US009546164B2

(12) United States Patent
Andrez et al.

(10) Patent No.: US 9,546,164 B2
(45) Date of Patent: Jan. 17, 2017

(54) SUBSTITUTED BENZAMIDES AND METHODS OF USE THEREOF

(71) Applicants: GENENTECH, INC., South San Francisco, CA (US); XENON PHARMACEUTICALS INC., Burnaby (CA)

(72) Inventors: Jean-Christophe Andrez, Burnaby (CA); Paul Robert Bichler, Burnaby (CA); Chien-An Chen, Shanghai (CN); Sultan Chowdhury, Burnaby (CA); Shannon Marie Decker, Burnaby (CA); Christoph Martin Dehnhardt, Burnaby (CA); Thilo Focken, Burnaby (CA); Michael Edward Grimwood, Burnaby (CA); Ivan William Hemeon, Burnaby (CA); Qi Jia, Burnaby (CA); Jun Li, South San Francisco, CA (US); Zhiguo Liu, Shanghai (CN); Daniel F. Ortwine, South San Francisco, CA (US); Brian Safina, South San Francisco, CA (US); Daniel Sutherlin, South San Francisco, CA (US); Tao Sheng, Burnaby (CA); Shaoyi Sun, Burnaby (CA); Andrew D. White, Shanghai (CN); Michael Scott Wilson, Burnaby (CA); Alla Yurevna Zenova, Burnaby (CA); Jiuxiang Zhu, Shanghai (CN)

(73) Assignees: GENENTECH, INC., South San Francisco, CA (US); XENON PHARMACEUTICALS INC., Burnaby, BC (CA)

( * ) Notice: Subject to any disclaimer, the term of this patent is extended or adjusted under 35 U.S.C. 154(b) by 0 days.

(21) Appl. No.: 14/603,273

(22) Filed: Jan. 22, 2015

(65) Prior Publication Data

US 2015/0252038 A1    Sep. 10, 2015

Related U.S. Application Data

(63) Continuation of application No. PCT/CN2014/092269, filed on Nov. 26, 2014.

(30) Foreign Application Priority Data

Nov. 27, 2013  (WO) ............... PCT/CN2013/001452
Nov. 28, 2013  (WO) ............... PCT/CN2013/088062
Nov. 3, 2014   (WO) ............... PCT/CN2014/090171

(51) Int. Cl.
*C07D 211/32* (2006.01)
*C07D 211/54* (2006.01)
(Continued)

(52) U.S. Cl.
CPC ........... *C07D 453/02* (2013.01); *A61K 31/337* (2013.01); *A61K 31/397* (2013.01);
(Continued)

(58) Field of Classification Search
CPC ... C07D 211/32; C07D 211/54; C07D 211/60; C07D 265/30; C07D 403/04; C07D 403/12; C07D 453/02; C07D 233/68; C07D 237/08; C07D 241/04; C07D 205/04; C07D 207/12; C07D 305/08; C07D 401/06; C07D 401/12; C07D 487/08
(Continued)

(56) References Cited

U.S. PATENT DOCUMENTS 3,705,185  A   12/1972  Moore et al.
5,171,748  A   12/1992  Roberts et al.
(Continued)

FOREIGN PATENT DOCUMENTS

CN   101466665 A   6/2009
CN   101643458     2/2010
(Continued)

OTHER PUBLICATIONS

Ikuma et al. "Preparation of 3- . . . " CA159:371450 (2013).*
Leeman et al. "Preparation of 4-benz . . . " CA122:250214 (2000).*
Fed. Reg. v.76(27), p. 7162-7175, slides 1, 64-67 (2011).*
Patani et al. "Bioisosterism: a rational . . . " Chem. Rev. 96, 3147-3176 (1996).*
Amaya et al., "The Voltage-Gated Sodium Channel Nav1.9 is an Effector of Peripheral Inflammatory Pain Hypersensitivity", *J. Neurosci*, 26(50), 12852-12860 (2006).
Arcangeli et al., "Targeting Ion Channels in Cancer: A Novel Frontier in Antineoplastic Therapy", *Current Medicinal Chemistry* 16, 66-93 (2009).
(Continued)

*Primary Examiner* — Celia Chang
(74) *Attorney, Agent, or Firm* — Viksnins Harris & Padys PLLP

(57) ABSTRACT

The invention provides compounds having the general formula I:

and pharmaceutically acceptable salts thereof, wherein the variables $R^A$, $R^{AA}$, subscript n, ring A, $X^2$, L, subscript m, $X^1$, $R^1$, $R^2$, $R^3$, $R^4$, $R^5$, and $R^N$ have the meaning as described herein, and compositions containing such compounds and methods for using such compounds and compositions.

38 Claims, No Drawings

(51) Int. Cl.

| | |
|---|---|
| C07D 233/68 | (2006.01) |
| C07D 453/02 | (2006.01) |
| A61K 31/337 | (2006.01) |
| A61K 31/397 | (2006.01) |
| A61K 31/4015 | (2006.01) |
| A61K 31/415 | (2006.01) |
| A61K 31/4412 | (2006.01) |
| A61K 31/495 | (2006.01) |
| C07D 237/08 | (2006.01) |
| C07D 241/04 | (2006.01) |
| C07D 205/04 | (2006.01) |
| C07D 207/12 | (2006.01) |
| C07D 211/42 | (2006.01) |
| C07D 305/08 | (2006.01) |
| C07D 401/06 | (2006.01) |
| C07D 401/12 | (2006.01) |
| C07D 403/12 | (2006.01) |
| C07D 403/04 | (2006.01) |
| C07D 487/08 | (2006.01) |
| C07D 265/30 | (2006.01) |
| C07D 211/60 | (2006.01) |

(52) U.S. Cl.
CPC ........ *A61K 31/4015* (2013.01); *A61K 31/415* (2013.01); *A61K 31/4412* (2013.01); *A61K 31/495* (2013.01); *C07D 205/04* (2013.01); *C07D 207/12* (2013.01); *C07D 211/32* (2013.01); *C07D 211/42* (2013.01); *C07D 211/54* (2013.01); *C07D 211/60* (2013.01); *C07D 233/68* (2013.01); *C07D 237/08* (2013.01); *C07D 241/04* (2013.01); *C07D 265/30* (2013.01); *C07D 305/08* (2013.01); *C07D 401/06* (2013.01); *C07D 401/12* (2013.01); *C07D 403/04* (2013.01); *C07D 403/12* (2013.01); *C07D 487/08* (2013.01)

(58) Field of Classification Search
USPC ........ 544/238; 546/133, 200, 208, 211, 221; 548/518, 950, 953; 514/210.01, 210.17, 514/210.2, 210.21, 252.03, 323 M, 326, 327
See application file for complete search history.

(56) References Cited

U.S. PATENT DOCUMENTS

| | | | |
|---|---|---|---|
| 5,573,653 A | 11/1996 | Bandlish | |
| 5,580,982 A | 12/1996 | O'Malley | |
| 5,753,653 A | 5/1998 | Bender et al. | |
| 6,096,771 A | 8/2000 | Kojima | |
| 7,262,304 B2 | 8/2007 | Ueno et al. | |
| 7,291,638 B2 | 11/2007 | Lee | |
| 7,858,639 B2 | 12/2010 | Sun | |
| 8,153,814 B2 | 4/2012 | Beaudoin | |
| 8,193,194 B2 * | 6/2012 | Martinborough | C07C 311/51 514/253.06 |
| 8,642,660 B2 | 2/2014 | Goldfarb | |
| 8,889,741 B2 | 11/2014 | Shinozuka | |
| 8,933,236 B2 * | 1/2015 | Chowdhury | C07D 413/12 546/124 |
| 8,952,169 B2 | 2/2015 | Andrez et al. | |
| 9,102,621 B2 * | 8/2015 | Brown | C07D 213/30 |
| 2006/0069093 A1 | 3/2006 | Scarborough et al. | |
| 2007/0088015 A1 | 4/2007 | Silva et al. | |
| 2008/0161303 A1 | 7/2008 | Zhang et al. | |
| 2008/0312286 A1 | 12/2008 | Pinkerton et al. | |
| 2009/0012103 A1 | 1/2009 | Abelman et al. | |
| 2010/0179137 A1 | 7/2010 | Kamikubo et al. | |
| 2010/0197655 A1 | 8/2010 | Beaudoin et al. | |
| 2010/0286110 A1 | 11/2010 | Fyfe et al. | |
| 2011/0092703 A1 | 4/2011 | Sakuma et al. |
| 2012/0004714 A1 | 1/2012 | Kleve et al. |
| 2012/0010182 A1 | 1/2012 | Brown et al. |
| 2012/0010183 A1 | 1/2012 | Bell et al. |
| 2012/0010207 A1 | 1/2012 | Bell et al. |
| 2012/0196869 A1 | 8/2012 | Hadida-Ruah et al. |
| 2013/0324525 A1 | 12/2013 | Abelman et al. |
| 2013/0338111 A1 | 12/2013 | Beaudoin et al. |
| 2014/0213616 A1 | 7/2014 | Hadida-Ruah et al. |
| 2014/0296266 A1 | 10/2014 | Hu et al. |
| 2015/0291514 A1 | 10/2015 | Brown et al. |

FOREIGN PATENT DOCUMENTS

| | | |
|---|---|---|
| EP | 0179619 | 9/1990 |
| EP | 0516392 | 12/1992 |
| EP | 2184278 | 5/2010 |
| WO | WO 90/08128 A1 | 7/1990 |
| WO | 0039077 A2 | 7/2000 |
| WO | WO 03/059882 A1 | 7/2003 |
| WO | 2004014913 | 2/2004 |
| WO | 2004052869 A1 | 6/2004 |
| WO | WO 2004/092145 A1 | 10/2004 |
| WO | 2005013914 | 2/2005 |
| WO | 2005032488 | 4/2005 |
| WO | 2006015158 | 2/2006 |
| WO | 2006020830 | 2/2006 |
| WO | 2006039212 | 4/2006 |
| WO | 2006122800 | 11/2006 |
| WO | WO 2006/121097 A1 | 11/2006 |
| WO | 2007030582 | 3/2007 |
| WO | WO 2007/045572 A1 | 4/2007 |
| WO | WO 2007/062078 A2 | 5/2007 |
| WO | 2007067994 A1 | 6/2007 |
| WO | 2007120647 A2 | 10/2007 |
| WO | 2008094602 | 8/2008 |
| WO | 2008097991 A1 | 8/2008 |
| WO | 2008118758 | 10/2008 |
| WO | 2009012242 | 1/2009 |
| WO | WO 2009/010784 A1 | 1/2009 |
| WO | WO 2009/157399 A1 | 12/2009 |
| WO | WO 2010/022055 A2 | 2/2010 |
| WO | 2010079443 | 7/2010 |
| WO | 2011014462 A1 | 2/2011 |
| WO | 2011016234 A1 | 2/2011 |
| WO | 2011037192 A1 | 3/2011 |
| WO | 2011063001 | 5/2011 |
| WO | WO 2011/059042 A1 | 5/2011 |
| WO | 2011088201 A1 | 7/2011 |
| WO | 2011100433 | 8/2011 |
| WO | WO 2011/153588 A1 | 12/2011 |
| WO | 2012004664 | 1/2012 |
| WO | 2012007883 | 1/2012 |
| WO | WO 2012/004706 A2 | 1/2012 |
| WO | WO 2012/004714 A2 | 1/2012 |
| WO | WO 2012/007836 A1 | 1/2012 |
| WO | WO 2012/007861 A1 | 1/2012 |
| WO | WO 2012/007868 A2 | 1/2012 |
| WO | WO 2012/007869 A2 | 1/2012 |
| WO | WO 2012/007877 A2 | 1/2012 |
| WO | WO 2012/035023 A1 | 3/2012 |
| WO | WO 2012/039657 A1 | 3/2012 |
| WO | 2012085650 | 6/2012 |
| WO | WO 2012/095781 A1 | 7/2012 |
| WO | WO 2013/025883 A1 | 2/2013 |
| WO | 2013056232 | 4/2013 |
| WO | 2013072758 A1 | 5/2013 |
| WO | WO 2013/063459 A1 | 5/2013 |
| WO | WO 2013/064983 A1 | 5/2013 |
| WO | WO 2013/064984 A1 | 5/2013 |
| WO | WO 2013/086229 A1 | 6/2013 |
| WO | WO 2013/088315 A1 | 6/2013 |
| WO | WO 2013/102826 A1 | 7/2013 |
| WO | 2013161801 | 8/2013 |
| WO | WO 2013/118805 A1 | 8/2013 |
| WO | WO 2013/118854 A1 | 8/2013 |
| WO | WO 2013/122897 A1 | 8/2013 |
| WO | WO 2013/134518 A1 | 9/2013 |
| WO | WO 2013/146969 A1 | 10/2013 |

(56) References Cited

FOREIGN PATENT DOCUMENTS

| WO | WO 2013/177224 A1 | 11/2013 |
| --- | --- | --- |
| WO | WO 2014/008458 A2 | 1/2014 |
| WO | WO 2014/014050 A1 | 1/2014 |
| WO | 2014066490 | 5/2014 |
| WO | 2014066491 | 5/2014 |
| WO | 2014096941 | 6/2014 |
| WO | 2014151472 | 9/2014 |
| WO | WO 2014/144545 A2 | 9/2014 |
| WO | WO 2014/153037 A1 | 9/2014 |
| WO | 2015051043 | 4/2015 |
| WO | 2015078374 | 6/2015 |

OTHER PUBLICATIONS

Bach et al., "A novel series of piperazinyl-pyridine ureas as antagonists of the purinergic P2T12 receptor", Bioorganic & Medicinal Chemistry Letters 21, 2877-2881 (2011).

Banks et al., "The Reaction of N-Alkylhydroxamic Acids with Sulphinyl Chlorides", J. Chem. Soc. Perkin Trans. II, 1211-1216 (1986).

Bean et al., "Lidocaine Block of Cardiac Sodium Channels", J. Gen. Physiol. 81, 613-642 (1983).

Binder et al., "Disease Mechanisms in Neuropathic Itch", Nature Clinical Practice Neurology 4(6), 329-337 (2008).

Black et al., "Changes in the expression of tetrodotoxin-sensitive sodium channels within dorsal root ganglia neurons in inflammatory pain", Pain, 108(3), 237-247.

Blair et al., "Roles of tetrodotoxin (TTX)-sensitive Na+ current, TTX-resistant Na+ current, and Ca2+ current in the action potentials of nociceptive sensory neurons", J. Neurosci, 22, 10277-10290 (2002).

Brackenbury and Djamgoz, "Activity-dependent regulation of voltage-gated Na+ channel expression in Mat-LyLu rat prostate cancer cell line", J. Physiol 573.2, 343-356 (2006).

Caldwell et al., "Sodium channel Nav1.6 is localized at nodes of Ranvier, dendrites, and synapses", Proc. Natl. Acad., 97(10), 5616-5620 (2000).

CAS Registry Nos. 1027529-26-5, 1027209-51-3 and 1026292-79-4, 1 page (2015).

Catterall, "From ionic currents to molecular mechanisms: the structure and function of voltage-gated sodium channels", Neuron, 26, 13-25 (2000).

Catterall, "Structural biology: A 3D view of sodium channels", Nature, vol. 409, 988-991 (2001).

Catterall, "Molecular mechanisms of gating and drug block of sodium channels", Novartis Foundation Symposium 241, 206-225 (2002).

Cestele et al., "Molecular mechanisms of neurotoxin action on voltage-gated sodium channels", Biochimie 82, 883-892 (2000).

Chan et al., "Rh(II)-Catalyzed Intermolecular Oxidative Sulfamidation of Aldehydes: A Mild Efficient Synthesis of N-Sulfonylcarboxamides", J. Am. Chem. Soc., 129, 14106-14107 (2007).

Chioni et al., "A novel adhesion molecule in human breast cancer cell lines: Voltage-gated Na+ channel β1 subunit", Int'l J. Biochem. Cell Biol. 41, 1216-1227 (2009).

Chung and Chung, "Sodium channels and neuropathic pain", Novartis Foundation Symposium 261, 19-31 (2004).

Clare et al., "Voltage-gated sodium channels as therapeutic targets" Drug Discovery Today 5(11), 506-520 (2000).

Cox et al., "An SCN9A channelopathy causes congenital inability to experience pain", Nature 444, 894-898 (2006).

Daeniker et al., "234. Uber bicyclische Sulfonamide", Helvetica Chimica ACTA, vol. 45 (6), 1972-1981 (1962).

Database Reaxys, XP002692384, Accession No. XRN: 6729065, 6731122, 1 page, (D. Bertoia et al., "Base promoted ring-opening reactions of 2-p-tolyl-5,6-dihydro-1,4,3-oxathizaine 4,4-dioxides", Gazetta Chimica Italiana, vol. 118 (6), 435-440 (1988)).

Devor et al., "Na+ Channel Immunolocalization in Peripheral Mammalian Axons and Changes following Nerve Injury and Neuroma Formation", J. Neurosci, 13(5), 1976-1992 (1993).

Dib-Hajj et al., "NaN, a novel voltage-gated Na channel is expressed preferentially in peripheral sensory neurons and down-regulated after axotomy", Proc. Natl Acad Sci, 95, 8963-8968 (1998).

Dib-Hajj et al., "Genetics and Molecular Pathophysiology of NaV1.7-related Pain Syndromes", Advances in Genetics 63, 85-110 (2008).

Dickore, "Synthese and reaktionen von 1.3.4-oxathiazolin-3-dioxyden", Justus Liebigs Annalen Der Chemie, vol. 671, 135-146, XP055053742, Compounds IVa, IVb, IVd, V, VI (1964).

Diss et al. "Expression profiles of voltage-gated sodium channel α-subunit genes in rat and human prostate cancer cell lines", The Prostate 48, 165-178 (2001).

Diss et al. "A potential novel marker for human prostate cancer: voltage-gated sodium channel expression in vivo", Prostate Cancer and Prostatic Diseases 8, 266-273 (2005).

Diss et al. "Identification and characterization of the promoter region of the NaV1.7 voltage-gated sodium channel gene (SCN9A)", Mol. Cell. Neurosci. 37, 537-547 (2008).

Dong et al., "Small interfering RNA-mediated selective knockdown of NaV1.8 tetrodotoxin-resistant sodium channel reverses mechanical allodynia in neuropathic rats", Neuroscience, 146, 812-821 (2007).

England et al., "Isoform-selective voltage-gated Na(+) channel modulators as next-generation analgesics", Future Med Chem, 2, 775-790 (2010).

Estacion et al., "A sodium channel gene SCN9A polymorphism that increases nociceptor excitability", Annals of Neurol, 66(6), 862-866 (2009).

Fishman et al. "Intravenous lidocaine for treatment-resistant pruritus", American J. of Medicine 102, 584-585 (1997).

Fraser et al., "Voltage-gated sodium channel expression and potentiation of human breast cancer metastasis", Clin. Cancer Res. 11(15), 5381-5389 (2005).

Goldberg et al., "Loss-of-function mutations in the Nav1.7 gene underlie congenital indifference to pain in multiple human populations", Clin. Genet., 71, 311-319 (2007).

Goldin et al., "Nomenclature of Voltage-Gated Sodium Channels", Neuron, vol. 28, 365-368 (2000).

Gould et al., "Development of inflammatory hypersensitivity and augmentation of sodium channels in rat dorsal root ganglia", Brain Res., 824(2), 296-299 (1999).

Hains et al., "Upregulation of Sodium Channel Nav1.3 and Functional Involvement in Neuronal Hyperexcitability Associated with Central Neuropathic Pain after Spinal Cord Injury", Journal of Neuroscience 23(26), 8881-8892 (2003).

Ikoma et al., "Neuronal sensitization for histamine-induced itch in lesional skin of patients with atopic dermatitis", Arch. Dermatol. 139, 1445-1458 (2003).

Ikoma et al., "The neurobiology of itch", Nature Reviews Neuroscience 7, 535-547 (2006).

Kis-Toth et al., "Voltage-gated sodium channel NaV1.7 maintains the membrane potential and regulates the activation and chemokine-induced migration of a monocyte-derived dendritic cell subset", J. Immunology 187, 1273-1280 (2011).

Klugbauer et al., "Structure and functional expression of a new member of the tetrodotoxin-sensitive voltage-activated sodium channel family from human neuroendocrine cells", EMBO J. 14(6), 1084-1090 (1995).

Kutt et al., "A Comprehensive Self-Consistent Spectrophotometric Acidity Scale of Neutral Bronsted Acids in Acetonitrile", J. Org. Chem. 71, 2829-2838 (2006).

Lai et al., "Inhibition of neuropathic pain by decreased expression of the tetrodotoxin-resistant sodium channel, NaV1.8", Pain, 95, 143-152 (2002).

Lai et al., "The role of voltage-gated sodium channels in neuropathic pain", Current Opinion in Neurobiology 13, 291-297 (2003).

Liu et al., "Mutations in cardiac sodium channels: clinical implications", Am. J. Pharmacogenomics, 3(3), 173-179 (2003).

(56) References Cited

OTHER PUBLICATIONS

Mao et al., "Systemic lidocaine for neuropathic pain relief", *Pain* 87, 7-17 (2000).
Massah et al., "Synthesis, in vitro antibacterial and carbonic anyydrase II inhibitory activities of N-acylsulfonamides using silica sulfuric acid as an efficient catalyst under both solvent-free and heterogeneous conditions", *Bioorganic & Medicinal Chemistry* 16, 5465-5472 (2008).
Meisler et al., "Sodium channel gene family: epilepsy mutations, gene interactions and modifier effects", *Journal of Physiology*, 588, 1841-1848 (2010).
Morinville et al., "Distribution of the voltage-gated sodium channel NaV1.7 in the rat: expression in the autonomic and endocrine systems" *J. Comparative Neurology* 504, 680-689 (2007).
Oaklander et al., "Intractable post-herpetic itch and cutaneous deafferentation after facial singles", *Pain* 96, 9-12 (2002).
Patent Cooperation Treaty, International Searching Authority, Search Report and Written Opinion for PCT/CN2014/092269, 17 pages, Feb. 17, 2015.
Priest et al., "Contribution of the tetrodotoxin-resistant voltage-gated sodium channel Nav1.9 to sensory transmission and nociceptive behavior", *Proc Natl Acad Sci*, 102(26), 9382-8387 (2005).
Priest, "Future potential and status of selective sodium channel blockers for the treatment of pain", *Current Opinion in Drug Discovery and Development*, 12(5), 682-692 (2009).
Raymond et al., "Expression of Alternatively Spliced Sodium Channel α-Subunit Genes: Unique Splicing Patterns Are Observed in Dorsal Root Ganglia", *J. Biol. Chem.*, 279, 46234-46241 (2004).
Reimann et al., "Pain perception is altered by a nucleotide polymorphism in SCN9A", *Proc Natl Acad Sci*, 107(11), 5148-5153 (2010).
Roberts et al., "Novel Aryl and Heteroaryl Acyl Microwave-Assisted Palladium-Catalyzed Carbonylation", *Organic Letters*, vol. 12(6), 1264-1267 (2010).
Roberts et al., "Molybdenum-Mediated Carbonylaiton of Aryl Halides with Nucleophiles Using Microwave Irradiation", *Organic Letters*, vol. 12 (19), 4280-4283 (2010).
Ruan et al., "Sodium channel mutations and arrhythmias", *Nature Reviews Cardiology*, 6, 337-348 (2009).
Rugiero et al., "Selective Expression of a Persistent Tetrodotoxin-Resistant Na+ Current and Nav1.9 Subunit in Myenteric Sensory Neurons", *J. Neurosci*, 23(7), 2715-2725 (2003).
Sangameswaran et al., "A Novel Tetrodotoxin-sensitive, Voltage-gated Sodium Channel Expressed in Rat and Human Dorsal Root Ganglia", *J. Biol. Chem.*, 272(23), 14805-14809 (1997).
Sato et al., "The voltage-sensitive sodium channel is a bell-shaped molecule with several cavities", *Nature* 409, 1047-1051 (2001).
Smith et al., "Sodium channel protein expression enhances the invasiveness of rat and human prostate cancer cells", *FEBS Letters*, 423, 19-24 (1998).
Tamaoka, "Paramyotonia Congenita and Skeletal Sodium Channelopathy", *Internal Medicine* vol. 42 (2), 769-770 (2003).
Tanelian and Brose, "Neuropathic pain can be relieved by drugs that are use-dependent sodium channel blockers: lidocaine, carbamazepine and mexiletine", *Anesthesiology*, 74(5), 949-951 (1991).
Termin et al., "Chapter 3 Recent Advances in Voltage-Gated Sodium Channel Blockers: Therapeutic Potential as Drug Targets in the CNS", *Annual Reports in Medicinal Chemistry*, 43, 43-60 (2008).
Toledo-Aral et al., "Identification of PN1, a predominant voltage-dependent sodium channel expressed principally in peripheral neurons", *Proc. Natl. Acad. Sci*, 94, 1527-1532 (1997).
Villamil et al., "Efficacy of lidocaine in the treatment of pruritus in patients with chronic cholestatic liver disease", *Am. J. Med*, 118, 1160-1163 (2005).
Wallace et al., "Efficacy of oral mexiletine for neuropathic pain with allodynia: a double-blind, placebo-controlled, crossover study", *Reg. Anesth. Pain Med.*, 25, 459-467 (2000).

Wood et al., "Voltage-gated sodium channels and pain pathways", *J. Neurobiol.*, 61(1), 55-71 (2004).
Xiao and Bennett, "C-fiber spontaneous discharge evoked by chronic inflammation is suppressed by a long-term infusion of lidocaine yielding nanogram per milliliter plasma levels", *Pain* 137, 218-228 (2008).
Yang et al., "Mutations in SCN9A, encoding a sodium channel alpha subunit, in patients with primary erythermalgia", *J. Med. Genet.*, 41(3), 171-174 (2004).
Yu et al., "The VGL-Chanome: A Protein Superfamily Specialized for Electrical Signaling and Ionic Homeostasis", *Sci. STKE*, 253, p. re15 (2004).
Yu et al., "Sodium Channel Beta4, a New Disulfide-Linked Auxiliary Subunit with Similarity to Beta2", *Journal of Neuroscience*, vol. 23(20), 7577-7585 (2003).
Yu et al., "Reduced sodium current in GABAergic interneurons in a mouse model of severe myoclonic epilepsy in infancy", *Nature Neuroscience* 9, 1142-1149 (2006).
Zhao et al., "Voltage-gated sodium channel expression in rat and human epidermal keratinocytes: evidence for a role in pain", *Pain*, 139, 90-105 (2008).
Zuliani et al., "Sodium channel blockers for neuropathic pain", *Epert Opinion on Therapeutic Patents*, vol. 20 (6), 755-779 (2010).
Braga et al., "Making crystals from crystals: a green route to crystal engineering and polymorphism", Chem Commun J Roy Soc Chem, 3635-3645 (2005).
Catron et al, "Preparation of 4-[4-[2-phenylcclohexen-1-en-1-yl)methyl]piperazin-1-ul]-N-(phenylsulfonyl) benzamides and 4-[4-[ (2-phenylcyclohexen-1-en-1-yl)methyl]piperazin-1-7l]-N-(3-pyridylsulfonlyl)benzamides as apoptosis-inducing agent-containing solid dispersions useful in treatment of cancer", CAPLUS 2012:637301, 156:638098, 2 pages (2012).
Hayes et al., "Na(V)1.7 Paint Control: A Novel Target", Neurosurgery 73, N16 (2013).
"Improper Markush", Fed Reg V. 76(27), 7162-7175, Slide 1, 64-67 (2011).
Prodrug "Dictionary" 1-2, Internet (2002).
PubChem, Compound Summary for CID 14280666, N-(1,2-benzoxazol-3-yl) methanesulfonamide, https://pubchem.ncbi.nim.nih.gov/summary/summary.cgi?cid=14280666, 3 pages (2007).
Sakuma et al., "Preparation of piperazine . . . ", CA150:260220 (2009).
Schmelz, "Itch and pain", Neuroscience and Biobehaviorial Reviews, 34, 171-176 (2010).
Seddon, "Pseudopolymorph: A Polemic", Crystal Growth and Design vol. 4(6), 1087 (2004).
Silos-Santiago, "Drugs in Clinical Development for Neuropathic Pain", presented at First World Conference Abdominal and Pelvic Pain, Amsterdam, pp. 1-23 (Jun. 6, 2013).
Vippagunta et al., "Crystal Solids", Adv Drug Del Rev vol. 48, 3-26 (2001).
Wolff Burger's Medicinal Chemistry and Drug Discovery Fifth Edition, vol. 1: Principles and Practice, 975-977 (1995).
Chemical Abstracts_1, XP002744143, Database accession No. 1321299-48-2 Abstract (Aug. 22, 2011).
Chemical Abstracts_2, XP002744144, Database accession No. 1320435-32-2 Abstract (Aug. 22, 2011).
Chemical Abstracts_3, XP002744145, Database accession No. 1319619-74-3 Abstract (Aug. 18, 2011).
Chemical Abstracts_4, XP002744146, Database accession No. 1294599-14-6 Abstract (May 15, 2011).
Chemical Abstracts_5, XP002744147, Database accession No. 1051238-85-7 Abstract (Sep. 21, 2008).
Chemical Abstracts_6, XP002744148, Database accession No. 1051172-94-1 Abstract (Sep. 21, 2008).
Chemical Abstracts_7, XP002744149, Database accession No. 1301192-24-4 (May 26, 2011).
Chemical Abstracts_8, XP002744150, Database accession No. 1299653-84-3 Abstract (May 24, 2011).
Chemical Abstracts_9, XP002744151, Database accession No. 299214-10-0 (May 24, 2011).
Chemical Abstracts_10, XP002744152, Database accession No. 1288553-28-5 Abstract (May 1, 2011).

(56) References Cited

OTHER PUBLICATIONS

Chemical Abstracts_11, XP002744153, Database accession No. 1278399-39-5 Abstract (Apr. 11, 2011).
Chemical Abstracts_12, XP002744154, Database accession No. 1297052-59-5 Abstract (May 19, 2011).
Chemical Abstracts_13, XP002744155, Database accession No. 1277490-84-2 Abstract (Apr. 10, 2011).
Daeniker et al., "234. Uber bicyclische Sulfonamide", Helvetica Chimica ACTA, vol. 45 (6), 1972-1981 (1962). [English Translation.].
Dickore, "Synthese and reaktionen von 1.3.4-oxathiazolin-3-dioxyden", Justus Liebigs Annalen Der Chemie, vol. 671, 135-146, XP055053742, Compounds IVa, IVb, IVd, V, VI (1964). [English Translation.].
Li et al., "Recent advances in the structure-activity relationship study of small-molecule sodium channel blockers with analgesic effects", Acta Pharmaceutica Sinica, vol. 44, (2), 101-108 (2009). [English Translation.].
Chemical Abstract Service, STN Registry Database No. 891026-77-0 [entered STN: Jul. 9, 2006].
Chemical Abstract Service, STN Registry Database No. 892698-09-8 [entered STN: Jul. 14, 2006].
Deng, et al., "Dynamic 1-15 Receptor-Based Pharmacophore Model Development and Its Application in Designing Novel HIV-1 Integrase Inhibitors", Journal of Medicinal Chemistry. vol. 48. No. 5, 1496-1505 (2005), Supporting Information, S1-S14. XP055285519. DOI: 10.1021j0049410e (2005).
Kuo, et al., "Application of CoMFA and CoMSIA 3D-QSAR and Docking Studies in Optimization of Mercaptobenzenesulfonamides as HIV-1 Integrase Inhibitors", Journal of Medicinal Chemistry. American Chemical Society. US. vol. 47. No. 2, 385-399 (2003).
File CAPLUS, Registry No. 1333872-40-4, entered STN: Sep. 29, 2011.
Lamoureux, et al., "Use of the adamantane structure in medicinal chemistry", Curr Med Chem 17(26), 2967-2978 (2010).

\* cited by examiner

SUBSTITUTED BENZAMIDES AND METHODS OF USE THEREOF

RELATED APPLICATIONS

This application is a continuation of international patent application number PCT/CN2014/092269, filed Nov. 26, 2014, and claims priority to international patent application number PCT/CN2014/090171, filed Nov. 3, 2014, and international patent application number PCT/CN2013/088062, filed Nov. 28, 2013, and international patent application number PCT/CN2013/001452, filed Nov. 27, 2013, all of which are incorporated by reference in their entirety.

The present invention relates to organic compounds useful for therapy and/or prophylaxis in a mammal, and in particular to inhibitors of sodium channel (e.g., NAV1.7) that are useful for treating sodium channel-mediated diseases or conditions, such as pain, as well as other diseases and conditions associated with the mediation of sodium channels.

Voltage-gated sodium channels, transmembrane proteins that initiate action potentials in nerve, muscle and other electrically excitable cells, are a necessary component of normal, sensation, emotions, thoughts and movements (Catterall, W. A., Nature (2001), Vol. 409, pp. 988-990). These channels consist of a highly processed alpha subunit that is associated with auxiliary beta subunits. The pore-forming alpha subunit is sufficient for channel function, but the kinetics and voltage dependence of channel gating are in part modified by the beta subunits (Goldin et al., Neuron (2000), Vol. 28, pp. 365-368). Electrophysiological recording, biochemical purification, and molecular cloning have identified, ten different sodium channel alpha subunits and four beta subunits (Yu, F. H., et al., Sci. STKE (2004), 253; and Yu, F. H., et al., Neurosci. (2003), 20:7577-85).

The hallmarks of sodium channels include rapid activation and inactivation when the voltage across the plasma membrane of an excitable cell is depolarized (voltage-dependent gating), and efficient and selective conduction of sodium ions through conducting pores intrinsic to the structure of the protein (Sato, C., et al., Nature (2001), 409:1047-1051). At negative or hyperpolarized membrane potentials, sodium channels are closed. Following membrane depolarization, sodium channels open rapidly and then inactivate. Channels only conduct currents in the open state and, once inactivated, have to return to the resting state, favoured by membrane hyperpolarization, before they can reopen. Different sodium channel subtypes vary in the voltage range over which they activate and inactivate as well as their activation and inactivation kinetics.

The sodium channel family of proteins has been extensively studied and shown to be involved in a number of vital body functions. Research in this area has identified variants of the alpha subunits that result in major changes in channel function and activities, which can ultimately lead to major pathophysiological conditions. The members of this family of proteins are denoted NaV1.x, where x=1 to 9, NaV1.1 and NaV1.2 are highly expressed in the brain (Raymond, C. K., et al., J. Biol. Chem. (2004), 279(44):46234-41) and are vital to normal brain function. Some loss of function mutations in NaV1.1 in humans result in epilepsy, apparently because many of these channels are expressed in inhibitory neurons (Yu, F. H., et al., Nat Neurosci (2006), 9 (9), 1142-9). Thus, block of NaV1.1 in the CNS may be counter-productive because it can produce hyperexcitability. However, NaV1.1 is also expressed in the peripheral nervous system and block may afford analgesic activity.

NaV1.3 is expressed primarily in the fetal central nervous system. It is expressed at very low levels or not at all in the peripheral nervous system, but expression is unregulated in the dorsal horn sensory neurons of rats after nervous system injury (Mains, B. D., et al., J. Neurosci. (2003), 23(26): 8881-92). Thus, it is an inducible target for treatment of pain following nerve injury.

NaV1.4 is expressed primarily is skeletal muscle (Raymond, C. K., et al., op. cit). Mutations in this gene have been shown to have profound effects on muscle function including paralysis, (Tamaoka A., Intern. Med. (2003), (9):769-70).

NaV1.5, is expressed mainly in cardiac myocytes (Raymond, C. K., et al., op. cit), including atria, ventricles, the sino-atrial node, atrio-ventricular node and cardiac Purkinje fibers. The rapid upstroke of the cardiac action potential and the rapid impulse conduction through cardiac tissue is due to the opening of NaV1.5. Abnormalities in the function of NaV1.5 can result in the genesis of a variety of cardiac arrhythmias. Mutations in human NaV1.5 result in multiple arrhythmic syndromes, including, for example, long QT3 (LQT3), Brugada syndrome (BS), an inherited cardiac conduction defect, sudden unexpected nocturnal death syndrome (SUNDS) and sudden infant death syndrome (SIDS) (Liu, H., et al. Am. J. Pharmacogenomics (2003), 3(3): 173-9). Sodium channel blocker therapy has been used extensively in treating cardiac arrhythmias.

NaV1.6 is a widely distributed voltage-gated sodium channel found throughout the central and peripheral nervous systems. It is expressed at high density in the nodes of Ranvier of myelinated neurons (Caldwell, J. H., et al., Proc. Natl. Acad. Sci USA (2000), 97(10): 5616-20).

NaV1.7 is a tetrodotoxin-sensitive voltage-gated sodium channel encoded by the gene SCN9A. Human NaV1.7 was first cloned from neuroendocrine cells (Klugbauer, N., et al., 1995 EMBO J., 14 (6): 1084-90.) and rat NaV1.7 was cloned from a pheochromocytoma PC12 cell line (Toledo-Aral, J. J., et al., Proc. Natl. Acad. Sci. USA (1997), 94:1527-1532) and from rat dorsal root ganglia (Sangameswaran, L., et al., (1997), J. Biol. Chem., 272 (23); 14805-9). NaV1.7 is expressed primarily in the peripheral nervous system, especially nociceptors and olfactory neurons and sympathetic neurons. The inhibition, or blocking, of NaV1.7 has been shown to result in analgesic activity. Knockout of NaV1.7 expression in a subset of sensory neurons that are predominantly nociceptive results in resistance to inflammatory pain (Nassar, et al., op. cit.). Likewise, loss of function mutations in humans results in congenital indifference to pain (CIP), in which the individuals are resistant to both inflammatory and neuropathic pain (Cox, J. J., et al., Nature (2006); 444:894-898; Goldberg, Y. P., et al., Clin. Genet. (2007); 71:311-319. Conversely, gain of function mutations in NaV1.7 have been established in two human heritable pain conditions, primary erythromelalgia and familial rectal pain, (Yang, Y., et al., J. Med. Genet. (2004), 41(3): 171-4). In addition, a single nucleotide polymorphism (R1150W) that has very subtle effects on the time- and voltage-dependence of channel gating has large effects on pain perception (Estacion, M., et al., 2009. Ann. Neurol 66: 862-6; Reimann, F., et al., Proc Natl Acad Sci USA (2010), 107: 5148-53). About 10% of the patients with a variety of pain conditions have the allele conferring greater sensitivity to pain and thus might be more likely to respond to block of NaV1.7. Because NaV1.7 is expressed in both sensory and sympathetic neurons, one might expect that enhanced pain perception would be accompanied by cardiovascular abnormalities such as hypertension, but no correlation has been reported. Thus, both the CIP mutations and SNP analysis suggest that human pain responses are more sensitive to changes in NaV1.7 currents than are perturbations of autonomic function.

NaV1.8 is expressed, primarily in sensory ganglia of the peripheral nervous system, such as the dorsal root ganglia (Raymond, C. K., at al., op. cit.). There are no identified human mutations for NaV1.8 that produce altered pain responses. NaV1.8 differs from most neuronal NaV's in that it is insensitive to block by tetrodotoxin. Thus, one can isolate the current carried by this channel with tetrodotoxin. These studies have shown that a substantial portion of total sodium current is NaV1.8 in some dorsal root ganglion neurons (Blair, N. T., et al., J Neurosci (2002), 22: 10277-90). Knock-down of NaV1.8 in rats has been achieved by using antisense DNA or small interfering RNAs and virtually complete reversal of neuropathic pain was achieved in the spinal nerve ligation and chronic constriction injury models (Dong, X. W., et al., Neuroscience (2007), 146: 812-21; Lai J., et al. Pain (2002), 95: 143-52). Thus, NaV1.8 is considered a promising target for analgesic agents based upon the limited tissue distribution of this NaV isoform and the analgesic activity produced by knock-down of channel expression.

NaV1.9 is also a tetrodotoxin insensitive, sodium channel expressed primarily in dorsal root ganglia neurons (Dib-Hajj, S. D., et al. (see Dib-Hajj, S. D., et al., Proc. Natl. Acad. Sci. USA (1998), 95(15):8963-8). It is also expressed in enteric neurons, especially the myenteric plexus (Rugiero, F., et al., J Neurosci (2003), 23:2715-25). The limited tissue distribution of this NaV isoform suggests that is may be a useful target for analgesic agents (Lai, J., et al., op. cit; Wood, J. N., et al., op. cit.; Chung, J. M., et al., op. cit.). Knock-out of NaV1.9 results in resistance to some forms of inflammatory pain (Amaya, F., et al., J Neurosci (2006), 26: 12852-60; Priest, B. T., et al. Proc Natl Acad Sci USA (2005). 102:9382-7).

This closely related family of proteins has long been recognized as targets for therapeutic intervention. Sodium channels are targeted by a diverse array of pharmacological agents. These include neurotoxins, antiarrhythmics, anticonvulsants and local anesthetics (England, S., et al., Future Med Chem (2010), 2: 775-90; Termin, A., et al., Annual Reports in Medicinal Chemistry (2008), 43: 43-60). All of the current pharmacological agents that act on sodium channels have receptor sites on the alpha subunits. At least six distinct receptor sites for neurotoxins and one receptor site for local anesthetics and related drugs have been identified (Cesteèle, S., et al., Biochimie (2000), Vol 82, pp. 883-892).

The small molecule sodium channel blockers or the local anesthetics and related antiepileptic and antiarrhythmic drugs interact with overlapping receptor sites located in the inner cavity of the pore of the sodium channel (Catterall, W. A., Neuron (2000), 26:13-25). Amino acid residues in the S6 segments from at least three of the four domains contribute to this complex drug receptor site, with the IVS6 segment playing the dominant role. These regions are highly conserved and as such most sodium channel blockers known to date interact with similar potency with all channel, subtypes. Nevertheless, it has been possible to produce sodium channel blockers with therapeutic selectivity and a sufficient therapeutic window for the treatment of epilepsy (e.g., lamotrignine, phenytoin and carbamazepine) and certain cardiac arrhythmias (e.g., lignocaine, tocainide and mexiletine). However, the potency and therapeutic index of these blockers is not optimal and have limited the usefulness of these compounds in a variety of therapeutic areas where a sodium channel blocker would be ideally suited.

Sodium channel blockers have been shows to be useful in the treatment of pain, including acute, chronic, inflammatory and/or neuropathic pain (see, e.g., Wood, J. N., et al., J. Neurobiol. (2004), 61(1), 55-71. Preclinical evidence demonstrates that sodium channel blockers can suppress neuronal firing in peripheral and central sensory neurons, and it is via this mechanism that they are considered to be useful for relieving pain. In some instances, abnormal or ectopic firing can original from injured or otherwise sensitized neurons. For example, it has been shown that sodium channels can accumulate in peripheral nerves at sites of axonal injury and may function as generators of ectopic firing (Devor et al., J. Neurosci. (1993), 132: 1976). Changes in sodium channel expression and excitability have also been shown in animal models of inflammatory pain where treatment with proinflammatory materials (CFA, Carrageenan) promoted pain-related behaviors and correlated with increased expression of sodium channel subunits (Gould et al., Brain Res., (1999), 824(2); 296-99; Black et al., Pain (2004), 108(3): 237-47). Alterations in either the level of expression or distribution of sodium channels, therefore, may have a major influence on neuronal excitability and pain-related behaviors.

Controlled infusions of lidocaine, a known sodium channel blocker, indicate that the drug is efficacious against neuropathic pain, but has a narrow therapeutic index. Likewise, the orally available local anesthetic, mexiletine, has dose-limiting side effects (Wallace, M. S., et al., Reg. Anesth. Pain Med. (2000), 25: 459-67). A major focus of drug discovery targeting voltage-gated sodium channels has been on strategies for improving the therapeutic index. One of the leading strategies is to identify selective sodium channel blockers designed to preferentially block NaV1.7, NaV1.8, NaV1.9 and/or NaV1.3. These are the sodium channel isoforms preferentially expressed in sensory neurons and unlikely to be involved in generating any dose-limiting side effects. For example, there is concern that blocking of NaV1.5 would be arrhythmogenic, so that selectivity of a sodium channel blocker against NaV1.5 is viewed as highly desirable. Furthermore, nearly 700 mutations of the SCN1A gene that codes for NaV2.1 have been identified in patients with Severe Myoclonic Epilepsy of Infancy (SMEI), making this the most commonly mutated gene in human epilepsy. Half of these mutations result in protein truncation (Meisler, M. H., et al., The Journal of Physiology (2010), 588: 1841-8). Thus, selectivity of a sodium channel blocker against NaV1.1 is also desirable.

In addition to the strategies of identifying selective sodium channel blockers, there is the continuing strategy of identifying therapeutic agents for the treatment of neuropathic pain. There has been some degree of success in treating neuropathic pain symptoms by using medications originally approved as anticonvulsants, such as gabapentin, and more recently pregabalm. However, pharmacotherapy for neuropathic pain has generally had limited success for a variety of reasons: sedation, especially by drugs first developed as anticonvulsants or anti-depressants, addiction or tachyphylaxis, especially by opiates, or lack of efficacy, especially by NSAIDs and anti-inflammatory agents. Consequently, there is still a considerable need to explore novel treatment modalities for neuropathic pain, which includes, but is not limited to, post-herpetic neuralgia, trigeminal neuralgia, diabetic neuropathy, chronic lower back pain, phantom limb pain, and pain resulting from cancer and chemotherapy, chronic pelvic pain, complex regional pain syndrome and related neuralgias.

There are a limited number of effective sodium channel blockers for the treatment of pain with a minimum of adverse side effects which are currently in the clinic. There is also an unmet medical need to treat neuropathic pain and other sodium channel associated pathological states effectively and without adverse side effects due to the blocking of sodium channels not involved in nociception. The present invention provides methods to meet these critical needs.

In one aspect the present invention provides for novel compounds. In a first embodiment of such compounds (Embodiment 1; abbreviated as "E1") the invention provides for a compound of formula I:


I or a pharmaceutically acceptable salt thereof, wherein:

$R^1$ is $C_{1-8}$alkyl, $C_{2-8}$alkenyl, $C_{1-8}$haloalkyl, $C_{1-8}$alkoxy, $C_{3-8}$carbocycle, C-linked $C_{2-7}$heterocycle, or $-NR^{1A}R^{1B}$, wherein $R^{1A}$ and $R^{1B}$ are each independently selected from the group consisting of hydrogen, $C_{1-8}$alkyl, $C_{1-8}$alkoxy, and wherein $R^{1A}$ and $R^{1B}$ are optionally combined to form a 3 to 8 membered heterocyclic ring optionally comprising 1 additional heteroatom selected from N, O and S; and wherein $R^1$ is optionally substituted with from 1 to 5 substituents selected from the group consisting of $C_{1-4}$alkyl, $C_{1-4}$haloalkyl F, Cl, Br, I, $-OH$, $-CN$, $-NO_2$, $-NR^{1a}R^{1b}$, $-OR^{R1a}$, $-SR^{R1a}$, $-Si(R^{R1a})_3$ and $C_{3-6}$carbocycle; wherein $R^{1a}$ and $R^{1b}$ are independently selected from the group consisting of hydrogen, $C_{1-8}$alkyl, $C_{1-8}$haloalkyl;

$R^N$ is hydrogen, $C_{1-4}$alkyl or $C_{1-4}$haloalkyl;

$R^2$ is selected from the group consisting of H, F, Cl, Br, I, $-CN$, $C_{1-8}$alkyl, $C_{1-8}$haloalkyl and $C_{1-8}$alkoxy;

$R^3$ is selected from the group consisting of H, F, Cl, Br, I, $-CN$, $C_{1-8}$alkyl, $C_{1-8}$haloalkyl and $C_{1-8}$alkoxy;

$R^4$ is selected from the group consisting of H, F, Cl, Br, I, $-CN$, $C_{1-8}$alkyl, $C_{1-8}$haloalkyl and $C_{1-8}$alkoxy;

$R^5$ is selected from the group consisting of H, F, Cl, Br, I, $-CN$, $C_{1-8}$alkyl, $C_{1-8}$haloalkyl, $C_{1-8}$alkoxy, $C_{1-8}$cycloalkyl and $C_{2-7}$heterocycle, wherein said $C_{3-8}$cycloalkyl and $C_{2-7}$heterocycle is optionally substituted with 1-3 substituents selected from F, Cl, Br and I;

L is a linker selected from the group consisting of $C_{1-4}$alkylene, $C_{2-4}$alkenylene and $C_{2-4}$alkynylene, wherein L is optionally substituted with from 1 to 3 substituents selected from the group consisting of $=O$, $C_{1-4}$alkyl halo, and $C_{1-4}$haloalkyl;

the subscript m represents the integer 0 or 1;

$X^1$ and $X^2$ are each independently selected from the group consisting of absent, $-O-$, $-S(O)-$, $-S(O)_2-$ and $-N(R^X)-$ wherein $R^x$ is H, $C_{1-8}$alkyl, $C_{1-8}$alkanoyl, or $-S(O)_2(C_{1-8}$alkyl), and wherein if the subscript m is 0 then one of $X^1$ or $X^2$ is absent;

the subscript n is an integer from 0 to 5;

the ring A is a $C_{2-11}$heterocycle comprising a nitrogen atom and further optionally comprising 1-2 heteroatoms selected from N, O and S;

each $R^{AA}$ is independently selected from the group consisting of $C_{1-6}$alkyl $C_{1-6}$haloalkyl, $C_{1-6}$heteroalkyl, CN, F, Cl, Br and I; and $R^A$ is selected from the group consisting of $-(X^{RB})_{0-1}$ $OR^{A1}$, $C_{6-10}$aryl-$(X^{RA})-$, $C_{1-20}$heteroaryl-$(X^{RA})-$, $C_{3-12}$carbocycle-$(X^{RA})-$, $-R^{A2}$, $-S(O)_2-R^{A2}$, and $C_{2-11}$heterocycle-$(X^{RA})-$, wherein said $C_{6-10}$aryl, $C_{5-9}$heteroaryl, $C_{3-12}$carbocycle and $C_{2-11}$heterocycle of $R^A$ is optionally substituted with from 1 to 5 substituents selected from, F, Cl, Br, I, $-NH_2$, $-OH$, $-CN$, $-NO_2$, $C_{1-4}$alkyl, $C_{1-4}$haloalkyl, $C_{1-4}$alkoxy, $C_{1-4}$(halo)alkoxy, $C_{1-4}$alkylamino, $C_{1-4}$dialkylamino, $C_{1-4}$alkanoyl, $C_{1-4}$alkyl-OC$(=O)-$, $C_{1-4}$alkyl-S(O)$_2-$, $C_{3-6}$carbocycle, and phenyl that is optionally substituted with one or more substituents selected from fluoro, chloro, and bromo; $R^{A1}$ is selected from the group consisting of hydrogen, $C_{1-8}$alkyl, $C_{2-8}$alkenyl, $C_{1-8}$haloalkyl, $C_{3-8}$cycloalkyl, phenyl and benzyl; $R^{A2}$ is selected from me group consisting of $C_{1-8}$alkyl that is optionally substituted with one or more substituents selected from oxo ($=O$), fluoro, amino, $C_{1-4}$alkylamino and $C_{1-4}$dialkylamino; $X^{RA}$ is selected from the group consisting of absent, $-O-$, $-S-$, $-N(H)-$, $-N(C_{1-4}$alkyl)-, $-S(O)-$, $-S(O)_2-$, $-C(=O)-$, $C_{1-4}$alkylene, $C_{1-4}$heteroalkylene, $C_{2-4}$alkenylene and $C_{2-4}$alkynylene; $X^{RB}$ is selected from the group consisting of absent, $C_{1-4}$alkylene, $C_{1-4}$heteroalkylene, $C_{2-4}$alkenylene and $C_{2-4}$alkynylene; wherein any $C_{1-4}$alkylene, $C_{1-4}$heteroalkylene, $C_{2-4}$alkenylene and $C_{2-4}$alkynylene of $X^{RA}$ or $X^{RB}$ is optionally substituted with 1 to 3 substituents selected from the group consisting of $C_{1-4}$alkyl, $C_{1-4}$haloalkyl, $C_{1-4}$heteroalkyl, oxo ($=O$), hydroxy, and phenyl that is optionally substituted with 1 to 5 substituents selected from, F, Cl, Br, I, $-NH_2$, $-OH$, $-CN$, $-NO_2$, $C_{1-4}$alkyl, $C_{1-4}$haloalkyl, $C_{1-4}$alkoxy, $C_{1-4}$(halo)alkoxy, $C_{1-4}$alkylamino and $C_{1-4}$dialkylamino; or wherein $X^{RA}$ or $X^{RB}$ is optionally substituted with 2 substituents that combine to form a 3 to 5 membered carbocycle or a 3-5 membered heterocycle;

provided the compound of formula I is not:

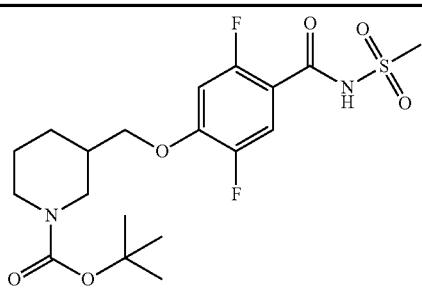

tert-butyl 3-((2,5-difluoro-4-((methylsulfonyl)carbamoyl)phenoxy)methyl)piperidine-1-carboxylate -continued
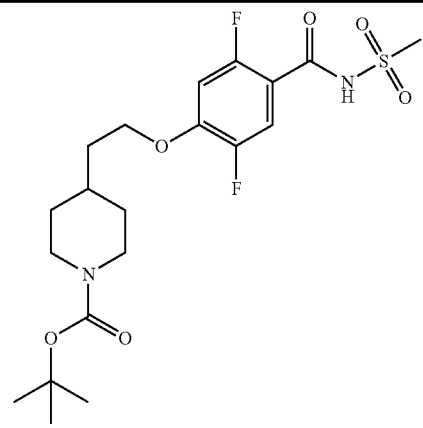
tert-butyl 4-(2-(2,5-difluoro-4-((methylsulfonyl)carbamoyl)phenoxy)ethyl)piperidine-1-carboxylate
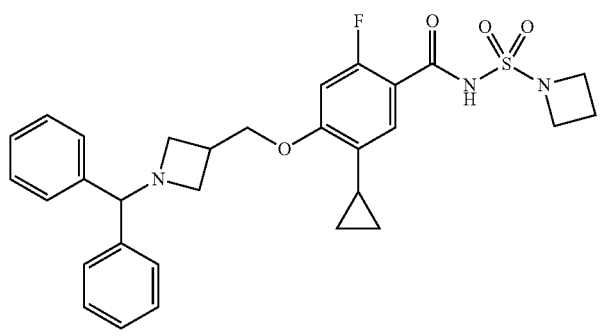 [SMILES: O=C(NS(=O)(=O)N1CCC1)c1cc(C2CC2)c(OCC2CN(C(c3ccccc3)c3ccccc3)C2)cc1F]
N-(azetidin-1-ylsulfonyl)-4-[(1-benzhydrylazetidin-3-yl)methoxy]-5-cyclopropyl-2-fluoro-benzamide
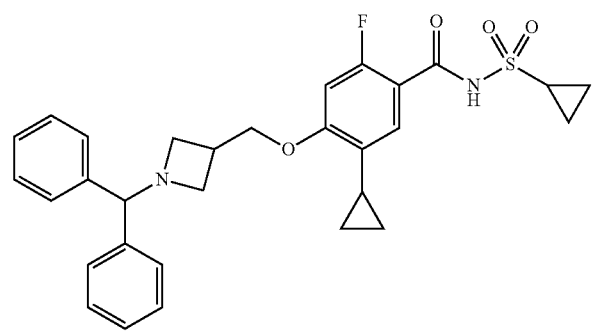 [SMILES: O=C(NS(=O)(=O)C1CC1)c1cc(C2CC2)c(OCC2CN(C(c3ccccc3)c3ccccc3)C2)cc1F]
4-[(1-benzhydrylazetidin-3-yl)methoxy]-5-cyclopropyl-N-cyclopropylsulfonyl-2-fluoro-benzamide
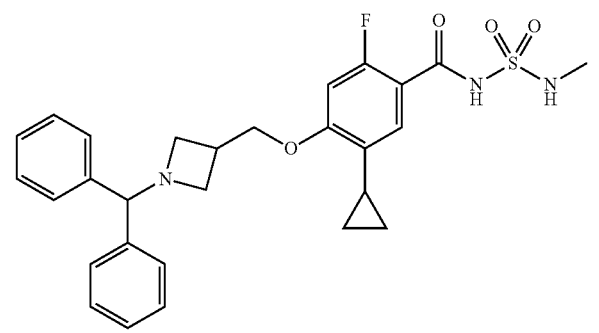 [SMILES: CNS(=O)(=O)NC(=O)c1cc(C2CC2)c(OCC2CN(C(c3ccccc3)c3ccccc3)C2)cc1F]
4-[(1-benzhydrylazetidin-3-yl)methoxy]-5-cyclopropyl-2-fluoro-N-(methylsulfamoyl)benzamide -continued

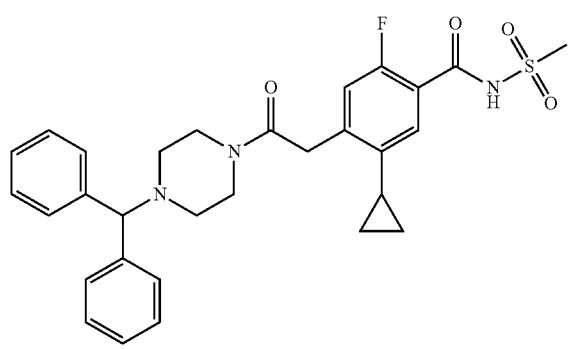 [SMILES: CS(=O)(=O)NC(=O)c1cc(C2CC2)c(CC(=O)N2CCN(C(c3ccccc3)c3ccccc3)CC2)cc1F]

4-[2-(4-benzhydrylazetidin-1-yl)-2-oxo-ethyl]-5-cyclopropyl-2-fluoro-N-methylsulfonyl-benzamide

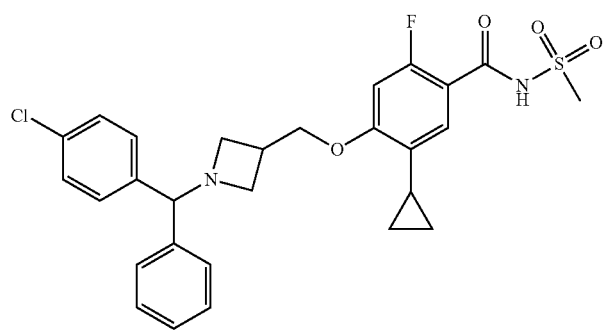 [SMILES: CS(=O)(=O)NC(=O)c1cc(C2CC2)c(OCC2CN(C(c3ccccc3)c3ccc(Cl)cc3)C2)cc1F]

4-[[1-[(4-chlorophenyl)-phenyl-methyl]azetidin-3-yl]methoxy]-5-cyclopropyl-2-fluoro-N-methylsulfonyl-benzamide

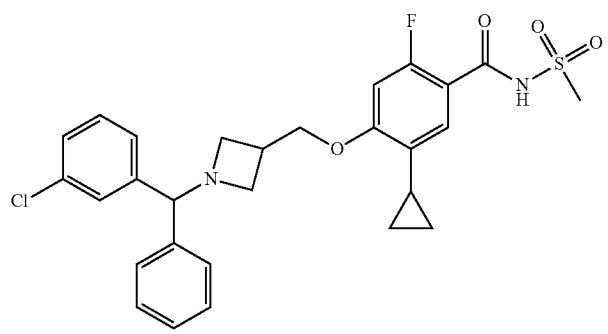 [SMILES: CS(=O)(=O)NC(=O)c1cc(C2CC2)c(OCC2CN(C(c3ccccc3)c3cccc(Cl)c3)C2)cc1F]

4-[[1-[(3-chlorophenyl)-phenyl-methyl]azetidin-3-yl]methoxy]-5-cyclopropyl-2-fluoro-N-methylsulfonyl-benzamide

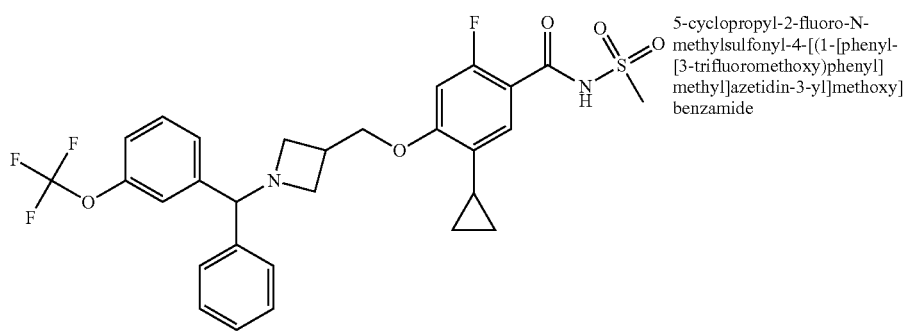

5-cyclopropyl-2-fluoro-N-methylsulfonyl-4-[(1-[phenyl-[3-trifluoromethoxy)phenyl]methyl]azetidin-3-yl]methoxy]benzamide

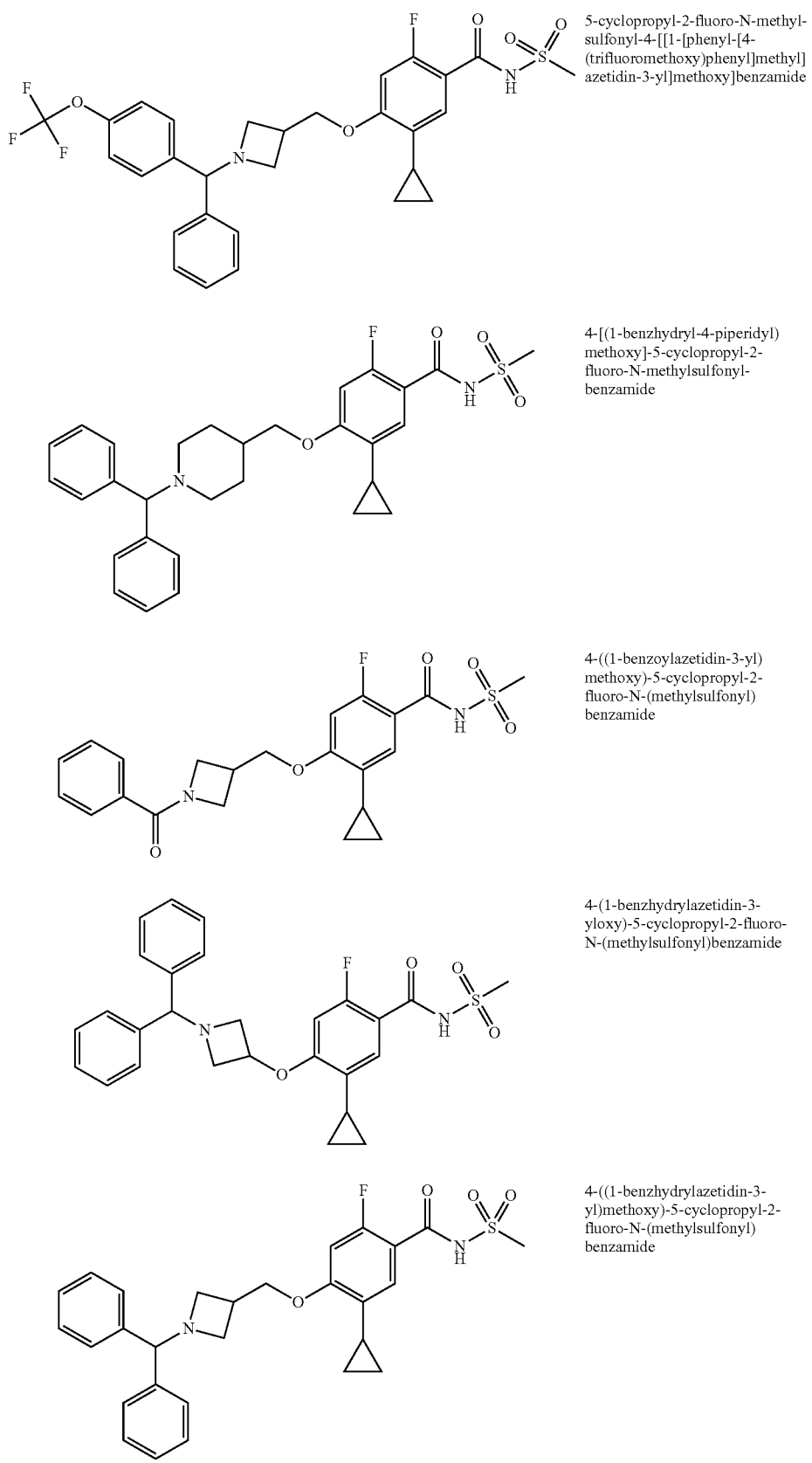

5-cyclopropyl-2-fluoro-N-methyl-sulfonyl-4-[[1-[phenyl-[4-(trifluoromethoxy)phenyl]methyl]azetidin-3-yl]methoxy]benzamide 4-[(1-benzhydryl-4-piperidyl)methoxy]-5-cyclopropyl-2-fluoro-N-methylsulfonyl-benzamide 4-((1-benzoylazetidin-3-yl)methoxy)-5-cyclopropyl-2-fluoro-N-(methylsulfonyl)benzamide 4-(1-benzhydrylazetidin-3-yloxy)-5-cyclopropyl-2-fluoro-N-(methylsulfonyl)benzamide 4-((1-benzhydrylazetidin-3-yl)methoxy)-5-cyclopropyl-2-fluoro-N-(methylsulfonyl)benzamide

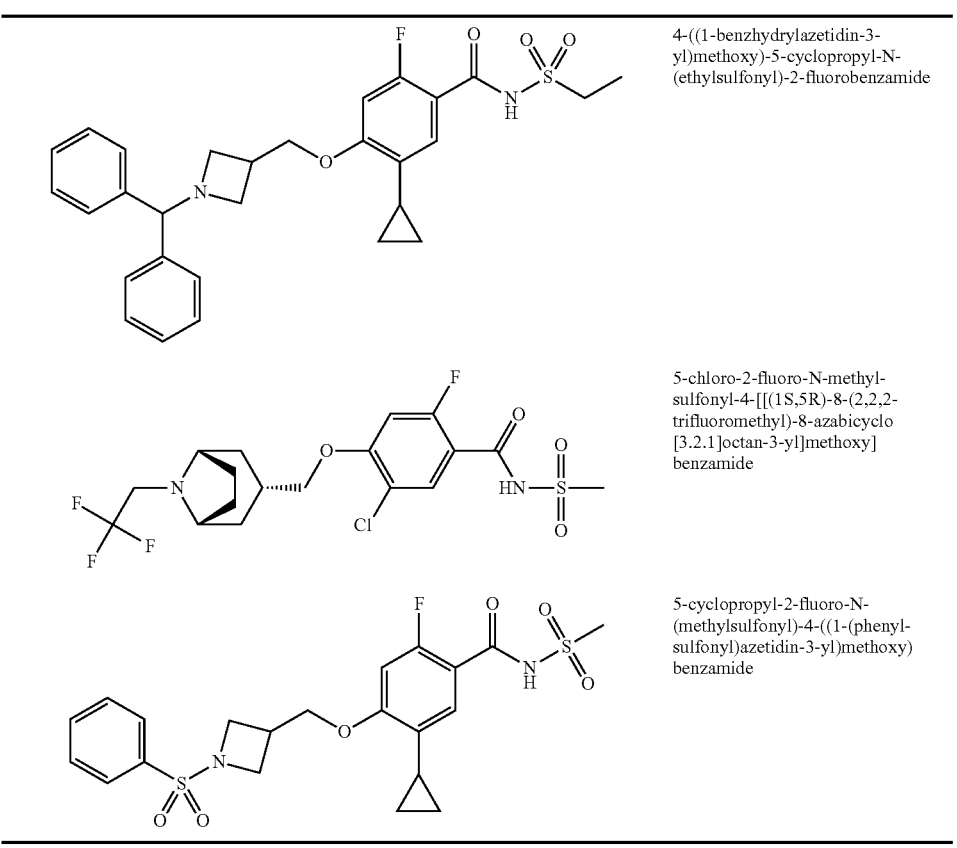

E2 The compound or salt of E1 wherein:

$R^1$ is $C_{1-8}$alkyl, $C_{2-8}$alkenyl, $C_{1-8}$haloalkyl, $C_{1-4}$alkoxy, $C_{3-8}$carbocycle, C-linked $C_{2-7}$heterocycle, or $-NR^{1A}R^{1B}$, wherein $R^{1A}$ and $R^{1B}$ are each independently selected from the group consisting of hydrogen, $C_{1-8}$alkyl, $C_{1-8}$alkoxy, and wherein $R^{1A}$ and $R^{1B}$ are optionally combined to form a 3 to 8 membered heterocyclic ring optionally comprising 1 additional heteroatom selected from N, O and S; and wherein $R^1$ is optionally substituted with from 1 to 5 substituents selected from the group consisting of $C_{1-4}$alkyl, $C_{1-4}$haloalkyl, F, Cl, Br, I, $-$OH, $-$CN, $-$NO$_2$, $-$NR$^{R1a}$R$^{R1b}$, $-$OR$^{R1a}$, $-$SR$^{R1a}$, $-$Si(R$^{R1a}$)$_3$ and $C_{3-6}$carbocycle; wherein $R^{R1a}$ and $R^{R1b}$ are independently selected from the group consisting of hydrogen, $C_{1-8}$alkyl, $C_{1-8}$haloalkyl;

$R^N$ is hydrogen, $C_{2-8}$alkyl or $C_{1-4}$haloalkyl;

$R^2$ is selected from the group consisting of H, F, Cl, Br, I, $-$CN, $C_{1-8}$alkyl, $C_{1-8}$haloalkyl and $C_{1-8}$alkoxy;

$R^3$ is selected from the group consisting of H, F, Cl, Br, I, $-$CN, $C_{1-8}$alkyl, $C_{1-8}$haloalkyl and $C_{1-8}$alkoxy;

$R^4$ is selected from the group consisting of H, F, Cl, Br, I, $-$CN, $C_{1-8}$alkyl, $C_{1-8}$haloalkyl and $C_{1-8}$alkoxy;

$R^5$ is selected from the group consisting of H, F, Cl, Br, I, $-$CN, $C_{1-8}$alkyl, $C_{1-8}$haloalkyl, $C_{1-8}$alkoxy, $C_{3-8}$cycloalkyl and $C_{2-7}$heterocycle, wherein said $C_{3-8}$cycloalkyl and $C_{2-7}$heterocycle is optionally substituted with 1-3 substituents selected from F, Cl, Br and I;

L is a linker selected from the group consisting of $C_{1-4}$alkylene, $C_{2-4}$alkenylene and $C_{2-4}$alkynylene, wherein L is optionally substituted with from 1 to 3 substituents selected from the group consisting of $=$O, $C_{1-4}$alkyl, halo, and $C_{1-4}$haloalkyl;

the subscript m represents the integer 0 or 1;

$X^1$ and $X^2$ are each independently selected from the group consisting of absent, $-$O$-$, $-$S(O)$-$, $-$S(O)$_2$$-$ and $-$N(R$^X$)$-$ wherein R$^X$ is H, $C_{1-8}$alkyl, $C_{1-8}$alkanoyl, or $-$S(O)$_2$(C$_{1-8}$alkyl), and wherein if the subscript m is 0 then one of $X^1$ or $X^2$ is absent;

the subscript n is an integer from 0 to 5;

the ring A is a $C_{2-11}$heterocycle comprising a nitrogen atom and further optionally comprising 1-2 heteroatoms selected from N, O and S;

each $R^{AA}$ is independently selected from the group consisting of $C_{1-6}$alkyl, $C_{1-6}$haloalkyl, $C_{1-6}$heteroalkyl, F, Cl, Br and I; and $R^A$ is selected from the group consisting of $-$(X$^{RB}$)$_{0-1}$OR$^{A1}$, $C_{6-10}$aryl-(X$^{RA}$)$-$, $C_{5-9}$heteroaryl-(X$^{RA}$)$-$, $C_{3-12}$carbocycle-(X$^{RA}$)$-$, $-$R$^{A2}$, $-$S(O)$_2$$-$R$^{A2}$, and $C_{2-11}$heterocycle-(X$^{RA}$)$-$, wherein said $C_{6-10}$aryl, $C_{5-9}$heteroaryl, $C_{3-12}$carbocycle and $C_{2-11}$heterocycle of $R^A$ is optionally substituted with from 1 to 5 substituents selected from, F, Cl, Br, I, $-$NH$_2$, $-$OH, $-$CN, $-$NO$_2$C$_{1-4}$alkyl, $C_{1-4}$haloalkyl, $C_{1-4}$alkoxy, $C_{1-4}$(halo)alkoxy, $C_{1-4}$alkylamino, $C_{1-4}$dialkylamino, $C_{1-4}$alkanoyl, $C_{1-4}$alkyl-OC($=$O)$-$, $C_{1-4}$alkyl-S(O)$_2$$-$, $C_{3-6}$carbocycle, and phenyl that is optionally substituted with one or more substituents selected from fluoro, chloro, and bromo; $R^{A1}$ is selected from the group consisting of hydrogen, $C_{1-8}$alkyl, $C_{2-8}$alkenyl, $C_{1-8}$haloalkyl, $C_{3-8}$cycloalkyl, phenyl and benzyl; $R^{A2}$ is selected from the group consisting of $C_{1-8}$alkyl that is optionally substituted with one or more substituents selected from oxo ($=$O), fluoro, amino, $C_{1-4}$alkylamino and $C_{1-4}$dialkylamino; $X^{RA}$ is selected from the group consisting of absent, —O—, —S—, —N(H)—, —N(C$_{3-8}$alkyl)-, —S(O)—, —S(O)$_2$—, —C(=O)—, C$_{1-4}$alkylene, C$_{1-4}$heteroalkylene, C$_{2-4}$alkenylene and C$_{2-4}$alkynylene; X$^{RB}$ is selected from the group consisting of absent, C$_{1-4}$alkylene, C$_{1-4}$heteroalkylene, C$_{2-4}$alkenylene and C$_{2-4}$alkynylene; wherein any C$_{1-4}$alkylene, C$_{1-4}$heteroalkylene, C$_{2-4}$alkenylene and C$_{2-4}$alkynylene of X$^{RA}$ or X$^{RB}$ is optionally substituted with 1 to 3 substituents selected from the group consisting of C$_{1-4}$alkyl, C$_{1-4}$haloalkyl, C$_{1-4}$heteroalkyl, oxo (=O), and phenyl that is optionally substituted with 1 to 5 substitutents selected from, F, Cl, Br, I, —NH$_2$, —OH, —CN, —NO$_2$, C$_{1-4}$alkyl, C$_{1-4}$haloalkyl, C$_{1-4}$alkoxy, C$_{1-4}$(halo)alkoxy, C$_{1-4}$alkylamino and C$_{1-4}$dialkylamino; or wherein X$^{RA}$ or X$^{RB}$ is optionally substituted with 2 substituents that combine to form a 3 to 5 membered carbocycle or a 3-5 membered heterocycle;

E3 The compound or salt of E1 or E2 wherein:

R$^1$ is C$_{1-8}$alkyl, C$_{2-8}$alkenyl, C$_{1-8}$haloalkyl, C$_{1-8}$alkoxy, C$_{3-8}$carbocycle, C-linked C$_{2-7}$heterocycle, or —NR$^{1A}$R$^{1B}$, wherein R$^{1A}$ and R$^{1B}$ are each independently selected from the group consisting of hydrogen, C$_{1-8}$alkyl, C$_{1-8}$alkoxy, and wherein R$^{1A}$ and R$^{1B}$ are optionally combined to form a 3 to 8 membered heterocyclic ring optionally comprising 1 additional heteroatom selected from N, O and S; and wherein R$^1$ is optionally substituted with from 1 to 5 substituents selected from the group consisting of C$_{1-4}$alkyl, C$_{1-4}$haloalkyl F, Cl, Br, I, —OH, —CN, —NO$_2$, —NR$^{R1a}$R$^{R1b}$, —OR$^{R1a}$, —Si(R$^{R1a}$)$_3$ and C$_{3-6}$carbocycle; wherein R$^{R1a}$ and R$^{R1b}$ are independently selected from the group consisting of hydrogen, C$_{1-8}$alkyl, C$_{1-8}$haloalkyl;

R$^N$ is hydrogen, C$_{1-4}$alkyl or C$_{1-4}$haloalkyl;

R$^2$ is selected from the group consisting of H, F, Cl, Br, I, —CN, C$_{1-8}$alkyl, C$_{1-8}$haloalkyl and C$_{1-8}$alkoxy;

R$^3$ is selected from the group consisting of H, F, Cl, Br, I, —CN, C$_{1-8}$alkyl, C$_{1-8}$haloalkyl and C$_{1-8}$alkoxy;

R$^4$ is selected from the group consisting of H, F, Cl, Br, I, —CN, C$_{1-8}$alkyl, C$_{1-8}$haloalkyl and C$_{1-8}$alkoxy;

R$^5$ is selected from the group consisting of H, F, Cl, Br, I, —CN, C$_{1-8}$alkyl, C$_{1-8}$haloalkyl, C$_{1-8}$alkoxy, C$_{3-8}$cycloalkyl and C$_{2-7}$heterocycle, wherein said C$_{3-8}$cycloalkyl and C$_{2-7}$heterocycle is optionally substituted with 1-3 substituents selected from F, Cl, Br and I;

L is a linker selected from the group consisting of C$_{1-4}$alkylene, C$_{2-4}$alkenylene and C$_{2-4}$alkynylene, wherein L is optionally substituted with from 1 to 3 substituents selected from the group consisting of =O, C$_{1-4}$alkyl, halo, and C$_{1-4}$haloalkyl;

the subscript m represents the integer 0 or 1;

X$^1$ and X$^2$ are each independently selected from the group consisting of absent, —O—, —S(O)—, —S(O)$_2$— and —N(R$^X$)— wherein R$^x$ is H, C$_{1-8}$alkyl, C$_{1-8}$alkanoyl, or —S(O)$_2$(C$_{1-8}$alkyl), and wherein if the subscript m is 0 then one of X$^1$ or X$^2$ is absent;

the subscript n is an integer from 0 to 5;

the ring A is a C$_{2-11}$heterocycle comprising a nitrogen atom and further optionally comprising 1-2 heteroatoms selected from N, O and S;

each R$^{AA}$ is independently selected from the group consisting of C$_{1-6}$alkyl, C$_{1-6}$haloalkyl, C$_{1-6}$heteroalkyl, F, Cl, Br and I; and R$^A$ is selected from the group consisting of —(X$^{RB}$)$_{0-1}$OR$^{A1}$, C$_{6-10}$aryl-(X$^{RA}$)—, C$_{5-9}$heteroaryl-(X$^{RA}$)—, C$_{3-12}$carbocycle-(X$^{RA}$)— and C$_{2-11}$heterocycle-(X$^{RA}$)—, wherein said C$_{6-10}$aryl, C$_{5-9}$heteroaryl, C$_{3-12}$carbocycle and C$_{2-11}$heterocycle of R$^A$ is optionally substituted with from 1 to 5 substituents selected from, F, Cl, Br, I, —NH$_2$, —OH, —CN, —NO$_2$ C$_{1-4}$alkyl, C$_{1-4}$haloalkyl, C$_{1-4}$alkoxy, C$_{1-4}$(halo)alkoxy, C$_{1-4}$alkylamino, C$_{1-4}$dialkylamino, C$_{1-4}$alkanoyl, C$_{1-4}$alkyl-OC(=O)—, C$_{1-4}$alkyl-S(O)$_2$—, C$_{3-6}$carbocycle, R$^{A1}$ is selected from the group consisting of hydrogen, C$_{1-8}$alkyl, C$_{2-8}$alkenyl, C$_{1-8}$haloalkyl, C$_{3-8}$cycloalkyl, phenyl and benzyl; X$^{RA}$ is selected from the group consisting of absent, —O—, —S—, —N(H)—, —N(C$_{1-4}$alkyl)-, —S(O)—, —C(=O)—, C$_{1-4}$alkylene, C$_{1-4}$heteroalkylene, C$_{2-4}$alkenylene and C$_{2-4}$alkynylene; X$^{RB}$ is selected from the group consisting of absent, C$_{1-4}$alkylene, C$_{1-4}$heteroalkylene, C$_{2-4}$alkenylene and C$_{2-4}$alkynylene; wherein any C$_{1-4}$alkylene, C$_{1-4}$heteroalkylene, C$_{2-4}$alkenylene and C$_{2-4}$alkynylene of X$^{RA}$ or X$^{RB}$ is optionally substituted with 1 to 3 substituents selected from the group consisting of C$_{1-4}$alkyl, C$_{1-4}$haloalkyl, C$_{1-4}$heteroalkyl, oxo (=O), and phenyl that is optionally substituted with 1 to 5 substitutents selected from, F, Cl, Br, I, —NH$_2$, —OH, —CN, —NO$_2$, C$_{1-4}$alkyl, C$_{1-4}$haloalkyl, C$_{1-4}$alkoxy, C$_{1-4}$(halo)alkoxy, C$_{1-4}$alkylamino and C$_{1-4}$dialkylamino; or wherein X$^{RA}$ or X$^{RB}$ is optionally substituted with 2 substituents that combine to form a 3 to 5 membered carbocycle or a 3-5 membered heterocycle.

E4 The compound of E1, E2, or E3 wherein the compound has the formula Ia:

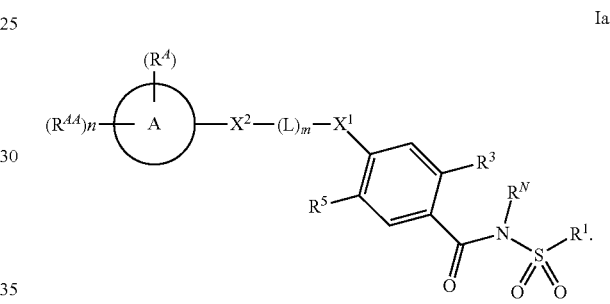

E5 The compound of E1, E2, or E3, wherein the compound has the formula Ib:

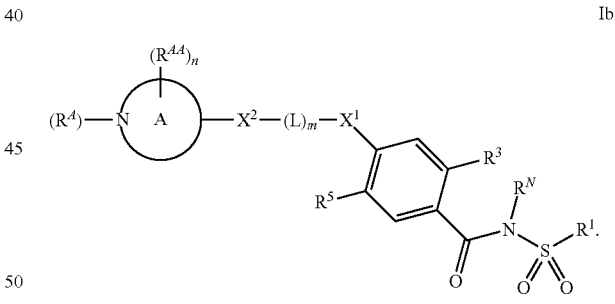

E6 The compound of E1, E2, or E3, wherein the compound has the formula Ic:

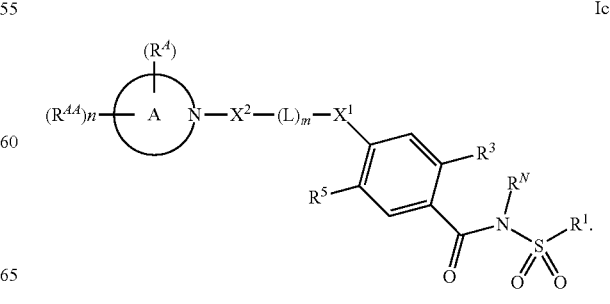

E7 The compound of E1, E2, E3, E4, E5, or E6 wherein $R^1$ is selected from the group consisting of $C_{1-8}$alkyl, $C_{1-8}$haloalkyl, $C_{3-8}$carbocycle, $C_{2-7}$heterocycle, and —$NR^{1A}R^{1B}$, wherein $R^{1A}$ and $R^{1B}$ are each independently selected from the group consisting of $C_{1-8}$alkyl and $C_{1-4}$alkoxy, and wherein $R^{1A}$ and $R^{1B}$ are optionally combined to form a 3 to 6 membered heterocyclic ring; and wherein $R^1$ is optionally substituted with from 1 to 5 substituents selected from the group consisting of $C_{1-4}$alkyl, $C_{1-4}$haloalkyl, F, Cl, Br, I, —OH, —$OR^{R1a}$, —$SR^{R1a}$, —$Si(R^{R1a})_3$, and $C_{3-5}$carbocycle; wherein $R^{R1a}$ and $R^{R1b}$ are independently selected from the group consisting of hydrogen, $C_{1-8}$alkyl, $C_{1-8}$haloalkyl E8 The compound of E1, E2, E3, E4, E5, or E6 wherein $R^1$ is methyl, cyclopropyl, cyclopropylmethyl, 1-azetidinyl, 1-methylcycloprop-1-yl, difluoromethyl, N-methylamino, ethyl, 2-methoxyeth-1-yl, 2-trimethylsilyleth-1-yl, propyl, 1,1,1-trifluoroprop-3-yl, butyl, morpholino, pyrrolidino, or 3-fluoroazetidin-1-yl.

E9 The compound of E1, E2, E3, E4, E5, or E6 wherein $R^1$ is methyl, cycloptopyl, 1-azetidinyl or 2-methoxyethyl.

E10 The compound of E1, E2, E3, E7, E8, or E9 wherein $R^2$ is H.

E11 The compound of E1, E2, E3, E4, E5, E6, E7, E8, E9 or E10 wherein $R^3$ is F, Cl, or Br.

E12 The compound of E1, E2, E3, E4, E5, E6, E7, E8, E9, or E10 wherein $R^3$ is F.

E13 The compound of E1, E2, E3, E7, E8, E9, E10, E11, or E12 wherein $R^4$ is H.

E14 The compound of E1, E2, E3, E4, E5, E6, E7, E8, E9, E10, E11, E12, or E13 wherein $R^5$ is $C_{3-5}$cycloalkyl.

E15 The compound of E1, E2, E3, E4, E5, E6, E7, E8, E9, E10, E11, E12, or E13 wherein $R^5$ is cyclopropyl.

E16 The compound of E1, E2, E3, E4, E5, E6, E7, E8, E9, E10, E11, E12, E13, E14, or E15 wherein $X^1$ is —O— or —N(H)—; $X^2$ is absent; the subscript m is 1; and -(L)- is an optionally substituted group selected from the group consisting of $C_{1-4}$alkylene, $C_{2-4}$alkenylene or $C_{2-4}$alkynylene.

E17 The compound of E1, E2, E3, E4, E5, E6, E7, E8, E9, E10, E11, E12, E13, E14, or E15 wherein $X^1$ is —O— or —N(H)—; $X^2$ is absent; the subscript m is 1; and -(L)- is selected from the group consisting of —CH$_2$—, —C(=O)—, —C(H)(CH$_3$)—, —CH$_2$—CH$_2$—, —CH$_2$—C(H)(CH$_3$)—, —C(H)(CH$_3$)—C(H)$_2$)—, —CH$_2$CH$_2$CH$_2$—, —CH$_2$—C(H)(CH$_3$)—CH$_2$— or —CH$_2$CH$_2$CH$_2$CH$_2$—.

E18 The compound of E1, E2, E3, E4, E5, E6, E7, E8, E9, E10, E11, E12, E13, E14, or E15 wherein $X^1$ is —O—; the subscript m is 1 and -(L)- is —CH$_2$— or —CH$_2$—CH$_2$—.

E19 The compound of E1, E2, E3, E4, E5, E6, E7, E8, E9, E10, E11, E12, E13, E14, or E15 wherein $X^1$ is absent; $X^2$ is —O— or —N(H)—; the subscript m is 1; and -(L)- is selected from the group consisting of —C(H)$_2$—, —C(=O)—, —C(H)(CH$_3$)—, —CH$_2$—CH$_2$—, —CH$_2$—C(H)(CH$_3$)—, —C(H)(CH$_3$)—C(H)$_2$)—, —CH$_2$CH$_2$CH$_2$—, —CH$_2$—C(H)(CH$_3$)—CH$_2$— or —CH$_2$CH$_2$CH$_2$CH$_2$—.

E20 The compound of E1, E2, E3, E4, E5, E6, E7, E8, E9, E10, E11, E12, E13, E14, or E15 wherein $X^1$ and $X^2$ is absent; the subscript m is 1; and -(L)- is selected from the group consisting of —C(H)$_2$—, —C(=O)—, —C(H)(CH$_3$)—, —CH$_2$—CH$_2$—, —CH$_2$—C(H)(CH$_3$)—, —C(H)(CH$_3$)—C(H)$_2$)—, —CH$_2$CH$_2$CH$_2$—, —CH$_2$—C(H)(CH$_3$)—CH$_2$— or —CH$_2$CH$_2$CH$_2$CH$_2$—.

E21 The compound of E1, E2, E3, E4, E5, E6, E7, E8, E9, E10, E11, E12, E13, E14, or E15 wherein m is 0; $X^1$ is selected from —O—, and —N(H)—; and $X^2$ is absent.

E22 The compound of E1, E2, E3, E4, E5, E6, E7, E8, E9, E10, E11, E12, E13, E14, E15, E16, E17, E18, E19, E20, or E21 wherein A is optionally substituted and is selected from azetidine, pyrrolidine, piperidine, morpholine, homopiperazine, and piperazine.

E23 The compound E1, E2, E3, E4, E5, E6, E7, E8, E9, E10, E11, E12, E13, E14, E15, E16, E17, E18, E19, E20, or E21 of wherein:

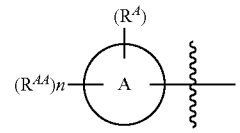

is selected from the group consisting of:

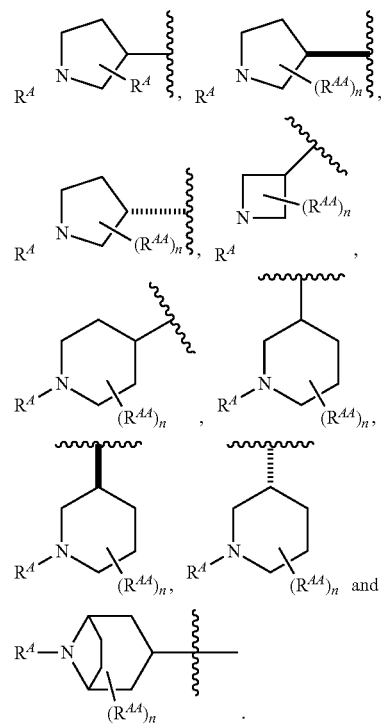

E24 The compound of E1, E2, E3, E4, E5, E6, E7, E8, E9, E10, E11, E12, E13, E14, E15, E16, E17, E18, E19, E20, or E21 wherein:

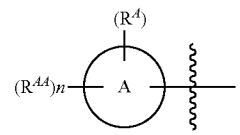

is selected from the group consisting of:

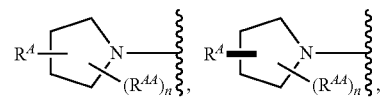

-continued

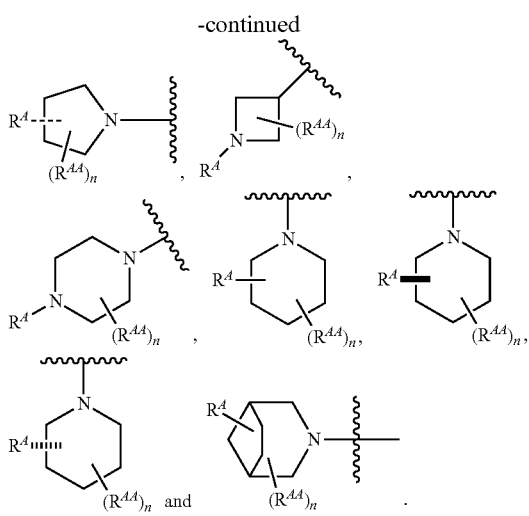

E25 The compound of E1, E2, E3, E4, E5, E6, E7, E8, E9, E10, E11, E12, E13, E14, E15, E16, E17, E18, E19, E20, E21, E22, E23, or E24 wherein $R^{AA}$ is selected from the group consisting of methyl, trifluoromethyl, CN, F, Cl, Br, and I.

E26 The compound of E1, E2, E3, E4, E5, E6, E7, E8, E9, E10, E11, E12, E13, E14, E15, E16, E17, E18, E19, E20, E21, E22, E23, or E24 wherein $R^{AA}$ is selected from the group consisting of methyl, trifluoromethyl, ethyl, F, Cl, Br, and I.

E27 The compound of E1, E2, E3, E4, E5, E6, E7, E8, E9, E10, E11, E12, E13, E14, E15, E16, E17, E18, E19, E20, E21, E22, E23, E24, E25, or E26 wherein $R^A$ is selected from the group consisting of phenyl-$(X^{RA})$—, wherein said phenyl is optionally substituted with from 1 to 5 substituents selected from, F, Cl, Br, —NH$_2$, —OH, —CN, —NO$_2$, $C_{1-4}$alkyl, $C_{1-4}$haloalkyl, $C_{1-4}$alkoxy, $C_{1-4}$alkylamino, $C_{1-4}$dialkylamino, phenyl, $C_{1-4}$alkanoyl, $C_{1-4}$alkyl-OC(=O)— and $C_{3-6}$carbocycle; and wherein $X^{RA}$ is selected from the group consisting of absent, —O—, —S—, —N(H)—, —N($C_{1-4}$alkyl)-, $C_{1-4}$alkylene, $C_{1-4}$heteroalkylene, $C_{2-4}$alkenylene and $C_{2-4}$alkynylene; and wherein $X^{RA}$ is optionally substituted with 1 to 3 substituents selected from the group consisting of $C_{1-4}$alkyl, $C_{1-4}$haloalkyl, $C_{1-4}$heteroalkyl, and phenyl, that is optionally substituted with 1 to 5 substitutents selected from, F, Cl, Br, I, —NH$_2$, —OH, —CN, —NO$_2$, $C_{1-4}$alkyl, $C_{1-4}$haloalkyl, $C_{1-4}$alkoxy, $C_{1-4}$alkylamino and $C_{1-4}$dialkylamino.

E28 The compound of E1, E2, E3, E4, E5, E6, E7, E8, E9, E10, E11, E12, E13, E14, E15, E16, E17, E18, E19, E20, E21, E22, E23, E24, E25, or E26 wherein $R^A$ is phenyl-$(X^{RA})$—, wherein said phenyl is optionally substituted with from 1 to 5 substitutents selected from, F, Cl, $C_{1-4}$alkyl, —CN, $C_{1-6}$carbocycle and $C_{1-4}$haloalkyl; wherein $X^{RA}$ is selected from the group consisting of absent and $C_{1-4}$alkylene; and wherein $X^{RA}$ is optionally substituted with 1 to 3 substituents selected from the group consisting of $C_{1-4}$alkyl- and phenyl that is optionally substituted with 1 to 5 substitutents selected from, F, Cl, $C_{1-4}$alkyl, and $C_{1-4}$haloalkyl.

E29 The compound of E1, E2, E3, E4, E5, E6, E7, E8, E9, E10, E11, E12, E13, E14, E15, E16, E17, E18, E19, E20, E21, E22, E23, E24, E25, or E26 wherein $R^A$ is —$(X^{RB})_{0-1}$OR$^{41}$; R$^{41}$ is selected from the group consisting of hydrogen, $C_{1-4}$alkyl, $C_{2-8}$alkenyl, $C_{1-8}$haloalkyl, $C_{3-8}$cycloalkyl, phenyl and benzyl: and $X^{RB}$ is selected from the group consisting of absent and $C_{1-4}$alkylene that is optionally substituted with 1 to 3 substituents selected from the group consisting of $C_{1-4}$alkyl, $C_{1-4}$haloalkyl, $C_{1-4}$heteroalkyl, oxo (=O), and phenyl that is optionally substituted with 1 to 5 substituents selected from, F, Cl Br, I, —NH$_2$, —OH, —CN, —NO$_2$, $C_{1-4}$alkyl, $C_{1-4}$haloalkyl, $C_{1-4}$alkoxy, $C_{1-4}$(halo)alkoxy, $C_{1-4}$alkylamino and $C_{1-4}$dialkylamino.

E30 The compound of E1, E2, E3, E4, E5, E6, E7, E8, E9, E10, E11, E12, E13, E14, E15, E16, E17, E18, E19, E20, E21, E22, E23, E24, E25, or E26 wherein $R^A$ is selected from the group consisting of

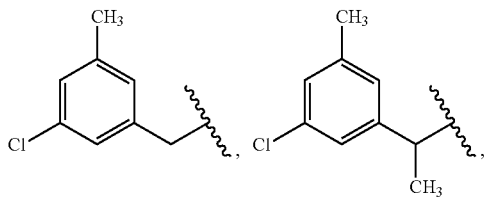

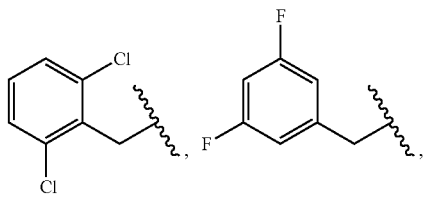

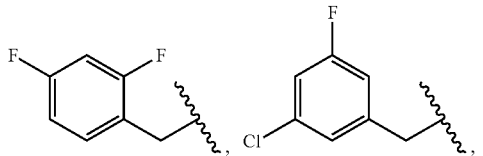

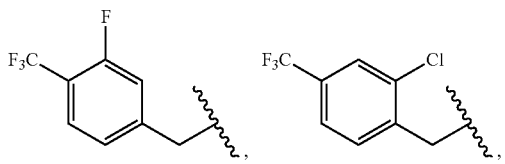

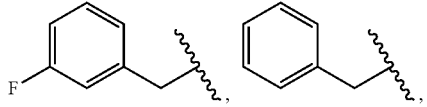

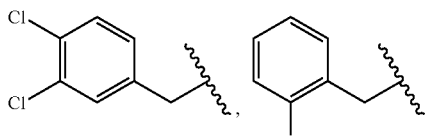

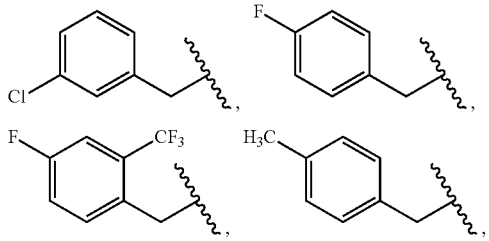

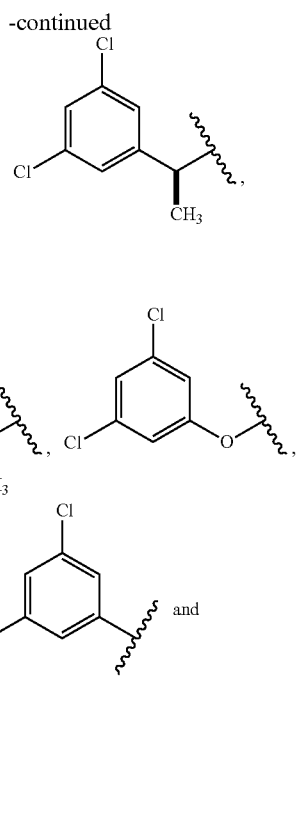

E31 The compound of E1, E2, E3, E4, E5, E6, E7, E8, E9, E10, E11, E12, E13, E14, E15, E16, E17, E18, E19, E20, E21, E22, E23, E24, E25, or E26 wherein $R^A$ is selected from the group consisting of

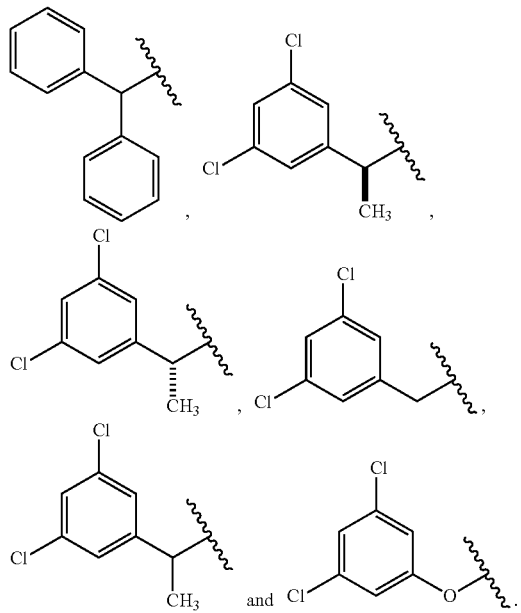

E32 The compound of E1, E2, E3, E4, E5, E6, E7, E8, E9, E10, E11, E12, E13, E14, E15, E16, E17, E18, E19, E20, E21, E22, E23, E24, E25, or E26 wherein $R^A$ is selected from the group consisting of phenyl, phenylmethyl, pyrazolyl, pyrazolylmethyl, cyclobutyl, cyclohexylmethyl, cyclopentyl, cyclopentylmethyl, cyclobutyl, cyctobutylmethyl, pyrimidinyl, pyrimidinylmethyl, pyrazinyl, pyrazinylmethyl, pyridazinyl, pyridazinylmethyl, indolinyl, indolinylmethyl, isoindolinyl, and isoindolinylmethyl, and wherein $R^A$ is optionally substituted with from 1 to 5 substituents selected from, F, Cl, Br, I, —NH$_2$, —OH, —CN, —NO$_2$, $C_{1-4}$alkyl, $C_{1-4}$haloalkyl, $C_{1-4}$alkoxy, $C_{1-4}$(halo)alkoxy, $C_{1-4}$alkylamino, $C_{1-4}$dialkylamino, $C_{1-4}$alkanoyl, $C_{1-4}$alkyl-OC(=O)—, $C_{1-4}$alkyl-S(O)$_2$—, $C_{3-6}$carbocycle, and phenyl that is optionally substituted with one or more substituents selected from fluoro, chloro, and bromo.

E33 The compound of claim E1, E2, E3, E4, E5, E6, E7, E8, E9, E10, E11, E12, E13, E14, E15, E16, E17, E18, E19, E20, E21, E22, E23, E24, E25, or E26 wherein $R^A$ is selected from the group consisting of —(X$^{RB}$)$_{0-1}$OR$^{41}$, $C_{6-10}$aryl-(X$^{RA}$)—, $C_{1-20}$heteroaryl-(X$^{RA}$)—, $C_{3-12}$carbocycle-(X$^{RA}$)— and $C_{2-11}$heterocycle-(X$^{RA}$)—, wherein said $C_{6-10}$aryl, $C_{5-9}$heteroaryl, $C_{3-12}$carbocycle and $C_{2-11}$heterocycle of $R^A$ is optionally substituted with from 1 to 5 substituents selected from, F, Cl, Br, I, —NH$_2$, —OH, —CN, —NO$_2$, $C_{1-4}$alkyl, $C_{1-4}$haloalkyl, $C_{1-4}$alkoxy, $C_{1-4}$alkylamino, $C_{1-4}$dialkylamino, phenyl, $C_{1-4}$alkanoyl, $C_{1-4}$alkyl-OC(=O)— and $C_{3-6}$carbocycle; $R^{41}$ is selected from the group consisting of hydrogen, $C_{1-8}$alkyl, $C_{3-8}$alkenyl, $C_{1-8}$haloalkyl, $C_{3-8}$cycloalkyl, phenyl and benzyl; $X^{RA}$ is selected from the group consisting of absent, —O—, —S—, —N(H)—, —N($C_{1-4}$alkyl)-, $C_{1-4}$alkylene, $C_{1-4}$heteroalkylene, $C_{2-4}$alkenylene and $C_{2-4}$alkynylene; and $X^{RB}$ is selected from the group consisting of absent, $C_{1-4}$alkylene, $C_{1-4}$heteroalkylene, $C_{2-4}$alkenylene and $C_{2-4}$alkynylene; wherein any $C_{1-4}$alkylene, $C_{1-4}$heteroalkylene, $C_{2-4}$alkenylene and $C_{2-4}$alkynylene of $X^{RA}$ or $X^{RB}$ is optionally substituted with 1 to 3 substituents selected from the group consisting of $C_{1-4}$ alkyl, $C_{1-4}$haloalkyl, and $C_{1-4}$heteroalkyl.

E34 The compound of E1, E2, E3, E4, E5, E6, E7, E8, E9, E10, E11, E12, E13, E14, E15, E16, E17, E18, E19, E20, E21, E22, E23, E24, E25, or E26 wherein $R^A$ is selected from the group consisting of —(X$^{RB}$)$_{0-1}$OR$^{41}$, $C_{6-10}$aryl-(X$^{RA}$)—, $C_{5-9}$heteroaryl-(X$^{RA}$)—, $C_{3-12}$carbocycle-(X$^{RA}$)— and $C_{2-11}$heterocycle-(X$^{RA}$)—, wherein said $C_{6-10}$aryl, $C_{5-9}$heteroaryl, $C_{3-12}$carbocycle and $C_{2-11}$heterocycle of $R^A$ is optionally substituted with from 1 to 5 substituents selected from, F, Cl, Br, I, —NH$_2$, —OH, —CN, —NO$_2$, $C_{1-4}$alkyl, $C_{1-4}$haloalkyl, $C_{1-4}$alkoxy, $C_{1-4}$alkylamino, $C_{1-4}$dialkylamino, phenyl, $C_{1-4}$alkanoyl, $C_{1-4}$alkyl-OC(=(— and $C_{3-6}$carbocycle; $R^{41}$ is selected from the group consisting of hydrogen. $C_{1-8}$alkyl, $C_{2-8}$alkenyl, $C_{1-8}$haloalkyl, $C_{3-8}$cycloalkyl, phenyl and benzyl; $X^{RA}$ is selected from the group consisting of absent, —O—, —S—, —N(H)—, —N($C_{1-4}$alkyl)-, $C_{1-4}$alkylene, $C_{1-4}$heteroalkylene, $C_{2-4}$alkenylene and $C_{2-4}$alkynylene; and $X^{RB}$ is selected from the group consisting of absent, $C_{1-4}$alkylene, $C_{1-4}$heteroalkylene, $C_{2-4}$alkenylene and $C_{2-4}$alkynylene; whereas any $C_{1-4}$alkylene, $C_{1-4}$heteroalkylene, $C_{2-4}$alkenylene and $C_{2-4}$alkynylene of $X^{RA}$ or $X^{RB}$ is optionally substituted with 1 to 3 substituents selected from the group consisting of $C_{1-4}$alkyl, $C_{1-4}$haloalkyl, and $C_{1-4}$heteroalkyl.

E35 The compound of E1, E2, E3, E4, E5, E6, E7, E8, E9, E10, E11, E12, E13, E14, E15, E16, E17, E18, E19, E20, E21, E22, E23, E24, E25, or E26 wherein $R^A$ is $C_{6-10}$aryl-(X$^{RA}$)—, wherein said $C_{6-10}$aryl, of $R^A$ is optionally substituted with from 1 to 5 substituents selected from, F, Cl, Br, I, —NH$_2$, —OH, —CN, —NO$_2$, $C_{1-4}$alkyl, $C_{1-4}$haloalkyl, $C_{1-4}$alkoxy, $C_{1-4}$(halo)alkoxy, $C_{1-4}$alkylamino, $C_{1-4}$dialkylamino, phenyl, $C_{1-4}$alkanoyl, $C_{1-4}$alkyl-OC(=O)—, $C_{1-4}$alkyl-S(O)$_2$—, and $C_{3-6}$carbocycle; and $X^{RA}$ is selected from the group consisting of —C(=O)—, $C_{1-4}$alkylene, C$_{1-4}$heteroalkylene, C$_{2-4}$alkenylene and C$_{2-4}$alkynylene; wherein any C$_{1-4}$alkylene, C$_{1-4}$heteroalkylene, C$_{2-4}$alkenylene and C$_{2-4}$alkynylene of X$^{RA}$ is optionally substituted with 1 to 3 substituents selected from the group consisting of C$_{1-4}$alkyl, C$_{1-4}$haloalkyl, C$_{1-4}$heteroalkyl, oxo (=O), and phenyl that is optionally substituted with 1 to 5 substituents selected from, F, Cl, Br, I, —NH$_2$, —OH, —CN, —NO$_2$, C$_{1-4}$alkyl, C$_{1-4}$haloalkyl, C$_{1-4}$alkoxy, C$_{1-4}$(halo)alkoxy, C$_{1-4}$alkylamino and C$_{1-4}$dialkylamino.

E36 The compound of E1, E2, E3, E4, E5, E6, E7, E8, E9, E10, E11, E12, E13, E14, E15, E16, E17, E18, E19, E20, E21, E22, E23, E24, E25, or E26 wherein R$^A$ is phenyl —(X$^{RA}$)—, wherein said phenyl is optionally substituted with from 1 to 5 substitutents selected from, F, Cl, —CN, C$_{1-4}$alkyl, C$_{1-4}$haloalkyl, C$_{1-4}$alkoxy, and C$_{1-4}$(halo)alkoxy; and X$^{RA}$ is C$_{1-4}$alkylene that is optionally substituted with 1 to 3 substituents selected from the group consisting of C$_{1-4}$alkyl, C$_{1-4}$haloalkyl, C$_{1-4}$heteroalkyl, oxo (=O), and phenyl that is optionally substituted with 1 to 5 substitutents selected from, F, Cl, Br, I, —NH$_2$, —OH, —CN, —NO$_2$, C$_{1-4}$alkyl, C$_{1-4}$haloalkyl, C$_{1-4}$alkoxy, C$_{1-4}$(halo)alkoxy, C$_{1-4}$alkylamino and C$_{1-4}$dialkylamino.

E37 The compound of E1, E2, E3, E7, E8, E9, E16, E17, E18, E19, E20, E21, E22, E23, E24, E25, E26, E27, E28, E29, E30, E31, E32, E33, E34, E33, or E36 wherein the compound has the formula Id:

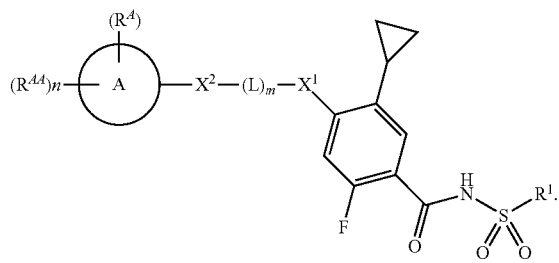

E38 The compound of E37 wherein R$^1$ is methyl, ethyl, cyclopropyl, or 1-azetidinyl.

E39 The compound of E37 or E38 wherein —X$^2$-(L)$_m$-X$^1$— is —O—, —CH$_2$—, —CH$_2$—O—, or —CH$_2$CH$_2$—O—.

E40 The compound of E37, E38, or E39 wherein;

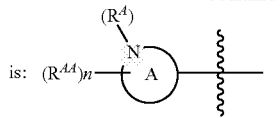

E41 The compound of E37, E38, or E39 wherein:

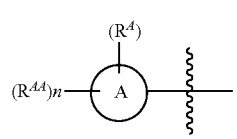

is:

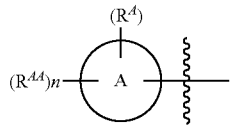

E42 The compound of E37, E38, or E39 wherein A is optionally substituted azetidine, pyrrolidine, piperidine, morpholine, homopiperazine, and piperazine.

E43 The compound of E37, E38, or E39 wherein:

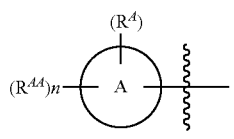

is selected from the group consisting of:

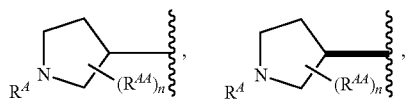

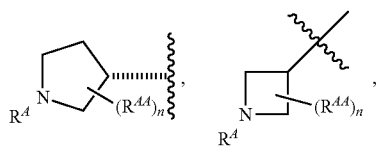

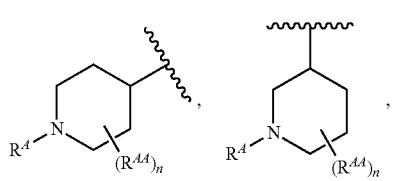

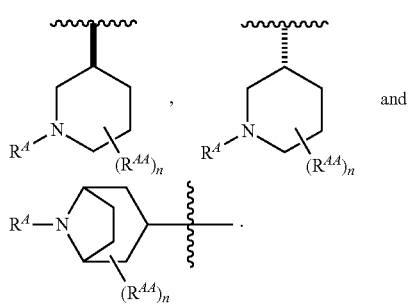

E44 The compound of E1, E2, E3, E4, E5, E6, E7, E8, E9, E10, E11, E12, E13, E14, E15, E16, E17, E18, E19, E20, E37, E38, or E39 wherein:

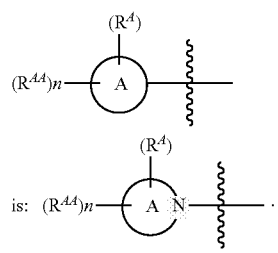

is selected from the group consisting of:
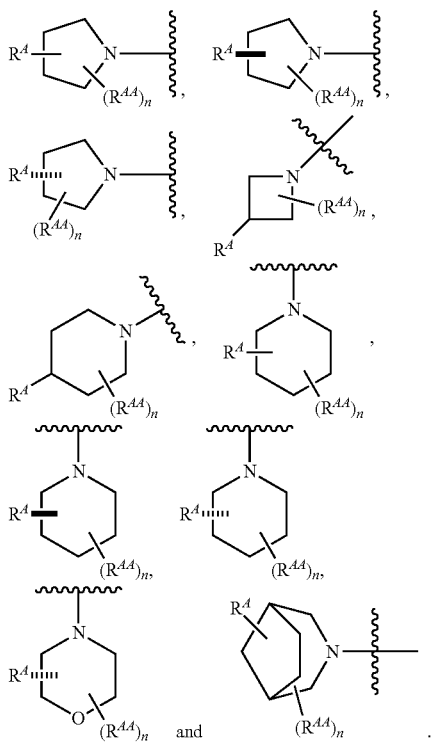
E45 The compound of E1, E2, E3, E4, E7, E8, E9, E10, E11, E12, E13, E14, E15, E25, E26, E27, E28, E29, E30, E31, E32, E33, E34, E35, E36, E37, or E38 wherein:
has the formula:
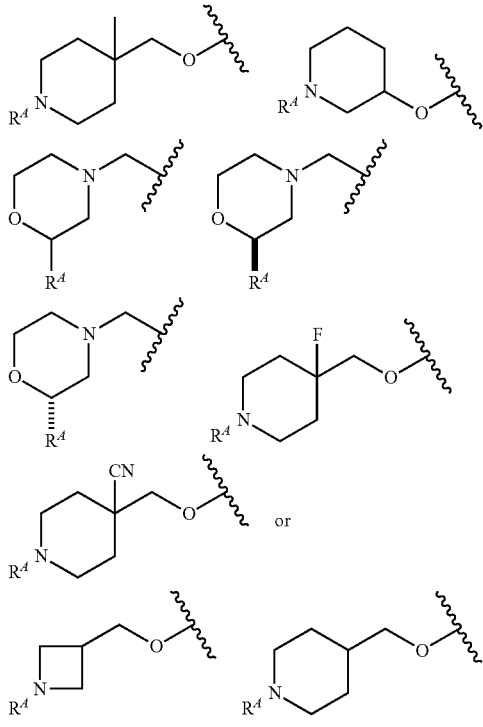
E46 The compound of E41, wherein
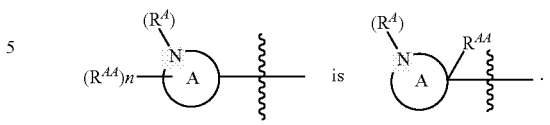
E47 The compound of claim E46, wherein $R^{RA}$ is selected from the group consisting of hydrogen, F, Cl and $C_{1-4}$haloalkyl.
E48 The compound of E1, E2, E3, E4, E5, E6, E7, E8, E9, E10, E11, E12, E13, E14, E15, E16, E17, E18, E19, E20, E21, E22, E23, E24, E25, E26, E37, E38, E39, E40, E41, E42, E43, E44, E45, E46, or E47 wherein $R^A$ is
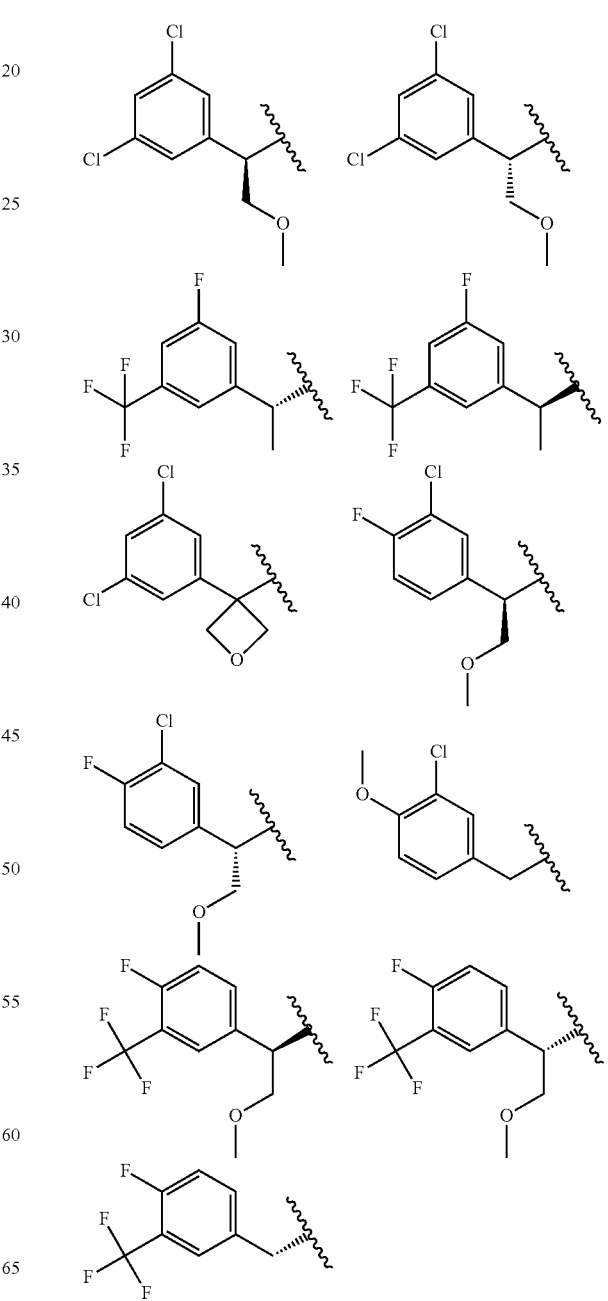

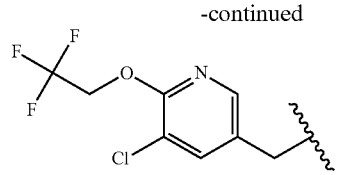
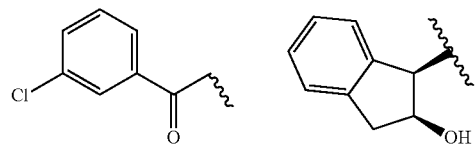
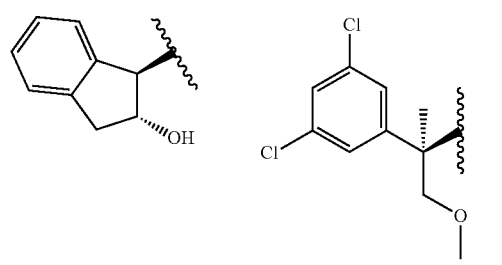
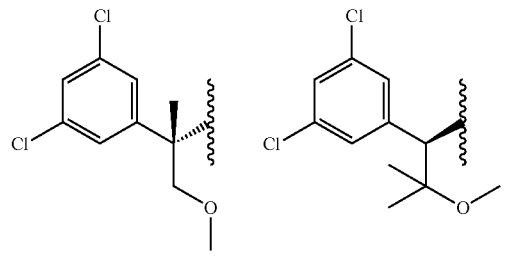
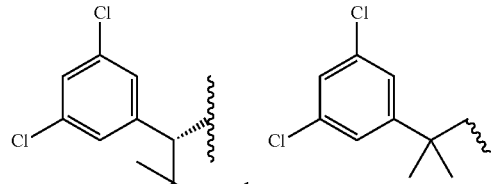
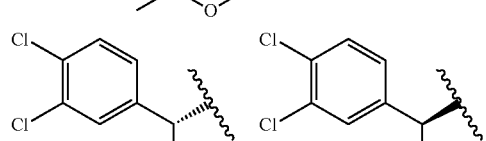
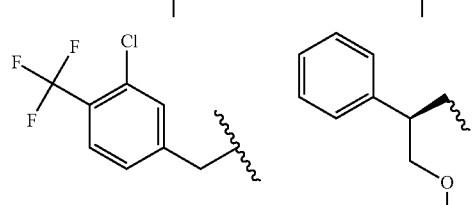
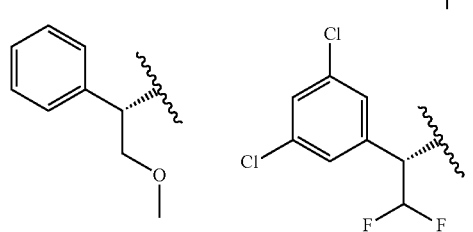
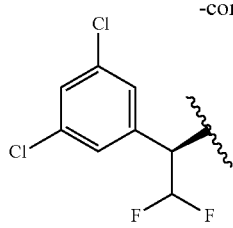

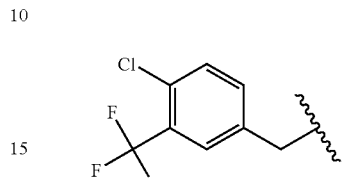
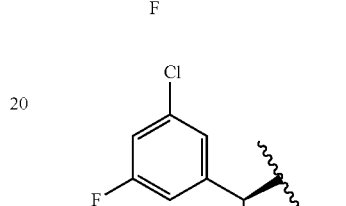
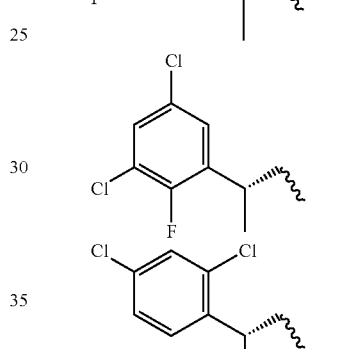
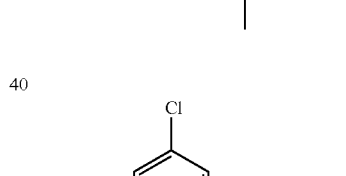
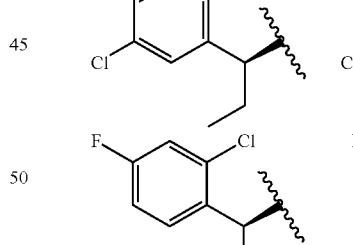
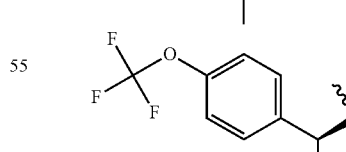
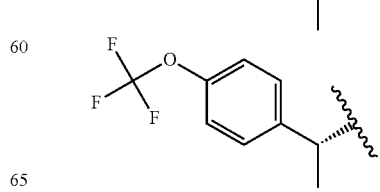

-continued
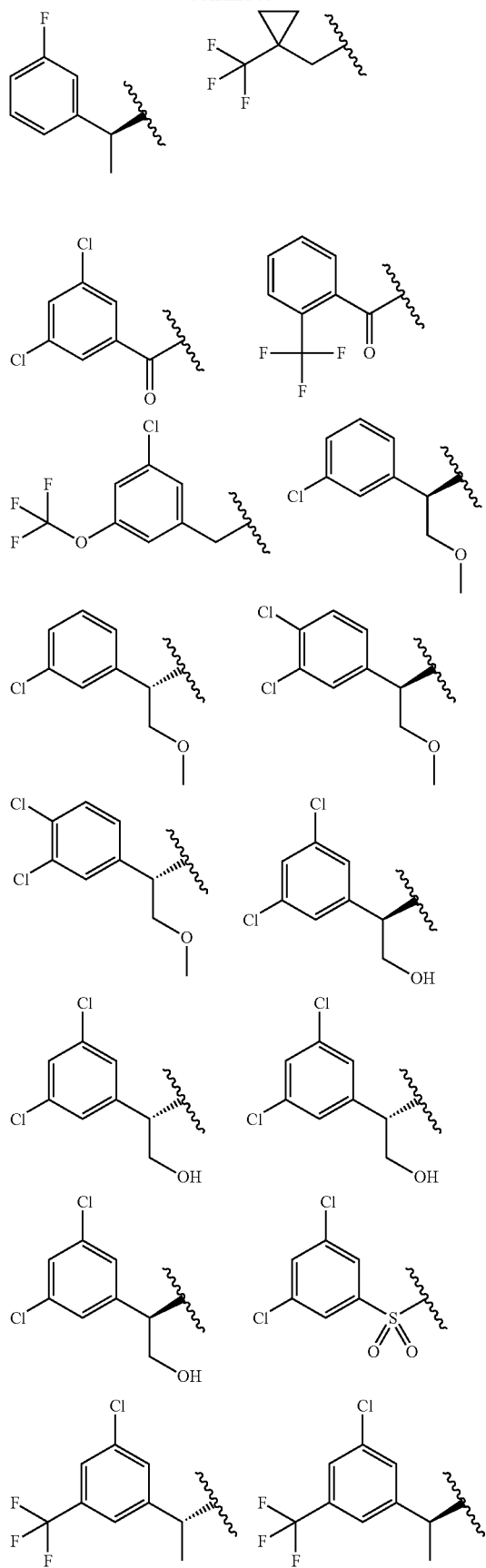
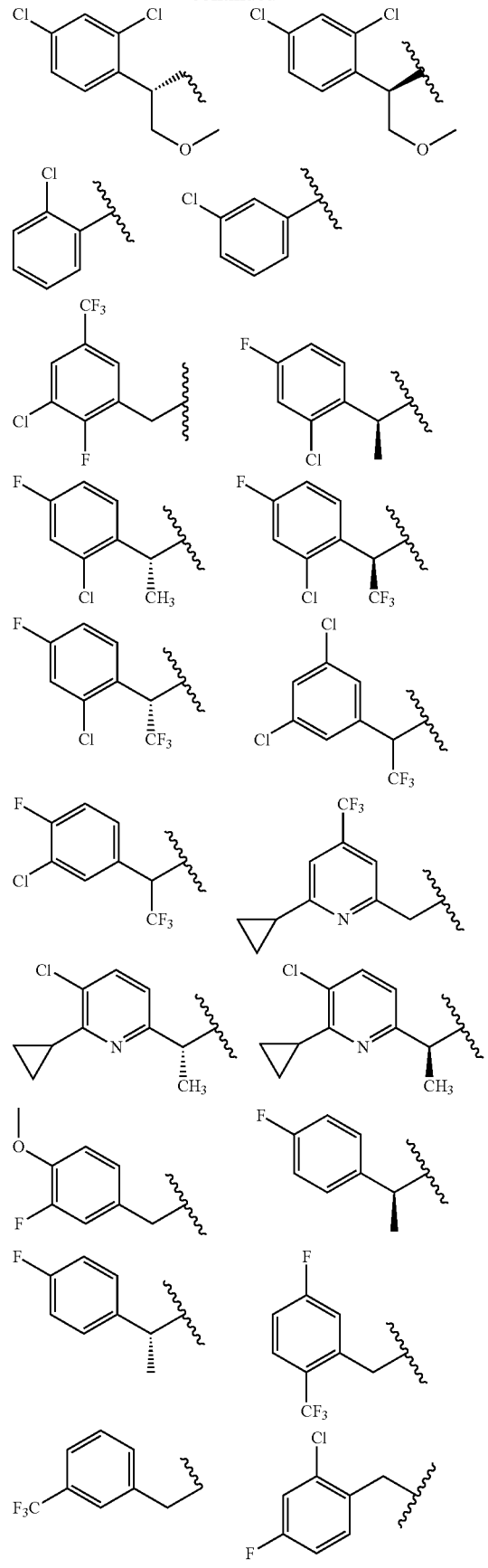

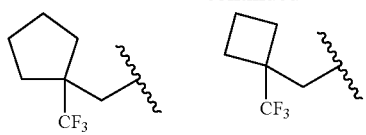
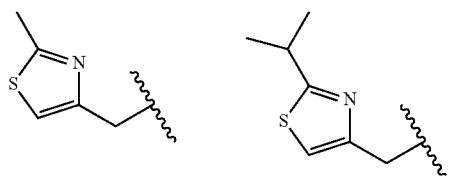
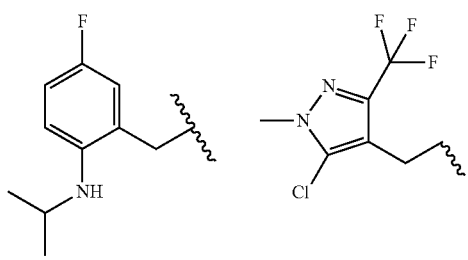
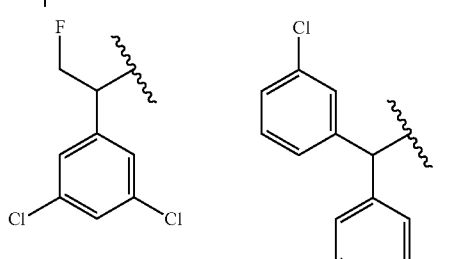
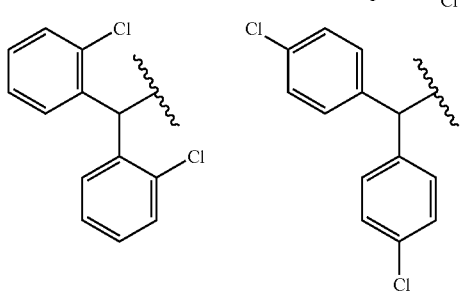
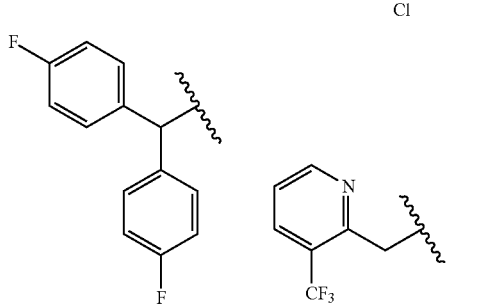
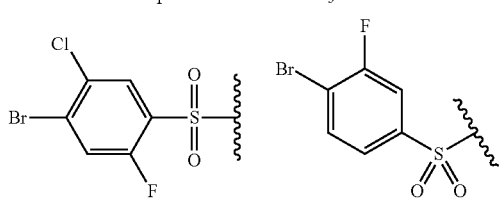
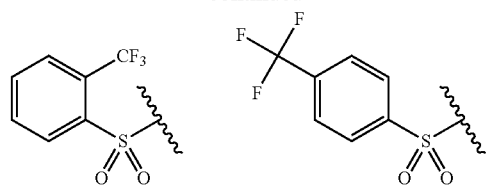
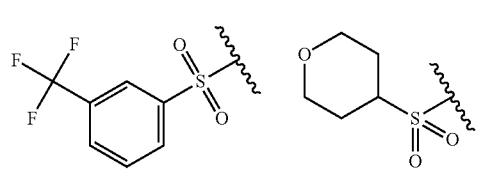
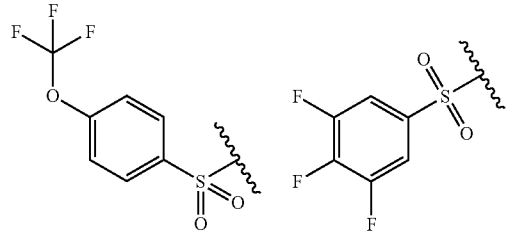
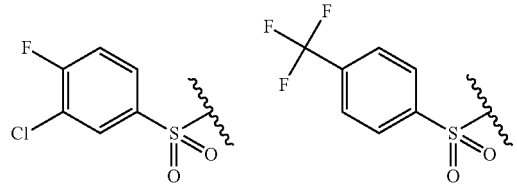
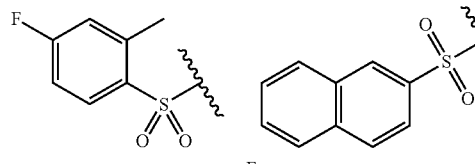
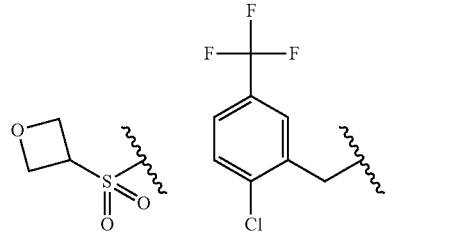
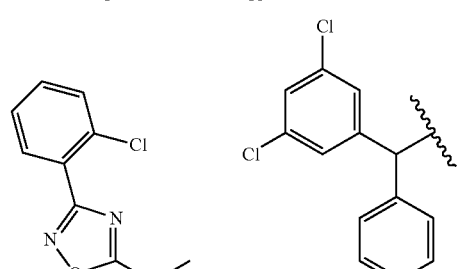
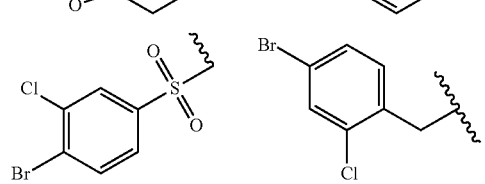

-continued
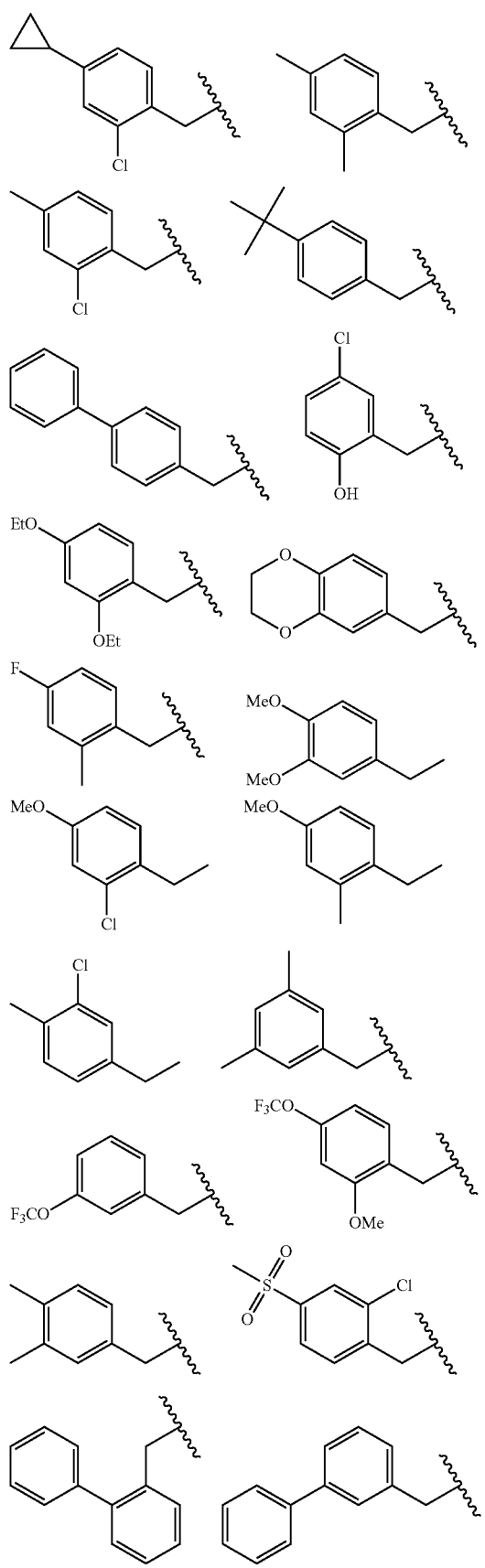
-continued
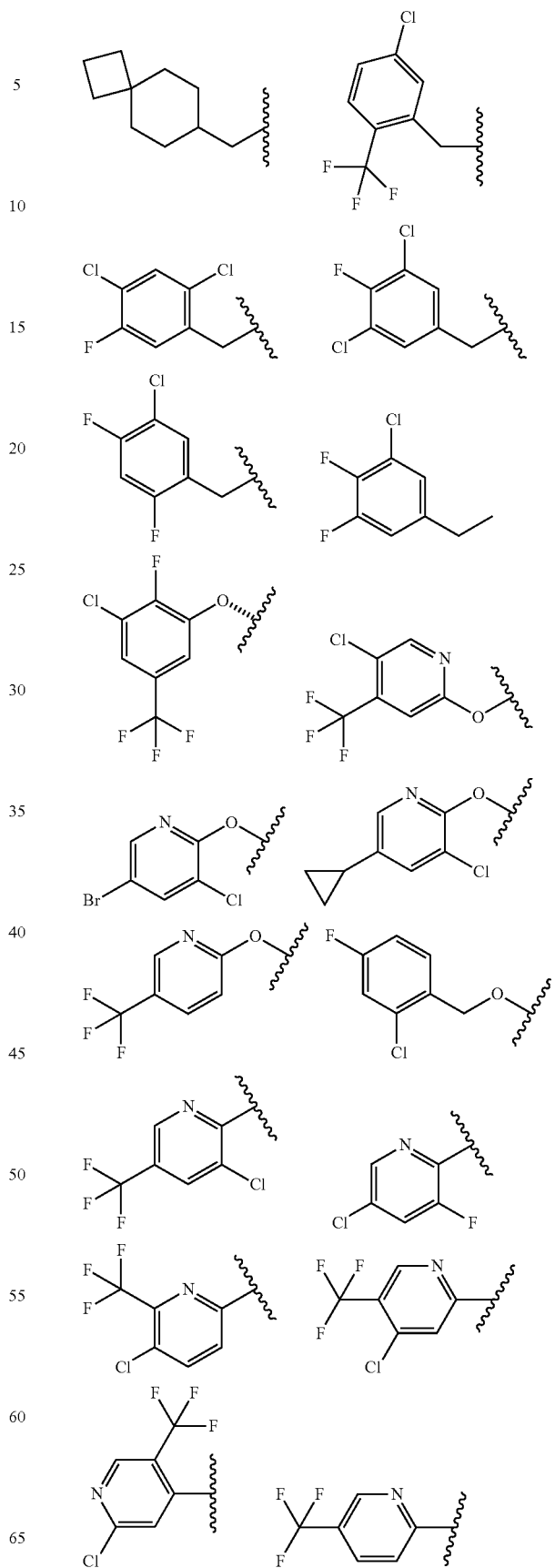

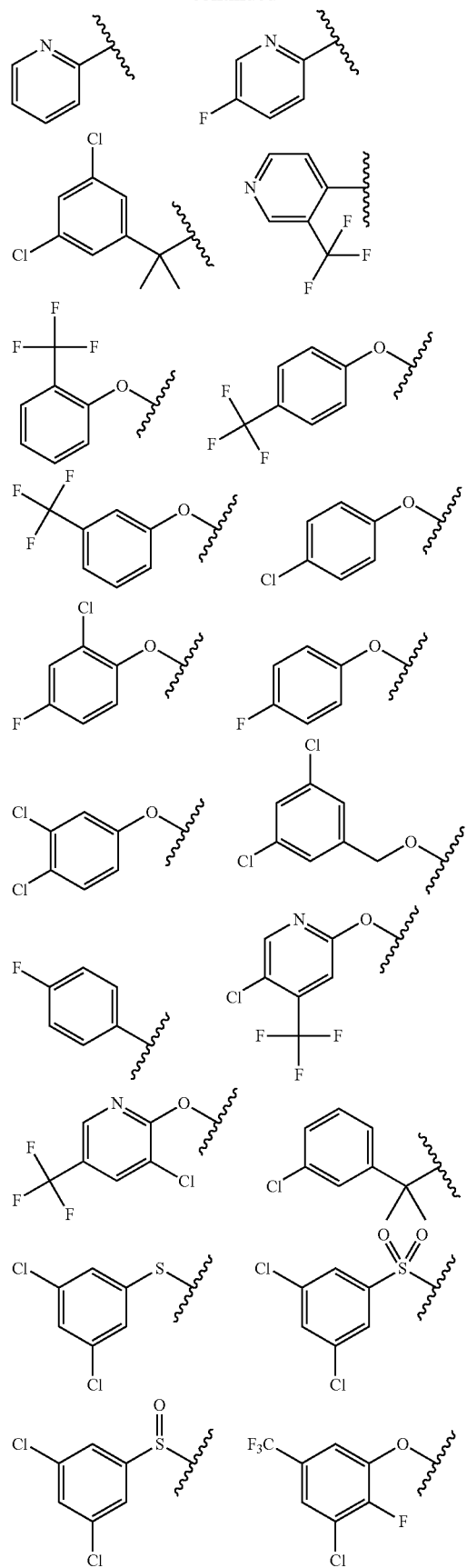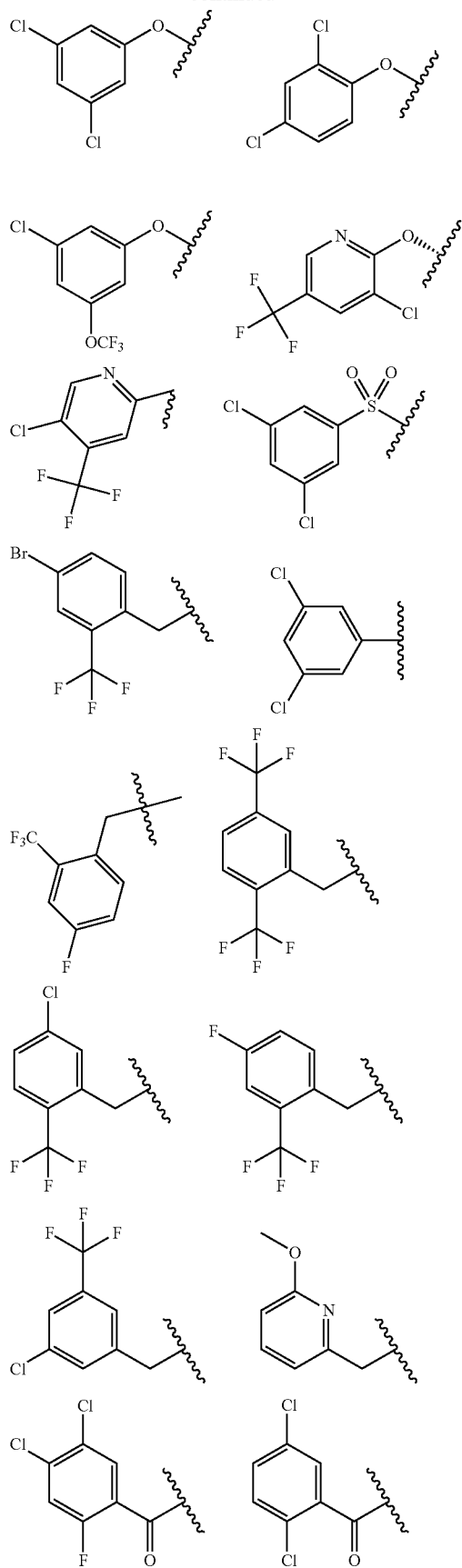

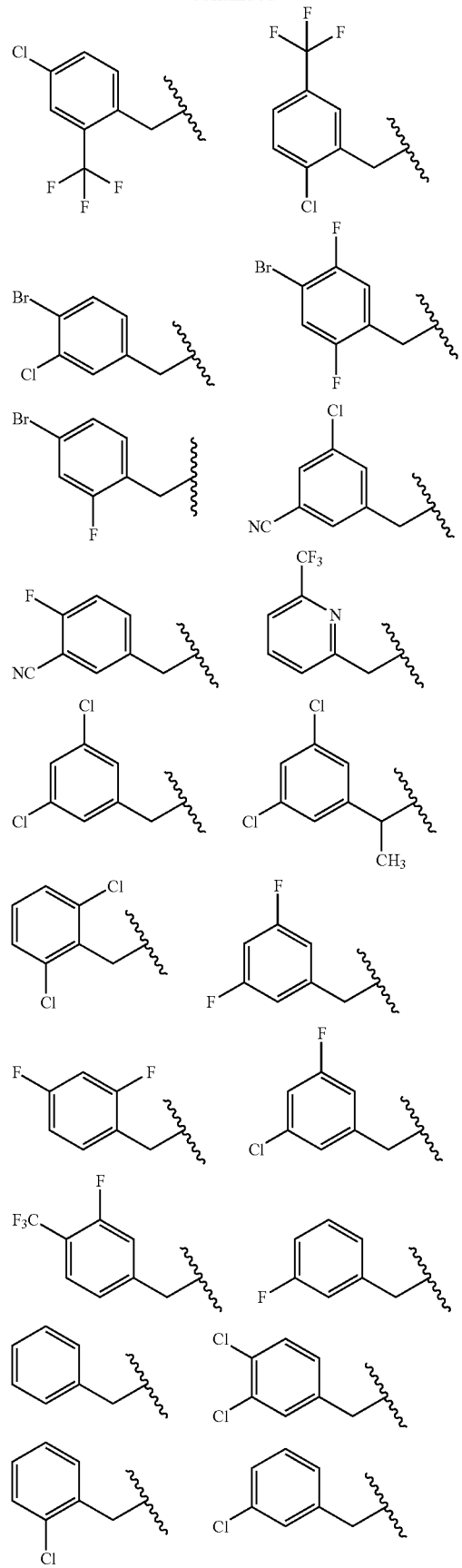
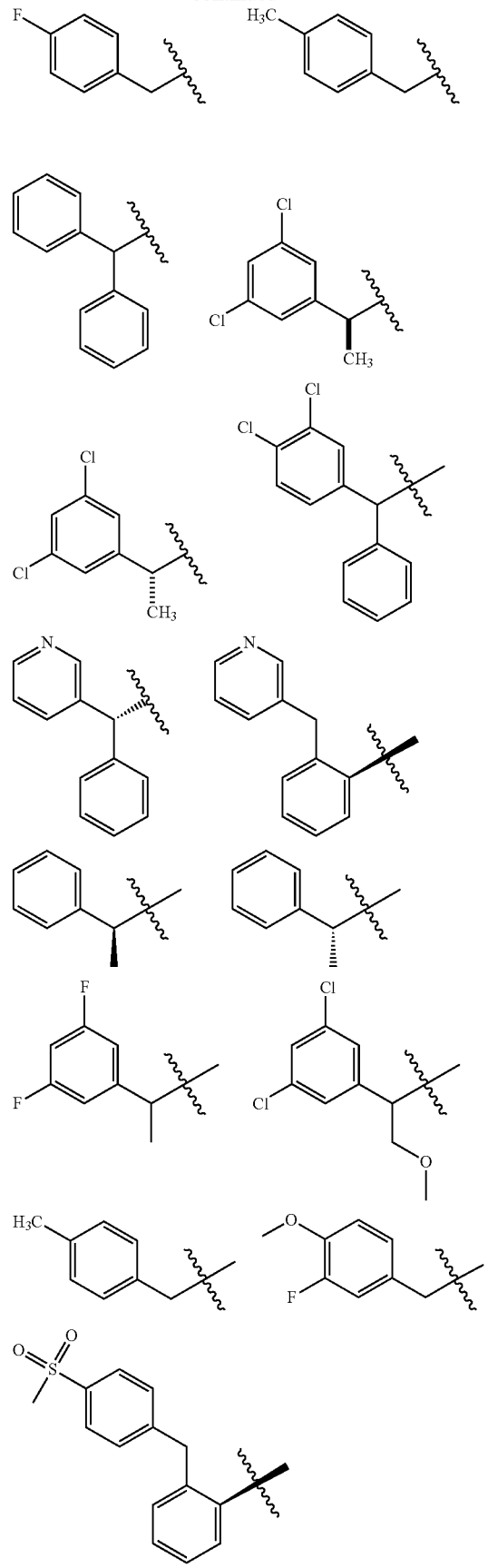

-continued
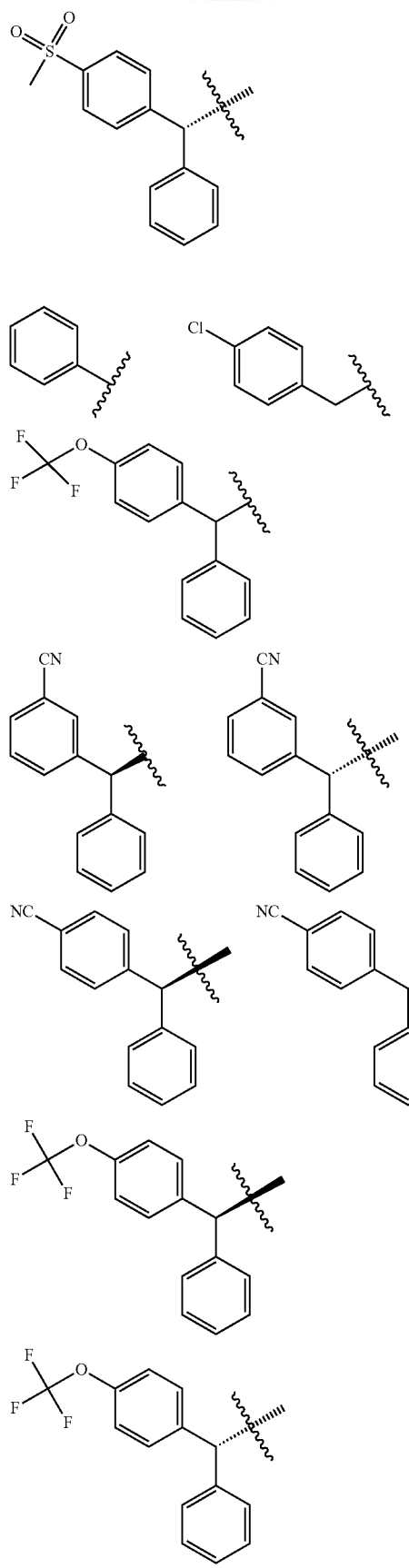
-continued
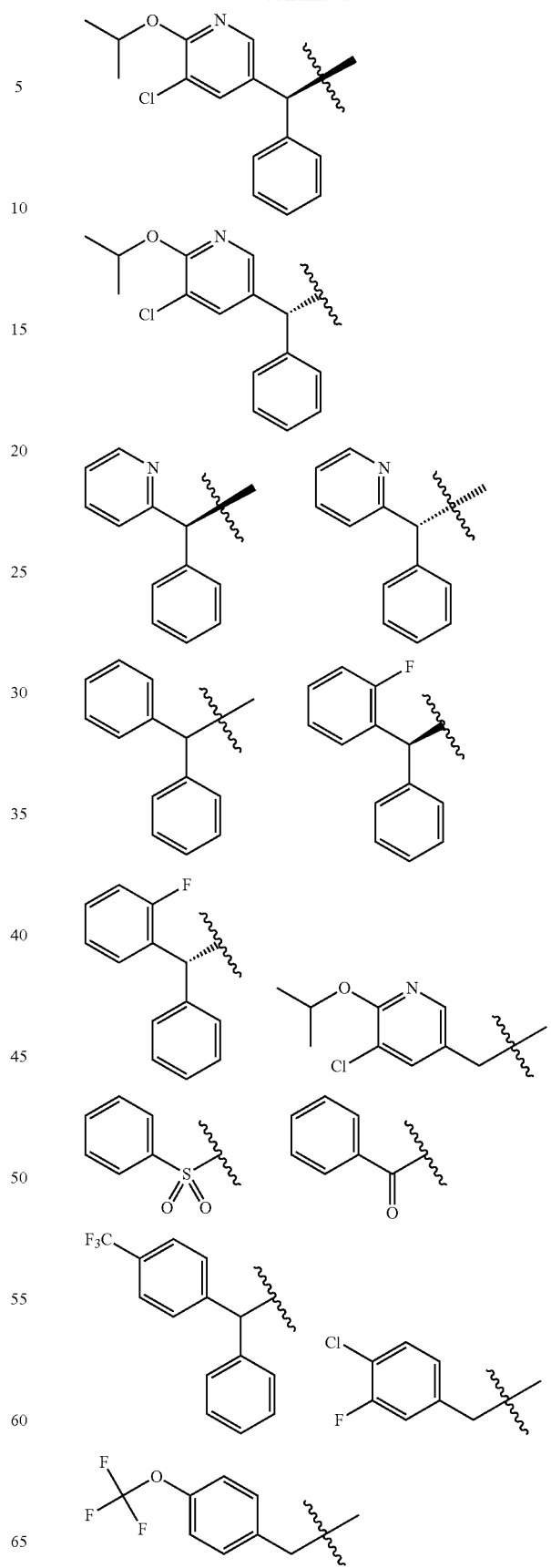

-continued
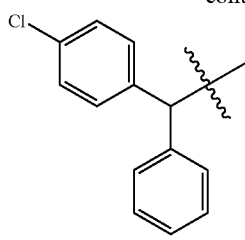
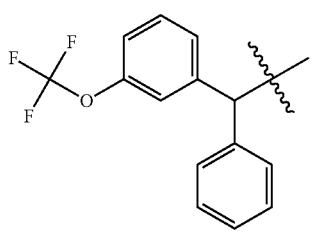
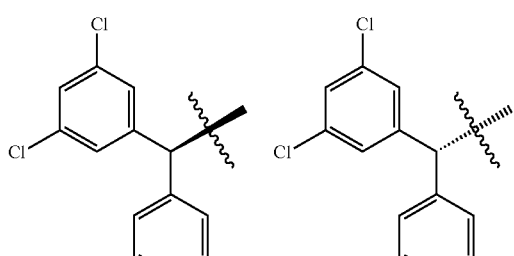
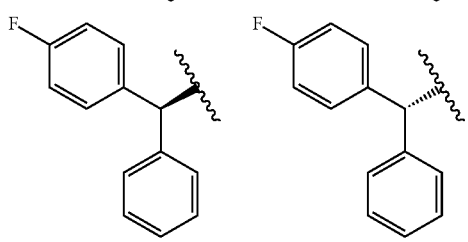
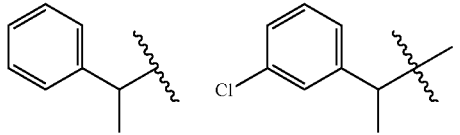
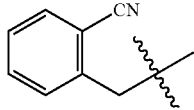
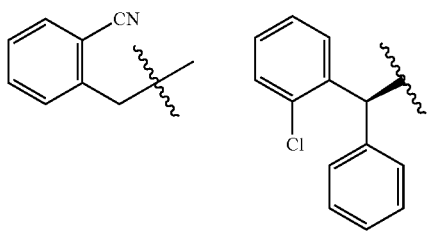
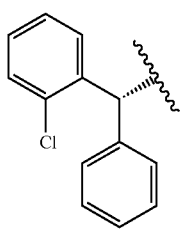
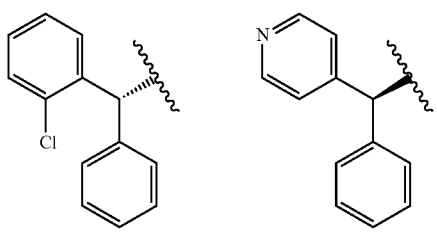
-continued
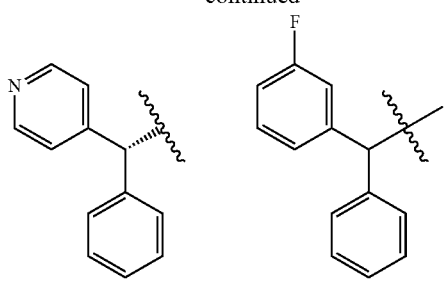
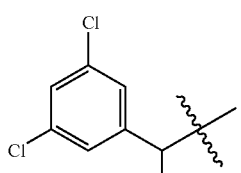
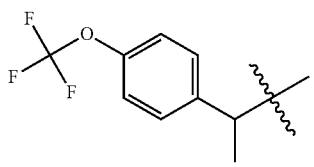
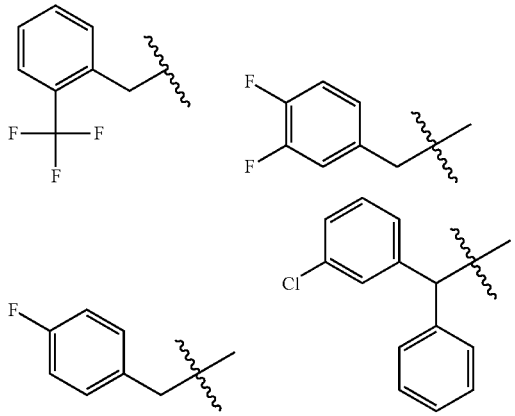
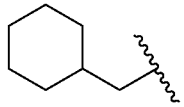
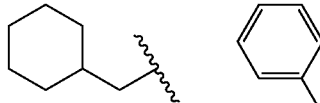
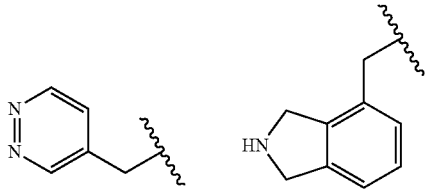
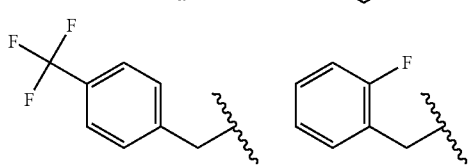

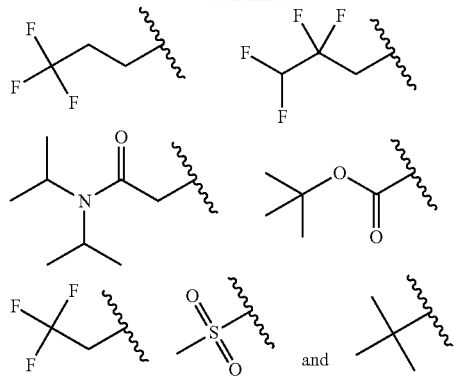
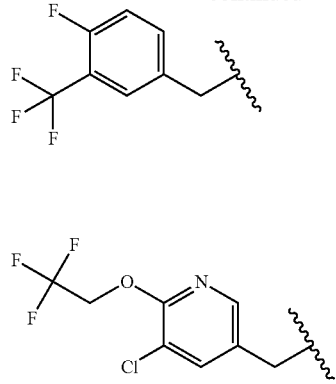
E49 The compound of E1, E2, E3, E4, E5, E6, E7, E8, E9, E10, E11, E12, E13, E14, E15, E16, E17, E18, E19, E20, E21, E22, E23, E24, E25, E26, E37, E38, E39, E40, E41, E42, E43, E44, E45, E46, or E47 wherein $R^A$ is
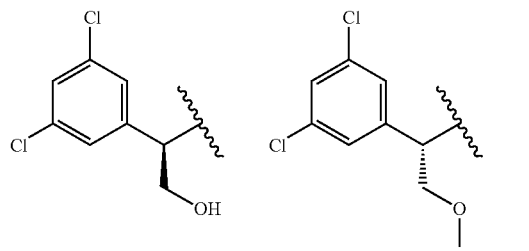
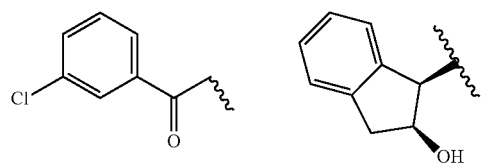
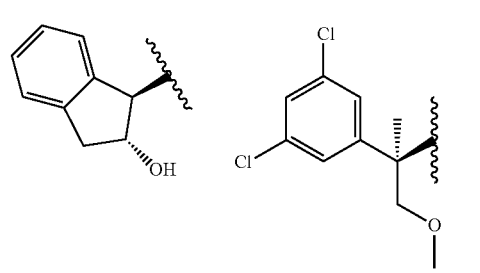
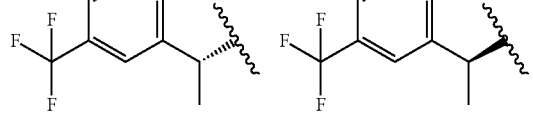
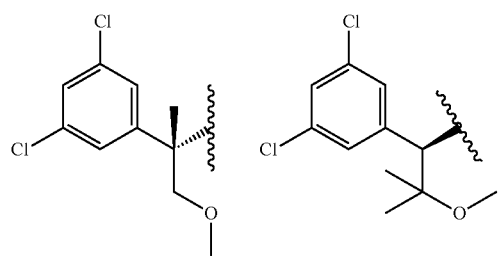
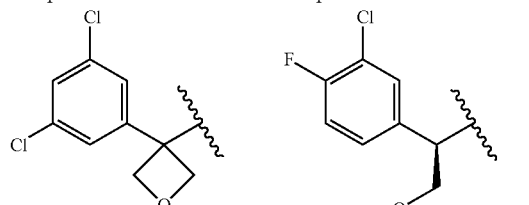
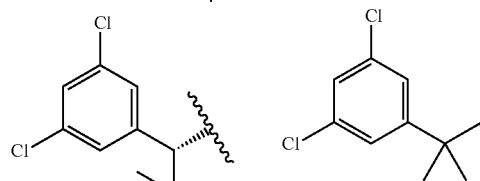
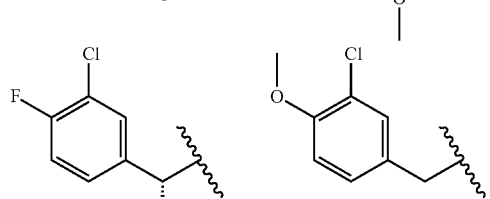
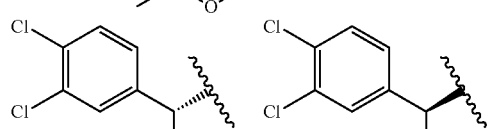
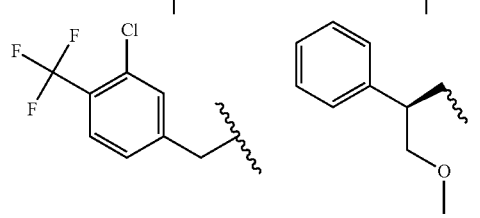
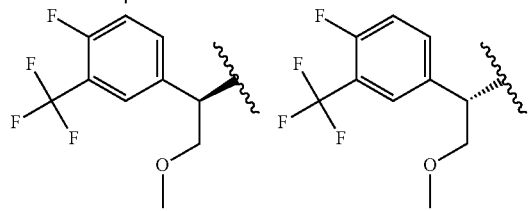

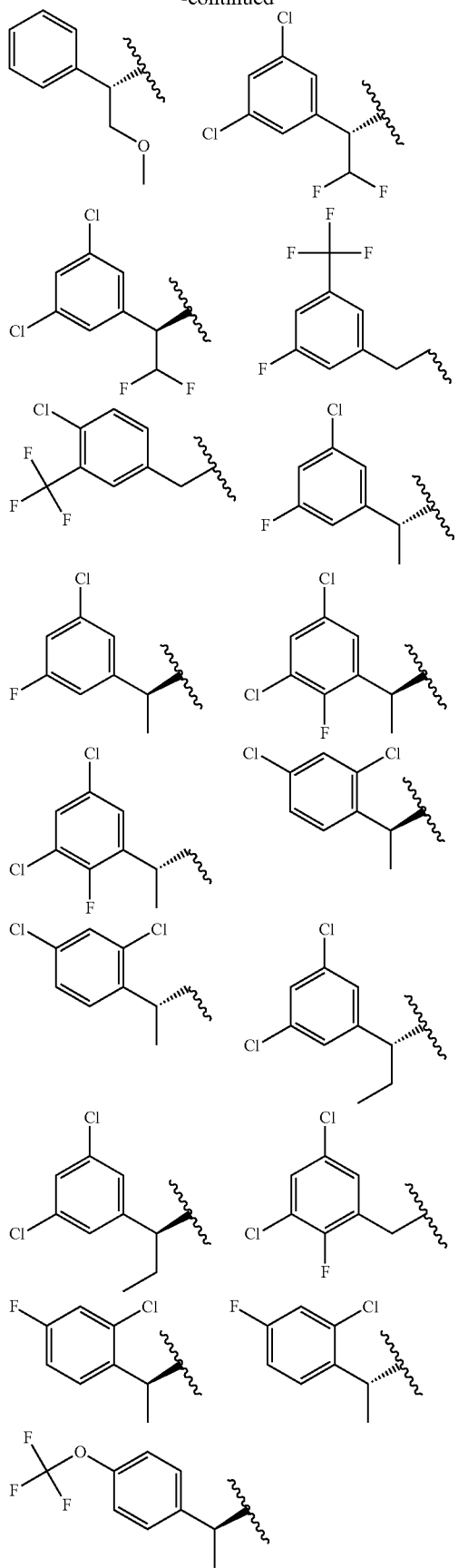
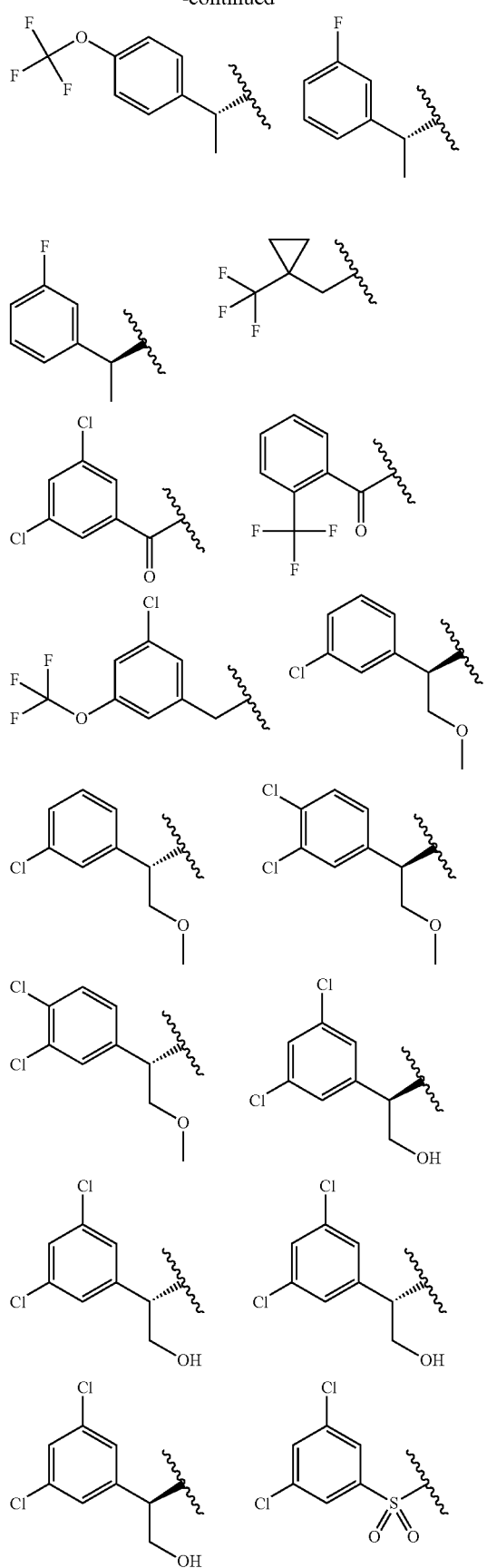

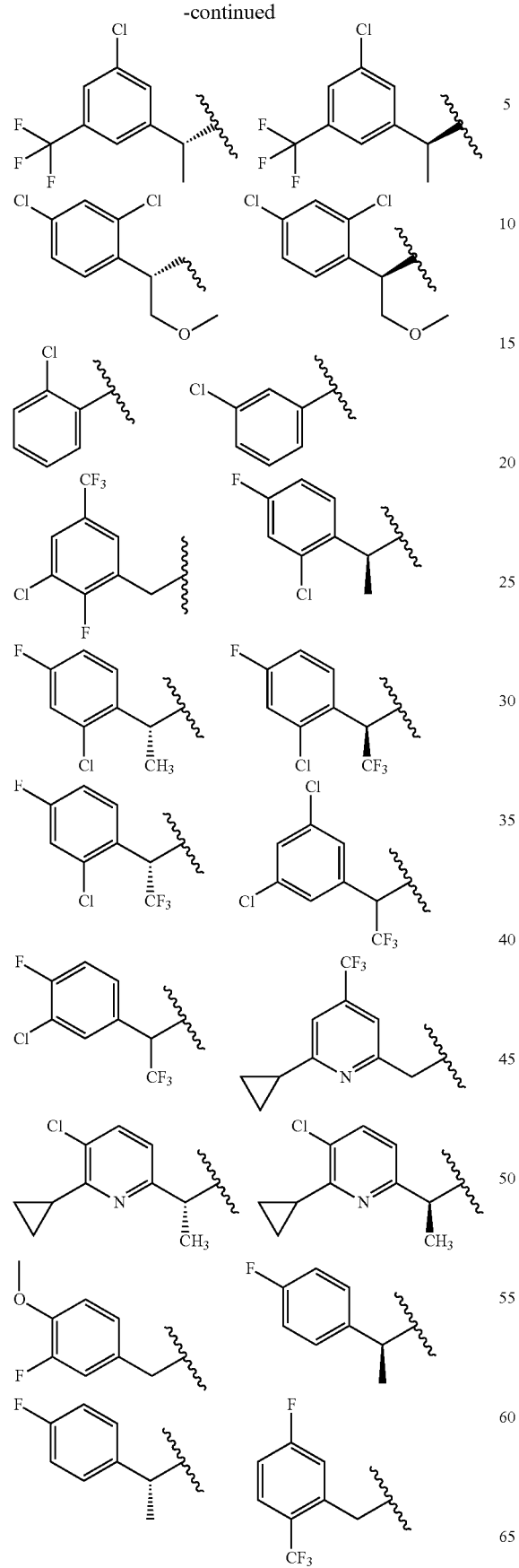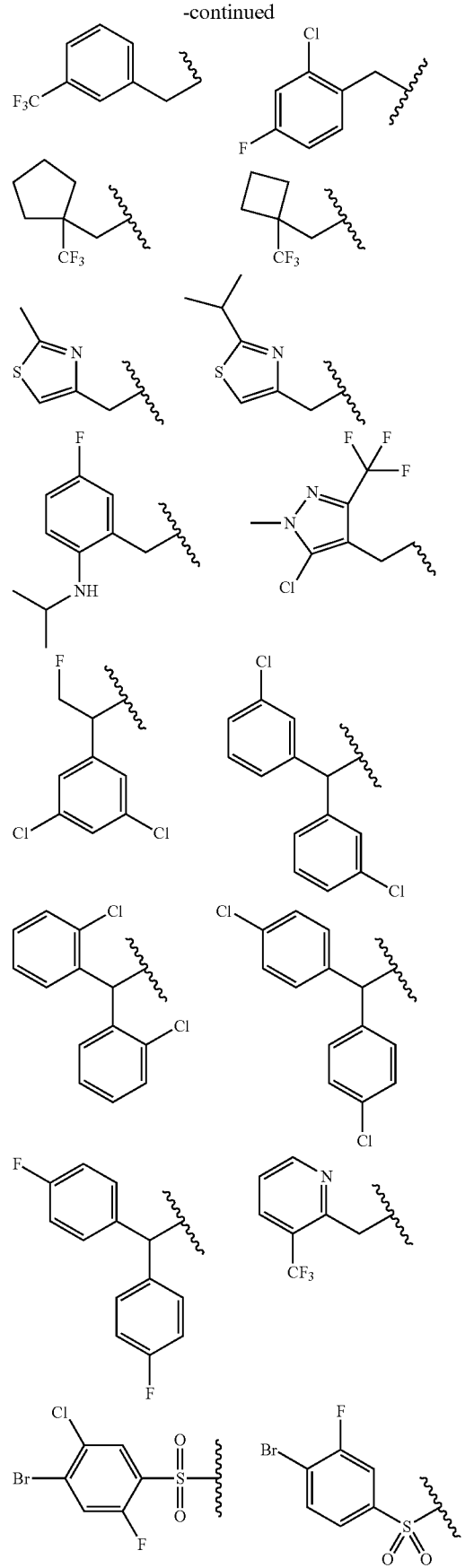

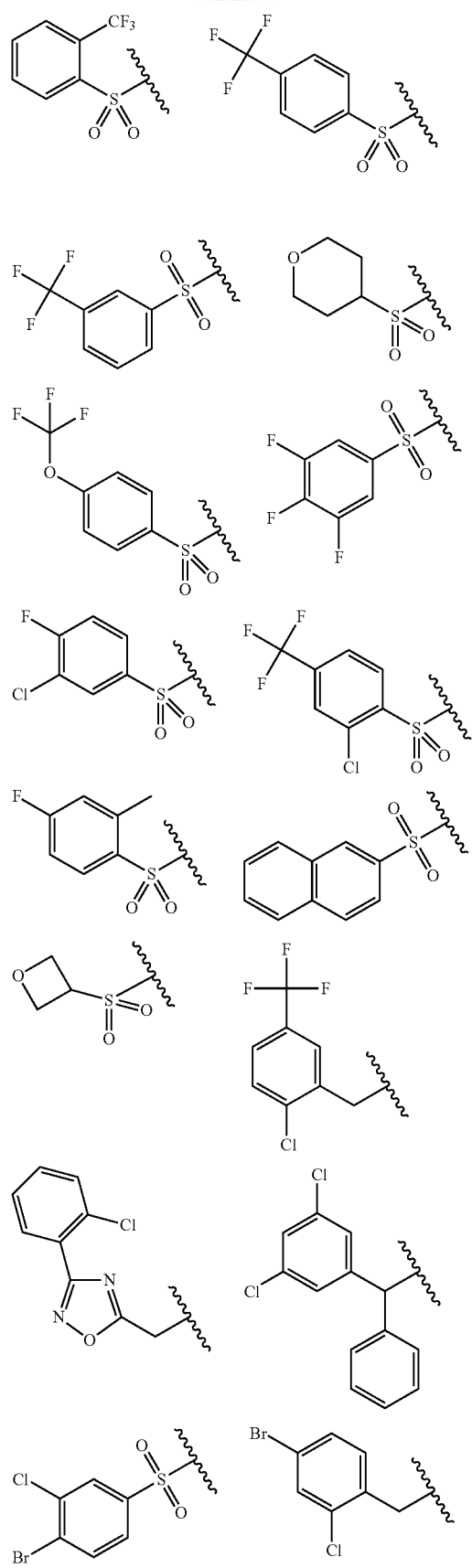
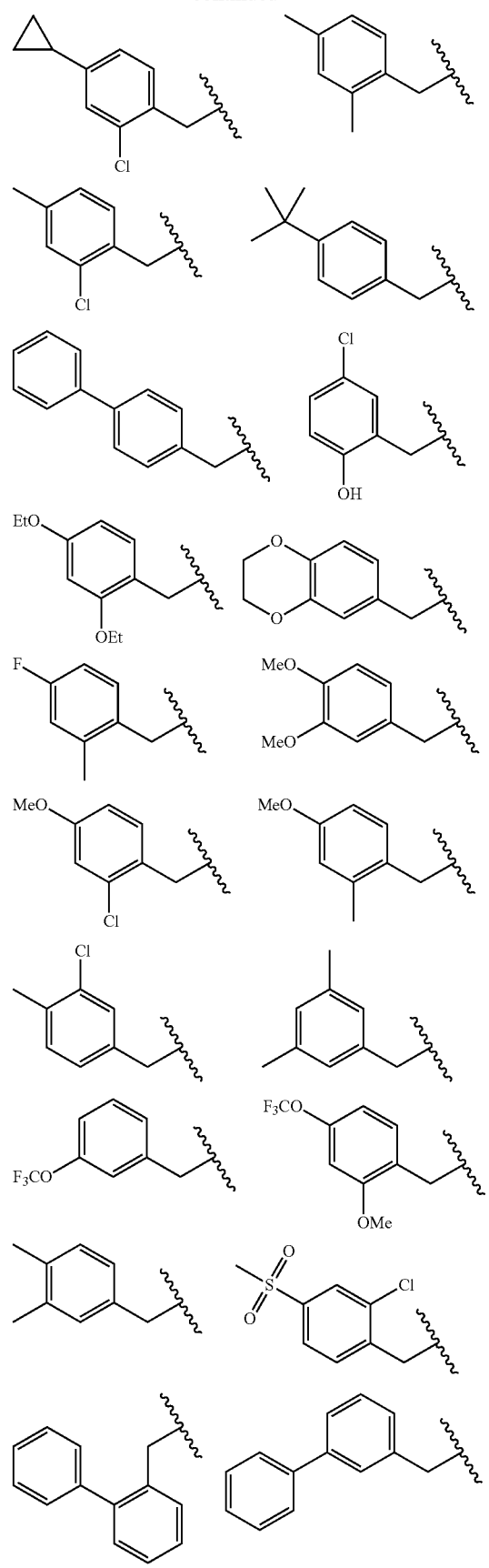

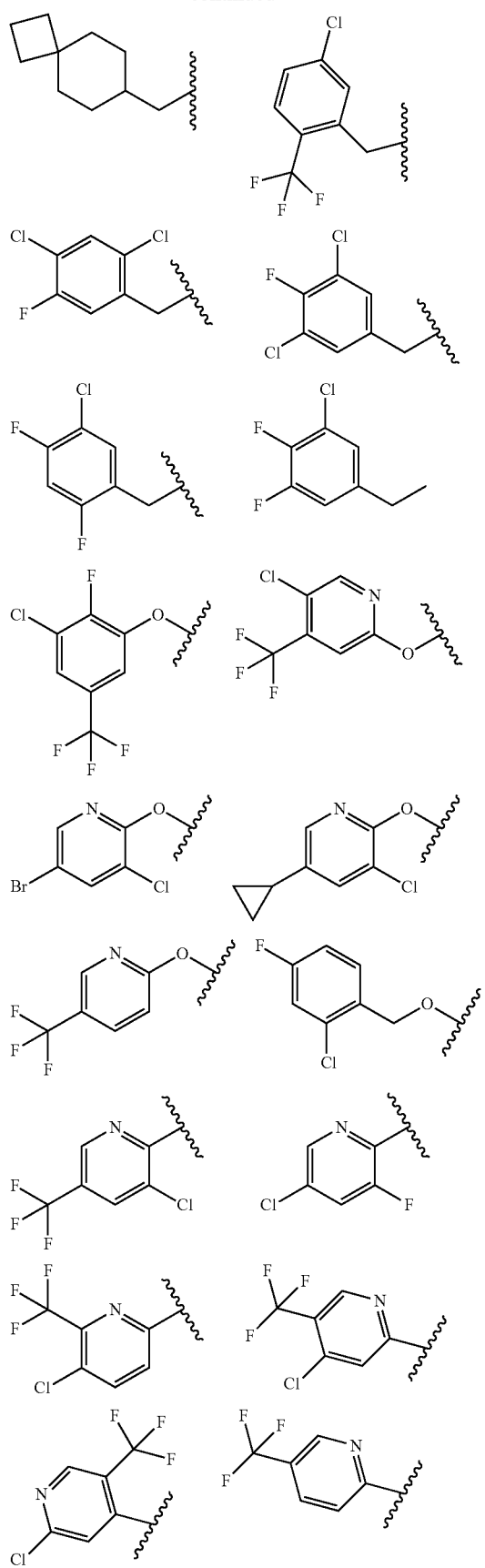
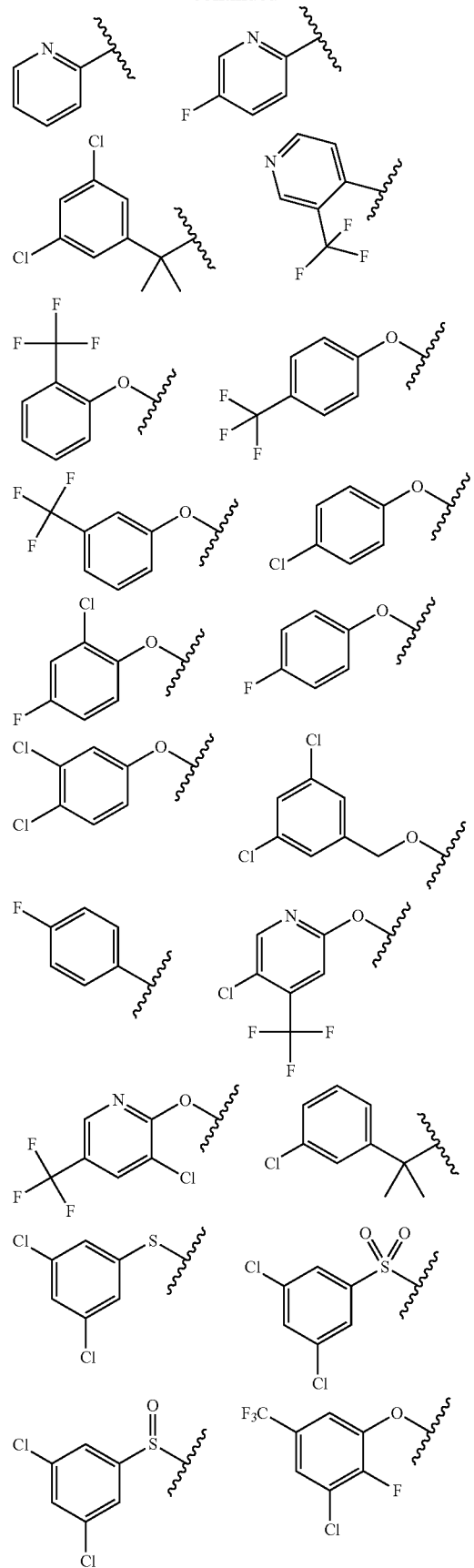

-continued
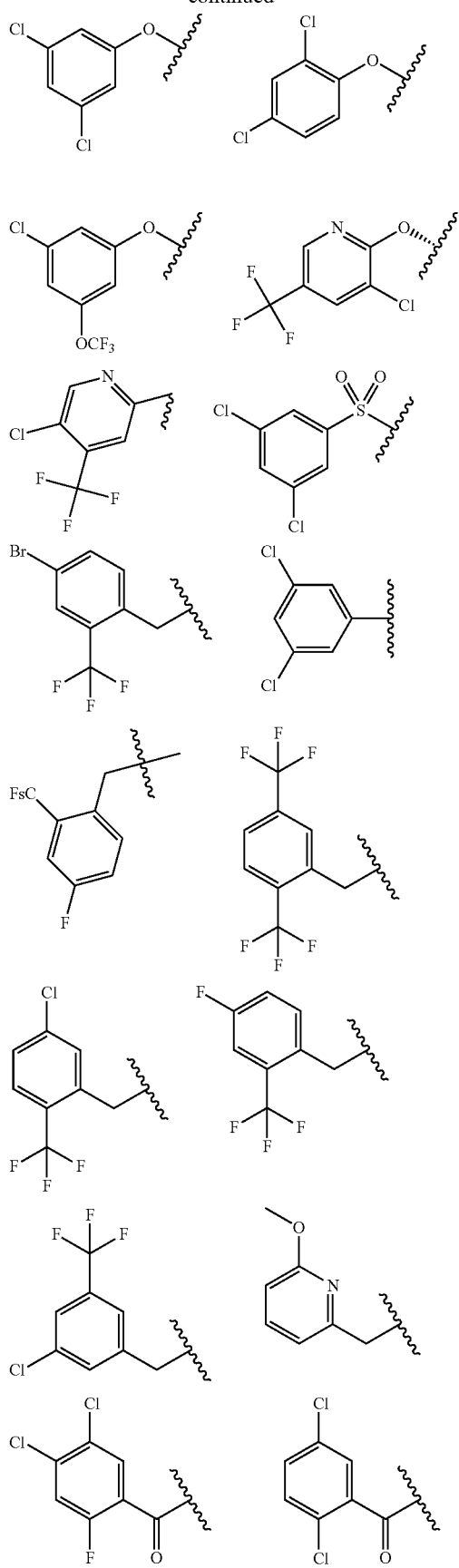
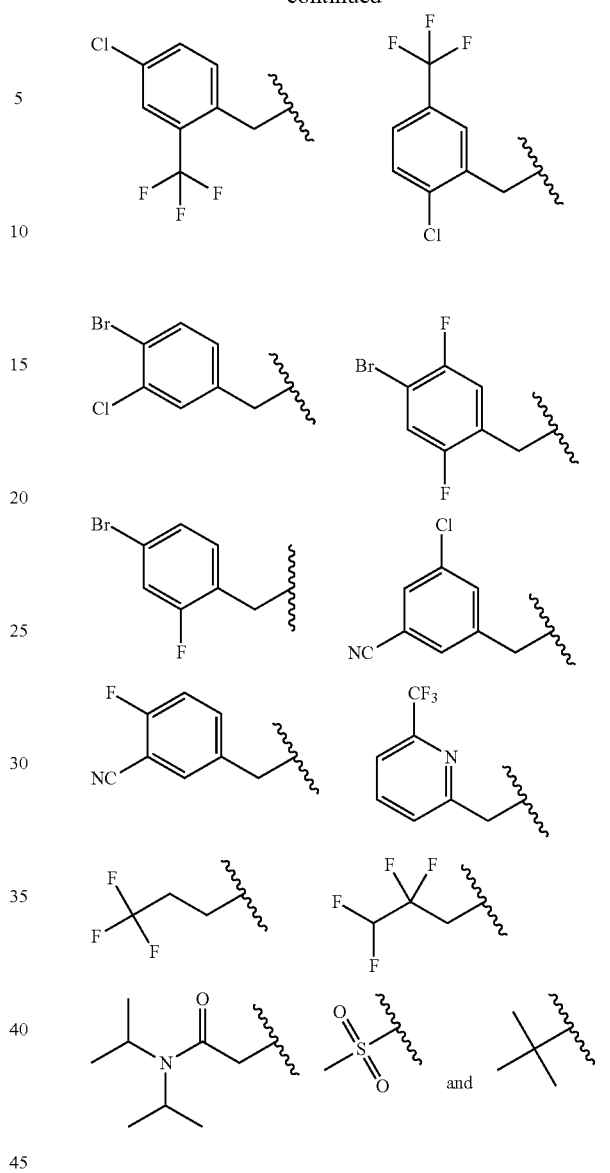
E50 The compound of E1 which is selected from:
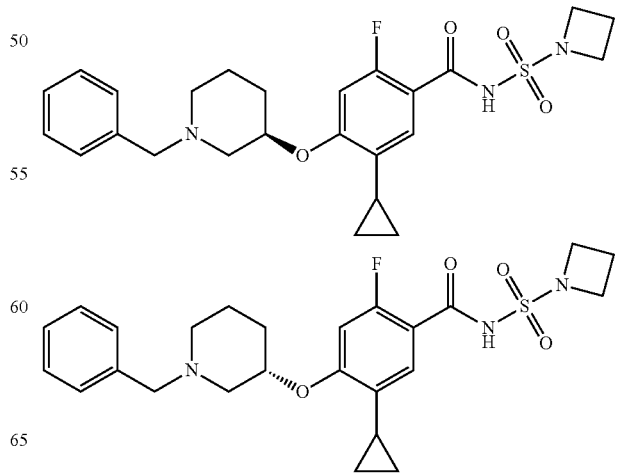

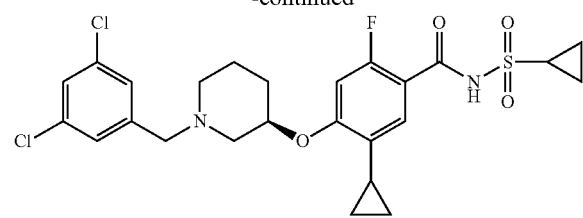
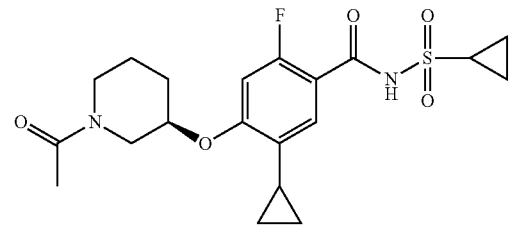
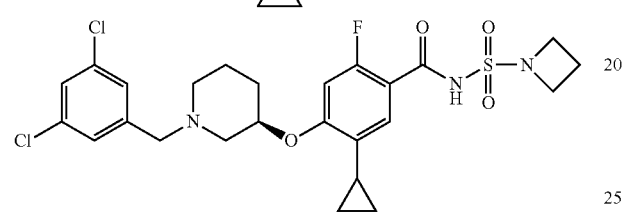
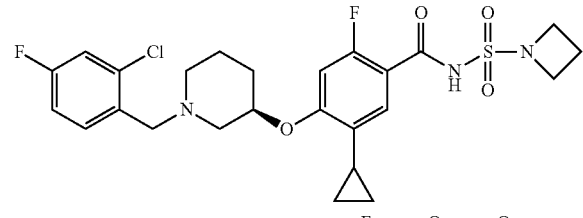
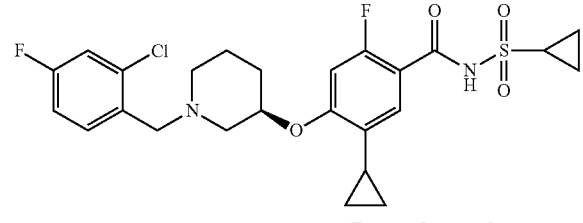
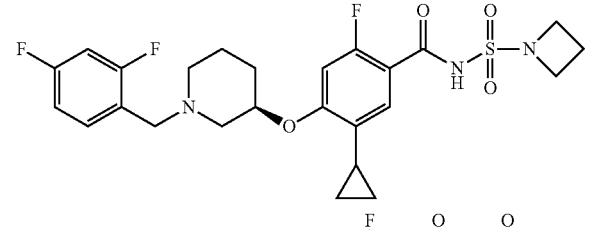
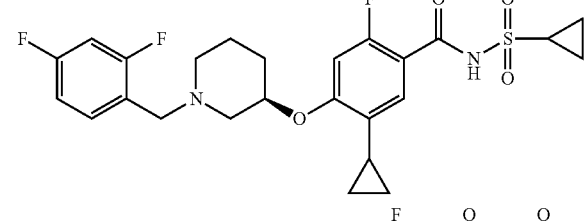
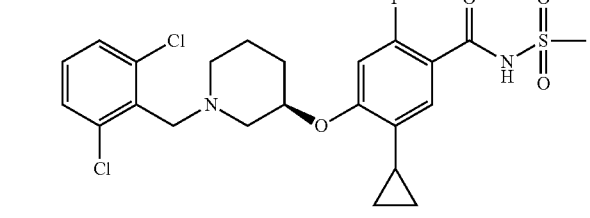
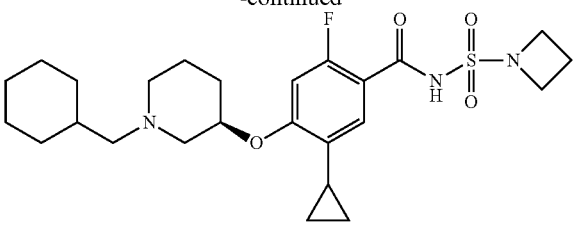
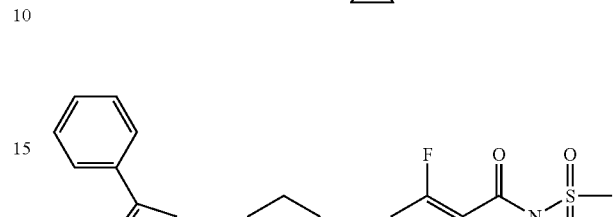

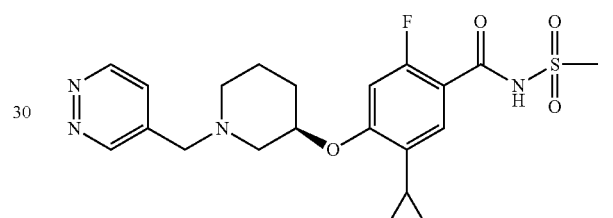
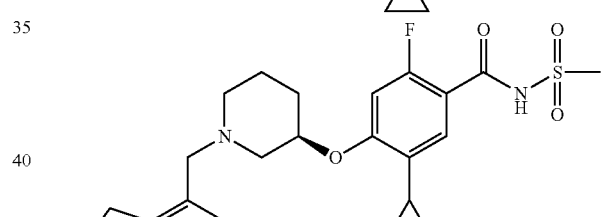
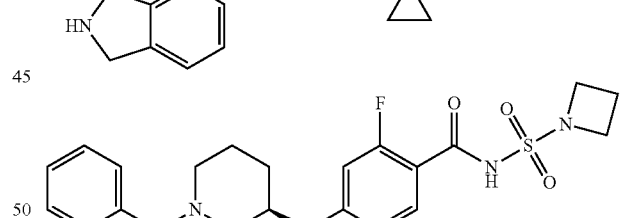
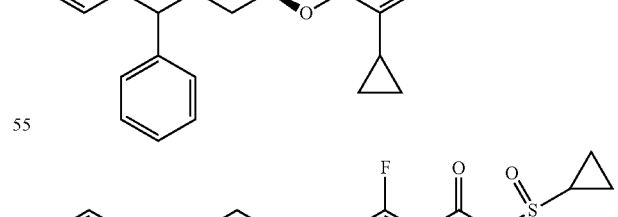
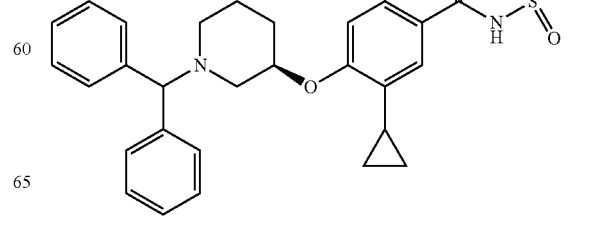

57
-continued
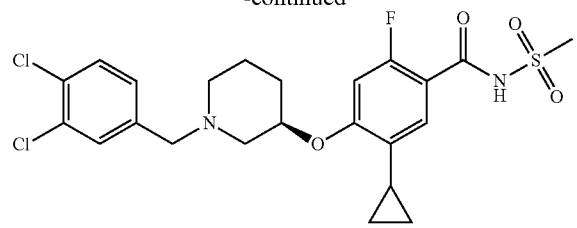
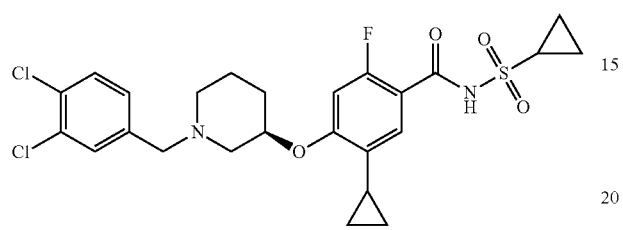
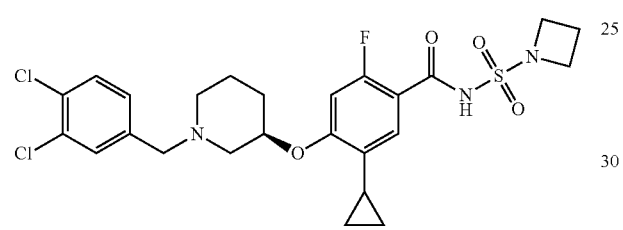
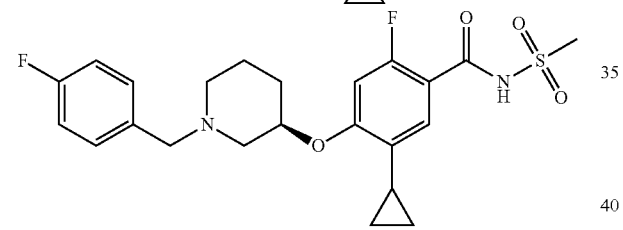
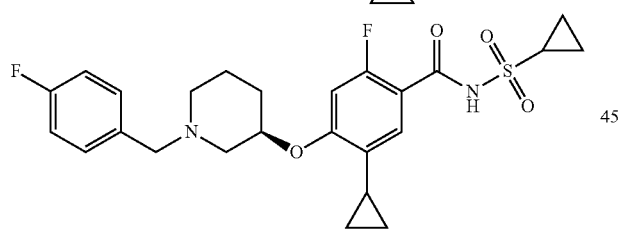
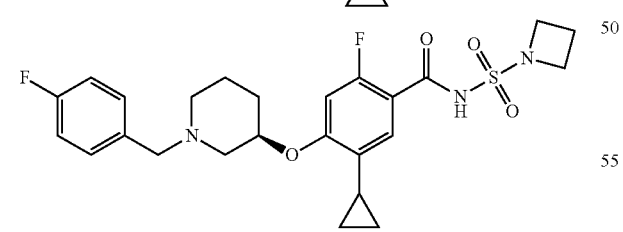
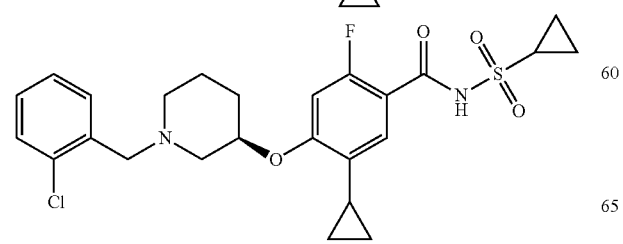
58
-continued
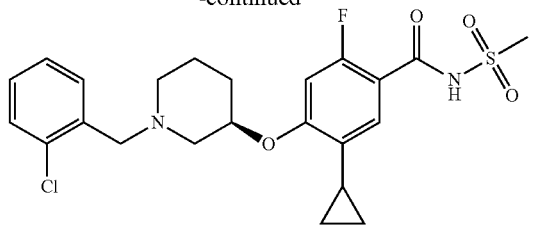
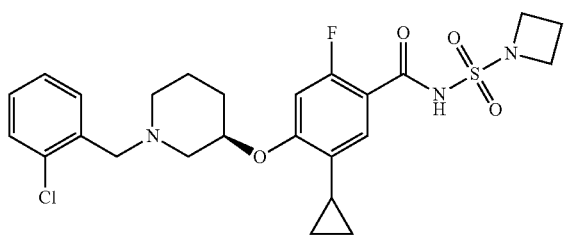
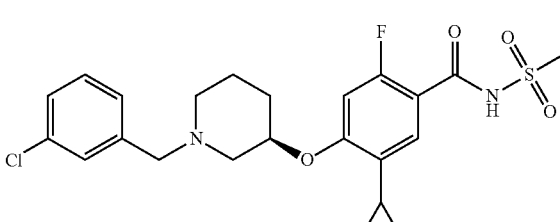
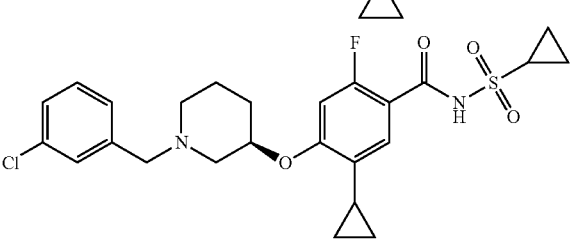
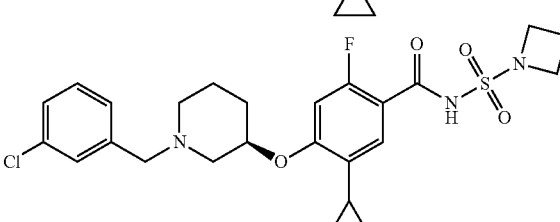
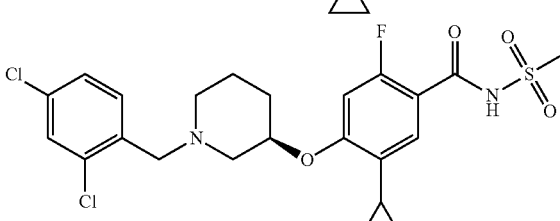
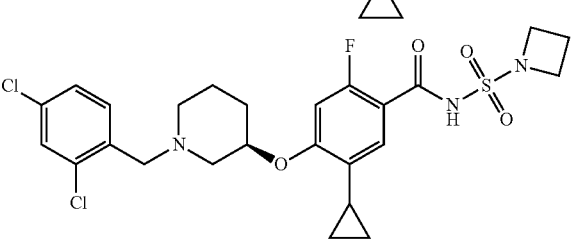

59
-continued
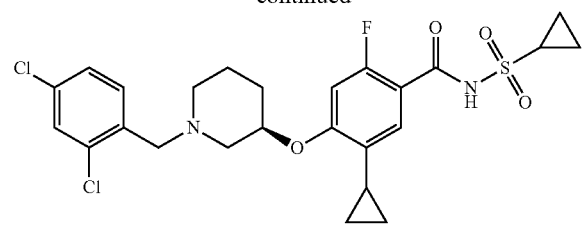
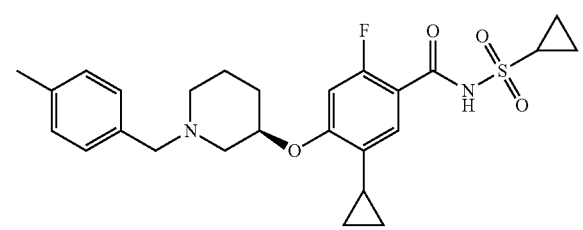
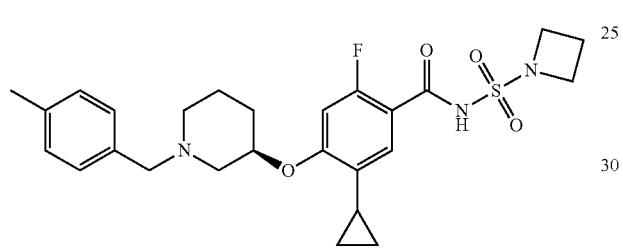
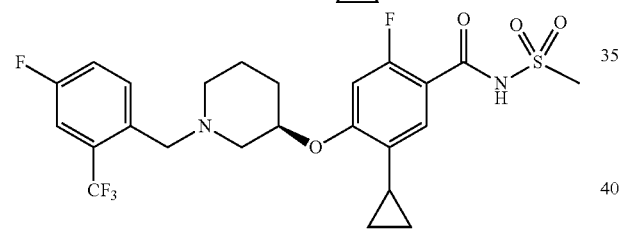
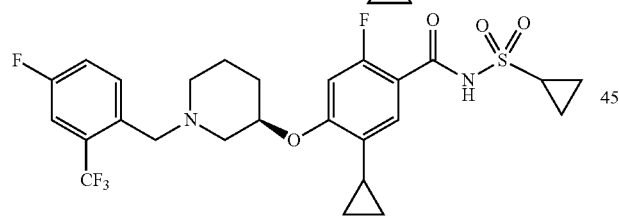
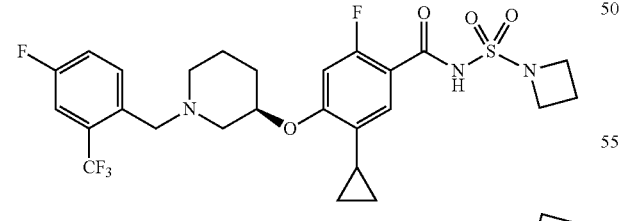
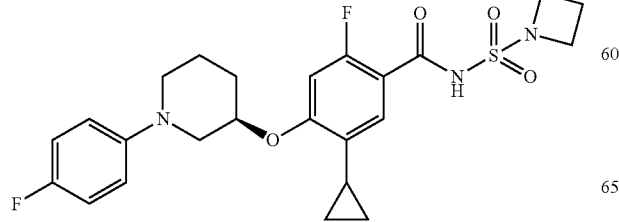
60
-continued
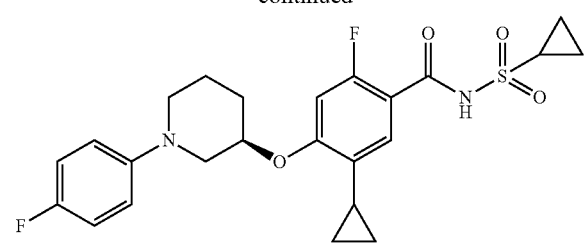
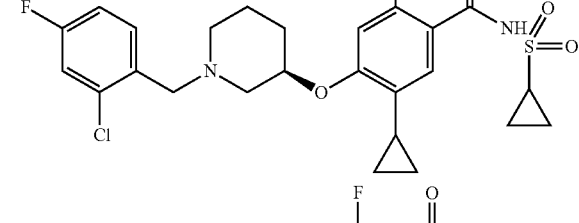
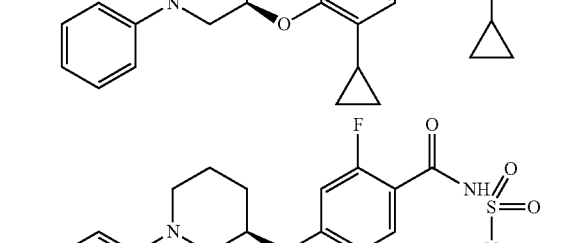
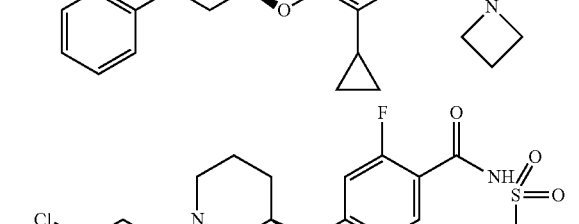
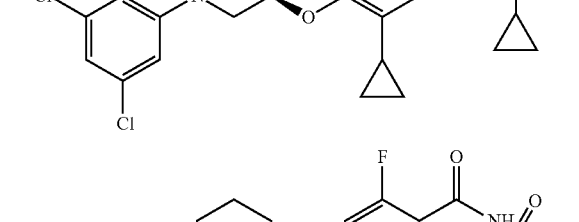
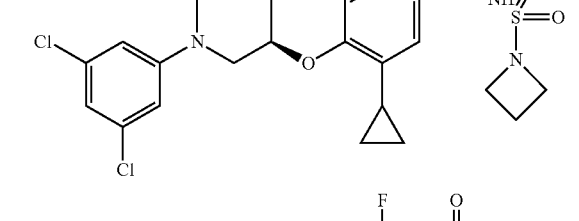
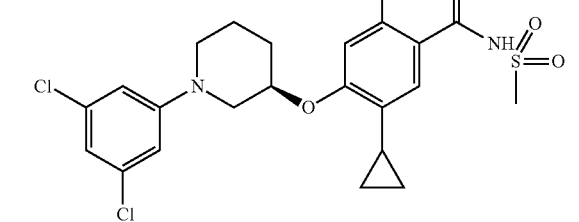

61
-continued
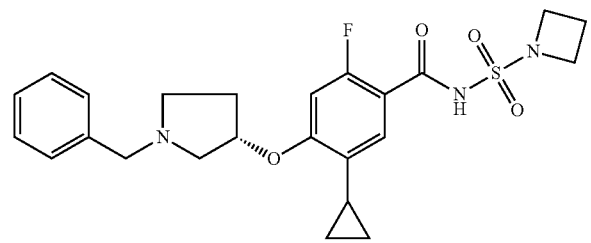
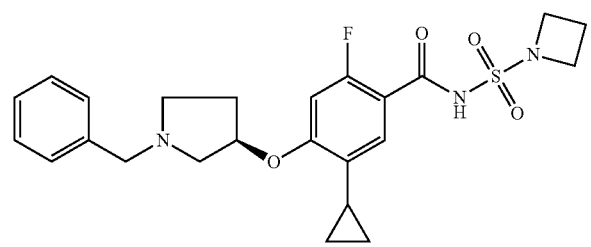
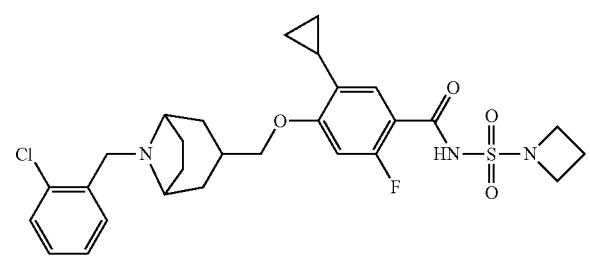
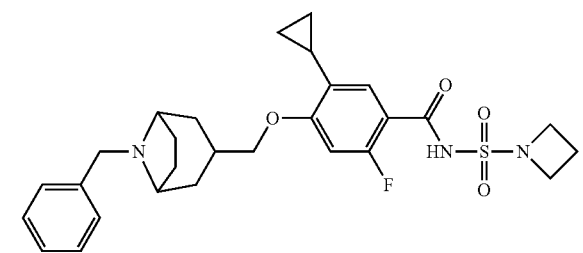
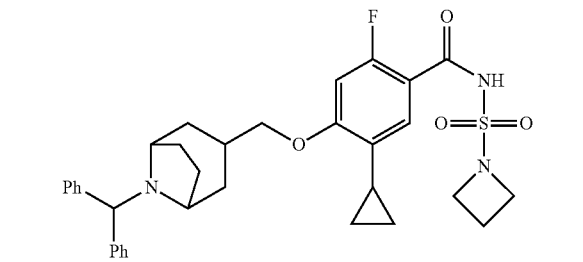
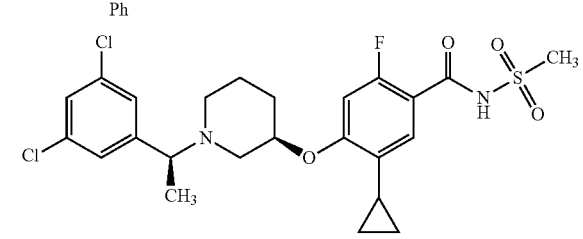
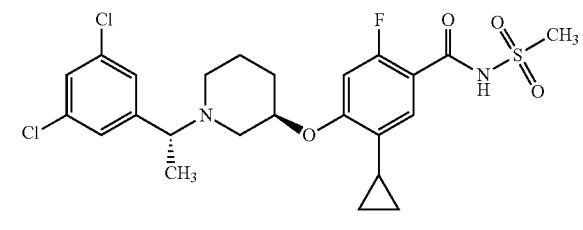
62
-continued
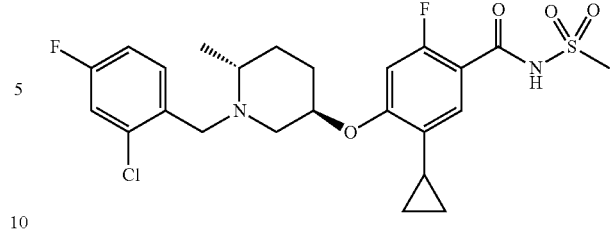
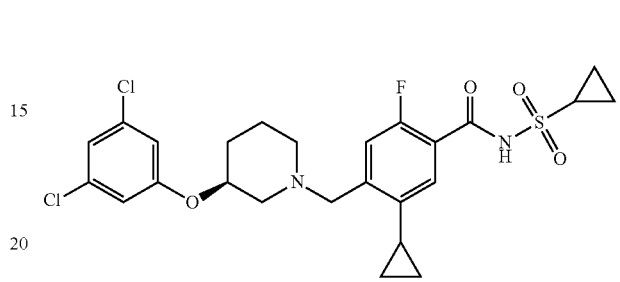
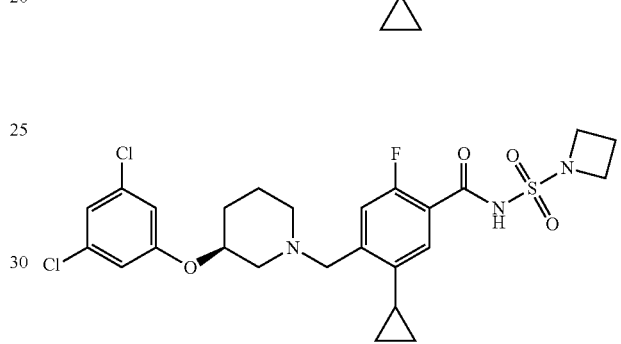
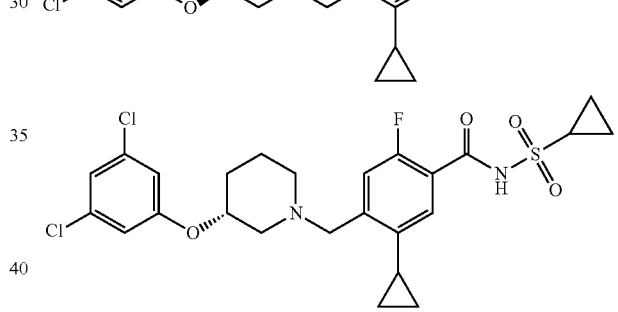
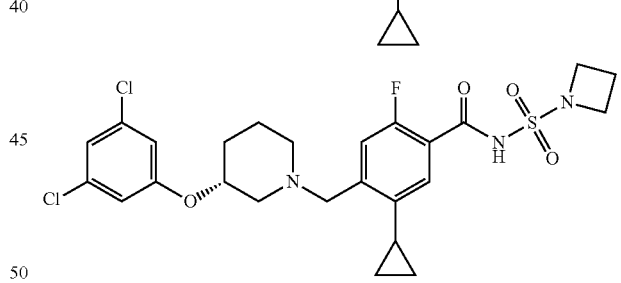
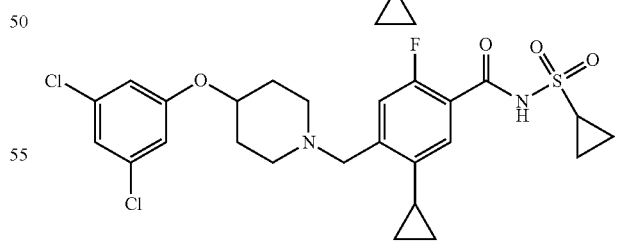
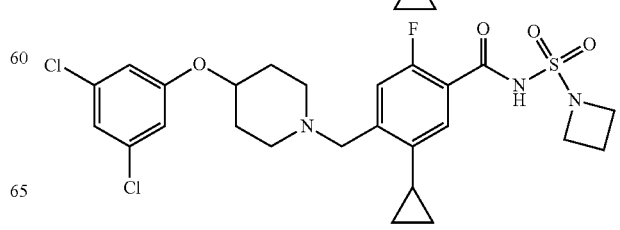

63
-continued
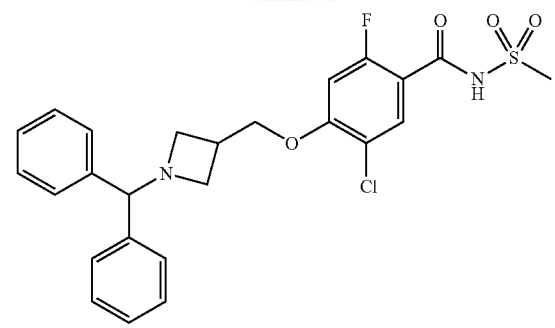
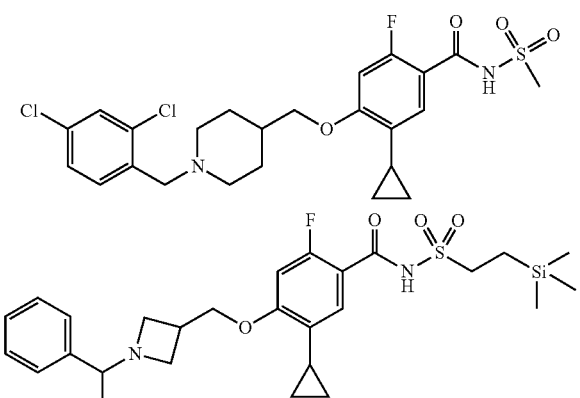
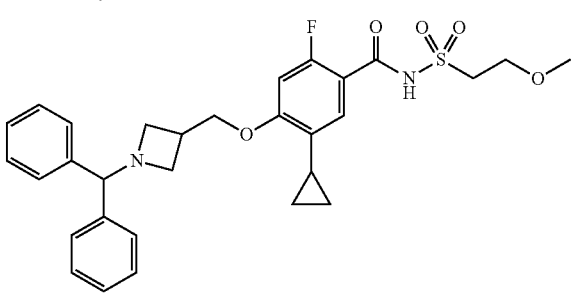
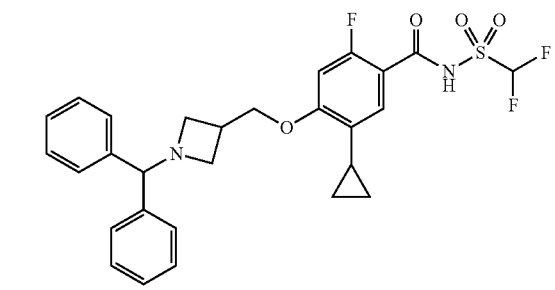
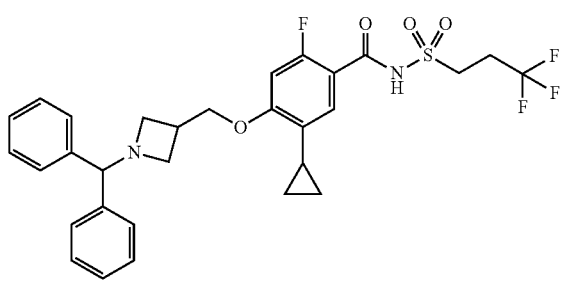
64
-continued
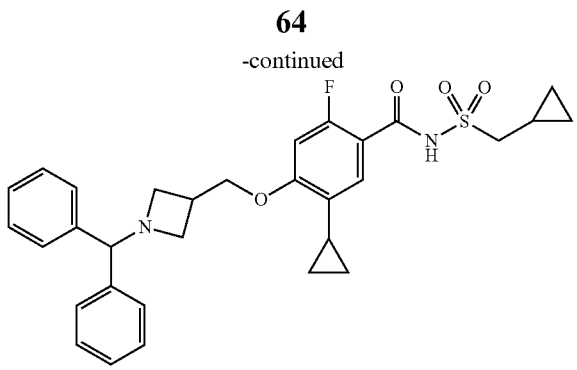
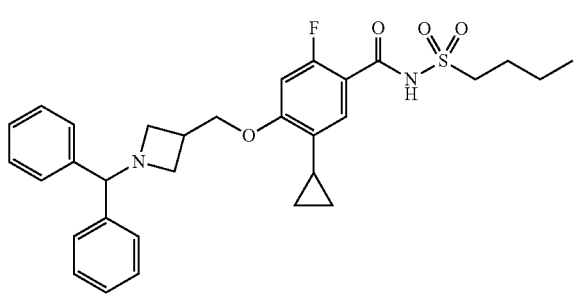
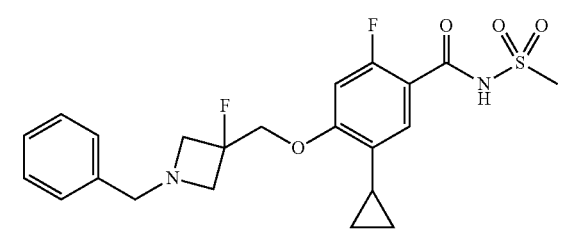
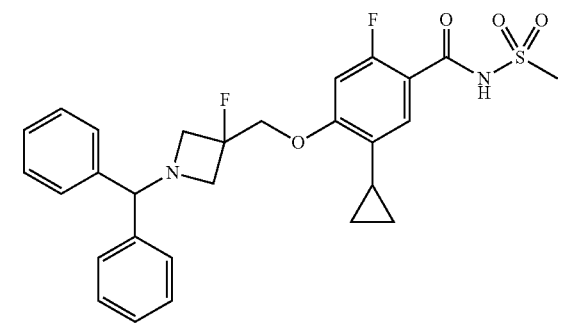
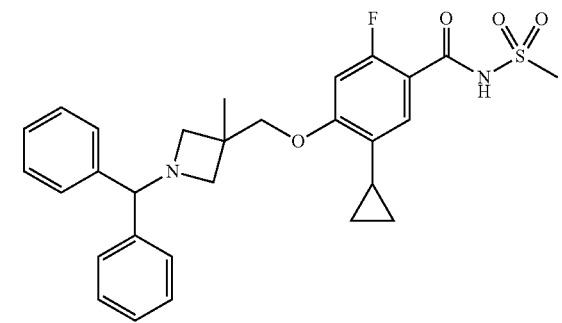

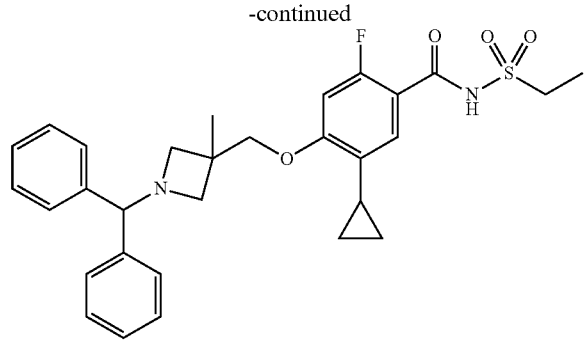
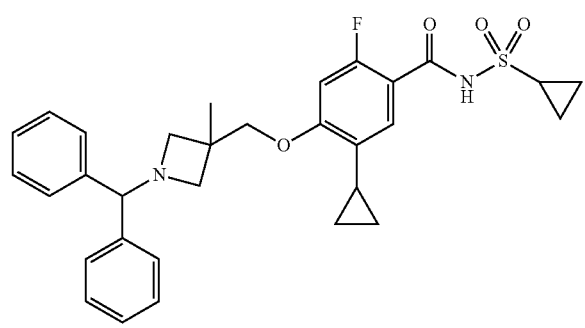
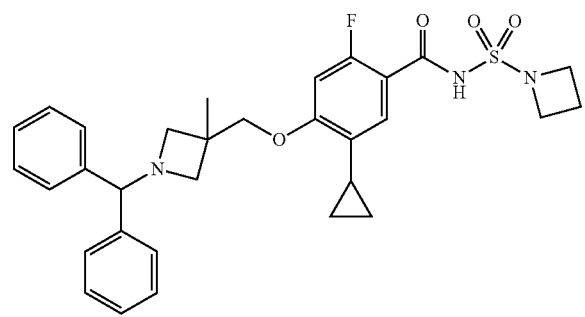
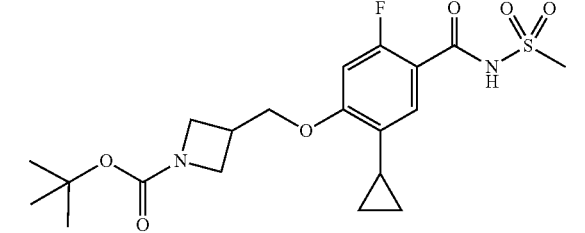
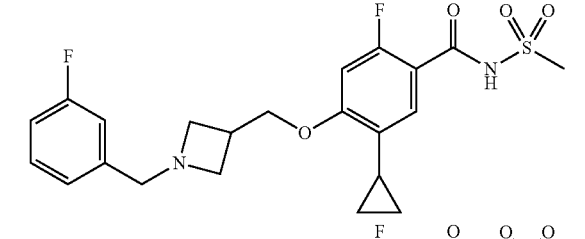
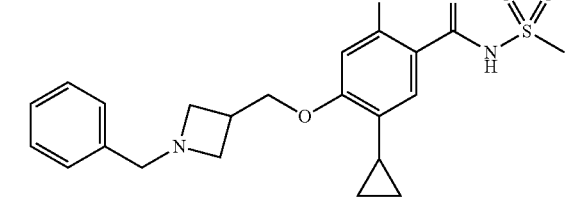
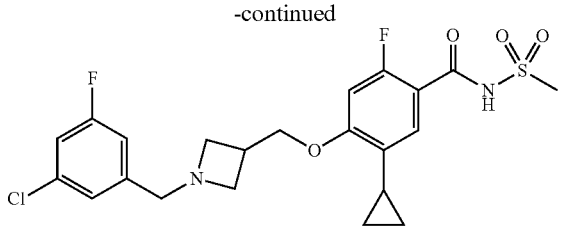
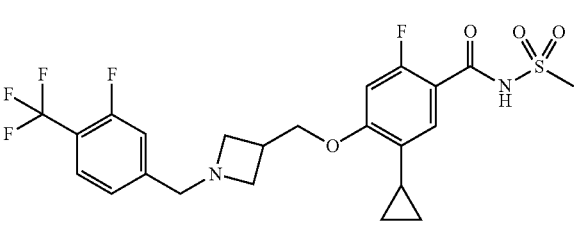
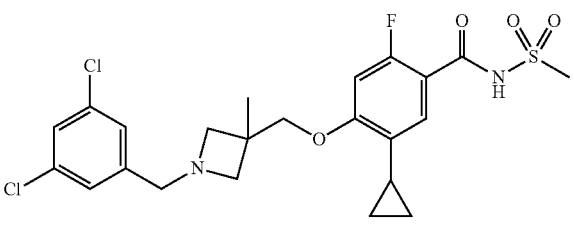
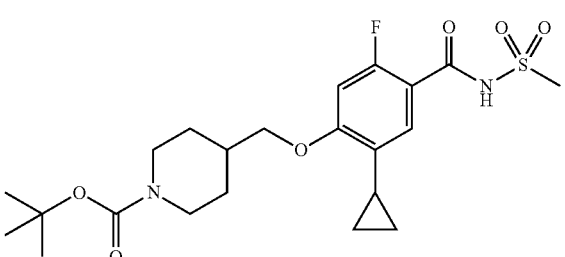
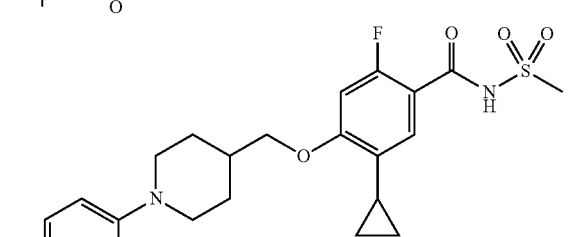
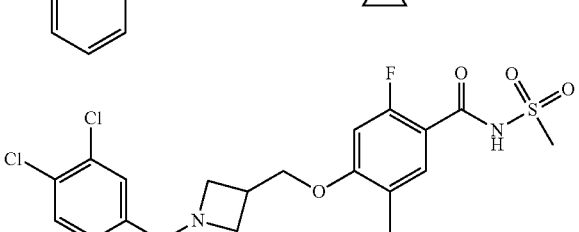
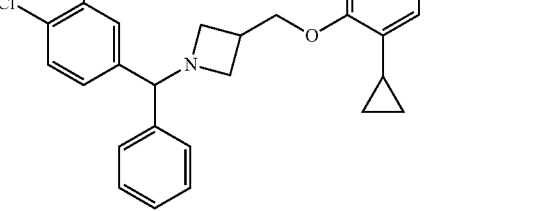

67
-continued
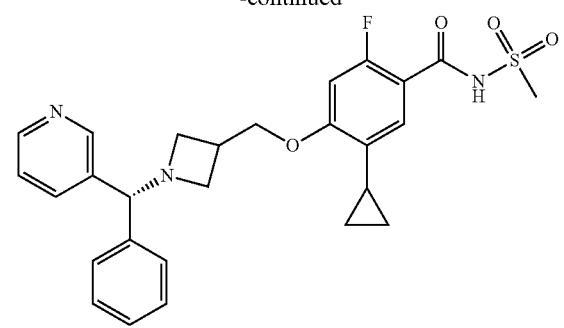
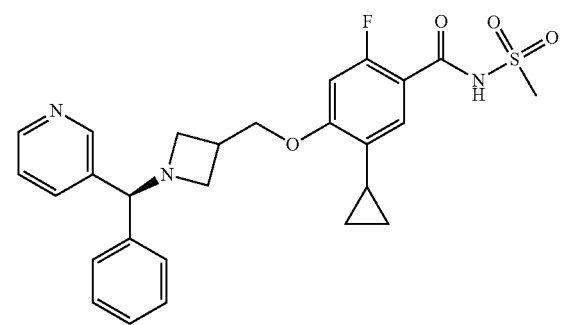
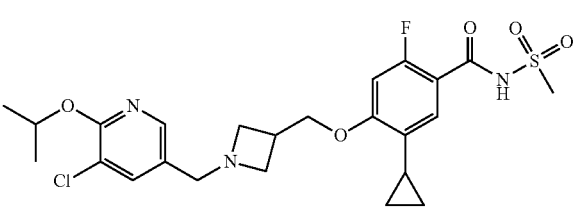
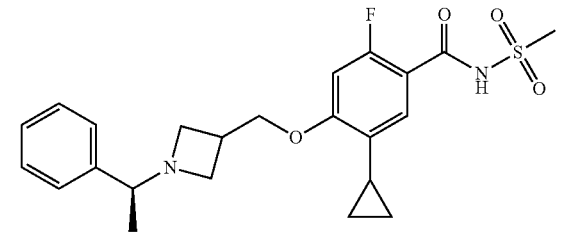
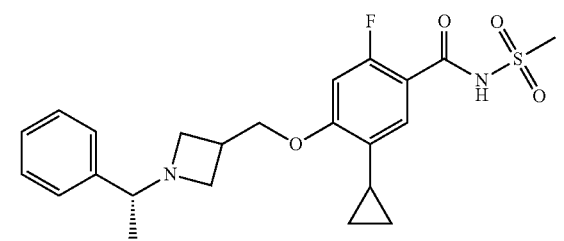
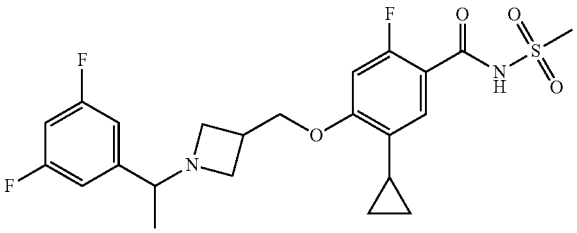
68
-continued
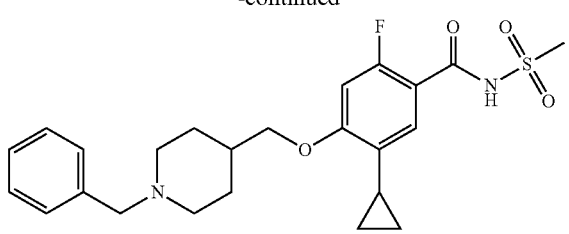
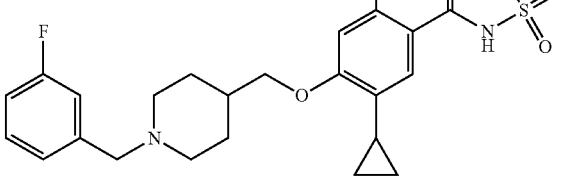
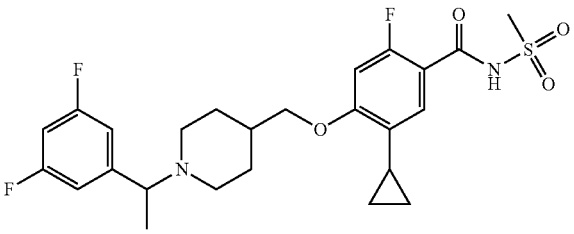
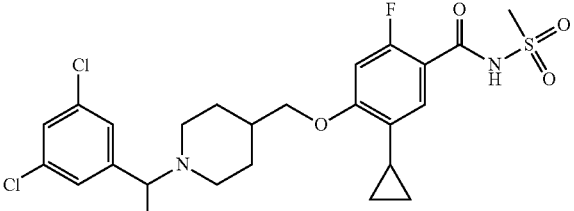
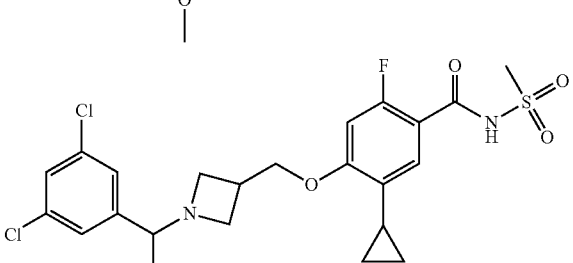
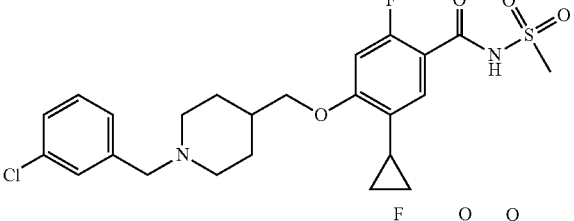
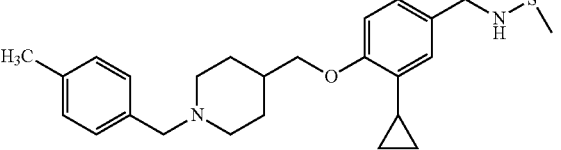

69
-continued
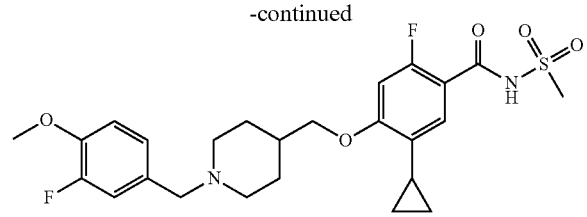
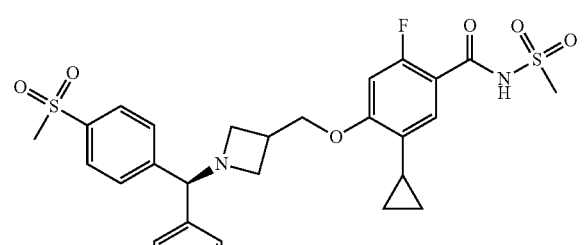
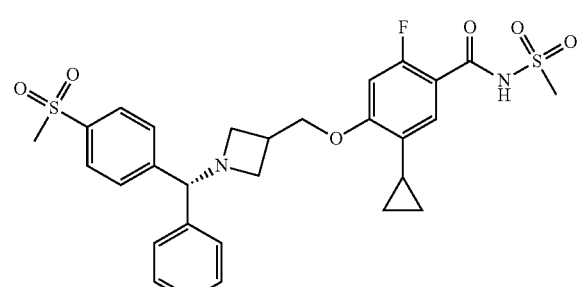
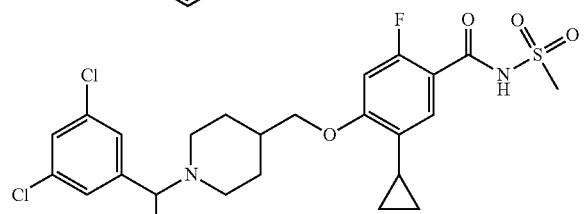
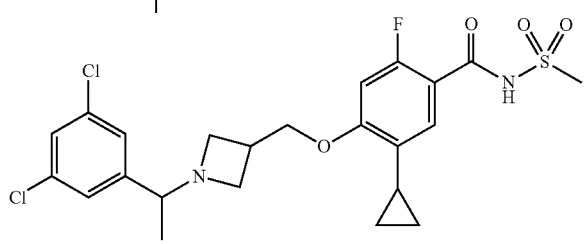
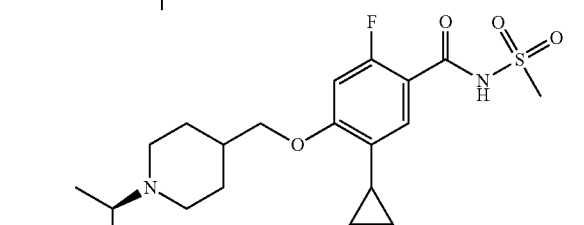
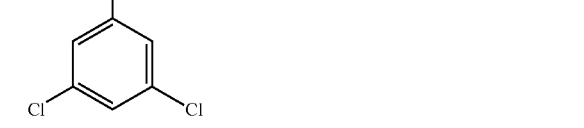
70
-continued
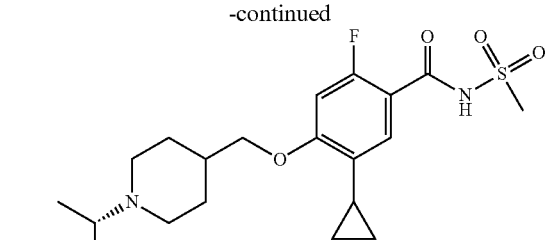
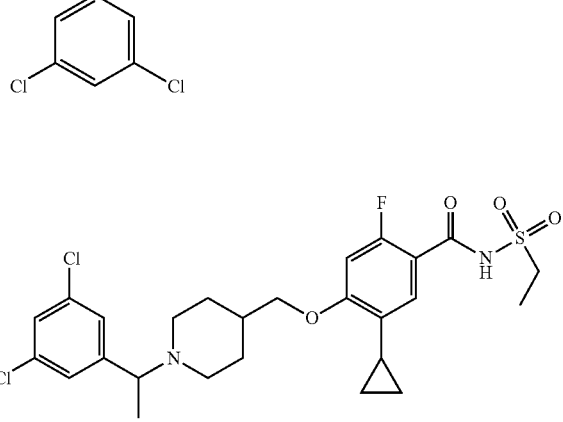
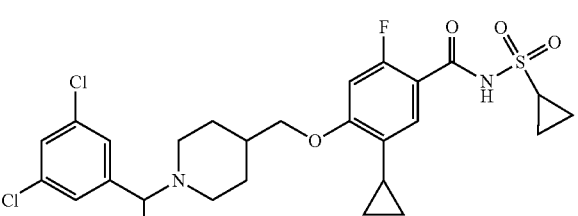
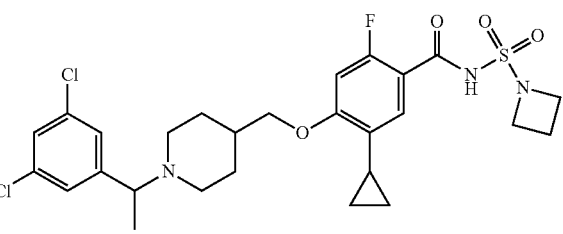
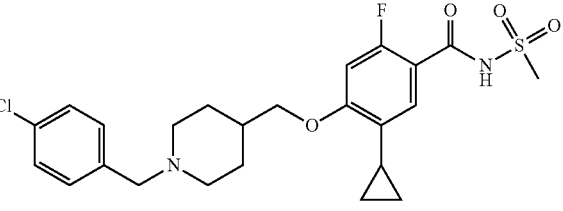
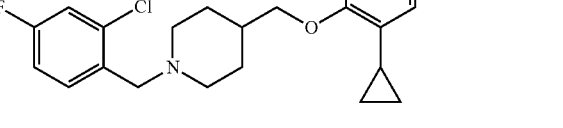

71
-continued
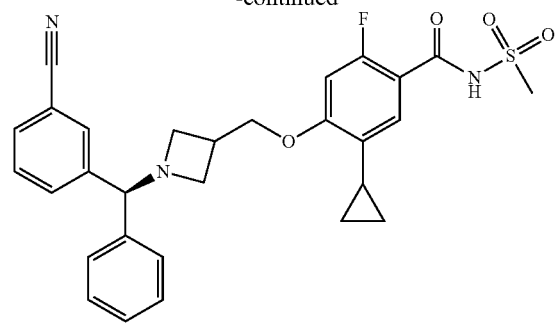
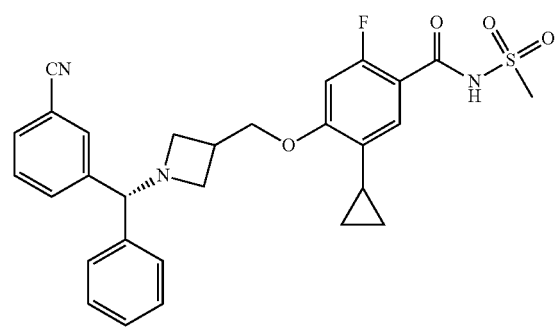
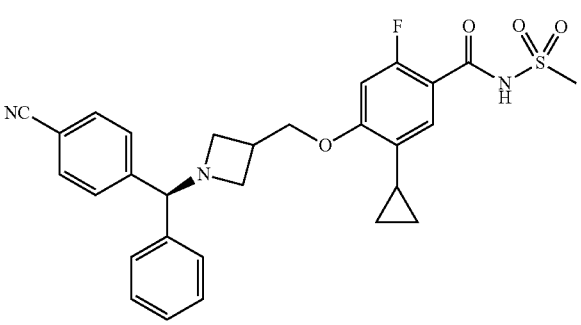
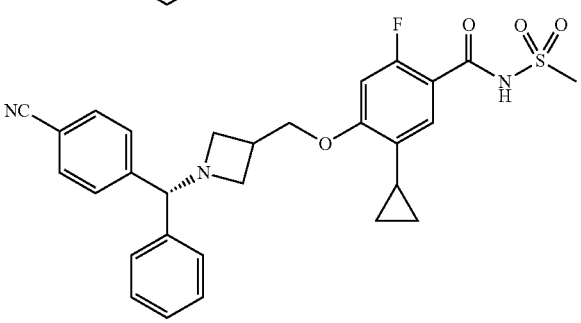
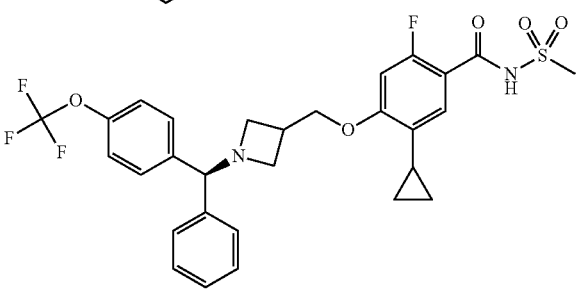
72
-continued
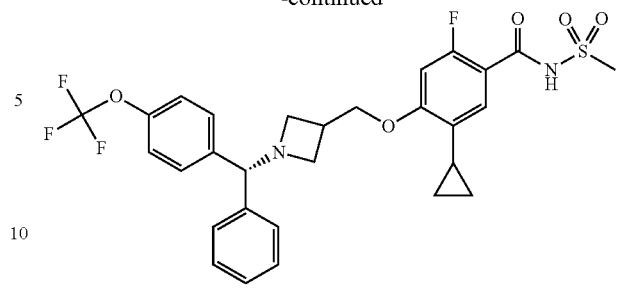
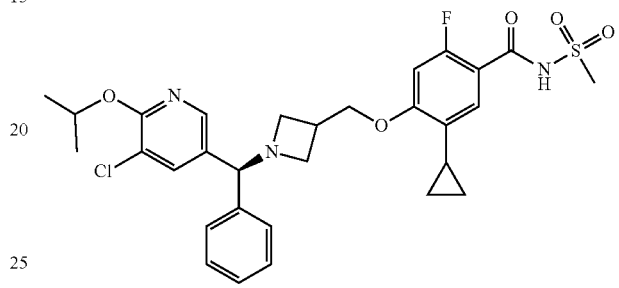
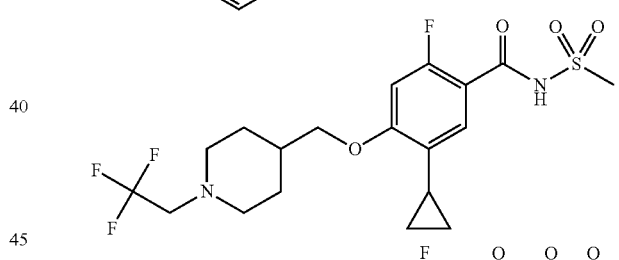
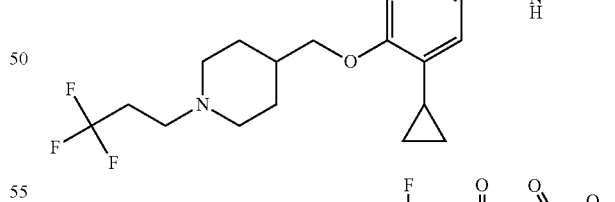
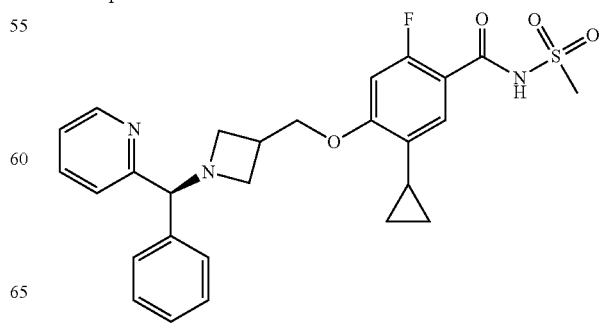

-continued
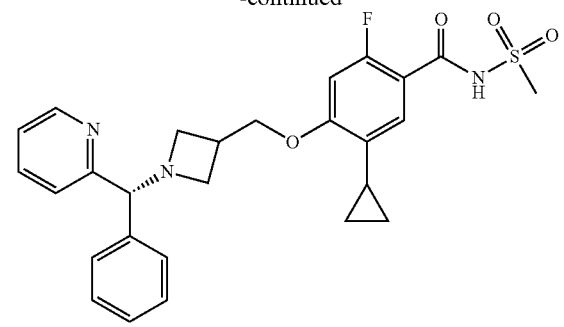
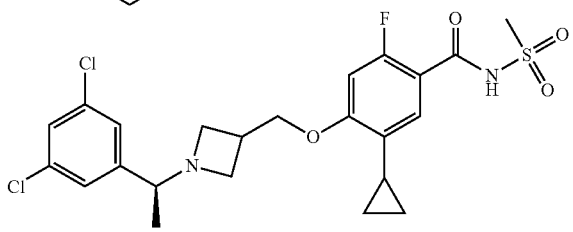

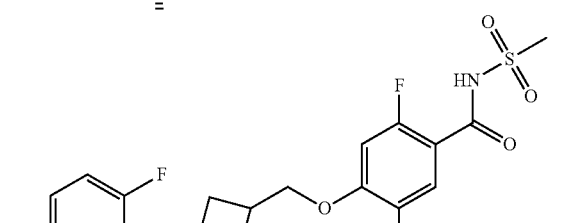
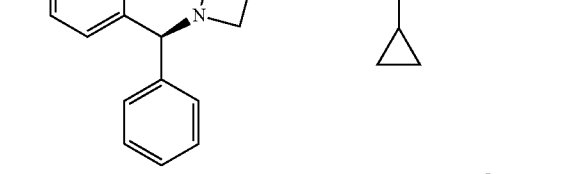
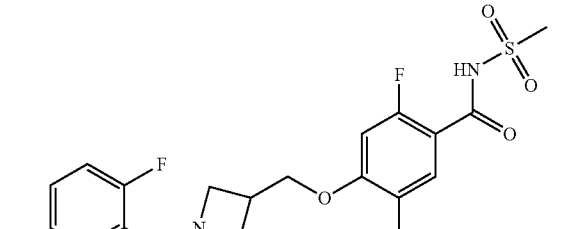
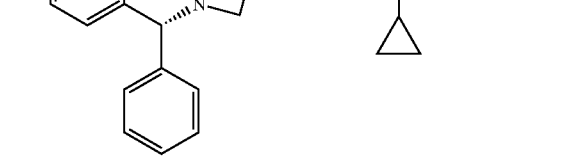
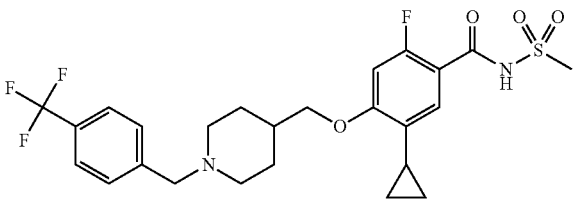
-continued
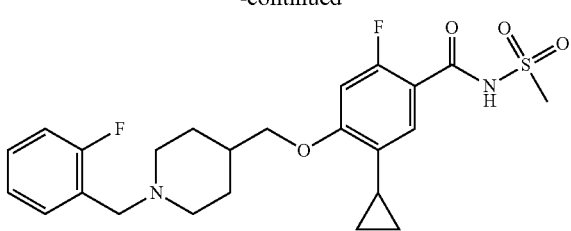
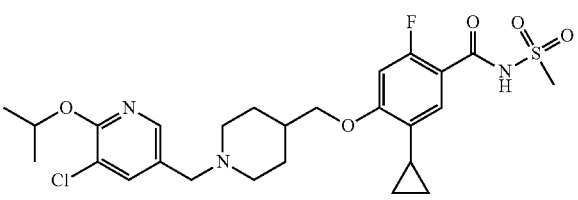
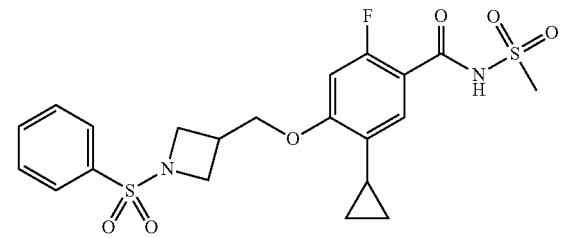
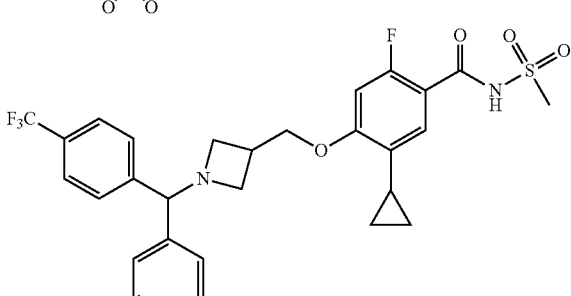
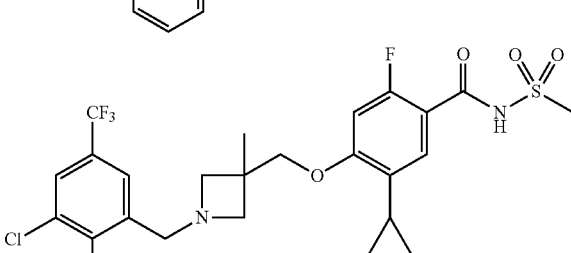
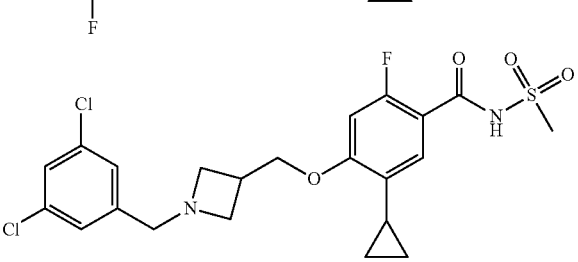
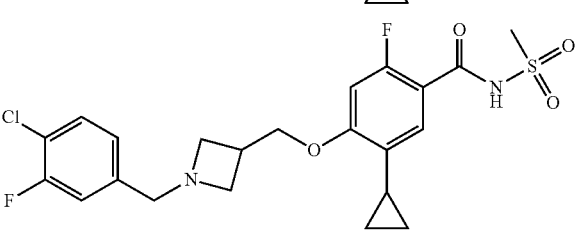

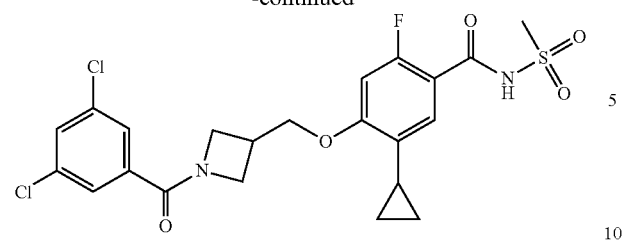

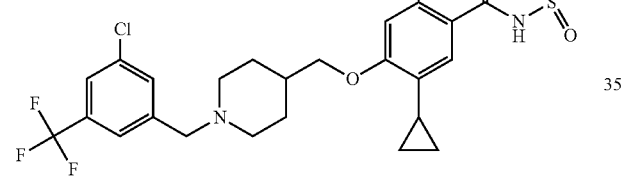
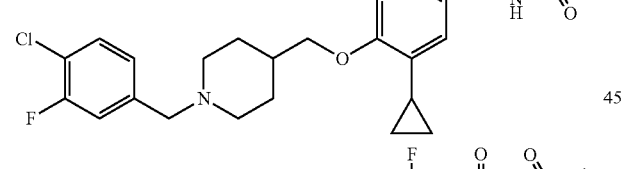
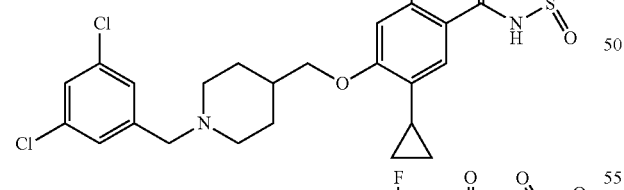
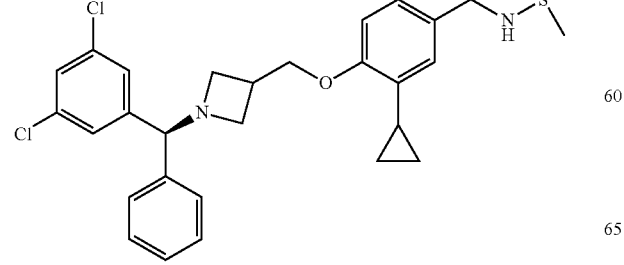
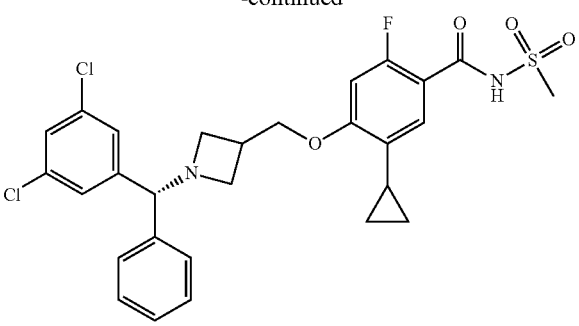
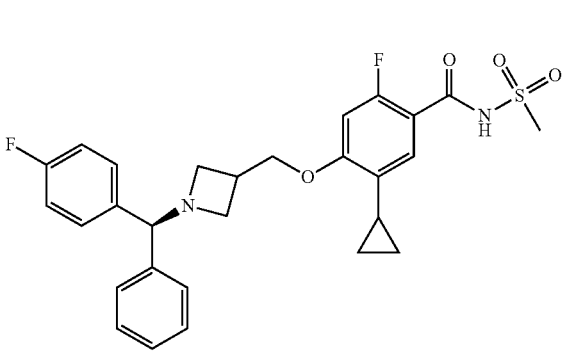
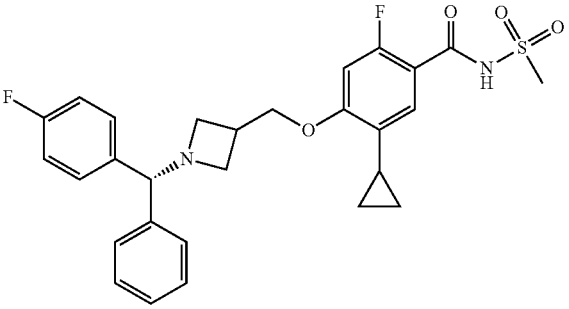
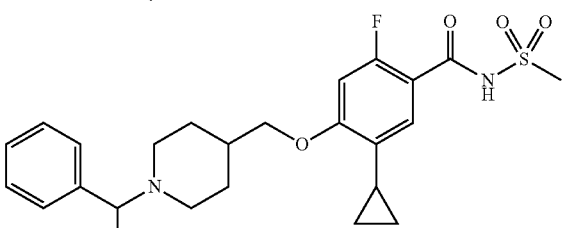
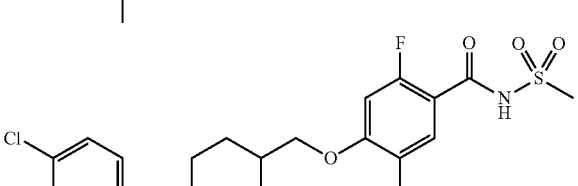
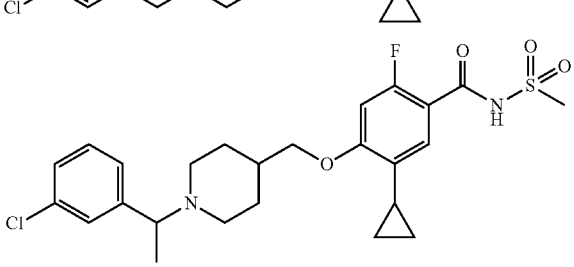

77
-continued
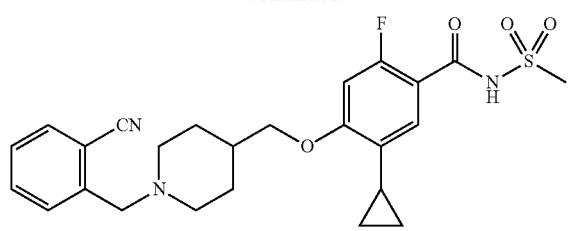
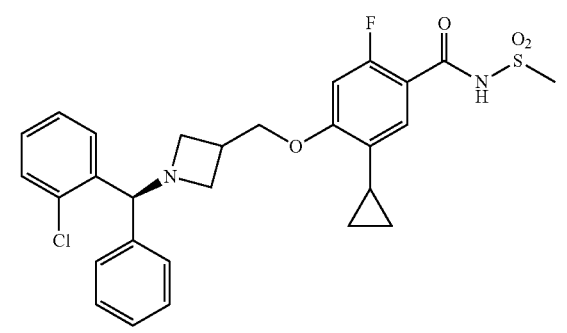
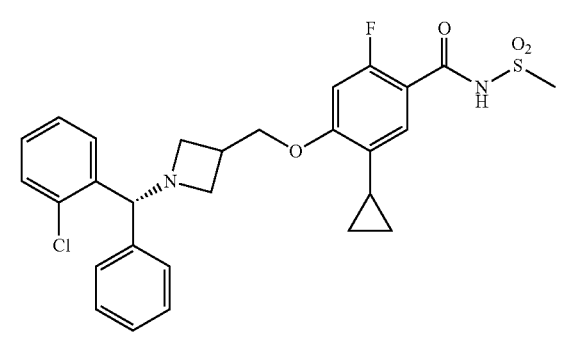
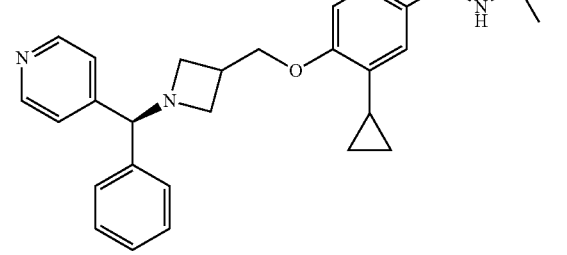
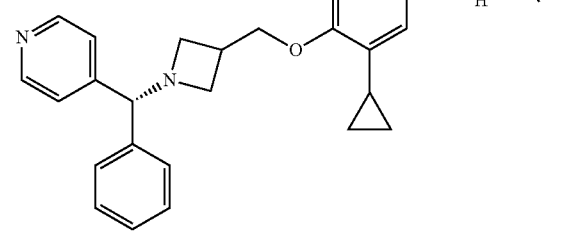
78
-continued
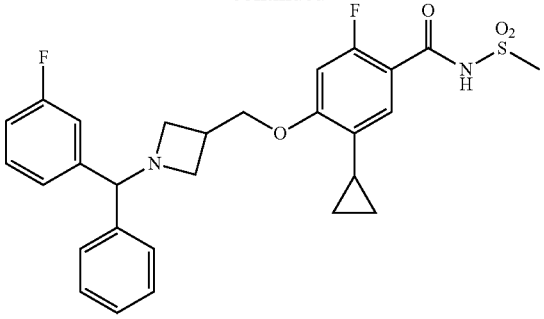
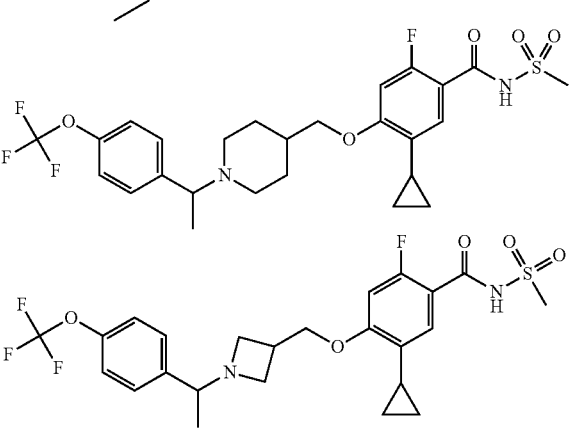
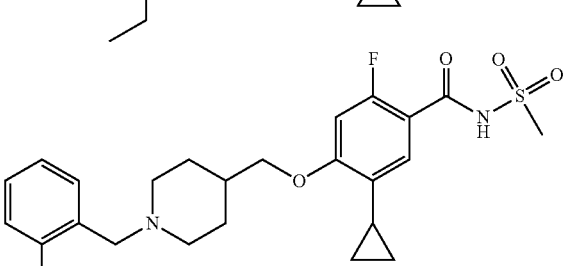
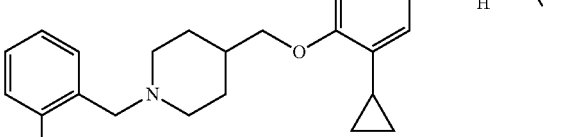
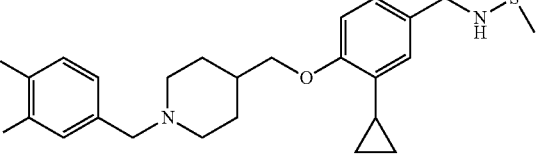

79
-continued
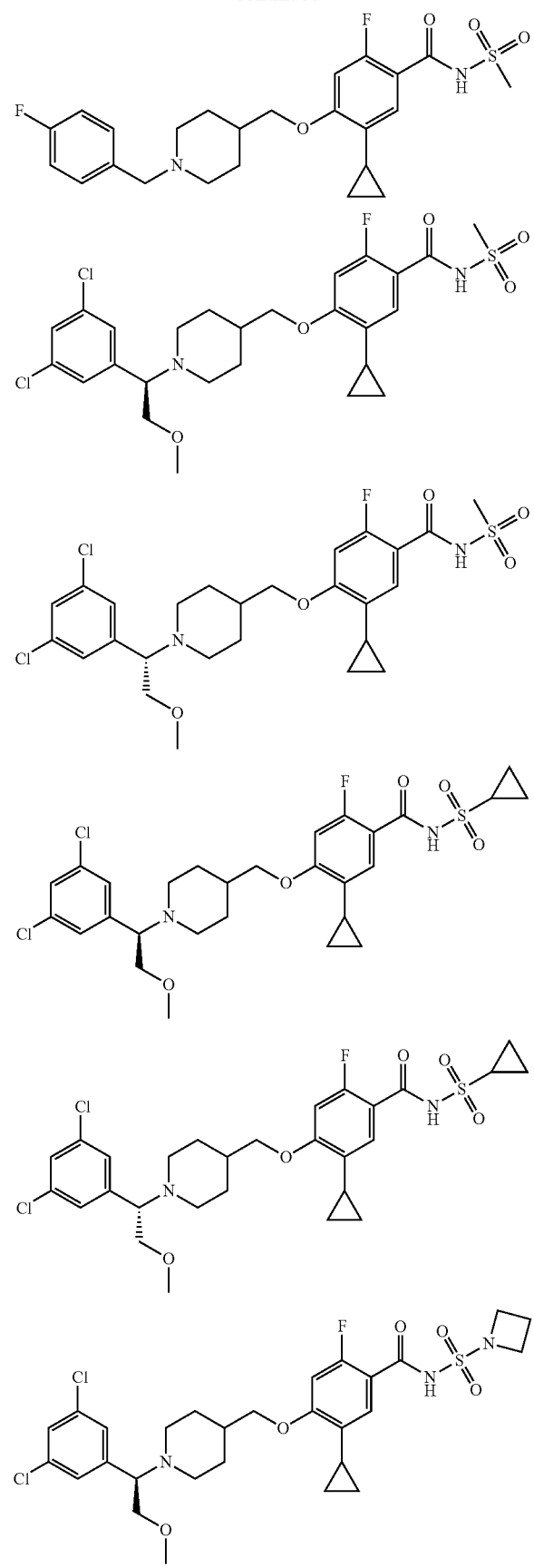
80
-continued
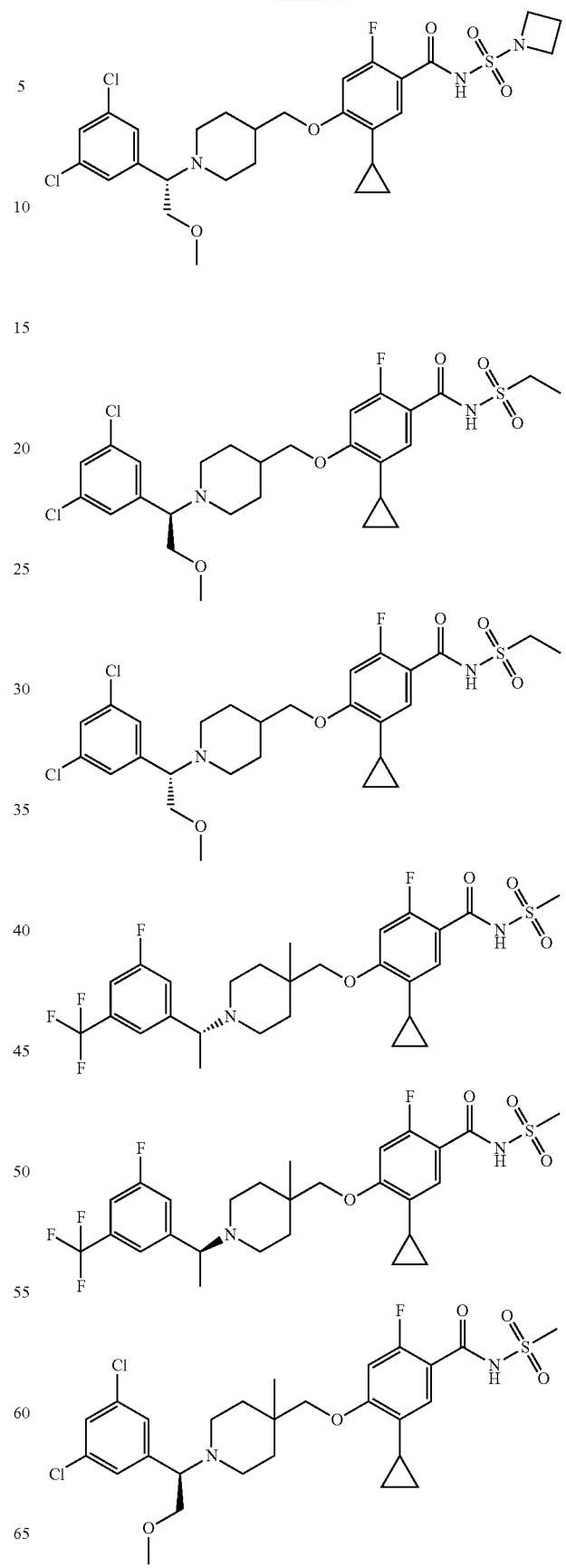

81
-continued
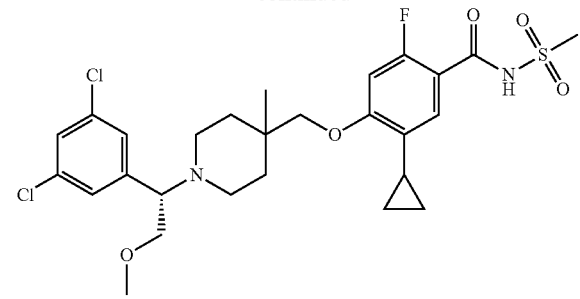
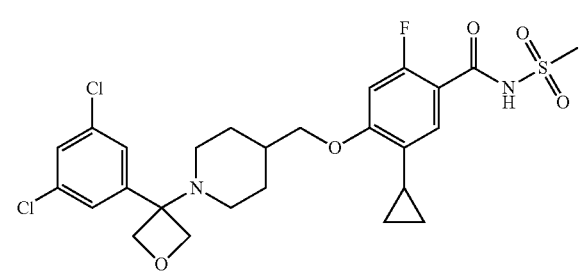
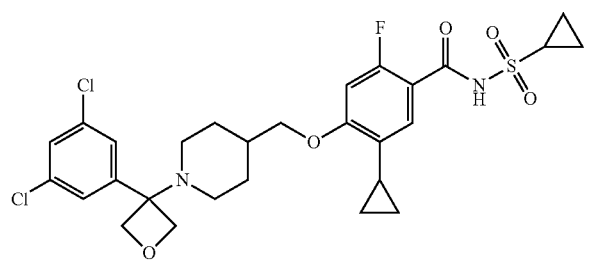
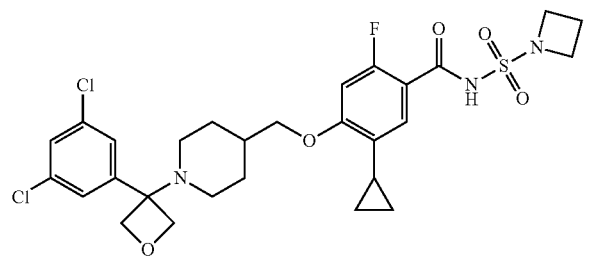
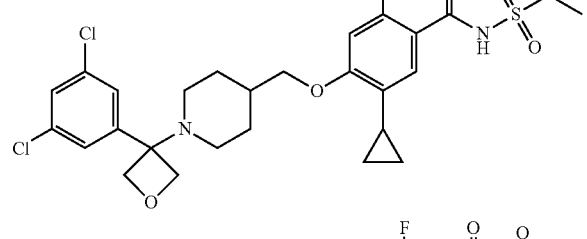
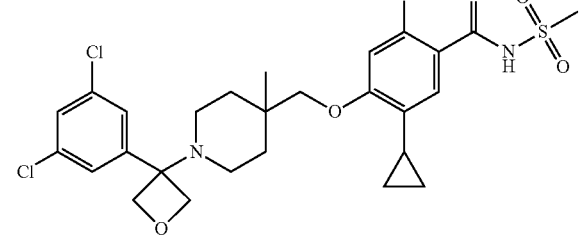
82
-continued
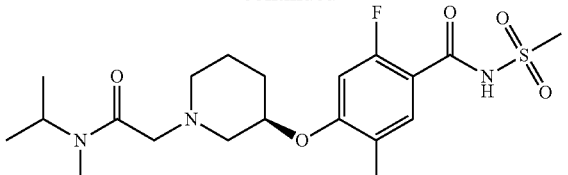
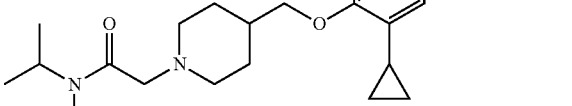
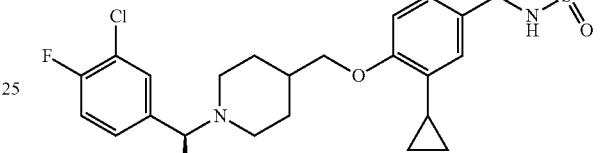
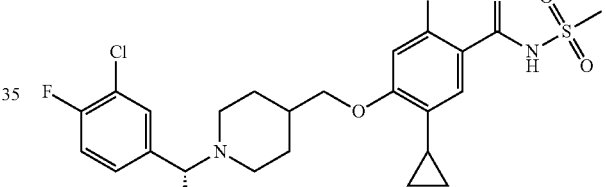
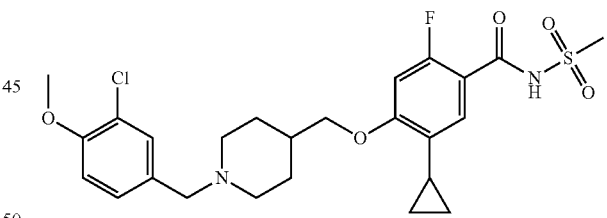
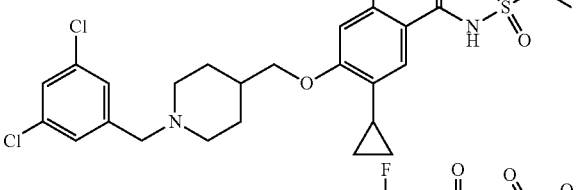
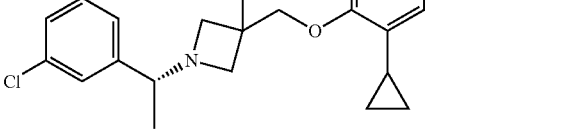

83
-continued
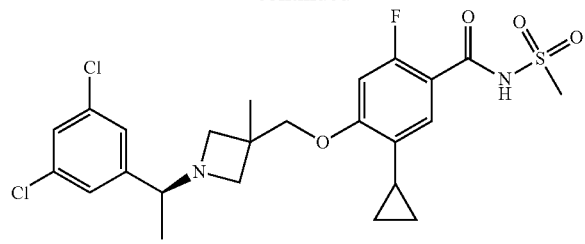
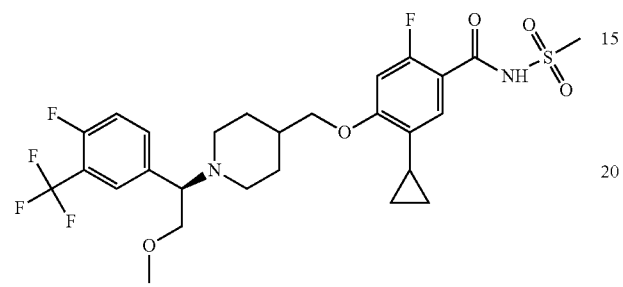
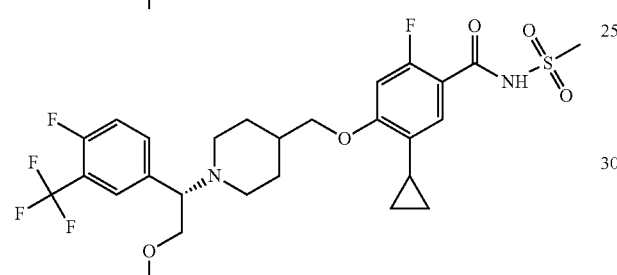
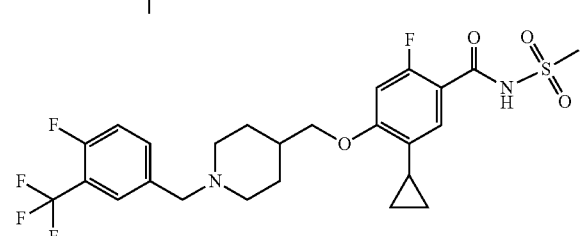
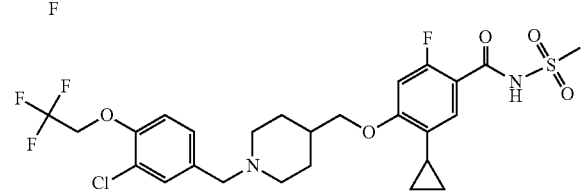
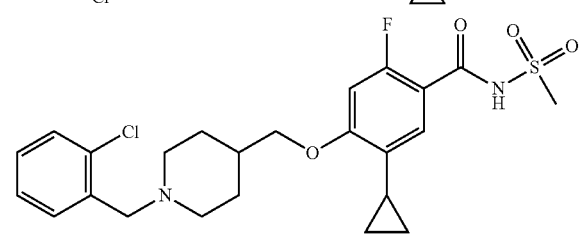
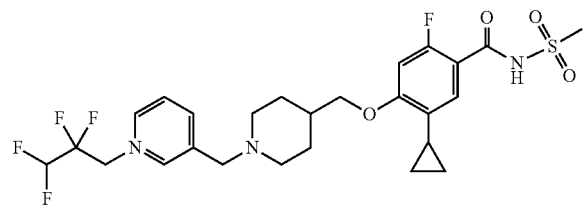
84
-continued
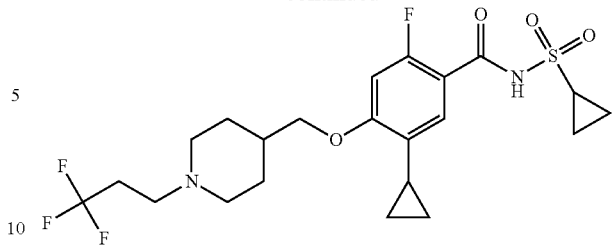
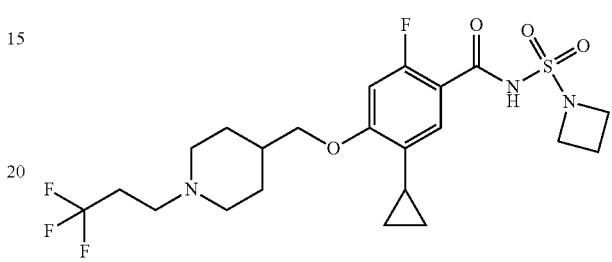
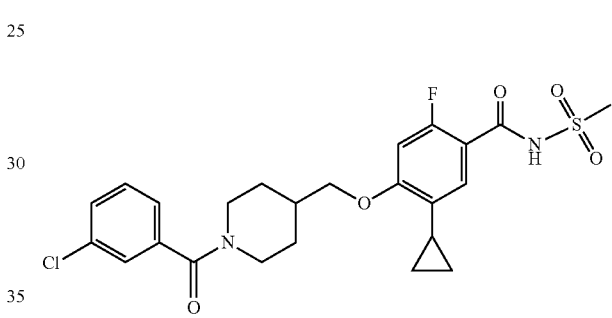
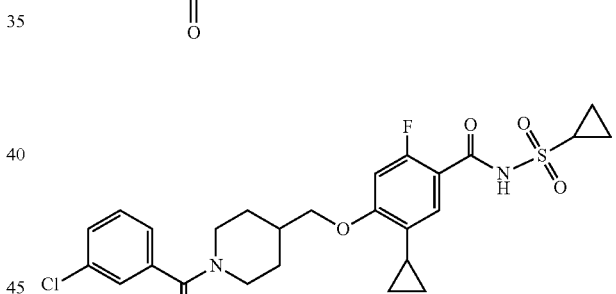
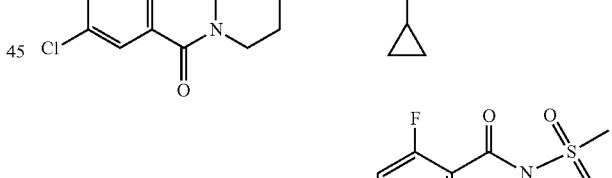
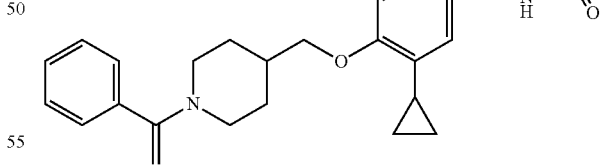
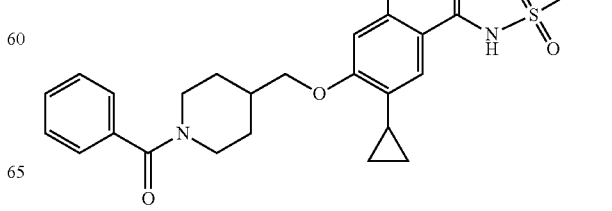

85
-continued
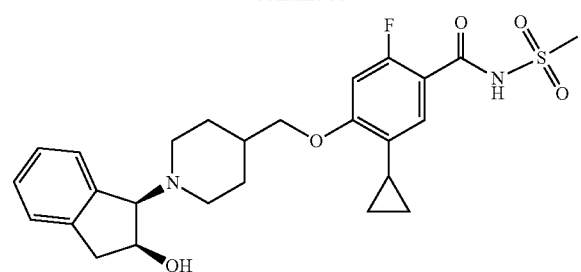
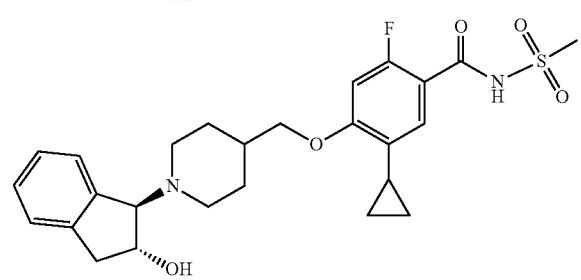
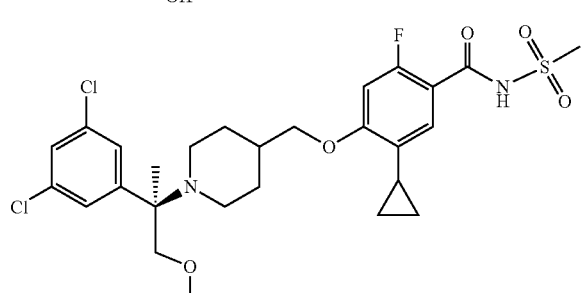
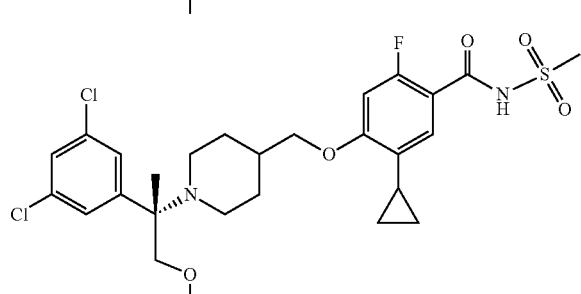
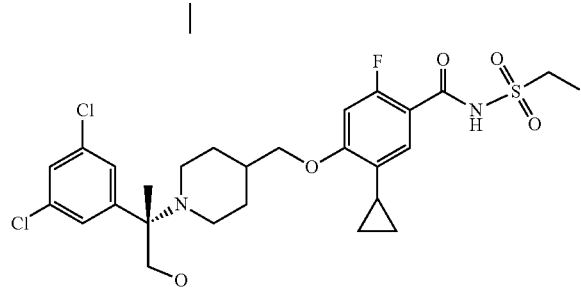
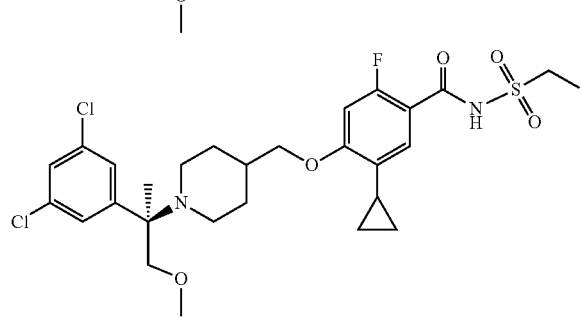
86
-continued
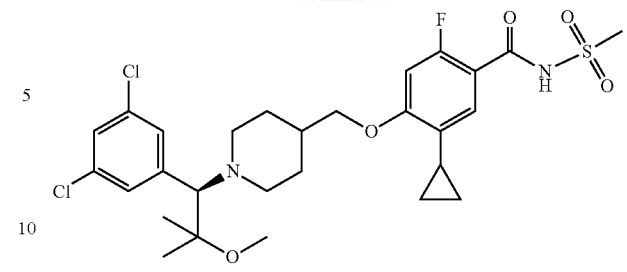
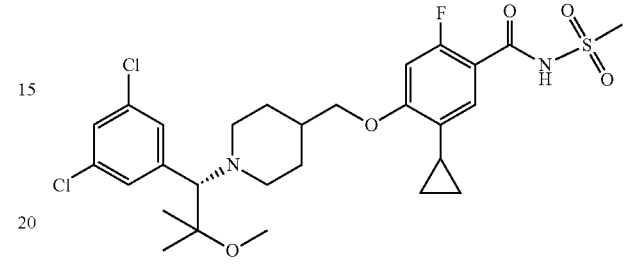
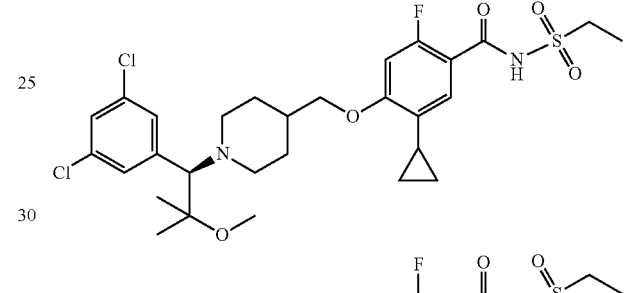
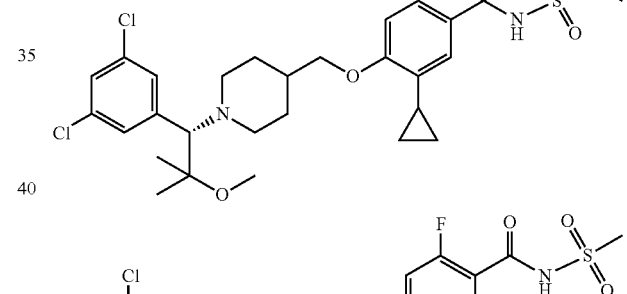
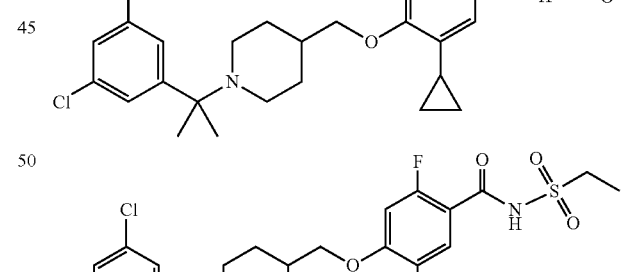
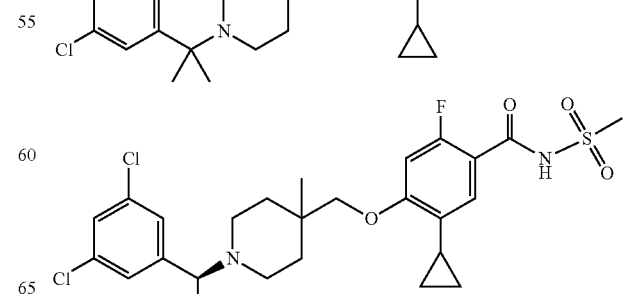

87
-continued
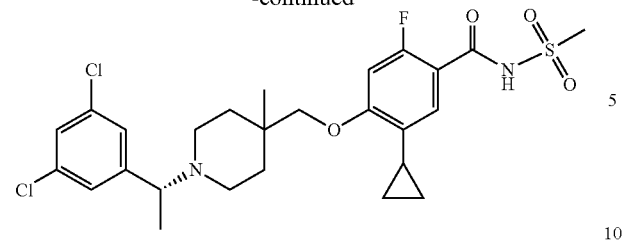
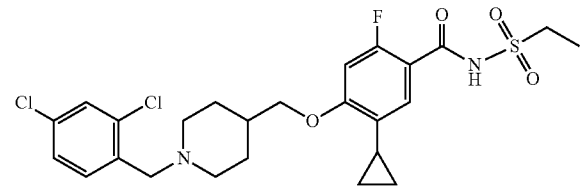
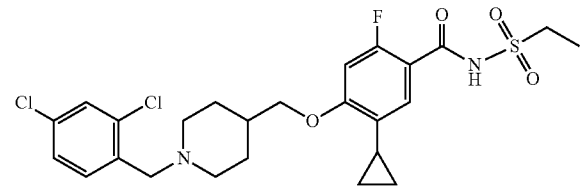
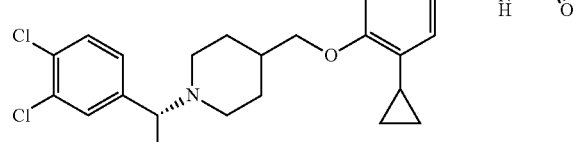
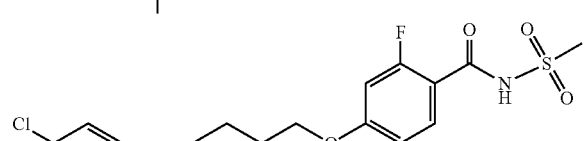
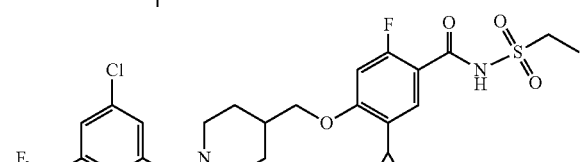
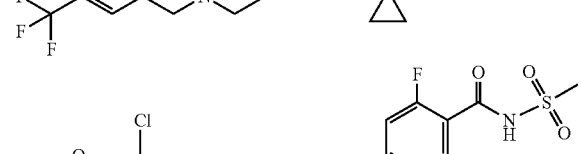
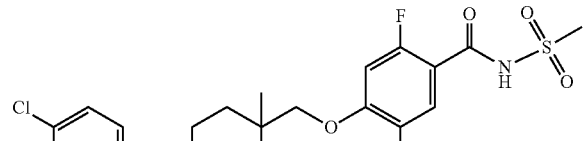
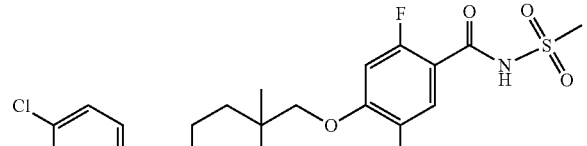
88
-continued
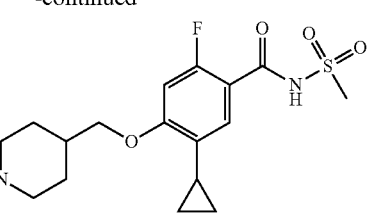
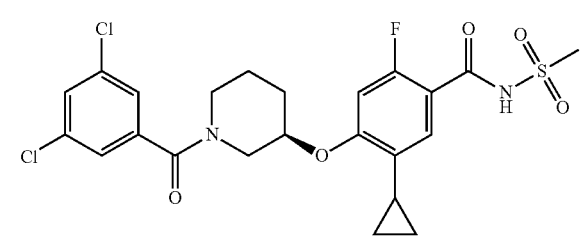
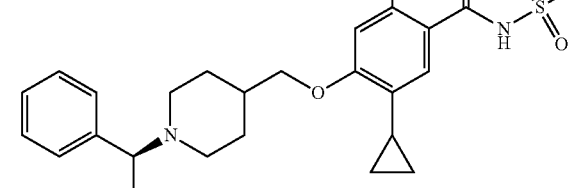
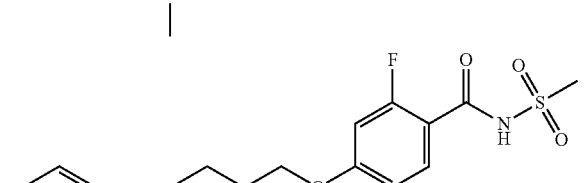
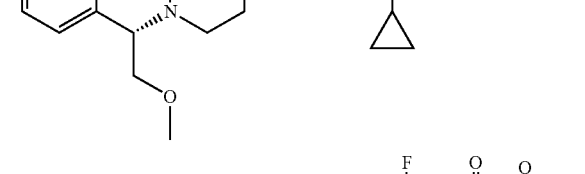
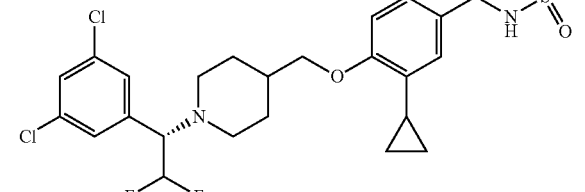
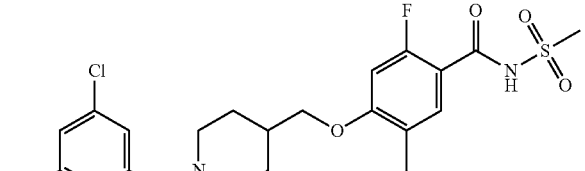

89
-continued
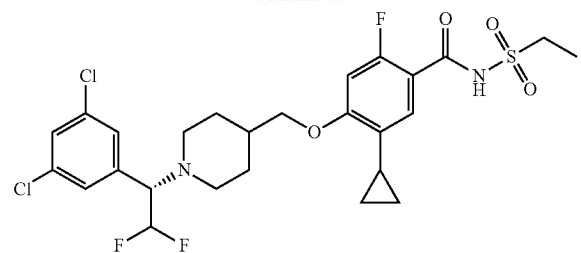
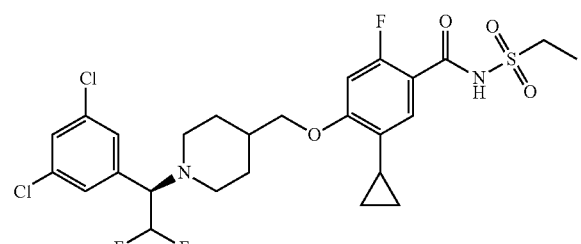
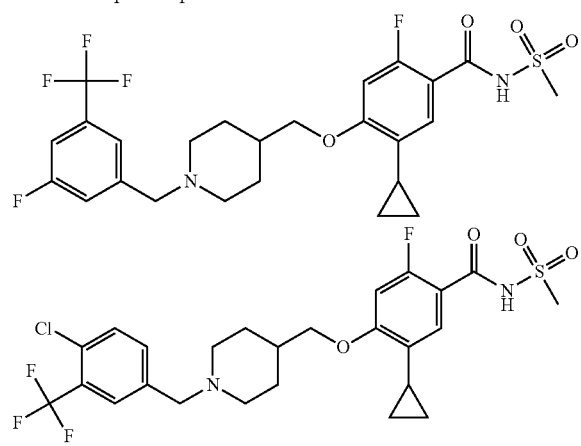
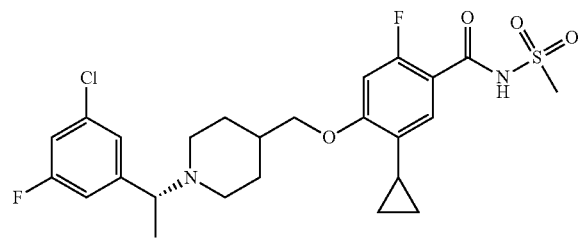
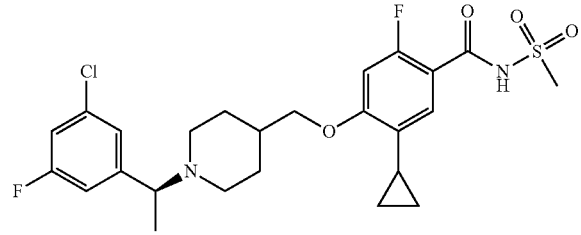
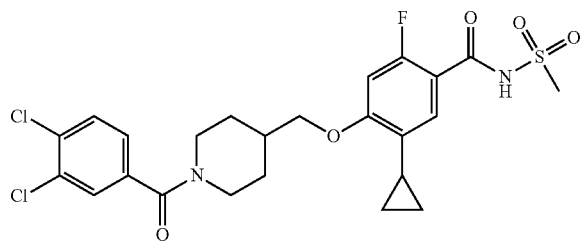
90
-continued
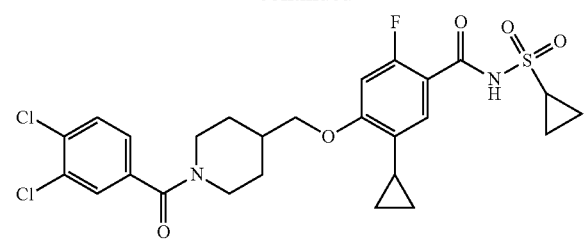
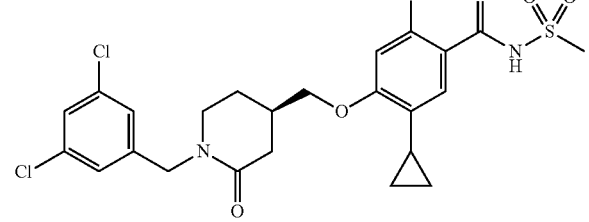
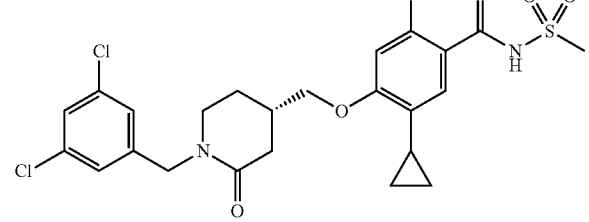
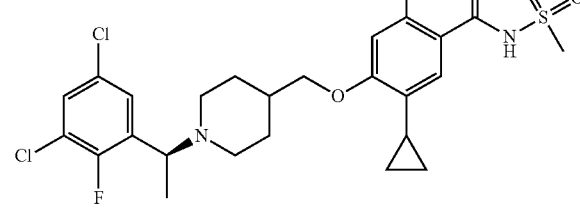
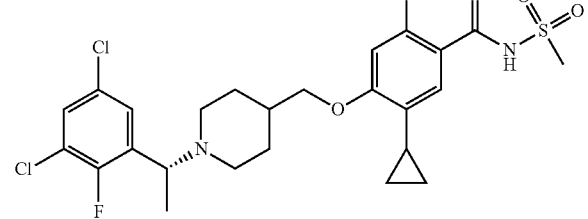
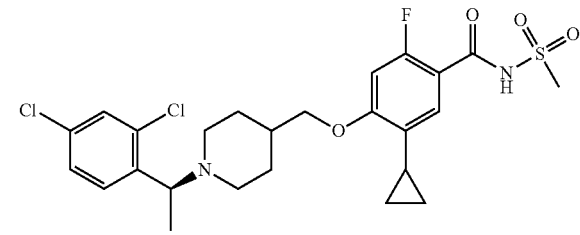
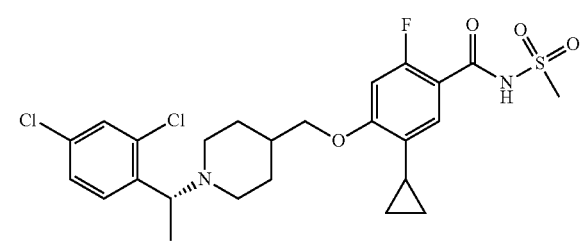

91
-continued
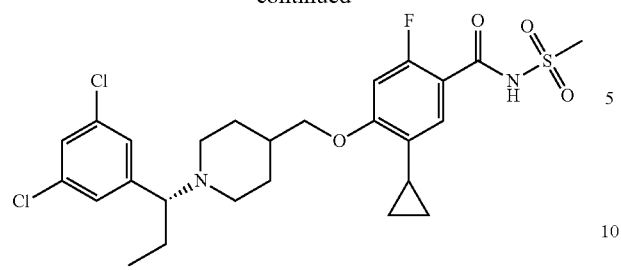
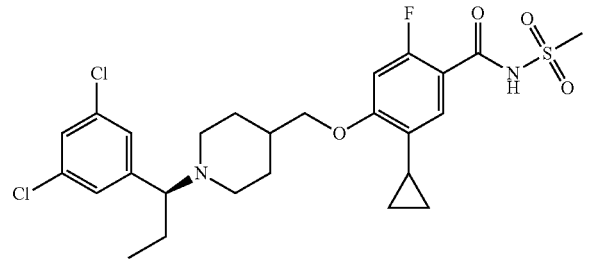
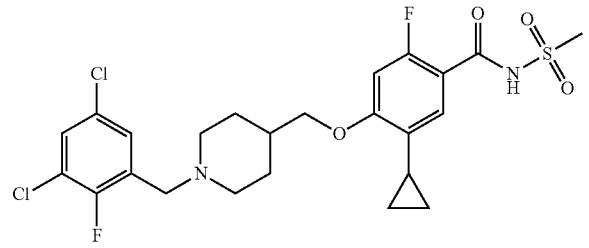
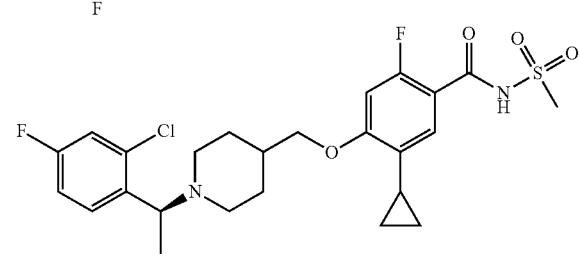
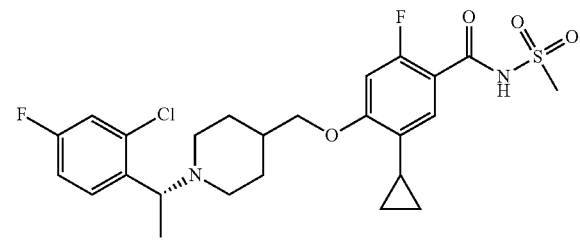
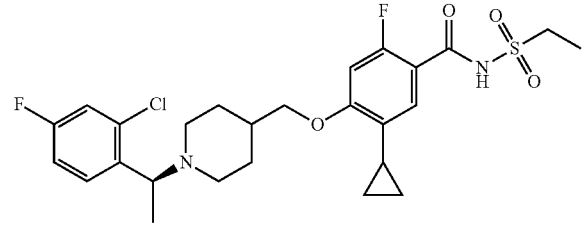
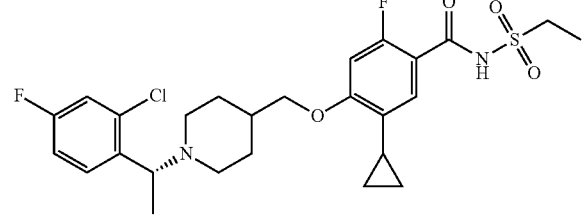
92
-continued
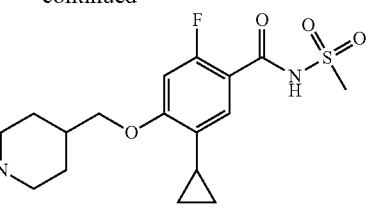
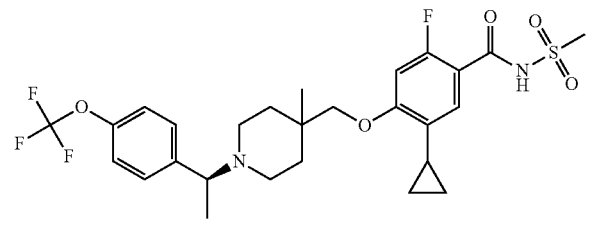
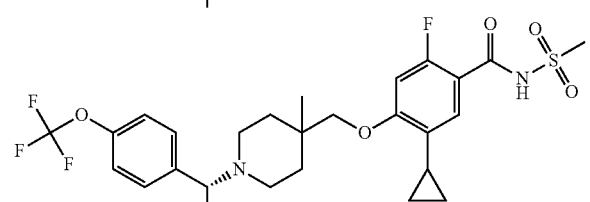
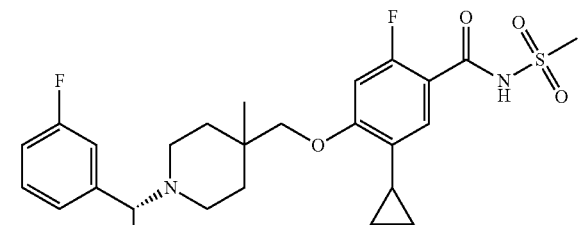
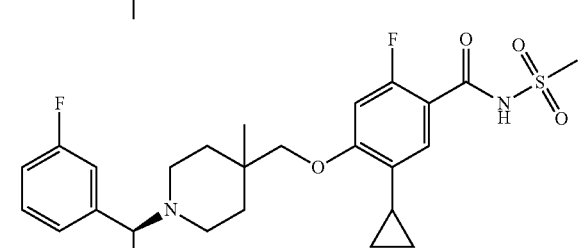
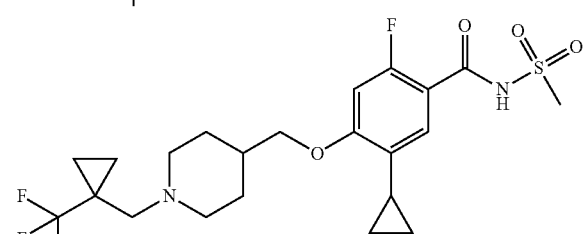
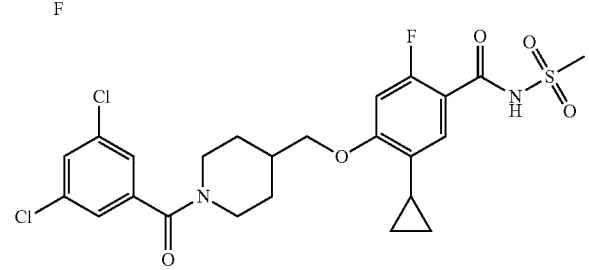

-continued
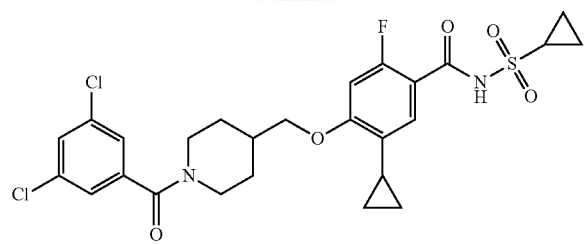
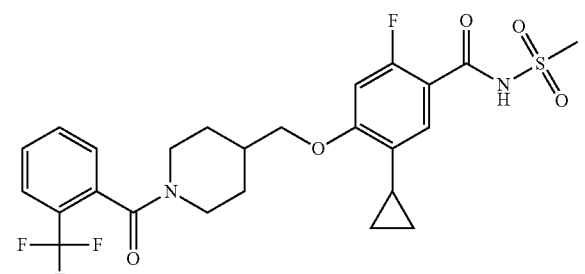
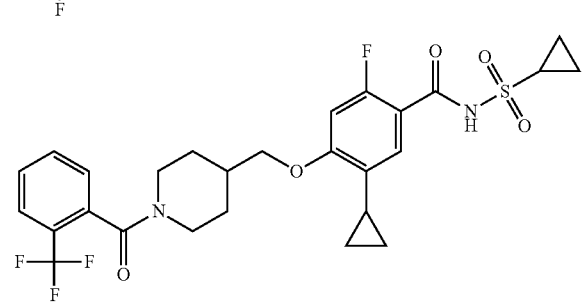
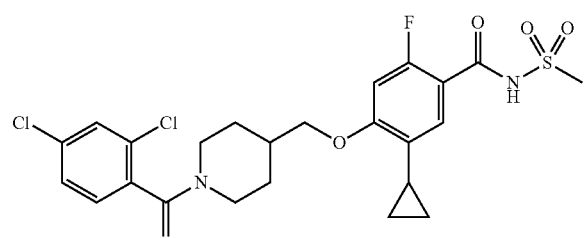
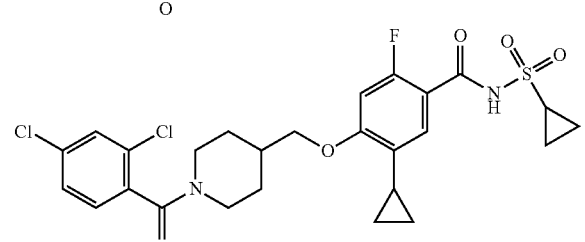
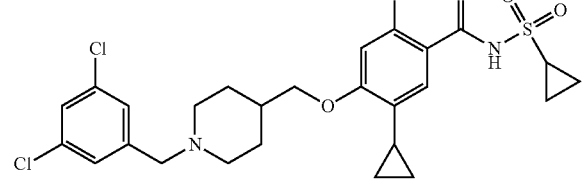
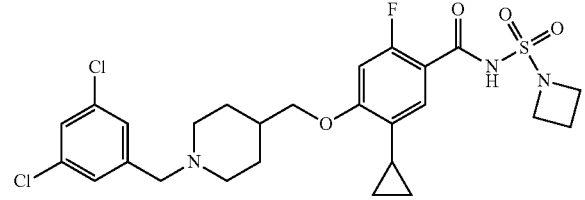
-continued
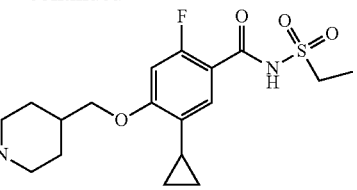
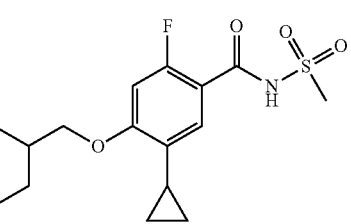
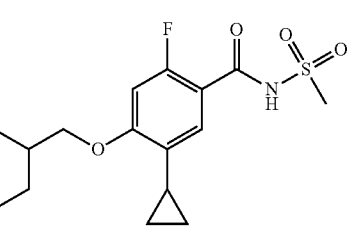
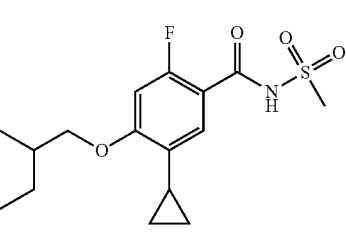
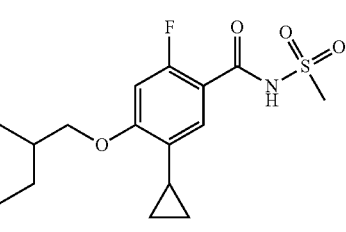
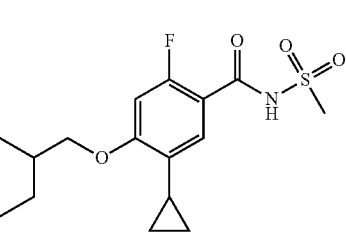

95
-continued
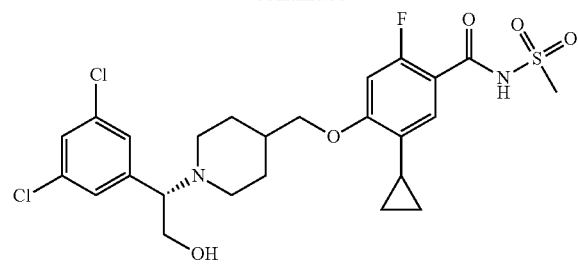
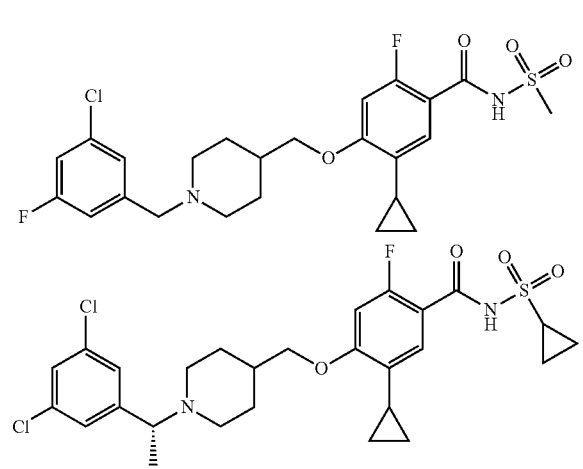
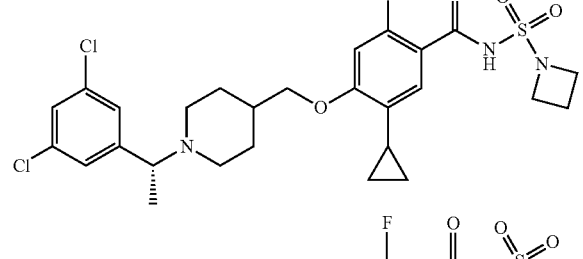
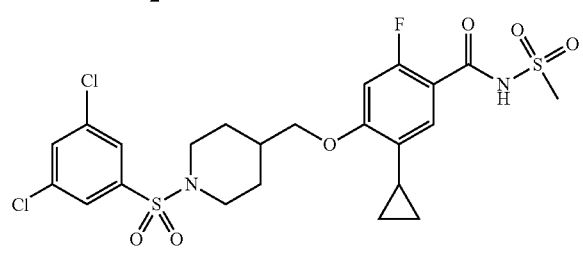
96
-continued
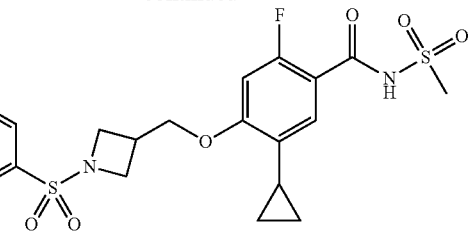
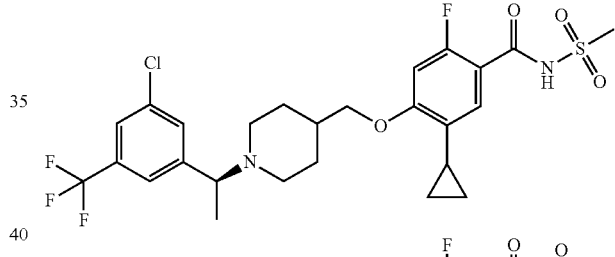
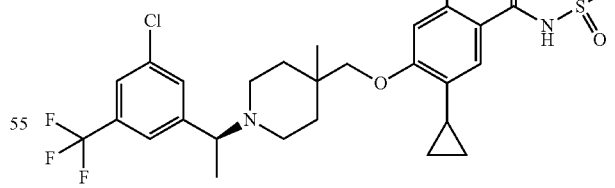
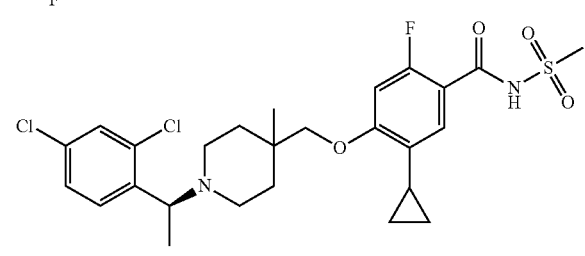

97
-continued
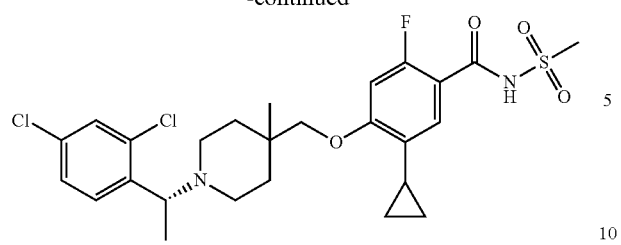
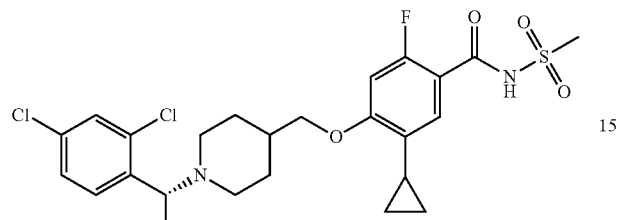
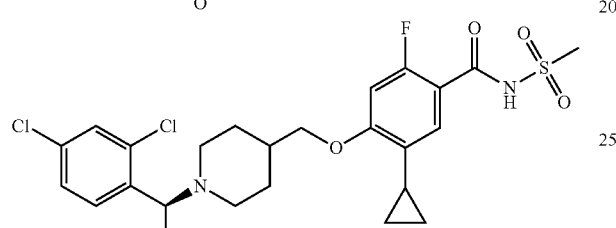
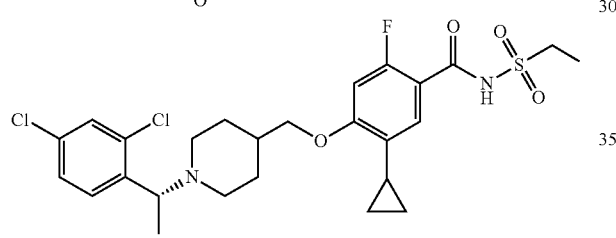
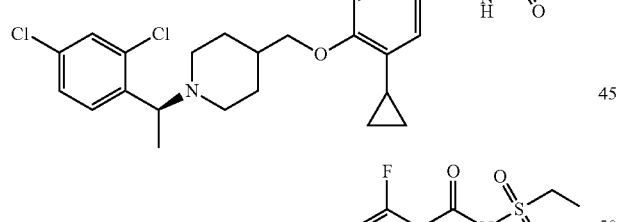
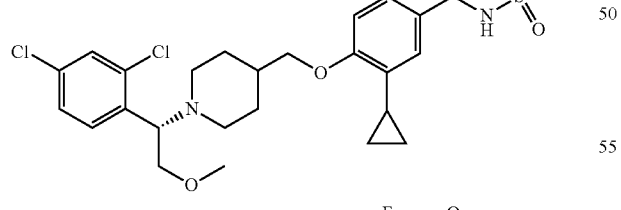
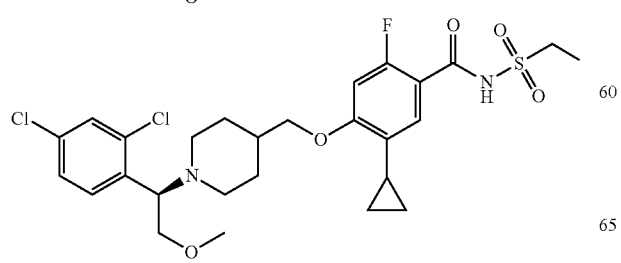
98
-continued
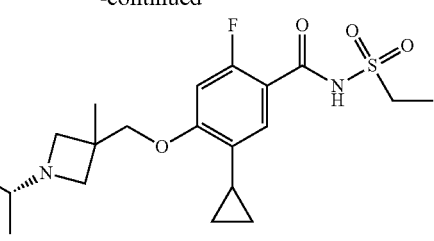
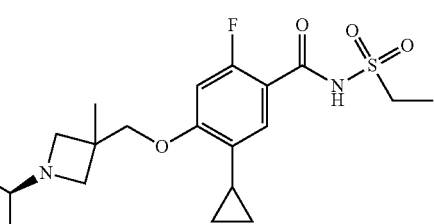
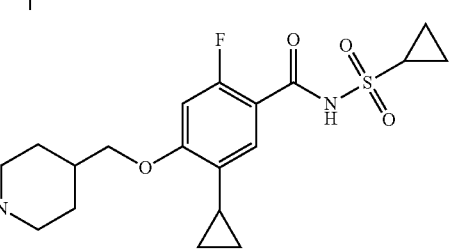
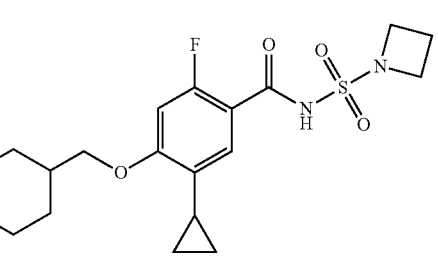
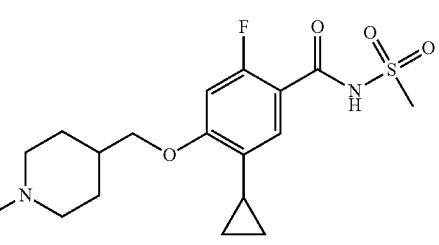
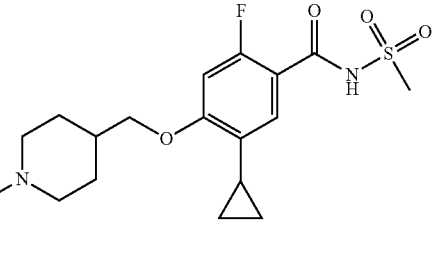

99
-continued
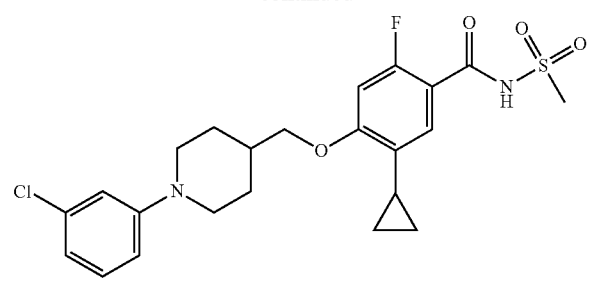
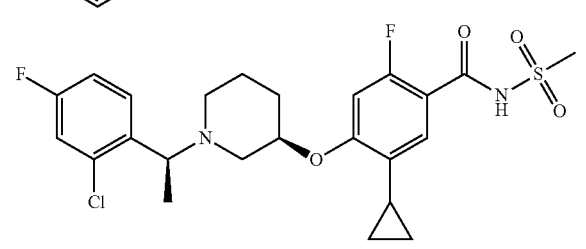
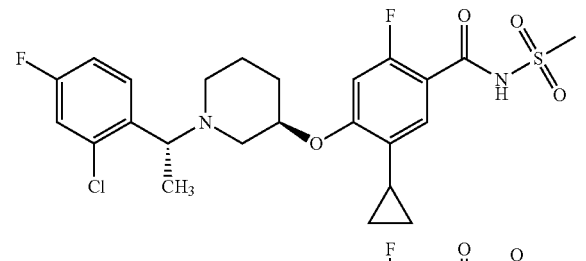
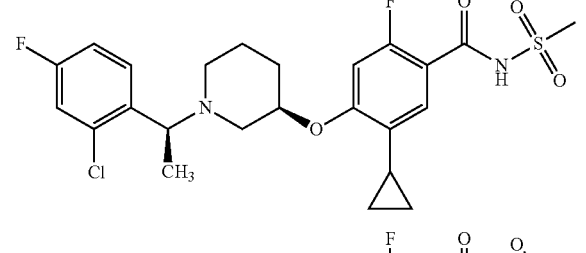
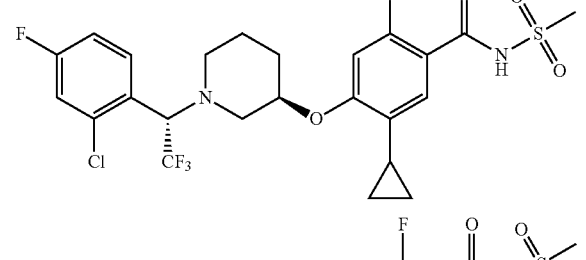
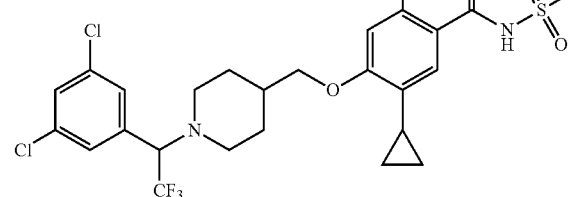
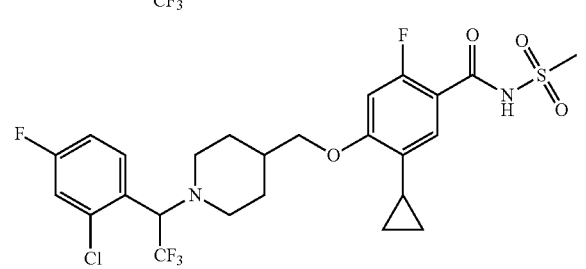
100
-continued
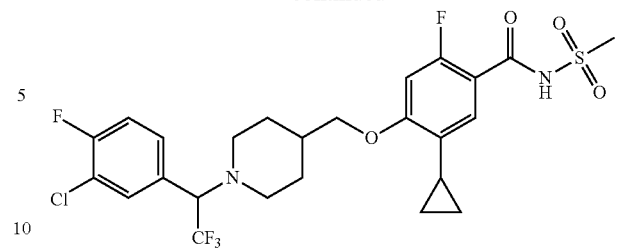
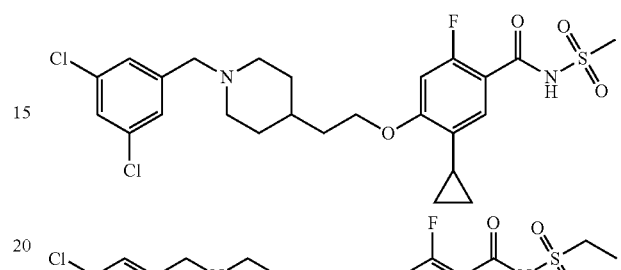
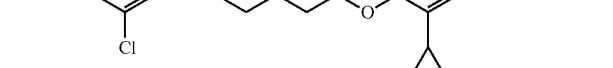
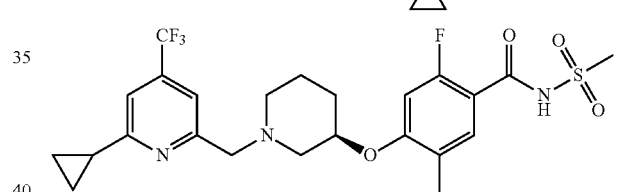
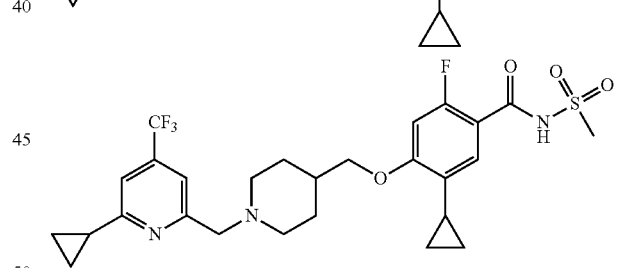
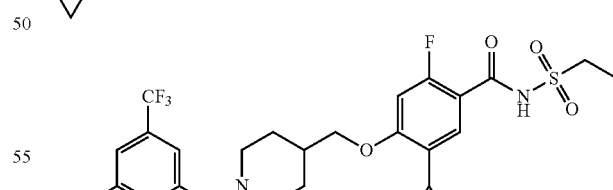
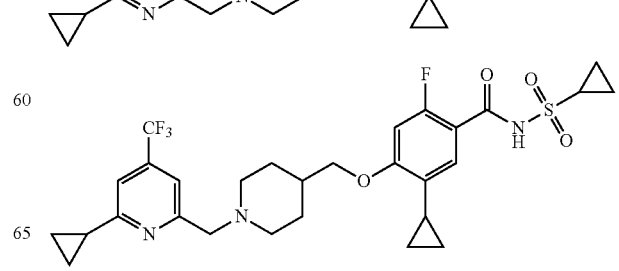

101
-continued
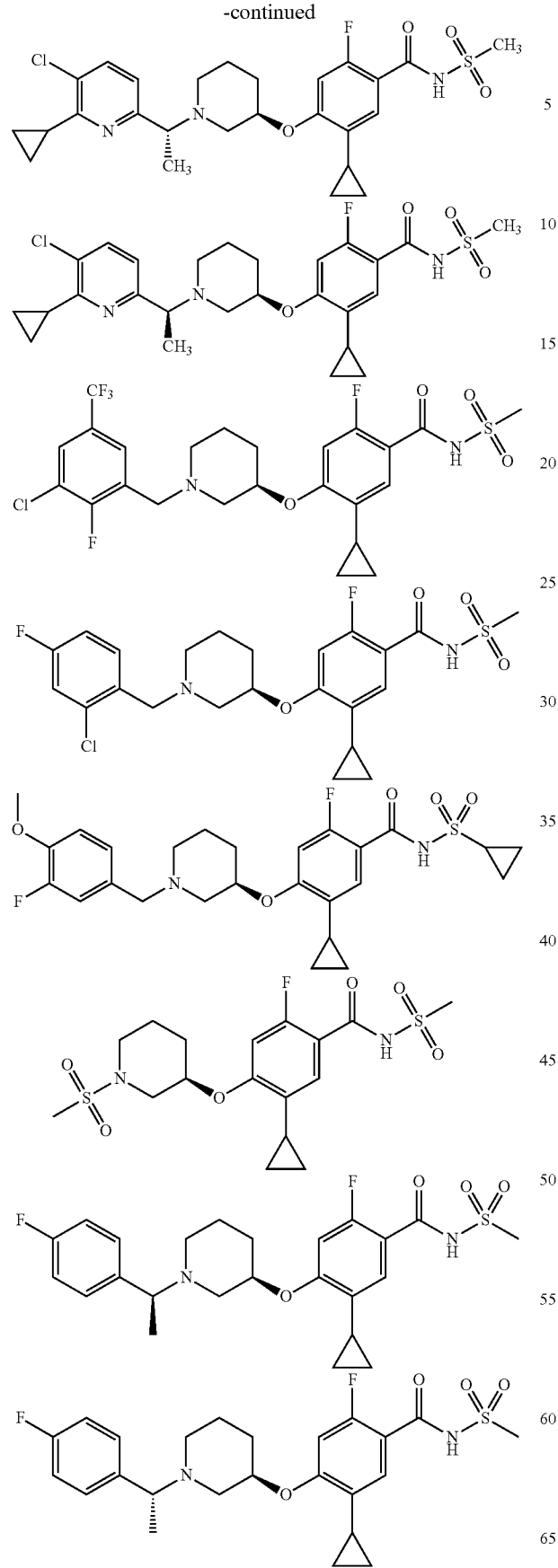
102
-continued
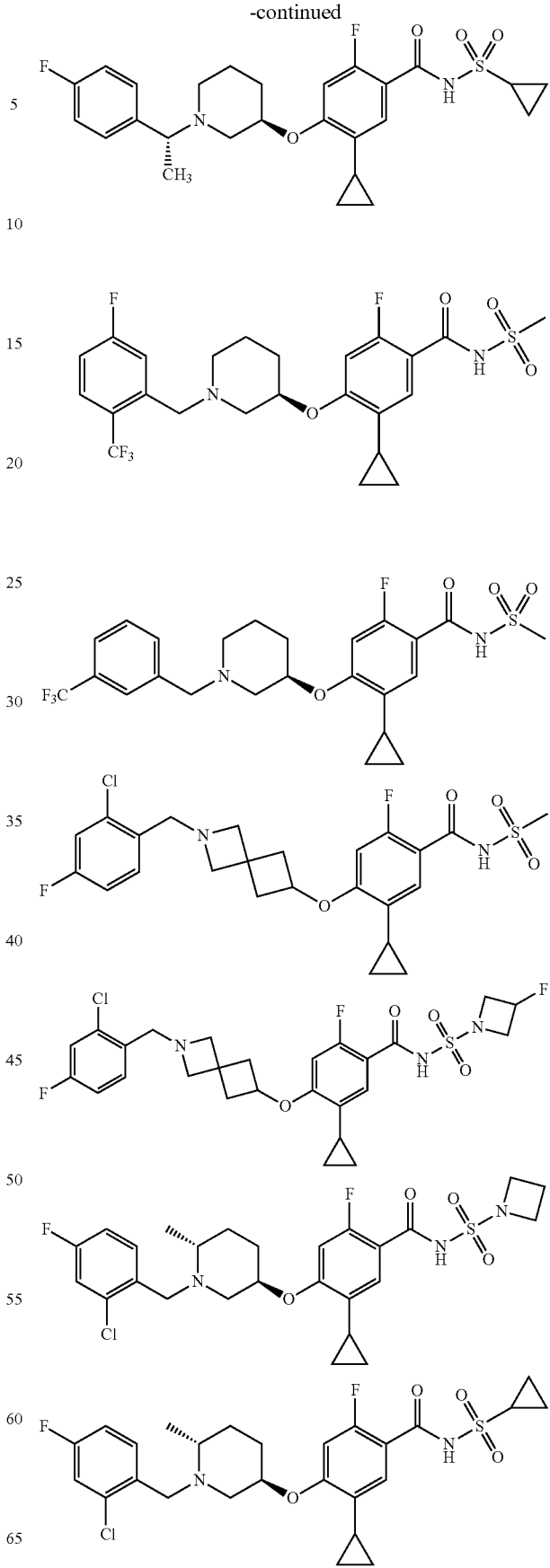

103
-continued
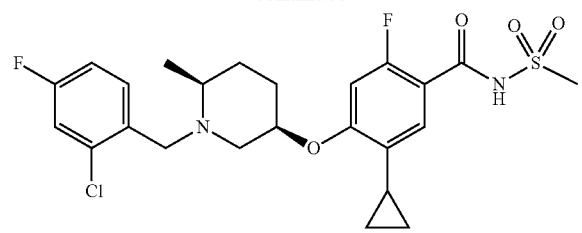
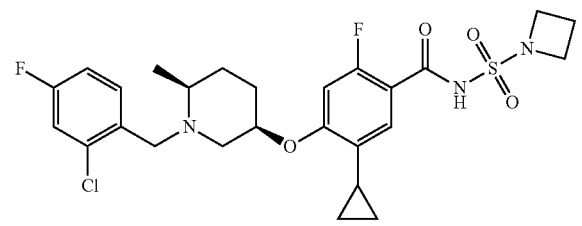
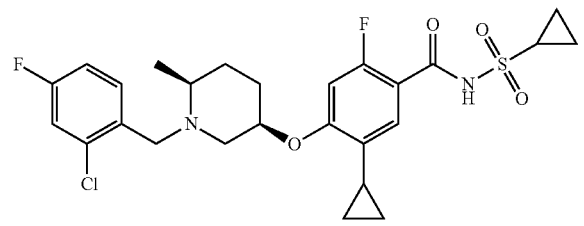
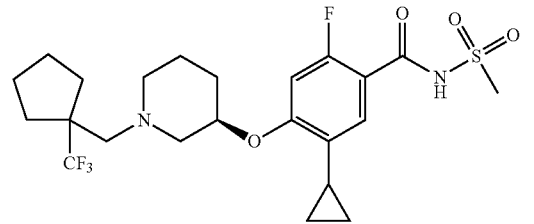
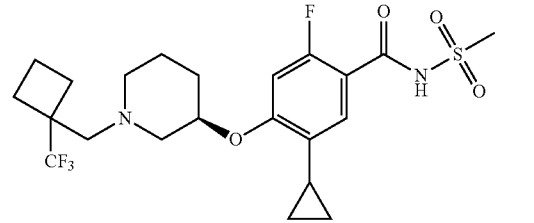
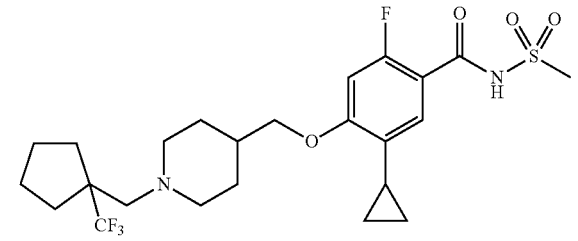
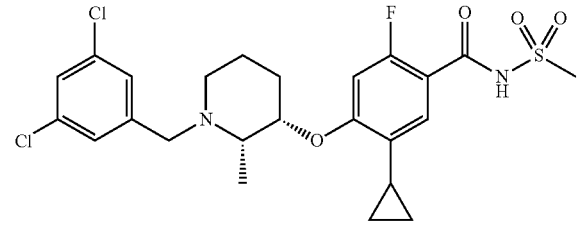
104
-continued
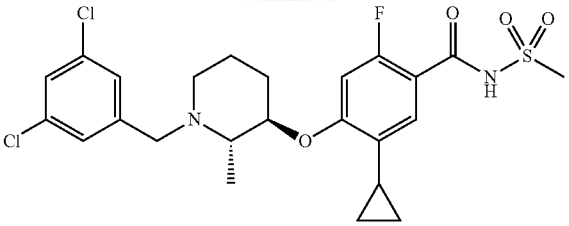
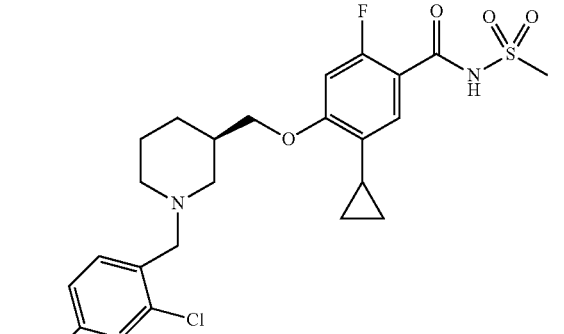
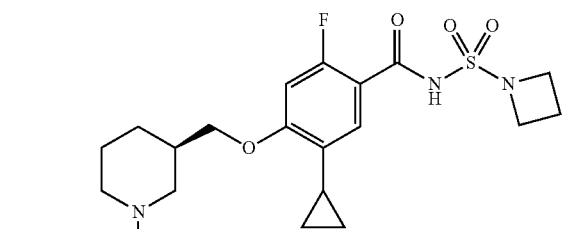
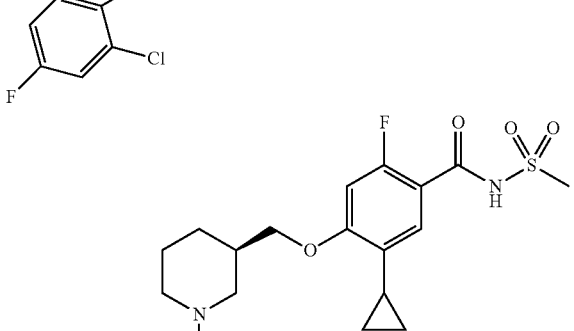
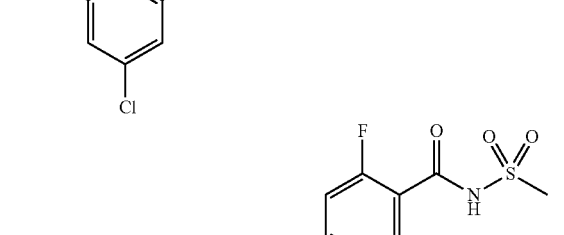
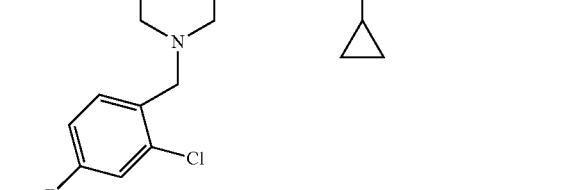

105
-continued
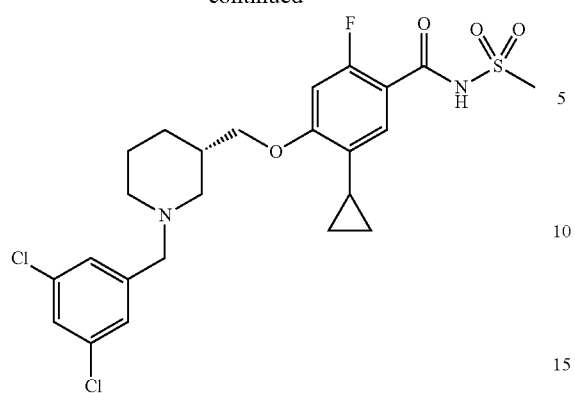
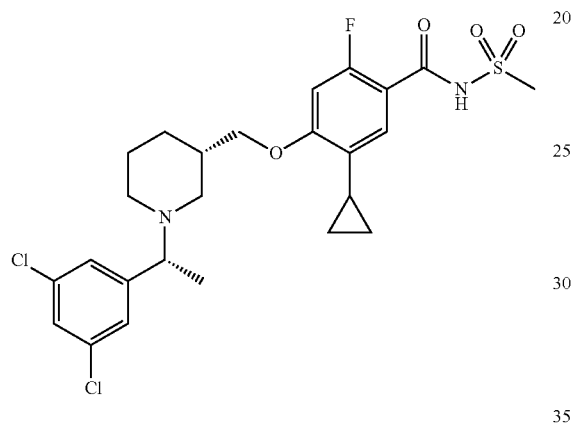
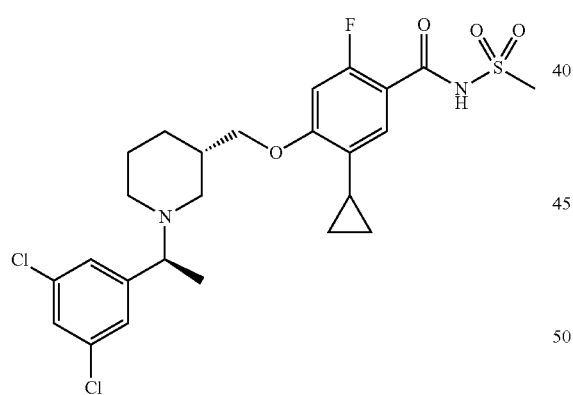
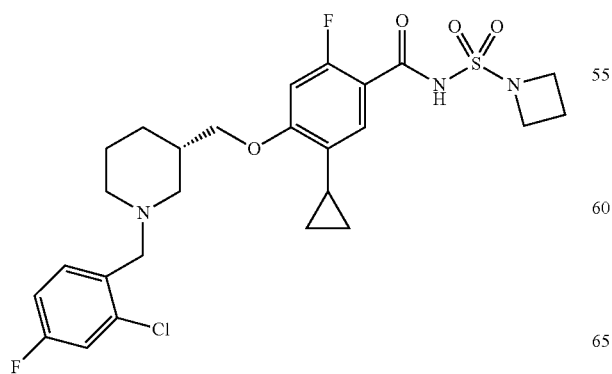
106
-continued
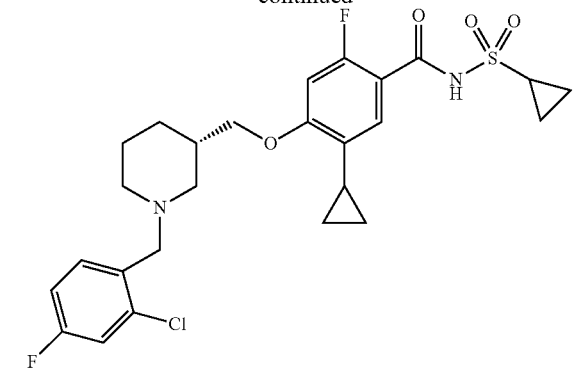
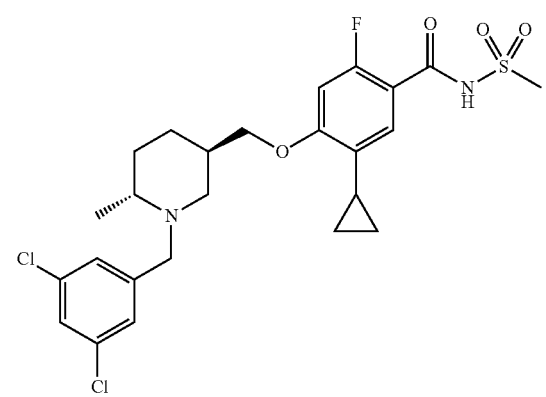
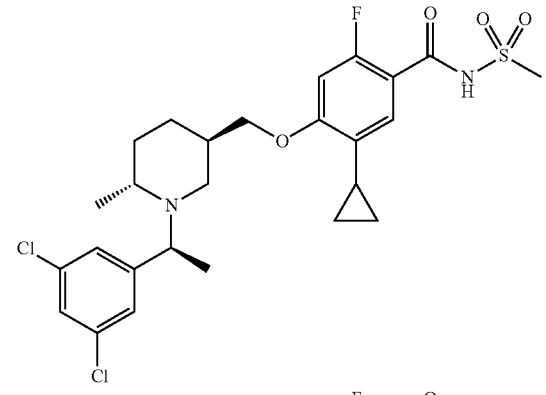
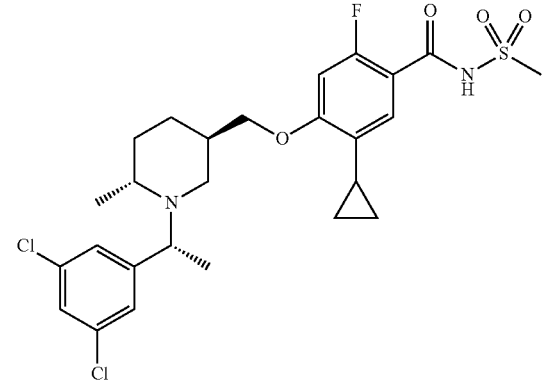

107
-continued
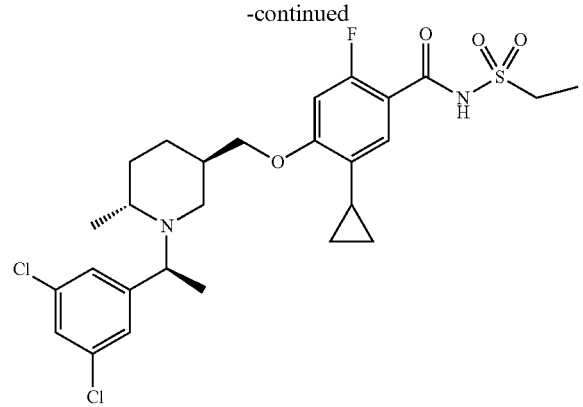
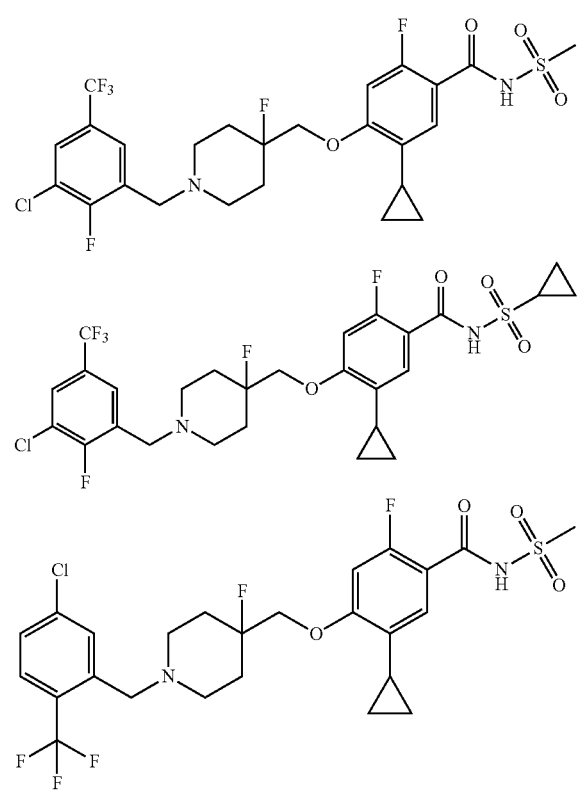
108
-continued
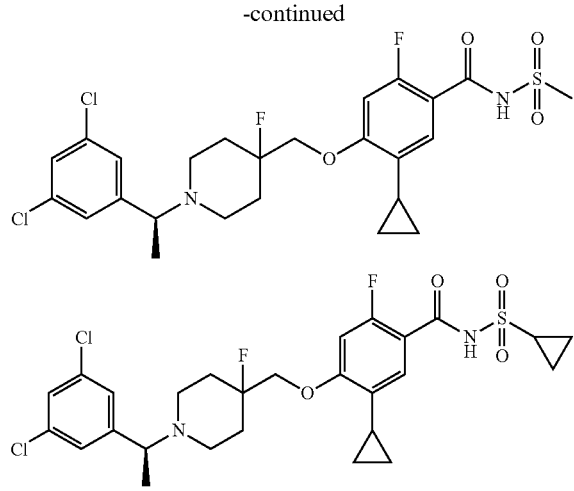
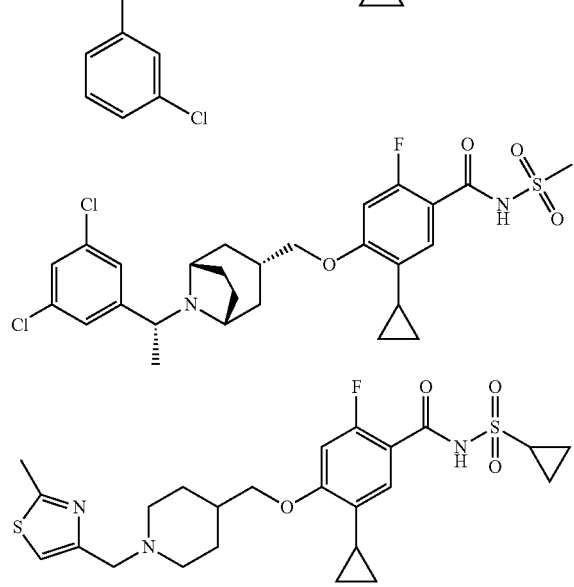
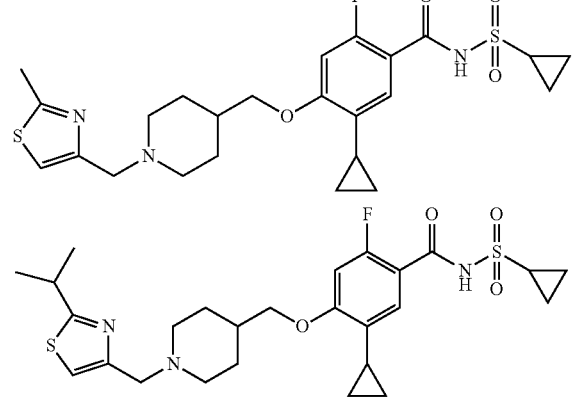

109
-continued
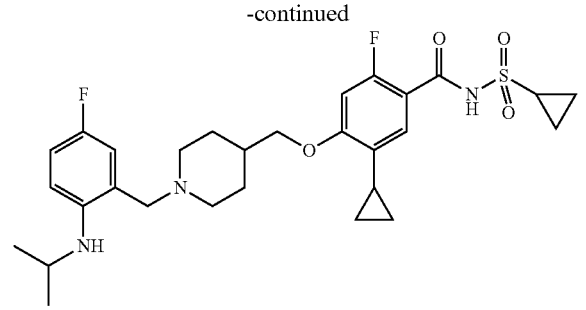
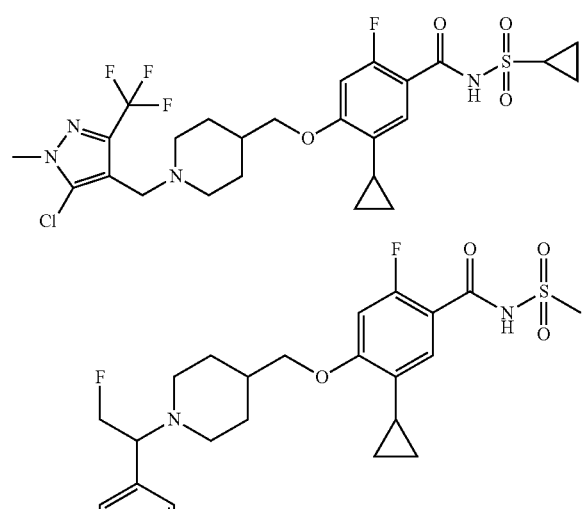
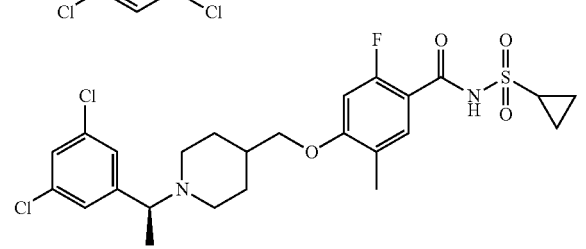
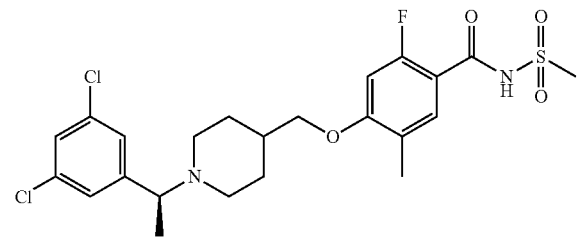
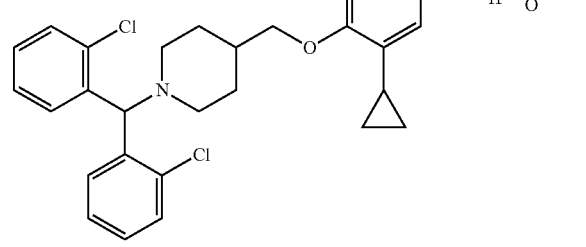
110
-continued
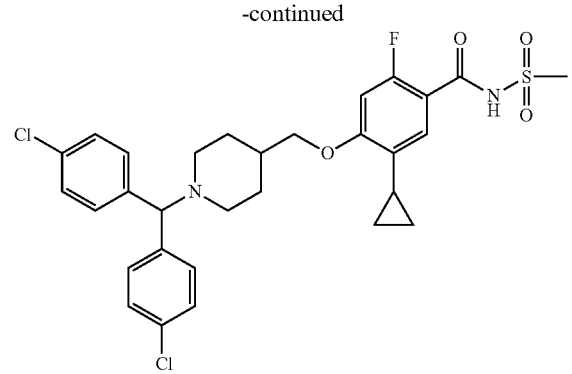
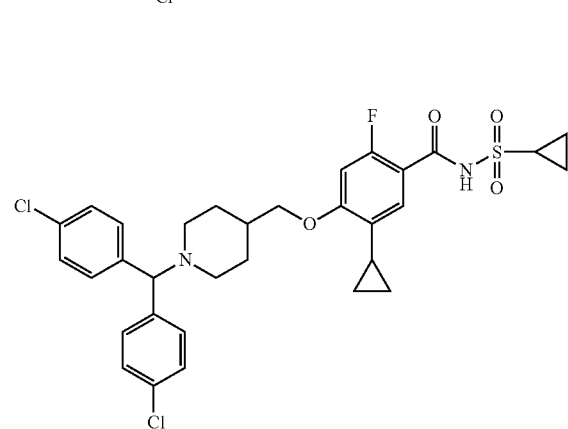
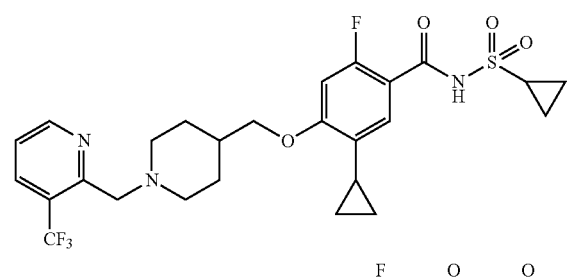
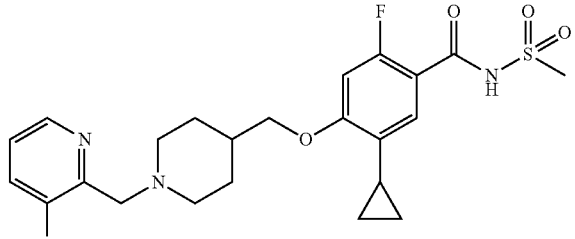
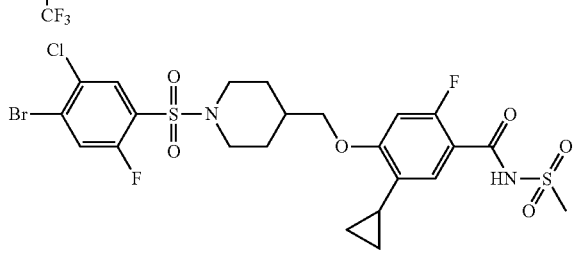
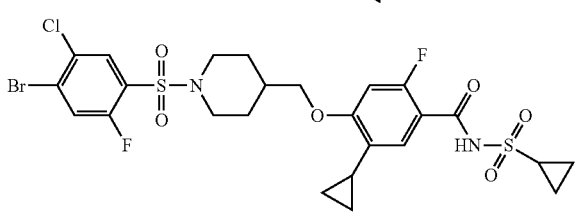

111
-continued
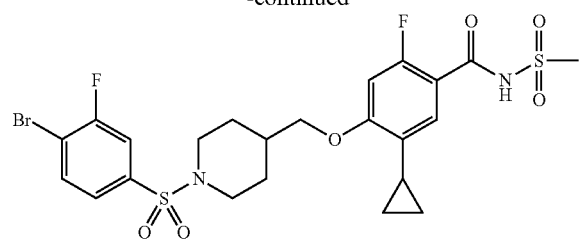
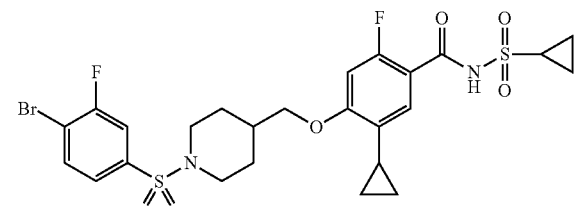
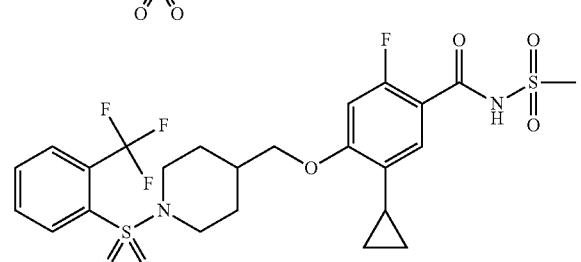
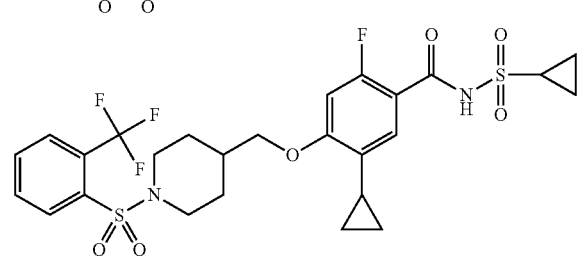
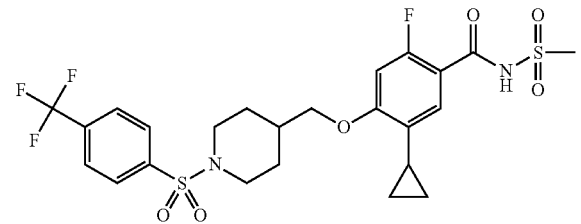
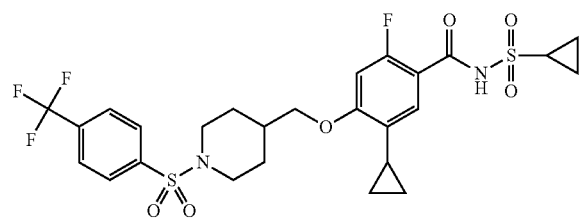
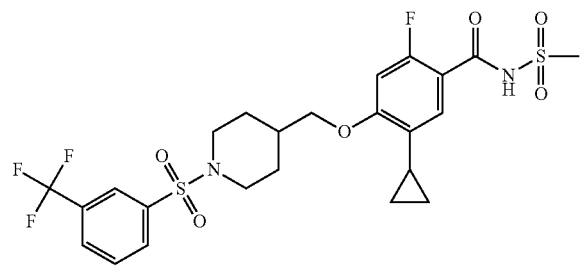
112
-continued
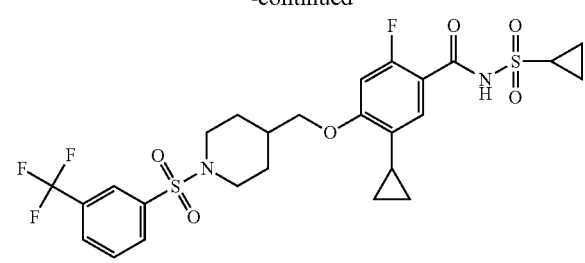
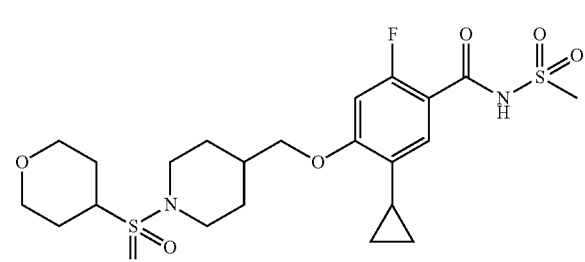
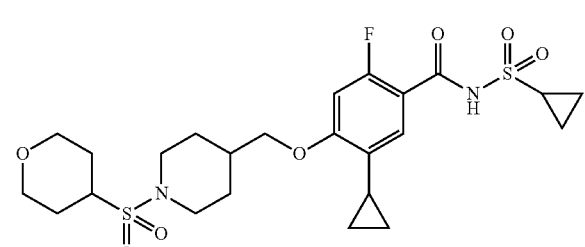
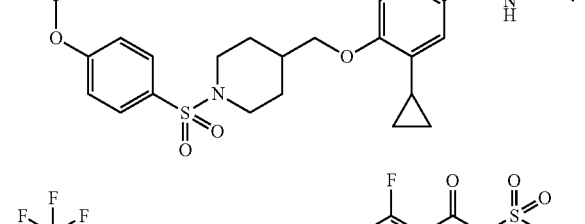
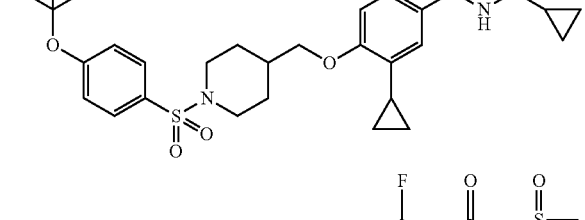
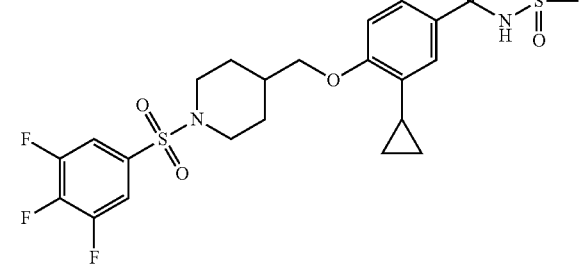

113
-continued
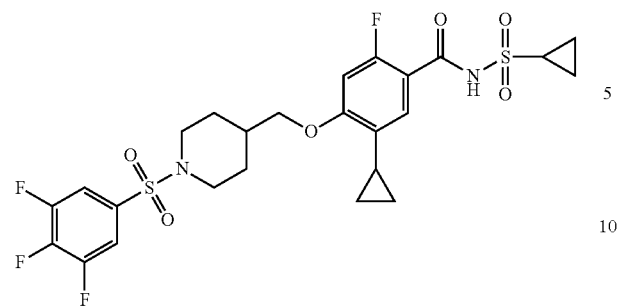
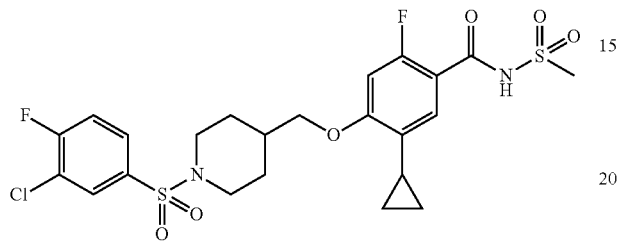

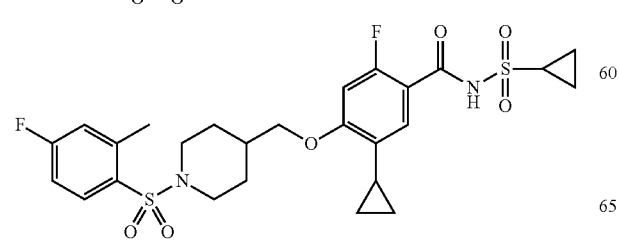
114
-continued
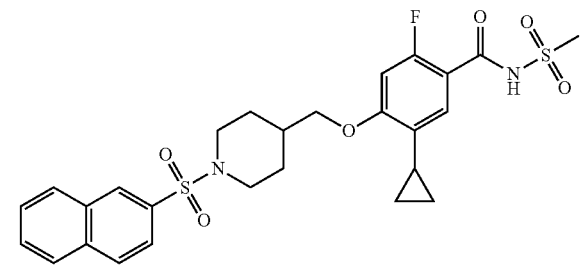
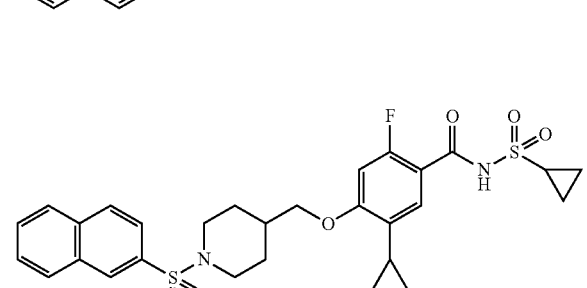
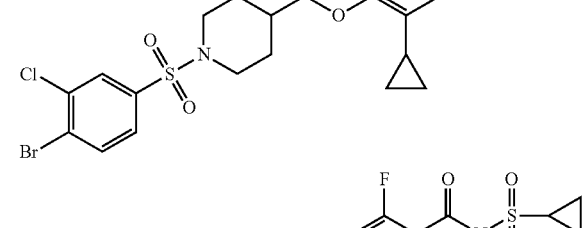
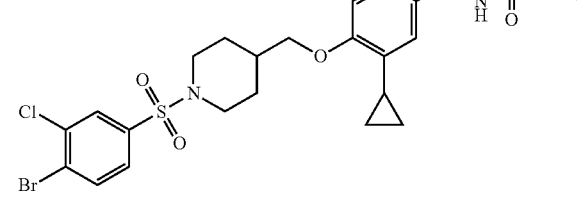
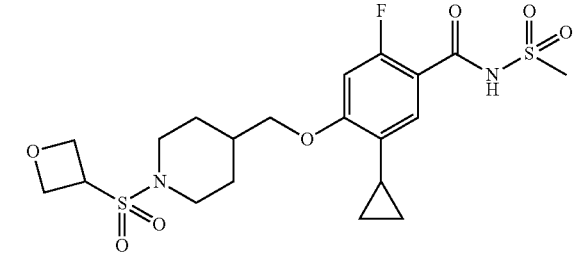
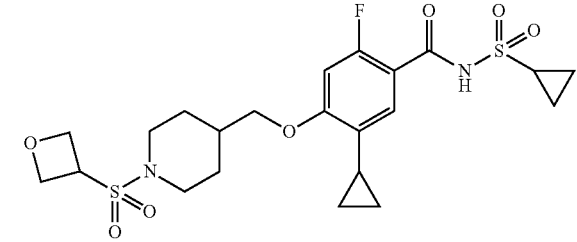

115
-continued
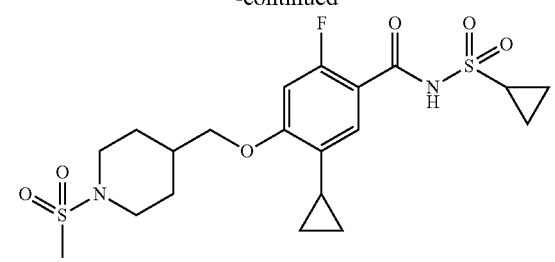
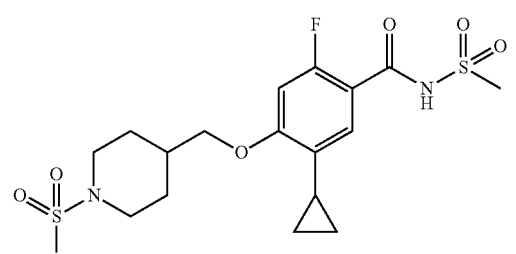
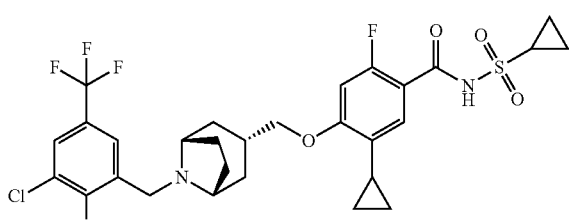
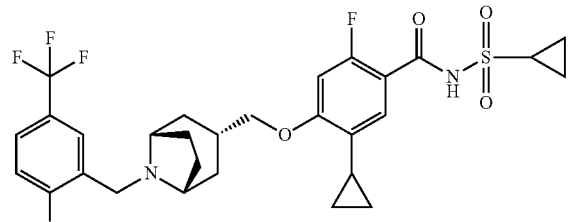
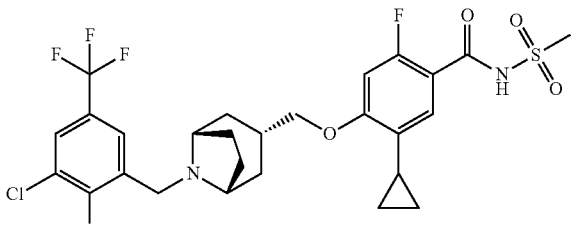
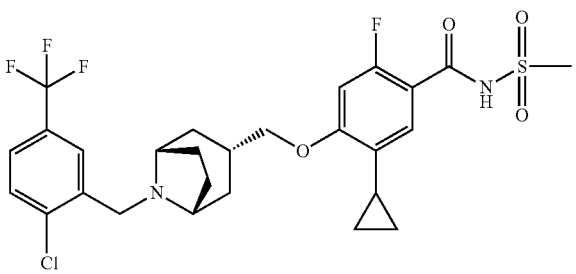
116
-continued
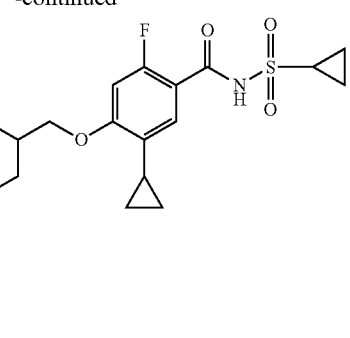
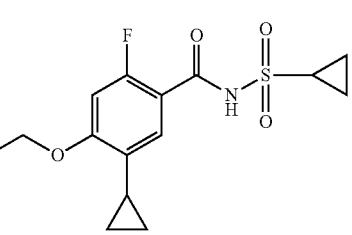
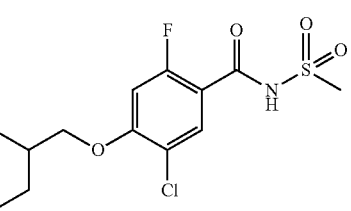
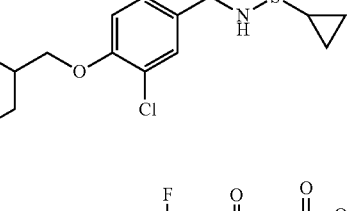
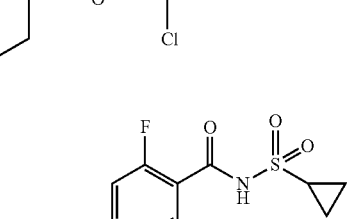

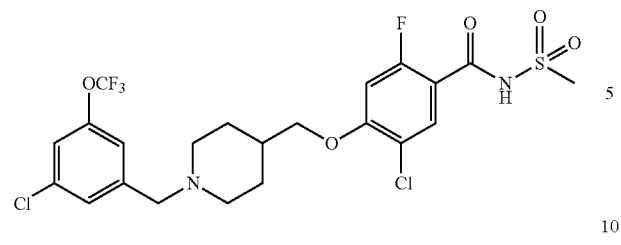
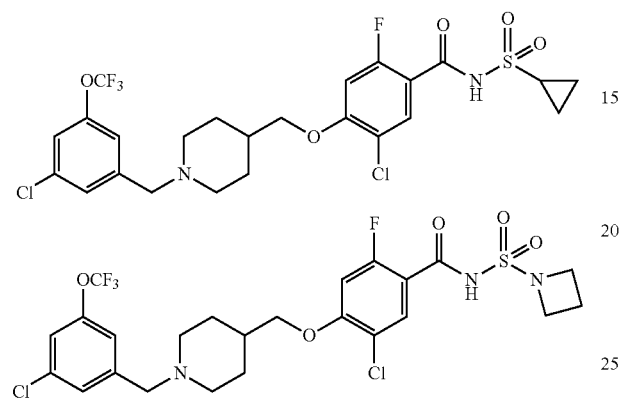
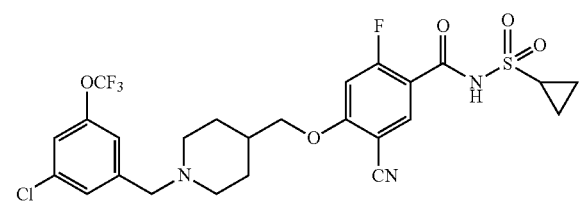
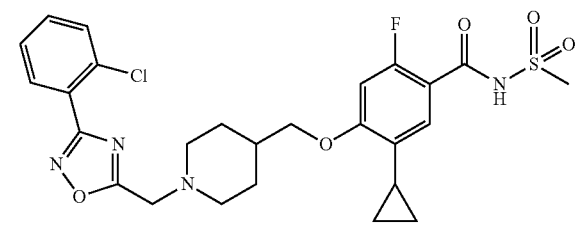
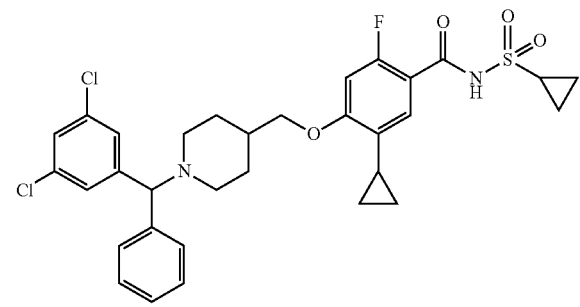
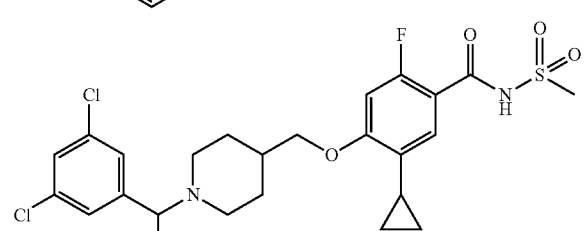
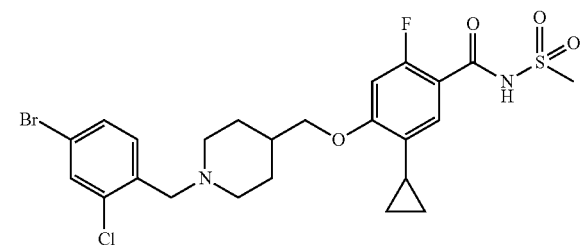
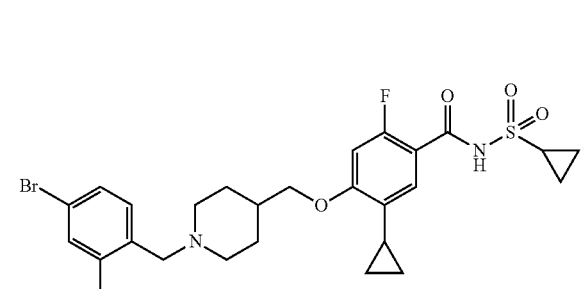
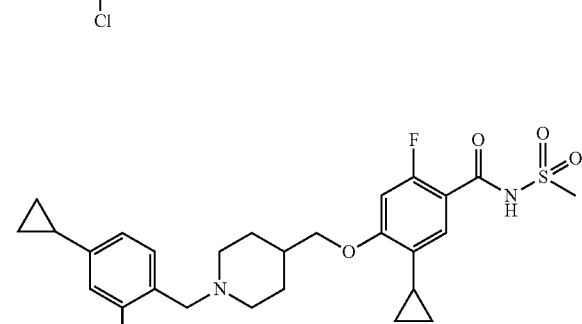
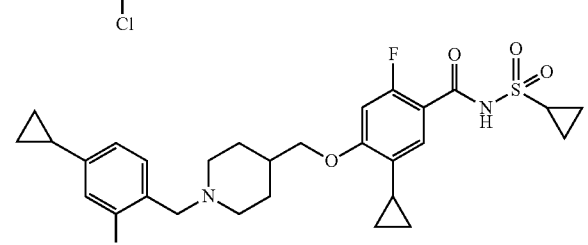
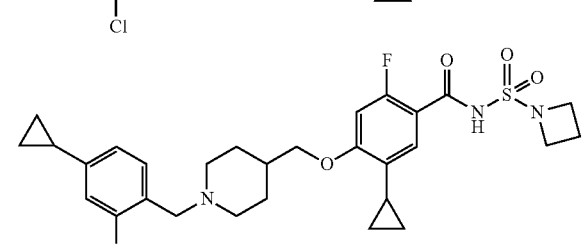
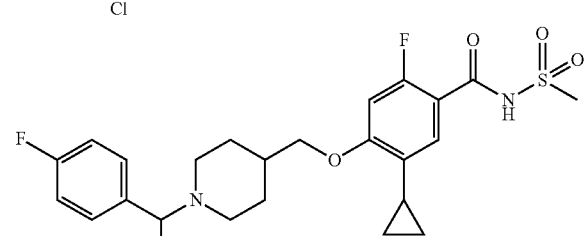

119
-continued
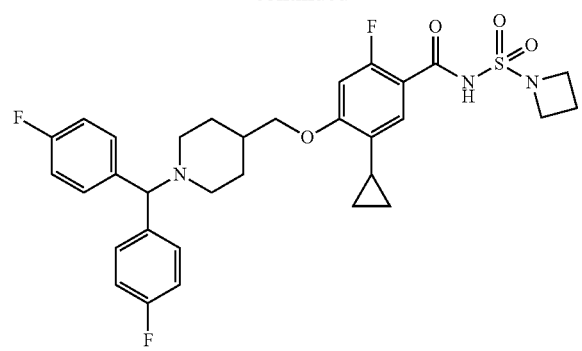
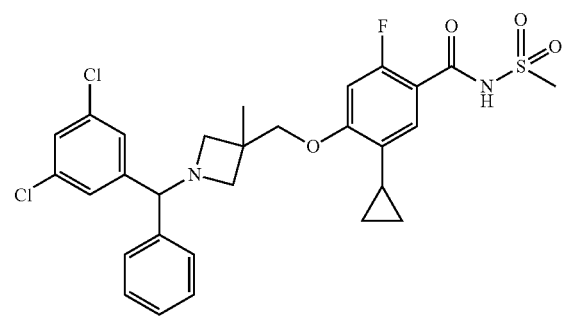
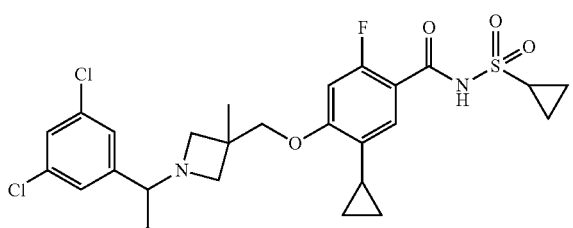
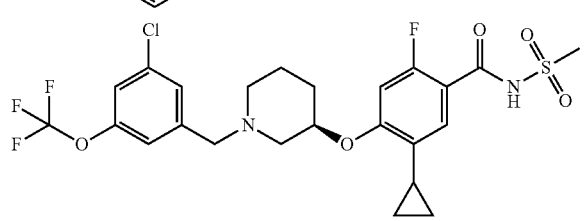

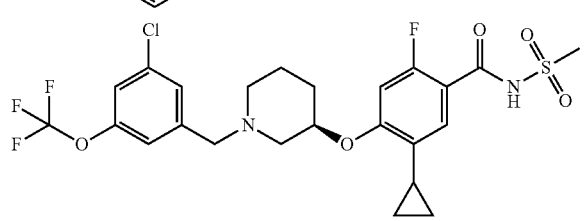
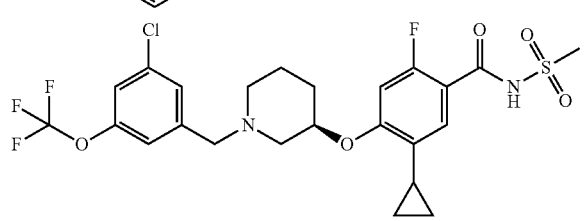
120
-continued
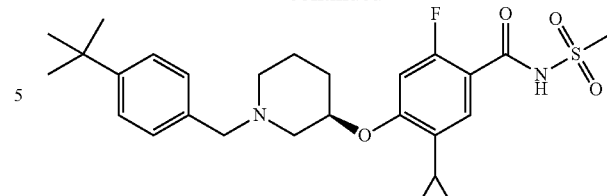
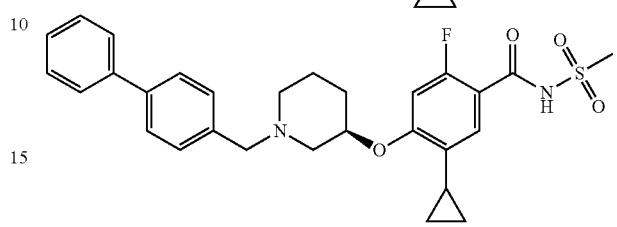
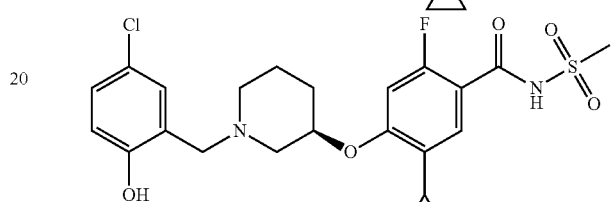
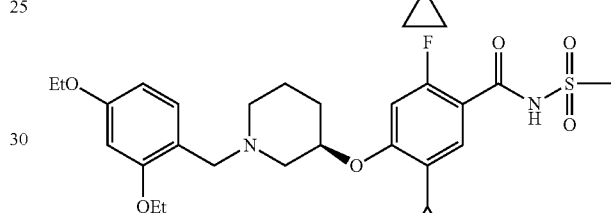

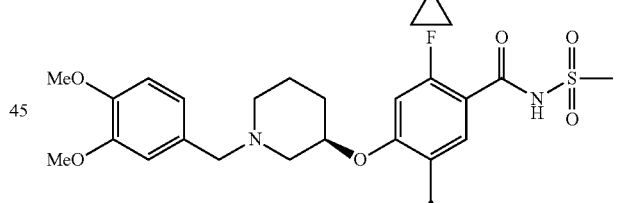
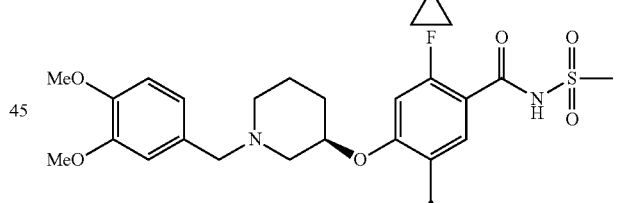

121
-continued
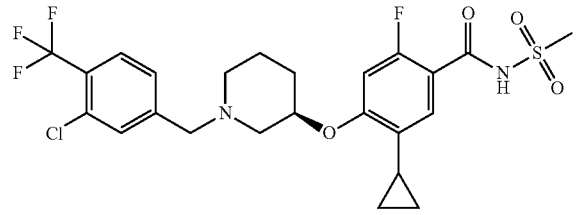
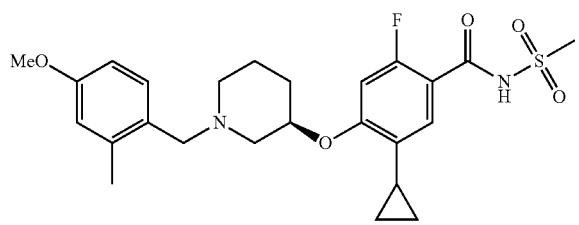

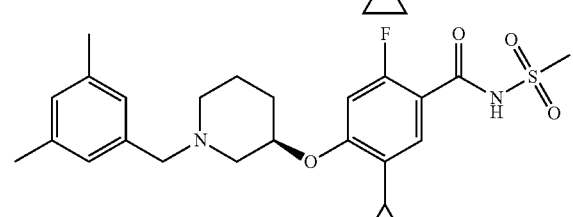
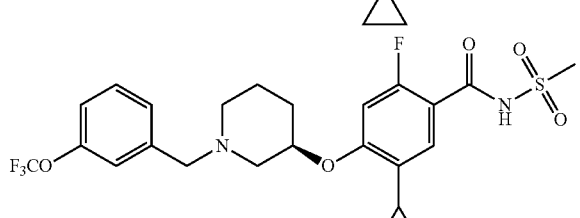
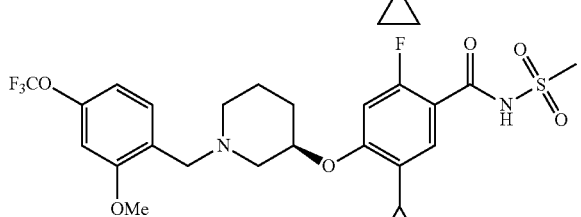
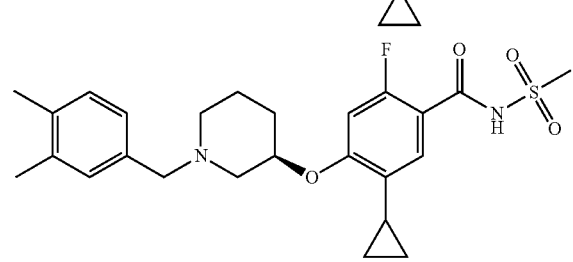
122
-continued
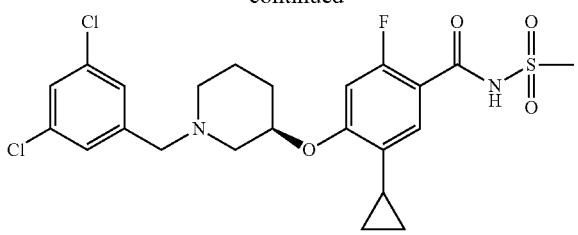
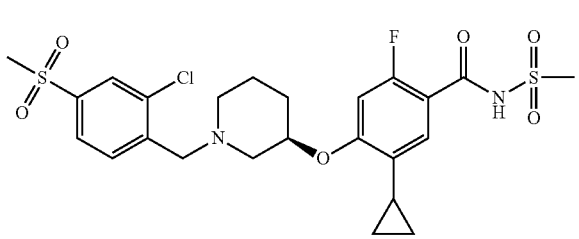
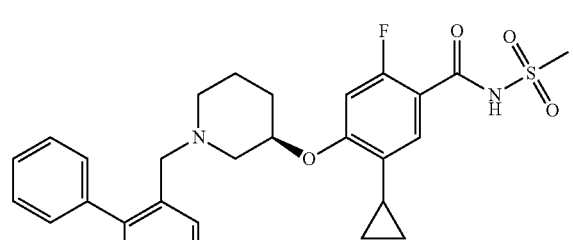
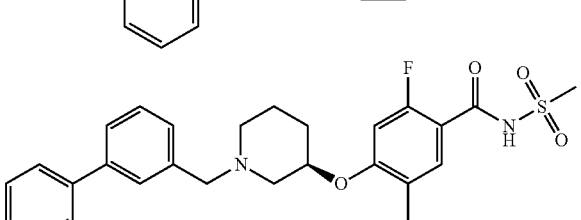
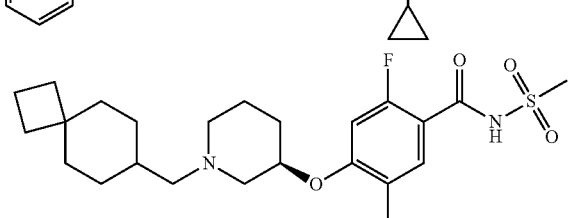
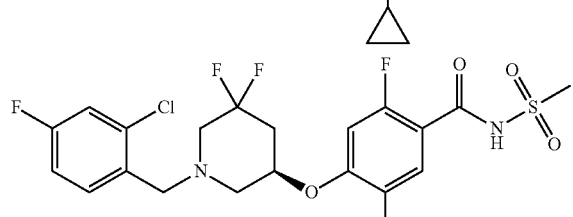
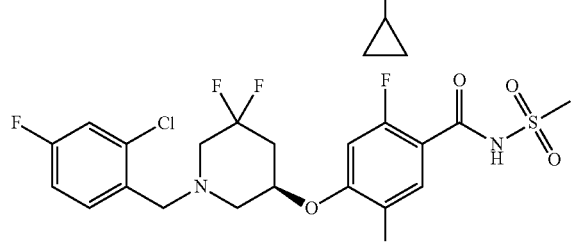

123
-continued
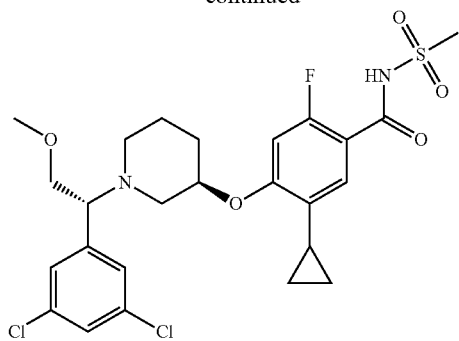
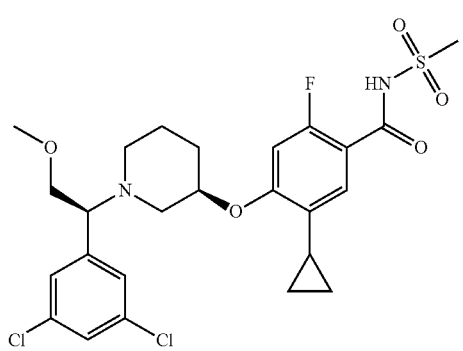
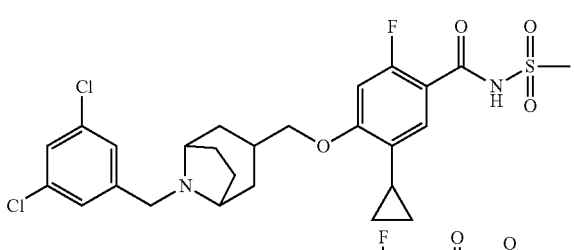

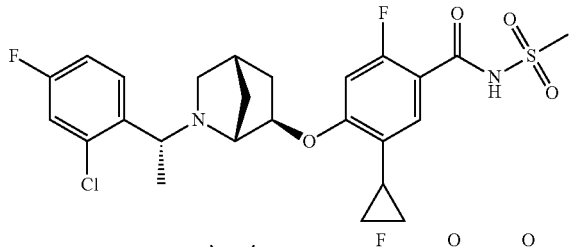
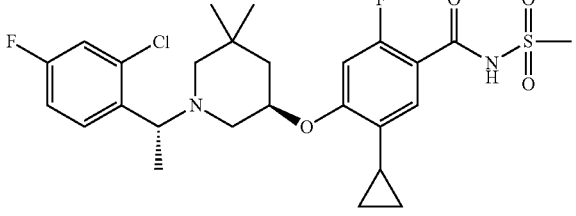
124
-continued
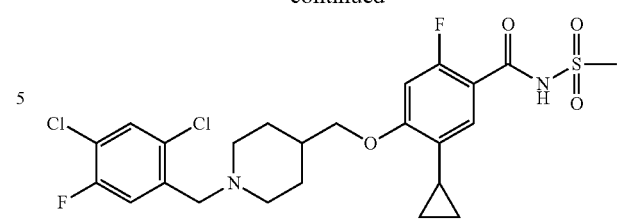
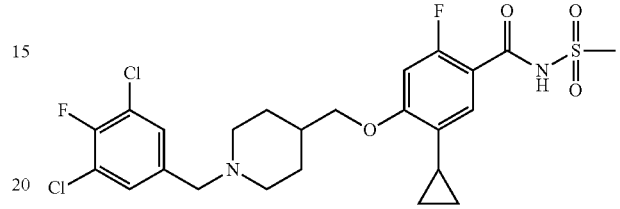

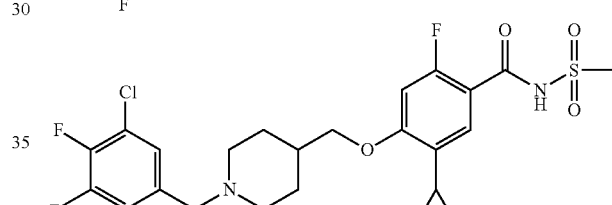
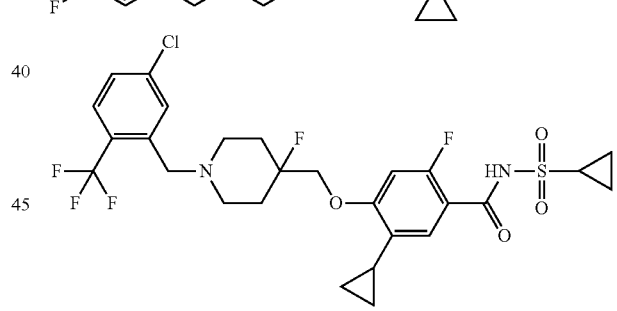
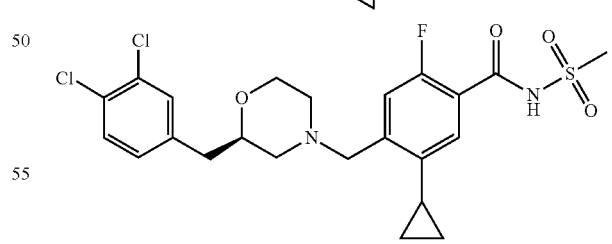
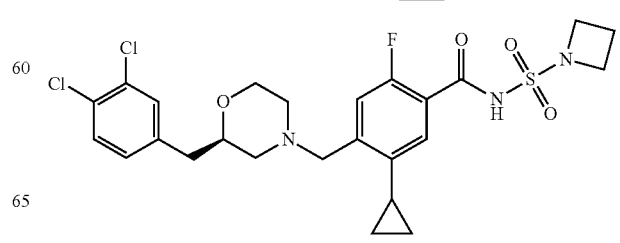

125
-continued
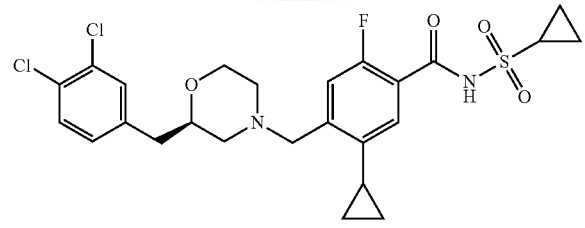
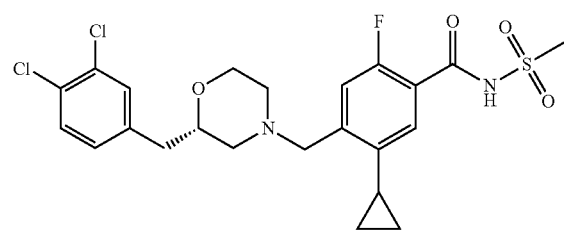
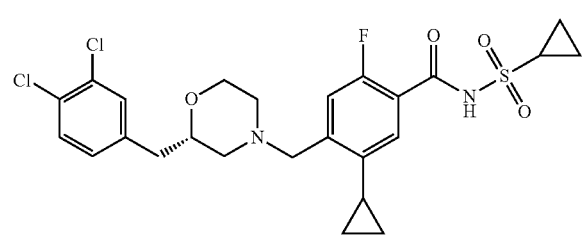
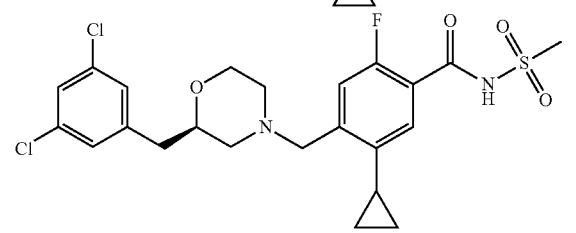
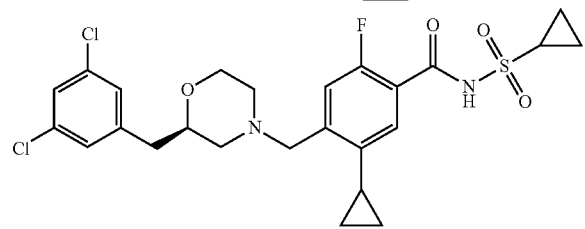
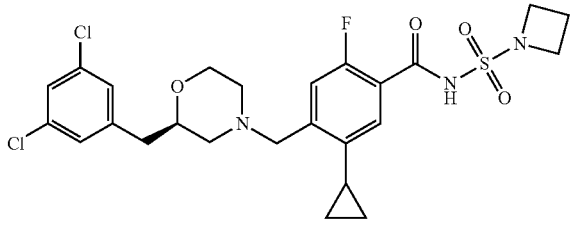
126
-continued
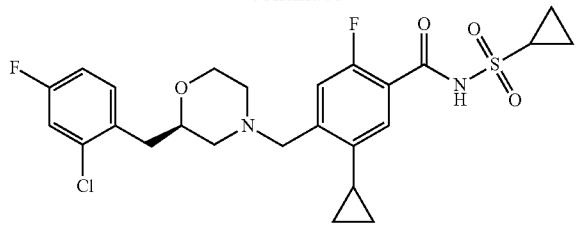
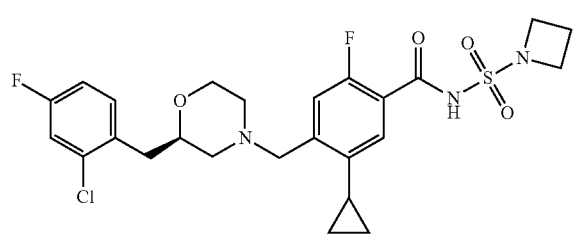
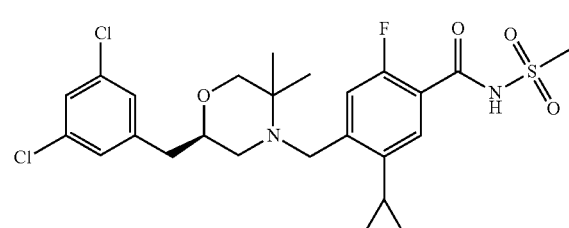
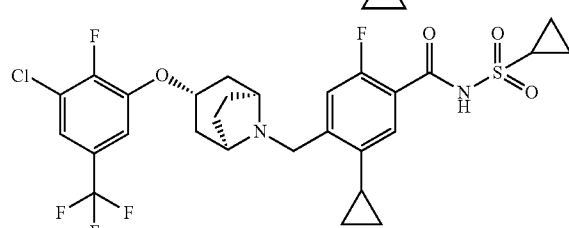
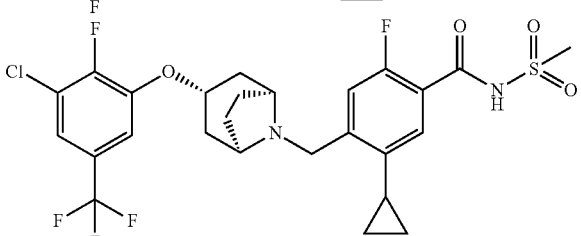
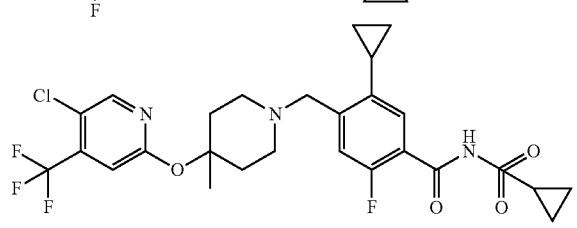

127
-continued
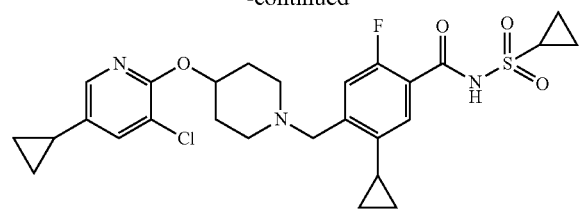
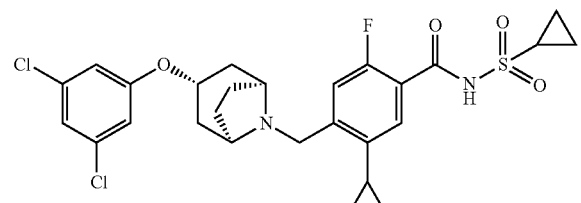
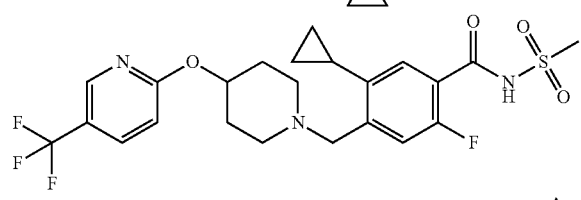
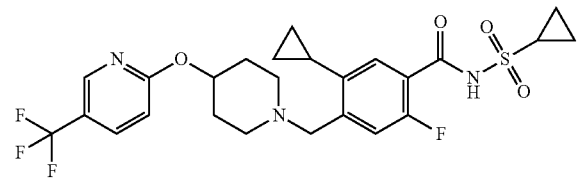
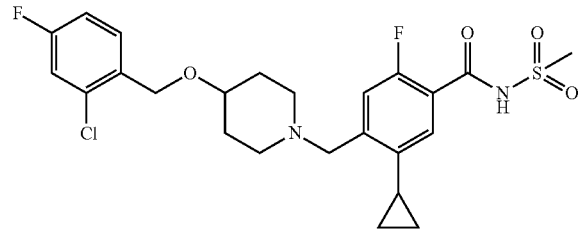
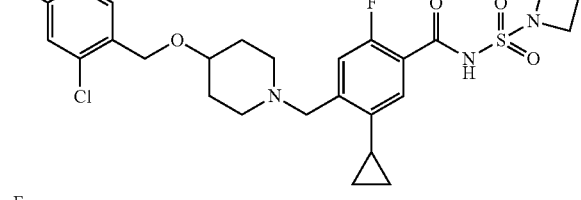
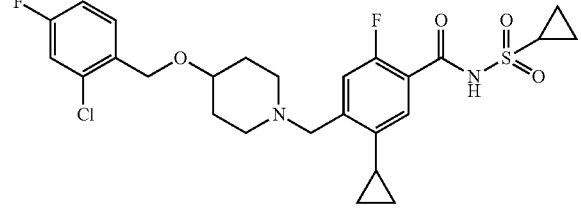
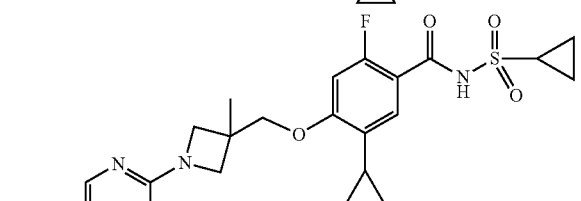
128
-continued
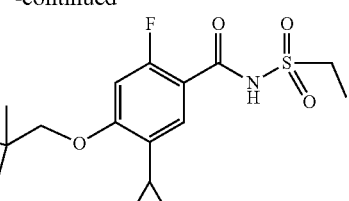
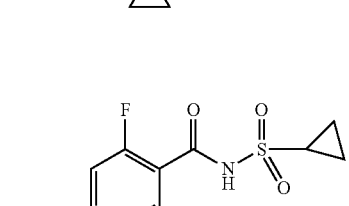
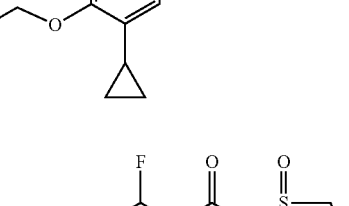
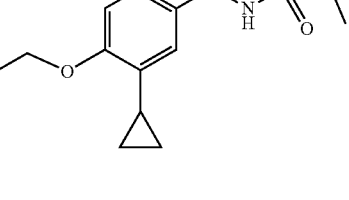
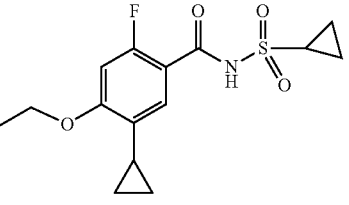

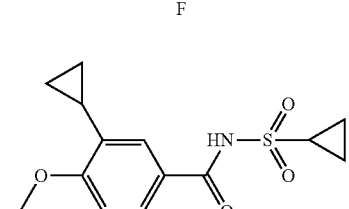
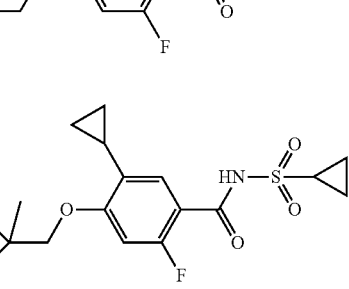

129
-continued
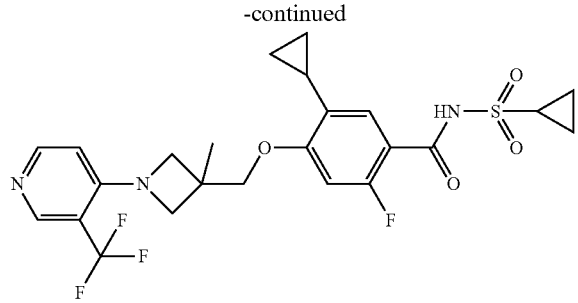
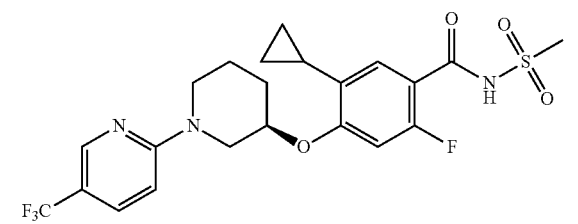
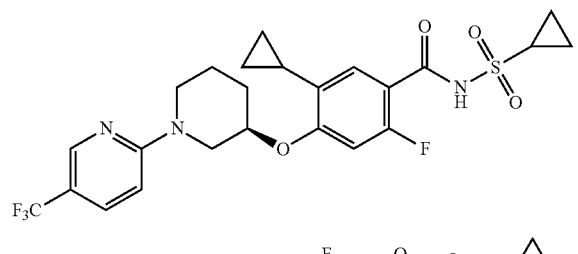
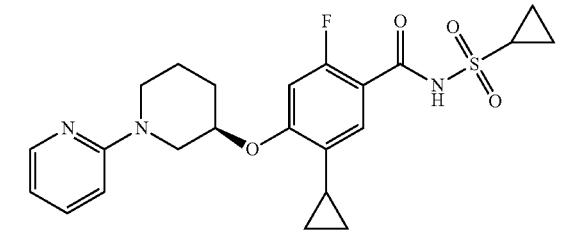
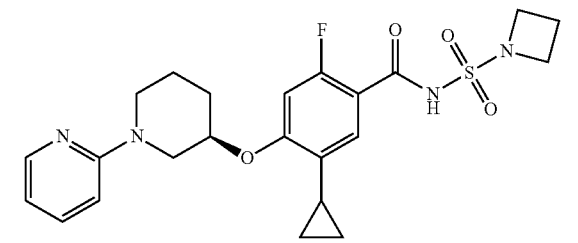
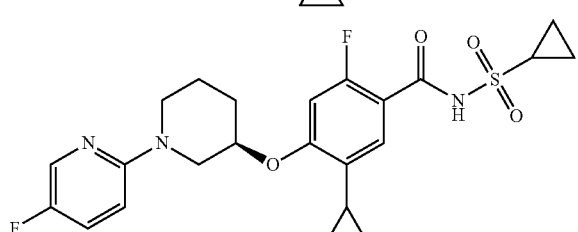
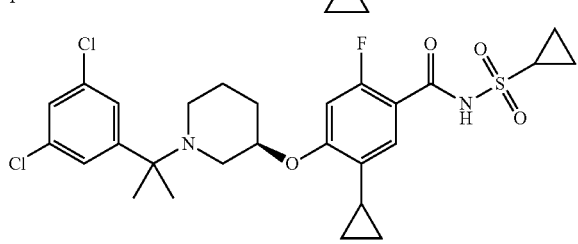
130
-continued
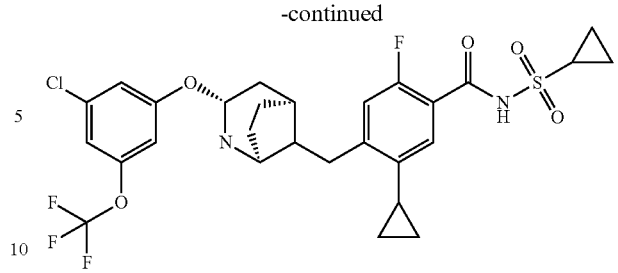
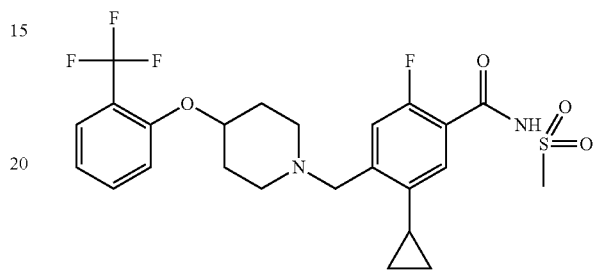
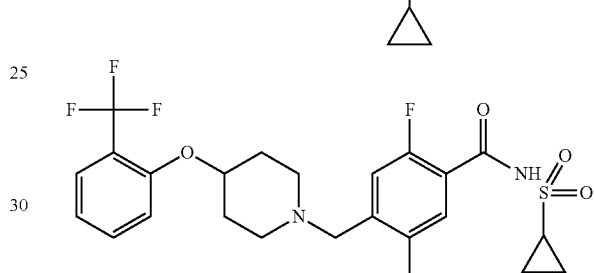
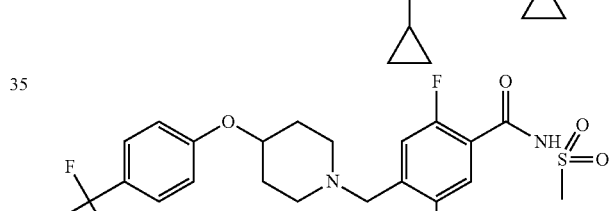
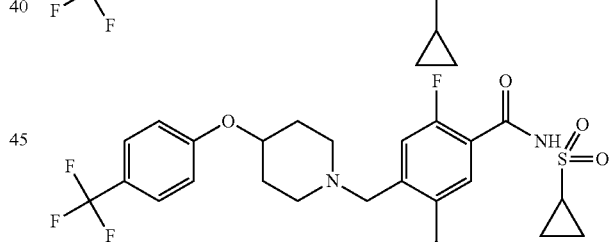
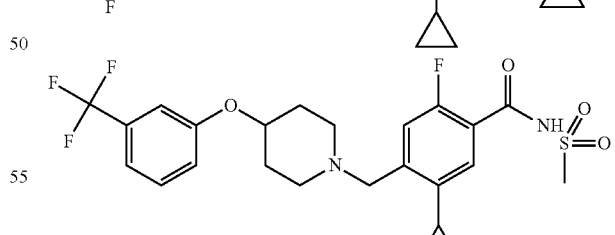
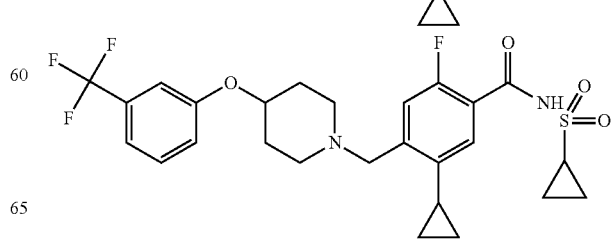

131
-continued
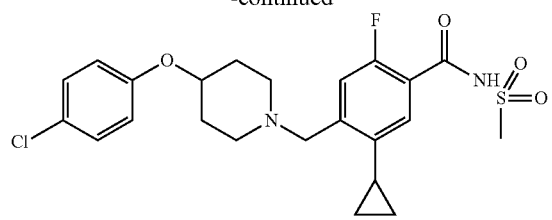
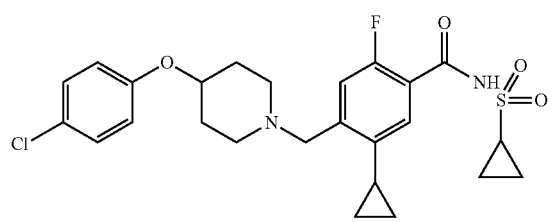
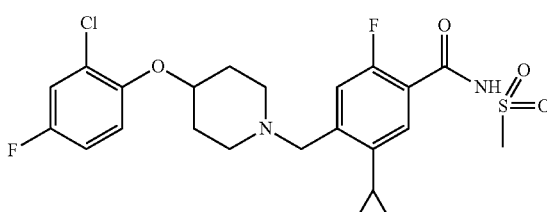
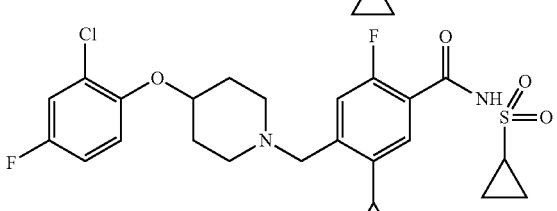
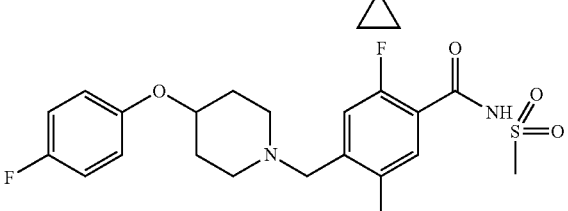
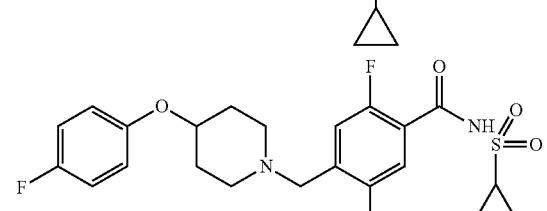
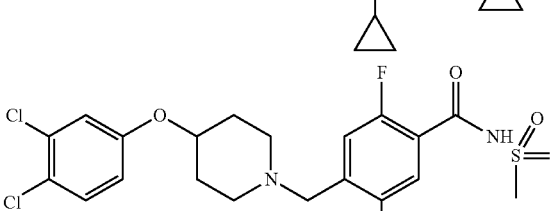
132
-continued
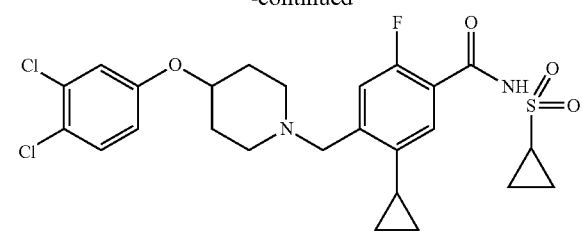
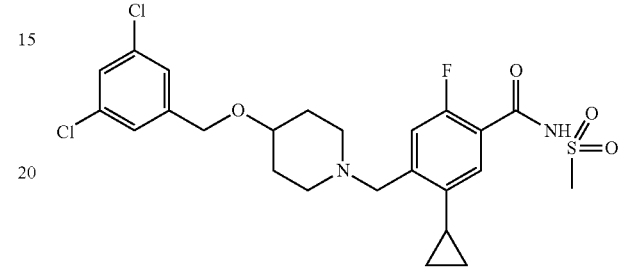
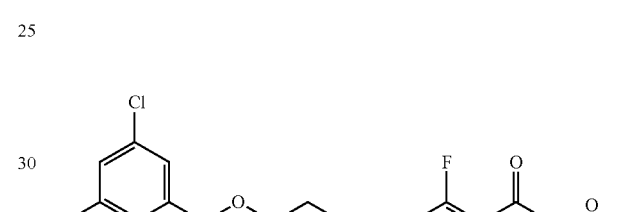
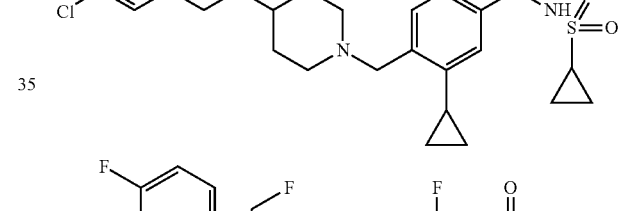
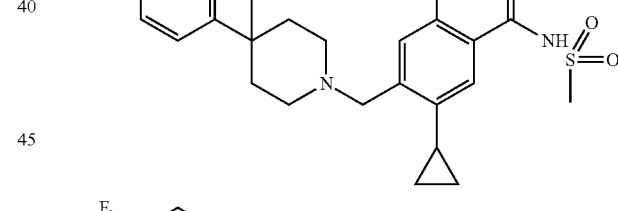
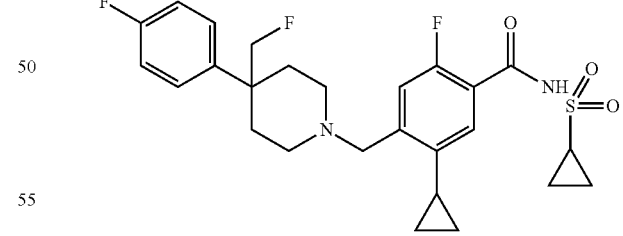
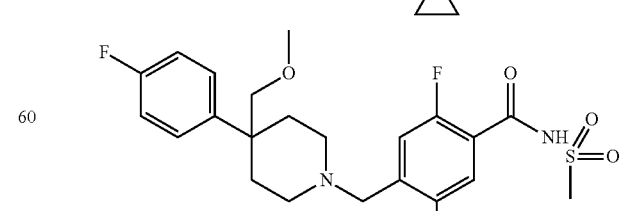

133
-continued
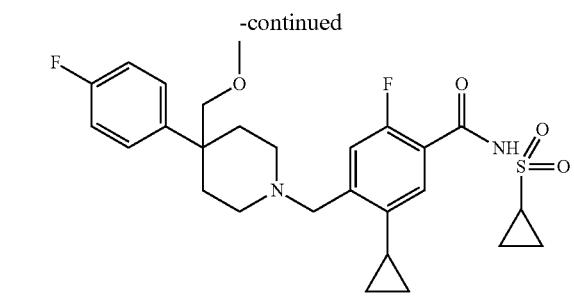
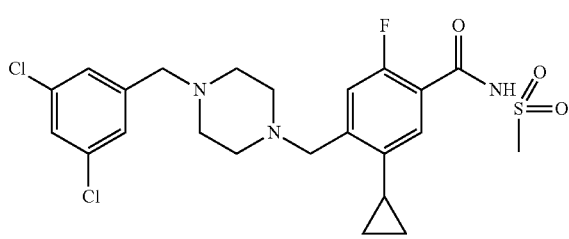
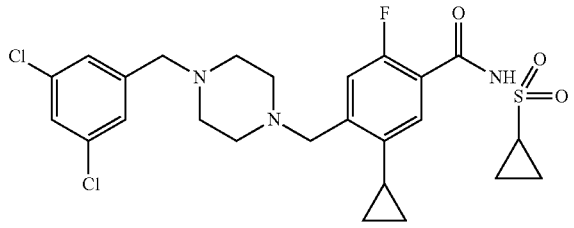
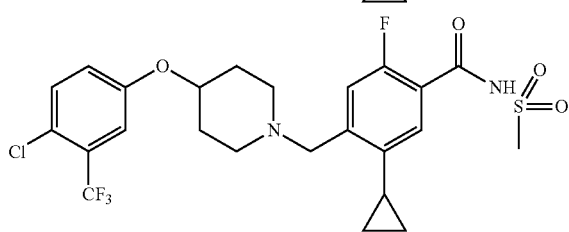
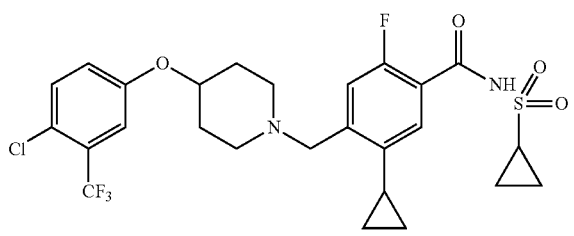
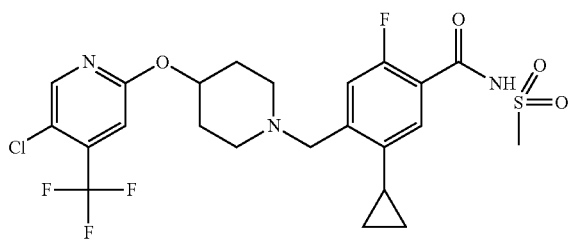
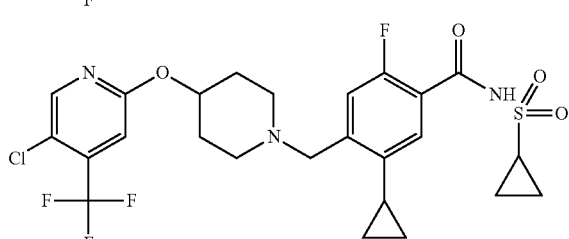
134
-continued
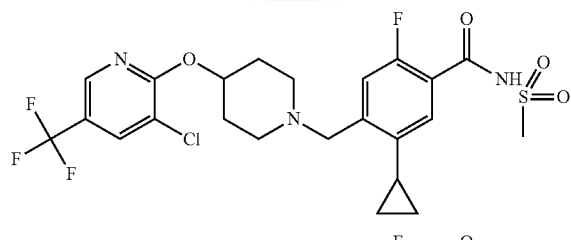
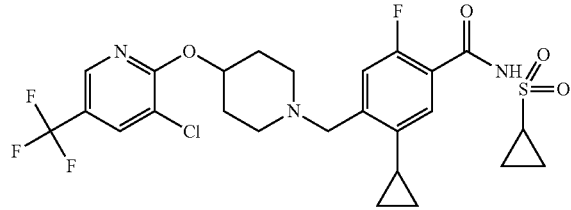
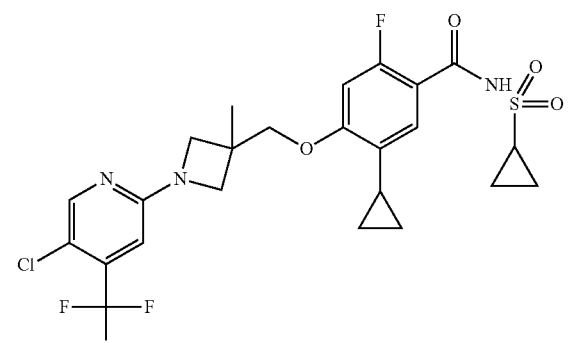
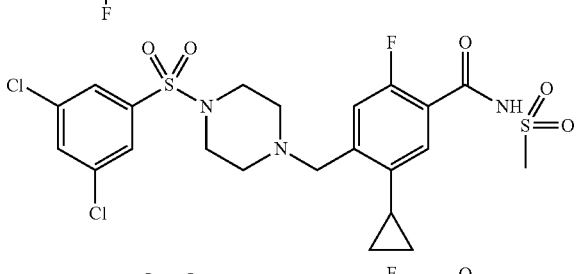
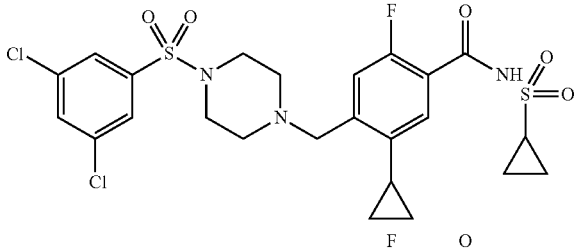
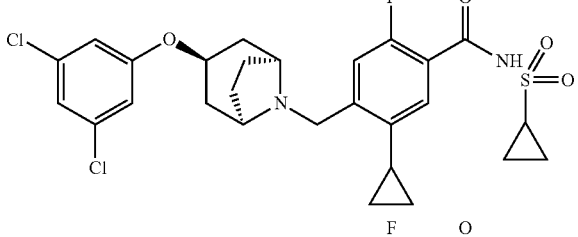
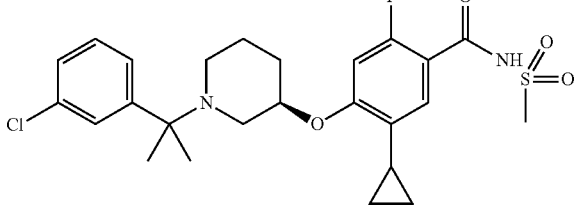

135
-continued
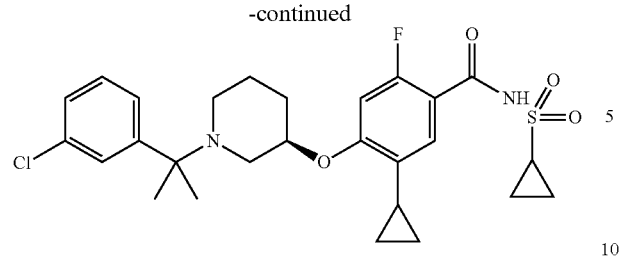
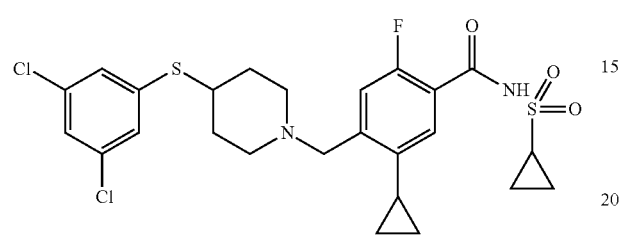
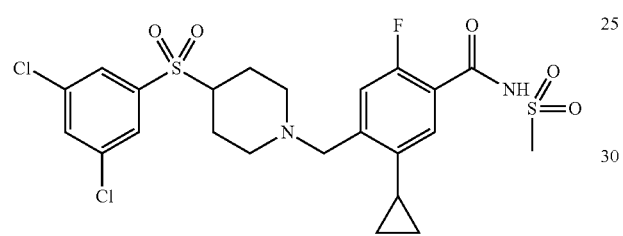
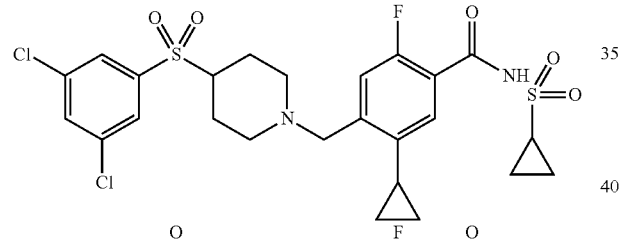

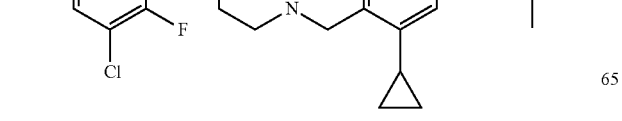
136
-continued
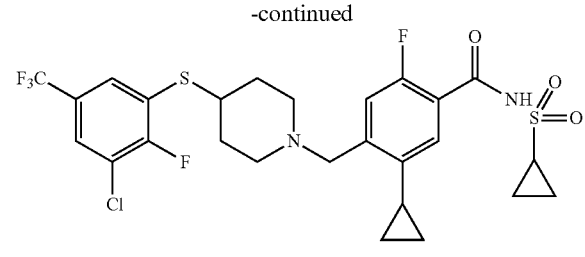
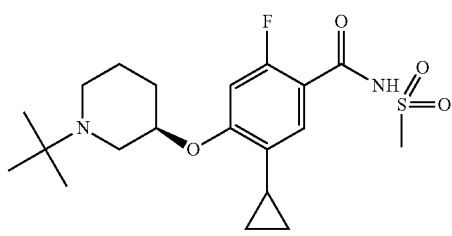
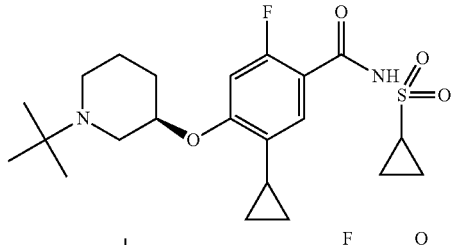
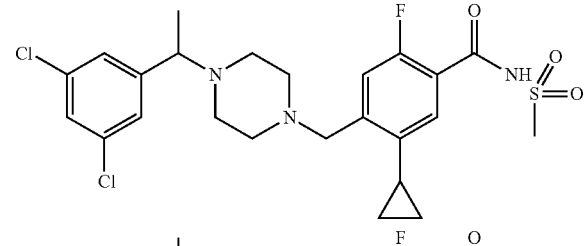
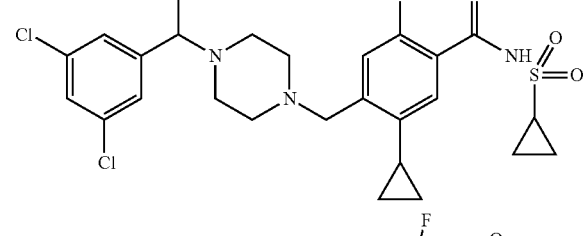
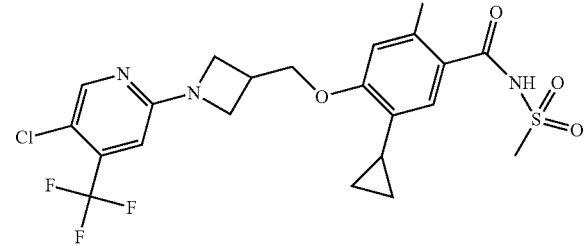
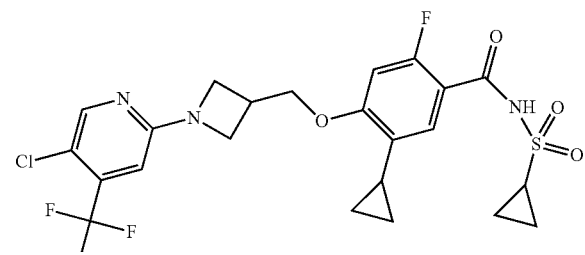

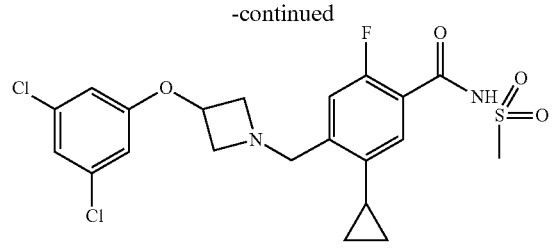
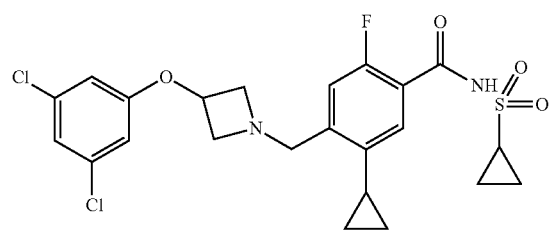
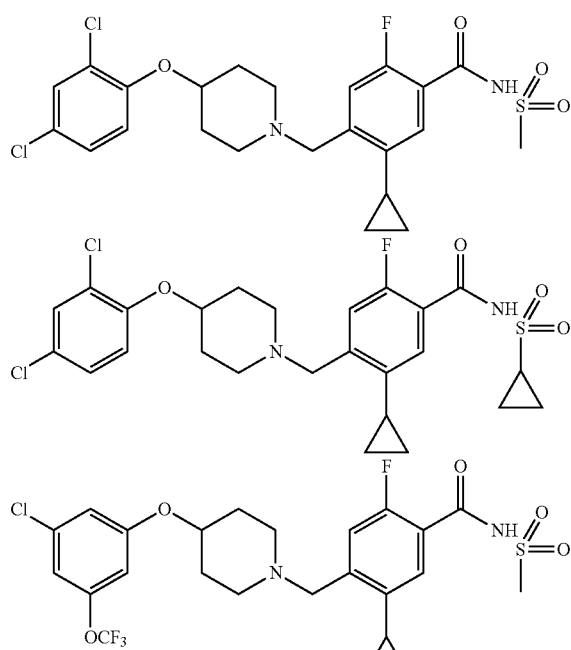
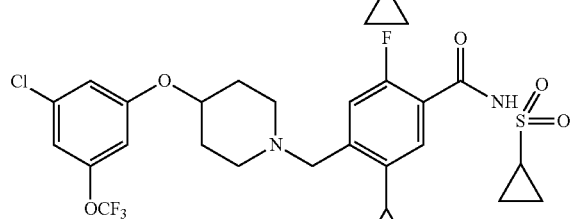
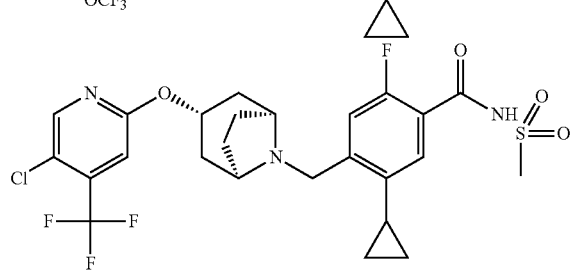
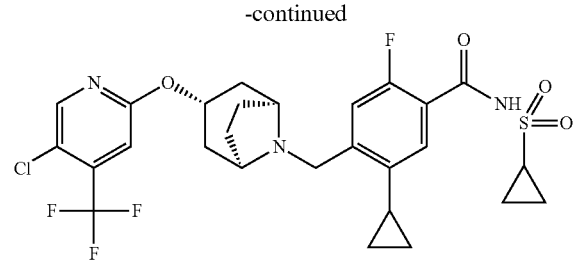
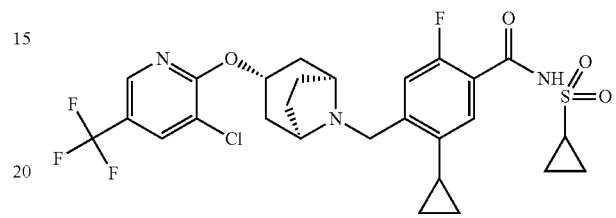
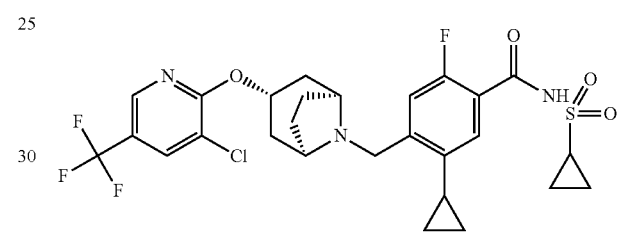
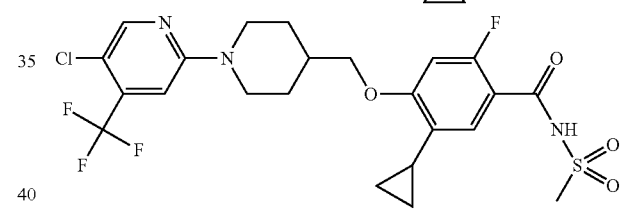
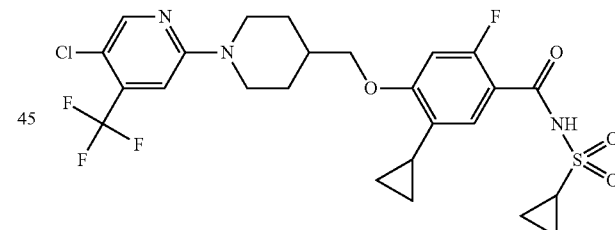
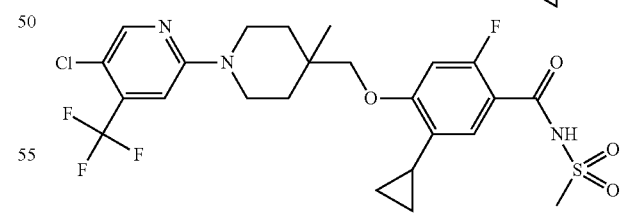
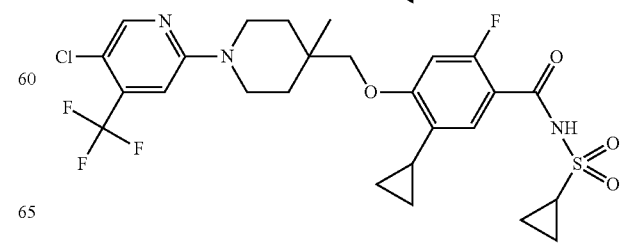

139
-continued
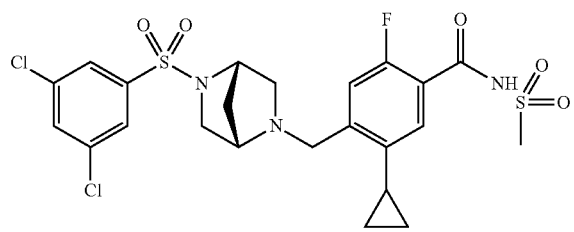
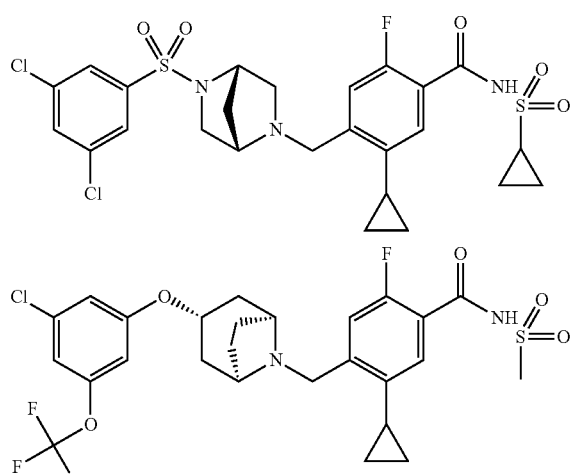
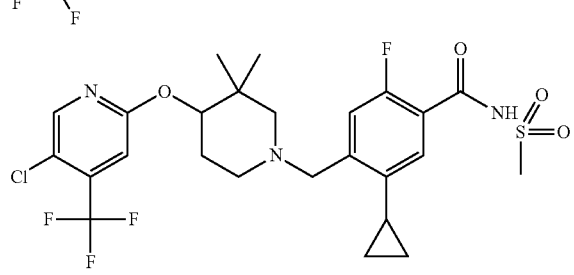
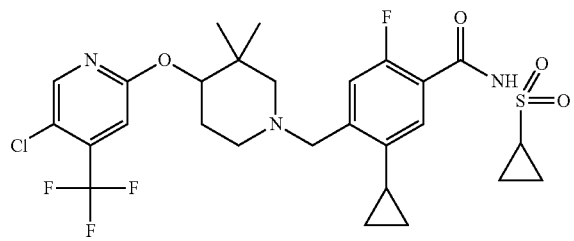
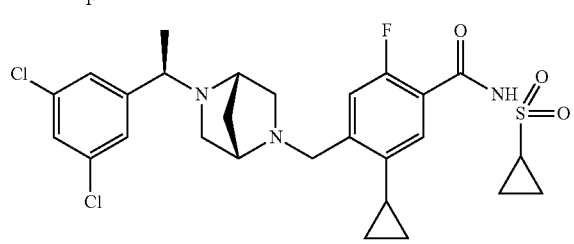
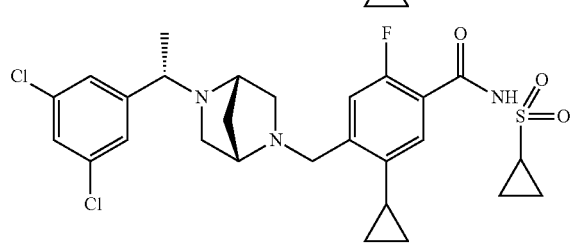
140
-continued
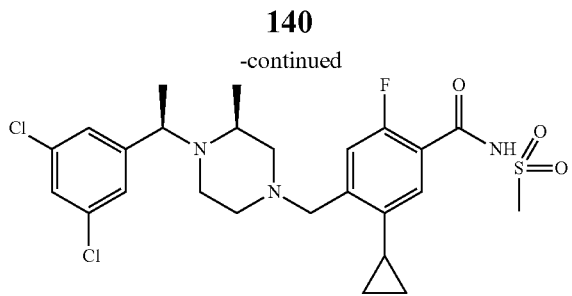
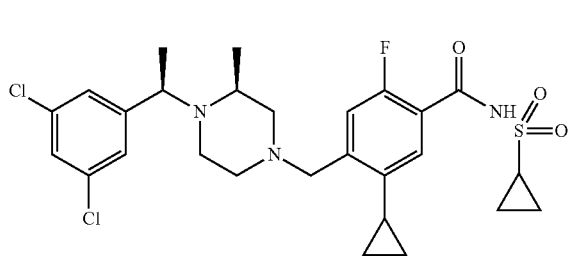
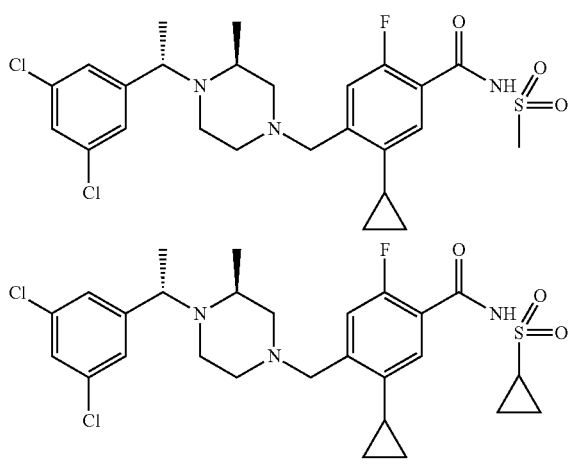
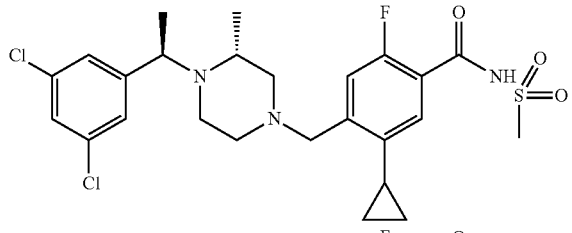
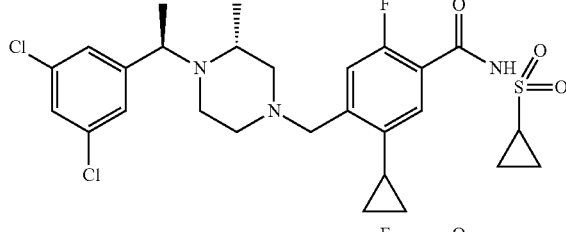
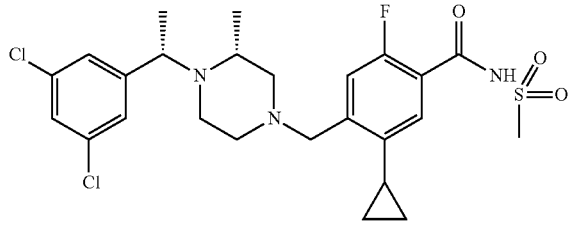

141
-continued
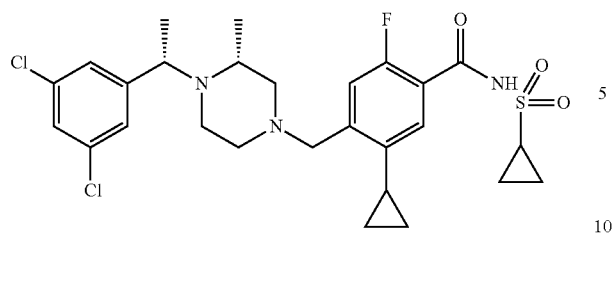
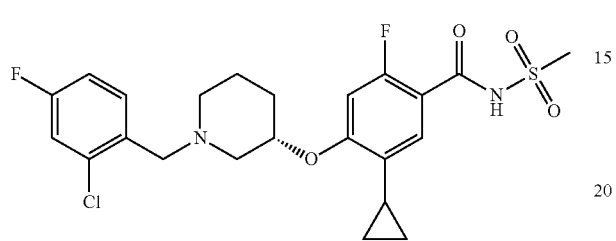
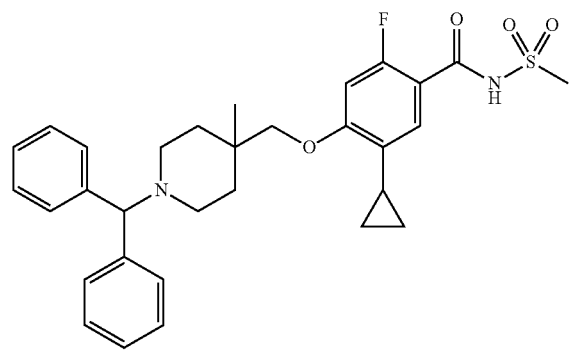
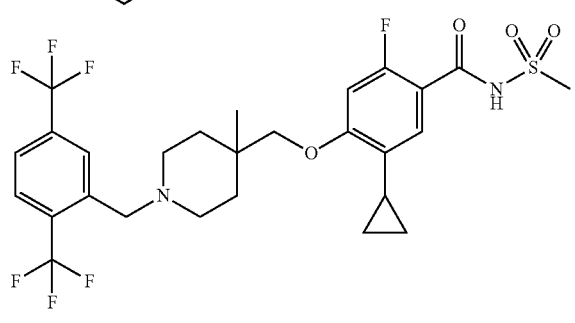
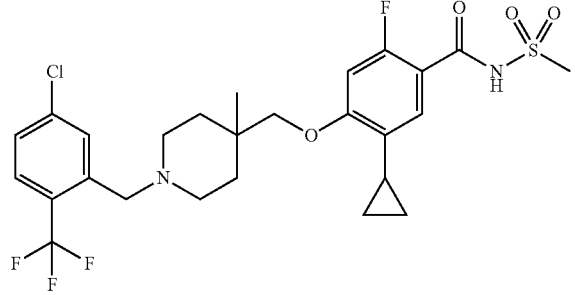
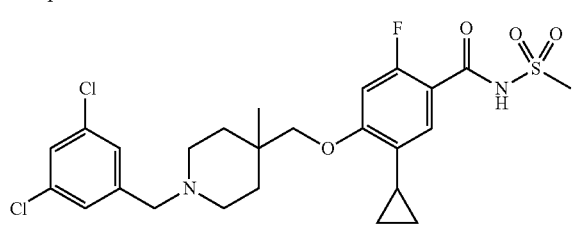
142
-continued
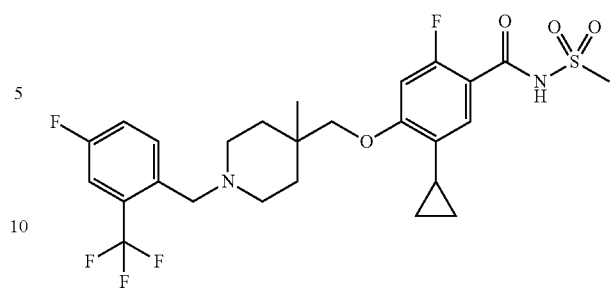
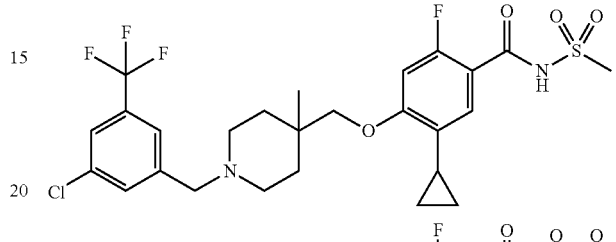
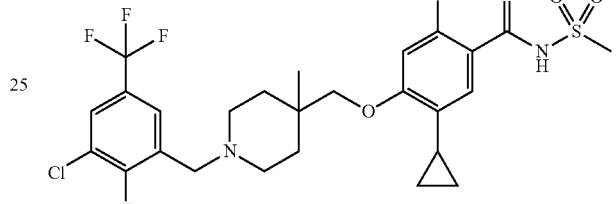
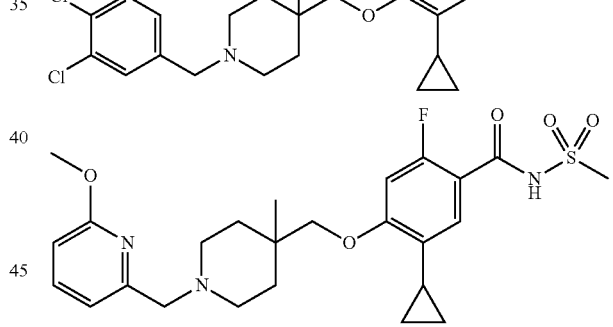
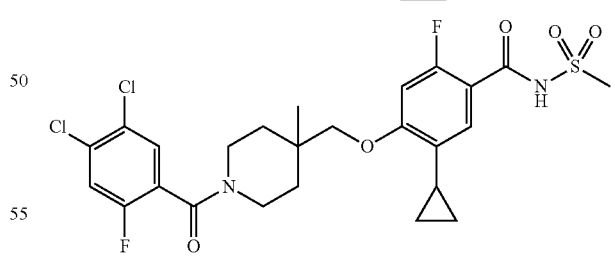
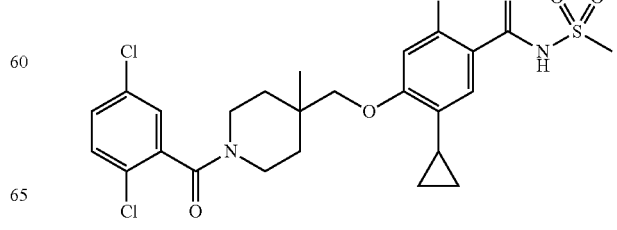

143
-continued
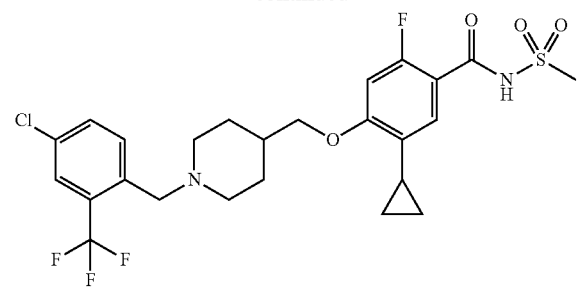
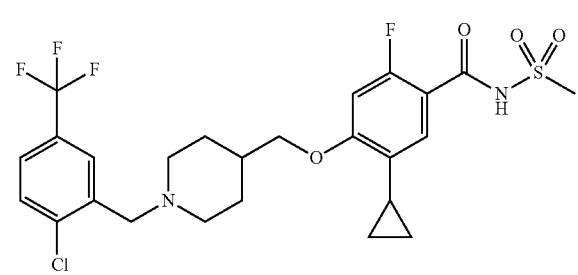
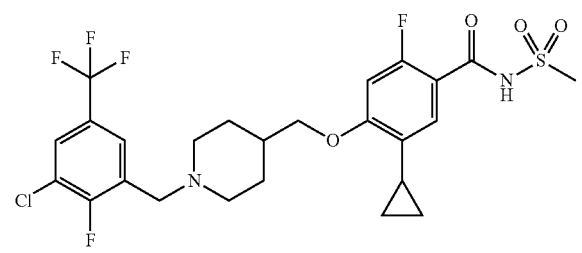
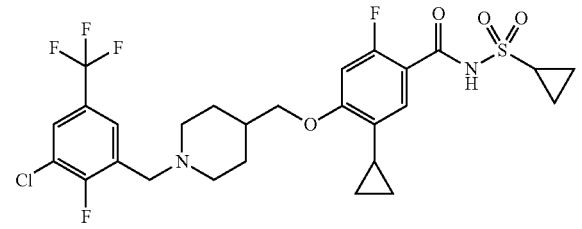
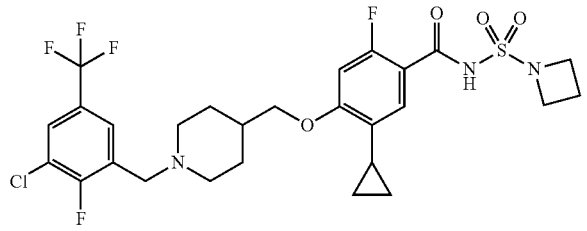
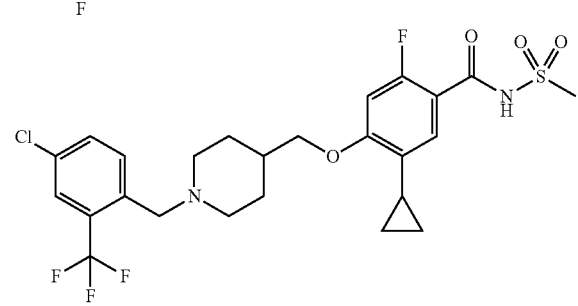
144
-continued
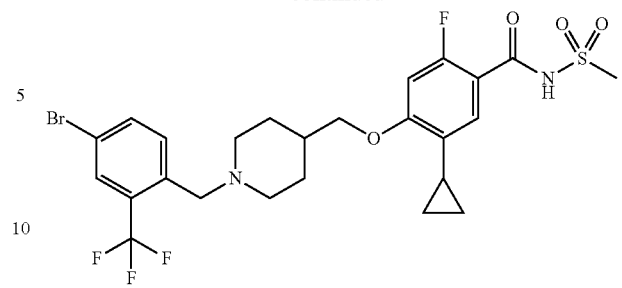
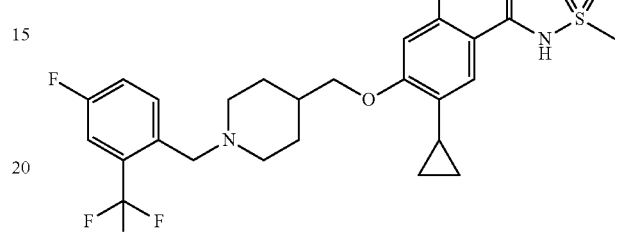
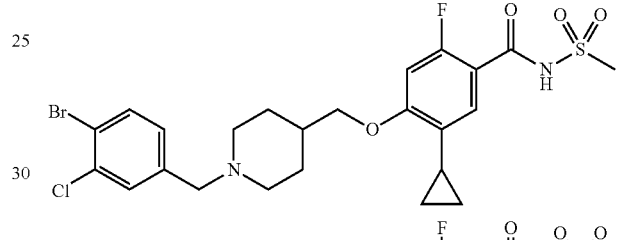
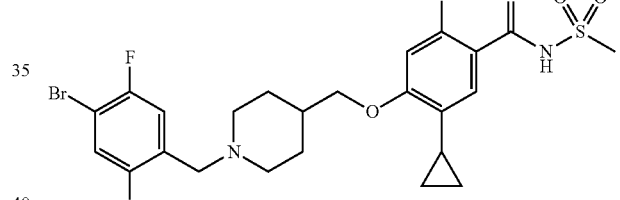
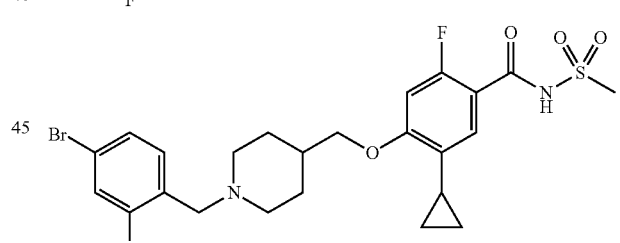
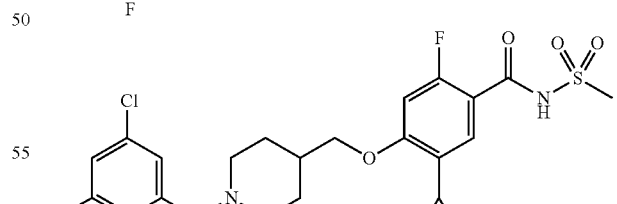
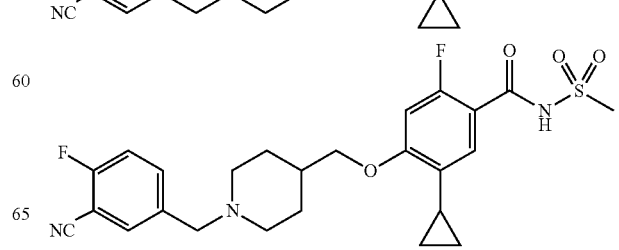

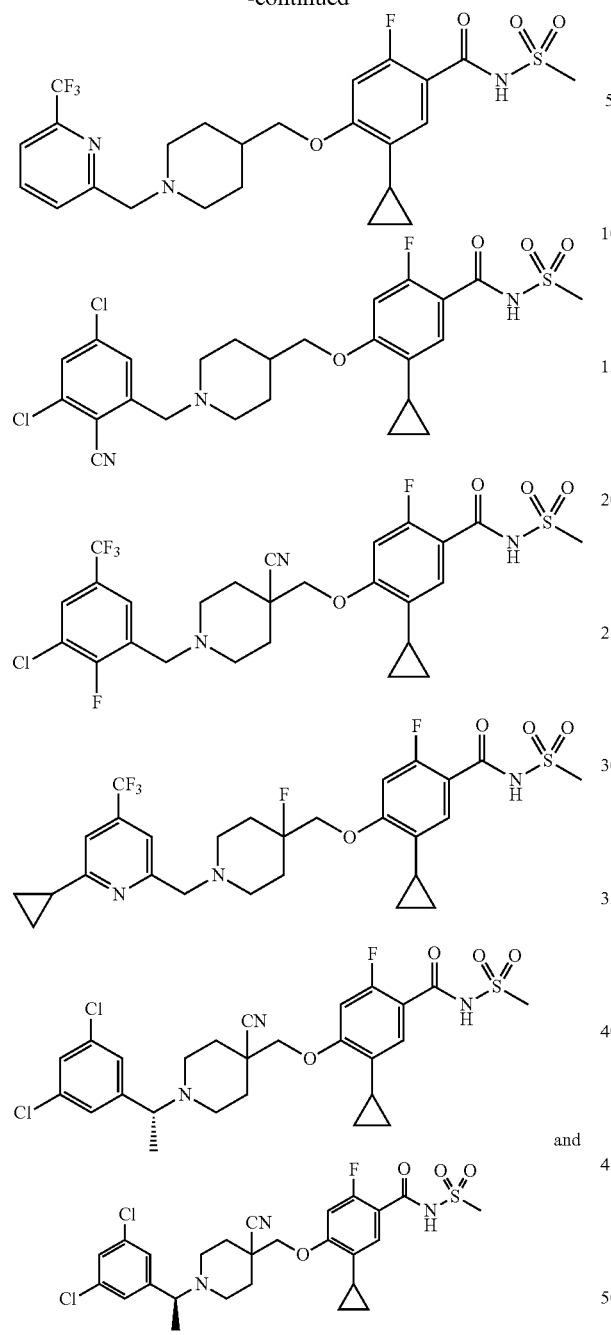
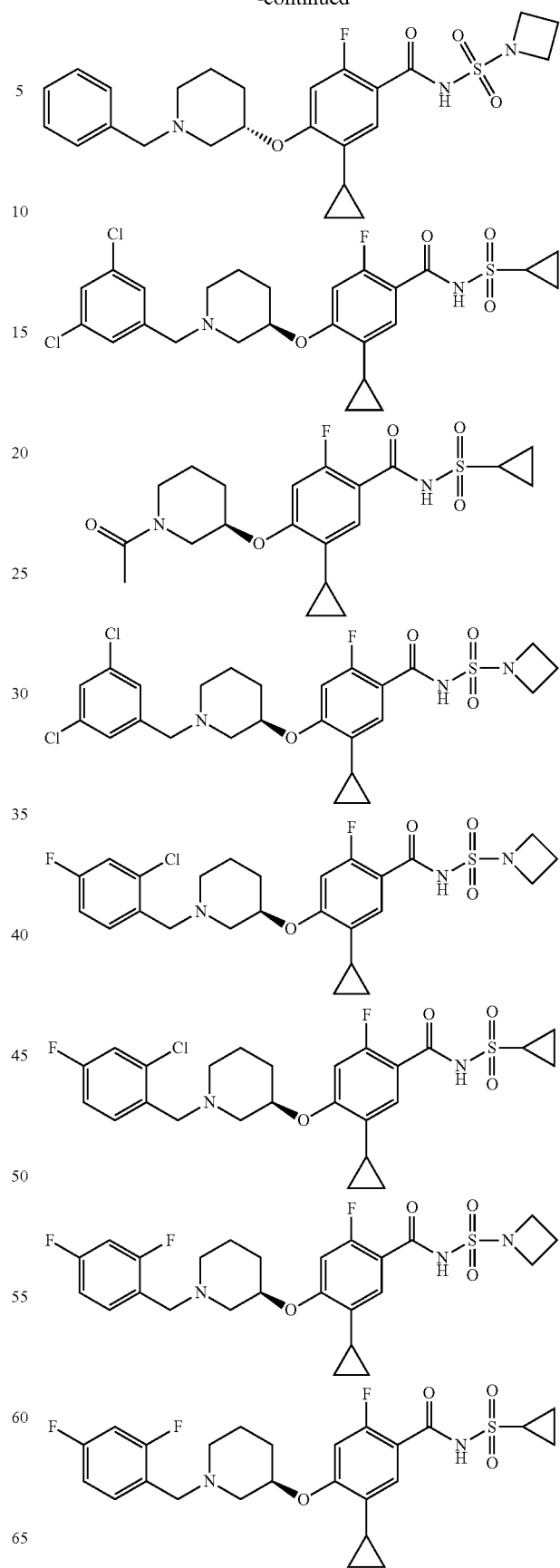
and salts thereof.
E51 The compound of E1, which is selected from:

147
-continued
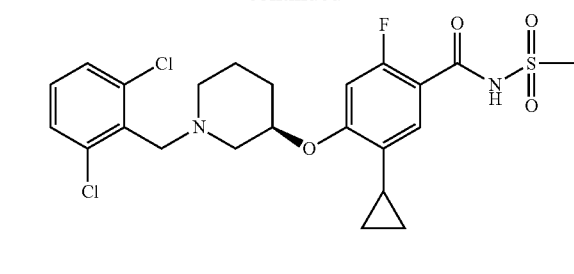
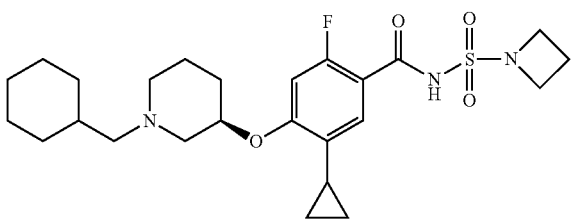
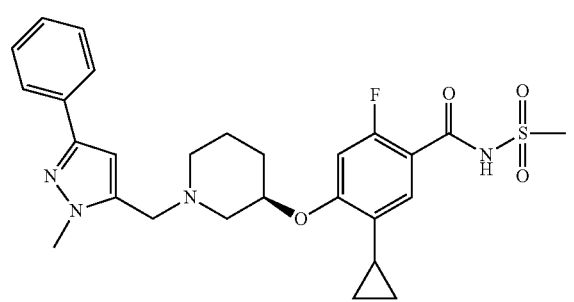
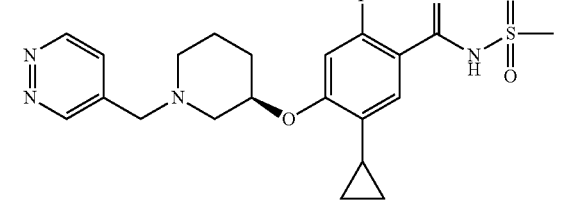
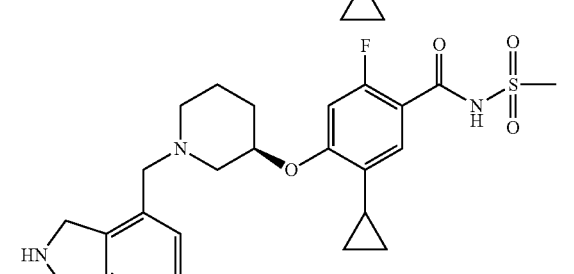
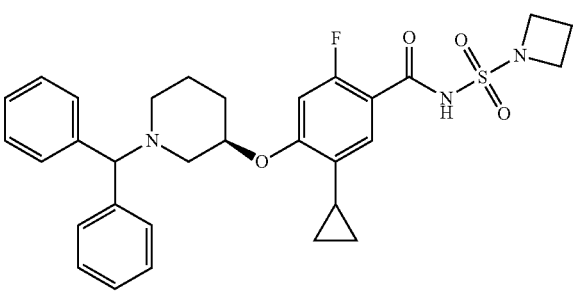
148
-continued
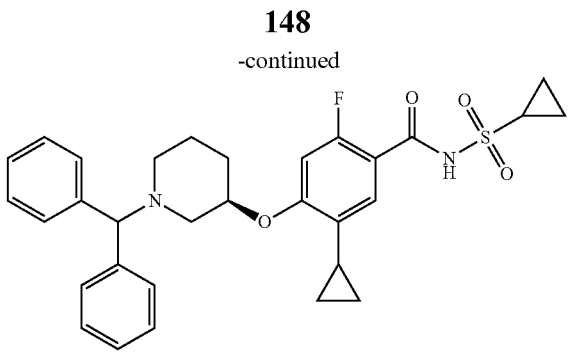
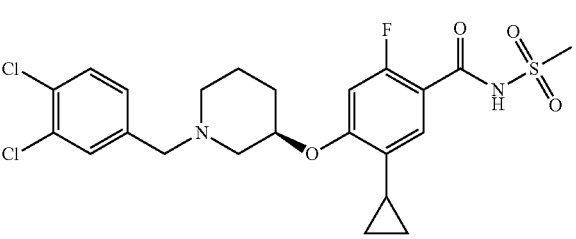
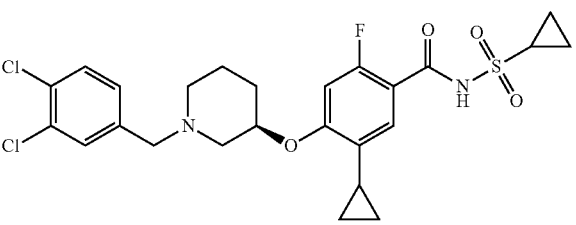
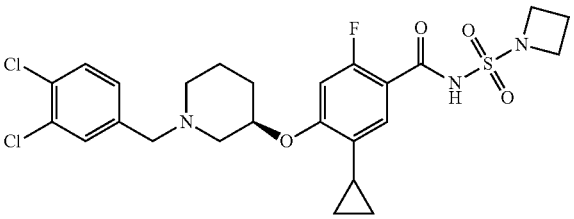
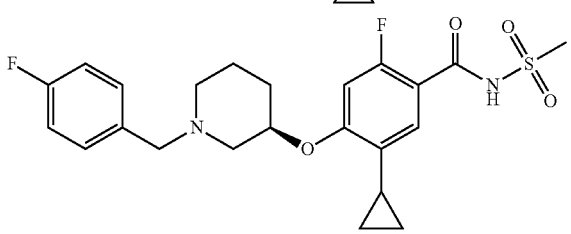
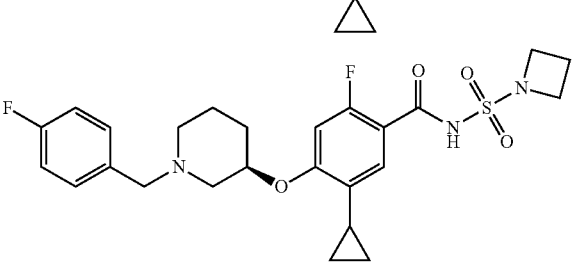

149
-continued
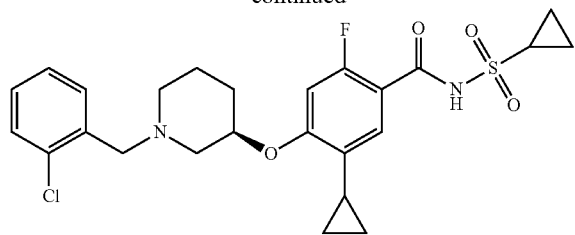
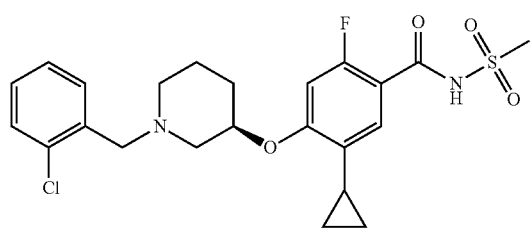
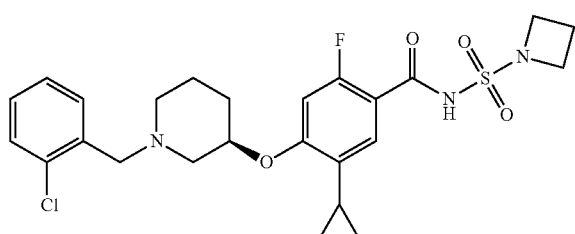
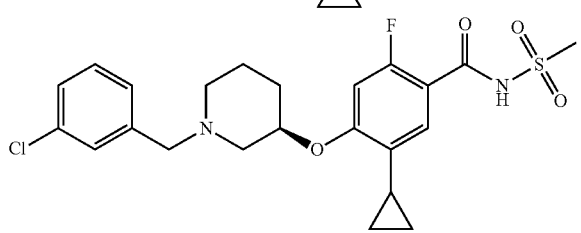
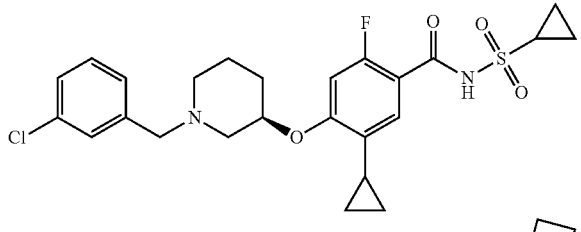
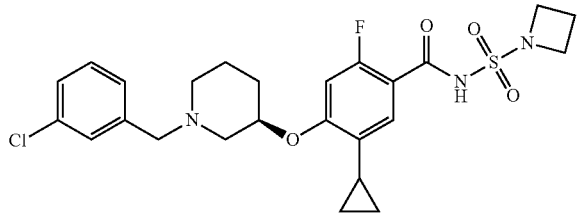
150
-continued
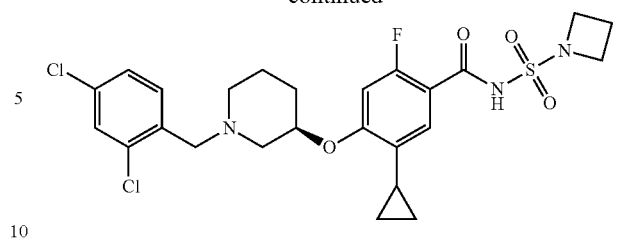
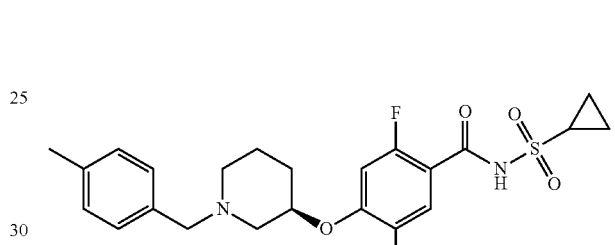
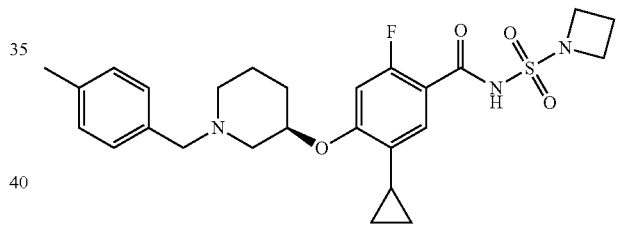
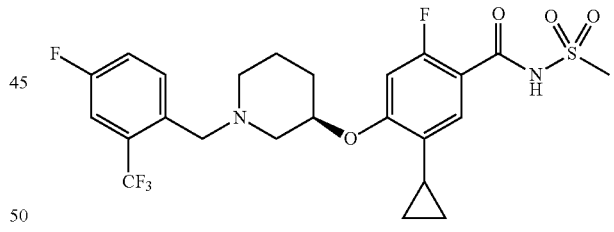
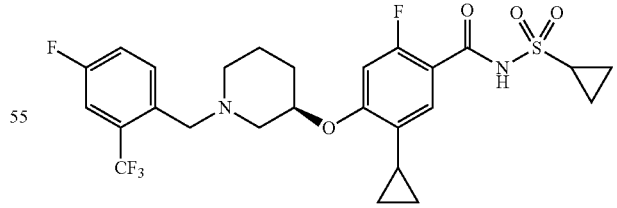

151
-continued
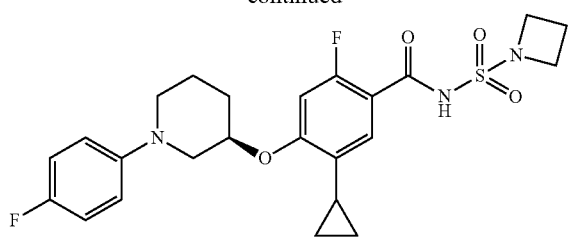
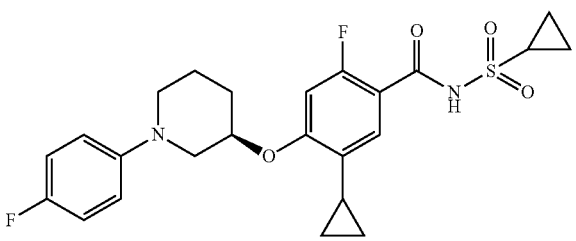
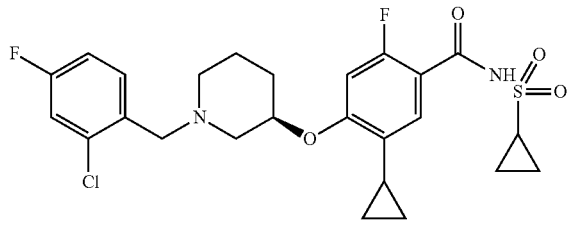
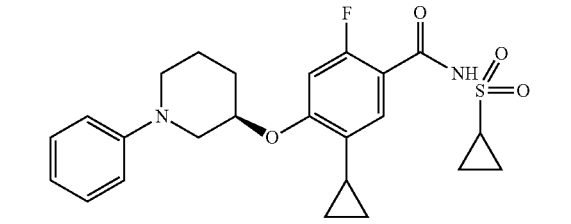
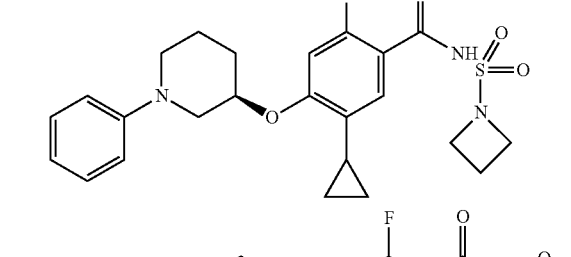

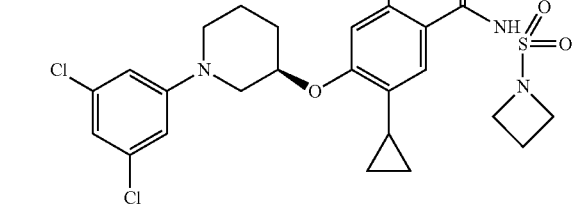
152
-continued
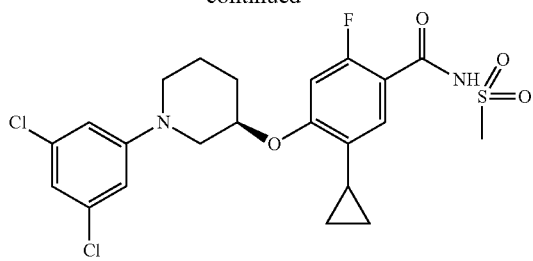
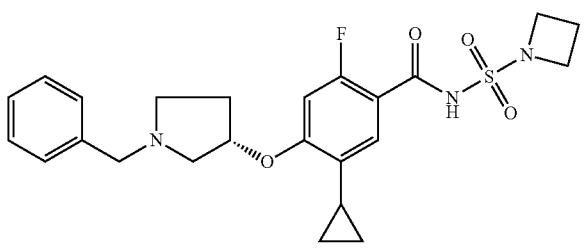
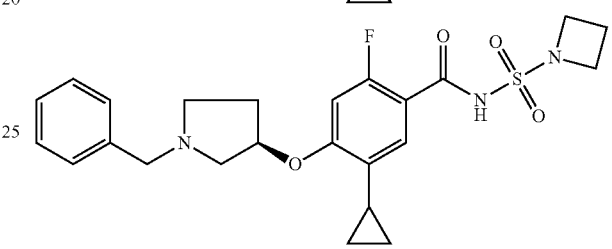
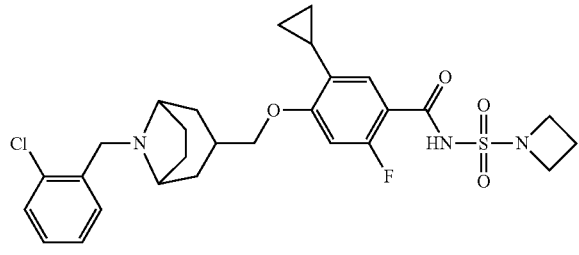
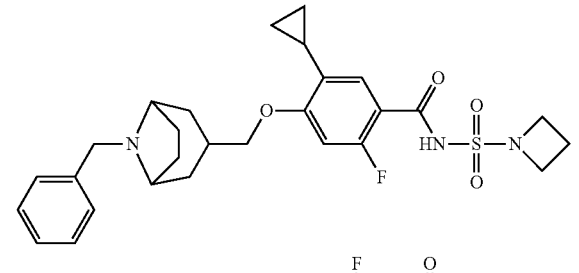
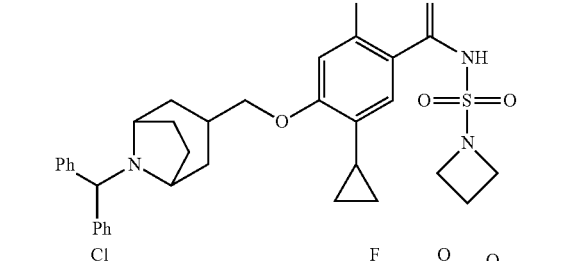
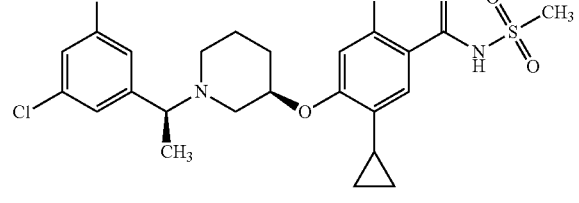

153
-continued
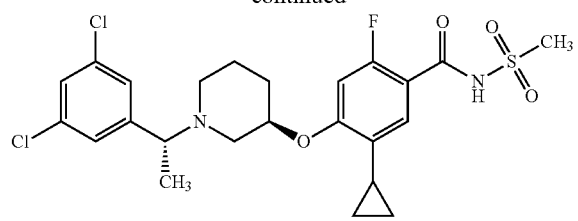
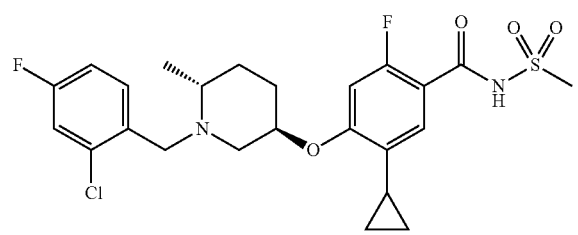
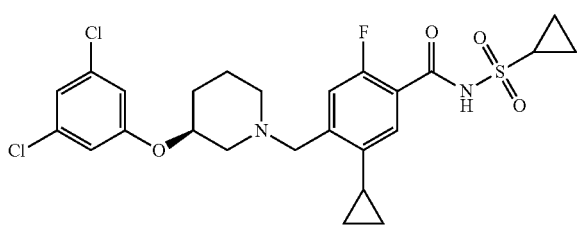
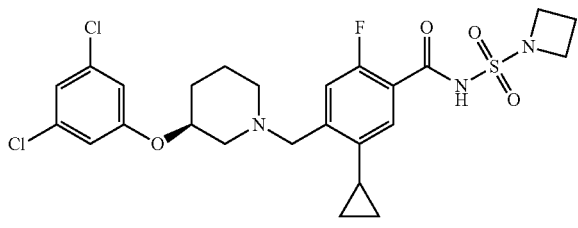
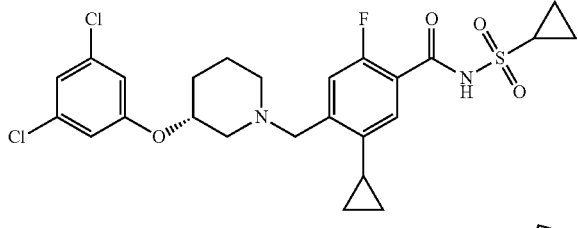
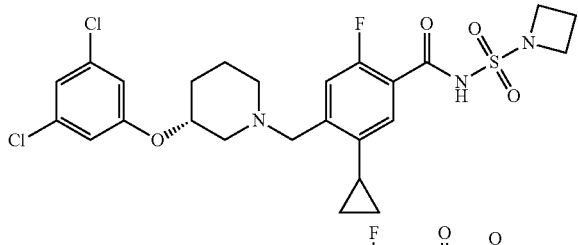
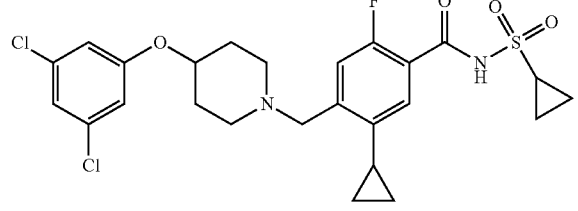
154
-continued
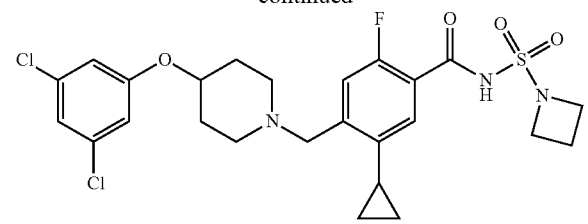
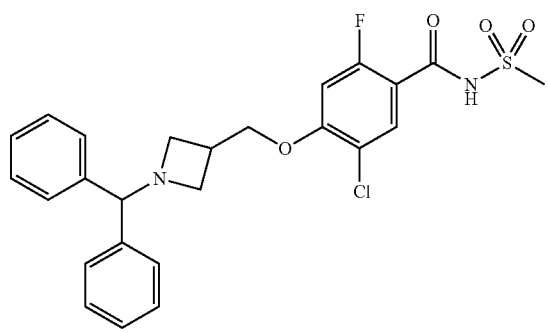
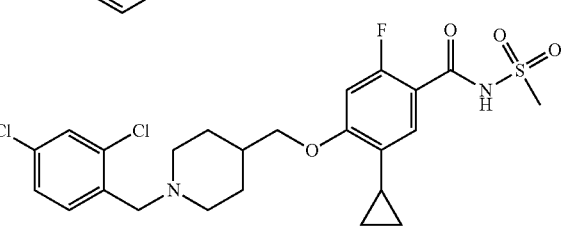
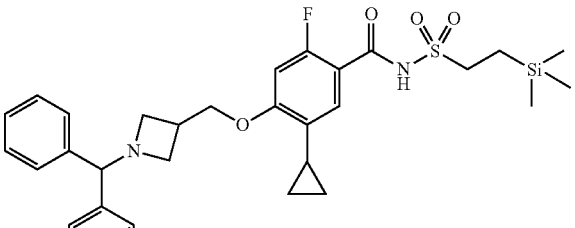
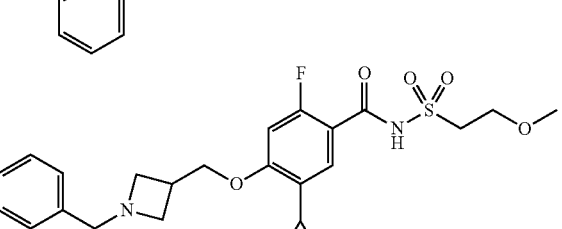
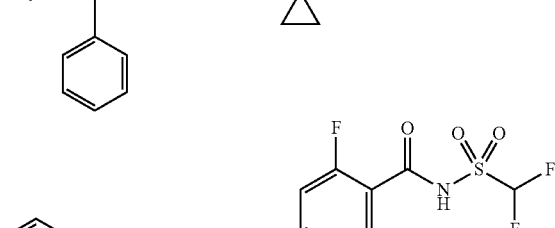

155
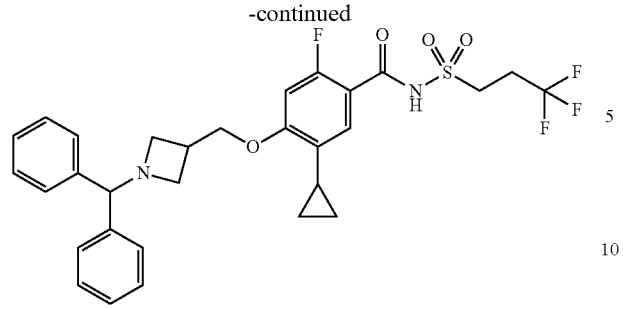
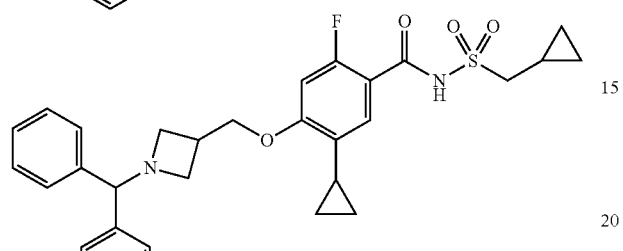
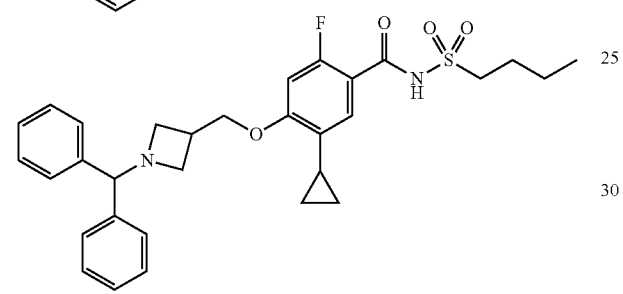
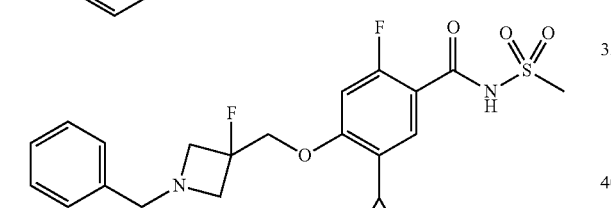
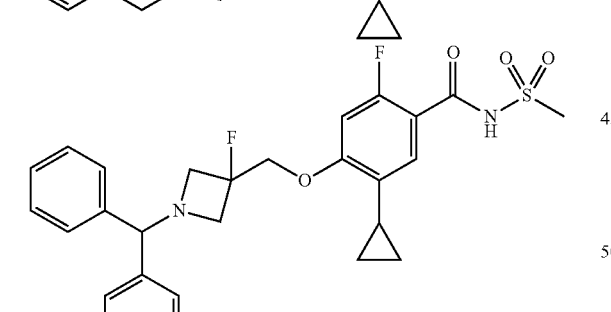
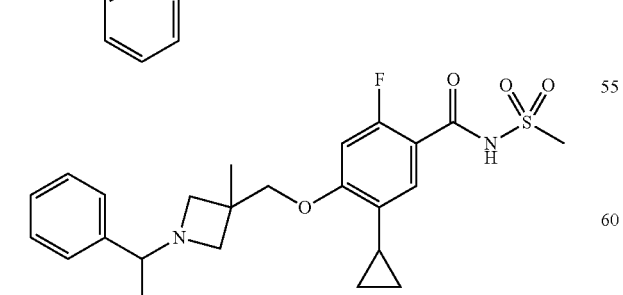
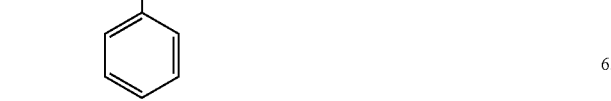
156
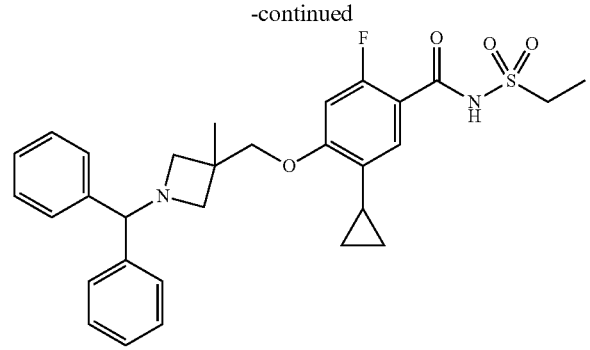
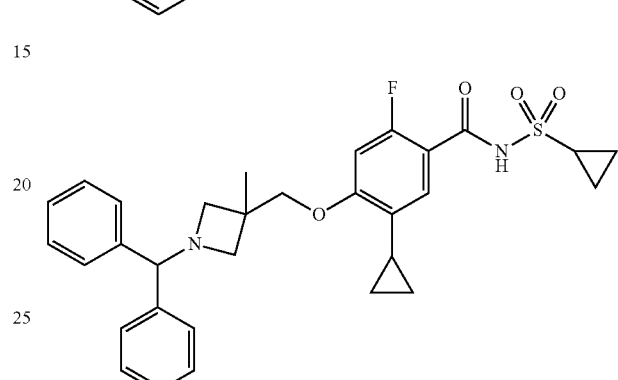
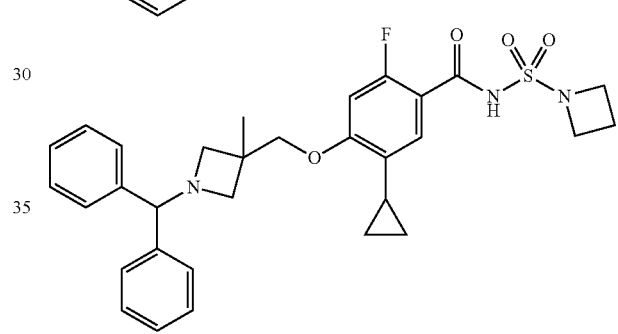
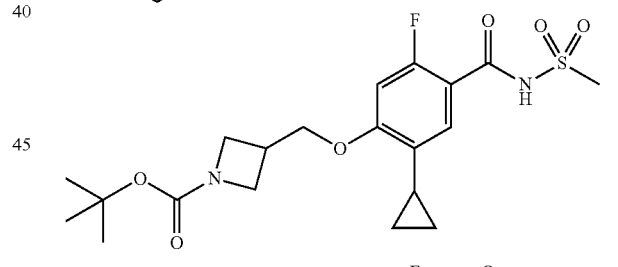
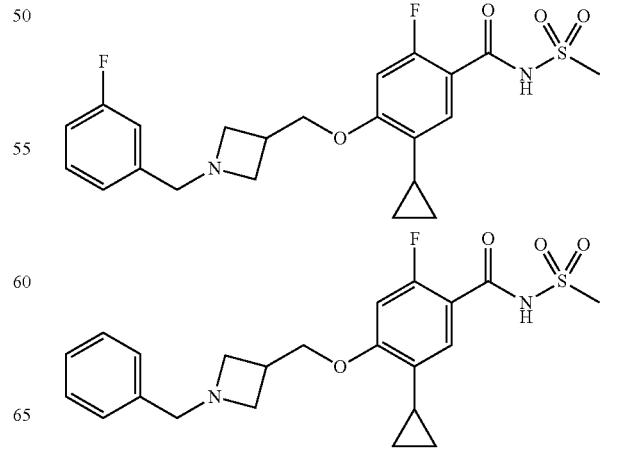

157
-continued
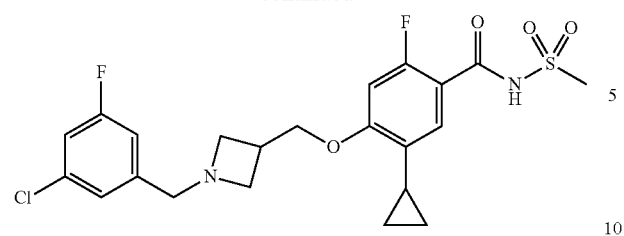
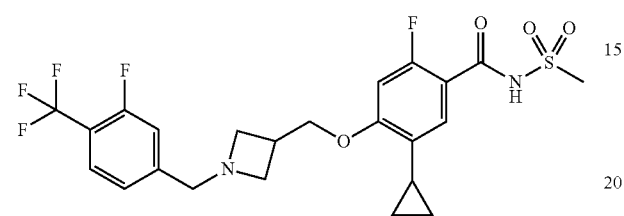
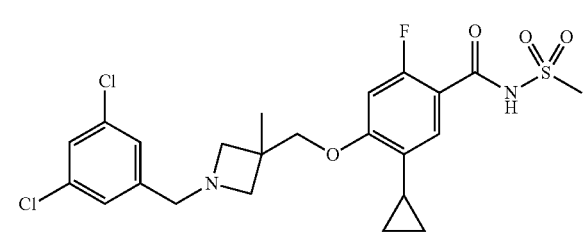
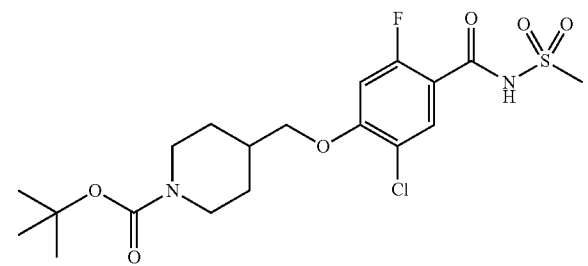
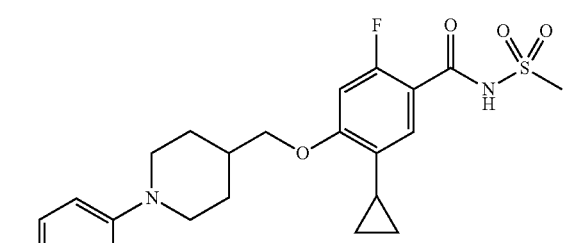
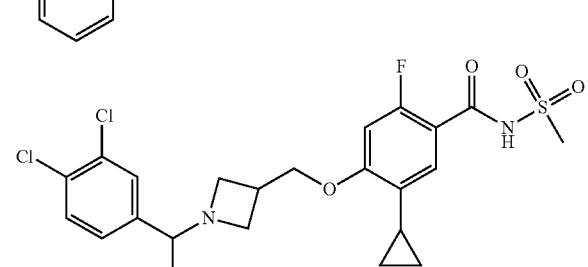
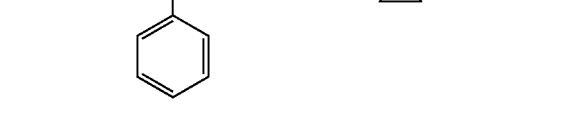
158
-continued
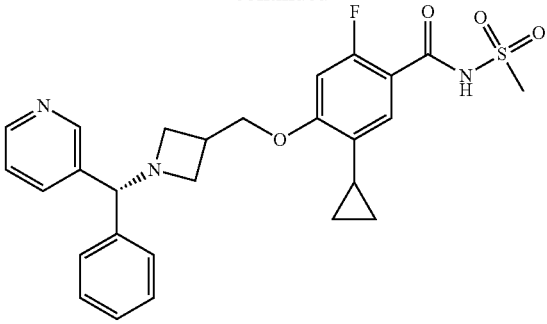
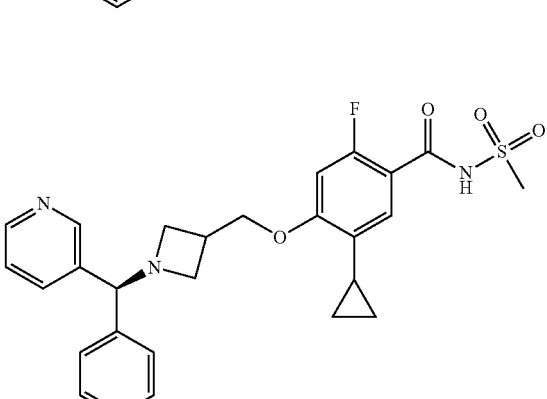
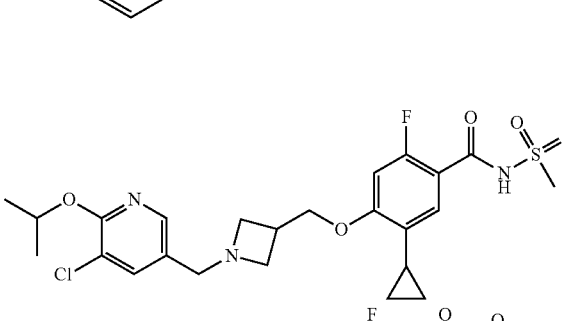
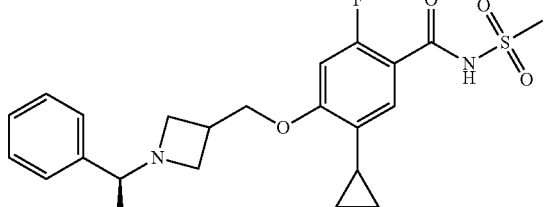
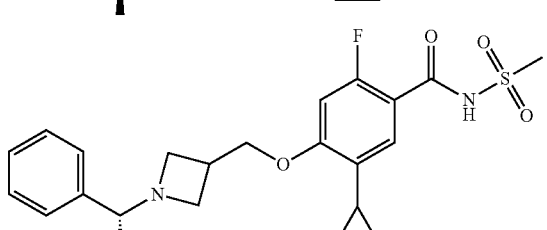
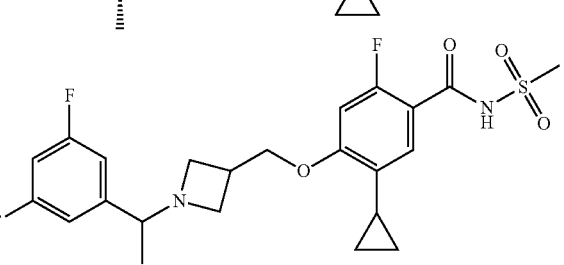

159
-continued
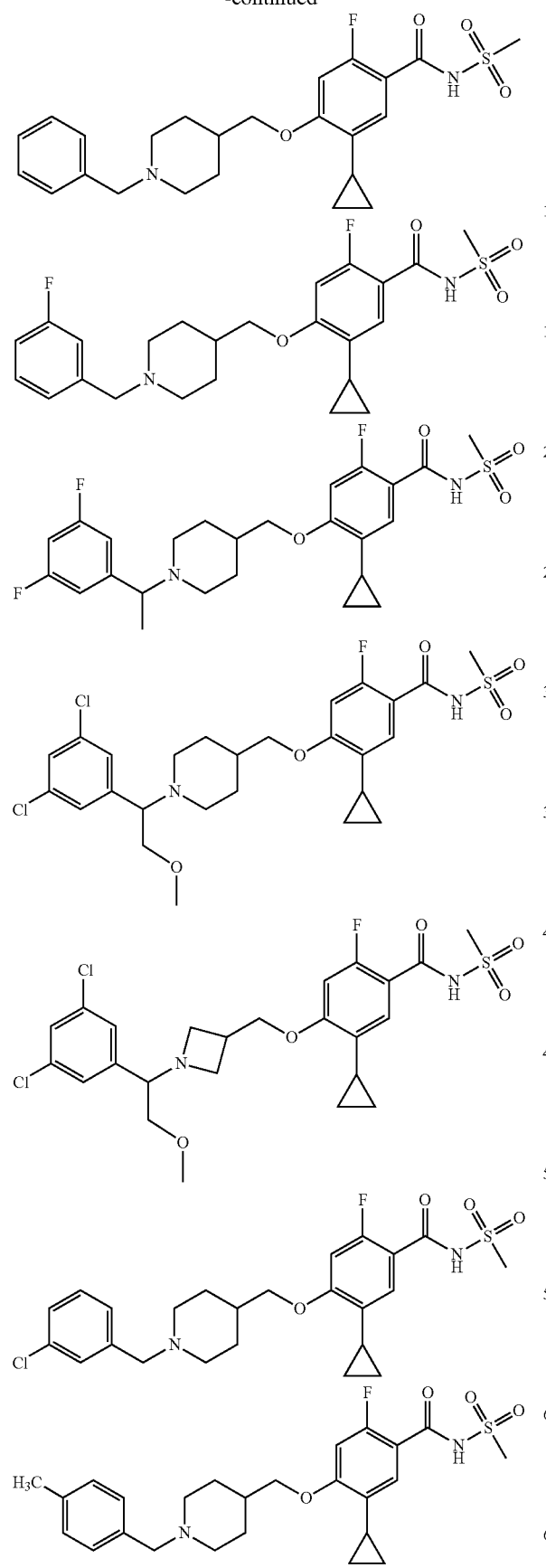
160
-continued
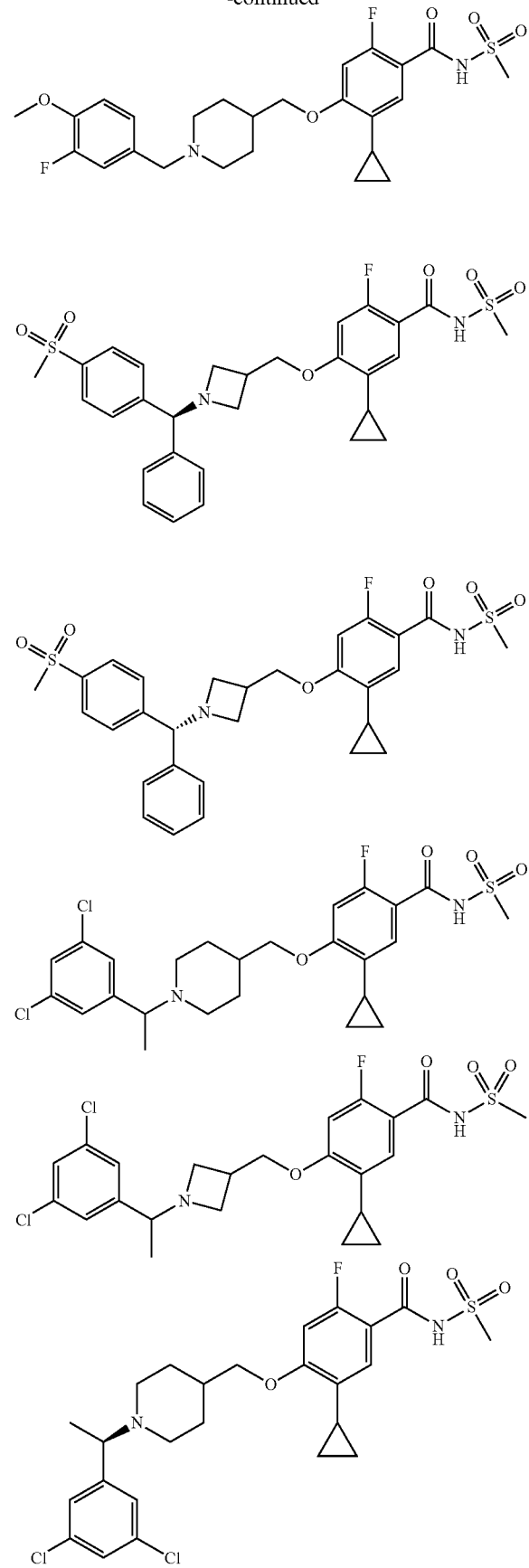

161
-continued
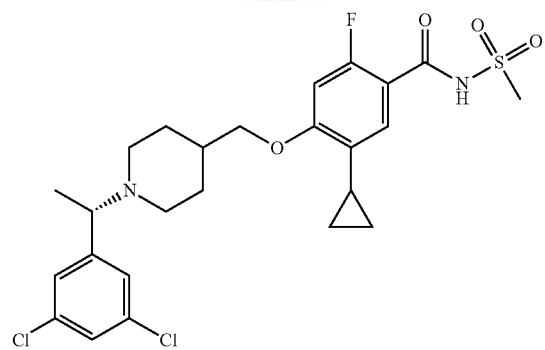
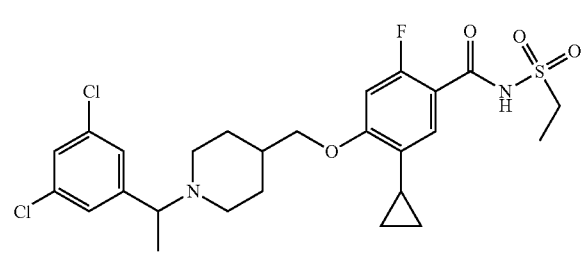
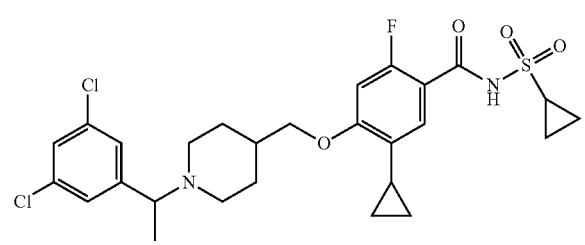
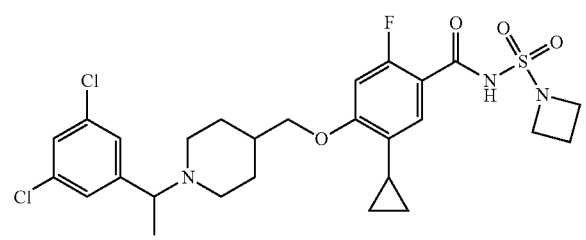
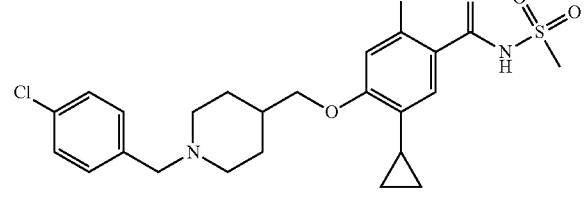
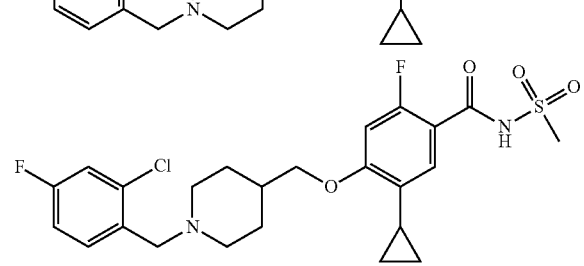
162
-continued
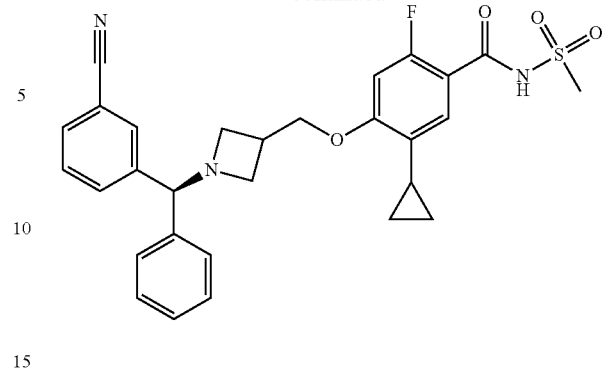
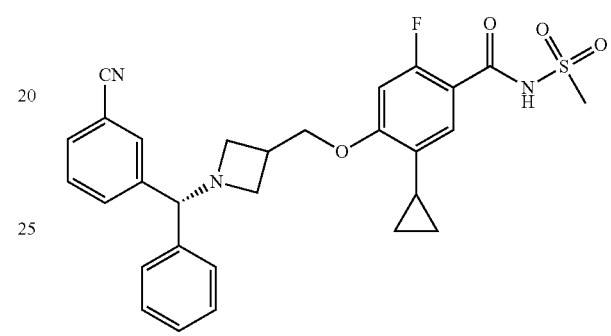
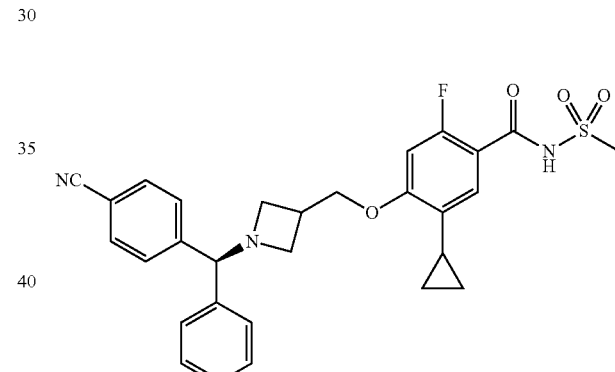
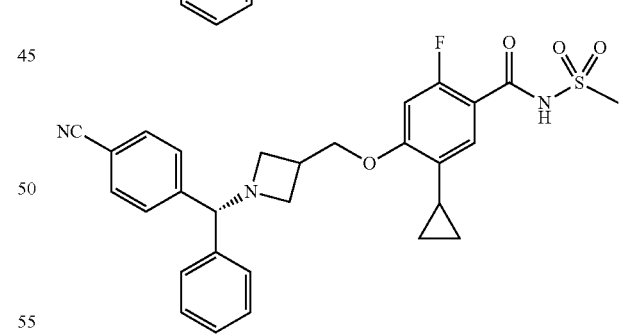
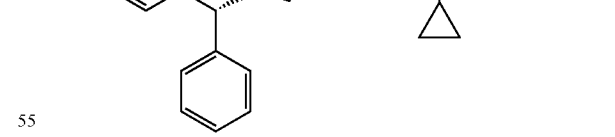
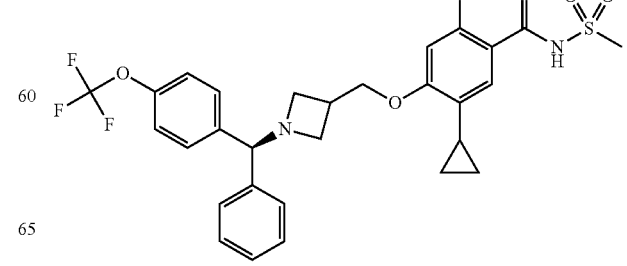

163
-continued
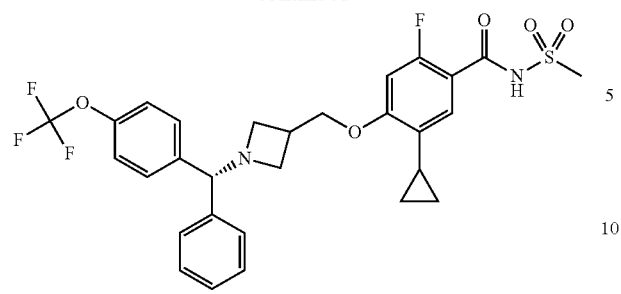
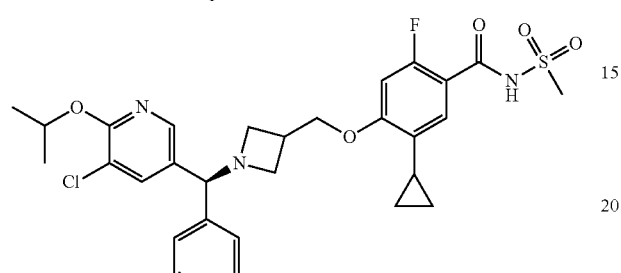
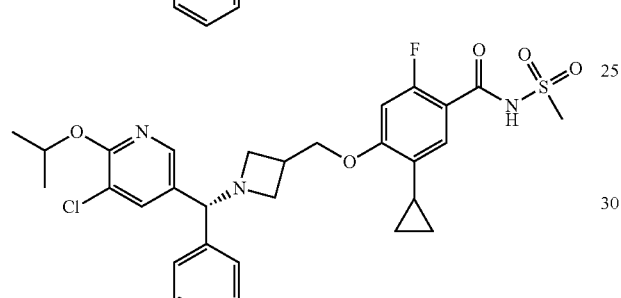
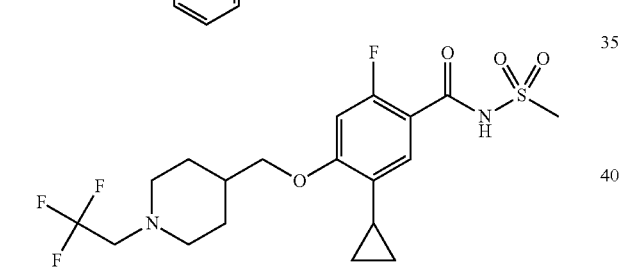
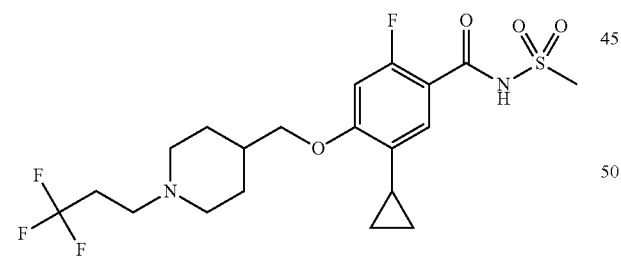
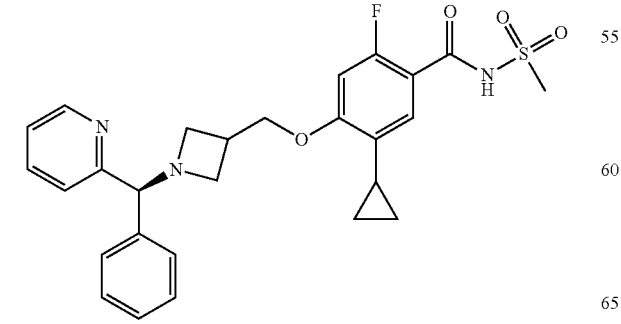
164
-continued
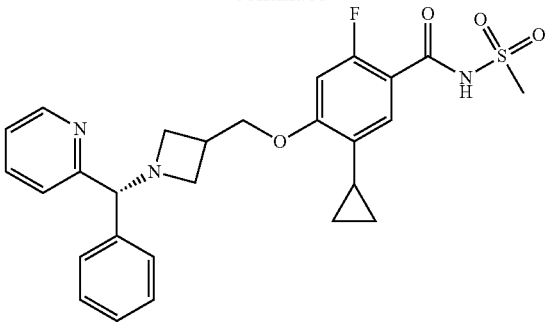
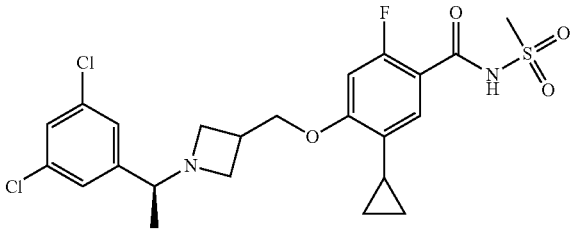
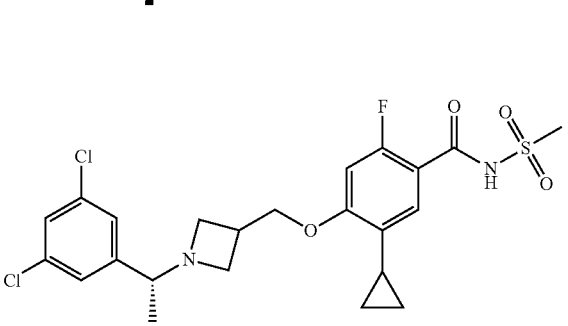
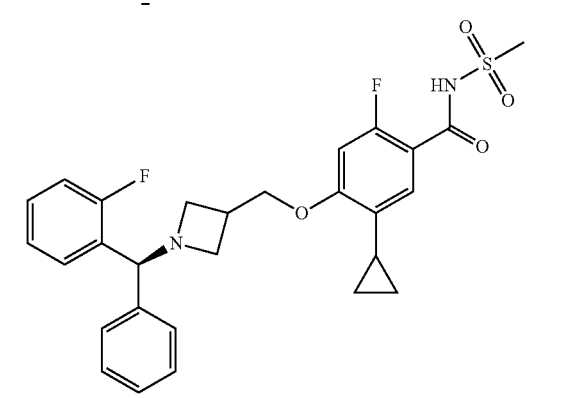
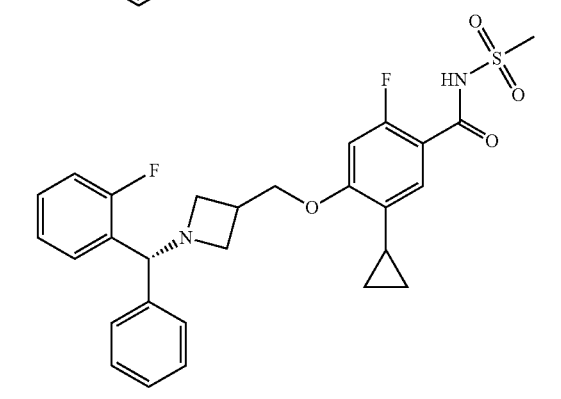

165
-continued
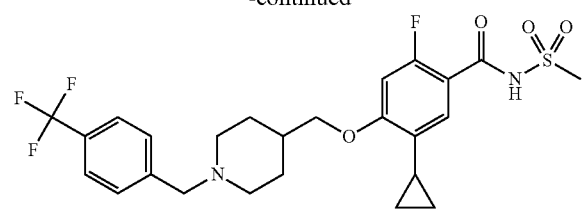
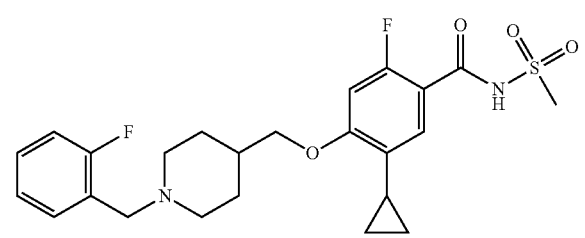
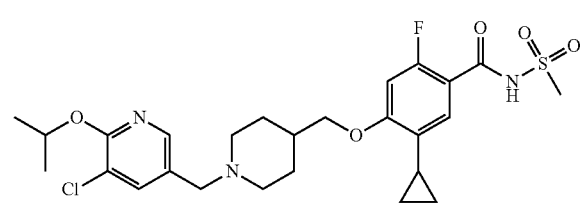
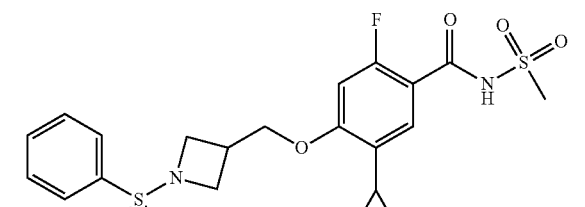
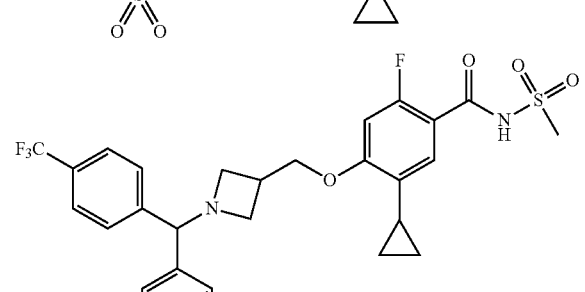
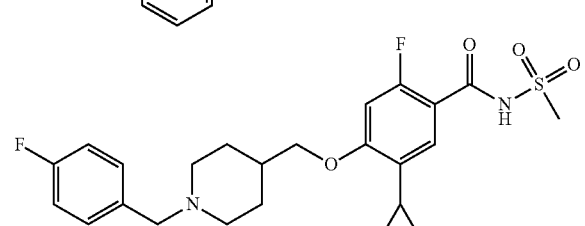
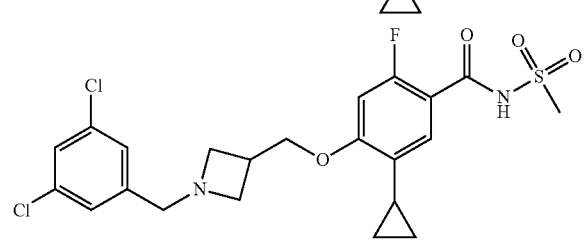
166
-continued
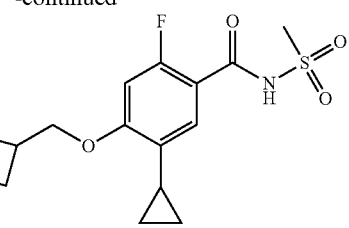
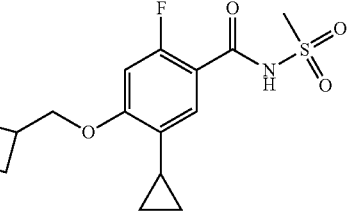
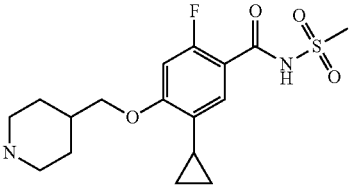
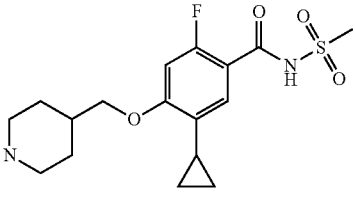
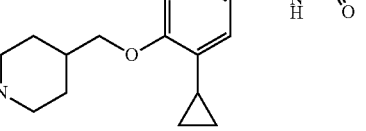
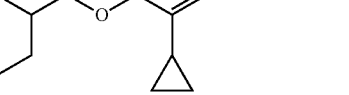
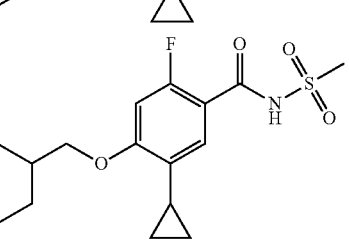

167
-continued
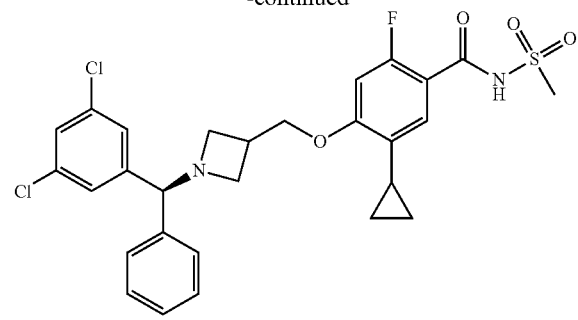
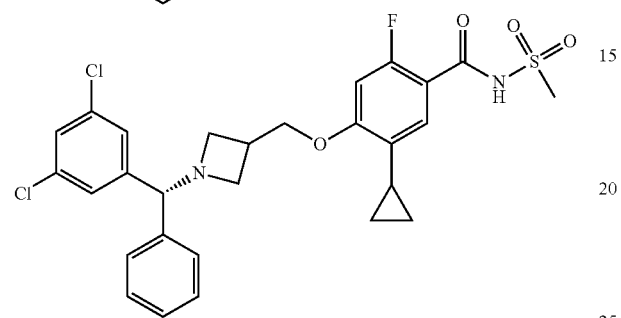
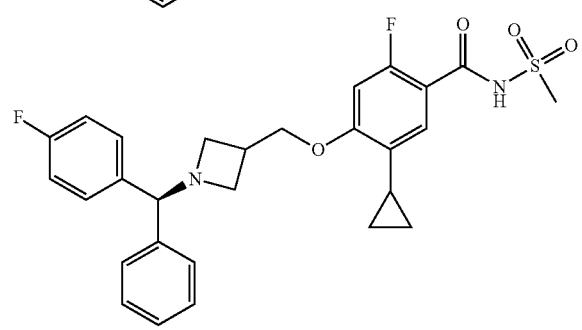
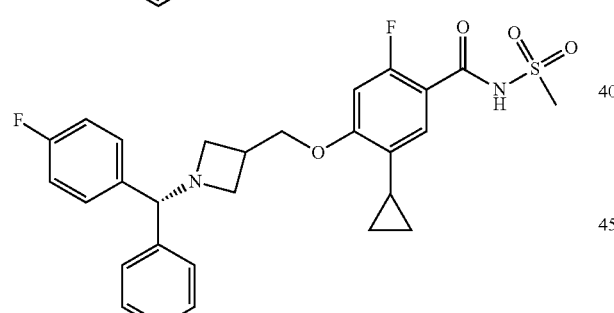
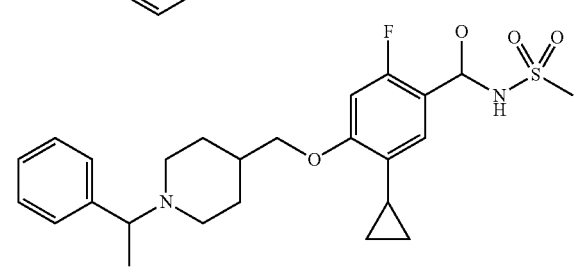
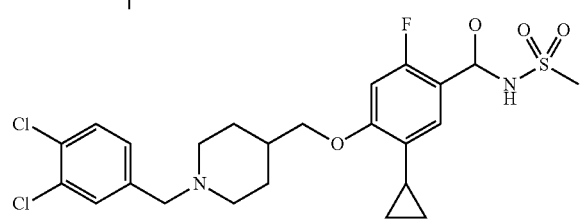
168
-continued
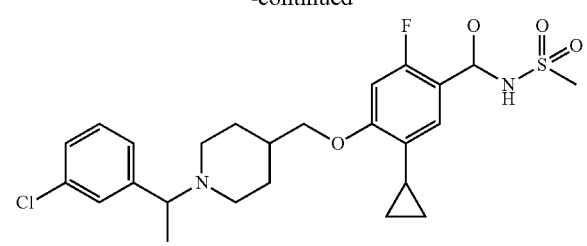
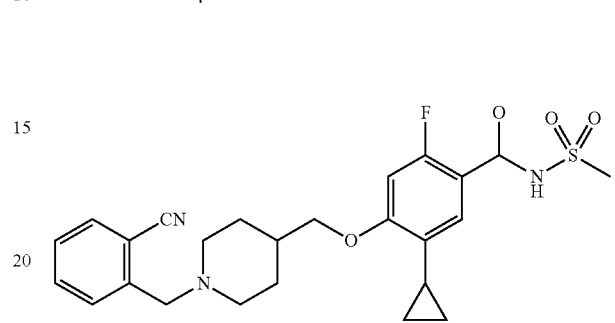
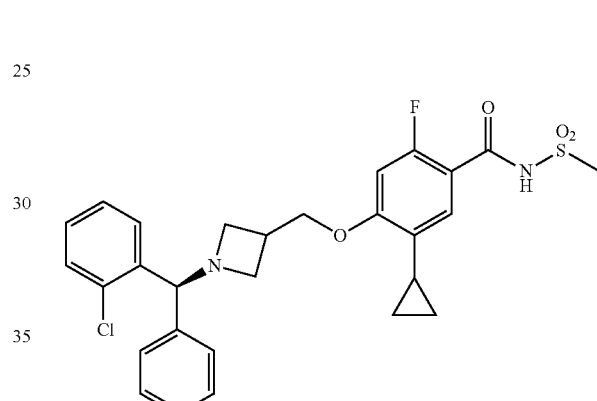
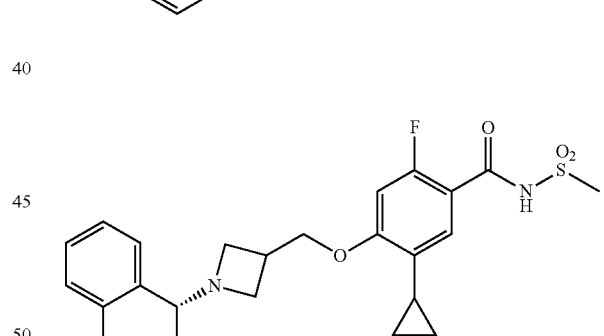
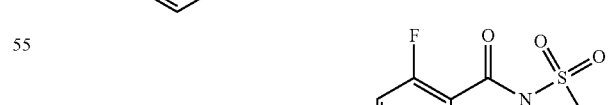
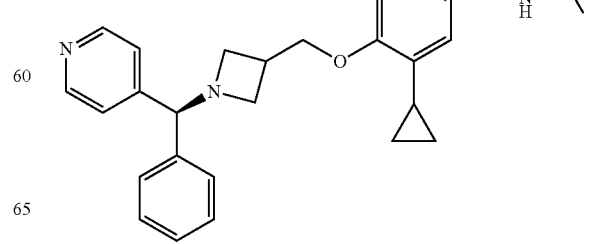

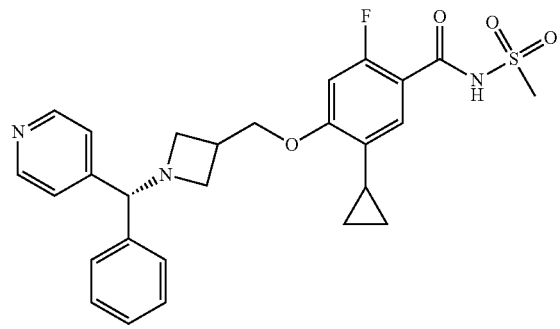
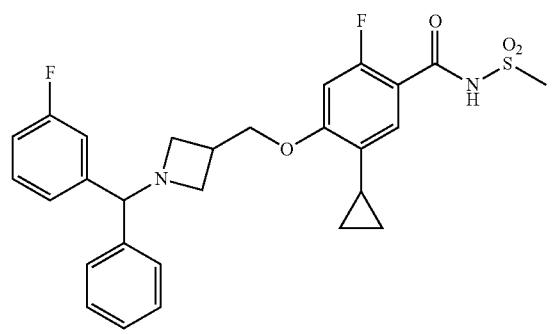
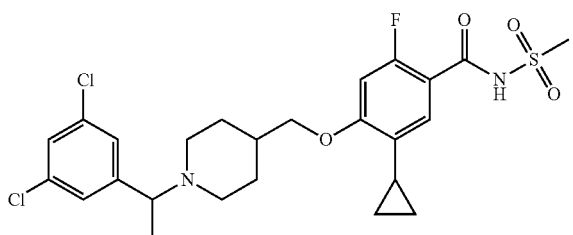
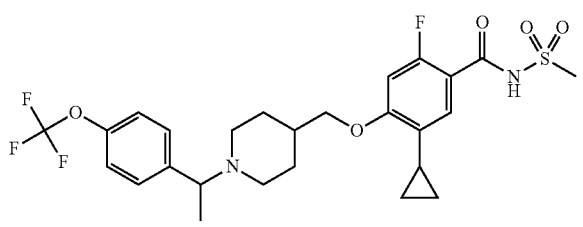
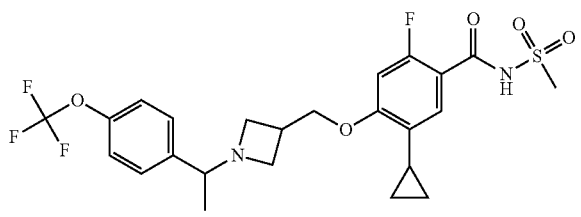
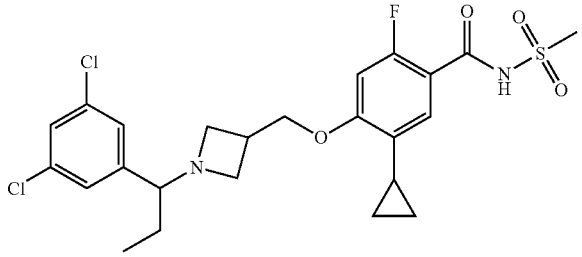
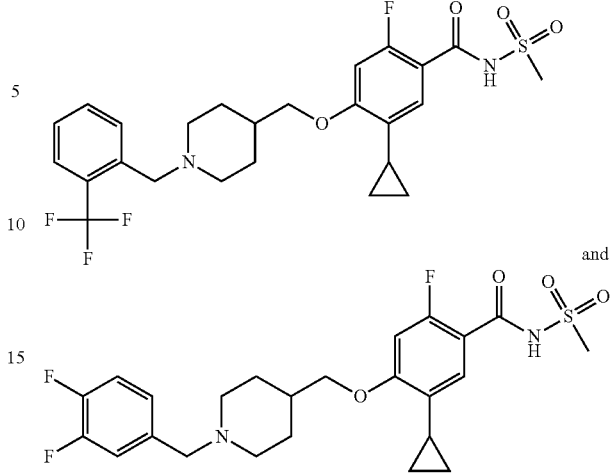

and salts thereof.

E52 The compound of E1, which is selected from the compounds of Examples 162-593 and the free bases and salts thereof.

E53 The compound of claim E1, E2, E3, E4, E5, E6, E7, E8, E9, E10, E11, E12, E13, E14, E15, E16, E17, E18, E19, E20, E21, E22, E23, E24, E25, or E26 wherein $R^A$ is selected from the group consisting of benzyl 3,5-dichlorobenzyl, N-acetylpiperidin-3-yl, 2-chloro-4-fluorobenzyl, 2,4-difluorobenzyl, 2,6-dichlorobenzyl, N-(cyclohexylmethyl)piperidin-3-yl, 1-methyl-3-phenyl-1H-pyrazol-5-ylmethyl, pyridazin-4-ylmethyl, isoindolin-4-ylmethyl, alpha-phenylbenzyl, 3,4-dichlorobenzyl, 4-fluorobenzyl, 2-chlorobenzyl, 3-chlorobenzyl, 2,4-dichlorobenzyl, 4-methylbenzyl, 2-(trifluoromethyl)-4-fluorobenzyl, 4-fluorophenyl, phenyl, 3,5-dichlorphenyl, benzyl, alpha-methyl-3,5-dichlorobenzyl 3,5-dichlorophenoxy, tert-butoxycarbonyl, 3-fluorobenzyl, 3-chloro-5-fluorobenzyl, and 4-(trifluoromethyl)-3-fluorobenzyl.

E54 The compound of E1, E2, E3, E4, E5, E6, E7, E8, E9, E10, E11, E12, E13, E14, E15, E16, E17, E18, E19, E20, E21, E22, E23, E24, E25, or E26 wherein $R^A$ is selected from the group consisting of:

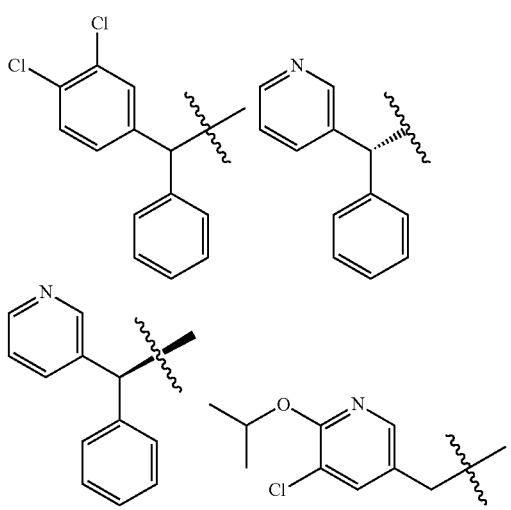

171
-continued
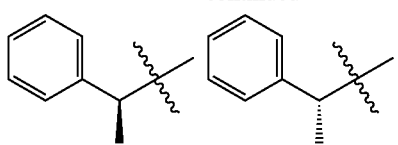
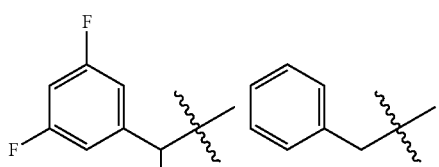
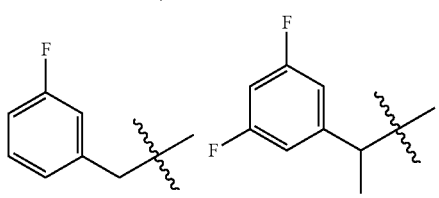
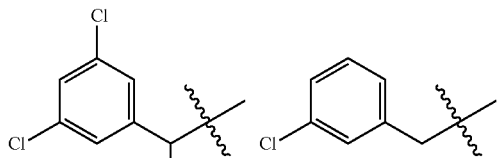
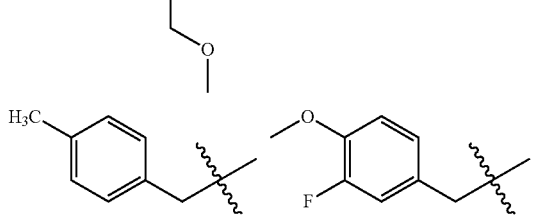
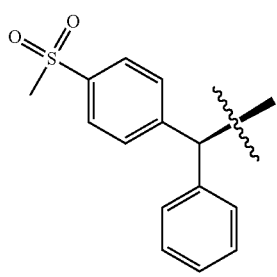
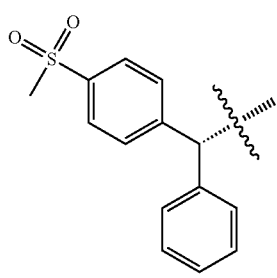
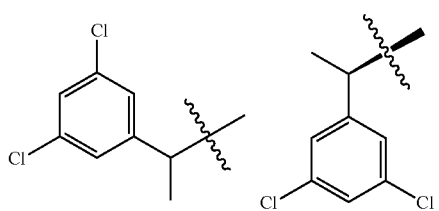
172
-continued
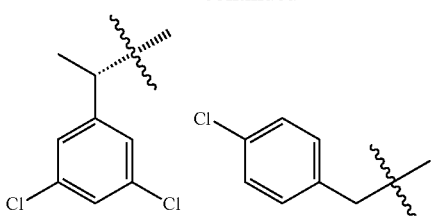
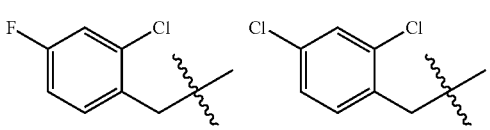
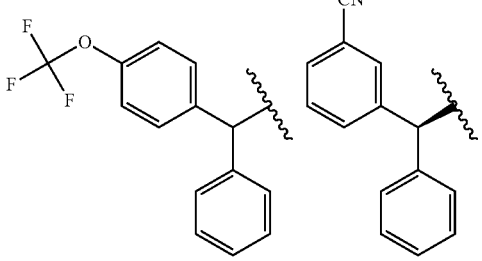
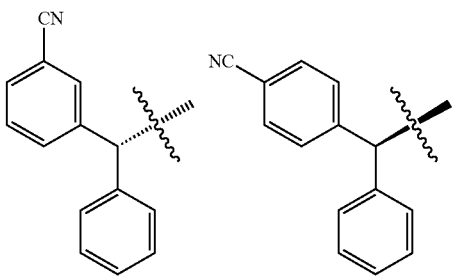
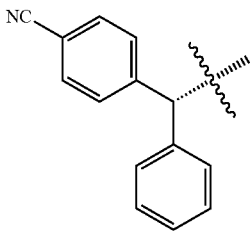
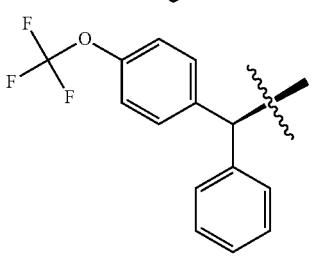
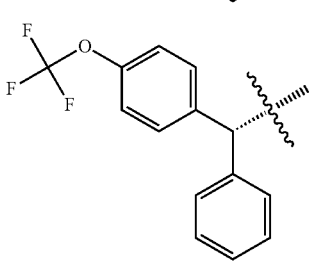

173
-continued
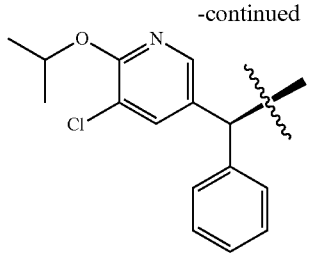
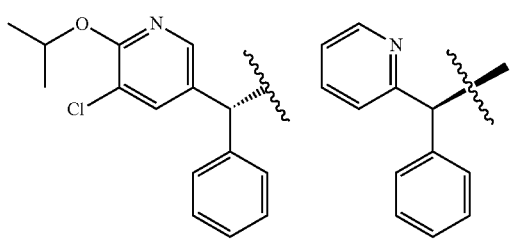
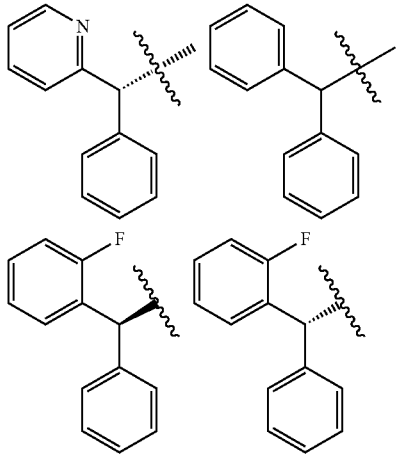
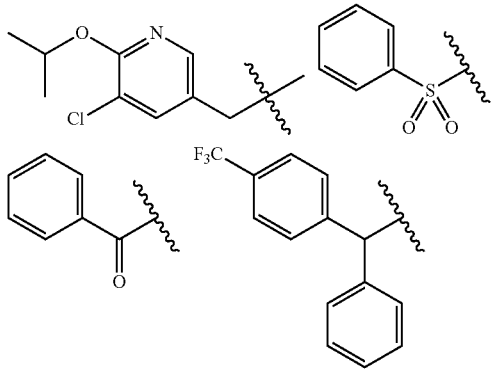
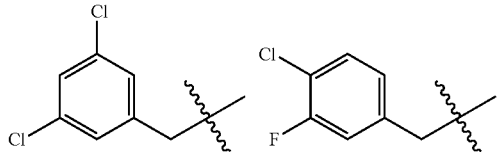
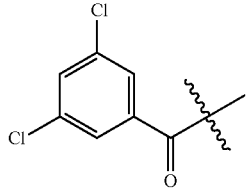
174
-continued
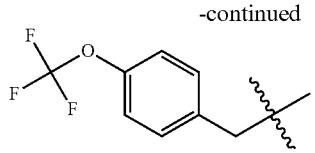
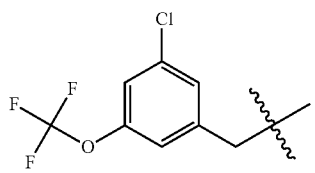
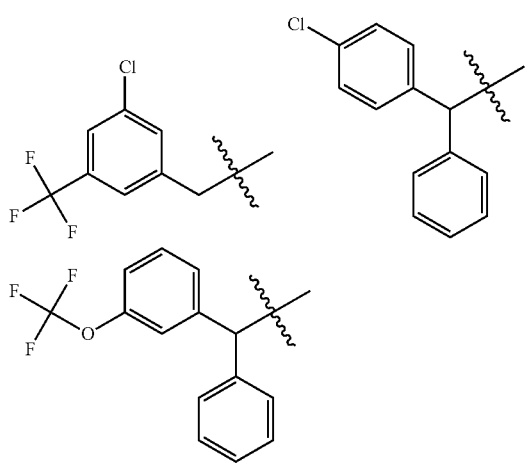
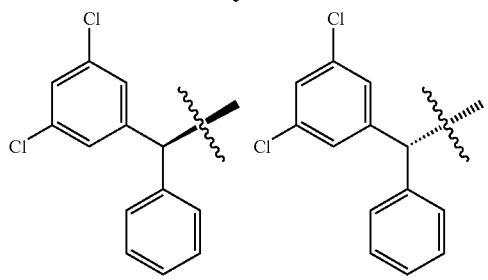
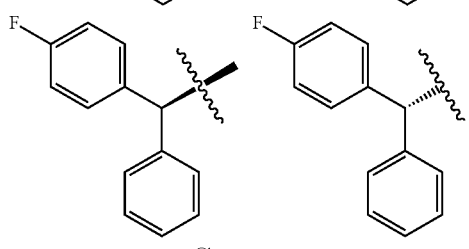
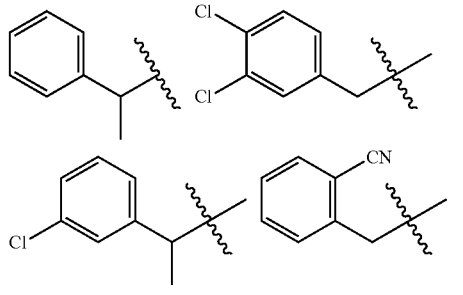

-continued

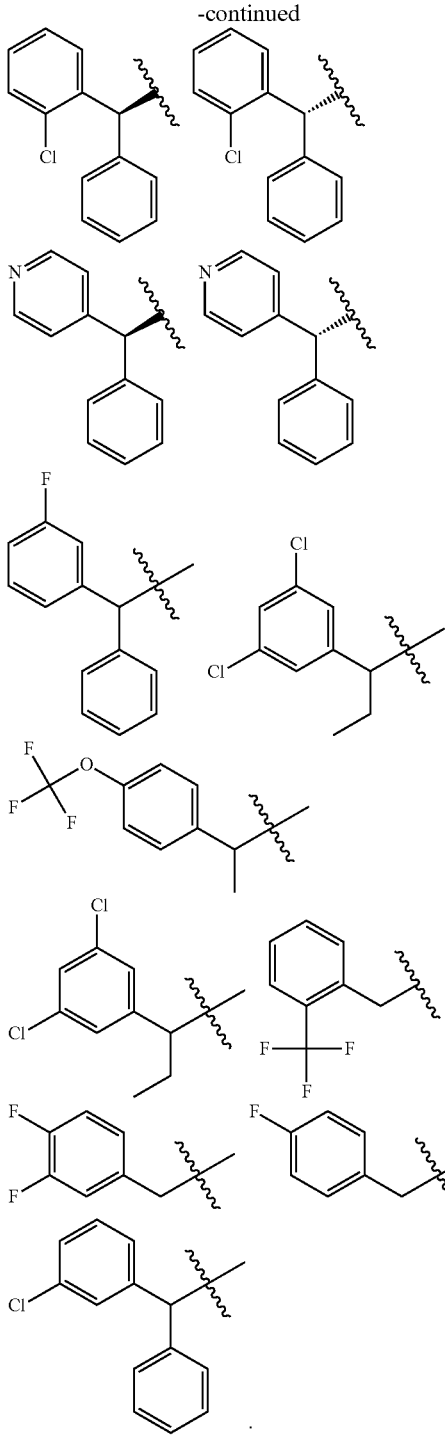

E55 The compound of E1, E2, E3, E4, E5, E6, E7, E8, E9, E10, E11, E12, E13, E14, E15, E16, E17, E18, E19, E20, E21, E22, E23, E24, E25, or E26 wherein $R^A$ is $C_{6-10}$aryl-$(X^{RA})$—, wherein said $C_{6-10}$aryl, of $R^A$ is optionally substituted with from 1 to 5 substituted selected from, F, Cl, Br, I, —NH$_2$, —OH, —CN, —NO$_2$, $C_{1-4}$alkyl, $C_{1-4}$haloalkyl, $C_{1-4}$alkoxy, $C_{1-4}$(halo)alkoxy, $C_{1-4}$alkylamino, $C_{1-4}$dialkylamino, phenyl, $C_{1-4}$alkanoyl, $C_{1-4}$alkyl-OC(=O)—, $C_{1-4}$alkyl-S(O)$_2$—, and $C_{3-6}$carbocycle; and $X^{RA}$ is $C_{1-4}$alkylene that is optionally substituted with 1 to 3 substituents selected from the group consisting of $C_{1-4}$alkyl, $C_{1-4}$haloalkyl, $C_{1-4}$heteroalkyl, oxo (=O), and phenyl that is optionally substituted with 1 to 5 substitutents selected from, F, Cl, Br, I, —NH$_2$, —OH, —CN, —NO$_2$, $C_{1-4}$alkyl, $C_{1-4}$haloalkyl, $C_{1-4}$alkoxy, $C_{1-4}$(halo)alkoxy, $C_{1-4}$alkylamino and $C_{1-4}$dialkylamino.

E56 The compound of E1, E2, E3, E4, E5, E6, E7, E8, E9, E10, E11, E12, E13, E14, E15, E16, E17, E18, E19, E20, E21, E22, E23, E24, E25, or E26 wherein $R^A$ is

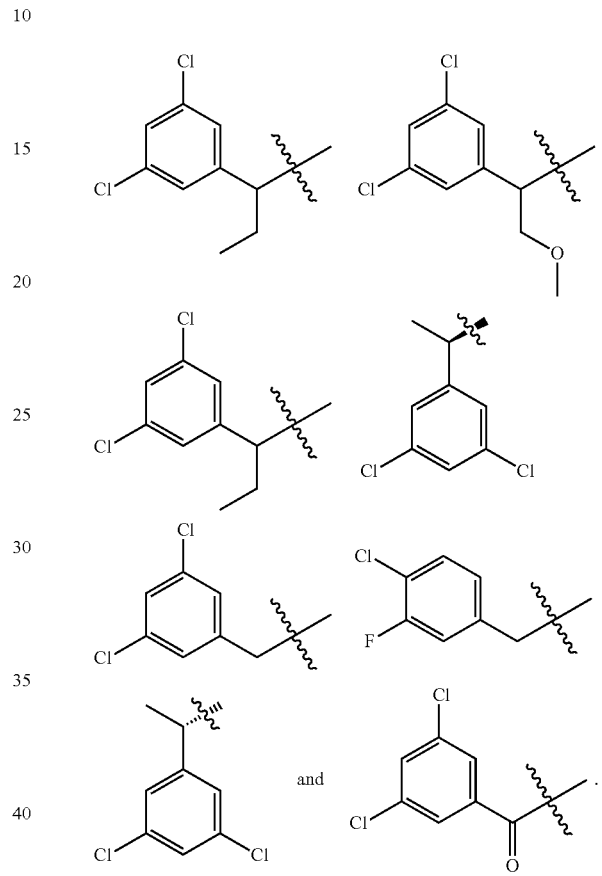

E57 The compound of E1, E2, E3, E4, E5, E6, E7, E8, E9, E10, E11, E12, E13, E14, E15, E16, E17, E18, E19, E20, E21, E22, E23, E24, E25, or E26 wherein $R^A$ is

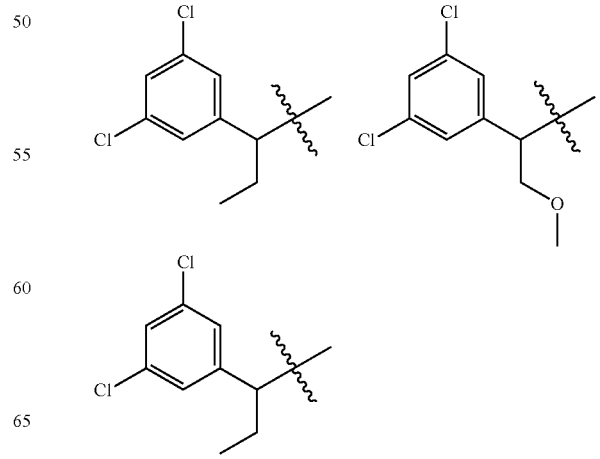

177
-continued

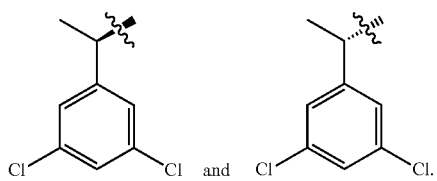

E58 The compound of E1, E2, E3, E4, E5, E6, E7, E8, E9, E10, E11, E12, E13, E14, E15, E16, E17, E18, E19, E20, E21, E22, E23, E24, E25, E26, E37, E38, E39, E40, E41, E42, E43, E44, E45, E46, or E47 wherein $R^A$ is

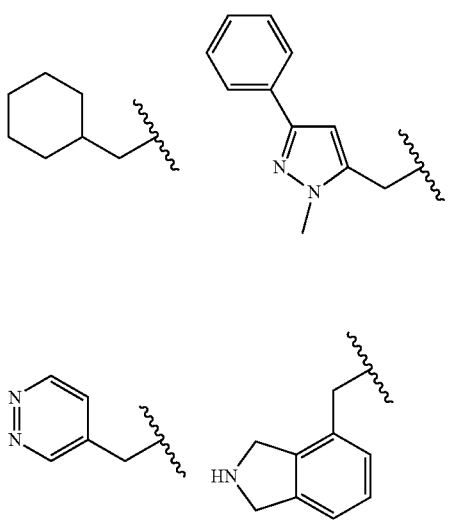

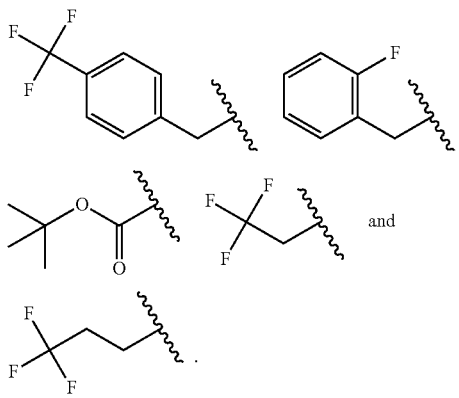

E59 The compound of E1, which is selected from:

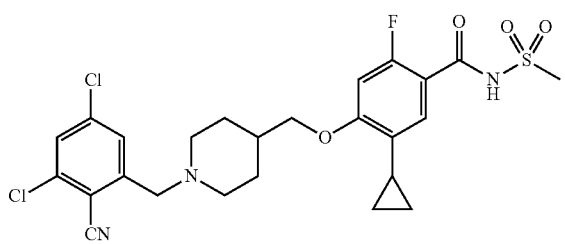

178
-continued

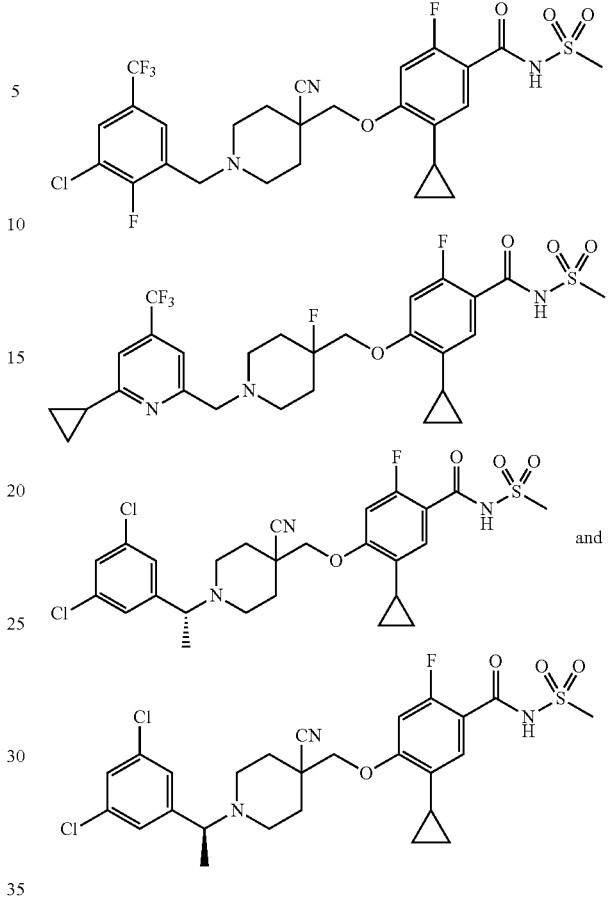

and salts thereof.

In another aspect the present invention provides for a pharmaceutical composition comprising a compound of formula I or a pharmaceutically acceptable salt thereof, and a pharmaceutically acceptable excipient.

In another aspect the present invention, provides for a method of treating a disease or condition in a mammal selected from the group consisting of pain, depression, cardiovascular diseases, respiratory diseases, and psychiatric diseases, and combinations thereof, wherein the method comprises administering to the mammal in need thereof a therapeutically effective amount of a compound of formula I, or a pharmaceutically acceptable salt thereof. In another aspect of the present invention said disease or condition is selected from the group consisting of neuropathic pain, inflammatory pain, visceral pain, cancer pain, chemotherapy pain, trauma pain, surgical pain, post-surgical pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, dental pain, peripheral nerve injury or a combination thereof, in another aspect of the present invention said disease or condition is selected from the group consisting of pain associated with HIV, HIV treatment induced neuropathy, trigeminal neuralgia, post-herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritis, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxi related illnesses, familial erythromelalgia, primary erythromelalgia, familial rectal pain, cancer, epilepsy, partial and general tonic seizures, restless leg syndrome, arrhythmias, fibromyalgia, neuroprotection under ischaemic conditions cause by stroke or neural trauma, tach-arrhythmias, atrial fibrillation and ventricular fibrillation.

In another aspect the present invention provides for a method of treating pain in a mammal by the inhibition of ion flux through a voltage-dependent sodium channel in the mammal, wherein the method comprises administering to the mammal in need thereof a therapeutically effective amount of a compound of formula I, or a pharmaceutically acceptable salt thereof.

In another aspect the present invention provides for a method of decreasing ion flux through a voltage-dependent sodium channel in a cell in a mammal, wherein the method comprises contacting the cell with a compound of formula I, or a pharmaceutically acceptable salt thereof.

In another aspect the present invention provides for a method of treating pruritus in a mammal, wherein the method comprises administering to the mammal in need thereof a therapeutically effective amount of a compound of formula I, or a pharmaceutically acceptable salt thereof.

In another aspect the present invention provides for a method of treating cancer in a mammal, wherein the method comprises administering to the mammal in need thereof a therapeutically effective amount a compound of formula I, of a pharmaceutically acceptable salt thereof.

In another aspect the present invention provides for a method of treating, but not preventing, pain in a mammal, wherein the method comprises administering to the mammal in need thereof a therapeutically effective amount of a compound of formula I, or a pharmaceutically acceptable salt thereof. In another aspect of the present invention the pain is selected from the group consisting of neuropathic pain, inflammatory pain, visceral pain, cancer pain, chemotherapy pain, trauma pain, surgical pain, post-surgical pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, dental pain, peripheral nerve injury or a combination thereof. In another aspect the present invention the pain is associated with a disease or condition selected from the group consisting of HIV, HIV treatment induced neuropathy, trigeminal neuralgia, post-herpetic neuralgia, eudynia, heat sensitivity, tosarcoidosis, irritable bowel syndrome, Crohns disease, pain associated with multiple sclerosis (MS), amyotrophic lateral Sclerosis (ALS), diabetic neuropathy, peripheral neuropathy, arthritis, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel taxi related illnesses, familial erythromelalgia, primary erythromelalgia, familial rectal pain, cancer, epilepsy, partial and general tonic seizures, restless leg syndrome, arrhythmias, fibromyalgia, neuroprotection under ischaemic conditions cause by stroke or neural trauma, tach-arrhythmias, atrial fibrillation and ventricular fibrillation.

In another aspect the present, invention provides for a method of treating, but not preventing, acute pain or chronic pain is a mammal, wherein the method comprises administering to the mammal in need thereof a therapeutically effective amount of a compound of formula I, or a pharmaceutically acceptable salt thereof.

In another aspect the present invention provides for a method of treating, but not preventing, neuropathic pain or inflammatory pain in a mammal, wherein the method comprises administering to the mammal in need thereof a therapeutically effective amount of a compound of formula I, or a pharmaceutically acceptable salt thereof.

In another aspect the present invention provides for a method for the treatment or prophylaxis of pain, depression, cardiovascular disease, respiratory disease, or psychiatric disease, or a combinations thereof, in an animal which method comprises administering an effective amount of a compound of formula I, or a pharmaceutically acceptable salt thereof.

In another aspect the present invention provides for a compound of formula I, or a pharmaceutically acceptable salt thereof for the use as a medicament for the treatment of diseases and disorders selected from the group consisting of pain, depression, cardiovascular diseases, respiratory diseases, and psychiatric diseases, or a combination thereof.

In another aspect the present invention provides for the use of a compound of formula I, or a pharmaceutically acceptable salt thereof for the manufacture of a medicament for the treatment of diseases and disorders selected from the group consisting of pain, depression, cardiovascular diseases, respiratory diseases, and psychiatric diseases, or a combination thereof.

In another aspect the present invention provides for the invention as described herein.

DETAILED DESCRIPTION OF THE INVENTION

Definitions

As used herein, the term "alkyl", by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, iso-propyl, n-butyl t-butyl, iso-butyl, sec-butyl, n-pentyl, n-hexyl, n-heptyl, n-octyl, and the like. The term "alkenyl" refers to an unsaturated alkyl radical having one or more double bonds. Similarly, the term "alkynyl" refers to an unsaturated, alkyl radical having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "heteroalkyl," by itself or in combination with another term, means, unless otherwise stated, a stable straight or branched chain hydrocarbon radical, consisting of the stated number of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S can be placed at any interior position, of the heteroalkyl group. The heteroatom Si can be placed at any position, of the heteroalkyl group, including the position at which the alkyl group is attached to the remainder of the molecule. A "heteroalkyl" can contain up to three units of unsaturation, and also include mono- and poly-halogenated variants, or combinations thereof. Examples include —$CH_2$—$CH_2$—

O—CH$_3$, —CH$_2$—CH$_2$—O—CF$_3$, —CH$_2$—CH$_2$—NH—CH$_3$, —CH$_2$—CH$_2$—N(CH$_3$)—CH$_3$, —CH$_2$—S—CH$_2$—CH$_3$, —S(O)—CH$_3$, —CH$_2$—CH$_2$—S(O)$_2$—CH$_3$, —CH=CH—O—CH$_3$, —Si(CH$_3$)$_3$—CH$_2$—CH=N—OCH$_3$, and —CH=CH=N(CH$_3$)—CH$_3$. Up to two heteroatoms can be consecutive, such as, for example, —CH$_2$—NH—OCH$_3$ and —CH$_2$—O—Si(CH$_3$)$_3$.

The term "alkylene" by itself or as part of another substituent means a divalent radical derived from an alkane (including branched alkane), as exemplified by —CH$_2$CH$_2$CH$_2$CH$_2$— and —CH(CH$_2$)CH$_2$CH$_2$—. Typically, an alkyl (or alkylene) group will have from 1 to 24 carbon atoms, with those groups having 10 or fewer carbon atoms being preferred in the present invention, "Alkenylene" and "alkynylene" refer to the unsaturated forms of "alkylene" having double or triple bonds, respectively. "Alkylene" and "alkenylene" and "alkynylene" are also meant so include mono and poly-halogenated variants.

The term, "heteroalkylene" by itself or as part of another substituent means a divalent radical, saturated or unsaturated or polyunsaturated, derived from heteroalkyl, as exemplified by CH$_2$—CH$_2$—S—CH$_2$CH$_2$— and —CH$_2$—S—CH$_2$—CH$_2$—NH—CH$_2$—, —O—CH$_2$CH=CH—, —CH$_2$—CH=C(H)CH$_2$—O–CH$_2$— and —S—CH$_2$—C≡C—. For heteroalkylene groups, heteroatoms can also occupy either or both of the chain termini (e.g., alkyleneoxy, alkylenedioxy, alkyleneamino, alkylenediamino, and the like). The term "heteroalkylene" is also meant to include mono and poly-halogenated variants.

The terms "alkoxy," "alkylamino" and "alkylthio", are used in their conventional sense, and refer to those alkyl groups attached to the remainder of the molecule via an oxygen atom ("oxy"), an amino group ("amino") or thio group, and further include mono- and poly-halogenated variants thereof. Additionally, for dialkylamino groups, the alkyl portions can be the same or different.

The terms "halo" or "halogen," by themselves or as part of another substituent, mean, unless otherwise stated, a fluorine, chlorine, bromine, or iodine atom. The term "(halo)alkyl" is meant to include both a "alkyl" and "haloalkyl" substituent Additionally, the term "haloalkyl," is meant to include monohaloalkyl and polyhaloalkyl. For example, the term "C$_{1-4}$haloalkyl" is mean to include trifluoromethyl, 2,2,2-trifluoroethyl, 4-chlorobutyl, 3-bromopropyl, difluoromethyl and the like.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, naphthyl, 1,2,3,4-tetrahydronaphthyl, anthracenyl, and the like.

The term "carbocycle" or "carbocyclyl" refers to a single saturated (i.e., cycloalkyl) or a single partially unsaturated (e.g., cycloalkenyl, cycloaalkadienyl, etc.) all carbon ring having 3 to 7 carbon atoms (i.e., (C$_3$-C$_7$)carbocycle). The term "carbocycle" or "carbocyclyl" also includes multiple condensed, saturated and partially unsaturated all carbon ring systems (e.g., ring systems comprising 2, 3 or 4 carbocyclic rings). Accordingly, carbocycle includes multicyclic carbocyles such as a bicyclic carbocycles (e.g., bicyclic carbocycles having about 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms so form a bridged connection (e.g., norbomane, bicyclo[2.2.2]octane, etc). The "carbocycle" or "carbocycly" can also be optionally substituted with one or more (e.g., 1, 2 or 3) oxo groups, in one embodiment the term carbocycle includes a C$_{3-12}$carbocycle. In one embodiment the term carbocycle includes a C$_{3-8}$carbocycle. In one embodiment the term carbocycle includes a C$_{3-6}$carbocycle. In one embodiment the term carbocycle includes a C$_{3-5}$carbocycle. Non-limiting examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, bicyclo[2.2.1]heptane, pinane, admantane, norborene, spirocyclic C$_{5-12}$alkane, and 1-cyclohex-3-enyl.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example a naphthyridinyl such as 1,8-naphthyridinyl), heterocycles, (to form for example a 1,2,3,4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements, it is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system, including a heteroaryl, heterocycle, aryl or carbocycle portion of the multiple condensed ring system, it is also to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, qiunolyl, isoquinolyl, benzothiazolyl, benzoxaxolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclo-penta[1,2-c]pyrazole.

The term "heterocyclyl" or "heterocycle" as used herein refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The term, "heterocycle" also includes multiple condensed ring systems (e.g., ring systems comprising 2, 3 or 4 rings) wherein a single heterocycle ring (as defined above) can be condensed with one or more groups selected from heterocycles (to form for example a 1,8-decahydronapthyridinyl), carbocycles (to form for example a decahydroquinolyl) and aryls to form the multiple condensed ring system. Thus, a heterocycle (a single saturated or single partially unsaturated ring or multiple condensed ring system) has about 2-20 carbon atoms and 1-6 heteroatoms within the heterocycle ring. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position, of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g., a nitrogen). In one embodiment the term heterocycle includes a $C_{2-20}$ heterocycle. In one embodiment the term heterocycle includes a $C_{2-7}$-heterocycle. In one embodiment the term heterocycle includes a $C_{2-5}$ heterocycle. In one embodiment the term heterocycle includes a $C_{2-4}$ heterocycle. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one N-methylpiperidine, imidaxolidine, pyrazolidine, butyrolactam, valerolactam, imidazolidinone, hydantoin, dioxolane, phthalimide, 1,4-dioxane, thiomorpholine, thiomorpholine-S-oxide, thiomorpholine-S,S-oxide, pyran, 3-pyrroline, thiopyran, pyrone, tetrahydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R,4R)-2-oxa-5-azabicyclo[2.2.2]octane and pyrrolidin-2-one.

The above terms (e.g., "alkyl," "aryl" and "heteroaryl"), in some embodiments, will include both substituted and unsubstituted forms of the indicated radical. Preferred substituents for each type of radical are provided below.

Substituents for the alkyl radicals (including those groups often referred to as alkylene, alkenyl, alkynyl, heteroalkylcarbocycle, and heterocyclyl) can be a variety of groups including, but not limited to, -halogen, —OR', —NR'R", —SR', —SiR'R"R''', —OC(O)R', —C(O)R', —CO$_2$R', —CONR'R", —OC(O)NR'R", —NR"C(O)R', —NR'''C(O)NR'R", —NR"C(O)$_2$R', —NHC(NH$_2$)=NH, —NR'C(NH$_2$)=NH, —NHC(NH$_2$)=NR', —NR'''C(NR'R")=N—CN, —NR'''C(NR'R")=NOR', —NHC(NH$_2$)=NR', —S(O)R', —S(O)$_2$R', —S(O)$_2$NR'R", —NR'S(O)$_2$R", —NR'''S(O)$_2$NR'R", —CN, —NO$_2$, —(CH$_2$)$_{1-4}$—OR', —(CH$_2$)$_{1-4}$—NR'R", —(CH$_2$)$_{1-4}$—CH$_2$)$_{1-4}$—SR', —(CH$_2$)$_{1-4}$—SiR'R"R''', —(CH$_2$)$_{1-4}$—OC(O)R', —(CH$_2$)$_{1-4}$—C(O)R', —(CH$_2$)$_{1-4}$—CO$_2$R', —(CH$_2$)$_{1-4}$CONR'R", in a number ranging from zero to (2m'+1), where m' is the total number of carbon atoms in such radical. R', R" and R''' each independently refer groups including, for example, hydrogen, unsubstituted $C_{1-6}$alkyl, unsubstituted heteroalkyl, unsubstituted aryl, aryl substituted with 1-3 halogens, unsubstituted $C_{1-6}$alkyl, $C_{1-6}$alkoxy or $C_{1-6}$thioalkoxy groups, or unsubstituted aryl-$C_{1-4}$alkyl groups, unsubstituted heteroaryl, substituted heteroaryl, among others. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. Other substitutents for alkyl radicals, including heteroalkyl, alkylene, include for example, =O, =NR', =N—OR', =N—CN, =NH, wherein R' include substituents as described above.

Similarly, substituents for the aryl and heteroaryl groups are varied and are generally selected from the group including, but not limited to halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'C(O)NR"R''', —NHC(NH$_2$)=NH, —NR'C(NH$_2$)=NH, —NHC(NH$_2$)=NR', —S(O)R', —S(O)$_2$R', —S(O)$_2$NR'R", —NR'S(O)$_2$R", —N$_3$, perfluoro-$C_{1-4}$alkoxy, and perfluoro-$C_{1-4}$alkyl, —(CH$_2$)$_{1-4}$—OR', —(CH$_2$)$_{1-4}$—NR'R", —(CH$_2$)$_{1-4}$—SR', —(CH$_2$)$_{1-4}$—SiR'R"R''', —(CH$_2$)$_{1-4}$—OC(O)R', —(CH$_2$)$_{1-4}$—C(O)R', —(CH$_2$)$_{1-4}$—CO$_2$R', —(CH$_2$)$_{1-4}$CONR'R", in a number ranging from zero to the total number of open valences on the aromatic ring system; and where R', R" and R''' are independently selected from hydrogen, $C_{1-6}$alkyl, $C_{3-6}$carbocycle, $C_{2-6}$alkenyl, $C_{2-6}$alkynyl, unsubstituted aryl and heteroaryl, (unsubstituted aryl)-$C_{1-4}$alkyl, and unsubstituted aryloxy-$C_{1-4}$alkyl. Other suitable substituents include each of the above aryl substituents attached to a ring atom by an alkylene tether of from 1-4 carbon atoms. When a substituent for the aryl or heteroaryl group contains an alkylene linker (e.g., —$(CH_2)_{1-4}$—NR'R"), the alkylene linker includes halo variants as well. For example, the linker "—$(CH_2)_{1-4}$—" when used as part of a substituent is meant to include difluoromethylene, 1,2-difluoroethylene, etc.

As used herein, the term "heteroatom" is meant to include oxygen (O), nitrogen (N), sulfur (S) and silicon (Si).

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line "∿" that intersects a bond in a chemical structure indicates the point of attachment of the bond that the wavy bond intersects in the chemical structure to the remainder of a molecule.

As used herein, the term "C-linked" means that the group that the term describes is attached the remainder of the molecule through a ring carbon atom.

As used herein, the term "N-linked" means that the group that the term describes is attached to the remainder of the molecule through a ring nitrogen atom.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been so stereoselection or stereospecificity in a chemical reaction or process. The terms "racemic mixture" and "racemate" refer to an equimolar mixture of two enantiomeric species, devoid of optical activity.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-tritrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis $4^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturedly-occurring amines and the like, such as arginine, betaine, caffeine, choline, N,N'-dibenzylethylenediamines diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Serge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylptenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as ($C_{1-6}$)alkanoyloxymethyl, 1-(($C_{1-6}$)alkanoyloxy)ethyl, 1-methyl-1-(($C_{1-6}$)alkanoyloxy)ethyl, ($C_{1-6}$)alkoxycarbonyloxymethyl, N—($C_{1-6}$)alkoxycarbonylaminomethyl, succinoyl, ($C_{1-6}$)alkanoyl, alpha-amino($C_{1-4}$)alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs;" by H. Bundgaard p. 113-191 (1991); c) H. Bundgaard, Advanced Drug Delivery Reviews, 8:1-38 (1992): d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention, possess asymmetric carbon atoms (optical centers) or double bonds; the racemates, diastereomers, geometric isomers, regioisomers and individual isomers (e.g., separate enantiomers) are all intended to be encompassed within the scope of the present invention.

The compounds of the present invention can also contain unnatural proportions of atomic isotopes at one or more of the atoms that constitute such compounds. For example, the present invention also embraces isotopically-labeled variants of the present invention which are identical to those recited herein, bur the for the fact that one or more atoms are replace by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated, in to compounds of the invention include isotopes of hydrogen, carbon, nitrogen, oxygen, phosphorous, sulfur, fluorine, chlorine and iodine, such as $^2$H ("D"), $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{125}$I and $^{125}$I. Certain isotopically labeled compounds of the present invention (e.g., those labeled with $^3$H or $^{14}$C) are useful in compound and/or substrate tissue distribution assays. Tritiated ($^3$H) and carbon-14 ($^{14}$C) isotopes are useful for their ease of preparation and detectability. Further substitution with heavier isotopes such as deuterium (i.e., $^2$H) may afford certain therapeutic advantages resulting from greater metabolic stability (e.g., increased in vivo half-life or reduced dosage requirements) and hence may be preferred is some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting an isotopically labeled reagent for a non-isotopically labeled reagent.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation, of symptoms, diminishment of extent of disease or disorder, stabilized (i.e., not worsening) state of disease or disorder, delay or slowing of disease progression, amelioration, or palliation of the disease state or disorder, and remission, (whether partial or total), whether delectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" or "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

In another embodiment, the compound is selected from compounds of formula I as described in the Examples herein and salts thereof.

Synthesis of Compounds

Compounds of formula (I) may be prepared by the process illustrated in Schemes 1 and 2. Compounds of formula (I), wherein $X^1$ is O, S, or NH, may be prepared by the processes illustrated in Scheme 1.

Scheme 1

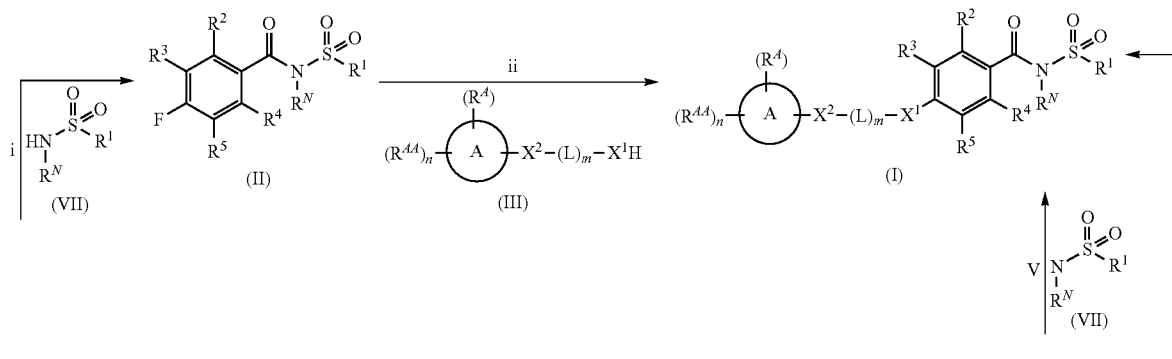

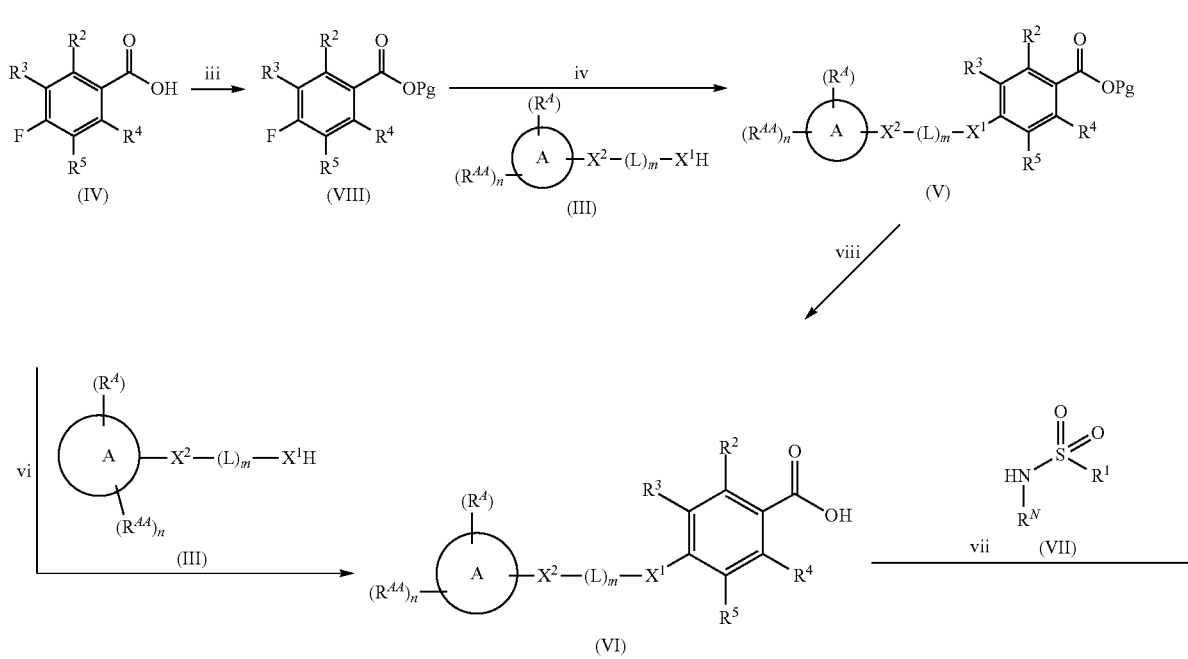

Compounds of formula (I) can be made from compounds of formula (II) by displacement with formula (III) and a base (reaction step ii in Scheme 1). Suitable conditions include potassium tert-butoxide or cesium carbonate in DMSO, NaH in DMF, or $K_2CO_3$ in DMF. Formula (II) can be made according to step (i) by activation of the acid group of formula (IV) with reagents such as oxalyl chloride, carbonyl di-imidazole (CDI), propylphosphonic anhydride, a uronium based amide coupling agent or a carbodiimide reagent followed by displacement with a sulfonamide of formula (VII) in the presence of a nucleophilic base such as 4-dimethylaminopyridine. Illustrative conditions comprise N,N-dimethylaminopropyl-N-ethylcarbodiimide and 4-dimethylamino-pyridine with N,N-diisopropylethylamine.

Alternatively, compounds of formula (I) can be made from compounds of formula (IV) by reversing steps (i) and (ii) as described in Scheme 1, Illustrative conditions for steps vi and vii are as previously described in steps (ii) and (i), respectively.

Compounds of formula (I) can also be made from compounds of formula (V) according to step (v) by displacement of the ester with compounds of formula (VII) and a suitable base such as potassium tert-butoxide, NaH or DBU. Compounds of formula (I) can also be made from compounds of formula (v) by a two steps sequence (see steps viii and vii in Scheme 1). Compounds of formula (V) can be made from compounds of formula (VIII) according to step (iv) via a nucleophilic substitution reaction using compounds of formula (III) and a base as described in step ii. Compounds of formula (VIII) can be made from compounds of formula (IV) according to step (iii) using protecting group methodology as described in references such as 'Greene's Protective Groups in Organic Synthesis'. When Pg is tolyl, illustrative conditions comprise thionyl chloride or carbonyldiimidazole with para-cresol. When Pg is tert-butyl, illustrative conditions comprise di-tert butyl dicarbonate and 4-dimethylaminopyridine in tert-butanol. Compounds of formula (I), wherein $R^5$ is $C_{1-8}$ alkyl, $C_{1-8}$haloalkyl, $C_{1-8}$alkoxy, $C_{3-8}$cycloalkyl or $C_{2-7}$heterocycloalkyl can be prepared by the process illustrated in Scheme 2. In certain embodiment, W groups in compounds of formula (IX, X and XI) are an ester or cyano group.

Scheme 2

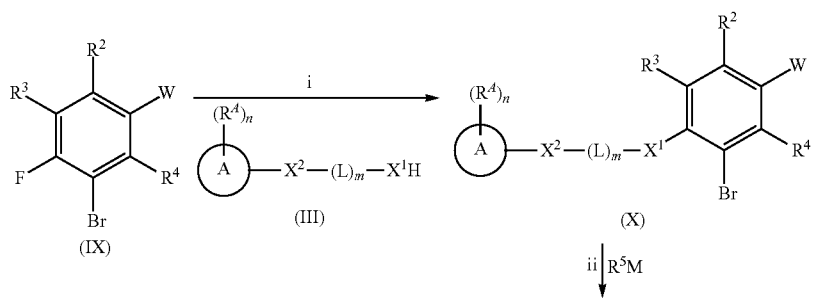

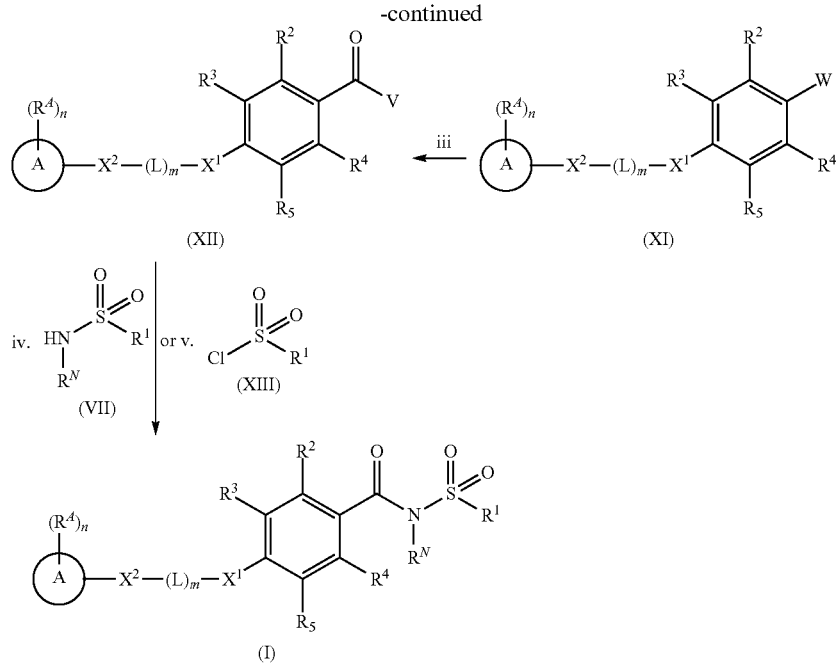

Compounds of formula (I) can be prepared from compounds of formulae (XII) (—V═OH) according to reaction step (iv) by activation of the acid group with reagents such as oxalyl chloride, carbonyl di-imidazole (CDI), a uronium based amide coupling agent, propylphosphonic anhydride or a carbodiimide reagent followed by displacement with a suitable sulfonamide of formula (VII) in the presence of a nucleophilic base such as 4-dimethylaminopyridine.

Alternatively, compounds of formula (I) can be prepared from compounds of formula (XII) (—V═NH$_2$) according to reaction step (v) by displacement of a sulfonyl chloride of formula (XIII) under basic reaction conditions.

Compounds of formula (XII) can be prepared by hydrolysis of the nitrile functional group in compounds of formula (XI, W═CN) or by hydrosis of the ester functional group in compounds of formula (XI, W═CO$_2$Pg) by either acidic or basic methods according to step (iii) as required.

Compounds of formula (XI) can be prepared from compounds of formula (X) by palladium-catalyzed coupling of a compound of formula (R$_5$M) according to step (ii). Conveniently the coupling is effective with a boronic acid or ester of formula (R$_5$M). The coupling reaction can be carried out with a variety of palladium catalysts such as palladium acetate or tetrakistriphenylphosphine palladium (0) in various solvents and in the presence of bases such as sodium and potassium carbonate, cesium fluoride or potassium phosphate. Compounds of formula (X) can be prepared under similar conditions as described for the preparation of compounds of formula (V), (VI) and (I) in Scheme 1.

Pharmaceutical Compositions and Administration

In addition to one or more of the compounds provided above (or stereoisomers, geometric isomers, tautomers, solvates, metabolites, isotopes, pharmaceutically acceptable salts, or prodrugs thereof), the invention also provides for compositions and medicaments comprising a compound of formula I or and embodiment thereof and at least one pharmaceutically acceptable carrier, diluent or excipient.

The compositions of the invention can be used to selectively inhibit NaV1.7 in patients (e.g. humans).

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In one embodiment, the invention provides for pharmaceutical compositions for medicaments) comprising a compound, of formula I or an embodiment thereof, and its stereoisomers, geometric isomers, tautomers, solvates, metabolites, isotopes, pharmaceutically acceptable salts, or prodrugs thereof) and a pharmaceutical acceptable carrier, diluent or excipient. In another embodiment, the invention provides for preparing compositions (or medicaments) comprising compounds of the invention, in another embodiment, the invention provides for administering compounds of formula I or its embodiments and compositions comprising compounds of formula I or an embodiment thereof to a patient (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered, will be governed by such considerations, and is the minimum amount necessary to inhibit NaV1.7 activity as required to prevent or treat the undesired disease or disorder, such as for example, pain. For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, intracerebral, intraocular, intralesional or subcutaneous administration.

The compositions comprising compounds of formula I or an embodiment thereof are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage forms and Drug Delivery Systems. Philadelphia: Lippincott, Williams & Wilkins, 2004; Gennaro, Alfonso R, et al. Remington: The Science and Practice of Pharmacy, Philadelphia: Lippincott, Williams & Wilkins, 2000; and Rowe, Raymond C. Handbook of Pharmaceutical Excipients, Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention, or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general safe solvents are non-toxic aqueous solvents such as water and other non-toxic solvents that are soluble or miscible in water. Suitable aqueous solvents include wafer, ethanol, propylene glycol, polyethylene glycols (e.g., PEG 400, PEG 300), etc, and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydropbilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of formula I or an embodiment thereof) can also be entrapped in microcapsules prepared, for example, by coacervation techniques or by interracial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philadelphia, Pa.

Sustained-release preparations of a compound of the invention (e.g., compound of formula I or an embodiment thereof) can be prepared. Suitable examples of sustained-release preparations include semipermeable matrices of solid hydrophobic polymers containing a compound of formula I or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102.324A). Ordinarily, the liposomes are of the small (about 200-800 Angstroms) unilamelar type in which the lipid content is greater than about 30 mol % cholesterol, the selected proportion being adjusted for the optimal therapy.

The formulations include those suitable for the administration routes detailed herein. The formulations can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) 21$^{st}$ Edition, Lippincott Williams & Wilkins, Philadelphia, Pa. Such methods include the step of bringing into association the active ingredient with the carrier which constitutes one or more accessory ingredients.

In general the formulations are prepared by uniformly and intimately bringing into association the active ingredient with liquid carriers, diluents or excipients or finely divided solid carriers, diluents or excipients, or both, and then, if necessary, shaping the product. A typical formulation is prepared by mixing a compound of the present invention and a carrier, diluent or excipient. The formulations can be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

In one example, compounds of formula I or an embodiment, thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I (or an embodiment thereof) is formulated in an acetate buffer, at pH 5. In another embodiment, the compounds of formula I or an embodiment thereof are sterile. The compound may be stored, for example, as a solid or amorphous composition, as a lyophilized formulation or as an aqueous solution.

Formulations of a compound of the invention (e.g., compound of formula I or an embodiment thereof) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant inert diluent, preservative, surface active or dispersing agent. Molded tablets can be made by molding in a suitable machine a mixture of the powdered active ingredient moistened with an inert liquid diluent. The tablets can optionally be coated or scored and Optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of formula I or an embodiment thereof) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-330 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base. If desired, the aqueous phase of the Cretan base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

In one aspect of topical applications, it is desired to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical, vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

Aqueous suspensions of a compound of the invention (e.g., compound of formula I or an embodiment thereof) contain the active materials in admixture with excipients suitable for the manufacture of aqueous suspensions. Such excipients include a suspending agent such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylate oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

Formulations of a compound of the invention (e.g., compound of formula I or an embodiment thereof) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are wafer, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration, to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sixes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment of disorders as described below.

The formulations can be packaged in unit-dose or multi-dose containers, for example sealed ampoules and vials, and can be stored in a freeze-dried (lyophilized) condition requiring only the addition of the sterile liquid carrier, for example water, for infection immediately prior to use. Extemporaneous injection solutions and suspensions are prepared from sterile powders, granules and tablets of the kind previously described. Preferred unit dosage formulations are those containing daily dose or unit daily sub-dose, as herein above recited, or an appropriate fraction thereof of the active ingredient.

When the binding target is located in the brain, certain embodiments of the invention provide for a compound of formula I (or an embodiment thereof) to traverse the blood-brain barrier. Certain neurodegenerative diseases are associated with an increase in permeability of the blood-brain barrier, such that a compound of formula I (or an embodiment thereof) can be readily introduced so the brain. When the blood-brain barrier remains intact, several art-known approaches exist for transporting molecules across it, including, but not limited to, physical methods, lipid-based methods, and receptor and channel-based methods.

Physical methods of transporting a compound of formula I (or an embodiment thereof) across the blood-brain barrier include, hot are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91: 2076-2080, 1994), and implanting a delivery device in the brain (see, e.g., Gill et al., Nature Med. 9:589-595, 2003; and Gliadel Wafers™ Guildford, Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I (or an embodiment thereof) across the blood-brain barrier include, but are not limited to, encapsulating the a compound of formula I (or an embodiment thereof) in liposomes that are coupled to antibody binding fragments that bind to receptors on the vascular endothelium of the blood-brain barrier (see, e.g., U.S. Patent Application Publication No. 2002/0025313), and coating a compound of formula I (or an embodiment thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Application Publication Nos. 2002/0005259, 2003/0162595, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of formula I (or an embodiment thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain, embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord., 2: 143, 1987.

A compound of formula I (or an embodiment thereof) used in the invention are formulated, dosed, and administered in a fashion consistent with good medical practice. Factors for consideration in this contest include the particular disorder being treated, the particular mammal being treated, the clinical condition of the individual patient, the cause of the disorder, the site of delivery of the agent, the method of administration, the scheduling of administration, and other factors known to medical practitioners. A compound of formula I for an embodiment thereof) need not be, but is optionally formulated with one or more agent currently used to prevent or treat the disorder in question. The effective amount of such other agents depends on the amount of a compound of the invention, present in the formulation, the type of disorder or treatment, and other factors discussed above.

These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a compound of formula I (or an embodiment thereof) (when used alone or in combination with other agents) will depend on the type of disease to be treated, the properties of the compound, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments. Depending on the type and severity of the disease, about 1 µg/kg to 15 mg/kg (e.g., 0.1 mg/kg-10 mg/kg) of compound can be an initial candidate dosage for administration to the patient, whether, for example, by one or more separate administrations, or by continuous infusion. One typical daily dosage might range from about 1 µg kg to 100 mg/kg or snore, depending on the factors mentioned above. For repeated administrations over several days or longer, depending on the condition, the treatment would generally be sustained until a desired suppression of disease symptoms occurs. One exemplary dosage of a compound of formula I (or an embodiment thereof) would be in the range from about 0.05 mg/kg to about 10 mg/kg. Thus, one or more doses of about 0.5 mg/kg, 2.0 mg/kg, 4.0 mg/kg, or 10 mg/kg for any combination thereof) may be administered to the patient. Such doses may be administered intermittently, e.g., every week or every three weeks (e.g., such that the patient receives from about two to about twenty, or, e.g., about six doses of the antibody). An initial higher loading dose, followed by one or more lower doses may be administered. An exemplary dosing regimen comprises administering an initial loading dose of about 4 mg/kg, followed by a weekly maintenance dose of about 2 mg kg of the compound. However, other dosage regimens may be useful. The progress of this therapy is easily monitored by conventional techniques and assays.

Other typical daily dosages might range from, for example, about 1 g/kg to up to 100 mg/kg or more (e.g., about 1 µg kg to 1 mg/kg, about 1 µg/kg to about 5 mg/kg, about 1 mg kg to 10 mg/kg, about 5 mg/kg to about 200 mg/kg, about 50 mg/kg to about 150 mg/mg, about 100 mg/kg to about 500 mg/kg, about 100 mg/kg to about 400 mg/kg, and about 200 mg/kg to about 400 mg/kg), depending on the factors mentioned above. Typically, the clinician will administer a compound until a dosage is reached that results in improvement in or, optimally, elimination of one or more symptoms of the treated disease or condition. The progress of this therapy is easily monitored by conventional assays. One or more agent provided herein may be administered together or at: different times (e.g., one agent is administered prior to the administration of a second agent). One or more agent may be administered to a subject using different techniques (e.g., one agent may be administered orally, while a second agent is administered via intramuscular injection or intranasally). One or more agent may be administered such that the one or more agent has a pharmacologic effect in a subject at the same time. Alternatively, one or more agent may be administered, such that the pharmacological activity of the first administered agent is expired prior the administration of one or more secondarily administered agents (e.g., 1, 2, 3, or 4 secondarily administered agents).

Indications and Methods of Treatment

The compounds of the invention modulate, preferably inhibit, ion flux through a voltage-dependent sodium channel in a mammal, (e.g. a human). Any such modulation, whether it be partial or complete inhibition or prevention of ion flux, is sometimes referred to herein as "blocking" and corresponding compounds as "blockers" or "inhibitors". In general, the compounds of the invention modulate the activity of a sodium channel downwards by inhibiting the voltage-dependent activity of the sodium channel, and/or reduce or prevent sodium ion flux across a cell membrane by preventing sodium channel activity such as ion flax.

The compounds of the invention inhibit the ion flux through a voltage-dependent sodium channel. In one aspect, the compounds are state or frequency dependent modifiers of the sodium channels, having a low affinity for the rested/closed state and a high affinity for the inactivated state. Without being bound by any particular theory, it is thought that these compounds are likely to interact with overlapping sites located in the inner cavity of the sodium conducting pore of the channel similar to that described for other state-dependent sodium channel blockers (Cestèle, S., et al., op. cit.). These compounds may also be likely to interact with sites outside of the inner cavity and have allosteric effects on sodium ion conduction through the channel pore.

Any of these consequences may ultimately be responsible for the overall therapeutic benefit provided by these compounds.

Accordingly, the compounds of the invention, are sodium channel blockers and are therefore useful for treating diseases and conditions in mammals, for example humans, and other organisms, including all those diseases and conditions which are the result of aberrant voltage-dependent sodium channel biological activity or which may be ameliorated by modulation of voltage-dependent sodium channel biological activity. In particular, the compounds of the invention, i.e., the compounds of formula (I) and embodiments and (or stereoisomers, geometric isomers, tautomers, solvates, metabolites, isotopes, pharmaceutically acceptable salts, or prodrugs thereof), are useful for treating diseases and conditions in mammals, for example humans, which are the result of aberrant voltage-dependent NaV1.7 biological activity or which may be ameliorated by the modulation, preferably the inhibition, of NaV1.7 biological activity. In certain aspects, the compounds of the invention selectively inhibit NaV1.7 over NaV1.5.

As defined herein, a sodium channel-mediated disease or condition refers to a disease or condition in a mammal, preferably a human, which is ameliorated upon modulation of the sodium channel and includes, but is not limited, to, pain, central nervous conditions such as epilepsy, anxiety, depression and bipolar disease; cardiovascular conditions such as arrhythmias, atrial fibrillation and ventricular fibrillation; neuromuscular conditions such as restless leg syndrome and muscle paralysis or tetanus; neuroprotection against stroke, neural trauma and multiple sclerosis; and channelopathies such as erythromyalgia and familial rectal pain syndrome.

In one aspect, the present invention relates to compounds, pharmaceutical, compositions and methods of using the compounds and pharmaceutical compositions for the treatment of sodium channel-mediated diseases in mammals, preferably humans and preferably diseases and conditions related to pain, central nervous conditions such as epilepsy, anxiety, depression and bipolar disease; cardiovascular conditions such as arrhythmias, atrial fibrillation and ventricular fibrillation; neuromuscular conditions such as restless leg syndrome and muscle paralysis or tetanus; neuroprotection, against stroke, neural trauma and multiple sclerosis; and channelopathies such as erythromyalgia and familial rectal pain syndrome, by administering to a mammal, for example a human, in need of such treatment an effective amount of a sodium channel blocker modulating, especially inhibiting, agent.

A sodium channel-mediated disease or condition also includes pain associated with HIV, HIV treatment induced neuropathy, trigeminal neuralgia, glossopharyngeal neuralgia, neuropathy secondary to metastatic infiltration, adiposis dolorosa, thalamic lesions, hypertension, autoimmune disease, asthma, drag addiction (e.g., opiate, benzodiazepine, amphetamine, cocaine, alcohol, butane inhalation), Alzheimer, dementia, age-related memory impairment, Korsakoff syndrome, restenosis, urinary dysfunction, incontinence, Parkinson's disease, cerebrovascular ischemia, neurosis, gastrointestinal disease, sickle cell anemia, transplant rejection, heart failure, myocardial infarction, reperfusion injury, intermittant claudication, angina, convulsion, respiratory disorders, cerebral or myocardial ischemias, long-QT syndrome, Catecholeminergic polymorphic ventricular tachycardia, ophthalmic diseases, spasticity, spastic paraplegia, myopathies, myasthenia gravis, paramyotonia congenita, hyperkalemic periodic paralysis, hypokalemic periodic paralysis, alopecia, anxiety disorders, psychotic disorders, mania, paranoia, seasonal affective disorder, panic disorder, obsessive compulsive disorder (CCD), phobias, autism, Aspergers Syndrome, Retts syndrome, disintegrative disorder, attention deficit disorder, aggressivity, impulse control disorders, thrombosis, pre clampsia, congestive cardiac failure, cardiac arrest, Freidrich's ataxia, Spinocerebellear ataxia, myelopathy, radiculopathy, systemic lupus erythamatosis, granulomatous disease, olivo-ponto-cerebellar atrophy, spinocerebellar ataxia, episodic ataxia, myokymia, progressive pallidal atrophy, progressive supranuclear palsy and spasticity, traumatic brain injury, cerebral, oedema, hydrocephalus injury, spinal cord injury, anorexia nervosa, bulimia, Prader-Willi syndrome, obesity, optic neuritis, cataract, retinal haemorrhage, ischaemic retinopathy, retinitis pigmentosa, acute and chronic glaucoma, macular degeneration, retinal artery occlusion. Chorea, Huntington's chorea, cerebral edema, proctitis, post-herpetic neuralgia, eudynia, heat sensitivity, sarcoidosis, irritable bowel syndrome, Tourette syndrome, Lesch-Nyhan Syndrome, Brugado syndrome, Liddle syndrome, Crohns disease, multiple sclerosis and the pain associated with multiple sclerosis (MS), amyotrophic lateral sclerosis (ALS), disseminated sclerosis, diabetic neuropathy, peripheral neuropathy, charcot marie tooth syndrome, arthritic, rheumatoid arthritis, osteoarthritis, chondrocalcinosis, atherosclerosis, paroxysmal dystonia, myasthenia syndromes, myotonia, myotonic dystrophy, muscular dystrophy, malignant hyperthermia, cystic fibrosis, pseudoaidosteronism, rhabdomyolysis, mental, handicap, hypothyroidism, bipolar depression, anxiety, schizophrenia, sodium channel toxin related illnesses, familial erythromelalgia, primary erythromelalgia, rectal pain, cancer, epilepsy, partial and general tonic seizures, febrile seizures, absence seizures (petit mal), myoclonic seizures, atonic seizures, clonic seizures, Lennox Gastaut, West Syndrome (infantile spasms), multiresistant seizures, seizure prophylaxis (anti-epileptogenic), familial Mediterranean fever syndrome, gout, restless leg syndrome, arrhythmias, fibromyalgia, neuroprotection under ischaemic conditions caused by stroke or neural trauma, tachy-arrhythmias, atrial fibrillation and ventricular fibrillation and as a general or local anaesthetic.

As used herein, the term "pain" refers to all categories of pain and is recognized to include, but is not limited to, neuropathic pain, inflammatory pain, nociceptive pain, idiopathic pain, neuralgic pain, orofacial pain, burn pain, burning mouth syndrome, somatic pain, visceral pain, myofacial pain, dental pain, cancer pain, chemotherapy pain, trauma pain, surgical pain, post-surgical pain, childbirth pain, labor pain, chronic regional pain syndrome (CRPS), reflex-sympathetic dystrophy, brachial plexus avulsion, neurogenic bladder, acute pain (e.g., musculoskeletal and post-operative pain), chronic pain, persistent pain, peripherally mediated pain, centrally mediated pain, chronic headache, migraine headache, familial hemiplegic migraine, conditions associated with cephalic pain, sinus headache, tension headache, phantom limb pain, peripheral nerve injury, pain following stroke, thalamic lesions, radiculopathy, HIV pain, postherpetic pain, non-cardiac chest pain, irritable bowel syndrome and pain associated with bowel disorders and dyspepsia, and combinations thereof.

Furthermore, sodium channel blockers have clinical uses in addition, to pain. The present invention therefore also relates to compounds, pharmaceutical compositions and methods of using the compounds and pharmaceutical compositions for the treatment of diseases or conditions such as cancer and pruritus (itch).

Pruritus, commonly known as itch, is a common dermatological condition. While the exact causes of pruritus are complex and incompletely understood, there has long been evidence that itch involves sensory neurons, especially C fibers, similar to those that mediate pain (Schmelz, M., et al., J. Neurosci. (1997), 17: 8003-8). In particular, it is believed that sodium influx through voltage-gated sodium channels is essential for the propagation of itch sensation from the skin. Transmission of the itch impulses results in the unpleasant sensation that elicits the desire or reflex to scratch.

Multiple causes and electrical pathways for eliciting itch are known, in humans, pruritus can be elicited by histamine or PAR-2 agonists such as mucunain that activate distinct populations of C fibers (Namer, B., et al., J. Neurophysiol. (2008), 100; 2062-9). A variety of neurotrophic peptides are known to mediate itch in animal models (Wang, H., and Yosipovitch, G., International Journal of Dermatology (2010), 49: 1-11). Itch can also be elicited by opioids, evidence of distinct pharmacology from that of pain responses.

There exists a complex Interaction between itch and pain responses that arises in pan from the overlapping sensory input from the skin (Ikoma, A. et al., Arch. Dermatol. (2003), 139: 1475-8) and also from the diverse etiology of both pain and pruritis. Pain responses can exacerbate itching by enhancing central sensitization or lead to inhibition of painful scratching. Particularly severe forms of chronic Itch occur when pain responses are absent, as in the case of post-herpetic itch (Oaklander, A. L., et al., Pain (2002), 96: 9-12).

The compounds of the invention can also be useful for treating pruritus. The rationale for treating itch with inhibitors of voltage-gated sodium channels, especially NaV1.7, is as follows:

The propagation of electrical activity in the C fibers that sense pruritinergic stimulants requires sodium entry through voltage-gated sodium channels.

NaV1.7 is expressed in the C fibers and kerotinocytes in human skin (Zhao, P., et al., Pain (2008), 139:90-105).

A gain of function mutation of NaV1.7 (L858F) that causes erythromelalgia also causes chronic itch (Li, Y., et al., Clinical and Experimental Dermatology (2009), 34: e313-e4).

Chronic itch can be alleviated with treatment by sodium channel blockers, such as the local anesthetic lidocaine (Oaklander, A. L., et al., Pain (2002), 96: 9-12; Villamil, A. G., et al., The American Journal of Medicine (2005), 118: 1160-3). In these reports, lidocaine was effective when administered either intravenously or topically (a Lidoderm patch). Lidocaine can have multiple activities at the plasma concentrations achieved when administered systemically, but when administered topically, the plasma concentrations are only about 1 $\mu$M (Center for Drug Evaluation and Research NDA 20-612). At these concentrations, lidocaine Is selective for sodium channel block and inhibits spontaneous electrical activity in C fibers and pain responses in animal models (Xiao, W. H., and Bennett, G. J., Pain (2008). 137: 218-28). The types of itch or skin imitation, include, but are not limited to:

psoriatic pruritus, itch due to hemodyalisis, aguagenic pruritus, and itching caused by skin disorders (e.g., contact dermatitis), systemic disorders, neuropathy, psychogenic factors or a mixture thereof;

itch caused by allergic reactions, insect bites, hypersensitivity (e.g., dry skin, acne, eczema, psoriasis), inflammatory conditions or injury;

itch associated with vulvar vestibulitis; and skin irritation or inflammatory effect from administration of another therapeutic such as, for example, antibiotics, antivirals and antihistamines.

The compounds of the invention are also useful in treating certain cancers, such as hormone sensitive cancers, such as prostate cancer (adenocarcinoma), breast cancer, ovarian cancer, testicular cancer and thyroid neoplasia, in a mammal, preferably a human. The voltage gated sodium channels have been demonstrated to be expressed in prostate and breast cancer cells. Up-regulation of neonatal NaV1.5 occurs as an integral part of the metastatic process in human breast cancer and could serve both as a novel marker of the metastatic phenotype and a therapeutic target (Clin. Cancer Res. (2005), August 1; 11(15): 5381-9). Functional expression of voltage-gated sodium channel alpha-subunits, specifically NaV1.7, is associated with strong metastatic potential in prostate cancer (CaP) in vitro. Voltage-gated sodium channel alpha-subunits immunostaining, using antibodies specific to the sodium channel alpha subunit was evident in prostatic tissues and markedly stronger in CaP vs non-CaP patients (Prostate Cancer Prostatic Dis., 2005; 8(3):266-73). See also Diss, J. K. J., et al., Mol. Cell. Neurosci. (2008), 37:532-547 and Kis-Toth, K., et al., The Journal of immunology (2011), 187; 1273-1280.

In consideration, of the above, in one embodiment, the present invention provides a method for treating a mammal for, or protecting a mammal from developing, a sodium channel-mediated disease, especially pain, comprising administering to the mammal, especially a human, in need thereof a therapeutically effective amount of a compound of the invention or a pharmaceutical composition comprising a therapeutically effective amount of a compound of the invention wherein the compound modulates the activity of one or more voltage-dependent sodium channels.

In another embodiment: of the invention is a method of treating a disease or a condition in a preferably a human, wherein the disease or condition is selected from the group consisting of pain, depression, cardiovascular diseases, respiratory diseases, and psychiatric diseases, and combinations thereof, and wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof and a pharmaceutically acceptable excipient.

One embodiment of this embodiment is wherein the disease or condition is selected from the group consisting of neuropathic pain, inflammatory pain, visceral pain, cancer pain, chemotherapy pain, trauma pain, surgical pain, post surgical pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, peripheral nerve injury, and combinations thereof.

Another embodiment of this embodiment is wherein the disease or condition is selected from the group consisting of pain associated with HIV, HIV treatment induced neuropathy, trigeminal neuralgia, post herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritic, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, familial erythromelalgia, primary erythromelalgia, familial rectal pain, cancer, epilepsy, partial and general tonic seizures, restless leg syndrome, arrhythmias, fibromyalgia, neuroprotection under ischaemic conditions caused by stroke or neural trauma, tachy arrhythmias, atrial fibrillation and ventricular fibrillation.

Another embodiment of the invention is a method of treating, but not preventing, pain in a mammal, wherein the method comprises administering to the mammal in need thereof a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical, composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

One embodiment of this embodiment is a method wherein the pain is selected from the group consisting of neuropathic pain, inflammatory pain, visceral pain, cancer pain, chemotherapy pain, trauma pain, surgical pain, post surgical pain, childbirth pain, labor pain, denial pain, chronic pain, persistent pain, peripherally mediated pain, centrally mediated pain, chronic headache, migraine headache, sinus headache, tension headache, phantom limb pain, peripheral nerve injury, trigeminal neuralgia, post herpetic neuralgia, eudynia, familial erythromelalgia, primary erythromelalgia, familial rectal pain or fibromyalgia, and combinations thereof.

Another embodiment of this embodiment is a method wherein the pain is associated with a disease or condition selected from HIV, HIV treatment, induced neuropathy, heat sensitivity, tosarcoidosis, irritable bowel syndrome, Crohns disease, multiple sclerosis, amyotrophic lateral sclerosis, diabetic neuropathy, peripheral neuropathy, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, neurogenic bladder, ulcerative colitis, cancer, epilepsy, partial and general tonic seizures, restless leg syndrome, arrhythmias, ischaemic conditions caused by stroke or neural trauma, tachy arrhythmias, atrial fibrillation and ventricular fibrillation.

Another embodiment of the invention is the method of treating pain in a mammal, preferably a human, by the inhibition of ion flax through a voltage dependent sodium channel in the mammal, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof or a pharmaceutical composition comprising a therapeutically effective amount of a compound of the invention, as set forth above, as a stereoisomer, enantiomer or tautomer thereof or mixtures thereof or a pharmaceutically acceptable salt, solvate or prodrug thereof, and a pharmaceutically acceptable excipient.

Another embodiment of the invention, is the method of treating pruritus in a mammal, preferably a human, wherein the method comprises administering to the mammal is need, thereof a therapeutically effective amount of an embodiment of a compound of the invention, as set forth above, as a stereoisomer, enantiomer or tautomer thereof or mixtures thereof or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention, is the method of treating cancer in a mammal, preferably a human, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of decreasing ion flux through a voltage dependent sodium channel in a cell in a mammal, wherein the method comprises contacting the cell with an embodiment of a compound of the invention, as set forth above, as a stereoisomer, enantiomer or tautomer thereof or mixtures thereof, or a pharmaceutically acceptable salt, solvate or prodrug thereof.

Another embodiment of the invention, is the method of selectively inhibiting a first voltage-gated sodium channel over a second voltage-gated sodium channel in a mammal, wherein, the method comprises administering to the mammal an inhibitory amount of a compound of formula (I), or an embodiment of a compound of formula (I).

Another embodiment of the invention is the method of selectively inhibiting NaV1.7 in a mammal or a mammalian cell as compared to NaV1.5, wherein the method comprises administering to the mammal in need thereof an inhibitory amount of a compound of formula (I) or an embodiment of an embodiment thereof.

For each of the above embodiments described related to treating diseases and conditions in a mammal, the present invention also contemplates relatedly a compound of formula I or an embodiment thereof for the use as a medicament in the treatment of such diseases and conditions.

For each of the above embodiments described related to treating diseases and conditions in a mammal, the present invention also contemplates relatedly the use of a compound of formula I or an embodiment thereof for the manufacture of a medicament for the treatment of such diseases and conditions.

Another embodiment of the invention, is a method of using the compounds of formula (I) as standards or controls in in vitro or in vivo assays in determining the efficacy of test compounds in modulating voltage-dependent sodium channels.

In another embodiment of the invention, the compounds of formula (I) are isotopically-labeled by having one or more atoms therein replaced by art atom having a different atomic mass or mass number. Such isotopically-labeled (i.e., radiolabeled) compounds of formula (I) are considered to be within the scope of this invention. Examples of isotopes that can be incorporated into the compounds of formula (I) Include isotopes of hydrogen, carbon, nitrogen, oxygen, phosphorous, sulfur, fluorine, chlorine, and iodine, such as, but not limited to, $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These isotopically-labeled compounds would be useful to help determine or measure the effectiveness of the compounds, by characterizing, for example, the site or mode of action on the sodium channels, or binding affinity to pharmacologically important site of action on the sodium channels, particularly NaV1.7. Certain isotopically-labeled compounds of formula (I), for example, those incorporating a radioactive isotope, are useful in drug and/or substrate tissue distribution studies. The radioactive isotopes tritium, i.e. $^3H$, and carbon-14, i.e., $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

Testing Compounds

The assessment of the compounds of the invention in mediating, especially inhibiting, the sodium channel ion flux can be determined using the assays described hereinbelow. Alternatively, the assessment of the compounds in treating conditions and diseases in humans may be established in industry standard animal models for demonstrating the efficacy of compounds in treating pain. Animal models of human neuropathic pain conditions have been developed, that result in reproducible sensory deficits (allodynia, hyperalgesia, and spontaneous pain) over a sustained period of time that can be evaluated by sensory testing. By establishing the degree of mechanical, chemical, and temperature induced allodynia and hyperalgesia present, several physiopathological conditions observed in humans can be modeled allowing the evaluation of pharmacotherapies.

In rat models of peripheral nerve injury, ectopic activity in the injured nerve corresponds to the behavioural signs of pain, in these models, intravenous application of the sodium channel blocker and local anesthetic lidocaine can suppress the ectopic activity and reverse the tactile allodynia at concentrations that do not affect general behaviour and motor function (Mao, J. and Chen, L. L., Pain (2000), 87:7-17). Allometric scaling of the doses effective in these rat models, translates into doses similar to those shown to be efficacious in humans (Tanelian, D. L. and Brose, W. G., Anesthesiology (1991), 74(5):949-951). Furthermore, Lidoderm®, lidocaine applied in the form of a dermal patch, is currently an FDA approved treatment for post-herpetic neuralgia (Devers, A. and Glaler, B. S., Clin. J. Pain (2000), 16(3):205-8).

The present invention readily affords many different means for identification of sodium channel modulating agents that are useful as therapeutic agents, identification of modulators of sodium channel can be assessed using a variety of in vitro and in vivo assays, e.g., measuring current, measuring membrane potential, measuring ion flux, (e.g., sodium or guanidinium), measuring sodium concentration, measuring second messengers and transcription levels, and using e.g., voltage-sensitive dyes, radioactive tracers, and patch-clamp electrophysiology.

One such protocol involves the screening of chemical agents for ability to modulate the activity of a sodium channel thereby identifying it as a modulating agent.

A typical assay described in Bean et al., J. General Physiology (1983), 83:613-642, and Leuwer, M., et al., Br. J. Pharmacol (2004), 141(1):47-54, uses patch-clamp techniques to study the behaviour of channels. Such techniques are known to those skilled in the art, and may be developed, using current technologies, into low or medium throughput assays for evaluating compounds for their ability to modulate sodium channel behaviour.

Throughput of test compounds is an important consideration in the choice of screening assay to be used. In some strategies, where hundreds of thousands of compounds are to be tested, if is not desirable to use low throughput means, in other cases, however, low throughput is satisfactory to identify important, differences between a limited number of compounds. Often it will be necessary to combine assay types to identify specific sodium channel modulating compounds.

Electrophysiological assays using patch clamp techniques is accepted as a gold standard for detailed characterization of sodium channel compound interactions, and as described in Bean et al., op. cit. and Leuwer, M., et al., op. cit. There is a manual low-throughput screening (LTS) method which can compare 2-10 compounds per day; a recently developed system for automated medium-throughput screening (MTS) at 20-50 patches (i.e. compounds) per day; and a technology from Molecular Devices Corporation (Sunnyvale, Calif.) which permits automated high-throughput screening (MTS) at 1000-3000 patches (i.e. compounds) per day.

One automated patch-clamp system utilizes planar electrode technology to accelerate the rate of drug discovery. Planar electrodes are capable of achieving high-resistance, cells-attached seals followed by stable, low-noise whole-cell recordings that are comparable to conventional recordings. A suitable instrument is the PatchXpress 7000A (Axon Instruments Inc, Union City, Calif.). A variety of cell lines and culture techniques, which include adherent cells as well as cells growing spontaneously in suspension are ranked for seal success rate and stability, immortalized cells (e.g. HEK and CHO) stably expressing high levels of the relevant sodium ion channel can be adapted into high-density suspension cultures.

Other assays can be selected which allow the investigator to identify compounds which block specific states of the channel, such as the open state, closed state or the resting state, or which block transition from open to closed, closed to resting or resting to open. Those skilled in the art are generally familiar with such assays.

Binding assays are also available. Designs include traditional radioactive filler based binding assays or the confocal based fluorescent system available from Evotec OAI group of companies (Hamburg, Germany), both of which are HTS.

Radioactive flux assays can also be used. In this assay, channels are stimulated to open with veratridine or aconitine and held in a stabilized open state with a toxin, and channel blockers are identified by their ability to prevent ion influx. The assay can use radioactive 22[Na] and 14[C] guanidinium ions as tracers. FlashPlate & Cytostar-T plates in living cells avoids separation steps and are suitable for HTS. Scintillation plate technology has also advanced this method to HTS suitability. Because of the functional aspects of the assay, the information content is reasonably good.

Yet another format measures the redistribution of membrane potential using the FLIPR system membrane potential kit (HTS) available from Molecular Dynamics (a division of Amersham Biosciences, Piscataway, N.J.). This method is limited to slow membrane potential changes. Some problems may result from the fluorescent background of compounds. Test compounds may also directly influence the fluidity of the cell membrane and lead to an increase in intracellular dye concentrations. Still, because of the functional aspects of the assay, the information content is reasonably good.

Sodium dyes can be used to measure the rate or amount of sodium ion influx through a channel. This type of assay provides a very high information content regarding potential channel blockers. The assay is functional and would measure Na+ influx directly. CoroNa Red, SBFI and/or sodium green (Molecular Probes, inc. Eugene, Oreg.) can be used to measure Na influx; all are Na responsive dyes. They can be used in combination with the FLIPR instrument. The use of these dyes in a screen has not been previously described in the literature. Calcium dyes may also have potential in this format.

In another assay, FRET based voltage sensors are used to measure the ability of a test compound to directly block Na influx. Commercially available HTS systems include the VIPR™ II FRET system (Life Technologies, or Aurora Biosciences Corporation, San Diego, Calif., a division of Vertex Pharmaceuticals, Inc.) which may be used in conjunction with FRET dyes, also available from Aurora Biosciences. This assay measures sub-second responses to voltage changes. There is no requirement for a modifier of channel function. The assay measures depolarization and hyperpolarizations, and provides ratiometric outputs for quantification. A somewhat less expensive MTS version of this assay employs the FLEXstation™ (Molecular Devices Corporation) in conjunction with FRET dyes from Aurora Biosciences. Other methods of testing the compounds disclosed herein, are also readily known and available to those skilled in the art.

Modulating agents so identified are then tested in a variety of in vivo models so as to determine if they alleviate pain, especially chronic pain or other conditions such as cancer and pruritus (itch) with minimal, adverse events. The assays described below in the Biological Assays Section are useful in assessing the biological activity of the instant compounds.

Typically, the efficacy of a compound of the invention is expressed by its IC50 value ("Inhibitory Concentration—50%"), which is the measure of the amount of compound required to achieve 50% inhibition of the activity of the target sodium channel over a specific time period. For example, representative compounds of the present invention have demonstrated IC50's ranging from less than 100 nanomolar to less than 10 micromolar in the patch voltage clamp NaV1.7 electrophysiology assay described herein.

In another aspect of the invention, the compounds of the invention can be used in in vitro or in vivo studies as exemplary agents for comparative purposes to find other compounds also useful in treatment of, or protection from, the various diseases disclosed herein.

Another aspect of the invention relates to inhibiting NaV1.1, NaV1.2, NaV1.3, NaV1.4, NaV1.5, NaV1.6, NaV1.7, NaV1.8, or NaV1.9 activity, preferably NaV1.7 activity, in a biological sample or a mammal, preferably a human, which method comprises administering to the mammal, preferably a human, or contacting said biological sample with a compound of formula (I) or a pharmaceutical composition comprising a compound of formula (I). The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of NaV1.1, NaV1.2, NaV1.3, NaV1.4, NaV1.5, NaV1.6, NaV1.7, NaV1.8, or NaV1.9 activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

The compounds of the invention (or stereoisomers, geometric isomers, tautomers, solvates, metabolites, isotopes, pharmaceutically acceptable salts, or prodrugs thereof) and/or the pharmaceutical compositions described herein which comprise a pharmaceutically acceptable excipient and one or more compounds of the invention, can be used in the preparation of a medicament for the treatment of sodium channel-mediated disease or condition in a mammal.

Combination Therapy

The compounds of the invention may be usefully combined with one or more other compounds of the invention or one or more other therapeutic agent or as any combination thereof in the treatment of sodium channel-mediated diseases and conditions. For example, a compound of the invention may be administered simultaneously, sequentially or separately in combination with other therapeutic agents, including, bat not limited to:

opiates analgesics, e.g., morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine;

non-opiate analgesics, e.g., acetomeniphen, salicylates (e.g., aspirin);

nonsteroidal antiinflammatory drugs (NSAIDs), e.g., ibuprofen, naproxen, fenoprofen, ketoprofen, celecoxib, diclofenac, diflusinal, etodolac, fenbofen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac;

anticonvulsants, e.g., carbamazepine, oxcarbazepine, lamotrigine, valproate, topiramate, gabapentin and pregabalin;

antidepressants such as tricyclic antidepressants, e.g., amitriptyline, clomipramine, despramine, imipramine and nortriptyline;

COX-2 selective inhibitors, e.g., celecoxib, rofecoxib, parecoxib, valdecoxib, deracoxib, etoricoxib, and lumiracoxib;

alpha-adrenergics, e.g., doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline;

barbiturate sedatives, e.g., amobarbital, aprobarbital, butabarbital, butabital, mephobarbital, metharbital, methohexital, pentobarbital, phenobartital, secobarbital, talbutal, theamylal and thiopental;

tachykinin (NK) antagonist, particularly an NK-3, NK-2 or NK-1 antagonist, e.g., (αR, 9R)-7-[3,5-bis(trifluoromethyl)benzyl)]-8,9,10,11-tetrahydro-9-methyl-5-(4-methylphenyl)-7H-[1,4]diazoe ino[2,1-g][1.7]-naphthyridine-6-13-dione (TAK-637), 5-[[2R,3S)-2-[(1R)-1-[3,5-bis(trifluoromethylphenyl]ethoxy-3-(4-fluorophenyl-4-morpholinyl]-methyl]-1,2-dihydro-3H-1,2,4-triazol-3-one (MK-869), aprepitant, lanepitant, dapitant or 3-[[2-methoxy5-(trifluoromethoxy)phenyl]-methylamino]-2-phenylpiperidine (2S,3S);

coal-tar analgesics, in particular paracetamol;

serotonin reuptake inhibitors, e.g., paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefaxodone, cericlamine, trazodone and fluoxetine;

noradrenaline (norepinephrine) reuptake inhibitors, e.g., maprotiline, lofepramine, mirtazepine, oxaprotiline, fezolamine, tomoxetine, mianserin, buprorion, buprorion metabolite hydroxybuproprion, nomifensine and viloxazine (Vivalian®)), especially a selective noradrenaline reuptake inhibitor such as reboxetine, in particular (S,S)-reboxetine, and venlafaxine duloxetine neuroleptics sedative/anxiolytics;

dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine;

acetylcholinesterase inhibitors such as donepezil;

5-HT13 antagonists such as ondansetron;

metabotropic glutamate receptor (mGluR) antagonists;

local anaesthetic such as mexiletine and lidocaine;

corticosteroid such as dexamethasone;

antiarrhythimics, e.g., mexiletine and phenytoin;

muscarinic antagonists, e.g., tolterodine, propiverine, tropsium t chloride, darifenacin, solifenacin, temiverine and ipratropium;

cannabinoids;

vanilloid receptor agonists (e.g., resinferatoxin) or antagonists (e.g., capsazepine);

sedatives, e.g., glutethimide, meprobamate, methaqualone, and dichloralphenazone;

anxiolytics such as benzodiazepines, antidepressant such as mirtazapine, topical agents (e.g., lidocaine, capsacin and resiniferotoxin);

muscle relaxants such as benzodiazepines, baclofen, carisoprodol, chlorzoxazone, cyclobenzaprine, methocarbamol and orphrenadine;

anti-histamines or H1 antagonists;

NMDA receptor antagonists;

5-HT receptor agonists/antagonists;

PDEV inhibitors;

Tramadol®;

cholinergic (nicotine) analgesics;

alpha-2-delta ligands;

prostaglandin E2 subtype antagonists;

leukotriene B4 antagonists;

5-lipoxygenase inhibitors; and

5-HT3 antagonists.

Sodium channel-mediated, diseases and conditions that may be treated and/or prevented using such combinations include but not limited to, pain, central and peripherally mediated, acute, chronic, neuropathic as well as other diseases with associated pain and other central nervous disorders such as epilepsy, anxiety, depression and bipolar disease; or cardiovascular disorders such as arrhythmias, atrial fibrillation and ventricular fibrillation; neuromuscular disorders such as restless leg syndrome and muscle paralysis or tetanus; neuroprotection against stroke, neural trauma and multiple sclerosis; and channelopathies such as erythromyalgia and familial rectal pain syndrome.

As used herein "combination" refers to any mixture or permutation of one or more compounds of the invention and one or more other compounds of the invention or one or more additional therapeutic agent. Unless the contest makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

The invention will be more fully understood, by reference to the following examples. They should not, however, be construed as limiting the scope of the invention.

EXAMPLES

These examples serve to provide guidance to a skilled artisan to prepare and use the compounds, compositions and methods of the invention. While particular embodiments of the present invention are described, the skilled artisan will appreciate that various changes and modifications can be made without departing from the spirit and scope of the inventions.

The chemical reactions in the examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, for example, by appropriately protecting interferring group, by utilizing other suitable reagents known in the art, for example, by appropriately protecting interferring groups by utilizing other suitable reagents known in the art other than those described, and/or by making routine modifications of reaction conditions.

In the examples below, unless otherwise indicated all temperatures are set forth in degrees Celcius. Commercially available reagents were purchased from suppliers such as Aldrich Chemical Company, Lancaster, TCI or Maybridge and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. $^1$H NMR spectra were obtained in deuterated $CDCl_3$, $d_6$-DMSO, $CH_3OD$ or $d_6$-acetone solvent solutions (reported in ppm) using or trimethylsilane (TMS) or residual non-deuterated solvent peaks as the reference standard. When peak multiplicities are reported, the following abbreviates are used: s (singlet), d (doublet), t (triplet), q (quartet), m (multiplet, br (broadened), dd (doublet of doublets), dt (doublet of triplets). Coupling constants, when given, ar reported in Hz (Hertz).

All abbreviations used to describe reagents, reaction conditions or equipment are intended to be consistent with the definitions set forth in the "List of standard abbreviates and acronyms". The chemical names of discrete compounds of the invention were obtained using the structure naming feature of ChemDraw naming program.

LCMS Analytical Methods

Final compounds were analyzed using three different LC/MS conditions, with UV detector monitoring at 214 nm and 254 nm, and mass spectrometry scanning 110-800 amu in ESI+ ionization mode.

LC/MS Method A (8.0 mm LC-MS Run): XBridge C18 column (4.6×50 mm, 3.5 μm, 40° C.); mobile phase: A=10 mM ammonium hydrogen carbonate in water, B=acetonitrile; gradient: 0.0-8.0 mm, 5%-95% B; flow rate=1.2 mL/min.

LC/MS Method B (8.0 mm LC-MS Run): XBridge C18 column (4.6×50 mm, 3.5 μm, 40° C.); mobile phase: A=0.1% ammonia in water, B=acetonitrile; gradient: 0.0-8.0 min, 5%-95% B; flow rate=1.2 mL/min.

LC/MS Method C (8.0 min LC-MS Run): XBridge C18 column (4.6×50 mm, 3.5 μm, 40° C.); mobile phase: A=0.1% TFA in water, B=acetonitrile; gradient: 0.0-8.0 mm, 5%-95% B; flow rate=1.2 mL/min.

LC/MS Method D: Agilent SB C18, 2.1×30 mm, 1.8 μm; mobile phase; A water (0.05% TFA), B $CH_3CN$ (0.05% TFA); gradient: 3% B (0.3 min), followed by 3-95% B (6.5 min), 95% B (1.5 min); flow rate: 0.4 mL/min; oven temperature 25° C.

LC/MS Method C: Acquity BEH C18, 2.1×50 mm, 1.8 μm; mobile phase: A water (0.1% FA), B $CH_3CN$ (0.1% FA); gradient: 3% B (0.4 min), followed by 3-95% B (7.5 min), 95% B (0.5 min); flow rate: 0.5 mL/min; oven temperature 25° C.

LC/MS Method F: Agilent SB C18, 2.1×30 mm, 1.8 μm; mobile phase: A water (0.05% TFA), B $CH_3CN$ (0.05% TFA); gradient: 3% B (0.3 min), followed by 3-95% B (6.5 min), 95% B (0.5 min); flow rate: 0.4 mL/min; oven temperature 25° C.

LC/MS Method G: Acquity BEH C18, 2.1×50 mm, 1.8 μm; mobile phase: A water (0.1% FA), B $CH_3CN$ (0.1% FA); gradient: 3% B (0.4 min), followed by 3-95% B (7.5 min), 95% B (0.5 min); flow rate: 0.5 mL/min; oven temperature 25° C.

ABBREVIATIONS

MeCN Acetonitrile
EtOAc Ethyl acetate
DCE Dichloroethane
DCM Dichloromethane
DIPEA Diisopropylethylamine
DEA Diethylamme
DMAP 4-dimethylaminopyridine
DMF N,N-Dimethylformamide
DMSO Dimethyl sulfoxide
FA Formic acid
IPA Isopropyl alcohol
TFA Trifluoroacetic acid
EDCl 1-Ethyl-3-(3-dimethylaminopropyl)carbodiimide hydrochloride
HCl Hydrochloric acid
HPLC High Pressure Liquid Chromatography
LCMS Liquid Chromatography Mass Spectrometry
MeOH Methanol
NMP N-methyl-2-pyrrolidone
RPHPLC Reverse phase high pressure liquid chromatography
RT Retention time
THF Tetrahydrofuran

EXAMPLES

Example 1

Synthesis (R)—N-(azetidin-1-ylsulfonyl)-4-((1-benzylpiperidin-3-yl)oxy)-5-cyclopropyl-2-fluorobenzamide

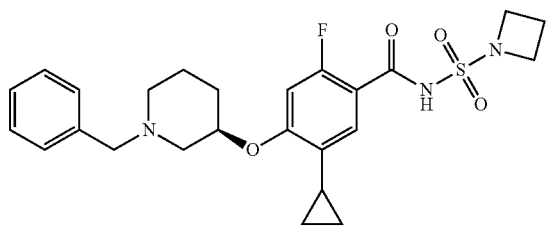 [SMILES: O=C(NS(=O)(=O)N1CCC1)c1cc(C2CC2)c(O[C@@H]2CCCN(Cc3ccccc3)C2)cc1F]

Step 1. Preparation of (R)-tert-butyl 4-((1-benzylpiperidin-3-yl)oxy)-5-chloro-2-fluorobenzoate

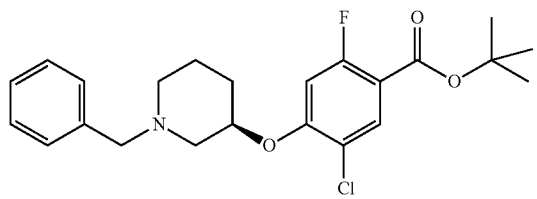 [SMILES: CC(C)(C)OC(=O)c1cc(Cl)c(O[C@@H]2CCCN(Cc3ccccc3)C2)cc1F]

To a solution of (R)-1-benzylpiperidin-3-ol (0.38 g, 2.00 mmol) and tert-butyl 5-chloro-2,4-difluorobenzoate (0.50 g, 2.00 mmol) in anhydrous dimethyl sulfoxide (6 mL) was added cesium carbonate (2.16 g, 4.00 mmol). The reaction mixture was stirred at 70° C. for 2 hours under an atmosphere of nitrogen and then cooled to ambient temperature and quenched by addition of 10 mL of water. The mixture was extracted with ethyl acetate (3×15 mL); the organic layers were combined and washed with brine (15 mL), dried over anhydrous magnesium sulfate, filtered and concentrated. The residue was purified by column chromatography eluting with a gradient of ethyl acetate in hexanes (0 to 25%) to give the title compound (0.66 g, 78%) as a white solid: $^1$H NMR (300 MHz, CDCl$_3$) d 7.85 (d, J=7.74 Hz, 1H), 7.36-7.18 (m, 5H), 6.63 (d, J=12.2 Hz, 1H), 4.49-4.31 (m, 1H), 3.57 (s, 2H), 3.10-2.96 (m, 1H), 2.82-2.66 (m, 1H), 2.27 (m, 1H), 2.20-2.02 (m, 2H), 1.92-1.75 (m, 1H), 1.73-1.59 (m, 1H), 1.60-1.50 (m, 10H).

Step 2. Preparation of (R)-tert-butyl-4-((1-benzylpiperidin-3-yl)oxy)-5-cyclopropyl-2-fluorobenzoate

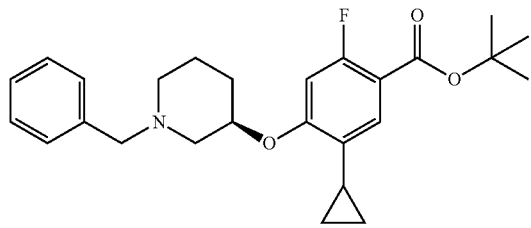 [SMILES: CC(C)(C)OC(=O)c1cc(C2CC2)c(O[C@@H]2CCCN(Cc3ccccc3)C2)cc1F]

To a solution of (R)-tert-butyl-4-((1-benzylpiperidin-3-yl)oxy)-5-chloro-2-fluorobenzoate (0.38 g, 0.90 mmol) and cyclopropylboronic acid (0.12 g, 1.35 mmol) in toluene (3 mL) and water (0.3 mL) was added potassium phosphate tribasic (0.64 g, 1.80 mmol), palladium (II) acetate (0.02 g, 0.09 mmol), and tricyclohexyl phosphonium tetrafluoroborate (0.07 g, 0.18 mmol) and the mixture was degassed thoroughly and the reaction vessel filled up with nitrogen before heating at 115° C. for 40 min under microwave irradiation. The reaction mixture was then cooled to ambient temperature and quenched by addition of 10 mL of water. The mixture was then extracted with diethyl ether (2×15 mL). The organic layers were combined, concentrated and The residue was purified by column chromatography (10 to 30% gradient of ethyl acetate in hexanes) to give the title compound (0.37 g, 98%) as a colorless oil: $^1$H NMR (300 MHz, CDCl$_3$) d7.36 (d, J=8.4 Hz, 1H), 7.33-7.13 (m, 5H), 6.53 (d, J=12.8 Hz, 1H), 4.44-4.30 (m, 1H), 3.61-3.49 (m, 2H), 3.09-2.94 (m, 1H), 2.76-2.63 (m, 1H), 2.31-1.96 (m, 4H), 1.90-1.60 (m, 3H), 1.59-1.54 (m, 9H), 0.92-0.83 (m, 2H), 0.67-0.60 (m, 2H); MS(ES+) m/z 426.2 (M+1).

Step 3. Preparation of (R)—N-(azetidin-1-ylfulfonyl)-4-((1-benzylpiperidin-3-yl)oxy)-5-cyclopropyl-2-fluorobenzamide

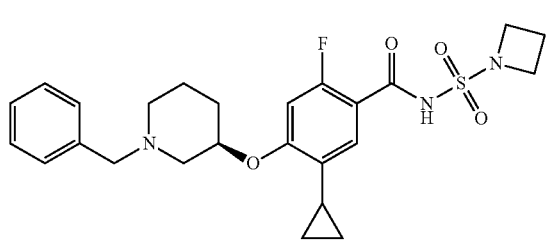 [SMILES: O=C(NS(=O)(=O)N1CCC1)c1cc(C2CC2)c(O[C@@H]2CCCN(Cc3ccccc3)C2)cc1F]

To a solution of (R)-tert-butyl 4-((1-benzylpiperidin-3-yl)oxy)-5-cyclopropyl-2-fluorobenzoate (0.127 g, 0.30 mmol) in dichloromethane (1 mL) was added trifluoroacetic acid (1 mL). After stirring at ambient temperature for 1 hour, the reaction mixture was concentrated, diluted with dichloromethane (10 mL) and washed with aqueous hydrochloric acid (1.0 N, 10 mL). The aqueous layers was extracted with dichloromethane (10 mL), the organic layers were combined, dried over anhydrous sodium sulfate, filtered and concentrated to give the corresponding carboxylic acid which was used directly for the next step. To a solution of the carboxylic acid (0.11 g, 0.30 mmol) in dichloromethane (2 mL) was added 1-ethyl-3-(3-dimethylaminopropyl)carbodiimide (0.124 g, 0.48 mmol) and 4-dimethylaminopyridine (0.091 g, 0.75 mmol) and azetidine sulfonamide (0.052 g, 0.39 mmol). The reaction mixture was stirred at ambient temperature for 16 hours and then diluted with dichloromethane (10 mL) and washed with aqueous hydrochloric acid (1.0 N, 10 mL). The aqueous layer was extracted with dichloromethane (10 mL); the organic layers were combined, dried over anhydrous sodium sulfate, filtered and concentrated. The residue was first purified by column chromatography eluting with a gradient of methanol in dichloromethane (0% to 15%) and further purified by preparative HPLC (gradient of acetonitrile in water) to give the title compound as a white solid (0.021 g, 54%): $^1$H NMR (300 MHz, CDCl$_3$) d 7.54 (d, J=9.1 Hz, 1H), 7.33-7.22 (m, 5H), 6.56 (d, J=14.5 Hz, 1H), 4.48-4.34 (m, 1H), 4.22 (t, J=7.7 Hz, 4H), 3.57 (s, 2H), 3.07-2.93 (m, 1H), 2.78-2.67

(m, 1H), 2.35-2.13 (m, 4H), 2.13-1.99 (m, 2H), 1.91-1.78 (m, 1H), 1.76-1.46 (m, 2H), 0.95-0.85 (m, 2H), 0.69-0.61 (m, 2H). MS(ES+) m/z: 488.1 (M+1); MS(ES−) m/z 486.2 (M−1).

Example 2

Synthesis of (S)—N-(azetidin-1-ylsulfonyl)-4-((1-benzylpiperidin-3-yl)oxy)-5-cyclopropyl-2-fluorobenzamide

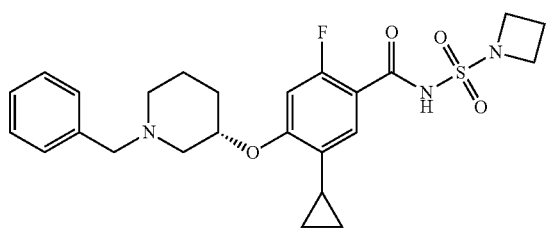 [SMILES: O=C(NS(=O)(=O)N1CCC1)c1cc(C2CC2)c(O[C@H]2CCCN(Cc3ccccc3)C2)cc1F]

Following the procedure as described in Example 1 step 1 to step 3, and making variation as required to replace (R)-1-benzylpiperidin-3-ol with (S)-1-benzylpiperidin-3-ol, the title compound was obtained as a white solid (0.012 g, 45%); $^1$H NMR (300 MHz, CDCl$_3$) d 7.54 (d, J=9.15 Hz, 1H), 7.33-7.22 (m, 5H) 6.56 (d, J=14.5 Hz, 1H), 4.48-4.34 (m, 1H), 4.22 (t, J=7.7 Hz, 4H), 3.57 (s, 2H), 3.07-2.93 (m, 1H), 2.78-2.67 (m, 1H), 2.35-2.13 (m, 4H), 2.13-1.99 (m, 2H), 1.91-1.78 (m, 1H), 1.76-1.46 (m, 2H), 0.95-0.85 (m, 2H), 0.69-0.61 (m, 2H); MS(ES+) m/z 488.1 (M+1); MS(ES−) m/z 486.2 (M−1).

Example 3

Synthesis of (R)-5-cyclopropyl-N-(cyclopropylsulfonyl)-4-((1-(3,5-dichlorobenzyl)piperidin-3-yl)oxy)-2-fluorobenzamide

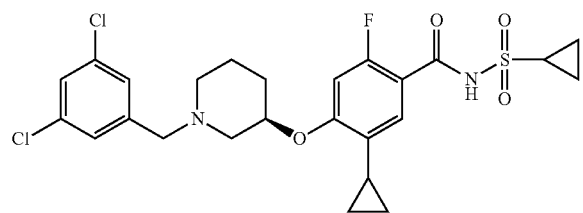 [SMILES: O=C(NS(=O)(=O)C1CC1)c1cc(C2CC2)c(O[C@@H]2CCCN(Cc3cc(Cl)cc(Cl)c3)C2)cc1F]

Step 1. Preparation of (R)-tert-butyl 3-(4-(tert-butoxycarbonyl)-2-chloro-5-fluorophenoxy)piperidine-1-carboxylate

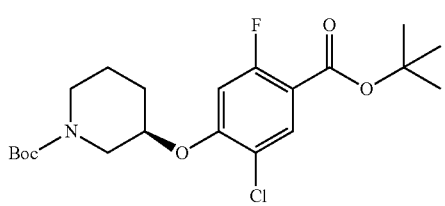 [SMILES: CC(C)(C)OC(=O)c1cc(Cl)c(O[C@@H]2CCCN(C(=O)OC(C)(C)C)C2)cc1F]

To a solution of (R)-tert-butyl 3-hydroxypiperidine-1-carboxylate (10.05 g, 50.00 mmol) and tert-butyl 5-chloro-2,4-difluorobenzoate (13.02 g, 52.50 mmol) in anhydrous DMSO (200 mL) was added cesium carbonate (40.62 g, 75.00 mmol). The reaction mixture was stirred at 70° C. for 1 hour under an atmosphere of nitrogen, and then cooled to ambient temperature and quenched by addition of 50 mL of water. The mixture was extracted with ethyl acetate (3×100 mL); the organic layers were combined and washed with brine (150 mL), dried over anhydrous magnesium sulfate, filtered and concentrated. The crude material (22.50 g, 99%) was used directly for the next step without further purification: MS(ES+) m/z 430.2, 431.2 (M+1).

Step 2. Preparation of (R)-tert-butyl 3-(4-(tert-butoxycarbonyl)-2-cyclopropyl-5-fluorophenoxy)piperidine-1-carboxylate

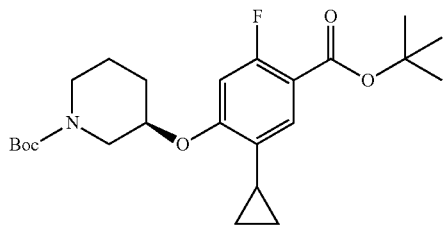 [SMILES: CC(C)(C)OC(=O)c1cc(C2CC2)c(O[C@@H]2CCCN(C(=O)OC(C)(C)C)C2)cc1F]

To a solution of (R)-tert-butyl 3-(4-(tert-butoxycarbonyl)-2-chloro-5-fluorophenoxy)piperidine-1-carboxylate (22.50 g, 50.00 mmol) and cyclopropylboronic acid (7.22 g, 83.90 mmol) in toluene (150 mL) and water (15 mL) was added potassium phosphate tribasic (39.53 g, 111.90 mmol), palladium (II) acetate (1.25 g, 5.60 mmol), and tricyclohexyl phosphonium tetrafluoroborate (4.10 g, 11.20 mmol). The mixture was degassed thoroughly and the reaction vessel filled up with nitrogen before heating at 115° C. for 16 hours. The reaction mixture was then cooled to ambient temperature and quenched by addition of 100 mL of water. The mixture was extracted with diethyl ether (2×100 mL). The organic layers were combined, concentrated. The residue was purified by column chromatography (10 to 30% gradient of ethyl acetate in hexanes) to give the title compound as an colorless oil (16.50 g, 75%). $^1$H NMR (300 MHz, CDCl$_3$) d 7.36 (d, J=8.4 Hz, 1H), 6.55 (d, J=12.6 Hz, 1H), 4.37-4.21 (m, 1H), 3.81-3.32 (m, 4H), 2.03-1.76 (m, 5H), 1.55 (s, 9H), 0.92-0.79 (m, 2H), 0.73-0.50 (m, 2H).

Step 3. Preparation of (R)-5-cyclopropyl-2-fluoro-4-(piperidin-3-yloxy)benzoic acid, trifluoroacetic acid salt

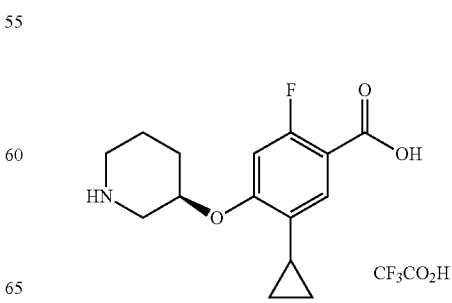

To a solution of (R)-tert-butyl 3-(4-(tert-butoxycarbonyl)-2-cyclopropyl-5-fluorophenoxy)-piperidine-1-carboxylate (9.5 g, 21.8 mmol) in dichloromethane (200 mL), was added trifluoroacetic acid (40 ml). The reaction mixture was stirred at ambient temperature for 3 hours and then concentrated in vacuo. The residue was purified by column chromatography (5% to 100% methanol in water on C18 column) afforded the title compound as colorless solid (5.3 g, 64%): $^1$H NMR (300 MHz, DMSO-$d_6$) δ 9.83 (brs, 2H), 7.27 (d, J=8.5 Hz, 1H), 7.02 (d, J=13.1 Hz, 1H), 4.76 (brs, 1H), 3.36-3.32 (m, 1H), 3.22-3.16 (m, 1H), 3.04 (brs, 2H), 2.27-2.18 (m, 1H), 1.96-1.66 (m, 4H), 0.92-0.87 (m, 2H), 0.66-0.52 (m, 2H); MS(ES+) m/z 280.3 (M+1); MS(ES−) m/z 278.4 (M−1).

Step 4. Preparation of (R)-5-cyclopropyl-4-((1-(3,5-dichlorobenzyl)piperidin-3-yl)oxy)-2-fluorobenzoic acid hydrochloride

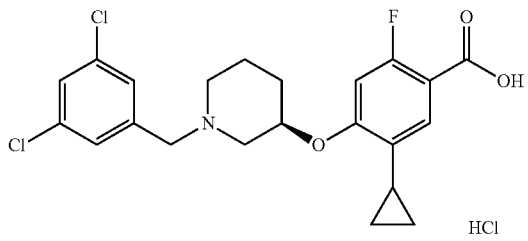 [SMILES: O=C(O)c1cc(C2CC2)c(O[C@@H]2CCCN(Cc3cc(Cl)cc(Cl)c3)C2)cc1F ; Cl]

To a stirred solution of (R)-5-cyclopropyl-2-fluoro-4-(piperidin-3-yloxy)benzoic acid trifluoroacetate (0.20 g, 0.53 mmol) in tetrahydrofuran (1 mL) under an atmosphere of nitrogen were introduced 3,5-dichlorobenzaldehyde (0.11 g, 0.64 mmol) and sodium triacetoxyborohydride (0.31 g, 0.96 mmol) and the mixture was stirred for 16 hours. Aqueous hydrochloric acid (1M, 5 mL) was added and the mixture was extracted with ethyl acetate (3×10 mL) and concentrated. The residue was purified by column chromatography eluting with 5% methanol in dichloromethane to give the title compound as an oil (0.16 g, 63%); MS(ES+) m/z 438.1, 440.1 (M+1): MS(ES−) m/z 436.1, 438.1 (M−1).

Step 5. Preparation of (R)-5-cyclopropyl-N-(cyclopropylsulfonyl)-4-((1-(3,5-dichlorobenzyl)piperidin-3-yl)oxy)-2-fluorobenzamide

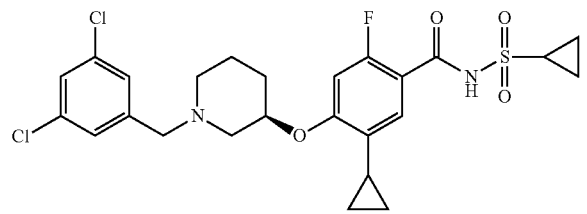 [SMILES: O=C(NS(=O)(=O)C1CC1)c1cc(C2CC2)c(O[C@@H]2CCCN(Cc3cc(Cl)cc(Cl)c3)C2)cc1F]

To a solution of (R)-5-cyclopropyl-4-((1-(3,5-dichlorobenzyl)piperidin-3-yl)oxy)-2-fluorobenzoic acid hydrochloride (0.07 g, 0.17 mmol) in dichloromethane (1 mL) was added 1-ethyl-3-(3-dimethylaminopropyl)carbodiimide (0.04 g, 0.25 mmol) and 4-dimethylaminopyridine (0.05 g, 0.42 mmol) and cyclopropylsulfonamide (0.02 g, 0.17 mmol). The reaction mixture was stirred at ambient temperature for 16 hours and then diluted with dichloromethane (1.0 mL) and washed with aqueous hydrochloric acid (1M, 10 mL). The aqueous layer was extracted with dichloromethane (10 mL), the organic layers were combined, dried over anhydrous sodium sulfate, filtered and concentrated to give an oil which was purified over silica gel chromatography (0 to 15% gradient of methanol containing 1% ammonia solution in dichloromethane) to give the title compound (0.02 g, 20%): $^1$H NMR (300 MHz, CDCl$_3$) d 7.41 (d, J=12.6 Hz, 1H), 7.23-7.18 (m, 3H), 6.54 (d, J=12.6 Hz, 1H), 4.49-4.33 (m, 1H), 3.56-3.39 (m, 2H), 2.94-2.81 (m, 1H), 2.68-2.53 (m, 1H), 2.46-2.31 (m, 1H), 2.31-2.16 (m, 1H), 2.11-1.97 (m, 2H), 1.92-1.78 (m, 1H), 1.73-1.52 (m, 3H), 0.98-0.79 (m, 6H), 0.72-0.57 (m, 2H); MS(ES+) m/z 541.1, 543.1 (M+1); MS(ES−) m/z 539.2, 541.2 (M−1).

Example 4

Synthesis of (R)-4-((1-acetylpiperidin-3-yl)oxy)-5-cyclopropyl-N-(cyclopropylsulfonyl)-2-fluorobenzamide

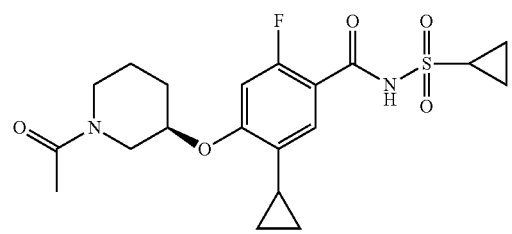 [SMILES: CC(=O)N1CCC[C@@H](Oc2cc(F)c(C(=O)NS(=O)(=O)C3CC3)cc2C2CC2)C1]

This compound was isolated as a side product during the synthesis of Example 3 in step 5 (0.02 g, 24%) as a colorless solid: $^1$H NMR (300 MHz, DMSO-$d_6$) d 7.21-7.00 (m, 2H), 4.83-4.52 (m, 1H), 4.06-3.93 (m, 1H), 3.86-3.69 (m, 1H), 3.63-3.38 (m, 2H), 3.13-2.93 (m, 2H), 1.99-1.76 (m, 5H), 1.72-1.36 (m, 2H), 1.29-1.03 (m, 4H), 0.90-0.79 (m, 2H), 0.69-0.60 (m, 2H); MS(ES+) m/z 425.2 (M+1); MS(ES−) m/z 423.3 (M−1).

Example 5

Synthesis of (R)—N-(azetidin-1-ylsulfonyl)-5-cyclopropyl-4-((1-(3,5-dichlorobenzyl)piperidin-3-yl)oxy)-2-fluoroenzamide

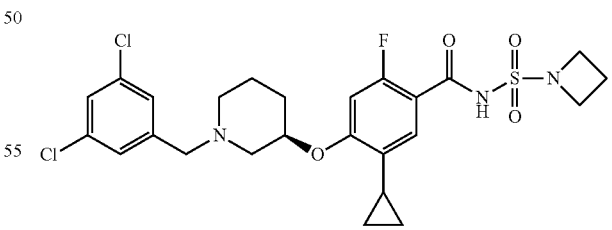

Following the procedure as described in Example 3 step 5, and making variation as required to replace cyclopropylsulfonamide with azetidine-1-sulfonamide, the title compound was obtained (0.02 g, 25%) as a colorless solid: $^1$H NMR (300 MHz, DMSO-$d_6$) δ 11.63-11.45 (m, 1H), 7.46-7.40 (m, 1H), 7.38-7.29 (m, 2H), 7.11 (d, J=8.36 Hz, 1H), 6.97 (d, J=13.0 Hz, 1H), 4.68-4.53 (m, 1H), 4.05-3.92 (m, 4H), 3.63-3.43 (m, 2H), 2.74-2.63 (m, 1H), 2.44-2.25 (m, 2H), 2.20-1.99 (m, 3H), 1.93-1.67 (m, 2H), 1.63-1.48 (m, 3H), 0.96-0.79 (m, 2H), 0.77-0.60 (m, 2H); MS(ES+) m/z 556.1, 558.1 (M+1); MS(ES−) m/z 554.2, 556.2 (M−1).

Example 6

Synthesis of (R)—N-(azetidin-1-ylsulfonyl)-4-((1-(2-chloro-4-fluorobenzyl)piperidin-3-yl)oxy)-5-cyclopropyl-2-fluoroenzamide

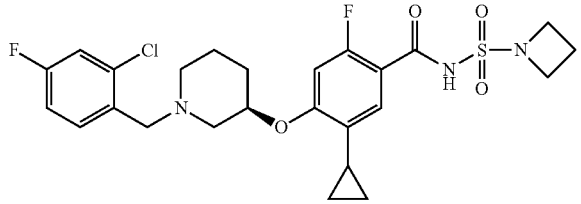 [SMILES: O=C(NS(=O)(=O)N1CCC1)c1cc(C2CC2)c(O[C@@H]2CCCN(Cc3ccc(F)cc3Cl)C2)cc1F]

Following the procedure as described in Example 3 steps 4 and 5, and making variations as required to replace 3,5-dichlorobenzaldehyde with 2-chloro-4-fluorobenzaldehyde and cyclopropylsulfonamide with azetidine-1-sulfonamide, the title compound was obtained (0.035 g, 50%) as a colorless solid; $^1$H NMR (300 MHz, DMSO-$d_6$) δ 11.62-11.47 (m, 1H), 7.45-7.40 (m, 1H), 7.38-7.28 (m, 2H), 7.11 (d, J=8.3 Hz, 1H), 4.68-4.53 (m, 1H), 4.05-3.92 (m, 4H), 3.62-3.42 (m, 2H), 2.75-2.63 (m, 1H), 2.44-2.26 (m, 1H), 2.20-2.00 (m, 3H), 1.90-1.67 (m, 2H), 1.63-1.48 (m, 3H), 0.94-0.81 (m, 2H), 0.76-0.62 (m, 2H); MS(ES+m/z 540.1, 542.1 (M+1); MS(ES−) m/z 538.2, 540.2 (M−1).

Example 7

Synthesis of (R)-4-((1-(2-chloro-4-fluorobenzyl)piperidin-3-yl)oxy)-5-cyclopropyl-N-(cyclopropylsulfonyl)-2-fluorobenzamide

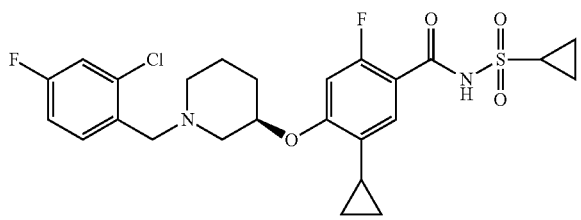 [SMILES: O=C(NS(=O)(=O)C1CC1)c1cc(C2CC2)c(O[C@@H]2CCCN(Cc3ccc(F)cc3Cl)C2)cc1F]

Following the procedures as described in Example 3 steps 4 and 5, and making variation as required to replace 3,5-dichlorobenzaldehyde with 2-chloro-4-fluorobenzaldehyde, the title compound was obtained (0.038 g, 37%) as a colorless solid; $^1$H NMR (300 MHz, DMSO-$d_6$) δ 11.89-11.60 (m, 1H), 7.49 (dd, J=8.5, 6.5 Hz, 1H), 7.37 (dd, J=8.8, 2.6 Hz, 1H), 7.17-7.05 (m, 2H), 6.98 (d, J=13.2 Hz, 1H), 4.68-4.50 (m, 1H), 3.63-3.52 (m, 2H), 3.11-2.97 (m, 1H), 2.84-2.70 (m, 1H), 2.61-2.49 (m, 2H), 2.43-2.29 (m, 1H), 2.12-1.98 (m, 1H), 1.98-1.65 (m, 2H), 1.64-1.45 (m, 2H), 1.13-1.02 (m, 4H), 0.91-0.81 (m, 2H), 0.72-0.62 (m, 2H); MS(ES+) m/z 525.1, 527.1 (M+1); MS(ES−) m/z 523.2, 525.2 (M−1).

Example 8

Synthesis of (R)—N-(azetidin-1-ylsulfonyl)-5-cyclopropyl-4-((1-(2,4-difluorobenzyl)-piperidin-3-yl)oxy)-2-fluorobenzamide

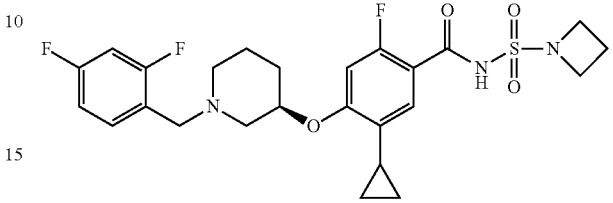

Following the procedures as described in Example 3 steps 4 and 5, and making variations as required to replace 3,5-dichlorobenzaldehyde with 2,4-difluorobenzaldehyde and cyclopropylsulfonamide with azetidine-1-sulfonamide, the title compound was obtained (0.048 g, 57%) as a colorless solid: $^1$H NMR (300 MHz, DMSO-$d_6$) δ 11.95-11.21 (m, 1H), 7.44 (dd, J=15.4, 8.53 Hz, 1H), 7.26-6.81 (m, 4H), 4.67-4.52 (m, 1H), 4.08-3.97 (m, 4H), 3.62-3.54 (m, 2H), 2.90-2.77 (m, 1H), 2.64-2.53 (m, 1H), 2.46-2.22 (m, 2H), 2.22-2.05 (m, 3H), 2.01-1.87 (m, 1H), 1.85-1.69 (m, 1H), 1.68-1.39 (m, 2.1), 0.95-0.82 (m, 2H), 0.76-0.64 (m, 2H); MS(ES+) m/z 524.1 (M+1); MS(ES−) m/z 522.2 (M−1).

Example 9

Synthesis of (R)-5-cyclopropyl-N-(cyclopropylsulfonyl)-4-((1-(2,4-difluorobenzyl)-piperidin-3-yl)oxy)-2-fluorobenzamide

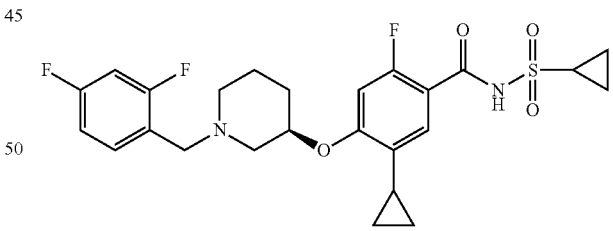

Following the procedures as described in Example 3 steps 4 and 5, and making variation as required to replace 3,5-dichlorobenzaldehyde with 2,4-difluorobenzaldehyde, the ride compound was obtained (0.035 g, 39%) as a colorless solid: $^1$H NMR (300 MHz, DMSO-$d_6$) δ 11.87-11.57 (m, 1H), 7.51-7.3 (m, 1H), 7.26-6.95 (m, 4H), 4.67-4.51 (m, 1H), 3.62-3.55 (m, 2H), 3.13-3.09 (m, 1H), 2.90-2.77 (m, 1H), 2.65-2.52 (m, 1H), 2.45-2.16 (m, 2H), 2.11-2.01 (m, 1H), 1.99-1.87 (m, 1H), 1.83-1.68 (m, 1H), 1.67-138 (m, 2H), 1.14-1.01 (m, 4H), 0.93-0.83 (m, 2H), 0.75-0.61 (m, 2H); MS(ES+) m/z 509.2 (M+1); MS(ES−) m/z 507.3 (M−1).

Example 10

Synthesis of (R)-5-cyclopropyl-4-((1-(2,6-dichlorobenzyl)piperidin-3-yl)oxy)-2-fluoro-N-(methylsulfonyl)benzamide

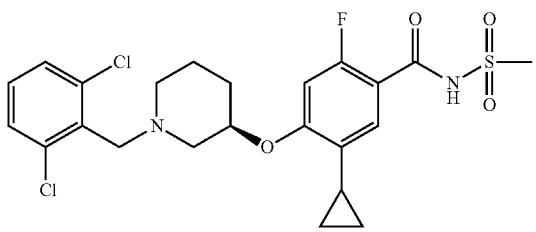 [SMILES: CS(=O)(=O)NC(=O)c1cc(C2CC2)c(O[C@@H]2CCCN(Cc3c(Cl)cccc3Cl)C2)cc1F]

Following the procedures as described in Example 3 steps 4 and 5, and making variations as required to replace 3,5-dichlorobenzaldehyde with 2,6-dichlorobenzaldehyde and cyclopropylsulfonamide with methylsulfonamide, the title compound was obtained (0.018 g, 13%) as a colorless solid: $^1$H NMR (300 MHz, DMSO-d$_6$) δ 7.46-734 (m, 2H), 7.28 (dd, J=8.8, 7.18 Hz, 1H), 7.14 (d, J=8.8 Hz, 1H), 4.39-4.24 (m, 1H), 3.67 (m, 2H), 2.94-2.80 (m, 1H), 2.80-2.72 (m, 3H), 2.61-2.53 (m, 1H), 2.44-2.37 (m, 1H), 2.37-2.23 (m, 1H), 2.05-1.83 (m, 2H), 1.78-1.60 (m, 1H), 1.54-1.36 (m, 2H), 0.86-0.73 (m, 2H), 0.36-0.42 (m, 2H): MS(ES+) m/z 515.2-517.2 (M+1); MS(ES−) m/z 513.3, 515.3 (M−1).

Example 11

Synthesis of (R)—N-(azetidin-1-ylsulfonyl)-4-((1-(cyclohexylmethyl)piperidin-3-yl)oxy)-5-cyclopropyl-2-fluorobenzamide

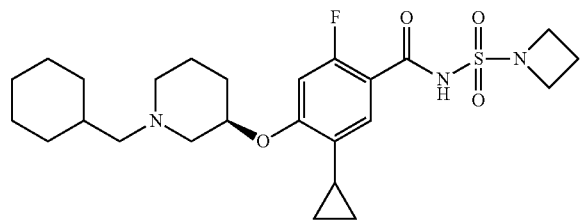 [SMILES: O=C(NS(=O)(=O)N1CCC1)c1cc(C2CC2)c(O[C@@H]2CCCN(CC3CCCCC3)C2)cc1F]

Following the procedures as described in Example 3 steps 4 and 5, and making variations as required to replace 3,5-dichlorobenzaldehyde with cyclohexanecarbaldehyde and cyclopropylsulfanamide with azetidine-1-sulfonamide, the title compound was obtained (0.041 g, 51%) as a colorless solid: $^1$H NMR (300 MHz, acetonitrile-d$_6$) δ 7.36-7.26 (m, 1H), 7.07-6.95 (m, 1H), 5.01-4.88 (m, 1H), 4.18-4.08 (m, 4H), 2.98-2.83 (m, 2H), 2.31-2.15 (m, 7H), 1.84-1.57 (m, 9H), 1.36-1.11 (m, 4H), 1.08-0.87 (m, 4H), 0.70-0.62 (m, 2H); MS(ES+) m/z 494.3 (M+1); MS(ES−) m/z 492.4 (M−1).

Example 12

Synthesis of (R)-5-cyclopropyl-2-fluoro-4-((1-((1-methyl-3-phenyl-1H-pyrazol-5-yl)methyl)piperidin-3-yl)oxy)-N-(methylsulfonyl)benzamide

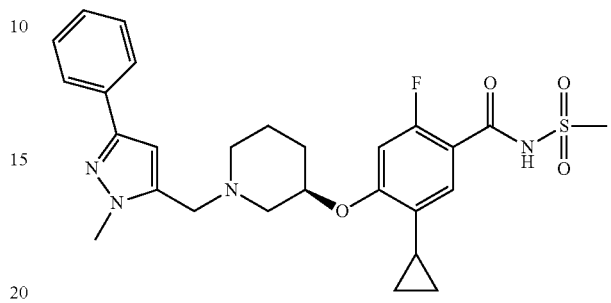

Following the procedures as described in Example 3 steps 4 and 5, and making variations as required to replace 3,5-dichlorobenzaldehyde with 1-methyl-3-phenyl-1H-pyrazole-5-carbaldehyde and cyclopropylsulfonamide with methylsulfonamide, the title compound was obtained (0.023 g, 39%) as a colorless solid: $^1$H NMR (300 MHz, DMSO-d$_6$) δ 7.75-7.61 (m, 2H), 7.33 (t, J=7.5 Hz, 2H), 7.25-7.13 (m, 231), 6.81-6.67 (m, 1H), 6.52 (d, J=3.3 Hz, 1H), 4.53-4.41 (m, 1H), 3.79 (s, 3H), 3.61-3.50 (m, 2H), 2.88-2.74 (m, 4H), 2.31-2.19 (m, 1H), 2.07-1.83 (m, 3H), 1.79-1.68 (m, 1H), 1.57-1.38 (m, 3H), 0.86-0.78 (m, 2H), 0.58-0.48 (m, 2H); MS(ES+) m/z 527.3 (M+1); MS(ES−) m/z 525.3 (M−1).

Example 13

Synthesis of (R)-5-cyclopropyl-2-fluoro-N-(methylsulfonyl)-4-((1-(pyridazin-4-ylmethyl)piperidin-3-yl)oxy)benzamide

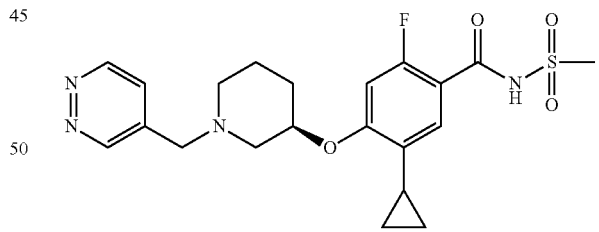

Following the procedures as described in Example 3 steps 4 and 5, and making variations as required to replace 3,5-dichlorobenzaldehyde with 1-methyl-3-phenyl-1H-pyrazole-5-carbaldehyde and cyclopropylsulfonamide with methylsulfonamide, the title compound was obtained (0.035 g, 40%) as a colorless solid: $^1$H NMR (300 MHz, CDCl$_3$) δ 8.87-8.82 (m, 1H), 8.75 (dd, J=5.2, 0.8 Hz, 1H), 7.23-718 (m, 1H), 7.08 (d, J=8.8 Hz, 1H), 0.36 (d, J=13.5 Hz, 1H), 4.28-4.16 (m, 1H), 3.35 (d, J=15.0 Hz, 1H), 3.26 (d, J=15.0 Hz, 1H), 2.88 (s, 3H), 2.59-2.48 (m, 1H), 2.38-2.02 (m, 4H), 1.85-1.6 (m, 2H), 1.46-1.29 (m, 3H), 0.68-0.59 (m, 2H), 0.46-0.34 (m, 2H); MS(ES+) m/z 449.1 (M+1).

Example 14

Synthesis of (R)-5-cyclopropyl-2-fluoro-4-((1-(isoindolin-4-ylmethyl)piperidin-3-yl)oxy)-N-(methylsulfonyl)benzamide

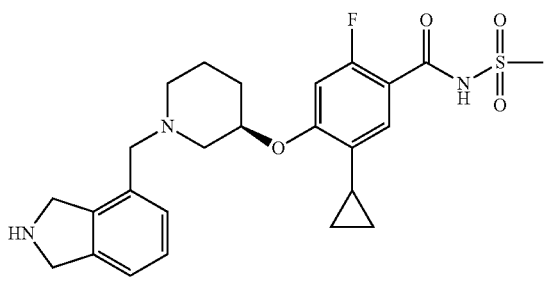 [SMILES: CS(=O)(=O)NC(=O)c1cc(C2CC2)c(O[C@@H]2CCCN(Cc3cccc4c3CNC4)C2)cc1F]

Step 1. Preparation of (R)-tert-butyl 4-((3-(2-cyclopropyl-5-fluoro-4-((methylsulfonyl)carbamoyl)phenoxy)piperidin-1-yl)methyl)isoindoline-2-carboxylate

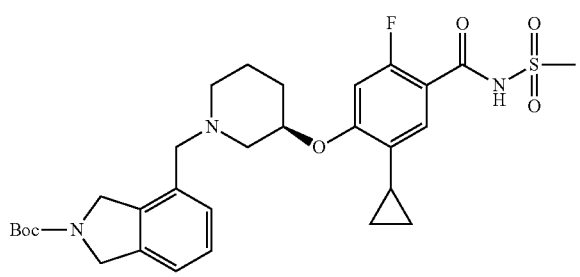 [SMILES: CC(C)(C)OC(=O)N1Cc2cccc(CN3CCC[C@@H](Oc4cc(F)c(C(=O)NS(C)(=O)=O)cc4C4CC4)C3)c2C1]

Following the procedures as described in Example 3 steps 4 and 5, and making variations as required to replace 3,5-dichlorobenzaldehyde with tert-butyl 4-formylisoindoline-2-carboxylate and cyclopropylsulfonamide with methylsulfonamide, the title compound was obtained (0.030 g, 16%): MS(ES+) m/z 588.2 (M+1).

Step 2. Preparation of (R)-5-cyclopropyl-2-fluoro-4-((1-(isoindolin-4-ylmethyl)-piperidin-3-yl)oxy)-N-(methylsulfonyl)benzamide

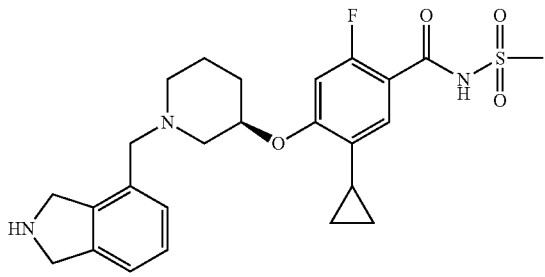 [SMILES: CS(=O)(=O)NC(=O)c1cc(C2CC2)c(O[C@@H]2CCCN(Cc3cccc4c3CNC4)C2)cc1F]

To a stirred solution of (R)-tert-butyl 4-((3-(2-cyclopropyl-5-fluoro-4-((methylsulfonyl)-carbamoyl)phenoxy)piperidin-1-yl)methyl)isoindoline-2-carboxylate (0.030 g, 0.051 mmol) in dichloromethane (1 mL) was added trifluoroacetic acid (0.3 mL) and the mixture was stirred at ambient temperature for 1 hour and then concentrated. The residue was purified by silica gel chromatography (0 to 15% gradient of methanol plus 1% ammonia solution in dichloromethane) to give the title compound (0.01 g, 38%): $^1$H NMR (300 MHz, MeOD-$d_4$) d 2.41-7.18 (m, 4H), 0.69 (d, J=13.1 Hz, 1H), 4.77-4.54 (m, 2H), 4.53-4.43 (m, 1H), 3.61-3.55 (m, 2H), 3.54-3.40 (m, 1H), 3.37-3.03 (m, 4H), 2.88-2.79 (m, 1H), 2.61-2.52 (m, 1H), 2.51-2.41 (m, 1H), 2.38-2.26 (m, 1H), 2.10-1.99 (m, 2H), 1.94-1.82 (m, 1H), 1.78-1.70 (m, 1H), 1.69-1.56 (m, 1H), 0.94-0.85 (m, 2H), 0.70-0.57 (m, 2H): MS(ES+) m/z 488.3 (M+1); MS(ES−) m/z 486.4 (M−1).

Example 15

Synthesis of (R)—N-(azetidin-1-ylsulfonyl)-4-((1-benzhydrylpiperidin-3-yl)oxy)-5-cyclopropyl-2-fluorobenzamide

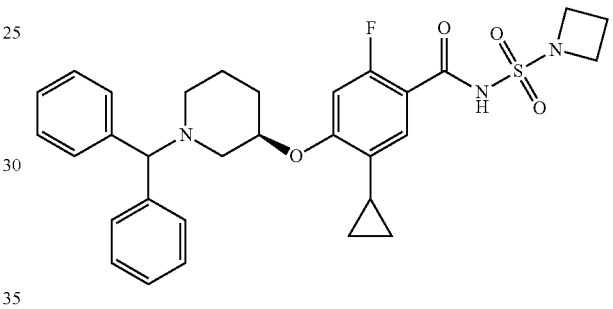

Step 1. Preparation of (R)-4-((1-benzhydrylpiperidin-3-yl)oxy)-5-cyclopropyl-2-fluorobenzoic acid

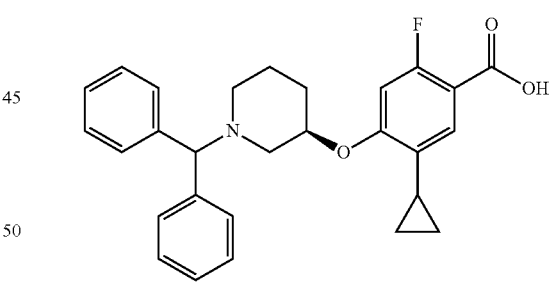

To a stirred solution of (R)-5-cyclopropyl-2-fluoro-4-(piperidin-3-yloxy)benzoic acid trifluoroacetate (0.20 g, 0.53 mmol) in acetonitrile (2 mL) under an atmosphere of nitrogen were added (bromomethylene)dibenzene (0.16 g, 0.64 mmol), potassium carbonate (0.17 g, 1.28 mmol) and sodium iodide (0.09 g, 0.64 mmol) and the mixture was stirred at reflux for 16 hours. Alter cooled to ambient temperature, 1M aqueous hydrochloric acid (5 mL) was added slowly and the mixture was extracted with ethyl, acetate (3×10 mL) and concentrated. The residue was purified over silica gel chromatography elating with 30% ethyl acetate (containing 1% Formic acid) in hexanes to give compound the title compound as an oil (0.16 g, 70%): MS(ES+) m/z 446.1 (M+1).

Step 2. Preparation of (R)—N-(azetidin-1-ylsulfonyl)-4-((1-benzhydrylpiperidin-3-yl)oxy)-5-cyclopropyl-2-fluorobenzamide

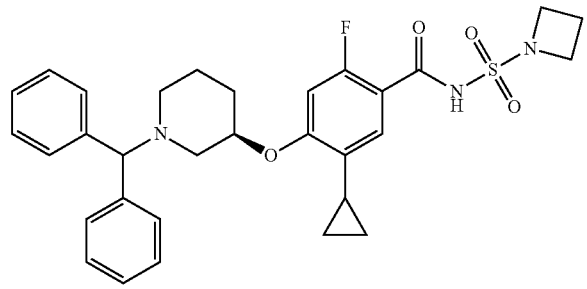 [SMILES: O=C(NS(=O)(=O)N1CCC1)c1cc(C2CC2)c(O[C@@H]2CCCN(C(c3ccccc3)c3ccccc3)C2)cc1F]

Following the procedure as described in Example 3 step 5, and making variations as required to replace cyclopropylsulfonamide with azetidine-1-sulfonamide, the title compound was obtained (0.035 g, 34%) as a colorless solid: $^1$H NMR (300 MHz, DMSO-d$_6$) δ 11.65-11.53 (m, 1H), 7.43-7.35 (m, 2H), 7.31-7.19 (m, 4H), 7.19-7.05 (m, 5H), 6.86 (d, J=13.0 Hz, 1H), 4.71-4.57 (m, 1H), 4.39-4.33 to, 1H), 4.08-3.95 (m, 4H), 2.62-2.49 (m, 1H), 2.44-2.21 (m, 3H), 2.20-2.05 (m, 3H), 1.94-1.70 (m, 2H), 1.67-1.48 (m, 2H), 0.96-0.87 (m, 2H), 0.79-0.69 (m, 2H): MS (ES+) m/z 564.3 (M+1); MS(ES−) m/z 562.4 (M−1).

Example 16

Synthesis of (R)-4-((1-benzhydrylpiperidin-3-yl)oxy)-5-cyclopropyl-N-(cyclopropylsulfonyl)-2-fluorobenzamide

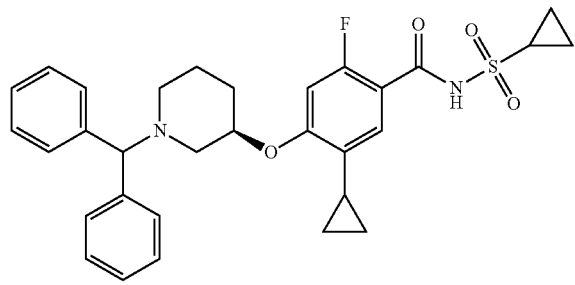 [SMILES: O=C(NS(=O)(=O)C1CC1)c1cc(C2CC2)c(O[C@@H]2CCCN(C(c3ccccc3)c3ccccc3)C2)cc1F]

Following the procedure as described in Example 15 step 2, and making variations as required to replace azetidine-1-sulfonamide with cyclopropylsulfonamide, the title compound was obtained (0.048 g, 52%) as a colorless solid: $^1$H NMR (300 MHz, DMSO-d$_6$) δ 11.90-11.73 (m, 1H), 7.43-7.34 (m, 2H), 7.31-7.20 (m, 4H), 7.19-7.04 (m, 5H), 6.86 (d, J=13.2 Hz, 1H), 4.73-4.55 (m, 1H), 4.40-4.32 (m, 1H), 3.12-2.99 (m, 1H), 2.62-2.49 (m, 1H), 2.44-2.21 (m, 3H), 2.20-2.05 (m, 1H), 1.94-1.71 (m, 2H), 1.68-1.46 (m, 1H), 1.15-1.02 (m, 4H), 0.96-0.87 (m, 2H), 0.79-0.68 (m, 2H); MS(ES+) m/z 549.3 (M+1); MS(ES−) m/z 547.4 (M−1).

Example 17

Synthesis of (R)-5-cyclopropyl-4-((1-(3,4-dichlorobenzyl)piperidin-3-yl)oxy)-2-fluoro-N-(methylsulfonyl)benzamide

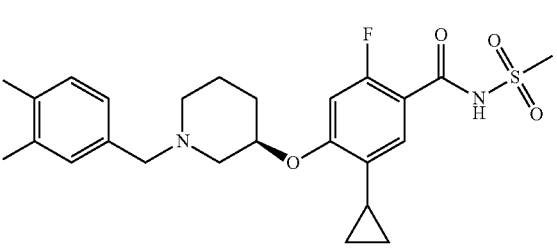

Step 1. Preparation of (R)-5-cyclopropyl-4-((1-(3,4-dichlorobenzyl)piperidin-3-yl)oxy)-2-fluorobenzoic acid

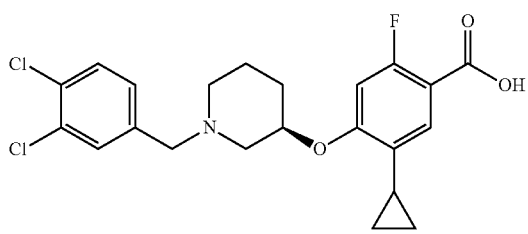 [SMILES: O=C(O)c1cc(C2CC2)c(O[C@@H]2CCCN(Cc3ccc(Cl)c(Cl)c3)C2)cc1F]

To a solution of (R)-5-cyclopropyl-2-fluoro-4-(piperidin-3-yloxy)benzoic acid (0.40 g, 1.43 mmol) and 3,4-dichlorobenzaldehyde (0.30 g, 1.72 mmol) in tetrahydroforan (2 mL) was added sodium triacetoxyborohydrate (0.55 g, 2.58 mmol). The reaction mixture was stirred at ambient temperature for 2 hours, and concentrated in vacuo. The residue was diluted with ethyl acetate (50 mL), washed with aqueous ammonium chloride (25% solution, 2×25 mL); dried over anhydrous sodium sulfate and concentrated in vacuo. The crude product was purified by column chromatography (5% to 100% methanol in water on C18 column) afforded the title compound as colorless solid (0.42 g, 56%); MS(ES+) m/z 438.2, 440.2 (M+1); MS(ES−) m/z 436.3, 438.3 (M−1).

Step 2. Preparation of (R)-5-cyclopropyl-4-((1-(3,4-dichlorobenzyl)piperidin-3-yl)oxy)-2-fluoro-N-(methylsulfonyl)benzamide To a mixture of (R)-5-cyclopropyl-4-((1-(3,4-dichlorobenzyl)piperidin-3-yl)oxy)-2-fluorobenzoic acid (0.10 g, 0.23 mmol), 1-ethyl-(3-dimethylaminopropyl)carbodiimide (0.10 g, 0.52 mmol) and 4-dimethylaminopyridine (0.06 g, 0.52 mmol) in anhydrous dichloromethane (2 mL) was added methanesulfonamide (0.03 g, 0.34 mmol) at ambient temperature. The resulting mixture was stirred at ambient temperature for 16 hours. The mixture was diluted with ethyl acetate (50 mL), washed with aqueous ammonium, chloride (25% solution, 2×2.5 mL), dried over anhydrous sodium sulfate, and filtered.

The filtrate was concentrated in vacuo, the crude product was purified by silica gel column chromatography using 10-100% ethyl acetate in hexanes as an eluent to afford the title compound as colorless solid (0.07 g, 58%): $^1$H NMR (300 MHz, DMSO-$d_6$) δ 11.74 (brs, 1H), 7.57-7.53 (m, 2H), 7.29 (dd, J=1.8, 8.3 Hz, 1H), 7.14 (d, J=8.4 Hz, 1H), 6.99 (d, J=13.2 Hz, 1H), 4.63-4.61 (m, 1H), 3.61 (d, J=14.0 Hz, 1H), 3.53 (d, J=14.0 Hz, 1H), 3.29 (s, 3H), 2.79-2.75 (m, 1H), 2.55-2.32 (m, 3H), 2.12-2.03 m, 1H), 1.92-1.89 (m, 1H), 1.83-1.77 (m, 1H), 1.63-1.53 (m, 2H), 0.93-0.85 (m, 2H), 0.76-0.65 (m, 2H); MS(ES−) m/z 515.2, 517.2 (M+1); MS(ES−) m/z 513.1, 515.1 (M−1).

Example 18

Synthesis of (R)-5-cyclopropyl-N-(cyclopropylsulfonyl)-4-((1-(3,4-dichlorobenzyl)-piperidin-3-yl)oxy)-2-fluorobenzamide

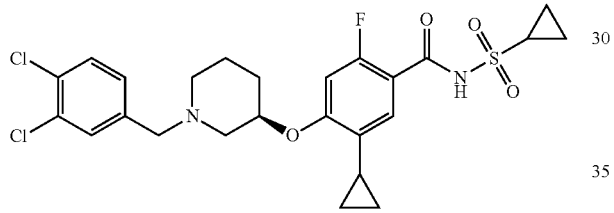

Following the procedure as described in Example 17 step 2, and making variations as required to replace methanesulfonamide with cyclopropanesulfonamide, the title compound was obtained as colorless solid (0.06 g, 51%): $^1$H NMR (300 MHz, DMSO-$d_6$) δ 11.72 (brs, 1H), 7.56-7.53 (m, 2H), 7.25 (dd, J=1.8, 8.3 Hz, 1H), 7.13 (d, J=8.4 Hz, 1H), 7.00 (d, J=13.2 Hz, 1H), 4.63-4.61 (m, 1H), 3.60 (d, J=14.0 Hz, 1H), 3.51 (d, J=14.0 Hz, 1H), 3.11-3.02 (m, 1H), 2.77-2.74 (m, 1H), 2.54-2.34 (m, 361), 2.13-2.03 (m, 1H), 1.92-1.77 (m, 1.60-1.56 (m, 2H), 0.12-1.07 (m, 4H), 0.92-0.88 (m, 2H), 0.74-0.69 (m, 2H); MS(ES+) m/z 541.2, 543.2 (M+1); MS(ES−) m/z 539.1, 541.1 (M−1).

Example 19

Synthesis of (R)—N-(azetidin-1-ylsulfonyl)-5-cyclopropyl-4-((1-(3,4-dichlorobenzyl)piperidin-3-yl)oxy)-2-fluorobenzamide

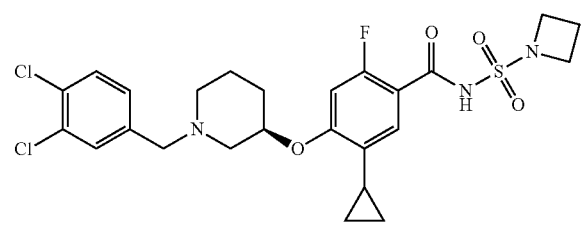 [SMILES: O=C(NS(=O)(=O)N1CCC1)c1cc(C2CC2)c(O[C@@H]2CCCN(Cc3ccc(Cl)c(Cl)c3)C2)cc1F]

Following the procedure as described in Example 17 step 2, and making variations as required to replace methanesulfonamide with azetidine-1-sulfonamide, the title compound was obtained as colorless solid (0.01 g, 11%): $^1$H NMR (300 MHz, CDCl$_3$) δ 8.65 (brs, 1H), 7.58 (d, J=9.1 Hz, 1H), 7.44-7.35 (m, 2H), 7.16-7.14 (m, 1H), 6.58 (d, J=14.1 Hz, 1H), 4.44 (brs, 1H), 4.27-4.22 (m, 4H), 3.56-3.45 (m, 2H), 2.92-2.88 (m, 1H), 2.67-2.63 (m, 1H), 2.41-2.22 (m, 4H), 2.12-2.03 (m, 2H), 1.91-1.87 (m, 1H), 1.68-1.63 (m, 2H), 0.97-0.91 (m, 2H), 0.71-0.67 (m, 2H); MS(ES+) m/z 556.2, 558.2 (M+1); MS(ES−) m/z 554.2, 556.2 (M−1).

Example 20

Synthesis of (R)-5-cyclopropyl-2-fluoro-4-((1-(4-fluorobenzyl)piperidin-3-yl)oxy)-N-(methlysulfonyl)benzamide

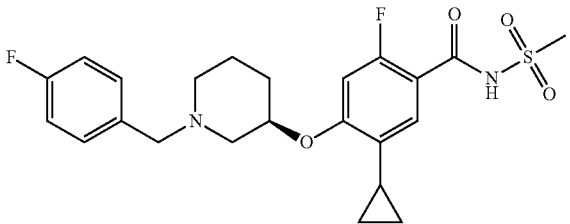

Step 1. Preparation of ((R)-5-cyclopropyl-2-fluoro-4-((1-(4-fluorobenzyl)piperidin-3-yl)oxy)benzoic acid

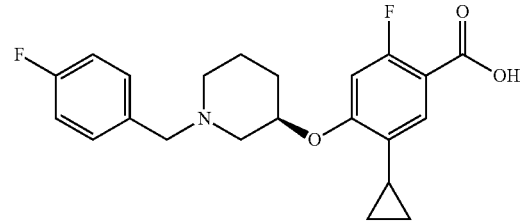 [SMILES: O=C(O)c1cc(C2CC2)c(O[C@@H]2CCCN(Cc3ccc(F)cc3)C2)cc1F]

Following the procedure as described in Example 17 step 1, and making variations as required to replace 3,4-dichlorobenzaldehyde with 4-fluorobenzaldehyde, the title compound was obtained as colorless solid (0.22 g, 41%): MS(ES+) m/z 388.2 (M+1); MS(ES−) m/z 386.2 (M−1).

Step 2. Preparation of ((R)-5-cyclopropyl-2-fluoro-4-((1-(4-fluorobenzyl)piperidin-3-yl)oxy)-N-(methylsulfonyl)benzamide

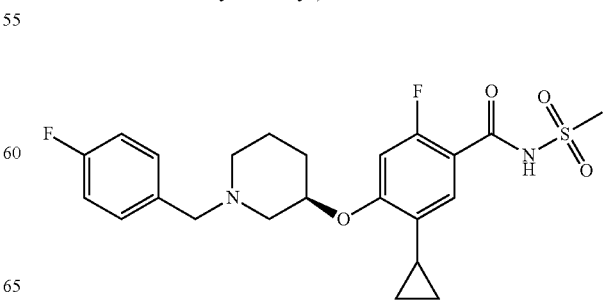

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with (R)-5-cyclopropyl-2-fluoro-4-((1-(4-fluorobenzyl)piperidin-3-yl)oxy)benzoic acid, the title compound was obtained as colorless solid (0.01 g, 14%): $^1$H NMR (300 MHz, DMSO-$d_6$) δ 11.68 (brs, 1H), 7.36-7.31 (m, 2H), 7.15-7.09 (m, 3H), 6.93 (d, J=13.1 Hz, 1H), 4.59-4.55 (m, 1H), 3.62-3.50 (m, 2H), 3.21 (m, 3H), 2.94-2.81 (m, 1H), 2.60-2.56 (m, 1H), 2.44-2.26 (m, 2H), 2.10-2.01 (m, 1H), 1.98-1.92 (m, 1H), 1.82-1.76 (m, 1H), 1.64-1.46 (m, 2H), 0.90-0.87 (m, 2H), 0.69-0.65 (m, 2H); MS(ES+) m/z 465.3 (M+1); MS(ES−) m/z 463.2 (M−1).

Example 21

Synthesis of (R)-5-cyclopropyl-N-(cyclopropylsulfonyl)-2-fluoro-4-((1-(4-fluorobenzyl)piperidin-3-yl)oxy)benzamide

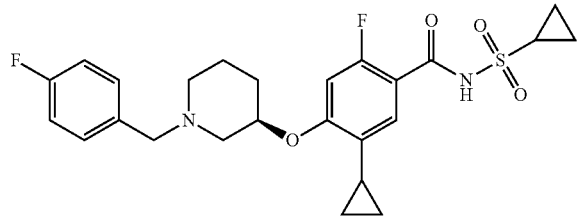 [SMILES: O=C(NS(=O)(=O)C1CC1)c1cc(C2CC2)c(O[C@@H]2CCCN(Cc3ccc(F)cc3)C2)cc1F]

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with (R)-5-cyclopropyl-2-fluoro-4-((1-(4-fluorobenzyl)piperidin-3-yl)oxy)benzoic acid and methanesulfonamide with cyclopropanesulfonamide, the title compound was obtained as colorless solid (0.05 g, 51%): $^1$H NMR (300 MHz, DMSO-$d_6$) δ 11.62 (brs, 1H), 7.36-7.31 (m, 2H), 7.15-7.09 (m, 3H), 6.97 (d, J=13.2 Hz, 1H), 4.62-4.57 (m, 1H), 3.63-3.52 (m, 2H), 3.09-3.01 (m, 1H), 2.83-2.80 (m, 1H), 2.60-2.56 (m, 1H), 2.42-2.27 (m, 2H), 2.11-2.02 (m, 1H), 1.98-1.92 (m, 1H), 1.82-1.76 (m, 1H), 1.61-1.50 (m, 2H), 1.10-1.06 (m, 4H), 0.91-0.87 (m, 2H), 0.71-0.67 (m, 2H); MS(ES+) m/z 491.3 (M+1); MS(ES−) m/z 489.3 (M−1).

Example 22

Synthesis of (R)—N-azetidin-1-ylsulfonyl)-5-cyclopropyl-2-fluoro-4-((1-(4-fluorobenzyl)piperidin-3-yl)oxy)benzamide

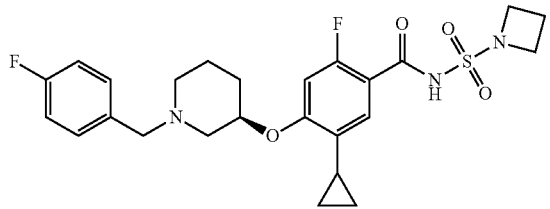 [SMILES: O=C(NS(=O)(=O)N1CCC1)c1cc(C2CC2)c(O[C@@H]2CCCN(Cc3ccc(F)cc3)C2)cc1F]

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with (R)-5-cyclopropyl-2-fluoro-4-((1-(4-fluorobenzyl)piperidin-3-yl)oxy)benzoic acid and methanesulfonamide with azetidine-1 sulfonamide, the title compound was obtained as colorless solid (0.04 g, 44%): $^1$H NMR (300 MHz, DMSO-$d_6$) δ 11.48 (brs, 1H), 7.35-731 (m, 2H), 7.14-7.09 (m, 3H), 6.98 (d, J=13.0 Hz, 1H), 4.60-4.58 (m, 1H), 4.01 (t, J=7.7 Hz, 4H), 3.62-3.50 (m, 2H), 2.82-2.79 (m, 1H), 2.60-2.56 (m, 1H), 2.41-2.26 (m, 2H), 2.20-2.04 (m, 3H), 1.98-1.92 (m, 1H), 1.82-1.76 (m, 1H), 1.64-1.46 (m, 2H), 0.91-0.85 (m, 2H), 0.72-0.68 (m, 2H); MS(ES+) m/z 506.3 (M+1); MS(ES−) m/z 504.3 (M−1).

Example 23

Synthesis of (R)-4-((1-(2-chlorobenzyl)piperidin-3-yl)oxy)-5-cyclopropyl-N-(cyclopropylsulfonyl)-2-fluorobenzamide

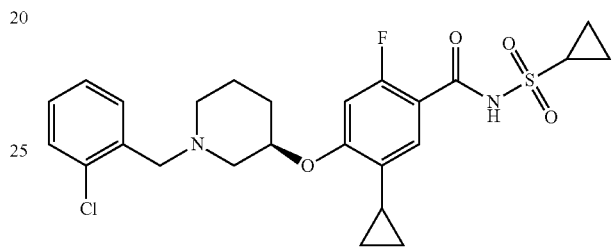

Step 1. Preparation of (R)-5-cyclopropyl-2-fluoro-4-((1-(2-chlorobenzyl)piperidin-3-yl)oxy)benzoic acid

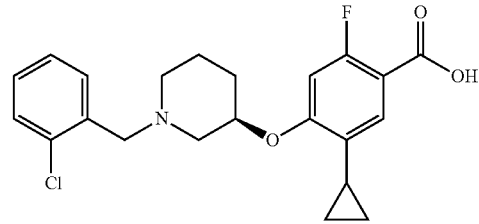 [SMILES: O=C(O)c1cc(C2CC2)c(O[C@@H]2CCCN(Cc3ccccc3Cl)C2)cc1F]

Following the procedure as described in Example 17 step 1, and making variations as required to replace 3,4-dichlorobenzaldehyde with 2-chlorobenzaldehyde, the title compound was obtained as colorless solid (0.28 g, 41%): MS(ES+) m/z 404.2, 406.2 (M+1); MS(ES−) m/z 402.2, 404.2 (M−1).

Step 2. Preparation of (R)-4-((1-(2-chlorobenzyl)piperidin-3-yl)oxy)-5-cyclopropyl-N-(cyclopropylsulfonyl)-2-fluorobenzamide

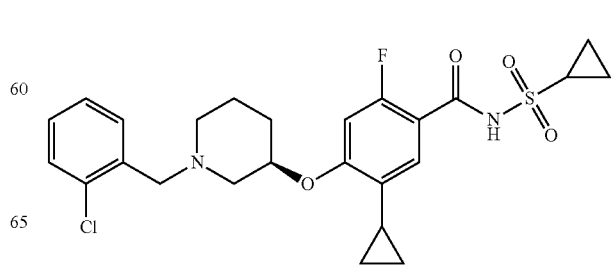

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with (R)-5-cyclopropyl-2-fluoro-4-((1-(2-chlorobenzyl)piperidin-3-yl)oxy)benzoic acid and methanesulfonamide with cyclopropanesulfonamide, the title compound was obtained as colorless solid (0.09 g, 98%): ¹H NMR (300 MHz, DMSO-d₆) δ 11.71 (brs, 1H), 7.48-7.45 (m, 1H), 7.39-7.36 (m, 1H), 7.24-7.21 (m, 2H), 7.08 (d, J=8.4 Hz, 1H), 6.97 (d, J=13.2 Hz, 1H), 4.60-4.58 (m, 1H), 3.59 (s, 2H), 3.07-2.99 (m, 1H), 2.79-2.76 (m, 1H), 2.58-2.51 (m, 1H), 2.50-2.36 (m, 2H), 2.10-2.00 (m, 1H), 1.92-1.88 (m, 1H), 1.81-1.75 (m, 1H), 1.58-1.51 (m, 2H), 1.08-1.04 (m, 4H), 0.87-0.83 (m, 2H), 0.68-0.65 (m, 2H): MS(ES+) m/z 507.3, 509.3 (M+1); MS(ES−) m/z 505.3, 507.3 (M−1).

Example 24

Synthesis of (R)-4-((1-(2-chlorobenzyl)piperidin-3-yl)oxy)-5-cyclopropyl-2-fluoro-N-(methylsulfonyl)benzamide

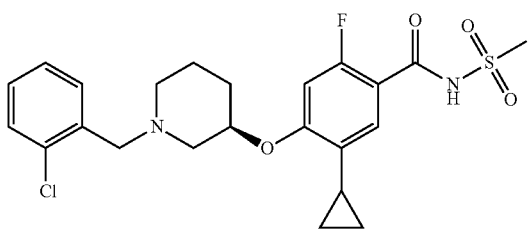 [SMILES: CS(=O)(=O)NC(=O)c1cc(C2CC2)c(O[C@@H]2CCCN(Cc3ccccc3Cl)C2)cc1F]

Following the procedure as described in Example 17 step 3, and making variations as required to replace (R)-5-cyclopropyl-4-((1-(3,4-dichlorobenzyl)piperidin-3-yl)oxy)-2-fluorobenzoic acid with (R)-5-cyclopropyl-2-fluoro-4-((1-(2-chlorobenzyl)piperidin-3-yl)oxy)benzoic acid, the title compound was obtained as colorless solid (0.05 g, 58%): ¹H NMR (300 MHz, DMSO-d₆) δ 11.79 (brs, 1H), 7.52-2.49 (m, 1H), 7.43-7.39 (m, 1H), 7.28-7.24 (m, 2H), 7.13 (d, J=8.4 Hz, 1H), 7.00 (d, J=13.2 Hz, 1H), 4.64-4.561 (m, 1H), 3.64 (s, 2H), 3.31 (s, 3H), 2.83-2.80 (m, 1H), 2.63-2.57 (m, 1H), 2.53-2.38 (m, 2H), 2.13-2.04 (m, 1H), 1.95-1.92 (m, 1H), 1.84-1.77 (m, 1H), 1.62-1.57 (m, 2H), 0.92-0.85 (m, 2H), 0.72-0.68 (m, 2H); MS(ES+) m/z 481.2, 483.2 (M+1); MS(ES−) m/z 479.3, 481.3 (M−1).

Example 25

Synthesis of (R)—N-(azetidin-1-ylsulfonyl)-4-((1-(2-chlorobenzyl)piperidin-3-yl)oxy)-5-cyclopropyl-2-fluorobenzamide

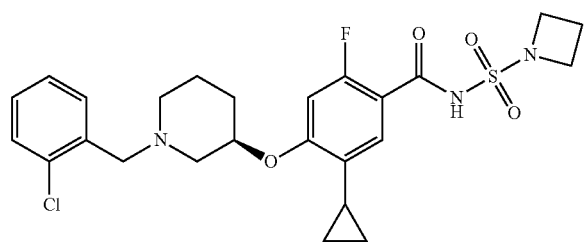 [SMILES: O=C(NS(=O)(=O)N1CCC1)c1cc(C2CC2)c(O[C@@H]2CCCN(Cc3ccccc3Cl)C2)cc1F]

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with (R)-5-cyclopropyl-2-fluoro-4-((1-(2-chlorobenzyl)piperidin-3-yl)oxy)benzoic acid and methanesulfonamide with azetidine-1-sulfonamide, the title confound was obtained as colorless solid (0.07 g, 74%): ¹H NMR (300 MHz, DMSO-d₆) δ 11.56 (brs, 1H), 7.53-7.49 (m, 1H), 7.43-7.38 (m, 1H), 7.29-7.23 (m, 2H), 7.13 (d, J=8.3 Hz, 1H), 7.02 (d, J=13.0 Hz, 1H), 4.64-4.62 (m, 1H), 4.03 (t, J=7.7 Hz, 4H), 3.63 (s, 2H), 2.84-2.80 (m, 1H), 2.62-2.57 (m, 1H), 2.49-2.39 (m, 2H), 2.21-2.05 (m, 3H), 1.95-1.92 (m, 1H), 1.84-1.79 (m, 1H), 1.62-1.54 (m, 2H), 0.92-0.87 (m, 2H), 0.73-0.69 (m, 2H); MS(ES+) m/z 522.3, 524.2 (M+1); MS(ES−) m/z 520.3, 522.3 (M−1).

Example 26

Synthesis of (R)-4-((1-(3-chlorobenzyl)piperidin-3-yl)oxy)-5-cyclopropyl-2-fluoro-N-(methylsulfonyl)benzamide acid

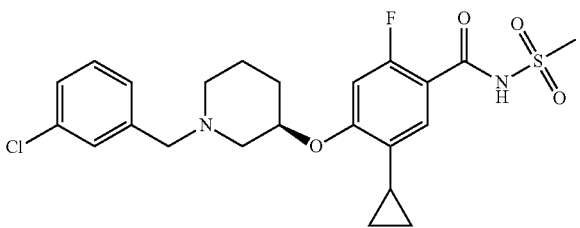 [SMILES: CS(=O)(=O)NC(=O)c1cc(C2CC2)c(O[C@@H]2CCCN(Cc3cccc(Cl)c3)C2)cc1F]

Step 1. Preparation of (R)-4-((1-(3-chlorobenzyl)piperidin-3-yl)oxy)-5-cyclopropyl-2-fluorobenzoic acid

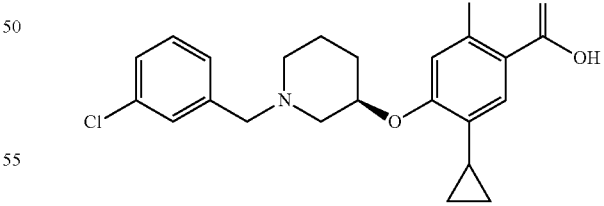

Following the procedure as described in Example 17 step 1, and making variations as required to replace 3,4-dichlorobenzaldehyde with 3-chlorobenzaldehyde, the title compound was obtained as colorless solid (0.23 g, 41%): MS(ES+) m/z 404.2, 406.2 (M+1); MS(ES−) m/z 402.2, 404.2 (M−1).

237

Step 2. Preparation of (R)-4-((1-(3-chlorobenzyl)piperidin-3-yl)oxy)-5-cyclopropyl-N-(cyclopropylsulfonyl)-2-fluorobenzamide

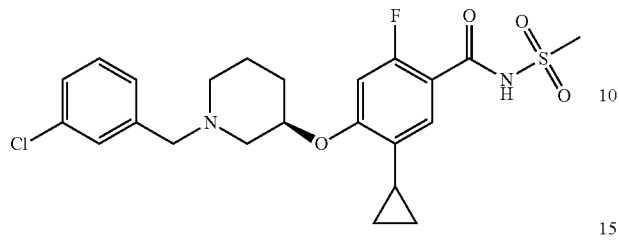

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with (R)-5-cyclopropyl-2-fluoro-4-((1-(3-chlorobenzyl)piperidin-3-yl)oxy)benzoic acid, the title compound was obtained as colorless solid (0.04 g, 51%): $^1$H NMR (300 MHz, DMSO-$d_6$) δ 11.71. (brs, 1H), 7.39-7.25 (m, 4H), 7.13 (d, J=8.4 Hz, 1H), 6.99 (d, J=13.1 Hz, 1H), 4.63-4.61 (m, 1H), 3.66-3.54 (m, 2H), 3.29 (s, 3H), 2.81-2.78 (m, 1H), 2.59-2.36 (m, 3H), 2.11-2.03 (m, 1H), 1.93-1.89 (m, 1H), 1.83-1.77 (m, 1H), 1.63-1.53 (m, 2H), 0.92-0.88 (m, 2H), 0.72-0.68 (m, 2H): MS(ES+) m/z 481.2, 483.2 (M+1); MS(ES−) m/z 479.3, 481.3 (M−1).

Example 27

Synthesis of (R)-4-((1-(3-chlorobenzyl)piperidin-3-yl)oxy)-5-cyclopropyl-N-(cyclopropylsulfonyl)-2-fluorobenzamide

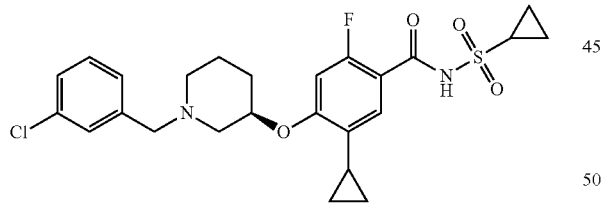

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with (R)-5-cyclopropyl-2-4-4-((1-(3-chlorobenzyl)piperidin-3-yl)oxy)benzoic acid and methanesulfonamide with cyclopropanesulfonamide, the title compound was obtained as colorless solid (0.06 g, 65%): $^1$M NMR (300 MHz, DMSO-$d_6$) δ 11.71 (brs, 1H), 7.38-7.24 (m, 4H), 7.12 (d, J=8.4 Hz, 1H), 6.99 (d, J=13.2 Hz, 1H), 4.63-4.61 (m, 1H), 3.63-3.51 (m, 2H), 3.10-3.01 (m, 2H), 2.79-2.75 (m, 1H), 2.57-2.33 (m, 3H), 2.13-2.04 (m, 1H), 1.93-1.77 (m, 2H), 1.61-1.52 (m, 2H), 1.11-1.06 (m, 4H), 0.92-0.89 (m, 2H), 0.72-0.68 (m, 2H); MS(ES+) m/z 507.2, 509.2 (M+1); MS(ES−) m/z 505.3, 507.3 (M−1).

238

Example 28

Synthesis of (R)—N-(azetidin-1-ylsulfonyl)-4-((1-(3-chlorobenzyl)piperidin-3-yl)oxy)-5-cyclopropyl-2-fluorobenzamide

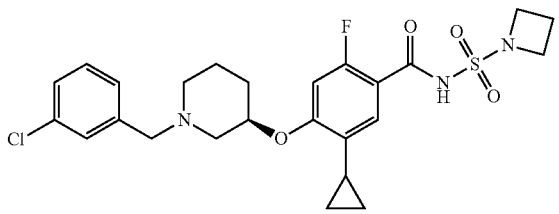 [SMILES: O=C(NS(=O)(=O)N1CCC1)c1cc(C2CC2)c(O[C@@H]2CCCN(Cc3cccc(Cl)c3)C2)cc1F]

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with (R)-5-cyclopropyl-2-fluoro-4-((1-(3-chlorobenzyl)piperidin-3-yl)oxy)benzoic acid and methanesulfonamide with azetidine-1-sulfonamide, the title compound was obtained as colorless solid (0.02 g, 22%); $^1$H NMR (300 MHz, DMSO-$d_6$) δ 11.55 (brs, 1H), 7.37-7.24 (m, 4H), 7.14 (d, J=8.4 Hz, 1H), 6.98 (d, J=13.0 Hz, 1H), 4.61-4.59 (m, 1H), 3.99 (t, J=7.6 Hz, 4H), 3.61-3.49 (m, 2H), 2.78-2.74 (m, 1H), 2.54-2.27 (m, 3H), 2.18-2.04 (m, 3H), 1.95-1.90 (m, 1H), 1.82-1.76 (m, 1H), 160-1.52 (m, 2H), 0.93-0.85 (m, 2H), 0.72-0.68 (m, 2H); MS(ES+) m/z 522.2, 524.2 (M+1); MS(ES−) m/z 520.3, 522.3 (M−1).

Example 29

Synthesis of (R)-5-cyclopropyl-4-((1-(2,4-dichlorobenzyl)piperidin-3-yl)oxy)-2-fluoro-N-(methylsulfonyl)benzamide

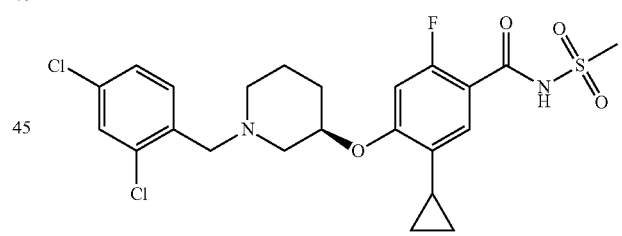

Step 1. Preparation of (R)-5-cyclopropyl-4-((1-(2,4-dichlorobenzyl)piperidin-3-yl)oxy)-2-fluorobenzoic acid

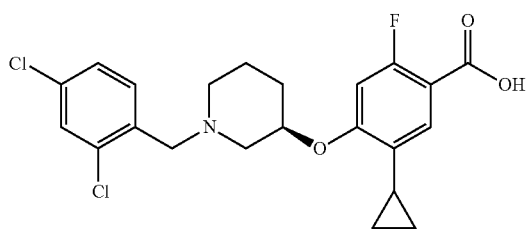 [SMILES: O=C(O)c1cc(C2CC2)c(O[C@@H]2CCCN(Cc3ccc(Cl)cc3Cl)C2)cc1F]

Following the procedure as described in Example 17 step 1, and making variations as required to replace 3,4-dichlorobenzaldehyde with 2,4-dichlorobenzaldehyde, the title compound was obtained as colorless solid (0.35 g, 56%); MS(ES+) m/z 438.2, 440.2 (M+1); MS(ES−) m/z 436.2, 438.2 (M−1).

Step 2. Preparation of (R)-5-cyclopropyl-4-((1-(2,4-dichlorobenzyl)piperidin-3-yl)oxy)-2-fluoro-N-(methylsulfonyl)benzamide

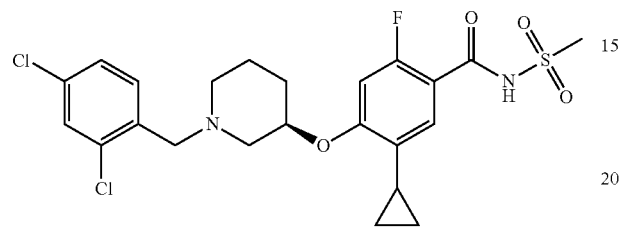

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with (R)-5-cyclopropyl-2-4-4-((1-(2,4-dichlorobenzyl)piperidin-3-yl)oxy)benzoic acid, the title compound was obtained as colorless solid (0.02 g, 25%): $^1$H NMR (300 MHz, DMSO-d$_6$) δ 11.84 (brs, 1H), 7.57 (d, J=2.1 Hz, 1H), 7.50 (d, J=8.3 Hz, 1H), 7.33 (dd, J=2.1 Hz, 8.3 Hz, 1H), 7.13 (d, J=8.4 Hz, 1H), 6.99 (d, J=13.2 Hz, 1H), 4.63-4.61 (m, 1H), 3.59 (s, 2H), 3.30 (s, 3H), 2.81-2.76 (m, 1H), 2.58-2.39 (m, 3H), 2.12-2.04 (m, 1H), 1.94-1.77 (m, 2H), 1.61-1.53 (m, 2H), 0.91-0.88 (m, 2H), 0.72-0.69 (m, 2H); MS(ES+) m/z 515.1, 517.1 (M+1); MS(ES−) m/z 513.2, 515.2 (M−1).

Example 30

Synthesis of (R)—N-(azetidin-1-ylsulfonyl)-5-cyclopropyl-4-((1-(2,4-dichlorobenzyl)piperidin-3-yl)oxy)-2-fluorobenzamide

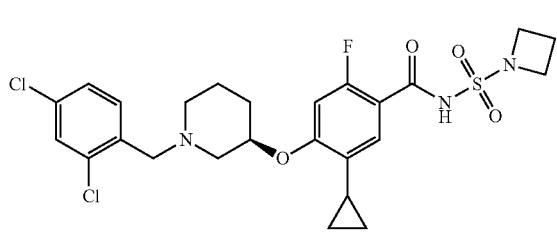 [SMILES: O=C(NS(=O)(=O)N1CCC1)c1cc(C2CC2)c(O[C@@H]2CCCN(Cc3ccc(Cl)cc3Cl)C2)cc1F]

Following the procedure as described in Example 17 step 2, and making variations as required to replace (R)-5-cyclopropyl-4-((1-(3,4-dichlorobenzylpiperidin-3-yl)oxy)-2-fluorobenzoic acid with (R)-5-cyclopropyl-2-fluoro-4-((1-(2,4-dichlorobenzyl)piperidin-3-yl)oxy)benzoic acid and methanesulfonamide with azetidine-1-sulfonamide, the title compound was obtained as colorless solid (0.06 g, 64%): $^1$H NMR (300 MHz, DMSO-d$_6$) δ 11.58 (brs, 1H), 7.56 (d, J=2.1 Hz, 1H), 7.50 (d, J=8.4 Hz, 1H), 7.33 (dd, J=2.1 Hz, 8.3 Hz, 1H), 7.13 (d, J=8.4 Hz, 1H), 7.01 (d, J=13.1 Hz, 1H), 4.63-4.61 (m, 1H), 4.03 (t, J=7.7 Hz, 4H), 3.59 (s, 2H), 2.79-2.76 (m, 1H), 2.58-2.39 (m, 3H), 2.21-2.04 (m, 3H), 1.94-1.79 (m, 2H), 1.59-1.56 (m, 2H), 0.92-0.88 (m, 2H), 0.73-0.69 (m, 2H); MS(ES+) m/z 556.2, 558.2 (M+1); MS(ES−) m/z 554.3, 556.3 (M−1).

Example 31

Synthesis of (R)-5-cyclopropyl-N-(cyclopropylsulfonyl)-4-((1-(2,4-dichlorobenzyl)piperidin-3-yl)oxy)-2-fluorobenzamide

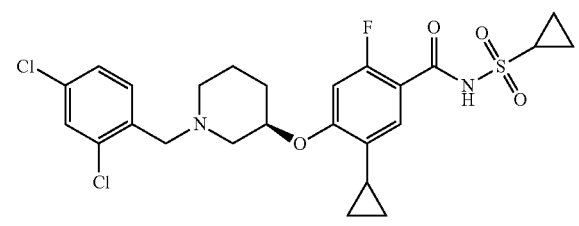 [SMILES: O=C(NS(=O)(=O)C1CC1)c1cc(C2CC2)c(O[C@@H]2CCCN(Cc3ccc(Cl)cc3Cl)C2)cc1F]

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with (R)-5-cyclopropyl-2-fluoro-4-((1-(2,4-dichlorobenzyl)piperidin-3-yl)oxy)benzoic acid and methanesulfonamide with cyclopropanesulfonamide, the title compound was obtained as colorless solid (0.05 g, 48%): $^1$H NMR (300 MHz, DMSO-d$_6$) δ 11.79 (brs, 1H), 7.57 (d, J=2.1 Hz, 1H), 7.50 (d, J=8.3 Hz, 1H), 7.33 (dd, J=2.1 Hz, 8.3 Hz, 1H), 7.12 (d, J=8.4 Hz, 1H), 7.01 (d, J=13.2 Hz, 1H), 4.63-4.61 (m, 1H), 3.59 (s, 2H), 3.11-3.03 (m, 1H), 2.80-2.76 (m, 1H), 2.58-2.39 (m, 3H), 2.12-2.04 (m, 1H), 1.94-1.77 (m, 2H), 1.60-1.55 (m, 2H), 1.12-1.07 (m, 4H), 0.91-0.88 (m, 2H), 0.72-0.69 (m, 2H); MS(ES+) m/z 541.2, 543.1 (M+1); MS(ES−) m/z 539.3, 542.2 (M−1).

Example 32

Synthesis of (R)-5-cyclopropyl-N-(cyclopropylsulfonyl)-2-fluoro-4-((1-(4-methylbenzyl)piperidin-3-yl)oxy)benzamide

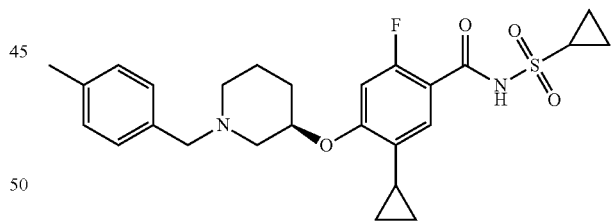

Step 1. Preparation of (R)-5-cyclopropyl-2-4-fluoro-((1-(4-methylbenzyl)piperidin-3-yl)oxy)benzoic acid

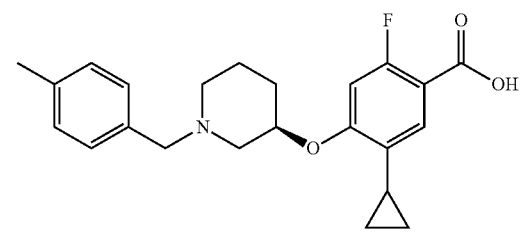 [SMILES: Cc1ccc(CN2CCC[C@@H](Oc3cc(F)c(C(=O)O)cc3C3CC3)C2)cc1]

Following the procedure as described in Example 17 step 1, and making variations as required to replace 3,4-dichlorobenzaldehyde with 4-methylbenzaldehyde, the title compound was obtained as colorless solid (0.24 g, 44%): MS(ES-+) m/z 384.3 (M+1); MS(ES−) m/z 382.3 (M−1).

Step 2. Preparation of (R)-5-cyclopropyl-N-(cyclopropylsulfonyl)-2-fluoro-4-((1-(4-methylbenzyl)piperidin-3-yl)oxy)benzamide

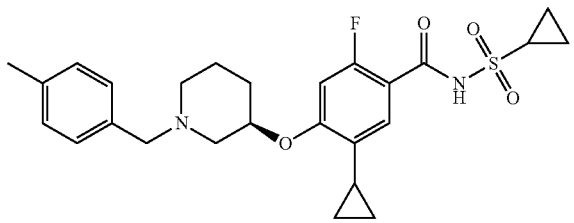 [SMILES: Cc1ccc(CN2CCC[C@@H](Oc3cc(F)c(C(=O)NS(=O)(=O)C4CC4)cc3C3CC3)C2)cc1]

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with (R)-5-cyclopropyl-2-fluoro-4-((1-(4-methylbenzyl)piperidin-3-yl)oxy)benzoic acid and methanesulfonamide with cyclopropanesulfonamide, the title compound was obtained as colorless solid (0.01 g, 18%): $^1$H NMR (300 MHz, DMSO-$d_6$) δ 11.46 (brs, 1H), 7.20-7.09 (m, 5H), 6.96 (d, J=13.1 Hz, 1H), 4.59-4.57 (m, 1H), 3.63-3.52 (m, 2H), 3.08-3.00 (m, 1H), 2.86-2.82 (m, 1H), 2.63-2.59 (m, 1H), 2.43-2.33 (m, 2H), 2.26 (s, 3H), 2.11-2.02 (m, 1H), 1.98-1.92 (m, 1H), 1.82-1.77 (m, 1H), 1.64-1.49 (m, 2H), 1.08-1.03 (m, 4H), 0.90-0.87 (m, 2H), 0.70-0.66 (m, 2H); MS(ES+) m/z 487.2 (M+1); MS(ES−) m/z 485.3 (M−1).

Example 33

Synthesis of (R)—N-(azetidin-1-ylsulfonyl)-5-cyclopropyl-2-4-fluoro-((1-(4-methylbenzyl)piperidin-3-yl)oxy)benzamide

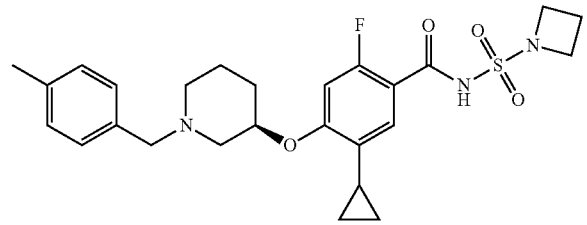 [SMILES: Cc1ccc(CN2CCC[C@@H](Oc3cc(F)c(C(=O)NS(=O)(=O)N4CCC4)cc3C3CC3)C2)cc1]

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with (R)-5-cyclopropyl-2-fluoro-4-((1-(4-methylbenzyl)piperidin-3-yl)oxy)benzoic acid and methanesulfonamide with azetidine-1-sulfonamide, the title compound was obtained as off-white solid (0.05 g, 54%): $^1$H NMR (300 MHz, DMSO-$d_6$) δ 11.28 (brs, 1H), 7.25-7.12 (m, 5H), 7.00 (d, J=13.0 Hz, 1H), 4.66-4.64 (m, 1H), 4.01 (t, J=7.7 Hz, 4H), 3.75-3.63 (m, 2H), 2.96-2.02 (m, 1H), 2.71-2.67 (m, 1H), 2.56-2.42 (m, 2H), 2.27 (s, 3H), 2.19- 2.05 (m, 3H), 1.99-1.80 (m, 2H), 1.69-1.50 (m, 2H), 0.92-0.86 (m, 2H), 0.71-0.68 (m, 2H); MS(ES+) m/z 502.2 (M+1); MS(ES−) m/z 500.3 (M−1).

Example 34

Synthesis of (R)-5-cyclopropyl-2-fluoro-4-((1-(4-fluoro-2-(trifluoromethyl)benzyl)piperidin-3-yl)oxy)-N-(methylsulfonyl)benzamide

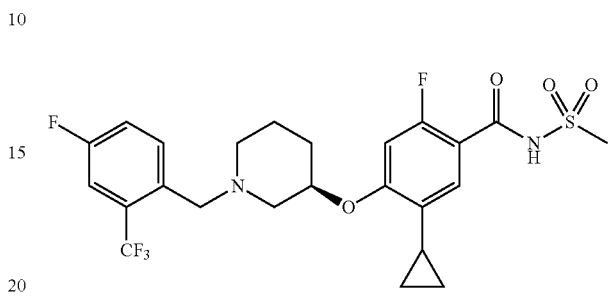

Step 1. Preparation of (R)-methyl 5-cyclopropyl-2-fluoro-4-(piperidin-3-yloxy)benzoate

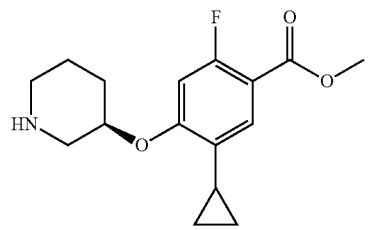 [SMILES: COC(=O)c1cc(C2CC2)c(O[C@@H]2CCCNC2)cc1F]

To a solution of (R)-tert-butyl 3-(4-(tert-butoxycarbonyl)-2-cyclopropyl-5-fluorophenoxy)piperidine-1-carboxylate (22.50 g, 51.80 mmol) in anhydrous methanol (400 mL), was added sulfuric acid (10.0 ml). The reaction mixture was refluxed for 16 hours and then concentrated in vacuo. The pH of the residue was adjusted to 8-9 with 1M aqueous sodium hydroxide solution, and extracted with ethyl acetate (2×300 mL). Organic layers were combined, washed with saturated sodium bicarbonate solution (50 mL), brine solution (50 mL), dried over anhydrous sodium sulfate and concentrated in vacuo. The crude product was purified by column chromatography (5% to 20% methanol in dichloromethane) afforded the title compound as an oil (10.00 g, 66%): MS (ES+) m/z 294.3 (M+1).

Step 2. Preparation of (R)-methyl 5-cyclopropyl-2-fluoro-4-((1-(4-fluoro-2-(trifluoromethyl)-benzyl)piperidin-3-yl)oxy)benzoate

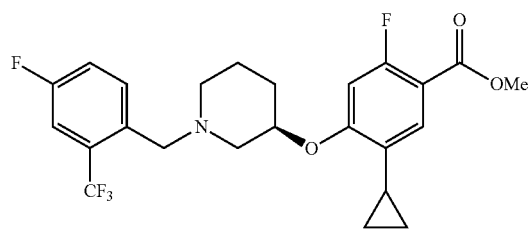 [SMILES: COC(=O)c1cc(C2CC2)c(O[C@@H]2CCCN(Cc3ccc(F)cc3C(F)(F)F)C2)cc1F]

To a solution of (R)-methyl 5-cyclopropyl-2-fluoro-4-(piperidin-3-yloxy)benzoate (0.225 g, 0.768 mmol) in anhydrous dimethylformamide (10 mL) was added potassium carbonate (0.269 g, 1.95 mmol) and 1-(bromomethyl)-4-fluoro-2-(trifluoromethyl)benzene (0.13 ml, 0.84 mmol). The mixture was stirred at ambient temperature for 1 hour, then poured into water (50 mL) and extracted with ethyl acetate (3×30 mL). The combined organic layer was washed with water (2×30 mL), brine (30 mL), dried over anhydrous sodium sulfate, filtered and concentrated in vacuo. The residue was purified by column chromatography (0 to 30% ethyl acetate in hexanes) to give the title compound (0.286 g, 79%): MS(ES+) m/z 470.2 (M+1).

Step 3. Preparation of (R)-5-cyclopropyl-2-fluoro-4-((1-(4-fluoro-2-(trifluoromethyl)benzyl)piperidin-3-yl)oxy)-N-(methylsulfonyl)benzamide

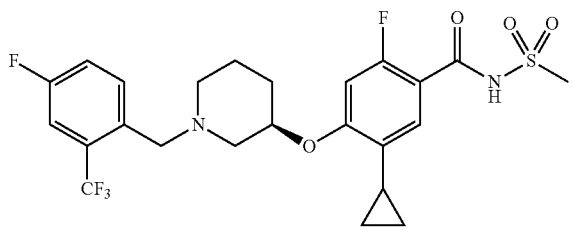 [SMILES: CS(=O)(=O)NC(=O)c1cc(C2CC2)c(O[C@@H]2CCCN(Cc3ccc(F)cc3C(F)(F)F)C2)cc1F]

To a solution of (R)-methyl 5-cyclopropyl-2-fluoro-4-((1-(4-fluoro-2-(trifluoromethyl)-benzyl)piperidin-3-yl)oxy) benzoate (0.525 g, 1.12 mmol) in water and tetrahydrofuran (1:1, 20 mL) was added lithium hydroxide (0.265 g, 11.10 mmol). The mixture was heated to reflux for 2 hours and then stirred for an additional 16 hours at ambient temperature before neutralized with a 1 M aqueous hydrochloric acid solution. The aqueous layer was then extracted with ethyl acetate (3×30 mL). The combined organic layers were washed with brine (30 mL), dried over anhydrous sodium sulfate, filtered and concentrated in vacuo. The crude product was used directly for the next step without further purification. To a solution of crude (R)-5-cyclopropyl-2-fluoro-4-((1-(4-fluoro-2-(trifluoromethyl)benzyl)piperidin-3-yl)oxy)benzoic acid (0.161 g, 0.354 mmol) in anhydrous dichloromethane (5 mL) was added 1-ethyl-3-(3-dimethylaminopropyl)carbodiimide hydrochloride (0.212 g, 1.11 mmol), 4-dimethylaminopyridine (0.199 g, 1.63 mmol) and methanesulfonamide (0.105 g, 1.11 mmol). The mixture was stirred at ambient temperature for 32 hours, then diluted with ethyl-acetate (50 mL) and washed with a 5% aqueous hydrochloric acid solution (2×25 mL). The combined aqueous layers were extracted with ethyl acetate (3×50 mL). The combined organic layers were then washed with water (50 mL) and brine (50 mL); dried over anhydrous sodium sulfate; filtered and concentrated in vacuo. The residue was purified by column chromatography (0 to 100% ethyl acetate (containing 0.2% acetic acid) in hexanes) to afford the title compound (0.033 g, 17%). $^1$H NMR (300 MHz, DMSO-$d_6$) δ 11.87 (brs, 1H), 7.84-7.79 (m, 1H), 7.58-7.54 (m, 1H), 7.46-7.40 (m, 1H), 7.13 (d, J=8.4 Hz, 1H), 6.99 (d, J=13.2 Hz, 1H), 4.63 (brs, 1H), 3.63 (m, 2H), 3.32 (s, 3H), 2.74-2.70 (m, 1H), 2.44-2.32 (m, 2H), 2.14-2.05 (m, 1H), 1.98-1.74 (m, 3H), 1.66-1.53 (m, 2H), 0.97-0.87 (m, 2H), 0.76-0.67 (m, 2H); $^{19}$F NMR (282 MHz, DMSO-$d_6$) δ−114.1, −113.1, −58.4; MS(ES+) m/z 533.2 (M+H).

Example 35

Synthesis of (R)-5-cyclopropyl-N-(cyclopropylsulfonyl)-2-fluoro-4-((1-(4-fluoro-2-(trifluoromethyl)benzyl)piperidin-3-yl)oxy)benzamide

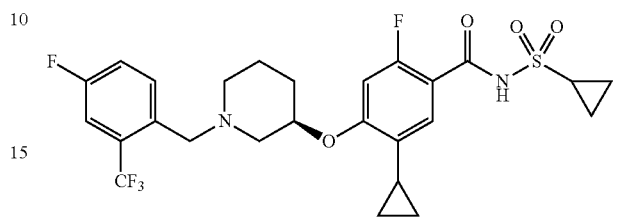

Following the procedure as described in example 34 step 3 and making variations as required to replace methanesulfonamide with cyclopropylsulfonamide, the title compound was obtained (0.04 g, 20%): $^1$H NMR (300 MHz, DMSO-$d_6$) δ 11.81 (brs, 1H), 7.83-7.79 (m, 1H), 7.58-7.54 (m, 1H), 7.46-7.40 (m, 1H), 7.12 (d, J=8.4 Hz, 1H), 6.99 (d, J=13.2 Hz, 1H), 4.63 (brs, 1H), 3.62 (m, 2H), 3.11-3.03 (m, 1H), 2.73-2.69 (m, 1H), 2.44-2.32 (m, 1H), 2.16-2.03 (m, 1H), 1.99-1.73 (m, 2H), 1.67-1.53 (m, 2H), 1.23 (s, 2H), 1.13-1.08 (m, 4H), 0.93-0.86 (m, 2H), 0.77-0.65 (m, 2H); $^{19}$F NMR (282 MHz, DMSO-$d_6$) δ−114.1, −112.8, −58.4; MS (ES+) m/z 559.2 (M+H).

Example 36

Synthesis of (R)—N-(azetidin-1-ylsulfonyl)-5-cyclopropyl-2-fluoro-4-((1-(4-fluoro-2-(trifluoromethyl)benzyl)piperidin-3-yl)oxy)benzamide

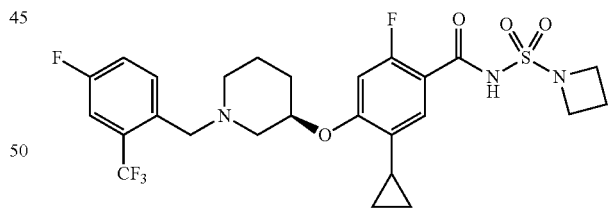

Following the procedure as described in example 34 step 3 and making variations as required to replace methanesulfonamide with azetidine-1-sulfonamide the title compound was obtained (0.053 g, 26%); $^1$H NMR (300 MHz, DMSO-$d_6$) δ 11.60 (br s, 1H), 7.83-7.78 (m, 1H), 7.58-7.54 (m, 1H), 7.46-7.40 (m, 1H), 7.14 (d, J=8.3 Hz, 1H), 6.99 (d, J=13.1 Hz, 1H), 4.63 (br s, 1H), 4.04 (t, J=7.7 Hz, 4H), 3.63 (m, 2H), 2.73-2.69 (m, 1H), 2.45-2.33 (m, 2H), 2.21-2.06 (m, 3H), 1.96-1.74 (m, 2H), 1.67-1.52 (m, 2H), 1.23 (s, 1H), 0.93-0.89 (m, 2H), 0.79-0.67 (m, 2H) $^1$F NMR (282 MHz, DMSO-$d_6$) δ−114.1, −113.1, −58.4; MS (ES+) m/z 574.2 (M+H).

Example 37

Synthesis of (R)—N-(azetidin-1-ylsulfonyl)-5-cyclopropyl-2-fluoro-4-((1-(4-fluorophenyl)piperidin-3-yl)oxy)benzamide, trifluoroacetic acid salt

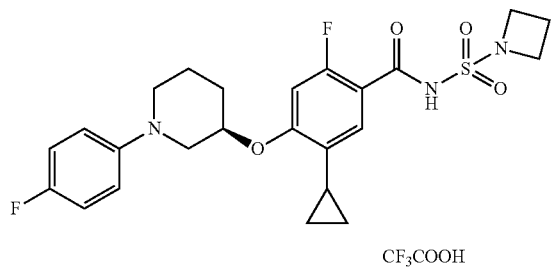

CF₃COOH

Step 1. Preparation of (R)-methyl 5-cyclopropyl-2-fluoro-4-((1-(4-fluorophenyl)piperidin-3-yl)oxy)benzoate

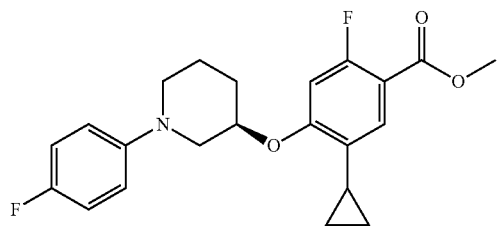 [SMILES: COC(=O)c1cc(C2CC2)c(O[C@@H]2CCCN(c3ccc(F)cc3)C2)cc1F]

To a mixture of (R)-methyl 5-cyclopropyl-2-fluoro-4-(piperidin-3-yloxy)benzoate (0.587 g, 2.0 mmol), 4-fluorophenylboronic acid (0.56 g, 4.0 mmol), and copper(II) acetate (0.363 g, 2.0 mmol in anhydrous dichloromethane (8 mL) was added triethylamine (0.56 mL, 4.0 mmol) and the reaction mixture was stirred for 72 hours at ambient temperature under an atmosphere of dry air. The mixture was filtered through a plug of celite, the filter cake was washed with a mixture of dichloromethane and methanol (1:1, 20 mL), and the combined filtrate was concentrated in vacuo. Purification of the residue by column chromatography (0 to 50% ethyl acetate in hexanes) afforded the title compound as a light yellow oil (0.448 g, 58%); $^1$H NMR (300 MHz, CDCl₃) δ 7.42 (d, J=8.4 Hz, 1H), 6.97-6.81 (m, 4H), 6.62 (d, J=12.8 Hz, 1H), 4.54-4.45 (m, 1H), 3.86 (s, 3H), 3.63-3.55 (m, 1H), 3.36-3.26 (m, 1H), 3.01 (dd, J=11.9, 8.0 Hz, 1H), 2.89 (ddd, J=12.0, 9.3, 2.9 Hz, 1H), 2.21-2.09 (m, 1H), 2.04-1.91 (m, 2H), 1.84-1.64 (m, 1H), 1.60-1.53 (m, 1H), 0.90-0.81 (m, 2H), 0.65-0.59 (m, 2H); MS (ES+) m/z 388.3 (M+1).

Step 2. Preparation of (R)-5-cyclopropyl-2-fluoro-4-((1-(4-fluoro)phenyl)piperidin-3-yl)oxy)benzoic acid

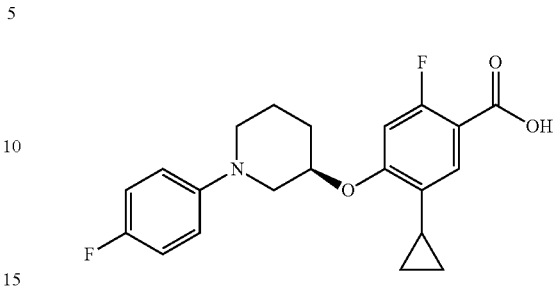

To a mixture of (R)-methyl 5-cyclopropyl-2-fluoro-4-((1-(4-fluorophenyl)piperidin-3-yl)oxy)benzoate (0.448 g, 1.16 mmol) in tetrahydrofuran (10 mL) was added a solution of lithium hydroxide (0.139 g, 5.8 mmol) in water (3 mL). The reaction mixture was stirred for 16 hours at ambient temperature and subsequently for 1 hour at 60° C. After cooling to ambient temperature, the reaction mixture was adjusted to pH 1 with 1 N hydrochloric acid solution and extracted with dichloromethane (3×20 mL). The combined organic phase was washed with brine (5 mL), dried over anhydrous sodium sulfate, and filtered. Concentration of the filtrate in vacuo gave the title compound as a yellowish oil (0.43 g, 99%), which was used without further purification: MS (ES+) m/z 374.3 (M+1).

Step 3. Preparation of (R)—N-(azetidin-1-ylfulfonyl)-5-cyclopropyl-2-fluoro-4-((1-(4-fluorophenyl)piperidin-3-yl)oxy)benzamide, trifluoroacetic acid salt

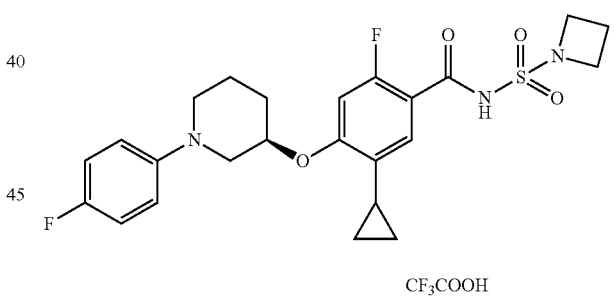

CF₃COOH

To a mixture of (R)-5-cyclopropyl-2-fluoro-4-((1-(4-fluorophenyl)piperidin-3-yl)oxy)benzoic acid (0.215 g, 0.58 mmol), N-(3-dimethylaminopropyl)-N'-ethylcarbodiimide hydrochloride (0.167 g, 0.87 mmol), and 4-(dimethylamino)pyridine (0.213 g, 1.74 mmol) in anhydrous dichloromethane was added azetidine-1-sulfonamide (0.119 g, 0.87 mmol). The reaction mixture was stirred for 48 hours at ambient temperature. The mixture was diluted with ethyl acetate (100 mL) and then quenched by addition of 1 N hydrochloric acid solution (10 mL). The organic phase was washed with 1 N hydrochloric acid solution (5 mL), water (5 mL) and brine (5 mL); dried over anhydrous sodium sulfate and filtered. Concentration of the filtrate gave a residue which was purified first by column chromatography (0 to 50% ethyl acetate in hexanes) and then by reverse-phase preparative HPLC to afford the title compound as an off-white solid (0.168 g, 48%): $^1$H NMR (300 MHz, DMSO-d$_6$) δ 11.61 (s, 1H), 7.30 (brs, 1H), 7.18-6.93 (m, 6H), 4.78-4.68 (m, 1H), 4.04 (t, J=7.7, 7.7 Hz, 4H), 3.52 (dd, J=12.2, 2.7 Hz, 1H), 3.31-3.18 (m, 2H), 3.13-3.03 (m, 1H), 2.23-2.10 (m, 2H), 2.10-1.99 (m, 1H), 1.99-1.84 (m, 2H), 1.76-1.61 (m, 2H), 0.86-0.77 (m, 2H), 0.70-0.62 (m, 2H); $^{19}$F NMR (282 MHz, DMSO-d$_6$) δ−75.0, −112.9, −125.2; MS (ES−) m/z 490.3 (M−1).

Example 38

Synthesis of (R)-5-cyclopropyl-N-(cyclopropylsulfonyl)-2-fluoro-4-((1-(4-fluorophenyl)piperidin-3-yl)oxy)benzamide

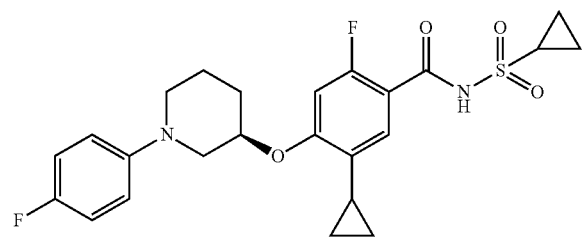 [SMILES: O=C(NS(=O)(=O)C1CC1)c1cc(C2CC2)c(O[C@@H]2CCCN(c3ccc(F)cc3)C2)cc1F]

Following the procedure as described in Example 37 Step 3 and making variations as required to replace azetidine-1-sulfonamide with cyclopropanesulfonamide and purification by column chromatography (0 to 50% ethyl acetate in hexanes), the title compound was obtained as a colorless solid (0.177 g, 64%): $^1$H NMR (300 MHz, DMSO-d$_6$) δ 11.82 (s, 1H), 7.18-6.89 (m, 6H), 4.77-4.66 (m, 1H), 3.50 (dd, J=12.3, 2.9 Hz, 1H), 3.29-3.15 (m, 2H), 3.13-3.01 (m, 2H), 2.09-1.99 (m, 1H), 1.97-1.81 (m, 2H), 1.75-1.60 (m, 2H), 1.16-1.06 (m, 4H), 0.86-0.77 (m, 2H), 0.69-0.61 (m, 2H); $^{19}$F NMR (282 MHz, DMSO-d$_6$) δ−112.63, −125.87; MS (ES−) m/z 475.3 (M−1).

Example 39

Synthesis of (R)-5-chloro-4-((1-(2-chloro-4-fluorobenzyl)piperidin-3-yl)oxy)-N-(cyclopropylsulfonyl)-2-fluorobenzamide, trichloroacetic acid salt

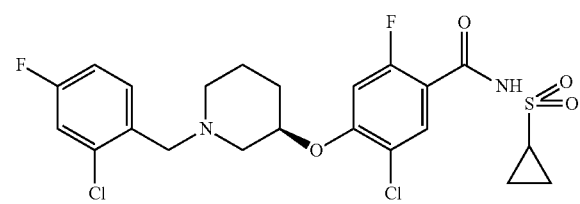

Step 1. Preparation of (R)-5-chloro-4-fluorobenzyl)piperidin-3-yl)oxy)-2-fluorobenzoic acid

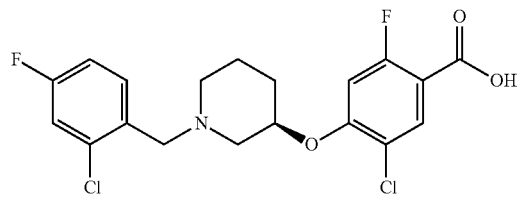 [SMILES: O=C(O)c1cc(Cl)c(O[C@@H]2CCCN(Cc3ccc(F)cc3Cl)C2)cc1F]

To a mixture of (R)-methyl 5-chloro-4-((1-(2-chloro-4-fluorobenzyl)piperidin-3-yl)oxy)-2-fluorobenzoate (0.15 g, 0.35 mmol) in tetrahydrofuran (20 mL) and water (20 mL) was added lithium hydroxide monohydrate (0.15 g, 3.5 mmol). The reaction mixture was heated to reflux for 4 hours. The reaction mixture was diluted with ethyl acetate (80 mL), washed with 1 M hydrochloric acid solution (50 mL) and brine (2×50 mL); dried over anhydrous sodium sulfate, filtered and concentrated in vacuo to provide the title compound as a solid (0.15 g, quant.): MS (ES+) m/z 414.2, 416.2 (M+1).

Step 2. Preparation of (R)-5-chloro-4-((1-(2-chloro-4-fluorobenzyl)piperidin-3-yl)oxy)-N-(cyclopropylsulfonyl)-2-fluorobenzamide, trifluoroacetic acid salt

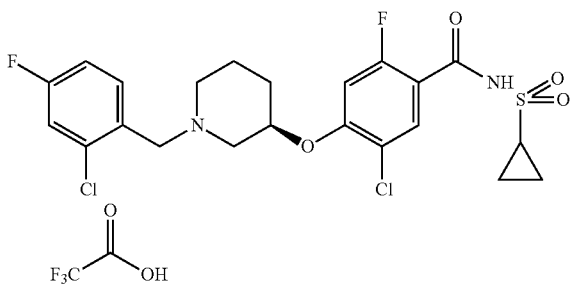

A mixture of (R)-5-chloro-4-((1-(2-chloro-4-fluorobenzyl)piperidin-3-yl)oxy)-2-fluorobenzoic acid (0.15 g, 0.35 mmol), cyclopropanesulfonamide (0.064 g, 0.53 mmol), N-(3-dimethylaminopropyl)-N'-ethylcarbodiimide hydrochloride (0.10 g, 0.53 mmol), and 4-dimethylaminopyridine (0.13 g, 1.05 mmol) in dichloromethane (20 mL) was stirred at ambient temperature for 18 hours. The reaction was concentrated in vacuo and the residue was first purified by flash chromatography (0 to 4% methanol in dichloromethane), then by reverse phase HPLC (acetonitrile in water+ 0.1% TFA) to provide the title compound (0.03 g, 17%): $^1$H NMR (300 MHz, DMSO-d$_6$) δ 12.03 (brs, 1H), 9.45 (brs, 1H), 7.77 (d, J=7.6 Hz, 1H), 7.74-7.64 (m, 1H), 7.60-7.49 (m, 1H), 7.41-7.26 (m, 2H), 4.85-4.67 (m, 1H), 4.53-3.99 (m, 5H), 3.43-3.29 (m, 1H), 3.18-2.99 (m, 2H), 2.01-1.88 (m, 1H), 1.81-1.56 (m, 2H), 1.15-1.04 (m, 4H); MS (ES+) m/z 519.1, 521.1 (M+H).

Example 40

Synthesis of (R)-5-cyclopropyl-N-(cyclopropylsulfonyl)-2-fluoro-4-((1-phenylpiperidin-3-yl)oxy)benzamide

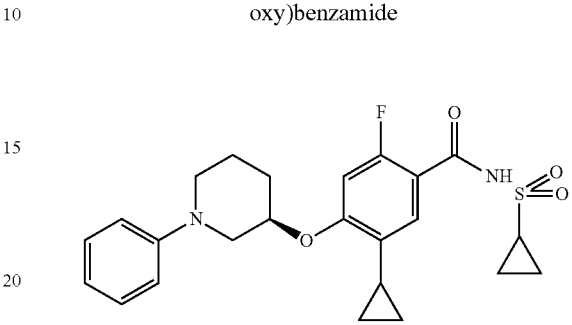

Step 1. Preparation of (R)-methyl 5-cyclopropyl-2-fluoro-4-((1-phenylpiperidin-3-yl)oxy)benzoate

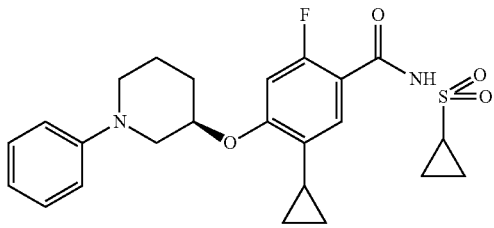

To a degassed mixture of (R)-methyl 5-cyclopropyl-2-fluoro-4-(piperidin-3-yloxy)benzoate (0.76 g, 2.68 mmol), iodobenzene (1.49 ml, 13.4 mmol), L-proline (0.62 g, 5.36 mmol), and potassium carbonate (1.88 g, 13.4 mmol) in anhydrous dimethylsulfoxide (30 mL) was added copper (I) iodide (0.51 g, 2.68 mmol). The resulting mixture was heated to 75° C. under nitrogen for 2 hours. And then iodobenzene (1.0 mL, 9.0 mmol) was added to the reaction mixture stirring was continued at 75° C. under nitrogen for 24 hours. The reaction mixture was diluted with ethyl acetate (100 mL), washed with water (50 mL), saturated ammonium chloride (3×50 mL) and brine (50 mL); dried over anhydrous sodium sulfate, filtered and concentrated in vacuo. The residue was purified by flash chromatography ($R_f$=0.2 in 9:1 hexanes:ethyl acetate) to provide the title compound as an oil (0.74 g, 75%): $^1$H NMR (300 MHz, CDCl$_3$) δ 7.46-7.39 (m, 1H), 7.31-7.17 (m, 3H), 6.95-6.88 (m, 1H), 6.86-6.79 (m, 1H), 6.63 (d, J=12.8 Hz, 1H), 4.55-4.44 (m, 1H), 3.87 (s, 3H), 3.76-3.68 (m, 1H), 3.48-3.39 (m, 1H), 3.10 (dd, J=13.1, 8.0 Hz, 1H), 3.03-2.93 (m, 1H), 2.21-2.12 (m, 1H), 2.03-1.91 (m, 2H), 1.56-1.66 (m, 2H), 0.89-0.82 (m, 2H), 0.65-0.57 (m, 2H); MS (ES+) m/z 370.2 (M+H).

Step 2. Preparation of (R)-5-cyclopropyl-2-fluoro-4-((1-phenylpiperidin-3-yl)oxy)benzoic acid

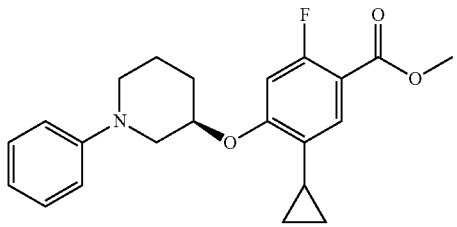 [SMILES: COC(=O)c1cc(C2CC2)c(O[C@@H]2CCCN(c3ccccc3)C2)cc1F]

Following the procedure as described in Example 39 step 1 and making variation as required to replace (R)-methyl 5-chloro-4-((1-(2-chloro-4-fluorobenzyl)piperidin-3-yl)oxy)-2-fluorobenzoate with (R)-methyl 5-cyclopropyl-2-fluoro-4-((1-phenylpiperidin-3-yl)oxy)benzoate, the title compound was obtained as a colorless solid (0.61 g, 86%): MS (ES+) m/z 356.2 (M+H).

Step 3. Preparation of (R)-5-cyclopropyl-N-(cyclopropylsulfonyl)-2-fluoro-4-((1-phenylpiperidin-3-yl)oxy)benzamide

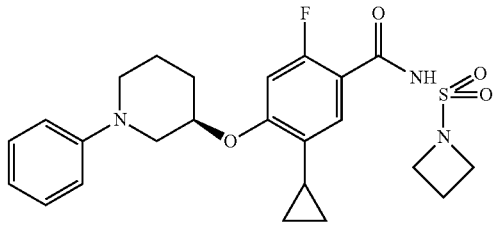

Following the procedure as described in Example 39 step 2 and making variation as required to replace (R)-5-chloro-4-((1-(2-chloro-4-fluorobenzyl)piperidin-3-yl)oxy)-2-fluorobenzoic acid with (R)-5-cyclopropyl-2-fluoro-4-((1-phenylpiperidin-3-yl)oxy)benzoic acid and purification by flash chromatography [($R_f$=0.2 in 2:1 hexanes:ethyl acetate (containing 0.2% acetic acid)], the title compound was obtained as a colorless solid (0.075 g, 18%): $^1$H NMR (300 MHz, DMSO-d$_6$) δ 11.78 (brs, 1H), 7.17-7.02 (m, 4H), 6.90-6.84 (m, 2H), 6.72-6.65 (m, 1H), 4.72-4.64 (m, 1H), 3.56-3.48 (m, 1H), 3.29-3.20 (m, 2H), 3.15-3.07 (m, 1H), 3.07-2.98 (m, 1H), 2.05-1.96 (m, 1H), 1.91-1.79 (m, 2H), 1.73-1.58 (m, 2H), 1.11-1.03 (m, 4H), 0.79-0.72 (m, 2H), 0.63-0.56 (m, 2H); MS (ES+) m/z 459.2 (M+H).

Example 41

Synthesis of (R)—N-(azetidin-1-ylsulfonyl)-5-cyclopropyl-2-fluoro-4-((1-phenylpiperidin-3-yl)oxy)benzamide

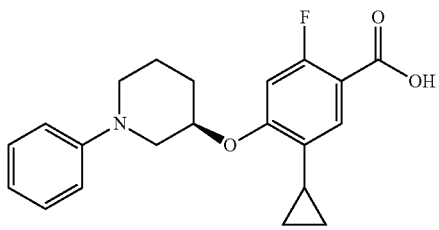 [SMILES: O=C(O)c1cc(C2CC2)c(O[C@@H]2CCCN(c3ccccc3)C2)cc1F]

Following the procedure as described in Example 39 step 2 and making variations as required to replace (R)-5-chloro-4-((1-(2-chloro-4-fluorobenzyl)piperidin-3-yl)oxy)-2-fluorobenzoic acid and cyclopropanesulfonamide with 1-azetidinesulfamide and purification by flash chromatography [($R_f$=0.2 in 2:1 hexanes:ethyl acetate (containing 0.2% acetic acid)], the title compound was obtained as a colorless solid (0.08 g, 20%): $^1$H NMR (300 MHz, DMSO-d$_6$) δ 11.57 (brs, 1H), 7.18-7.03 (m, 4H), 6.91-6.49 (m, 2H), 6.72-6.65 (m, 1H), 4.72-4.63 (m, 1H), 4.00 (t, J=7.6 Hz, 4H), 3.56-3.48 (m, 1H), 3.28-3.19 (m, 2H), 3.15-3.05 (m, 1H), 2.12 (quintet, J=7.6 Hz, 2H), 2.05-1.95 (m, 1H), 1.91-1.78 (m, 2H), 1.73-1.58 (m, 2H), 0.80-0.71 (m, 2H), 0.65-0.57 (m, 2H); MS (ES+) m/z 474.25 (M+H).

Example 42

Synthesis of (R)-5-cyclopropyl-N-(cyclopropylsulfonyl)-4-((1-(3,5-dichlorophenyl)piperidin-3-yl)oxy)-2-fluorobenzamide

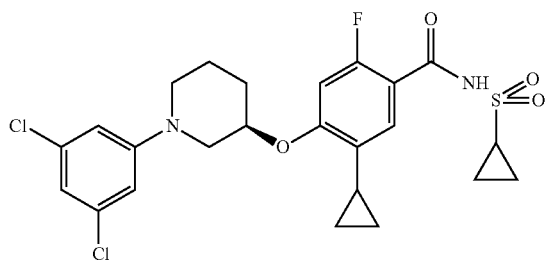

Step 1. Preparation of (R)-methyl 5-cyclopropyl-4-((1-(3,5-dichlorophenyl)piperidin-3-yl)oxy)-2-fluorobenzoate

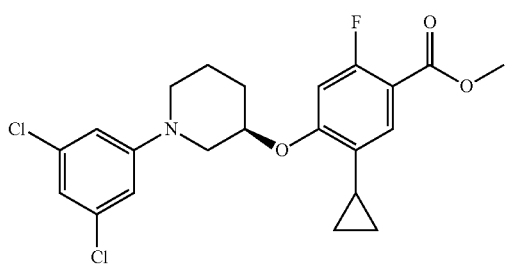 [SMILES: COC(=O)c1cc(C2CC2)c(O[C@@H]2CCCN(c3cc(Cl)cc(Cl)c3)C2)cc1F]

Following the procedure as described in Example 40 step 1 and making variation as required to replace iodobenzene with 1,3-dichloro-5-iodobenzene, the title compound was obtained as a colorless oil (1.08 g, 47%): $^1$H NMR (300 MHz, CDCl$_3$) δ 7.39 (d, J=8.3 Hz, 1H), 6.74-6.69 (m, 3H), 6.57 (d, J=12.7 Hz, 1H), 4.52-4.43 (m, 1H), 3.86 (s, 3H), 3.59 (dd, J=12.8, 3.07 Hz, 1H), 3.39-3.29 (m, 2H), 3.24-3.12 (m, 1H), 2.15-2.04 (m, 1H), 2.00-1.91 (m, 1H), 1.90-1.78 (m, 2H), 1.75-162 (m, 1H), 0.86-0.77 (m, 2H), 0.60-0.53 (m, 2H); MS(ES+) m/z 438.2, 440.2 (M+H).

Step 2. Preparation of (R)-5-cyclopropyl-4-((1-(3,5-dichlorophenyl)piperidin-3-yl)oxy)-2-fluorobenzoic acid

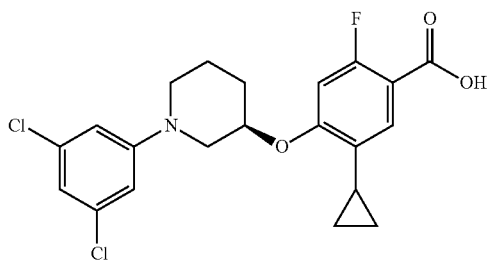 [SMILES: O=C(O)c1cc(C2CC2)c(O[C@@H]2CCCN(c3cc(Cl)cc(Cl)c3)C2)cc1F]

Following the procedure as described in Example 39 step 1 and making variation as required to replace (R)-methyl 5-chloro-4-((1-(2-chloro-4-fluorobenzyl)piperidin-3-yl)oxy)-2-fluorobenzoate with (R)-methyl 5-cyclopropyl-4-((1-(3,5-dichlorophenyl)piperidin-3-yl)oxy)-2-fluorobenzoate, the title compound was obtained as a colorless solid (1.04 g, quant.): MS (ES+) m/z 424.2, 426.2 (M+H).

Step 3. Preparation of (R)-5-cyclopropyl-N-(cyclopropylsulfonyl)-4-((1-(3,5-dichlorophenyl)piperidin-3-yl)oxy)-2-fluorobenzamide

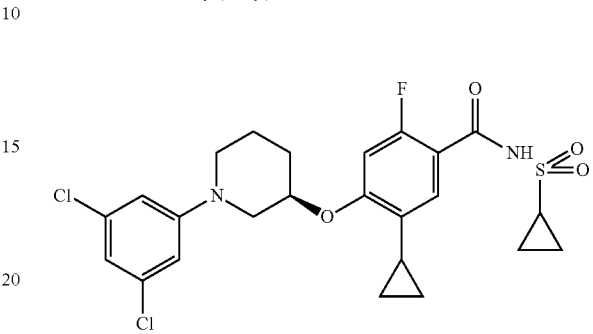

Following the procedure as described in Example 39 step 2 and making variation as required to replace (R)-5-chloro-4-((1-(2-chloro-4-fluorobenzyl)piperidin-3-yl)oxy)-2-fluorobenzoic acid with (R)-5-cyclopropyl-4-((1-(3,5-dichlorophenyl)piperidin-3-yl)oxy)-2-fluorobenzoic acid and purification by flash chromatography [(R$_f$=0.25 in 2:1 hexanes:ethyl acetate (containing 0.2% acetic acid)), the title compound was obtained as a colorless solid (0.175 g, 47%): $^1$H NMR (300 MHz, DMSO-d$_6$) δ 11.77 (brs, 1H), 7.06 (d, J=13.2 Hz, 1H), 7.01 (d, J=8.3 Hz, 1H), 6.85 (d, J=1.8 Hz, 2H), 6.69 (dd, J=1.7, 1.7 Hz, 1H), 4.73-4.65 (m, 1H), 3.73-3.63 (m, 1H), 3.57-3.49 (m, 1H), 3.48-3.39 (m, 2H), 3.27-3.21 (m, 1H), 3.08-2.97 (m, 1H), 2.00-1.88 (m, 1H), 1.84-1.71 (m, 1H), 1.67-1.59 (m, 1H), 1.57-1.46 (m, 1H), 1.13-1.03 (m, 4H), 0.70-0.60 (m, 2H), 0.57-0.48 (m, 2H); MS (ES+) m/z 527.1, 529.1 (M+H).

Example 43

Synthesis of (R)—N-(azetidin-1-ylsulfonyl)-5-cyclopropyl-4-((1-(3,5-dichlorophenyl)piperidin-3-yl)oxy)-2-fluorobenzamide

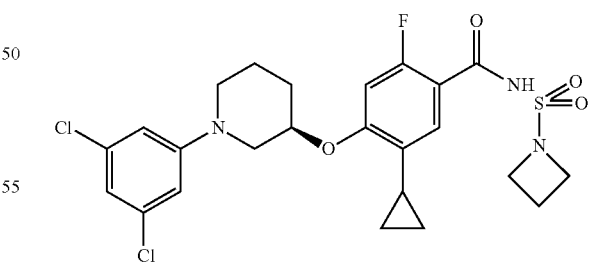

Following the procedure as described in Example 39 step 2 and making variation as required to replace (R)-5-chloro-4-((1-(2-chloro-4-fluorobenzyl)piperidin-3-yl)oxy)-2-fluorobenzoic acid with (R)-5-cyclopropyl-4-((1-(3,5-dichlorophenyl)piperidin-3-yl)oxy)-2-fluorobenzoic acid and cyclopropanesulfonamide with 1-azetidinesulfamide and purification by flash chromatography (R$_f$=0.25 in 2:1 hexanes:ethyl acetate (+0.2% acetic acid)), the title compound was obtained as a colorless solid (0.16 g, 42%): $^1$H NMR (300 MHz, DMSO-$d_6$) δ 11.55 (br s, 1H), 7.09-7.00 (m, 2H), 6.86 (d, J=1.7 Hz, 2H), 6.71-6.68 (m, 1H), 4.72-4.65 (m, 1H), 3.99 (t, J=7.7 Hz, 4H), 3.67 (dd, J=13.7, 5.5 Hz, 1H), 3.52 (dd, J=13.7, 2.3 Hz, 1H), 3.48-3.39 (m, 1H), 3.27-3.21 (m, 1H), 2.11 (p, J=7.7 Hz, 2H), 1.99-1.88 (m, 1H), 1.84-1.71 (m, 2H), 1.68-1.59 (m, 1H), 1.58-1.46 (m, 1H), 0.69-0.61 (m, 2H), 0.57-0.50 (m, 2H); MS (ES+) m/z 542.2, 544.1 (M+H).

Example 44

Synthesis of (R)-5-cyclopropyl-4-((1-(3,5-dichlorophenyl)piperidin-3-yl)oxy)-2-fluoro-N-(methylsulfonyl)benzamide

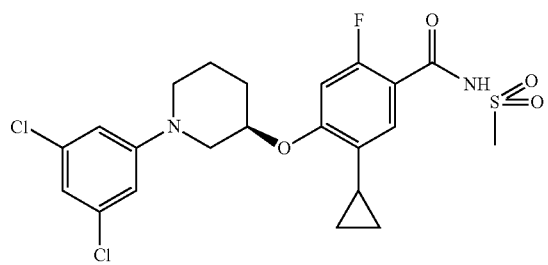

Following the procedure as described in Example 39 step 2 and making variations as required to replace (R)-5-chloro-4-((1-(2-chloro-4-fluorobenzyl)piperidin-3-yl)oxy)-2-fluorobenzoic acid with (R)-5-cyclopropyl-4-((1-(3,5-dichlorophenyl)piperidin-3-yl)oxy)-2-fluorobenzoic acid and cyclopropanesulfonamide with methanesulfonamide and purification by flash chromatography ($R_f$=0.15 in 2:1 hexanes:ethyl acetate (+0.2% acetic acid)), the title compound was obtained as a colorless solid (0.15 g, 42%): $^1$H NMR (300 MHz, DMSO-$d_6$) δ 11.83 (brs, 1H), 7.08-6.99 (m, 2H), 6.85 (d, J=1.7 Hz, 2H), 6.70-6.68 (m, 1H), 4.72-4.65 (m, 1H), 3.68 (dd, J=13.7, 5.4 Hz, 1H), 3.53 (dd, J=13.7, 2.4 Hz, 1H), 3.48-3.38 (m, 1H), 3.30 (s, 3H), 3.26-3.21 (m, 1H), 1.99-1.88 (m, 1H), 1.83-1.70 (m, 2H), 169-1.59 (m, 1H), 1.57-1.45 (m, 1H), 0.59-0.61 (m, 2H), 0.57-0.49 (m, 2H); MS (ES+) m/z 501.1, 503.1 (M+H)

Example 45

Synthesis of (S)—N-(azetidin-1-ylsulfonyl)-4-((1-benzylprrolidin-3-yl)oxy)-5-cyclopropyl-2-fluorobenzamide

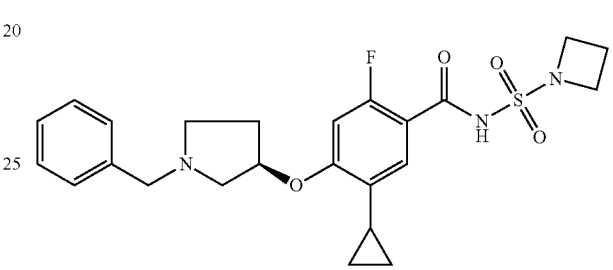

Following the procedures as described is Example 3 steps 1 to 5, and making variations as required to replace (R)-tert-butyl 3-hydroxypiperidine-1-carboxylate with (S)-tert-butyl 3-hydroxypyrrolidine-1-carboxylate, 3,5-dichlorobenzaldehyde with benzaldehyde and cyclopropylsulfonamide with azetidine-1-sulfonamide, the title compound was obtained (0.027 g, 5%): $^1$H NMR (300 MHz, DMSO-$d_6$) d 7.40-7.17 (m, 5H), 7.13 (d, J=8.8 Hz, 1H), 6.69 (d, J=12.61 Hz, 1H), 5.00-4.87 (m, 1H), 3.86-3.71 (m, 4H), 3.65-3.59 (m, 2H), 2.98-2.84 (m, 1H), 2.78-2.56 (m, 3H), 2.37-1.77 (m, 5H), 0.92-0.78 (m, 2H), 0.62-0.52 (m, 2H); MS(ES+) m/z 474.2 (M+1); MS(ES−) m/z 472.3 (M−1).

Example 46

Synthesis of (R)—N-(azetidin-1-ylsulfonyl)-4-((1-benzylpyrrolidin-3-yl)oxy)-5-cyclopropyl-2-fluorobenzamide Following the procedures as described in Example 3 steps 1 to 5, and making variations as required to replace (R)-tert-butyl 3-hydroxypiperidine-1-carboxylate with (R)-tert-butyl 3-hydroxypyrrolidine-1-carboxylate, 3,5-dichlorobenzaldehyde with benzaldehyde and cyclopropylsulfonamide with azetidine-1-sulfonamide, the title compound was obtained (0.095 g, 27%): $^1$H NMR (300 MHz, DMSO-$d_6$) d 7.45-7.18 (m, 5H), 7.10 (d, J=8.3 Hz, 1H), 6.82 (d, J=12.7 Hz, 1H), 5.07-4.94 (m, 1H), 3.98-3.87 (m, 4H), 3.76 (s, 2H), 3.06 (dd, J=11.0, 5.8 Hz, 1H), 2.91-2.74 (m, 2H), 2.72-2.57 (m, 1H), 2.34 (dt, J=13.9, 7.1 Hz, 1H), 2.17-1.94 (m, 3H), 1.93-1.79 (m, 1H), 0.90-0.77 (m, 2H), 0.67-0.56 (m, 2H); MS(ES+) m/z 474.2 (M+1); MS(ES−) m/z 472.3 (M−1).

Example 47

Synthesis of N-(azetidin-1-ylsulfonyl)-4-((8-(2-chlorobenzyl)-8-azabicyclo[3.2.1]octan-3-yl)methoxy)-5-cyclopropyl-2-fluorobenzamide

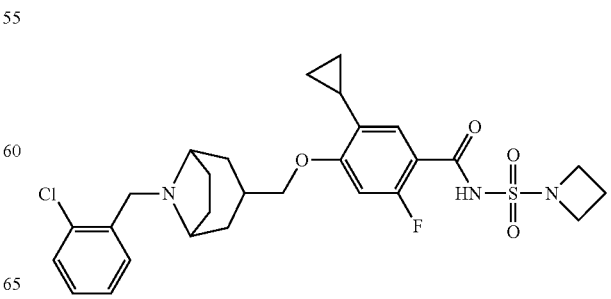

Step 1. Preparation of benzyl 3-(hydroxymethyl)-8-azabicyclo[3.2.1]octane-8-carboxylate

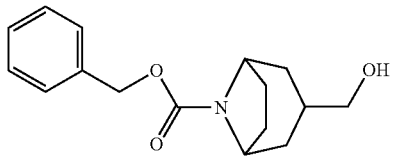 [SMILES: O=C(OCc1ccccc1)N1C2CCC1CC(CO)C2]

To a solution of 8-Azabicyclo[3.2.1]octan-3-ylmethanol (1.00 g, 7.09 mmol) in dichloromethane (15 mL) and a saturated aqueous sodium bicarbonate solution (10 mL) at 0° C. was added benzyl chloroformate (1.26 g, 7.45 mmol) and the reaction mixture was stirred at 0° C. for 30 mm. The reaction mixture was then extracted with dichloromethane (3×100 mL). The organic layers were combined and washed with brine (150 mL); dried over anhydrous sodium sulfate, filtered and concentrated to give the title compound, which was used directly for the next step. (1.50 g, 73%). $^1$H NMR (300 MHz, CDCl$_3$) d 7.43-7.24 (m, 5H), 5.15-5.09 (m, 2H), 4.59-4.57 (m, 1H), 4.40-4.27 (m, 2H), 3.41 (m, 2H), 2.14-1.90 (m, 3H), 1.88-1.80 (m, 1H), 1.73-1.48 (m, 4H).

Step 2. Preparation of benzyl 3-((4-(tert-butoxycarbonyl)-2-chloro-5-fluorophenoxy)methyl)-8-azabicyclo[3.2.1]octane-8-carboxylate

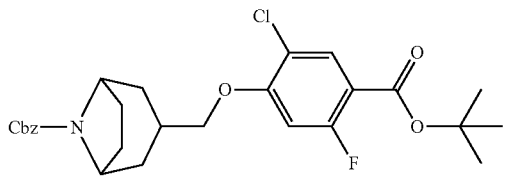 [SMILES: CC(C)(C)OC(=O)c1cc(Cl)c(OCC2CC3CCC(C2)N3C(=O)OCc2ccccc2)cc1F]

To a solution of benzyl 3-(hydroxymethyl)-8-azabicyclo[3.2.1]octane-8-carboxylate (1.92 g, 7.00 mmol) in anhydrous dimethylsulfoxide (15 mL) was added cesium carbonate (5.69 g, 10.50 mmol) and tert-butyl 5-chloro-2,4-difluorobenzoate (1.82 g, 7.35 mmol). The reaction mixture was stirred at 70° C. for 16 hours; cooled to ambient temperature and acidified to pH=1 with 5% aqueous hydrochloric acid solution and extracted with ethyl acetate (2×15 mL), the combined organics were washed with brine (15 mL); dried over anhydrous sodium sulfate; filtered and concentrated in vacuo. Purification of the residue by column chromatography (0 to 10% gradient of ethyl acetate in hexanes) afforded the title compound (2.00 g, 54%): $^1$H NMR (300 MHz, CDCl$_3$) d 7.85 (d, J=7.6 Hz, 1H), 7.39-7.26 (m, 5H), 6.56 (d, J=12.1 Hz, 1H), 5.13 (s, 2H), 4.46-4.28 (m, 2H), 3.81-3.73 (m, 2H), 2.54-2.32 (m, 1H), 2.03-1.96 (m, 4H), 1.79-1.65 (m, 4H), 1.60-1.51 (m, 9H); MS(ES+) m/z 504.2, 506.2 (M+1).

Step 3. Preparation of benzyl 3-((4-(tert-butoxycarbonyl)-2-cyclopropyl-5-fluorophenoxy)methyl)-8-azabicyclo[3.2.1]octane-8-carboxylate

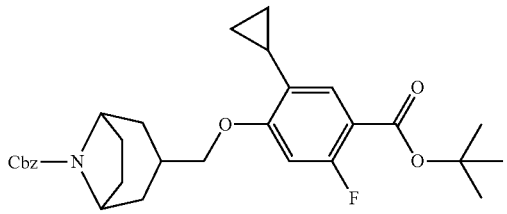 [SMILES: CC(C)(C)OC(=O)c1cc(C2CC2)c(OCC2CC3CCC(C2)N3C(=O)OCc2ccccc2)cc1F]

To a solution of benzyl 3-((4-(tert-butoxycarbonyl)-2-chloro-5-fluorophenoxy)-methyl)-8-azabicyclo[3.2.1]octane-8-carboxylate (1.50 g, 2.98 mmol), cyclopropylboronic acid (0.38 g, 4.46 mmol), potassium phosphate (2.10 g, 5.95 mmol) and tricyclohexylphosphine tetrafluoroborate (0.22 g, 0.60 mmol) in toluene (15 mL) and water (1.5 mL) under a nitrogen atmosphere was added palladium acetate (0.06 g, 0.30 mmol). The reaction mixture was heated at reflux for 16 hours, and then cooled to ambient temperature. Water (50 mL) was added and the mixture was extracted with diethyl ether (2×100 mL), the combined organics were washed with brine (30 mL); dried over anhydrous sodium sulfate and concentrated in vacuo. Purification of the residue by column chromatography (10 to 30% gradient of ethyl acetate in hexanes) afforded the title compound (1.05 g: 66%). $^1$H NMR (300 MHz, CDCl$_3$) δ 7.48 (d, J=8.4 Hz, 1H), 6.58 (d, 12.9 Hz, 1H), 3.87 (dd, J=6.9, 2.3 Hz, 2H), 2.17-1.91 (m, 3H), 1.76-1.31 (m, 8H), 0.98-0.84 (m, 5H), 0.67-0.58 (m, 2H).

Step 4. Preparation of benzyl 3-((4-((azetidin-1-ylsulfonyl)carbamoyl)-2-cyclopropyl-5-fluorophenoxy)methyl)-8-azabicyclo[3.2.1]octane-8-carboxylate

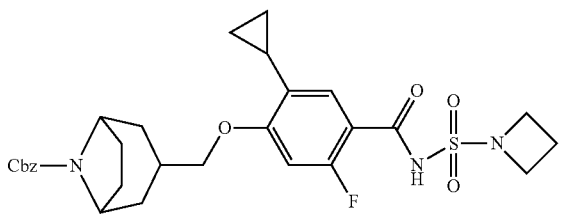 [SMILES: O=C(NS(=O)(=O)N1CCC1)c1cc(C2CC2)c(OCC2CC3CCC(C2)N3C(=O)OCc2ccccc2)cc1F]

To a stirred solution of benzyl 3-((4-(tert-butoxycarbonyl)-2-cyclopropyl-5-fluorophenoxy)methyl)-8-azabicyclo[3.2.1]octane-8-carboxylate (0.56 g, 1.19 mmol) in dichloromethane (5 mL) at 0° C. was added trifluoroacetic acid (1 mL) and the mixture was stirred for 1.5 hours at ambient temperature and then concentrated. The residue was further concentrated 2 times with toluene (5 mL) and then diluted with dichloromethane (5 mL). To this solution was added N-(3-dimethylaminopropyl)-N'-ethylcarbodiimide hydrochloride (0.426 g, 1.65 mmol) and 4-(dimethylamino)pyridine (0.335 g, 2.75 mmol) azetidine-1-sulfonamide (0.165 g, 1.21 mmol). The reaction mixture was stirred at room temperature for 16 hours and then diluted with dichloromethane (10 mL) and washed with aqueous hydrochloric acid (1M, 10 mL). The aqueous layer was extracted with Step 5. Preparation of 4-(8-azabicyclo[3.2.1]octan-3-ylmethoxy)-N-(azetidin-1-ylsulfonyl)-5-cyclopropyl-2-fluorobenzamideate

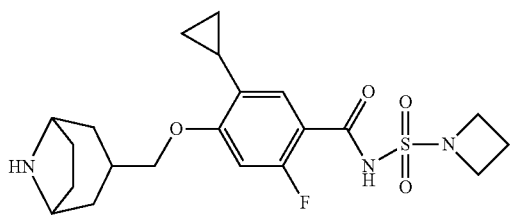 [SMILES: O=C(NS(=O)(=O)N1CCC1)c1cc(C2CC2)c(OCC2CC3CCC(C2)N3)cc1F]

To a stirred solution of benzyl 3-((4-((azetidin-1-ylsulfonyl)carbamoyl)-2-cyclopropyl-5-fluorophenoxy)methyl)-8-azabicyclo[3.2.1]octane-8-carboxylate (0.46 g, 0.81 mmol) in degassed ethyl acetate was added palladium 20% on carbon (0.050 g). The reaction mixture was stirred for 2 hours under an atmosphere of hydrogen. The reaction mixture was then filtered over a plug of silica gel and rinsed (2×15 mL) with a solution of 20% methanol and 2% acetic acid in dichloromethane. The filtrate was concentrated to give the title compound (0.2 g, 56%). ¹H NMR (300 MHz, MeO-d₄) δ 7.37-7.13 (m, 1H), 6.87-6.61 (m, 1H), 4.33-3.73 (m, 7H), 3.38-3.23 (m, 1H), 2.68-1.64 (m, 12H), 1.03-0.75 (m, 2H), 0.69-0.51 (m, 2H).

Step 6. Preparation of N-(azetidin-1-ylsulfonyl)-4-((8-(2-chlorobenzyl)-8-azabicyclo[3.2.1]octan-3-yl)methoxy)-5-cyclopropyl-2-fluorobenzamide

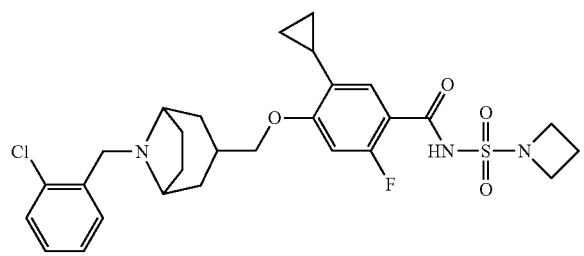 [SMILES: O=C(NS(=O)(=O)N1CCC1)c1cc(C2CC2)c(OCC2CC3CCC(C2)N3Cc2ccccc2Cl)cc1F]

To a stirred solution of 4-(8-azabicyclo[3.2.1]octan-3-ylmethoxy)-N-(azetidin-1-ylsulfonyl)-5-cyclopropyl-2-fluorobenzamideate (50 mg, 0.11 mmol) in tetrahydrofuran (1 mL) under an atmosphere of nitrogen were introduced (19 mg, 0.14 mmol) and sodium triacetoxyborohydride (66 mg, 0.21 mmol) and the mixture was stirred for 16 hours, 1N aqueous hydrochloric acid (5 mL) was added and the mixture was extracted with ethyl acetate (3×10 mL) and concentrated. The residue was purified by chromatography eluting with 5% methanol in dichloromethane to give the title compound, which was lyophilized to give a white solid (0.035 g, 29%). ¹H NMR (300 MHz, DMSO-d₆) δ 7.71 (d, J=6.5 Hz, 1H), 7.44 (d, J=7.3 Hz, 1H), 7.40-7.28 (m, 2H), 7.12 (d, J=8.3 Hz, 1H), 6.86 (d, J=12.7 Hz, 1H), 4.00-3.79 (m, 8H), 3.55-3.42 (m, 2H), 2.33-1.94 (m, 6H), 1.83-1.60 (m, 6H), 0.90-0.80 (m, 2H), 0.68-0.56 (m, 2H), MS(ES+) m/z 562.2, 564.2 (M+1); MS(ES−) m/z 560.3, 562.3 (M−1).

Example 48

Synthesis of N-(azetidin-1-ylsulfonyl)-4-((8-benzyl-8-azabicyclo[3.2.1]octan-3-yl)methoxy)-5-cyclopropyl-2-fluorobenzamide

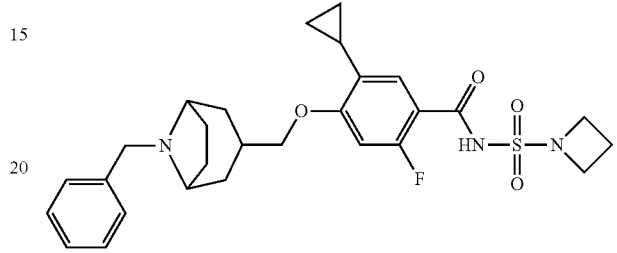

Following the procedure as described in Example 4 step 6, and making variation as required to replace 2-chlorobenzaldehyde with benzaldehyde, the title compound was obtained as a white solid (0.025 g, 41%). ¹H NMR (300 MHz, DMSO-d₆) δ 7.66-7.52 (m, 2H), 7.47-7.36 (m, 3H), 7.22-7.1.2 (m, 1H), 6.82-6.71 (m, 1H), 4.18-4.01 (m, 2H), 3.97-3.62 (m, 8H), 2.42-2.16 (m, 3H), 2.14-1.71 (m, 9H), 0.91-0.76 (m, 2H), 0.63-0.52 (m, 2H); MS(ES+) m/z 528.2 (M+1).

Example 49

Synthesis of N-(azetidin-1-ylsulfonyl)-4-((8-benzhydryl-8-azabicyclo[3.2.1]-octan-3-yl)methoxy)-5-cyclopropyl-2-fluorobenzamide

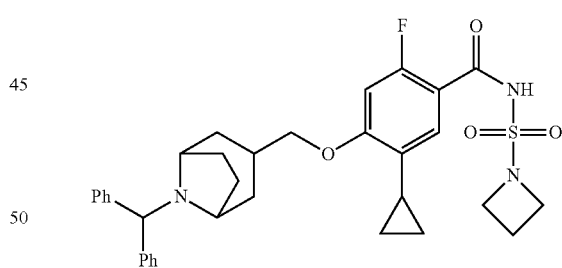

To a stirred solution of 4-(8-azabicyclo[3.2.1]octan-3-ylmethoxy)-N-(azetidin-1-ylsulfonyl)-5-cyclopropyl-2-fluorobenzamideate (0.05 g, 011 mmol) in acetonitrile (2 mL) under an atmosphere of nitrogen was added (bromomethylene)dibenzene (0.034 g, 0.14 mmol), potassium carbonate (0.038 g, 0.27 mmol) and sodium iodide (0.021 g, 0.14 mmol). Else reaction mixture was stirred at reflux for 16 hours and then cooled to ambient temperature. 1N aqueous hydrochloric acid (5 mL) was added and the mixture was extracted with ethyl acetate (3×10 mL) and concentrated. The residue was first purified by column chromatography during with 30% ethyl acetate (containing 1% formic acid) in hexanes and then purified by reverse phase chromatography cutting with a gradient of acetonitrile in water (containing 0.1% trifluoroacetic acid) and finally crystallized in isopropyl alcohol to give the title compound (0.03 g, 43%): $^1$H NMR (300 MHz, DMSO-$d_6$) d 12.18-11.67 (m, 1H), 8.75-8.53 (m, 1H), 7.98-7.76 (m, 4H), 7.61-7.49 (m, 1H), 7.47-7.30 (m, 6H), 6.59 (d, J=14.1 Hz, 1H), 4.77-4.65 (m, 1H), 4.28-4.17 (m, 4H), 4.07-3.98 (m, 2H), 3.97-3.89 (m, 2H), 2.90-2.56 (m, 3H), 2.51-2.34 (m, 3H), 2.24 (m, 2H), 2.12-2.01 (m, 2H), 1.95-1.81 (m, 2H), 0.90-0.76 (m, 2H), 0.67-0.55 (m, 2H); MS(ES+) m/z 564.3 (M+1); MS(ES−) m/z 562.3.

Example 50

Synthesis of (5-cyclopropyl-4-(((R)-1-((S)-1-(3,5-dichlorophenyl)ethyl)piperidin-3-yl)oxy)-2-fluoro-N-(methylsulfonyl)benzamide

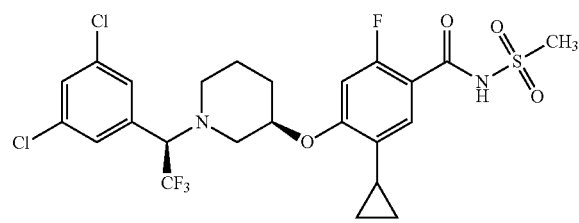 [SMILES: C[C@@H](c1cc(Cl)cc(Cl)c1)N1CCC[C@@H](Oc2cc(F)c(C(=O)NS(C)(=O)=O)cc2C2CC2)C1]

Step 1. Preparation of methyl 5-cyclopropyl-4-(((R)-1-((S)-1-(3,5-dichlorophenyl)ethyl)-piperidin-3-yl)oxy)-2-fluorobenzoate and methyl 5-cyclopropyl-4-(((R)-1-((R)-1-(3,5-dichlorophenyl)ethyl)piperidin-3-yl)oxy)-2-fluorobenzoate

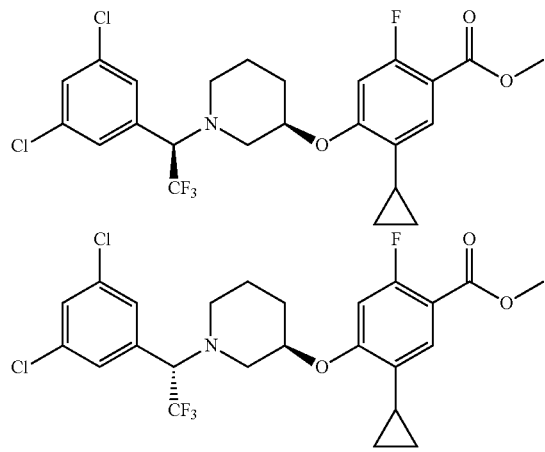

To a mixture of (R)-methyl 5-cyclopropyl-2-fluoro-4-(piperidin-3-yloxy)benzoate (0.52 g, 1.77 mmol), potassium carbonate (0.73 g, 5.30 mmol) and sodium iodide (0.26 g, 1.77 mmol) in acetonitrile (50 mL) was added 1,3-dichloro-5-(1-chloroethyl)benzene (0.37 g, 1.77 mmol). The reaction mixture was heated at reflux for 16 hours, and concentrated in vacuo. To the he residue was added 25% aqueous ammonium chloride solution (40 mL) and extracted with ethyl acetate (2×70 mL). The combined organic layer was washed with brine (40 mL), dried over anhydrous sodium sulfate and concentrated in vacuo. The residue was purified by column chromatography (0-20% ethyl acetate its hexanes) afforded the title compound. The first eluting fraction was arbitrarily assigned as methyl 5-cyclopropyl-4-(((R)-1-((S)-1-(3,5-dichlorophenyl)ethylpiperidin-3-yl)oxy)-2-fluorobenzoate (0.18 g, 22%); $^1$H NMR (300 MHz, CDCl$_3$) δ 7.42 (d, J=8.4 Hz, 1H), 7.22-7.21 (m, 3H), 6.54 (d, J=12.9 Hz, 1H), 4.39-4.37 (m, 1H), 3.87 (s, 3H), 3.47 (q, J=6.6 Hz, 1H), 2.97-2.94 (m, 1H), 2.57-2.54 (m, 1H), 2.35-2.23 (m, 2H), 2.11-1.98 (m, 2H), 1.85-1.77 (m, 1H), 1.65-1.51 (m, 2H), 1.31 (d, J=6.7 Hz, 3H), 0.94-0.90 (m, 2H), 0.68-0.63 (m, 2H); MS(ES+) m/z 466.1, 468.1 (M+1). The second elating fraction was arbitrarily assigned as methyl 5-cyclopropyl-4-(((R)-1-((R)-1-(3,5-dichlorophenyl)ethyl)piperidin-3-yl)oxy)-2-fluorobenzoate (0.18 g, 22%); $^1$H NMR (300 MHz, CDCl$_3$) δ 7.42 (d, J=8.4 Hz, 1H), 7.22-7.21 (m, 3H), 6.54 (d, J=12.9 Hz, 1H), 4.39-4.37 (m, 1H), 3.87 (s, 3H), 3.47 (q, J=6.6 Hz, 1H), 2.97-2.94 (m, 1H), 2.57-2.54 (m, 1H), 2.35-2.23 (m, 2H), 2.11-1.98 (m, 2H), 1.85-1.77 (m, 1H), 1.65-1.51 (m, 2H), 1.31 (d, J=6.7 Hz, 3H), 0.94-0.90 (m, 2H), 0.68-0.63 (m, 2H); MS(ES+) m/z 466.1, 468.1 (M+1).

Step 2. Preparation of 5-cyclopropyl-4-(((R)-1-((S)-1-(3,5-dichlorophenyl)ethyl)-piperidin-3-yl)oxy)-2-fluorobenzoic acid

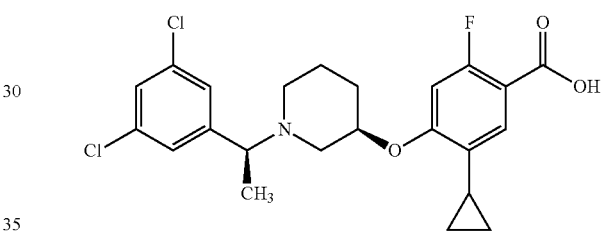

To a mixture of 5-cyclopropyl-4-(((R)-1-((S)-1-(3,5-dichlorophenyl)ethyl)-piperidin-3-yl)oxy)-2-fluorobenzoate (0.20 g, 0.43 mmol) in tetrahydrafurane (30 mL) and water (5 mL) was added lithium hydroxide (0.10 g, 4.3 mmol). The reaction mixture was heated to reflux for 16 hours and adjusted pH to 7 with 1N aqueous hydrochloric acid solution, extracted with ethyl acetate (2×50 mL), the combined organics were washed with 25% aqueous ammonium chloride solution (2×30 mL), dried over anhydrous sodium sulfate and concentrated in vacuo. Purification of the residue by column chromatography (20%-100% ethyl acetate in hexanes) afforded the title compound (0.15 g, 77%); MS(ES+) m/z 452.1, 454.1 (M+1); MS(ES−) m/z 450.2, 452.2 (M−1).

Step 3. Preparation of (5-cyclopropyl-4-(((R)-1-((S)-1-(3,5-dichlorophenyl)ethyl)-piperidin-3-yl)oxy)-2-fluoro-N-(methylsulfonyl)benzamide

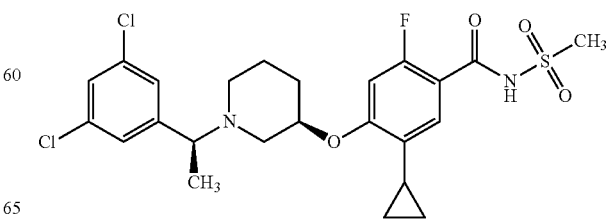

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with 5-cyclopropyl-4-(((R)-1-((S)-1-(3,5-dichlorophenyl)ethyl)piperidin-3-yl)oxy)-2-fluorobenzoic acid, the title compound was obtained as colorless solid (0.05 g, 33%): ¹H NMR (300 MHz, DMSO-d$_6$) δ 11.87 (brs, 1H), 7.46-7.37 (m, 3H), 7.13 (d, J=8.4 Hz, 1H), 6.95 (d, J=13.2 Hz, 1H), 4.59-4.57 (m, 1H), 3.63-3.62 (m, 1H), 3.28 (s, 3H), 2.77-2.73 (m, 1H), 2.43-2.33 (m, 3H), 2.13-2.03 (m, 1H), 2.18-1.73 (m, 2H), 1.55-1.53 (m, 2H), 1.27 (d, J=6.7 Hz, 3H), 0.91-0.88 (m, 2H), 0.73-0.66 (m, 2H); MS(ES+) m/z 529.1, 531.1 (M+1); MS(ES−) m/z 527.2, 529.2 (M−1).

Example 51

Synthesis of (5-cyclopropyl-4-(((R)-1-((R)-1-(3,5-dichlorophenyl)ethyl)piperidin-3-yl)oxy)-2-fluoro-N-(methylsulfonyl)benzamide

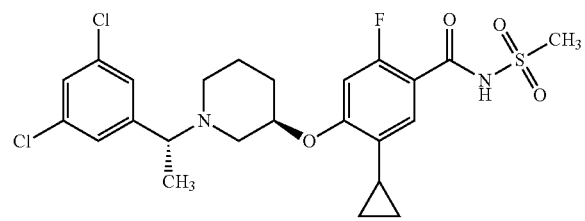 [SMILES: C[C@H](c1cc(Cl)cc(Cl)c1)N1CCC[C@@H](Oc2cc(F)c(C(=O)NS(C)(=O)=O)cc2C2CC2)C1]

Step 1. Preparation of 5-cyclopropyl-4-(((R)-1-((R)-1-(3,5-dichlorophenyl)ethyl)-piperidin-3-yl)oxy)-2-fluorobenzoic acid

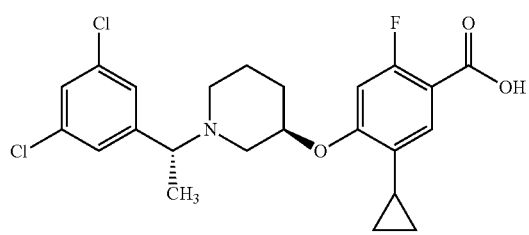 [SMILES: C[C@H](c1cc(Cl)cc(Cl)c1)N1CCC[C@@H](Oc2cc(F)c(C(=O)O)cc2C2CC2)C1]

Following the procedure as described in Example 50 step 2 and making variations as required to replace 5-cyclopropyl-4-(((R)-1-((S)-1-(3,5-dichlorophenyl)ethyl)piperidin-3-yl)oxy)-2-fluorobenzoate with 5-cyclopropyl-4-((R)-1-((R)-1-(3,5-dichlorophenyl)ethyl)-piperidin-3-yl)oxy-2-fluorobenzoate, the title compound was obtained as beige color solid (0.18 g, 2%): MS(ES+) m/z 452.2, 454.2 (M+1); MS (ES−) m/z 450.2, 452.2 (M−1).

Step 2. Preparation of (5-cyclopropyl-4-(((R)-1-((R)-1-(3,5-dichlorophenyl)ethylpiperidin-3-yl)oxy)-2-fluoro-N-(methylsulfonyl)benzamide

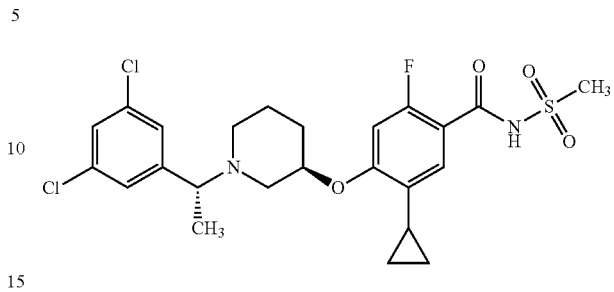

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with 5-cyclopropyl-4-(((R)-1-((R)-1-(3,5-dichlorophenyl)ethyl-piperidin-3-yl)oxy)-2-fluorobenzoic acid, the title compound was obtained as colorless solid (0.06 g, 30%): ¹H NMR (300 MHz, DMSO-d$_6$) δ 11.87 (brs, 1H), 7.47-7.40 (m, 3H), 7.12 (d, J=8.4 Hz, 1H), 6.96 (d, J=13.2 Hz, 1H), 4.58-4.56 (m, 1H), 3.68 (q, J=6.3 Hz, 1H), 3.29 (s, 3H), 2.80-2.77 (m, 1H), 2.60-2.56 (m, 1H), 2.37-2.20 (m, 2H), 2.08-2.03 (m, 1H), 1.91-1.74 (m, 2H), 1.57-1.46 (m, 2H), 1.27 (d, J=6.7 Hz, 3H), 0.90-0.87 (m, 2H), 0.75-0.63 (m, 2H); MS(ES+) m/z 529.1, 531.1 (M+1); MS(ES−) m/z 527.2, 529.2 (M−1).

Example 52

Synthesis of 4-((3R,6R)-1-(2-chloro-4-fluorobenzyl)-6-methylpiperidin-3-yl)oxy)-5-cyclopropyl-2-fluoro-N-(methylsulfonyl)benzamide

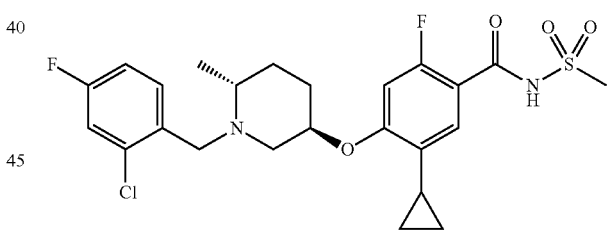

Step 1. Preparation of (2R,5R)-benzyl 5-hydroxy-2-methylpiperidine-1-carboxylate

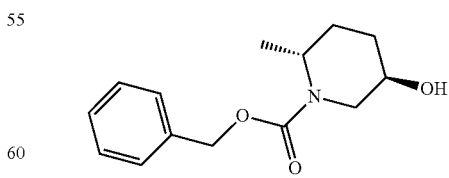

To a cooled (0° C.) solution of (3R,6R)-6-methylpiperidin-3-ol (1.06 g, 9.19 mmol) (Ian A. O'Neil et al., *Synlett*, 2000, 5, 695) and triethylamine (1.35 mL, 9.65 mmol) in dichloromethane (60 mL) was added benzyl chloroformate (1.38 mL, 9.65 mmol) dropwise. The reaction mixture was stirred at ambient temperature for 16 h, diluted with aqueous saturated ammonium chloride solution (35 mL), and extracted with ethyl acetate (3×70 mL). The combined organic layers were washed with brine (100 mL), dried over anhydrous magnesium sulfate, filtered and concentrated in vacuo. The residue was purified by column chromatography cutting with a gradient of ethyl acetate in hexanes (0 to 60%) to give the title compound (1.30 g, 57%) as a colorless oil: $^1$H NMR (300 MHz, CDCl$_3$) δ 7.40-7.29 (m, 5H), 5.14 (s, 2H), 4.57-4.45 (m, 1H), 4.13-4.02 (m, 1H), 3.94 (s, 1H), 3.18-3.03 (m, 1H), 2.19-2.03 (m, 1H), 1.88-1.62 (m, 3H), 1.39-1.26 (m, 1H), 1.19-1.13 (m, 3H); MS(ES+) m/z 250.2 (M+1).

Step 2. Preparation of (2R,5R)-benzyl 5-(4-(tert-butoxycarbonyl)-2-chloro-5-fluorophenoxy)-2-methylpiperidine-1-carboxylate

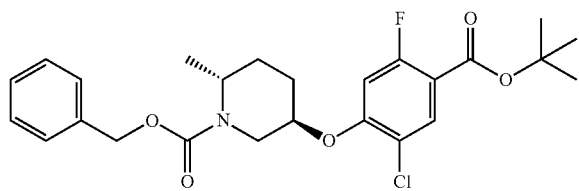 [SMILES: C[C@@H]1CC[C@@H](Oc2cc(F)c(C(=O)OC(C)(C)C)cc2Cl)CN1C(=O)OCc1ccccc1]

Following the procedure as described in Example 1 step 1, and making variation as required to replace (R)-1-benzylpiperidin-3-ol with (2R,5R)-benzyl 5-hydroxy-2-methylpiperidine-1-carboxylate, the title compound was obtained (1.80 g, 72%) as a colorless oil: $^1$H NMR (300 MHz, CDCl$_3$) δ 7.84-7.77 (m, 1H), 7.32-7.08 (m, 5H), 6.64-6.53 (m, 1H), 5.09-4.92 (m, 2H), 4.69-4.56 (m, 1H), 4.46 (s, 1H), 4.39-4.29 (m, 1H), 3.19-3.07 (m, 1H), 2.32-2.16 (m, 1H), 2.01-1.89 (m, 2H), 1.56 (s, 9H), 1.41-1.31 (m, 1H), 1.24-1.18 (m, 3H); MS(ES+) m/z 478.2 (M+1).

Step 3. Preparation of (2R,5R)-benzyl 5-(4-(tert-butoxycarbonyl)-2-cyclopropyl-5-fluorophenoxy)-2-methylpiperidine-1-carboxylate

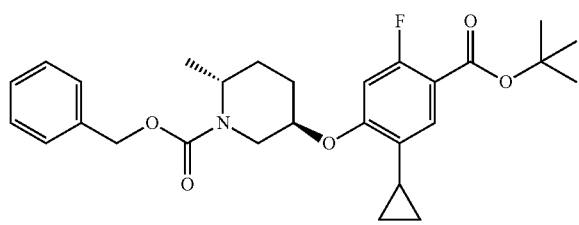 [SMILES: C[C@@H]1CC[C@@H](Oc2cc(F)c(C(=O)OC(C)(C)C)cc2C2CC2)CN1C(=O)OCc1ccccc1]

Following the procedure as described in Example 1 step 2, and making variation as required to replace (R)-tert-butyl 4-((1-benzylpiperidin-3-yl)oxy)-5-chloro-2-fluorobenzoate with (2R,5R)-benzyl 5-(4-(tert-butoxycarbonyl)-2-chloro-5-fluorophenoxy)-2-methylpiperidine-1-carboxylate, the title compound was obtained (1.62 g, 89%) as a colorless oil. $^1$H NMR (300 MHz, CDCl$_3$) δ 7.39-7.32 (m, 1H), 7.30-7.03 (m, 5H), 6.52-6.41 (m, 1H), 5.06-4.92 (m, 2H), 4.68-4.55 (m, 1H), 4.46 (s, 1H), 4.42-4.29 (m, 1H), 3.20-3.07 (m, 1H), 2.27-2.08 (m, 1H), 2.04-1.82 (m, 3H), 1.56 (s, 9H), 1.42-1.31 (m, 1H), 1.24-1.19 (m, 3H), 0.83-0.73 (m, 2H), 0.58-0.47 (m, 2H); MS(ES+) m/z 484.3 (M+1).

Step 4. Preparation of tert-butyl 5-cyclopropyl-2-fluoro-4-(((3R,6R)-6-methylpiperidin-3-yl)oxy)benzoate

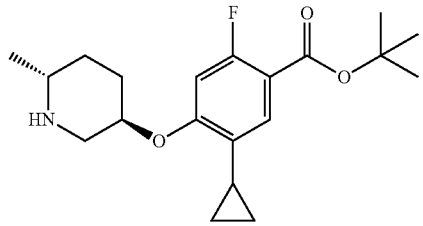 [SMILES: C[C@@H]1CC[C@@H](Oc2cc(F)c(C(=O)OC(C)(C)C)cc2C2CC2)CN1]

To a solution of (2R,5R)-benzyl 5-(4-(tert-butoxycarbonyl)-2-cyclopropyl-5-fluorophenoxy)-2-methylpiperidine-1-carboxylate (1.62 g, 3.35 mmol) in ethyl acetate (15 mL) and methanol (30 mL) was added 10% palladium on carbon (0.5 g). The reaction mixture was stirred at ambient temperature under hydrogen temperature using a balloon for 1 h and filtered through a pad of Celite. The filtrate was concentrated in vacuo to give the title compound (0.94 g, 80%) as colorless oil: MS(ES+) m/z 350.3 (M+1).

Step 5. Preparation of tert-butyl 4-(((3R,6R)-1-(2-chloro-4-fluorobenzyl)-6-methylpiperidin-3-yl)oxy)-5-cyclopropyl-2-fluorobenzoate

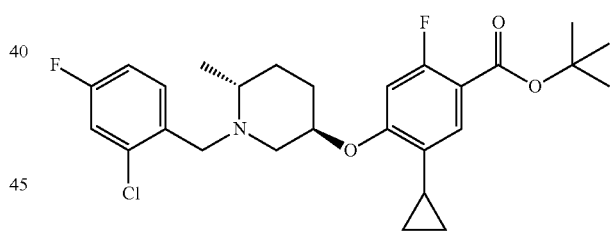

Following the procedure as described in Example 34 step 2, and making variations as required to replace (R)-methyl 5-cyclopropyl-2-fluoro-4-(piperidin-3-yloxy)benzoate with tert-butyl 5-cyclopropyl-2-fluoro-4-(((3R,6R)-6-methylpiperidin-3-yl)oxy)benzoate, and to replace 1-(bromomethyl)-4-fluoro-2-(trifluoromethyl)benzene with 1-(bromomethyl)-2-chloro-4-fluorobenzene, the title compound was obtained (1.29 g, 98%) as a colorless oil: $^1$H NMR (300 MHz, CDCl$_3$) δ 7.58-7.48 (m, 1H), 7.36-7.29 (m, 1H), 7.11-7.03 (m, 1H), 7.00-6.90 (m, 1H), 6.50-6.39 (m, 1H), 4.36-4.23 (m, 1H), 4.09-3.92 (m, 1H), 3.43-3.32 (m, 1H), 3.10-2.99 (m, 1H), 2.58-2.41 (m, 1H), 2.29-2.11 (m, 2H), 2.04-1.83 (m, 2H), 1.64-1.39 (m, 11H), 1.21-1.10 (m, 3H), 0.94-0.80 (m, 2H), 0.65-0.55 (m, 2H); MS(ES+) m/z 492.2, 494.2 (M+1).

Step 6. Preparation of 4-(((3R,6R)-1-(2-chloro-4-fluorobenzyl)-6-methylpiperidin-3-yl)oxy)-5-cyclopropyl-2-fluorobenzoic acid

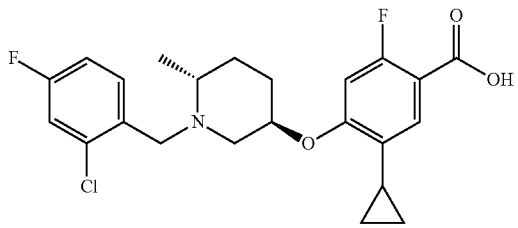 [SMILES: C[C@@H]1CC[C@@H](Oc2cc(F)c(C(=O)O)cc2C2CC2)CN1Cc1ccc(F)cc1Cl]

Following the procedure as described in Example 3 step 3, and making variations as required to replace (R)-tert-butyl 3-(4-(tert-butoxycarbonyl)-2-cyclopropyl-5-fluorophenoxy)piperidin-1-carboxylate with of tert-butyl 4-(((3R,6R)-1-(2-chloro-fluorobenzyl)-6-methylpiperidin-3-yl)oxy)-5-cyclopropyl-2-fluorobenzoate, the title compound was obtained (1.10 g, 97%) as a colorless solid: MS(ES+) m/z 436.2, 438.2 (M+1).

Step 7. Preparation of 4-(((3R,6R)-1-(2-chloro-4-fluorobenzyl)-2-methylpiperidin-3-yl)oxy)-5-cyclopropyl-2-fluoro-N-(methylsulfonyl)benzamide

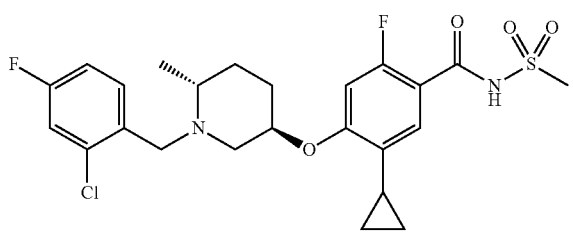 [SMILES: C[C@@H]1CC[C@@H](Oc2cc(F)c(C(=O)NS(C)(=O)=O)cc2C2CC2)CN1Cc1ccc(F)cc1Cl]

Following the procedure as described in Example 17 step 3, and making variation as required to replace (R)-5-cyclopropyl-4-((1-(3,4-dichlorobenzyl)piperidin-3-yl)-oxy)-2-fluorobenzoic acid with 4-(((3R,6R)-1-(2-chloro-4-fluorobenzyl)-6-methylpiperidin-3-yl)oxy)-5-cyclopropyl-2-fluorobenzoic acid, the title compound was obtained (0.065 g, 22%) as a colorless solid: ¹H NMR (300 MHz, CDCl₃) δ 8.80-8.56 (m, 1H, 7.59-7.46 (m, 2H), 7.12-7.05 (m, 1H), 7.01-6.89 (m, 1H), 6.54-6.40 (m, 1H), 4.38-4.26 (m, 1H), 4.06-3.95 (m, 1H), 3.46-3.33 (m, 4H), 3.09-3.00 (m, 1H), 2.59-2.45 (m, 1H), 2.32-2.11 (m, 2H), 2.09-1.86 (m, 2H), 1.70-1.41 (m, 2H), 1.22-1.16 (m, 3H), 0.96-0.85 (m, 2H), 0.67-0.59 (m, 2H); MS(ES+) m/z 513.1, 515.1 (M+1).

Example 53

Synthesis of (S)-5-cyclopropyl-N-(cyclopropylsulfonyl)-4-((3-(3,5-dichlorophenoxy)-piperidin-1-yl)methyl)-2-fluorobenzamide

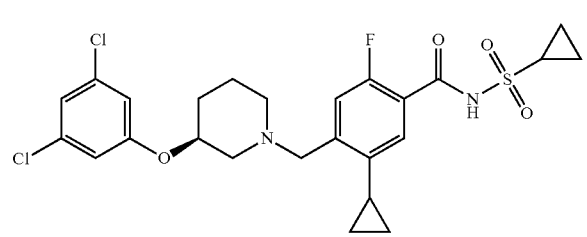 [SMILES: O=C(NS(=O)(=O)C1CC1)c1cc(C2CC2)c(CN2CCC[C@H](Oc3cc(Cl)cc(Cl)c3)C2)cc1F]

Step 1. Preparation of (S)-tert-butyl 3-(3,5-dichlorophenoxy)piperidine-1-carboxylate

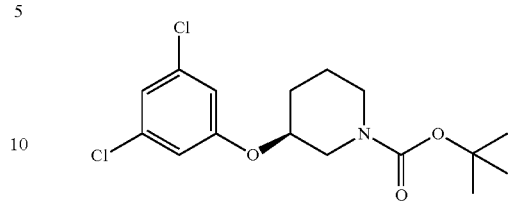

A mixture of (S)-tert-butyl 3-hydroxypiperidine-1-carboxylate (1.00 g, 4.97 mmol), 3,5-dichloroidobenzene (1.36 g, 4.97 mmol), copper(I) iodide (0.142 g, 0.75 mmol), 3,4,7,8-tetramethyl-1,10-phenanthroline (0.352 g, 1.49 mmol), molecular sieves 4 Å (1.00 g), and cesium carbonate (4.86 g, 14.9 mmol) is toluene (6 mL) was degassed and then heated to 90° C. for 16 hours. After cooling to ambient temperature, the mixture was filtered through a plug of celite. The filter cake was washed with dichloromethane (100 mL), and the combined filtrate concentrated in vacuo. Purification of the residue by column chromatography (0 to 30% ethyl acetate in hexanes) afforded the title compound as a colorless oil: (1.20 g, 70%): MS(ES+) m/z 346.1, 348.1 (M+1).

Step 2. Preparation of (S)-3-(3,5-dichlorophenoxy)piperidine, trifluoroacetic acid salt

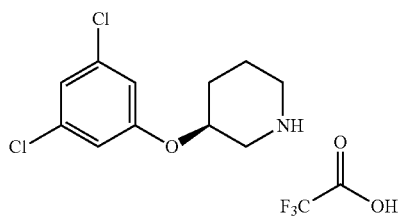

A solution of (S)-tert-butyl 3-(3,5-dichlorophenoxy)piperidine-1-carboxylate (1.17 g, 3.38 mmol) in dichloromethane (30 mL) was treated with trifluoroacetic acid (10 mL). The mixture was stirred at ambient temperature for 1 hour and then concentrated in vacuo to provide the title compound as an oil (1.22 g, quant.): MS(ES+) m/z 246.2, 248.1 (M+1).

Step 3. Preparation of (S)-tert-butyl 5-cyclopropyl-4-((3-(3,5-dichlorophenoxy)piperidin-1-yl)methyl)-2-fluorobenzoate

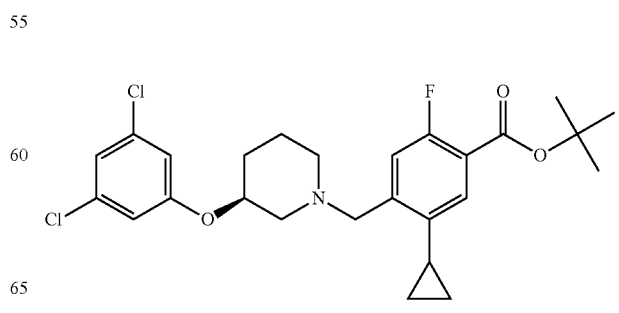

A mixture of tert-butyl 5-cyclopropyl-2-fluoro-4-(((methylsulfonyl)oxy)methyl)benzoate (0.64 g, 1.86 mmol), (S)-3-(3,5-dichlorophenoxy)piperidine, trifluoroacetic acid salt (0.74 g, 2.05 mmol), and potassium carbonate (0.64 g, 465 mmol) in anhydrous dimethylformamide (15 mL) was stirred at ambient temperature for 18 hours. The reaction mixture was diluted with ethyl acetate (100 mL), washed with water (80 mL), saturated ammonium chloride (2×80 mL), brine (80 mL), dried over anhydrous sodium sulfate, filtered the solid, and concentrated in vacuo. The residue was purified by flash chromatography (0 to 25% ethyl acetate in hexanes) to provide the title compound as an oil (0.70 g, 76%): $^1$H NMR (300 MHz, CDCl$_3$) d 7.48 (d, J=7.3 Hz, 1H), 7.15 (d, J=11.8 Hz, 1H), 6.90-6.87 (m, 1H), 6.76-6.73 (m, 2H), 4.35-4.23 (m, 1H), 3.72-3.58 (m, 2H), 2.97-2.88 (m, 1H), 2.71-2.61 (m, 1H), 2.31-2.12 (m, 2H), 2.06-1.88 (m, 2H), 1.85-1.74 (m, 1H), 1.70-1.38 (m, 11H), 0.94-0.82 (m, 2H), 0.64-0.54 (m, 2H); MS(ES+) m/z 494.3, 496.3 (M+1).

Step 4 Preparation of (S)-5-cyclopropyl-4-((3-(3,5-dichlorophenoxy)piperidin-1-yl)methyl)-2-fluorobenzoic acid

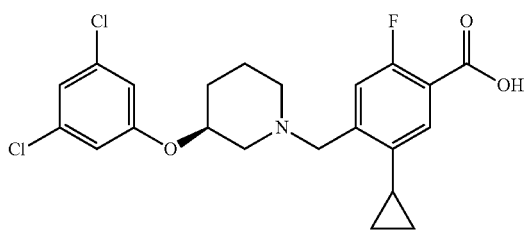 [SMILES: O=C(O)c1cc(C2CC2)c(CN2CCC[C@H](Oc3cc(Cl)cc(Cl)c3)C2)cc1F]

A solution of (S)-tert-butyl 5-cyclopropyl-4-((3-(3,5-dichlorophenoxy)piperidin-1-yl)methyl)-2-fluorobenzoate (1.04 g, 2.10 mmol) in dichloromethane (30 mL) was treated with trifluoroacetic acid (10 ml). The resulting solution was stirred at ambient temperature for 1 hour and then concentrated in vacuo to provide the title compound as a colorless solid (0.92 g, quant.): MS(ES+) m/z 438.1, 440.1 (M+1).

Step 5. Preparation of (S)-5-cyclopropyl-N-(cyclopropylsulfonyl)-4-((3-(3,5-dichlorophenoxy)piperidin-1-yl)methyl)-2-fluorobenzamide

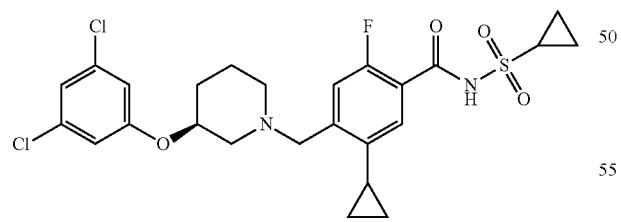

A mixture of (S)-5-cyclopropyl-4-((3-(3,5-dichlorophenoxy)piperidin-1-yl)methyl)-2-fluorobenzoic acid (0.30 g, 0.68 mmol), cyclopropanesulfonamide (0.12 g, 1.02 mmol), 1-ethyl-3-(3-dimethylaminopropyl)-carbodiimide (0.20 g, 1.02 mmol), and 4-dimethylaminopyridin (0.25 g, 2.04 mmol) in dichloromethane (12 mL) was stirred at ambient temperature for 24 hours. The reaction mixture was treated with acetic acid (1.0 mL) and purified by flash chromatography (0 to 30% ethyl acetate (containing 0.2% acetic acid) in hexanes) to provide the title compound as a colorless solid (0.175 g, 48%): $^1$H NMR (300 MHz, DMSO-d$_6$) δ 11.93 (br s, 1H), 7.24 (d, J=11.7 Hz, 1H), 7.18 (d, J=7.0 Hz, 1H), 7.09-7.07 (m, 1H), 7.01 (d, J=1.9 Hz, 2H), 4.61-4.51 (m, 1H), 3.69 (s, 2H), 3.08-2.99 (m, 1H), 2.85-2.77 (m, 1H), 2.63-2.52 (m, 1H), 2.41-2.21 (m, 2H), 2.05-1.97 (m, 1H), 1.96-1.84 (m, 1H), 1.78-1.67 (m, 1H), 1.63-1.51 (m, 1H), 1.49-1.34 (m, 1H), 1.11-1.03 (m, 4H), 0.91-0.79 (m, 2H), 0.68-0.56 (m, 2H); MS(ES+) m/z 541.2, 543.2 (M+1).

Example 54

Synthesis of (S)—N-(azetidin-1-ylsulfonyl)-5-cyclopropyl-4-((3-(3,5-dichlorophenoxy)piperidin-1-yl)methyl)-2-fluorobenzamide, acetic acid salt

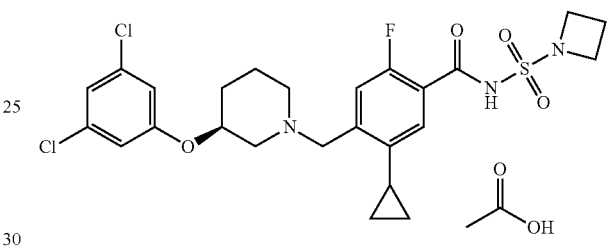

Following the procedure as described in Example 53, step 5, and making variation as required to replace cyclopropanesulfonamide with azetidine-1-sulfonamide, the title compound was obtained as a colorless solid (0.16 g, 42%): $^1$H NMR (300 MHz, CDCl$_3$) δ 8.74 (br s, 1H), 7.72 (d, J=7.9 Hz, 1H), 7.35-7.26 (m, 1H), 6.91 (s, 1H), 6.77 (s, 2H), 4.39-4.28 (m, 1H), 4.24 (t, J=7.7 Hz, 4H), 3.77-3.65 (m, 2H), 2.96-2.86 (m, 1H), 2.74-2.62 (m, 1H), 2.39-2.19 (m, 4H), 2.08 (s, 3H), 1.98-1.79 (m, 3H), 1.72-1.44 (m, 3H), 1.00-0.88 (m, 2H), 0.71-0.59 (m, 2H): MS (ES+) m/z 556.2, 558.2 (M+1).

Example 55

Synthesis of (R)-5-cyclopropyl-N-(cyclopropylsulfonyl)-4-((3-(3,5-dichlorophenoxy)piperidin-1-yl)methyl)-2-fluorobenzamide

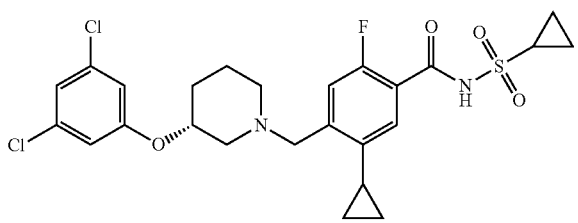 [SMILES: O=C(NS(=O)(=O)C1CC1)c1cc(C2CC2)c(CN2CCC[C@@H](Oc3cc(Cl)cc(Cl)c3)C2)cc1F]

Step 1. Preparation of (R)-tert-butyl 3-(3,5-dichlorophenoxy)piperidine-1-carboxylate

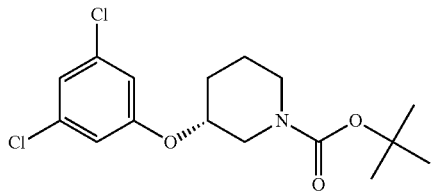 [SMILES: CC(C)(C)OC(=O)N1CCC[C@@H](Oc2cc(Cl)cc(Cl)c2)C1]

Following the procedure as described in Example 53 step 1 and making variation as required to replace (S)-tert-butyl 3-hydroxypiperidine-1-carboxylate with (R)-tert-butyl 3-hydroxypiperidine-1-carboxylate, the title compound was obtained as a colorless oil (0.461 g, 83%): $^1$H NMR (300 MHz, CDCl$_3$) d 6.91-6.87 (m, 1H), 6.76-6.74 (m, 2H), 4.23-4.12 (m, 1H), 3.92-3.03 (m, 4H), 2.01-1.88 (m, 1H), 1.85-1.63 (m, 2H), 1.55-1.27 (m, 10H).

Step 2. Preparation of (R)-3-(3,5-dichlorophenoxy)piperidine, trifluoroacetic acid salt

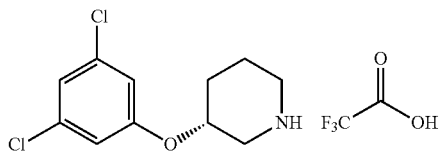 [SMILES: Clc1cc(Cl)cc(O[C@@H]2CCCNC2)c1 ; O=C(O)C(F)(F)F]

Following the procedure as described in Example 53 step 2, and making variation as required to replace (S)-tert-butyl 3-(3,5-dichlorophenoxy)piperidine-1-carboxylate with (R)-tert-butyl 3-(3,5-dichlorophenoxy)piperidine-1-carboxylate, the title compound was obtained as an oil (0.43 g, quant): MS (ES+) m/z 246.2, 248.2 (M+1).

Step 3. Preparation of (R)-tert-butyl 5-cyclopropyl-4-((3-(3,5-dichlorophenoxy)piperidin-1-yl)methyl)-2-fluorobenzoate

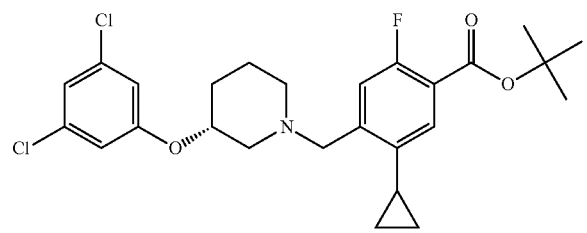 [SMILES: CC(C)(C)OC(=O)c1cc(C2CC2)c(CN2CCC[C@@H](Oc3cc(Cl)cc(Cl)c3)C2)cc1F]

Following the procedure as described in Example 53 step 3, and making variation as required to replace (S)-3-(3,5-dichlorophenoxy)piperidine, trifluoroacetic acid salt with (R)-3-(3,5-dichlorophenoxy)piperidine, trifluoroacetic acid salt, the title compound was obtained as an oil (0.38 g, 72%); $^1$H NMR (300 MHz, CDCl$_3$) δ 7.48 (d, J=7.3 Hz, 1H), 7.15 (d, J=11.7 Hz, 1H), 6.90-6.87 (m, 1H), 6.76-6.73 (m, 2H), 4.35-4.24 (m, 1H), 3.72-3.58 (m, 2H), 2.97-2.88 (m, 1H), 2.71-2.61 (m, 1H), 2.31-2.12 (m, 2H), 2.08-1.98 (m, 1H), 1.97-1.88 (m, 1H), 1.85-1.75 (m, 1H), 1.68-1.39 (m, 11H), 0.93-0.84 (m, 2H), 0.64-0.56 (m, 2H); MS (ES+) m/z 494.3, 496.3 (M+1).

Step 4. Preparation of (R)-5-cyclopropyl-4-((3-(3,5-dichlorophenoxy)piperidin-1-yl)methyl)-2-fluorobenzoic acid

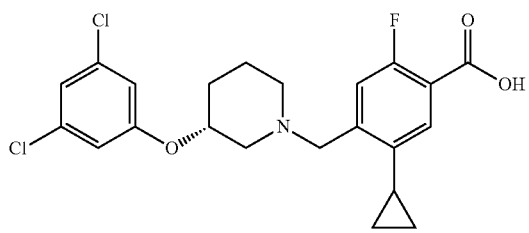 [SMILES: O=C(O)c1cc(C2CC2)c(CN2CCC[C@@H](Oc3cc(Cl)cc(Cl)c3)C2)cc1F]

Following the procedure as described in Example 53 step 4, and making variation as repaired to replace (S)-tert-butyl 5-cyclopropyl-4-((3-(3,5-dichlorophenoxy)piperidin-1-yl)methyl)-2-fluorobenzoate with (R)-tert-butyl 5-cyclopropyl-4-((3-(3,5-dichlorophenoxy)piperidin-1-yl)methyl)-2-fluorobenzoate, the title compound was obtained as an colorless solid (0.34 g, quant.): MS(ES+) m/z 438.1, 440.1 (M+1).

Step 5. Preparation of (R)-5-cyclopropyl-N-(cyclopropylsulfonyl)-4-((3-(3,5-dichlorophenoxy)-piperidin-1-yl)methyl)-2-fluorobenzamide

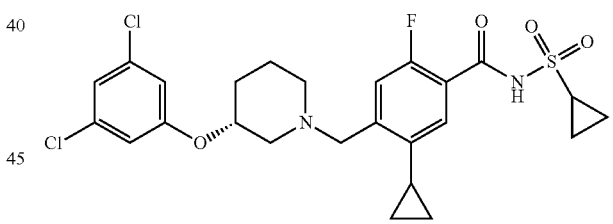

Following the procedure as described in Example 53 step 5, and making variation as required to replace (S)-5-cyclopropyl-4-((3-(3,5-dichlorophenoxy)piperidin-1-yl)methyl)-2-fluorobenzoid acid with (R)-5-cyclopropyl-4-((3-(3,5-dichlorophenoxy)piperidin-1-yl)methyl)-2-fluorobenzoic acid, the title compound was obtained as a colorless solid (0.12 g, 57%): $^1$H NMR (300 MHz, CDCl$_3$) δ 8.85-8.67 (m, 1H), 7.72 (d, J=7.7 Hz, 1H), 7.29 (d, J=14.0 Hz, 1H), 6.91 (s, 1H), 6.75 (s, 2H), 4.37-4.26 (m, 1H), 3.78-3.61 (m, 2H), 3.13-3.03 (m, 1H), 2.94-2.85 (m, 1H), 2.72-2.61 (m, 1H), 2.37-2.18 (m, 2H), 2.09-1.98 (m, 1H), 1.97-1.79 (m, 2H), 1.71-1.49 (m, 2H), 1.48-1.41 (m, 2H), 1.18-1.09 (m, 2H), 0.99-0.88 (m, 2H), 0.70-0.59 (m, 2H); MS (ES+) m/z 541.2, 543.2 (M+1).

Example 56

Synthesis of (R)—N-(azetidin-1-ylsulfonyl)-5-cyclopropyl-4-((3-(3,5-dichlorophenoxy)piperidin-1-yl)methyl)-2-fluorobenzamide

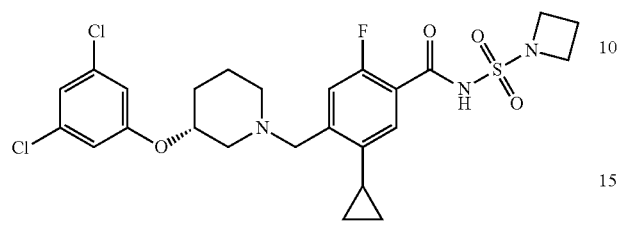

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with (R)-5-cyclopropyl-4-((3-(3,5-dichlorophenoxy)piperidin-1-yl)methyl)-2-fluorobenzoic acid and cyclopropanesulfonamide with azetidine-1-sulfonamide, the title compound was obtained as a colorless solid (0.30 g, 58%): $^1$H NMR (300 MHz, CDCl$_3$) 8.80-8.62 (m, 1H), 7.73 (d, J=7.3 Hz, 1H), 7.35-7.26 (m, 1H), 6.91 (s, 1H), 6.76 (s, 2H), 4.38-4.28 (m, 1H), 4.23 (S, J=7.7 Hz, 4H), 3.77-3.62 (m, 2H), 2.95-2.86 (m, 1H), 2.72-2.62 (m, 1H), 2.37-2.18 (m, 3H), 2.06-1.99 (m, 1H), 1.97-1.88 (m, 1H), 1.86-1.79 (m, 1H), 1.72-1.45 (m, 3H), 1.01-0.89 (m, 2H), 0.71-0.59 (m, 2H); MS (ES+) m/z 556.2, 558.2 (M+1).

Example 57

Synthesis of 5-cyclopropyl-N-(cyclopropylsulfonyl)-4-((4-(3,5-dichlorophenoxy)piperidin-1-yl)methyl)-2-fluorobenzamide, trifluoroacetic acid salt

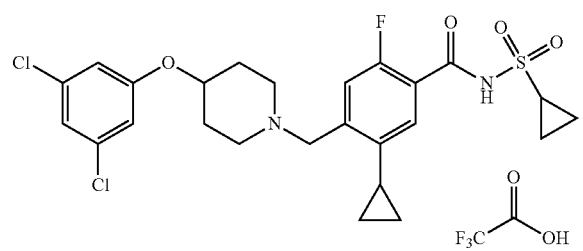

Step 1. Preparation of tert-butyl 4-(3,5-dichlorophenoxy)piperidin-1-carboxylate

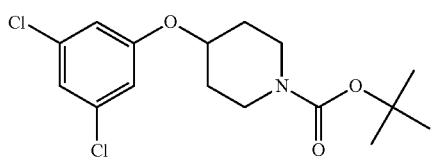 [SMILES: CC(C)(C)OC(=O)N1CCC(Oc2cc(Cl)cc(Cl)c2)CC1]

Following the procedure as described in Example 53 step 1, and making variations as required to replace (S)-tert-butyl 3-hydroxypiperidine-1-carboxylate with tert-butyl 4-hydroxypiperidine-1-carboxylate, the title compound was obtained as an oil (0.84 g, 41%): $^1$H NMR (300 MHz, CDCl$_3$) δ 6.92-6.89 (m, 1H), 6.77-6.74 (m, 2H), 4.44-4.34 (m, 1H), 3.69-3.58 (m, 2H), 3.37-3.25 (m, 2H), 1.93-1.80 (m, 2H), 1.75-1.63 (m, 2H), 1.43 (s, 9H).

Step 2. Preparation of 4-(3,5-dichlorophenoxy)piperidine, trifluoroacetic acid salt

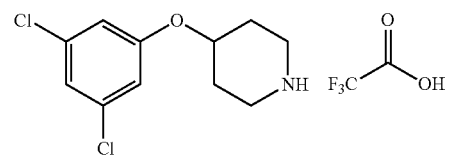 [SMILES: Clc1cc(Cl)cc(OC2CCNCC2)c1 ; O=C(O)C(F)(F)F]

Following the procedure as described in Example 53 step 2, and making variation as required to replace (S)-tert-butyl 3-(3,5-dichlorophenoxy)piperidine-1-carboxylate with tert-butyl 4-(3,5-dichlorophenoxy)piperidine-1-carboxylate, the title compound was obtained as an oil (0.88 g, quant.): MS (ES+m/z 246.2, 248.2 (M+1).

Step 3. Preparation of tert-butyl 5-cyclopropyl-4-((4-(3,5-dichlorophenoxy)piperidin-1-yl)methyl)-2-fluorobenzoate

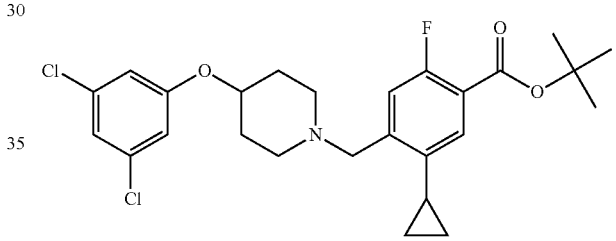

Following the procedure as described in Example 53 step 3. and making variation as required to replace (S)-3-(3,5-dichlorophenoxy)piperidine, trifluoroacetic acid salt with 4-(3,5-dichlorophenoxy)piperidine, trifluoroacetic acid salt, the title compound was obtained, as an oil (0.74 g, 62%): $^1$H NMR (500 MHz, CDCl$_3$) δ 7.48 (d, J=7.3 Hz, 1H), 7.17 (d, J=11.8 Hz, 1H), 6.92-6.88 (m, 1H), 6.79-6.74 (m, 2H), 4.35-4.25 (m, 1H), 3.65 (s, 2H), 2.75-2.64 (m, 2H), 2.42-2.30 (m, 2H), 1.77-1.90 (m, 3H), 1.86-1.73 (m, 2H), 1.55 (s, 9H), 0.96-0.87 (m, 2H), 0.65-0.57 (m, 2H); MS (ES+) m/z 494.3, 496.3 (M+1).

Step 4. Preparation of 5-cyclopropyl-4-((4-(3,5-dichlorophenoxy)piperidin-1-yl)methyl)-2-fluorobenzoic acid

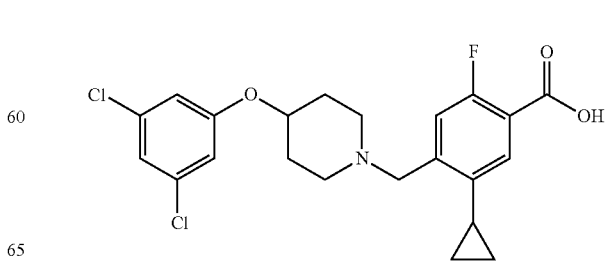

Following the procedure as described in Example 53 step 4, and making variation as required to replace (S)-tert-butyl 5-cyclopropyl-4-((3-(3,5-dichlorophenoxy)piperidin-1-yl)methyl)-2-fluorobenzoate with tert-butyl 5-cyclopropyl-4-((4-(3,5-dichlorophenoxy)piperidin-1-yl)methyl)-2-fluorobenzoate, the title compound was obtained as an colorless solid (0.66 g, quant.): MS (ES+) m/z 438.2, 440.2 (M+1).

Step 5. Preparation of 5-cyclopropyl-N-(cyclopropylsulfonyl)-4-((4-(3,5-dichlorophenoxy)-piperidin-1-yl)methyl)-2-fluorobenzamide, trifluoroacetic acid salt

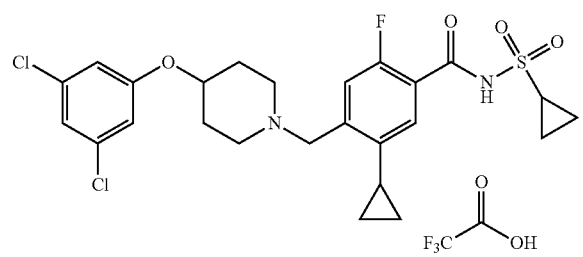

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-((4-(3,5-dichlorophenoxy)piperidin-1-yl)methyl)-2-fluorobenzoic acid and purification by reverse phase HPLC, the title compound was obtained as a colorless solid (0.20 g, 49%): $^1$H NMR (300 MHz, DMSO-d$_6$) δ 12.25 (brs, 1H), 9.76 (brs, 1H), 7.52 (d, J=10.9 Hz, 1H), 7.24 (d, J=6.7 Hz, 1H), 7.20-7.06 (m, 1H), 4.90-4.77 (m, 1H), 4.56 (s, 2H), 3.55-3.41 (m, 1H), 3.34-3.18 (m, 3H), 3111-3.01 (m, 1H), 2.30-1.92 (m, 4H), 1.86-1.72 (m, 1H), 1.15-1.06 (m, 4H), 1.03-0.95 (m, 2H), 0.80-0.72 (m, 2H); MS (ES+) m/z 541.2, 543.2 (M+1).

Example 58

Synthesis of N-(azetidin-1-ylsulfonyl)-5-cyclopropyl-4-((4-(3,5-dichlorophenoxy)piperidin-1-yl)methyl)-2-fluorobenzamide, trifluoroacetic acid salt

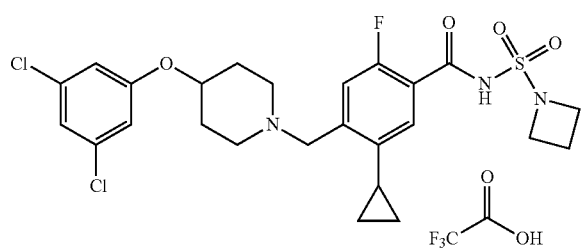

Following the procedure as described in Example 53 step 5, and making variations as required to replace (S)-5-cyclopropyl-4-((3-(3,5-dichlorophenoxy)piperidin-1-yl)methyl)-2-fluorobenzoic acid with 5-cyclopropyl-4-((4-(3,5-dichlorophenoxy)piperidin-1-yl)methyl)-2-fluorobenzoic acid and cyclopropanesulfonamide with azetidine-1-sulfonamide and purification by reverse phase HPLC, the title compound was obtained as a colorless solid (0.19 g, 46%): $^1$H NMR (300 MHz, DMSO-d$_6$) δ 12.00 (brs, 1H), 9.69 (brs, 1H), 7.52 (d, J=10.8 Hz, 1H), 7.26 (d, J=6.5 Hz, 1H), 7.20-7.07 (m, 3H), 4.89-4.79 (m, 1H), 4.56 (s, 2H), 4.03 (t, 7.6 Hz, 4H), 3.54-3.42 (m, 1H), 3.39-3.18 (m, 3H), 2.24-2.09 (m, 4H), 2.08-1.98 (m, 2H), 1.87-1.70 (or, 1H), 1.04-0.96 (m, 2H), 0.82-0.74 (m, 2H); MS (ES+) m/z 556.2, 558.2 (M+1).

Example 59

Synthesis of 4-((1-benzhydrylazetidin-3-yl)methoxy)-5-chloro-2-fluoro-N-(methylsulfonyl)benzamide

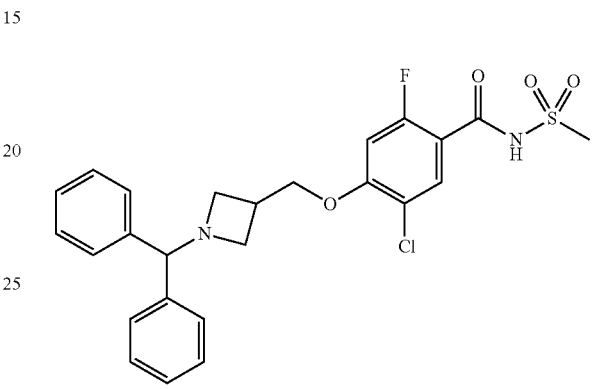

To a solution of (1-benzhydrylazetidin-3-yl)methanol (40.4 mg, 0.159 mmol) and 5-chloro-2,4-difluoro-N-methylsulfonyl-benzamide (43.0 mg, 0.159 mmol) in DMSO (0.80 mL) as rt was added potassium tert-butoxide in 1:10 THF-DMSO (0.38 mL, 0.93 M). The mixture was stirred at rt for 1 jr. LCMS showed major product. Diluted with EtOAc, the contents were washed with 1:4 mixture of 1M HCl and 1M NaH$_2$PO$_4$ (2×) and brine (1×), dried (Na$_2$SO$_4$). After filtration and concentration, the crude was purified with HPLC (55.7 mg). LCMS (Method D): RT=5.37 min, m/z: 503.2 [M+H]$^+$. $^1$H NMR (400 MHz, DMSO-d6) δ 7.79 (d, J=7.5 Hz, 1H), 7.47-7.40 (m, 4H), 7.32 (t, J=7.5 Hz, 4H), 7.2-7.15 (m, 3H), 4.78 (s, 1H), 4.29 (d, J=6.1 Hz, 2H), 3.45 (s, 2H), 3.20 (s, 3H), 2.96 (s, 1H).

Example 60

Synthesis of 4-((1-benzhydrylazetidin-3-yl)methoxy)-5-cyclopropyl-2-fluoro-N-((2-(trimethylsilyl)ethyl)sulfonyl)benzamide

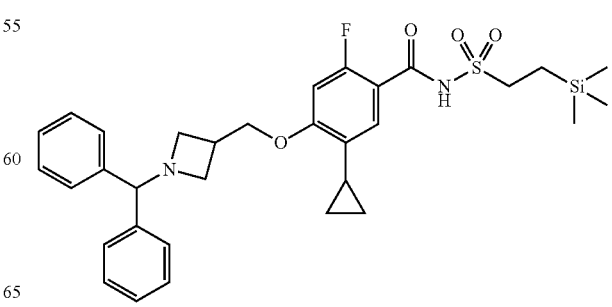

Step 1: Preparation of tert-butyl 4-((1-benzhydry-lazetidin-3-yl)methoxy)-5-chloro-2-fluorobenzoate To solution of (1-benzhydrylazetidin-3-yl)methanol (1.141 g) and tert-butyl 5-chloro-2,4-difluoro-benzoate (1.244 g, ~90% pure) in DMSO (13.5 mL) at 14° C. (bath) was added potassium tert-butoxide (0.606 g). The mixture was stirred at rt for 1 hr. Diluted with EtOAc, the contents were washed with dilute NaHCO$_3$ (2×) and brine (1×), and dried (Na$_2$SO$_4$). After filtration and concentration, the crude was purified with silica gel flash chromatography (0-40% EtOAc/heptane) to give the product (1.359 g, 63%).

Step 2: Preparation of tert-butyl 4-((1-benzhydry-lazetidin-3-yl)methoxy)-5-cyclopropyl-2-fluoroben-zoate A mixture of tert-butyl 4-((1-benzhydrylazetidin-3-yl)methoxy)-5-chloro-2-fluorobenzoate (1.35 g), cyclopropyl-boronic acid (506 mg), potassium phosphate (1.52 g), and potassium fluoride (163 mg) in toluene (16.8 mL) and water (0.56 mL) was purge with nitrogen. Tricyclohexylphosphine tetrafluoroborate (213 mg) and palladium acetate (64 mg) were added. The mixture was heated at 90° C. for 7 hours. The mixture was diluted with EtOAc and filtered. The filtrate was concentrated. The residue was purified with silica gel flash chromatography (0-20% EtOAc/heptane with 0.5% Et$_3$N) to give the product (1.092 g, 80%).

Step 3: Preparation, 4-((1-benzhydrylazetidin-3-yl)methoxy)-5-cyclopropyl-2-fluorobenzoic acid A mixture of tert-butyl 4-((1-benzhydrylazetin-3-yl)methoxy)-5-cyclopropyl-2-fluorobenzoate (248 mg) and potassium hydroxide (228 mg) in DMSO (2.0 mL) was stirred at rt for 16 hr. The contents were acidified with 1M NaH$_2$PO$_4$. Solid was collected with filtration, washed with water, and dried under vacuum (171 mg, 78%).

Step 4: Preparation of 4-((1-benzhydrylazetidin-3-yl)methoxy)-5-cyclopropyl-2-fluoro-N-((2-(trimeth-ylsilyl)ethyl)sulfonyl)benzamide A mixture of 4-((1-benzhydrylazetidin-3-yl)methoxy)-5-cyclopropyl-2-fluorobenzoic acid (26.2 mg), 2-(trimethylsi-lyl)ethanesulfonamide (44.0 mg), HBTU (30.9 mg), and DIPEA (0.053 mL) in DCE (0.83 mL) was heated at 40° C. for 16 hr. Acidified with 0.5 M NaH$_2$PO$_4$, the contents were extracted with DCM (2×). The combined extracts were dried (Na$_2$SO$_4$). The crude was purified with HPLC (18.0 mg, 50%). LCMS (Method D): RT=5.47 min, m/z: 595.2 [M+H]$^+$. $^1$H NMR (400 MHz, DMSO-d6) δ 11.66 (s, 1H), 7.45-7.36 (m, 4H), 7.25 (t, J=7.5 Hz, 4H), 7.19-7.08 (m, 3H), 6.93 (d, J=12.7 Hz, 1H), 4.45 (s, 1H), 4.19 (d, J=6.2 Hz, 2H), 3.38-3.29 (m, 2H), 2.99 (s, 2H), 2.84 (s, 1H), 2.07-1.97 (m, 1H), 0.93-0.81 (m, 4H), 0.66-0.59 (m, 2H), 43.00 (s, 7H), −0.03 (s, 4H).

Example 61

Synthesis of 4-((1-benzhydrylazetidin-3-yl)methoxy)-5-cyclopropyl-2-fluoro-N-((2-methoxy-ethyl)sulfonyl)benzamide

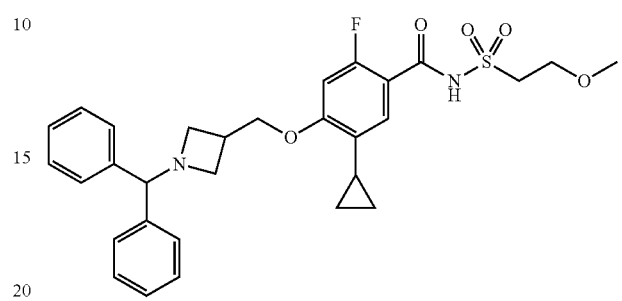

The compound was prepared in a similar manner to Example 60 from 4-((1-benzhydrylazetidin-3-yl)-methoxy)-5-cyclopropyl-2-fluorobenzoic acid and 2-methoxyethane-sulfonamide. LCMS (Method D): RT=4.53 min, m/z: 553.2 [M+H]$^+$. $^1$H NMR (400 MHz, DMSO-d6) δ 7.46-7.37 (m, 4H), 7.33-7.23 (m, 4H), 7.21-7.12 (m, 3H), 6.84 (d, J=12.6 Hz, 1H), 4.48 (s, 1H), 4.18 (d, J=6.1 Hz, 2H), 3.64 (t, J=6.6 Hz, 3H), 3.51 (s, 2H), 3.26 (s, 2H), 3.21 (s, 3H), 3.14 (s, 1H), 3.02 (d, J=6.5 Hz, 2H), 2.92-2.79 (m, 1H), 2.10-1.98 (m, 1H), 1.25 (q, J=7.6, 6.4 Hz, 6H) 0.94-0.83 (m, 2H), 0.66-0.55 (m, 2H).

Example 62

Synthesis of 4-((1-benzhydrylazetidin-3-yl)methoxy)-5-cyclopropyl-N-((difluoromethyl)-sulfo-nyl-2-fluorobenzamide

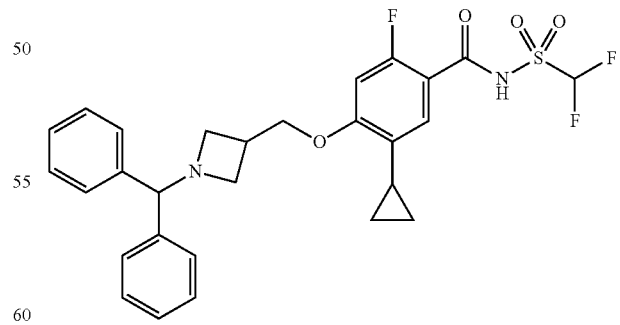

The compound was prepared in a similar manner to Example 60 from 4-((1-benzhydrylazetidin-3-yl)methoxy)-5-cyclopropyl-2-fluorobenzoic acid and difluoromethane-sulfonamide. LCMS (Method E): RT=3.95 mm, m/z: 545.2 [M+H]$^+$.

Example 63

Synthesis of 4-((1-benzhydrylazetidin-3-yl)methoxy)-5-cyclopropyl-2-fluoro-N-((3,3,3-trifluoropropyl)sulfonyl)benzamide

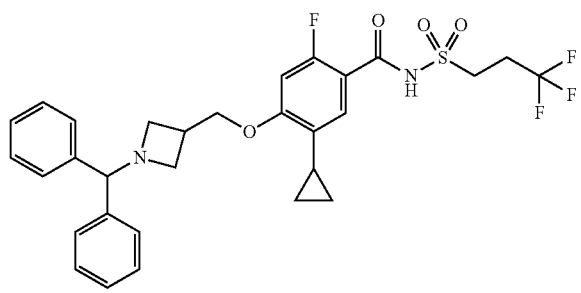 [SMILES: O=C(NS(=O)(=O)CCC(F)(F)F)c1cc(C2CC2)c(OCC2CN(C(c3ccccc3)c3ccccc3)C2)cc1F]

The compound was prepared in a similar manner to Example 60 from 4-((1-benzhydrylazetidin-3-yl)methoxy-5-cyclopropyl-2-fluorobenzoic acid and 3,3,3-trifluoropropane-1-sulfonamide. LCMS (Method E): RT=5.14 min, m/z: 591.2 [M+H]$^+$. 1H NMR (400 MHz, DMSO-d6) δ 7.44 (d, J=7.2 Hz, 4H), 7.40-7.30 (m, 4H), 7.26 (s, 2H), 7.21 (d, J=8.4 Hz, 1H), 6.88 (d, J=1.2.7 Hz, 1H), 4.22 (d, J=6.2 Hz, 2H), 3.53 (s, 3H), 2.76-2.60 (m, 2H), 2.09-1.98 (m, 1H), 0.93-0.82 (m, 2H), 0.66-0.57 (m, 2H).

Example 64

Synthesis of 4-((1-benzhydrylazetidin-3-yl)methoxy)-5-cyclopropyl-N-((cyclopropylmethyl)sulfonyl)-2-fluorobenzamide

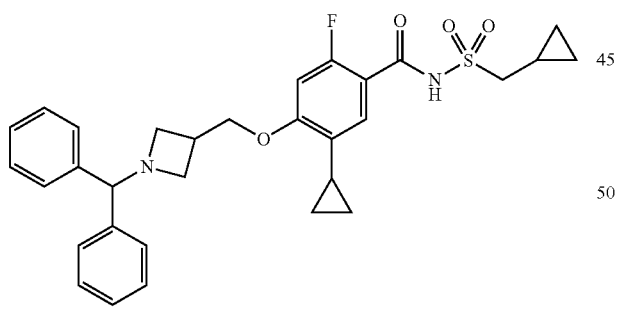

The compound was prepared in a similar manner to Example 60 from 4-((1-benzhydrylazetidin-3-yl)methoxy-5-cyclopropyl-2-fluorobenzoic acid and cyclopropylmethanesulfonamide. LCMS (Method E): RT=4.89 min, m/z: 549.2 [M+H]$^+$. $^1$H NMR (400 MHz, DMSO-d6) δ 11.84 (s, 1H), 7.46-7.37 (m, 4H), 7.28 (t, J=7.6 Hz, 4H), 7.23-7.10 (m, 3H), 6.95 (d, J=12.8 Hz, 1H), 4.49 (s, 1H), 4.22 (d, J=6.2 Hz, 2H), 3.37 (d, J=7.1 Hz, 2H), 3.02 (s, 2H), 2.94-2.80 (m, 1H), 2.10-1.99 (m, 1H), 1.11-0.97 (m, 1H), 0.94-0.84 (m, 2H), 0.71-0.63 (m, 2H), 0.60-0.52 (m, 2H), 0.37-0.28 (m, 2H), 2H hidden under water

Example 65

Synthesis of 4-((1-benzhydrylazetidin-3-yl)methoxy)-N-(butylsulfonyl)-5-cyclopropyl-2-fluorobenzamide

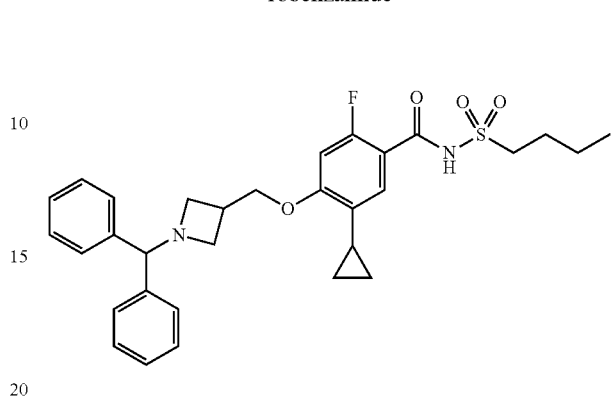

The compound was prepared in a similar manner to Example 60 from 4-((1-benzhydrylazetidin-3-yl)methoxy)-5-cyclopropyl-2-flurobenzoic acid and butane-1-sulfonamide. LCMS (Method B); RT=5.08 min, m/z: 551.2 [M+H]$^+$. $^1$H NMR (400 MHz, DMSO-d6) δ 11.75 (s, 1H), 7.42 (dd, J=8.2, 1.4 Hz, 4H), 7.27 (dd, J=8.3, 6.9 Hz, 4H), 7.21-7.11 (m, 3H), 6.92 (d, J=12.7 Hz, 1H), 4.47 (s, 1H), 4.20 (d, J=6.2 Hz, 2H), 3.37 (t, J=7.9 Hz, 2H), 3.01 (t, J=6.6 Hz, 2H), 2.93-2.81 (m, 1H), 2.09-1.99 (m, 1H), 1.71-1.59 (m, 2H), 1.45-1.34 (m, 2H), 0.94-0.83 (m, 5H), 0.69-0.59 (m, 2H), 2H hidden under water

Example 66

Synthesis of 4-((1-benzyl-3-fluoroazetidin-3-yl)methoxy)-5-cyclopropyl-2-fluoro-N-(methylsulfonyl)benzamide

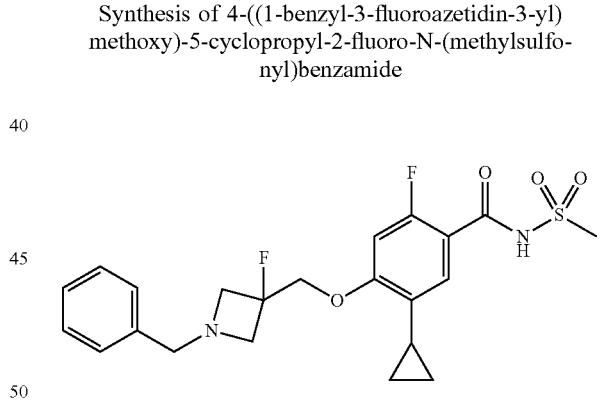

Step 1: Preparation of 4-((1-(tert-butoxycarbonyl)-3-fluoroazetidin-3-yl)methoxy)-5-chloro-2-fluorobenzoic acid To a solution of tert-butyl 3-fluoro-3-(hydroxymethyl)azetidine-1-carboxylate (0.161 g, 0.784 mmol) and 5-chloro-2,4-difluoro-benzoic acid (151 mg, 0.784 mmol) in dimethyl sulfoxide (4.00 mL/mmol, 44.1 mmol, 99.8 mass %) at 14° C. (bath) was added potassium tert-butoxide (194 mg, 1.73 mmol). The mixture was stirred at that temp for 5 min then at rt for 30 min. Diluted with EtOAc, the contents were washed with 1:4 mixture of 0.3M HCl and 0.3M NaH$_2$PO$_4$ (3×) and brine, and dried (Na)SO$_4$. After filtration and concentration, the white solid crude (327 mg) was used as-is.

Step 2: Preparation of tert-butyl 3-((2-chloro-4-(ethoxycarbonyl)-5-fluorophenoxy)methyl)-3-fluoro-azetidine-1 carboxylate To a suspension, of product from step 1 (278 mg) and potassium carbonate (185 mg, 1.32 mmol) in N,N-dimethylformamide (2.65 mL) was added iodoethane (156 mg, 0.99 mmol). The mixture was heated at 50° C. for 2 hr. LCMS showed completion. Diluted with EtOAc (50 mL), the contents were washed with diluted NaHCO$_3$ (2×) and brine, and dried (Na$_2$SO$_4$). After filtration and concentration, the residue was purified with silica gel flash chromatography (0-40% EtOAc/heptane) to give the product (141 mg).

Step 3: Preparation of ethyl 4-((1-benzyl-3-fluoro-azetidin-3-yl)methoxy)-5-cyclopropyl-2-fluorobenzoate A mixture of product from step 2 (57 mg, 0.14 mmol) and trifluoroacetic acid (0.28 mL, 3.6 mmol) in dichloromethane (0.83 mL) was stirred at 0° C. for 30 min then at rt for 2 h. The contents were concentrated and used as-is.

Step 4: Preparation of ethyl 4-((1-benzyl-3-fluoro-azetidin-3-yl)methoxy)-5-cyclopropyl-2-fluorobenzoate To the residue from step 3 was added dichloromethane (0.83 mL), followed by N,N-diisopropylethylamine (0.19 mL, 1.1 mmol) and benzyl bromide (26 mg, 0.15 mmol). The mixture was stirred at rt for 16 hr. Dilute aq Na$_2$CO$_3$ was added. The contents were extracted with DCM (2×). The combined extracts were dried (Na$_2$SO$_4$). The crude was purified with silica gel flash chromatography (0-25% EtOAc/heptane) to give the product as viscous oil (43.8 mg).

Step 5: Preparation of 4-((1-benzyl-3-fluoroazeti-din-3-yl)methoxy)-5-cyclopropyl-2-fluorobenzoic acid A mixture of product from previous step (41.7 mg, 0.104 mmol) and potassium hydroxide (11.7 mg, 0.208 mmol) in methanol (0.62 mL) and water (0.16 mL) was stirred at rt for 3 hr then heated at 50° C. for 1.5 hr. Diluted with water and acidified with 1M NaH$_2$PO$_4$, the contents were extracted with DCM (3×). The combined extracts were dried (Na$_2$SO$_4$) and concentrated. The crude (37.6 mg) was used as-is.

Step 6: Preparation of 4-((1-benzyl-3-fluoroazeti-din-3-yl)methoxy)-5-cyclopropyl-2-fluoro-N-(methylsulfonyl)benzamide A mixture of product from previous step (37.6 mg. 0.101 mmol), methanesulfonamide (28.7 mg, 0.302 mmol), N,N-diisopropylethylamine (0.089 mL, 0.503 mmol), and HBTU ((51.2 mg, 0.131 mmol) in 1,2-dichloroethane (1 mL) was stirred at 50° C. for 2 hr then at 65° C. for 1 hr. To the mixture was added 1M NaH$_2$PO$_4$. The contents were extracted with DCM (2×). The combined extracts were dried (Na$_2$SO$_4$). The crude was purified with HPLC (23.0 mg, 50.7%). LCMS (Method D): RT=4.24 min, m/z: 451.1 [M+H]$^+$. $^1$H NMR (400 MHz, DMSO-d6) δ 7.39-7.22 (m, 5H), 7.17 (d, J=8.3 Hz, 1H), 7.01 (d, J=12.7 Hz, 1H), 4.43 (d, J=23.8 Hz, 2H), 3.74 (s, 2H), 3.59 (dd, J=13.3, 9.1 Hz, 2H), 3.25 (s, 3H), 2.06-1.95 (m, 1H), 0.92-0.82 (m, 2H), 0.71-0.62 (m, 2H).

Example 67

Synthesis of 4-((1-benzyl-3-fluoroazetidin-3-yl)methoxy)-5-cyclopropyl-2-fluoro-N-(methylsulfonyl)benzamide

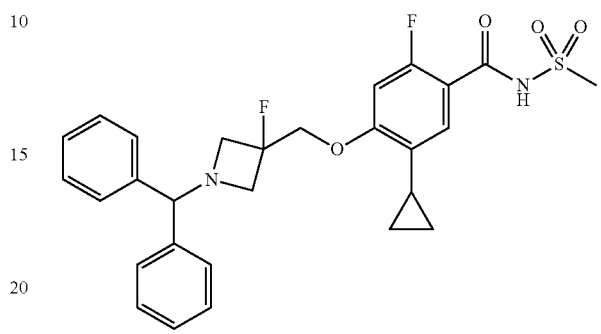

The compound was prepared in a similar manner to Example 66 while in step 3 benzyl bromide being replaced by bromodiphenylmethane and DCM being replaced by DMF. LCMS (Method D): RT=4.67 min, m/z: 427.2 [M+H]+. $^1$H NMR (400 MHz, DMSO-d6) δ 11.90 (s, 1H), 7.49-7.40 (m, 4H), 7.29 (dd, J=8.4-6.8 Hz, 4H), 7.23-7.13 (m, 3H), 7.02 (d, J=12.7 Hz, 1H), 4.60 (s, 1H), 4.48 (d, J=23.1 Hz, 2H), 3.49-3.38 (m, 2H), 3.27-3.15 (m, 5H), 2.06-1.91 (m, 1H), 0.90-0.79 (m, 2H), 0.70-0.60 (m, 2H).

Example 68

Synthesis of 4-((1-benzhydryl-3-methylazetidin-3-yl)methoxy)-5-cyclopropyl-2-fluoro-N-(methylsulfonyl)benzamide

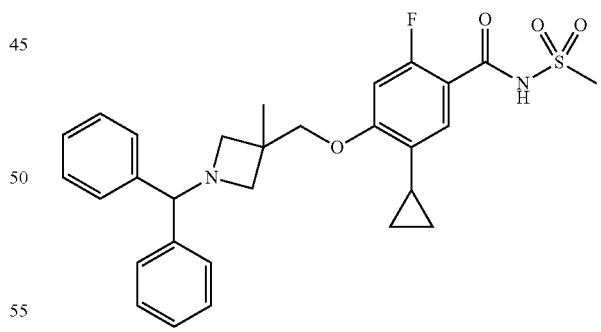

Step 1: Preparation of tert-butyl 3-((4-(tert-butoxycarbonyl)-2-chloro-5-fluorophenoxy)methyl)-3-methylazetidine-1-carboxylate The compound was prepared from tert-butyl 3-(hydroxymethyl)-3-methylazetidine-1-carboxylate and tert-butyl 5-chloro-2,4-difluorobenzoate in a similar manner to step 1 of Example 60.

Step 2: Preparation of tert-butyl 3-((4-(tert-butoxycarbonyl)-2-cyclopropyl-5-fluorophenoxy)methyl)-3-methylazetidine-1-carboxylate The compound was prepared from tert-butyl 3-((4-(tert-butoxycarbonyl)-2-chloro-5-fluorophenoxy)methyl-3-methylazetidine-1-carboxylate in a similar manner to step 2 of Example 60.

Step 3: Preparation of tert-butyl 5-cyclopropyl-2-fluoro-4-((3-methylazetidin-3-yl)methoxy)benzoate To a solution of tert-butyl 3-[(4-tert-butoxycarbonyl-2-cyclopropyl-5-fluorophenoxy)methyl]-3-methyl-azetidine-1-carboxylate (73.3 mg, 0.168 mmol) in acetonitrile (1.35 mL) at 7° C. (bath) was added p-toluenesulfonic acid hydrate (38.4 mg, 0.202 mmol). After 10 min, the mixture was stirred at rt for 20 hr. Tert-butyl acetate (0.23 mL) and p-toluenesulfonic acid hydrate (16.0 mg, 0.842 mmol) were added. After 1 hr, acetonitrile (3 mL) and $K_2CO_3$ was added (500 mg). After well mixing, the contents were diluted with EtOAc and filtered. The filtrated was concentrated. The residue was used as-is.

Step 4: Preparation of tert-butyl 4-((1-benzhydryl-3-methylazetidin-3-yl)methoxy)-5-cyclopropyl-2-fluorobenzoate A mixture of tert-butyl 5-cyclopropyl)-2-fluoro-4-[(3-methylazetidin-3-yl)methoxy]benzoate (56.3 mg, 0.168 mmol), bromodiphenylmethane (62.3 mg, 0.252 mmol), and cesium carbonate (164 mg, 0.504 mmol) in acetonitrile (1.68 mL) was heated at 50° C. for 16 hr. The contents were concentrated. The residue was suspended in water and extracted with DCM (2×). The combined extracts were dried ($Na_2SO_4$). The crude was purified with silica gel flash chromatography (0-30% EtOAc/heptane) to give the product (96.9 mg).

Step 5: Preparation of 4-((1-benzhydryl-3-methylazetidin-3-yl)methoxy)-5-cyclopropyl-2-fluorobenzoic acid A mixture of product from previous step (96.9 mg) and potassium hydroxide (86.7 mg, 1.55 mmol) in DMSO (1.93 mL) was stirred at rt for 40 hr. Acidified with 0.5M $NaH_2PO_4$, the contents were extracted with DCM (3×). The combined extracts were dried ($Na_2SO_4$) and concentrated. The crude was used as-is (103 mg).

Step 6: Preparation of 4-((1-benzhydryl-3-methylazetidin-3-yl)methoxy)-5-cyclopropyl-2-fluorobenzoic acid The compound was prepared in a similar manner to step 4 of Example 60 from 4-((1-benzhydryl-3-methylazetidin-3-yl)methoxy)-5-cyclopropyl-2-fluorobenzoic acid and methanesulfonamide. LCMS (Method D): RT=4.49 min, m/z: 523.2 [M+H]+. 1H NMR (400 MHz, DMSO-d6) δ 11.83 (s, 1H), 7.48-7.38 (m, 4H), 7.28 (t, J=7.6 Hz, 4H), 7.23-7.13 (m, 3H), 6.98 (d, J=12.8 Hz, 1H), 4.53 (s, 1H), 4.11 (s, 2H), 3.17 (s, 2H), 2.88 (d, J=11.8 Hz, 2H), 2.12-2.00 (m, 1H), 1.35 (s, 3H), 0.94-0.85 (m, 2H), 0.72-0.62 (m, 2H).

Example 69

Synthesis of 4-((1-benzhydryl-3-methylazetidin-3-yl)methoxy)-5-cyclopropyl-N-(ethylsulfonyl)-2-fluorobenzamide

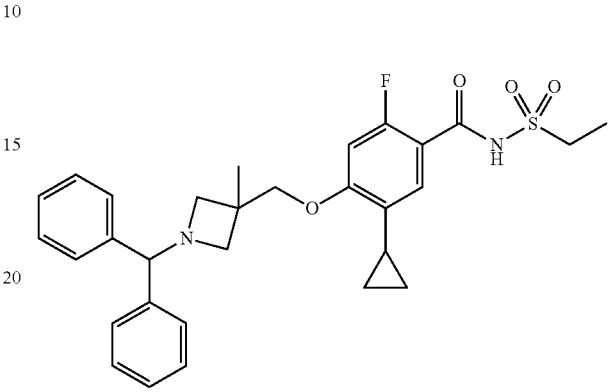

The compound was prepared in a similar manner to step 4 of Example 60 from 4-((1-benzhydryl-3-methylazetidin-3-yl)methoxy)-5-cyclopropyl-2-fluorobenzoic acid and ethanesulfonamide. LCMS (Method D): RT=4.63 min, m/z: 537.2 [M+H]+. 1H NMR (400 MHz, DMSO-d6) δ 11.75 (s, 1H), 7.47-7.37 (m, 4H), 7.28 (t, J=7.5 Hz, 4H), 7.18 (t, J=7.3 Hz, 3H), 6.99 (d, J=12.8 Hz, 1H), 4.50 (s, 1H), 4.10 (s, 2H), 3.50-3.38 (m, 2H), 3.15 (s, 2H), 2.95-2.81 (m, 2H), 2.12-1.99 (m, 1H), 1.35 (s, 3H), 1.24 (t, J=7.4 Hz, 3H), 0.94-0.83 (m, 2H), 0.71-0.60 (m, 2H).

Example 70

Synthesis of 4-((1-benzhydryl-3-methylazetidin-3-yl)methoxy)-5-cyclopropyl-N-(cyclopropylsulfonyl)-2-fluorobenzamide

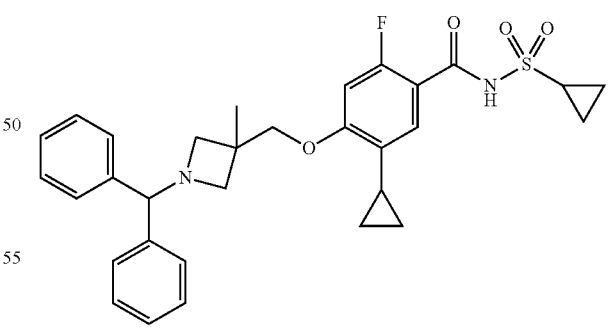

The compound was prepared in a similar manner to step 4 of Example 60 from 4-((1-benzhydryl-3-methylazetidin-3-yl)methoxy)-5-cyclopropyl-2-fluorobenzoic acid and cyclopropanesulfonamide. LCMS (Method E): RT=4.69 min, m/z: 549.2 [M+H]+. 1H NMR (400 MHz, DMSO-d6) δ 11.79 (s, 1H), 7.46-7.38 (m, 4H), 7.32-7.23 (m, 4H), 7.22-7.13 (m, 3H), 6.94 (d, J=12.8 Hz, 1H), 4.50 (s, 1H), 4.09 (s, 2H), 3.14 (d, J=7.1 Hz, 2H), 3.07-2.96 (m, 1H), 2.92-2.80 (m, 2H), 2.13-2.00 (m, 1H), 1.30-1.20 (m, 3H), 1.03 (d, J=17.8 Hz, 4H), 0.94-0.83 (m, 2H), 0.69-0.60 (m, 2H).

Example 71

Synthesis of N-(azetidin-1-ylsulfonyl)-4-((1-benzhydryl-3-methylazetidin-3-yl)methoxy)-5-cyclopropyl-2-fluorobenzamide

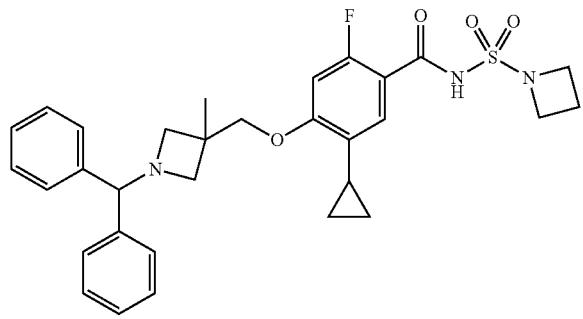 [SMILES: CC1(COc2cc(F)c(C(=O)NS(=O)(=O)N3CCC3)cc2C2CC2)CN(C(c2ccccc2)c2ccccc2)C1]

The compound was prepared in a similar manner to step 4 of Example 60 from 4-((1-benzhydryl-3-methylazetidin-3-yl)methoxy)-5-cyclopropyl-2-fluorobenzoic acid and azetidine-1-sulfonamide. LCMS (Method D): RT=4.74 min, m/z: 564.2 [M+H]+.

Example 72

Synthesis of tert-butyl 3-((2-cyclopropyl-5-fluoro-4-((methylsulfonyl)carbamoyl)phenoxy)methyl)azetidine-1-carboxylate

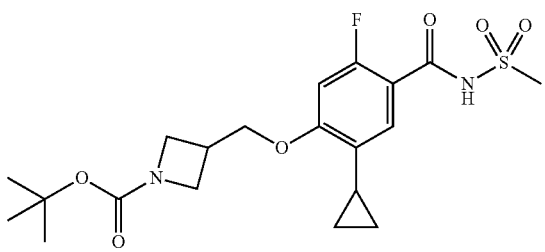 [SMILES: CC(C)(C)OC(=O)N1CC(COc2cc(F)c(C(=O)NS(C)(=O)=O)cc2C2CC2)C1]

Steps 1-2: Preparation of tert-butyl 3-((4-tert-butoxycarbonyl)-5-fluorophenoxy)methyl)azetidine-1-carboxylate The compound was prepared from tert-butyl-3-(hydroxymethyl)azetidine-1-carboxylate and tert-butyl 5-chloro-2,4-difluorobenzoate in a similar manner to steps 1-2 of Example 60.

Step 3: Preparation of 4-((1-(tert-butoxycarbonyl)azetidin-3-yl)methoxy)-5-cyclopropyl-2-fluorobenzoic acid To a mixture of tert-butyl 3-[(4-tert-butoxycarbonyl-2-cyclopropyl-5-fluorophenoxy)-methyl]azetidine-1-carboxylate (0.711 g, 1.69 mmol) and potassium hydroxide (1.14 g, 20.2 mmol) in methanol (8.43 mL) was slowly added water (0.84 mL). The resulting mixture was heated at 60° C. for 16 hr. LCMS showed completion. The contents were diluted with water and acidified with 1:4 mixture of 1M HCl and 1M NaH$_2$PO$_4$, and extracted with DCM (2×). The combined DCM solutions were dried (Na$_2$SO$_4$). After filtration and concentration, the crude was used as-is.

Step 4: Preparation of tert-butyl 3-((2-cyclopropyl-5-fluoro-4-((methylsulfonyl)carbamoyl)phenoxy)methyl)azetidine-1-carboxylate The compound was prepared in a similar manner to step 4 of Example 60 from 4-((1-(tert-butoxycarbonyl)azetidin-3-yl)methoxy)-5-cyclopropyl-2-fluorobenzoic acid and methanesulfonamide. $^1$H NMR (400 MHz, DMSO-d6) δ 11.88 (s, 1H), 7.17 (d, J=8.3 Hz, 1H), 6.97 (d, J=12.8 Hz, 1H), 4.29-4.15 (m, 2H), 3.96 (s, 2H), 3.85-3.71 (m, 2H), 3.31 (s, 3H), 3.06-2.93 (m, 1H), 2.04-1.89 (m, 1H), 1.36 (s, 9H), 0.93-0.80 (m, 2H), 0.74-0.59 (m, 2H).

Example 73

Synthesis of 5-cyclopropyl-2-fluoro-4-((1-(3-fluorobenzyl)azetidin-3-yl)methoxy)-N-(methylsulfonyl)benzamide

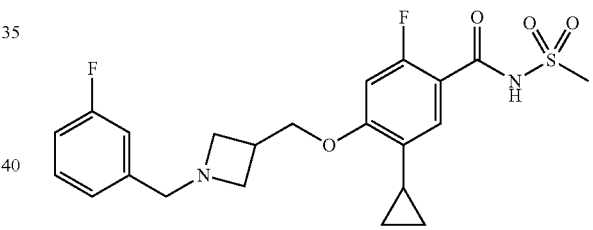

A mixture of tert-butyl 3-[[2-cyclopropyl-5-fluoro-4-(methylsulfonylcarbamoyl)phenoxy]-methyl]azetidine-1-carboxylate (39.2 mg, 0.0753 mmol, Example 77) and trifluoroacetic acid (0.15 mL, 1.9 mmol) in dichloromethane (0.45 mL) was stirred at 0° C. for 10 min then at rt for 1 h. The contents were concentrated. To the residue was added 1,2-dichloroethane (1.5 mL). The mixture was cooled at 0° C. N,N-diisopropylethylamine (0.158 mL, 0.904 mmol) was added, followed by 3-fluorobenzaldehyde (28.0 mg, 0.226 mmol) and sodium triacetoxyborohydride (63.8 mg, 0.301 mmol). The mixture was stirred at rt for 20 hr. Diluted with 0.5M NaH$_2$PO$_4$, the contents were extracted with 1:5 mixture of IPA-DCM (3×). The combined org solutions were dried (Na$_2$SO$_4$). The crude purified with HPLC (10.9 mg). LCMS (Method E): RT=3.29 min, m/z: 451.1 [M+H]+. $^1$H NMR (400 MHz, DMSO-d6) δ 7.43 (q, J=7.4 Hz, 1H), 7.27-7.12 (m, 4H), 6.85 (d, J=12.7 Hz, 1H), 4.19 (d, J=6.1 Hz, 2H), 3.98 (s, 2H), 3.74 (s, 2H), 3.56 (s, 2H), 3.06 (s, 4H), 2.11-1.97 (m, 1H), 0.94-0.82 (m, 2H), 0.66-0.57 (m, 2H).

Example 74

Synthesis of -((1-benzylazetidin-3-yl)methoxy)-5-cyclopropyl-2-fluoro-N-(methylsulfonyl)benzamide

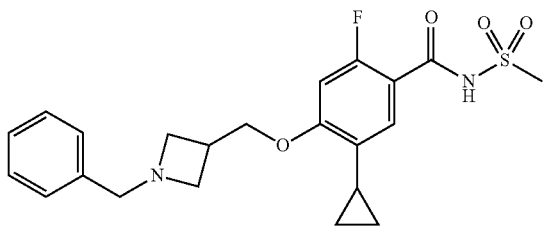 [SMILES: CS(=O)(=O)NC(=O)c1cc(C2CC2)c(OCC2CN(Cc3ccccc3)C2)cc1F]

The compound was prepared in a similar manner to Example 73 from tert-butyl 3-[[2-cyclopropyl-5-fluoro-4-(methylsulfonylcarbamoyl)phenoxy]methyl]azetidine-1-carboxylate and benzaldehyde. LCMS (Method D): RT=3.88 min, m/z: 433.2 [M+H]+. 1H NMR (400 MHz, DMSO-d6) δ 7.49-7.31 (m, 5H), 7.23 (d, J=8.5 Hz, 1H), 6.80 (d, J=12.7 Hz, 1H), 4.18 (d, J=6.1 Hz, 2H), 4.08 (s, 2H), 3.92-3.78 (m, 2H), 3.68 (d, J=8.1 Hz, 2H), 3.18-3.05 (m, 1H), 2.99 (s, 3H), 2.11-1.94 (m, 1H), 0.94-0.81 (m, 2H), 0.65-0.53 (m, 2H).

Example 75

Synthesis of 4-((1-(3-chloro-5-fluorobenzyl)azetidin-3-yl)methoxy)-5-cyclopropyl-2-fluoro-N-(methylsulfonyl)benzamide

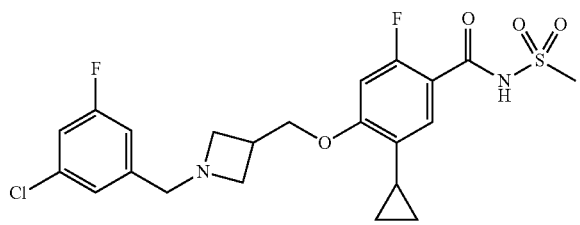 [SMILES: CS(=O)(=O)NC(=O)c1cc(C2CC2)c(OCC2CN(Cc3cc(F)cc(Cl)c3)C2)cc1F]

The compound was prepared in a similar manner to Example 73 from tert-butyl 3-[[2-cyclopropyl-5-fluoro-4-(methylsulfonylcarbamoyl)phenoxy]methyl]azetidine-1-carboxylate and 3-chloro-5-fluorobenzaldehyde. LCMS (Method D); RT=4.15 min, m/z: 485.2 [M+H]+. 1H NMR (400 MHz, DMSO-d6) δ 7.41-7.34 (m, 1H), 7.29 (s, 1H), 7.24-7.15 (m, 2H), 6.90 (d, J=12.8 Hz, 1H), 4.20 (d, J=6.2 Hz, 2H), 3.88 (s, 2H), 3.65 (t, J=8.1 Hz, 2H), 3.44 (t, J=7.4 Hz, 2H), 3.17 (s, 3H), 3.08-2.95 (m, 1H), 2.04 (tt, J=8.6, 5.3 Hz, 1H), 0.94-0.83 (m, 2H), 0.69-0.60 (m, 2H).

Example 76

Synthesis of 5-cyclopropyl-2-fluoro-4-((1-(3-fluoro-4-(trifluoromethyl)benzyl)azetidin-3-yl)methoxy)-N-(methylsulfonyl)benzamide

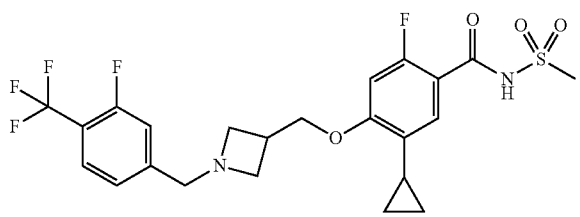 [SMILES: CS(=O)(=O)NC(=O)c1cc(C2CC2)c(OCC2CN(Cc3ccc(C(F)(F)F)c(F)c3)C2)cc1F]

The compound was prepared in a similar manner to Example 73 from tert-butyl 3-[[2-cyclopropyl-5-fluoro-4-(methylsulfonylcarbamoyl)phenoxy]methyl]azetidine-1-carboxylate and 3-fluoro-4-(trifluoromethyl)benzaldehyde. LCMS (Method D): RT=4.33 mm, m/z: 519.2 [M+]+. 1H NMR (400 MHz, DMSO-d6) δ 7.76 (t, J=7.8 Hz, 1H), 7.45 (d, J=11.9 Hz, 1H), 7.37 (d, J=8.1 Hz, 1H), 7.19 (d, J=8.4 Hz, 1H), 6.91 (d, J=12.8 Hz, 1H), 4.21 (d, J=16.2 Hz, 2H), 3.87 (s, 2H), 3.87 (s, 2H), 3.58 (t, J=7.9 Hz, 2H), 3.18 (s, 3H), 3.05-2.93 (m, 1H), 2.06-1.98 (m, 1H), 0.94-0.85 (m, 2H), 0.68-0.61 (m, 2H).

Example 77

Synthesis of 5-cyclopropyl-4-((1-(3,5-dichlorobenzyl)-3-methylazetidin-3-yl)methoxy)-2-fluoro-N-(methylsulfonylbenzamide

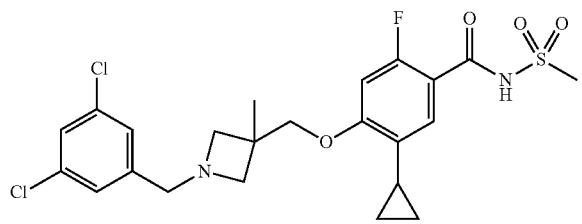 [SMILES: CC1(COc2cc(F)c(C(=O)NS(C)(=O)=O)cc2C2CC2)CN(Cc2cc(Cl)cc(Cl)c2)C1]

Steps 1-4; Preparation of tert-butyl 3-((2-cyclopropyl-5-fluoro-4-((methylsulfonyl)carbamoyl)phenoxy)methyl)-3-methylazetidine-1-carboxylate The compound was prepared in a similar manner to Example 72 while in step 1 tert-butyl 3-(hydroxymethyl)azetidine-1-carboxylate was replaced by tert-butyl 3-(hydroxymethyl)-3-methylazetidine-1-carboxylate.

Step 5: Preparation of 5-cyclopropyl-4-((1-(3,5-dichlorobenzyl)-3-methylazetidin-3-yl)methoxy)-2-fluoro-N-(methylsulfonyl)benzamide The compound was prepared in a similar manner to Example 73 from tert-butyl 3-((2-cyclopropyl-5-fluoro-4-((methylsulfonyl)carbamoyl)phenoxy)methyl)-3-methylazetidine-1-carboxylate and 3,5-dichlorobenzaldehyde. LCMS (Method D): RT=4.42 min, m/z: 515.2 [M+H]+. 1H NMR (400 MHz, DMSO-d6) δ 7.54 (t, J=2.0 Hz, 1H), 7.39 (d, J=1.9 Hz, 2H), 7.22 (d, J=8.4 Hz, 1H), 6.91 (d, J=12.8 Hz, 1H), 4.08 (s, 2H), 3.84 (s, 2H), 3.49 (s, 2H), 3.17 (s, 3H), 2.09-1.98 (m, 1H), 1.37 (s, 3H), 0.94-0.83 (m, 2H), 0.70-0.59 (m, 2H).

Example 78

Synthesis of tert-butyl 4-((2-chloro-5-fluoro-4-((methylsulfonyl)carbamoyl)phenoxy)-methyl)piperidine-1-carboxylate

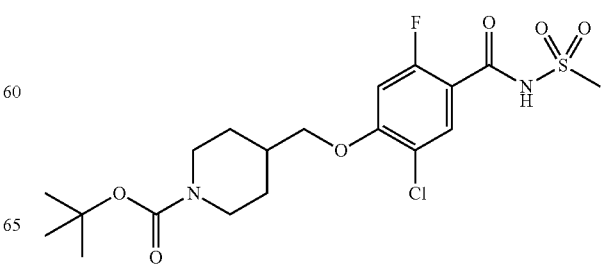

The compound was prepared in a similar manner to Example 59 from tert-butyl 4-(hydroxymethyl)-piperidine-1-carboxylate and 5-chloro-2,4-difluoro-N-methylsulfonyl-benzamide. LCMS (Method D): RT=6.67 min, m/z: 409.1. [M+H]+. 1H NMR (400 MHz, DMSO-d6) δ 7.77 (d, J=7.7 Hz, 1H), 7.13 (d, J=12.3 Hz, 1H), 4.08-3.88 (m, 4H), 3.13 (s, 3H), 2.74 (d, J=9.9 Hz, 2H), 1.97 (q, J=7.2, 5.8 Hz, 1H), 1.81-1.68 (m, 2H), 1.40 (s, 9H), 1.19 (qd, J=12.4, 4.1 Hz, 2H).

Example 79

Synthesis of 5-cyclopropyl-2-fluoro-N-(methylsulfonyl)-4-((1-phenylpiperidin-4-yl)methoxy)benzamide

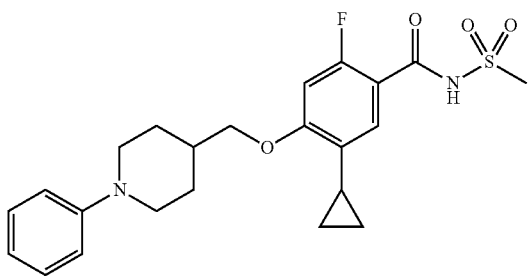 [SMILES: CS(=O)(=O)NC(=O)c1cc(C2CC2)c(OCC2CCN(c3ccccc3)CC2)cc1F]

The compound was prepared in a similar manner to Example 60 from (1-phenylpiperidin-4-yl)methanol and 5-chloro-2,4-difluoro-N-methylsulfonyl-benzamide.

LCMS (Method E): RT=4.68 min, m/z: 447.2 [M+H]+. 1H NMR (400 MHz, DMSO-d6) δ 11.82 (s, 1H), 7.26-7.11 (m, 3H), 7.00-6.89 (m, 3H), 6.74 (t, J=7.2 Hz, 1H), 4.00 (d, J=6.2 Hz, 2H), 3.79-3.67 (m, 2H), 3.29 (s, 3H), 2.78-2.65 (m, 2H), 2.07-1.92 (m, 2H), 1.87 (d, J=11.9 Hz, 2H), 1.55-1.41 (m, 2H), 0.94-0.83 (m, 2H), 0.72-0.61 (m, 2H).

Example 88

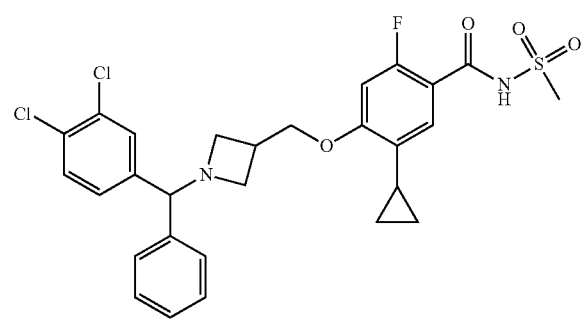

5-Cyclopropyl-4-((1-((3,4-dichlorophenyl)(phenyl)methyl)azetidin-3-yl)methoxy)-2-fluoro-N-(methylsulfonyl)benzamide

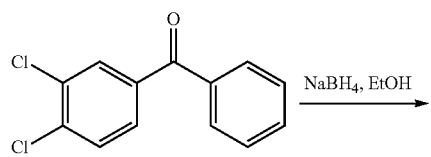

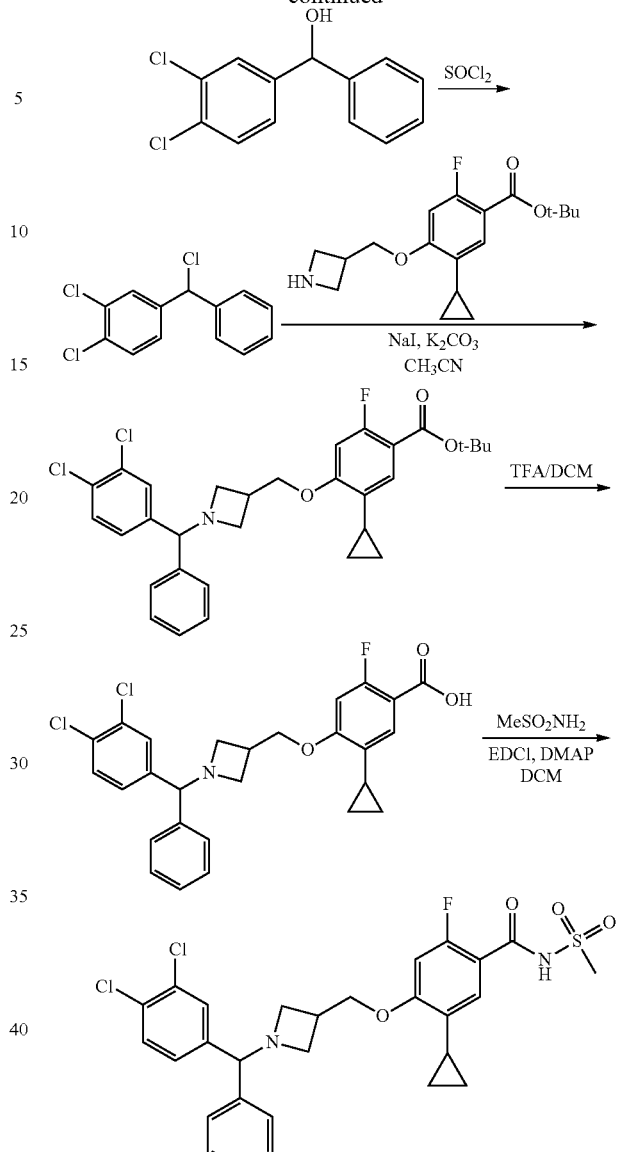

Step 1

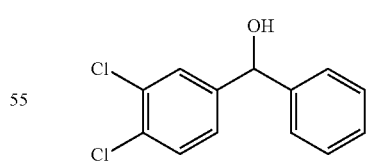

(3,4-Dichlorophenyl)(phenyl)methanol

A mixture of (3,4-dichlorophenyl)(phenyl)methanone (2.0 g, 8.0 mmol) and sodium borohydride (456 mg, 12 mmol) in EtOH (10 mL) was stirred at 25° C. for 2 h. After removal of the solvent, the residue was diluted with water (20 mL) and extracted with EtOAc (20 mL×3). The combined organic layers were washed with brine (20 mL), dried over anhydrous sodium sulfate, filtered and concentrated to give the desired product (2.0 g, 100%) as yellow oil. LCMS (ESI) m/z: 251.1 [M−H].

Step 2

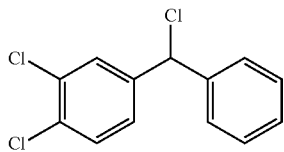 [SMILES: Clc1ccc(C(Cl)c2ccccc2)cc1Cl]

1,2-Dichloro-4-(chloro(phenyl)methyl)benzene

A solution of (3,4-dichlorophenyl)(phenyl)methanol (2.0 g, 7.9 mmol) in thionyl chloride (10 mL) was stirred at 60° C. for 3 h. After cooling to room temperature, the reaction mixture was concentrated and purified by silica gel column (elating with petroleum, ether/ethyl acetate-100/1) to give the desired product (1.6 g, 76%) as yellow oil.

Step 3

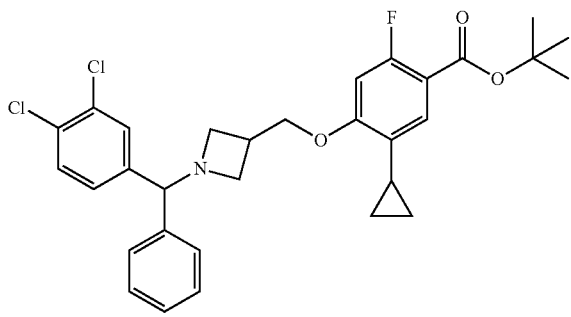 [SMILES: CC(C)(C)OC(=O)c1cc(C2CC2)c(OCC2CN(C(c3ccccc3)c3ccc(Cl)c(Cl)c3)C2)cc1F]

tert-Butyl 5-cyclopropyl-4-((1-((3,4-dichlorophenyl)(phenyl)methyl)-azetidin-3-yl)methoxy)-2-fluorobenzoate A mixture of methyl tert-butyl 4-(azetidin-3-ylmethoxy)-5-cyclopropyl-2-fluorobenzoate (100 mg, 0.31 mmol), 1,2-dichloro-4-(chloro(phenyl)methyl)benzene (126 mg, 0.47 mmo), sodium iodide (93 mg, 0.62 mmol) and potassium carbonate (128 mg, 0.93 mmol) in MeCN (10 mL) was stirred at 80° C. for 16 h. After cooling to room temperature, the reaction mixture was diluted with EtOAc (100 mL) and brine (50 mL). The organic layer was separated and washed with brine (50 mL), dried over anhydrous sodium sulfate, filtered and concentrated. The residue was purified by silica gel chromatography (eluting with petroleum, ether/ethyl acetate=4/1) to give the target compound (100 mg, 58%) as a pale yellow oil. LCMS (ESI) m/z: 556.0 [M+H]⁺.

Step 4

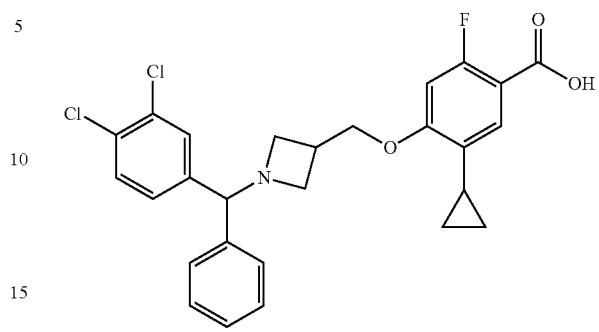

5-Cyclopropyl-4-((1-((3,4-dichlorophenyl)(phenyl)methyl)azetidin-3-yl)methoxy-2-fluorobenzoic acid Trifluoroacetic acid (1 mL) was added to a solution of tert-butyl 5-cyclopropyl-4-((1-((3,4-dichlorophenyl)(phenyl)methyl)azetidin-3-yl)methoxy-2-fluorobenzoate (100 mg, 0.18 mmol) in DCM (2 mL) and the reaction stirred at room temperature for 1 h. The mixture was then concentrated to give the desired product (80 mg, crude) as a pale yellow solid. LCMS (ESI): 500.0 [M−H]⁻.

Step 5

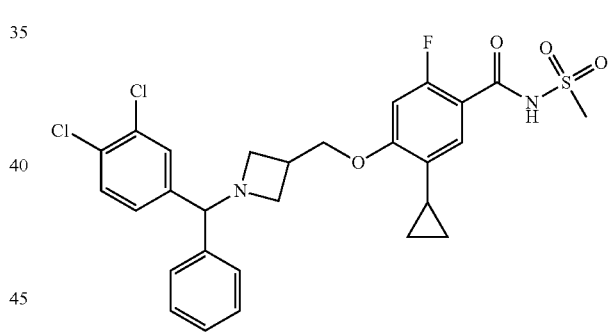

5-Cyclopropyl-4-((1-((3,4-dichlorophenyl)(phenyl)methyl)azetidin-3-yl)methoxy)-2-fluoro-N-(methylsulfonyl)benzamide 1. A mixture of 5-cyclopropyl-4-((1-((3,4-dichlorophenyl)(phenyl)methyl)-azetidin-3-yl)methoxy-2-fluorobenzoic acid (80 mg, 0.16 mmol), methanesulfonamide (23 mg, 0.24 mmol), EDCl (61 mg, 0.32 mmol) and DMAP (39 mg, 0.32 mmol) in DCM (4 mL) was stirred at 25° C. for 16 h. The reaction mixture was diluted with EtOAc (100 mL), washed with HCl (2.0 M, 20 mL) and brine (50 mL), dried over anhydrous sodium sulfate, filtered and concentrated. The residue was purified by reverse phase combiflash (30-40% MeCN in 0.1% NH₄HCO₃) to give the target product (35 mg, 38%) as an off-white solid, LCMS (ESI) Method A: RT=6.24 min, m/z: 577.2 [M+H]⁺. ¹H NMR (500 MHz, MeOD-d₄) δ7.60 (d, J=2.0 Hz, 1H), 7.48-7.24 (m, 8H), 6.85 (d, J=13.0 Hz, 1H), 4.58 (s, 1H), 4.23 (d, J=6.0 Hz, 2H), 3.48-3.42 (m, 2H), 3.32 (s, 3H), 3.27-3.21 (m, 2H), 3.06-3.00 (m, 1H), 2.13-2.09 (m, 1H), 0.97-0.94 (m, 2H), 0.70-0.67 (m, 2H).

Example 81

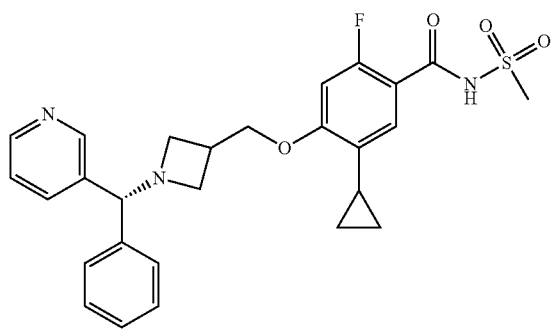 [SMILES: CS(=O)(=O)NC(=O)c1cc(C2CC2)c(OCC2CN([C@H](c3ccccc3)c3cccnc3)C2)cc1F]

(R)-5-Cyclopropyl-2-fluoro-N-(methylsulfonyl)-4-((1-(phenyl(pyridin-3-yl)methyl)azetidin-3-yl)methoxy)benzamide

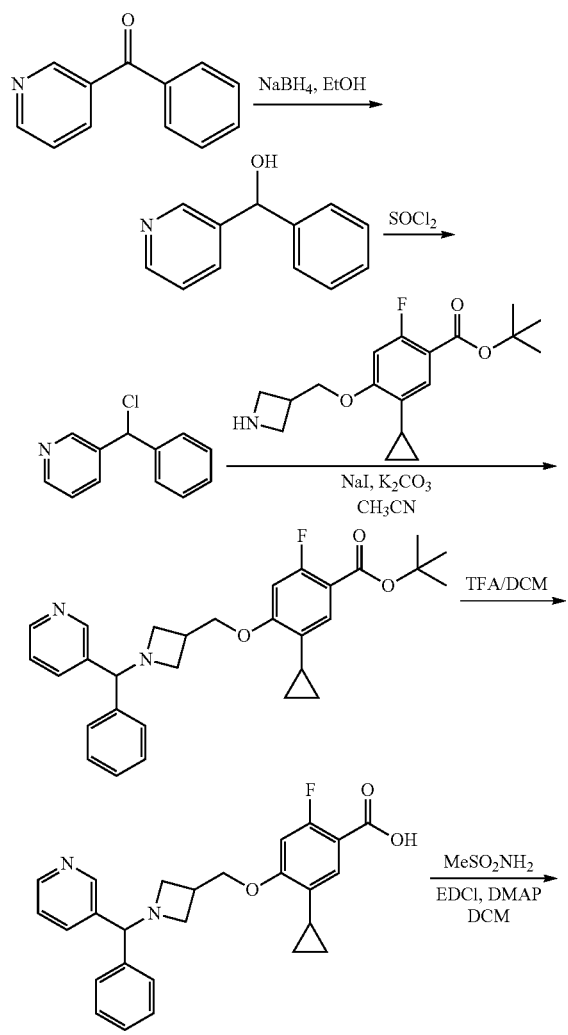

-continued

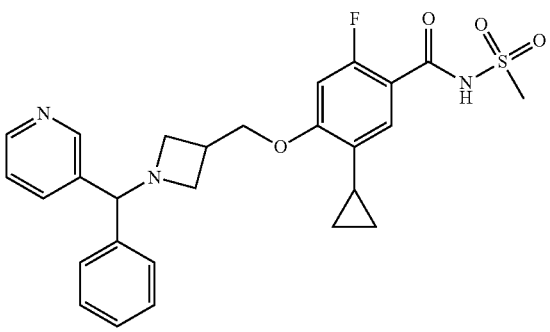

Step 1

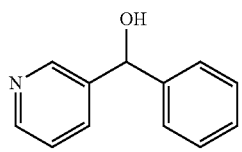 [SMILES: ClC(c1ccccc1)c1cccnc1]

Phenyl(pyridin-3-yl)methanol

A mixture of phenyl(pyridin-3-yl)methanone (2.0 g, 11 mmol) and sodium borohydride (623 mg, 16 mmol) in EtOH (30 ml) was stirred at 25° C. for 2 h. The mixture was then concentrated, diluted with water (20 mL) and extracted with EtOAc (20 mL×3). The combined organic layers were washed with brine (20 mL), dried over anhydrous sodium sulfate, filtered and concentrated to give the desired product (2.0 g, 100%) as yellow oil. LCMS (ESI): m/z 184.3 [M+H]$^+$.

Step 2

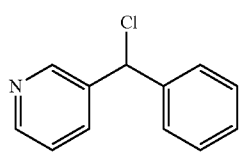

3-(Chloro(phenyl)methyl)pyridine

A solution of phenyl(pyridin-3-yl)methanol (1.5 g, 8.1 mmol) in thionyl chloride (10 mL) was stirred at 80° C. for 16 h. The mixture was then cooled to room temperature, concentrated and purified by silica gel chromatography (eluting with DCM/MeOH from 100/1 to 20/1) to give the desired product (1.5 g, 94%) as a brown solid. LCMS (ESI): m/z 204.3 [M+H]$^+$.

Step 3

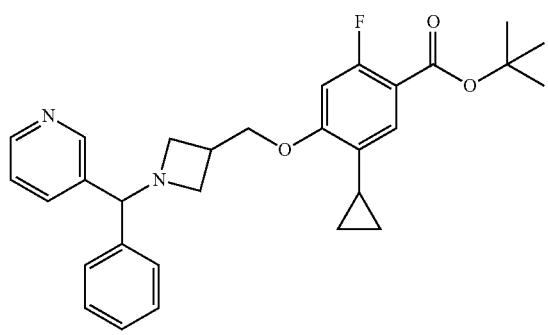 [SMILES: CC(C)(C)OC(=O)c1cc(C2CC2)c(OCC2CN(C(c3ccccc3)c3cccnc3)C2)cc1F]

tert-butyl 5-Cyclopropyl-2-fluoro-4-((1-(phenyl(pyridin-3-yl)methyl)azetidin-3-yl)methoxy)benzoate The compound was synthesized as described in step 3, Example 80. LCMS (ESI) m/z: 489.1 [M+H]$^+$.

Step 4

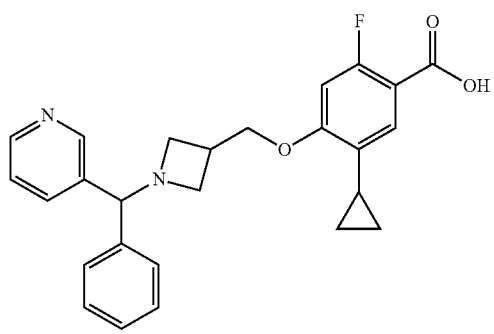 [SMILES: O=C(O)c1cc(C2CC2)c(OCC2CN(C(c3ccccc3)c3cccnc3)C2)cc1F]

5-Cyclopropyl-2-fluoro-4-((1-(phenyl(pyridin-3-yl)methyl)azetidin-3-yl)methoxy)benzoic acid The compound was synthesized as described in step 4, Example 80. LCMS (ESI) m/z: 433.1 [M+H]$^+$.

Step 5

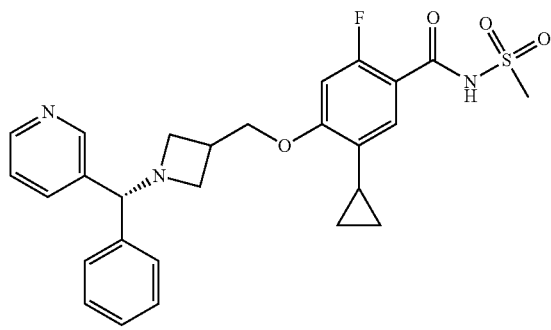 [SMILES: CS(=O)(=O)NC(=O)c1cc(C2CC2)c(OCC2CN([C@H](c3ccccc3)c3cccnc3)C2)cc1F]

(R)-5-Cyclopropyl-2-fluoro-N-(methylsulfonyl)-4-((1-(phenyl(pyridin-3-yl)methyl)azetidin-3-yl)methoxybenzamide The compound was synthesized as described in step 5, Example 80. The enantiomer was separated by chiral SFC from the racemate. Chiral HPLC (column: OJ-H, 4.6×250 mm, 5 μm; mobile Phase: A: supercritical CO$_2$, B: MeOH, A:B=75:25; flow: 3 mL/min; column temperature: 40° C.; Rt=4.83 mm). LCMS (ESI) Method B: RT=4.56 min, m/z: 510.2 [M+H]$^+$; $^1$H NMR (500 MHz, DMSO-d$_6$) δ 11.90 (s, 1H), 8.66 (s, 1H), 8.43 (s, 1H), 7.80 (d, J=8.0 Hz, 1H), 7.45-7.44 (m, 2H), 7.32-7.29 (m, 3H), 7.22-7.16 (m, 2H), 6.92 (d, J=13.0 Hz, 1H), 4.55 (s, 1H), 4.21 (d, J=6.5 Hz, 2H), 3.29-3.24 (m, 2H), 3.22 (s, 3H), 3.04-3.00 (m, 2H), 2.90-2.84 (m, 1H), 2.08-2.02 (m, 1H), 0.91-0.87 (m, 2H), 0.66-0.63 (m, 2H).

Example 82

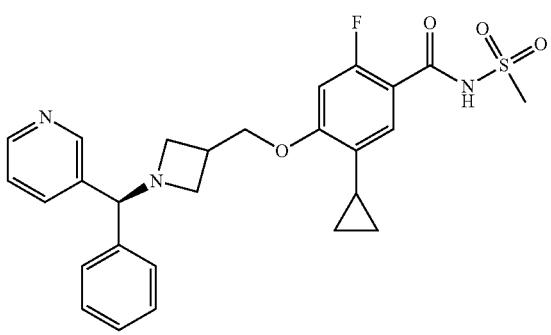 [SMILES: CS(=O)(=O)NC(=O)c1cc(C2CC2)c(OCC2CN([C@@H](c3ccccc3)c3cccnc3)C2)cc1F]

(S)-5-Cyclopropyl-2-fluoro-N-(methylsulfonyl)-4-((1-(phenyl(pyridin-3-yl)methylazetidin-3-yl)methoxybenzamide The compound was synthesized as described in Example 81. Chiral HPLC (column: OJ-H, 4.6×250 mm, 5 μm; mobile Phase: A: supercritical CO$_2$, B: MeOH, A:B=75:25; flow: 3 mL/min; column temperature; 40° C.; RT=4.08 min). LCMS (ESI) Method B: RT=4.56 min, m/z: 510.2 [M+H]$^+$. $^1$H NMR (500 MHz, DMSO-d$_6$) δ 11.90 (s, 1H), 8.64 (s, 1H), 7.79 (d, J=8.0 Hz, 1H), 7.45-7.44 (m, 2H), 7.32-7.29 (m, 3H), 7.22-7.16 (m, 2H), 6.92 (d, J=13.0 Hz, 1H), 4.55 (s, 1H), 4.21 (d, J=6.5 Hz, 2H), 3.29-3.24 (m, 2H), 3.20 (s, 3H), 3.04-3.00 (m, 2H), 2.90-2.84 (m, 1H), 2.07-2.02 (m, 1H), 0.91-0.87 (m, 2H), 0.66-0.63 (m, 2H).

Example 83

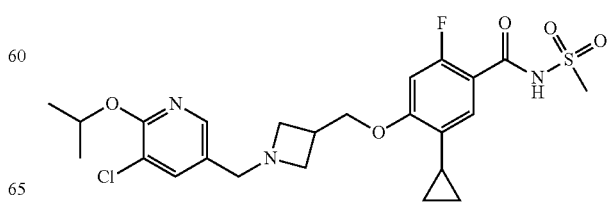

4-((1-((5-Chloro-6-isopropoxypyridin-3-yl)methyl)azetidin-3-yl)methoxy)-5-cyclopropyl-2-fluoro-N-(methylsulfonyl)benzamide

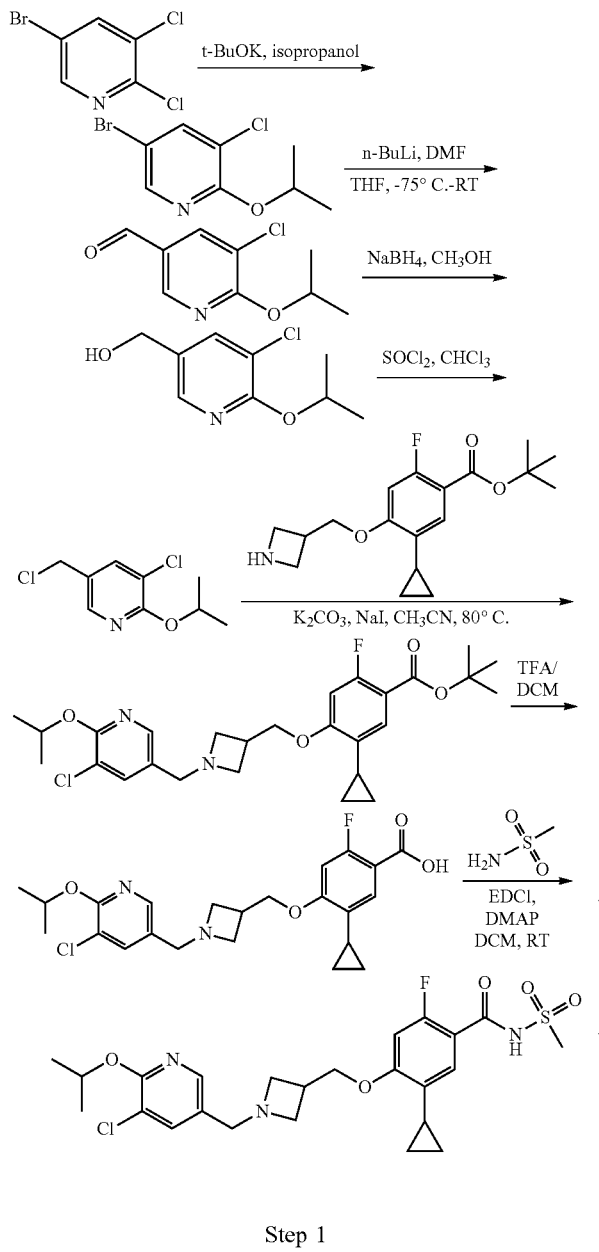

Step 1

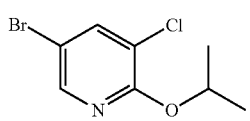

5-Bromo-3-chloro-2-isopropoxypyridine

A mixture of potassium tert-butoxide (10 g, 88.8 mmol) in isopropanol (15 mL) was stirred at 95° C. for 3 h, 5-bromo-2,3-dichloropyridine (5 g, 22.2 mmol) wax then added. The reaction mixture was refluxed overnight then partitioned between ethyl acetate and water. The organic layer was washed with water, brine, dried over anhydrous sodium sulfate, filtered, and concentrated. The residue was purified by silica column chromatography (eluting with petroleum ether/ethyl acetate=100/1) to give 5-bromo-3-chloro-2-isopropoxypyridine (3.2 g, 58% yield) as colorless oil. $^1$H-NMR (500 MHz, DMSO-$d_6$): δ 8.25-8.20 (m, 2H), 5.27-5.23 (m, 1H), 1.32 (d, J=5.5 Hz, 6H).

Step 2

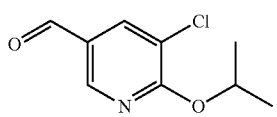

5-Chloro-6-isopropoxynicotinaldehyde n-BuLi (2.5 M, 9.6 ml, 24 mmol) was added dropwise to a solution of 5-bromo-2,3-dichloropyridine (3.0 g, 12 mmol) in anhydrous THF (20 mL) at −78° C. The resulting mixture was stirred at this temperature for 10 min then DMF (2.0 g, 36 mmol) was added at −50° C. The mixture was warmed to room temperature and partitioned with EtOAc (100 mL) and 1N HCl (10 mL). The organic layer was washed with saturated brine (50 mL), dried over anhydrous sodium sulfate, filtered and concentrated. The residue was purified by silica gel chromatography (elating with petroleum ether/ethyl acetate=50/1) to give 5-chloro-6-isopropoxynicotinaldehyde (700 mg, 29% yield) as colorless oil. $^1$H-NMR (500 MHz, DMSO-$d_6$); δ 9.94 (s, 1H), 8.70 (d, J=1.5 Hz, 1H), 8.24 (d, J=2.0 Hz, 1H) 5.40-5.31 (m, 1H), 1.37 (d, J=6.0 Hz, 6H).

Step 3

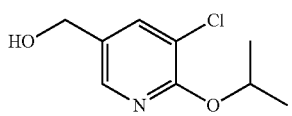

(5-Chloro-6-isopropoxypyridin-3-yl)methanol

The compound was synthesized as described in step 1, Example 80. LCMS (ESI) m/z: 200.1 [M−H]⁺.

Step 4

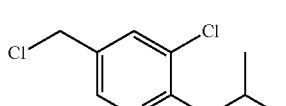

3-Chloro-3-(chloromethyl)-2-isopropoxypyridine

The compound was synthesized as described in step 2, Example 80.

Step 5

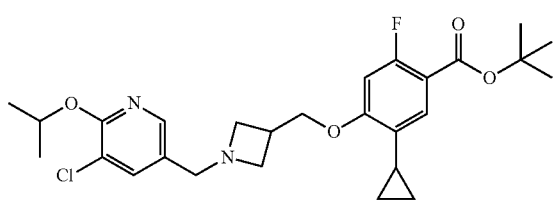 [SMILES: CC(C)Oc1ncc(CN2CC(COc3cc(F)c(C(=O)OC(C)(C)C)cc3C3CC3)C2)cc1Cl]

tert-butyl 4-((1-((5-Chloro-6-isopropoxypyridin-3-yl)methyl)azetidin-3-yl)methoxy-5-cyclopropyl-2-fluorobenzoate The compound was synthesized as described in step 3, Example 80. LCMS (ESI) m/z: 505.1 [M+H]$^+$.

Step 2

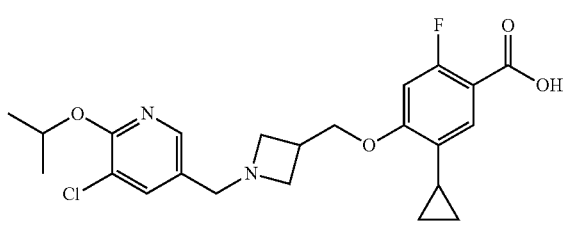 [SMILES: CC(C)Oc1ncc(CN2CC(COc3cc(F)c(C(=O)O)cc3C3CC3)C2)cc1Cl]

4-((1-((5-Chloro-6-isopropoxypyridin-3-yl)methyl)azetidin-3-yl)methoxy-5-cyclopropyl-2-fluorobenzoic acid The compound was synthesized as described in step 4, Example 80. LCMS (ESI) m/z: 449.1 [M+H]$^+$.

Step 7

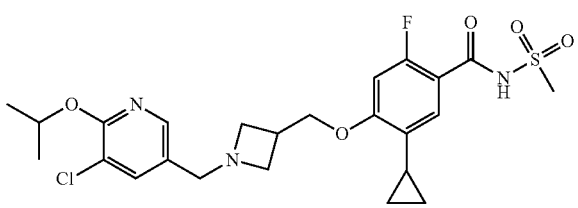 [SMILES: CC(C)Oc1ncc(CN2CC(COc3cc(F)c(C(=O)NS(C)(=O)=O)cc3C3CC3)C2)cc1Cl]

4-((1-((5-Chloro-6-isopropoxypyridin-3-yl)methyl)azetidin-3-yl)methoxy)-5-cyclopropyl-2-fluoro-N-(methylsulfonyl) benzamide The compound was synthesized as described is step 5, Example 80. LCMS (ESI) Method A: RT=5.06 min, m/z: 526.2 [M+H]$^+$. $^1$H NMR (500 MHz, DMSO-d$_6$): δ 7.99 (d, J=2.0 Hz, 1H), 7.55 (d, J=2.0 Hz, 1H). 7.23 (d, J=9.0 Hz, 1H), 6.71 (d, J=13.0 Hz, 1H), 5.28-5.26 (m, 1H), 4.11 (d, J=6.0 Hz, 2H), 3.55 (s, 2H), 3.39-3.33 (m, 2H), 3.13-3.11 (m, 2H), 2.86-2.83 (m, 4H), 2.00 (m, 1H), 1.31 (d, J=6.0 Hz, 6H), 0.88-0.85 (m, 2H), 0.56-0.53 (m, 2H).

Example 84

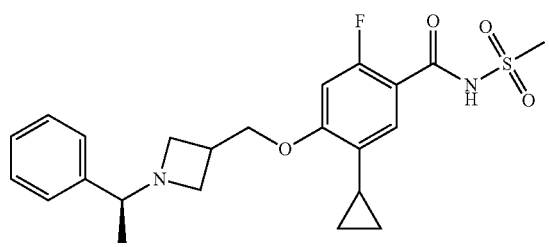 [SMILES: C[C@@H](c1ccccc1)N1CC(COc2cc(F)c(C(=O)NS(C)(=O)=O)cc2C2CC2)C1]

(S)-5-Cyclopropyl-2-fluoro-N-(methylsulfonyl)-4-((1-(1-phenylethyl)azetidin-3-yl)methoxy)benzamide

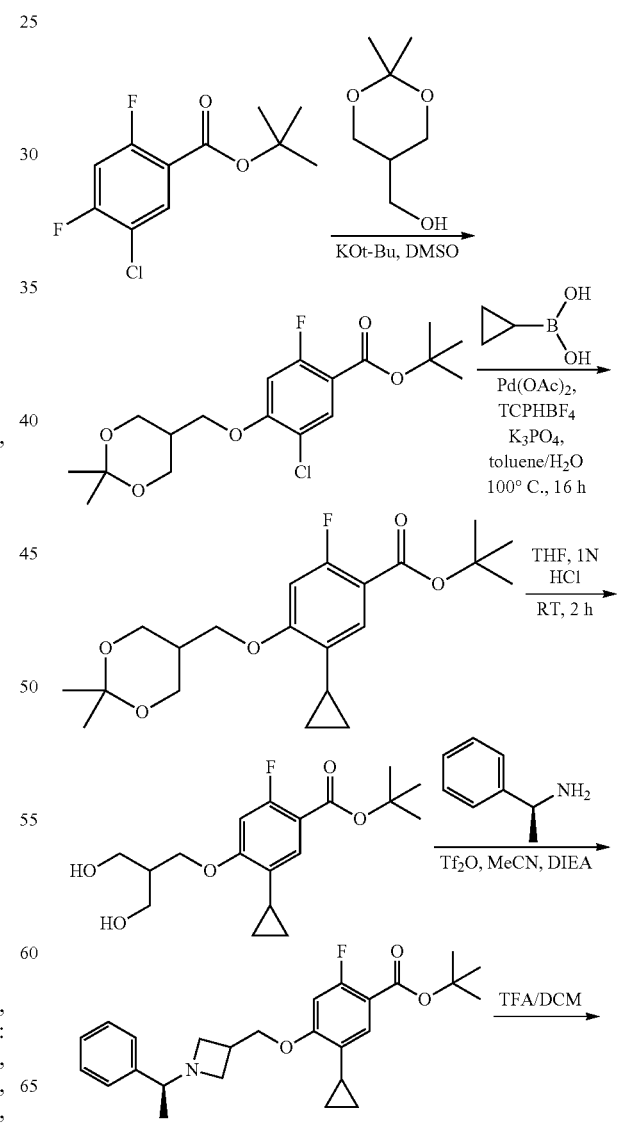

-continued

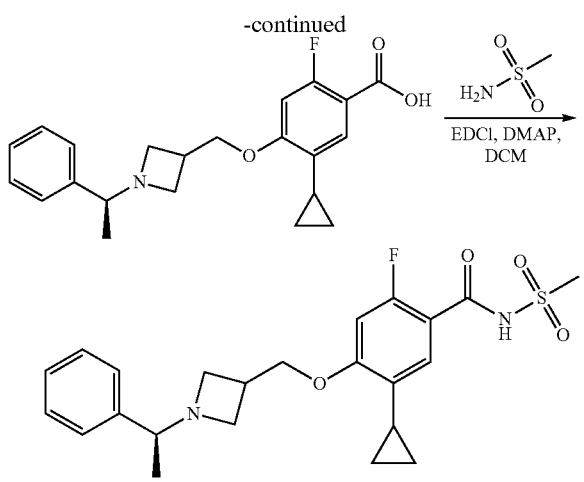

5-yl)methoxy)-2-fluorobenzoate (375 mg, 1 mmol), cyclopropylboronic acid (176 mg, 2 mmol), potassium phosphate (1.06 g, 5 mmol) and tricyclohexylphosphine tetrafluoroborate (74 mg, 0.2 mmol) in toluene (5 mL) and water (0.25 mL) under a nitrogen atmosphere. The reaction mixture was heated at 100° C. for 16 hours then cooled to room temperature. The mixture was then diluted with water (200 mL) and extracted with ethyl acetate (100 mL×3). The combined organics were washed with brine, dried over anhydrous sodium sulfate and concentrated in vacuo. The residue was purified by silica gel chromatography (elating with petroleum ether/ethyl acetate-5/1) to afford tert-butyl 5-cyclopropyl-4-((2,2-dimethyl-1,3-dioxan-5-yl)methoxy)-2-fluorobenzoate (350 mg, yield: 92%) as a white solid.

Step 3

Step 1

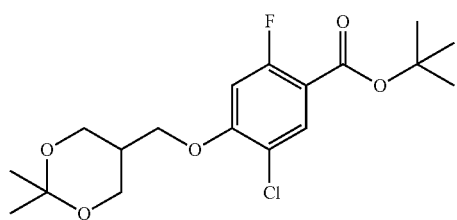 [SMILES: CC(C)(C)OC(=O)c1cc(Cl)c(OCC2COC(C)(C)OC2)cc1F]

tert-Butyl 5-chloro-4-((2,2-dimethyl-1,3-dioxan-5-yl)methoxy)-2-fluorobenzoate

Potassium tert-butoxide (7.8 g, 70 mmol) was added to a solution of (2,2-dimethyl-1,3-dioxan-5-yl)methanol (9.3 g, 63.7 mmol) and tert-butyl 5-chloro-2,4-difluorobenzoate (16.6 g, 66.9 mmol) in DMSO (200 mL) at 14° C. After stirring at room temperature for 1 h, the reaction mixture was diluted with water (500 mL) and extracted with EtOAc (200 mL×3). The combined organics were washed with brine, dried over anhydrous sodium sulfate and concentrated. The residue was purified by silica gel chromatography (during with petroleum ether/ethylacetate, 5/1) to afford the target compound (16.4 g, yield: 69%) as a white solid.

Step 2

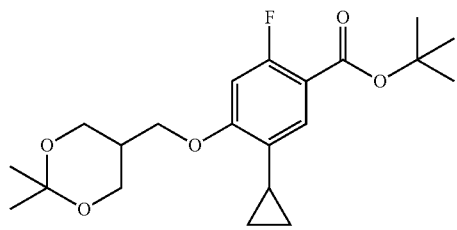 [SMILES: CC(C)(C)OC(=O)c1cc(C2CC2)c(OCC2COC(C)(C)OC2)cc1F]

tert-Butyl 5-cyclopropyl-4-((2,2-dimethyl-1,3-dioxan-5-yl)methoxy)-2-fluorobenzoate Palladium acetate (23 mg, 0.1 mmol) was added to a mixture of tert-butyl 5-chloro-4-((2,2-dimethyl-1,3-dioxan-

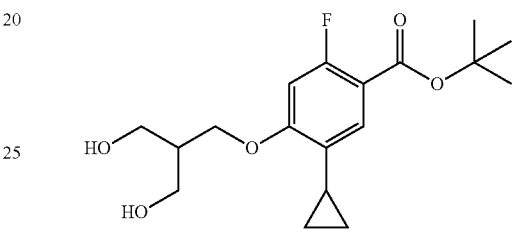

tert-Butyl 5-cyclopropyl-2-fluoro-4-(3-hydroxy-2-(hydroxymethyl)propoxy)benzoate A solution of tert-butyl 5-cyclopropyl-4-((2,2-dimethyl-1,3-dioxan-5-yl)methoxy)-2-fluorobenzoate (350 mg, 0.92 mmol) in a mixture of THF (10 mL) and HCl (1 M, 10 mL) was stirred at room temperature for 2 h. The reaction mixture was diluted with DCM (20 ml×2) and washed with saturated aqueous NaHCO₃ (10 mL). The combined organic layers were dried over anhydrous sodium sulfate, filtered and concentrated. The residue was purified by silica gel column chromatography (eluting with hexanes/ethyl acetate=2/1) to give tert-butyl5-cyclopropyl-2-fluoro-4-(3-hydroxy-2-(hydroxymethyl)propoxy)benzoate (300 mg, yield: 965) as a yellow solid. LCMS (ESI) m/z: 339.1 [M−H]⁻.

Step 4

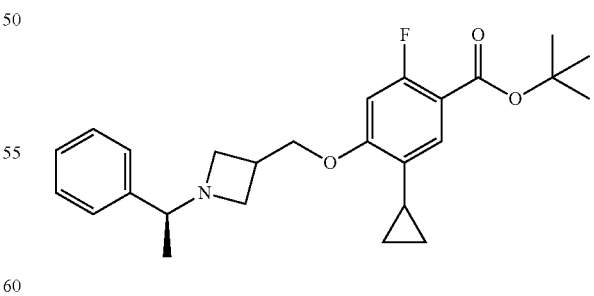

(S)-tert-Butyl 5-cyclopropyl-2-fluoro-4-((1-(1-phenylethyl)azetidin-3-yl)methoxy)benzoate Trifluoromethanesulfonic anhydride (200 mg, 0.71 mmol) was added dropwise to a 0° C. mixture of tert-butyl 5-cyclopropyl-2-fluoro-4-(3-hydroxy-2-(hydroxymethyl)- propoxy)benzoate (60 mg, 0.18 mmol) and N,N-diisopropylethylamine (91 mg, 0.71 mmol) in acetonitrile (5 mL). The mixture was stirred at 0° C. for 1 h, then (S)-1-phenylethanamine (21 mg, 0.18 mmol) added, and the solution stirred for a further 1 h at room temperature. The reaction was quenched with water (10 mL) and extracted with ethyl acetate (10 mL×3). The combined organic layers were washed with brine (10 mL), dried over anhydrous sodium sulfate, filtered and concentrated. The crude product was purified by silica column chromatography (eluting with petroleum ether/ethyl acetate=10/1) to give (S)-tert-butyl 5-cyclopropyl-2-fluoro-4-((1-(1-phenylethyl)azetidin-3-yl)methoxy)benzoate (32 mg, 43%) as an oil. LCMS (ESI): m/z: 426.8 [M+H]$^+$.

Step 5

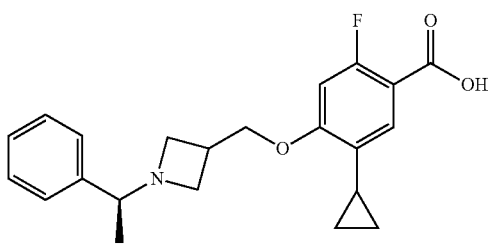 [SMILES: C[C@@H](c1ccccc1)N1CC(COc2cc(F)c(C(=O)O)cc2C2CC2)C1]

(S)-5-Cyclopropyl-2-fluoro-4-((1-(1-phenylethyl)azetidin-3-yl)methoxy)benzoic acid The compound was synthesized as described in step 4, Example 80, LCMS (ESI) m/z: 370.1 [M+H]$^+$.

Step 6

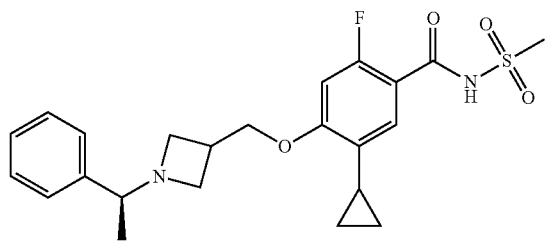

(S)-5-Cyclopropyl-2-fluoro-N-(methylsulfonyl)-4-((1-(1-phenylethyl)azetidin-3-yl)methoxy)benzamide The compound was synthesized as described in step 5, Example 80. LCMS (ESI) Method A: RT=4.31 min, m/z: 447.0 [M+H]$^+$. $^1$H NMR (500 MHz, DMSO-d$_6$): δ 7.37-7.32 (m, 5H), 7.20 (d, J=8.5 Hz, 1H), 6.83 (d, J=12.5 Hz, 1H), 4.17 (d, J=6.5 Hz, 2H), 3.75-3.46 (m, 5H), 3.04 (s, 3H), 3.00-2.98 (m, 1H), 2.03-2.00 (m, 1H), 1.29 (d, J=5.0 Hz, 3H), 0.88-0.87 (m, 2H), 0.62-0.59 (m, 2H).

Example 85

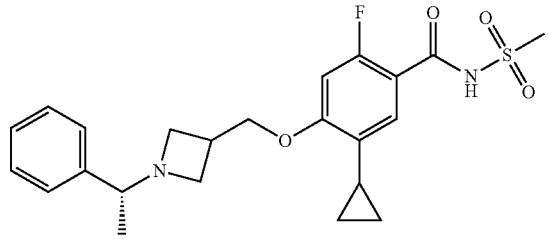 [SMILES: C[C@H](c1ccccc1)N1CC(COc2cc(F)c(C(=O)NS(C)(=O)=O)cc2C2CC2)C1]

(R)-5-Cyclopropyl-2-fluoro-N-(methylsulfonyl)-4-((1-(1-phenylethyl)azetidin-3-yl)methoxy)benzamide The compound was synthesized as described to Example 5, LCMS (ESI) Method A: RT=4.32 min, m/z: 447.0 [M+H]$^+$. $^1$H NMR (500 MHz, DMSO-d$_6$): δ 7.39-7.33 (m, 5H), 7.20 (d, J=8.5 Hz, 1H), 6.82 (d, J=12.5 Hz, 1H), 4.17 (d, J=5.5 Hz, 3H), 3.93-3.49 (m, 5H), 3.04 (s, 3H), 3.02-2.98 (m, 1H), 2.04-2.00 (m, 1H), 1.29 (d, J=6.0 Hz, 3H), 0.88-0.85 (m, 2H), 0.62-0.59 (m, 2H).

Example 86

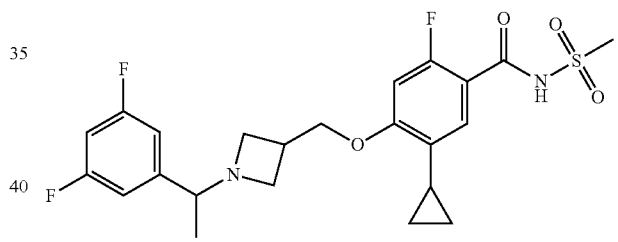

5-Cyclopropyl-4-((1-(1-(3,5-difluorophenyl)ethyl)azetidin-3-yl)methoxy)-2-fluoro-N-(methylsulfonyl)benzamide

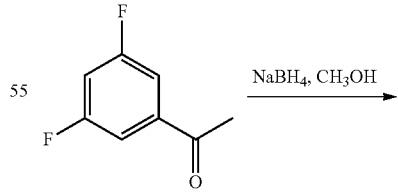

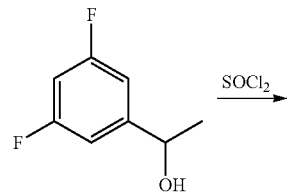

303
-continued
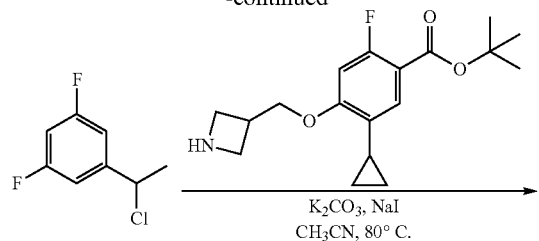
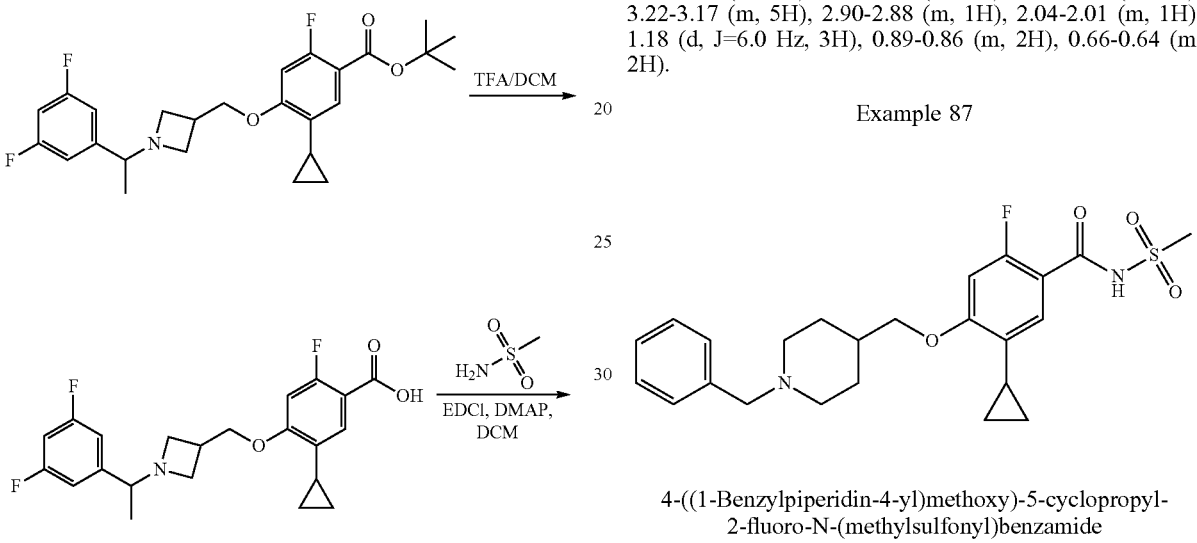
304
-continued
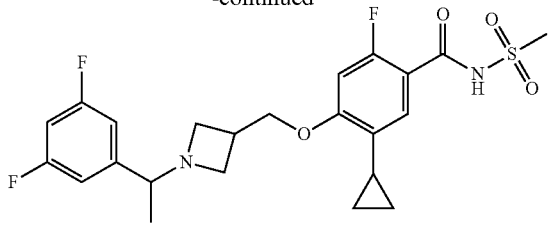
The compound was synthesized as described in Example 80. LCMS (ESI) Method A: RT=4.79 mm, m/z: 483.0 [M+H]⁺. ¹H NMR (500 MHz, DMSO-$d_6$): δ 7.18-7.07 (m, 4H), 6.91 (d, J=13.0 Hz, 1H), 4.19 (d, J=6.0 Hz, 2H), 3.64-3.63 (m, 1H), 3.52-3.49 (m, 1H), 3.40-3.33 (m, 1H), 3.22-3.17 (m, 5H), 2.90-2.88 (m, 1H), 2.04-2.01 (m, 1H), 1.18 (d, J=6.0 Hz, 3H), 0.89-0.86 (m, 2H), 0.66-0.64 (m, 2H).
Example 87
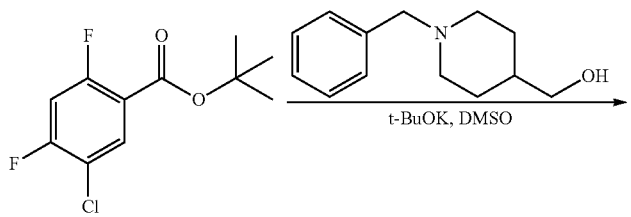
4-((1-Benzylpiperidin-4-yl)methoxy)-5-cyclopropyl-2-fluoro-N-(methylsulfonyl)benzamide
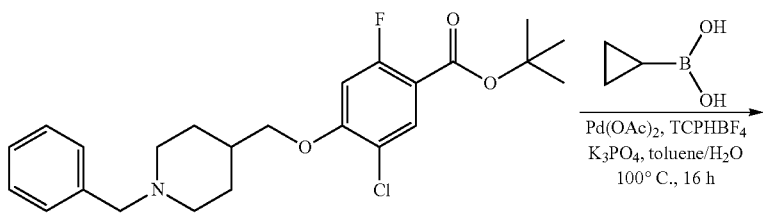
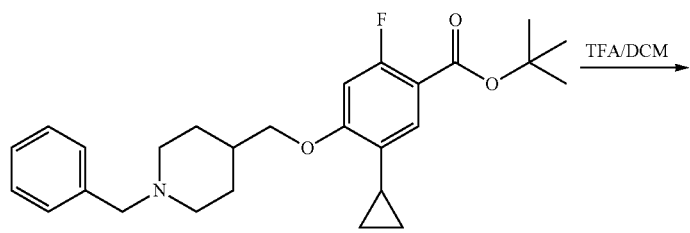

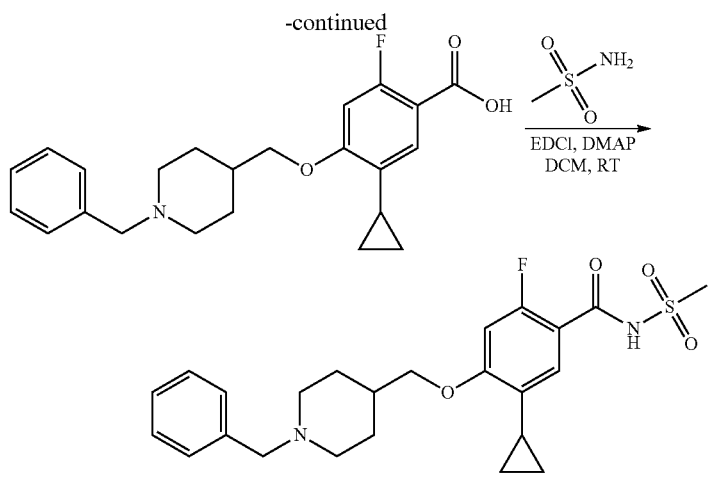

Step 1

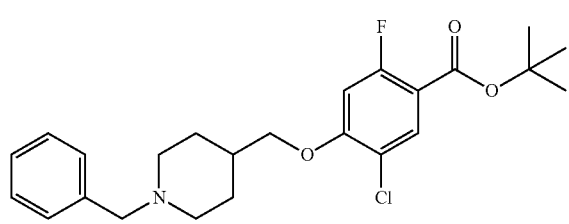 [SMILES: CC(C)(C)OC(=O)c1cc(Cl)c(OCC2CCN(Cc3ccccc3)CC2)cc1F]

tert-Butyl 4-((1-benzylpiperidin-4-yl)methoxy)-5-chloro-2-fluorobenzoate

Potassium tert-butoxide (135 mg, 1.12 mmol) was added to a mixture of tert-butyl 5-chloro-2,4-difluorobenzoate (300 mg, 0.93 mmol) and (1-benzylpiperidin-4-yl) methanol (230 g, 1.12 mmol) in DMSO (5 mL) at 15° C. After stirring at room temperature for 1 h, the mixture was diluted with EtOAc, washed with brine, dried over Na$_2$SO$_4$, filtered and concentrated. The resulting residue was purified by silica gel column chromatography (during with petroleum ether/ethyl acetate=10/1) to give the desired product (105 mg, 26% yield) as an oil. LCMS (ESI); m/z 434.0 [M+H]$^+$.

Step 2

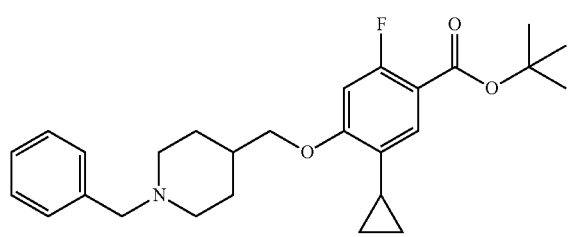 [SMILES: CC(C)(C)OC(=O)c1cc(C2CC2)c(OCC2CCN(Cc3ccccc3)CC2)cc1F]

tert-Butyl 4-((1-benzylpiperidin-4-yl)methoxy)-5-cyclopropyl-2-fluorobenzoate

Palladium acetate (8 mg, 0.037 mmol) was added to a solution of tert-butyl 4-((1-benzylpiperidin-4-yl)methoxy)-5-chloro-2-fluorobenzoate (160 mg, 0.37 mmol), cyclopropylboronic acid (41 mg, 0.55 mmol), potassium phosphate (157 mg, 0.74 mmol) and tricyclohexylphosphine tetrafluoroborate (27 mg, 0.074 mmol) in toluene (2 mL) and water (0.1 mL) under a nitrogen atmosphere. The reaction mixture was heated at 100° C. for 18 hours then cooled to room temperature. The mixture was diluted with water (10 mL) and extracted with ethyl acetate (10 mL×3). The combined organic layers were washed with brine (10 mL), dried over anhydrous sodium sulfate, filtered and concentrated. The residue was purified by silica gel chromatography (eluting with petroleum ether/ethyl acetate=10/1) to give the desired product (110 mg, 68% yield) as an oil. LCMS (ESI): m/z 440.0 [M+H]$^+$.

Step 3

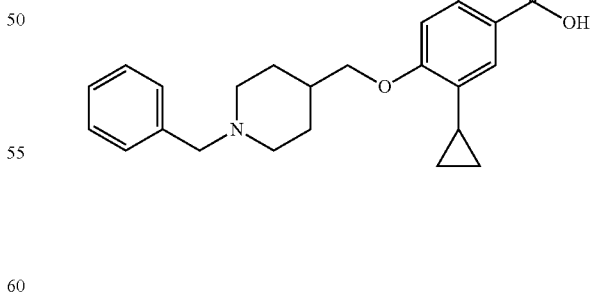

4-((1-Benzylpiperidin-4-yl)methoxy)-5-cyclopropyl-2-fluorobenzoic acid

The synthetic procedure was same as the step 4 of Example 80. LCMS (ESI) m/z: 384.0 [M+H]$^+$.

Step 4
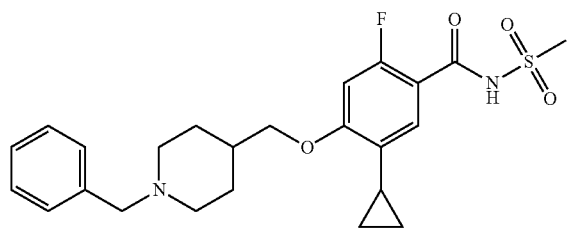 [SMILES: CS(=O)(=O)NC(=O)c1cc(C2CC2)c(OCC2CCN(Cc3ccccc3)CC2)cc1F]
4-((1-benzylpiperidin-4-yl)methoxy)-5-cyclopropyl-2-fluoro-N-(methylsulfonyl)benzamide
The compound was synthesized as described in step 5 of Example 80. LCMS (ESI) Method A: RT=4.76 min, m/z: 461.1 [M+H]+. 1H NMR (500 MHz, DMSO-$d_6$): δ 7.41-7.35 (m, 5H), 7.19 (d, J=8.5 Hz, 1H), 6.78 (d, J=12.5 Hz, 1H), 3.91 (d, J=6.0 Hz, 2H), 3.89 (s, 2H), 3.13-3.11 (m, 2H), 3.02 (s, 3H), 2.52-2.50 (m, 2H), 2.02-1.97 (m, 1H), 1.93-1.86 (m, 3H), 1.51-1.45 (m, 2H), 0.89-0.85 (m, 2H), 0.60-0.57 (m, 2H).
Example 88
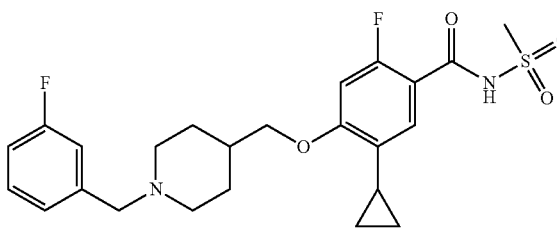
4-((1-(3-Fluorobenzyl)piperidin-4-yl)methoxy)-5-cyclopropyl-2-fluoro-N-(methylsulfonyl)benzamide
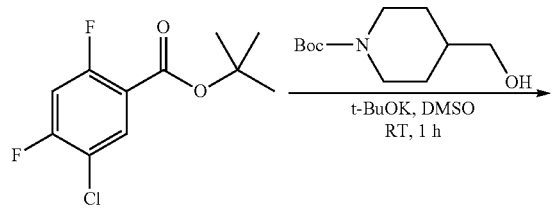
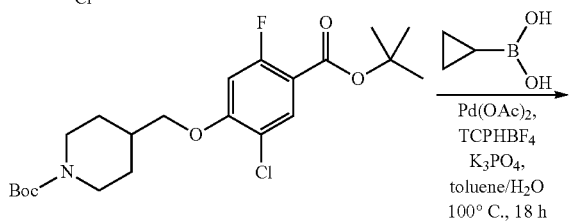
Step 1
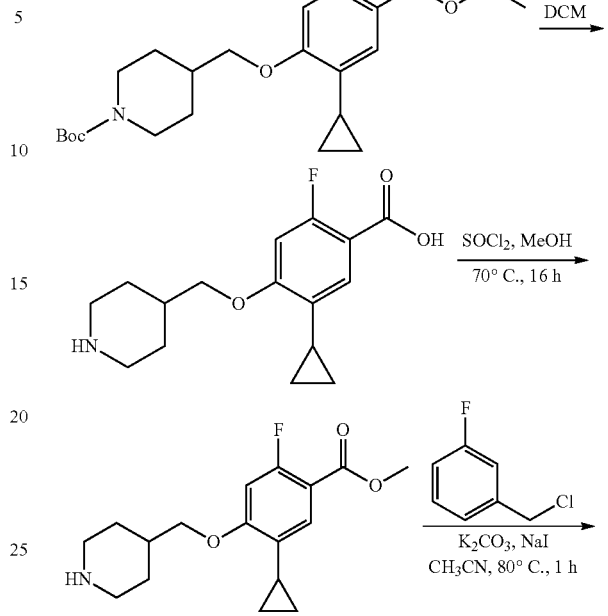
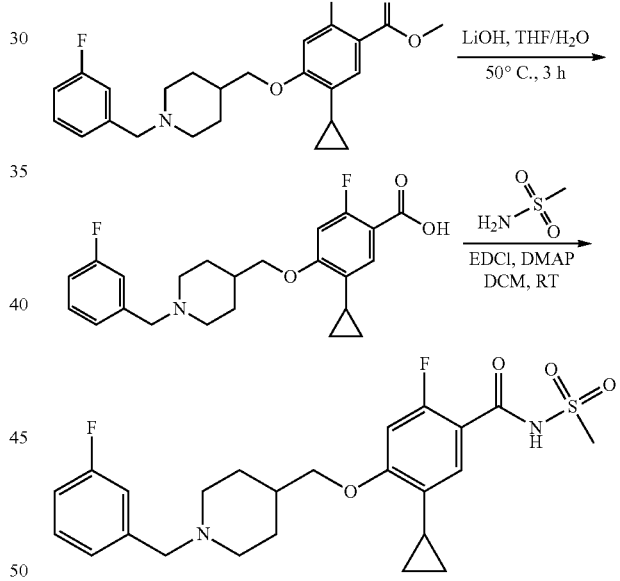
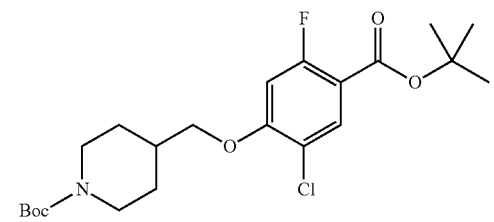 [SMILES: CC(C)(C)OC(=O)c1cc(Cl)c(OCC2CCN(C(=O)OC(C)(C)C)CC2)cc1F]

tert-butyl 4-((4-(tert-Butoxycarbonyl)-2-chloro-5-fluorophenoxy)-methyl)piperidine-1-carboxylate Potassium tert-butoxide (6.2 g, 55.6 mmol) was added to a solution of tert-butyl 4-(hydroxymethyl)piperidine-1-carboxylate (10.0 g, 46.3 mmol) and tert-butyl 5-chloro-2,4-difluorobenzoate (12.6 g, 50.9 mmol) in DMSO (200 mL). After stirring at room temperature for 1 h, the reaction mixture was diluted with water (500 mL) and extracted with EtOAc (200 mL×3). The combined organic layers were washed with brine, dried over anhydrous sodium sulfate, filtered and concentrated. The residue was purified by silica gel column chromatography (eluting with petroleum ether/ethyl acetate, from 20/1 to 5/1) to afford the target compound (12.3 g, yield; 60%) as a pale yellow liquid, LCMS (ESI) m/z: 331.9. [M−111]+.

Step 2

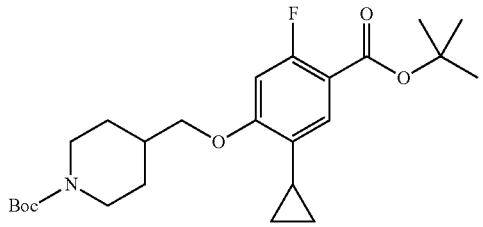 [SMILES: CC(C)(C)OC(=O)c1cc(C2CC2)c(OCC2CCN(C(=O)OC(C)(C)C)CC2)cc1F]

tert-Butyl 4-((4-(tert-butoxycarbonyl)-2-cyclopropyl-5-fluorophenoxy)-methyl)piperidine-1-carboxylate Palladium acetate (672 mg, 3 mmol) was added to a solution of tert-butyl 4-((4-(tert-butoxycarbonyl)cyclohexyl)methoxy)-5-chloro-2-fluorobenzoate (13.3 g, 30 mol), cyclopropylboronic acid (5.16 g, 60 mmol), potassium phosphate (25.5 g, 120 mmol) and tricyclohexylphosphine tetrafluoroborate (2.2 g, 6 mmol) in toluene (200 mL) and water (10 mL) under a nitrogen atmosphere. The reaction mixture was heated at 100° C. for 16 hours then cooled to room temperature. The mixture was diluted with water (200 mL) was and extracted with ethyl acetate (100 mL×3). The combined organic layers were washed with brine, dried over anhydrous sodium sulfate, filtered and concentrated. The residue was purified by silica gel column chromatography (eluting with petroleum ether/ethyl acetate, from 10/1 to 2/1) to afford the target compound (10.8 g, yield: 80%) as a pale yellow liquid. LCMS (ESI) m/z: 338.0 [M−111]+.

Step 3

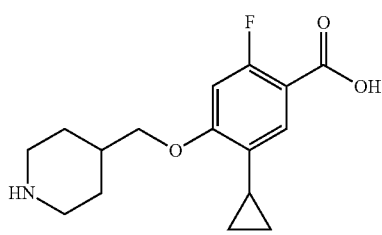 [SMILES: O=C(O)c1cc(C2CC2)c(OCC2CCNCC2)cc1F]

5-Cyclopropyl-2-fluoro-4-(piperidin-4-ylmethoxy)benzoic acid

A solution of tert-butyl 4-((4-(tert-butoxycarbonyl)-2-cyclopropyl-5-fluorophenoxy)methylpiperidine-1-carboxylate (11.0 g, 24.5 mmol) in DCM (20 mL) and TFA (20 ml) was stirred at room temperature for 1 h. The reaction was quenched with saturated aqueous sodium bicarbonate and extracted with DCM (50 mL×3). The combined organic layers were dried over anhydrous sodium sulfate, filtered and concentrated to give target compound (6.5 g, yield: 90%) as a white solid which was used in the next step without further purification. LCMS (ESI) m/z: 294.1 [M+H]+.

Step 4

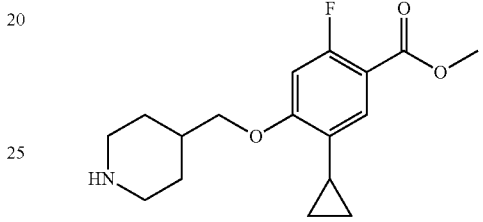

Methyl 5-cyclopropyl-2-fluoro-4-(piperidin-4-ylmethoxy)benzoate

Thionyl chloride (8 ml) was added dropwise to a solution of 5-cyclopropyl-2-fluoro-4-(piperidin-4-ylmethoxy)benzoic acid (5.0 g, 17 mmol) in MeOH (80 ml). After stirring at 70° C. for 16 h, the solution was concentrated to give a brown solid, which was recrystallized (petroleum ether/ethyl acetate=5/1) to give the target compound as a gray solid (yield: 80%). LCMS (ESI) m/z: 308.1 [M+H]+.

Step 5

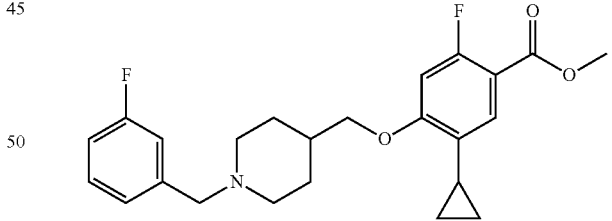

Methyl 4-((1-(3-fluorobenzyl)piperidin-4-yl)methoxy)-5-cyclopropyl-2-fluorobenzoate A mixture of methyl 5-cyclopropyl-2-fluoro-4-(piperidin-4-ylmethoxy)benzoate (100 mg, 0.33 mmol), 1-(chloromethyl)-3-fluorobenzene (48 mg, 0.33 mmol), sodium iodide (149 mg, 0.99 mmol) and potassium carbonate (137 mg, 0.99 mmol) in MeCN (10 mL) was stirred at 80° C. for 1 h. The reaction mixture was diluted with EtOAc (100 mL) and brine (50 mL). The organic layer was separated, washed with brine (50 mL), dried over anhydrous sodium sulfate, filtered and concentrated. The residue was purified by silica gel chromatography (elating with petroleum ether/ EtOAc=5/1) to give the target compound (110 mg, 81%) as a pale yellow oil. LCMS (ESI) m/z: 416.0 [M+H]⁺.

Step 6

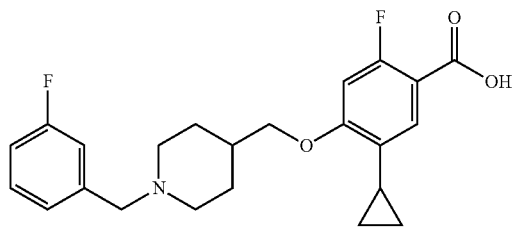 [SMILES: O=C(O)c1cc(C2CC2)c(OCC2CCN(Cc3cccc(F)c3)CC2)cc1F]

4-((1-(3-Fluorobenzyl)piperidin-4-yl)methoxy)-5-cyclopropyl-2-fluorobenzoic acid A mixture of methyl 4-((1-(3-fluorobenzyl)piperidin-4-yl)methoxy)-5-cyclopropyl-2-fluorobenzoate (110 mg, 0.27 mmol) and lithium hydroxide (64 mg, 2.7 mmol) in THF (5 mL) and water (5 mL) was stirred at 50° C. for 3 h. After cooling to room temperature, the mixture was adjusted to a pH of 2-3 with HCl (2M) then extracted with EtOAc (10×2 mL). The combined organic layers were washed with brine (10 mL), dried over anhydrous sodium sulfate, filtered and concentrated to give the product (68 mg, 64%) as a pale yellow solid. LCMS (ESI) m/z: 402.1 [M+H]⁺.

Step 7

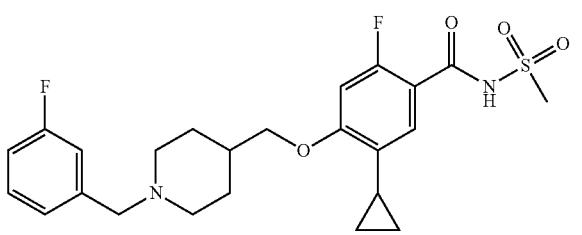 [SMILES: CS(=O)(=O)NC(=O)c1cc(C2CC2)c(OCC2CCN(Cc3cccc(F)c3)CC2)cc1F]

4-((1-(3-Fluorobenzyl)piperidin-4-yl)methoxy)-5-cyclopropyl-2-fluoro-N-(methylsulfonyl)benzamide The compound was synthesized as described in step 5 of Example 80. LCMS (ESI) Method A: RT=5.02 min, m/z: 479.0 [M+H]⁺. ¹H NMR (500 MHz, DMSO-d₆): δ 7.43-7.42 (m, 1H), 7.41-7.13 (m, 4H), 6.81 (d, J=12.5 Hz, 1H), 3.92 (d, J=6.0 Hz, 2H), 3.74 (s, 2H), 3.18 (s, 3H), 3.07-2.99 (m, 2H), 2.30-2.28 (m, 2H), 2.04-1.98 (m, 1H), 1.87-1.82 (m, 3H), 1.47-1.24 (m, 2H), 0.89-0.85 (m, 2H), 0.62-0.59 (m, 2H).

Example 89

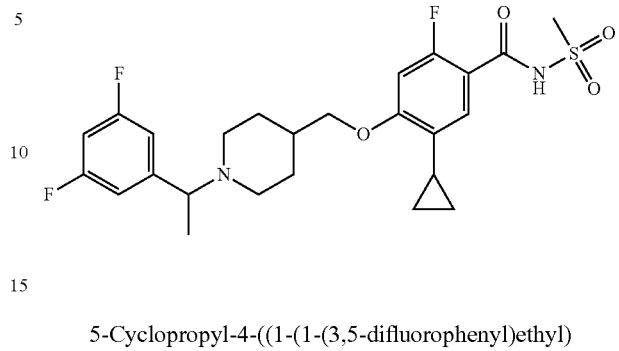

5-Cyclopropyl-4-((1-(1-(3,5-difluorophenyl)ethyl)piperidin-4-yl)methoxy)-2-fluoro-N-(methylsulfonyl)benzamide The compound was synthesized as described in Example 88. LCMS (ESI) Method A: RT=5.39 min, m/z: 511.0 [M+H]⁺. ¹H NMR (500 MHz, DMSO-d₆): δ 7.17-7.10 (m, 4H), 6.85 (d, J=13.0 Hz, 1H), 3.91 (d, J=6.0 Hz, 2H), 3.81-3.74 (m, 1H), 3.16 (s, 3H), 3.11-3.08 (m, 1H), 2.92-2.90 (m, 1H), 2.20-2.10 (m, 2H), 2.03-1.97 (m, 1H), 1.85-1.78 (m, 3H), 1.45-1.36 (m, 5H), 0.89-0.85 (m, 2H), 0.64-0.61 (m, 2H).

Example 90

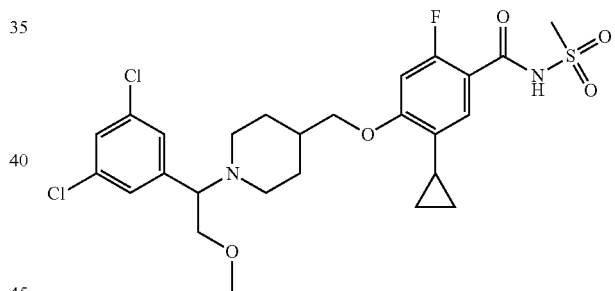

5-Cyclopropyl-4-((1-(1-(3,5-dichlorophenyl)-2-methoxyethyl)piperidin-4-yl)methoxy)-2-fluoro-N-(methylsulfonyl)benzamide

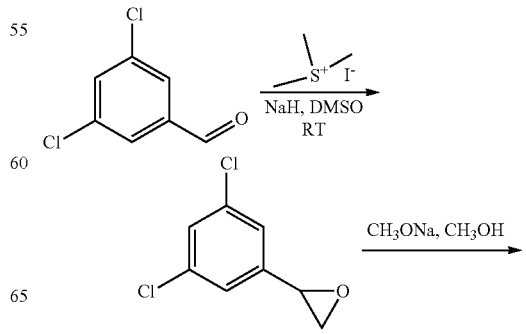

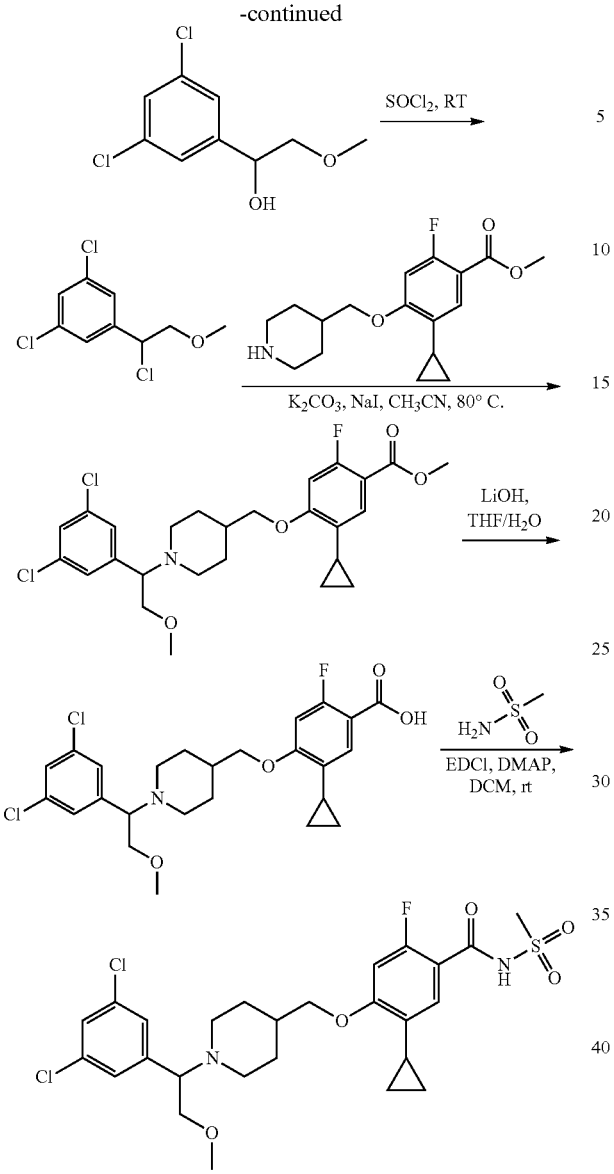

h. The mixture was then quenched with water (40 mL) and extracted with EtOAc (20 mL×3). The combined organic layers were washed with brine (40 mL), dried over anhydrous sodium sulfate, filtered and concentrated. The crude product was used in the next step without further purification.

Step 2

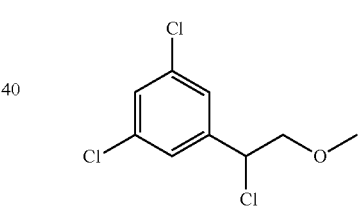

1-(3,5-Dichlorophenyl)-2-methoxyethanol 2-(3,5-Dichlorophenyl)oxirane (1 g, crude) was added to a solution of sodium (1.2 g, 53 mmol) in methanol (50 mL) and the mixture heated at 60° C. for 1 h. After cooling to room temperature, the mixture was diluted with water (50 mL) and extracted with EtOAc (20 mL×3). The combined organic layers were washed with brine (40 mL), dried over anhydrous sodium sulfate, filtered and concentrated. The residue was purified by silica gel chromatography (eluting with petroleum ether/EtOAc=50/1) to give the target compound (160 mg, 14%) as a pale yellow oil. LCMS (ESI) m/z: 219.0 [M−H]+.

Step 3

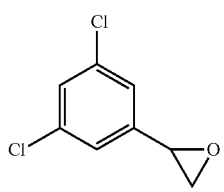 [SMILES: Clc1cc(Cl)cc(C2CO2)c1]

1,3-dichloro-5-(1-chloro-2-methoxyethyl)benzene

The compound was synthesized as described in step 2 of Example 80.

Step 4

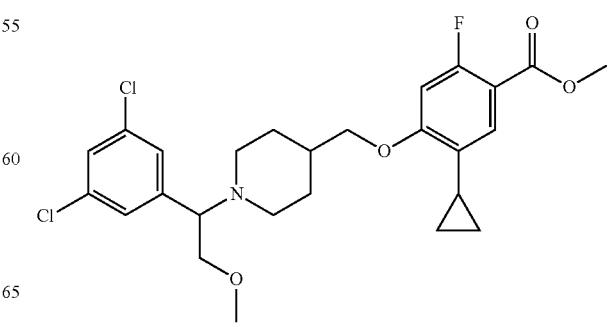

Step 1

2-(3,5-Dichlorophenyl)oxirane

Sodium hydride (280 mg, 6.9 mmol) was added to an ice-cooled solution of trimethylsulfonium iodide (1.4 g, 6.9 mmol) in DMSO (40 mL), After stirring at room temperature for 30 min, 3,5-dichlorobenzaldehyde (1 g, 5.7 mmol) was added and mixture stirred further at room temperature for 1

315

Methyl 5-cyclopropyl-4-((1-(1-(3,5-dichlorophenyl)-2-methoxyethyl)piperidin-4-yl)methoxy)-2-fluorobenzoate The compound was synthesized as described in step 5 of Example 88. LCMS (ESI) m/z: 510.1 [M+H]⁺.

Step 5

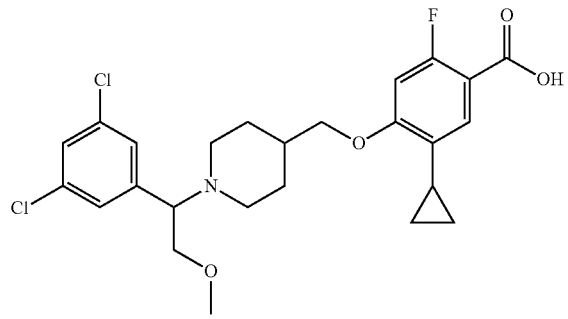 [SMILES: COCC(c1cc(Cl)cc(Cl)c1)N1CCC(COc2cc(F)c(C(=O)O)cc2C2CC2)CC1]

5-Cyclopropyl-4-((1-(1-(3,5-dichlorophenyl)-2-methoxyethyl)piperidin-4-yl)methoxy)-2-fluorobenzoic acid The compound was synthesized as described in step 6 of Example 88. LCMS (ESI) m/z: 496.1 [M+H]⁺.

Step 6

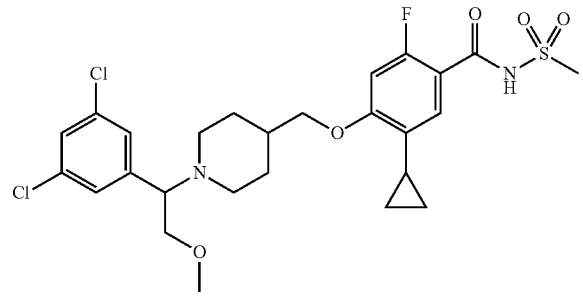 [SMILES: COCC(c1cc(Cl)cc(Cl)c1)N1CCC(COc2cc(F)c(C(=O)NS(C)(=O)=O)cc2C2CC2)CC1]

5-Cyclopropyl-4-((1-(1-(3,5-dichlorophenyl)-2-methoxyethyl)piperidin-4-yl)methoxy)-2-fluoro-N-(methylsulfonyl)benzamide The compound was synthesized as described in step 5 of Example 80. LCMS (ESI) Method A: RT=5.78 min, m/z: 572.9 [M+H]⁺. ¹H NMR (500 mHz, DMSO-d₆): δ 11.73 (brs, 1H), 7.50-7.49 (m, 1H), 7.39-7.38 (m, 2H), 7.16 (d, J=8.0 Hz, 1H), 6.82 (d, J=13.0 Hz, 1H), 3.88 (d, J=5.5 Hz, 2H), 3.73-3.65 (m, 3H), 3.22 (s, 3H), 3.14 (s, 3H), 2.99-2.97 (m, 1H), 2.81-2.79 (m, 1H), 2.11-2.07 (m, 1H), 2.02-1.95 (m, 2H), 1.79-1.71 (m, 3H), 1.38-1.28 (m, 2H), 0.89-0.85 (m, 2H), 0.63-0.60 (m, 2H).

316

Example 91

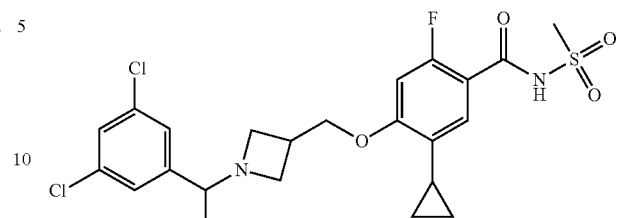

5-Cyclopropyl-4-((1-(1-(3,5-dichlorophenyl)-2-methoxyethyl)azetidin-3-yl)methoxy)-2-fluoro-N-(methylsulfonyl)benzamide

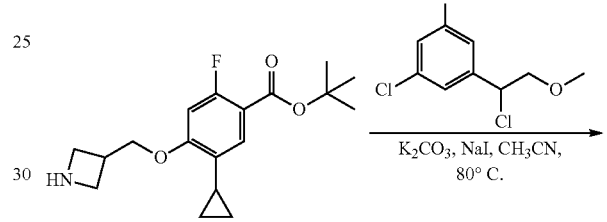

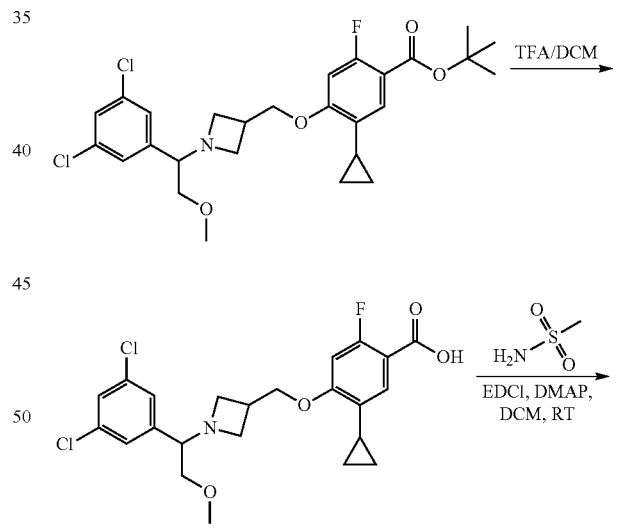

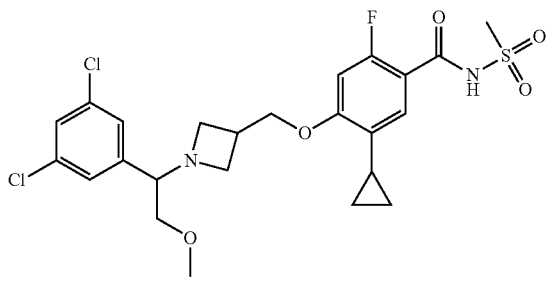

Step 1

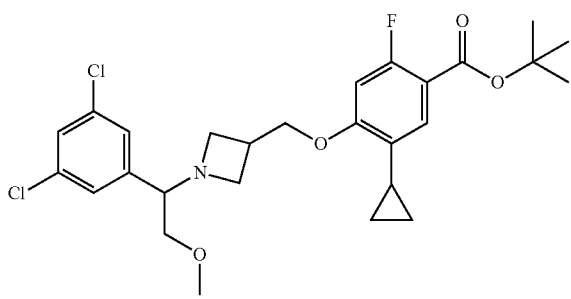 [SMILES: COCC(c1cc(Cl)cc(Cl)c1)N1CC(COc2cc(F)c(C(=O)OC(C)(C)C)cc2C2CC2)C1]

tert-Butyl 5-cyclopropyl-4-((1-(1-(3,5-dichlorophenyl)-2-methoxyethyl)-azetidin-3-yl)methoxy)-2-fluorobenzoate The compound was synthesized as described in step 3 of Example 80. LCMS (ESI) m/z: 524.0 [M+H]$^+$.

Step 2

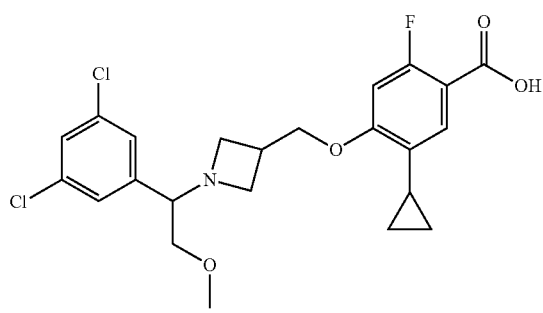 [SMILES: COCC(c1cc(Cl)cc(Cl)c1)N1CC(COc2cc(F)c(C(=O)O)cc2C2CC2)C1]

5-Cyclopropyl-4-((1-(1-(3,5-dichlorophenyl)-2-methoxyethyl)azetidin-3-yl)methoxy)-2-fluorobenzoic acid The compound was synthesized as described in step 4 of Example 80. LCMS (ESI) m/z: 467.9 [M+H]$^+$.

Step 3

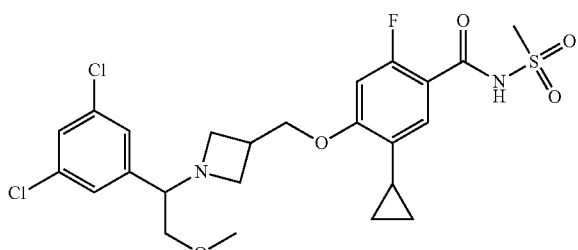

5-Cyclopropyl-4-((1-(1-(3,5-dichlorophenyl)-2-methoxyethyl)azetidin-3-yl)methoxy)-2-fluoro-N-(methylsulfonyl)benzamide The compound was synthesized as described in step 5 of Example 80. LCMS (ESI) Method A: RT=5.26 min, m/z: 544.8 [M+H]$^+$. $^1$H NMR (500 MHz, DMSO-d$_6$): δ 7.50 (m, 1H), 7.35 (m, 2H), 7.17 (d, J=8.0 Hz, 1H), 6.89 (d, J=13.0 Hz, 1H), 4.16 (d, J=6.0 Hz, 2H), 3.60 (m, 1H), 3.48-3.45 (m, 1H), 3.42-3.32 (m, 3H), 3.20 (s, 3H), 3.18 (s, 3H), 3.15-3.12 (m, 1H), 3.09-3.07 (m, 1H), 2.87-2.85 (m, 1H), 2.04-2.00 (m, 1H), 0.89-0.87 (m, 2H), 0.64-0.63 (m, 2H).

Example 92

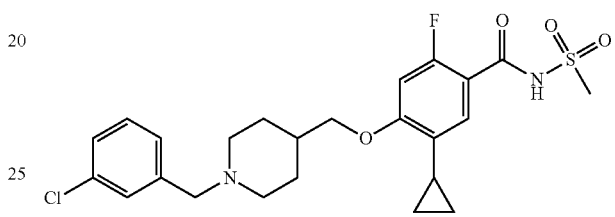

4-((1-(3-Chlorobenzyl)piperidin-3-yl)methoxy)-5-cyclopropyl-2-fluoro-N-(methylsulfonyl)benzamide The compound was synthesized as described in Example 88. LCMS (ESI) Method A: RT=5.35 min, m/z 494.9[M+H]$^+$. $^1$H NMR (500 MHz, DMSO-d$_6$): δ 7.42-7.31 (m, 4H), 7.19-7.17 (d, J=8.5 Hz, 1H), 6.81-6.79 (d, J=13.0 Hz, 1H), 3.92-3.91 (m, 2H), 3.68 (br s, 2H), 3.04-2.96 (m, 5H), 2.24-2.22 (m, 2H), 2.02-1.99 (m, 1H), 1.84-1.81 (d, J=12.5 Hz, 3H), 1.43-1.40 (m, 2H), 0.89-0.86 (m, 2H), 0.61-0.58 (m, 2H).

Example 93

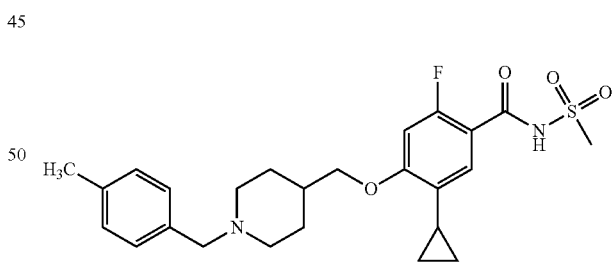

5-Cyclopropyl-2-fluoro-4-((1-(4-methylbenzyl)piperidin-4-yl)methoxy)-N-(methylsulfonyl)benzamide The compound was synthesized as described in Example 88. LCMS (ESI) Method A: RT=4.88 min, m/z 475.0 [M+H]$^+$. $^1$H NMR (500 MHz, DMSO-d$_6$): δ 7.31-7.29 (d, J=7.5 Hz, 2H), 7.23-7.18 (m, 3H), 6.79-6.77 (d, J=12.5 Hz, 1H), 3.92 (m, 4H), 3.16-3.14 (m, 2H), 3.00 (s, 3H), 2.50 (s, 2H), 2.31 (s, 3H), 2.01-1.87 (m, 4H), 1.50-1.48 (m, 2H), 0.88-0.86 (m, 2H), 0.59-0.58 (m, 2H).

Example 94

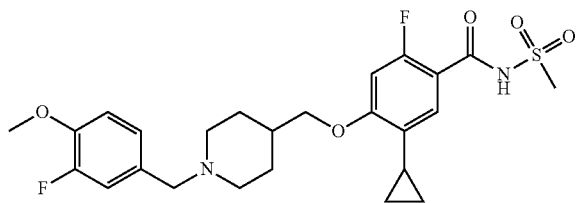 [SMILES: COc1ccc(CN2CCC(COc3cc(F)c(C(=O)NS(C)(=O)=O)cc3C3CC3)CC2)cc1F]

5-Cyclopropyl-2-fluoro-4-((1-(3-fluoro-4-methoxy-benzyl)piperidin-4-yl)methoxy)-N-(methylsulfonyl)benzamide The compound was synthesized as described in Example 88. LCMS (ESI) Method A: RT=4.70 min, m/z 509.0[M+H]$^+$. $^1$H NMR (500 MHz, DMSO-d$_6$): δ 7.29-7.27 (d, J=12.5 Hz, 1H), 7.19-7.18 (d, J=6.0 Hz, 3H), 6.81-6.78 (d, J=13.0 Hz, 1H), 3.92 (m, 2H), 3.86 (m, 5H), 3.14-3.12 (m, 2H), 3.04 (s, 3H), 2.50 (s, 2H), 2.00-1.86 (m, 4H), 1.50-1.48 (m, 2H), 0.88-0.86 (m, 2H), 0.60-0.59 (m, 2H).

Example 95

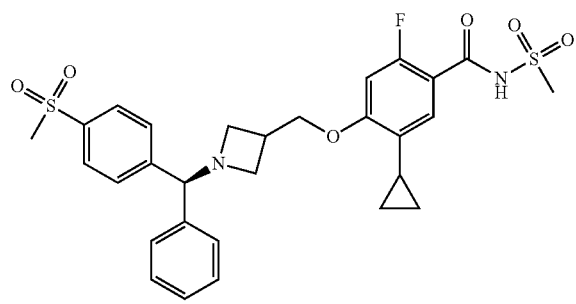 [SMILES: CS(=O)(=O)NC(=O)c1cc(C2CC2)c(OCC2CN([C@@H](c3ccccc3)c3ccc(S(C)(=O)=O)cc3)C2)cc1F]

(S)-5-Cyclopropyl-2-fluoro-N-(methylsulfonyl)-4-((1-((4-(methylsulfonyl)phenyl)(phenyl)methyl)azetidin-3-yl)methoxy)benzamide The compound was synthesized as described in Example 81. LCMS (ESI) Method A: RT=4.99 min, m/z 587.3 [M+H]$^+$. $^1$H NMR (500 MHz, MeOD-d$_4$): δ 7.90 (d, J=8.0 Hz, 2H), 7.73 (d, J=8.5 Hz, 2H), 7.45 (d, J=7.0 Hz, 2H), 7.37-7.25 (m, 3H), 7.23 (d, J=7.0 Hz, 1H), 6.76 (d, J=12.5 Hz, 1H), 4.66 (s, 1H), 4.20 (d, J=6.0 Hz, 2H), 3.47-3.33 (m, 2H), 3.24-3.16 (m, 5H), 3.09 (s, 3H), 3.03-3.00 (m, 1H), 2.10 (t, J=10.5 Hz, 1H), 0.94-0.90 (m, 2H), 0.70-0.67 (m, 2H).

Example 96

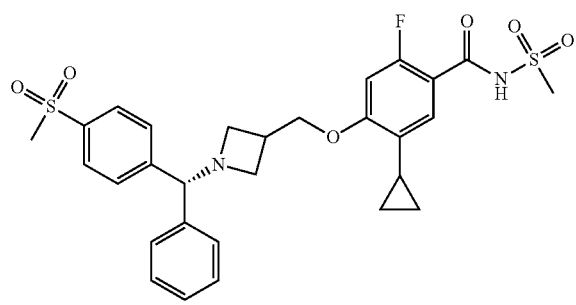 [SMILES: CS(=O)(=O)NC(=O)c1cc(C2CC2)c(OCC2CN([C@H](c3ccccc3)c3ccc(S(C)(=O)=O)cc3)C2)cc1F]

(R)-5-Cyclopropyl-2-fluoro-N-(methylsulfonyl)-4-((1-((4-(methylsulfonyl)phenyl)(phenyl)methyl)azetidin-3-yl)methoxy)benzamide The compound was synthesized as described in Example 81. LCMS (ESI) Method A: RT=4.99 min, m/z 587.2 [M+H]$^+$. $^1$H NMR (500 MHz, MeOD-d$_4$): δ 7.91 (d, J=8.5 Hz, 2H), 7.74 (d, J=8.0 Hz, 2H), 7.45 (d, J=7.0 Hz, 2H), 7.34-7.31 (m, 3H), 7.26 (d, J=7.0 Hz, 1H), 6.85 (d, J=13.0 Hz, 1H), 4.71 (s, 1H), 4.25 (d, J=6.0 Hz, 2H), 3.50-3.43 (m, 2H), 3.34-3.21 (m, 5H), 3.09 (s, 3H), 3.06-3.04 (m, 1H), 2.10 (t, J=10.5 Hz, 1H), 0.97-0.93 (m, 2H), 0.70-0.67 (m, 2H).

Example 97

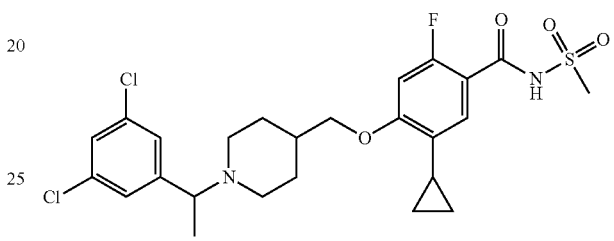

5-Cyclopropyl-4-((1-(1-(3,5-dichlorophenyl)ethyl)piperidin-4-yl)methoxy)-2-fluoro-N-(methylsulfonyl)benzamide The compound was synthesized as described in Example 88. LCMS (ESI) Method A: RT=6.17 min, m/z 543.0 [M+H]$^+$. $^1$H NMR (500 MHz, MeOD-d$_4$): δ 7.51 (s, 3H), 7.35 (d, J=8.5 Hz, 1H), 6.63 (d, J=12.5 Hz, 1H), 4.14 (s, 1H), 3.82 (s, 2H), 3.54 (d, J=10.0 Hz, 1H), 3.21 (d, J=12.5 Hz, 4H), 2.66-2.62 (m, 2H), 2.09-2.00 (m, 4H), 1.69-1.59 (m, 5H), 0.88 (m, 2H), 0.63 (m, 2H).

Example 98

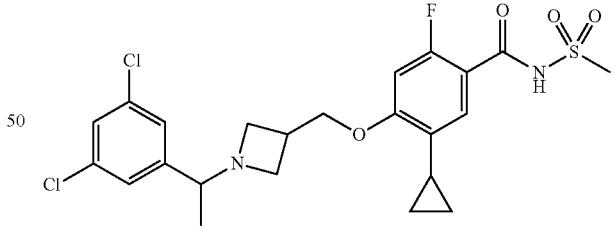

5-Cyclopropyl-4-((1-(1-(3,5-dichlorophenyl)ethyl)azetidin-3-yl)methoxy)-2-fluoro-N-(methylsulfonyl)benzamide The compound was synthesized as described its Example 80. LCMS (ESI) Method A: RT=5.51 min, m/z 515.0[M+H]$^+$. $^1$H NMR (500 MHz, MeOD-d$_4$): δ 7.43 (s, 1H), 7.38-7.35 (m, 3H), 6.77 (d, J=13.0 Hz, 1H), 4.20-4.17 (m, 2H), 3.79 (s, 2H), 3.58 (d, J=7.0 Hz, 1H), 3.49 (d, J=4.0 Hz, 1H), 3.25 (s, 1H), 3.11 (t, J=13.0 Hz, 1H), 2.09-2.06 (m, 1H), 1.36 (d, J=6.5 Hz, 3H), 0.94 (m, 2H), 0.68 (m, 2H).

Example 99

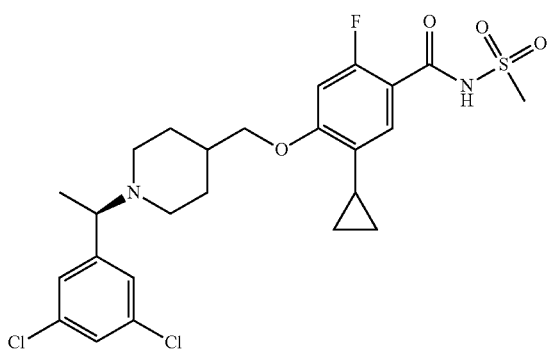 [SMILES: C[C@H](c1cc(Cl)cc(Cl)c1)N1CCC(COc2cc(F)c(C(=O)NS(C)(=O)=O)cc2C2CC2)CC1]

(R)-5-Cyclopropyl-4-((1-(1-(3,5-dichlorophenyl)
ethyl)piperidin-4-yl)methoxy)-2-fluoro-N-(methyl-
sulfonyl)-benzamide The compound was synthesized as described in Example 88. The enantiomer was separated by chiral SFC from the racemate. Chiral HPLC (column: AD-3, 4.6×150 mm, 3 μm; mobile Phase: n-hexane (0.1% DEA)/EtOH 0.1% DEA)=90/10; flow: 1 mL/min; column temperature: 40° C.; RT=6.59 min). LCMS (ESI) Method A: RT=6.13 min, m/z 543.0[M+H]$^+$. $^1$H NMR (500 MHz, MeOD-d$_4$): δ 7.51 (s, 1H), 7.40 (d, J=1.5 Hz, 2H), 7.17 (d, J=8.5 Hz, 1H), 6.82 (d, J=12.5 Hz, 1H), 3.91 (d, J=5.5 Hz, 2H), 3.70 (t, J=4.0 Hz, 1H), 3.32 (s, 3H), 3.03 (d, J=8.5 Hz, 1H), 2.86 (t, J=12.0 Hz; 1H), 2.05-1.99 (m, 3H), 1.83-1.76 (m, 3H), 1.40-1.33 (m, 5H), 0.89-0.86 (m, 2H), 0.63-0.59 (m, 2H).

Example 109

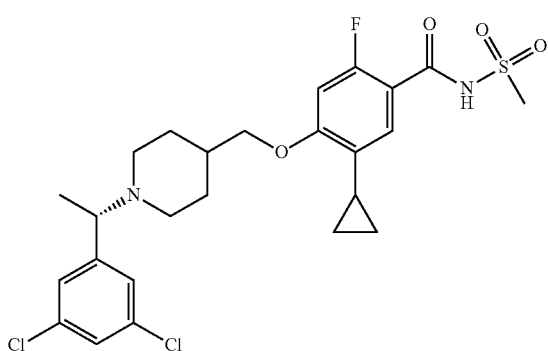 [SMILES: C[C@@H](c1cc(Cl)cc(Cl)c1)N1CCC(COc2cc(F)c(C(=O)NS(C)(=O)=O)cc2C2CC2)CC1]

(S)-5-Cyclopropyl-4-((1-(1-(3,5-dichlorophenyl)
ethyl)piperidin-4-yl)methoxy)-2-fluoro-N-(methyl-
sulfonyl)benzamide The compound was synthesized as described in Example 99. Chiral HPLC (column: AD-3, 4.6×150 mm, 3 μm; mobile Phase: n-hexane (0.1% DEA)/EtOH 0.1% DEA)=90/10; flow: 1 mL/min; column temperature: 40° C.; RT=9.38 mm). LCMS (ESI) Method A: RT=6.06 min, m/z 542.9[M+H]$^+$. $^1$H NMR (500 MHz, MeOD-d$_4$): δ 7.50 (s, 1H), 7.39 (s, 2H), 7.19 (d, J=8.5 Hz, 1H), 6.78 (d, J=12.5 Hz, 1H), 3.89 (d, J=5.5 Hz, 2H), 3.65 (s, 1H), 3.03-2.99 (m, 4H), 2.84 (d, J=11.0 Hz, 1H), 2.04-1.98 (m, 3H), 1.82-1.75 (m, 3H), 1.38-1.31 (m 5H), 0.88-0.85 (m, 2H), 0.61-0.57 (m, 2H).

Example 101

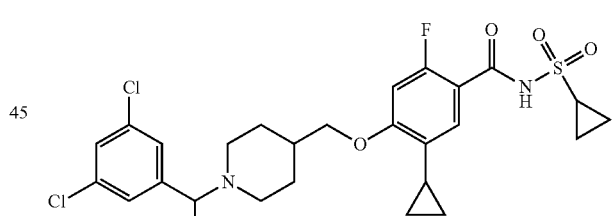

5-Cyclopropyl-4-((1-(1-(3,5-dichlorophenyl)ethyl)
piperidin-4-yl)methoxy)-N-(ethylsulfonyl)-2-fluo-
robenzamide The compound was synthesized as described in Example 88. LCMS (ESI) Method A: RT=6.22 min, m/z 557.0 [M+H]$^+$. $^1$H NMR (500 MHz, DMSO-d$_6$): δ 7.52 (s, 1H), 7.42 (s, 2H), 7.14 (d, J=9.0 Hz, 1H), 6.89 (d, J=12.5 Hz, 1H), 3.92 (d, J=6.0 Hz, 2H), 3.75 (s, 1H), 3.38 (d, J=7.0 Hz, 2H), 3.06 (d, J=10.0 Hz, 1H), 2.89 (d, J=9.5 Hz, 1H), 2.12-1.99 (m, 3H), 1.84-1.77 (m, 3H), 1.40-1.35 (m, 5H), 1.21 (d, J=14.5 Hz, 3H), 0.89-0.85 (m, 2H), 0.65-0.62 (m, 2H).

Example 162

5-Cyclopropyl-N-(cyclopropylsulfonyl)-4-((1-(1-(3,
5-dichlorophenyl)-ethyl)piperidin-4-yl)methoxy)-2-
fluorobenzamide The compound was synthesized as described in Example 88. LCMS (ESI) Method A: RT=6.26 min, m/z 569.0 [M+H]$^+$. $^1$H NMR (500 MHz, DMSO-d$_6$) δ 7.52 (s, 1H), 7.41 (s, 2H), 7.14 (d, J=8.0 Hz, 1H), 6.90 (d, J=13.0 Hz, 1H), 3.93 (d, J=5.5 Hz, 2H), 3.73 (s, 1H), 3.06-3.02 (m, 2H), 2.89 (d, J=8.5 Hz, 1H), 2.11-1.99 (m, 3H), 1.84-1.77 (m, 3H), 1.41-1.34 (m, 5H), 1.06-1.01 (m, 4H), 0.90-0.86 (m, 2H), 0.65-0.62 (m, 2H).

Example 103

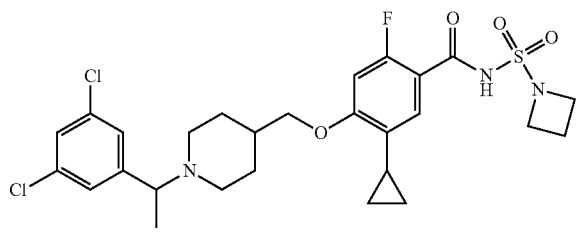 [SMILES: CC(c1cc(Cl)cc(Cl)c1)N1CCC(COc2cc(F)c(C(=O)NS(=O)(=O)N3CCC3)cc2C2CC2)CC1]

N-(Azetidin-1-ylsulfonyl)-5-cyclopropyl-4-((1-(1-(3, 5-dichlorophenyl)-ethyl)piperidin-4-yl)methoxy)-2-fluorobenzamide The compound was synthesized as described in Example 88. LCMS (ESI) Method A: RT=6.34 min: m/z 583.9 [M+H]$^+$. $^1$H NMR (500 MHz, DMSO-d$_6$): δ 7.48 (s, 1H), 7.38 (d, J=1.5 Hz, 2H), 7.19 (d, J=7.5 Hz, 1H), 6.81 (d, J=12.5 Hz, 1H), 3.88 (d, J=22.5 Hz, 6H), 3.61 (d, J=6.5 Hz, 1H), 2.97 (d, J=10.5 Hz, 1H), 2.81 (d, J=10.0 Hz, 1H), 2.08-1.96 (m, 5H), 1.82-1.74 (m, 3H), 1.37-1.30 (m, 5H), 0.88 (m, 2H), 0.61 (m, 2H).

Example 104

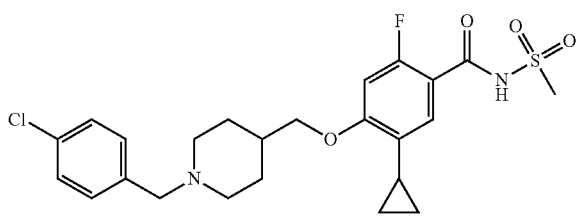 [SMILES: CS(=O)(=O)NC(=O)c1cc(C2CC2)c(OCC2CCN(Cc3ccc(Cl)cc3)CC2)cc1F]

4-((1-(4-Chlorobenzyl)piperidin-4-yl)methoxy)-5-cyclopropyl-2-fluoro-N-(methylsulfonyl)benzamide The compound was synthesized as described in Example 88. LCMS (ESI) Method A: RT=5.29 min, m/z 494.9 [M+H]$^+$. $^1$H NMR (500 MHz, DMSO-d$_6$): δ 7.41 (d, J=8.0 Hz, 2H), 7.36 (d, J=8.5 Hz, 2H), 7.20 (t, J=8.5 Hz, 1H), 6.74 (d, J=13.0 Hz, 1H), 3.90 (d, J=5.5 Hz, 2H), 3.61 (s, 2H), 2.93 (d, J=9.0 Hz, 5H), 2.16 (s, 2H), 1.99 (d, J=5.5 Hz, 1H), 1.80 (d, J=11.0 Hz, 3H), 1.40 (d, J=11.0 Hz, 2H), 0.87-0.86 (m, 2H), 0.56 (m, 2H).

Example 105

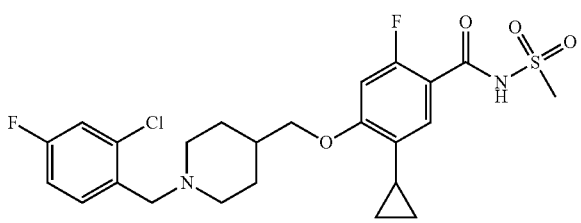 [SMILES: CS(=O)(=O)NC(=O)c1cc(C2CC2)c(OCC2CCN(Cc3ccc(F)cc3Cl)CC2)cc1F]

4-((1-(2-Chloro-4-fluorobenzyl)piperidin-4-yl)methoxy)-5-cyclopropyl-2-fluoro-N-(methylsulfonyl)benzamide The compound was synthesized as described in Example 88. LCMS (ESI) Method A: RT=5.69 min m/z 513.0 [M+H]$^+$. $^1$H NMR (500 MHz, DMSO-d$_6$): δ 7.57 (t, J=15.0 Hz, 1H), 7.45 (t, J=9.0 Hz, 1H), 7.27-7.24 (m, 1H), 7.16 (d, J=8.5 Hz, 1H), 6.89 (d, J=12.5 Hz, 1H), 3.95 (d, J=5.5 Hz, 2H), 3.70 (s, 2H), 3.21 (s, 3H), 2.97 (d, J=10.5 Hz, 2H), 2.28 (t, J=22 Hz, 2H), 2.02 (t, J=10.0 Hz, 1H), 1.87-1.81 (m, 3H), 1.41 (d, J=11.5 Hz, 2H), 0.89 (m, 2H), 0.64 (m, 2H).

Example 106

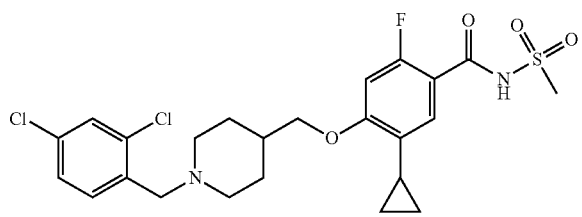

5-Cyclopropyl-4-((1-(2,4-dichlorobenzyl)piperidin-4-yl)methoxy)-2-fluoro-N-(methylsulfonyl)benzamide The compound was synthesized as described in Example 88. LCMS (ESI) Method A: RT=6.03 min, m/z 528.8[M+H]$^+$. $^1$H NMR (500 MHz, DMSO-d$_6$): δ 7.61 (s, 1H), 7.54 (d, J=8.0 Hz, 1H), 7.45 (t, J=9.0 Hz, 1H), 7.15 (d, J=8.5 Hz, 1H), 6.90 (d, J=13.0 Hz, 1H), 3.95 (d, J=6.0 Hz, 2H), 3.67 (s, 2H), 3.23 (s, 3H), 2.94 (d, J=10.5 Hz, 2H), 2.24 (t, J=22 Hz, 2H), 2.03-1.99 (m, 1H), 1.86-1.80 (m, 3H), 1.13-1.37 (m, 2H), 0.89 (m, 2H), 0.65 (m, 2H).

Example 107

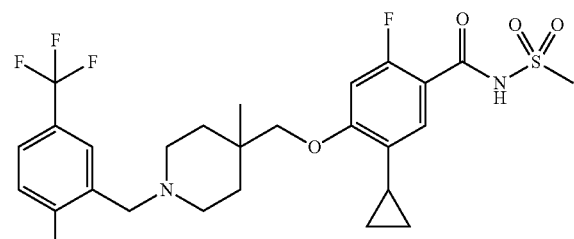

4-((1-(2,5-bis(trifluoromethyl)benzyl)-4-methylpiperidin-4-yl)methoxy)-5-cyclopropyl-2-fluoro-N-(methylsulfonyl)benzamide The compound was prepared in a similar manner to Example 73 starting from tert-butyl 4-((2-cyclopropyl-5-fluoro-4-((methylsulfonyl)carbamoyl)phenoxy)methyl)-4-methylpiperidin-1-carboxylate (Example 73 step 1-2) and 2,5-bis(trifluoromethyl)benzaldehyde. LCMS (Method F):

RT=4.76 min, m/z: 577.2 [M+H]⁺. ¹H NMR (400 MHz, DMSO-d6) δ 11.76 (s, 1H), 8.15 (d, J=1.7 Hz, 1H), 7.96 (d, J=8.2 Hz, 1H), 7.85 (dd, J=8.3, 1.5 Hz, 1H), 7.18 (d, J=8.3 Hz, 1H), 6.96 (d, J=12.9 Hz, 1H), 3.86 (s, 2H), 3.77 (s, 2H), 2.64-2.53 (m, 2H), 2.47-2.36 (m, 2H), 2.08-1.98 (m, 1H), 1.81-1.68 (m, 2H), 1.52-1.39 (m, 2H), 1.09 (s, 3H), 0.94-0.83 (m, 2H), 0.71-0.62 (m, 2H).

Example 108

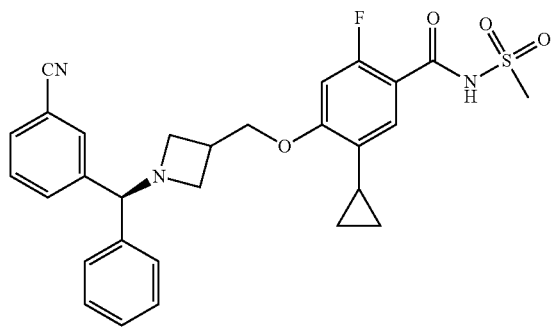 [SMILES: CS(=O)(=O)NC(=O)c1cc(C2CC2)c(OCC2CN([C@@H](c3ccccc3)c3cccc(C#N)c3)C2)cc1F]

(S)-4-((1-((3-Cyanophenyl)(phenyl)methyl)azetidin-3-yl)methoxy)-5-cyclopropyl-2-fluoro-N-(methylsulfonyl)benzamide The compound was synthesized as described in Example 81. Chiral HPLC (column: OJ-H, 4.6×250 mm, 5 μm; mobile Phase: A: supercritical CO₂, B: MeOH, A:B=75:25; (low: 2.25 mL/min; column temperature: 36° C.; RT=6.85 min). LCMS (ESI) Method A: RT=5.66, m/z: 534.2 [M+H⁺]. ¹H NMR (500 MHz, MeOD-d4): δ 7.82 (s, 1H), 7.77 (d, J=8.0 Hz, 1H), 7.60 (d, J=7.5 Hz, 1H), 7.52-7.49 (s, 1H), 7.45-7.43 (m, 2H), 7.35-7.32 (m, 3H), 7.27-7.24 (m, 1H), 6.85 (d, J=13.0 Hz, 1H), 4.63 (s, 1H), 4.24 (d, J=6.5 Hz, 2H), 3.47-3.43 (m, 2H), 3.33 (s, 3H), 3.23-3.20 (m, 2H), 3.04-3.02 (m, 1H), 2.13-2.10 (m, 1H), 0.97-0.94 (m, 2H), 0.70-0.67 (m, 2H).

Example 109

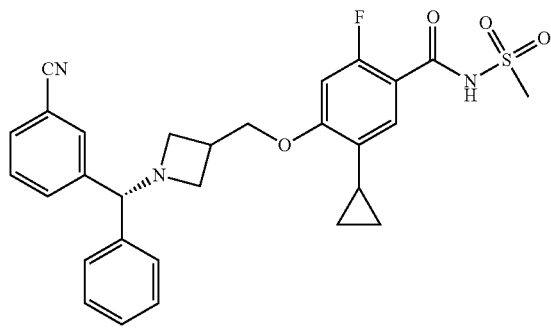 [SMILES: CS(=O)(=O)NC(=O)c1cc(C2CC2)c(OCC2CN([C@H](c3ccccc3)c3cccc(C#N)c3)C2)cc1F]

(R)-4-((1-((3-Cyanophenyl)(phenyl)methyl)azetidin-3-yl)methoxy)-5-cyclopropyl-2-fluoro-N-(methylsulfonyl)benzamide The compound was synthesized as described in Example 81. Chiral HPLC (column: OJ-H, 4.6×250 mm, 5 μm; mobile Phase: A: supercritical CO₂, B: MeOH, A:B=75:25; flow: 2.25 mL/min; column temperature: 36° C.; RT=8.24 mm). LCMS (ESI) Method A: RT=534 min, m/z: 534.3 [M+H⁺]. ¹H NMR (500 MHz, MeOD-d4): δ 7.82 (s, 1H), 7.77 (d, J=8.5 Hz, 1H), 7.60 (d, J=7.5 Hz, 1H), 7.52-7.49 (m, 1H), 7.45-7.43 (m, 2H), 7.35-7.32 (m, 3H), 7.27-7.24 (m, 1H), 6.85 (d, J=12.5 Hz, 1H), 4.63 (s, 1H), 4.24 (d, J=6.0 Hz, 2H), 3.47-3.41 (m, 2H), 3.33 (s, 3H), 3.23-3.20 (m, 2H), 3.04-3.02 (m, 1H), 2.12-2.09 (m, 1H), 0.96-0.94 (m, 2H), 0.69-0.68 (m, 2H).

Example 110

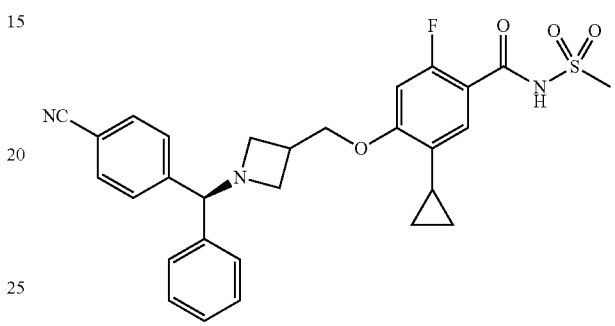

(S)-4-((1-((4-Cyanophenyl)(phenyl)methyl)azetidin-3-yl)methoxy)-5-cyclopropyl-2-fluoro-N-(methylsulfonyl)benzamide The compound was synthesized as described in Example 81. Chiral HPLC (column: AD-H, 4.6×250 mm, 5 μm; mobile Phase: A: supercritical CO₂, B: MeOH (0.1% DEA), A:B=65:35; flow: 1.95 mL/min; column temperature: 40° C.; RT=4.13 mm). LCMS (ESI) Method A: RT=5.64 mm, m/z: 534.2 [M+H⁺]. ¹H NMR (500 MHz, MeOD-d4): δ 7.69-7.64 (m, 4H), 7.43 (d, J=7.0 Hz, 2H), 7.34-7.31 (m, 3H), 7.26-7.23 (m, 1H), 6.84 (d, J=13.0 Hz, 1H), 4.65 (s, 1H), 4.23 (d, J=6.0 Hz, 2H), 3.48-3.40 (m, 2H), 3.31 (s, 3H), 3.25-3.18 (m, 2H), 3.05-3.01 (m, 1H), 2.12-2.08 (m, 1H), 0.97-0.93 (m, 2H), 0.70-0.67 (m, 2H).

Example 111

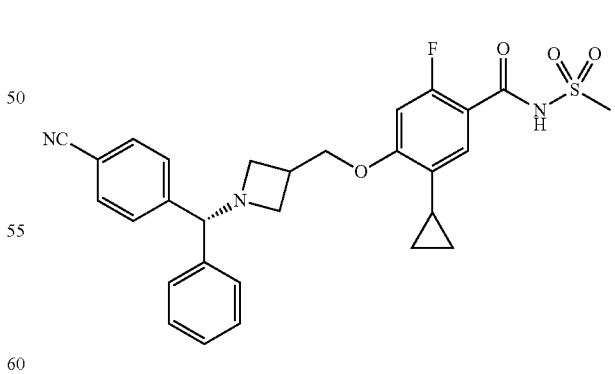

(R)-4-((1-((4-Cyanophenyl)(phenyl)methyl)azetidin-3-yl)methoxy)-5-cyclopropyl-2-fluoro-N-(methylsulfonyl)benzamide The compound was synthesized as described in Example 81. Chiral HPLC (column: AD-H, 4.6×250 mm, 5 μm;

mobile Phase: A: supercritical $CO_2$, B: MeOH (0.1% DEA), A:B=65:35; flow: 1.95 mL/min; column temperature: 40° C.; RT=6.36 min). LCMS (ESI) Method. A: RT=5.64 min, m/z: 534.2 [M+H$^+$]. $^1$H NMR (500 MHz, MeOD-d4): δ 7.69-7.64 (m, 4H), 7.43 (d, J=7.5 Hz, 2H), 7.34-7.30 (m, 3H), 7.26-7.23 (m, 1H), 6.82 (d, J=13.0 Hz, 1H), 4.63 (s, 1H), 4.22 (d, J=5.5 Hz, 2H), 3.47-3.39 (m, 2H), 3.29 (s, 3H), 3.24-3.16 (m, 2H), 3.95-3.00 (m, 1H), 2.13-2.07 (m, 1H), 0.96-0.92 (m, 2H), 0.70-0.66 (m, 2H).

Example 112

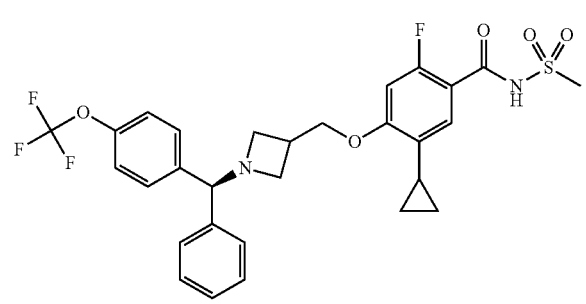 [SMILES: CS(=O)(=O)NC(=O)c1cc(C2CC2)c(OCC2CN([C@@H](c3ccccc3)c3ccc(OC(F)(F)F)cc3)C2)cc1F]

(S)-5-Cyclopropyl-2-fluoro-N-(methylsulfonyl)-4-((1-(phenyl(4-(trifluoromethoxy)phenyl)methyl)azetidin-3-yl)methoxy)benzamide The compound was synthesized as described in Example 81. Chiral HPLC (column: OJ-H, 4.6×250 mm, 5 μm; mobile Phase: A: supercritical $CO_2$, B: MeOH (0.1% DEA), A:B=80:20; flow: 2.4 mL/min; column temperature: 40° C.; RT=3.62 min). LCMS (ESI) Method A: RT=6.36 min, m/z: 593.2 [M+H$^+$]. $^1$H NMR (500 MHz, MeOD-d4): δ 7.55-7.53 (m, 2H), 7.44-7.42 (m, 2H), 7.34-7.31 (m, 3H), 7.26-7.22 (m, 3H), 6.80 (d, J=12.0 Hz, 1H), 4.63 (s, 1H), 4.21 (d, J=6.0 Hz, 2H), 3.47-3.45 (m, 2H), 3.33-3.31 (m, 5H), 3.10-3.00 (m, 1H), 2.10-2.09 (m, 1H), 0.95-0.92 (m, 2H), 0.68-0.67 (m, 2H).

Example 113

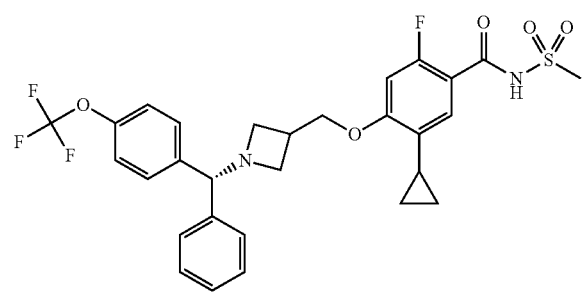 [SMILES: CS(=O)(=O)NC(=O)c1cc(C2CC2)c(OCC2CN([C@H](c3ccccc3)c3ccc(OC(F)(F)F)cc3)C2)cc1F]

(R)-5-Cyclopropyl-2-fluoro-N-(methylsulfonyl)-4-((1-(phenyl(4-(trifluoromethoxy)phenyl)methyl)azetidin-3-yl)methoxy)benzamide The compound was synthesized as described in Example 81. Chiral HPLC (column: OJ-H, 4.6×250 mm, 5 μm; mobile Phase: A: supercritical $CO_2$, B: MeOH (0.1% DEA), A:B=80:20; flow: 2.4 mL/min; column temperature: 40° C.; RT=4.11 min). LCMS (ESI) Method B: RT=6.38 min, m/z: 593.2 [M+H$^+$]. $^1$H NMR (500 MHz, MeOD-d4): δ 7.55-7.53 (m, 2H), 7.44-7.42 (m, 2H), 7.36-7.32 (m, 3H), 7.27-7.23 (m, 3H), 6.84 (d, J=12.5 Hz, 1H), 4.71 (s, 1H), 4.23 (d, J=6.0 Hz, 2H), 3.53-3.51 (m, 2H), 3.40-3.20 (m, 5H), 3.08-3.07 (m, 1H), 2.12-2.09 (m, 1H), 0.97-0.93 (m, 2H), 0.70-0.67 (m, 2H).

Example 114

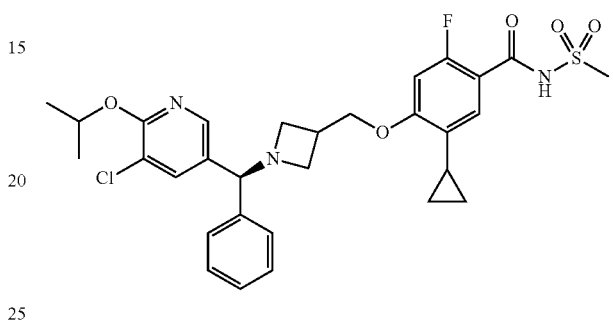

(S)-4-((1-((5-Chloro-6-isopropoxypyridin-3-yl)(phenyl)methyl)azetidin-3-yl)methoxy)-5-cyclopropyl-2-fluoro-N-(methylsulfonyl)benzamide The compound was synthesized as described in Example 81. Chiral HPLC (column: OJ-H, 4.6×250 mm, 5 μm; mobile Phase: A: supercritical $CO_2$, B: MeOH (0.1% DEA), A:B=75:25; flow: 2.25 mL/min; column temperature: 40° C.; RT=4.49 min). LCMS (ESI) Method. A: RT=5.88 min, m/z: 602.1 [M+H$^+$]. $^1$H NMR (500 MHz, MeOD-d4): δ 8.04 (d, J=5.0 Hz, 1H), 7.46 (m, 2H), 7.36-7.25 (m, 5H), 6.84 (d, J=13.0 Hz, 1H), 5.34-5.29 (m, 1H), 5.01 (s, 1H), 4.19 (d, J=5.5 Hz, 2H), 3.53-3.50 (m, 1H), 3.30-3.28 (m, 5H), 3.15-3.12 (m, 1H), 3.04-3.01 (m, 1H), 2.19-2.15 (m, 1H), 1.36 (d, J=6.5 Hz, 3H), 1.32 (d, J=6.5 Hz, 3H), 1.01-0.97 (m, 2H), 0.71-0.70 (m, 2H).

Example 115

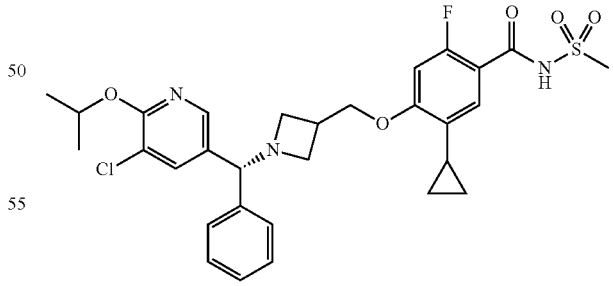

(R)-4-((1-((5-Chloro-6-isopropoxypyridin-3-yl)(phenyl)methyl)azetidin-3-yl)methoxy)-5-cyclopropyl-2-fluoro-N-(methylsulfonyl)benzamide The compound was synthesized as described in Example 81. Chiral HPLC (column: OJ-H, 4.6×250 mm, 5 μm; mobile Phase: A: supercritical $CO_2$, B: MeOH (0.1% DEA), A:B=75:25; flow: 2.25 mL/min; column temperature: 40° C.; RT=4.49 min). LCMS (ESI) Method A: RT=5.56 min, m/z: 602.2 [M+H$^+$]. $^1$H NMR (500 MHz, MeOD-d4): δ 8.04 (d, J=5.0 Hz, 1H), 7.46 (m, 2H), 7.36-7.25 (m, 5H), 6.85 (d, J=13.0 Hz, 1H), 5.34-5.30 (m, 1H), 5.01 (s, 1H), 4.19 (d, J=5.0 Hz, 2H), 3.53-3.50 (m, 1H), 3.32-3.30 (m, 5H), 3.15-3.12 (m, 1H), 3.04-3.01 (m, 1H), 2.19-2.15 (m, 1H), 1.36 (d, J=6.5 Hz, 3H), 1.32 (d, J=6.5 Hz, 3H), 1.01-0.97 (m, 2H), 0.71-0.70 (m, 2H).

Example 116

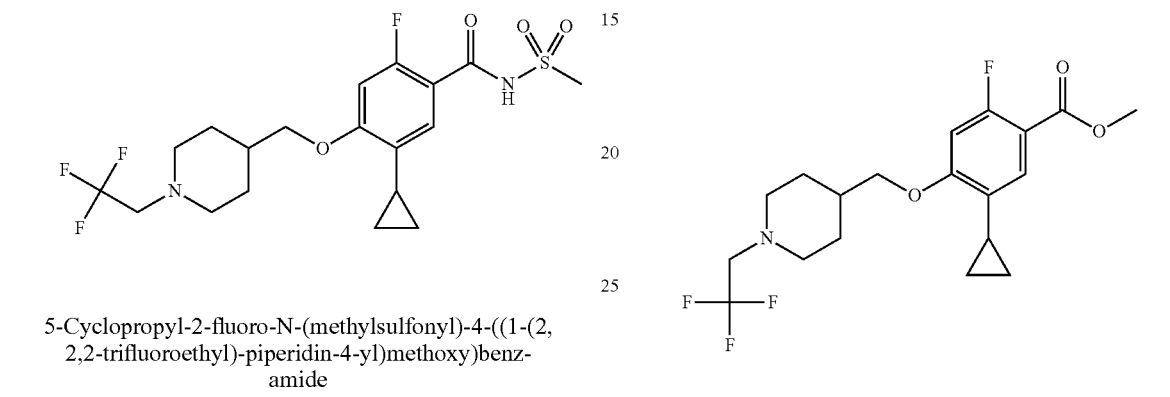

5-Cyclopropyl-2-fluoro-N-(methylsulfonyl)-4-((1-(2,2,2-trifluoroethyl)-piperidin-4-yl)methoxy)benzamide

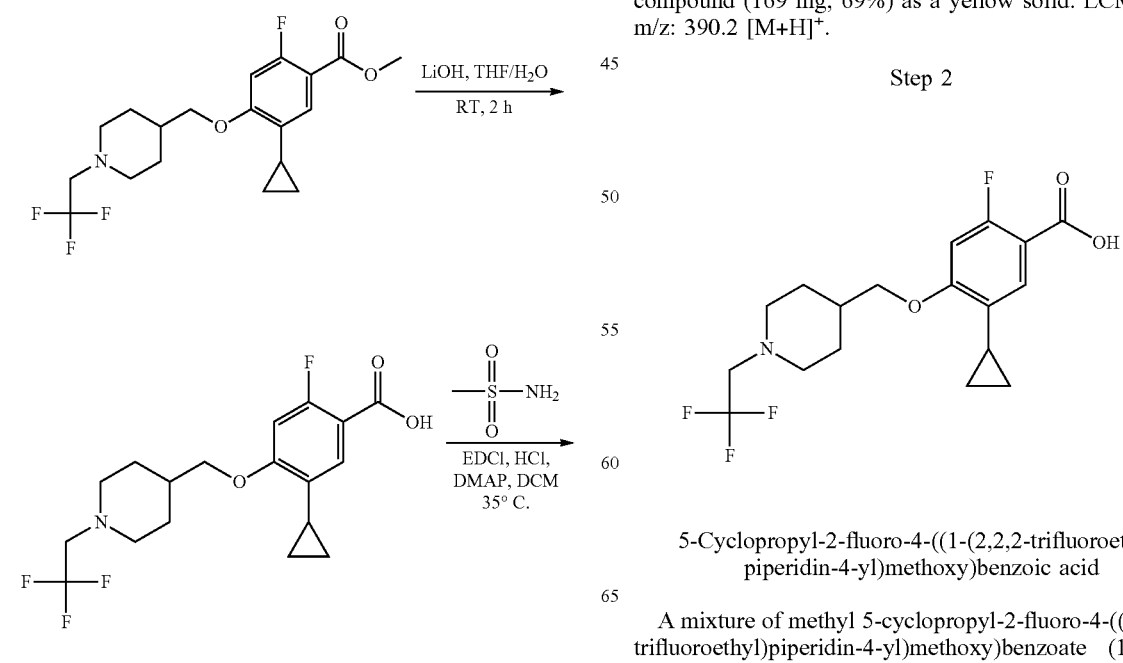

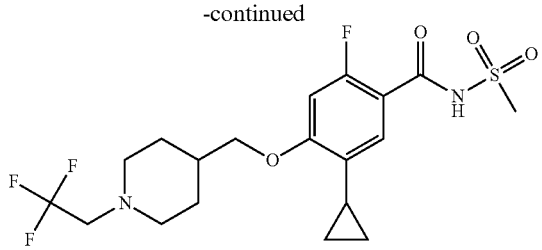

Step 1

Methyl 5-cyclopropyl-2-fluoro-4-((1-(2,2,2-trifluoroethyl)piperidin-4-yl)methoxy)benzoate A mixture of methyl 5-cyclopropyl-2-fluoro-4-(piperidin-4-ylmethoxy)benzoate (180 mg, 0.59 mmol), 2,2,2-trifluoroethyl trifluoromethanesulfonate (151 mg, 0.65 mmol) and DIPEA (152 mg, 1.18 mmol) in THF (15 mL) was stirred at 60° C. for 2 h. The reaction mixture was diluted with ethyl acetate (30 mL), washed with brine (50×2 mL), dried over anhydrous sodium sulfate, filtered and concentrated. The residue was purified by silica gel chromatography (eluting with petroleum ether/ethyl acetate=5/1) to give the target compound (169 mg; 69%) as a yellow solid. LCMS (ESI) m/z: 390.2 [M+H]$^+$.

Step 2

5-Cyclopropyl-2-fluoro-4-((1-(2,2,2-trifluoroethyl)piperidin-4-yl)methoxy)benzoic acid A mixture of methyl 5-cyclopropyl-2-fluoro-4-((1-(2,2,2-trifluoroethyl)piperidin-4-yl)methoxy)benzoate (160 mg, 0.4 mmol) and lithium hydroxide (250 mg, 10.0 mmol) in THF (10 mL) and H$_2$O (10 mL) was stirred at room temperature for 2 h. The mixture was diluted with EtOAc (50 mL), washed with HCl (2.0 M, 10 mL), brine (50×2 mL), dried over anhydrous sodium, sulfate, filtered and concentrated to give the target compound (120 mg) as yellow solid which was used in the next step without further purification. LCMS (ESI) m/z: 376.0 [M+H]$^+$.

Step 3

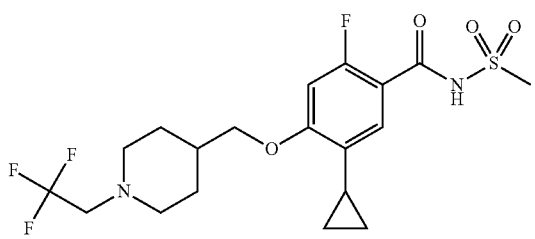 [SMILES: CS(=O)(=O)NC(=O)c1cc(C2CC2)c(OCC2CCN(CC(F)(F)F)CC2)cc1F]

5-Cyclopropyl-2-fluoro-N-(methylsulfonyl)-4-((1-(2,2,2-trifluoroethyl)-piperidin-4-yl)methoxy)benzamide A mixture of 5-cyclopropyl-2-fluoro-4-((1-(2,2,2-trifluoroethyl)piperidin-4-yl)methoxy)benzoic acid (120 mg, 0.32 mmol), methanesulfonamide (45.6 mg, 0.48 mmol), EDCl (92 mg, 0.48 mmol) and DMAP (59 mg, 0.48 mmol) in DCM (20 mL) was stirred at 25° C. for 16 h. The reaction mixture was diluted with EtOAc (100 mL), washed with HCl (2.0 M, 20 mL), brine (50×2 mL), dried over anhydrous sodium sulfate, filtered and concentrated. The residue was purified by reverse phase combiflash (25%-30% MeCN in 0.5% NH$_4$HCO$_3$) to give the target product (65.0 mg, 45%) as a white solid. LCMS (ESI) Method A: RT=5.97 min, m/z: 453.1 [M'H]$^+$. $^1$H-NMR (500 MHz, MeOH-d$_4$): δ 7.36 (d, J=8.5 Hz, 1H), 6.65 (d, J=12.5 Hz, 1H), 3.90 (d, J=5.5 Hz, 2H), 3.11-3.05 (m, 7H), 2.46-2.42 (m, 2H), 2.08-2.06 (m, 1H), 1.89-1.86 (m, 3H), 1.55-1.52 (m, 2H), 0.91-0.87 (m, 2H), 0.67-0.65 (m, 2H).

Example 117

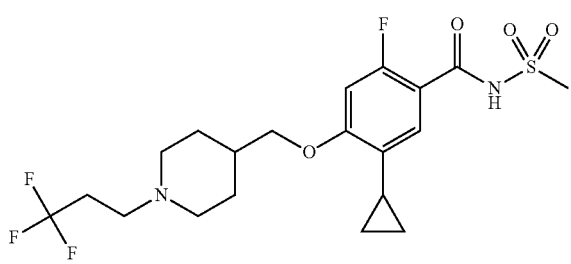 [SMILES: CS(=O)(=O)NC(=O)c1cc(C2CC2)c(OCC2CCN(CCC(F)(F)F)CC2)cc1F]

5-Cyclopropyl-2-fluoro-N-(methylsulfonyl)-4-((1-(3,3,3-trifluoropropyl)piperidin-4-yl)methoxy)benzamide The compound was synthesized as described in Example 37. LCMS (ESI) Method A: RT=4.66 min, m/z: 467.0 [M+H]$^+$. $^1$H-NMR (500 MHz, MeOD-d$_4$): δ 7.24 (d, J=8.5 Hz, 1H), 6.56 (d, J=12.5 Hz, 1H), 3.81, (d, J=5.5 Hz, 2H), 3.01 (s, 3H), 2.96-2.94 (m, 2H), 2.60 (m, 2H), 2.39-2.33 (m, 2H), 2.11-2.07 (m, 2H), 1.97-1.93 (m, 1H), 1.84-1.81 (m, 2H), 1.47-1.42 (m, 2H), 1.22-1.20 (m, 1H), 0.79-0.76 (m, 2H), 0.54-0.53 (m, 2H).

Example 118

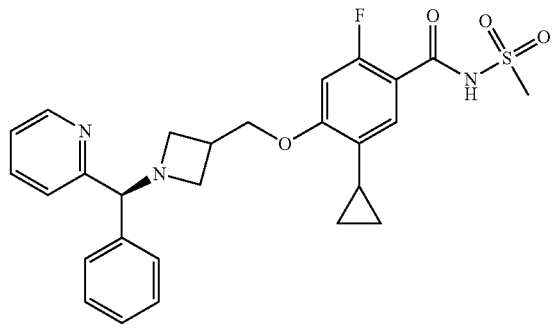 [SMILES: CS(=O)(=O)NC(=O)c1cc(C2CC2)c(OCC2CN([C@@H](c3ccccc3)c3ccccn3)C2)cc1F]

(S)-5-Cyclopropyl-2-fluoro-N-(methylsulfonyl)-4-((1-(phenyl(pyridin-2-yl)methyl)azetidin-3-yl)methoxy)benzamide The compound was synthesized as described in Example 81. Chiral HPLC (column: AD-H, 4.6×250 mm, 5 μm; mobile Phase: A: supercritical CO$_2$, B: MeOH (0.1% DEA), A:B: 75:25; flow: 2.25 mL/min; column temperature: 40° C.; RT=4.55 min), LCMS (ESI) Method A: RT=4.86 min, m/z 510.3 [M+H]$^+$. $^1$H NMR (500 MHz, CDCl$_3$): δ 8.51 (d, J=3.0 Hz, 1H), 7.62-7.57 (m, 2H), 7.50-7.47 (m, 3H), 7.29-7.22 (m, 4H), 7.11 (s, 1H), 6.61 (d, J=14.5 Hz, 1H), 4.61 (s, 1H), 4.20 (d, J=6.0 Hz, 2H), 3.41 (s, 5H), 3.14 (s, 1H), 3.01 (s, 1H), 2.04 (m, 1H), 0.94 (m, 2H), 0.65 (m, 2H).

Example 119

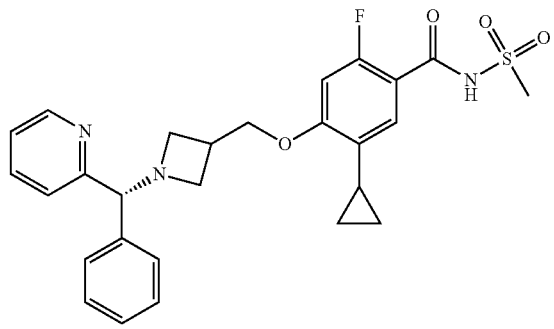 [SMILES: CS(=O)(=O)NC(=O)c1cc(C2CC2)c(OCC2CN([C@H](c3ccccc3)c3ccccn3)C2)cc1F]

(S)-5-Cyclopropyl-2-fluoro-N-(methylsulfonyl)-4-((1-(phenyl(pyridin-2-yl)methyl)azetidin-3-yl)methoxy)benzamide The compound was synthesized as described in Example 81. Chiral HPLC (column: AD-H, 4.6×250 mm, 5 μm; mobile Phase A: supercritical CO$_2$, B: MeOH (0.1% DEA), A:B=75:25; flow: 2.25 mL/min; column temperature: 40°

C.; RT=5.70 min). LCMS (ESI) Method A: RT=4.86 min m/z: 510.3 [M+H]+. 1H NMR (500 MHz, CDCl3): δ 8.50 (d, J=4.5 Hz, 1H), 7.64-7.57 (m, 2H), 7.50-7.47 (m, 3H), 7.31-7.21 (m, 4H), 7.12-7.10 (m, 1H), 6.60 (d, J=14.5 Hz, 1H), 4.60 (s, 1H), 4.20 (d, J=6.0 Hz, 2H), 3.41 (s, 5H), 3.15 (s, 1H), 3.0.1 (s, 1H), 2.06-2.01 (m, 1H), 0.93 (m, 2H), 0.65 (m, 2H).

Example 120

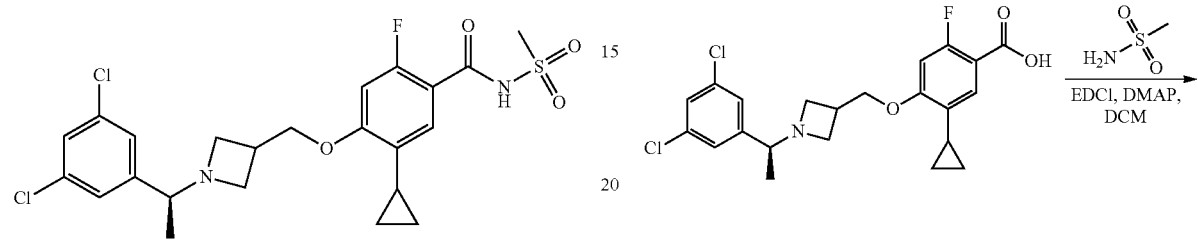

(S)-5-Cyclopropyl-4-((1-(1-(3,5-dichlorophenyl)ethyl)azetidin-3-yl)methoxy)-2-fluoro-N-(methylsulfonyl)benzamide

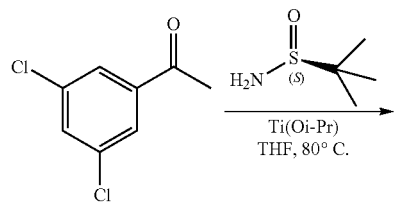

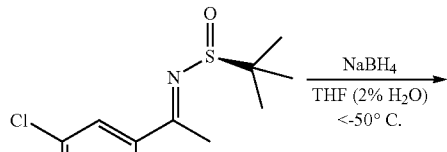

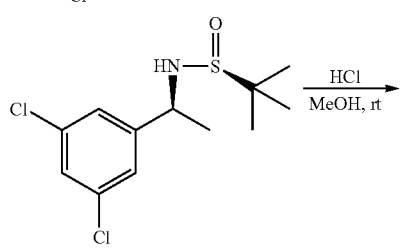

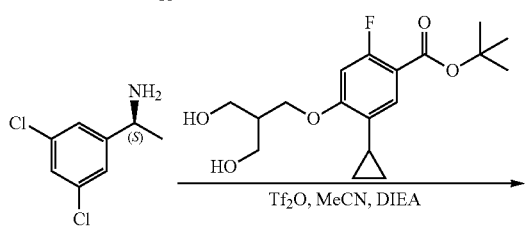

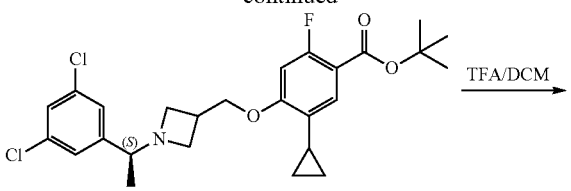

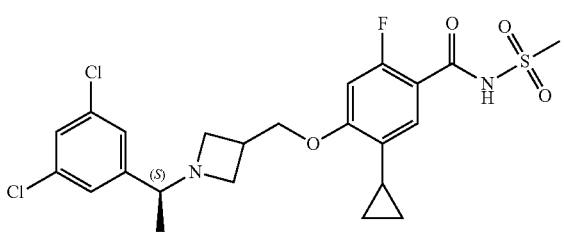

Step 1

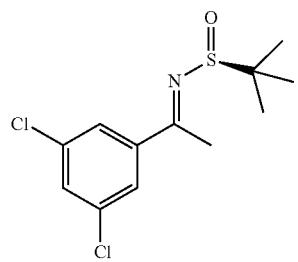 [SMILES: C/C(=N\[S@@](=O)C(C)(C)C)c1cc(Cl)cc(Cl)c1]

(S,E)-N-(1-(3,5-Dichlorophenyl)ethylidene)-2-methylpropane-2-sulfinamide

Tetraisopropoxytitanium (6.14 g, 21.2 mmol) was added to a solution of 3,5-dichlorophenyl ethanone (1.0 g, 5.3 mmol) and (S)-2-methylpropane-2-sulfinamide (1.28 g, 10.6 mmol) in dry THF (20 mL). After stirring at 80° C. for 16 h, ethyl acetate (15 mL) and brine was added to quench the reaction. The white precipitate was filtered and the filtrate was concentrated and purified by silica gel chromatography (elating with ethyl acetate/petroleum ether=1/10) to give the target compound as a yellow solid (1.24 g, 80%). LCMS (ESI): m/z 292.0 [M+H]+.

Step 2

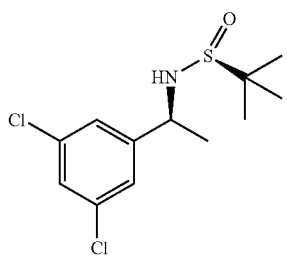 [SMILES: C[C@H](N[S@@](=O)C(C)(C)C)c1cc(Cl)cc(Cl)c1]

(S)—N—(S)-1-(3,5-Dichlorophenyl)ethyl)-2-methylpropane-2-sulfinamide

Sodium borohydride (0.49 g, 12.9 mmol) was added to a solution of (S,E)-N-(1-(3,5-dichlorophenyl)ethylidene)-2-methylpropane-2-sulfinamide (1.24 g, 4.3 mmol) in THF (20 mL, with 2% H₂O) at −60° C. After stirring at room temperature for 3 h, the solvent was removed under reduced pressure and the crude product was purified by silica gel chromatography (eluting with ethyl acetate/petroleum ether=1/12) to afford target compound (1.07 g, 85%) as white solid. LCMS (ESI): m/z 294.0 [M+H]⁺. ¹H-NMR (CDCl₃, 500 MHz): δ 7.28 (t, J=2.0 Hz, 1H), 7.23 (d, J=2.0 Hz, 2H), 4.48 (m, 1H), 3.41 (d, J=2.5 Hz, 1H), 1.49 (d, J=6.5 Hz, 3H), 1.24 (s, 9H).

Step 3

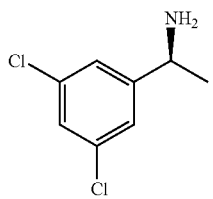

(S)-1-(3,5-Dichlorophenyl)ethanamine hydrochloride

HCl (1M in MeOH, 10 mL) was added to a solution of (S)—N—(S)-1-(3,5-dichlorophenyl)ethyl)-2-methylpropane-2-sulfinamide (1.07 g, 3.66 mmol) in MeOH (5 ml). After stirring at room temperature for 2 h, the mixture was diluted with ethyl acetate (30 mL). The resultant white precipitate was filtered and washed with ethyl acetate (10 mL) to provide the target compound (820 mg, 99%) as a white solid. LCMS (ESI): m/z 190.0 [M+H]⁺.

Step 4

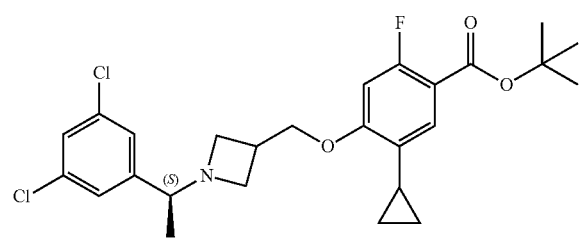

(S)-tert-Butyl 5-cyclopropyl-4-((1-(1-(3,5-dichlorophenyl)ethyl)azetidin-3-yl)methoxy)-2-fluorobenzoate The compound was synthesized as described in step 4 of Example 5, LCMS (ESI): m/z 494.1 [M+H]⁺.

Step 5

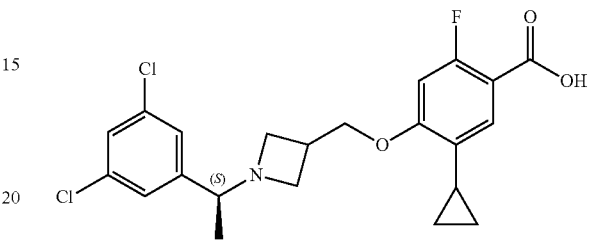

(S)-5-Cyclopropyl-4-((1-(1-(3,5-dichlorophenyl)ethyl)azetidin-3-yl)methoxy)-2-fluorobenzoic acid The compound was synthesized as described in step 5 of Example 5. LCMS (ESI): m/z 438.1 [M+H]⁺.

Step 6

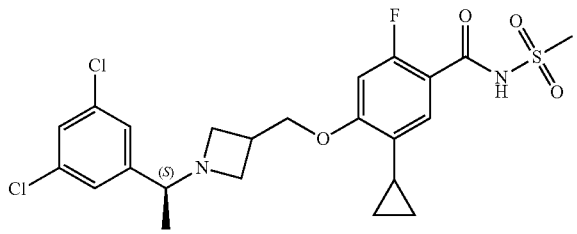

(S)-5-Cyclopropyl-4-((1-(1-(3,5-dichlorophenyl)ethyl)azetidin-3-yl)methoxy)-2-fluoro-N-(methylsulfonyl)benzamide The compound was synthesized as described in step 6 of Example 5. Chiral HPLC (column: OZ-H, 4.6×250 mm, 5 μm; mobile Phase: A: supercritical CO₂, B: MeOH (0.1% DEA), A: 8-65:35; flow: 1.95 mL/min; column temperature: 40° C.; RT=7.28 min). LCMS (ESI) Method A: RT=5.55 min m/z 514.9 [M+H]⁺. ¹H-NMR (CDCl₃, 500 MHz): δ 7.58 (d, J=9.0 Hz, 1H), 7.23 (m, 1H), 7.19 (d, J=2.0 Hz, 2H), 6.59 (d, J=14.5 Hz, 1H), 4.17 (m, 2H), 3.38 (m, 4H), 3.30 (m, 2H), 3.07 (m, 2H), 2.92 (m, 1H), 2.02 (m, 1H), 1.18 (d, 3H), 0.94 (m, 2H), 0.66 (m, 2H).

Example 121

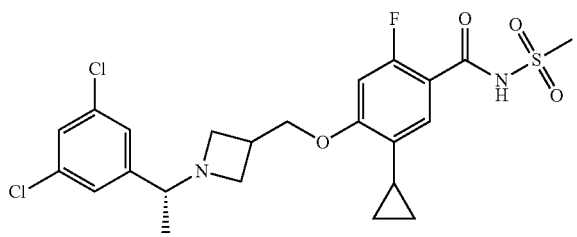 [SMILES: C[C@H](c1cc(Cl)cc(Cl)c1)N1CC(COc2cc(F)c(C(=O)NS(C)(=O)=O)cc2C2CC2)C1]

(R)-5-Cyclopropyl-4-((1-(1-(3,5-dichlorophenyl)
ethyl)azetidin-3-yl)methoxy)-2-fluoro-N-(methylsulfonyl)benzamide The compound was synthesized as described in Example 41. Chiral HPLC (column: OZ-H, 4.6×250 mm. 5 μm; mobile Phase: A: supercritical $CO_2$, B: MeOH (0.1% DEA), A:B=65:35; flow: 1.95 mL/min; column temperature: 40° C.; RT=5.37 min). LCMS (ESI) Method A: RT=5.41 min m/z 514.8 [M+H]$^+$. $^1$H-NMR (CDCl$_3$, 500 MHz): δ 7.58 (d, J=9.0 Hz, 1H), 7.23 (m, 1H), 7.19 (d, J=2.0 Hz, 2H), 6.59 (d, J=14.5 Hz, 1H), 4.17 (m, 2H), 3.38 (m, 4H), 3.30 (m, 2H), 3.07 (m, 2H), 2.92 (m, 1H), 2.02 (m, 1H), 1.18 (d, 3H), 0.94 (m, 2H), 0.66 (m, 2H).

Example 122

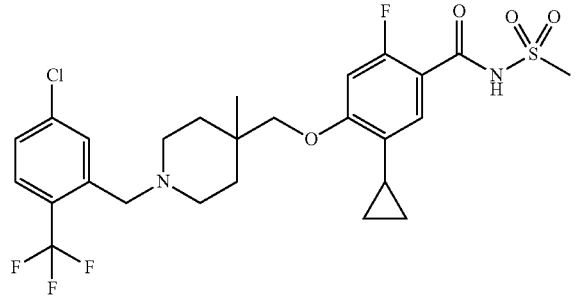 [SMILES: CC1(COc2cc(F)c(C(=O)NS(C)(=O)=O)cc2C2CC2)CCN(Cc2cc(Cl)ccc2C(F)(F)F)CC1]

4-((1-(5-chloro-2-(trifluoromethyl)benzyl)-4-methylpiperidin-4-yl)methoxy)-5-cyclopropyl-2-fluoro-N-methylsulfonyl)benzamide The compound was prepared in a similar manner to Example 73 starting from tert-butyl 4-((2-cyclopropyl-5-fluoro-4-((methylsulfonyl)carbamoyl)phenoxy)methyl)-4-methylpiperidine-1-carboxylate (Example 73 step 1-2) and 5-chloro-2-(trifluoromethyl)benzaldehyde. LCMS (Method F): RT=4.76 min, m/z: 577.2 [M+H]$^+$.

Example 123

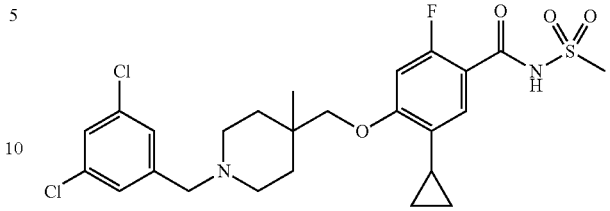

5-cyclopropyl-4-((1-(3,5-dichlorobenzyl)-4-methylpiperidin-4-yl)methoxy)-2-fluoro-N-(methylsulfonyl)benzamide The compound was prepared in a similar manner to Example 73 starting from tert-butyl 4-((2-cyclopropyl-5-fluoro-4-((methylsulfonyl)carbamoyl)phenoxy)methyl)-4-methylpiperidine-1-carboxylate (Example 73 step 1-2) and 3,5-dichlorobenzaldehyde. LCMS (Method F); RT=4.64 min, m/z: 543.2 [M+H]$^+$. $^1$H NMR (400 MHz, DMSO-d6) δ 7.54 (t, J=1.9 Hz, 1H), 7.41 (d, J=2.0 Hz, 2H), 7.20 (d, J=8.4 Hz, 1H), 6.90 (d, J=12.9 Hz, 1H), 3.84 (s, 2H), 3.72 (s, 2H), 3.19 (s, 3H), 2.76-2.61 (m, 2H), 2.06-1.96 (m, 1H), 1.76-1.64 (m, 2H), 1.50 (d, J=14.0 Hz, 2H), 1.09 (s, 3H), 0.94-0.83 (m, 2H), 0.69-0.59 (m, 2H).

Example 124

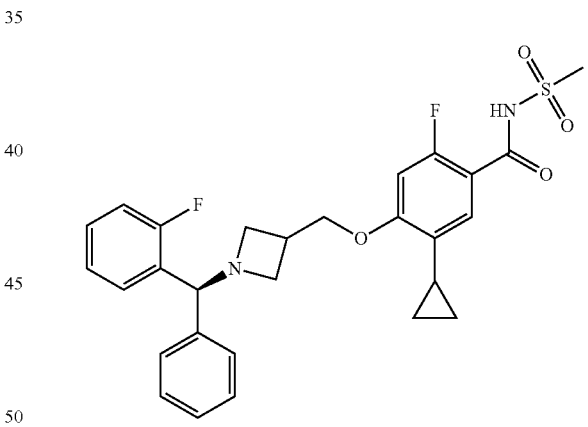

(S)-5-Cyclopropyl-2-fluoro-4-((1-((2-fluorophenyl)(phenyl)methyl)azetidin-3-yl)methoxy)-N-(methylsulfonyl)benzamide The compound was synthesized as described in Example 81. Chiral HPLC (column: OJ-H, 4.6×250 mm, 5 μm; mobile Phase: A: supercritical $CO_2$, B: MeOH (0.1% DEA), A; B=85:15; flow: 2.25 mL/min; column temperature: 40° C.; RT=14.2 min), LCMS (ESI) Method A: RT=5.48 min, m/z: 527.2 [M+H]$^+$. $^1$H-NMR (500 MHz, DMSO-d$_6$): δ7.64-7.62 (m, 1H), 7.43-7.03 (m, 9H), 6.81 (d, J=12.5 Hz, 1H), 5.00 (s, 1H), 4.18 (d, J=5.0 Hz, 2H), 3.55-3.46 (m, 3H), 3.28 (m, 4H), 3.07-3.05 (m, 1H), 2.16-2.13 (m, 1H), 0.98-0.96 (m, 2H), 0.69-0.68 (m, 2H).

Example 125

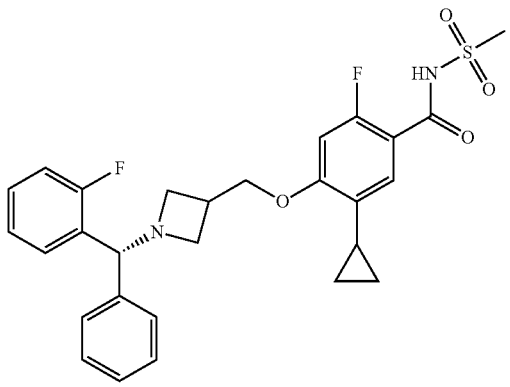 [SMILES: CS(=O)(=O)NC(=O)c1cc(C2CC2)c(OCC2CN([C@H](c3ccccc3)c3ccccc3F)C2)cc1F]

(R)-5-Cyclopropyl-2-fluoro-4-((1-((2-fluorophenyl)(phenyl)methyl)azetidin-3-yl)methoxy)-N-(methylsulfonyl)benzamide The compound was synthesized as described in Example 81. Chiral HPLC (column: OJ-H, 4.6×250 mm, 5 μm; mobile Phase: A: supercritical CO₂, B: MeOH (0.1% DEA), A:B=85:15; flow: 2.25 mL/min; column temperature: 40° C.; RT=16.3 min), LCMS (ESI) Method A: RT=5.69 min, m/z: 527.2 [M+H]⁺. ¹H-NMR (500 MHz, DMSO-d₆): δ7.64-7.61 (m, 1H), 7.43-7.03 (m, 9H), 6.83 (d, J=13.0 Hz, 1H), 5.05 (s, 1H), 4.19 (d, J=5.5 Hz, 2H), 3.59-3.40 (m, 4H), 3.28 (s, 3H), 3.10-3.08 (m, 1H), 2.17-2.13 (m, 1H), 0.98-0.96 (m, 2H), 0.71-0.68 (m, 2H).

Example 126

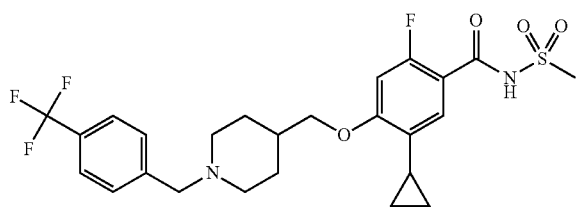 [SMILES: CS(=O)(=O)NC(=O)c1cc(C2CC2)c(OCC2CCN(Cc3ccc(C(F)(F)F)cc3)CC2)cc1F]

5-Cyclopropyl-2-fluoro-N-(methylsulfonyl)-4-((1-(4-(trifluoromethyl)benzylpiperidin-4-yl)methoxy)benzamide The compound was synthesized as described in Example 88. LCMS (ESI) Method A: RT=5.54 min, m/z: 528.9 [M+H]⁺. ¹H-NMR (500 MHz, DMSO-d₆): δ7.74-7.58 (m, 4H), 7.16 (d, J=8.5 Hz, 1H), 6.86 (d, J=12.5 Hz, 1H), 3.94 (d, J=6.0 Hz, 2H), 3.79 (s, 2H), 3.16 (s, 3H), 2.99-2.98 (m, 2H), 2.29-2.26 (m, 2H), 2.02-1.99 (m, 1H), 1.88-1.82 (m, 3H), 1.44-1.42 (m, 2H), 0.89-0.86 (m, 2H), 0.64-0.61 (m, 2H).

Example 127

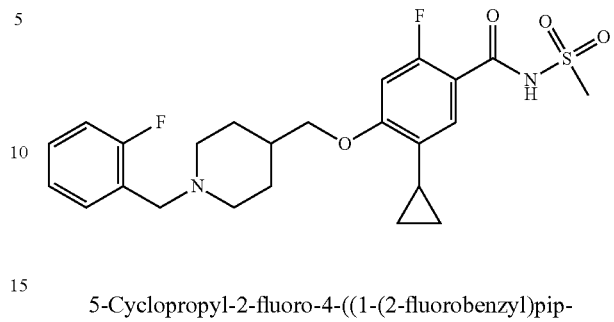

5-Cyclopropyl-2-fluoro-4-((1-(2-fluorobenzyl)piperidin-4-yl)methoxy)-N-(methylsulfonyl)benzamide The compound was synthesized as described in Example 88. LCMS (ESI) Method A: RT=4.89 min, m/z: 479.0 [M+H]⁺. ¹H-NMR (500 MHz, MeOH-d₄,): δ7.46-736 (m, 2H), 7.23-7.16 (m, 3H), 6.83 (d, J=12.5 Hz, 1H), 3.92-3.91 (m, 2H), 3.76 (s, 2H), 3.11 (s, 3H), 3.03-3.01 (m, 2H), 2.33-2.30 (m, 2H), 2.02-1.82 (m, 4H), 1.46-1.42 (m, 2H), 0.89-0.86 (m, 2H), 0.62-0.60 (m, 2H).

Example 128

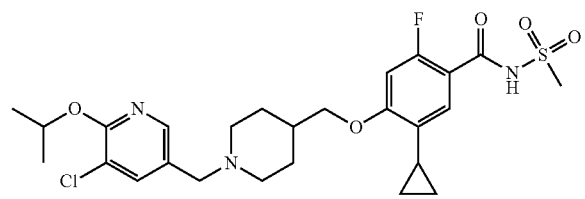 [SMILES: CC(C)Oc1ncc(CN2CCC(COc3cc(F)c(C(=O)NS(C)(=O)=O)cc3C3CC3)CC2)cc1Cl]

4-((1-((5-Chloro-6-isopropoxypyridin-3-yl)methyl)piperidin-4-yl)methoxy)-5-cyclopropyl-2-fluoro-N-(methylsulfonyl)benzamide The compound was synthesized as described in Example 88. LCMS (ESI) Method A: RT=5.86 min, m/z: 553.8 [M+H]⁺. ¹H-NMR (500 MHz, DMSO-d₆,): δ8.06 (d, J=5.0 Hz, 1H), 7.16-6.88 (m, 3H), 5.30-5.28 (m, 1H), 3.94 (d, J=6.0 Hz, 2H), 3.60 (s, 2H), 3.21 (s, 3H), 2.89-2.87 (m, 2H), 2.16-2.12 (m, 2H), 2.03-2.01 (m, 1H), 1.80-1.78 (m, 3H), 1.41-1.39 (m, 2H), 1.31 (d, J=6.5 Hz, 6H), 0.90-0.87 (m, 2H), 0.66-0.63 (m, 2H).

Example 129

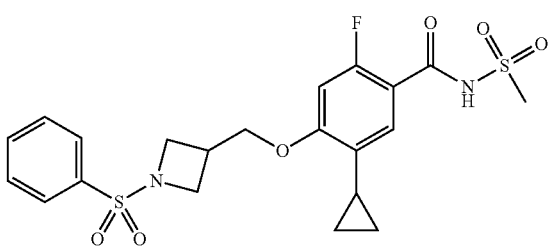 [SMILES: CS(=O)(=O)NC(=O)c1cc(C2CC2)c(OCC2CN(S(=O)(=O)c3ccccc3)C2)cc1F]

5-Cyclopropyl-2-fluoro-N-(methylsulfonyl)-4-((1-(phenylsulfonyl)-azetidin-3-yl)methoxy)benzamide

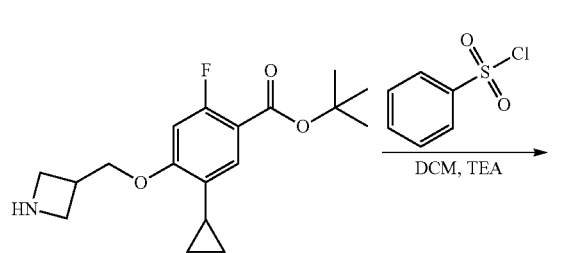

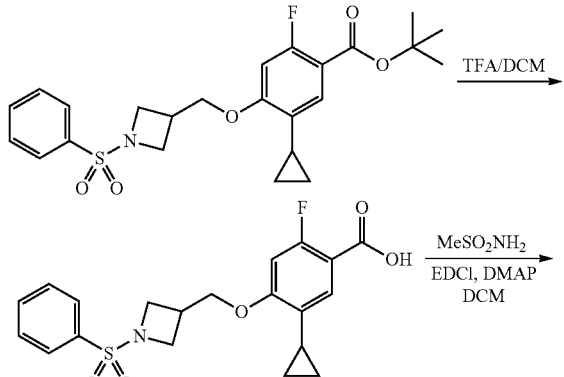

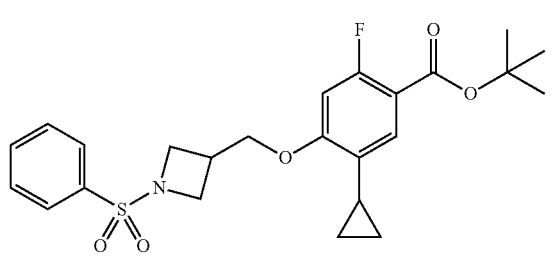 [SMILES: CC(C)(C)OC(=O)c1cc(C2CC2)c(OCC2CN(S(=O)(=O)c3ccccc3)C2)cc1F]

Step 1 tert-Butyl 5-cyclopropyl-2-fluoro-4-((1-(phenylsulfonyl)azetidin-3-yl)methoxy)benzoate Benzenesulfonyl chloride (54 mg, 0.31 mol) was added to a mixture of tert-butyl 4-(azetidin-3-ylmethoxy)-5-cyclopropyl-2-fluorobenzoate (100 mg, 0.31 mmol) and triethylamine (94 mg, 0.93 mmol) in DCM (10 ml). After stirring at room temperature for 2 h, the mixture was quenched with water (10 ml), extracted with DCM (10 ml×3), dried over sodium sulfate, filtered and concentrated to give target compound as a yellow solid. (112 mg, 78%). LCMS (ESI) m/z: 462.1 [M+H]$^+$.

Step 2

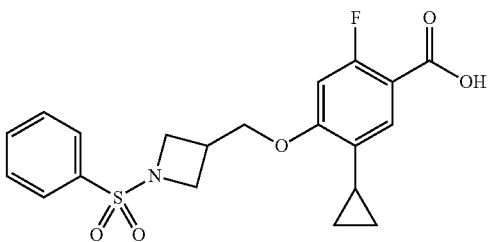 [SMILES: O=C(O)c1cc(C2CC2)c(OCC2CN(S(=O)(=O)c3ccccc3)C2)cc1F]

5-Cyclopropyl-2-fluoro-4-((1-(phenylsulfonyl)azetidin-3-yl)methoxy)benzoic acid

The compound was synthesized as described in step 3 of Example 88.

Step 3

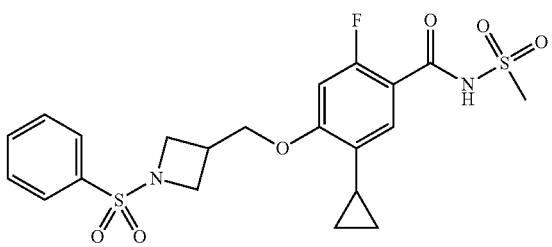 [SMILES: CS(=O)(=O)NC(=O)c1cc(C2CC2)c(OCC2CN(S(=O)(=O)c3ccccc3)C2)cc1F]

5-Cyclopropyl-2-fluoro-N-(methylsulfonyl)-4-((1-(phenylsulfonyl)azetidin-3-yl)methoxy)benzamide The compound was synthesized as described in step 5 of Example 80. LCMS (ESI) Method A: RT=4.60 min, m/z: 483.2 [M+H]$^+$. $^1$H-NMR (500 MHz, DMSO-d$_6$,): δ7.89-7.66 (m, 5H), 7.26 (d, J=8.0 Hz, 1H), 6.76 (d, J=12.5 Hz, 1H), 4.02 (d, J=5.5 Hz, 2H), 3.97-3.94 (m, 2H), 3.83-3.81 (m, 2H), 3.36 (s, 3H), 2.99-2.96 (m, 1H), 1.91-1.88 (m, 1H), 0.91-0.88 (m, 2H), 0.63-0.60 (m, 2H).

Example 130

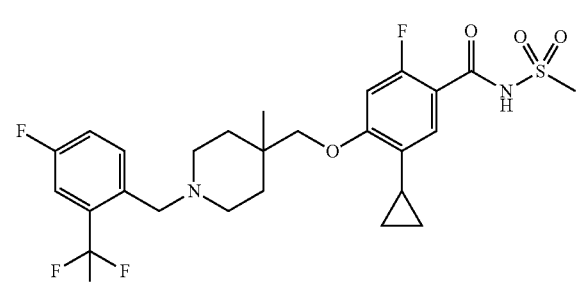

5-cyclopropyl-2-fluoro-4-((1-(4-fluoro-2-(trifluoromethyl)benzyl)-4-methylpiperidin-4-yl)methoxy)-N-(methylsulfonyl)benzamide The compound was prepared in a similar manner to Example 73 starting from tert-butyl 4-((2-cyclopropyl-5-fluoro-4-((methylsulfonyl)carbamoyl)phenoxy)methyl)-4-methylpiperidine-1-carboxylate (Example 73 step 1-2) and 4-fluoro-2-trifluoromethylbenzaldehyde. LCMS (Method F): RT=4.62 min, m/z: 561.2 [M+H]+. 1H NMR (400 MHz, DMSO-d6) δ 11.68 (s, 1H), 7.87-7.78 (n 1H), 7.62-7.49 (m, 2H), 7.18 (d, J=8.3 Hz, 1H), 6.95 (d, J=13.0 Hz, 1H), 3.85 (s, 2H), 3.66 (s, 2H), 3.28 (s, 3H), 2.61-2.52 (m, 2H), 2.46-2.36 (m, 2H), 2.06-1.95 (m, 1H), 1.74-1.61 (m, 2H), 1.47 (d, J=13.3 Hz, 2H), 1.09 (s, 3H), 0.93-0.84 (m, 2H), 0.70-0.61 (m, 2H).

Example 131

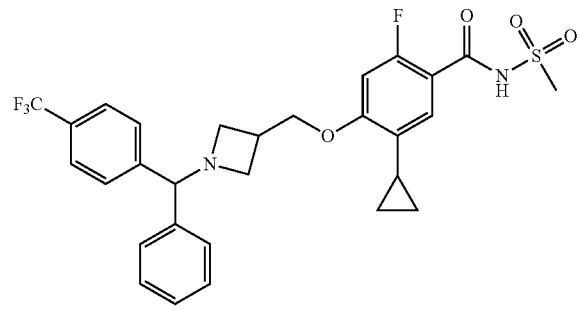 [SMILES: CS(=O)(=O)NC(=O)c1cc(C2CC2)c(OCC2CN(C(c3ccccc3)c3ccc(C(F)(F)F)cc3)C2)cc1F]

5-Cyclopropyl-2-fluoro-N-(methylsulfonyl)-4-((1-(phenyl(4-(trifluoromethyl)phenyl)methyl)-azetidin-3-yl)methoxy)benzamide The compound was synthesized as described in Example 80. LCMS (ESI) Method A: RT=6.00 min, m/z: 577.3 [M+H]+. 1H NMR (500 MHz, MeOD-d4): δ 7.65-7.60 (m, 4H), 7.44-7.43 (m, 2H), 7.34-7.31 (m, 3H), 7.25-7.23 (m, 1H), 6.81-6.78 (m, 1H), 4.65 (s, 1H), 4.21 (d, J=6.0 Hz, 2H), 3.48-3.41 (m, 2H), 3.29-3.10 (m, 5H), 3.04-3.01 (m, 1H), 2.12-2.08 (m, 1H), 0.96-0.68 (m, 2H), 0.67 (s, 2H).

Example 132

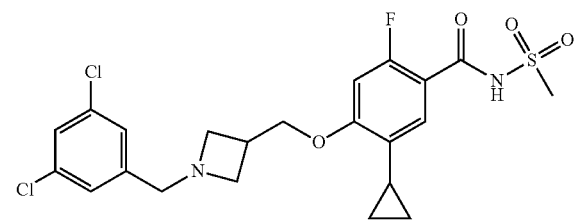 [SMILES: CS(=O)(=O)NC(=O)c1cc(C2CC2)c(OCC2CN(Cc3cc(Cl)cc(Cl)c3)C2)cc1F]

5-Cyclopropyl-4-((1-(3,5-dichlorobenzyl)azetidin-3-yl)methoxy)-2-fluoro-N-(methylsulfonyl)benzamide The compound was synthesized as described in Example 80. LCMS (ESI) Method A: RT=5.26 min, m/z: 501.1 [M+H]+. 1H NMR (500 MHz, DMSO-d6): δ 7.56 (s, 1H), 7.41-7.41 (m, 2H), 7.20-7.18 (m, 1H), 6.90-6.88 (m, 1H), 4.20-4.18 (d, J=6.5 Hz, 2H), 3.85 (s, 2H), 3.63 (s, 2H), 3.42 (s, 2H), 3.14 (s, 3H), 3.02-3.00 (m, 1H), 2.06-2.02 (m, 1H), 0.91-0.87 (m, 2H), 0.65-0.62 (m, 2H).

Example 133

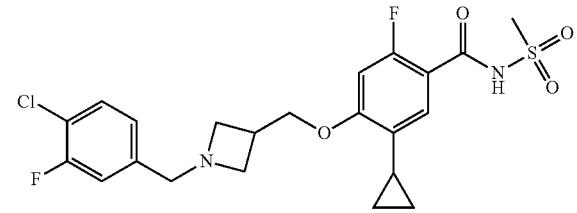 [SMILES: CS(=O)(=O)NC(=O)c1cc(C2CC2)c(OCC2CN(Cc3ccc(Cl)c(F)c3)C2)cc1F]

4-((1-(4-Chloro-3-fluorobenzyl)azetidin-3-yl)methoxy)-5-cyclopropyl-2-fluoro-N-(methylsulfonyl)benzamide The compound was synthesized as described in Example 80. LCMS (ESI) Method A: RT=4.81 min, m/z: 485.0 [M+H]+. 1H NMR (500 MHz, DMSO-d6): δ 7.58 (t, J=8.0 Hz, 1H), 7.38 (d, J=9.5, 1H), 7.22-7.19 (m, 2H), 6.86 (d, J=12.5 Hz, 1H), 4.19 (d, J=6.0 Hz, 2H), 3.87 (s, 2H), 3.63 (s, 2H), 3.40 (s, 2H), 3.10 (s, 3H), 3.02-3.00 (m, 1H), 2.04-2.00 (m, 1H), 0.90-0.86 (m, 2H), 0.64-0.61 (m, 2H).

Example 134

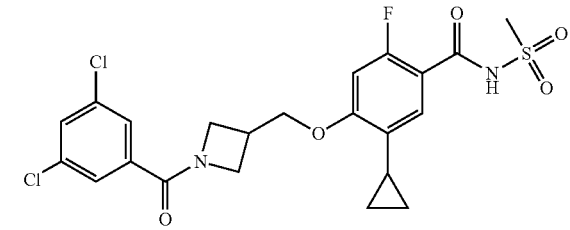 [SMILES: CS(=O)(=O)NC(=O)c1cc(C2CC2)c(OCC2CN(C(=O)c3cc(Cl)cc(Cl)c3)C2)cc1F]

5-Cyclopropyl-4-((1-(3,5-dichlorobenzoyl)azetidin-3-yl)methoxy)-2-fluoro-N-(methylsulfonyl)benzamide

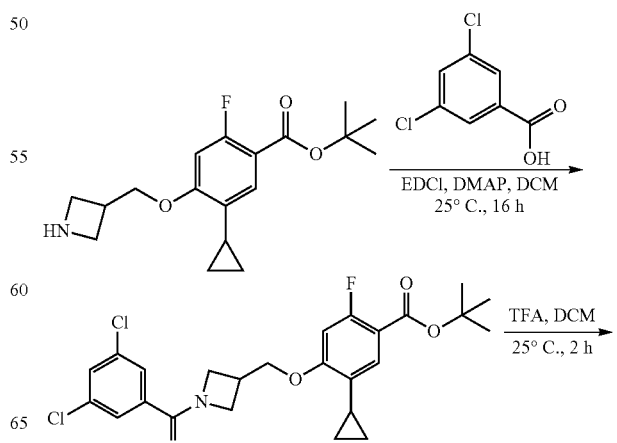

345
-continued

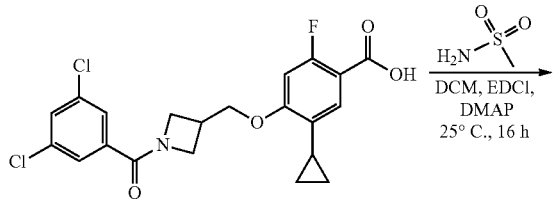

Step 1

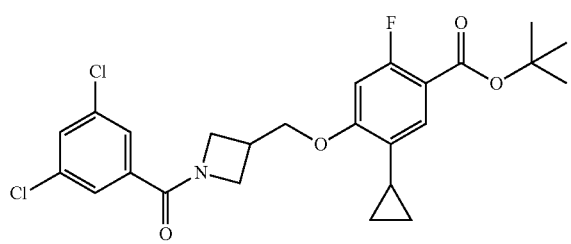 [SMILES: CC(C)(C)OC(=O)c1cc(C2CC2)c(OCC2CN(C(=O)c3cc(Cl)cc(Cl)c3)C2)cc1F]

tert-Butyl 5-cyclopropyl-4-((1-(3,5-dichlorobenzoyl)
azetidin-3-yl)methoxy)-2-fluorobenzoate A mixture of 3,5-dichlorobenzoic acid (100 mg, 0.52 mmol), tert-butyl 4-(azetidin-3-ylmethoxy)-5-cyclopropyl-2-fluorobenzoate (140 mg, 0.44 mmol), EDCI (140 mg, 0.72 mmol) and DMAP (27 mg, 0.22 mmol) in DCM (5 mL) was stirred at room temperature for 18 h. The mixture was diluted with DCM (10 mL) and washed with HCl (2N, 15 mL×2). The organic layer was dried over anhydrous sodium sulfate, filtered and concentrated. The residue was purified by silica gel chromatography feinting with petroleum ether/EtOAc=4/1) to give the target compound (200 mg, 92%) as a white solid. LCMS (ESI) m/z: 437.9 [M+H–56]⁺.

Step 2

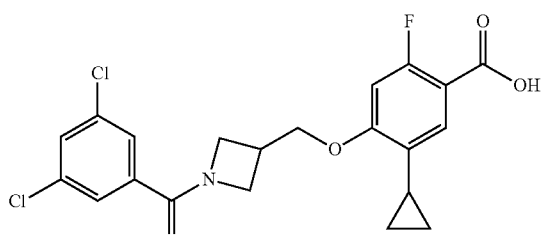

346
5-Cyclopropyl-4-((1-(3,5-dichlorobenzoyl)azetidin-3-yl)methoxy)-2-fluorobenzoic acid The compound was synthesized as described in step 3 of Example 88. LCMS (ESI) m/z: 438.0 [M+H]⁺.

Step 3

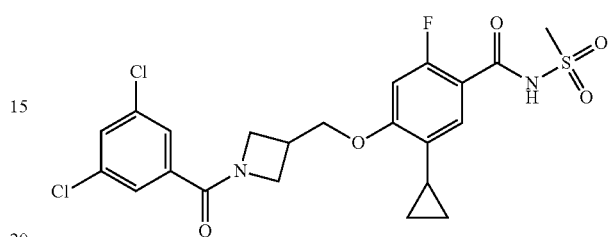

5-Cyclopropyl-4-((1-(3,5-dichlorobenzoyl)azetidin-3-yl)methoxy)-2-fluoro-N-(methylsulfonyl)benzamide The compound was synthesized as described in step 5 of Example 80. LCMS (ESI) Method A: RT=4.65 min, m/z: 515.0 [M+H]⁺. ¹H NMR (500 MHz, DMSO-d₆): δ 11.90 (s, 1H), 7.80 (t, J=1.5 Hz, 1H), 7.58 (d, J=2.0 Hz, 2H), 7.15 (d, J=8.0 Hz, 1H), 6.96 (d, J=12.5 Hz, 1H), 4.52 (t, J=8.5 Hz, 1H), 4.27-4.16 (m, 4H), 3.99-3.97 (m, 1H), 3.28 (s, 3H), 3.12-3.09 (m, 1H), 1.95-1.89 (m, 1H), 0.89-0.84 (m, 1H), 0.76-0.60 (m, 3H).

Example 135

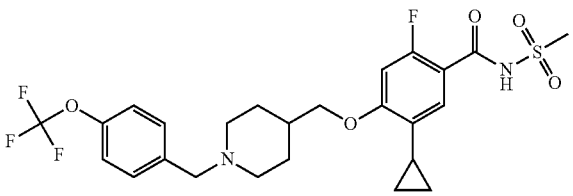 [SMILES: CS(=O)(=O)NC(=O)c1cc(C2CC2)c(OCC2CCN(Cc3ccc(OC(F)(F)F)cc3)CC2)cc1F]

5-Cyclopropyl-2-fluoro-N-(methylsulfonyl)-4-((1-(4-(trifluoromethoxy)benzyl)piperidin-4-yl)methoxybenzamide The compound was synthesized as described in Example 88. LCMS (ESI) Method A: RT=5.55 min, m/z: 544.8 [M+H]⁺. ¹H NMR (500 MHz, DMSO-d₆): δ 7.51 (d, J=8.5 Hz, 2H), 7.38 (d, J=8.0 Hz, 2H), 7.17 (d, J=8.5 Hz, 1H), 6.83 (d, J=12.5 Hz, 1H), 3.92 (d, J=6.5 Hz, 2H), 3.827 (s, 2H), 3.11 (s, 3H), 3.05 (d, J=11.0 Hz, 2H), 2.41-2.37 (m, 2H), 2.03-1.98 (m, 1H), 1.90-1.85 (m, 3H), 1.48-1.42 (m, 2H), 0.89-0.85 (m, 2H), 0.63-0.60 (m, 2H).

Example 136

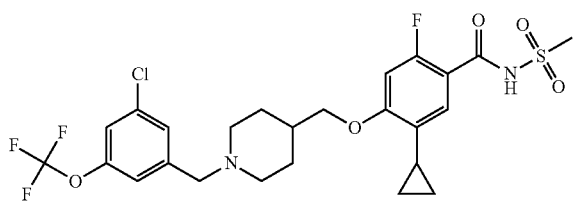 [SMILES: CS(=O)(=O)NC(=O)c1cc(C2CC2)c(OCC2CCN(Cc3cc(Cl)cc(OC(F)(F)F)c3)CC2)cc1F]

4-((1-(3-Chloro-5-(trifluoromethoxy)benzyl)piperidin-4-yl)methoxy)-5-cyclopropyl-2-fluoro-N-(methylsulfonyl)benzamide The compound was synthesized as described in Example 88. LCMS (ESI) Method A: RT=6.15 min, m/z: 578.8 [M+H]$^+$. $^1$H NMR (500 MHz, DMSO-d$_6$): δ 7.48 (s, 2H), 7.35 (s, 1H), 7.15 (d, J=8.0 Hz, 1H), 6.87 (d, J=13.5 Hz, 1H), 3.93 (d, J=5.5 Hz, 2H), 3.67 (s, 2H), 3.18 (s, 3H), 2.90 (d, J=10 Hz, 2H), 2.20-2.15 (m, 2H), 2.07-1.98 (m, 1H), 1.88-1.80 (m, 3H), 1.44-1.36 (m, 2H), 0.89-0.86 (m, 2H), 0.65-0.62 (m, 2H).

Example 137

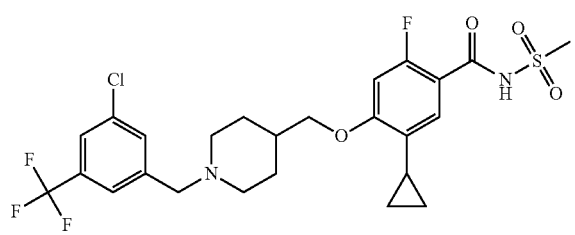 [SMILES: CS(=O)(=O)NC(=O)c1cc(C2CC2)c(OCC2CCN(Cc3cc(Cl)cc(C(F)(F)F)c3)CC2)cc1F]

4-((1-(3-Chloro-5-(trifluoromethyl)benzyl)piperidin-4-yl)methoxy)-5-cyclopropyl-2-fluoro-N-(methylsulfonyl)benzamide The compound was synthesized as described in Example 88. LCMS (ESI) Method A: RT=6.06 min, m/z: 562.8 [M+H]$^+$. $^1$H NMR (500 MHz, DMSO-d$_6$): δ 7.76 (s, 2H), 7.73 (s, 1H), 7.67 (s, 1H), 7.18 (d, J=8.5 Hz, 1H), 6.82 (d, J=11.5 Hz, 1H), 3.93 (d, J=5.5 Hz, 2H); 3.67 (s, 2H), 3.10 (s, 3H), 2.89 (d, J=10.5 Hz, 2H), 2.16-2.12 (m, 2H), 2.03-1.99 (m, 1H), 1.84-1.79 (m, 3H), 1.43-1.36 (m, 2H), 0.89-0.86 (m, 2H), 0.63-0.60 (m, 2H).

Example 138

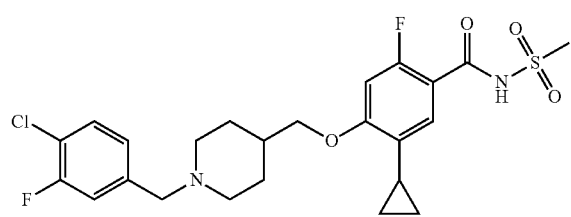 [SMILES: CS(=O)(=O)NC(=O)c1cc(C2CC2)c(OCC2CCN(Cc3ccc(Cl)c(F)c3)CC2)cc1F]

4-((1-(4-Chloro-3-fluorobenzyl)piperidin-4-yl)methoxy)-5-cyclopropyl-2-fluoro-N-(methylsulfonyl)benzamide The compound was synthesized as described in Example 88. LCMS (ESI) Method A: RT=4.72 min m/z: 513.2 [M+H]$^+$. $^1$H NMR (500 MHz, DMSO-d$_6$): δ 7.56-7.23 (m, 1H), 7.60-7.58 (m, 1H), 7.38 (d, J=8.0 Hz, 1H), 7.13 (d, J=8.0 Hz, 1H), 6.97 (d, J=12.5 Hz, 1H), 4.32 (s, 2H), 3.98 (s, 2H), 3.42-3.34 (m, 2H), 3.33 (s, 3H), 2.97 (s, 2H), 2.06-1.97 (m, 4), 1.58-1.56 (m, 2H), 0.90-0.86 (m, 2H), 0.70-0.67 (m, 2H).

Example 139

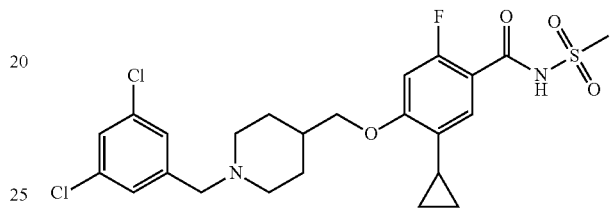

5-Cyclopropyl-4-((1-(3,5-dichlorobenzyl)piperidin-4-yl)methoxy)-2-fluoro-N-(methylsulfonyl)benzamide The compound was synthesized as described in Example 88. LCMS (ESI) Method A: RT=5.75 min, m/z: 528.8 [M+H]$^+$. $^1$H NMR (500 MHz, DMSO-d$_6$): δ 7.53 (s, 1H), 7.40 (s, 2H), 7.16 (d, J=8.5 Hz, 1H), 6.84 (d, J=12.0 Hz, 1H), 3.93 (d, J=5.5 Hz, 2H), 3.64-3.61 (m, 2H), 3.14 (s, 3H), 2.93-2.91 (m, 2H), 2.17-2.16 (m, 2H), 2.03-2.00 (m, 1H), 1.82-1.80 (m, 3H), 1.41-1.39 (m, 2H), 0.90-0.86 (m, 2H), 0.63-0.62 (d, 2H).

Example 140

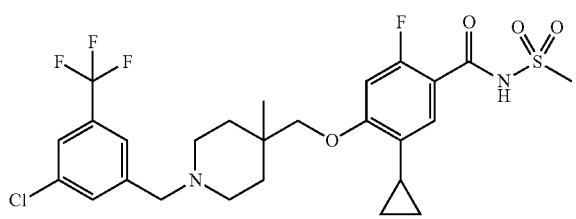 [SMILES: CC1(COc2cc(F)c(C(=O)NS(C)(=O)=O)cc2C2CC2)CCN(Cc2cc(Cl)cc(C(F)(F)F)c2)CC1]

4-((1-(3-chloro-5-(trifluoromethyl)benzyl)-4-methylpiperidin-4-yl)methoxy)-5-cyclopropyl-2-fluoro-N-(methylsulfonyl)benzamide The compound was prepared in a similar manner to Example 73 starting from tert-butyl 4-((2-cyclopropyl-5-fluoro-4-((methylsulfonyl)carbamoyl)phenoxy)methyl)-4-methylpiperidine-1-carboxylate (Example 73 step 1-2) and 3-chloro-5-(trifluoromethyl)benzaldehyde. LCMS (Method G): RT=5.81, min, m/z: 577.2 [M+H]$^+$. $^1$H NMR (400 MHz, DMSO-d6) δ 7.81-7.65 (m, 3H), 7.20 (d, J=8.4 Hz, 1H), 6.90 (d, J=12.9 Hz, 1H), 3.84 (s, 2H), 3.76 (s, 2H), 3.20 (s, 3H), 2.72-2.58 (m, 2H), 2.07-1.96 (m, 1H), 1.78-1.65 (m, 2H), 1.56-1.43 (m, 2H), 1.09 (s, 3H), 0.92-0.83 (m, 2H), 0.68-0.59 (m, 2H).

Example 141

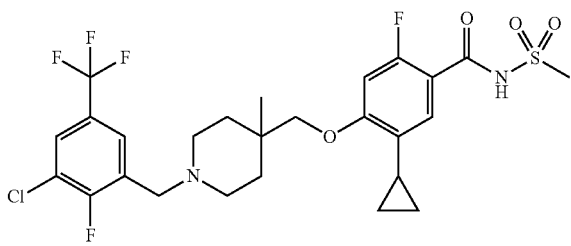

4-((1-(3-chloro-2-fluoro-5-(trifluoromethyl)benzyl)-4-methylpiperidin-4-yl)methoxy)-5-cyclopropyl-2-fluoro-N-(methylsulfonyl)benzamide The compound was prepared in a similar manner to Example 73 starting from tert-butyl 4-((2-cyclopropyl-5-fluoro-4-((methylsulfonyl)carbamoyl)phenoxy)methyl)-4-methylpiperidine-1-carboxylate (Example 73 step 1-2) and 3-chloro-2-fluoro-5-(trifluoromethyl)benzaldehyde. LCMS (Method G): RT=6.67 min, m/z: 595.14 [M+H]$^+$. $^1$H NMR (400 MHz, DMSO-d6) δ 11.58 (s, 1H), 8.02 (dd, J=6.4, 2.3 Hz, 1H), 7.80 (dd, J=5.9, 2.3 Hz, 1H), 7.19 (d, J=8.5 Hz, 1H), 6.91 (d, J=12.9 Hz, 1H), 3.84 (s, 2H), 3.75 (s, 2H), 3.24 (s, 3H), 2.72-2.57 (m, 2H), 2.08-1.96 (m, 1H), 1.77-1.62 (m, 2H), 1.53-1.40 (m, 2H), 1.07 (s, 3H), 0.93-0.82 (m, 2H), 0.69-0.59 (m, 2H).

Example 142

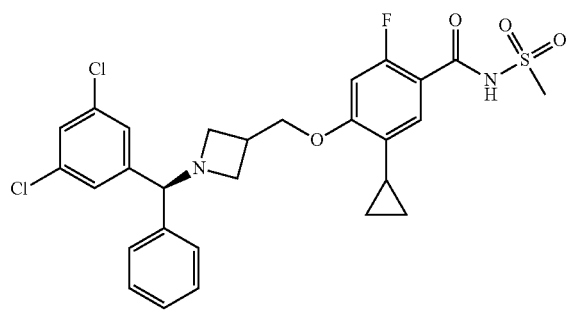 [SMILES: CS(=O)(=O)NC(=O)c1cc(C2CC2)c(OCC2CN([C@@H](c3ccccc3)c3cc(Cl)cc(Cl)c3)C2)cc1F]

(S)-5-Cyclopropyl-4-((1-((3,5-dichlorophenyl)(phenyl)methyl)azetidin-3-yl)methoxy)-2-fluoro-N-(methylsulfonyl)benzamide The compound was synthesized as described in Example 81. Chiral HPLC (column: OJ-H, 4.6×250 mm, 5 μm; mobile Phase: A: supercritical CO$_2$, B: MeOH, A:B=65:35; flow: 1.95 mL/min; column temperature: 40° C.; RT=4.15 min). LCMS (ESI) Method A: RT=6.20 min, m/z: 577.2 [M+H]$^+$. $^1$H-NMR NMR (500 MHz, MeOD-d$_4$): δ7.30-7.28 (m, 4H), 7.23-7.20 (m, 3H), 7.17-7.12 (m, 2H), 6.70 (d, J=12.5 Hz, 1H), 4.42 (s, 1H), 4.10 (d, J=7.0 Hz, 2H), 3.33-3.26 (m, 2H), 3.16 (s, 3H), 3.10-3.05 (m, 2H), 2.90-2.87 (m, 1H), 2.00-1.96 (m, 1H), 0.86-0.80 (m, 2H), 0.56-0.54 (m, 2H).

Example 143

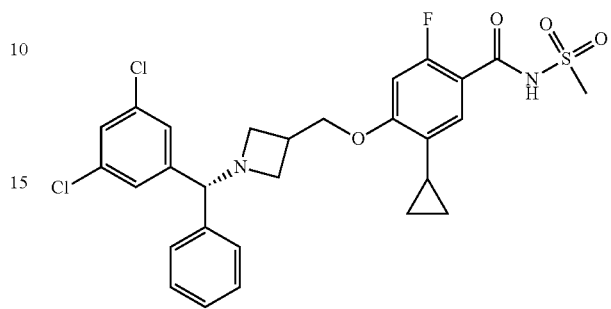

(R)-5-(Cyclopropyl-4-((1-((3,5-dichlorophenyl)(phenyl)methyl)azetidin-3-yl)methoxy)-2-fluoro-N-(methylsulfonyl)benzamide The compound was synthesized as described in Example 81. Chiral HPLC (column: OJ-H, 4.6×250 mm, 5 μm; mobile Phase: A: supercritical CO$_2$, B: MeOH, A:B=65:35; flow: 1.95 mL/min; column temperature: 40° C.; RT=5.47 min). LCMS (ESI) Method A: RT=6.19 min, m/z: 577.2 [M+H]$^+$. $^1$H-NMR (500 MHz, MeOD-d$_4$): δ7.30-7.28 (m, 4H), 7.23-7.20 (m, 3H), 7.17-7.12 (m, 2H), 6.70 (d, J=12.5 Hz, 1H), 4.42 (s, 1H), 4.10 (d, J=7.0 Hz, 2H), 3.33-3.26 (m, 2H), 3.16 (s, 3H), 3.10-3.05 (m, 2H), 2.90-2.87 (m, 1H), 2.00-1.96 (m, 1H), 0.86-0.80 (m, 2H), 0.56-0.54 (m, 2H).

Example 144

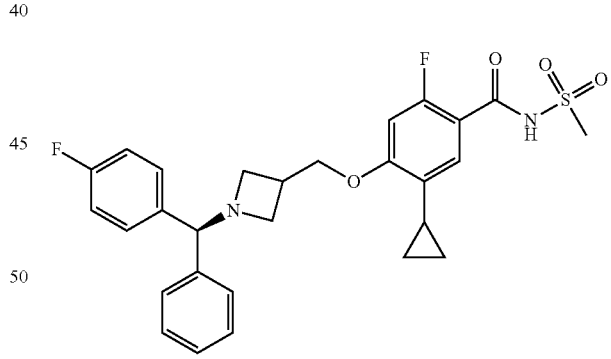

(S)-5-Cyclopropyl-2-fluoro-4-((1-((4-fluorophenyl)(phenyl)methyl)azetidin-3-yl)methoxy)-N-(methylsulfonyl)benzamide The compound was synthesized as described in Example 81. Chiral HPLC (column: OJ-H, 4.6×250 mm, 5 μm; mobile Phase: A: supercritical CO$_2$, B: MeOH (0.1% DEA), A:B=75:25; flow: 2.25 mL/min; column temperature: 40° C.; RT=5.77 min). LCMS (ESI) Method A: RT=4.83 min, m/z: 527.2 [M+H]$^+$. $^1$H-NMR (500 MHz, MeOH-d$_4$): δ 7.35-7.29 (m, 4H), 7.24-7.20 (m, 3H), 7.16-7.12 (m, 1H), 6.97-6.93 (m, 2H), 6.67 (d, J=13.0 Hz, 1H), 4.63 (s, 1H), 4.08 (d, J=6.0 Hz, 2H), 3.45-3.43 (m, 2H), 3.25-3.22 (m, 2H), 3.15 (s, 3H), 2.98-2.95 (m, 1H), 1.99-1.95 (m, 1H), 0.84-0.79 (m, 2H), 0.56-0.54 (m, 2H).

Example 145

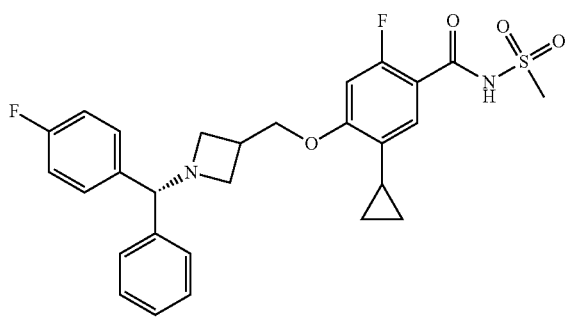 [SMILES: CS(=O)(=O)NC(=O)c1cc(C2CC2)c(OCC2CN([C@H](c3ccccc3)c3ccc(F)cc3)C2)cc1F]

(R)-5-Cyclopropyl-2-fluoro-4-((1-((4-fluorophenyl)(phenyl)methyl)-azetidin-3-yl)methoxy)-N-(methylsulfonyl)benzamide The compound was synthesized as described in Example 81. Chiral HPLC (column: OJ-H, 4.6×250 mm, 5 μm; mobile Phase: A: supercritical CO₂, B: MeOH (0.1% DEA), A:B=25:25; flow: 2.25 mL/min; column temperature: 40° C.; RT=6.50 min). LCMS (ESI) Method A: RT=4.79 min, m/z: 527.2 [M+H]⁺. ¹H-NMR (500 MHz, MeOH-d₄): δ 7.35-7.29 (m, 4H), 7.24-7.20 (m, 3H), 7.16-7.12 (m, 1H), 6.97-6.93 (m, 2H), 6.67 (d, J=13.0 Hz, 1H), 4.63 (s, 1H), 4.08 (d, J=6.0 Hz, 2H), 3.45-3.43 (m, 2H), 3.25-3.22 (m, 2H), 3.15 (s, 3H), 2.98-2.95 (m, 1H), 1.99-1.95 (m, 1H), 0.84-0.79 (m, 2H), 0.56-0.54 (m, 2H).

Example 146

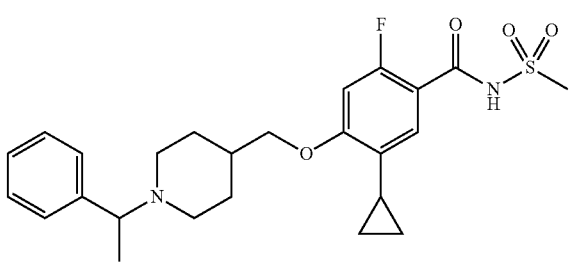 [SMILES: CC(c1ccccc1)N1CCC(COc2cc(F)c(C(=O)NS(C)(=O)=O)cc2C2CC2)CC1]

5-Cyclopropyl-2-fluoro-N-(methylsulfonyl)-4-((1-(1-phenylethyl)-piperidin-4-yl)methoxy)benzamide The compound was synthesized as described is Example 88. LCMS (ESI) Method A: RT=4.70 min, m/z: 476.2 [M+H]⁺. 1H-NMR (500 MHz, DMSO-d₆): δ 7.42-7.36 (m, 5H), 7.18 (d, J=8.0 Hz, 1H), 6.78 (d, J=13.0 Hz, 1H), 4.04 (brs, 1H), 3.90 (d, J=5.0 Hz, 2H), 3.32 (s, 3H), 3.02 (m, 4H), 2.02-1.97 (m, 1H), 1.90-1.84 (m, 3H), 1.50-1.49 (m, 5H), 0.88-0.83 (m, 2H), 0.60-0.57 (m, 2H).

Example 147

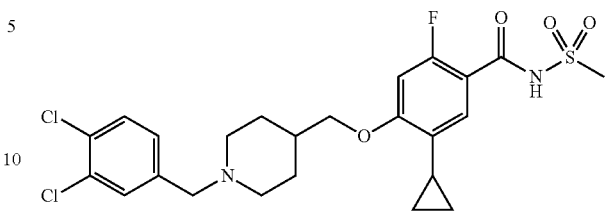

5-Cyclopropyl-4-((1-(3,4-dichlorobenzyl)piperidin-4-yl)methoxy)-2-fluoro-N-(methylsulfonyl)benzamide The compound was synthesized as described in Example 88. LCMS (ESI) Method A: RT=5.75 min, m/z: 528.9 [M+H]⁺. ¹H-NMR (500 MHz, DMSO-d₆): δ 7.64-7.63 (m, 2H), 7.37-7.36 (m, 1H), 7.17-7.16 (m, 1H), 6.85 (d, J=13.0 Hz, 1H), 3.94 (s, 2H), 3.72 (s, 2H), 3.15 (s, 3H), 3.00-2.98 (m, 2H), 2.29 (s, 2H), 2.02-2.01 (m, 1H), 1.85-1.82 (m, 3H), 1.44-1.42 (m, 2H), 0.88-0.87 (m, 2H), 0.63 (s, 2H).

Example 148

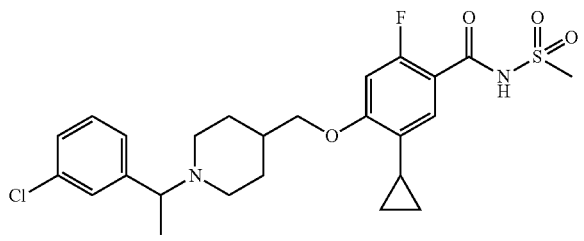 [SMILES: CC(c1cccc(Cl)c1)N1CCC(COc2cc(F)c(C(=O)NS(C)(=O)=O)cc2C2CC2)CC1]

4-((1-(1-(3-Chlorophenyl)ethyl)piperidin-4-yl)methoxy)-5-cyclopropyl-2-fluoro-N-(methylsulfonyl)benzamide The compound was synthesized as described in Example 88. LCMS (ESI) Method A: RT=5.52 min, m/z: 508.9 [M+H]⁺. ¹H-NMR (500 MHz, DMSO-d₆): δ 7.46-7.31 (m, 4H), 7.17 (d, J=8.5 Hz, 1H), 6.83 (d, J=12.5 Hz, 1H), 3.92-3.91 (m, 3H), 3.31-3.27 (m, 4H), 3.17-3.16 (m, 1H), 2.98-2.96 (m, 1H), 2.27-2.26 (m, 1H), 2.02-1.98 (m, 1H), 1.88-1.80 (m, 3H), 1.46-1.41 (m, 5H), 0.89-0.85 (m, 2H), 0.63-0.60 (m, 2H).

Example 149

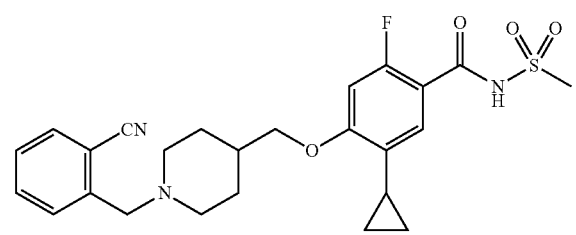 [SMILES: CS(=O)(=O)NC(=O)c1cc(C2CC2)c(OCC2CCN(Cc3ccccc3C#N)CC2)cc1F]

4-((1-(2-Cyanobenzyl)piperidin-4-yl)methoxy)-5-cyclopropyl-2-fluoro-N-(methylsulfonyl)benzamide The compound was synthesized as described in Example 88. LCMS (ESI) Method A: RT=4.86 min, m/z: 486.0 [M+H]+. 1H-NMR (500 MHz, DMSO-d6): δ 7.83-7.81 (m, 1H), 7.71-7.67 (m, 1H), 7.60-7.59 (m, 1H), 7.50-7.47 (m, 1H), 7.15 (d, J=8.0 Hz, 1H), 6.91 (d, J=12.5 Hz, 1H), 3.94 (d, J=6.0 Hz, 2H), 3.70 (s, 2H), 3.25 (s, 3H), 2.90-2.88 (m, 2H), 2.19-2.15 (m, 2H), 2.03-2.00 (m, 1H), 1.84-1.78 (m, 3H), 1.42-1.34 (m, 2H), 0.90-0.86 (m, 2H), 0.66-0.63 (m, 2H).

Example 150

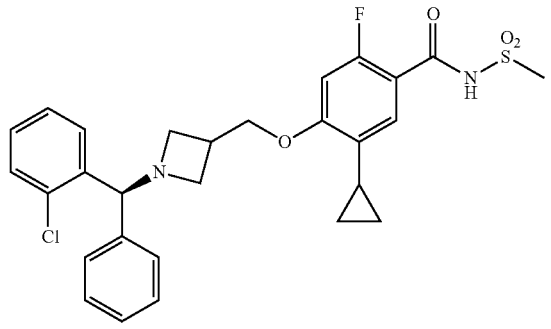 [SMILES: CS(=O)(=O)NC(=O)c1cc(C2CC2)c(OCC2CN([C@@H](c3ccccc3)c3ccccc3Cl)C2)cc1F]

(S)-4-((1-((2-Chlorophenyl)(phenyl)methyl)azetidin-3-yl)methoxy)-5-cyclopropyl-2-fluoro-N-(methylsulfonyl)benzamide The compound was synthesized as described in Example 81. Chiral HPLC (column: OJ-H, 4.6×250 mm, 5 μm; mobile Phase: A: supercritical CO2, B: MeOH (0.1% DEA), A:B=65:35; flow: 1.95 mL/min; column temperature: 40° C.; RT=4.38 min), LCMS (ESI) Method A: RT=6.04 min, m/z: 543.2 [M+H]+. 1H NMR (500 MHz, DMSO-d6) δ 11.89 (s, 1H), 7.81 (d, J=6.6 Hz, 1H), 7.39 (dd, J=19.1, 7.6 Hz, 4H), 7.29 (t, J=7.6 Hz, 2H), 7.23 (dd, J=13.4, 7.6 Hz, 2H), 7.16 (d, J=8.3 Hz, 1H), 6.95 (d, J=12.6 Hz, 1H), 4.88 (s, 1H), 4.18 (d, J=5.7 Hz, 2H), 3.30-3.29 (m, 1H), 3.29-3.23 (m, 3H), 3.15 (s, 2H), 2.93 (s, 2H), 2.10 (s, 1H), 0.91 (t, J=8.9 Hz, 2H), 0.69 (s, 2H).

Example 151

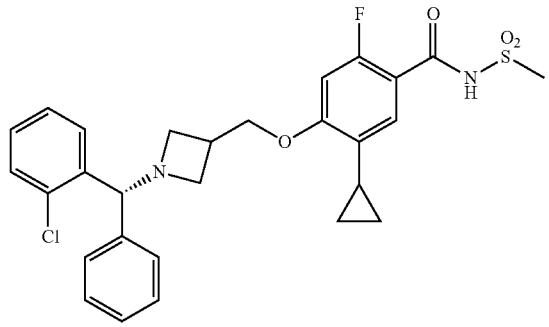 [SMILES: CS(=O)(=O)NC(=O)c1cc(C2CC2)c(OCC2CN([C@H](c3ccccc3)c3ccccc3Cl)C2)cc1F]

(R)-4-((1-((2-Chlorophenyl)(phenyl)methyl)azetidin-3-yl)methoxy)-5-cyclopropyl-2-fluoro-N-(methylsulfonyl)benzamide The compound was synthesized as described in Example 81. Chiral HPLC (column: OJ-H, 4.6×250 mm, 5 μm; mobile Phase: A: supercritical CO2, B: MeOH (0.1% DEA), A:B=65:35; flow: 1.95 mL/min; column temperature: 40° C.; RT=5.23 min). LCMS (ESI) Method A: RT=6.11 min, m/z: 543.2 [M+H]+. 1H NMR (500 MHz, DMSO-d6) δ 11.89 (s, 1H), 7.81 (d, J=6.6 Hz, 1H), 7.39 (dd, J=19.1, 7.6 Hz, 4H), 7.29 (t, J=7.6 Hz, 2H), 7.23 (dd, J=13.4, 7.6 Hz, 2H), 7.16 (d, J=8.3 Hz, 1H), 6.95 (d, J=12.6 Hz, 1H), 4.88 (s, 1H), 4.18 (d, J=5.7 Hz, 2H), 3.30-3.29 (m, 1H), 3.29-3.23 (m, 3H), 3.15 (s, 2H), 2.93 (s, 2H), 2.10 (s, 1H), 0.91 (t, J=8.9 Hz, 2H), 0.69 (s, 2H).

Example 152

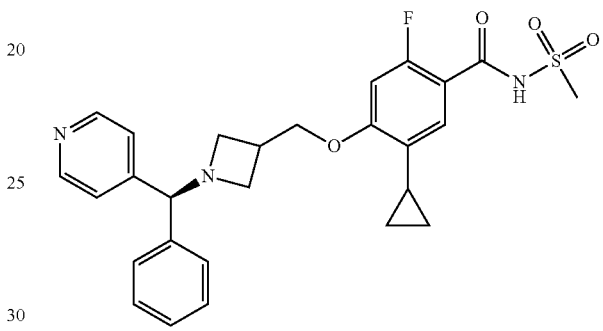

(S)-5-Cyclopropyl-2-fluoro-N-(methylsulfonyl)-4-((1-(phenyl(pyridin-4-yl)methyl)azetidin-3-yl)methoxy)benzamide The compound was synthesized as described in Example 81. Chiral HPLC (column: AD-H, 4.6×250 mm, 5 μm; mobile Phase: A: supercritical CO2, B: MeOH (0.1% DEA), A:B=65:35; flow: 1.95 mL/min; column temperature: 40° C.; RT=4.20 min). LCMS (ESI) Method A: RT=4.72 min, m/z: 510.3 [M+H]+. 1H NMR (500 MHz, MeOD-d4) δ 8.46 (d, J=5.1 Hz, 2H), 7.54 (d, J=5.9 Hz, 2H), 7.44 (d, J=7.3 Hz, 2H), 7.33 (t, J=7.5 Hz, 3H), 7.26 (t, J=7.3 Hz, 1H), 6.83 (d, J=12.8 Hz, 1H), 4.59 (s, 1H), 4.23 (d, J=6.0 Hz, 2H), 3.49 (t, J=7.7 Hz, 1H), 3.39 (t, J=7.6 Hz, 1H), 3.30 (s, 3H), 3.26-3.22 (m, 1H), 3.17 (t, J=6.9 Hz, 1H), 3.06-3.00 (m, 1H), 2.13-2.05 (m, 1H), 0.97-0.92 (m, 2H), 0.68 (d, J=4.3 Hz, 2H).

Example 153

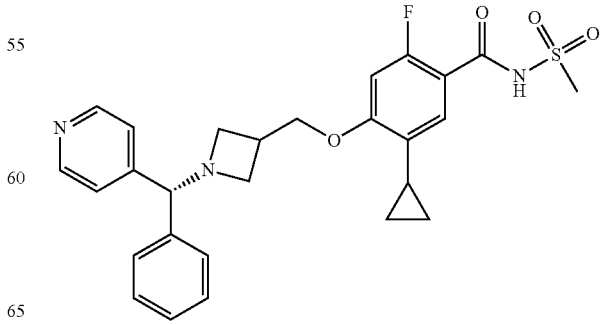

(R)-5-Cyclopropyl-2-fluoro-N-(methylsulfonyl)-4-((1-(phenyl(pyridin-4-yl)methyl)azetidin-3-yl)methoxy)benzamide The compound was synthesized as described in Example 81. Chiral HPLC (column: AD-H, 4.6×250 mm, 5 μm; mobile Phase: A: supercritical CO₂: B: MeOH (0.1% DEA), A:B=65:35; flow: 1.95 mL/min; column temperature: 40° C.; RT=7.60 min). LCMS (ESI) Method B: RT=4.70 min, m/z: 510.3 [M+H]⁺. ¹H NMR (500 MHz, MeOD-d₄) δ 8.34 (d, J=4.6 Hz, 2H), 7.41 (d, J=5.8 Hz, 2H), 7.32 (d, J=7.3 Hz, 2H), 7.21 (t, J=7.5 Hz, 3H), 7.13 (t, J=7.3 Hz, 1H), 6.70 (d, J=12.8 Hz, 1H), 4.47 (s, 1H), 4.11 (d, J=6.1 Hz, 2H), 3.37 (t, J=7.7 Hz, 1H), 3.27 (t, J=7.7 Hz, 1H), 3.17 (s, 3H), 3.14-3.10 (m, 2H), 3.07-3.03 (m, 1H), 2.02-1.92 (m, 1H), 0.86-0.78 (m, 2H), 0.55 (d, J=4.3 Hz, 2H).

Example 154

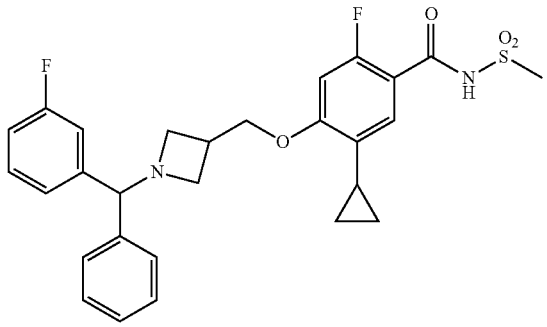 [SMILES: CS(=O)(=O)NC(=O)c1cc(C2CC2)c(OCC2CN(C(c3ccccc3)c3cccc(F)c3)C2)cc1F]

5-Cyclopropyl-2-fluoro-4-((1-((3-fluorophenyl)(phenyl)methyl)azetidin-3-yl)methoxy)-N-(methylsulfonyl)benzamide The compound was synthesized as described in Example 80. LCMS (ESI) Method B: RT=5.84 min, m/z: 527.2 [M+H]⁺. ¹H NMR (500 MHz, MeOD-d₄) δ 7.43 (d, J=7.3 Hz, 2H), 7.34 (dd, J=7.9, 5.0 Hz, 4H), 7.26 (dd, J=7.4, 4.4 Hz, 2H), 7.19 (d, J=9.9 Hz, 1H), 6.98 (t, J=8.5 Hz, 1H), 6.83 (d, J=12.9 Hz, 1H), 4.66 (s, 1H), 4.22 (d, J=5.9 Hz, 2H), 3.56-3.45 (m, 2H), 3.32-3.32 (m, 2H), 3.30 (s, 3H), 3.06 (s, 1H), 2.11 (t, J=6.9 Hz, 1H), 0.98-0.91 (m, 2H), 0.69 (q, J=5.9 Hz, 2H).

Example 155

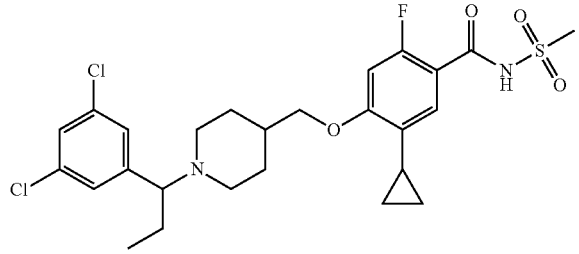 [SMILES: CCC(c1cc(Cl)cc(Cl)c1)N1CCC(COc2cc(F)c(C(=O)NS(C)(=O)=O)cc2C2CC2)CC1]

5-Cyclopropyl-4-((1-(1-(3,5-dichlorophenyl)propyl)piperidin-4-yl)methoxy)-2-fluoro-N-(methylsulfonyl)benzamide The compound was synthesized as described in Example 88. LCMS (ESI) Method A: RT=6.40 min, m/z: 556.8 [M+H]⁺. ¹H NMR (500 MHz, DMSO-d₆) δ 7.52 (s, 1H), 7.34 (s, 2H), 7.16 (d, J=8.4 Hz, 1H), 6.80 (d, J=12.8 Hz, 1H), 3.87 (d, J=5.9 Hz, 2H), 3.51 (s, 1H), 3.10 (s, 3H), 3.03 (s, 1H), 2.91 (s, 1H), 1.99 (s, 2H), 1.88 (s, 2H), 1.76 (d, J=14.0 Hz, 4H), 1.35 (m, 2H), 0.89-0.81 (m, 2H), 0.72 (t, J=7.2 Hz, 3H), 0.60 (d, J=4.1 Hz, 2H).

Example 156

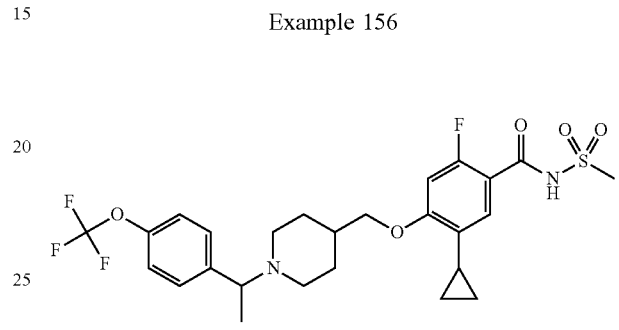

5-Cyclopropyl-2-fluoro-N-methylsulfonyl)-4-((1-(1-(4-(trifluoromethoxy)-phenyl)ethyl)piperidin-4-yl)methoxy)benzamide The compound was synthesized as described in Example 88. LCMS (ESI) Method A: RT=5.68 min, m/z: 558.9 [M+H]⁺. ¹H NMR (500 MHz, MeOD-d₄) δ 7.63 (s, 2H), 7.37 (m, 3H), 6.58 (s, 1H), 4.33 (s, 1H), 3.70 (m, 3H), 3.16 (s, 3H), 2.76 (s, 2H), 2.00 (m, 4H), 1.85-1.47 (m, 6H), 0.86 (s, 2H), 0.63 (s, 2H).

Example 157

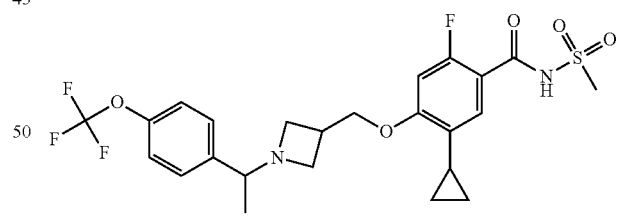

5-Cyclopropyl-2-fluoro-N-(methylsulfonyl)-4-((1-(1-(4-(trifluoromethoxy)-phenyl)ethyl)azetidin-3-yl)methoxy)benzamide The compound was synthesized as described in Example 80. LCMS (ESI) Method A: RT=5.24 min, m/z: 516.9 [M+H]⁺. ¹H NMR (500 MHz, MeOD-d₄) δ 7.50 (d, J=8.6 Hz, 2H), 7.28 (m, 3H), 6.49 (d, J=12.3 Hz, 1H), 4.92 (m, 2H), 4.05 (m, 1H), 3.77 (m, 2H), 3.44-3.35 (m, 2H), 3.26 (m, 1H), 3.22 (s, 3H), 2.12 (m, 1H), 1.35 (d, J=6.5 Hz, 3H), 0.98-0.88 (m, 2H), 0.68 (m, 2H).

Example 158

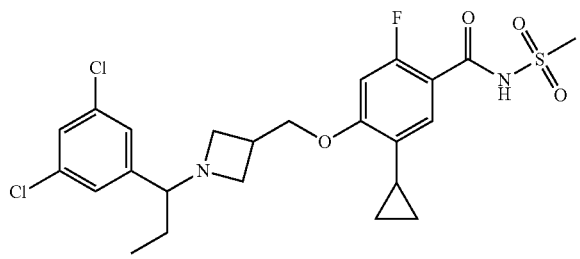 [SMILES: CCC(c1cc(Cl)cc(Cl)c1)N1CC(COc2cc(F)c(C(=O)NS(C)(=O)=O)cc2C2CC2)C1]

5-Cyclopropyl-4-((1-(1-(3,5-dichlorophenyl)propyl)azetidin-3-yl)methoxy)-2-fluoro-N-(methylsulfonyl)benzamide The compound was synthesized as described in Example 80. LCMS (ESI) Method A: RT=5.74 min, m/z: 529.0 [M+H]+. $^1$H NMR (500 MHz, MeOD-d$_4$) δ 7.50-7.41 (m, 1H), 7.40-7.30 (m, 3H), 6.83-6.69 (m, 1H), 4.18 (s, 2H), 3.76 (m, 1H), 3.47 (m, 4H), 3.24 (s, 3H), 3.09 (m, 1H), 2.08 (m, 1H), 1.88 (m, 1H), 1.56 (m, 1H), 0.93 (m, 2H), 0.76 (m, 3H), 0.68 (s, 2H).

Example 159

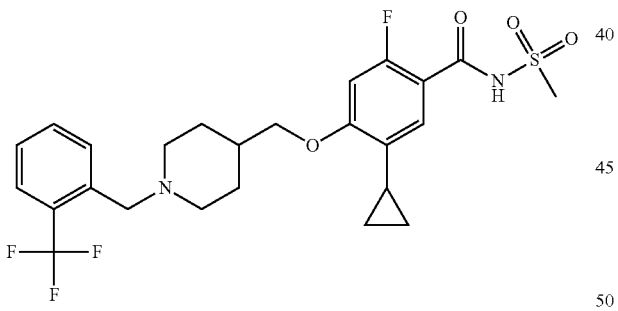

5-Cyclopropyl-2-fluoro-N-(methylsulfonyl)-4-((1-(2-(trifluoromethyl)-benzyl)piperidin-4-yl)methoxy)benzamide The compound was synthesized as described in Example 88. LCMS (ESI) Method A: RT=5.94 min, m/z: 529.0 [M+H]+. $^1$H NMR (500 MHz, MeOD-d$_4$) δ 7.88 (d, J=7.8 Hz, 1H), 7.73 (d, J=7.9 Hz, 1H), 7.66 (t, J=7.6 Hz, 1H), 7.50 (t, J=7.6 Hz, 1H), 7.35 (s, 1H), 6.72 (d, J=12.9 Hz, 1H), 3.93 (m, 4H), 3.22 (m, 3H), 3.12 (m, 2H), 2.43 (m, 2H), 2.07 (m, 1H), 2.01 (m, 1H), 1.95 (m, 2H), 1.68-1.55 (m, 2H), 0.91 (m, 2H), 0.65 (m, 2H).

Example 160

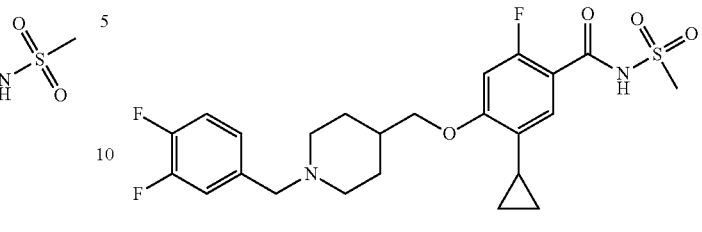

5-Cyclopropyl-4-((1-(3,4-difluorobenzyl)piperidin-4-yl)methoxy)-2-fluoro-N-(methylsulfonyl)benzamide The compound was synthesized as described in Example 88. LCMS (ESI) Method A: RT=4.46 min, m/z: 497.2 [M+H]+. $^1$H NMR (500 MHz, DMSO-d$_6$) δ 7.43 (m, 2H), 7.25-7.13 (m, 2H), 6.83 (d, J=12.8 Hz, 1H), 3.93 (d, J=5.9 Hz, 2H), 3.70 (s, 2H), 3.11 (s, 3H), 2.99 (m, 2H), 2.28 (m, 2H), 2.05-1.96 (m, 1H), 1.83 (m, 3H), 1.42 (m, 2H), 0.87 (m, 2H), 0.61 (m, 2H).

Example 161

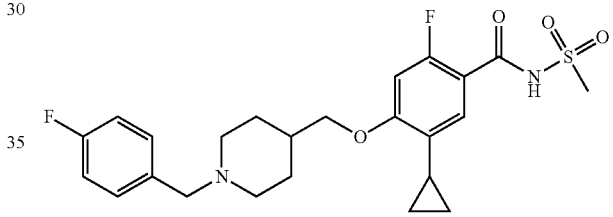

5-Cyclopropyl-2-fluoro-4-((1-(4-fluorobenzyl)piperidin-4-yl)methoxy)-N-(methylsulfonyl)benzamide The compound was synthesized as described in Example 88, LCMS (ESI) Method A: RT=4.90 min, m/z: 479.0 [M+H]+. $^1$H NMR (500 MHz, DMSO-d$_6$) δ 7.46-7.39 (m, 2H), 7.20 (m, 3H), 6.80 (d, J=12.8 Hz, 1H), 3.92 (d, J=6.0 Hz, 2H), 3.80 (m, 2H), 3.04 (m, 5H), 2.40 (m, 2H), 2.00 (m, 1H), 1.86 (m, 3H), 1.45 (m, 2H), 0.87 (m, 2H), 0.59 (m, 2H).

Example 162

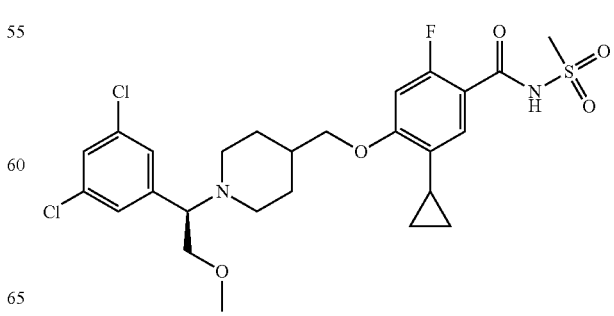

(R)-5-cyclopropyl-4-((1-(1-(3,5-dichlorophenyl)-2-methoxyethyl)piperidin-4-yl)methoxy)-2-fluoro-N-(methylsulfonyl)benzamide Step 1

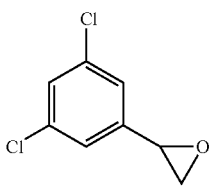 [SMILES: Clc1cc(Cl)cc(C2CO2)c1]

2-(3,5-Dichlorophenyl)oxirane

The compound was synthesized as described in step 1 of Example 90.

Step 2

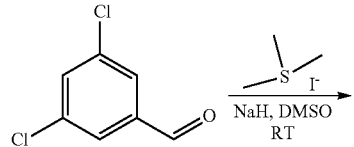

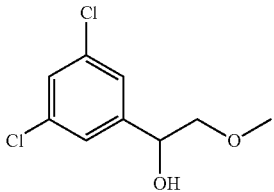

1-(3,5-Dichlorophenyl)-2-methoxyethanol

The compound was synthesized as described in step 2 of Example 90.

Step 3

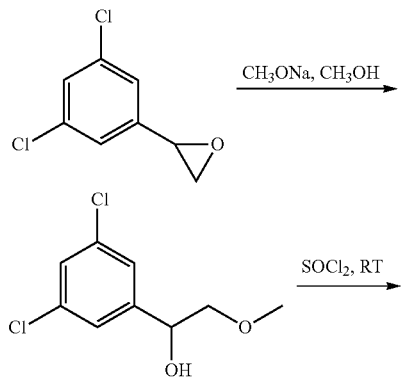

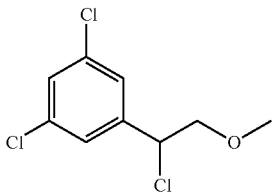

1,3-Dichloro-5-(1-chloro-2-methoxyethyl)benzene

The compound was synthesized as described in step 2 of Example 80.

Step 4

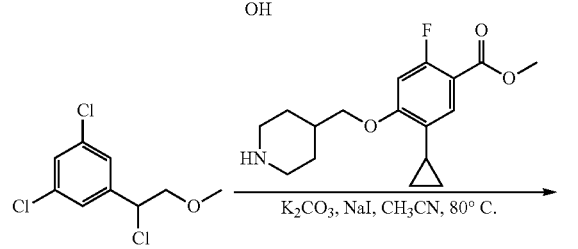

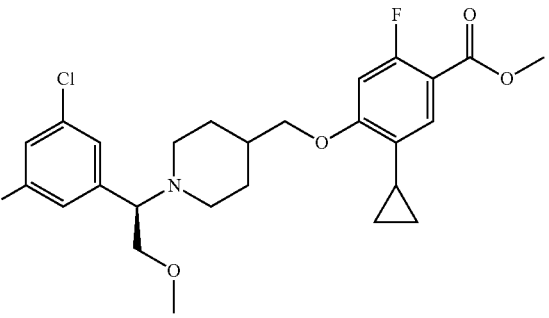

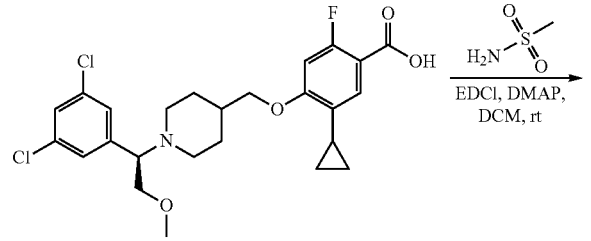

(R)-methyl 5-cyclopropyl-4-((1-(1-(3,5-dichlorophenyl)-2-methoxyethyl)piperidin-4-yl)methoxy)-2-fluorobenzoate The compound was synthesized as described in step 5 of Example 88. The enantiomer was separated by chiral SFC from the racemate, the first eluting fraction was arbitrarily assigned as (R)-methyl 5-cyclopropyl-4-((1-(1-(3,5-dichlorophenyl)-2-methoxyethyl)piperidin-4-yl)methoxy)-2-fluorobenzoate. Chiral HPLC (column: AD-H, 4.6×250 mm, 5 µm: mobile Phase: A: supercritical $CO_2$, B: EtOH, A:B=85:15; flow: 3 mL/min; column temperature: 40° C.; RT=3.89 min). LCMS (ESI) m/z: 510.1 $[M+H]^+$.

Step 5

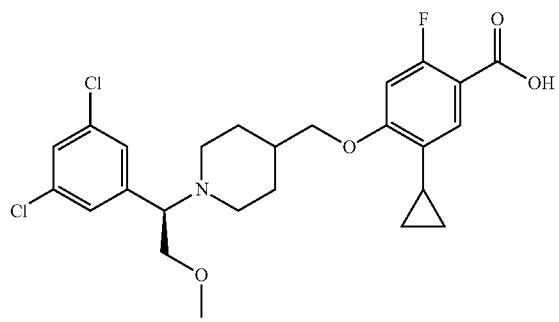 [SMILES: COC[C@@H](c1cc(Cl)cc(Cl)c1)N1CCC(COc2cc(F)c(C(=O)O)cc2C2CC2)CC1]

(R)-5-cyclopropyl-4-((1-(1-(3,5-dichlorophenyl)-2-methoxyethyl)piperidin-4-yl)methoxy)-2-fluorobenzoic acid The compound was synthesized as described in step 6 of Example 88. LCMS (ESI) m/z: 496.1 $[M+H]^+$.

Step 6

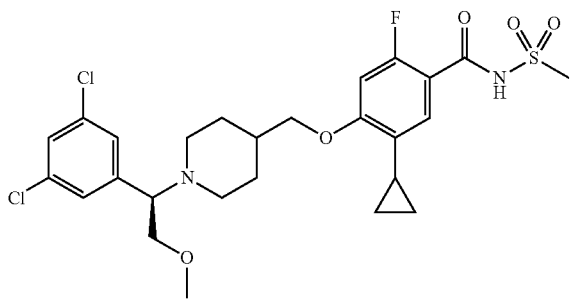 [SMILES: COC[C@@H](c1cc(Cl)cc(Cl)c1)N1CCC(COc2cc(F)c(C(=O)NS(C)(=O)=O)cc2C2CC2)CC1]

(R)-5-cyclopropyl-4-((1-(1-(3,5-dichlorophenyl)-2-methoxyethyl)piperidin-4-yl)methoxy)-2-fluoro-N-(methylsulfonyl)benzamide The compound was synthesized as described in step 5 of Example 80. Chiral HPLC (column: OJ-H, 4.6×250 mm, 5 µm; mobile Phase: A: supercritical $CO_2$, B: MeOH, A:B=85:15; flow: 2.55 mL/min; column temperature: 39.8° C.; RT=6.09 min). LCMS (ESI) Method A: RT-5.79 min, m/z: 572.8 $[M+H]^+$. $^1$H NMR (500 MHz, DMSO-$d_6$): δ 11.65 (brs, 1H), 7.51-7.50 (m, 1H), 7.41-7.40 (m, 2H), 7.14 (d, J=9.0 Hz, 1H), 6.88 (d, J=13.0 Hz, 1H), 3.91 (d, J=5.5 Hz, 2H), 3.78-3.67 (m, 3H), 3.25 (s, 3H), 3.23 (s, 3H), 3.03-3.01 (m, 1H), 2.84-2.82 (m, 1H), 2.16-2.12 (m, 1H), 2.06-1.97 (m, 2H), 1.80-1.73 (m, 3H), 1.41-1.31 (m, 2H), 0.89-0.86 (m, 2H), 0.66-0.63 (m, 2H).

Example 163

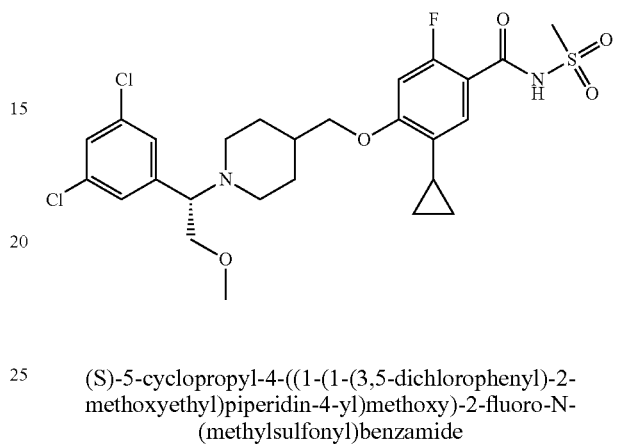

(S)-5-cyclopropyl-4-((1-(1-(3,5-dichlorophenyl)-2-methoxyethyl)piperidin-4-yl)methoxy)-2-fluoro-N-(methylsulfonyl)benzamide The compound was synthesized as described in Example 162. The enantiomer was arbitrarily assigned as (S)-5-cyclopropyl-4-((1-(1-(3,5-dichlorophenyl)-2-methoxyethyl)piperidin-4-yl)methoxy)-2-fluoro-N-(methylsulfonyl)benzamide. Chiral HPLC (column: OJ-H, 4.6×250 mm, 5 µm; mobile Phase: A: supercritical $CO_2$, B: MeOH, A:B=85:15; flow: 2.55 mL/min; column temperature; 40.6° C.; RT=6.48 min). LCMS (ESI) Method A: RT=5.79 min, m/z: 572.8 $[M+H]^+$. $^1$H NMR (500 MHz, DMSO-$d_6$): δ 11.63 (brs, 1H), 7.52-7.5.1 (m, 1H), 7.41-7.40 (m, 2H), 7.14 (d, J=8.5 Hz, 1H), 6.89 (d, J=12.5 Hz, 1H), 3.91 (d, J=6.0 Hz, 2H), 3.79-3.68 (m, 3H), 3.25 (s, 3H), 3.23 (s, 3H), 3.03-3.02 (m, 1H), 2.85-2.82 (m, 1H), 2.17-2.13 (m, 1H), 2.95-1.97 (m, 2H), 1.80-1.73 (m, 3H), 1.41-1.31 (m, 2H), 0.89-0.86 (m, 2H), 0.66-0.63 (m, 2H).

Example 164

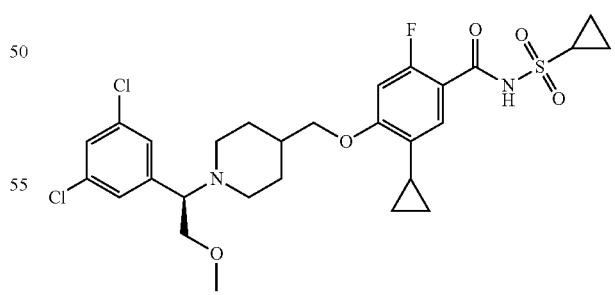

(R)-5-cyclopropyl-N-(cyclopropylsulfonyl)-4-((1-(1-(3,5-dichlorophenyl)-2-methoxyethyl)piperidin-4-yl)methoxy)-2-fluorobenzamide The compound was synthesized as described in Example 162. The enantiomer was arbitrarily assigned as (R)-5- cyclopropyl-N-(cyclopropylsulfonyl)-4-((1-(1-(3,5-dichlorophenyl)-2-methoxyethyl)piperidin-4-yl)methoxy-2-fluorobenzamide. Chiral HPLC (column: AD-H, 4.6×250 mm, 5 µm; mobile Phase: A: supercritical $CO_2$, B: MeOH, A:B=80:20; flow: 2.4 mL/min; column temperature: 38.0° C.; RT=13.16 min). LCMS (ESI) Method A: RT=6.27 min, m/z: 598.8 $[M+H]^+$. $^1$H NMR (500 MHz, DMSO-$d_6$): δ11.67 (brs, 1H), 7.50 (s, 1H), 7.39 (s, 2H), 7.13 (d, J=8.0 Hz, 1H), 6.89 (d, J=12.5 Hz, 1H), 3.91 (d, J=5.5 Hz, 2H), 3.74-3.67 (m, 3H), 3.23 (s, 3H), 3.06-2.98 (m, 2H), 2.82-2.80 (m, 1H), 2.12-2.08 (m, 1H), 2.03-1.97 (m, 2H), 1.79-1.72 (m, 3H), 1.39-1.23 (m, 2H), 1.08-1.03 (m, 4H), 0.89-0.86 (m, 2H), 0.65-0.64 (m, 2H).

Example 165

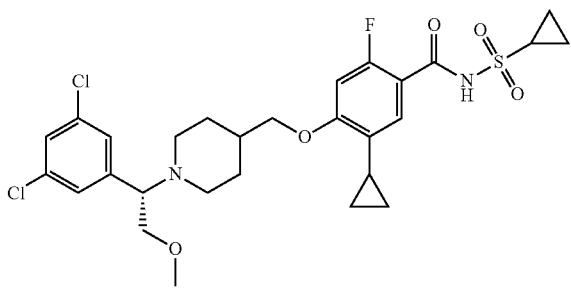 [SMILES: COC[C@H](c1cc(Cl)cc(Cl)c1)N1CCC(COc2cc(F)c(C(=O)NS(=O)(=O)C3CC3)cc2C2CC2)CC1]

(S)-5-cyclopropyl-N-(cyclopropylsulfonyl)-4-((1-(1-(3,5-dichlorophenyl)-2-methoxyethyl)piperidin-4-yl)methoxy)-2-fluorobenzamide The compound was synthesized as described in Example 163. The enantiomer was arbitrarily assigned as (S)-5-cyclopropyl-N-(cyclopropylsulfonyl)-4-((1-(1-(3,5-dichlorophenyl)-2-methoxyethyl)piperidin-4-yl)methoxy)-2-fluorobenzamide. Chiral HPLC (column: AD-H, 4.6×250 mm, 5 µm; mobile Phase: A: supercritical $CO_2$, B: MeOH, A:B=80:20; flow: 2.4 mL/min; column temperature: 39.7° C.; RT=11.96 min). LCMS (ESI) Method A: RT=6.19 min, m/z: 598.9 $[M+H]^+$. $^1$H NMR (500 MHz, DMSO-$d_6$): δ 11.69 (brs, 1H), 7.50 (s, 1H), 7.39 (s, 2H), 7.13 (d, J=8.0 Hz, 1H), 6.89 (d, J=13.0 Hz, 1H), 3.90 (d, J=6.0 Hz, 2H), 3.73-3.67 (m, 3H), 3.22 (s, 3H), 3.06-2.98 (m, 2H), 2.82-2.80 (m, 1H), 2.11-2.07 (m, 1H), 2.03-1.96 (m, 2H), 1.79-1.72 (m, 3H), 1.37-1.23 (m, 2H), 1.07-1.02 (m, 4H), 0.89-0.85 (m, 2H), 0.65-0.62 (m, 2H).

Example 166

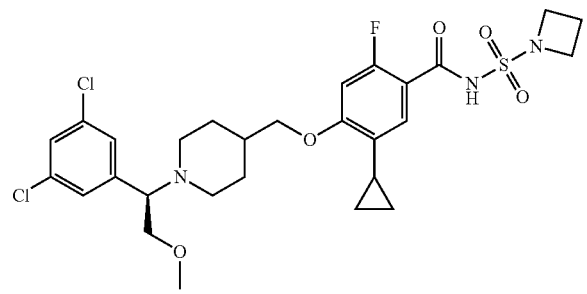 [SMILES: COC[C@@H](c1cc(Cl)cc(Cl)c1)N1CCC(COc2cc(F)c(C(=O)NS(=O)(=O)N3CCC3)cc2C2CC2)CC1]

(R)—N-(azetidin-1-ylsulfonyl)-5-cyclopropyl-4-((1-(1-(3,5-dichlorophenyl)-2-methoxyethyl)piperidin-4-yl)methoxy)-2-fluorobenzamide The compound was synthesized as described in Example 162. The enantiomer was arbitrarily assigned as (R)—N-(azetidin-1-ylsulfonyl)-5-cyclopropyl-4-((1-(1-(3,5-dichlorophenyl)-2-methoxyethyl)piperidin-4-yl)methoxy)-2-fluorobenzamide. Chiral HPLC (column: (s,s-whelk-ol, 4.6×250 mm, 5 µm; mobile Phase: A: n-hexane, B: MeOH, A:B=80:20; flow: 1 mL/min; column temperature: 40° C.; RT=11.97 min). LCMS (ESI) Method A: RT=6.34 min, m/z: 614.0 $[M+H]^+$. $^1$H NMR (500 MHz, DMSO-$d_6$): δ 11.52 (brs, 1H), 7.50-7.49 (m, 1H), 7.39-7.38 (m, 2H), 7.15 (d, J=8.5 Hz, 1H), 6.87 (d, J=12.5 Hz, 1H), 3.97-3.94 (m, 4H), 3.90 (d, J=6.5 Hz, 2H), 3.74-3.66 (m, 3H), 3.22 (s, 3H), 2.99-2.97 (m, 1H), 2.81-2.79 (m, 1H), 2.15-2.06 (m, 3H), 2.02-1.94 (m, 2H), 1.79-1.69 (m, 3H), 1.37-1.28 (m, 2H), 0.89-0.86 (m, 2H), 0.66-0.63 (m, 2H).

Example 167

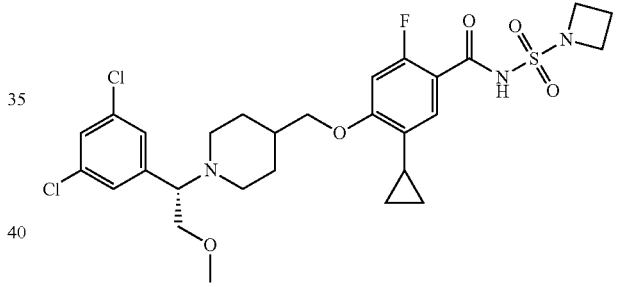

(S)—N-(azetidin-1-ylsulfonyl)-5-cyclopropyl-4-((1-(1-(3,5-dichlorophenyl)-2-methoxyethyl)piperidin-4-yl)methoxy)-2-fluorobenzamide The compound was synthesized as described in Example 163. The enantiomer was arbitrarily assigned as (S)—N-(azetidin-1-ylfulfonyl)-5-cyclopropyl-4-((1-(1-(3,5-dichlorophenyl)-2-methoxyethyl)piperidin-4-yl)methoxy-2-fluorobenzamide. Chiral HPLC (column: (s,s-whelk-ol, 4.6×250 mm, 5 µm; mobile Phase: A: n-hexane, B: MeOH, A:B=80:20; flow: 1 mL/min; column temperature: 40° C.; RT=12.14 min). LCMS (ESI) Method A: RT=6.36 min, m/z: 614.0 $[M+H]^+$. $^1$H NMR (500 MHz, DMSO-$d_6$): δ 7.49-7.48 (m, 1H), 7.38-7.37 (m, 2H), 7.18 (d, J=9.0 Hz, 1H), 6.87 (d, J=12.5 Hz, 1H), 3.88-3.85 (m, 6H), 3.72-3.65 (m, 3H), 3.21 (s, 3H), 2.98-2.96 (m, 1H), 2.80-2.78 (m, 1H), 2.09-1.92 (m, 5H), 1.79-1.71 (m, 3H), 1.37-1.28 (m, 2H), 0.89-0.86 (m, 2H), 0.62-0.59 (m, 2H).

Example 168

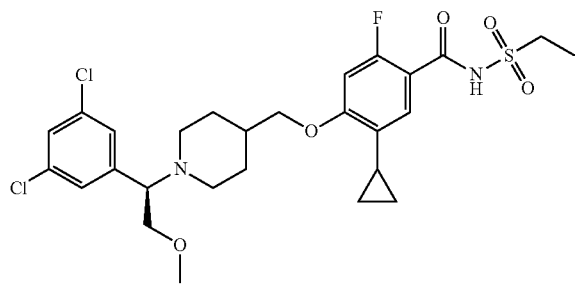 [SMILES: CCS(=O)(=O)NC(=O)c1cc(C2CC2)c(OCC2CCN([C@@H](COC)c3cc(Cl)cc(Cl)c3)CC2)cc1F]

(R)-5-cyclopropyl-4-((1-(1-(3,5-dichlorophenyl)-2-methoxyethyl)piperidin-4-yl)methoxy)-N-(ethylsulfonyl)-2-fluorobenzamide The compound was synthesized as described in Example 162. The enantiomer was arbitrarily assigned as (R)-5-cyclopropyl-4-((1-(1-(3,5-dichlorophenyl)-2-methoxyethyl)piperidin-4-yl)methoxy)-N-(ethylsulfonyl)-2-fluorobenzamide. LCMS (ESI) Method A: RT=5.99 min. m/z: 587.3 [M+H]$^+$. $^1$H NMR (400 MHz, DMSO-d$_6$): δ 7.49-7.48 (m, 1H), 7.38-7.37 (m, 2H), 7.16 (d, J=8.8 Hz, 1H), 6.77 (d, J=12.8 Hz, 1H), 3.87 (d, J=6.0 Hz, 2H), 3.73-3.65 (m, 3H), 3.21-3.19 (m, 5H), 2.98-2.95 (m, 1H), 2.80-2.77 (m, 1H), 2.06-1.94 (m, 3H), 1.79-1.70 (m, 3H), 1.36-1.26 (m, 2H), 1.15 (t, J=7.4 Hz, 3H), 0.89-0.84 (m, 2H), 0.61-0.57 (m, 2H).

Example 169

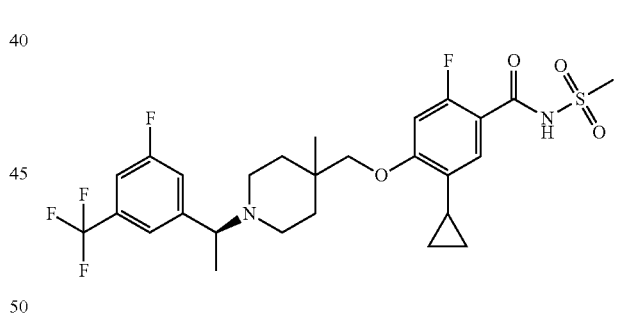

(S)-5-cyclopropyl-4-((1-(1-(3,5-dichlorophenyl)-2-methoxyethyl)piperidin-4-yl)methoxy)-N-(ethylsulfonyl)-2-fluorobenzamide The compound was synthesized as described in Example 163. The enantiomer was arbitrarily assigned as (S)-5-cyclopropyl-4-((1-(1-(3,5-dichlorophenyl)-2-methoxyethyl)piperidin-4-yl)methoxy)-N-(ethylsulfonyl)-2-fluorobenzamide. LCMS (ESI) Method A: RT=5.99 min, m/z: 587.2 [M+H]$^+$. $^1$H NMR (400 MHz, DMSO-d$_6$): δ 7.49-7.48 (m, 1H), 7.38-7.37 (m, 2H), 7.16 (d, J=8.4 Hz, 1H), 6.77 (d, J=12.8 Hz, 1H), 3.87 (d, J=6.0 Hz, 2H), 3.73-3.65 (m, 3H), 3.24-3.19 (m, 5H), 2.98-2.95 (m, 1H), 2.80-2.77 (m, 1H), 2.09-1.91 (m, 3H), 1.79-1.67 (m, 3H), 1.36-1.26 (m, 2H), 1.16 (t, J=7.4 Hz, 3H), 0.89-0.84 (m, 2H), 0.61-0.57 (m, 2H).

Example 170

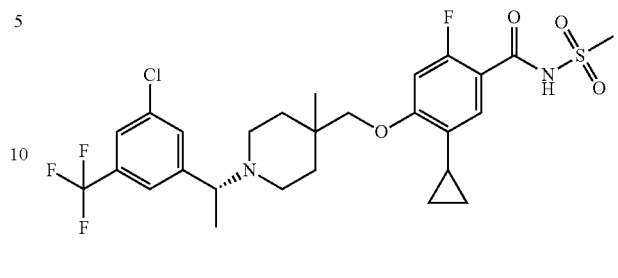

(R)-5-cyclopropyl-2-fluoro-4-((1-(1-(3-fluoro-5-(trifluoromethyl)phenyl)ethyl)-4-methylpiperidin-4-yl)methoxy)-N-(methylsulfonyl)benzamide The compound was synthesized as described in Example 88. The enantiomer was separated by chiral SFC from the racemate, the first eluting fraction was arbitrarily assigned as (R)-5-cyclopropyl-2-fluoro-4-((1-(1-(3-fluoro-5-(trifluoromethyl)phenyl)ethyl)-4-methylpiperidin-4-yl)methoxy)-N-(methylsulfonyl)benzamide. Chiral HPLC (column: IC-H, 4.6×250 mm, 5 µm; mobile Phase: A: supercritical CO$_2$, B: MeOH, A:B=75:25; flow: 2.25 mL/min; column temperature: 40° C.; RT=4.46 min). LCMS (ESI) Method A: RT=6.13 min, m/z: 575.2 [M+H]$^+$. $^1$H NMR (400 MHz, DMSO-d$_6$): δ 11.45 (brs, 1H), 7.58-7.54 (m, 3H), 7.20 (d, J=8.4 Hz, 1H), 6.87 (d, J=13.2 Hz, 1H), 3.80 (m, 3H), 3.18 (s, 3H), 2.68-2.66 (m, 1H), 2.56-2.54 (m, 2H), 2.39-2.33 (m, 1H), 2.04-1.97 (m, 1H), 1.71-1.66 (m, 2H), 1.50-1.44 (m, 2H), 1.37 (d, J=6.8 Hz, 3H), 1.04 (s, 3H), 0.89-0.85 (m, 2H), 0.65-0.61 (m, 2H).

Example 171

(S)-5-cyclopropyl-2-fluoro-4-((1-(1-(3-fluoro-5-(trifluoromethyl)phenyl)ethyl)-4-methylpiperidin-4-yl)methoxy)-N-(methylsulfonyl)benzamide The compound was synthesized as described in Example 170. The enantiomer was separated by chiral SFC from the racemate, the second eluting fraction was arbitrarily assigned as (S)-5-cyclopropyl-2-fluoro-4-((1-(1-(3-fluoro-5-(trifluoromethyl)phenyl)ethyl)-4-methylpiperidin-4-yl)methoxy)-N-(methylsulfonyl)benzamide. Chiral HPLC (column: IC-H, 4.6×250 mm, 5 µm; mobile Phase: A: supercritical CO$_2$, B: MeOH, A:B=75:25; flow: 2.25 mL/min; column temperature: 39.9° C.; RT=4.96 min). LCMS (ESI) Method A: RT=6.11 min, m/z: 575.3 [M+H]$^+$. $^1$H NMR (400 MHz, DMSO-d$_6$): δ 7.58-7.54 (m, 3H), 7.19 (d, J=8.4 Hz, 1H), 6.87 (d, J=12.8 Hz, 1H), 3.80 (m, 3H), 3.17 (s, 3H), 2.71-2.67 (m, 1H), 2.56-2.54 (m, 2H), 2.38-2.32 (m, 1H), 2.04-1.97 (m, 1H), 1.71-1.66 (ms 2H), 1.49-1.44 (m, 2H), 1.37 (d, J=6.8 Hz, 3H), 1.04 (s, 3H), 0.89-0.85 (m, 2H), 0.64-0.61 (m, 2H).

Example 172

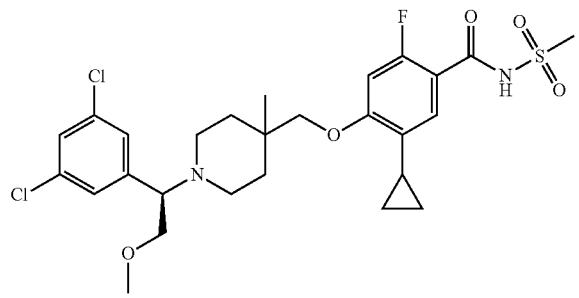 [SMILES: COC[C@@H](c1cc(Cl)cc(Cl)c1)N1CCC(C)(COc2cc(F)c(C(=O)NS(C)(=O)=O)cc2C2CC2)CC1]

(R)-5-cyclopropyl-4-((1-(1-(3,5-dichlorophenyl)-2-methoxyethyl)-4-methylpiperidin-4-yl)methoxy)-2-fluoro-N-(methylsulfonyl)benzamide

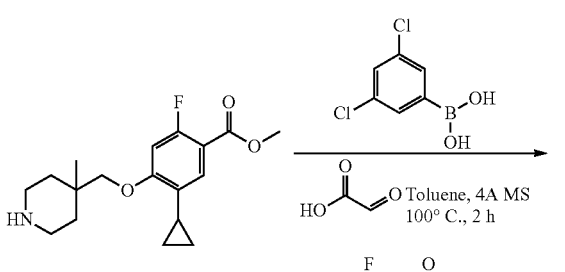

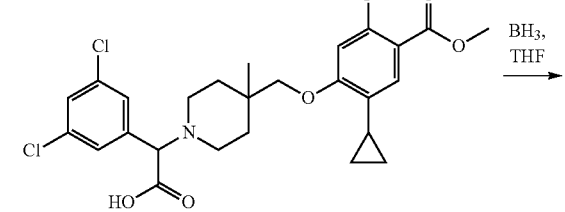

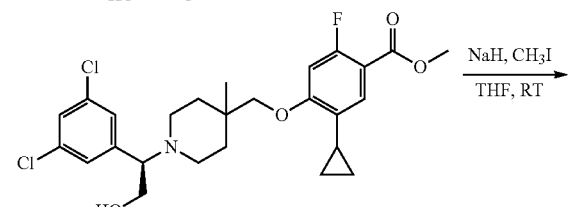

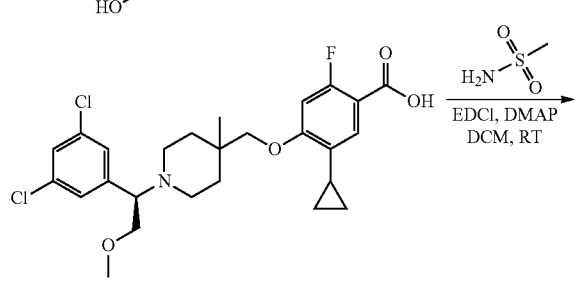

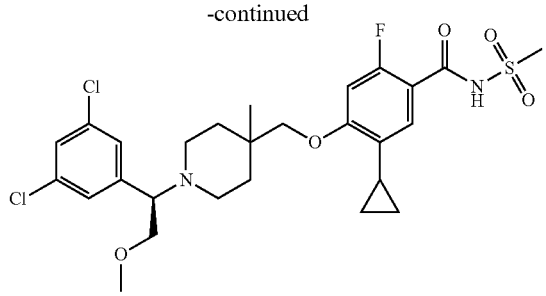

Step 1

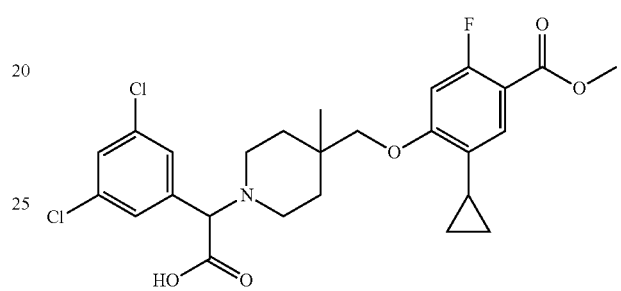

2-(4-((2-Cyclopropyl-5-fluoro-4-(methoxycarbonyl)phenoxy)methyl)-4-methylpiperidin-1-yl)-2-(3,5-dichlorophenyl)acetic acid A mixture of methyl 5-cyclopropyl-2-methyl-4-((4-methylpiperidin-4-yl)methoxy)benzoate (1.8 g, 5.6 mmol), 3,5-dichylorophenylboronic acid (1.6 g, 8.4 mmol), 2-oxoacetic acid (638 mg, 8.4 mmol) and 1.8 g of 4 A molecular sieve in toluene (30 mL) was stirred at 100° C. for 2 h. The mixture was then filtered, washed with DCM (20 mL) and concentrated. The residue was purified by silica gel chromatography (eluting with DCM/MeOH from 100/1 to 10/1) to afford the target compound (2.8 g, 96%) as a white solid. LCMS (ESI) m/z: 524.0 [M+H]⁺.

Step 2

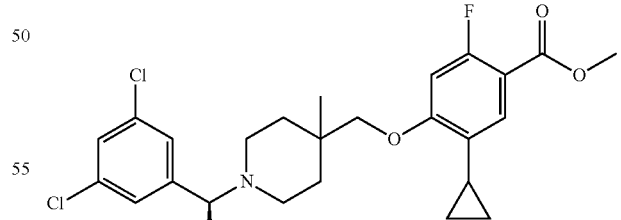

(R)-methyl 5-cyclopropyl-4-((1-(1-(3,5-dichlorophenyl)-2-hydroxyethyl)-4-methylpiperidin-4-yl)methoxy)-2-fluorobenzoate A mixture of 2-(4-((2-cyclopropyl-5-fluoro-4-(methoxycarbonyl)phenoxy)methyl)-4-methylpiperidin-1-yl)-2-(3,5- dichlorophenyl)acetic acid (2.0 g, 3.8 mmol) in borane-THF (20 mL) was stirred at room temperature for 2 h, quenched with MeOH (20 mL) and concentrated. The residue was purified by silica gel chromatography (eluting with DCM/MeOH from 300/1 to 100/1) to afford the racemate (2.8 g, 96%) as an oil. The enantiomer was separated by chiral SFC from the racemate. The enantiomer was arbitrarily assigned as (R)-methyl 5-cyclopropyl-4-((1-(1-(3,5-dichlorophenyl)-2-hydroxyethyl)-4-methylpiperidin-4-yl)methoxy)-2-fluorobenzoate. Chiral HPLC (column: OZ-H, 4.6×250 mm, 5 μm; mobile Phase: A: n-Hexane, B: EtOH, A:B=85:15; flow: 3 mL/min; column temperature: 40° C.; RT=6.83 min), LCMS (ESI) m/z: 510.1 [M+H]$^+$.

Step 3

(R)-5-cyclopropyl-4-((1-(3,5-dichlorophenyl)-2-methoxyethyl)-4-methylpiperidin-4-yl)methoxy)-2-fluorobenzoic acid To a solution of (R)-methyl 5-cyclopropyl-4-((1-(1-(3,5-dichlorophenyl)-2-hydroxyethyl)-4-methylpiperidin-4-yl) methoxy)-2-fluorobenzoate (100 mg, 0.2 mmol) in THF (5 mL) was added sodium hydride (30 mg, 0.98 mmol) at 0° C. The mixture was stirred at room temperature for 30 min, then methyl iodide (56 mg, 0.39 mmol) was added. The mixture was stirred for another 16 h, quenched with water (15 mL), acidified with HCl (1 M) to pH 2-3, and extracted with EtOAc (20 mL×3). The combined organic layers were washed with brine (20 mL) and dried over anhydrous sodium sulfate. The solvent was distilled off under reduce pressure to afford a yellow solid. LCMS (ESI) m/z: 510.1 [M+H]$^+$.

Step 4

(R)-5-cyclopropyl-4-((1-(3,5-dichlorophenyl)-2-methoxyethyl)-4-methylpiperidin-4-yl)methoxy)-2-fluoro-N-(methylsulfonyl)benzamide The compound was synthesized as described in step 5 of Example 80. Chiral HPLC (column: OZ-H, 4.6×250 mm, 5 μm; mobile Phase: A: supercritical CO$_2$, B: MeOH, A:B=65:35; flow; 1.95 mL/min; column, temperature: 40° C.; RT=5.13 min), LCMS (ESI) Method A: RT=6.28 min, m/z: 587.2 [M+H]$^+$. $^1$H NMR (400 MHz, DMSO-d$_6$): δ 11.69 (brs, 1H), 7.50 (s, 1H), 7.41 (s, 2H), 7.18 (d, J=8.4 Hz, 1H), 6.90 (d, J=12.8 Hz, 1H), 3.79-3.69 (m, 5H), 3.23 (s, 3H), 3.22 (s, 3H), 2.67-2.66 (m, 1H), 2.58-2.50 (m, 1H), 2.50-2.35 (m, 2H), 2.03-1.97 (m, 1H), 1.58-1.62 (m, 2H), 1.49-1.37 (m, 2H), 1.01 (s, 3H), 0.90-0.86 (m, 2H), 0.65-0.62 (m, 2H).

Example 173

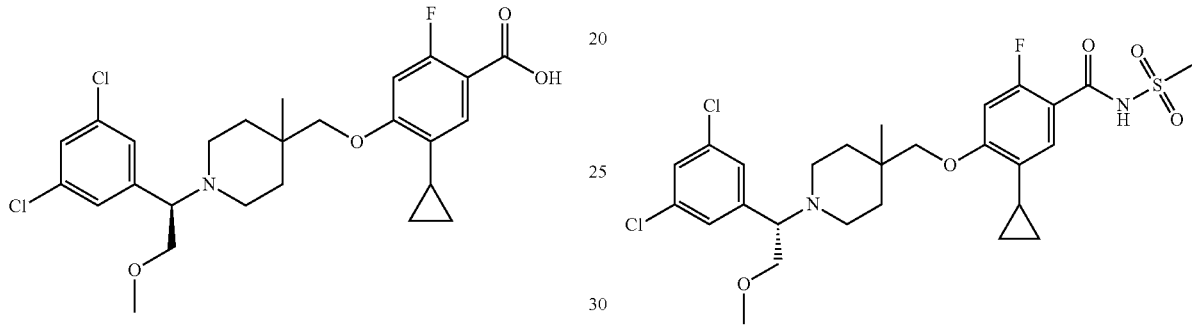

(S)-5-cyclopropyl-4-((1-(1-(3,5-dichlorophenyl)-2-methoxyethyl)-4-methylpiperidin-4-yl)methoxy)-2-fluoro-N-(methylsulfonyl)benzamide The compound was synthesized as described in Example 172. The enantiomer was arbitrarily assigned as (S)-5-cyclopropyl-4-((1-(1-(3,5-dichlorophenyl)-2-methoxyethyl)-4-methylpiperidin-4-yl)methoxy)-2-fluoro-N-(methylsulfonyl)benzamide Chiral HPLC (column: OZ-B, 4.6×250 mm, 5 μm; mobile Phase: A: supercritical CO$_2$, B: MeOH, A:B=65:35; flow; 1.95 mL/min; column temperature: 40.1° C.; RT=4.52 mm). LCMS (ESI) Method A: RT=6.28 min, m/z: 587.2 [M+H]$^+$. $^1$H NMR (400 MHz, DMSO-d$_6$): δ 11.64 (brs, 1H), 7.50 (s, 1H), 7.41 (s, 2H), 7.18 (d, J=8.4 Hz, 1H), 6.89 (d, J=12.8 Hz, 1H), 3.78-3.66 (m, 5H), 3.22 (s, 6H), 2.67-2.66 (m, 1H), 2.58-2.50 (m, 1H), 2.45-2.33 (m, 2H), 2.03-1.97 (m, 1H), 1.68-1.62 (m, 2H), 1.49-1.37 (m, 2H), 1.01 (s, 3H), 0.90-0.86 (m, 2H), 0.65-0.62 (m, 2H).

Example 174

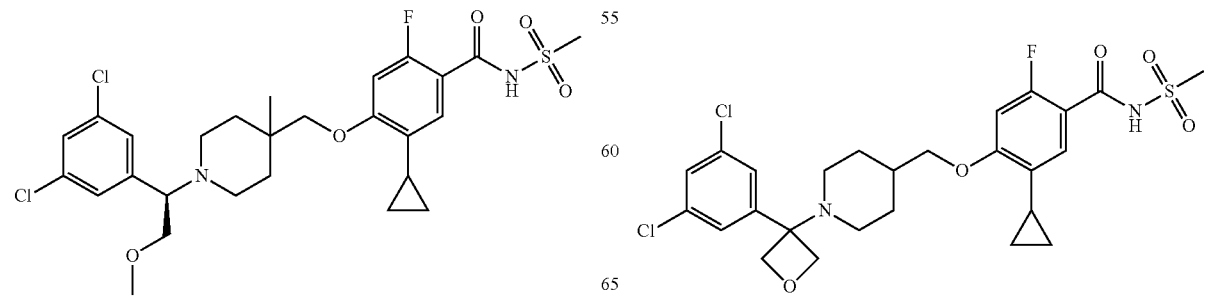

5-Cyclopropyl-4-((1-(3-(3,5-dichlorophenyl)oxetan-3-yl)piperidin-4-yl)methoxy)-2-fluoro-N-(methylsulfonyl)benzamide

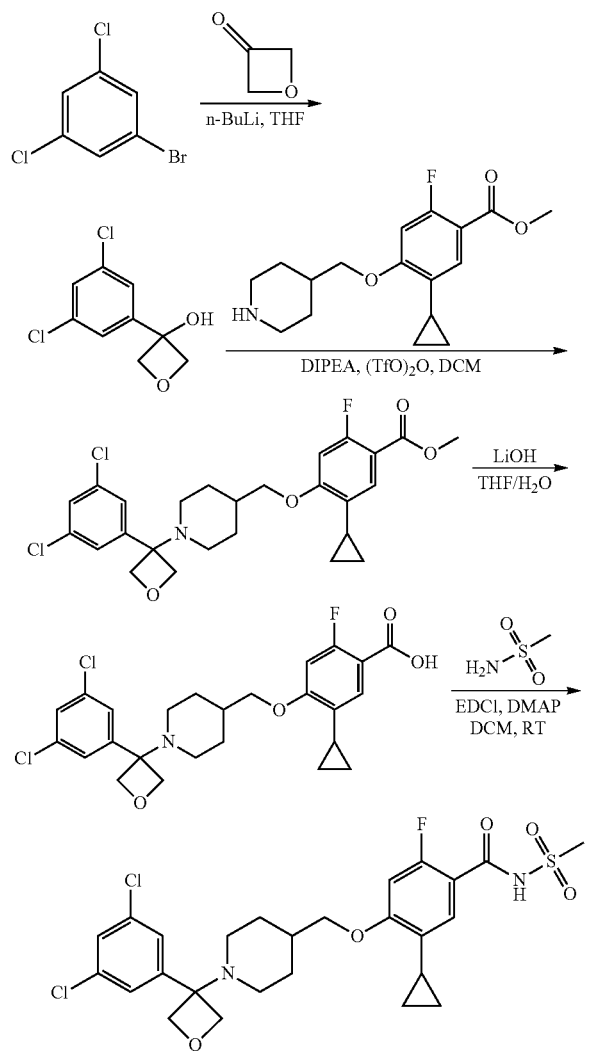

Step 1

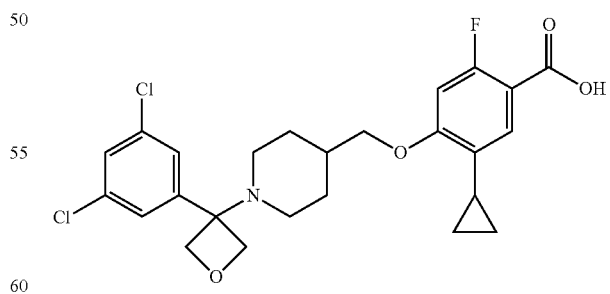

3-(3,5-Dichlorophenyl)oxetan-3-ol

To a solution of 1-bromo-3,5-dichlorobenzene (1.0 g, 4.5 mmol) in dry THF (20 mL) was added n-BuLi (2.2 mL, 5.4 mmol) dropwise and the mixture stirred 30 min at −78° C. Oxetan-3-one (386 mg, 5.4 mmol) was then added and the mixture was left to warm to room temperature. The mixture was then quenched with aqueous ammonium chloride (20 mL) and extracted with EtOAc (20 mL×3). The combined organic layers were washed with brine (20 mL), dried over anhydrous sodium sulfate and concentrated. The residue was purified by silica gel chromatography (eluting with ethyl acetate/petroleum ether=1/10) to afford the target compound (0.7 g, 71%) as an oil. LCMS (ESI) m/z: 217.1 [M−H]⁻.

Step 2

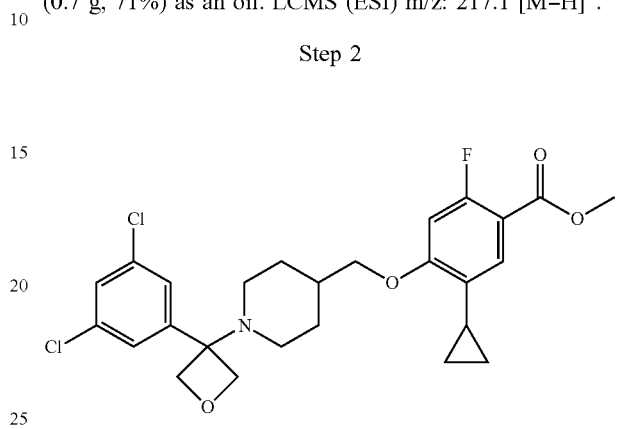

Methyl 5-cyclopropyl-4-((1-(3-(3,5-dichlorophenyl)oxetan-3-yl)piperidin-4-yl)methoxy)-2fluorobenzoate To solution of 3-(3,5-dichlorophenyl)oxetan-3-ol (400 mg, 1.8 mmol) and DIPEA (1.4 g, 11 mmol) in DCM (10 mL), trifluoromethanesulfonic anhydride (0.9 mL, 5.5 mmol) was added dropwise at −20° C. The mixture was then stirred at room temperature for 3 h, and methyl 5-cyclopropyl-2-fluoro-4-(piperidin-4-ylmethoxy)benzoate (280 mg, 0.92 mmol) in acetonitrile (10 mL) was added. Then the reaction mixture was stirred at room temperature for another 16 h. The mixture was then concentrated in vacuo and the residue purified by silica gel chromatography (eluting with ethyl acetate/petroleum ether=1/3) to afford the target compound (320 mg, 69%) as an oil. LCMS (ESI) m/z: 508.1 [M+H]⁺.

Step 3

5-Cyclopropyl-4-((1-(3-(3,5-dichlorophenyl)oxetan-3-yl)piperidin-4-yl)methoxy)-2-fluorobenzoic acid The compound was synthesized as described in step 6 of Example 88. LCMS (ESI) m/z: 494.1 [M+H]⁺.

Step 4

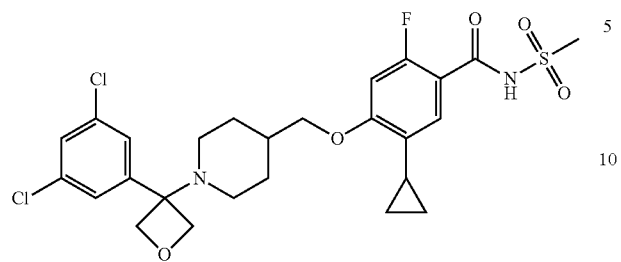

5-Cyclopropyl-4-((1-(3-(3,5-dichlorophenyl)oxetan-3-yl)piperidin-4-yl)methoxy)-2-fluoro-N-(methylsulfonyl)benzamide The compound was synthesized as described in step 5 of Example 80, LCMS (ESI) Method A: RT=5.76 min, m/z: 571.2 [M+H]+. 1H NMR (400 MHz, DMSO-d6): δ 11.82 (brs, 1H), 7.47-7.44 (m, 2H), 7.39-7.37 (m, 1H), 7.15 (d, J=84 Hz, 1H), 6.88 (d, J=13.2 Hz, 1H), 3.90 (d, J=6.0 Hz, 2H), 3.24 (m, 1H), 3.23 (s, 3H), 3.02-2.94 (m, 2H), 2.87-2.79 (m, 3H), 2.15-2.08 (m, 2H), 2.02-1.98 (m, 1H), 1.75-1.69 (m, 3H), 1.33-1.30 (m, 2H), 0.90-0.85 (m, 2H), 0.66-0.62 (m, 2H).

Example 176

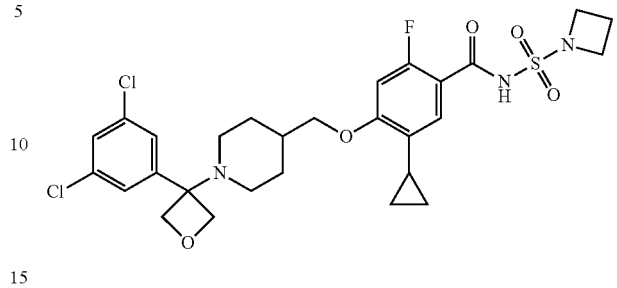

N-azetidin-1-ylsulfonyl)-5-cyclopropyl-4-((1-(3-(3,5-dichlorophenyl)oxetan-3-yl)piperidin-4-yl)methoxy)-2-fluorobenzamide The compound was synthesized as described in Example 174. LCMS (ESI) Method A: RT=6.06 min, m/z: 612.5 [M+H]+. 1H NMR (400 MHz, MeOD-d4): δ7.41-7.38 (m, 2H), 7.34-7.30 (m, 2H), 6.75 (d, J=13.2 Hz, 1H), 4.12-3.91 (m, 4H), 3.91 (d, J=6.0 Hz, 2H), 3.31 (m, 1H), 3.16-3.07 (m, 2H), 2.93-2.91 (m, 3H), 2.28-2.20 (m, 4H), 2.09-2.05 (m, 1H), 1.86-1.80 (m, 3H), 1.52-1.49 (m, 2H), 0.95-0.90 (m, 2H), 0.68-0.64 (m, 2H).

Example 175

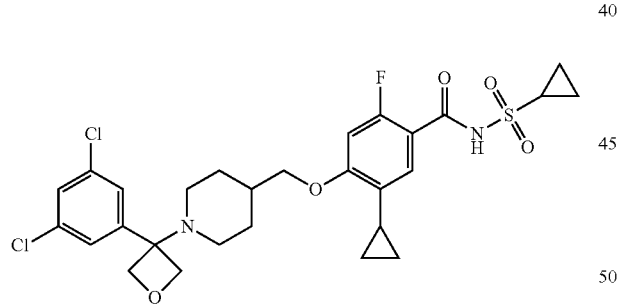

5-Cyclopropyl-N-(cyclopropylsulfonyl)-4-((1-(3-(3,5-dichlorophenyl)oxetan-3-yl)piperidin-4-yl)methoxy)-2-fluorobenzamide The compound was synthesized as described in Example 174. LCMS (ESI) Method A: RT=5.91 min, m/z: 597.2 [M+H]+. 1H NMR (400 MHz, DMSO-d6): δ 11.79 (brs. 1H), 7.47-7.44 (m, 2H), 7.39-7.35 (m, 1H), 7.15 (d, J=8.4 Hz, 1H), 6.85 (d, J=12.8 Hz, 1H), 3.89 (d, J=5.6 Hz, 2H), 3.23-3.22 (m, 1H), 3.01-2.93 (m, 3H), 2.87-2.79 (m, 3H), 2.12-2.37 (m, 2H), 2.01-1.97 (m, 1H), 1.72-1.69 (m, 3H), 1.33-1.30 (m, 2H), 1.03-0.97 (m, 4H), 0.90-0.85 (m, 2H), 0.65-0.61 (m, 2H).

Example 177

5-Cyclopropyl-4-((1-(3-(3,5-dichlorophenyl)oxetan-3-yl)piperidin-4-yl)methoxy)-N-(ethylsulfonyl)-2-fluorobenzamide The compound was synthesized as described in Example 174. LCMS (ESI) Method A: RT=6.86 min, m/z: 585.2 [M+H]+. 1H NMR (400 MHz, MeOD-d4): δ7.42-7.39 (m, 2H), 7.34-7.28 (m, 2H), 6.87 (d, J=13.2 Hz, 1H), 3.92 (d, J=6.0 Hz, 2H), 3.51-3.45 (m, 2H), 3.35 (s, 1H), 3.21-3.13 (m, 2H), 2.98-2.92 (m, 3H), 2.34-2.67 (m, 2H), 2.09-2.05 (m, 1H), 1.90-1.82 (m, 3H), 1.57-1.51 (m, 2H), 1.37 (d, J=7.4 Hz, 3H), 0.95-0.90 (m, 2H), 0.68-0.64 (m, 2H).

Example 178

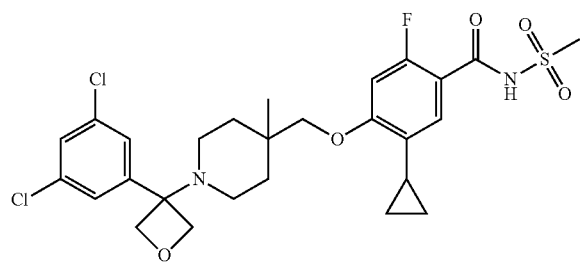

5-Cyclopropyl-4-((1-(3-(3,5-dichlorophenyl)oxetan-3-yl)-4-methylpiperidin-4-yl)methoxy)-2-fluoro-N-(methylsulfonyl)benzamide The compound was synthesized in a similar manner to Example 174 from methyl 5-cyclopropyl-2-fluoro-4-((4-methylpiperidin-4-yl)methoxy)benzoate and 3-(3,5-Dichlorophenyl)oxetan-3-ol. LCMS (ESI) Method A: RT=5.91 min, m/z; 585.3 [M+H]$^+$. $^1$H NMR (400 MHz, DMSO-d$_6$): δ7.47-7.44 (m, 2H), 7.39-7.35 (m, 1H), 7.23-7.19 (m, 1H), 6.84 (d, J=10.8 Hz, 1H), 3.76 (s, 2H), 3.23-3.22 (m, 1H), 3.12 (s, 3H), 2.87-2.76 (m, 3H), 2.69-2.61 (m, 2H), 2.45-2.39 (m, 2H), 2.03-1.95 (m, 1H), 1.66-1.61 (m, 2E), 1.38-1.33 (m, 2H), 1.93 (s, 3H), 0.88-0.85 (m, 2H), 0.61-0.60 (m, 2H).

Example 179

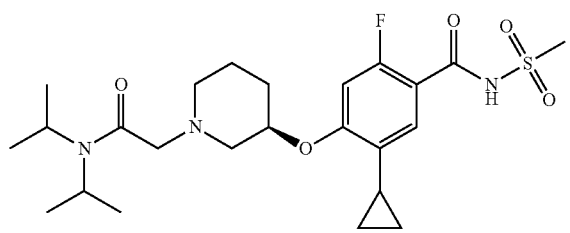 [SMILES: CC(C)N(C(=O)CN1CCC[C@@H](Oc2cc(F)c(C(=O)NS(C)(=O)=O)cc2C2CC2)C1)C(C)C]

(R)-5-Cyclopropyl-4-((1-(2-(diisopropylamino)-2-oxoethyl)piperidin-3-yloxy)-2-fluoro-N-(methylsulfonyl)benzamide

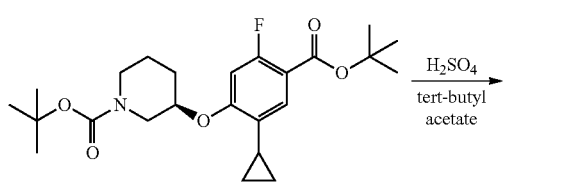

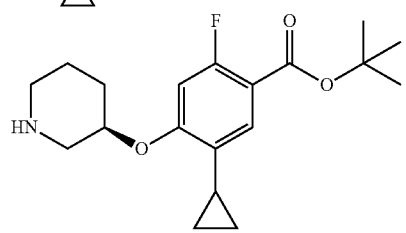

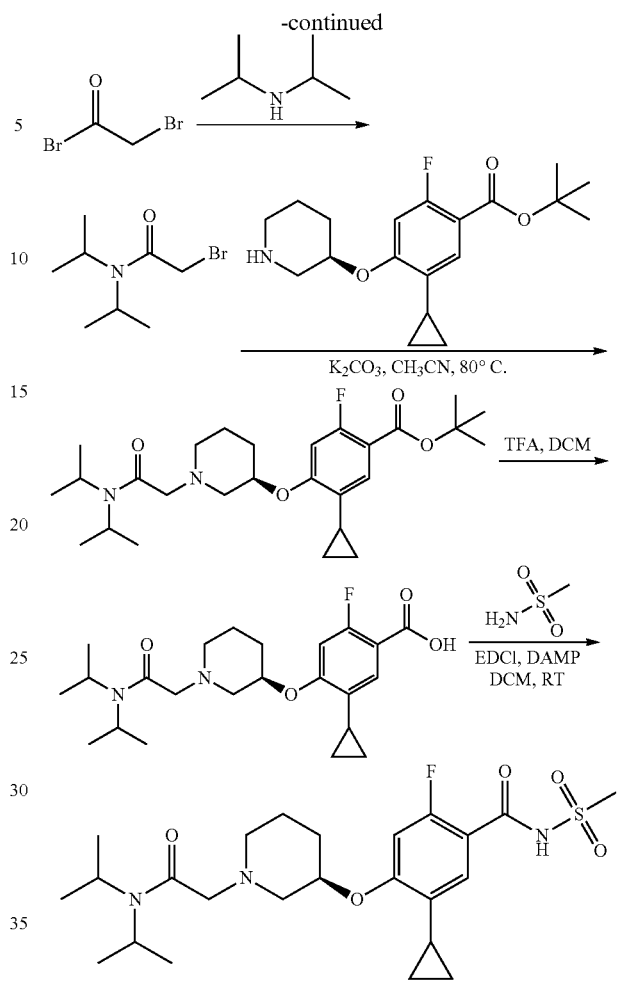

Step 1

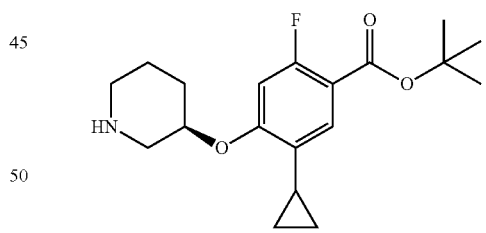

(R)-tert-butyl 5-cyclopropyl-2-fluoro-4-(piperidin-3-yloxy)benzoate

To a solution of (R)-tert-butyl 3-(4-tert-butoxycarbonyl)-2-cyclopropyl-5-fluorophenoxy)piperidin-1-carboxylate (1.0 g, 2.3 mmol) in tert-butylacetate (4 mL) was added sulfuric acid (0.6 mL, 11.5 mmol) at room temperature. The reaction mixture was stirred for 2 h, quenched with aqueous ammonium bicarbonate (10 mL) and extracted with ethyl acetate (20 ml×3). The combined organic layers were distilled off under reduced pressure to afford the target compound (500 mg, 65%) as a pale yellow oil. LCMS (ESI) m/z: 336.0 [M+H]$^+$.

Step 2

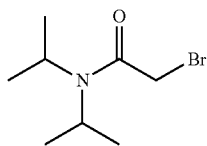

2-Bromo-N,N-diisopropylacetamide

Diisopropylamine (1.0 g, 5.0 mmol) was added to a solution of 2-bromoacetyl bromide (1.0 g, 10.0 mmol) in DCM (30 mL) at 0° C. The reaction mixture was left to warm to room temperature and stirred for 1 h, then quenched with saturated ammonium chloride, extracted with DCM (20 mL×3), washed with brine (20 mL), dried over anhydrous sodium sulfate, filtered and concentrated. The residue was purified by silica gel chromatography (eluting with petroleum ether/ethyl acetate=10/1) to afford the target compound (810 mg, 81%) as a pale yellow oil. LCMS (ESI) m/z: 222.0 [M+H]$^+$. $^1$H NMR (500 MHz, CDCl$_3$-d) δ3.98-3.95 (m, 1H), 3.81 (s, 2H), 3.45-3.42 (m, 1H), 1.40-1.38 (m, 6H), 1.28-1.25 (m, 6H).

Step 3

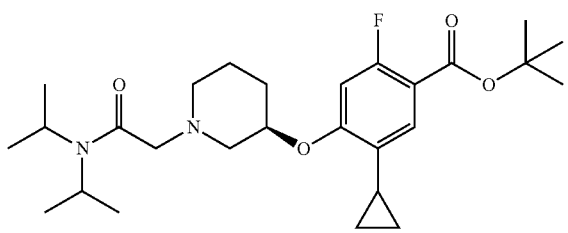 [SMILES: CC(C)N(C(=O)CN1CCC[C@@H](Oc2cc(F)c(C(=O)OC(C)(C)C)cc2C2CC2)C1)C(C)C]

(R)-tert-butyl 5-cyclopropyl-4-(1-(2-(diisopropylamino)-2-oxoethyl)piperidin-3-yloxy)-2-fluorobenzoate A mixture of (R)-tert-butyl 5-cyclopropyl-2-fluoro-4-(piperidin-3-yloxy)benzoate (56 mg, 0.17 mmol), 2-bromo-N,N-diisopropylacetamide (44 mg, 0.20 mmol) and potassium carbonate (69 mg, 0.50 mmol) in acetonitrile (2 mL) was heated at 80° C. for 16 h. The reaction mixture was filtered, washed with ethyl acetate (10 mL) and concentrated. The residue was purified by silica gel chromatography (eluting with petroleum ether/ethyl acetate=5/1) to afford the target compound (61 mg, 75%) as a pale yellow oil. LCMS (ESI) m/z: 477.0 [M+H]$^+$.

Step 4

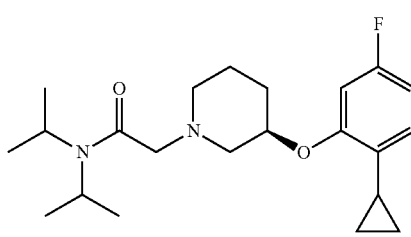

(R)-5-cyclopropyl-4-(1-(2-(diisopropylamino)-2-oxoethyl)piperidin-3-yloxy)-2-fluorobenzoic acid The compound was synthesized as described in step 4, Example 80. LCMS (ESI) m/z: 421.1 [M+H]$^+$.

Step 5

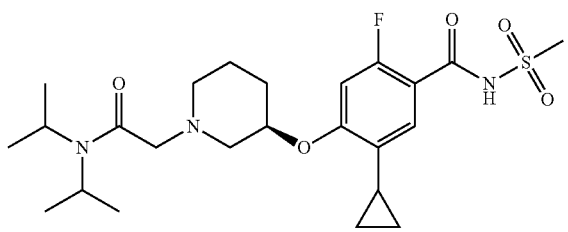 [SMILES: CC(C)N(C(=O)CN1CCC[C@@H](Oc2cc(F)c(C(=O)NS(C)(=O)=O)cc2C2CC2)C1)C(C)C]

(R)-5-cyclopropyl-4-(1-(2-(diisopropylamino)-2-oxoethyl)piperidin-3-yloxy)-2-fluoro-N-(methylsulfonyl)benzamide The compound was synthesized as described in step 5, Example 80. LCMS (ESI) Method A: RT=4.61 min, m/z: 498.0 [M+H]$^+$. $^1$H NMR (500 MHz, DMSO-d$_6$) δ 7.14 (d, J=8.5 Hz, 1H), 6.92 (d, J=13.0 Hz, 1H), 4.58 (m, 1H), 4.09 (m, 1H), 3.41-3.38 (m, 3H), 3.15 (s, 3H), 2.97 (m, 1H), 2.70-2.63 (m, 2H), 2.49-2.46 (m, 1H), 2.07 (m, 1H), 1.95 (m, 1H), 1.83 (m, 1H), 1.64-1.57 (m, 2H), 1.28-1.24 (m, 6H), 1.14-1.10 (m, 6H), 0.89-0.85 (m, 2H), 0.68-0.61 (m, 2H).

Example 180

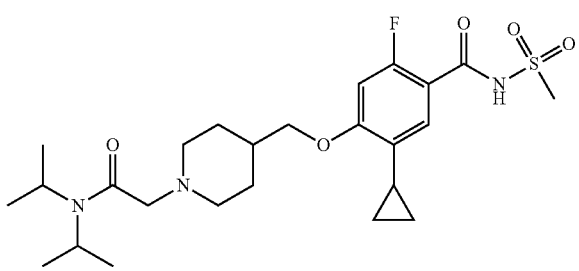 [SMILES: CC(C)N(C(=O)CN1CCC(COc2cc(F)c(C(=O)NS(C)(=O)=O)cc2C2CC2)CC1)C(C)C]

5-Cyclopropyl-4-((1-(2-(diisopropylamino)-2-oxoethyl)piperidin-4-yl)methoxy)-2-fluoro-N-(methylsulfonyl)benzamide

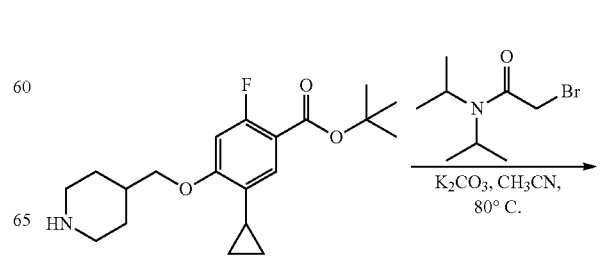

379

-continued

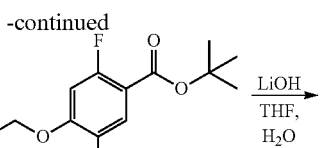

Step 1

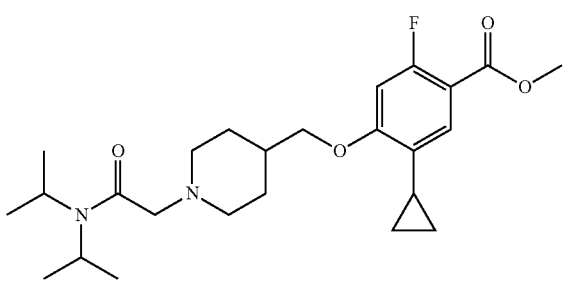 [SMILES: COC(=O)c1cc(C2CC2)c(OCC2CCN(CC(=O)N(C(C)C)C(C)C)CC2)cc1F]

Methyl 5-cyclopropyl-4-((1-(2-(diisopropylamino)-2-oxoethyl)piperidin-4-yl)methoxy)-2-fluorobenzoate The compound was synthesized as described in step 3 of Example 179. LCMS (ESI) m/z: 449.1 [M+H]⁺.

Step 2

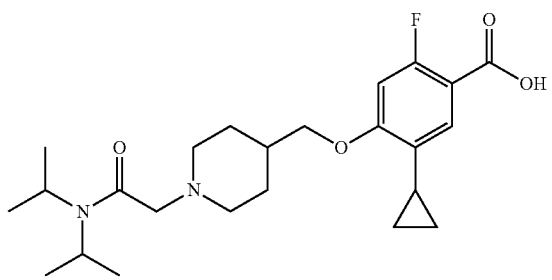 [SMILES: CC(C)N(C(=O)CN1CCC(COc2cc(F)c(C(=O)O)cc2C2CC2)CC1)C(C)C]

380

5-Cyclopropyl-4-((1-(2-(diisopropylamino)-2-oxoethyl)piperidin-4-yl)methoxy)-2-fluorobenzoic acid The compound was synthesized as described in step 6 of Example 88. LCMS (ESI) m/z: 435.1 [M+H]⁺.

Step 3

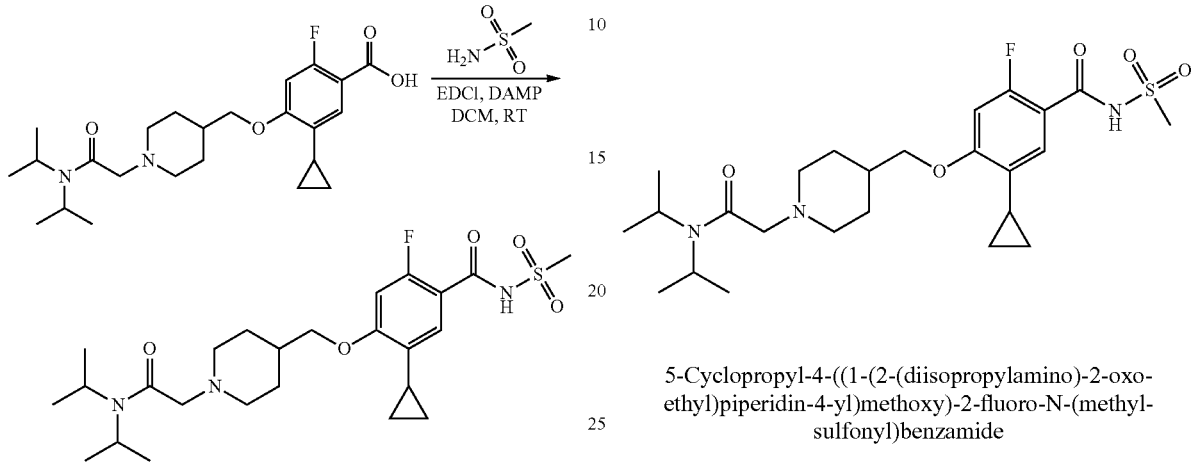

5-Cyclopropyl-4-((1-(2-(diisopropylamino)-2-oxoethyl)piperidin-4-yl)methoxy)-2-fluoro-N-(methylsulfonyl)benzamide The compound was synthesized as described in step 5 of Example 80. LCMS (ESI) Method A: RT=4.52 min, m/z: 512.0 [M+H]⁺. ¹H NMR (500 MHz, DMSO-d₆) δ 7.21 (d, J=8.5 Hz, 1H), 6.77 (d, J=12.0 Hz, 1H), 3.93-3.77 (m, 5H), 3.51-3.49 (m, 1H), 3.23 (m, 2H), 2.96 (s, 3H), 2.75-2.57 (m, 2H), 2.04-1.88 (m, 4H), 1.69-1.56 (m, 2H), 1.33-1.32 (at, 6H), 1.16-1.15 (m, 6H), 0.89-0.85 (m, 2H), 0.60-0.57 (m, 2H).

Example 181

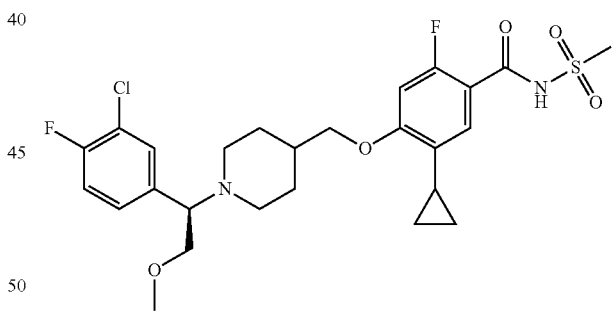

(R)-4-((1-(1-(3-chloro-4-fluorophenyl)-2-methoxyethyl)piperidin-4-yl)methoxy)-5-cyclopropyl-2-fluoro-N-methylsulfonyl)benzamide The compound was synthesized as described in Example 172. The enantiomer was arbitrarily assigned as (R)-4-((1-(1-(3-chloro-4-fluorophenyl)-2-methoxyethyl)-4-yl)methoxy)-5-cyclopropyl-2-fluoro-N-(methylsulfonyl)benzamide. Chiral HPLC (column: OJ-H, 4.6×250 mm, 5 µm; mobile Phase: A: supercritical CO₂, B: MeOH, A:B=75:25; flow: 2.25 mL/min; column temperature: 41.7° C.; RT=2.97 min). LCMS (ESI) Method A: RT=5.51 min, m/z: 557.3 [M+H]⁺. ¹H NMR (400 MHz, DMSO-d₆): δ 11.58 (brs, 1H), 7.55 (d, J=6.0 Hz, 1H), 7.41-7.36 (m, 2H), 7.15 (d, J=8.4 Hz, 1H), 6.85 (d, J=12.8 Hz, 1H), 3.89 (d, J=6.0 Hz, 2H), 3.78-3.70 (m, 3H), 3.23 (s, 3H), 3.17 (s, 3H), 3.05-3.03 (m, 1H), 2.85-2.82 (m, 1H), 2.15-2.12 (m, 1H), 2.03-1.97 (m, 2H), 1.80-1.72 (m, 3H), 1.41-1.31 (m, 2H), 0.89-0.85 (m, 2H), 0.64-0.60 (m, 2H).

Example 182

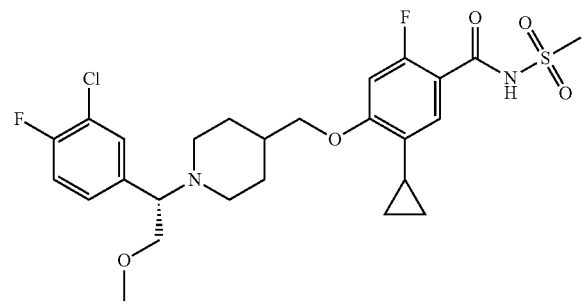 [SMILES: COC[C@H](c1ccc(F)c(Cl)c1)N1CCC(COc2cc(F)c(C(=O)NS(C)(=O)=O)cc2C2CC2)CC1]

(S)-4-((1-(1-(3-chloro-4-fluorophenyl)-2-methoxy-ethyl)piperidin-4-yl)methoxy)-5-cyclopropyl-2-fluoro-N-(methylsulfonyl)benzamide The compound was synthesized as described in Example 172. The enantiomer was arbitrarily assigned as (S)-4-((1-(1-(3-chloro-4-fluorophenyl)-2-methoxyethyl)piperidin-4-yl)methoxy)-5-cyclopropyl-2-fluoro-N-(methylsulfonyl)benzamide. Chiral HPLC (column: OJ-H, 4.6×250 mm, 5 μm; mobile Phase: A: supercritical $CO_2$, B: MeOH, A:B=75:25; flow: 2.25 mL/min; column temperature: 39.5° C.; RT=3.58 min). LCMS (ESI) Method A: RT=3.50 min, m/z: 557.3 [M+H]$^+$, $^1$H NMR (400 MHz, DMSO-d$_6$): δ 11.60 (brs, 1H), 7.55 (d, J=6.8 Hz, 1H), 7.41-7.36 (m, 2H), 7.15 (d, J=8.4 Hz, 1H), 6.85 (d, J=12.8 Hz, 1H), 3.89 (d, J=5.6 Hz, 2H), 3.78-3.70 (m, 3H), 3.23 (s, 3H), 3.17 (s, 3H), 3.05-3.03 (m, 1H), 2.85-2.82 (m, 1H), 2.20-2.12 (m, 1H), 2.03-1.97 (m, 2H), 1.80-1.72 (m, 3H), 1.41-1.31 (m, 2H), 0.89-0.85 (m, 2H), 0.64-0.60 (m, 2H).

Example 183

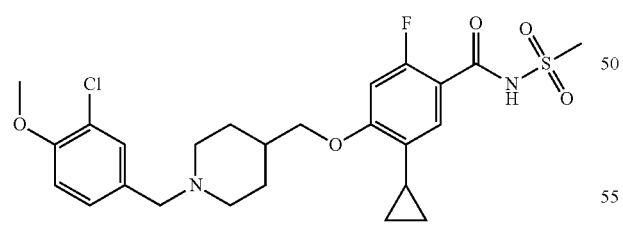

4-((1-(3-Chloro-4-methoxybenzyl)piperidin-4-yl)methyoxy)-5-cyclopropyl-2-fluoro-N-(methylsulfonyl)benzamide The compound was synthesized as described in Example 88. LCMS (ESI) Method A: RT=5.08 min, m/z: 525.2 [M+H]$^+$. $^1$H NMR (400 MHz, MeOD-d$_4$) δ10.51 (brs, 1H), 7.48 (s, 1H), 7.35-7.33 (m, 1H), 7.20-7.16 (m, 2H), 6.89 (d, J=12.8 Hz, 1H), 3.92 (d, J=5.6 Hz, 2H), 3.86 (s, 3H), 3.82 (s, 2H), 3.11-3.08 (m, 2H), 3.01 (s, 3H), 2.50-2.39 (m, 2H), 2.03-1.97 (m, 1H), 1.91-1.85 (m, 3H), 1.48-1.45 (m, 2H), 0.89-0.85 (m, 2H), 0.61-0.57 (m, 2H).

Example 184

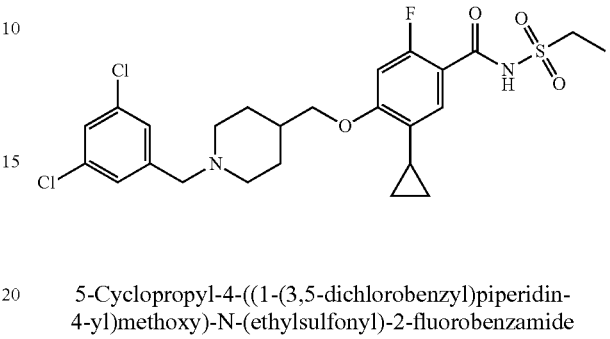

5-Cyclopropyl-4-((1-(3,5-dichlorobenzyl)piperidin-4-yl)methoxy)-N-(ethylsulfonyl)-2-fluorobenzamide The compound was synthesized as described in Example 88. LCMS (ESI) Method A: RT=6.34 min, m/z: 543.2 [M+H]$^+$. $^1$H NMR (400 MHz, MeOD-d$_4$) δ11.47 (brs, 1H), 7.54-7.52 (m, 1H), 7.40-7.39 (m, 2H), 7.15-7.13 (m, 1H), 6.90-6.87 (m, 1H), 3.93 (d, J=6.0 Hz, 2H), 3.62 (m, 2H), 3.35-3.32 (m, 2H), 2.93-2.90 (m, 2H), 2.19-1.99 (m, 3H), 1.82-1.79 (m, 3H), 1.44-1.38 (m, 2H), 1.22-1.18 (m, 3H), 0.90-0.85 (m, 2H), 0.61-0.57 (m, 2H).

Example 185

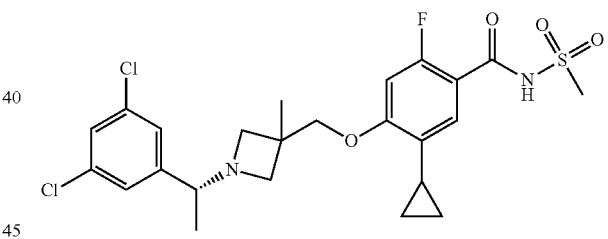

(R)-5-cyclopropyl-4-((1-(1-(3,5-dichlorophenyl)ethyl)-3-methylazetidin-3-yl)methoxy)-2-fluoro-N-(methylsulfonyl)benzamide The compound was synthesized as described in Example 81. The enantiomer was separated by chiral SFC from the racemate, the first eluting fraction was arbitrarily assigned as (R)-5-cyclopropyl-4-((1-(1-(3,5-dichlorophenyl)ethyl)-3-methylazetidin-3-yl)methoxy)-2-fluoro-N-(methylsulfonyl)benzamide. Chiral HPLC (column: OZ-H, 4.6×250 mm, 5 μm; mobile Phase: A: supercritical $CO_2$, B: MeOH (0.5% DEA), A:B=70:30; flow: 3 mL/min; column temperature: 38.5° C.; RT=5.7 min). LCMS (ESI) Method C: RT=5.48 min, m/z: 528.8 [M+H]$^+$. $^1$H NMR (400 MHz, MeOD-d$_4$) δ7.44 (s, 1H), 7.39-7.35 (m, 3H), 6.81 (d, J=12.4 Hz, 1H), 4.10-4.04 (m, 2H): 3.83-3.81 (m, 1H), 3.65-3.59 (m, 2H), 3.40-3.38 (m, 1H), 3.27-3.25 (m, 4H), 2.10-2.07 (m, 1H), 1.48 (s, 3H), 1.37-1.35 (m, 3H), 0.95-0.93 (m, 2H), 0.69-0.68 (m, 2H).

Example 186

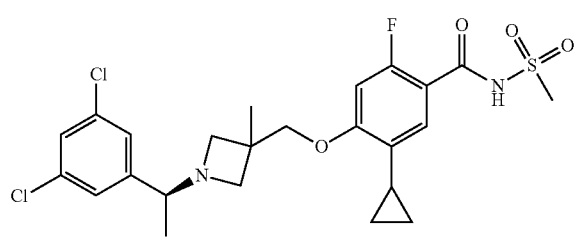 [SMILES: C[C@@H](c1cc(Cl)cc(Cl)c1)N1CC(C)(COc2cc(F)c(C(=O)NS(C)(=O)=O)cc2C2CC2)C1]

(R)-5-cyclopropyl-4-((1-(1-(3,5-dichlorophenyl)ethyl)-3-methylazetidin-3-yl)methoxy)-2-fluoro-N-(methylsulfonyl)benzamide The compound was synthesized as described in Example 81. The enantiomer was separated by chiral SFC from the racemate, the second eluting fraction was arbitrarily assigned as (S)-5-cyclopropyl-4-((1-(1-(3,5-dichlorophenyl)ethyl)-3-methylazetidin-3-yl)methoxy)-2-fluoro-N-(methylsulfonyl)benzamide. Chiral HPLC (column: OZ-H, 4.6×250 mm, 5 μm; mobile Phase: A: supercritical $CO_2$, B: MeOH (0.5% DEA), A:B=70:30; flow: 3 mL/min; column temperature; 38.5° C.: RT=8.13 min). LCMS (ESI) Method C: RT=5.42 min, m/z: 528.7 $[M+H]^+$. $^1$H NMR (400 MHz, MeOD-$d_4$) δ 7.42 (s, 1H), 7.38-7.36 (m, 3H), 6.81 (d, J=12.8 Hz, 1H), 4.10-4.03 (m, 2H), 3.79-3.77 (m, 1H), 3.60-3.50 (m, 2H), 3.34-3.32 (m, 1H), 3.25-5.23 (m, 4H) 2.09-2.05 (m, 1H), 1.47 (s, 3H), 1.35-1.30 (m, 3H), 0.97-0.91 (m, 2H), 0.68-0.66 (m, 2H).

Example 187

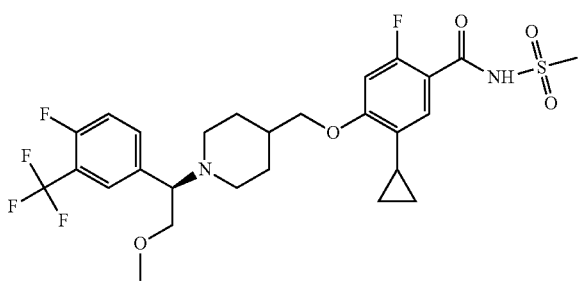 [SMILES: COC[C@@H](c1ccc(F)c(C(F)(F)F)c1)N1CCC(COc2cc(F)c(C(=O)NS(C)(=O)=O)cc2C2CC2)CC1]

(R)-5-cyclopropyl-2-fluoro-4-((1-(1-(4-fluoro-3-(trifluoromethyl)phenyl)-2-methoxyethyl)piperidin-4-yl)methoxy)-N-(methylsulfonyl)benzamide The compound was synthesized as described in Example 172. The enantiomer was separated by chiral SFC from the racemate, the first eluting fraction was arbitrarily assigned as (R)-5-cyclopropyl-2-fluoro-4-((1-(1-(4-fluoro-3-(trifluoromethyl)phenyl)-2-methoxyethyl)piperidin-4-yl)methoxy)-N-(methylsulfonyl)benzamide. Chiral HPLC (column: AD-H, 4.6×250 mm, 5 μm; mobile Phase: A: supercritical $CO_2$, B: MeOH (0.1% DEA), A:B=80:20; flow; 3 mL/min; column temperature: 39.5° C.; RT=3.55 min). LCMS (ESI) Method C: RT=4.82 min, m/z 591.0 $[M+H]^+$, $^1$H NMR (400 MHz, DMSO-$d_6$) δ 7.72-7.70 (m, 2H), 7.51-7.46 (m, 1H), 7.15 (d, J=8.4 Hz, 1H), 6.87 (d, J=12.8 Hz, 1H), 3.91-3.84 (m, 5H), 3.28-3.27 (m, 1H), 3.22-3.21 (m, 5H), 3.06-3.03 (m, 1H), 2.83-2.81 (m, 1H), 2.16-1.96 (m, 3H), 1.77-1.72 (m, 3H), 1.40-1.30 (m, 2H), 0.89-0.84 (m, 2H), 0.65-0.61 (m, 2H).

Example 188

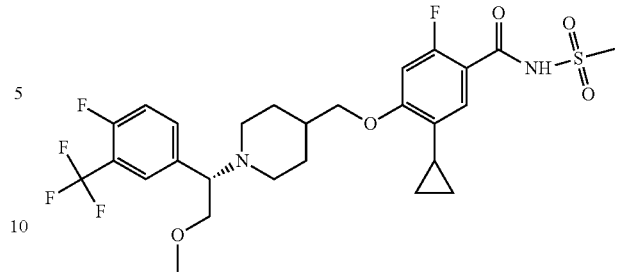

(S)-5-cyclopropyl-2-fluoro-4-((1-(1-(4-fluoro-3-(trifluoromethyl)phenyl)-2-methoxyethyl)piperidin-4-yl)methoxy)-N-(methylsulfonyl)benzamide The compound was synthesized as described in Example 172. The enantiomer was separated by chiral SFC from the racemate, the second eluting fraction was arbitrarily assigned as (S)-5-cyclopropyl-2-fluoro-4-((1-(1-(4-fluoro-3-(trifluoromethyl)phenyl)-2-methoxyethyl)piperidin-4-yl)methoxy)-N-(methylsulfonyl)benzamide. Chiral HPLC (column: AD-H, 4.6×250 mm, 5 μm; mobile Phase: A: supercritical $CO_2$, B: MeOH (0.1% DEA), A:B=80:20; flow; 3 mL/min; column temperature: 39.5° C.: RT=6.51 min). LCMS (ESI) Method C: RT=4.83 min, m/z 591.1 $[M+H]^+$. $^1$H NMR (400 MHz, DMSO-$d_6$) δ 7.72-7.70 (m, 2H), 7.51-7.46 (m, 1H), 7.15 (d, J=8.4 Hz, 1H), 6.87 (d, J=13.2 Hz, 1H), 3.91-3.72 (m, 4H), 3.29-3.28 (m, 1H), 3.23-3.21 (m, 5H), 3.05-3.02 (m, 1H), 2.83-2.81 (m, 2H), 2.02-1.96 (m, 3H), 1.81-1.72 (m, 3H), 1.40-1.30 (m, 2H), 0.89-0.84 (m, 2H), 0.66-0.62 (m, 2H).

Example 189

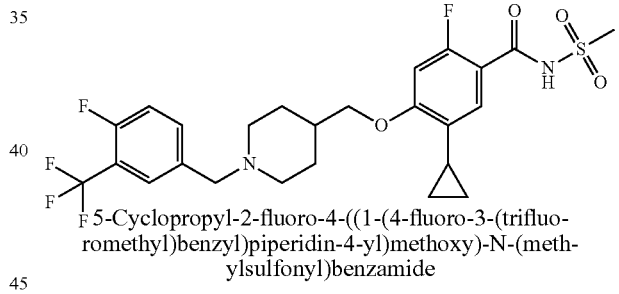

5-Cyclopropyl-2-fluoro-4-((1-(4-fluoro-3-(trifluoromethyl)benzyl)piperidin-4-yl)methoxy)-N-(methylsulfonyl)benzamide The compound was synthesized as described in Example 88. LCMS (ESI) Method C: RT=3.95 min, m/z: 547.0 $[M+H]^+$. $^1$H NMR (400 MHz, DMSO-$d_6$) δ 7.73-7.72 (m, 2H), 7.52-7.47 (m, 1H), 7.18 (d, J=8.8 Hz, 1H), 6.80 (d, J=12.8 Hz, 1H), 3.92 (d, J=5.6 Hz, 2H), 3.68 (s, 2H), 3.04 (s, 3H), 2.94-2.91 (m, 2H), 2.03-1.99 (m, 3H), 1.83-1.80 (m, 3H), 1.44-1.38 (m, 2H), 0.89-0.86 (m, 2H), 0.60-0.59 (m, 2H).

Example 190

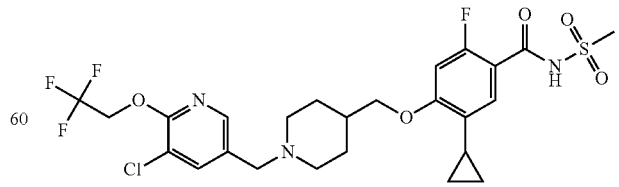

4-((1-((5-Chloro-6-(2,2,2-trifluoroethoxy)pyridin-3-yl)methyl)piperidin-4-yl)methoxy)-5-cyclopropyl-2-fluoro-N-(methylsulfonyl)benzamide

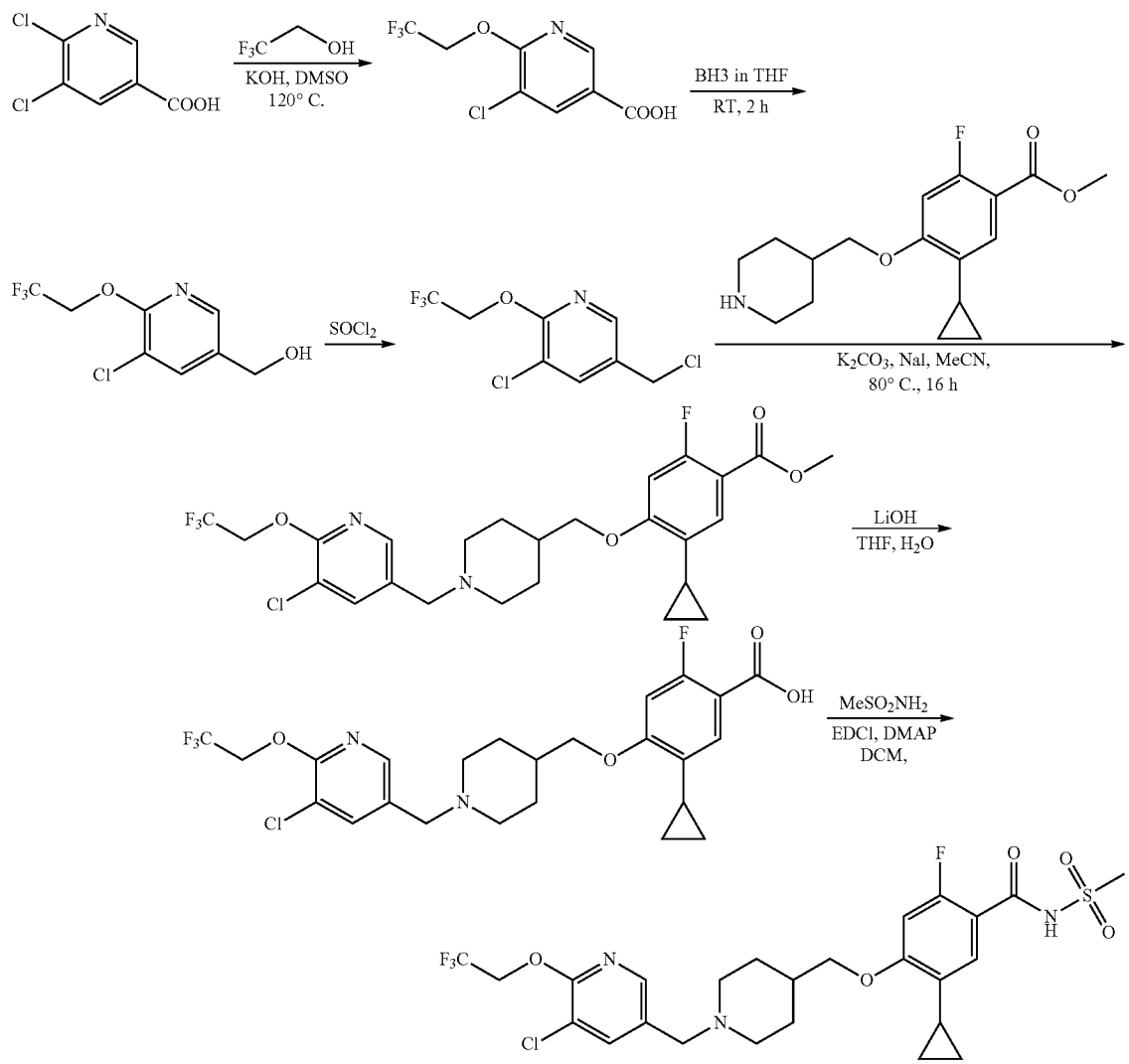

Step 1

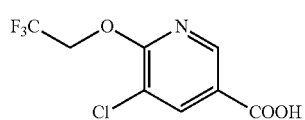 [SMILES: O=C(O)c1cnc(OCC(F)(F)F)c(Cl)c1]

5-Chloro-6-(2,2,2-trifluoroethoxy)nicotinic acid

A mixture of 2,2,2-trifluoroethanol (1.0 g, 5.2 mmol) and potassium hydroxide (824 mg, 15.6 mmol) in DMSO (15 mL) was stirred at 120° C. for 24 h. The reaction mixture was acidified with HCl (1M), extracted with DCM (30 mL×3), dried over anhydrous sodium sulfate and concentrated. The crude compound (960 mg) was used in next step without further purification. LCMS (ESI) m/z: 255.8 [M+H]$^+$.

Step 2

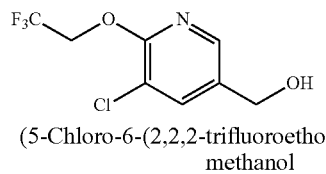

(5-Chloro-6-(2,2,2-trifluoroethoxy)pyridin-3-yl) methanol

The compound was synthesized as described in step 2 of Example 172. LCMS (ESI) m/z: 241.9 [M+H]$^+$.

Step 3

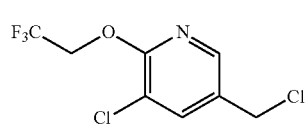

3-Chloro-5-(chloromethyl)-2-(2,2,2-trifluoroethoxy) pyridine

The compound was synthesized as described in step 2 of Example 80.

Step 4

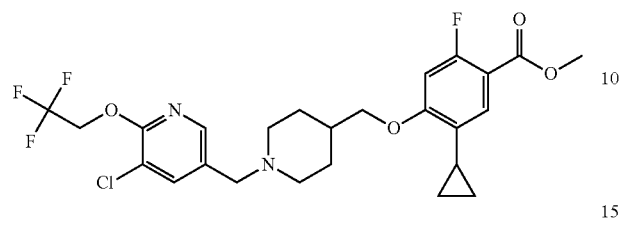

Methyl 4-((1-((5-chloro-6-(2,2,2-trifluoroethoxy)
pyridin-3-yl)methyl)piperidin-4-yl)methoxy)-5-cyclopropyl-2-fluorobenzoate The compound was synthesized as described in step 3 of Example 80. LCMS (ESI) m/z: 531.0 [M+H]+.

Step 5

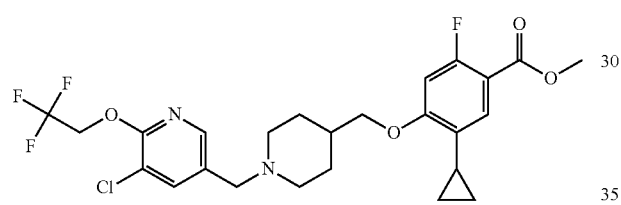

4-((1-((5-Chloro-6-(2,2,2-trifluoroethoxy)pyridin-3-yl)methyl)piperidin-4-yl)methoxy)-5-cyclopropyl-2-fluorobenzoic acid The compound was synthesized as described in step 6 of Example 88. LCMS (ESI) m/z: 517.0 [M+H]+.

Step 6

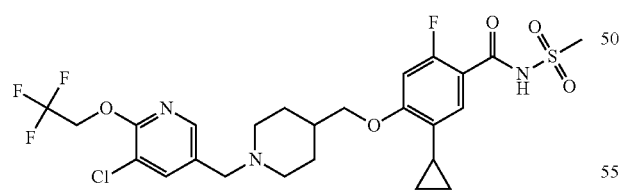

4-((1-((5-Chloro-6-(2,2,2-trifluoroethoxy)pyridin-3-yl)methyl)piperidin-4-yl)methoxy)-5-cyclopropyl-2-fluoro-N-(methylsulfonyl)benzamide The compound was synthesized as described in step 5 of Example 80, LCMS (ESI) Method A: RT=5.70 min, m/z 594.0 [M+H]+. 1H NMR (500 MHz, MeOD-d4) δ 8.14-8.11 (m, 1H), 7.97-7.94 (m, 1H), 7.35-7.34 (m, 1H), 6.70-6.66 (m, 1H), 5.0-4.94 (m, 2H), 3.90-3.71 (m, 4H), 3.30-3.15 (m, 5H), 2.50-2.49 (m, 2H), 2.07-1.93 (m, 4H), 1.61-1.55 (m, 2H), 0.90-0.89 (m, 2H), 0.65-0.63 (m, 2H).

Example 191

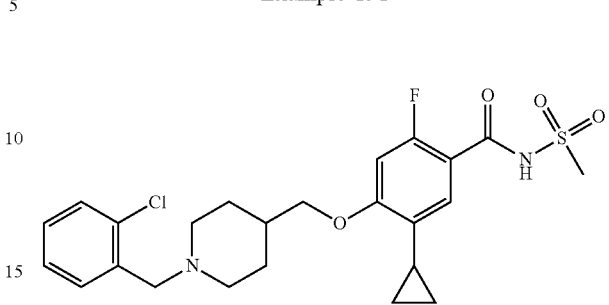

4-((1-(2-Chlorobenzyl)piperidin-4-yl)methoxy)-5-cyclopropyl-2-fluoro-N-(methylsulfonyl)benzamide The compound was synthesized as described in Example 88. LCMS (ESI) Method A: RT=5.67 min, m/z: 495.0 [M+H]+. 1H NMR (500 MHz, MeOD-d4): δ 7.58-7.57 (m, 1H), 7.47-7.46 (m, 1H), 7.36-7.33 (m, 3H), 6.68 (d, J=12.0 Hz, 1H), 3.94-3.90 (m, 4H), 3.27-3.12 (m, 5H), 2.54-2.47 (m, 1H), 2.08-1.95 (m, 4H), 1.63-1.60 (m, 2H), 1.28-1.25 (m, 1H), 0.91-0.87 (m, 2H), 0.67-0.64 (m, 2H).

Example 192

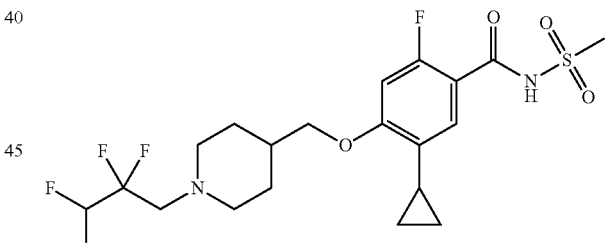

5-Cyclopropyl-2-fluoro-N-(methylsulfonyl)-4-((1-(2,2,3,3-tetrafluoropropyl)piperidin-4-yl)methoxy)benzamide The compound was synthesized as described in Example 116. LCMS (ESI) Method A: RT=5.34 min, m/z: 485.1 [M+H]+. 1H NMR (500 MHz, DMSO-d6): δ 11.87 (s, 3H), 7.15 (d, J=9.0 Hz, 1H), 6.90 (d, J=13.0 Hz, 1H), 6.58-6.37 (m, 1H), 3.92 (d, J=6.0 Hz, 2H), 3.23 (s, 3H), 3.0-2.89 (m, 4H), 2.32-2.27 (m, 2H), 2.03-2.0 (m, 1H), 1.78-1.74 (m, 3H), 1.40-1.32 (m, 2H), 0.91-0.87 (m, 2H), 0.66-0.63 (m, 2H).

Example 193

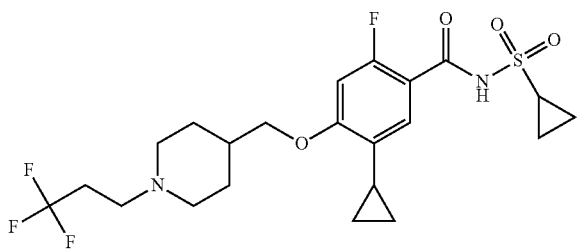 [SMILES: O=C(NS(=O)(=O)C1CC1)c1cc(C2CC2)c(OCC2CCN(CCC(F)(F)F)CC2)cc1F]

5-Cyclopropyl-N-(cyclopropylsulfonyl)-2-fluoro-4-
((1-(3,3,3-trifluoropropyl)piperidin-4-yl)methoxy)
benzamide The compound was synthesized as described in Example 116. LCMS (ESI) Method A: RT=4.98 min, m/z: 493.0 [M+H]+. $^1$H NMR (500 MHz, DMSO-$d_6$) δ 7.15 (d, J=8.0 Hz, 1H), 6.88 (d, J=12.5 Hz, 1H), 3.94 (d, J=5.5 Hz, 2H), 3.04-3.00 (m, 3H), 2.65-2.63 (m, 2H), 2.56-2.50 (m, 2H), 2.17-2.12 (m, 2H), 2.04-1.99 (m, 1H), 1.82-1.79 (m, 3H), 1.42-1.35 (m, 2H), 1.06-0.97 (m, 4H), 0.90-0.87 (m, 2H), 0.65-0.62 (m, 2H).

Example 194

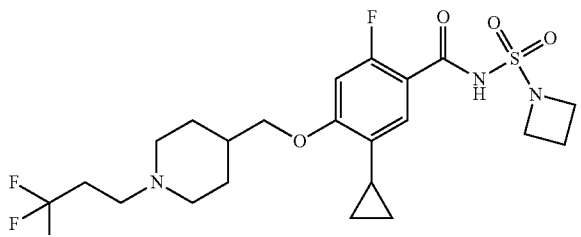

N-(azetidin-1-ylsulfonyl)-5-cyclopropyl-2-fluoro-4-
((1-(3,3,3-trifluoropropyl)piperidin-4-yl)methoxy)
benzamide The compound was synthesized as described in Example 116. LCMS (ESI) Method A: RT=5.13 min, m/z: 508.0 [M+H]+. $^1$H NMR (500 MHz, DMSO-$d_6$) δ 7.17 (d, J=8.5 Hz, 1H), 6.87 (d, J=13.0 Hz, 1H), 3.94-3.93 (m, 6H), 2.98-2.96 (m, 2H), 2.61-2.58 (m, 2H), 2.52-2.50 (m, 1H), 2.49-2.48 (m, 1H), 2.12-2.01 (m, 5H), 1.38-1.35 (m, 3H), 0.90-0.87 (m, 2H), 0.90-0.87 (m, 2H), 0.65-0.62 (m, 2H).

Example 195

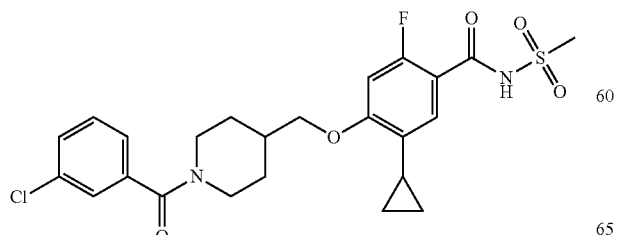

4-((1-(3-Chlorobenzoyl)piperidin-4-yl)methoxy)-5-
cyclopropyl-2-fluoro-N-(methylsulfonyl)benzamide The compound was synthesized as described in step Example 134, LCMS (ESI) Method A: RT=4.61 min, m/z: 509.0 [M+H]+. $^1$H NMR (500 MHz, DMSO-$d_6$) δ 11.87 (s, 1H), 7.53-7.43 (m, 3H), 7.34 (d, J=8.0 Hz, 1H), 7.15 (d, J=8.5 Hz, 1H), 6.96 (d, J=10.4 Hz, 1H), 4.51-4.49 (m, 1H), 3.99 (d, J=4.4 Hz, 2H), 3.57-3.51 (m, 1H), 3.28 (s, 3H), 3.12-3.04 (m, 1H), 2.89-2.81 (m, 1H), 2.13-1.72 (m, 4H), 1.32-1.23 (m, 2H), 0.91-0.84 (m, 2H), 0.68-0.64 (m, 2H).

Example 196

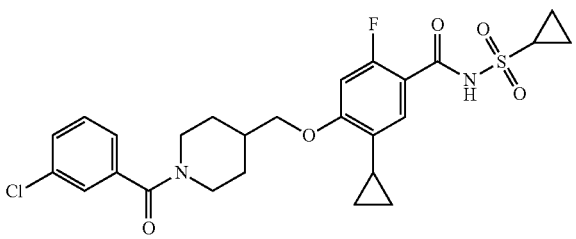 [SMILES: O=C(NS(=O)(=O)C1CC1)c1cc(C2CC2)c(OCC2CCN(C(=O)c3cccc(Cl)c3)CC2)cc1F]

4-((1-(3-Chlorobenzoyl)piperidin-4-yl)methoxy)-5-
cyclopropyl-N-(cyclopropylsulfonyl)-2-fluorobenz-
amide The compound was synthesized as described in step Example 134. LCMS (ESI) Method A: RT=4.74 min, m/z: 535.0 [M+H]+. $^1$H NMR (500 MHz, DMSO-$d_6$) δ 11.87 (s, 1H), 7.53-7.43 (m, 3H), 7.34 (d, J=8.0 Hz, 1H), 7.15 (d, J=8.5 Hz, 1H), 6.96 (d, J=12.5 Hz, 1H), 4.52-4.50 (m, 1H), 4.00 (d, J=5.0 Hz, 2H), 3.58-3.32 (m, 1H), 3.13-3.00 (m, 2H), 2.85-2.83 (m, 1H), 2.14-1.90 (m, 4H), 1.34-1.33 (m, 2H), 1.24-1.22 (m, 4H), 0.91-0.87 (m, 2H), 0.69-0.66 (m, 2H).

Example 197

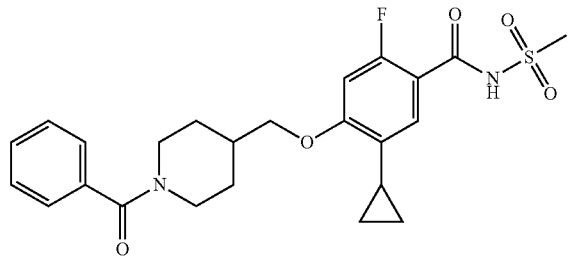 [SMILES: CS(=O)(=O)NC(=O)c1cc(C2CC2)c(OCC2CCN(C(=O)c3ccccc3)CC2)cc1F]

4-((1-Benzoylpiperidin-4-yl)methoxy)-5-cyclopro-
pyl-2-fluoro-N-(methylsulfonyl)benzamide The compound was synthesized as described in step Example 134. LCMS (ESI) Method A: RT=4.17 min, m/z: 475.0 [M+H]+. $^1$H NMR (500 MHz, DMSO-$d_6$) δ 11.87 (s, 1H), 7.45-7.44 (m, 3H), 7.38-7.36 (m, 2H), 7.15 (d, J=8.5 Hz, 1H), 6.96 (d, J=13.0 Hz, 1H), 4.0-3.99 (m, 1H), 3.99 (d, J=4.4 Hz, 2H), 3.62-3.60 (m, 1H), 3.32 (s, 3H), 3.17-3.09

(m, 1H), 3.02-3.01 (m, 1H), 2.13-1.76 (m, 4H), 1.32-1.24 (m, 2H), 0.91-0.84 (m, 2H), 0.69-0.63 (m, 2H).

Example 198

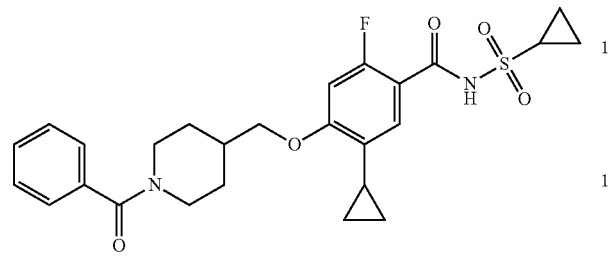

4-((1-Benzoylpiperidin-4-yl)methoxy)-5-cyclopropyl-N-(cyclopropylsulfonyl)-2-fluorobenzamide The compound was synthesized as described in step Example 134. LCMS (ESI) Method A: RT=4.38 min, m/z: 501.0 [M+H]⁺. ¹H NMR (500 MHz, DMSO-$d_6$) δ11.81 (s, 1H), 7.45-7.44 (m, 3H), 7.38-7.36 (m, 2H), 7.15 (d, J=8.0 Hz, 1H), 6.93 (d, J=13.0 Hz, 1H), 4.52-4.51 (m, 1H), 3.98 (d, J=4.8 Hz, 2H), 3.62-3.60 (m, 1H), 3.09-3.01 (m, 2H), 2.83-2.81 (m, 1H), 2.14-1.71 (m, 4H), 1.32-1.31 (m, 2H), 1.07-1.03 (m, 4H), 0.90-0.84 (m, 2H), 0.56-0.61 (m, 2H).

Example 199

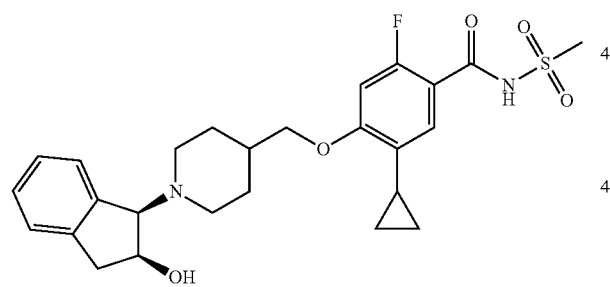

5-Cyclopropyl-2-fluoro-4-((1-((1R,2S)-2-hydroxy-2,3-dihydro-1H-inden-1-yl)piperidin-4-yl)methoxy)-N-(methylsulfonyl)benzamide

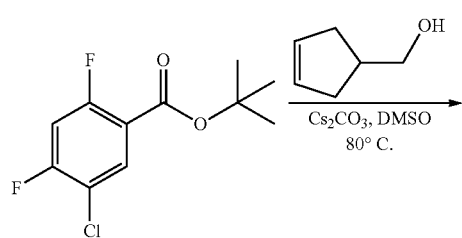

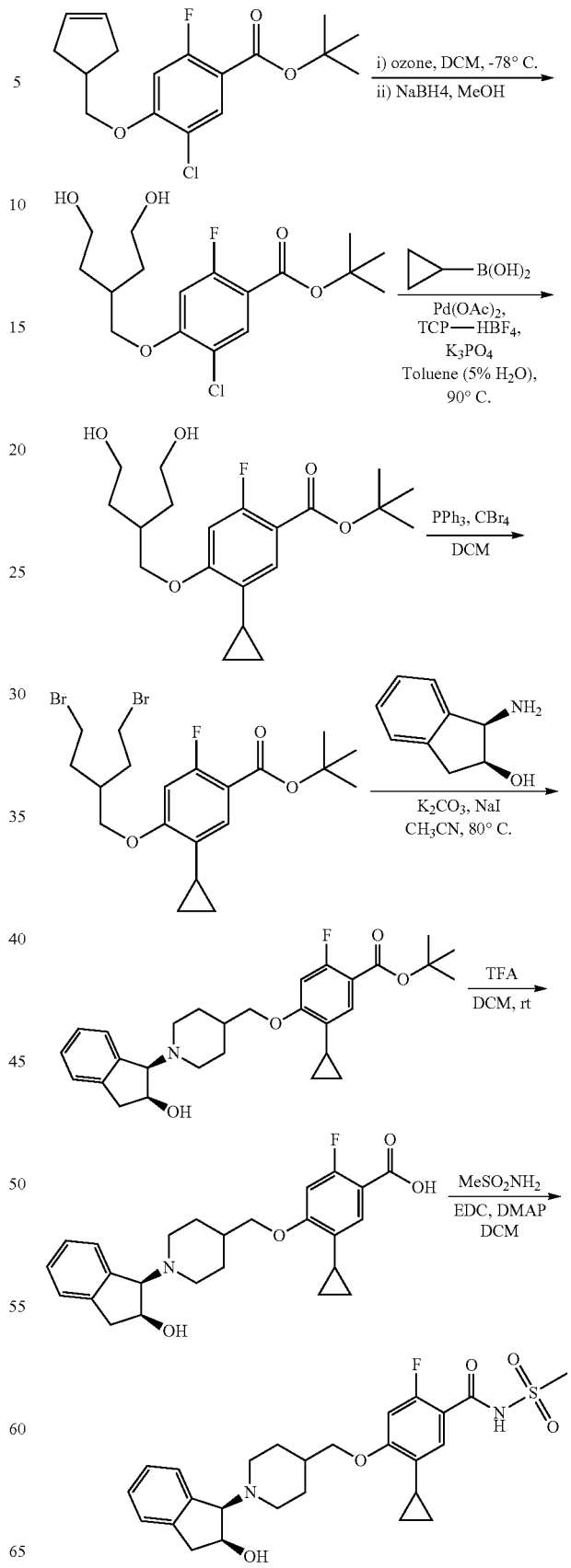

Step 1

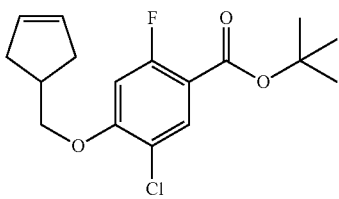 [SMILES: CC(C)(C)OC(=O)c1cc(Cl)c(OCC2CC=CC2)cc1F]

tert-Butyl 5-chloro-4-(cyclopent-3-en-1-ylmethoxy)-2-fluorobenzoate

A mixture of cyclopent-3-enylmethanol (0.9 g, 9.2 mmol), tert-butyl 5-chloro-2,4-difluorobenzoate (2.3 g, 9.3 mmol) and cesium carbonate (6.0 g, 18.4 mmol) in DMSO (20 mL) was stirred at 80° C. for 10 h. The reaction mixture was diluted with EtOAc (50 mL) and brine (100 mL). The organic layer was washed by brine (30 mL×3), dried over anhydrous sodium sulfate, filtered and concentrated. The residue was purified by flash column (petroleum ether) to afford the title compound as a white solid (2.1 g, 70%).

Step 2

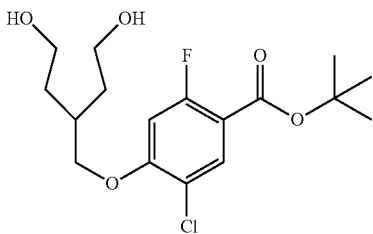 [SMILES: CC(C)(C)OC(=O)c1cc(Cl)c(OCC(CCO)CCO)cc1F]

tert-Butyl 5-chloro-2-fluoro-4-(4-hydroxy-2-(2-hydroxyethyl)butoxy)benzoate

Ozone was bubbled into a solution of tert-butyl 5-chloro-4-(cyclopent-3-enylmethoxy)-2-fluorobenzoate (1.63 g, 5 mmol) in dry DCM (50 mL) at −78° C. until the solution turned blue. Then the reaction was purged with nitrogen gas until the reaction mixture turned colorless. Sodium borohydride (0.76 g, 20 mmol) and methanol (50 mL) was then added and the resultant mixture allowed to warm to room temperature and stirred for 5 h. The mixture was then concentrated in vacuo and the residue purified by silica gel chromatography (elating with 50% ethyl acetate in petroleum ether) to afford the title compound as a colorless oil (1.63 g, 90%).

Step 3

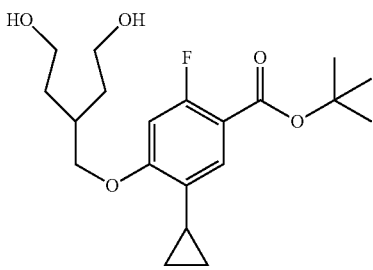 [SMILES: CC(C)(C)OC(=O)c1cc(C2CC2)c(OCC(CCO)CCO)cc1F]

tert-Butyl 5-cyclopropyl-2-fluoro-4-(4-hydroxy-2-(2-hydroxyethyl)butoxy)benzoate A mixture of tert-butyl 5-chloro-2-fluoro-4-(4-hydroxy-2-(2-hydroxyethyl)butoxy)benzoate (1.09 g, 4 mmol), cyclopropylboronic acid (0.515 g, 6 mmol), diacetoxypalladium (0.067 g, 0.3 mmol) and potassium phosphate (1.3 g, 6 mmol) in toluene (30 mL) and H$_2$O (1.5 mL) was stirred at 90° C. for (16 h. The reaction mixture was filtered, concentrated in vacuo and the residue purified by silica gel chromatography (elating with 40% ethyl acetate in petroleum ether) to afford the target compound as a colorless oil (0.77 g, 70%).

Step 4

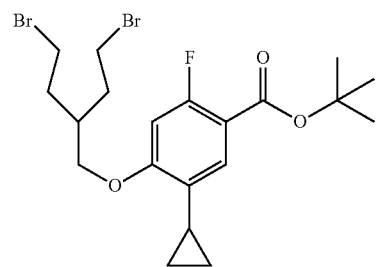 [SMILES: CC(C)(C)OC(=O)c1cc(C2CC2)c(OCC(CCBr)CCBr)cc1F]

tert-Butyl 4-(4-bromo-2-(2-bromoethyl)butoxy)-5-cyclopropyl-2-fluorobenzoate

A mixture of tert-butyl 5-cyclopropyl-2-fluoro-4-(4-hydroxy-2-(2-hydroxyethyl)butoxy)benzoate (0.73 g, 2 mmol), triphenylphosphine (2.1 g, 8 mmol), carbon tetrabromide (2.65 g, 8 mmol) in DCM (30 mL) was stirred at room temperature for 20 h. The mixture was concentrated in vacuo and the residue purified by silica gel chromatography (eluting with 10% ethyl acetate in petroleum ether) to afford the target compound as a pale yellow oil (0.84 g, 85%).

Step 5

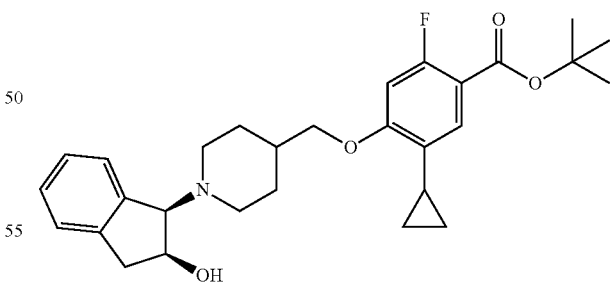

tert-butyl 5-cyclopropyl-2-fluoro-4-((1-((1R,2S)-2-hydroxy-2,3-dihydro-1H-inden-1-yl)piperidin-4-yl)methoxy)benzoate A mixture of tert-butyl 4-(4-bromo-2-(2-bromoethyl)butoxy)-5-cyclopropyl-2-fluorobenzoate (0.84 g, 1.7 mmol), 1R,2S)-1-amino-2,3-dihydro-1H-inden-2-ol (0.253 g, 1.7 mmol), potassium carbonate (0.47 g, 3.4 mmol) and sodium iodide (0.026 g, 0.17 mmol) in acetonitrile (10 mL) was stirred at 80° C. for 8 h. The reaction mixture was quenched with brine (40 mL), extracted with ethyl acetate (10 mL×3), dried over anhydrous sodium sulfate, and concentrated. The residue was purified by silica gel chromatography (eluding with 15% ethyl acetate in petroleum ether) to afford the target compound, as a white solid (0.712 g, 87%). MS(ESI): m/z 482.3[M+1]$^+$.

Step 6

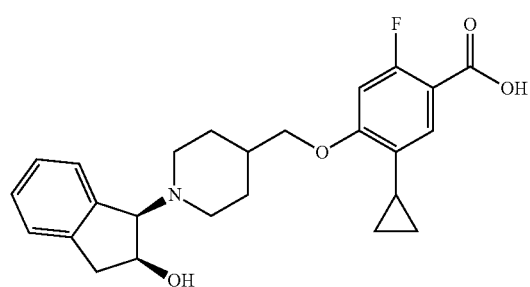 [SMILES: O=C(O)c1cc(C2CC2)c(OCC2CCN([C@@H]3c4ccccc4C[C@@H]3O)CC2)cc1F]

5-Cyclopropyl-2-fluoro-4-((1-((1R,2S)-2-hydroxy-2,
3-dihydro-1H-inden-1-yl)piperidin-4-yl)methoxy)
benzoic acid The compound was synthesized as described in step 3 of Example 88. LCMS (ESI) m/z: 426.2 [M+H]$^+$.

Step 7

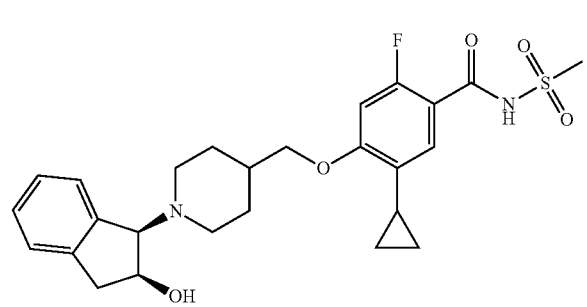 [SMILES: CS(=O)(=O)NC(=O)c1cc(C2CC2)c(OCC2CCN([C@@H]3c4ccccc4C[C@@H]3O)CC2)cc1F]

5-Cyclopropyl-2-fluoro-4-((1-((1R,2S)-2-hydroxy-2,
3-dihydro-1H-inden-1-yl)piperidin-4-yl)methoxy)-
N-(methylsulfonyl)benzamide The compound was synthesized as described in step 5 of Example 80. LCMS (ESI): Method A: RT=4.71 min, m/z: 593.2[M+H]$^+$. $^1$HNMR (500 MHz, DMSO-d$_6$) δ 7.43 (d, J=7.6 Hz, 1H), 7.33-7.21 (m, 3H), 7.21 (d, J=8.4 Hz, 1H), 6.72 (d, J=2.8 Hz, 1H), 4.65-4.60 (m, 1H), 4.32 (s, 1H), 3.88 (d, J=5.6 Hz, 2H), 3.27-3.25 (m, 2H), 3.13-3.04 (m, 3H), 2.91-2.83 (m, 4H), 2.03-1.96 (m, 1H), 1.88-1.80 (m, 3H), 1.57-1.48 (m, 2H), 0.88-0.83 (m, 2H), 0.58-0.54 (m, 2H).

Example 200

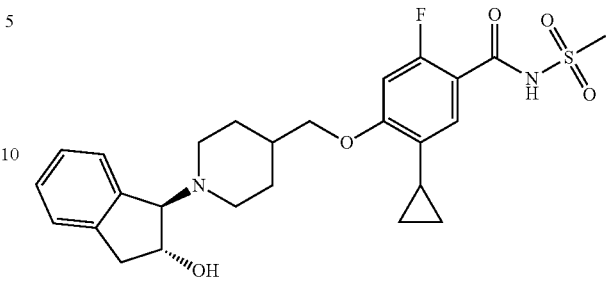

5-Cyclopropyl-2-fluoro-4-((1-((1R,2R)-2-hydroxy-2,
3-dihydro-1H-inden-1-yl)piperidin-4-yl)methoxy)-
N-(methylsulfonyl)benzamide The compound was synthesized as described in Example 199. LCMS (ESI) Method A: RT=4.30 min, m/z: 503.2 [M+H]$^+$. $^1$H NMR (400 MHz, DMSO-d$_6$) δ7.35-7.33 (m, 1H), 7.25-7.24 (m, 3H), 7.17 (d, J=8.4 Hz, 1H), 6.85 (d, J=12.8 Hz, 1H), 5.18-5.16 (m, 1H), 4.60-4.58 (m, 1H), 4.19-4.17 (m, 1H), 3.93 (d, J=6.0 Hz, 1H), 3.31-3.29 (m, 1H), 3.26-3.12 (m, 5H), 2.77-2.66 (m, 3H), 2.05-2.00 (m, 1H), 1.89-1.79 (m, 3H), 1.48-1.36 (m, 2H), 0.90-0.82 (m, 2H), 0.64-0.60 (m, 2H).

Example 201

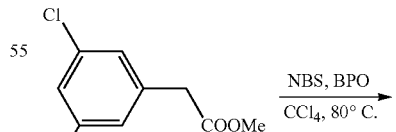

(R)-5-cyclopropyl-4-((1-(2-(3,5-dichloro)-1-
methoxypropan-2-yl)piperidin-4-yl)methoxy)-2-
fluoro-N-(methylsulfonyl)benzamide

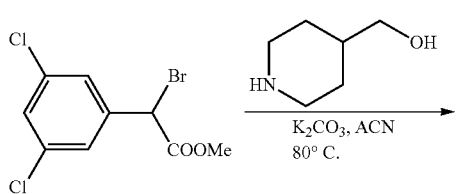

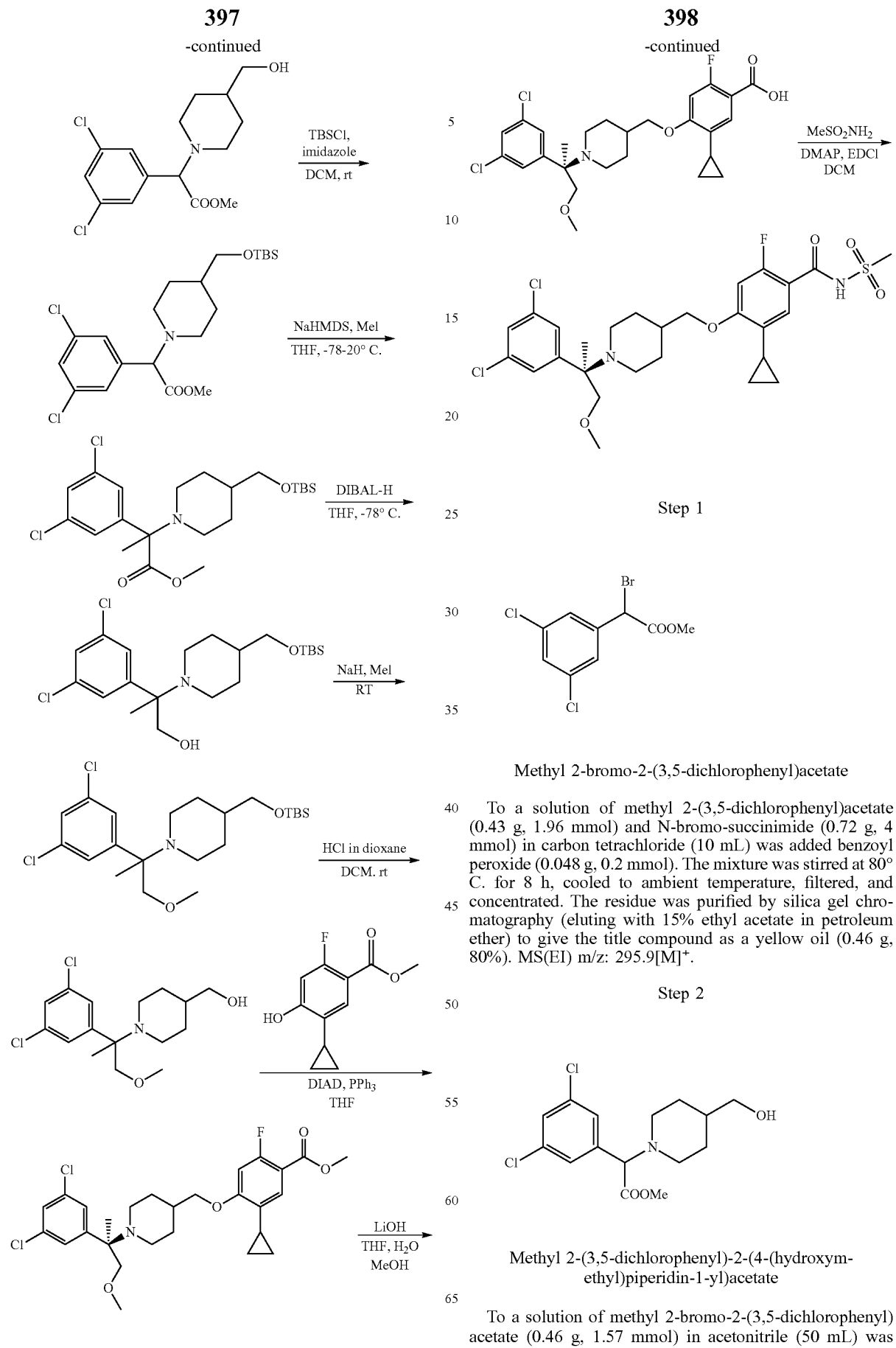

Step 1

Methyl 2-bromo-2-(3,5-dichlorophenyl)acetate

To a solution of methyl 2-(3,5-dichlorophenyl)acetate (0.43 g, 1.96 mmol) and N-bromo-succinimide (0.72 g, 4 mmol) in carbon tetrachloride (10 mL) was added benzoyl peroxide (0.048 g, 0.2 mmol). The mixture was stirred at 80° C. for 8 h, cooled to ambient temperature, filtered, and concentrated. The residue was purified by silica gel chromatography (eluting with 15% ethyl acetate in petroleum ether) to give the title compound as a yellow oil (0.46 g, 80%). MS(EI) m/z: 295.9[M]$^{+}$.

Step 2

Methyl 2-(3,5-dichlorophenyl)-2-(4-(hydroxymethyl)piperidin-1-yl)acetate

To a solution of methyl 2-bromo-2-(3,5-dichlorophenyl) acetate (0.46 g, 1.57 mmol) in acetonitrile (50 mL) was added potassium carbonate (0.65 g, 4.7 mmol) and piperidin-4-yl-methanol (0.37 g, 3.2 mmol). The reaction mixture was stirred at 80° C. for 4 h, diluted with dichloromethane (30 mL) and washed with brine (20 mL×3). The combined organic layers were dried over anhydrous sodium sulfate, filtered and concentrated to give me erode product as a colorless oil (0.51 g) which was used directly without further purification, LCMS (ESI) m/z: 332.1 [M+1]$^+$.

Step 3

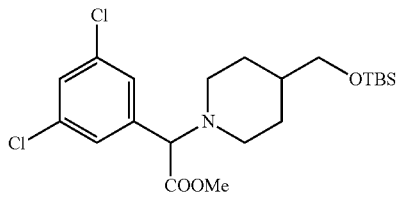 [SMILES: COC(=O)C(c1cc(Cl)cc(Cl)c1)N1CCC(CO[Si](C)(C)C(C)(C)C)CC1]

Methyl 2-(4-(((tert-butyldimethylsilyl)oxy)methyl)piperidin-1-yl)-2-(3,5-dichlorophenyl)acetate To a solution of methyl 2-(3,5-dichlorophenyl)-2-(4-(hydroxymethyl)piperidin-1-yl)acetate (0.51 g, 1.54 mmol, crude) in dichloromethane (20 mL) was added imidazole (0.35 g, 5.14 mmol) and tert-butylchlorodimethylsilane (0.47 g, 3.1 mmol). The mixture was stirred at room temperature for 2 h, then filtered, concentrated and purified by silica gel chromatography (eluting with 5% ethyl acetate in petroleum ether) to give the title compound (0.6 g, 86%) as a colorless oil. LCMS (ESI) m/z: 446.1 [M+1]$^+$.

Step 4

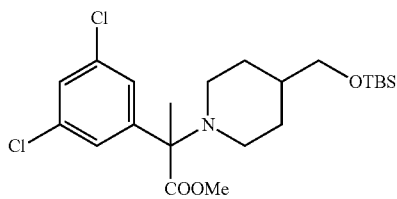 [SMILES: COC(=O)C(C)(c1cc(Cl)cc(Cl)c1)N1CCC(CO[Si](C)(C)C(C)(C)C)CC1]

Methyl 2-(4-(((tert-butyldimethylsilyl)oxy)methyl)piperidin-1-yl)-2-(3,5-dichlorophenyl)propanoate To a solution of methyl 2-(4-(((tert-butyldimethylsilyl)oxy)methyl)piperidin-1-yl)-2-(3,5-dichlorophenyl)acetate (0.58 g, 1.3 mmol) in dry THF (10 mL) at −78° C., was added sodium bis(trimethylsilyl) amide (1M in THF, 2.6 mL). The resultant mixture was maintained at −78+C. and stirred for 1 hour. Methyl iodide (0.55 g, 3.0 mmol) was then added and the mixture allowed to warm to room temperature overnight. The mixture was diluted with EtOAc (15 mL) and brine (30 mL), extracted with EtOAc (10 mL×3), dried over anhydrous sodium, sulfate, filtered and concentrated. The residue was purified by silica gel chromatography (eluting with 5% EtOAc in petroleum ether) to afford the title compound as a colorless oil (0.49 g, 82%). LCMS (ESI) m/z: 460.1 [M+1]$^+$.

Step 5

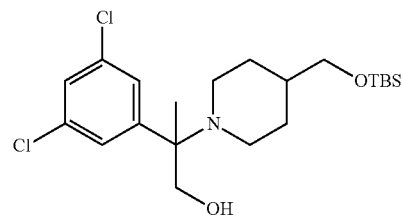 [SMILES: CC(CO)(c1cc(Cl)cc(Cl)c1)N1CCC(CO[Si](C)(C)C(C)(C)C)CC1]

2-(4-((tert-Butyldimethylsilyl)oxy)methyl)piperidin-1-yl)-2-(3,5-dichlorophenyl)propan-1-ol To a solution of methyl 2-(4-((tert-butyldimethylsilyloxy)methyl)piperidin-1-yl)-2-(3,5-dichlorophenyl)propanoate (0.49 g, 1.06 mmol) in THF (20 mL) at −78° C., diisobutyl aluminium hydride (1M in THF, 4.3 mL) was added dropwise. The resultant mixture was allowed to warm to room temperature and stirred for 16 h. The mixture was quenched with brine and the white precipitate filtered and washed with EtOAc (30 mL). The combined organic layers were dried over anhydrous sodium sulfate and concentrated to give the title compound which was used in next step without former purification. LCMS (ESI) m/z: 432.1 [M+1]$^+$.

Step 6

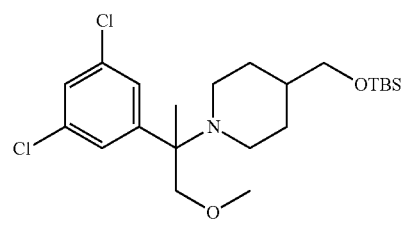 [SMILES: COCC(C)(c1cc(Cl)cc(Cl)c1)N1CCC(CO[Si](C)(C)C(C)(C)C)CC1]

4-(((tert-Butyldimethylsilyl)oxy)methyl)-1-(2-(3,5-dichlorophenyl)-1-methoxypropan-2-yl)piperidin To a solution of 2-(4-((tert-butyldimethylsilyloxy)methyl)piperidin-1-yl)-2-(3,5-dichlorophenyl)propan-1-ol (0.46 g, 1.06 mmol, crude) in dry THF (20 mL) was added sodium hydride (60% in mineral oil, 0.4 g, 10 mmol) under N$_2$ atmosphere at room temperature. Methyl iodide (1.41 g, 10 mmol) was added after 2 h and the resultant mixture was stirred overnight. The mixture was quenched with water (20 mL), extracted with EtOAc (10 mL×3), dried over sodium sulfate and concentrated. The residue was purified by silica gel chromatography (eluting with 8% EtOAc in petroleum ether) to afford the title compound as a viscous oil (0.4 g, 85%). LCMS (ESI) m/z: 446.1 [M+1]$^+$.

Step 7

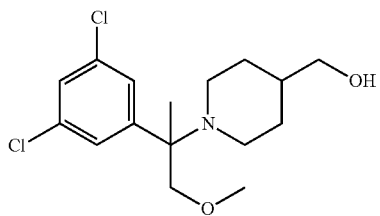 [SMILES: COCC(C)(c1cc(Cl)cc(Cl)c1)N1CCC(CO)CC1]

(1-(2-(3,5-Dichlorophenyl)-1-methoxypropan-2-yl)piperidin-4-yl)methanol

To a solution of 4-((tert-butyldimethylsilyloxy)methyl)-1-(2-(3,5-dichlorophenyl)-1-methoxypropan-2-yl)piperidin (0.4 g, 0.9 mmol) in DCM (20 mL), HCl in methanol (4M, 2 mL) was added dropwise. The mixture was stirred at room temperature for 2 h and concentrated in vacuo to give the title compound as a pale yellow oil. LCMS (ESI) m/z: 332.1 [M+1]⁺.

Step 8

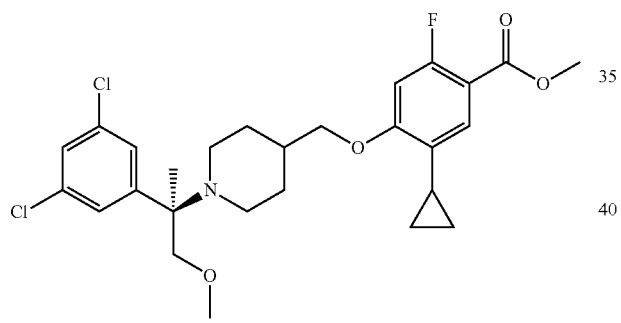 [SMILES: COC[C@@](C)(c1cc(Cl)cc(Cl)c1)N1CCC(COc2cc(F)c(C(=O)NS(C)(=O)=O)cc2C2CC2)CC1]

(R)-methyl 5-cyclopropyl-4-((1-(2-(3,5-dichlorophenyl)-1-methoxypropan-2-yl)piperidin-4-yl)methoxy)-2-fluorobenzoate A mixture of (1-(2-(3,5-dichlorophenyl)-1-methoxypropan-2-yl)piperidin-4-yl)methanol (0.298 g, 0.9 mmol), methyl 5-cyclopropyl-2-fluoro-4-hydroxybenzoate (0.19 g, 0.9 mmol), triphenylphosphine (0.472 g, 1.8 mmol) and diisopropyl azodiformate (0.365 g, 1.8 mmol) in dry THF (10 mL) was stirred under an N₂ atmosphere for 24 h. The reaction mixture was filtered, concentrated in vacuo, and the residue was purified by silica gel chromatography (eluting with 10% EtOAc in petroleum ether) to give the racemate (0.33 g, 70%). The enantiomer was separated by chiral SFC from the racemate. The enantiomer was arbitrarily assigned as (R)-methyl 5-cyclopropyl-4-((1-(2-(3,5-dichlorophenyl)-1-methoxypropan-2-yl)piperidin-4-yl)methoxy)-2-fluorobenzoate. Chiral HPLC (column: AD-H, 4.6×250 mm, 5 µm; mobile Phase: A: supercritical $CO_2$, B: MeOH, A:B=90:10; flow: 3 mL/min; column temperature: 38.9° C., RT=4.36 min). LCMS (ESI) m/z: 524.1 [M+1]⁺.

Step 9

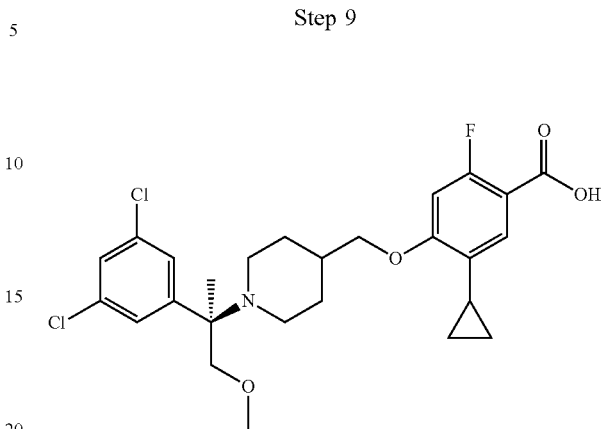

(R)-5-cyclopropyl-4-((1-(2-(3,5-dichlorophenyl)-1-methoxypropan-1-yl)piperidin-4-yl)methoxy)-2-fluorobenzoic acid The compound was synthesized as described in step 6 of Example 88. LCMS (ESI) m/z: 510.1 [M+1]⁺.

Step 10

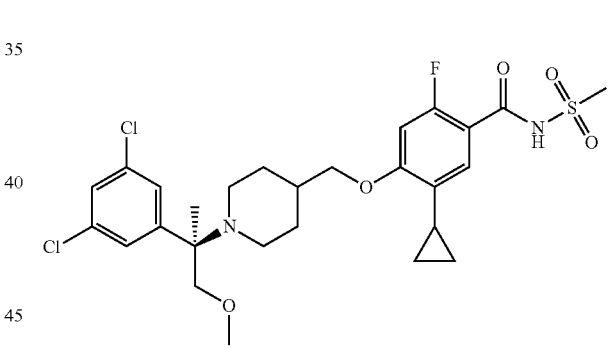

(S)-5-cyclopropyl-4-((1-(2-(3,5-dichlorophenyl)-1-methoxypropan-2-yl)piperidin-4-yl)methoxy)-2-fluoro-N-(methylsulfonyl)benzamide The compound was synthesized as described in step 5 of Example 80. The enantiomer was arbitrarily assigned as (R)-5-cyclopropyl-4-((1-(2-(3,5-dichlorophenyl)-1-methoxypropan-2-yl)piperidin-4-yl)methoxy)-2-fluoro-N-(methylsulfonyl)benzamide. LCMS (ESI): Method A: RT=6.39 min, m/z: 587.3[M+1]⁺. ¹HNMR (400 MHz, DMSO-d₆) δ 7.49 (d, J=1.6 Hz, 2H), 7.44 (m, 1H), 7.19 (d, J=8.8 Hz, 1H), 6.82 (d, J=12.4 Hz, 1H), 3.91 (d, J=5.6 Hz, 2H), 3.53-3.40 (m, 2H), 3.18 (s, 3H), 3.10 (s, 3H), 2.88 (d, J=9.6 Hz, 1H), 2.57 (m, 1H), 2.28-2.13 (m, 2H), 2.01-2.02 (m, 1H), 1.80-1.70 (m, 3H), 1.37-1.24 (m, 5H), 0.89-0.85 (ms 2H), 0.63-0.60 (m, 2H).

Example 202

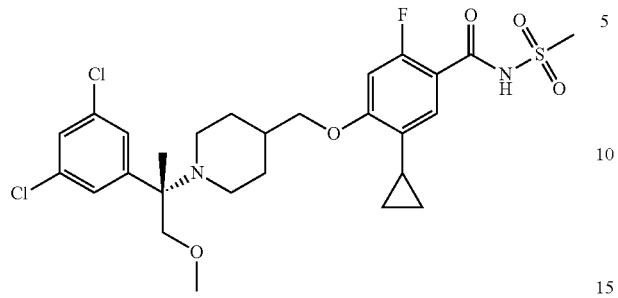

(S)-5-cyclopropyl-4-((1-(2-(3,5-dichlorophenyl)-1-methoxypropan-2-yl)piperidin-4-yl)methoxy)-2-fluoro-N-(methylsulfonyl)benzamide The compound was synthesized as described in Example 201. The enantiomer was arbitrarily assigned as (S)-5-cyclopropyl-4-((1-(2-(3,5-dichlorophenyl)-1-methoxypropan-2-yl)piperidin-4-yl)methoxy)-2-fluoro-N-(methylsulfonyl)benzamide. LCMS (ESI): Method A: RT=6.52 min, m/z: 587.2 [M+1]$^+$. $^1$HNMR (400 MHz, DMSO-d$_6$) δ 7.49 (d, J=2.0 Hz, 2H), 7.44 (m, 1H), 7.19 (d, J=8.8 Hz, 1H), 6.82 (d, J=12.8 Hz, 1H), 3.91 (d, J=6.0 Hz, 2H), 3.53-3.40 (m, 2H), 3.18 (s, 3H), 3.10 (s, 3H), 2.88 (d, J=9.6 Hz, 1H), 2.57 (m, 1H), 2.28-2.13 (m, 2H), 2.02-2.00 (m, 1H), 1.80-1.70 (m, 3H), 1.37-1.24 (m, 5H), 0.89-0.85 (m, 2H), 0.63-0.60 (m, 2H).

Example 203

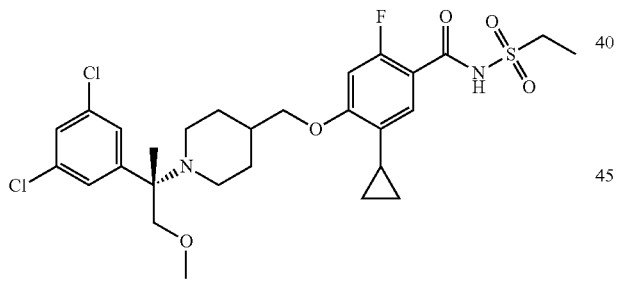

(S)-5-cyclopropyl-4-((1-(2-(3,5-dichlorophenyl)-1-methoxypropan-2-yl)piperidin-4-yl)methoxy)-N-(ethylsulfonyl)-2-fluorobenzamide The compound was synthesized as described in Example 201. The enantiomer was arbitrarily assigned as (S)-5-cyclopropyl-4-((1-(2-(3,5-dichlorophenyl)-1-methoxypropan-2-yl)piperidin-4-yl)methoxy-N-(ethylsulfonyl)-2-fluorobenzamide. LCMS (ESI): Method A: RT=6.19 min, m/z: 601.3 [M+H]$^+$. $^1$HNMR (400 MHz, DMSO-d$_6$) δ 7.49 (d, J=2.0 Hz, 2H), 7.44 (m, 1H), 7.19 (d, J=8.8 Hz, 1H), 6.82 (d, J=12.8 Hz, 1H), 3.91 (d, J=6.0 Hz, 2H), 3.53-3.40 (m, 2H), 3.18 (s, 3H), 3.10 (s, 3H), 3.08-3.06 (m, 2H), 2.88 (d, J=9.6 Hz, 1H), 2.58-2.56 (m, 1H), 2.28-2.13 (m, 2H), 2.02-2.00 (m, 1H), 1.80-1.70 (m, 3H), 1.37-1.24 (m, 5H), 0.89-0.85 (m, 2H), 0.63-0.60 (m, 2H).

Example 204

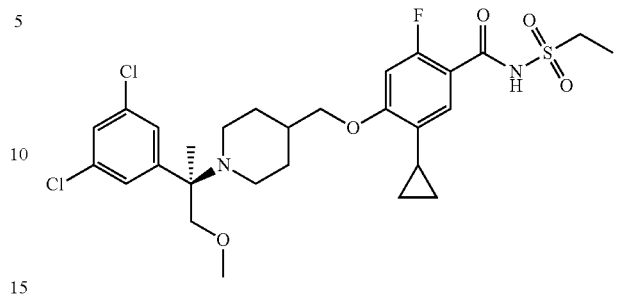

(S)-5-cyclopropyl-4-((1-(2-(3,5-dichlorophenyl)-1-methoxypropan-2-yl)piperidin-4-yl)methoxy)-N-(ethylsulfonyl)-2-fluorobenzamide The compound was synthesized as described in Example 201. The enantiomer was arbitrarily assigned as (S)-5-cyclopropyl-4-((1-(2-(3,5-dichlorophenyl)-1-methoxypropan-2-yl)piperidin-4-yl)methoxy)-N-(ethylsulfonyl)-2-fluorobenzamide. LCMS (ESI): Method A: RT=6.21 min, m/z: 601.2[M+1]$^+$. $^1$HNMR (400 MHz, DMSO-d$_6$) δ 7.49 (d, J=2.0 Hz, 2H), 7.44 (m, 1H), 7.19 (d, J=8.8 Hz, 1H), 6.82 (d, J=12.8 Hz, 1H), 3.91 (d, J=6.0 Hz, 2H), 3.53-3.40 (m, 2H), 3.18 (s, 3H), 3.10 (s, 3H), 3.08-3.06 (m, 2H), 2.88 (d, J=9.6 Hz, 1H), 2.58-2.56 (m, 1H), 2.28-2.13 (m, 2H), 2.02-2.00 (m, 1H), 1.80-1.70 (m, 3H), 1.37-1.24 (m, 5H), 0.89-0.85 (m, 2H), 0.63-0.60 (m, 2H).

Example 205

(R)-5-cyclopropyl-4-((1-(1-(3,5-dichlorophenyl)-2-methoxy-2-methylpropyl)piperidin-4-yl)methoxy)-2-fluoro-N-(methylsulfonyl)benzamide

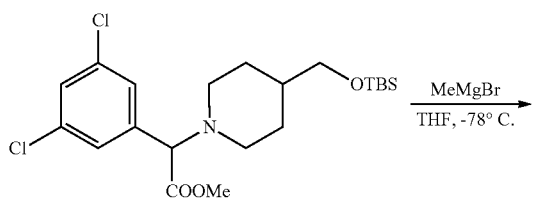

-continued

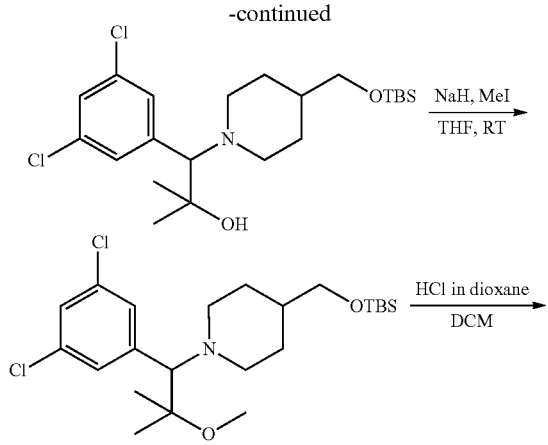

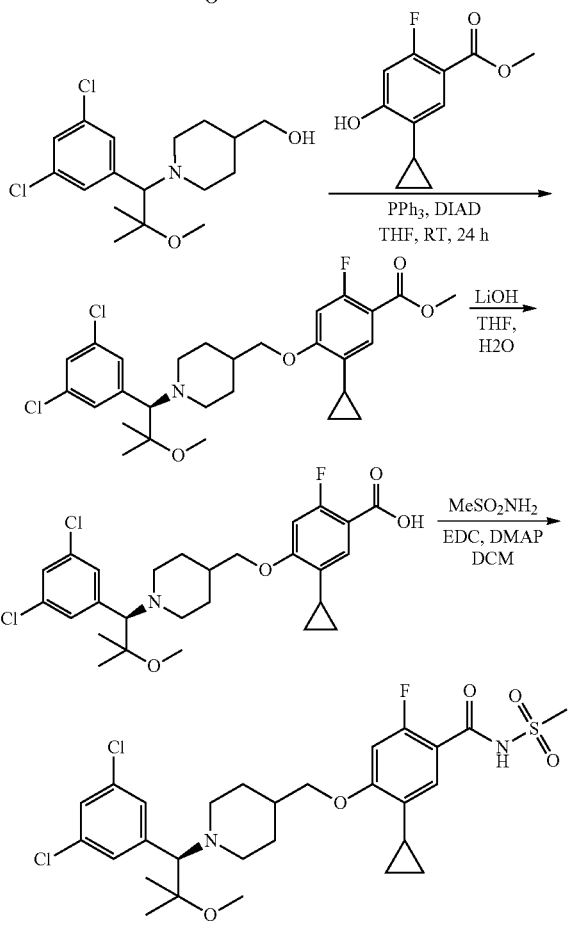

Step 1

1-(4-(((tert-Butyldimethylsilyl)oxy)methyl)piperidin-1-yl)-1-(3,5-dichlorophenyl)-2-methylpropan-2-ol To a solution of methyl 2-(4-((tert-butyldimethylsilyloxy)methyl)piperidin-1-yl)-2-(3,5-dichlorophenyl)acetate (0.58 g, 1.3 mmol) in dry THF (10 mL) at −78° C. was added methylmagnesium bromide (3M in THF, 2.6 mL). The resultant mixture was allowed to warm to room temperature and stirred overnight, quenched with water (20 mL), extracted with EtOAc (10 mL×3), dried over sodium sulfate, filtered and concentrated in vacuo. The residue was purified by silica gel chromatography (eluting with 5% EtOAc in petroleum ether) to afford title compound as a colorless oil (0.47 g, 81%). LCMS (ESI) m/z: 445.1. [M+1]$^+$.

Step 2

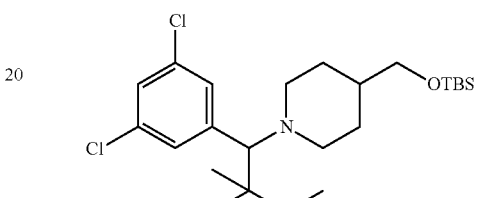

4-(((tert-Butyldimethylsilyl)oxy)methyl)-1-(1-(3,5-dichlorophenyl)-2-methoxy-2-methylpropyl)piperidine The compound was synthesized as described in step 6 of Example 201. LCMS (ESI) m/z: 460.2 [M+1]$^+$.

Step 3

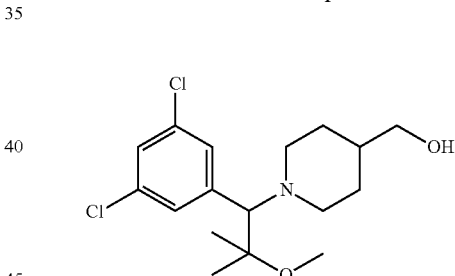

(1-(1-(3,5-Dichlorophenyl)-2-methoxy-2-methylpropyl)piperidin-4-yl)methanol

The compound was synthesized as described in step 7 of Example 201. LCMS (ESI) m/z: 346.1 [M+1]$^+$.

Step 4

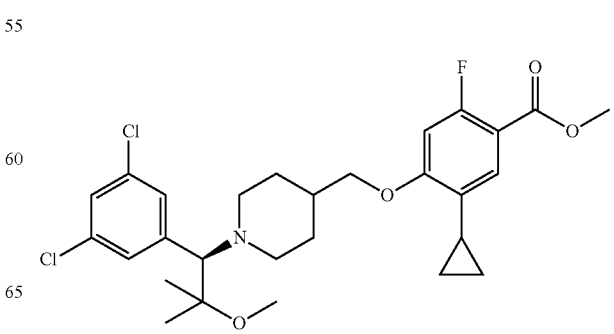

(R)-methyl 5-cyclopropyl-4-((1-(1-(3,5-dichlorophenyl)-2-methoxy-2-methylpropyl)piperidin-4-yl)methoxy-2-fluorobenzoate The compound was synthesized as described in step 8 of Example 201. The enantiomer was separated by chiral SFC from the racemate, the enantiomer was arbitrarily assigned as (R)-methyl 5-cyclopropyl-4-((1-(1-(3,5-dichlorophenyl)-2-methoxy-2-methylpropyl)piperidin-4-yl)methoxy)-2-fluorobenzoate. Chiral HPLC (column: AD-H, 4.6×250 mm, 5 μm; mobile Phase: A: supercritical $CO_2$, B: MeOH, A:B=85:15; flow: 3 mL/min; column temperature: 40.4° C., RT=2.85 min). LCMS (ESI) m/z: 538.1 [M+1]$^+$.

Step 5

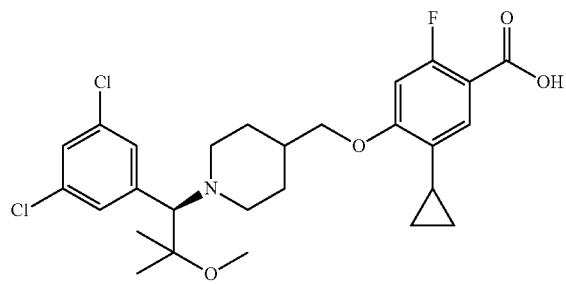 [SMILES: COC(C)(C)[C@@H](c1cc(Cl)cc(Cl)c1)N1CCC(COc2cc(F)c(C(=O)O)cc2C2CC2)CC1]

(R)-5-cyclopropyl-4-((1-(1-(3,5-dichlorophenyl)-2-methoxy-2-methylpropyl)piperidin-4-yl)methoxy)-2-fluorobenzoic acid The compound was synthesized as described in step 9 of Example 201. LCMS (ESI) m/z: 524.1 [M+1]$^+$.

Step 6

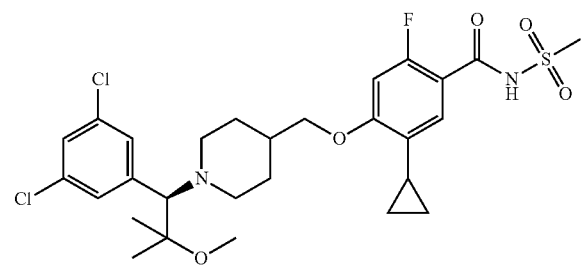 [SMILES: COC(C)(C)[C@@H](c1cc(Cl)cc(Cl)c1)N1CCC(COc2cc(F)c(C(=O)NS(C)(=O)=O)cc2C2CC2)CC1]

(R)-5-cyclopropyl-4-((1-(1-(3,5-dichlorophenyl)-2-methoxy-2-methylpropyl)piperidin-4-yl)methoxy)-2-fluoro-N-(methylsulfonyl)benzamide The compound was synthesized as described in step 9 of Example 201. The enantiomer was arbitrarily assigned as (R)-5-cyclopropyl-4-((1-(1-(3,5-dichlorophenyl)-2-methoxy-2-methylpropyl)piperidin-4-yl)methoxy)-2-fluoro-N-(methylsulfonyl)benzamide. LCMS (ESI): Method A: RT=6.95 min, m/z: 601.3 [M+1]$^+$. $^1$H NMR (400 MHz, DMSO-d$_6$) δ 11.83 (brs, 1H), 7.50-7.44 (m, 3H), 7.15-7.13 (m, 1H), 6.86 (d, J=12.8 Hz, 1H), 3.86-3.85 (m, 2H), 3.46-3.44 (m, 2H), 3.29 (s, 1H), 3.24 (s, 3H), 3.16 (s, 3H), 2.82 (d, J=10.8 Hz, 1H), 2.00-1.95 (m, 2H), 1.72-1.71 (m, 3H), 1.55-1.54 (m, 1H), 1.40-1.23 (m, 4H), 0.93 (s, 3H), 0.88-0.83 (m, 2H), 0.65-0.61 (m, 2H).

Example 206

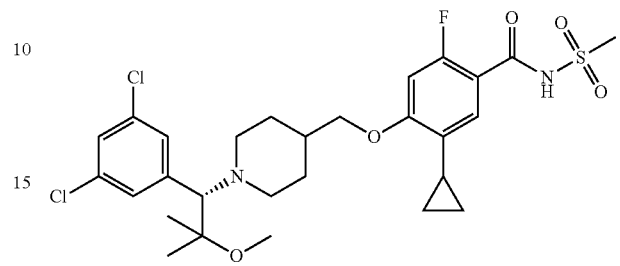

(S)-5-cyclopropyl-4-((1-(1-(3,5-dichlorophenyl)-2-methoxy-2-methylpropyl)piperidin-4-yl)methoxy)-2-fluoro-N-(methylsulfonyl)benzamide The compound was synthesized as described in Example 205. The anantiomer was arbitrarily assigned as (S)-5-cyclopropyl-4-((1-(1-(3,5-dichlorophenyl)-2-methoxy-2-methylpropyl)piperidin-4-yl)methoxy)-2-fluoro-N-methyl-sulfonyl)benzamide. LCMS (ESI): Method A: RT=6.95 min, m/z: 601.3 [M+1]$^+$. $^1$H NMR (400 MHz, DMSO-d$_6$) δ 11.83 (brs, 1H), 7.50-7.44 (m, 3H), 7.15-7.13 (m, 1H), 6.86 (d, J=12.8 Hz, 1H), 3.86-3.85 (m, 2H), 3.46-3.44 (m, 2H), 3.29 (s, 1H), 3.24 (s, 3H), 3.16 (s, 3H), 2.82 (d, J=10.8 Hz, 1H), 2.00-1.95 (m, 2H), 1.72-1.71 (m, 3H), 1.55-1.54 (m, 1H), 1.40-1.23 (m, 4H), 0.93 (s, 3H), 0.88-0.83 (m, 2H), 0.65-0.61 (m, 2H).

Example 207

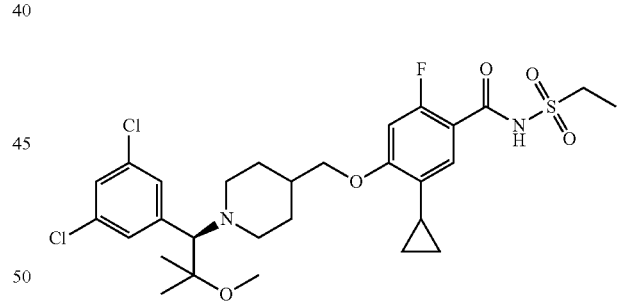

(R)-5-cyclopropyl-4-((1-(1-(3,5-dichlorophenyl)-2-methoxy-2-methylpropyl)piperidin-4-yl)methoxy)-N-(ethylsulfonyl)-2-fluorobenzamide The compound was synthesized as described in Example 205. The enantiomer was arbitrarily assigned as (R)-5-cyclopropyl-4-((1-(1-(3,5-dichlorophenyl)-2-methoxy-2-methylpropyl)piperidin-4-yl)methoxy)-N-(ethylsulfonyl)-2-fluorobenzamide. LCMS (ESI): Method A: RT=7.04 min, m/z: 615.3 [M+1]$^+$. $^1$H NMR (400 MHz, DMSO-d$_6$) δ 7.49 (d, J=2.0 Hz, 2H), 7.44 (m, 1H), 7.19 (d, J=8.8 Hz, 1H), 6.82 (d, J=12.8 Hz, 1H), 3.91. (d, J=6.0 Hz, 2H), 3.53-3.40 (m, 2H), 3.42-3.37 (m, 2H), 3.18 (s, 3H), 3.10 (s, 3H), 3.07 (m, 2H), 2.88 (d, J=9.6 Hz, 1H), 2.57-2.56 (m, 1H), 2.28-2.13

(m, 2H), 2.01-2.00 (m, 1H), 1.80-1.70 (m, 3H), 1.37-1.24 (m, 5H), 0.89-0.85 (m, 2H), 0.63-0.60 (m, 2H).

Example 208

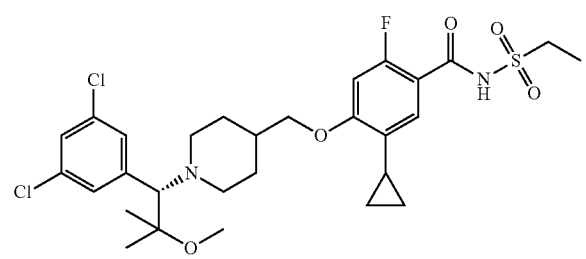 [SMILES: CCS(=O)(=O)NC(=O)c1cc(C2CC2)c(OCC2CCN([C@@H](c3cc(Cl)cc(Cl)c3)C(C)(C)OC)CC2)cc1F]

(S)-5-cyclopropyl-4-((1-(1-(3,5-dichlorophenyl)-2-methoxy-2-methylpropyl)piperidin-4-yl)methoxy)-N-(ethylsulfonyl)-2-fluorobenzamide The compound was synthesized as described in Example 205. The enantiomer was arbitrarily assigned as (S)-5-cyclopropyl-4-((1-(1-(3,5-dichlorophenyl)-2-methoxy-2-methylpropyl)piperidin-4-yl)methoxy)-N-(ethylsulfonyl)-2-fluorobenzamide. LCMS (ESI): Method A: RT=7.12 min, m/z: 615.2 [M+1]$^+$. $^1$H NMR (400 MHz, DMSO-d$_6$) δ 7.49 (d, J=2.0 Hz, 2H), 7.44 (m, 1H), 7.19 (d, J=8.8 Hz, 1H), 6.82 (d, J=12.8 Hz, 1H), 3.91 (d, J=6.0 Hz, 2H), 3.53-3.40 (m, 2H), 3.42-3.37 (m, 2H), 3.18 (s, 3H), 3.10 (s, 3H), 3.07-3.06 (m, 2H), 2.88 (d, J=9.6 Hz, 1H), 2.58-2.56 (m, 1H), 2.28-2.13 (m, 2H), 2.01-2.00 (m, 1H), 1.80-1.70 (m, 3H), 1.37-1.24 (m, 5H), 0.89-0.85 (m, 2H), 0.63-0.60 (m, 2H).

Example 209

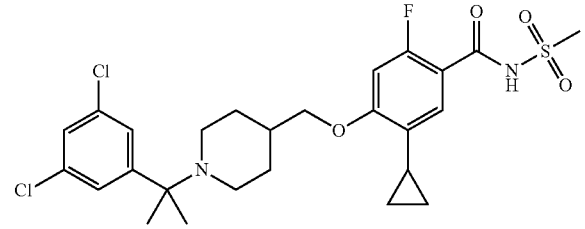 [SMILES: CC(C)(c1cc(Cl)cc(Cl)c1)N1CCC(COc2cc(F)c(C(=O)NS(C)(=O)=O)cc2C2CC2)CC1]

5-Cyclopropyl-4-((1-(1-(3,5-dichlorophenyl)-propan-2-yl)piperidin-4-yl)methoxy)-2-fluoro-N-(methylsulfonyl)benzamide

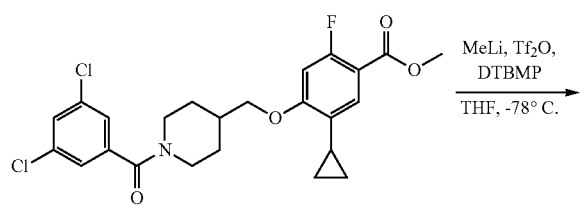

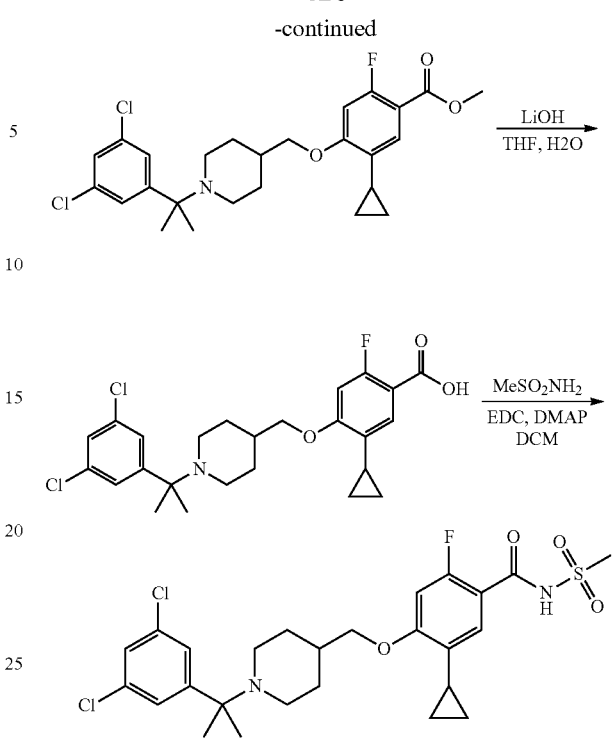

Step 1

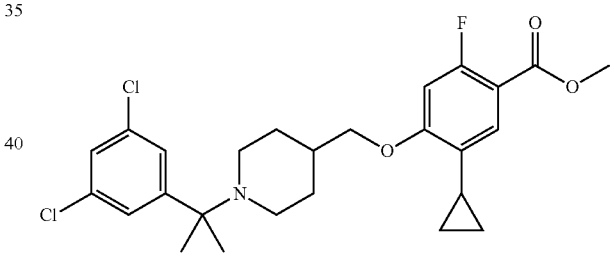

Methyl 5-cyclopropyl-4-((1-(2-(3,5-dichlorophenyl)propan-2-yl)piperidin-4-yl)methoxy)-2-fluorobenzoate To a solution of methyl 5-cyclopropyl-4-((1-(3,5-dichlorobenzoyl)piperidin-4-yl)methoxy)-2-fluorobenzoate (0.81 g, 1.7 mmol) and 2,6-di-tert-butyl-4-methylpyridine (1.4 g, 6.8 mmol) in dry THF (15 mL) under N$_2$ atmosphere, was added trifluoromethanesulfonic anhydride (0.4 mL) dropwise at −78° C. The mixture was stirred at −40° C. for 3 h followed by the addition of MeLi (3M in THF, 2.3 mL). The reaction mixture was allowed to warm to room temperature and stirred overnight, quenched with water (10 mL), extracted with EtOAc (10 mL×3), dried over anhydrous sodium sulfate, filtered and concentrated. The residue was purified by silica gel chromatography (eluting with 15% ethyl acetate in petroleum ether) to afford the target compound as a white solid (0.17 g, 20%). LCMS (ESI): m/z: 494.2 [M+1]$^+$.

Step 2

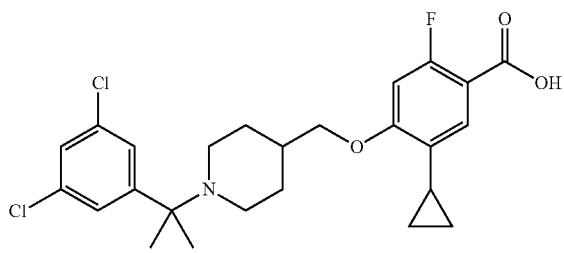 [SMILES: CC(C)(c1cc(Cl)cc(Cl)c1)N1CCC(COc2cc(F)c(C(=O)O)cc2C2CC2)CC1]

5-Cyclopropyl-4-((1-(2-(3,5-dichlorophenyl)propan-2-yl)piperidin-4-yl)methoxy)-2-fluorobenzoic acid The compound was synthesized as described in step 6 of Example 88. LCMS (ESI) m/z: 480.2 [M+1]$^+$.

Step 3

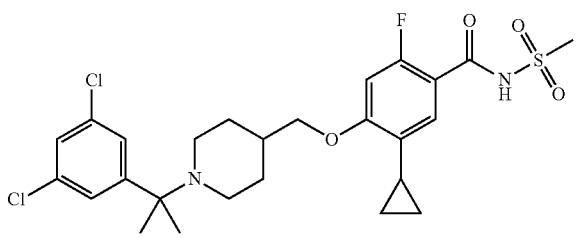 [SMILES: CC(C)(c1cc(Cl)cc(Cl)c1)N1CCC(COc2cc(F)c(C(=O)NS(C)(=O)=O)cc2C2CC2)CC1]

5-Cyclopropyl-4-((1-(2-(3,5-dichlorophenyl)propan-2-yl)piperidin-4-yl)methoxy)-2-fluoro-N-(methylsulfonyl)benzamide The compound was synthesized as described in step 5 of Example 80. LCMS (ESI): Method A: RT=7.01 min, m/z: 557.0 [M+1]$^+$. $^1$HNMR (500 MHz, DMSO-d$_6$) δ 7.51 (s, 2H), 7.44 (s, 1H), 7.21 (d, J=8.5 Hz, 1H), 6.76 (d, J=13.0 Hz, 1H), 3.90 (d, J=5.5 Hz, 2H), 3.00 (s, 3H), 2.75-2.73 (m, 2H), 2.12-2.10 (m, 2H), 2.01-1.98 (m, 1H), 1.78-1.76 (m, 3H), 1.35-1.23 (m, 8H) 0.89-0.85 (m, 2H), 0.60-0.57 (m, 2H).

Example 210

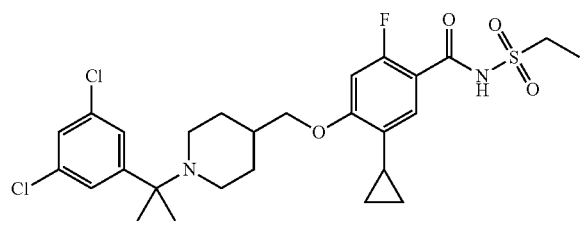 [SMILES: CCS(=O)(=O)NC(=O)c1cc(C2CC2)c(OCC2CCN(C(C)(C)c3cc(Cl)cc(Cl)c3)CC2)cc1F]

5-Cyclopropyl-4-((1-(2-(3,5-dichlorophenyl)propan-2-yl)piperidin-4-yl)methoxy)-N-(ethylsulfonyl)-2-fluorobenzamide The compound was synthesized as described in Example 209. LCMS (ESI): Method A: RT=6.81 min, m/z: 571.2 [M+1]$^+$. $^1$HNMR (400 MHz, DMSO-d$_6$) ε7.51 (s, 2H), 7.44 (s, 1H), 7.17 (d, J=8.8 Hz, 1H), 6.81 (d, J=12.8 Hz, 1H), 3.92 (d, J=5.2 Hz, 2H), 3.29-3.24 (m, 2H), 2.76-2.67 (m, 2H), 2.14-2.09 (m, 2H), 2.03-1.96 (m, 1H), 1.77-1.76 (m, 3H), 1.37-1.24 (m, 8H), 1.17 (t, J=7.6 Hz, 3H), 0.89-0.85 (m, 2H), 0.63-0.59 (m, 2H).

Example 211

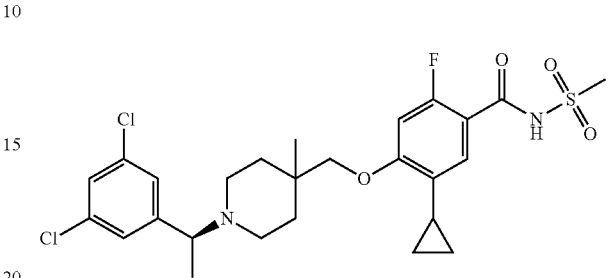

(S)-5-cyclopropyl-4-((1-(1-(3,5-dichlorophenyl)ethyl)-4-methylpiperidin-4-yl)methoxy)-2-fluoro-N-(methylsulfonyl)benzamide The compound was synthesized as described in Example 170. The enantiomer was separated by chiral SFC from the racemate, the second eluting fraction was arbitrarily assigned as (S)-5-cyclopropyl-4-((1-(1-(3,5-dichlorophenyl)ethyl)-4-methylpiperidin-4-yl)methoxy)-2-fluoro-N-(methylsulfonyl)benzamide. Chiral HPLC (column: IC 4.6×150 mm 5 μm; mobile Phase: A: supercritical CO$_2$, B: MeOH, A:B=70:30; flow: 3.0 mL/min; column temperature: 39.9° C.; RT=6.78 mm). LCMS (ESI) Method A: RT=5.50 min, m/z: 556.7 [M+H]$^+$. $^1$H NMR (400 MHz, DMSO-d$_6$): δ7.53-7.43 (m, 3H), 7.20 (d, J=8.4 Hz, 1H), 6.89 (d, J=12.4 Hz, 1H), 3.80 (s, 3H), 3.14 (s, 3H), 3.21-3.16 (m, 2H), 2.42-2.40 (m, 1H), 2.01-1.99 (m, 1H), 1.69-1.68 (m, 2H), 1.47-1.35 (m, 6H), 1.04 (s, 3H), 0.89-0.86 (m, 2H): 0.62-0.61 (m, 2H).

Example 212

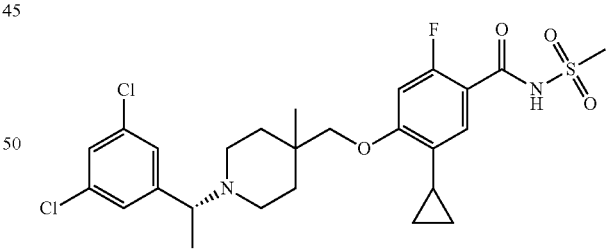

(R)-5-cyclopropyl-4-((1-(1-(3,5-dichlorophenyl)ethyl)-4-methylpiperidin-4-yl)methoxy)-2-fluoro-N-(methylsulfonyl)benzamide The compound was synthesized as described in Example 170. The enantiomer was separated by chiral SFC from the racemate, the first eluting fraction was arbitrarily assigned as (R)-5-cyclopropyl-4-((1-(1-(3,5-dichlorophenyl)ethyl)-4-methylpiperidin-4-yl)methoxy)-2-fluoro-N-(methylsulfonyl)benzamide. Chiral HPLC (column: IC 4.6×150 mm 5 μm; mobile Phase: A: supercritical CO$_2$, B: MeOH, A:B=70:

30; flow: 3.0 mL/min; column temperature: 39.9° C.; RT=5.75 min). LCMS (ESI) Method A: RT=5.46 min, m/z: 556.7 [M+H]+. 1H NMR (400 MHz, DMSO-d6): δ7.53-7.43 (m, 3H), 7.20 (d, J=8.4 Hz, 1H), 6.89 (d, J=12.4 Hz, 1H), 3.80 (s, 3H), 3.14 (s, 3H), 3.21-3.16 (m, 2H), 2.44-2.40 (m, 1H), 2.01-1.99 (m, 1H), 1.69-1.68 (m, 2H), 1.47-1.33 (m, 6H), 1.04 (s, 3H), 0.90-0.85 (m, 2H), 0.64-0.60 (m, 2H).

Example 213

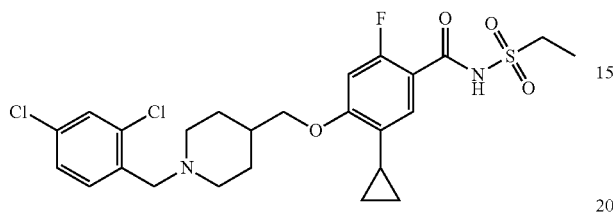

5-cyclopropyl-4-((1-(2,4-dichlorobenzyl)piperidin-4-yl)methoxy)-N-(ethylsulfonyl)-2-fluorobenzamide The compound was synthesized as described in Example 88. LCMS (ESI) Method A: RT=6.25 min, m/z: 542.8 [M+H]+. 1H NMR (400 MHz, DMSO-d6): δ7.60-7.51 (m, 3H), 7.13 (d, J=8.4 Hz, 1H), 6.91 (d, J=12.8 Hz, 1H), 3.94 (d, J=6.0 Hz, 2H), 3.62 (s, 2H), 3.40-3.37 (m, 2H), 2.92-2.90 (m, 2H), 2.20-1.79 (m, 6H), 1.42-1.37 (m, 2H), 1.23-1.19 (m, J=7.4 Hz, 3H), 0.89-0.86 (m, 2H), 0.66-0.63 (m, 2H).

Example 214

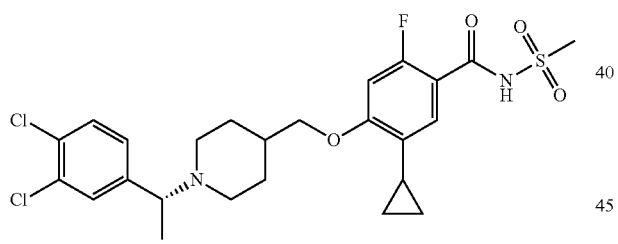

(R)-5-cyclopropyl-4-((1-(1-(3,4-dichlorophenyl)ethyl)piperidin-4-yl)methoxy)-2-fluoro-N-(methylsulfonyl)benzamide The compound was synthesized as described in Example 88. The enantiomer was separated by chiral SFC from the racemate, the first eluting fraction was arbitrarily assigned as (R)-5-cyclopropyl-4-((1-(1-(3,4-dichlorophenyl)ethyl)piperidin-4-yl)methoxy)-2-fluoro-N-(methylsulfonyl)benzamide. Chiral HPLC (column: AD-H, 4.6×250 mm, 5 μm; mobile Phase: A: supercritical CO2, B: MeOH, A:B=70:30; flow: 3.0 mL/min; column temperature: 37.7° C.; RT=6.44 min). LCMS (ESI) Method A: RT=6.11 min, m/z: 542.9 [M+H]+. 1H NMR (400 MHz, DMSO-d6): δ7.63-7.62 (m, 2H), 7.30-7.38 (m, 1H), 7.17 (d, J=6.4 Hz, 1H), 6.80 (d, J=10.4 Hz, 1H), 3.90 (d, J=4.4 Hz, 3H), 3.08 (s, 3H), 2.86-2.84 (m, 2H), 2.01-1.98 (m, 3H), 1.85-1.78 (m, 3H), 1.39-1.35 (m, 5H), 0.88-0.86 (m, 2H), 0.62-0.59 (m, 2H).

Example 215

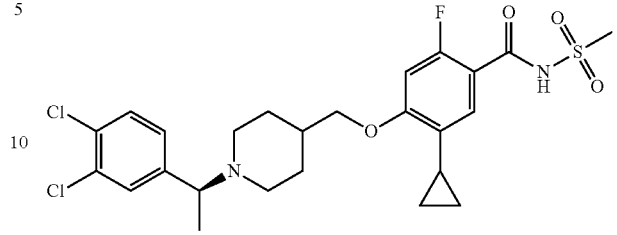

(S)-5-cyclopropyl-4-((1-(1-(3,4-dichlorophenyl)ethyl)piperidin-4-yl)methoxy)-2-fluoro-N-(methylsulfonyl)benzamide The compound was synthesized as described in Example 88. The enantiomer was separated by chiral SFC from the racemate, the second eluting fraction was arbitrarily assigned as (S)-5-cyclopropyl-4-((1-(1-(3,4-dichlorophenyl)ethyl)piperidin-4-yl)methoxy)-2-fluoro-N-(methylsulfonyl)benzamide. Chiral HPLC (column: AD-H, 4.6×250 mm, 5 μm; mobile Phase: A: supercritical CO2, B: MeOH, A:B=70:30; flow: 3.0 mL/min: column temperature: 37.7° C.; RT=10.00 min). LCMS (ESI) Method A: RT=6.11 min, m/z: 542.9 [M+H]+. 1H NMR (400 MHz, DMSO-d6): δ7.64-7.62 (m, 214), 7.38-7.36 (m, 1H), 7.17 (d, J=6.8 Hz, 1H), 6.80 (d, J=10.4 Hz, 1H), 3.91 (d, J=4.4 Hz, 3H), 3.10 (s, 3H), 2.92-2.91 (m, 2H), 2.19-1.17 (m, 2H), 2.01-1.78 (m, 4H), 1.42-1.35 (m, 5H), 0.88-0.86 (m, 2H), 0.64-0.61 (m, 2H).

Example 216

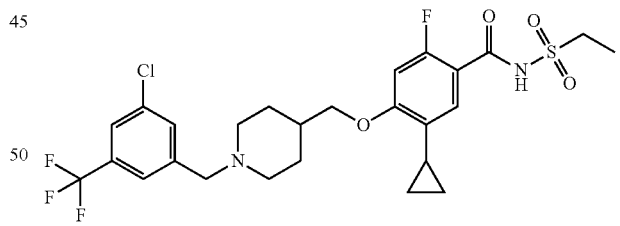

4-((1-(3-Chloro-5-(trifluoromethyl)benzyl)piperidin-4-yl)methoxy)-5-cyclopropyl-N-(ethylsulfonyl)-2-fluorobenzamide The compound was synthesized as described in Example 88. LCMS (ESI) Method A: RT=6.31 min, m/z: 576.8 [M+H]+. 1H NMR (400 MHz, DMSO-d6): δ7.77-7.67 (m, 3H), 7.14 (d, J=8.4 Hz, 1H), 6.88 (d, J=12.8 Hz, 1H), 3.94 (d, J=16 Hz, 2H), 3.68 (s, 2H), 3.35-3.33 (m, 2H), 2.91-2.88 (m, 2H), 2.14-1.79 (m, 6H), 1.40-1.38 (m, 2H), 1.20 (t, J=7.4 Hz, 3H), 0.89-0.86 (m, 2H), 0.66-0.63 (m, 2H).

Example 217

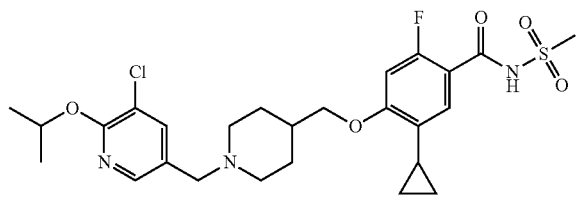 [SMILES: CC(C)Oc1ncc(CN2CCC(COc3cc(F)c(C(=O)NS(C)(=O)=O)cc3C3CC3)CC2)cc1Cl]

4-((1-((5-Chloro-6-isopropoxypyridin-3-yl)methyl)piperidin-4-yl)methoxy)-5-cyclopropyl-2-fluoro-N-(methylsulfonyl)benzamide The compound was synthesized as described in Example 190. LCMS (ESI) Method A: RT=5.88 min, m/z: 553.8 [M+H]$^+$. $^1$H NMR (400 MHz, DMSO-d$_6$): δ8.06 (d, J=4.0 Hz, 1H), 7.15 (d, J=9.6 Hz, 1H), 7.10 (d, J=4.4 Hz, 1 Hz), 6.89 (d, J=10.4 Hz, 1H), 5.30-5.28 (m, 1H), 3.95-3.94 (m, 2H), 3.60 (s, 2H), 3.21 (s, 3H), 2.89-2.87 (m, 2H), 2.16-2.51 (m, 2H), 2.03-2.01 (m, 1H), 1.80-1.78 (m, 3H), 1.41-1.39 (m, 2H), 1.31 (d, J=5.2 Hz, 6H), 0.91-0.87 (m, 2H), 0.66-0.63 (m, 2H).

Example 218

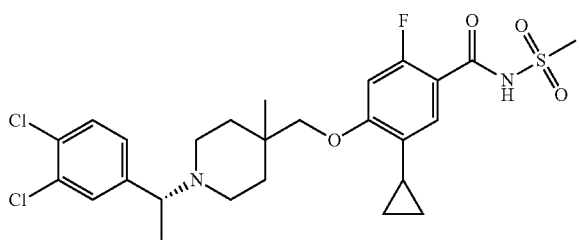 [SMILES: C[C@H](c1ccc(Cl)c(Cl)c1)N1CCC(C)(COc2cc(F)c(C(=O)NS(C)(=O)=O)cc2C2CC2)CC1]

(R)-5-cyclopropyl-4-((1-(1-(3,4-dichlorophenyl)ethyl)-4-methylpiperidin-4-yl)methoxy)-2-fluoro-N-(methylsulfonyl)benzamide The compound was synthesized as described in Example 170. The enantiomer was separated by chiral SFC from the racemate, the first eluting fraction was arbitrarily assigned as (R)-5-cyclopropyl-4-((1-(1-(3,4-dichlorophenyl)ethyl)-4-methylpiperidin-4-yl)methoxy)-2-fluoro-N-(methylsulfonyl)benzamide. Chiral HPLC (column: OJ-H (4.6×250 mm, 5 μm; mobile Phase: A: supercritical CO$_2$, B: MeOH, A;B=75:25; flow: 3.0 mL/min; column temperature: 40.0° C.; RT=4.18 min). LCMS (ESI) Method A: RT=6.25 min, m/z: 556.8 [M+H]$^+$. $^1$H NMR (300 MHz, DMSO-d$_6$): δ7.65-7.63 (m, 2H), 7.40-7.38 (m, 1H), 7.20 (d, J=8.1 Hz, 1H), 6.84 (d, J=12.9 Hz, 1H), 3.79-3.78 (m, 2H), 3.11 (s, 3H), 2.57-2.56 (m, 1H), 2.45-2.42 (m, 3H), 2.01-1.99 (m, 1H), 1.69-1.37 (m, 8H), 1.04 (s, 3H), 0.89-0.85 (m, 2H), 0.62-0.60 (m, 2H).

Example 219

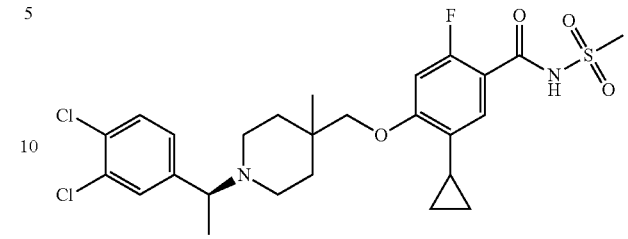

(S)-5-cyclopropyl-4-((1-(1-(3,4-dichlorophenyl)ethyl)-4-methylpiperidin-4-yl)methoxy)-2-fluoro-N-(methylsulfonyl)benzamide The compound was synthesized as described in Example 170. The enantiomer was separated by chiral SFC from the racemate, the second eluting fraction was arbitrarily assigned as (S)-5-cyclopropyl-4-((1-(1-(3,4-dichlorophenyl)ethyl-4-methylpiperidin-4-yl)methoxy)-2-fluoro-N-(methylsulfonyl)benzamide. Chiral HPLC (column: OJ-H (4.6× 250 mm, 5 μm; mobile Phase: A: supercritical CO$_2$, B: MeOH, A:B=75:25; flow: 3.0 mL/min; column temperature: 40.0° C.; RT=6.43 min). LCMS (ESI) Method A: RT=6.26 min, m/z: 556.8 [M+H]$^+$. $^1$H NMR (300 MHz, DMSO-d$_6$): δ7.65-7.63 (m, 2H), 7.40-7.38 (m, 1H), 7.20 (d, J=8.1 Hz, 1H), 6.83 (d, J=12.9 Hz, 1H), 3.79-3.78 (m, 2H), 3.11 (s, 3H), 2.57-2.56 (m, 1H), 2.45-2.42 (m, 3H), 2.01-1.99 (m, 1H), 1.69-1.37 (m, 8H), 1.04 (s, 3H), 0.88-0.8.6 (m, 2H), 0.62-0.60 (m, 2H).

Example 220

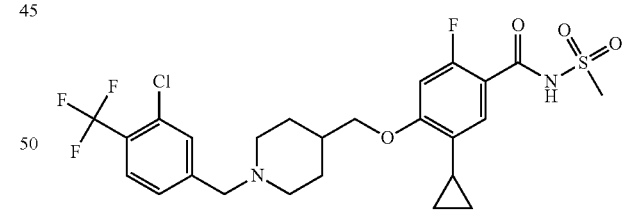

4-((1-(3-Chloro-4-(trifluoromethyl)benzyl)piperidin-4-yl)methoxy)-5-cyclopropyl-2-fluoro-N-(methylsulfonyl)benzamide The compound was synthesized as described in Example 88, LCMS (ESI) Method A: RT=6.25 min, m/z: 562.8 [M+H]$^+$. $^1$H NMR (400 MHz, DMSO-d$_6$): δ 7.86-7.84 (m, 1H), 7.69-7.52 (m, 2H), 7.15 (d, J=8.4 Hz, 1H), 6.88 (d, J=12.8 Hz, 1H), 3.94 (d, J=6.0 Hz, 2H), 3.72 (s, 2H), 3.20 (s, 3H), 2.95-2.92 (m, 2H), 2.20-1.80 (m, 6H), 1.43-1.40 (m, 2H), 0.90-0.86 (m, 2H), 0.66-0.63 (m, 2H).

Example 221

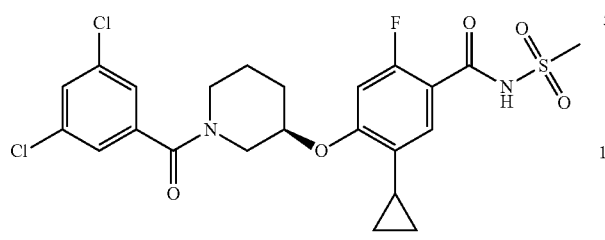

(R)-5-cyclopropyl-4-((1-(3,5-dichlorobenzoyl)piperidin-3-yl)oxy)-2-fluoro-N-(methylsulfonyl)benzamide The compound was synthesized as described in step Example 134. LCMS (ESI) Method A: RT=4.69 min, m/z: 528.8 [M+H]$^+$. $^1$H NMR (500 MHz, DMSO-d$_6$): δ 7.74-7.28 (m, 3H), 7.17 (d, J=8.0 Hz, 1H), 6.78 (d, J=12.5 Hz, 1H), 4.68-4.67 (m, 1H), 4.19-4.16 (m, 1H), 3.68-3.50 (m, 2H), 3.28-3.14 (m, 4H), 2.02-1.60 (m, 5H), 0.93-0.92 (m, 2H), 0.71-0.68 (m, 2H).

Example 222

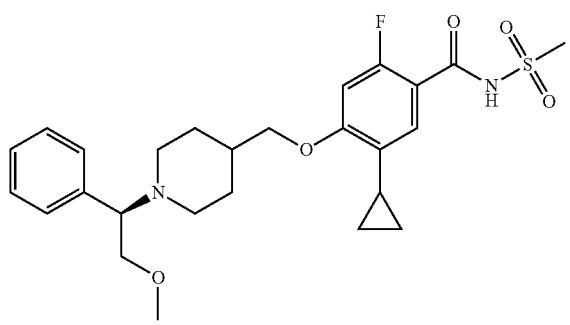 [SMILES: COC[C@@H](c1ccccc1)N1CCC(COc2cc(F)c(C(=O)NS(C)(=O)=O)cc2C2CC2)CC1]

(R)-5-cyclopropyl-2-fluoro-4-((1-(2-methoxy-1-phenylethyl)piperidin-4-yl)methoxy)-N-(methylsulfonyl)benzamide The compound was synthesized as described in Example 172. The enantiomer was separated by chiral SFC from the racemate, the first eluting fraction was arbitrarily assigned as (R)-5-cyclopropyl-2-fluoro-4-((1-(2-methoxy-1-phenylethyl)piperidin-4-yl)methoxy)-N-(methylsulfonyl)benzamide. Chiral HPLC (column: OJ-H, 4.6×250 mm, 5 μm; mobile Phase: A: supercritical CO$_2$, B: MeOH, A:B=75:25; flow: 3.0 mL/min; column temperature: 40.2° C.; RT=3.78 min). LCMS (ESI) Method A: RT=4.83 min, m/z: 505.0 [M+H]$^+$. $^1$H NMR (500 MHz, DMSO-d$_6$): δ7.36-7.32 (m, 5H), 7.16 (d, J=8.0 Hz, 1H), 6.82 (d, J=13.5 Hz, 1H), 3.90-3.71 (m, 5H), 3.29-3.25 (m, 4H), 3.11-2.90 (m, 4H), 2.35-1.75 (m, 6H), 1.49-1.38 (m, 2H), 0.88-0.85 (m, 2H), 0.61-0.60 (m, 2H).

Example 223

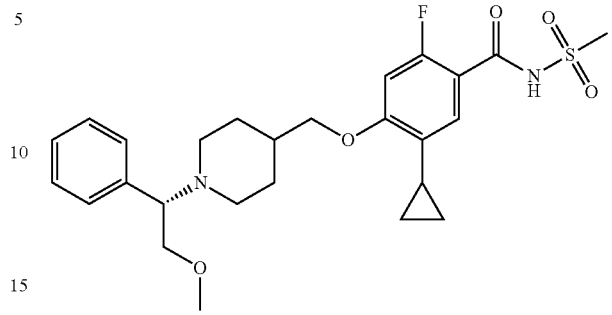

(S)-5-cyclopropyl-2-fluoro-4-((1-(2-methoxy-1-phenylethyl)piperidin-4-yl)methoxy)-N-(methylsulfonyl)benzamide The compound was synthesized as described in Example 172. The enantiomer was separated by chiral SFC from the racemate, the second eluting fraction was arbitrarily assigned as (S)-5-cyclopropyl-2-fluoro-4-((1-(2-methoxy-1-phenylethyl)piperidin-4-yl)methoxy)-N-(methylsulfonyl)benzamide. Chiral HPLC (column: OJ-H, 4.6×250 mm, 5 μm; mobile Phase: A: supercritical CO$_2$, B: MeOH, A:B=75:25; flow: 3.0 mL/min; column temperature: 40.2° C.; RT=5.20 min). LCMS (ESI) Method A: RT=4.83 min, m/z: 504.9 [M+H]$^+$. $^1$H NMR (500 MHz, DMSO-d$_6$) δ7.39-7.32 (m, 5H), 7.16 (d, 9.0 Hz, 1H), 6.82 (d, J=13.0 Hz, 1H), 3.90-3.69 (m, 5H), 3.31 (s, 3H), 3.11-2.90 (m, 5H), 2.01-1.75 (m, 6H), 1.49-1.38 (m, 2H), 0.88-0.85 (m, 2H); 0.62-0.59 (m, 2H).

Example 224

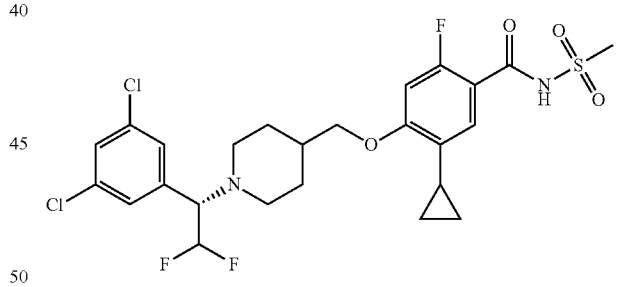

(S)-5-cyclopropyl-4-((1-(1-(3,5-dichlorophenyl)-2,2-difluoroethyl)piperidin-4-yl)methoxy)-2-fluoro-N-(methylsulfonyl)benzamide

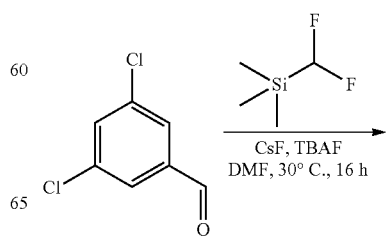

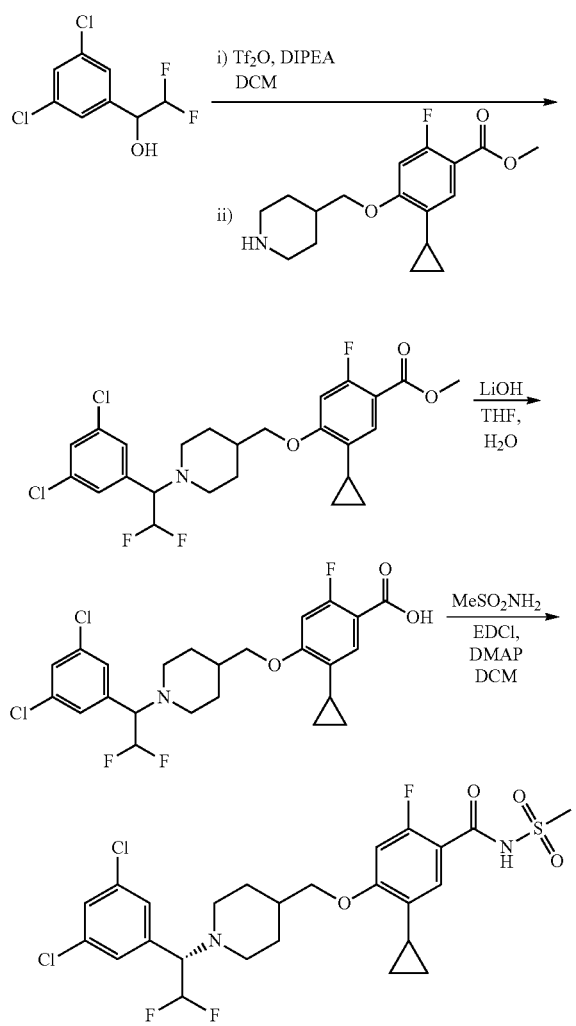

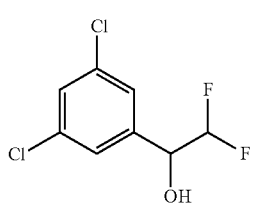 [SMILES: OC(c1cc(Cl)cc(Cl)c1)C(F)F]

1-(3,5-Dichlorophenyl)-2,2-difluoroethanol

A mixture of 3,5-dichlorobenzaldehyde (800 mg, 4.6 mmol), (difluoromethyl)trimethylsilane (850 mg, 6.8 mmol) and CsF (441 mg, 2.3 mmol) in DMF (20 mL) was stirred for 36 h at room temperature. The reaction mixture was diluted with ethyl acetate (50 mL), washed with brine (30 mL×3), dried over anhydrous sodium sulfate and concentrated. The residue was purified by silica gel chromatography (eluting with petroleum ether/ethyl acetate=10/1) to afford the title compound as a pale yellow oil (500 mg, 48%). LCMS (ESI) m/z: 225.0 [M−H]⁻.

Step 2

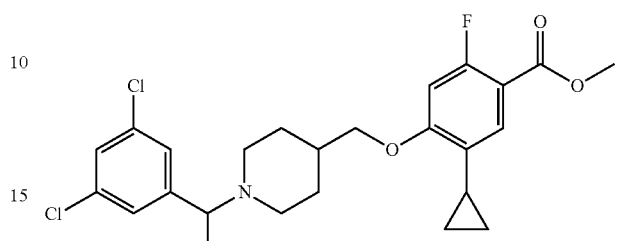

Methyl 5-cyclopropyl-4-((1-(1-(3,5-dichlorophenyl)-2,2-difluoroethyl)piperidin-4-yl)methoxy)-2-fluorobenzoate To a mixture of 1-(3,5-dichlorophenyl)-2,2-difluoroethanol (200 mg, 0.9 mmol) and DIPEA (270 mg, 2.7 mmol) in DCM (20 mL) was added trifluoromethanesulfonic anhydride (507 mg, 1.8 mmol) at 0° C., and the mixtures stirred for 2 h. Methyl 5-cyclopropyl-2-fluoro-4-(piperidin-4-ylmethoxy)benzoate (277 mg, 0.9 mmol) was then added at 0° C. and the mixture left to warm to room temperature and stirred for 16 h. The reaction was quenched with ethyl acetate (40 mL) and water (40 mL), extracted with ethyl acetate (20 mL×3), dried over anhydrous sodium sulfate and concentrated. The residue was purified by silica gel chromatography (eluting with petroleum ether/ethyl acetate=5/1) to afford the title compound, as a pale yellow oil. (230 mg, 20%).

Step 3

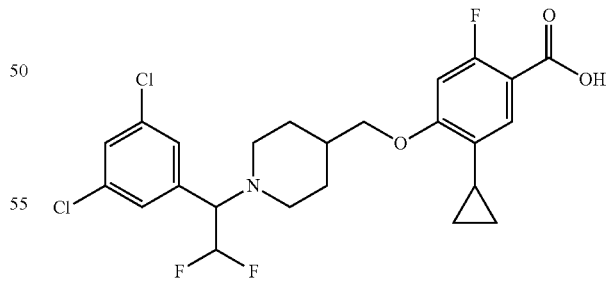

5-Cyclopropyl-4-((1-(1-(3,5-dichlorophenyl)-2,2-difluoroethyl)piperidin-4-yl)methoxy)-2-fluorobenzoic acid The compound was synthesized as described in step 6 of Example 88. LCMS (ESI) m/z: 502.1 [M+H]⁺.

Step 4

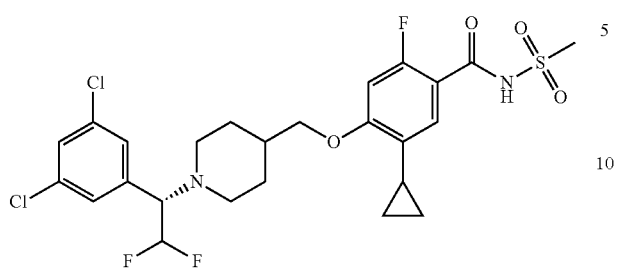

(S)-5-cyclopropyl-4-((1-(1-(3,5-dichlorophenyl)-2,2-difluoroethyl)piperidin-4-yl)methoxy)-2-fluoro-N-(methylsulfonyl)benzamide The compound was synthesized as described in step 5 of Example 80. The enantiomer was separated by chiral SFC from the racemate, the second eluting fraction was arbitrarily assigned as (S)-5-cyclopropyl-4-((1-(1-(3,5-dichlorophenyl)-2,2-difluoroethyl)piperidin-4-yl)methoxy)-2-fluoro-N-(methylsulfonyl)benzamide. Chiral HPLC (column: AD-H, 4.6×250 mm, 5 μm; mobile Phase: A: supercritical $CO_2$, B: MeOH, A:B=85:15; flow: 3.0 mL/min; column temperature: 40.1° C.; RT=15.85 mm). LCMS (ESI) Method A: RT=6.16 min, m/z: 579.0 [M+H]$^+$. $^1$H NMR (400 MHz, DMSO-$d_6$): δ7.62-7.47 (m, 3H), 7.14 (d, J=8.4 Hz, 1H), 6.89-6.65 (m, 2H), 4.04-3.89 (m, 3H), 5.29-3.24 (m, 3H), 2.98-2.92 (m, 2H), 2.17-2.15 (m, 1H), 2.00-1.73 (m, 5H), 1.35-1.32 (m, 2H), 0.89-0.84 (m, 2H), 0.66-0.62 (m, 2H).

Example 225

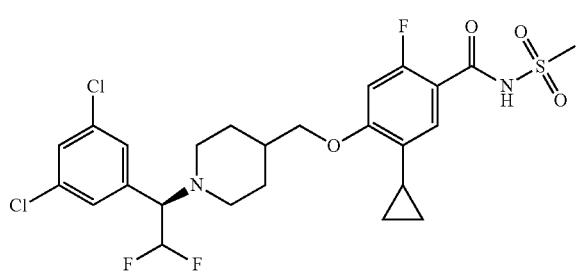

(S)-5-cyclopropyl-4-((1-(1-(3,5-dichlorophenyl)-2,2-difluoroethyl)piperidin-4-yl)methoxy)-2-fluoro-N-(methylsulfonyl)benzamide The compound was synthesized as described in Example 224. The enantiomer was separated by chiral SFC from the racemate, the first eluting fraction was arbitrarily assigned as (S)-5-cyclopropyl-4-((1-(1-(3,5-dichlorophenyl)-2,2-difluoroethyl)piperidin-4-yl)methoxy)-2-fluoro-N-(methylsulfonyl)benzamide. Chiral HPLC (column: AD-H, 4.6×250 mm, 5 μm: mobile Phase: A: supercritical $CO_2$, B: MeOH, A:B=85:15; flow: 3.0 mL/min; column temperature: 40.1° C.; RT=13.82 min). LCMS (ESI) Method A: RT=6.16 min, m/z: 579.0 [M+H]$^+$. $^1$H NMR (400 MHz, DMSO-$d_6$): δ7.62-7.42 (m, 3H), 7.14 (d, J=8.4 Hz, 1H), 6.77-6.65 (m, 2H), 4.04-3.85 (m, 3H), 3.29-3.27 (m, 1H), 3.02-2.92 (m, 4H), 2.16-2.14 (m, 1H), 2.00-1.68 (m, 5H), 1.39-1.29 (m, 2H), 0.88-0.83 (m, 2H), 0.60-0.58 (m, 2H).

Example 226

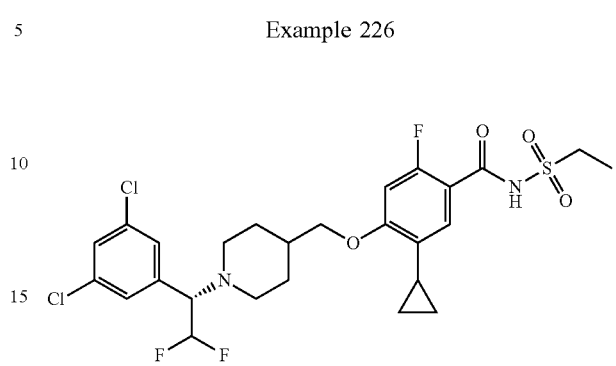

(S)-5-cyclopropyl-4-((1-(1-(3,5-dichlorophenyl)-2,2-difluoroethyl)piperidin-4-yl)methoxy)-N-(ethylsulfonyl)-2-fluorobenzamide The compound was synthesized as described in Example 224. The enantiomer was separated by chiral SFC from the racemate, the second eluting fraction was arbitrarily assigned as (S)-5-cyclopropyl-4-((1-(1-(3,5-dichlorophenyl)-2,2-difluoroethyl)piperidin-4-yl)methoxy)-N-(ethylsulfonyl)-2-fluorobenzamide. Chiral HPLC (column: AD-H, 4.6×250 mm, 5 μm; mobile Phase: A: supercritical $CO_2$, B: MeOH, A:B=85:15; flow: 3.0 mL/min; column temperature: 42.0° C.; RT=13.5 min). LCMS (ESI) Method A: RT=6.15 min, m/z: 593.2 [M+H]$^+$. $^1$H NMR (400 MHz, DMSO-$d_6$): δ7.62-7.61 (m, 1H), 7.47-7.46 (m, 2H), 7.12 (d, J=8.4 Hz, 1H), 6.90-6.58 (m, 2H), 4.08-3.89 (m, 3H), 3.39-3.37 (m, 2H), 3.01-2.92 (m, 2H), 2.15-2.13 (m, 1H), 1.98-1.72 (m, 4H), 1.35-1.19 (m, 6H), 0.87-0.84 (m, 2H), 0.62-0.60 (m, 2H).

Example 227

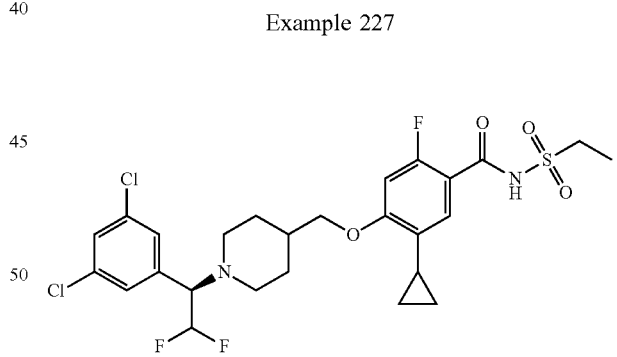

(R)-5-cyclopropyl-4-((1-(1-(3,5-dichlorophenyl)-2,2-difluoroethyl)piperidin-4-yl)methoxy)-N-(ethylsulfonyl)-2-fluorobenzamide The compound was synthesized as described in Example 224. The enantiomer was separated by chiral SFC from the racemate, the first eluting fraction was arbitrarily assigned as (R)-5-cyclopropyl-4-((1-(1-(3,5-dichlorophenyl)-2,2-difluoroethyl)piperidin-4-yl)methoxy)-N-(ethylsulfonyl)-2-fluorobenzamide. Chiral HPLC (column: AD-H, 4.6×250 mm, 5 μm; mobile Phase: A: supercritical $CO_2$, B: MeOH, A:B=85:15; flow: 3.0 mL/min; column temperature: 42.0°

C.; RT=12.33 min), LCMS (ESI) Method A: RT=6.15 min., m/z: 593.2 [M+H]$^+$. $^1$H NMR (400 MHz, DMSO-d$_6$): δ7.62-7.61 (m, 1H), 7.47-7.46 (m, 2H), 7.12 (d, J=8.4 Hz, 1H), 6.90-6.58 (m, 2H), 4.08-3.89 (m, 3H), 3.39-3.37 (m, 2H), 3.01-2.94 (m, 2H), 2.15-1.91 (m, 3H), 1.76-1.68 (m, 3H), 1.35-1.32 (m, 2H), 1.21 (t, J=7.4 Hz, 3H), 0.89-0.84 (m, 2H), 0.66-0.63 (m, 2H).

Example 228

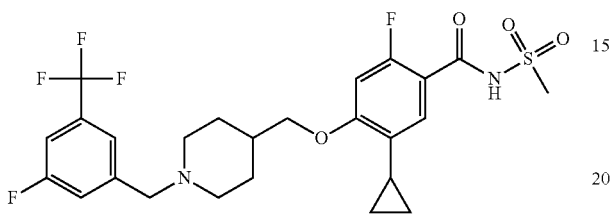

5-Cyclopropyl-2-fluoro-4-((1-(3-fluoro-5-(trifluoromethyl)benzyl)piperidin-4-yl)methoxy)-N-(methylsulfonyl)benzamide The compound was synthesized as described in Example 88. LCMS (ESI) Method A: RT=5.71 min, m/z 546.9[M+H]$^+$. $^1$H-NMR (500 MHz, DMSO-d$_6$): δ11.34 (s, 1H), 7.62-7.53 (m, 3H), 7.16 (d, J=9.0 Hz, 1H), 6.89 (d, J=13.0 Hz, 1H), 3.95 (d, J=6.0 Hz, 2H), 3.77 (s, 2H), 3.21 (s, 3H), 2.97-2.95 (m, 2H), 2.27-2.23 (m, 2H), 2.04-2.00 (m, 1H), 1.87-1.82 (m, 3H), 1.46-1.40 (m, 2H), 0.90-0.86 (m, 2H), 0.66-0.63 (m, 2H).

Example 229

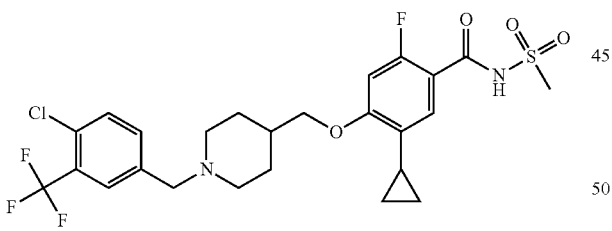

4-((1-(4-Chloro-3-(trifluoromethyl)benzyl)piperidin-4-yl)methoxy)-5-cyclopropyl-2-fluoro-N-(methylsulfonyl)benzamide The compound was synthesized as described in Example 88. LCMS (ESI) Method A: RT=5.88 min, m/z 563.0[M+H]$^+$. $^1$H-NMR (500 MHz, DMSO-d$_6$): δ11.24 (brs, 1H), 7.83 (s, 1H), 7.75 (d, J=8.0 Hz, 1H), 7.67 (d, J=8.0 Hz, 1H), 7.17 (d, J=8.5 Hz, 1H), 6.85 (d, J=12.5 Hz, 1H), 3.93 (d, J=6.0 Hz, 2H), 3.74 (s, 2H), 3.14 (s, 3H), 2.97-2.95 (m, 2H), 2.24 (s, 2H), 2.04-1.98 (m, 1H), 1.86-1.77 (m, 3H), 1.45-1.38 (m, 2H), 0.89-0.86 (m, 2H), 0.64-0.61 (m, 2H).

Example 230

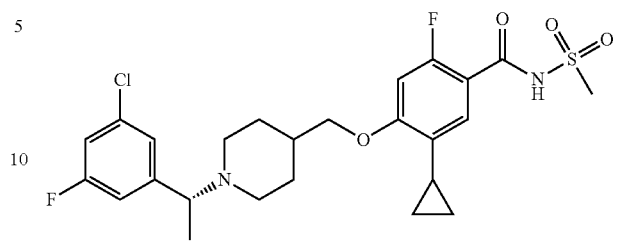

(R)-4-((1-(1-(3-chloro-5-fluorophenyl)ethyl)piperidin-4-yl)methoxy)-5-cyclopropyl-2-fluoro-N-(methylsulfonyl)benzamide The compound was synthesized as described in Example 88. The enantiomer was separated by chiral SFC from the racemate, the first eluting fraction was arbitrarily assigned as (R)-4-((1-(1-(3-chloro-5-fluorophenyl)ethyl)piperidin-4-yl)methoxy-5-cyclopropyl-2-fluoro-N-(methylsulfonyl)benzamide. Chiral HPLC (column: AD-H, 4.6×250 mm, 5 μm; mobile Phase: A: supercritical CO$_2$, B: MeOH (0.1% DEA), A:B=70:30; flow: 2.1 mL/min; column temperature: 40° C.; RT=4.01 min). LCMS (ESI) Method A: RT=5.99 min, m/z 527.2[M+H]$^+$. $^1$H-NMR (400 MHz, DMSO-d$_6$): δ7-35 (d, J=8.8 Hz, 1H), 7.30 (s, 1H), 7.21 (d, J=9.2 Hz, 1H), 7.17 (d, J=8.4 Hz, 1H), 6.83 (d, J=12.4 Hz, Hz, 3.91 (d, J=5.6 Hz, 2H), 3.74 (brs. 1H), 3.11 (s, 3H), 3.07-3.03 (m, 1H), 2.91-2.87 (m, 1H), 2.12-2.09 (m, 2H), 2.03-1.98 (m, 1H), 1.84-1.77 (m, 3H), 1.41-1.34 (m, 5H), 0.89-0.85 (m, 2H), 0.63-0.59 (m, 2H).

Example 231

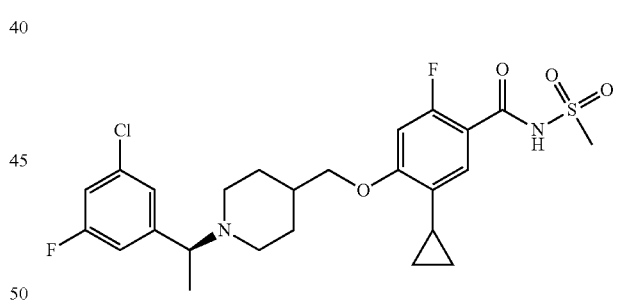

(S)-4-((1-(1-(3-chloro-5-fluorophenyl)ethyl)piperidin-4-yl)methoxy)-5-cyclopropyl-2-fluoro-N-(methylsulfonyl)benzamide The compound was synthesized as described in Example 88. The enantiomer was separated by chiral SFC from the racemate, the second eluting fraction was arbitrarily assigned as (R)-4-((1-(1-(3-chloro-5-fluorophenyl)ethyl)piperidin-4-yl)methoxy)-5-cyclopropyl-2-fluoro-N-(methylsulfonyl)benzamide. Chiral HPLC (column: AD-H, 4.6×250 mm, 5 μm; mobile Phase: A: supercritical CO$_2$, B: MeOH (0.1% DEA), A:B=70:30; flow: 2.1 mL/min; column temperature: 40° C.; RT=4.83 min). LCMS (ESI) Method A: RT=5.99 min, m/z 527.2[M+H]$^+$. $^1$H-NMR (400 MHz, DMSO-d$_6$): δ7.35 (d, J=8.8 Hz, 1H), 7.30 (s, 1H), 7.21 (d, J=9.2 Hz, 1H), 7.17 (d, J=8.4 Hz, 1H), 6.83 (d, J=12.4 Hz, 1H), 3.91 (d, J=5.6 Hz, 2H), 3.74 (brs, 1H), 3.11 (s, 3H), 3.07-3.03 (m, 1H), 2.91-2.87 (m, 1H), 2.12-2.09 (m, 2H), 2.03-1.98 (m, 1H), 1.84-1.77 (m, 3H), 1.41-1.34 (on 5H), 0.89-0.85 (m, 2H), 0.63-0.59 (m, 2H).

Example 232

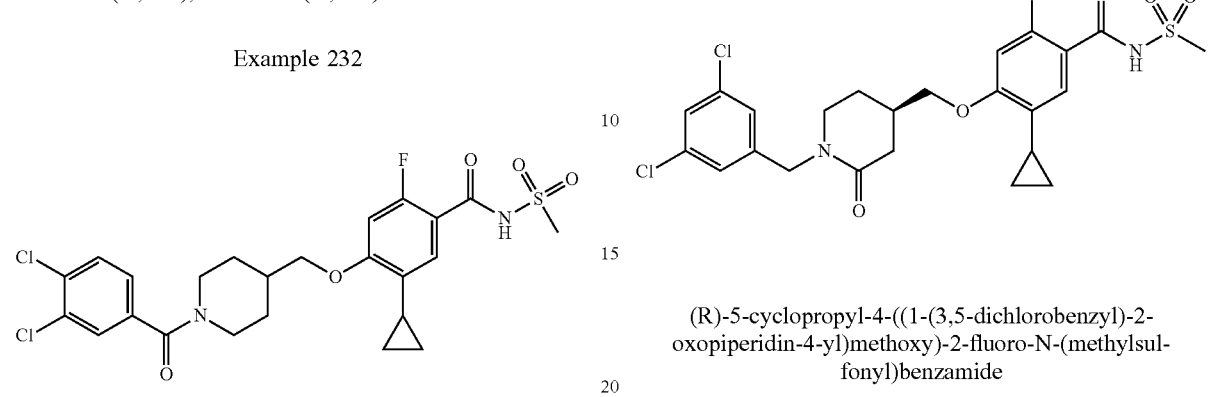

5-Cyclopropyl-4-((1-(3,4-dichlorobenzoyl)piperidin-4-yl)methoxy)-2-fluoro-N-(methylsulfonyl)benzamide The compound was synthesized as described in Example 134. LCMS (ESI) Method A: RT=5.03 min, m/z 542.8 [M+H]+. 1H-NMR (500 MHz, DMSO-d6): δ11.89 (s, 1H), 7.72 (d, J=8.0 Hz, 1H), 7.66 (d, J=2.0 Hz, 1H), 7.39-7.37 (m, 1H), 7.15 (d, J=90 Hz, 1H), 6.95 (d, J=12.5 Hz, 1H), 4.48 (brs, 1H), 3.98 (d, J=6.0 Hz, 2H) 3.56 (brs, 1H), 3.29 (s, 3H), 3.18-3.12 (m, 1H), 2.84-2.76 (m, 1H), 2.13-2.10 (m, 1H), 2.05-1.99 (m, 1H), 1.89-1.76 (m, 2H), 1.33 (brs, 2H), 0.91-0.87 (m, 2H), 0.68-0.65 (m, 2H).

Example 233

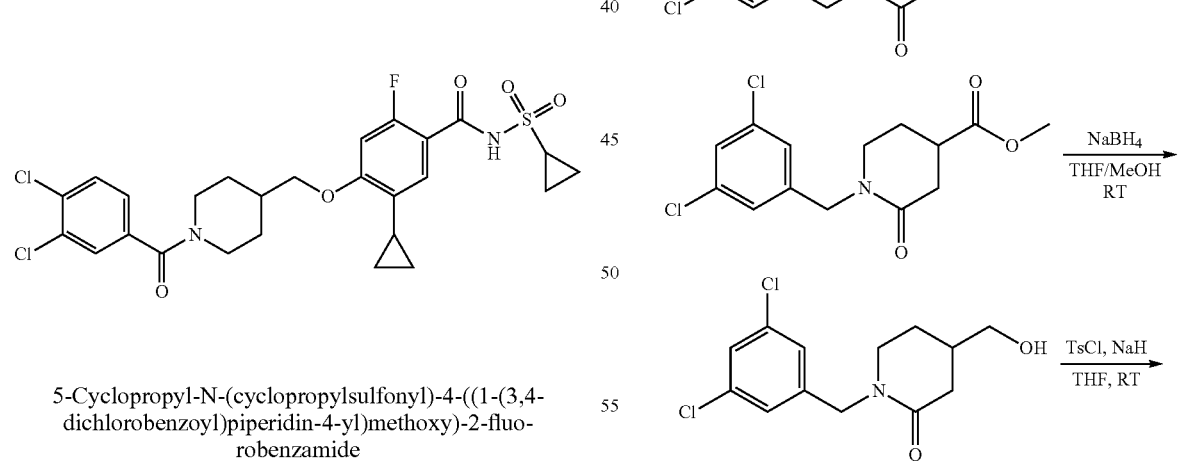

5-Cyclopropyl-N-(cyclopropylsulfonyl)-4-((1-(3,4-dichlorobenzoyl)piperidin-4-yl)methoxy)-2-fluorobenzamide The compound was synthesized as described in Example 134. LCMS (ESI) Method A: RT=5.18 min, m/z 568.8 [M+H]+. 1H-NMR (500 MHz, DMSO-d6): δ11.81 (s, 1H), 7.72 (d, =8.5 Hz, 1H), 7.66 (d, J=2.0 Hz, 1H), 7.39-7.37 (m, 1H), 7.14 (d, J=8.0 Hz, 1H), 6.97 (d, J=12.5 Hz, 1H), 4.48 (brs, 1H), 3.99 (d, J=5.0 Hz, 2H), 3.56 (brs, 1H), 3.12-3.04 (m, 2H), 2.84 (s, 1H), 2.13-2.12 (m, 1H), 2.04-1.99 (m, 1H), 1.89 (s, 1H), 1.77 (s, 1H), 1.33 (s, 2H), 1.12-1.07 (m, 4H), 0.91-0.87 (m, 2H), 0.68-0.65 (m, 2H).

Example 234

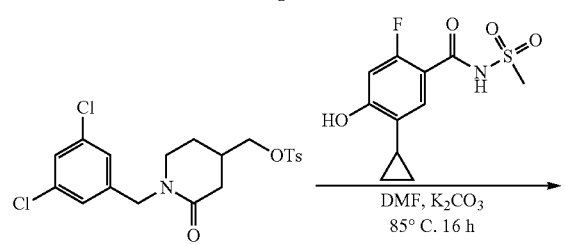

(R)-5-cyclopropyl-4-((1-(3,5-dichlorobenzyl)-2-oxopiperidin-4-yl)methoxy)-2-fluoro-N-(methylsulfonyl)benzamide -continued

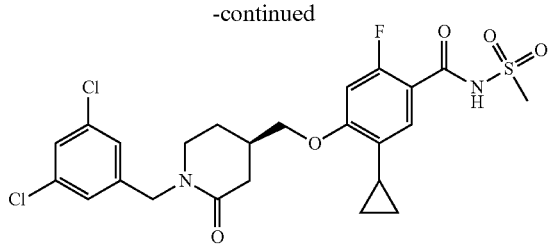

Step 1

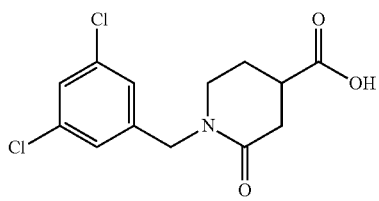 [SMILES: O=C(O)C1CCN(Cc2cc(Cl)cc(Cl)c2)C(=O)C1]

1-(3,5-Dichlorobenzyl)-2-oxopiperidine-4-carboxylic acid

A mixture of methyl 2-oxopiperidine-4-carboxylate (1.00 g, 6.36 mmol), 1,3-dichloro-5-(chloromethyl)benzene (1.49 g, 7.63 mmol) and potassium hydroxide (1.79 g, 31.8 mmol) in DMSO (30 mL) was stirred at room temperature for 4 h. The reaction was quenched with HCl (3.0 M, 50 mL) and ethyl acetate (150 mL). The organic layer was separated and washed with brine (50 mL×3), dried over anhydrous sodium sulfate, filtered and concentrated. The residue was purified by silica gel chromatography (eluting with 2% ethyl acetate in petroleum ether) to afford target compound as white solid (1.65 g, 85%). LCMS (ESI) m/z: 302.0 [M+H]$^+$.

Step 2

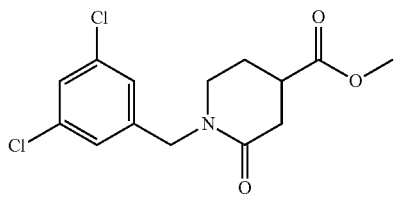 [SMILES: COC(=O)C1CCN(Cc2cc(Cl)cc(Cl)c2)C(=O)C1]

Methyl 1-(3,5-dichlorobenzyl)-2-oxopiperidine-4-carboxylate

A solution of 1-(3,5-dichlorobenzyl)-2-oxopiperidine-4-carboxylic acid (1.65 g, 5.46 mmol) in thionyl chloride (30 mL) was refluxed for 2 h. Then the solution was added dropwise to methanol (100 mL) at 0° C. and the mixture stirred at room temperature for 2 h. The mixture was concentrated in vacuo to afford the target compound as brown oil which was used without further purification. LCMS (ESI) m/z: 316.0 [M+H]$^+$.

Step 3

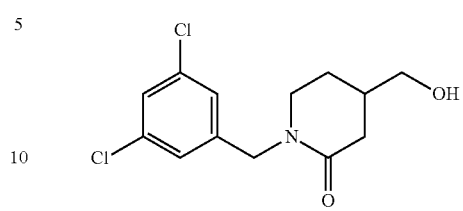

1-(3,5-Dichlorobenzyl)-4-(hydroxymethyl)piperidin-2-one

A mixture of methyl 1-(3,5-dichlorobenzyl)-2-oxopiperidine-4-carboxylate (1.80 g, 5.69 mmol) and sodium borohydride (1.08 g, 28.5 mmol) in THF (20 mL) and MeOH (10 mL) was stirred at room temperature for 16 h. The solvent was removed and the residue was purified by reverse phase chromatography (elating with 25-30% CH$_3$CN in 0.5% NH$_4$HCO$_3$) to give target compound as brown oil (630 mg, 38%). LCMS (ESI) m/z: 388.0 [M+H]$^+$.

Step 4

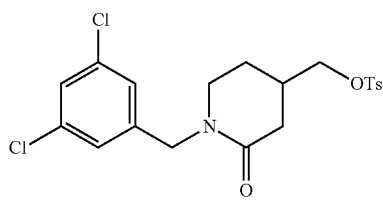 [SMILES: Cc1ccc(S(=O)(=O)OCC2CCN(Cc3cc(Cl)cc(Cl)c3)C(=O)C2)cc1]

(1-(3,5-Dichlorobenzyl)-2-oxopiperidin-4-yl)methyl 4-methylbenzenesulfonate

A mixture of 1-(3,5-dichlorobenzyl)-4-(hydroxymethyl)piperidin-2-one (630 mg, 2.19 mmol) and sodium hydride (437 mg, 10.9 mmol) in THF (30 mL) was stirred at room temperature for 30 min. Tosyl chloride (500 mg, 2.62 mmol) in THF (10 mL) was then added and the resulting mixture was stirred at room temperature for 16 h. The react was quenched with ice water, extracted with ethyl acetate (100 mL), washed with brine (50 mL×2), dried over anhydrous sodium sulfate, filtered and concentrated. The residue was purified by reverse phase chromatography (eluting with 50-60% CH$_3$CN in 0.5% NH$_4$HCO$_3$) to afford the target compound ax brown oil (380 mg, 39%). LCMS (ESI) m/z: 442.0 [M+H]$^+$.

Step 5

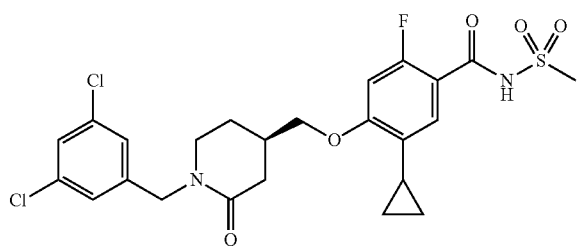 [SMILES: CS(=O)(=O)NC(=O)c1cc(C2CC2)c(OC[C@@H]2CCN(Cc3cc(Cl)cc(Cl)c3)C(=O)C2)cc1F]

(R)-5-cyclopropyl-4-((1-(3,5-dichlorobenzyl)-2-oxopiperidin-4-yl)methoxy)-2-fluoro-N-(methylsulfonyl)benzamide A mixture of (1-(3,5-dichlorobenzyl)-2-oxopiperidin-4-yl)methyl 4-methylbenzenesulfonate (380 mg, 0.859 mmol), potassium carbonate (1.19 g, 8.61 mmol) and 5-cyclopropyl-2-fluoro-4-hydroxy-N-(methylsulfonyl)benzamide (352 mg, 1.29 mmol), in DMF (20 mL) was stirred at 85° C. for 16 h. The reaction was quenched with ethyl acetate (100 mL) and HCl (2.0 M, 40 mL), washed with brine (50 mL×2), dried over anhydrous sodium sulfate, filtered and concentrated. The residue was purified by reverse phase chromatography (elating with 25-40% CH$_3$CN in 0.5% NH$_4$HCO$_3$) to afford the racemate as a white solid. The enantiomer was separated by chiral SFC from the racemate, the first eliding fraction was arbitrarily assigned as (R)-5-cyclopropyl-4-((1-(3,5-dichlorobenzyl)-2-oxopiperidin-4-yl)methoxy)-2-fluoro-N-(methylsulfonyl)benzamide. Chiral HPLC (column: AS-H, 4.6×250 mm, 5 μm; mobile Phase: A: supercritical CO$_2$, B: MeOH (0.1% DEA), A:B=75:25; flow: 2.25 mL/min; column temperature: 40° C.; RT=5.59 min). LCMS (ESI) Method A: RT=5.14 mm, m/z: 542.80 [M+H]$^+$. $^1$H-NMR (400 MHz, DMSO-d$_6$): δ11.92 (s, 1H), 7.53-7.52 (m, 1H), 7.31-7.29 (m, 2H), 7.15 (d, J=8.4 Hz, 1H), 6.95 (d, J=12.8 Hz, 1H), 4.56-4.47 (m, 2H), 4.00 (d, J=6.4 Hz, 2H), 3.32-3.30 (m, 2H), 3.28 (s, 3H), 2.57-2.51 (m, 1H), 2.44-2.39 (m, 1H), 2.30-2.24 (m, 1H), 2.07-1.98 (m, 2H), 1.69-1.63 (m, 1H), 0.92-0.87 (m, 2H), 0.69-0.65 (m, 2H).

Example 235

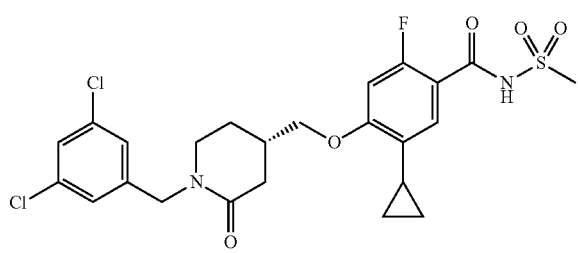 [SMILES: CS(=O)(=O)NC(=O)c1cc(C2CC2)c(OC[C@H]2CCN(Cc3cc(Cl)cc(Cl)c3)C(=O)C2)cc1F]

(S)-5-cyclopropyl-4-((1-(3,5-dichlorobenzyl)-2-oxopiperidin-4-yl)methoxy)-2-fluoro-N-(methylsulfonyl)benzamide The compound was synthesized as described in Example 234. The enantiomer was separated by chiral SFC from the racemate, the second elating fraction was arbitrarily assigned as (R)-5-cyclopropyl-4-((1-(3,5-dichlorobenzyl)-2-oxopiperidin-4-yl)methoxy)-2-fluoro-N-(methylsulfonyl)benzamide. Chiral HPLC (column: AS-H, 4.6×250 mm, 5 μm; mobile Phase: A: supercritical CO$_2$, B: MeOH (0.1% DEA), A:B=75:25; flow: 2.25 mL/min; column temperature: 40° C.; RT=7.28 min), LCMS (ESI) Method A: RT=5.12 min, m/z: 542.80 [M+H]$^+$. $^1$H-NMR (400 MHz, DMSO-d$_6$): δ11.92 (s, 1H), 7.53-7.52 (m, 1H), 7.31-7.29 (m, 2H), 7.15 (d, J=8.4 Hz, 1H), 6.95 (d, J=12.8 Hz, 1H), 4.56-4.47 (m, 2H), 4.00 (d, J=6.4 Hz, 2H), 3.32-3.30 (m, 2H), 3.28 (s, 3H), 2.57-2.51 (m, 1H), 2.44-2.39 (m, 1H), 2.30-2.24 (m, 1H), 2.07-1.98 (m, 2H), 1.69-1.63 (m, 1H), 0.92-0.87 (m, 2H), 0.69-0.65 (m, 2H).

Example 236

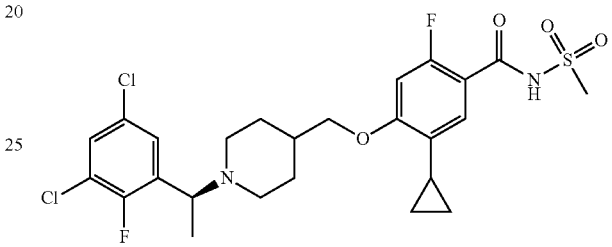

(R)-5-cyclopropyl-4-((1-(1-(3,5-dichloro-2-fluorophenyl)ethyl)piperidin-4-yl)methoxy)-2-fluoro-N-(methylsulfonyl)benzamide The compound was synthesized as described in Example 88. The enantiomer was separated by chiral SFC from the racemate, the second elating fraction was arbitrarily assigned as (S)-5-cyclopropyl-4-((1-(1-(3,5-dichloro-2-fluorophenyl)ethylpiperidin-4-yl)methoxy)-2-fluoro-N-(methylsulfonyl)benzamide. Chiral HPLC (column: AD-H, 4.6×250 mm, 5 μm; mobile Phase: A: supercritical CO$_2$, B: MeOH (0.1 DEA), A:B=65:35; flow: 1.95 mL/min; column temperature: 40.8° C.; RT=3.74 min). LCMS (ESI) Method A: RT=6.22 min, m/z: 561.2 [M+H]$^+$. $^1$H NMR (400 MHz, DMSO-d$_6$) δ 7.69 (dd, J=6.1, 2.6 Hz, 1H), 7.47 (dd, J=5.3, 2.6 Hz, 1H), 7.16 (d, J=8.5 Hz, 1H), 6.83 (d, J=12.8 Hz, 1H), 3.90-3.89 (m, 3H), 3.14 (s, 3H), 3.03-3.02 (m, 1H), 2.87-2.85 (m, 1H), 2.01-2.00 (m, 2H), 1.94-1.68 (m, 4H), 1.42-1.26 (m, 5H), 0.91-0.82 (m, 2H), 0.61 (d, J=5.1 Hz, 2H).

Example 237

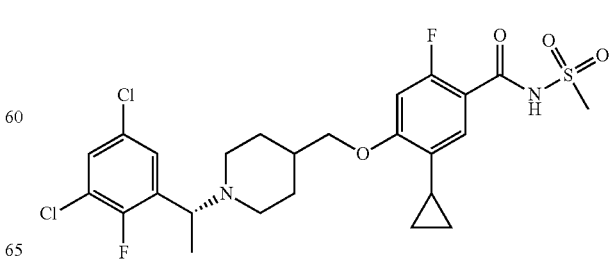

(R)-5-cyclopropyl-4-((1-(1-(3,5-dichloro-2-fluorophenyl)ethyl)piperidin-4-yl)methoxy)-2-fluoro-N-(methylsulfonyl)benzamide The compound was synthesized as described in Example 88. The enantiomer was separated by chiral SFC from the racemate, the first eluting fraction was arbitrarily assigned as (R)-5-cyclopropyl-4-((1-(1-(3,5-dichloro-2-fluorophenyl)ethylpiperidin-4-yl)methoxy)-2-fluoro-N-(methylsulfonyl)benzamide. Chiral HPLC (column: AD-H, 4.6×250 mm, 5 μm; mobile Phase: A: supercritical $CO_2$, B: MeOH (0.1 DEA), A:B=65:35; flow: 1.95 mL/min; column temperature: 40.8° C.; RT=3.11 min). LCMS (ESI) Method A: RT=5.83 min, m/z: 561.0 [M+H]$^+$. $^1$H NMR (400 MHz, DMSO-d$_6$) δ 7.69 (dd, J=6.1, 2.6 Hz, 1H), 7.47 (dd, J=5.3, 2.5 Hz, 1H), 7.16 (d, J=8.5 Hz, 1H), 6.82 (d, J=12.7 Hz, 1H), 3.88-3.91 (m, 3H), 3.12 (s, 3H), 3.03 (d, J=9.7 Hz, 1H), 2.86-2.85 (m, 1H), 1.99-1.97 (m, 2H), 1.93-1.69 (m, 4H), 1.40-1.25 (m, 5H), 0.86-0.84 (m, 2H), 0.61-0.60 (m, 2H).

Example 238

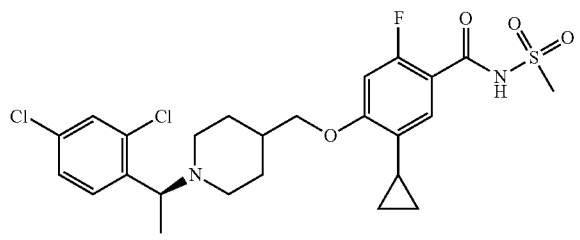 [SMILES: C[C@@H](c1ccc(Cl)cc1Cl)N1CCC(COc2cc(F)c(C(=O)NS(C)(=O)=O)cc2C2CC2)CC1]

(S)-5-cyclopropyl-4-((1-(1-(2,4-dichlorophenyl)ethyl)piperidin-4-yl)methoxy)-2-fluoro-N-(methylsulfonyl)benzamide The compound was synthesized as described in Example 88. The enantiomer was separated by chiral SFC from the racemate, the second eluting fraction was arbitrarily assigned as (S)-5-cyclopropyl-4-((1-(1-(2,4-dichlorophenyl)ethyl)piperidin-4-yl)methoxy)-2-fluoro-N-(methylsulfonyl)benzamide. Chiral HPLC (column: AS-H, 4.6×250 mm, 5 μm; mobile Phase: A: supercritical $CO_2$, B; MeOH (0.1% DEA), A:B=75:25; flow: 2.25 mL/min; column temperature: 38.1° C.; RT=4.08 min). LCMS (ESI) Method A: RT=6.43 mm, mm 542.9 [M+H]$^+$. $^1$H NMR (500 MHz, MeOD-d$_4$) δ 7.56 (d, J=8.5 Hz, 1H), 7.44 (d, J=2.1 Hz, 1H), 7.33 (dd, J=8.4, 2.1 Hz, 1H), 7.22 (d, J=8.3 Hz, 1H), 6.52 (d, J=12.8 Hz, 1H), 4.34 (brs, 1H), 3.74 (s, 2H), 3.45 (s, 1H), 3.06-3.04 (m, 3H), 2.97-2.96 (m, 1H), 2.52-2.29 (m, 2H), 1.93-1.90 (m, 3H), 1.80-1.79 (m, 1H), 1.56-1.55 (m, 1H), 1.42-1.40 (m, 4H), 0.80-0.73 (m, 2H), 0.51-0.50 (m, 2H).

Example 239

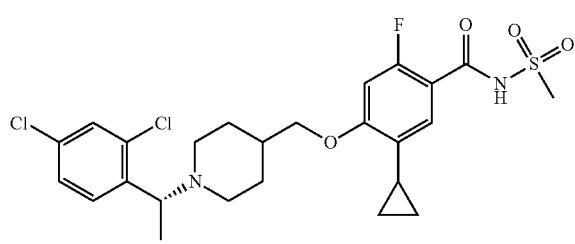 [SMILES: C[C@H](c1ccc(Cl)cc1Cl)N1CCC(COc2cc(F)c(C(=O)NS(C)(=O)=O)cc2C2CC2)CC1]

(R)-5-cyclopropyl-4-((1-(1-(2,4-dichlorophenyl)ethyl)piperidin-4-yl)methoxy)-2-fluoro-N-(methylsulfonyl)benzamide Use compound was synthesized as described in Example 88. The enantiomer was separated by chiral SFC from the racemate, the first eluting fraction was arbitrarily assigned as (R)-5-cyclopropyl-4-((1-(1-(2,4-dichlorophenyl)ethyl)piperidin-4-yl)methoxy)-2-fluoro-N-(methylsulfonyl)benzamide. Chiral HPLC (column: AS-H, 4.6×250 mm, 5 μm; mobile Phase: A: supercritical $CO_2$, B: MeOH (0.1% DEA), A:B=75:25; flow: 2.25 mL/min; column temperature: 41.5° C.; RT=2.87 min). LCMS (ESI) Method A: RT=6.48 min, m/z: 542.9 [M+H]$^+$. $^1$H NMR (500 MHz, MeOD-d$_4$) δ 7.56 (d, J=8.5 Hz, 1H), 7.44 (d, J=2.1 Hz, 1H), 7.33 (dd, J=8.4, 2.1 Hz, 1H), 7.22 (d, J=8.3 Hz, 1H), 6.52 (d, J=12.8 Hz, 1H), 4.34-4.33 (m, 1H), 3.74 (brs, 2H), 3.45-3.44 (m, 1H), 3.06 (s, 3H), 2.97-2.96 (m, 1H), 2.52-2.29 (m, 2H), 1.91-1.90 (m, 3H), 1.80 (m, 1H), 1.56 (m, 1H), 1.42 (m, 4H), 0.75 (m, 2H), 0.51 (m, 2H).

Example 240

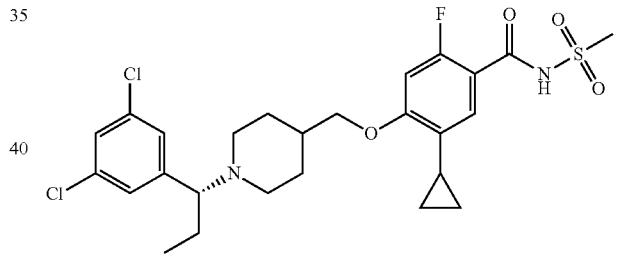

(R)-5-cyclopropyl-4-((1-(1-(3,5-dichlorophenyl)propyl)piperidin-4-yl)methoxy)-2-fluoro-N-(methylsulfonyl)benzamide The compound was synthesized as described in Example 88. The enantiomer was separated by chiral SFC from the racemate, the second eluting fraction was arbitrarily assigned as (R)-5-cyclopropyl-4-((1-(1-(3,5-dichlorophenyl)propyl)piperidin-4-yl)methoxy)-2-fluoro-N-(methylsulfonyl)benzamide. Chiral HPLC (column: OZ-H, 4.6×250 mm, 5 μm; mobile Phase: A: supercritical $CO_2$, B: MeOH (0.5% DEA), A:B=70:30; flow: 2.1 mL/min; column temperature: 41.0° C.; RT=10.67 min). LCMS (ESI) Method A: RT=6.42 min, m/z: 557.3 [M+H]$^+$. $^1$H NMR (400 MHz, DMSO-d$_6$) δ 7.52 (m, 1H), 7.34 (d, J=1.8 Hz, 2H), 7.16 (d, J=8.5 Hz, 1H), 6.81 (d, J=12.9 Hz, 1H), 3.88 (d, J=6.0 Hz, 2H), 3.53 (m, 1H), 3.13 (s, 3H), 3.05 (m, 1H), 2.93 (m, 1H), 2.01 (m, 4H), 1.76 (m, 4H), 1.34 (m, 2H), 0.86 (m, 2H), 0.72 (m, 3H), 0.60 (m, 2H).

Example 241

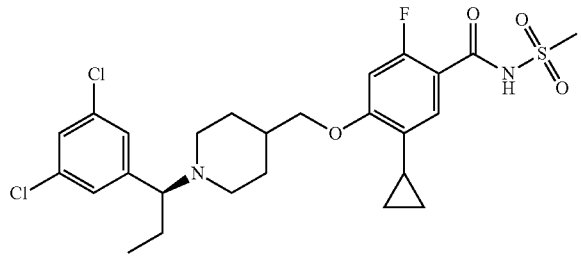 [SMILES: CC[C@@H](c1cc(Cl)cc(Cl)c1)N1CCC(COc2cc(F)c(C(=O)NS(C)(=O)=O)cc2C2CC2)CC1]

(S)-5-cyclopropyl-4-((1-(1-(3,5-dichlorophenyl)propyl)piperidin-4-yl)methoxy)-2-fluoro-N-(methylsulfonyl)benzamide The compound was synthesized as described in Example 88. The enantiomer was separated by chiral SFC from the racemate, the first eluting fraction was arbitrarily assigned as (S)-5-cyclopropyl-4-((1-(1-(3,5-dichlorophenyl)propyl)piperidin-4-yl)methoxy)-2-fluoro-N-(methylsulfonyl)benzamide. Chiral HPLC (column: OZ-H, 4.6×250 mm, 5 μm; mobile Phase: A: supercritical $CO_2$, B: MeOH (0.5% DEA), A:B=70:30; flow: 2.1 mL/min; column temperature: 39.3° C.; RT=9.34 min). LCMS (ESI) Method A: RT=6.35 min, m/z: 557.2 $[M+H]^+$. $^1$H NMR (400 MHz, DMSO-$d_6$) δ 7.52 (m, 1H), 7.34 (d, J=1.8 Hz, 2H), 7.16 (d, J=8.5 Hz, 1H), 6.81 (d, J=12.9 Hz, 1H), 3.88 (d, J=6.0 Hz, 2H), 3.53 (m, 1H), 3.13 (s, 3H), 3.05 (m, 1H), 2.93 (m, 1H), 2.01 (m, 4H), 1.76 (m, 4H), 1.34 (m, 2H), 0.85 (m, 2H), 0.72 (m, 3H), 0.61 (m, 2H).

Example 242

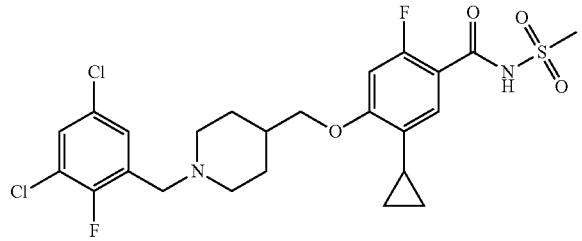 [SMILES: CS(=O)(=O)NC(=O)c1cc(C2CC2)c(OCC2CCN(Cc3cc(Cl)cc(Cl)c3F)CC2)cc1F]

5-Cyclopropyl-4-((1-(3,5-dichloro-2-fluorobenzyl)piperidin-4-yl)methoxy)-2-fluoro-N-(methylsulfonyl)benzamide The compound was synthesized as described in Example 88. LCMS (ESI) Method A: RT=5.98 min, m/z: 547.0 $[M+H]^+$; $^1$H NMR (400 MHz, DMSO-$d_6$) δ 7.72 (dd, J=6.1, 2.6 Hz, 1H), 7.47 (dd, J=5.5, 2.6 Hz, 1H), 7.16 (d, J=8.5 Hz, 1H), 6.85 (d, J=12.9 Hz, 1H), 3.92 (d, J=5.8 Hz, 2H), 3.63 (s, 2H), 3.16 (s, 5H), 2.89 (m, 2H), 2.12 (m, 2H), 2.01 (m, 1H), 1.79 (m, 3H), 1.38 (m, 2H), 0.85 (m, 2H), 0.63 (m, 2H).

Example 243

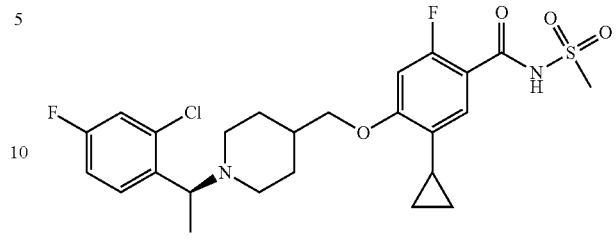

(S)-4-((1-(1-(2-chloro-4-fluorophenyl)ethyl)piperidin-4-yl)methoxy)-5-cyclopropyl-2-fluoro-N-(methylsulfonyl)benzamide The compound was synthesized as described in Example 88. The enantiomer was separated by chiral SFC from the racemate, the second during fraction was arbitrarily assigned as (S)-4-((1-(1-(2-chloro-4-fluorophenyl)ethylpiperidin-4-yl)methoxy)-5-cyclopropyl-2-fluoro-N-(methylsulfonyl)benzamide. Chiral HPLC (column: AD-H, 4.6×250 mm, 5 μm; mobile Phase: A: supercritical $CO_2$, B: MeOH (0.1% DEA), A:B=70:30; flow: 2.1 mL/min; column temperature: 41.6° C.; RT=5.88 min). LCMS (ESI) Method A: RT=5.88 min, m/z: 526.9 $[M+H]^+$. $^1$H NMR 500 MHz, DMSO-$d_6$) δ 7.61 (dd, J=8.6, 6.6 Hz, 1H), 7.41 (dd, J=8.8, 2.5 Hz, 1H), 7.24 (m, 1H), 7.16 (d, J=8.5 Hz, 1H), 6.84 (d, J=12.8 Hz, 1H), 3.91 (m, 3H), 3.15 (m, 4H), 2.75 (m, 1H), 2.12 (m, 1H), 2.01 (m, 2H), 1.75 (m, 3H), 1.39 (m, 1H), 1.28 (m, 4H), 0.87 (m, 2H), 0.62 (m, 2H).

Example 244

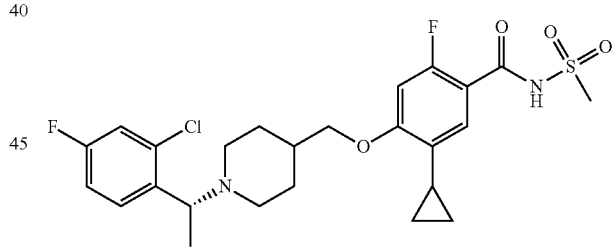

(R)-4-((1-(1-(2-chloro-4-fluorophenyl)ethylpiperidin-4-yl)methoxy)-5-cyclopropyl-2-fluoro-N-(methylsulfonyl)benzamide The compound was synthesized as described in Example 88. The enantiomer was separated by chiral SFC from the racemate, the first eluting fraction was arbitrarily assigned as (R)-4-((1-(1-(2-chloro-4-fluorophenyl)ethyl)piperidin-4-yl)methoxy)-5-cyclopropyl-2-fluoro-N-(methylsulfonyl)benzamide. Chiral HPLC (column: AD-H, 4.6×250 mm, 5 μm; mobile Phase: A: supercritical $CO_2$, B: MeOH (0.1% DEA), A:B=70:30; flow: 2.1 mL/min; column temperature: 38.1° C.; RT=3.41 min). LCMS (ESI) Method A: RT=5.88 min, m/z: 526.9 $[M+H]^+$. $^1$H NMR (500 MHz, DMSO-$d_6$) δ 7.65 (dd, J=8.6, 6.6 Hz, 1H), 7.43 (dd, J=8.8, 2.5 Hz, 1H), 7.27 (m, 1H), 7.15 (d, J=8.4 Hz, 1H), 6.88 (d, J=12.9 Hz, 1H), 4.03 (m, 3H), 3.21 (m, 4H), 2.81 (m, 1H), 2.17 (m, 2H), 2.01 (m, 1H), 1.81 (m, 3H), 1.44 (m, 1H), 1.33 (m, 4H), 0.88 (m, 2H), 0.64 (m, 2H).

Example 245

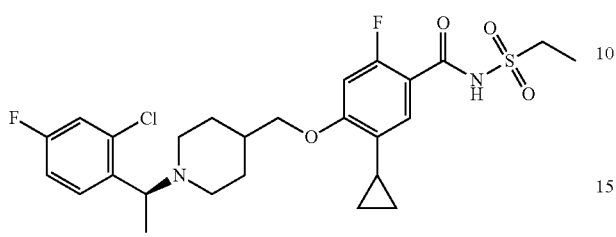

(S)-4-((1-(1-(2-chloro-4-fluorophenyl)ethylpiperidin-4-yl)methoxy)-5-cyclopropyl-N-(ethylsulfonyl)-2-fluorobenzamide The compound was synthesized as described in Example 88. The enantiomer was separated by chiral SFC from the racemate, the second eluting fraction was arbitrarily assigned as (S)-4-((1-(1-(2-chloro-4-fluorophenyl)ethylpiperidin-4-yl)methoxy)-5-cyclopropyl-N-(ethylsulfonyl)-2-fluorobenzenamide. Chiral HPLC (column: AD-H, 4.6×250 mm, 5 µm; mobile Phase: A: supercritical $CO_2$, B: MeOH (0.1% DEA), A:B=65:35; flow: 1.95 mL/min; column temperature: 39.6° C.; RT=3.31 min). LCMS (ESI) Method A: RT=5.85 min, m/z 541.3 [M+H]$^+$. $^1$H NMR (400 MHz, DMSO-$d_6$) δ 11.46 (s, 1H), 7.61 (dd, J=8.7, 6.5 Hz, 1H), 7.41 (dd, J=8.9, 2.6 Hz, 1H), 7.25 (m, 1H), 7.14 (d, J=8.4 Hz, 1H), 6.90 (d, J=12.9 Hz, 1H), 3.92 (d, J=6.1 Hz, 3H), 3.40 (m, 2H), 3.18 (m, 1H), 2.77 (m, 1H), 2.15 (s, 1H), 2.01 (m, 2H), 1.84 (m, 2H), 1.72 (m, 1H), 1.40 (m, 1H), 1.29 (m, 4H), 1.21 (t, J=7.4 Hz, 3H), 0.85 (m, 2H), 0.64 (m, 2H).

Example 246

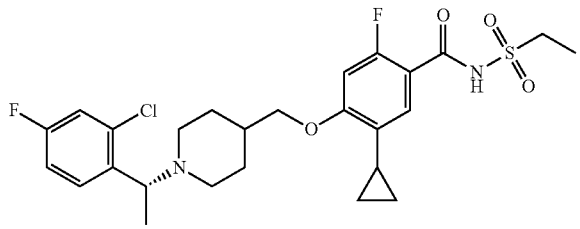 [SMILES: CCS(=O)(=O)NC(=O)c1cc(C2CC2)c(OCC2CCN([C@H](C)c3ccc(F)cc3Cl)CC2)cc1F]

(R)-4-((1-(1-(2-chloro-4-fluorophenyl)ethyl)piperidin-4-yl)methoxy)-5-cyclopropyl-N-(ethylsulfonyl)-2-fluorobenzamide The compound was synthesized as described in Example 88. The enantiomer was separated by chiral SFC from the racemate, the first eluting fraction was arbitrarily assigned as (R)-4-((1-(1-(2-chloro-4-fluorophenyl)ethyl)piperidin-4-yl)methoxy)-5-cyclopropyl-N-(ethylsulfonyl)-2-fluorobenzamide. Chiral HPLC (column: AD-H, 4.6×250 mm, 5 µm; mobile Phase: A: supercritical $CO_2$, B: MeOH (0.1% DEA), A:B=65:35; flow: 1.95 mL/min; column temperature: 40° C.; RT=2.62 min). LCMS (ESI) Method A: RT=5.86 min, m/z: 541.3 [M+H]$^+$. $^1$H NMR (400 MHz, DMSO-$d_6$) δ 11.46 (s, 1H), 7.61 (dd, J=8.7, 6.5 Hz, 1H), 7.41 (dd, J=8.9, 2.6 Hz, 1H), 7.25 (m, 1H), 7.14 (d, J=8.4 Hz, 1H), 6.90 (d, J=12.9 Hz, 1H), 3.92 (d, J=6.1 Hz, 3H), 3.40 (m, 2H), 3.18 (m, 1H), 2.77 (m, 1H), 2.15 (m, 1H), 2.01 (m, 2H), 1.84 (m, 2H), 1.72 (m, 1H), 1.40 (m, 1H), 1.29 (m, 4H), 1.21 (t, J=7.4 Hz, 3H), 0.85 (m, 2H), 0.64 (m, 2H).

Example 247

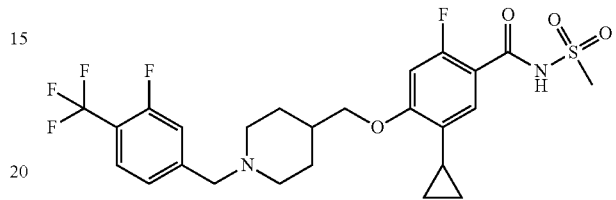

5-cyclopropyl-2-fluoro-4-((1-(3-fluoro-4-(trifluoromethyl)benzyl)piperidin-4-yl)methoxy)-N-(methylsulfonyl)benzamide The compound was synthesized as described in Example 88. LCMS (ESI) Method-A: RT=5.77 min, m/z: 547.2 [M+H]$^+$. $^1$H NMR (400 MHz, DMSO-$d_6$) δ 7.78 (m, 1H), 7.45 (m, 2H), 7.17 (d, J=8.4 Hz, 1H), 6.88 (d, J=12.9 Hz, 1H), 3.94 (d, J=5.0 Hz, 2H), 3.74 (s, 2H), 3.19 (s, 3H), 2.95 (m, 2H), 2.23 (m, 2H), 2.02 (m, 1H), 1.84 (m, 3H), 1.43 (m, 2H), 0.88 (m, 2H), 0.65 (m, 2H).

Example 248

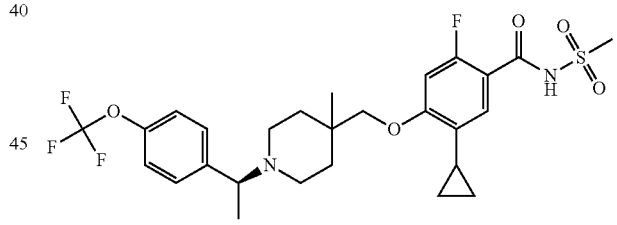

(S)-5-cyclopropyl-2-fluoro-4-((4-methyl-1-(1-(4-trifluoromethoxy)phenyl)ethyl)piperidin-4-yl)methoxy)-N-(methylsulfonyl)benzamide The compound was synthesized as described in Example 170. The enantiomer was separated by chiral SFC from the racemate, the second eluting fraction was arbitrarily assigned as (S)-5-cyclopropyl-2-fluoro-4-((4-methyl-1-(1-(4-(trifluoromethoxy)phenyl)ethyl)piperidin-4-yl)methoxy)-N-(methylsulfonyl)benzamide. Chiral HPLC (column: OJ-H, 4.6×250 mm, 5 µm; mobile Phase: A: supercritical $CO_2$, B: MeOH (0.1% DEA), A:B=80:20; flow: 2.4 mL/min; column temperature: 40.1° C.; RT=4.93 min). LCMS (ESI) Method A: RT=5.98 min, m/z: 573.3 [M+H]$^+$. $^1$H NMR (400 MHz, DMSO-$d_6$) δ 7.52 (d, J=8.1 Hz, 2H), 7.37 (d, J=8.1 Hz, 2H), 7.21 (d, J=8.5 Hz, 1H), 6.80 (d, J=12.8 Hz, 1H), 3.79 (brs, 2H), 3.30 (m, 1H), 3.04 (s, 3H), 2.61 (m, 1H), 2.49 (s, 3H), 1.99 (m, 1H), 1.70 (m, 2H), 1.46 (m, 5H), 1.04 (s, 3H), 0.87 (m, 2H), 0.59 (m, 2H).

Example 249

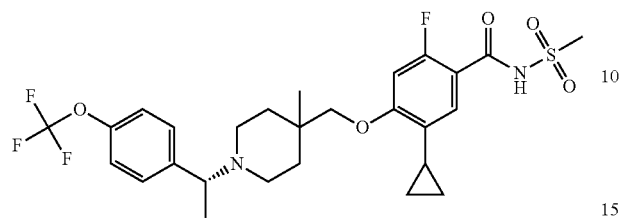

(R)-5-cyclopropyl-2-fluoro-4-((4-methyl-1-(1-(4-(trifluoromethoxy)phenyl)ethyl)piperidin-4-yl)methoxy)-N-(methylsulfonyl)benzamide The compound was synthesized as described in Example 170. The enantiomer was separated by chiral SFC from the racemate, the first eluting fraction was arbitrarily assigned as (R)-5-cyclopropyl-2-fluoro-4-((4-methyl-1-(1-(4-(trifluoromethoxy)phenyl)ethylpiperidin-4-yl)methoxy)-N-(methylsulfonyl)benzamide. Chiral HPLC (column: OJ-H, 4.6×250 mm, 5 μm; mobile Phase: A: supercritical CO$_2$, B: MeOH (0.1% DEA), A:B=80:20; flow: 2.4 mL/min; column temperature: 39.9° C.; RT=2.52 min). LCMS (ESI) Method A: RT=5.95 min, m/z: 573.3 [M+H]$^+$. $^1$H NMR (400 MHz, DMSO-d$_6$) δ 7.52 (m, 2H), 7.37 (m, 2H), 7.21 (d, J=8.5 Hz, 1H), 6.80 (d, J=12.8 Hz, 1H), 3.79 (brs, 2H), 3.31 (m, 1H), 3.04 (s, 3H), 2.61 (m, 1H), 2.49 (s, 3H), 1.99 (m, 1H), 1.70 (m, 2H), 1.46 (m, 5H), 1.04 (s, 3H), 0.87 (m, 2H), 0.59 (m, 2H).

Example 250

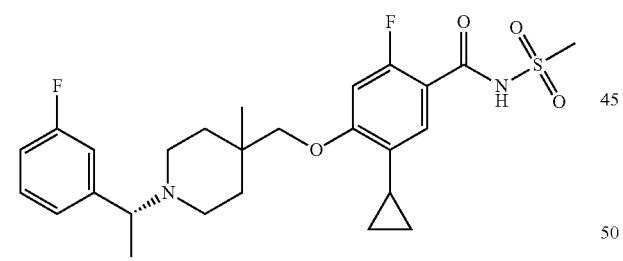

(R)-5-cyclopropyl-2-fluoro-4-((1-(1-(3-fluorophenyl)ethyl)-4-methylpiperidin-4-yl)methoxy)-N-(methylsulfonyl)benzamide The compound was synthesized as described in Example 170. The enantiomer was separated by chiral SFC from the racemate, the first eluting fraction was arbitrarily assigned as (R)-5-cyclopropyl-2-fluoro-4-((1-(1-(3-fluorophenyl)ethyl)-4-methylpiperidin-4-yl)methoxy)-N-(methylsulfonyl)benzamide. Chiral HPLC (column: OJ-H, 4.6×250 mm, 5 μm; mobile Phase: A: supercritical CO$_2$, B: MeOH (0.1% DEA), A:B=80:20; flow: 2.4 mL/min; column temperature: 38.8° C.; RT=4.89 min), LCMS (ESI) Method A: RT=5.42 mm, m/z: 507.3 [M+H]$^+$. $^1$H NMR (400 MHz, DMSO-d$_6$) δ 7.43 (m, 1H), 7.29 (m, 2H), 7.23 (d, J=8.6 Hz, 1H), 7.16 (m, 1H), 6.80 (d, J=12.8 Hz, 1H), 3.95 (m, 1H), 3.79 (s, 2H), 3.03 (s, 3H), 2.91 (m, 1H), 2.70 (m, 2H), 2.59 (m, 1H), 2.03 (m, 1H), 1.76 (m, 2H), 1.50 (m, 5H), 1.05 (s, 3H), 0.88 (m, 2H), 0.60 (m, 2H).

Example 251

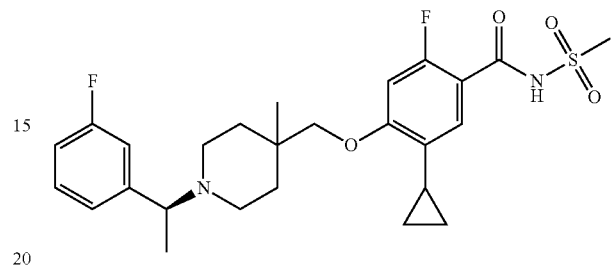

(S)-5-cyclopropyl-2-fluoro-4-((1-(1-(3-fluorophenyl)ethyl)-4-methylpiperidin-4-yl)methoxy)-N-(methylsulfonyl)benzamide The compound was synthesized as described in Example 170. The enantiomer was separated by chiral SFC from the racemate, the second eluting fraction was arbitrarily assigned as (S)-5-cyclopropyl-2-fluoro-4-((1-(1-(3-fluorophenyl)ethyl)-4-methylpiperidin-4-yl)methoxy)-N-(methylsulfonyl)benzamide. Chiral HPLC (column: OJ-H, 4.6×250 mm, 5 μm; mobile Phase: A: supercritical CO$_2$, B: MeOH (0.1% DEA), A:B=80:20; flow: 2.4 mL/min; column temperature: 40.6° C.; RT=6.92 min). LCMS (ESI) Method A: RT=5.42 min, m/z: 507.5 [M+H]$^+$. $^1$H NMR (400 MHz, DMSO-d$_6$) δ 7.43 (m, 1H), 7.29 (m, 2H), 7.23 (d, J=8.6 Hz, 1H), 7.16 (m, 1H), 6.80 (d, J=12.8 Hz, 1H), 3.95 (m, 1H), 3.79 (s, 2H), 3.03 (s, 3H), 2.91 (m, 1H), 2.70 (m, 2H), 2.59 (m, 1H), 2.03 (m, 1H), 1.76 (m, 2H), 1.50 (m, 5H), 1.05 (s, 3H, 0.85 (m, 2H), 0.60 (m, 2H).

Example 252

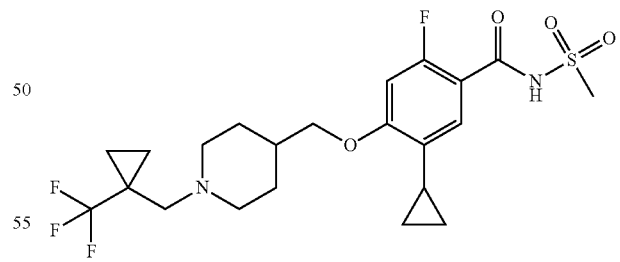

5-cyclopropyl-2-fluoro-N-(methylsulfonyl)-4-((1-((1-(trifluoromethyl)cyclopropyl)methyl)piperidin-4-yl)methoxy)benzamide The compound was synthesized as described in Example 88. LCMS (ESI) Method B: RT=5.42 min, m/z: 492.9 [M+H]$^+$. $^1$H NMR (500 MHz, DMSO-d$_6$) δ 7.16 (d, J=8.4 Hz, 1H), 6.90 (d, J=12.9 Hz, 1H), 3.94 (d, J=5.8 Hz, 2H), 3.24 (s, 3H), 3.01 (m, 2H), 2.59 (s, 2H), 2.03 (m, 3H), 1.79 (m, 3H), 1.37 (m, 2H), 0.99 (m, 2H), 0.88 (m, 2H), 0.76 (m, 2H), 0.66 (m, 2H).

Example 253

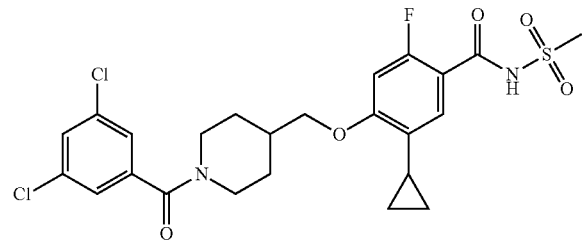 [SMILES: CS(=O)(=O)NC(=O)c1cc(C2CC2)c(OCC2CCN(C(=O)c3cc(Cl)cc(Cl)c3)CC2)cc1F]

5-Cyclopropyl-4-((1-(3,5-dichlorobenzoyl)piperidin-4-yl)methoxy)-2-fluoro-N-(methylsulfonyl)benzamide The compound was synthesized as described in Example 134. LCMS (ESI) Method A: RT=4.92 min, m/z 542.8 [M+H]$^+$. $^1$H NMR (500 MHz, DMSO-d$_6$) δ 7.71 (s, 1H), 7.45 (s, 2H), 7.15 (d, J=8.5 Hz, 1H), 6.92 (d, J=13.0 Hz, 1H), 4.49-4.47 (m, 1H), 3.97 (d, J=4.5 Hz, 2H), 3.53-3.50 (m, 1H), 3.26 (s, 3H), 3.15-3.12 (m, 1H), 2.85-2.84 (m, 1H), 2.14-2.10 (m, 1H), 2.05-1.99 (m, 1H), 1.89-1.88 (m, 1H), 1.78-1.75 (m, 1H), 1.35-1.32 (m, 2H), 0.89-0.88 (m, 2H), 0.66-0.65 (m, 2H).

Example 254

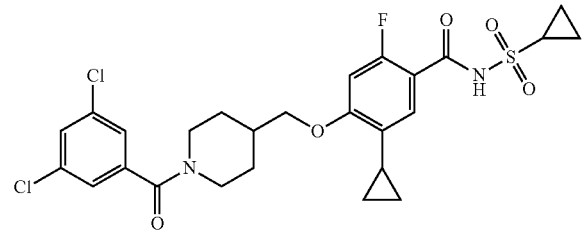 [SMILES: O=C(NS(=O)(=O)C1CC1)c1cc(C2CC2)c(OCC2CCN(C(=O)c3cc(Cl)cc(Cl)c3)CC2)cc1F]

5-Cyclopropyl-N-(cyclopropylsulfonyl)-4-((1-(3,5-dichlorobenzoyl)piperidin-4-yl)methoxy)-2-fluorobenzamide The compound was synthesized as described in Example 134. LCMS (ESI) Method A: RT=5.28 min, m/z: 569.0 [M+H]$^+$. $^1$H NMR (500 MHz, DMSO-d$_6$) δ 11.80 (s, 1H), 7.71 (s, 1H), 7.40 (m, 2H), 7.16 (d, J=8.0 Hz, 1H), 6.92 (d, J=12.1 Hz, 1H), 4.47 (m, 1H), 3.97 (m, 2H), 3.51 (m, 1H), 3.08 (m, 2H), 2.84 (m, 1H), 2.07 (m, 2H), 1.82 (m, 2H), 1.34 (m 2H), 1.01 (m, 4H), 0.89 (m, 2H), 0.62 (m, 2H).

Example 255

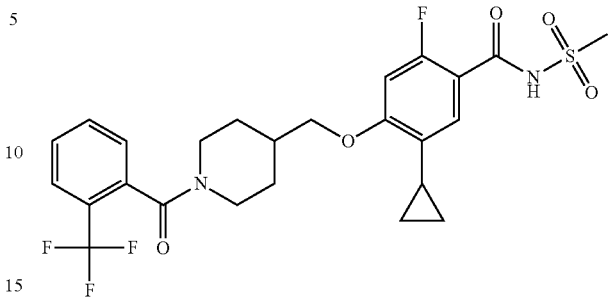

5-Cyclopropyl-2-fluoro-N-(methylsulfonyl)-4-((1-(2-trifluoromethyl)benzoyl)piperidin-4-yl)methoxy)benzamide The compound was synthesized as described in Example 134. LCMS (ESI) Method A: RT=4.54 min, m/z: 542.9 [M+H]$^+$. $^1$H NMR (500 MHz, MeOD-d$_4$) δ 7.82 (d, J=7.9 Hz, 1H), 7.75 (m, 1H), 7.67 (d, J=7.4 Hz, 1H), 7.46 (m, 1H), 7.31 (m, 1H), 6.82 (m, 1H), 4.77 (m, 1H), 4.01 (4.7-5.2 Hz, 2H), 3.43 (m, 1H), 3.33 (s, 3H), 3.17 (m, 1H), 2.96 (m, 1H), 2.20 (m, 1H), 2.07 (m, 2H), 1.81 (m, 1H), 1.42 (m, 2H), 0.94 (m, 2H), 0.66 (m, 2H).

Example 256

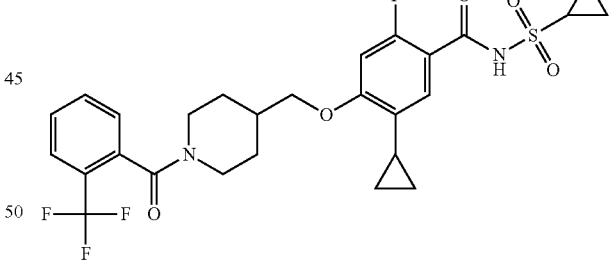

5-Cyclopropyl-N-(cyclopropylsulfonyl)-2-fluoro-4-((1-(2-(trifluoromethyl)benzoyl)piperidin-4-yl)methoxy)benzamide The compound was synthesized as described in Example 134. LCMS (ESI) Method A: RT=4.69 min, m/z: 568.9 [M+H]$^+$. $^1$H NMR (500 MHz, MeOD-d$_4$) δ 7.82 (m, 1H), 7.76 (m, 1H), 7.67 (m, 1H), 7.46 (m, 1H), 7.30 (m, 1H), 6.82 (dd, J=12.8, 4.8 Hz, 1H), 4.77 (m, 1H), 4.01 (m, 2H), 3.43 (m, 1H), 3.17 (m, 2H), 2.96 (m, 1H), 2.20 (m, 1H), 2.02 (m, 2H), 1.81 (m, 1H), 1.47 (m, 2H), 1.29 (m, 2H), 1.13 (m, 2H), 0.92 (m, 2H), 0.66 (m, 2H).

Example 257

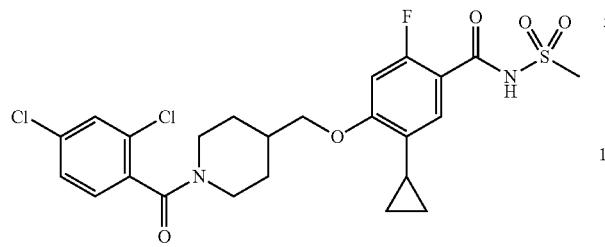

5-Cyclopropyl-4-((1-(2,4-dichlorobenzoyl)piperidin-4-yl)methoxy)-2-fluoro-N-(methylsulfonyl)benzamide The compound was synthesized as described in Example 134. LCMS (ESI) Method A: RT=4.82 min, m/z 542.8 [M+H]$^+$. $^1$H NMR (500 MHz, DMSO-d$_6$) δ 7.73-7.72 (m, 1H), 7.53-7.49 (m, 1H), 7.43-7.37 (m, 1H), 7.15 (d, J=8.5 Hz, 1H), 6.91 (d, J=13.0 Hz, 1H), 4.57-4.52 (m, 1H), 3.99-3.95 (m, 2H), 3.30-3.28 (m, 1H), 2.25 (s, 3H), 3.13-3.03 (m, 1H), 2.85-2.82 (m, 1H), 2.13-1.97 (m, 2H), 1.92-1.89 (m, 1H), 1.75-1.72 (m, 1H), 1.43-1.25 (m, 2H), 0.89-0.85 (m, 2H), 0.67-0.63 (m, 2H).

Example 258

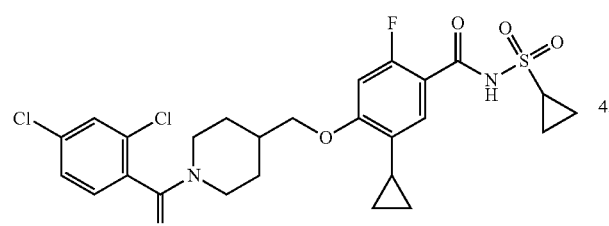

5-Cyclopropyl-N-(cyclopropylsulfonyl)-4-((1-(2,4-dichlorobenzoyl)piperidin-4-yl)methoxy)-2-fluorobenzamide The compound was synthesized as described in Example 134. LCMS (ESI) Method A: RT=5.00 min, m/z 568.8 [M+H]$^+$. $^1$H NMR (500 MHz, DMSO-d$_6$) δ 7.73 (s, 1H), 7.53-7.49 (m, 1H), 7.43-7.37 (m, 1H), 7.14 (d, J=8.5 Hz, 1H), 6.94 (d, J=13.0 Hz, 1H), 4.57-4.52 (m, 1H), 3.99-3.96 (m, 2H), 3.13-3.04 (m, 2H), 2.87-2.83 (m, 1H), 2.12-1.89 (m, 3H), 1.75-1.72 (m, 1H), 1.42-1.23 (m, 3H), 1.10-1.06 (m, 4H), 0.89-0.86 (m, 2H), 0.69-0.63 (m, 2H).

Example 259

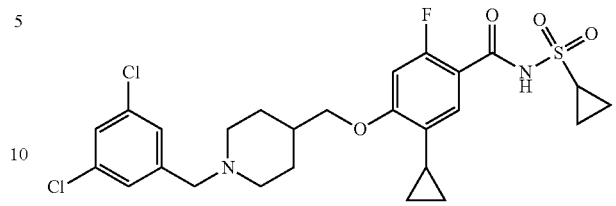

5-Cyclopropyl-N-(cyclopropylsulfonyl)-4-((1-(3,5-dichlorobenzyl)piperidin-4-yl)methoxy)-2-fluorobenzamide The compound was synthesized as described in Example 88. LCMS (ESI) Method A: RT=6.21 min, m/z 555.0 [M+H]$^+$. $^1$H NMR (500 MHz, DMSO-d$_6$) δ 7.52 (s, 1H), 7.39 (s, 2H), 7.14 (d, J=8.0 Hz, 1H), 6.89 (d, J=13.0 Hz, 1H), 3.94 (d, J=5.5 Hz, 2H), 3.62 (s, 2H), 3.05-2.90 (m, 1H), 2.91 (d, J=11.5 Hz, 2H), 2.16 (t, J=11.3 Hz, 2H), 2.03-1.99 (m, 1H), 1.82-1.79 (m, 3H), 1.43-1.37 (m, 2H), 1.05-0.99 (m, 4H), 0.90-0.86 (m, 2H), 0.65-0.62 (m, 2H).

Example 260

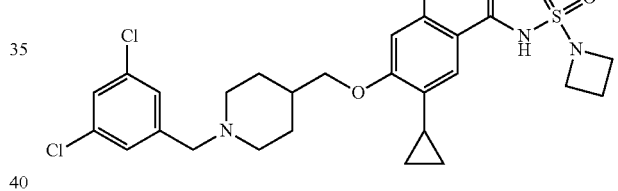

N-(azetidin-1-ylsulfonyl)-5-cyclopropyl-4-((1-(3,5-dichlorobenzyl)piperidin-4-yl)methoxy)-2-fluorobenzamide The compound was synthesized as described in Example 88. LCMS (ESI) Method A: RT=6.47 min, m/z 570.0 [M+H]$^+$. $^1$H NMR (500 MHz, DMSO-d$_6$) δ 7.52 (s, 1H), 7.39 (s, 2H), 7.15 (d, J=8.0 Hz, 1H), 6.90 (d, J=12.5 Hz, 1H), 3.98-3.94 (m, 1H), 3.60 (s, 2H), 2.90 (d, J=11.0 Hz, 2H), 2.15-2.11 (m, 4H), 2.03-2.01 (m, 1H), 1.82-1.79 (m, 3H), 1.43-1.37 (m, 2H), 0.90-0.87 (m, 2H), 0.66-0.64 (m, 2H).

Example 261

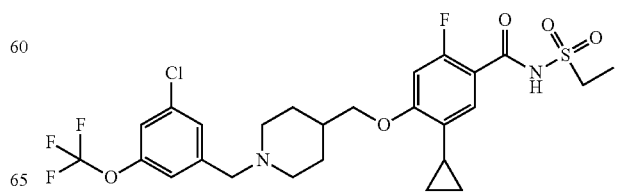

4-((1-(3-Chloro-5-(trifluoromethoxy)benzyl)piperidin-4-yl)methoxy)-5-cyclopropyl-N-(ethylsulfonyl)-2-fluorobenzamide The compound was synthesized as described in Example 88. LCMS (ESI) Method A: RT=6.34 min, m/z 593.3 [M+H]⁺. ¹H NMR (400 MHz, DMSO-d₆) δ 7.48 (s, 2H), 7.35 (s, 1H), 7.14 (d, J=8.4 Hz, 1H), 6.90 (d, J=12.8 Hz, 1H), 3.95 (d, J=6.0 Hz, 2H), 3.67 (s, 2H), 3.40-3.32 (m, 2H), 2.92 (d, J=10.4 Hz, 2H), 2.20-2.15 (m, 2H), 2.03-1.98 (m, 1H), 1.82-1.79 (m, 3H), 1.45-1.37 (m, 2H), 1.21 (t, J=7.4 Hz, 3H), 0.90-0.86 (m, 2H), 0.65-0.62 (m, 2H).

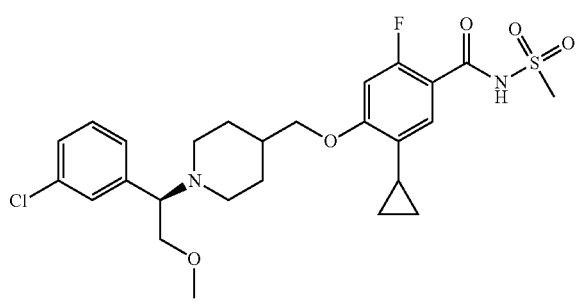 [SMILES: COC[C@@H](c1cccc(Cl)c1)N1CCC(COc2cc(F)c(C(=O)NS(C)(=O)=O)cc2C2CC2)CC1]

(R)-4-((1-(1-(3-chlorophenyl)-2-methoxyethyl)piperidin-4-yl)methoxy)-5-cyclopropyl-2-fluoro-N-(methylsulfonyl)benzamide The compound was synthesized as described in Example 172. The enantiomer was separated by chiral SFC from the racemate, the first elating fraction was arbitrarily assigned as (R)-4-((1-(1-(3-chlorophenyl)-2-methoxyethyl)piperidin-4-yl)methoxy)-5-cyclopropyl-2-fluoro-N-(methylsulfonyl)benzamide. Chiral HPLC (column: OJ-H, 4.6×250 mm, 5 μm; mobile Phase: A: supercritical CO₂, B: MeOH (0.1% DEA), A:B=75:25; flow: 3 mL/min; column temperature: 40° C.; RT=3.05 min). LCMS (ESI) Method A: RT=5.47 min, m/z 538.9 [M+H]⁺. ¹H NMR (400 MHz, DMSO-d₆): δ 7.41-7.30 (m, 4H), 7.15 (d, J=8.4 Hz, 1H), 6.86 (d, J=12.8 Hz, 1H), 3.89 (d, J=5.6 Hz, 2H), 3.81-3.78 (m, 1H), 3.73-3.71 (m, 2H), 3.23 (s, 3H), 3.18 (s, 3H), 3.09-3.06 (m, 1H), 2.87-2.84 (m, 1H), 2.22-2.16 (m, 1H), 2.10-2.06 (m, 1H), 2.03-2.96 (m, 1H), 1.81-1.73 (m, 3H), 1.45-1.26 (m, 2H), 0.89-0.84 (m, 2H), 0.65-0.61, (m, 2H).

Example 263

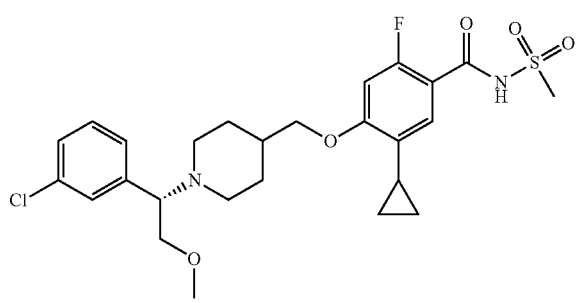 [SMILES: COC[C@H](c1cccc(Cl)c1)N1CCC(COc2cc(F)c(C(=O)NS(C)(=O)=O)cc2C2CC2)CC1]

(S)-4-((1-(1-(3-chlorphenyl)-2-methoxyethyl)piperidin-4-yl)methoxy)-5-cyclopropyl-2-fluoro-N-(methylsulfonyl)benzamide The compound was synthesized as described in Example 172. The enantiomer was separated by chiral SFC from the racemate, the second eluting fraction was arbitrarily assigned as (S)-4-((1-(1-(3-chlorophenyl)-2-methoxyethyl)piperidin-4-yl)methoxy)-5-cyclopropyl-2-fluoro-N-(methylsulfonyl)benzamide. Chiral HPLC (column: OJ-H, 4.6×250 mm, 5 μm; mobile Phase: A: supercritical CO₂, B: MeOH (0.1% DEA). A:B=75:25; flow: 3 mL/min; column temperature: 40° C.; RT=4.35 mm). LCMS (ESI) Method A: RT=5.46 min, m/z 539.0 [M+H]⁺. ¹H NMR (400 MHz, DMSO-d₆): δ 7.41-7.30 (m, 4H), 7.15 (d, J=8.4 Hz, 1H), 6.86 (d, J=12.8 Hz, 1H), 3.89 (d, J=5.0 Hz, 2H), 3.81-3.78 (m, 1H), 3.73-3.71 (m, 2H), 3.23 (s, 3H), 3.18 (s, 3H), 3.09-3.06 (m, 1H), 2.87-2.84 (m, 1H), 2.22-2.16 (m, 1H), 2.10-2.06 (m, 1H), 2.03-2.96 (m, 1H), 1.81-1.73 (m, 3H), 1.45-1.26 (m, 2H), 0.89-0.84 (m, 2H), 0.65-0.61 (m, 2H).

Example 264

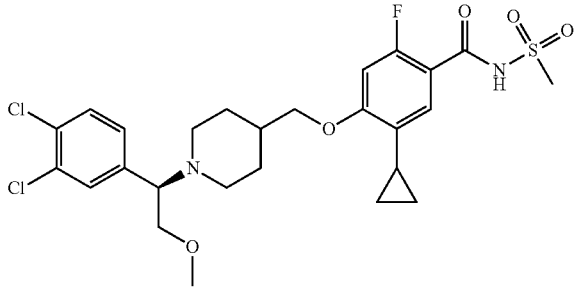 [SMILES: COC[C@@H](c1ccc(Cl)c(Cl)c1)N1CCC(COc2cc(F)c(C(=O)NS(C)(=O)=O)cc2C2CC2)CC1]

(R)-5-cyclopropyl-4-((1-(1-(3,4-dichlorophenyl)-2-methoxyethyl)piperidin-4-yl)methoxy)-2-fluoro-N-(methylsulfonyl)benzamide The compound was synthesized as described in Example 172. The enantiomer was separated by chiral SFC from the racemate, the first eluting fraction was arbitrarily assigned as (R)-5-cyclopropyl-4-((1-(1-(3,4-dichlorophenyl)-2-methoxyethyl)piperidin-4-yl)methoxy)-2-fluoro-N-(methylsulfonyl)benzamide. Chiral HPLC (column: OJ-H, 4.6×250 mm, 5 μm; mobile Phase: A: supercritical CO₂, B: MeOH (0.1% DEA), A:B=75:25; flow: 3 mL/min; column temperature: 40° C.; RT=3.71 min). LCMS (ESI) Method A: RT=5.74 min, m/z 573.0 [M+H]⁺. ¹H NMR (500 MHz, DMSO-d₆): δ 7.60-7.58 (m, 2H), 7.32 (d, J=8.5 Hz, 1H), 7.15 (d, J=8.0 Hz, 1H), 6.83 (d, J=13.0 Hz, 1H), 3.89 (d, J=6 Hz, 2H), 3.74-3.68 (m, 3H), 3.22 (s, 3H), 3.15 (s, 3H), 3.01-3.00 (m, 1H), 2.82-2.78 (m, 1H), 2.14-2.09 (m, 1H), 2.02-1.96 (m, 2H), 1.79-1.71 (m, 3H), 1.38-1.28 (m, 2H), 0.88-0.85 (m, 2H), 0.63-0.60 (m, 2H).

Example 265

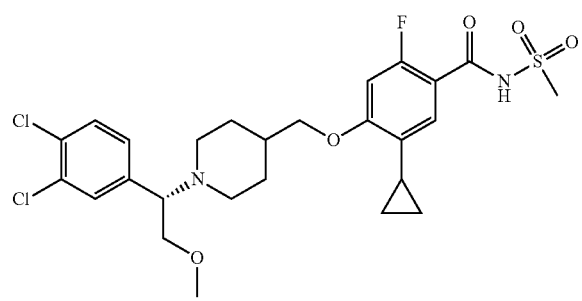 [SMILES: COC[C@H](c1ccc(Cl)c(Cl)c1)N1CCC(COc2cc(F)c(C(=O)NS(C)(=O)=O)cc2C2CC2)CC1]

(S)-5-cyclopropyl-4-((1-(1-(3,4-dichlorophenyl)-2-methoxyethyl)piperidin-4-yl)methoxy)-2-fluoro-N-(methylsulfonyl)benzamide The compound was synthesized as described in Example 172. The enantiomer was separated by chiral SFC from the racemate, the second eluting fraction was arbitrarily assigned as (S)-5-cyclopropyl-4-((1-(1-(3,4-dichlorophenyl)-2-methoxyethyl)piperidin-4-yl)methoxy)-2-fluoro-N-(methylsulfonyl)benzamide. Chiral HPLC (column: OJ-H, 4.6×250 mm, 5 μm; mobile Phase: A: supercritical $CO_2$, B: MeOH (0.1% DEA), A:B=75:25; flow: 3 mL/min; column temperature: 40° C.; RT=5.12 min). LCMS (ESI) Method A: RT=5.71 min, m/z 573.0 [M+H]$^+$. $^1$H NMR (500 MHz, DMSO-$d_6$); δ 7.60-7.58 (m, 2H), 7.32 (d, J=8.5 Hz, 1H), 7.15 (d, J=8.0 Hz, 1H), 0.83 (d, J=13.0 Hz, 1H), 3.89 (d, J=6 Hz, 2H), 3.74-3.68 (m, 3H), 3.22 (s, 3H), 3.15 (s, 3H), 3.01-3.00 (m, 1H), 2.82-2.78 (m, 1H), 2.14-2.09 (m, 1H), 2.02-1.96 (m, 2H), 1.79-1.71 (m, 3H), 1.38-1.28 (m, 2H), 0.88-0.85 (m, 2H), 0.63-0.60 (m, 2H).

Example 266

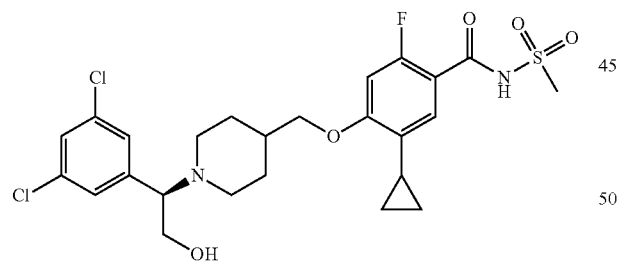

((R)-5-cyclopropyl-4-((1-(1-(3,5-dichlorophenyl)-2-hydroxyethyl)piperidin-4-yl)methoxy)-2-fluoro-N-(methylsulfonyl)benzamide

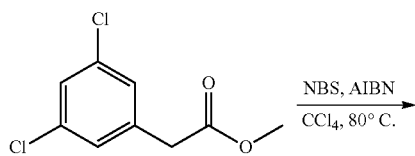

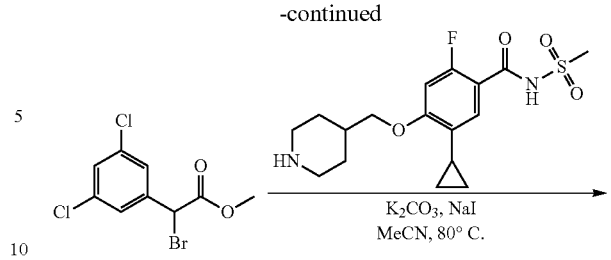

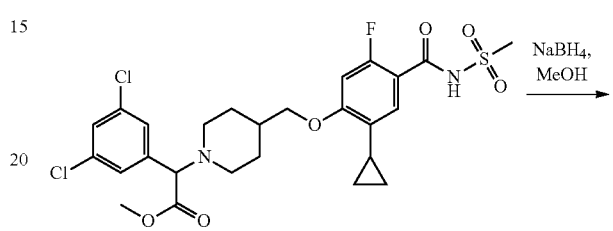

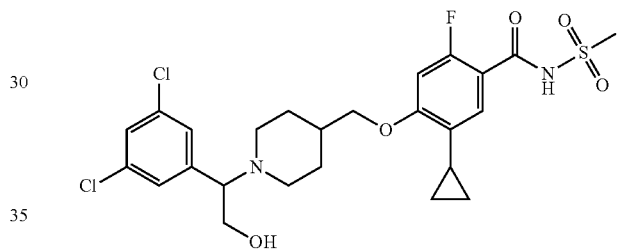

Step 1

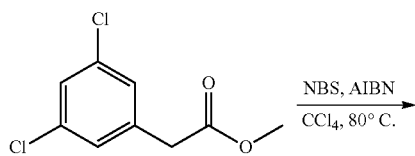

Methyl 2-bromo-2-(3,5-dichlorophenyl)acetate

A mixture of methyl 2-(3,5-dichlorophenyl)acetate (2.0 g, 9.11 mol), N-bromosuccinimide (6.5 g, 36.51 mmol) and 2,2'-azobis(2-methylpropionitrile) (600 mg, 3.64 mmol) in carbon tetrachloride (50 mL) was stirred at 80° C. for 16 h. The reaction mixture was diluted with dichloromethane (200 mL) and brine (50 mL). The organic layer was separated, washed with brine (50 mL), dried over anhydrous sodium sulfate, filtered and concentrated. The residue was purified by silica gel chromatography (eluting with 10% ethylacetate in petroleum ether) to afford the target compound (2.5 g, 92%) as a pale yellow oil.

Step 2

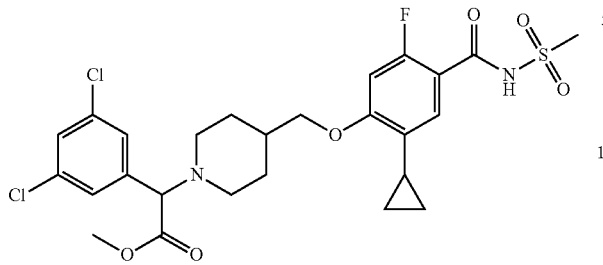

Methyl 2-(4-((2-cyclopropyl-5-fluoro-4-((methylsulfonyl)carbamoyl)phenoxy)methyl)piperidin-1-yl)-2-(3,5-dichlorophenyl)acetate The compound was synthesized as described in step 5 of Example 88. LCMS (ESI) m/z: 587.2 [M+H]⁺.

Step 3

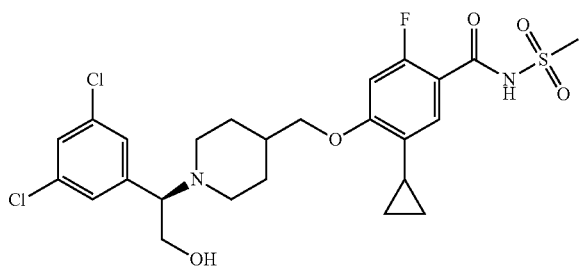 [SMILES: CS(=O)(=O)NC(=O)c1cc(C2CC2)c(OCC2CCN([C@@H](CO)c3cc(Cl)cc(Cl)c3)CC2)cc1F]

(R)-5-cyclopropyl-4-((1-(1-(3,5-dichlorophenyl)-2-hydroxyethyl)piperidin-4-yl)methoxy)-2-fluoro-N-(methylsulfonyl)benzamide A mixture of methyl 2-(4-((2-cyclopropyl-5-fluoro-4-(methylsulfonylcarbamoyl)phenoxy)methyl)piperidin-1-yl)-2-(3,5-dichlorophenyl)acetate (200 mg; 0.37 mmol) and sodium borohydride (142 mg, 3.7 mmol) in MeOH (5 mL) was stirred at 25° C. for 2 h. The mixture was then concentrated, diluted with water (20 mL) and extracted with DCM (20 mL×3). The combined organic layers were washed with brine (20 mL), dried over anhydrous sodium sulfate, filtered and concentrated. The residue was purified by reverse phase chromatography (eluting with 30-40% MeCN in 0.1% NH₄HCO₃) to afford the racemate (100 mg, 48.3%) as an white solid. The enantiomer was separated by chiral SFC from the racemate, the first eluting fraction was arbitrarily assigned as (R)-5-cyclopropyl-4-((1-(1-(3,5-dichlorophenyl)-2-hydroxyethyl)piperidin-4-yl)methoxy)-2-fluoro-N-(methylsulfonyl)benzamide. Chiral HPLC (column: OJ-H, 4.6×250 mm, 5 μm; mobile Phase: A: supercritical CO₂, B: MeOH (0.1% DEA), A:B=80:20; flow: 3 mL/min; column temperature: 40° C.; RT=5.25 min). LCMS (ESI) Method A: RT=5.28 min, m/z 559.0[M+H]⁺. ¹H NMR (400 MHz, DMSO-d₆): δ 7.52 (s, 1H), 7.42 (s, 2H), 7.15 (d, J=8.4 Hz, 1H), 0.85 (d, J=12.8 Hz, 1H), 4.77 (brs, 1H), 3.90 (d, J=5.6 Hz, 2H), 3.78 (s, 2H), 3.65-3.61 (m, 1H), 3.17-3.11) (m, 4H), 2.86-2.85 (m, 1H), 2.20-1.97 (m, 3H), 1.82-1.74 (m, 3H), 1.44-1.16 (m, 2H), 0.89-85 (m, 2H), 0.65-0.61 (m, 2H).

Example 267

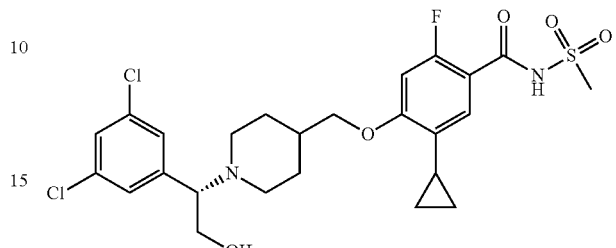

(S)-5-cyclopropyl-4-((1-(1-(3,5-dichlorophenyl)-2-hydroxyethyl)piperidin-4-yl)methoxy)-2-fluoro-N-(methylsulfonyl)benzamide The compound was synthesized as described in Example 266. The enantiomer was separated by chiral SFC from the racemate, the second eluting fraction was arbitrarily assigned as (R)-5-cyclopropyl-4-((1-(1-(3,5-dichlorophenyl)-2-hydroxyethyl)piperidin-4-yl)methoxy)-2-fluoro-N-(methylsulfonyl)benzamide. Chiral HPLC (column: OJ-H, 4.6×250 mm, 5 μm; mobile Phase: A: supercritical CO₂), B: MeOH (0.1% DEA), A:B=80:20; flow: 3 mL/min; column temperature: 40° C.; RT=6.45 min). LCMS (ESI) Method A: RT=5.35 min, m/z 559.1 [M+H]⁺. ¹H NMR (400 MHz, DMSO-d₆): δ 7.52 (s, 1H), 7.42 (s, 2H), 7.15 (d, J=8.4 Hz, 1H), 6.85 (d, J=12.8 Hz, 1H), 4.77 (br, 1H), 3.90 (d, J=5.6 Hz, 2H), 3.78 (s, 2H), 3.65-3.61 (m, 1H), 3.17-3.11 (m, 4H), 2.86-2.85 (m, 1H), 2.20-1.97 (m, 3H), 1.82-1.74 (m, 3H), 1.44-1.16 (m, 2H), 0.89-85 (m, 2H), 0.65-0.61 (m, 2H).

Example 268

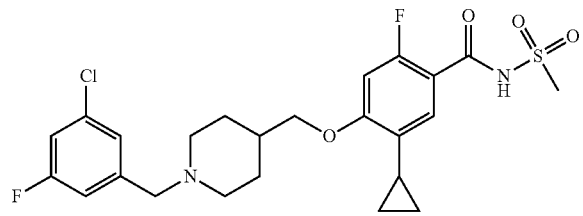 [SMILES: CS(=O)(=O)NC(=O)c1cc(C2CC2)c(OCC2CCN(Cc3cc(F)cc(Cl)c3)CC2)cc1F]

4-((1-(3-Chloro-5-fluorobenzyl)piperidin-4-yl)methoxy)-5-cyclopropyl-2-fluoro-N-(methylsulfonyl)benzamide The compound was synthesized as described in Example 88. LCMS (ESI) Method A: RT=5.75 min, m/z: 513.0 [M+H]⁺. ¹H NMR (400 MHz, DMSO-d₆): δ 7.35-7.34 (m, 1H), 7.28-7.27 (m, 1H), 7.20-7.16 (m, 2H), 6.86-6.83 (m, 1H), 3.94-3.92 (d, J=5.0 Hz, 2H), 3.63 (s, 2H), 3.13 (s, 3H), 2.94-2.91 (m, 2H), 2.19-2.15 (m, 2H), 2.01 (m, 1H), 1.82-1.80 (m, 3H), 1.42-1.40 (m, 2H), 0.89-0.86 (m, 2H), 0.64-0.62 (m, 2H).

Example 269

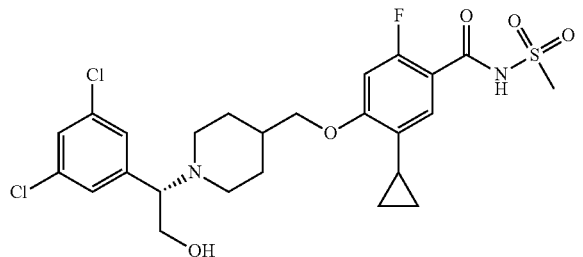 [SMILES: CS(=O)(=O)NC(=O)c1cc(C2CC2)c(OCC2CCN([C@H](CO)c3cc(Cl)cc(Cl)c3)CC2)cc1F]

(R)-5-cyclopropyl-N-(cyclopropylsulfonyl)-4-((1-(1-(3,5-dichlorophenyl)ethyl)piperidin-4-yl)methoxy)-2-fluorobenzamide

Step 1

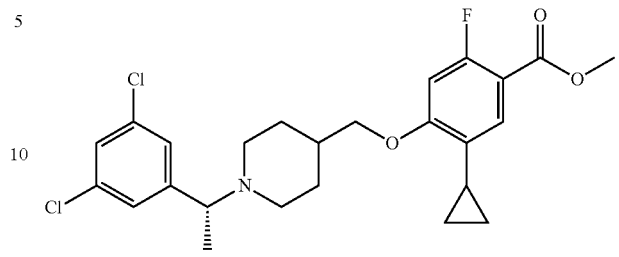

(R)-methyl 5-cyclopropyl-4-((1-(1-(3,5-dichlorophenyl)ethyl)piperidin-4-yl)methoxy)-2-fluorobenzoate The compound was synthesized as described in step 5 of Example 88. The enantiomer was separated by chiral SFC from the racemate, the enantiomer was arbitrarily assigned as (R)-methyl 5-cyclopropyl-4-((1-(1-(3,5-dichlorophenyl)ethyl)piperidin-4-yl)methoxy)-2-fluorobenzoate. Chiral HPLC (column: AD-H, 4.6×250 mm, 5 μm; mobile Phase: A: supercritical $CO_2$, B: MeOD (0.1% DEA), A:B=80:20; flow: 2.4 mL/min; column temperature: 39.9° C.; RT=4.49 min). LCMS (ESI) m/z: 480.1 $[M+H]^+$.

Step 2

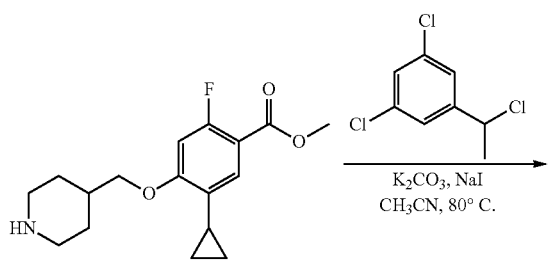

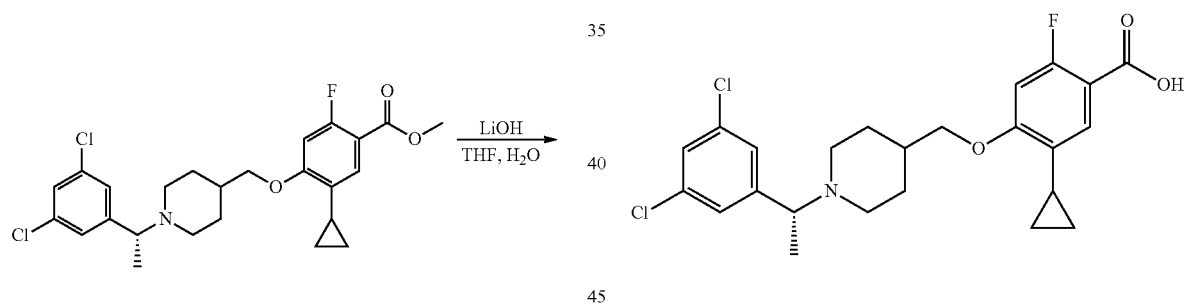

(R)-5-cyclopropyl-4-((1-(1-(3,5-dichlorophenyl)ethylpiperidin-4-yl)methoxy)-2-fluorobenzoic acid The compound was synthesized as described in step 6 of Example 88. LCMS (ESI) m/z: 466.0 $[M+H]^+$.

Step 3

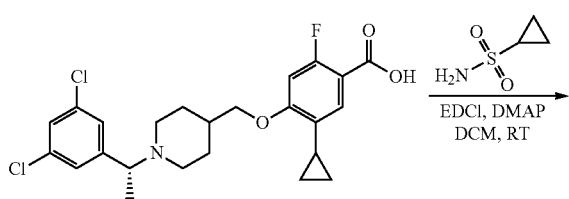

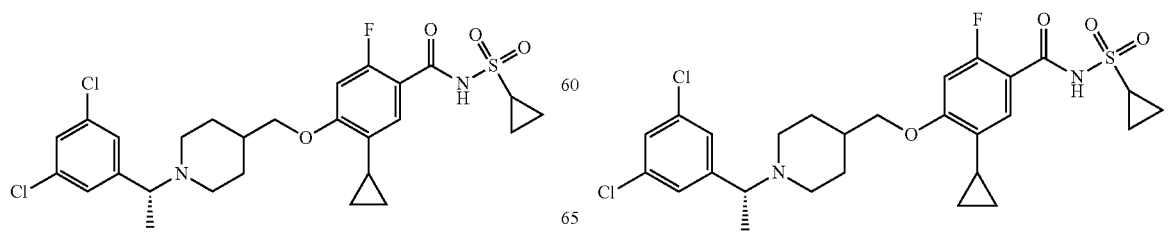

(R)-5-cyclopropyl-N-(cyclopropylsulfonyl)-4-((1-(1-(3,5-dichlorophenyl)ethyl)piperidin-4-yl)methoxy)-2-fluorobenzamide The compound was synthesized as described in step 5 of Example 80. The enantiomer was arbitrarily assigned as (R)-5-cyclopropyl-N-(cyclopropylsulfonyl)-4-((1-(1-(3,5-dichlorophenyl)ethyl)piperidin-4-yl)methoxy)-2-fluorobenzamide. LCMS (ESI) Method A: RT=6.52 min, m/z: 569.0 [M+H]⁺. ¹H-NMR (500 MHz, DMSO-d₆): δ 7.52 (m, 1H), 7.41 (m, 2H), 7.15-7.13 (d, J=5.0 Hz, 1H), 6.91-6.88 (d, J=13.0 Hz, 1H), 3.93-3.73 (m, 2H), 3.72-3.70 (m, 1H), 3.05-3.03 (m, 2H), 2.89-2.87 (m, 1H), 2.36-2.00 (m, 3H), 1.84-1.77 (m, 3H), 1.42-1.30 (m, 5H), 1.06-1.02 (m, 4H), 0.91-0.83 (m, 2H), 0.71-0.62 (m, 2H).

Example 270

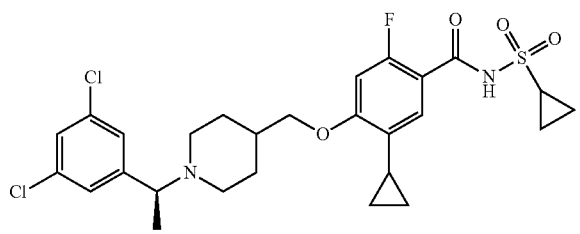 [SMILES: C[C@@H](c1cc(Cl)cc(Cl)c1)N1CCC(COc2cc(F)c(C(=O)NS(=O)(=O)C3CC3)cc2C2CC2)CC1]

(S)-5-cyclopropyl-N-(cyclopropylsulfonyl)-4-((1-(1-(3,5-dichlorophenyl)ethylpiperidin-4-yl)methoxy)-2-fluorobenzamide The compound was synthesized as described in Example 269. The enantiomer was arbitrarily assigned as (S)-5-cyclopropyl-N-(cyclopropylsulfonyl)-4-((1-(1-(3,5-dichlorophenyl)ethyl)piperidin-4-yl)methoxy)-2-fluorobenzamide. LCMS (ESI) Method A: RT=6.51 min, m/z: 569.0 [M+H]⁺. ¹H-NMR (500 MHz, DMSO-d₆): δ 7.52 (m, 1H), 7.41 (m, 2H), 7.15-7.13 (d, J=5.0 Hz, 1H), 6.90-6.88 (d, J=13.0 Hz, 1H), 3.93-3.73 (m, 2H), 3.72-3.71 (m, 1H), 3.05-3.03 (m, 2H), 2.89-2.87 (m, 1H), 2.21-1.98 (m, 3H), 1.84-1.77 (m, 3H), 1.42-1.30 (m, 5H), 1.29-0.98 (m, 4H), 0.91-0.83 (m, 2H), 0.71-0.62 (m, 2H).

Example 271

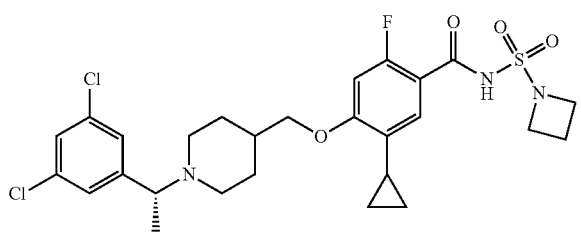 [SMILES: C[C@H](c1cc(Cl)cc(Cl)c1)N1CCC(COc2cc(F)c(C(=O)NS(=O)(=O)N3CCC3)cc2C2CC2)CC1]

(R)—N-(azetidin-1-ylsulfonyl)-5-cyclopropyl-4-((1-(1-(3,5-dichlorophenyl)ethyl)piperidin-4-yl)methoxy)-2-fluorobenzamide The compound was synthesized as described in Example 269. The enantiomer was arbitrarily assigned as (R)—N-(azetidin-1-ylsulfonyl)-5-cyclopropyl-4-((1-(1-(3,5-dichlorophenyl)ethylpiperidin-4-yl)methoxy)-2-fluorobenzamide. LCMS (ESI) Method A: RT=6.66 min, m/z: 584.0 [M+H]⁺. ¹H-NMR (500 MHz; DMSO-d₆): δ 7.49 (s, 1H), 7.39-7.38 (d, J=1.0 Hz, 2H), 7.19-7.17 (d, J=7.5 Hz, 1H), 6.86-6.83 (d, J=13.0 Hz, 1H), 3.91-3.90 (m, 6H), 3.64-3.63 (m, 1H), 2.98 (m, 1H), 2.84-2.82 (m, 1H), 2.11-1.98 (m, 5H), 1.82-1.75 (m, 3H), 1.36-1.31 (m, 5H), 0.88-0.86 (m, 2H), 0.63-0.62 (m, 2H).

Example 272

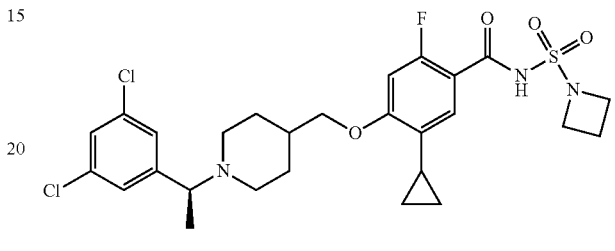

(S)—N-(azetidin-1-ylsulfonyl)-5-cyclopropyl-4-((1-(1-(3,5-dichlorophenyl)ethyl)piperidin-4-yl)methoxy)-2-fluorobenzamide The compound was synthesized as described in Example 269. The enantiomer was arbitrarily assigned as (S)—N-(azetidin-1-ylsulfonyl)-5-cyclopropyl-4-((1-(1-(3,5-dichlorophenyl)ethyl)piperidin-4-yl)methoxy)-2-fluorobenzamide. LCMS (ESI) Method A: RT=6.67 min, m/z: 584.0 [M+H]⁺. ¹H-NMR (500 MHz, DMSO-d₆): δ 7.49 (s, 1H), 7.39-7.38 (d, J=1.0 Hz, 2H), 7.19-7.17 (d, J=7.5 Hz, 1H), 6.83-6.80 (d, J=13.0 Hz, 1H), 3.91-3.86 (m, 6H), 3.64-3.63 (m, 1H), 2.98 (m, 1H), 2.82-2.80 (m, 1H), 2.11-1.98 (m, 5H), 1.82-1.75 (m, 3H), 1.36-1.31 (m, 5H), 0.88-0.86 (m, 2H), 0.63-0.62 (m, 2H).

Example 273

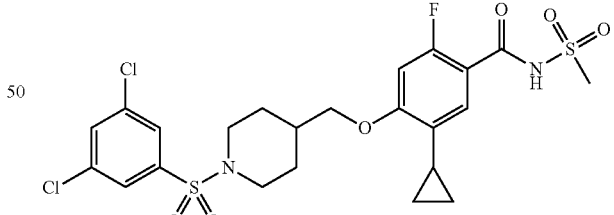

5-Cyclopropyl-4-((1-((3,5-dichlorophenyl)sulfonyl)piperidin-4-yl)methoxy)-2-fluoro-N-(methylsulfonyl)benzamide The compound was synthesized as described in Example 129. LCMS (ESI) Method A: RT=5.54 min, m/z: 579.0 [M+H]⁺. ¹H-NMR (500 MHz, DMSO-d₆): δ11.87 (brs, 1H), 8.13 (s, 1H), 8.04 (d, J=5.0 Hz, 2H), 7.14 (d, J=8.5 Hz, 1H), 6.90 (d, J=10.0 Hz, 1H), 3.94 (d, J=5 Hz, 2H), 3.75-3.74 (m, 2H), 3.26-3.22 (m, 3H), 3.46-3.36 (m, 2H), 1.99-1.85 (m, 4H), 1.42-1.35 (m, 2H), 0.89-0.83 (m, 2H), 0.67-0.62 (m, 2H).

Example 274

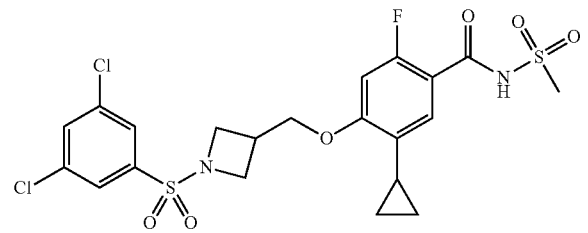 [SMILES: CS(=O)(=O)NC(=O)c1cc(C2CC2)c(OCC2CN(S(=O)(=O)c3cc(Cl)cc(Cl)c3)C2)cc1F]

5-Cyclopropyl-4-((1-((3,5-dichlorophenyl)sulfonyl)azetidin-3-yl)methoxy)-2-fluoro-N-(methylsulfonyl)benzamide The compound was synthesized as described in Example 129. LCMS (ESI) Method A: RT=5.01 min, m/z: 551.0 [M+H]$^+$. $^1$-NMR (500 MHz, DMSO-d$_6$): δ11.90 (brs, 1H), 8.09 (s, 1H), 7.84-7.83 (d, J=1.5 Hz, 2H), 7.15-7.13 (d, J=8.5 Hz, 1H), 6.89-6.87 (d, J=13.0 Hz, 1H), 4.08-4.06 (m, 2H), 3.96-3.92 (m, 2H), 3.78-3.75 (m, 2H), 3.24 (s, 3H), 3.02-3.96 (m, 1H), 1.81-1.76 (m, 1H), 0.83-0.79 (m, 2H), 0.63-0.61 (m, 2H).

Example 275

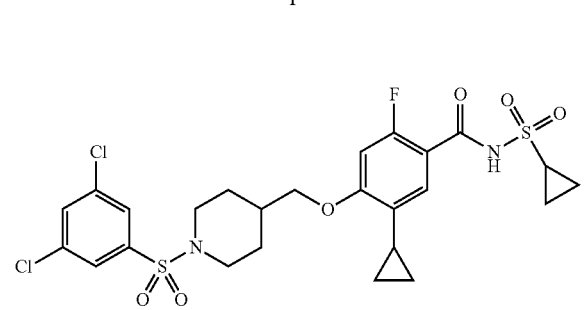

5-Cyclopropyl-N-(cyclopropylsulfonyl)-4-((1-((3,5-dichlorophenyl)sulfonyl)piperidin-4-yl)methoxy)-2-fluorobenzamide The compound was synthesized as described in Example 129. LCMS (ESI) Method A: RT=5.68 min, m/z: 604.8 [M+H]$^+$. $^1$H-NMR (500 MHz, DMSO-d$_6$): δ8.05 (s, 1H), 7.76 (d, J=2.5 Hz, 2H), 7.14-7.12 (d, J=8.5 Hz, 1H), 6.91-6.88 (d, J=13.0 Hz, 1H), 3.94-3.93 (d, J=5.0 Hz, 2H), 3.75-3.73 (m, 2H), 3.05-3.02 (m, 1H), 2.50-2.42 (m, 2H), 1.98-1.85 (m, 4H), 1.42-1.37 (ms 2H), 0.87-0.85 (m, 4H), 0.66-0.64 (m, 2H), 0.62-0.56 (m, 2H).

Example 276

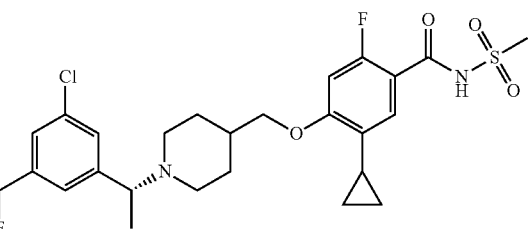

(R)-5-((1-(1-(3-chloro-5-(trifluoromethyl)phenyl)ethyl)piperidin-4-yl)methoxy)-5-cyclopropyl-2-fluoro-N-(methylsulfonyl)benzamide The compound was synthesized as described in Example 88. The enantiomer was separated by chiral SFC from the racemate, the first eluting fraction was arbitrarily assigned as (R)-4-((1-(1-(3-chloro-5-(trifluoromethyl)phenyl)ethyl)piperidin-4-yl)methoxy)-5-cyclopropyl-2-fluoro-N-(methylsulfonyl)benzamide. Chiral HPLC (column: AD-H, 4.6×250 mm, 5 µm; mobile Phase: A: supercritical CO$_2$, B: MeOD (0.1% DEA), A:B=80:20; flow: 2.4 mL/min; column temperature: 40.1° C.; RT=5.80 min). LCMS (ESI) Method A: RT=6.43 min, m/z: 577.0 [M+H]$^+$. $^1$H-NMR (400 MHz, MeOD-d$_4$): δ 7.80 (s, 1H), 7.73 (s, 2H), 7.34-7.32 (m, 1H), 6.67-6.64 (d, J=12.8 Hz, 1H), 4.05-4.03 (m, 1H). 3.86-3.85 (m, 2H), 3.44-3.42 (m, 1H), 3.21 (s, 3H), 3.11-3.08 (m, 1H), 2.49-2.44 (m, 2H), 2.05-1.93 (m, 4H), 1.66-1.54 (m, 5H), 0.91-0.87 (m, 2H), 0.83-0.80 (m, 2H).

Example 277

(S)-4-((1-(1-(3-chloro-5-(trifluoromethyl)phenyl)ethyl)piperidin-4-yl)methoxy)-5-cyclopropyl-2-fluoro-N-(methylsulfonyl)benzamide The compound was synthesized as described in Example 88. The enantiomer was separated by chiral SFC from the racemate, the second eluting fraction was arbitrarily assigned as (S)-4-((1-(1-(3-chloro-5-(trifluoromethyl)phenyl)ethyl)piperidin-4-yl)methoxy)-5-cyclopropyl-2-fluoro-N-(methylsulfonyl)benzamide. Chiral HPLC (column: AD-H, 4.6×250 mm, 5 µm; mobile Phase: A: supercritical CO$_2$, B: MeOD (0.1% DEA), A:B=80:20; flow: 2.4 mL/min; column temperature: 40.1° C.; RT=7.02 min). LCMS (ESI) Method A: RT=6.42 min, m/z: 577.0 [M+H]$^+$. $^1$H-NMR (400 MHz, MeOD-d$_4$): δ 7.79 (s, 1H), 7.74 (s, 2H), 7.34-7.32 (m, 1H), 6.71-6.65 (m, 1H), 4.11-4.05 (m, 1H), 3.88-3.83 (m, 2H), 3.46-3.45 (m, 1H), 3.23 (s, 3H), 3.15-3.11 (m, 1H), 2.51-2.48 (m, 2H), 2.04-1.93 (m, 4H), 1.69-1.51 (m, 5H), 0.91-0.86 (m, 2H), 0.73-0.68 (m, 2H).

Example 278

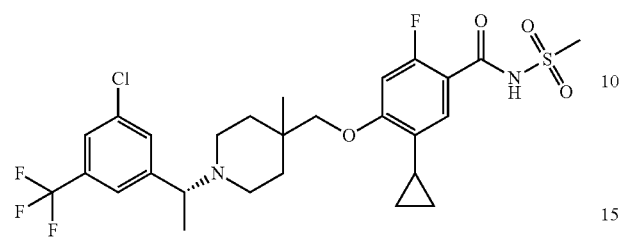

(R)-4-((1-(1-(3-chloro-5-(trifluoromethyl)phenyl)ethyl)-4-methylpiperidin-4-yl)methoxy)-5-cyclopropyl-2-fluoro-N-(methylsulfonyl)benzamide The compound was synthesized as described in Example 170. The enantiomer was separated by chiral SFC from the racemate, the second eluting fraction was arbitrarily assigned as (R)-4-((1-(1-(3-chloro-5-(trifluoromethyl)phenyl)ethyl)-4-methylpiperidin-4-yl)methoxy)-5-cyclopropyl-2-fluoro-N-(methylsulfonyl)benzamide. Chiral HPLC (column: AD-H, 4.6×250 mm, 5 μm; mobile Phase: A: supercritical $CO_2$, B: MeOD (0.1% DEA), A:B=80:20; flow: 2.4 mL/min; column temperature: 40.0° C.; RT=5.35 min). LCMS (ESI) Method A: RT=6.42 min, m/z: 591.2 [M+H]$^+$. $^1$H-NMR (400 MHz, MeOD-d$_4$): δ 7.77-7.72 (m, 3H), 7.36-7.34 (d, J=8.8 Hz, 1H), 6.76-6.68 (m, 1H), 4.00-3.95 (m, 1H), 3.81-3.78 (s, 2H), 3.23-3.22 (s, 3H), 3.10-3.02 (m, 1H), 2.78-2.67 (m, 3H), 2.08-2.02 (m, 1H), 1.94-1.84 (m, 2H), 1.68-1.55 (m, 5H), 1.16 (s, 3H), 0.92-0.88 (m, 2H), 0.67-0.63 (m, 2H).

Example 279

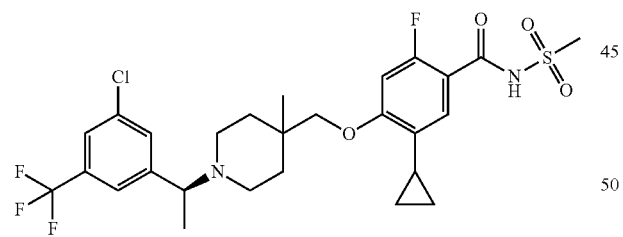

(S)-4-((1-(1-(3-chloro-5-(trifluoromethyl)phenyl)ethyl)-4-methylpiperidin-4-yl)methoxy)-5-cyclopropyl-2-fluoro-N-(methylsulfonyl)benzamide The compound was synthesized as described in Example 170. The enantiomer was separated by chiral SFC from the racemate, the first eluting fraction was arbitrarily assigned as (S)-4-((1-(1-(3-chloro-5-(trifluoromethyl)phenyl)ethyl)-4-methylpiperidin-4-yl)methoxy)-5-cyclopropyl-2-fluoro-N-(methylsulfonyl)benzamide. Chiral HPLC (column: AD-H, 4.6×250 mm, 5 μm; mobile Phase: A: supercritical $CO_2$, B: MeOD (0.1% DEA), A:B=80:20; flow: 2.4 mL/min; column temperature: 40.0° C.; RT=4.69 min). LCMS (ESI) Method A: RT=6.42 min, m/z: 591.3 [M+H]$^+$. $^1$H-NMR (400 MHz, MeOD-d$_4$): δ 7.79-7.72 (m, 3H), 7.36-7.34 (d, J=8.8 Hz, 1H), 6.76-6.68 (m, 1H), 4.00-3.95 (m, 1H), 3.81-3.78 (s, 2H), 3.23-3.22 (s, 3H), 3.07-3.05 (m, 1H), 2.78-2.67 (m, 3H), 2.08-2.02 (m, 1H), 1.94-1.84 (m, 2H), 1.69-1.53 (m, 5H), 1.16 (s, 3H), 0.92-0.88 (m, 2H), 0.67-0.63 (m, 2H).

Example 280

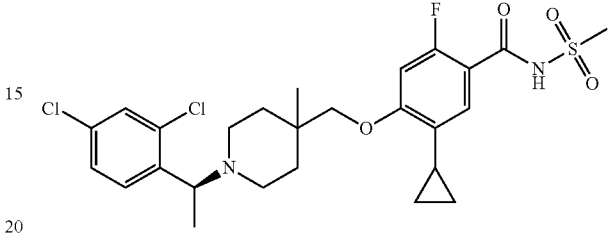

(S)-5-cyclopropyl-4-((1-(1-(2,4-dichlorophenyl)ethyl)-4-methylpiperidin-4-yl)methoxy)-2-fluoro-N-(methylsulfonyl)benzamide The compound was synthesized as described in Example 170. The enantiomer was separated by chiral SFC from the racemate, the first eluting fraction was arbitrarily assigned as (S)-5-cyclopropyl-4-((1-(1-(2,4-dichlorophenyl)ethyl)-4-methylpiperidin-4-yl)methoxy)-2-fluoro-N-(methylsulfonyl)benzamide. Chiral HPLC (column: AD-H, 4.6×250 mm, 5 μm; mobile Phase: A: supercritical $CO_2$, B: MeOD (0.1% DEA), A:B=70:30; flow: 2.4 mL/min; column temperature: 39.9° C.; RT=3.89 min). LCMS (ESI) Method A: RT=6.46 min, m/z: 557.2 [M+H]$^+$. $^1$H-NMR (400 MHz, MeOD-d$_4$): δ 7.68-7.66 (d, J=11.5 Hz, 1H), 7.57-7.56 (d, J=2.5 Hz, 1H), 7.46-7.42 (m, 1H), 7.38-7.36 (d, J=8.5 Hz, 1H), 6.75-6.72 (d, J=13.0 Hz, 1H), 4.47-4.46 (ms, 1H), 3.82 (s, 2H), 3.20-3.17 (m, 4H), 2.90-2.79 (m, 3H), 2.06-2.04 (m, 1H), 1.94-1.88 (m, 2H), 1.66 (s, 2H), 1.54-1.53 (d, J=7.0 Hz, 3H), 1.18 (s, 3H), 0.93-0.89 (m, 2H), 0.67-0.63 (m, 2H).

Example 281

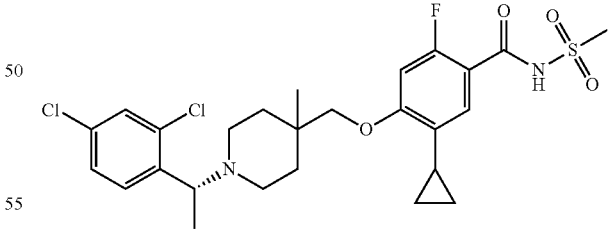

(R)-5-cyclopropyl-4-((1-(1-(2,4-dichlorophenyl)ethyl)-4-methylpiperidin-4-yl)methoxy)-2-fluoro-N-(methylsulfonyl)benzamide The compound was synthesized as described in Example 170. The enantiomer was separated by chiral SFC from the racemate, the second eluting fraction was arbitrarily assigned as (R)-5-cyclopropyl-4-((1-(1-(2,4-dichlorophenyl)ethyl)-4-methylpiperidin-4-yl)methoxy)-2-fluoro-N-

(methylsulfonyl)benzamide. Chiral HPLC (column: AD-H, 4.6×250 mm, 5 μm; mobile Phase: A: supercritical $CO_2$, B: MeOD (0.1% DEA), A:B=70:30; flow: 2.4 mL/min; column temperature: 39.9° C.; RT=5.67 min). LCMS (ESI) Method A: RT=6.46 min, m/z: 557.2 [M+H]$^+$. $^1$H-NMR (400 MHz, MeOD-$d_4$): δ 7.70-7.68 (d, J=11.5 Hz, 1H), 7.57-7.56 (d, J=2.5 Hz, 1H), 7.47-7.45 (m, 1H), 7.36-7.34 (d, J=8.5 Hz, 1H), 6.72-6.69 (d, J=13.0 Hz, 1H), 4.47-4.46 (m, 1H), 3.82 (s, 2H), 3.20-3.17 (m, 4H), 2.88-2.82 (m, 3H), 2.06-2.04 (m, 1H), 1.96-1.85 (m, 2H) 1.66 (s, 2H), 1.54-1.53 (d, J=7.0 Hz, 3H), 1.18 (s, 3H), 0.93-0.89 (m, 2H), 0.67-0.63 (m, 2H).

Example 282

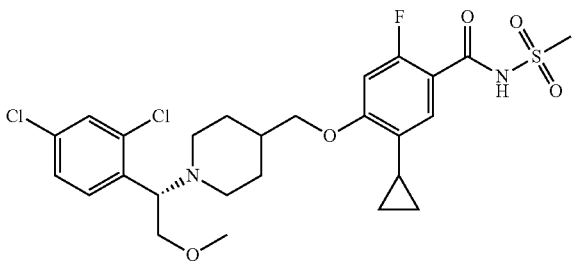 [SMILES: COC[C@H](c1ccc(Cl)cc1Cl)N1CCC(COc2cc(F)c(C(=O)NS(C)(=O)=O)cc2C2CC2)CC1]

(S)-5-cyclopropyl-4-((1-(1-(2,4-dichlorophenyl)-2-methoxyethyl)piperidin-4-yl)methoxy)-2-fluoro-N-(methylsulfonyl)benzamide The compound was synthesized as described in Example 172. The enantiomer was separated by chiral SFC from the racemate, the first eluting fraction was arbitrarily assigned as (S)-5-cyclopropyl-4-((1-(1-(2,4-dichlorophenyl)-2-methoxyethyl)piperidin-4-yl)methoxy)-2-fluoro-N-(methylsulfonyl)benzamide. Chiral HPLC (column: AS-H, 4.6×250 mm, 5 μm; mobile Phase: A: supercritical $CO_2$, S: MeOD (0.1% DEA), A:B=75:25; (low: 2.25 mL/min; column temperature: 40.3° C.; RT=2.95 min). LCMS (ESI) Method A: RT=6.00 min, m/z: 573.1 [M+H]$^+$. $^1$H-NMR (400 MHz, MeOD-$d_4$): δ7.69-7.66 (m, 1H), 7.55-7.54 (d, J=2.0 Hz, 1H), 7.41-7.39 (m, 1H), 7.33-7.31. (d, J=8.4 Hz, 1H), 6.75-6.71 (m, 1H), 4.41 (m, 1H), 3.94-3.92 (m, 2H), 3.77 (s, 2H), 3.43-3.32 (m, 4H), 3.24 (s, 3H), 2.98 (m, 1H), 2.55-2.41 (m, 2H), 2.08-1.86 (m, 4H), 1.67-1.51 (m, 2H), 0.93-9.89 (m, 2H), 0.66-0.64 (d, J=4.8 Hz, 2H).

Example 283

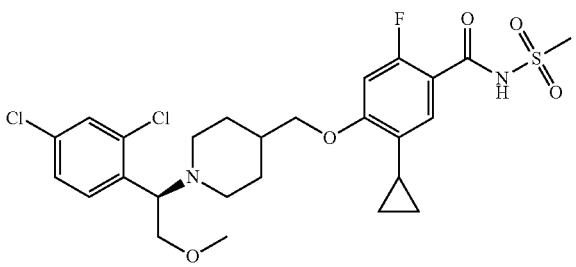 [SMILES: COC[C@@H](c1ccc(Cl)cc1Cl)N1CCC(COc2cc(F)c(C(=O)NS(C)(=O)=O)cc2C2CC2)CC1]

(R)-5-cyclopropyl-4-((1-(1-(2,4-dichlorophenyl)-2-methoxyethyl)piperidin-4-yl)methoxy)-2-fluoro-N-(methylsulfonyl)benzamide The compound was synthesized as described in Example 172. The enantiomer was separated by chiral SFC from the racemate, the second eluting fraction was arbitrarily assigned as (R)-5-cyclopropyl-4-((1-(1-(2,4-dichlorophenyl)-2-methoxyethyl)piperidin-4-yl)methoxy)-2-fluoro-N-(methylsulfonyl)benzamide. Chiral HPLC (column: AS-H, 4.6×250 mm, 5 μm; mobile Phase: A: supercritical $CO_2$, B: MeOH (0.1% DEA), A:B=75:25; flow: 2.25 mL/min; column temperature: 40.3° C.; RT=3.85 mm). LCMS (ESI) Method A: RT=6.01 min, m/z: 573.1 [M+]$^+$. $^1$H-NMR (400 MHz, MeOD-$d_4$): δ7.69-7.66 (m, 1H), 7.55-7.54 (d, J=2.0 Hz, 1H), 7.41-7.39 (m, 1H), 7.33-7.31 (d, J=8.4 Hz, 1H), 6.75-6.71 (m, 1H), 4.21 (m, 1H), 3.81-3.78 (m, 2H), 3.77 (s, 2H), 3.43-3.32 (m, 4H), 3.24 (s, 3H), 2.98 (m, 1H), 2.55-2.41 (m, 2H), 2.08-1.86 (m, 4H), 1.67-1.51 (m, 2H), 0.93-0.89 (m, 2H), 0.66-0.64 (m, 2H).

Example 284

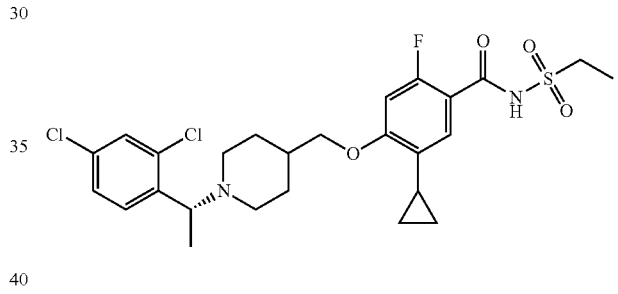

(R)-5-cyclopropyl-4-((1-(1-(2,4-dichlorophenyl)ethyl)piperidin-4-yl)methoxy)-N-(ethylsulfonyl)-2-fluorobenzamide The compound was synthesized as described in Example 88. The enantiomer was separated by chiral SFC from the racemate, the second eluting fraction was arbitrarily assigned as (R)-5-cyclopropyl-4-((1-(1-(2,4-dichlorophenyl)ethyl)piperidin-4-yl)methoxy)-N-(ethylsulfonyl)-2-fluorobenzamide. Chiral HPLC (column: AS-H, 4.6×250 mm, 5 μm; mobile Phase: A: supercritical $CO_2$, B: MeOD (0.1% DEA), A:B=75:25; flow: 2.25 mL/min; column temperature: 37.7° C.; RT=4.46 min). LCMS (ESI) Method A: RT=6.28 min, m/z: 557.1 [M+H]$^+$. $^1$H-NMR (400 MHz, MeOD-$d_4$): δ7.69-7.64 (m, 1H), 7.55-7.54 (m, 1H), 7.44-7.42 (d, J=8.4 Hz, 1H), 7.31-7.29 (d, J=8.4 Hz, 1H), 6.73-6.70 (d, J=12.8 Hz, 1H), 4.36-4.35 (m, 1H), 3.92-3.86 (m, 2H), 3.53-3.50 (m, 1H), 3.34-3.32 (m, 2H), 3.06-3.03 (m, 1H), 2.49-2.41 (m, 2H), 2.08-1.89 (m, 4H), 1.68-1.65 (m, 1H), 1.54-1.49 (m, 4H), 1.38-1.33 (s, 3H), 0.93-0.82 (m, 2H), 0.61-0.59 (m, 2H).

Example 285

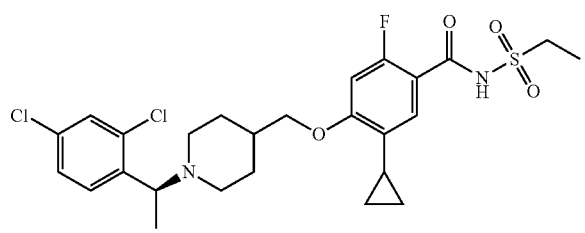 [SMILES: CCS(=O)(=O)NC(=O)c1cc(C2CC2)c(OCC2CCN([C@@H](C)c3ccc(Cl)cc3Cl)CC2)cc1F]

(S)-5-cyclopropyl-4-((1-(1-(2,4-dichlorophenyl)
ethyl)piperidin-4-yl)methoxy)-N-(ethylsulfonyl)-2-
fluorobenzamide The compound was synthesized as described in Example 88. The enantiomer was separated by chiral SFC from the racemate, the first eluting fraction was arbitrarily assigned as (S)-5-cyclopropyl-4-((1-(1-(2,4-dichlorophenyl)ethyl)piperidin-4-yl)methoxy)-N-(ethylsulfonyl)-2-fluorobenzamide. Chiral HPLC (column: AS-H, 4.6×250 mm, 5 μm; mobile Phase: A: supercritical $CO_2$, B: MeOD (0.1% DEA), A:B=75:25; flow: 2.25 mL/min; column temperature: 37.7° C.; RT=2.99 min). LCMS (ESI) Method A: RT=6.29 min, m/z: 557.2 [M+H]$^+$1. $^1$H-NMR (400 MHz, MeOD-d$_3$): δ7.71-7.65 (m, 1H), 7.56-7.55 (m, 1H), 7.46-7.42 (d, J=8.4 Hz, 1H), 7.31-7.30 (d, J=8.4 Hz, 1H), 6.73-6.70 (d, J=12.8 Hz, 1H), 4.49 (m, 1H), 3.89-3.86 (m, 2H), 3.58-3.55 (m, 1H), 3.34-3.32 (m, 2H), 3.06-3.03 (m, 1H), 2.49-2.41 (m, 2H), 2.08-1.89 (m, 4H), 1.68-1.65 (m, 1H), 1.54-1.49 (m, 4H), 1.38-1.33 (s, 3H), 0.93-0.82 (m, 2H), 0.61-0.59 (m, 2H).

Example 286

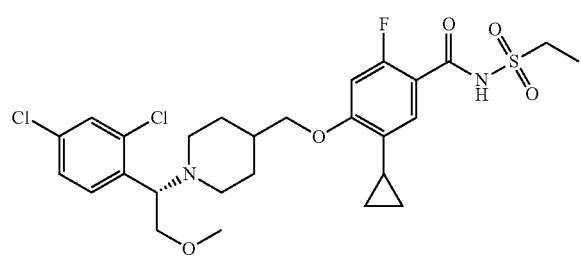 [SMILES: CCS(=O)(=O)NC(=O)c1cc(C2CC2)c(OCC2CCN([C@H](COC)c3ccc(Cl)cc3Cl)CC2)cc1F]

(S)-5-cyclopropyl-4-((1-(1-(2,4-dichlorophenyl)-2-
methoxyethyl)piperidin-4-yl)methoxy)-N-(ethylsul-
fonyl)-2-fluorobenzamide The compound was synthesized as described in Example 172. The enantiomer was separated by chiral SFC from the racemate, the first eluting fraction was arbitrarily assigned as (S)-5-cyclopropyl-4-((1-(1-(2,4-dichlorophenyl)-2-methoxy)ethylpiperidin-4-yl)methoxy)-N-(ethylsulfonyl)-2-fluorobenzamide. Chiral HPLC (column: AS-H, 4.6×250 mm, 5 μm; mobile Phase: A: supercritical $CO_2$, B: MeOD (0.1% DEA), A:B=75:25; flow: 2.25 mL/min; column temperature: 40.5° C.; RT=2.87 min). LCMS (ESI) Method A: RT=6.10 min, m/z: 587.0 [M+H]$^+$. $^1$H-NMR (400 MHz, DMSO-d$_6$): δ7.58-7.54 (m, 2H), 7.43-7.40 (m, 1H), 7.16-7.13 (d, J=10.5 Hz, 1H), 6.86-6.83 (d, J=12.8 Hz, 1H), 4.05-4.02 (m, 1H), 3.90-3.88 (m, 2H), 3.68-3.58 (m, 2H), 3.29-3.28 (m, 2H), 3.19 (s, 3H), 3.10-3.08 (m, 1H), 2.73-2.69 (m, 1H), 2.19-2.13 (m, 1H), 2.03-1.97 (m, 2H), 1.81-1.67 (m, 3H), 1.35-1.18 (m, 5H), 0.95-0.82 (m, 2H), 0.72-0.61 (m, 2H).

Example 287

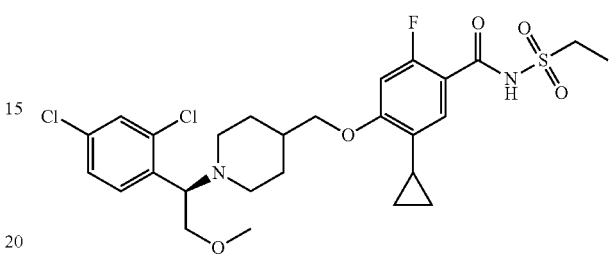

(R)-5-cyclopropyl-4-((1-(1-(2,4-dichlorophenyl)-2-
methoxyethyl)piperidin-4-yl)methoxy)-N-(ethylsul-
fonyl)-2-fluorobenzamide The compound was synthesized as described in Example 172. The enantiomer was separated by chiral SFC from the racemate, the second eluting fraction was arbitrarily assigned as (R)-5-cyclopropyl-4-((1-(1-(2,4-dichlorophenyl)-2-methoxyethyl)piperidin-4-yl)methoxy)-N-(ethylsulfonyl)-2-fluorobenzamide. Chiral HPLC (column: AS-H, 4.6×250 mm, 5 μm; mobile Phase: A: supercritical $CO_2$, B: MeOD (0.1% DEA), A:B=75:25; flow: 2.25 mL/min; column temperature: 40.5° C.; RT=3.66 min). LCMS (ESI) Method A: RT=6.10 min, m/z; 587.0 [M+H]$^+$. $^1$H-NMR (400 MHz, DMSO-d$_6$): δ7.58-7.54 (m, 2H), 7.43-7.40 (m, 1H), 7.16-7.14 (4, J=10.5 Hz, 1H), 6.86-6.82 (d, J=12.8 Hz, 1H), 4.05-4.02 (m, 1H), 3.90-3.88 (m, 2H), 3.67-3.58 (m, 2H), 3.30-3.28 (m, 2H), 3.19 (s, 3H), 3.10-3.08 (m, 1H), 2.71-2.60 (m, 1H), 2.18-2.13 (m, 1H), 2.03-1.97 (m, 2H), 1.81-1.67 (m, 3H), 1.35-1.18 (m, 5H), 0.89-0.81 (m, 2H), 0.61-0.59 (m, 2H).

Example 288

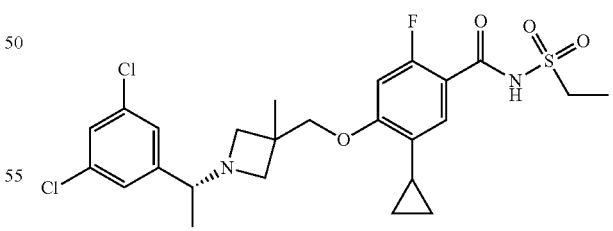

(R)-5-cyclopropyl-4-((1-(1-(3,5-dichlorophenyl)
ethyl)-3-methylazetidin-3-yl)methoxy)-N-(ethylsul-
fonyl)-2-fluorobenzoate The compound was synthesized as described in Example 68. The enantiomer was separated by chiral SFC from the racemate, the first eluting fraction was arbitrarily assigned as (R)-5-cyclopropyl-4-((1-(1-(3,5-dichlorophenyl)ethyl)-3- methylazetidin-3-yl)methoxy)-N-(ethylsulfonyl)-2-fluorobenzamide. Chiral HPLC (column: IC, 4.6×150 mm, 4.6×250 mm, 5 μm; mobile Phase: A: supercritical CO₂, B: MeOD (0.1% DEA), A:B=65:35: flow: 1.95 mL/min; column temperature: 39.9° C.; RT=2.73 min). LCMS (ESI) Method A: RT=6.04 min, m/z: 543.1 [M+H]⁺. ¹H-NMR (400 MHz, MeOD-d₄): δ7.42-7.33 (m, 4H), 6.83-6.76 (m, 1H), 4.10-4.04 (m, 2H), 3.81 (m, 1H), 3.64-3.45 (m, 2H), 3.43-3.36 (m, 2H), 3.36-3.35 (m, 1H), 3.12-3.22 (m, 1H), 2.09-2.06 (m, 1H), 1.47 (s, 3H), 1.39-1.30 (m, 6H), 0.94-0.92 (m, 2H), 0.70-0.65 (m, 2H).

Example 289

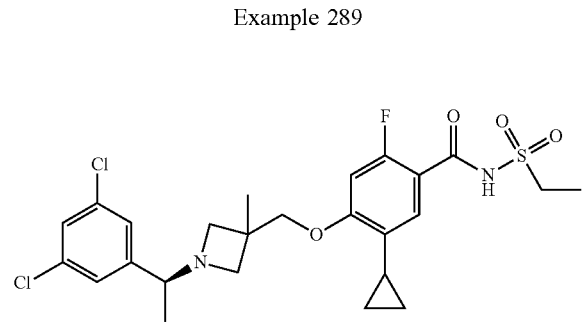

(S)-5-cyclopropyl-4-((1-(1-(3,5-dichlorophenyl)ethyl-3-methylazetidin-3-yl)methoxy)-N-(ethylsulfonyl)-2-fluorobenzamide The compound was synthesized as described in Example 68. The enantiomer was separated by chiral SFC from the racemate, the second eluting (faction was arbitrarily assigned as (S)-5-cyclopropyl-4-((1-(1-(3,5-dichlorophenyl)ethyl)-3-methylazetidin-3-yl)methoxy)-N-(ethylsulfonyl)-2-fluorobenzamide. Chiral HPLC (column: IC, 4.6×150 mm, 4.6×250 mm, 5 μm: mobile Phase: A: supercritical CO₂, B: MeOD (0.1% DEA), A:B=65:35; flow: 1.95 mL/min; column temperature: 39.9° C.; RT=3.22 min). LCMS (ESI) Method A: RT=6.04 min, m/z: 543.1 [M+H]⁺. ¹H-NMR (400 MHz, MeOD-d₄): δ7.40-7.33 (m, 4H), 6.84-6.76 (m, 1H), 4.10-4.04 (m, 2H), 3.72 (m, 1H), 3.55-3.43 (m, 2H), 3.45-3.33 (m, 2H), 3.36-3.35 (m, 1H), 3.12-3.22 (m, 1H), 2.09-2.06 (m, 1H), 1.47 (s, 3H), 1.39-1.30 (m, 6H), 0.94-0.92 (m, 2H), 0.71-0.63 (m, 2H).

Example 290

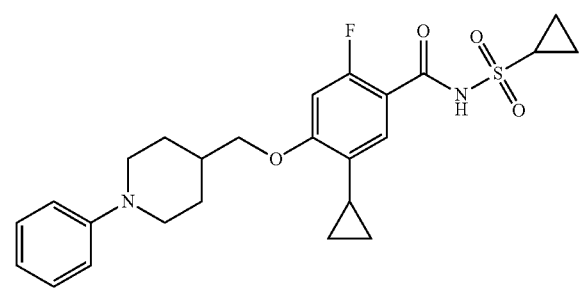 [SMILES: O=C(NS(=O)(=O)C1CC1)c1cc(C2CC2)c(OCC2CCN(c3ccccc3)CC2)cc1F]

5-Cyclopropyl-N-(cyclopropylsulfonyl)-2-fluoro-4-((1-phenylpiperidin-4-yl)methoxy)benzamide The compound was synthesized as described in Example 79. LCMS (ESI) Method A: RT=5.51 mm, m/z: 473.1 [M+H]⁺. ¹H-NMR (500 MHz, DMSO-d₆): δ7.27-7.23 (m, 1H), 7.25-7.23 (d, J=7 Hz, 2H), 7.04-7.03 (d, J=8.0 Hz, 2H), 6.87-6.84 (m, 1H), 6.78-6.75 (d, J=12.5 Hz, 1H), 4.00-3.99 (d, J=6.0 Hz, 2H), 3.77-3.75 (m, 2H), 3.26 (s, 1H), 2.82-1.72 (m, 2H), 2.09-1.99 (m, 4H), 1.71-1.65 (m, 2H), 1.23 (m, 2H), 1.06-1.05 (m, 2H), 0.93-0.66 (m, 2H), 0.65 (m, 2H).

Example 291

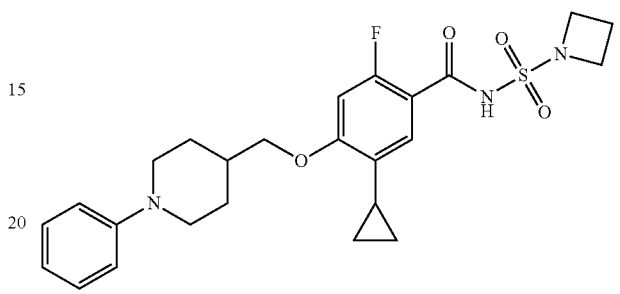

N-(azetidin-1-ylsulfonyl)-5-cyclopropyl-2-fluoro-4-((1-phenylpiperidin-4-yl)methoxy)benzamide The compound was synthesized as described in Example 79. LCMS (ESI) Method A: RT=5.40 min, m/z: 488.0 [M+H]⁺. ¹H-NMR (500 MHz, DMSO-d₆): δ7.23-7.18 (m, 3H), 6.95-6.94 (m, 2H), 6.75-6.69 (m, 2H), 3.93-3.92 (d, J=6.0 Hz, 2H), 3.75-3.73 (m, 2H), 3.68-3.65 (m, 4H), 2.72-2.68 (m, 2H), 2.01-1.89 (m, 6H), 1.49-1.46 (m, 2H), 0.87-0.84 (m, 2H), 0.54-0.52 (m, 2H).

Example 292

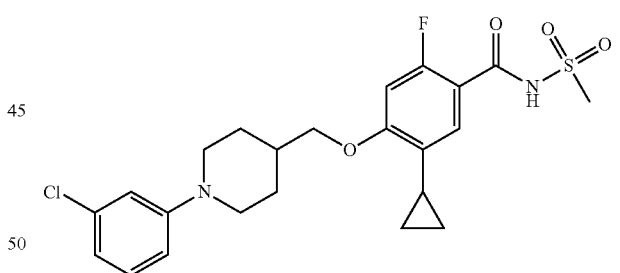

5-Cyclopropyl-4-((1-(3,5-dichlorophenyl)piperidin-4-yl)methoxy)-2-fluoro-N-(methylsulfonyl)benzamide The compound was synthesized as described in Example 79. LCMS (ESI) Method A: RT=6.07 min, m/z: 514.8 [M+H]⁺. ¹H-NMR (500 MHz, CDCl₃-D₄): δ7.20-7.19 (d, J=8.5 Hz, 1H), 6.93 (d, J=1.5 Hz, 2H), 6.82-6.79 (m, 2H), 3.95-3.94 (d, J=6.5 Hz, 2H), 3.86-3.83 (m, 2H), 3.04 (s, 3H), 2.82 (m. 2H), 1.98 (m, 2H), 1.84-1.82 (m, 2H), 1.43 (m, 2H), 0.86-0.84 (m, 2H), 0.60-0.59 (m, 2H).

Example 293

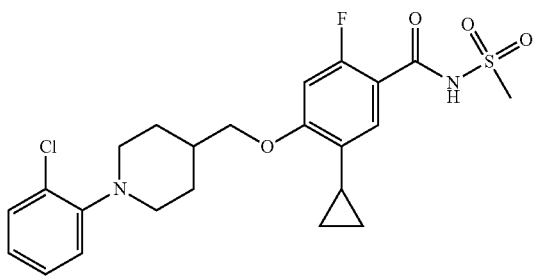 [SMILES: CS(=O)(=O)NC(=O)c1cc(C2CC2)c(OCC2CCN(c3ccccc3Cl)CC2)cc1F]

4-((1-(2-Chlorophenyl)piperidin-4-yl)methoxy)-5-cyclopropyl-2-fluoro-N-(methylsulfonyl)benzamide The compound was synthesized as described in Example 79. LCMS (ESI) Method A: RT=5.53 min, m/z: 480.9 [M+H]$^+$. $^1$H-NMR (500 MHz, DMSO-d$_6$): δ7.41-7.39 (m, 1H), 7.39-7.27 (m, 1H), 7.21-7.16 (m, 2H), 7.04-7.01 (m, 1H), 6.85-6.82 (m, 1H), 4.00-3.99 (d, J=5.5 Hz, 2H), 3.32 (m, 2H), 3.05-3.01 (m, 3H), 2.71-2.54 (m, 2H), 2.05-1.90 (m, 4H), 1.58-1.50 (m, 2H), 0.91-0.89 (m, 2H), 0.62-0.61 (m, 2H).

Example 294

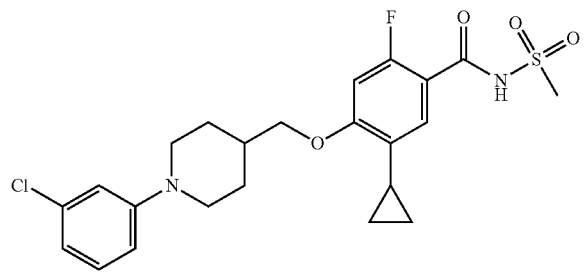 [SMILES: CS(=O)(=O)NC(=O)c1cc(C2CC2)c(OCC2CCN(c3cccc(Cl)c3)CC2)cc1F]

4-((1-(3-Chlorophenyl)piperidin-4-yl)methoxy)-5-cyclopropyl-2-fluoro-N-(methylsulfonyl)benzamide The compound was synthesized as described in Example 79. LCMS (ESI) Method A: RT=5.55 mm, m/z: 480.9 [M+H]$^+$. $^1$H-NMR (500 MHz, DMSO-d$_6$) δ7.20-7.17 (m, 2H), 6.94-6.90 (m, 3H), 6.74-6.72 (d, J=7.5 Hz 1H), 3.97-3.95 (d, J=6.5 Hz, 1H), 3.80-3.78 (m, 2H), 3.12-3.11 (s, 3H), 2.78-2.74 (m, 2H), 2.00-1.98 (m, 2H), 1.87-1.84 (m, 2H), 1.45-1.43 (m, 2H), 0.87-0.85 (m, 2H), 0.62-0.61 (m, 2H).

Example 295

Synthesis of 4-(((R)-1-((S)-1-(2-chloro-4-fluorophenyl)ethyl)piperidin-3-yl)oxy)-5-cyclopropyl-2-fluoro-N-(methylsulfonyl)benzamide

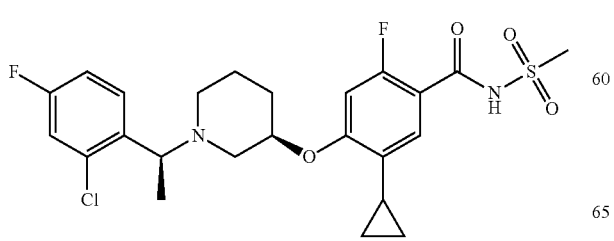

Step 1. Preparation of methyl 4-(((R)-1-((S)-1-(2-chloro-4-fluorophenyl)ethylpiperidin-3-yl)oxy)-5-cyclopropyl-2-fluorobenzoate and methyl 4-(((R)-1-((R)-1-(2-chloro-4-fluorophenyl)ethyl)piperidin-3-yl)oxy)-5-cyclopropyl-2-fluorobenzoate

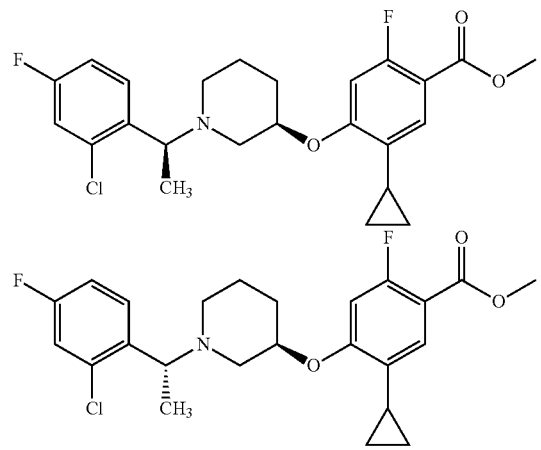

Following the procedure as described in Example 50 step 1, and making variations as required to replace 1,3-dichloro-5-(1-chloroethyl)benzene with 2-chloro-1-(1-chloroethyl)-4-fluorobenzene. The first eluting fraction was arbitrarily assigned as methyl 4-(((R)-1-((S)-1-(2-chloro-4-fluorophenyl)ethylpiperidin-3-yl)oxy)-5-cyclopropyl-2-fluorobenzoate was obtained as a colorless solid (0.17 g, 15%); 1H NMR (300 MHz, CDCl$_3$) δ7.50-7.42 (m, 2H), 7.06 (dd, J=2.6 Hz, 8.6 Hz, 1H), 6.87 (dt, J=2.5 Hz, 8.4 Hz, 1H), 6.52 (d, =12.9 Hz, 1H), 4.38-4.36 (m, 1H), 3.92 (q, J=6.6 Hz, 1H), 3.88 (s, 3H), 3.07-3.04 (m, 1H), 2.55-2.51 (m, 1H), 2.39-2.28 (m, 2H), 2.13-2.01 (m, 2H), 1.84-1.77 (m, 1H), 1.67-1.56 (m, 3H), 1.27 (d, J=6.5 Hz, 3H), 0.96-0.89 (m, 2H), 0.69-0.65 (m, 2H); MS(ES+) m/z 450.2, 452.2 (M+1).

The second eluting fraction was arbitrarily assigned as methyl 4-(((R)-1-((R)-1-(2-chloro-4-fluorophenyl)ethyl)piperidin-3-yl)oxy)-5-cyclopropyl-2-fluorobenzoate as a colorless solid (0.26 g, 22%): 1H NMR (300 MHz, CDCl$_3$) δ7.56-7.51 (m, 1H), 7.38 (d, J=8.4 Hz, 1H), 7.06-6.95 (m, 2H), 6.46 (d, J=13.0 Hz, 1H), 4.32-4.26 (m, 1H), 3.94 (q, =6.6 Hz, 1H), 3.86 (s, 3H), 2.96-2.89 (m, 2H), 2.39-1.83 (m, 6H), 1.68-1.45 (m, 2H), 1.27 (d, J=6.6 Hz, 3H), 0.90-0.84 (m, 2H), 0.64-0.59 (m, 2H); MS(ES+) m/z 450.2, 452.2 (M+1).

Step 2. Preparation of 4-(((R)-1-((S)-1-(2-chloro-4-fluorophenyl)ethyl)piperidin-3-yl)oxy)-5-cyclopropyl-2-fluorobenzoic acid

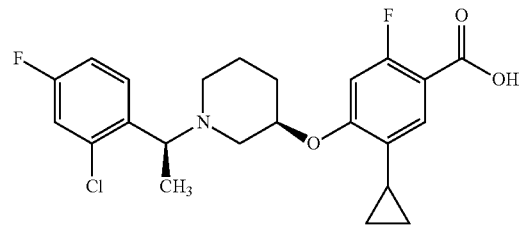 [SMILES: C[C@@H](c1ccc(F)cc1Cl)N1CCC[C@@H](Oc2cc(F)c(C(=O)O)cc2C2CC2)C1]

Following the procedure as described in Example 50 step 2, and making variations as required to replace methyl 5-cyclopropyl-4-(((R)-1-((S)-1-(3,5-dichlorophenyl)ethyl)-piperidin-3-yl)oxy)-2-fluorobenzoate with methyl 4-(((R)-1-((S)-1-(2-chloro-4-fluorophenyl)ethyl)piperidin-3-yl)oxy)-5-cyclopropyl-2-fluorobenzoate, the title compound was obtained as a colorless solid (0.04 g, 24%): MS(ES+) m/z 436.2, 438.2 (M+1); MS(ES−) m/z 434.3, 436.5 (M−1).

Step 3. Preparation of 4-(((R)-1-((S)-1-(2-chloro-4-fluorophenyl)ethyl)piperidin-3-yl)oxy)-5-cyclopropyl-2-4-N-(methylsulfonyl)benzamide

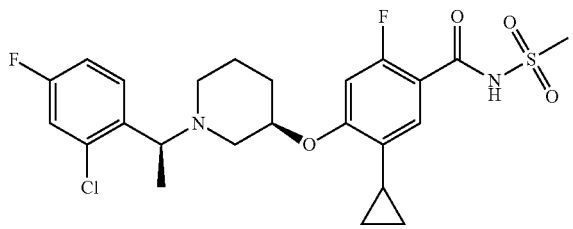 [SMILES: C[C@@H](c1ccc(F)cc1Cl)N1CCC[C@@H](Oc2cc(F)c(C(=O)NS(C)(=O)=O)cc2C2CC2)C1]

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with 4-(((R)-1-((S)-1-(2-chloro-4-fluorophenyl)ethyl)piperidin-3-yl)oxy)-5-cyclopropyl-2-fluorobenzoic acid, the title compound was obtained as a colorless solid (0.01 g, 32%); $^1$H NMR (300 MHz, DMSO-$d_6$) δ 11.85 (br s, 1H), 7.51 (dd, J=6.6 Hz, 8.6 Hz, 1H), 7.37 (dd, J=2.6 Hz, 8.9 Hz, 1H), 7.14 (d, J=8.4 Hz, 1H), 7.05 (dt, J=2.6 Hz, 8.6 Hz, 1H), 6.92 (d, J=13.1 Hz, 1H), 4.56-4.55 (m, 1H), 3.91-3.89 (m, 1H), 3.32 (s, 3H), 2.78-2.74 (m, 2H), 2.47-2.42 (m, 2H), 2.15-2.06 (m, 1H), 1.87-1.77 (m, 2H), 1.59-1.46 (m, 2H), 1.23 (d, J=6.4 Hz, 3H), 0.93-0.90 (m, 2H), 0.70-0.67 (m, 2H): MS(ES+) m/z 513.2, 515.1 (M+1): MS(ES−) m/z 511.2, 513.2 (M−1).

Example 296

Synthesis of 4-(((R)-1-((R)-1-(2-chloro-4-fluorophenyl)ethyl)piperidin-3-yl)oxy)-5-cyclopropyl-2-fluoro-N-(methylsulfonyl)benzamide

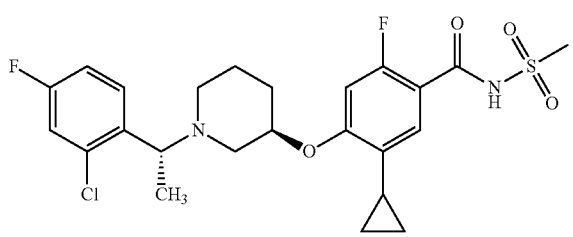

Step 1. Preparation of 4-(((R)-1-((R)-1-(2-chloro-4-fluorophenyl)ethyl)piperidin-3-yl)oxy)-5-cyclopropyl-2-fluorobenzoic acid

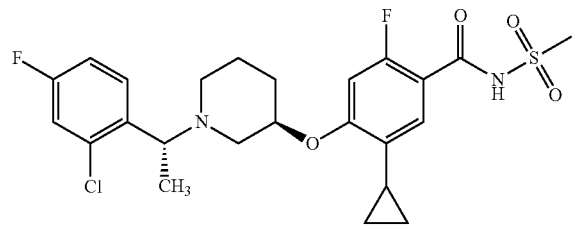

Following the procedure as described in Example 50 step 2 and making variations as required to replace methyl 5-cyclopropyl-4-(((R)-1-((S)-1-(3,5-dichlorophenyl)ethyl)piperidin-3-yl)oxy)-2-fluorobenzoate with methyl 4-(((R)-1-((R)-1-(2-chloro-4-fluorophenyl)ethyl)piperidin-3-yl)oxy)-5-cyclopropyl-2-fluorobenzoate, the title compound was obtained as a beige color solid (0.23 g, 99%); MS(ES+) m/z 436.2, 438.1 (M+1); MS(ES−) m/z 434.2, 436.2 (M−1).

Step 2. Preparation of 4-(((R)-1-((R)-1-(2-chloro-4-fluorophenyl)ethyl)piperidin-3-yl)oxy)-5-cyclopropyl-2-fluoro-N-(methylsulfonyl)benzamide Following the procedure as described in Example 17 step 2, and making variations as required to replace (R)-5-cyclopropyl-4-((1-(3,4-dichlorobenzyl)piperidin-3-yl)oxy)-2-fluorobenzoic acid with 4-(((R)-1-((R)-1-(2-chloro-4-fluorophenyl)ethyl)piperidin-3-yl)oxy)-5-cyclopropyl-2-fluorobenzoic acid, the title compound was obtained as a colorless solid (0.17 g, 48%): $^1$H NMR (300 MHz, DMSO-$d_6$) δ 11.82 (br s, 1H), 7.61 (dd, J=6.5 Hz, 8.7 Hz, 1H), 7.38 (dd, J=2.4 Hz, 8.8 Hz, 1H), 7.22 (dt, J=2.6 Hz, 8.5 Hz, 1H), 7.09 (d, J=8.4 Hz, 1H), 6.91 (d, J=13.1 Hz, 1H), 4.55-4.50 (m, 1H), 3.92 (q, J=6.3 Hz, 1H), 3.32 (s, 3H), 2.77-2.74 (m, 2H), 2.36-2.19 (m, 2H), 2.08-1.94 (m, 2H), 1.81-1.75 (m, 1H), 1.59-1.46 (m, 2H), 1.23 (d, J=6.6 Hz, 3H), 0.89-0.85 (m, 2H), 0.70-0.65 (m, 2H); MS(ES+) m/z 513.2, 515.1 (M+1); MS(ES−) m/z 511.2, 513.2 (M−1).

Example 297 and Example 298

Synthesis of 4-(((R)-1-((R)-1-(2-chloro-4-fluorophenyl)-2,2,2-trifluoroethyl)piperidin-3-yl)oxy)-5-cyclopropyl-2-fluoro-N-(methylsulfonyl)benzamide

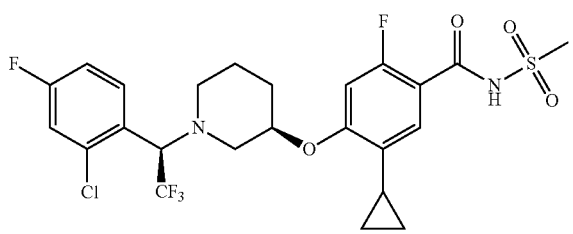 [SMILES: CS(=O)(=O)NC(=O)c1cc(C2CC2)c(O[C@@H]2CCCN([C@H](c3ccc(F)cc3Cl)C(F)(F)F)C2)cc1F]

And 4-(((R)-1-((S)-1-(2-chloro-4-fluorophenyl)-2,2,2-trifluoroethyl)piperidin-3-yl)oxy)-5-cyclopropyl-2-4-N-(methylsulfonyl)benzamide

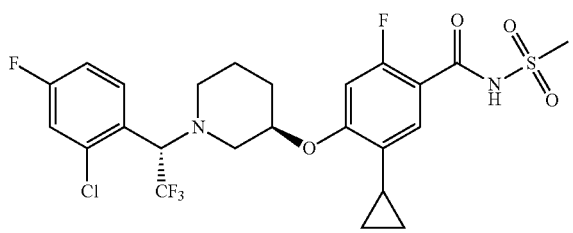

Step 1. Preparation of 1-(2-chloro-4-fluorophenyl)-2,2,2-trifluoroethyl trifluoromethanesulfonate

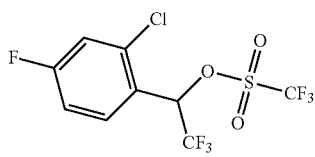 [SMILES: O=S(=O)(OC(c1ccc(F)cc1Cl)C(F)(F)F)C(F)(F)F]

To a solution of 1-(2-chloro-4-fluorophenyl)-2,2,2-trifluoroethanol (1.14 g, 5.00 mmol) and 2,6-dimethylpyridine (0.86 g, 8.00 mmol) in cyclohexane (10 mL) was added, dropwise trifluoromethanesulfonic anhydride (2.12 g, 7.50 mmol) at 10° C. The reaction mixture was stirred at auditions temperature for 5 hours, and diluted with hexanes (200 mL). The organic layer was washed with 1N aqueous hydrochloric acid solution (30 mL), 25% aqueous ammonium chloride solution (2×40 mL); dried over anhydrous sodium sulfate and concentrated in vacuo to afford the title compound as a colorless oil (1.30 g, 72%): $^1$H NMR (300 MHz, CDCl$_3$) δ7.66-7.61 (m, 1H), 7.26-7.22 (m, 1H), 7.19-7.12 (m, 1H), 6.46 (q, J=5.6 Hz, 1H).

Step 2. Preparation of methyl 4-(((3R)-1-(1-(2-chloro-4-fluorophenyl)-2,2,2-trifluoroethyl)piperidin-3-yl)oxy)-5-cyclopropyl-2-fluorobenzoate

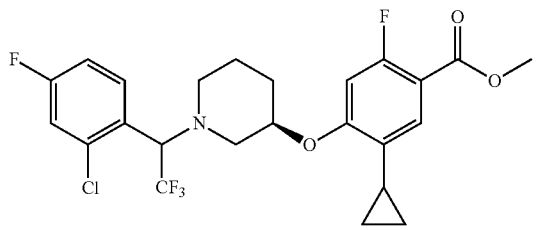 [SMILES: COC(=O)c1cc(C2CC2)c(O[C@@H]2CCCN(C(c3ccc(F)cc3Cl)C(F)(F)F)C2)cc1F]

To a mixture of (R)-methyl 5-cyclopropyl-2-fluoro-4-(piperidin-3-yloxy)benzoate (1.07 g, 3.66 mmol) and potassium carbonate (0.69 g, 4.99 mmol) in cyclohexane (10 mL) was added 1-(2-chloro-4-fluorophenyl)-2,2,2-trifluoroethyl trifluoromethanesulfonate (1.20 g, 3.33 mmol). The reaction mixture was heated at 70° C. for 72 hours, cooled to ambient temperature and diluted with ethyl acetate (250 mL). The organic layer was washed with 1N aqueous hydrochloric acid solution (30 mL) and 25% aqueous ammonium chloride solution (2×40 mL); dried over anhydrous sodium sulfate and concentrated in vacuo. The residue was purified by column chromatography (0-25% ethyl acetate in hexanes) afforded the title compound as a colorless oil (1.20 g, 71%); MS(ES+) m/z 504.1, 506.1 (M+1).

Step 3. Preparation of 4-(((3R)-1-(1-(2-chloro-4-fluorophenyl)-2,2,2-trifluoroethyl)piperidin-3-yl)oxy)-5-cyclopropyl-2-fluorobenzoic acid

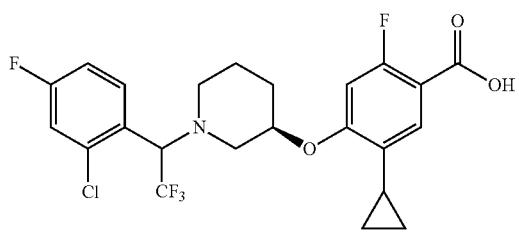

Following the procedure as described in Example 50 step 2 and making variations as required to replace methyl 5-cyclopropyl-4-(((R)-1-((S)-1-(3,5-dichlorophenyl)ethyl)-piperidin-3-yl)oxy)-2-fluorobenzoate and methyl with methyl 4-(((3R)-1-(1-(2-chloro-4-fluorophenyl)-2,2,2-trifluoroethyl)piperidin-3-yl)oxy)-5-cyclopropyl-2-fluorobenzoate, the title compound was obtained as a colorless oil (0.98 g, 92%): $^1$H NMR (300 MHz, CDCl$_3$) δ7.53-7.43 (m, 2H), 7.25-7.21 (m, 0.5H), 7.17-7.13 (m, 0.5H), 7.03-6.95 (m, 1H), 6.47 (d, J=12.9 Hz, 0.5H), 6.37 (d, J=12.9 Hz, 0.5H), 4.76-4.66 (m, 1H), 4.38-4.31 (m, 0.5H), 4.27-4.20 (m, 0.5H), 3.14-3.10 (m, 1H), 2.94-2.84 (m, 1H), 2.75-2.60 (m, 2H), 2.95-1.96 (m, 2H), 1.91-1.80 (m, 1H), 1.70-1.52 (m, 2H), 0.91-0.85 (m, 2H), 0.70-0.57 (m, 2H); MS(ES+) m/z 490.2, 492.2 (M+1); MS(ES−) m/z 488.2, 490.2 (M−1).

469

Step 4. Preparation of 4-(((R)-1-((R)-1-(2-chloro-4-fluorophenyl)-2,2,2-trifluoroethyl)piperidin-3-yl)oxy)-5-cyclopropyl-2-fluoro-N-(methylsulfonyl)benzamide

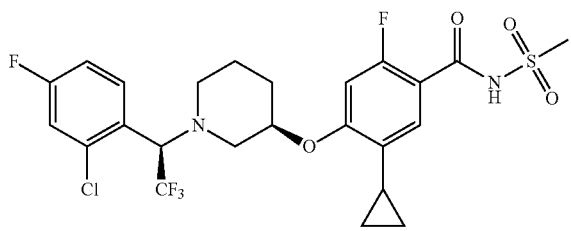

And 4-(((R)-1-((S)-1-(2-chloro-4-fluorophenyl)-2,2,2-trifluoroethyl)piperidin-3-yl)oxy)-5-cyclopropyl-2-fluoro-N-(methylsulfonyl)benzamide

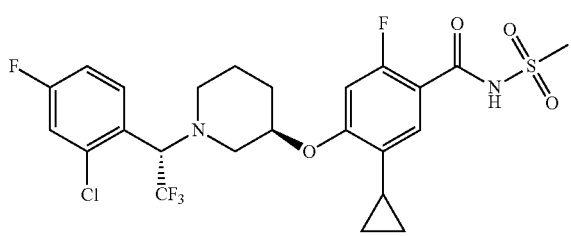

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with 4-(((3R)-1-(1-(2-chloro-4-fluorophenyl)-2,2,2-dichlorobenzyl)piperidin-3-yl)oxy)-5-cyclopropyl-2-fluorobenzoic acid. The residue was purified by preparative-HPLC, the first eluting fraction was arbitrarily assigned as 4-(((R)-1-((R)-1-(2-chloro-4-fluorophenyl)-2,2,2-trifluoroethyl)piperidin-3-yl)oxy)-5-cyclopropyl-2-fluoro-N-(methylsulfonyl)benzamide as a colorless solid (0.02 g, 4%): $^1$H NMR (300 MHz, CDCl$_3$) δ8.69 (d, J=16.0 Hz, 1H), 7.52-7.46 (m, 2H), 7.12 (dd, J=2.6 Hz, 8.4 Hz, 1H), 7.02-6.95 (m, 1H), 6.44 (d, J=14.6 Hz, 1H), 4.70 (q, J=8.8 Hz, 1H), 4.37-4.32 (m, 1H), 3.42 (s, 3H), 3.13-3.08 (m, 1H), 2.93-2.89 (m, 1H), 2.75-2.69 (m, 2H), 2.10-1.85 (m, 3H), 1.72-1.53 (m, 2H), 0.95-0.87 (m, 2H), 0.72-0.66 (m, 1H), 0.62-0.56 (m, 1H); MS(ES+) m/z 567.1, 569.1 (M+1); MS(ES−) m/z 565.1, 567.1 (M−1).

The second eluting fraction, was arbitrarily assigned as 4-(((R)-1-((S)-1-(2-chloro-4-fluorophenyl)-2,2,2-trifluoroethyl)piperidin-3-yl)oxy)-5-cyclopropyl-2-fluoro-N-(methylsulfonyl)benzamide as a colorless solid (0.01 g, 2%): $^1$H NMR (300 MHz, CDCl$_3$) δ8.68 (d, J=16.0 Hz, 1H), 7.57-7.51 (m, 2H), 7.26-7.22 (m, 1H), 7.04-6.97 (m, 1H), 6.38 (d, J=14.6 Hz, 1H), 4.73 (q, J=8.8 Hz, 1H), 4.31-4.23 (m, 1H), 3.41 (s, 3H), 3.16-3.12 (m, 1H), 2.91-2.85 (m, 1H), 2.78-2.60 (m, 2H), 2.09-1.99 (m, 2H), 1.70-1.54 (m, 3H), 0.94-0.91 (m, 2H), 0.67-0.63 (m, 2H); MS(ES+) m/z 567.1, 569.1 (M+1); MS(ES−) m/z 565.1, 567.1 (M−1).

470

Example 299

Synthesis of 5-cyclopropyl-4-((1-(1-(3,5-dichlorophenyl)-2,2,2-trifluoroethyl)piperidin-4-yl)methoxy)-2-fluoro-N-(methylsulfonyl)benzamide

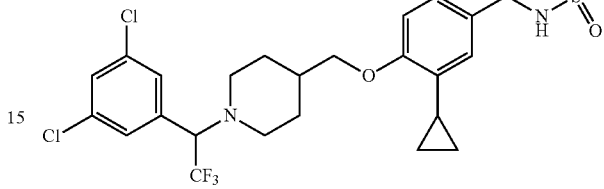

Step 1. Preparation of 1-(3,5-dichlorophenyl)-2,2,2-trifluoroethyl trifluoromethanesulfonate

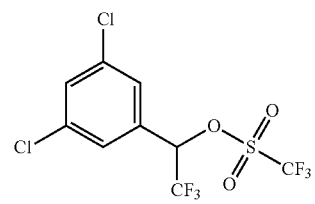 [SMILES: O=S(=O)(OC(c1cc(Cl)cc(Cl)c1)C(F)(F)F)C(F)(F)F]

Following the procedure as described in Example 297 step 1, and making variation as required to replace 1-(2-chloro-4-fluorophenyl)-2,2,2-trifluoroethanol with (1-(3,5-dichlorophenyl)-2,2,2-trifluoroethanol, the title compound was obtained as a colorless oil (1.30 g, 72%): $^1$H NMR (300 MHz, CDCl$_3$) δ7.66-7.671 (m, 1H), 7.19-7.12 (m, 2H), 6.46 (q, J=5.6 Hz, 1H).

Step 2. Preparation of tert-butyl 5-cyclopropyl-4-((1-(1-(3,5-dichlorophenyl)-2,2,2-trifluoroethyl)piperidin-4-yl)methoxy)-2-fluorobenzoate

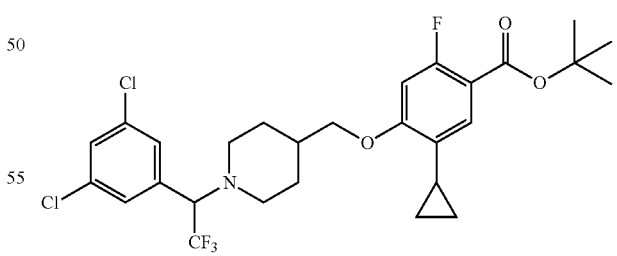

Following the procedure as described in Example 297 step 2, and making variations as required to replace (R)-methyl 5-cyclopropyl-2-fluoro-4-(piperidin-3-yloxy)benzoate with tert-butyl 5-cyclopropyl-2-fluoro-2-4-(piperidin-4-ylmethoxy)benzoate and to replace 1-(2-chloro-4-fluorophenyl)-2,2,2-trifluoroethyl trifluoromethanesulfonate with 1-(3,5-dichlorophenyl)-2,2,2-trifluoroethyl trifluoromethanesulfonate, the title compound was obtained as a colorless oil (1.20 g, 90%): $^1$H NMR (300 MHz, CDCl$_3$) δ7.37-7.29 (m, 4H), 6.47 (d, J=12.6 Hz, 1H), 4.49-4.01 (m, 1H), 3.80 (d, J=5.9 Hz, 2H), 2.99-2.93 (m, 2H), 2.47-2.29 (m, 2H), 2.01-1.92 (m, 1H), 1.84-1.81 (m, 3H), 1.55 (s, 9H), 1.50-1.33 (m, 2H), 0.89-0.83 (m, 2H), 0.63-0.57 (m, 2H).

Step 3. Preparation of 5-cyclopropyl-4-((1-(1-(3,5-dichlorophenyl)-2,2,2-trifluoroethyl)piperidin-4-yl)methoxy)-2-fluorobenzoic acid

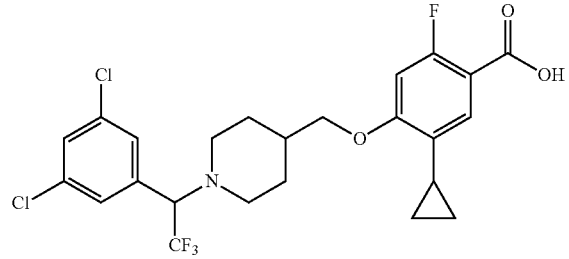 [SMILES: O=C(O)c1cc(C2CC2)c(OCC2CCN(C(c3cc(Cl)cc(Cl)c3)C(F)(F)F)CC2)cc1F]

To a solution of tert-butyl 5-cyclopropyl-4-((1-(1-(3,5-dichlorophenyl)-2,2,2-trifluoro)piperidin-4-yl)methoxy)-2-fluorobenzoate (1.10 g, 1.91 mmol) in dichloromethane (30 mL) was added trifluoroacetic acid (10 mL). The resulting solution was stirred at ambient temperature for 1 hour and then concentrated in vacuo to provide the title compound as a gummy solid (1.0 g, 99%): MS(ES+) m/z 520.1, 522.1 (M+1); MS(ES−) m/z 518.1, 520.1 (M−1).

Step 4. Preparation of 5-cyclopropyl-4-((1-(1-(3,5-dichlorophenyl)-2,2,2-trifluoroethyl)piperidin-4-yl)methoxy)-2-fluoro-N-(methylsulfonyl)benzamide

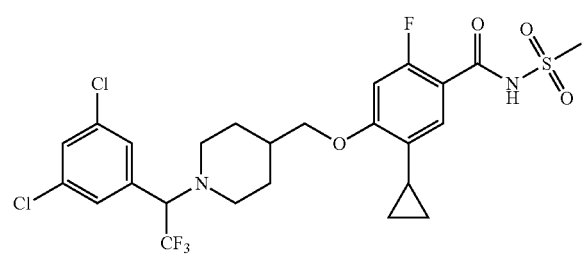 [SMILES: CS(=O)(=O)NC(=O)c1cc(C2CC2)c(OCC2CCN(C(c3cc(Cl)cc(Cl)c3)C(F)(F)F)CC2)cc1F]

Following the procedure as described in Example 3 step 5, and making variations as required to replace (R)-5-cyclopropyl-4-((1-(3,5-dichlorobenzyl)piperidin-3-yl)oxy)-2-fluorobenzoic acid with 5-cyclopropyl-4-((1-(1-3,5-dichlorophenyl)-2,2,2-trifluoroethyl)piperidin-4-yl)methoxy)-2-fluorobenzoic acid, and to replace cyclopropylsulfonamide with methanesulfonamide, the title compound was obtained as a colorless solid (0.35 g, 50%), $^1$H NMR (300 MHz, DMSO-d$_6$) δ 11.88 (br s, 1H), 7.72 (s, 1H), 7.45-7.44 (m, 2H), 7.12 (d, J=8.3 Hz, 1H), 6.93 (d, J=13.0 Hz, 1H), 4.77 (q, J=9.3 Hz, 1H), 3.91 (d, J=5.7 Hz, 2H), 3.33 (s, 3H), 3.00-2.99 (m, 2H), 2.33-2.25 (m, 1H), 2.04-1.95 (m, 2H), 1.79-1.70 (m, 3H), 1.41-1.30 (m, 2H), 0.90-0.84 (m, 2H), 0.69-0.64 (m, 2H); MS(ES+) m/z 597.1, 599.0 (M+1).

Example 300

Synthesis of 4-((1-(1-(2-chloro-4-fluorophenyl)-2,2,2-trifluoroethyl)piperidin-4-yl)methoxy)-5-cyclopropyl-2-fluoro-N-(methylsulfonyl)benzamide

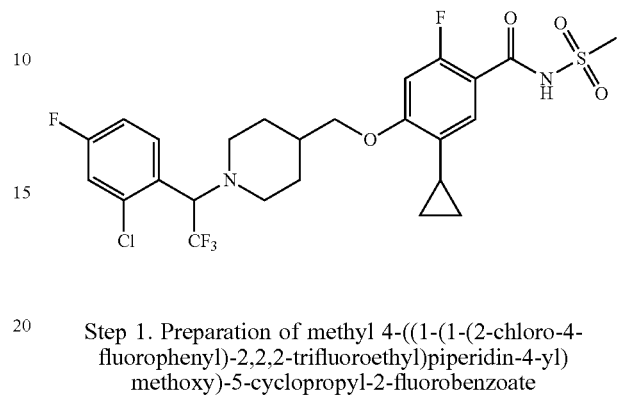

Step 1. Preparation of methyl 4-((1-(1-(2-chloro-4-fluorophenyl)-2,2,2-trifluoroethyl)piperidin-4-yl)methoxy)-5-cyclopropyl-2-fluorobenzoate

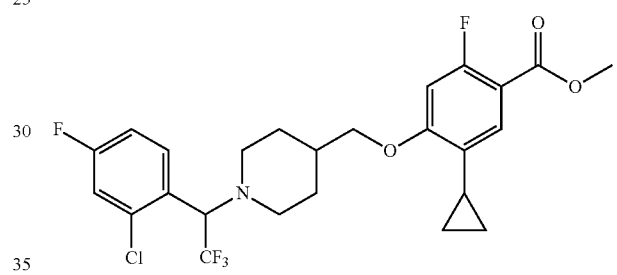

Following the procedure as described in Example 297 step 2, and making variation as required to replace (R)-methyl 5-cyclopropyl-2-fluoro-4-(piperidin-3-yloxy)benzoate with tert-butyl 5-cyclopropyl-2-fluoro-4-(piperidin-4-ylmethoxy)benzoate, the title compound was obtained as a colorless solid (0.80 g, 47%): $^1$H NMR (300 MHz, CDCl$_3$) δ7.59-7.54 (m, 1H), 7.43 (d, J=8.3 Hz, 1H), 7.20 (dd, J=2.6 Hz, 8.4 Hz, 1H), 7.03 (dt, J=2.6 Hz, 8.3 Hz, 1H), 6.51 (d, 7-12.7 Hz, 1H), 4.69 (q, J=8.7 Hz, 1H), 3.87 (s, 3H), 3.81 (d, J=6.0 Hz, 2H), 3.13-3.09 (m, 1H), 3.00-2.96 (m, 1H), 2.52 (t, J=11.2 Hz, 1H), 2.30 (t, J=11.1 Hz, 1H), 2.03-1.94 (m, 3H), 1.83-1.77 (m, 3H), 1.48-1.31 (m, 2H), 0.90-1.85 (m, 2H), 0.65-0.59 (m, 2H); MS(ES+) m/z 518.1, 520.1 (M+1).

Step 2. Preparation of 4-((1-(1-(2-chloro-4-fluorophenyl)-2,2,2-trifluoroethyl)piperidin-4-yl)methoxy)-5-cyclopropyl-2-fluorobenzoic acid

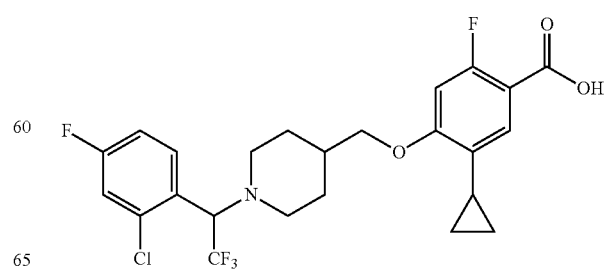

Following the procedure as described in Example 50 step 2 and making variations as required to replace methyl 5-cyclopropyl-4-(((R)-1-((S)-1-(3,5-dichlorophenyl)ethyl)piperidin-3-yl)oxy)-2-fluorobenzoate with methyl 4-((1-(1-(2-chloro-4-fluorophenyl)-2,2,2-trifluoroethyl)piperidin-4-yl)methoxy)-5-cyclopropyl-2-fluorobenzoate, the title compound was obtained as a colorless solid (0.75 g, 96%): $^1$H NMR (300 MHz, DMSO-$d_6$) δ12.82 (s, 1H), 7.65-7.59 (m, 2H), 7.36-7.28 (m, 2H), 6.87 (d, J=13.1 Hz, 1H), 4.84 (q, J=9.1 Hz, 1H), 3.90 (d, J=5.7 Hz, 2H), 3.07-2.95 (m, 2H), 2.49-2.40 (m, 1H), 2.20-2.13 (m, 1H), 2.02-1.93 (m, 1H), 1.77-1.74 (m, 3H), 1.33-1.27 (m, 2H), 0.93-0.83 (m, 2H), 0.59-0.54 (m, 2H); MS(ES+) m/z 504.1, 506.1 (M+1);

Step 3. Preparation of 4-((1-(1-(2-chloro-4-fluorophenyl)-2,2,2-trifluoroethyl)piperidin-4-yl)methoxy)-5-cyclopropyl-2-fluoro-N-(methylsulfonyl)benzamide

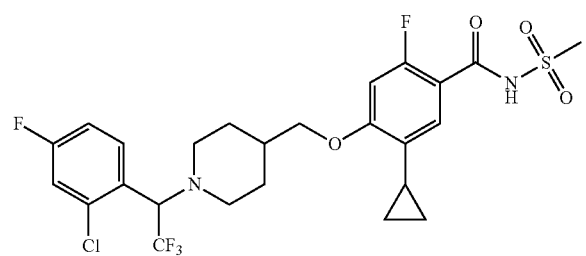 [SMILES: CS(=O)(=O)NC(=O)c1cc(C2CC2)c(OCC2CCN(C(c3ccc(F)cc3Cl)C(F)(F)F)CC2)cc1F]

Following the procedure as described in Example 3 step 5, and making variation as required to replace (R)-5-cyclopropyl-4-((1-(3,5-dichlorobenzyl)piperidin-3-yl)oxy)-2-fluorobenzoic acid with 4-((1-(1-(2-chloro-4-fluorophenyl)-2,2,2-trifluoroethyl)piperidin-4-yl)methoxy)-5-cyclopropyl-2-fluorobenzoic acid and to replace cyclopropylsulfonamide with methanesulfonamide, the title compound was obtained as a colorless solid (0.32 g, 56%): $^1$H NMR (300 MHz, DMSO-$d_6$) δ11.88 (br s, 1H), 7.65-7.59 (m, 2H), 7.33 (dt, J=2.7 Hz, 8.5 Hz, 1H), 7.12 (d, J=8.3 Hz, 1H), 6.93 (d, J=13.0 Hz, 1H), 4.84 (q, J=9.0 Hz, 1H), 3.91 (d, J=5.6 Hz, 2H), 3.33 (s, 3H), 3.01. (dd, J=11.1 Hz, 27.2 Hz, 2H), 2.49-2.40 (m, 1H), 2.16 (t, J=10.9 Hz, 1H), 2.03-1.94 (m, 1H), 1.77-1.74 (m, 3H), 1.38-1.27 (m, 2H), 0.90-0.83 (m, 2H), 0.68-0.63 (m, 2H); MS(ES+) m/z 581.2, 58.3.2 (M+1); MS(ES−) m/z 579.2, 581.2 (M−1).

Example 301

Synthesis 4-((1-(1-(3-chloro-4-fluorophenyl)-2,2,2-trifluoroethyl)piperidin-4-yl)methoxy)-5-cyclopropyl-2-fluoro-N-(methylsulfonyl)benzamide

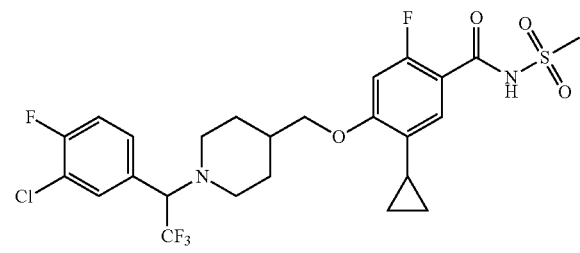 [SMILES: CS(=O)(=O)NC(=O)c1cc(C2CC2)c(OCC2CCN(C(c3ccc(F)c(Cl)c3)C(F)(F)F)CC2)cc1F]

Step 1. Preparation of 1-(3-chloro-4-fluorophenyl)-2,2,2-trifluoroethyl trifluoromethanesulfonate

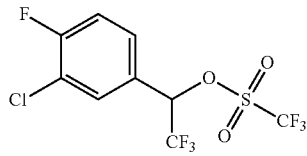 [SMILES: O=S(=O)(OC(c1ccc(F)c(Cl)c1)C(F)(F)F)C(F)(F)F]

Following the procedure as described in Example 297 step 1, and making variation as required to replace 1-(2-chloro-4-fluorophenyl)-2,2,2-trifluoroethanol with (1-(3-chloro-4-fluorophenyl)-2,2,2-trifluoroethanol, the title compound was obtained as a brown oil (4.60 g, 76%): $^1$H NMR (300 MHz, CDCl$_3$) δ7.58-7.55 (m, 1H), 7.42-7.37 (m, 1H), 7.29-7.24 (m, 1H), 5.78 (q, J=5.7 Hz, 1H).

Step 2. Preparation of tert-butyl 4-((1-(1-(3-chloro-4-fluorophenyl)-2,2,2-trifluoroethyl)piperidin-4-yl)methoxy)-5-cyclopropyl-2-fluorobenzoate

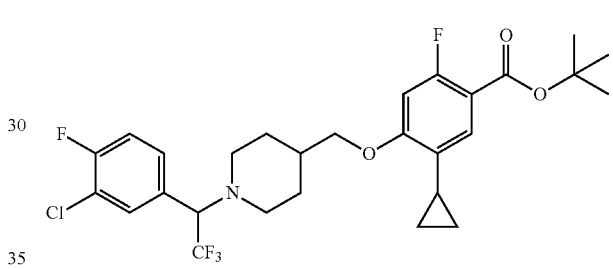

Following the procedure as described in Example 297 step 2, and making variation as required to replace (R)-methyl 5-cyclopropyl-2-fluoro-4-(piperidin-3-yloxy)benzoate with tert-butyl 5-cyclopropyl-2-fluoro-4-(piperidin-4-ylmethoxy)benzoate and to replace 1-(2-chloro-4-fluorophenyl)-2,2,2-trifluoroethyl trifluoromethanesulfonate with 1-(3-chloro-4-fluorophenyl)-2,2,2-trifluoroethyl trifluoromethanesulfonate, the title compound was obtained as a pale yellow oil (0.70 g, 54%): $^1$H NMR (300 MHz, CDCl$_3$) δ7.47-7.44 (m, 1H), 7.36 (d, J=8.4 Hz, 1H), 7.29-7.24 (m, 1H), 7.13 (t, J=8.6 Hz, 1H), 6.46 (d, J=12.6 Hz, 1H), 4.05 (q, J=8.7 Hz, 1H), 3.79 (d, J=5.9 Hz, 2H), 2.98-2.95 (m, 2H), 2.41 (t, J=11.2 Hz, 1H), 2.27 (d, J=11.4 Hz, 1H), 2.01-1.91 (m, 1H), 1.83-1.79 (m, 3H), 1.54 (m, 9H), 1.48-1.33 (m, 2H), 0.88-0.82 (m, 2H), 0.62-0.57 (m, 2H); MS(ES+) m/z 506.0, 508.0 (M+1).

Step 3. Preparation of 4-((1-(1-(3-chloro-4-fluorophenyl)-2,2,2-trifluoroethyl)piperidin-4-yl)methoxy)-5-cyclopropyl-2-fluorobenzoic acid

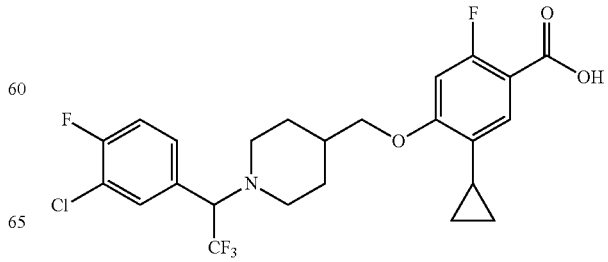

Following the procedure as described in Example 299 step 3, and making variation as required to replace tert-butyl 5-cyclopropyl-4-((1-(1-(3,5-dichlorophenyl)-2,2,2-trifluoroethyl)piperidin-4-yl)methoxy)-2-fluorobenzoate with tert-butyl 4-((1-(1-(3-chloro-4-fluorophenyl)-2,2,2-trifluoroethyl)piperidin-4-yl)methoxy)-5-cyclopropyl-2-fluorobenzoate, the title compound was obtained as a colorless solid (0.55 g, 87%): MS(ES+) m/z 504.1, 506.9 (M+1); MS(ES−) m/z 502.1, 504.1 (M−1).

Step 4. Preparation of 4-((1-(1-(3-chloro-4-fluorophenyl)-2,2,2-trifluoroethyl)piperidin-4-yl)methoxy)-5-cyclopropyl-2-fluoro-N-(methylsulfonyl)benzamide

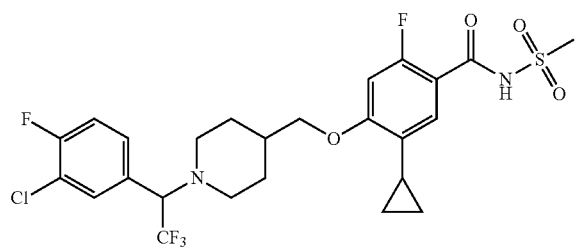 [SMILES: CS(=O)(=O)NC(=O)c1cc(C2CC2)c(OCC2CCN(C(c3ccc(F)c(Cl)c3)C(F)(F)F)CC2)cc1F]

Following the procedure as described in Example 3 step 5, and making variations as required to replace (R)-5-cyclopropyl-4-((1-(3,5-dichlorobenzyl)piperidin-3-yl)oxy)-2-fluorobenzoic acid with 4-((1-(1-(3-chloro-4-fluorophenyl)-2,2,2-trifluoroethyl)piperidin-4-yl)methoxy)-5-cyclopropyl-2-fluorobenzoic acid and to replace cyclopropylsulfonamide with methanesulfonamide, the title compound was obtained as a colorless solid (0.23 g, 39%): $^1$H NMR (300 MHz, DMSO-$d_6$) δ 11.88 (br s, 1H), 7.63-7.60 (m, 1H), 7.53-7.41 (m, 2H), 7.12 (d, J=8.3 Hz, 1H), 6.93 (d, J=13.0 Hz, 1H), 4.72 (q, J=9.4 Hz, 1H), 3.91 (d, J=5.9 Hz, 2H), 3.33 (s, 3H), 3.01-2.98 (m, 2H), 231-2.24 (m, 1H), 2.05-1.94 (m, 2H), 1.78-1.66 (m, 3H), 1.42-1.29 (m, 2H), 0.90-0.84 (m, 2H), 0.69-0.63 (m, 2H); MS(ES+) m/z 581.1, 583.1 (M+1); MS(ES−) m/z 579.1, 581.0 (M−1).

Example 302

Synthesis of 5-cyclopropyl-4-(2-(1-(3,5-dichlorobenzyl)piperidin-4-yl)ethoxy)-2-fluoro-N-(methylsulfonyl)benzamide, trifluoroacetic acid salt

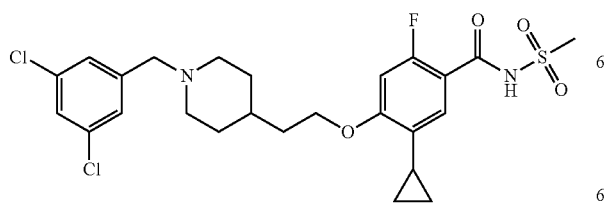

Step 1. Preparation of tert-butyl 4-(2-(4-tert-butoxycarbonyl)-2-chloro-5-fluorophenoxy)ethyl)piperidin-1-carboxylate

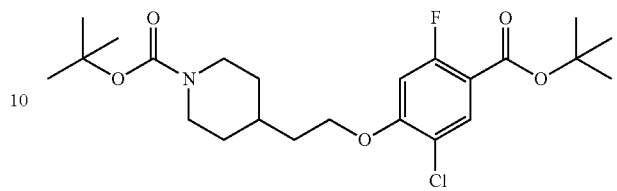

Following the procedure as described in Example 3 step 1, and making variation as required to replace (R)-tert-butyl 3-hydroxypiperidine-1-carboxylate with tert-butyl 4-(2-hydroxyethyl)piperidine-1-carboxylate, the title compound was obtained as a colorless oil. (3.80 g, 95%): MS(ES+) m/z 458.2, 460.2 (M+1).

Step 2. Preparation of tert-butyl 4-(2-(4-tert-butoxycarbonyl)-2-cyclopropyl-5-fluorophenoxy)ethyl)piperidine-1-carboxylate

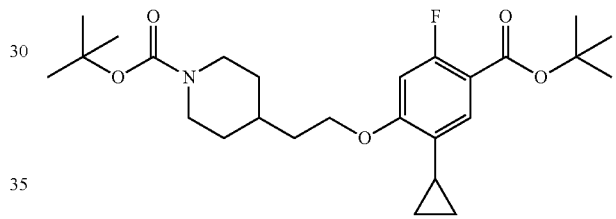

Following the procedure as described in Example 3 step 2, and making variation as required to replace (R)-tert-butyl 3-(4-(tert-butoxycarbonyl)-2-chloro-5-fluorophenoxy)piperidine-1-carboxylate with tert-butyl 4-(2-(4-(tert-butoxycarbonyl)-2-chloro-5-fluorophenoxy)ethyl)piperidine-1-carboxylate, the title compound was obtained as a light yellow oil (1.90 g, 95%): $^1$H NMR (300 MHz, CDCl$_3$) δ 7.34 (d, J=8.4 Hz, 1H), 6.48 (d, J=12.7 Hz, 1H), 4.10-3.99 (m, 4H), 2.67 (t, J=12.4 Hz, 2H), 2.01-1.92 (m, 1H), 1.80-1.63 (m, 5H), 1.53 (s, 9H), 1.42 (s, 9H), 1.22-1.11 (m, 2H), 0.89-0.82 (m, 2H), 0.62-0.57 (m, 2H): MS(ES+) m/z 464.3 (M+1).

Step 3. Preparation of 5-cyclopropyl-2-fluoro-4-(2-(piperidin-4-yl)ethoxy)benzoic acid

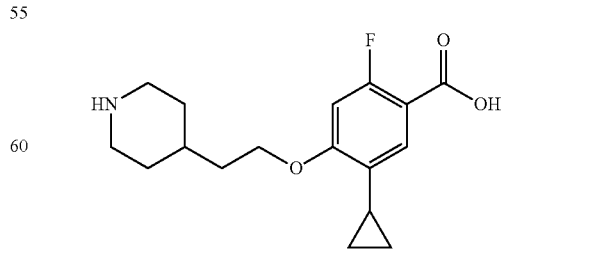

Following the procedure as described in Example 3 step 3, and making variation as required to replace (R)-tert-butyl 3-(4-(tert-butoxycarbonyl)-2-cyclopropyl-5-fluorophenoxy)-piperidine-1-carboxylate with tert-butyl 4-(2-(4-(tert-butoxycarbonyl)-2-cyclopropyl-5-fluorophenoxy)ethyl)piperidine-1-carboxylate, the title compound was obtained as trifluoroacetic acid salt (1.72 g, 99%): MS(ES+) m/z 308.1 (M+1).

Step 4. Preparation of 5-cyclopropyl-4-(2-(1-(3,5-dichlorobenzyl)piperidin-4-yl)ethoxy)-2-fluorobenzoic acid, trifluoroacetic acid salt

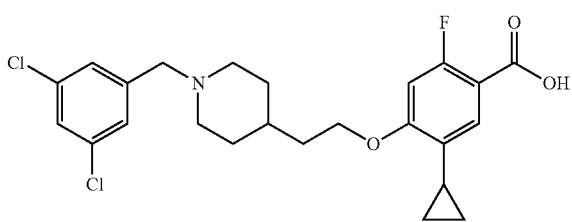 [SMILES: O=C(O)c1cc(C2CC2)c(OCCC2CCN(Cc3cc(Cl)cc(Cl)c3)CC2)cc1F]

Following the procedure as described in Example 3 step 4, and making variation as required to replace (R)-5-cyclopropyl-2-fluoro-4-(piperidin-4-yloxy)benzoic acid with 5-cyclopropyl-2-fluoro-4-(2-(piperidin-4-yl)ethoxy)benzoic acid, the title compound was obtained (1.37 g, 56%): $^1$M NMR (300 MHz, DMSO-d$_6$) δ12.87 (brs, 1H), 9.62 (br, 1H), 7.76 (s, 1H), 7.61-7.60 (m, 2H), 7.31 (d, J=8.5 Hz, 1H), 6.92 (d, J=13.1 Hz, 1H), 4.29-4.12 (m, 4H), 3.40-3.36 (m, 2H), 2.95-2.88 (m, 2H), 2.02-1.74 (m, 6H), 1.48-1.37 (m, 2H), 0.92-0.86 (m, 2H), 0.62-0.57 (m, 2H); MS(ES+) m/z 466.1, 468.0 (M+1).

Step 5. Preparation of 5-cyclopropyl-4-(2-(1-(3,5-dichlorobenzyl)piperidin-4-yl)ethoxy)-2-fluoro-N-(methylsulfonyl)benzamide, trifluoroacetic acid salt

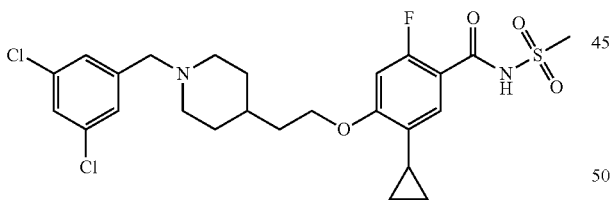

Following the procedure as described in Example 3 step 5, and making variation as required to replace (R)-5-cyclopropyl-4-((1-(3,5-dichlorobenzyl)piperidin-3-yl)oxy)-2-fluorobenzoic acid with 5-cyclopropyl-4-(2-(1-(3,5-dichlorobenzyl)piperidin-4-yl)ethoxy)-2-fluorobenzoic acid and cyclopropylsulfonamide with methanesulfonamide, the title compound was obtained as a colorless solid (0.02 g, 10%): $^1$H NMR (300 MHz, DMSO-d$_6$) δ11.87 (br s, 1H), 9.55 (br s, 1H), 7.74-7.72 (m, 1H), 7.58-7.57 (m, 2H), 7.09 (d, J=8.3 Hz, 1H), 6.95 (d, J=13.0 Hz, 1H), 4.26 (s, 2H), 4.10-4.08 (m, 2H), 3.37-3.33 (m, 2H), 3.30 (s, 3H), 2.94-2.86 (or, 2H), 2.01-1.89 (m, 3H), 1.72-1.68 (m, 3H), 1.45-1.37 (m, 2H), 0.88-0.82 (m, 2H), 0.67-0.62 (m, 2H); MS(ES+) m/z 543.0, 545.0 (M+1).

Example 303

Synthesis of 5-cyclopropyl-4-(2-(1-(3,5-dichlorobenzyl)piperidin-4-yl)ethoxy)-N-(ethylsulfonyl)-2-fluorobenzamide, trifluoroacetic acid salt

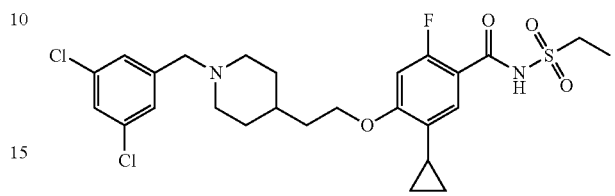

Following the procedure as described in Example 3 step 5, and making variation as required to replace (R)-5-cyclopropyl-4-((1-(3,5-dichlorobenzyl)piperidin-3-yl)oxy)-2-fluorobenzoic acid with 5-cyclopropyl-4-(2-(1-(3,5-dichlorobenzyl)piperidin-4-yl)ethoxy)-2-fluorobenzoic acid and to replace cyclopropylsulfonamide with ethanesulfonamide, the title compound was obtained as a colorless solid (0.06 g, 34%); $^1$H NMR (300 MHz, DMSO-d$_6$) δ11.78 (br s, 1H), 9.73 (br s, 1H), 7.73-7.72 (m, 1H), 7.58-7.57 (m, 2H), 7.09 (d, J=8.3 Hz, 1H), 6.94 (d, J=13.0 Hz, 1H), 4.26 (s, 2H), 4.10-4.08 (m, 2H), 3.44 (q, J=7.3 Hz, 2H), 3.37-3.33 (m, 2H), 2.94-2.86 (m, 2H), 2.01-1.88 (m, 3H), 1.72-1.68 (m, 3H), 1.45-1.37 (m, 2H), 1.21 (t, J=7.3 Hz, 3H), 0.88-0.82 (m, 2H), 0.67-0.62 (m, 2H); MS(ES+) m/z 557.0, 559.0 (M+1).

Example 304

Synthesis of 5-cyclopropyl-N-(cyclopropylsulfonyl)-4-(2-(1-(3,5-dichlorobenzyl)piperidin-4-yl)ethoxy)-2-fluorobenzamide, trifluoroacetic acid salt

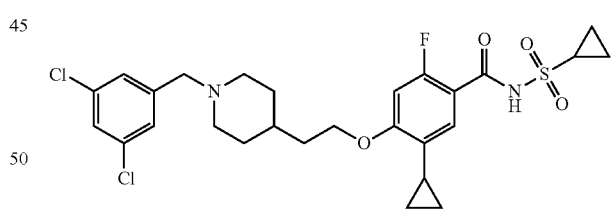

Following the procedure as described in Example 3 step 5, and making variation as required to replace (R)-5-cyclopropyl-4-((1-(3,5-dichlorobenzyl)piperidin-3-yl)oxy)-2-fluorobenzoic acid with 5-cyclopropyl-4-(2-(1-(3,5-dichlorobenzyl)piperidin-4-yl)ethoxy)-2-fluorobenzoic acid, the title compound was obtained as a colorless solid (0.10 g, 56%): $^1$H NMR (300 MHz, DMSO-d$_6$) δ11.81 (br s, 1H), 9.75 (br s, 1H), 7.73-7.72 (m, 1H), 7.58-7.57 (m, 1H), 7.09 (d, J=8.3 Hz, 1H), 6.95 (d, J=13.0 Hz, 1H), 4.26 (s, 2H), 4.10-4.08 (m, 2H), 3.37-3.33 (m, 2H), 3.08-3.00 (m, 1H), 2.94-2.86 (m, 2H), 2.01-1.89 (m, 3H), 1.72-1.68 (m, 3H), 1.45-1.37 (m, 2H), 1.10-1.05 (m, 4H), 0.88-0.82 (m, 2H), 0.67-0.62 (m, 2H); MS(ES+) m/z 568.9, 570.9 (M-1).

Example 305

Synthesis of (R)-5-cyclopropyl-4-((1-((6-cyclopropyl-4-(trifluoromethyl)pyridin-2-yl)methyl)piperidin-3-yl)oxy)-2-fluoro-N-(methylsulfonyl)benzamide

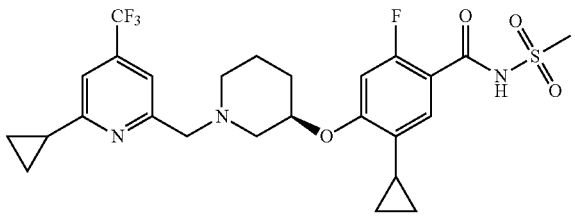 [SMILES: CS(=O)(=O)NC(=O)c1cc(C2CC2)c(O[C@@H]2CCCN(Cc3cc(C(F)(F)F)cc(C4CC4)n3)C2)cc1F]

Following the procedure as described in Example 50 step 1, and snaking variations as required to replace (R)-methyl 5-cyclopropyl-2-fluoro-4-(piperidin-3-yloxy)benzoate with (R)-5-cyclopropyl-2-fluoro-N-(methylsulfonyl)-4-(piperidin-3-yloxy)benzamide and to replace 1,3-dichloro-5-(1-chloroethyl)benzene with 2-(chloromethyl)-6-cyclopropyl-4-(trifluoromethyl)pyridine, the title compound was obtained as a colorless solid (0.17 g, 28%): $^1$H NMR (300 MHz, DMSO-d$_6$) δ11.71 (br s, 1H), 7.54 (s, 1H), 7.47 (s, 1H), 7.13 (d, J=8.4 Hz, 1H), 6.99 (d, J=13.2 Hz, 1H), 4.66 (br r s, 1H), 3.79-3.67 (m, 2H), 3.29 (s, 3H), 2.87-2.84 (m, 1H), 2.59-2.55 (m, 2H), 2.46-2.43 (m, 1H), 2.28-2.19 (m, 1H), 2.12-2.03 (m, 1H), 1.91-1.80 (m, 2H), 1.63-1.58 (m, 2H), 1.03-0.82 (m, 6H), 0.74-0.65 (m, 2H); MS(ES+) m/z 556.1 (M+1); MS(ES−) m/z 554.1 (M−1).

Example 306

Synthesis of 5-cyclopropyl-4-((1-((6-cyclopropyl-4-(trifluoromethyl)pyridin-2-yl)methyl)piperidin-4-yl)methoxy)-2-fluoro-N-(methylsulfonyl)benzamide

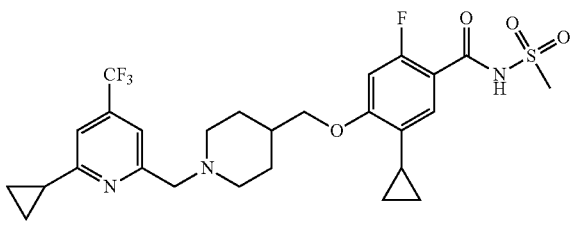 [SMILES: CS(=O)(=O)NC(=O)c1cc(C2CC2)c(OCC2CCN(Cc3cc(C(F)(F)F)cc(C4CC4)n3)CC2)cc1F]

Step 1. Preparation of tert-butyl 5-cyclopropyl-4-((1-((6-cyclopropyl-4-(trifluoromethyl)pyridin-2-yl)methyl)piperidin-4-yl)methoxy)-2-fluorobenzoate

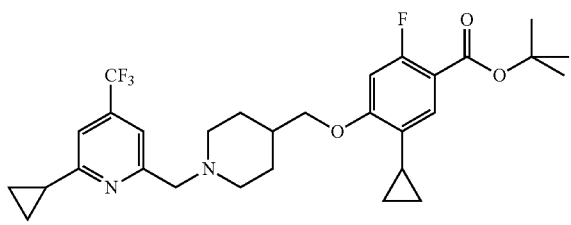 [SMILES: CC(C)(C)OC(=O)c1cc(C2CC2)c(OCC2CCN(Cc3cc(C(F)(F)F)cc(C4CC4)n3)CC2)cc1F]

Following the procedure as described in Example 50 step 1, and making variations as required to replace (R)-methyl 5-cyclopropyl-2-fluoro-4-(piperidin-3-yloxy)benzoate with tert-butyl 5-cyclopropyl-2-fluoro-4-(piperidin-4-ylmethoxy)benzoate and to replace 1,3-dichloro-5-(1-chloroethyl)benzene with 2-(chloromethyl)-6-cyclopropyl-4-(trifluoromethyl)pyridine, the title compound was obtained as a colorless solid (1.00 g, 64%): $^1$H NMR (300 MHz, CDCl$_3$) δ7.40-7.35 (m, 2H), 7.19 (s, 1H), 6.49 (d, J=12.7 Hz, 1H), 3.85 (d, J=5.9 Hz, 2H), 3.76 (s, 2H), 3.08-3.04 (m, 2H), 2.29-2.21 (m, 2H), 2.13-1.97 (m, 2H), 1.88-1.84 (m, 3H), 1.63-1.50 (m, 11H), 1.05-1.02 (m, 4H), 0.91-0.85 (m, 2H), 0.64-0.59 (m, 2H); MS(ES+) m/z 549.2 (M+1).

Step 2. Preparation of 5-cyclopropyl-4-((1-((6-cyclopropyl-4-(trifluoromethyl)pyridin-2-yl)methyl)piperidin-4-yl)methoxy)-2-fluorobenzoic acid, trifluoroacetic acid salt

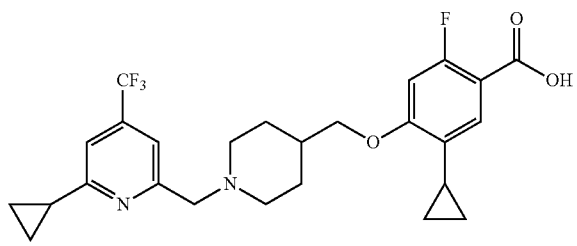 [SMILES: O=C(O)c1cc(C2CC2)c(OCC2CCN(Cc3cc(C(F)(F)F)cc(C4CC4)n3)CC2)cc1F]

Following the procedure as described in Example 3 step 3, and making variation as required to replace (R)-tert-butyl 3-(4-(tert-butoxycarbonyl)-2-cyclopropyl-5-fluorophenoxy)-piperidine-1-carboxylate with tert-butyl 5-cyclopropyl-4-((1-((6-cyclopropyl-4-(trifluoromethyl)pyridin-2-yl)methyl)piperidin-4-yl)methoxy)-2-fluorobenzoate, the title compound was obtained as a colorless oil (1.31 g, 99%): MS(ES+) m/z 493.0 (M+1).

Step 3. Preparation of 5-cyclopropyl-4-((1-((6-cyclopropyl-4-(trifluoromethyl)pyridin-2-yl)methyl)piperidin-4-yl)methoxy)-2-fluoro-N-(methylsulfonyl)benzamide

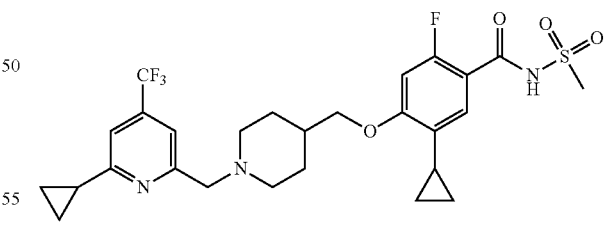

Following the procedure as described in Example 3 step 5, and making variation as required to replace (R)-5-cyclopropyl-4-((1-(3,5-dichlorobenzyl)piperidin-3-yl)oxy)-2-fluorobenzoic acid with 5-cyclopropyl-4-((1-((6-cyclopropyl-4-(trifluoromethyl)pyridin-2-yl)methyl)piperidin-4-yl)methoxy)-2-fluorobenzoic acid and to replace cyclopropylsulfonamide with methanesulfonamide, the title compound was obtained as a colorless solid (0.10 g, 28%): $^1$H NMR (300 MHz, DMSO-d$_6$) δ11.00 (br s, 1H), 7.60 (s, 1H), 7.48 (s, 1H), 7.13 (d, J=8.4 Hz, 1H), 6.83 (d, J=12.9 Hz, 1H), 3.92-3.87 (m, 4H), 3.11 (s, 3H), 3.05-3.01 (m, 2H), 2.45-2.37 (m, 2H), 2.28-2.23 (m, 1H), 2.01-1.96 (m, 1H), 1.83-1.80 (m, 3H), 1.51-1.39 (m, 2H), 1.02-0.96 (m, 4H), 0.88-0.81 (m, 1H), 0.62-0.57 (m, 2H); MS(ES+) m/z 570.0 (M+1); MS(ES−) m/z 568.0 (M−1).

Example 307

Synthesis of 5-cyclopropyl-4-((1-((6-cyclopropyl-4-(trifluoromethyl)pyridin-2-yl)methyl)piperidin-4-yl)methoxy)-N-(ethylsulfonyl)-2-fluorobenzamide

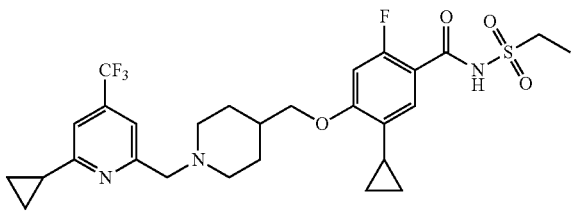 [SMILES: CCS(=O)(=O)NC(=O)c1cc(C2CC2)c(OCC2CCN(Cc3cc(C(F)(F)F)cc(C4CC4)n3)CC2)cc1F]

Following the procedure as described in Example 3 step 5, and making variation as required to replace (R)-5-cyclopropyl-4-((1-(3,5-dichlorobenzyl)piperidin-3-yl)oxy)-2-fluorobenzoic acid with 5-cyclopropyl-4-((1-((6-cyclopropyl-4-(trifluoromethyl)pyridin-2-yl)methyl)piperidin-4-yl)methoxy)-2-fluorobenzoic acid and to replace cyclopropylsulfonamide with ethanesulfonamide, the title compound was obtained as a colorless solid (0.14 g, 39%); $^1$H NMR (300 MHz, DMSO-$d_6$) δ11.15 (br s, 1H), 7.62 (s, 1H), 7.50 (s, 1H), 7.15 (d, J=8.4 Hz, 1H), 6.88 (d, J=12.0 Hz, 1H), 3.96-3.94 (m, 2H), 3.85 (s, 2H), 3.37-3.30 (m, 2H), 3.05-3.01 (m, 2H), 2.41-2.24 (m, 3H), 2.06-1.97 (m, 1H), 1.85-1.82 (m, 3H), 1.52-1.41 (m, 2H), 1.20 (t, J=7.3 Hz, 3H), 1.04-0.99 (m, 4H), 0.91-0.85 (m, 2H), 0.66-0.61 (m, 2H); MS(ES+) m/z 584.0 (M+): MS(ES−) m/z 582.1 (M−1).

Example 308

Synthesis of 5-cyclopropyl-4-((1-((6-cyclopropyl-4-(trifluoromethyl)pyridin-2-yl)methyl)piperidin-4-yl)methoxy)-N-(ethylsulfonyl)-2-fluorobenzamide

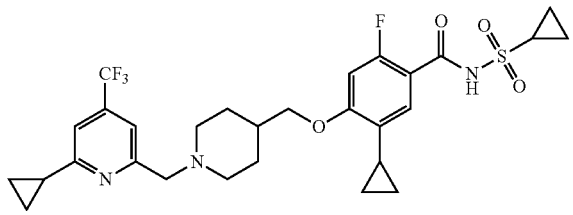 [SMILES: O=C(NS(=O)(=O)C1CC1)c1cc(C2CC2)c(OCC2CCN(Cc3cc(C(F)(F)F)cc(C4CC4)n3)CC2)cc1F]

Following the procedure as described in Example 3 step 5, and making variation as required to replace (R)-5-cyclopropyl-4-((1-(3,5-dichlorobenzyl)piperidin-3-yl)oxy)-2-fluorobenzoic acid with 5-cyclopropyl-4-((1-((6-cyclopropyl-4-(trifluoromethyl)piperidin-2-yl)methyl)piperidin-4-yl)methoxy)-2-fluorobenzoic acid, the title compound was obtained as a colorless solid (0.13 g, 36%): $^1$H NMR (300 MHz, DMSO-$d_6$) δ11.22 (br s, 1H), 7.61 (s, 1H), 7.49 (s, 1H), 7.15 (d, J=8.4 Hz, 1H), 6.89 (d, J=12.9 Hz, 1H), 3.95 (d, J=5.8 Hz, 2H), 3.83 (s, 2H), 3.04-2.99 (m, 3H), 2.38-2.24 (m, 3H), 2.07-1.97 (m, 1H), 1.85-1.81 (m, 3H), 1.52-1.41 (m, 2H), 1.04-0.99 (m, 8H), 0.91-0.85 (m, 2H), 0.66-0.61 (m, 2H); MS(ES+) m/z 596.1 (M+1); MS(ES−) m/z 594.2 (M−1).

Example 309

Synthesis of 4-(((R)-1-((R)-1-(5-chloro-6-cyclopropylpyridin-2-yl)ethyl)piperidin-3-yl)oxy)-5-cyclopropyl-2-fluoro-N-(methylsulfonyl)benzamide (arbitrarily assigned)

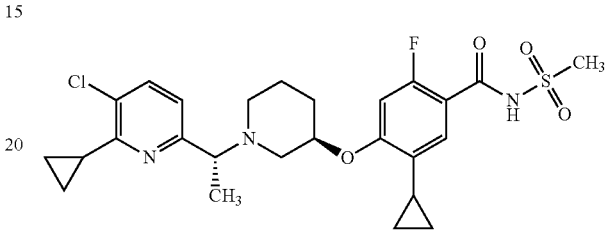

Step 1. Preparation of methyl 4-(((R)-1-((R)-1-(5-chloro-6-cyclopropylpyridin-2-yl)ethyl)piperidin-3-yl)oxy)-5-cyclopropyl-2-fluorobenzoate and methyl 4-(((R)-1-((S)-1-(5-chloro-6-cyclopropylpyridin-2-yl)ethyl)piperidin-3-yl)oxy)-5-cyclopropyl-2-fluorobenzoate

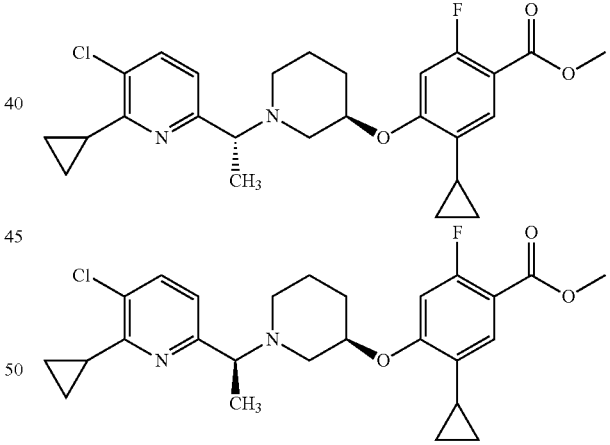

Following the procedure as described in Example 50 step 1 and making variations as required to replace 1,3-dichloro-5-(1-chloroethyl)benzene with 3-chloro-6-(1-chloroethyl)-2-cyclopropylpyridin. The residue was purified by preparative-HPLC, the first eluting fraction was arbitrarily assigned as methyl 4-(((R)-1-((R)-1-(5-chloro-6-cyclopropylpyridin-2-yl)ethyl)piperidin-3-yl)oxy)-5-cyclopropyl-2-fluorobenzoate (0.36 g, 50%): $^1$H NMR (300 MHz, CDCl$_3$) δ7.44 (d, J=8.2 Hz, 1H), 7.38 (d, J=8.4 Hz, 1H), 7.01 (d, J=8.2 Hz, 1H), 6.52 (d, J=12.9 Hz, 1H), 4.36-4.28 (m, 1H), 3.84 (s, 3H), 3.63 (q, J=6.8 Hz, 1H), 2.99-2.95 (m, 1H), 2.66-2.62 (m, 1H), 2.45-2.40 (m, 1H), 2.29-2.15 (m, 2H), 2.05-1.96 (m, 2H), 1.80-1.74 (m, 1H), 1.60-1.42 (m, 2H), 1.29 (d, J=6.8 Hz, 3H), 1.07-0.84 (m, 6H), 0.63-0.58 (m, 2H); MS(ES+) m/z 473.1, 475.1 (M+1).

The second eluting fraction was arbitrarily assigned as methyl 4-(((R)-1-((S)-1-(5-chloro-6-cyclopropylpyridin-2-yl)ethyl)piperidin-3-yl)oxy)-5-cyclopropyl-2-fluorobenzoate (0.36 g, 50%): $^1$H NMR (300 MHz, CDCl$_3$) δ7.45 (d, J=8.2 Hz, 1H), 7.41 (d, J=8.4 Hz, 1H), 7.04 (d, J=7.5 Hz, 1H), 6.53 (d, J=12.8 Hz, 1H), 4.35-4.29 (m, 1H), 3.85 (s, 3H), 3.67 (q, J=6.8 Hz, 1H), 3.039-3.00 (m, 1H), 2.72-2.68 (m, 1H), 2.49-2.41 (m, 1H), 2.28-2.13 (m, 2H), 2.05-1.96 (m, 2H), 1.82-1.77 (m, 1H), 1.64-1.38 (m, 2H), 1.31 (d, J=6.8 Hz, 3H), 1.06-0.86 (m, 6H), 0.65-0.60 (m, 2H); MS(ES+) m/z 473.1, 475.1 (M+1).

Step 2. Preparation of 4-(((R)-1-((R)-1-(5-chloro-6-cyclopropylpyridin-2-yl)ethyl)piperidin-3-yl)oxy)-5-cyclopropyl-2-fluorobenzoic acid

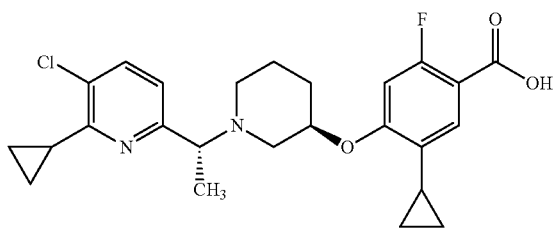 [SMILES: C[C@H](c1ccc(Cl)c(C2CC2)n1)N1CCC[C@@H](Oc2cc(F)c(C(=O)O)cc2C2CC2)C1]

Following the procedure as described in Example 50 step 2 and making variations as required to replace methyl 5-cyclopropyl-4-(((R)-1-((S)-1-(3,5-dichlorophenyl)ethyl)piperidin-3-yl)oxy)-2-fluorobenzoate with methyl 4-(((R)-1-((R)-1-(5-chloro-6-cyclopropylpyridin-2-yl)ethyl)piperidin-3-yl)oxy)-5-cyclopropyl-2-fluorobenzoate, the title compound was obtained as a pale yellow oil (0.06 g, 17%): (M+1); m/z 459.1, 461.1 (M+1); MS(ES−) m/z 457.1, 459.1 (M+1).

Step 3. Preparation of 4-(((R)-1-((R)-1-(5-chloro-6-cyclopropylpyridin-2-yl)ethyl)piperidin-3-yl)oxy)-5-cyclopropyl-2-fluoro-N-(methylsulfonyl)benzamide

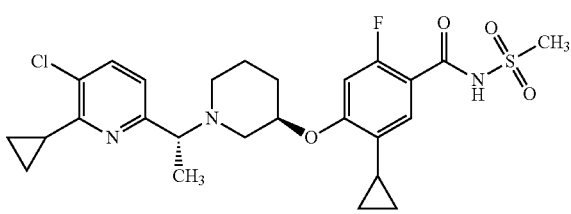 [SMILES: C[C@H](c1ccc(Cl)c(C2CC2)n1)N1CCC[C@@H](Oc2cc(F)c(C(=O)NS(C)(=O)=O)cc2C2CC2)C1]

Following the procedure as described in Example 3 step 5, and making variation as required to replace (R)-5-cyclopropyl-4-((1-(3,5-dichlorobenzyl)piperidin-3-yl)oxy)-2-fluorobenzoic acid with 4-(((R)-1-((R)-1-(5-chloro-6-cyclopropylpyridin-2-yl)ethyl)piperidin-3-yl)oxy)-5-cyclopropyl-2-fluorobenzoic acid and to replace cyclopropylsulfonamide with methanesulfonamide, the title compound was obtained as a colorless solid (0.01 g, 50%): $^1$H NMR (300 MHz, CDCl$_3$) δ 8.77 (br s, 1H), 7.67 (d, J=7.9 Hz, 1H), 7.53 (d, J=8.8 Hz, 1H), 7.10 (d, J=7.8 Hz, 1H), 6.87 (d, J=13.5 Hz, 1H), 4.86-4.82 (m, 1H), 4.66-4.64 (m, 1H), 3.95-3.92 (m, 1H), 3.68-3.64 (m, 1H), 3.38 (s, 3H), 2.95-2.86 (m, 1H), 2.60-2.55 (m, 2H), 2.36-2.31 (m, 1H), 2.13-2.07 (m, 2H), 1.92-1.87 (m, 1H), 1.69 (d, J=6.4 Hz, 3H), 1.62-1.51 (m, 1H), 1.10-0.86 (m, 6H), 0.62-0.60 (m, 2H): MS(ES+) m/z 536.1, 538.1 (M+1).

Example 310

Synthesis of 4-(((R)-1-((S)-1-(5-chloro-6-cyclopropylpyridin-2-yl)ethyl)piperidin-3-yl)oxy)-5-cyclopropyl-2-fluoro-N-(methylsulfonyl)benzamide

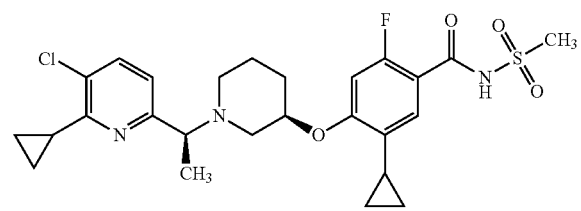 [SMILES: C[C@@H](c1ccc(Cl)c(C2CC2)n1)N1CCC[C@@H](Oc2cc(F)c(C(=O)NS(C)(=O)=O)cc2C2CC2)C1]

Step 1. Preparation of 4-(((R)-1-((S)-1-(5-chloro-6-cyclopropylpyridin-2-yl)ethyl)piperidin-3-yl)oxy)-5-cyclopropyl-2-fluorobenzoic acid

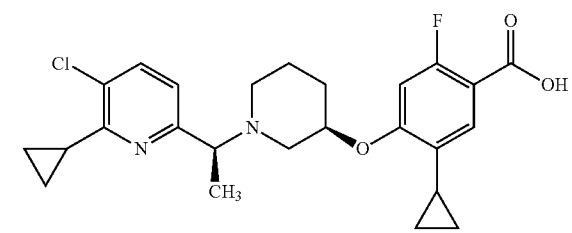 [SMILES: C[C@@H](c1ccc(Cl)c(C2CC2)n1)N1CCC[C@@H](Oc2cc(F)c(C(=O)O)cc2C2CC2)C1]

Following the procedure as described in Example 50 step 2 and making variations as required to replace methyl 5-cyclopropyl-4-(((R)-1-((S)-1-(3,5-dichlorophenyl)ethyl)piperidin-3-yl)oxy)-2-fluorobenzoate with methyl 4-(((R)-1-((S)-1-(5-chloro-6-cyclopropylpyridin-2-yl)ethyl)piperidin-3-yl)oxy)-5-cyclopropyl-2-fluorobenzoate, the title compound was obtained as a colorless solid (0.17 g, 49%): MS(ES+) m/z 459.1, 461.0 (M+1); MS(ES−) m/z 457.1, 459.1 (M−1).

Step 2. Preparation of 4-(((R)-1-((S)-1-(5-chloro-6-cyclopropylpyridin-2-yl)ethyl)piperidin-3-yl)oxy)-5-cyclopropyl-2-fluoro-N-(methylsulfonyl)benzamide

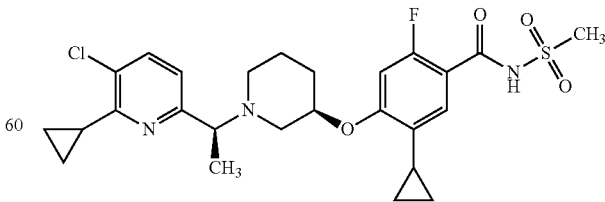

Following the procedure as described in Example 3 step 5, and making variation as required to replace (R)-5-cyclopropyl-4-((1-(3,5-dichlorobenzyl)piperidin-3-yl)oxy)-2- fluorobenzoic acid with 4-(((R)-1-((S)-1-(5-chloro-6-cyclopropylpyridin-2-yl)ethyl)piperidin-3-yl)oxy)-5-cyclopropyl-2-fluorobenzoic acid and to replace cyclopropylsulfonamide with methanesulfonamide, the title compound was obtained as a colorless solid (0.05 g, 44%): $^1$H NMR (300 MHz, CDCl$_3$) δ8.77 (br s, 1H), 7.67 (d, J=7.7 Mhz, 1H), 7.57 (d, J=8.0 Hz, 1H), 7.08 (d, J=7.4 Hz, 1H), 6.89 (d, J=13.6 Hz, 1H), 4.95-4.89 (m, 1H), 4.67-4.66 (m, 1H), 3.92-3.89 (m, 1H), 3.62-3.59 (m, 1H), 3.39 (s, 3H), 3.05-2.97 (m, 1H), 2.62-2.50 (m, 2H), 2.38-2.34 (m, 1H), 2.05-1.93 (m, 3H), 1.67 (d, J=4.4 Hz, 3H), 1.51-1.45 (m, 1H), 1.10-0.90 (m, 6H), 0.65-0.63 (m, 2H); MS(ES+) m/z 536.1, 538.1 (M+1).

Example 311

Synthesis of (R)-4-((1-(3-chloro-2-fluoro-5-(trifluoromethyl)benzyl)piperidin-3-yl)oxy)-5-cyclopropyl-2-fluoro-N-(methylsulfonyl)benzamide

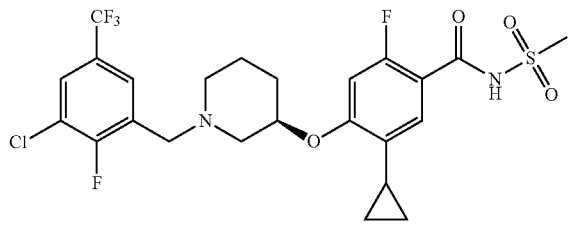 [SMILES: CS(=O)(=O)NC(=O)c1cc(C2CC2)c(O[C@@H]2CCCN(Cc3cc(C(F)(F)F)cc(Cl)c3F)C2)cc1F]

Following the procedure as described in Example 3 step 4, and making variation as required to replace (R)-5-cyclopropyl-2-fluoro-4-(piperidin-3-yloxy)benzoic acid trifluoroacetate with (R)-5-cyclopropyl-2-fluoro-N-(methylsulfonyl)-4-(piperidin-3-yloxy)benzamide and to replace 3,5-dichlorobenzaldehyde with 3-chloro-2-fluoro-5-(trifluoromethyl)benzaldehyde, the title compound was obtained as a colorless solid (0.18 g, 35%): $^1$H NMR (300 MHz, DMSO-d$_6$) δ11.80 (br s, 1H). 7.98 (dd, J=1.9 Hz, 6.3 Hz, 1H), 7.79 (dd, J=1.9 Hz, 5.6 Hz, 1H), 7.12 (d, J=8.4 Hz, 1H), 7.02 (d, J=13.2 Hz, 1H), 4.65-4.63 (m, 1H), 3.71 (d, J=2.0 Hz, 2H), 3.32 (s, 3H), 2.83-2.79 (m, 1H), 2.56-2.54 (m, 2H), 2.41-2.36 (m, 1H), 2.10-2.00 (m, 1H), 1.90-1.77 (m, 2H), 1.60-1.55 (m, 2H), 0.89-0.84 (m, 2H), 0.73-0.67 (m, 2H); MS(ES+) m/z 567.2, 569.0 (M+1); MS(ES−) m/z 565.1, 567.1 (M−1).

Example 312

Synthesis of (R)-4-((1-(2-chloro-4-fluorobenzyl)piperidin-3-yl)oxy)-5-cyclopropyl-2-fluoro-N-(methylsulfonyl)benzamide

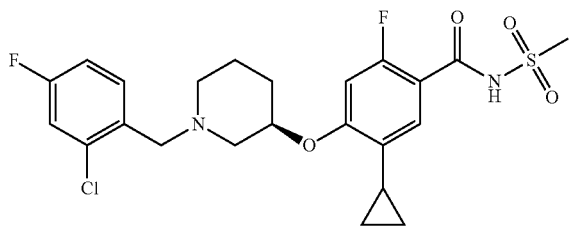

Following the procedure as described in Example 3 step 5, and making variation as required to replace (R)-5-cyclopropyl-4-((1-(3,5-dichlorobenzyl)piperidin-3-yl)oxy)-2-fluorobenzoic acid with (R)-4-((1-(2-chloro-4-fluorobenzyl)piperidin-3-yl)oxy)-5-cyclopropyl-2-fluorobenzoic acid and to replace cyclopropylsulfonamide with methanesulfonamide, the title compound was obtained as a colorless solid (0.05 g, 60%): $^1$H NMR (300 MHz, DMSO-d$_6$) δ11.79 (br s, 3H), 7.55-7.50 (m, 1H, 7.42-7.38 (m, 1H), 7.17-7.11 (m, 2H), 7.00 (d, J=13.2 Hz, 1H), 4.62-4.60 (m, 1H), 3.60 (s, 2H), 3.31 (s, 3H), 2.82-2.79 (m, 1H), 2.60-2.55 (m, 1H), 2.49-2.39 (m, 2H), 2.12-2.03 (m, 1H), 1.94-1.91 (m, 1H), 1.83-1.79 (m, 1H), 1.61-1.57 (m, 2H), 0.91-0.85 (m, 2H), 0.72-0.68 (m, 2H); MS(ES+) m/z 499.2, 501.2 (M+1); MS(ES−) m/z 497.3, 499.3 (M−1).

Example 313

Synthesis of (R)-5-cyclopropyl-N-(cyclopropylsulfonyl)-2-fluoro-4-((1-(3-fluoro-4-methoxybenzyl)piperidin-3-yl)oxy)benzamide

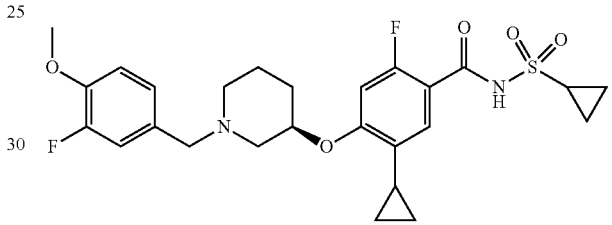

Following the procedure as described in Example 3 step 5, and making variation as required to replace (R)-5-cyclopropyl-4-((1-(3,5-dichlorobenzyl)piperidin-3-yl)oxy)-2-fluorobenzoic acid with (R)-5-cyclopropyl-2-fluoro-4-((1-(3-fluoro-4-methoxybenzyl)piperidin-3-yl)oxy)benzoic acid, the title compound was obtained as a colorless solid (0.03 g, 23%): $^1$H NMR (300 MHz, CDCl$_3$) δ7.55 (d, J=9.1 Hz, 1H): 7.11-6.86 (m, 3H), 6.60 (d, J=18.1 Hz, 1H), 4.50 (s, 1H), 3.88 (s, 3H), 3.53 (s, 2H), 3.12-3.05 (m, 1H), 3.02-2.91 (m, 1H), 2.83-2.66 (m, 1H), 2.44-2.20 (m, 2H), 2.15-1.98 (m, 2H), 1.95-1.82 (m, 2H), 1.66-1.53 (m, 2H), 1.48-1.42 (m, 2H), 1.17-1.13 (m, 2H), 0.96-0.88 (m, 2H), 0.69-0.64 (m, 2H); MS(ES+) m/z 521.2 (M+1), MS(ES+) m/z 519.3 (M−1).

Example 314

Synthesis of (R)-5-cyclopropyl-2-fluoro-N-(methylsulfonyl)-4-((1-(methylsulfonyl)piperidin-3-yl)oxy)benzamide

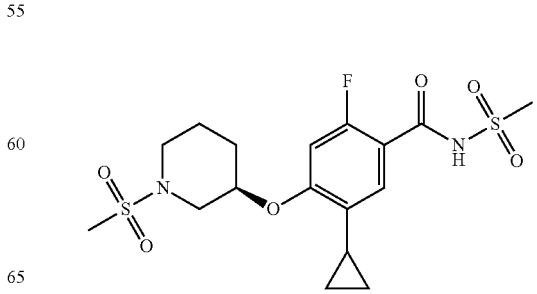

Following the procedure as described in Example 3 step 5, and making variation as required to replace (R)-5-cyclopropyl-4-((1-(3,5-dichlorobenzyl)piperidin-3-yl)oxy)-2-fluorobenzoic acid with (R)-5-cyclopropyl-2-fluoro-4-((1-(methylsulfonyl)piperidin-3-yl)oxy)benzoic acid and to replace cyclopropylsulfonamide with methanesulfonamide, the title compound was obtained as a colorless solid (0.07 g, 40%) $^1$H NMR (300 MHz, CDCl$_3$) δ 8.72 (d, J=15.9 Hz, 1H), 7.59 (d, J=9.0 Hz, 1H), 0.65 (d, J=14.2 Hz, 1H), 4.49 (brs, 1H), 3.74 (d, J=14.2 Hz, 1H), 3.51-3.45 (m, 5H), 3.41 (s, 3H), 3.25-3.12 (m, 2H), 2.83 (s, 3H), 2.11-2.01 (m, 3H), 1.85-1.79 (m, 2H), 0.94 (d, J=8.4 Hz, 2H), 0.66 (d, J=5.2 Hz, 2H); MS(ES+) m/z 435.1 (M+1); MS(ES−) m/z 433.2 (M−1).

Example 315

Synthesis of 5-cyclopropyl-2-fluoro-4-(((R)-1-((S)-1-(4-fluorophenyl)ethyl)piperidin-3-yl)oxy)-N-(methylsulfonyl)benzamide

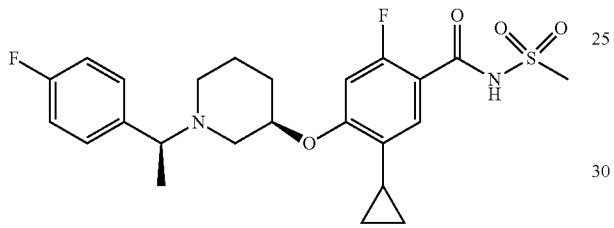

Step 1. Preparation of methyl 5-cyclopropyl-2-fluoro-4-(((R)-1-((S)-1-(4-fluorophenyl)ethyl)piperidin-3-yl)oxy)benzoate and methyl 5-cyclopropyl-2-fluoro-4-(((R)-1-((R)-1-(4-fluorophenyl)ethyl)piperidin-3-yl)oxy)benzoate

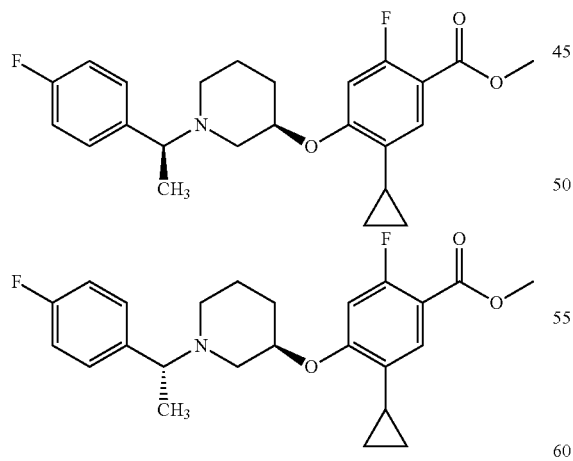

Following the procedure as described in Example 50 step 1, and making variations as required to replace 1,3-dichloro-5-(1-chloroethyl)benzene with 1-(1-chloroethyl)-4-fluorobenzene, the first eluting fraction was arbitrarily assigned as methyl 5-cyclopropyl-2-fluoro-4-(((R)-1-((S)-1-(4-fluorophenyl)ethyl)piperidin-3-yl)oxy)benzoate (0.50 g, 38%): $^1$H NMR (300 MHz, CDCl$_3$) δ7.41 (d, J=8.4 Hz, 1H), 7.27-7.22 (m, 2H), 6.95 (t, J=8.7 Hz, 2H), 6.53 (d, J=13 Hz, 1H), 4.39-4.32 (m, 1H), 3.86 (s, 3H), 3.54-3.46 (m, 1H), 3.02-3.00 (m, 1H), 2.62-2.59 (m, 1H), 2.25-1.96 (m, 4H), 1.83-1.76 (m, 1H), 1.63-1.43 (m, 2H), 1.32 (d, J=6.8 Hz, 3H), 0.91-0.88 (m, 2H), 0.66-0.62 (m, 2H); MS(ES+) m/z 416.2 (M+1).

The second eluting fraction was arbitrarily assigned as methyl 5-cyclopropyl-2-fluoro-4-(((R)-1-((R)-1-(4-fluorophenyl)ethyl)piperidin-3-yl)oxy)benzoate (0.50 g, 38%): $^1$H NMR (300 MHz, CDCl$_3$) δ 7.36 (d, J=8.4 Hz, 1H), 7.23-7.21 (m, 2H), 6.94 (t, J=8.9 Hz, 2H), 6.46 (d, J=12.9 Hz, 1H), 4.32-4.24 (m, 1H), 3.82 (s, 3H), 3.50 (q, J=6.7 Hz, 1H), 2.94-2.91 (m, 5H), 2.77-2.73 (m, 1H), 2.15-1.93 (m, 4H), 1.88-1.76 (m, 1H), 1.65-1.37 (m, 2H), 1.30 (d, J=6.8 Hz, 3H) 0.85-0.81 (m, 2H), 0.61-0.57 (m, 2H); MS(ES+) m/z 416.2 (M+1).

Step 2. Preparation of 5-cyclopropyl-2-fluoro-4-(((R)-1-((S)-1-(4-fluorophenyl)ethyl)piperidin-3-yl)oxy)benzoic acid

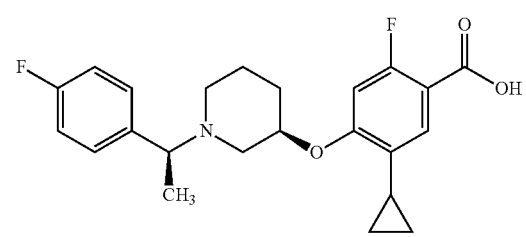 [SMILES: C[C@@H](c1ccc(F)cc1)N1CCC[C@@H](Oc2cc(F)c(C(=O)O)cc2C2CC2)C1]

Following the procedure as described in Example 50 step 2, and making variations as required to replace methyl 5-cyclopropyl-4-(((R)-1-((S)-1-(3,5-dichlorophenyl)ethyl)-piperidin-3-yl)oxy)-2-fluorobenzoate with methyl 5-cyclopropyl-2-fluoro-4-(((R)-1-((S)-1-(4-fluorophenyl)ethyl)piperidin-3-yl)oxy)benzoate, the title compound was obtained as a colorless solid (0.16 g, 33%): MS(ES+) m/z 402.2 (M+1); MS(ES−) m/z 400.2 (M−1).

Step 3. Preparation of methyl 5-cyclopropyl-2-fluoro-4-(((R)-1-((S)-1-(4-fluorophenyl)ethyl)piperidin-3-yl)oxy)-N-(methylsulfonyl)benzamide

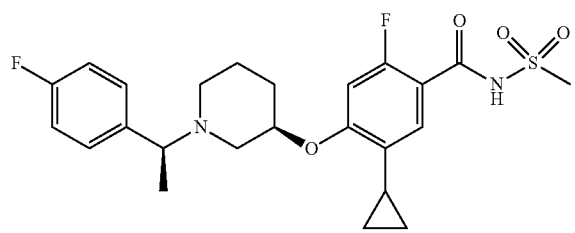 [SMILES: C[C@@H](c1ccc(F)cc1)N1CCC[C@@H](Oc2cc(F)c(C(=O)NS(C)(=O)=O)cc2C2CC2)C1]

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with 5-cyclopropyl-2-fluoro-4-(((R)-1-((S)-1-(4-fluorophenyl)ethyl)piperidin-3-yl)oxy)benzoic acid, the title compound was obtained as a colorless solid (0.12 g, 62%): $^1$H NMR (300 MHz, CDCl$_3$) δ8.99-8.66 (m, 1H), 7.56 (d, J=8.6 Hz, 1H), 7.45-7.42 (m, 2H), 7.19 (t, J=8.0 Hz, 2H), 6.96 (d, J=12.9 Hz, 1H), 5.01-4.86 (m, 1H), 4.61-4.47 (m, 1H), 4.06-3.92 (m, 1H), 3.59-3.46 (m, 1H), 3.41 (s, 3H), 2.59-2.42 (m, 2H), 2.39-2.28 (m, 1H), 2.23-2.00 (m, 2H), 1.97-1.87 (m, 1H), 1.81 (d, J=5.3 Hz, 3H), 1.64-1.46 (m, 1H), 0.93-0.88 (m, 2H), 0.64-0.60 (m, 2H); MS(ES+) m/z 479.1 (M+1); MS(ES−) m/z 477.2 (M−1).

Example 316

Synthesis of 5-cyclopropyl-2-fluoro-4-(((R)-1-((R)-1-(4-fluorophenyl)ethyl)piperidin-3-yl)oxy)-N-(methylsulfonyl)benzamide

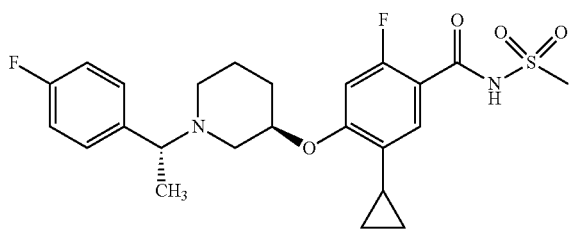 [SMILES: C[C@H](c1ccc(F)cc1)N1CCC[C@@H](Oc2cc(F)c(C(=O)NS(C)(=O)=O)cc2C2CC2)C1]

Step 1. Preparation of 5-cyclopropyl-2-fluoro-4-(((R)-1-((R)-1-(4-fluorophenyl)ethyl)piperidin-3-yl)oxy)benzoic acid

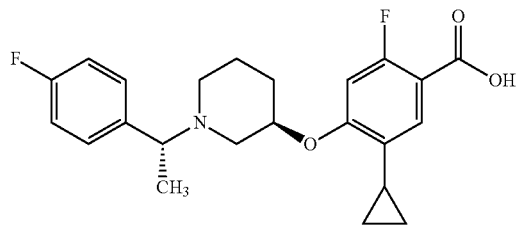 [SMILES: C[C@H](c1ccc(F)cc1)N1CCC[C@@H](Oc2cc(F)c(C(=O)O)cc2C2CC2)C1]

Following the procedure as described in Example 50 step 2 and making variations as required to replace methyl 5-cyclopropyl-4-(((R)-1-((S)-1-(3,5-dichlorophenyl)ethyl)piperidin-3-yl)oxy)-2-fluorobenzoate with methyl 5-cyclopropyl-2-fluoro-(((R)-1-((R)-1-(4-fluorophenyl)ethyl)piperidin-3-yl)oxy)benzoate, the title compound was obtained as a beige color solid (0.23 g, 99%); MS(ES−) m/z 400.2 (M−1); MS(ES+) m/z 402.2 (M+1).

Step 2. Preparation of 5-cyclopropyl-2-fluoro-4-(((R)-1-((R)-1-(4-fluorophenyl)ethyl)piperidin-3-yl)oxy)-N-(methylsulfonyl)benzamide

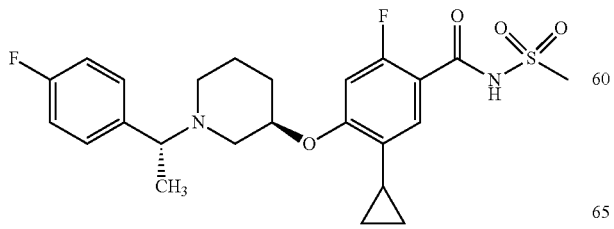 [SMILES: C[C@H](c1ccc(F)cc1)N1CCC[C@@H](Oc2cc(F)c(C(=O)NS(=O)(=O)C3CC3)cc2C2CC2)C1]

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with 5-cyclopropyl-2-fluoro-4-(((R)-1-((R)-1-(4-fluorophenyl)ethyl)piperidin-3-yl)oxy)benzoic acid, the title compound was obtained as a colorless solid (0.04 g, 15%) $^1$H NMR (300 MHz, CDCl$_3$) δ9.07-8.61 (m, 1H), 7.54 (d, J=8.7 Hz, 1H), 7.45-7.41 (m, 2H), 7.18 (t, J=8.26 Hz, 2H), 7.02-6.89 (m, 1H), 5.10-4.91 (m, 1H), 4.63-4.46 (m, 1H), 3.82-3.56 (m, 2H), 3.40 (s, 3H), 2.63-2.41 (m, 2H), 2.40-2.28 (m, 1H), 2.25-1.87 (m, 3H), 1.80 (d, J=6.3 Hz, 3H), 1.63-1.43 (m, 1H), 0.95-0.87 (m, 2H), 0.67-0.59 (m, 2H); MS(ES+) m/z 479.1 (M+1); MS(ES−) m/z 477.2 (M−1).

Example 317

Synthesis of 5-cyclopropyl-N-(cyclopropylsulfonyl)-2-fluoro-4-(((R)-1-((R)-1-(4-fluorophenyl)ethyl)piperidin-3-yl)oxy)benzamide

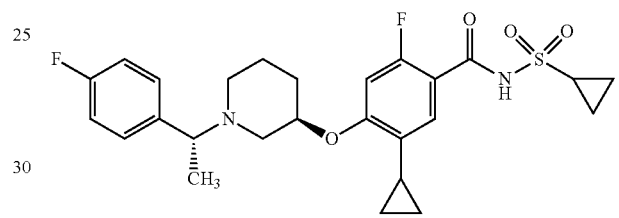

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with 5-cyclopropyl-2-fluoro-4-(((R)-1-((R)-1-(4-fluorophenyl)ethyl)piperidin-3-yl)oxy)benzoic acid and to replace methanesulfonamide with cyclopropylsulfonamide, the title compound was obtained as a colorless solid (0.01 g, 6%) $^1$H NMR (300 MHz, CDCl$_3$) δ8.91-8.63 (m, 1H), 7.61-7.51 (m, 1H), 7.49-7.38 (m, 2H), 7.19-7.12 (m, 2H), 7.04-6.89 (m, 1H), 5.12-4.88 (m, 1H), 4.63-4.46 (m, 1H), 3.86-3.52 (m, 2H), 3.17-3.02 (m, 1H), 2.69-2.28 (m, 3H), 2.23-1.89 (m, 3H), 1.89-1.85 (m, 3H), 1.50-1.41 (m, 3H), 1.21-1.10 (m, 2H), 0.96-0.85 (m, 2H), 0.69-0.58 (m, 2H); MS(ES+) m/z 505.2 (M+1); MS(ES−) m/z 503.2 (M+1).

Example 318

Synthesis of (R)-5-cyclopropyl-2-fluoro-4-((1-(5-fluoro-2-(trifluoromethyl)benzyl)piperidin-3-yl)oxy)-N-(methylsulfonyl)benzamide

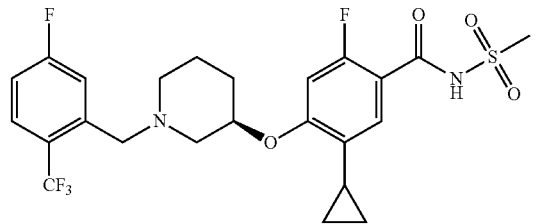 [SMILES: CS(=O)(=O)NC(=O)c1cc(C2CC2)c(O[C@@H]2CCCN(Cc3cc(F)ccc3C(F)(F)F)C2)cc1F]

Step 1. Preparation of (R)-methyl 5-cyclopropyl-2-fluoro-4-((1-(5-fluoro-2-(trifluoromethyl)benzyl)piperidin-3-yl)oxy)benzoate

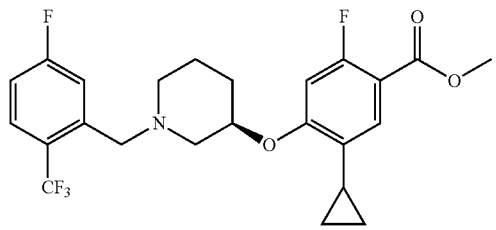 [SMILES: COC(=O)c1cc(C2CC2)c(O[C@@H]2CCCN(Cc3cc(F)ccc3C(F)(F)F)C2)cc1F]

Following the procedure as described in Example 50 step 1, and making variations as required to replace 1,3-dichloro-5-(1-chloroethyl)benzene with 2-(bromomethyl)-4-fluoro-1-(trifluoromethyl)benzene, the title compound was obtained as a colorless oil (0.20 g, 99%); MS(ES+) m/z 470.2 (M+1).

Step 2. Preparation of (R)-5-cyclopropyl-2-fluoro-4-((1-(5-fluoro-2-(trifluoromethyl)benzyl)piperidin-3-yl)oxy)benzoic acid

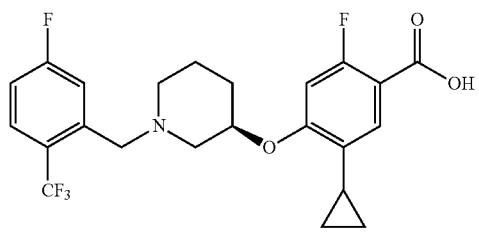 [SMILES: O=C(O)c1cc(C2CC2)c(O[C@@H]2CCCN(Cc3cc(F)ccc3C(F)(F)F)C2)cc1F]

Following the procedure as described in Example 50 step 2 and making variations as required to replace methyl 5-cyclopropyl-4-(((R)-1-((S)-1-(3,5-dichlorophenyl)ethyl)piperidin-3-yl)oxy)-2-fluorobenzoate with (R)-methyl 5-cyclopropyl-2-fluoro-4-((1-(5-fluoro-2-(trifluoromethyl)benzyl)piperidin-3-yl)oxy)benzoate, the title compound was obtained as a colorless oil (0.12 g, 59%): MS(ES+) m/z 456.1 (M+1); MS(ES−) m/z 454.2 (M−1).

Step 3. Preparation of (R)-5-cyclopropyl-2-fluoro-4-((1-(5-fluoro-2-(trifluoromethyl)benzyl)piperidin-3-yl)oxy)-N-(methylsulfonyl)benzamide

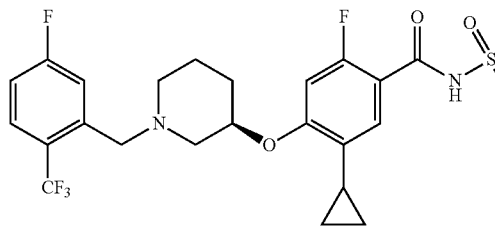

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with (R)-5-cyclopropyl-2-fluoro-4-((1-(5-fluoro-2-(trifluoromethyl)benzyl)piperidin-3-yl)oxy) benzoic acid, the title compound was obtained as a colorless solid (0.03 g, 18%): $^1$H NMR (300 MHz, CDCl$_3$) δ 8.99-8.55 (m, 1H), 7.78-7.74 (m, 2H), 7.56-7.53 (d, J=8.6 Hz, 1H), 7.27-7.22 (m, 1H), 4.97-4.83 (m, 1H), 4.61-4.56 (m, 1H), 4.37-4.33 (m, 1H), 3.81-3.57 (m, 1H), 3.38 (s, 3H), 3.35-3.25 (m, 1H), 3.03-2.78 (m, 2H), 2.37-2.22 (m, 1H), 2.17-1.98 (m, 3H), 1.87-1.69 (m, 1H), 0.92 (d, J=8.1 Hz, 2H), 0.68-0.56 (m, 2H); MS(ES+) m/z 533.2 (M+1); MS(ES−) m/z 531.2 (M−1).

Example 319

Synthesis of (R)-5-cyclopropyl-2-fluoro-N-(methylsulfonyl)-4-((1-(3-(trifluoromethyl)benzyl)piperidin-3-yl)oxy)benzamide

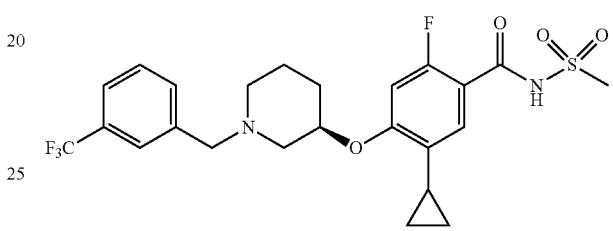

Step 1. Preparation of (R)-methyl 5-cyclopropyl-2-fluoro-4-((1-(3-(trifluoromethyl)benzyl)piperidin-3-yl)oxy)benzoate

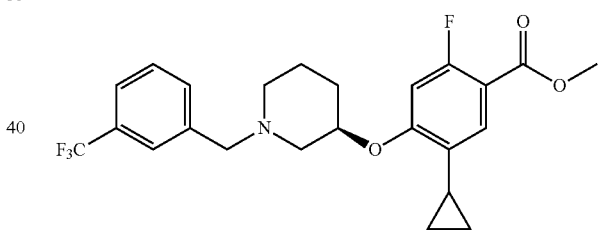

Following the procedure as described in Example 50 step 1, and making variations as required to replace 1,3-dichloro-5-(1-chloroethyl)benzene with 1-(chloromethyl)-3-(trifluoromethyl)benzene, the title compound was obtained as a colorless oil (0.24 g, 28%): MS(ES+) m/z 452.2 (M+1).

Step 2. Preparation of (R)-5-cyclopropyl-2-fluoro-4-((1-(3-(trifluoromethyl)benzyl)piperidin-3-yl)oxy) benzoic acid

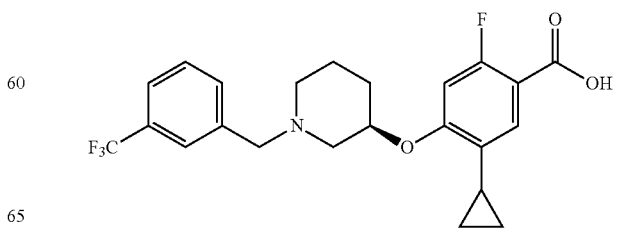

Following the procedure as described in Example 50 step 2 and making variations as required to replace methyl 5-cyclopropyl-4-(((R)-1-((S)-1-(3,5-dichlorophenyl)ethyl)piperidin-3-yl)oxy)-2-fluorobenzoate with (R)-methyl 5-cyclopropyl-2-fluoro-4-((1-(3-(trifluoromethyl)benzyl)piperidin-3-yl)oxy)benzoate, the title compound was obtained as colorless oil (0.25 g, 99%): MS(ES+) m/z 438.2 (M+1); MS(ES−) m/z 436.2 (M−1).

Step 3. Preparation of (R)-5-cyclopropyl-2-fluoro-N-(methylsulfonyl)-4-((1-(3-(trifluoromethyl)benzyl)piperidin-3-yl)oxy)benzamide

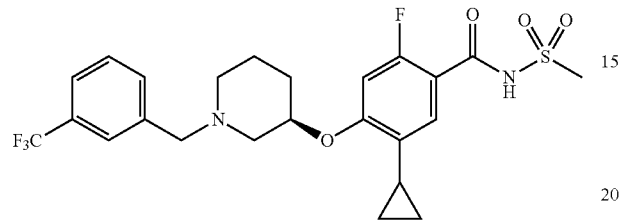

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with (R)-5-cyclopropyl-2-fluoro-4-((1-(3-(trifluoromethyl)benzyl)piperidin-3-yl)oxy)benzoic acid, the title compound was obtained as a colorless solid (0.04 g, 16%): $^1$H NMR (300 MHz, CDCl$_3$) δ9.03-8.68 (m, 1H), 7.76-7.67 (m, 4H), 7.56-7.54 (m, 1H), 6.95-6.71 (m, 1H), 4.96-4.78 (m, 1H), 4.47-4.23 (m, 2H), 4.02-3.72 (m, 1H), 3.40 (s, 3H), 2.96-2.58 (m, 2H), 2.43-2.26 (m, 1H), 2.21-1.91 (m, 3H), 1.83-1.56 (m, 2H), 0.98-0.80 (m, 2H), 0.68-0.51 (m, 2H); MS(ES+) m/z 515.1 (M+1).

Example 320

Synthesis of 4-((2-(2-chloro-4-fluorobenzyl)-2-azaspiro[3.3]heptan-6-yl)oxy)-5-cyclopropyl-2-fluoro-N-(methylsulfonyl)benzamide, trifluoroacetic acid salt

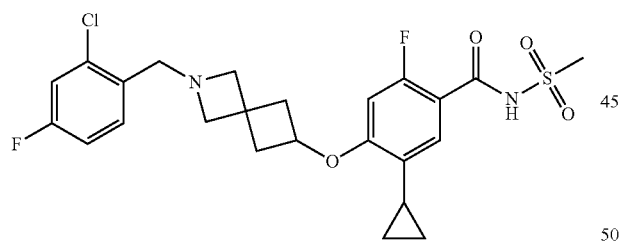

Step 1. Preparation of tert-butyl 6-(4-(tert-butoxycarbonyl)-2-chloro-5-fluorophenoxy)-2-azaspiro[3.3]heptane-2-carboxylate

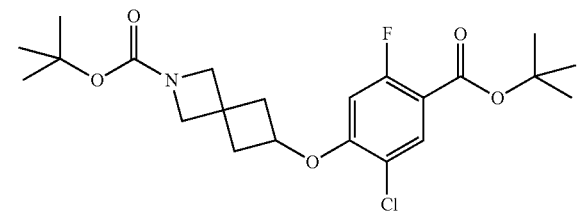 [SMILES: CC(C)(C)OC(=O)c1cc(Cl)c(OC2CC3(C2)CN(C(=O)OC(C)(C)C)C3)cc1F]

Following the procedure as described in Example 3 step 11 and making variation as required to replace (R)-tert-butyl 3-hydroxypiperidine-1-carboxylate with tert-butyl 6-hydroxy-2-azaspiro[3.3]heptane-2-carboxylate, the title compound was obtained as a colorless solid (2.36 g, 53%): $^1$H NMR (300 MHz, CDCl$_3$) δ7.85 (d, J=7.6 Hz, 1H), 6.42 (d, J=11.9 Hz, 1H), 4.64-4.55 (m, 1H), 3.95 (d, J=11.2 Hz, 4H), 2.78-2.71 (m, 2H), 2.44-2.37 (m, 2H), 1.55 (s, 9H), 1.42 (s, 9H); MS(ES+) m/z 442.1, 444.0 (M+1).

Step 2. Preparation of tert-butyl 6-(4-(tert-butoxycarbonyl)-2-cyclopropyl-5-fluorophenoxy)-2-azaspiro[3.3]heptane-2-carboxylate

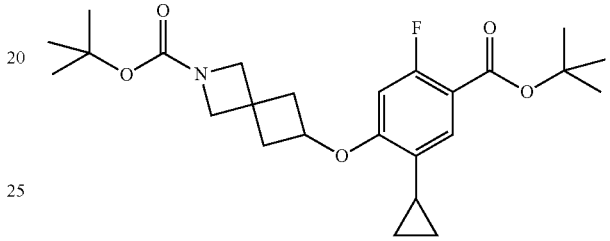

Following the procedure as described in Example 3 step 2, and making variation as required to replace (R)-tert-butyl 3-(4-(tert-butoxycarbonyl)-2-chloro-5-fluorophenoxy)piperidine-1-carboxylate with tert-butyl 6-(4-(tert-butoxycarbonyl)-2-chloro-5-fluorophenoxy)-2-azaspiro[3.3]heptane-2-carboxylate, the title compound was obtained as a colorless oil (0.96 g, 95%): $^1$H NMR (300 MHz, CDCl$_3$) δ7.31 (d, J=8.3 Hz, 1H), 6.28 (d, J=12.4 Hz, 1H), 4.61-4.52 (m, 1H), 3.94 (d, J=12.2 Hz, 4H), 2.75-2.68 (m, 2H), 2.37-2.30 (m, 2H), 2.01-1.93 (m, 1H), 1.54 (s, 9H), 1.41 (s, 9H), 0.90-0.82 (m, 2H), 0.63-0.57 (m, 2H); MS(ES+) m/z 448.2 (M+1).

Step 3. Preparation of 4-(2-azaspiro[3.3]heptan-6-yloxy)-5-cyclopropyl-2-fluorobenzoic acid, trifluoroacetic acid salt

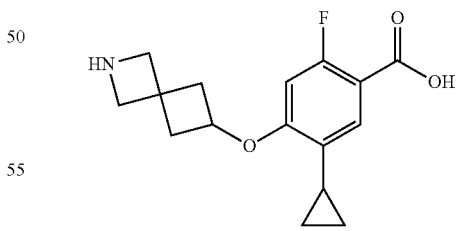

Following the procedure as described in Example 3 step 3, and making variation as required to replace (R)-tert-butyl 3-(4-(tert-butoxycarbonyl)-2-cyclopropyl-5-fluorophenoxy)-piperidin-1-carboxylate with tert-butyl 6-(4-(tert-butoxycarbonyl)-2-cyclopropyl-5-fluorophenoxy)-2-azaspiro[3.3]heptane-2-carboxylate, the title compound was obtained (0.86 g, 99%): MS(ES+) m/z 292.2 (M+1); MS(ES−) m/z 290.3 (M−1).

Step 4. Preparation of 4-((2-(2-chloro-4-fluorobenzyl)-2-azaspiro[3.3]heptan-6-yl)oxy)-5-cyclopropyl-2-fluorobenzoic acid, trifluoroacetic acid salt

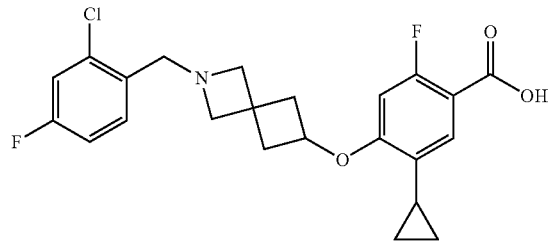 [SMILES: O=C(O)c1cc(C2CC2)c(OC2CC3(C2)CN(Cc2ccc(F)cc2Cl)C3)cc1F]

Following the procedure as described in Example 3 step 4, and making variation as required to replace (R)-5-cyclopropyl-2-fluoro-4-(piperidin-3-yloxy)benzoic acid with 4-(2-azaspiro[3.3]heptan-6-yloxy)-5-cyclopropyl-2-fluorobenzoic acid and to replace 3,5-dichlorobenzaldehyde with 2-chloro-4-fluorobenzaldehyde, the title compound was obtained as colorless solid (0.30 g, 37%): $^1$H NMR (300 MHz, DMSO-d$_6$) δ12.87 (br s, 1H), 10.35 (br s, 1H), 7.70-7.62 (m, 2H), 7.42-7.36 (m, 1H), 7.27 (d, J=8.4 Hz, 1H), 6.72 (d, J=12.9 Hz, 1H), 4.79-4.70 (m, 1H), 4.51-4.49 (m, 2H), 4.32-4.10 (m, 4H), 2.92-2.80 (m, 2H), 2.39-2.30 (m, 2H), 2.04-1.95 (m, 1H), 0.93-0.86 (m, 2H), 0.62-0.57 (m, 2H); MS(ES+) m/z 434.1, 436.1 (M+1); MS(ES−) m/z 432.2, 434.1 (M−1).

Step 5. Preparation of 4-((2-(2-chloro-4-fluorobenzyl)-2-azaspiro[3.3]heptan-6-yl)oxy)-5-cyclopropyl-2-fluoro-N-(methylsulfonyl)benzamide, trifluoroacetic acid salt Following the procedure as described in Example 3 step 5, and making variations as required to replace (R)-5-cyclopropyl-4-((1-(3,5-dichlorobenzyl)piperidin-3-yl)oxy)-2-fluorobenzoic acid with 4-((2-(2-chloro-4-fluorobenzyl)-2-azaspiro[3.3]heptan-6-yl)oxy)-5-cyclopropyl-2-fluorobenzoic acid and to replace cyclopropylsulfonamide with methanesulfonamide, the title compound was obtained as colorless solid (0.04 g, 22%): $^1$H NMR (300 MHz, CDCl$_3$) δ8.73 (br s, 1H), 7.59-7.52 (m, 2H), 7.25-7.21 (m, 1H), 7.14-7.08 (m, 1H), 6.31 (d, J=13.8 Hz, 1H), 4.66-4.62 (m, 1H), 4.52-4.40 (m, 4H), 3.95-3.93 (m, 2H), 3.40 (s, 3H), 3.06-3.00 (m, 1H), 2.86-2.80 (m, 1H), 2.60-2.45 (m, 2H), 2.02-1.93 (m, 1H), 0.96-0.90 (m, 2H), 0.60-0.61 (m, 2H); MS(ES+) m/z 511.1, 513.1 (M+1); MS(ES−) m/z 509.2, 511.2 (M+1).

Example 321

Synthesis of 4-((2-(2-chloro-4-fluorobenzyl)-2-azaspiro[3.3]heptan-6-yl)oxy)-5-cyclopropyl-2-fluoro-N-((3-fluoroazetidin-1-yl)sulfonyl)benzamide

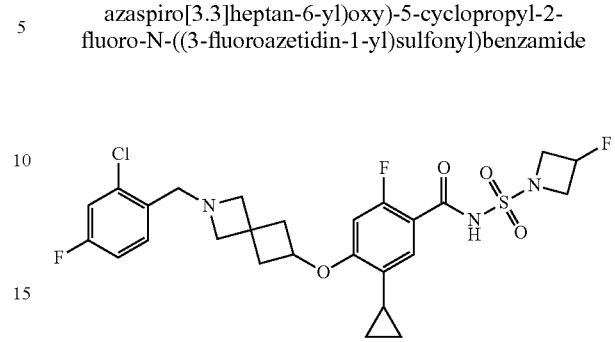

Following the procedure as described in Example 3 step 5, and making variations as required to replace (R)-5-cyclopropyl-4-((1-(3,5-dichlorobenzyl)piperidin-3-yl)oxy)-2-fluorobenzoic acid with 4-((2-(2-chloro-4-fluorobenzyl)-2-azaspiro[3.3]heptan-6-yl)oxy)-5-cyclopropyl-2-fluorobenzoic acid and to replace cyclopropylsulfonamide with 3-fluoroazetidine-1-sulfonamide, the title compound was obtained as colorless solid (0.08 g, 39%): $^1$H NMR (300 MHz, DMSO-d$_6$) δ11.48 (br s, 1H), 7.69-7.62 (m, 2H), 7.39 (dt, J=2.6 Hz, 8.4 Hz, 1H), 7.11 (d, J=8.2 Hz, 1H), 6.79 (d, J=12.7 Hz, 1H), 5.48-5.42 (m, 0.5H), 5.29-5.23 (m, 0.5H), 4.80-4.71 (m, 1H), 4.50 (s, 2H), 4.43-4.12 (m, 8H), 2.86 (br s, 2H), 2.37-2.30 (m, 2H), 2.06-1.97 (m, 1H), 0.93-0.86 (m, 2H), 0.71-0.66 (m, 2H); MS(ES+) m/z 570.1, 572.1. (M+1); MS(ES−) m/z 568.1, 570.1 (M−1).

Example 322

Synthesis of N-(azetidin-1-ylsulfonyl)-4-(((3R,6R)-1-(2-chloro-4-fluorobenzyl)-6-methylpiperidin-3-yl)oxy)-5-cyclopropyl-2-fluorobenzamide

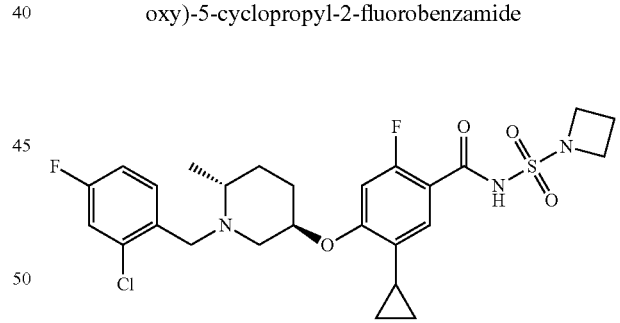

Following the procedure as described in Example 17 step 2, and making variations as required to replace of (R)-5-cyclopropyl-4-((1-(3,4-dichlorobenzyl)piperidin-3-yl)-oxy-2-fluorobenzoic acid with 4-(((3R,6R)-1-(2-chloro-4-fluorophenyl)-6-methylpiperidin-3-yl)oxy)-5-cyclopropyl-2-fluorobenzoic acid, and to replace methanesulfonamide with azetidine-1-sulfonamide, the title compound was obtained as a colorless solid (0.07 g, 23%): $^1$H NMR (300 MHz, CDCl$_3$) δ8.70-8.55 (m, 1H), 7.59-7.48 (m, 2H), 7.13-7.04 (m, 1H), 6.99-6.89 (m, 1H), 6.52-6.43 (m, 1H), 4.40-4.14 (m, 5H), 4.06-3.94 (m, 1H), 3.45-3.32 (m, 1H), 3.09-3.00 (m, 1H), 2.60-2.46 (m, 1H), 2.33-2.13 (m, 4H), 2.09-1.87 (m, 2H), 1.69-1.42 (m, 2H), 1.22-1.14 (m, 3H), 0.97-0.86 (m, 2H), 0.69-0.60 (m, 2H); MS(ES+) m/z 554.2, 556.2 (M+1).

Example 323

Synthesis of 4-(((3R,6R)-1-(2-chloro-4-fluorobenzyl)-6-methylpiperidin-3-yl)oxy)-5-cyclopropyl-N-(cyclopropylsulfonyl)-2-fluorobenzamide

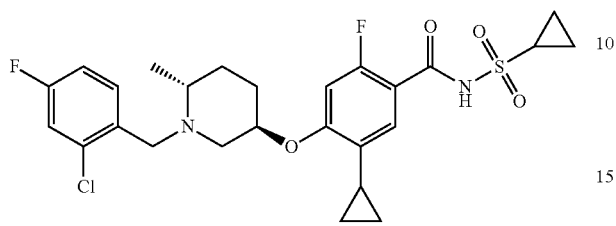

Following the procedure as described to Example 17 step 2, and making variations as required to replace (R)-5-cyclopropyl-4-((1-(3,4-dichlorobenzyl)piperidin-3-yl)-oxy)-2-fluorobenzoic acid with 4-(((3R,6R)-1-(2-chloro-4-fluorobenzyl)-6-methylpiperidin-3-yl)oxy)-5-cyclopropyl-2-fluorobenzoic acid, and to replace methanesulfonamide with cyclopropanesulfonamide, the title compound was obtained as a colorless solid (0.14 g, 44%); $^1$H NMR (300 MHz, CDCl$_3$) δ8.75-8.57 (m, 1H), 7.58-7.47 (m, 2H), 7.13-7.03 (m, 1H), 7.00-6.88 (m, 1H), 6.53-6.41 (m, 1H), 4.39-4.25 (m, 1H), 4.07-3.93 (m, 1H), 3.44-3.33 (m, 1H), 3.14-2.99 (m, 2H), 2.57-2.46 (m, 1H), 2.31-2.11 (m, 2H), 2.08-1.85 (m, 2H), 1.69-1.37 (m, 5H), 1.22-1.08 (m, 4H), 0.96-0.84 (m, 2H), 0.69-0.56 (m, 2H); MS(ES+) m/z 539.2, 541.2 (M+1).

Example 324

Synthesis of 4-(((3R,6S)-1-(2-chloro-4-fluorobenzyl)-6-methylpiperidin-3-yl)oxy)-5-cyclopropyl-2-fluoro-N-(methylsulfonyl)benzamide

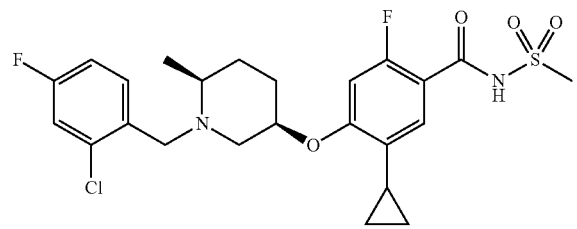 [SMILES: C[C@H]1CC[C@@H](Oc2cc(F)c(C(=O)NS(C)(=O)=O)cc2C2CC2)CN1Cc1ccc(F)cc1Cl]

Step 1. Preparation of (2S,5R)-benzyl 5-hydroxy-2-methylpiperidine-1-carboxylate

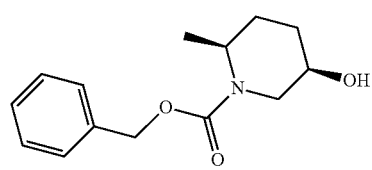 [SMILES: C[C@H]1CC[C@@H](O)CN1C(=O)OCc1ccccc1]

Following the procedure as described in Example 52 step 1, and making variations as required to replace (3R,6R)-6-methylpiperidin-3-ol with (3R,6S)-6-methylpiperidin-3-ol (Ian A. O'Neil et al., *Synlett*, 2000, 5, 695), the title compound was obtained (1.45 g, 27%) as a colorless oil: MS(ES+) m/z 250.2 (M+1).

Step 2. Preparation of (2S,5R)-benzyl 5-(4-(tert-butoxycarbonyl)-2-chloro-5-fluorophenoxy)-2-methylpiperidine-1-carboxylate

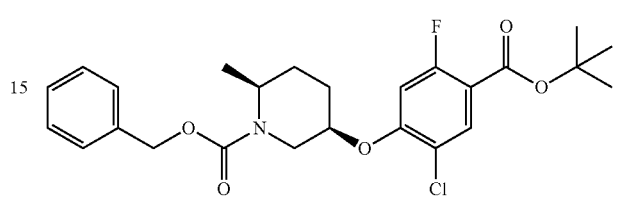

Following the procedure as described in Example 1 step 1, and making variation as required to replace (R)-1-benzylpiperidin-3-ol with (2S,5R)-benzyl 5-hydroxy-2-methylpiperidine-1-carboxylate, the title compound was obtained as a colorless oil (1.63 g, 59%): $^1$H NMR (300 MHz, CDCl$_3$) δ7.91-7.84 (m, 1H), 7.43-7.28 (m, 5H), 6.78-6.61 (m, 1H), 5.23-5.06 (m, 2H), 4.61-4.09 (m, 3H), 3.07-2.88 (m, 1H), 2.17-1.99 (m, 1H), 1.96-1.50 (m, 12H), 1.31-1.17 (m, 3H); MS(ES+) m/z 478.2, 480.2 (M+1).

Step 3. Preparation of (2S,5R)-benzyl 5-(4-(tert-butoxycarbonyl)-2-cyclopropyl-5-fluorophenoxy)-2-methylpiperidine-1-carboxylate

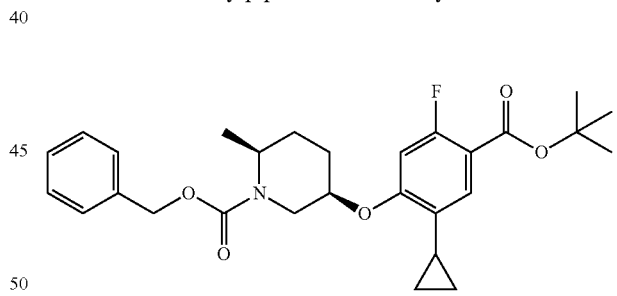

Following the procedure as described in Example 1 step 2, and making variation as required to replace (R)-tert-butyl 4-((1-benzylpiperidin-3-yl)oxy)-5-chloro-2-fluorobenzoate with (2S,5R)-benzyl 5-(4-(tert-butoxycarbonyl)-2-chloro-5-fluorophenoxy)-2-methylpiperidine-1-carboxylate, the title compound was obtained as a colorless oil (1.35 g, 82%): $^1$H NMR (300 MHz, CDCl$_3$) δ7.43-7.28 (m, 6H), 6.64-6.53 (m, 1H), 5.23-5.07 (m, 2H), 4.63-4.10 (m, 3H), 3.01-2.82 (m, 1H), 2.14-1.94 (m, 2H), 1.89-1.75 (m, 2H), 1.73-1.62 (m, 1H), 1.57 (s, 9H), 1.28-1.19 (m, 3R), 0.94-0.84 (m, 2H), 0.67-0.58 (m, 2H); MS(ES+) m/z 484.3 (M+1).

Step 4. Preparation of tert-butyl 5-cyclopropyl-2-fluoro-4-(((3R,6S)-6-methylpiperidin-3-yl)oxy)benzoate

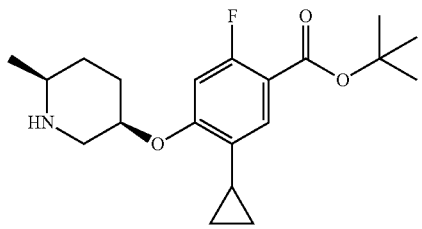 [SMILES: C[C@H]1CC[C@@H](Oc2cc(F)c(C(=O)OC(C)(C)C)cc2C2CC2)CN1]

Following the procedure as described in Example 52 step 4, and making variation as required to replace (2R,5R)-benzyl 5-(4-(tert-butoxycarbonyl)-2-cyclopropyl-5-fluorophenoxy)-2-methylpiperidine-1-carboxylate with (2S,5R)-benzyl 5-(4-(tert-butoxycarbonyl)-2-cyclopropyl-5-fluorophenoxy)-2-methylpiperidine-1-carboxylate, the title compound was obtained as a colorless oil (0.97 g, 99%): MS(ES+) m/z 350.3 (M+1).

Step 5. Preparation of tert-butyl 4-(((3R,6S)-1-(2-chloro-4-fluorobenzyl)-6-methylpiperidin-3-yl)oxy)-5-cyclopropyl-2-fluorobenzoate

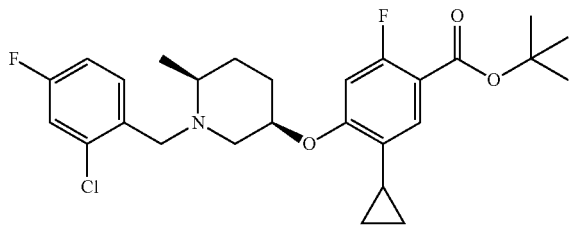 [SMILES: C[C@H]1CC[C@@H](Oc2cc(F)c(C(=O)OC(C)(C)C)cc2C2CC2)CN1Cc1ccc(F)cc1Cl]

Following the procedure as described in Example 34 step 2, and making variations as required to replace (R)-methyl 5-cyclopropyl-2-fluoro-4-(piperidin-3-yloxy)benzoate with tert-butyl 5-cyclopropyl-2-fluoro-4-((3R,6S)-6-methylpiperidin-3-yl)oxy)benzoate, and to replace 1-(bromomethyl)-4-fluoro-2-(trifluoromethyl)benzene with 1-(bromomethyl)-2-chloro-4-fluorobenzene, the title compound was obtained as a colorless oil (1.10 g, 82%): ¹H NMR (300 MHz, CDCl₃) δ7.53-7.43 (m, 1H), 7.41-7.34 (m, 1H), 7.08-6.99 (m, 1H), 6.86-6.73 (m, 1H), 6.48-6.36 (m, 1H), 4.48-4.34 (m, 1H), 3.93-3.76 (m, 1H), 3.50-3.36 (m, 1H), 2.97-2.81 (m, 1H), 2.79-2.65 (m, 1H), 2.58-2.42 (m, 1H), 2.22-2.04 (m, 1H), 2.01-1.66 (m, 4H), 1.57 (s, 9H), 1.19-1.09 (m, 3H), 0.97-0.87 (m, 2H), 0.75-0.62 (m, 2H); MS(ES+) m/z 492.3, 494.3 (M+1).

Step 6. Preparation of 4-(((3R,6S)-1-(2-chloro-4-fluorobenzyl)-6-methylpiperidin-3-yl)oxy)-5-cyclopropyl-2-fluorobenzoic acid

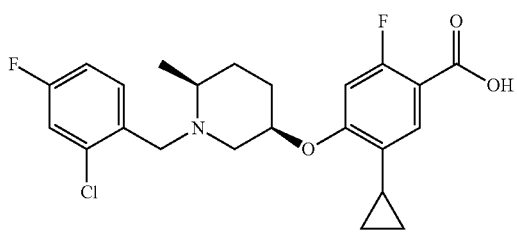 [SMILES: C[C@H]1CC[C@@H](Oc2cc(F)c(C(=O)O)cc2C2CC2)CN1Cc1ccc(F)cc1Cl]

Following the procedure as described in Example 3 step 3, and making variation as required to replace (R)-tert-butyl 3-(4-(tert-butoxycarbonyl)-2-cyclopropyl-5-fluorophenoxy)piperidine-1-carboxylate with tert-butyl 4-(((3R,6S)-1-2-chloro-4-fluorobenzyl)-6-methylpiperidin-3-yl)oxy)-5-cyclopropyl-2-fluorobenzoate, the title compound was obtained as a colorless solid (0.94 g, 96%): MS(ES+) m/z 436.2, 438.2 (M+1).

Step 7. Preparation of 4-(((3R,6S)-1-(2-chloro-4-fluorobenzyl)-6-methylpiperidin-3-yl)oxy)-5-cyclopropyl-2-fluoro-N-(methylsulfonyl)benzamide

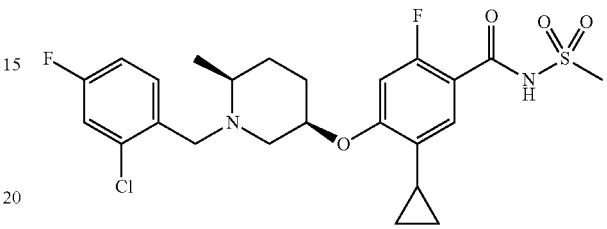

Following the procedure as described in Example 17 step 2, and making variation as required to replace (R)-5-cyclopropyl-4-((1-(3,4-dichlorobenzyl)piperidin-3-yl)-oxy)-2-fluorobenzoic acid with 4-(((3R,6S)-1-(2-chloro-4-fluorobenzyl)-6-methylpiperidin-3-yl)oxy)-5-cyclopropyl-2-fluorobenzoic acid, the title compound was obtained as a colorless solid (0.03 g, 9%); ¹H NMR (300 MHz, CDCl₃) δ8.77-8.58 (m, 1H), 7.62-7.53 (m, 1H), 7.48-7.40 (m, 1H), 7.08-6.99 (m, 1H), 6.82-6.72 (m, 1H), 6.49-6.38 (m, 1H), 4.47-4.37 (m, 1H), 3.92-3.79 (m, 1H), 3.49-3.35 (m, 4H), 2.96-2.81 (m, 1H), 2.80-2.67 (m, 1H), 2.56-2.43 (m, 1H), 2.20-2.05 (m, 1H), 2.03-1.66 (m, 4H), 1.19-1.07 (m, 3H), 1.02-0.87 (m, 2H), 0.78-0.60 (m, 2H); MS(ES+) m/z 513.2, 515.2 (M+1).

Example 325

Synthesis of N-(azetidin-1-ylsulfonyl)-4-(((3R,6S)-1-(2-chloro-4-fluorobenzyl)-6-methylpiperidin-3-yl)oxy)-5-cyclopropyl-2-fluorobenzamide

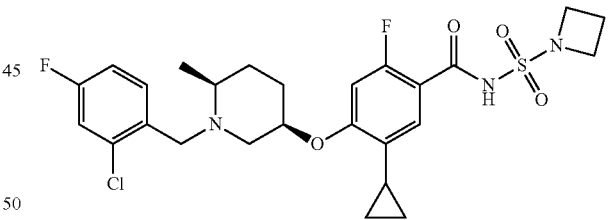

Following the procedure as described in Example 17 step 2, and making variations as required to replace (R)-5-cyclopropyl-4-((1-(3,4-dichlorobenzyl)piperidin-3-yl)-oxy)-2-fluorobenzoic acid with 4-(((3R,6S)-1-(2-chloro-4-fluorobenzyl)-6-methylpiperidin-3-yl)oxy)-5-cyclopropyl-2-fluorobenzoic acid, and to replace methanesulfonamide with azetidine-1-sulfonamide, the title compound was obtained as a colorless solid (0.08 g, 27%): ¹H NMR (300 MHz, CDCl₃) δ8.69-8.55 (m, 1H), 7.63-7.57 (m, 1H), 7.50-7.41 (m, 1H), 7.08-6.99 (m, 1H), 6.83-6.73 (m, 1H), 6.50-6.39 (m, 1H), 4.48-4.38 (m, 1H), 4.34-4.15 (m 4H), 3.92-3.81 (m, 1H), 3.48-3.36 (m, 1H), 2.94-2.83 (m, 1H), 2.78-2.67 (m, 1H), 2.54-2.45 (m, 1H), 2.34-2.20 (m, 2H), 2.19-2.08 (m, 1H), 2.04-1.67 (m, 4H), 1.20-1.10 (m, 3H), 1.01-0.89 (m, 2H), 0.80-0.64 (m, 2H); MS(ES+) m/z 554.0, 556.0 (M+1).

Example 326

Synthesis of 4-(((3R,6S)-1-(2-chloro-4-fluorobenzyl)-6-methylpiperidin-3-yl)oxy)-5-cyclopropyl-N-(cyclopropylsulfonyl)-2-fluorobenzamide

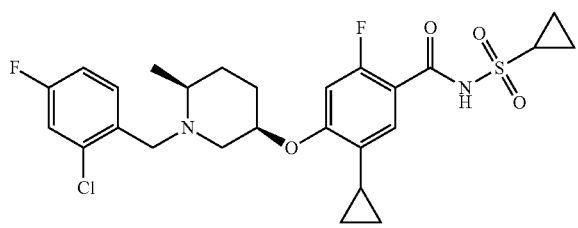 [SMILES: C[C@H]1CC[C@@H](Oc2cc(F)c(C(=O)NS(=O)(=O)C3CC3)cc2C2CC2)CN1Cc1ccc(F)cc1Cl]

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with 4-(((3R,6S)-1-(2-chloro-4-fluorobenzyl)-6-methylpiperidin-3-yl)oxy)-5-cyclopropyl-2-fluorobenzoic acid, and to replace methanesulfonamide with cyclopropanesulfonamide, the title compound was obtained as a colorless solid (0.11 g, 35%): $^1$H NMR (300 MHz, CDCl$_3$) δ 8.72-8.60 (m, 1H), 7.62-7.54 (m, 1H), 7.50-7.41 (m, 1H), 7.07-6.99 (m, 1H), 6.84-6.72 (m, 1H), 6.50-6.38 (m, 1H), 4.49-4.37 (m, 1H), 3.93-3.80 (m, 1H), 3.49-3.36 (m, 1H), 3.17-3.03 (m, 1H), 2.95-2.84 (m, 1H), 2.79-2.67 (m, 1H), 2.55-2.45 (m, 1H), 2.21-2.06 (m, 1H), 2.02-1.67 (m, 4H), 1.49-1.39 (m, 2H), 1.19-1.11 (m, 5H), 0.99-0.92 (m, 2H), 0.77-0.64 (m, 2H); MS(ES+) m/z 539.1, 541.1 (M+1).

Example 327

Synthesis of (R)-5-cyclopropyl-2-fluoro-N-(methylsulfonyl)-4-((1-((1-(trifluoromethyl)cyclopentyl)methyl)piperidin-3-yl)oxy)benzamide

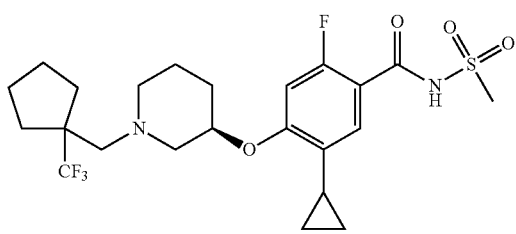 [SMILES: CS(=O)(=O)NC(=O)c1cc(C2CC2)c(O[C@@H]2CCCN(CC3(C(F)(F)F)CCCC3)C2)cc1F]

Step 1. Preparation of (R)-methyl 5-cyclopropyl-2-fluoro-4-((1-((1-(trifluoromethyl)cyclopentyl)methyl)piperidin-3-yl)oxy)benzoate

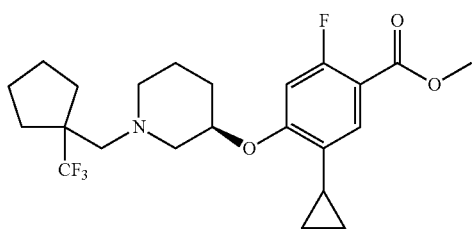 [SMILES: COC(=O)c1cc(C2CC2)c(O[C@@H]2CCCN(CC3(C(F)(F)F)CCCC3)C2)cc1F]

To a stirred solution of (R)-methyl 5-cyclopropyl-2-fluoro-4-(piperidin-3-yloxy)benzoate (1.84 g, 6.26 mmol) in acetone (31 mL) was added triethylamine (4.36 mL, 31.30 mmol), followed by addition of (1-(trifluoromethyl)cyclopentyl)methyl trifluoromethanesulfonate (1.84 g, 6.26 mmol) (A. Wolniewicz et al., *Journal of Fluorine Chemistry* 2001, 109, 95-102). The reaction mixture was stirred at reflux for 48 hours, cooled to ambient temperature, and concentrated in vacuo. The residue was diluted with ethyl acetate (70 mL), and washed with saturated aqueous sodium bicarbonate solution (30 mL). The layers were separated and the aqueous layer was extracted with ethyl acetate (2×70 mL). The combined organic layers were washed with brine (80 mL), dried over anhydrous magnesium sulfate, filtered and concentrated. The residue was purified by column chromatography eluting with a gradient of ethyl acetate in hexanes (0 to 25%) to give the title compound as a colorless oil (0.84 g, 30%): MS(ES+) m/z 444.4 (M+1).

Step 2. Preparation of (R)-5-cyclopropyl-2-fluoro-4-((1-((1-(trifluoromethyl)cyclopentyl)methyl)piperidin-3-yl)oxy)benzoic acid

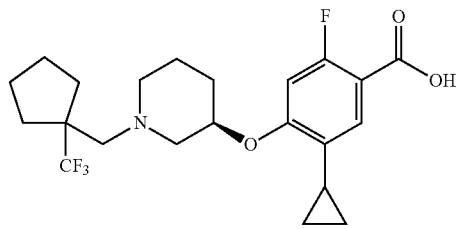 [SMILES: O=C(O)c1cc(C2CC2)c(O[C@@H]2CCCN(CC3(C(F)(F)F)CCCC3)C2)cc1F]

Following the procedure as described in Example 50 step 2, and making variations as required to replace methyl 4-((1-(3-fluorobenzyl)piperidin-4-yl)methoxy)-5-cyclopropyl-2-fluorobenzoate with (R)-methyl 5-cyclopropyl-2-fluoro-4-((1-((1-(trifluoromethyl)cyclopentyl)methyl)piperidin-3-yl)oxy)benzoate, the title compound was obtained as a colorless solid (0.78 g, 96%): MS(ES+) m/z 430.2 (M+1).

Step 3. Preparation of (R)-5-cyclopropyl-2-fluoro-N-(methylsulfonyl)-4-((1-((1-(trifluoromethyl)cyclopentyl)methyl)piperidin-3-yl)oxy)benzamide

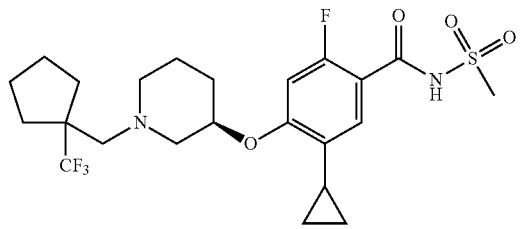 [SMILES: CS(=O)(=O)NC(=O)c1cc(C2CC2)c(O[C@@H]2CCCN(CC3(C(F)(F)F)CCCC3)C2)cc1F]

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with (R)-5-cyclopropyl-2-fluoro-4-((1-((1-(trifluoromethyl)cyclopentyl)methyl)piperidin-3-yl)oxy)benzoic acid, the title compound was obtained as a colorless solid (0.11 g, 17%); $^1$H NMR (300 MHz, CDCl$_3$)

δ 8.71 (s, 1H), 7.60-7.52 (m, 1H), 6.66-6.54 (m, 1H), 4.45-4.29 (m, 1H), 3.41 (s, 3H), 3.08-2.98 (m, 1H), 2.76-2.63 (m, 1H), 2.60-2.38 (m, 4H), 2.12-1.94 (m, 2H), 1.91-1.55 (m, 1H), 0.98-0.86 (m, 2H), 0.72-0.60 (m, 2H); MS(ES+) m/z 507.2 (M+1).

Example 328

Synthesis of (R)-5-cyclopropyl-2-fluoro-N-(methylsulfonyl)-4-((1-((1-(trifluoromethyl)cyclobutyl)methyl)piperidin-3-yl)oxy)benzamide

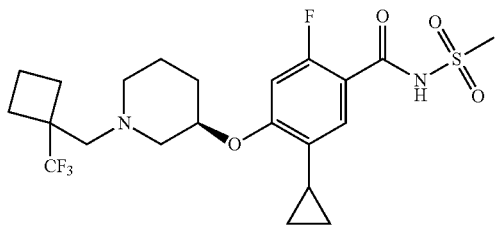 [SMILES: CS(=O)(=O)NC(=O)c1cc(C2CC2)c(O[C@@H]2CCCN(CC3(C(F)(F)F)CCC3)C2)cc1F]

Step 1. Preparation of (R)-methyl 5-cyclopropyl-2-fluoro-4-((1-((1-(trifluoromethyl)cyclobutyl)methyl)piperidin-3-yl)oxy)benzoate

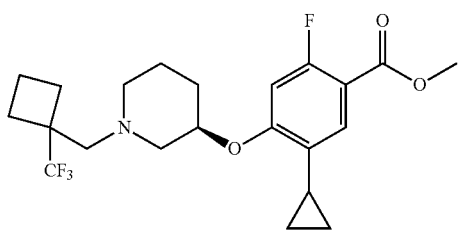 [SMILES: COC(=O)c1cc(C2CC2)c(O[C@@H]2CCCN(CC3(C(F)(F)F)CCC3)C2)cc1F]

To a mixture of (R)-methyl 5-cyclopropyl-2-fluoro-4-(piperidin-3-yloxy)benzoate (1.51 g, 5.15 mmol), (1-(trifluoromethyl)cyclobutyl)methyl trifluoromethanesulfonate (1.34 g, 4.68 mmol) (A. Wolniewicz et al., *Journal of Fluorine Chemistry*, 2001, 109, 95-102), and potassium carbonate (0.97 g, 7.02 mmol) in cyclohexane (35 ml) was stirred at reflux for 96 hours. The mixture was cooled to ambient temperature, diluted with hexanes (100 mL), washed with saturated aqueous sodium, bicarbonate solution (30 mL), brine (40 mL), dried over anhydrous magnesium sulfate, filtered and concentrated. The residue was purified by column chromatography eluting with a gradient of ethyl acetate is hexanes (0 to 25%) to give the title compound as a colorless oil (0.90 g, 39%): MS(ES+) m/z 430.2 (M+1).

Step 2. Preparation of (R)-5-cyclopropyl-2-fluoro-4-((1-((1-(trifluoromethyl)cyclobutyl)methyl)piperidin-3-yl)oxy)benzoic acid

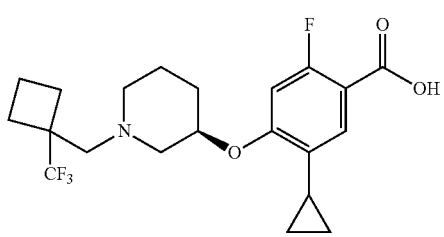 [SMILES: O=C(O)c1cc(C2CC2)c(O[C@@H]2CCCN(CC3(C(F)(F)F)CCC3)C2)cc1F]

Following the procedure as described in Example 50 step 2, and making variations as required to replace methyl 4-((1-(3-fluorobenzyl)piperidin-4-yl)methoxy)-5-cyclopropyl-2-fluorobenzoate with (R)-methyl 5-cyclopropyl-2-fluoro-4-((1-((1-(trifluoromethyl)cyclobutyl)methyl)piperidin-3-yl)oxy)benzoate, the title compound was obtained as a colorless solid (0.58 g, 67%): MS(ES+) m/z 416.2 (M+1).

Step 3. Preparation of (R)-5-cyclopropyl-2-fluoro-N-(methylsulfonyl)-4-((1-((1-(trifluoromethyl)cyclobutyl)methyl)piperidin-3-yl)oxy)benzamide

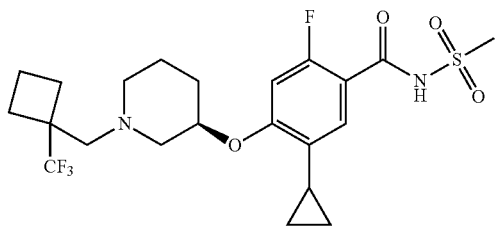 [SMILES: CS(=O)(=O)NC(=O)c1cc(C2CC2)c(O[C@@H]2CCCN(CC3(C(F)(F)F)CCC3)C2)cc1F]

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with (R)-5-cyclopropyl-2-fluoro-4-((1-((1-(trifluoromethyl)cyclobutyl)methyl)piperidin-3-yl)oxy)benzoic acid, the title compound was obtained as a colorless solid (0.24 g, 35%): $^1$H NMR (300 MHz, CDCl$_3$) δ 8.70 (s, 1H), 7.61-7.50 (m, 1H), 6.67-6.52 (m, 1H), 4.49-4.31 (m, 1H), 3.41 (s, 3H), 3.05-2.96 (m, 1H), 2.75-2.64 (m, 1H), 2.59 (s, 2H), 2.53-2.32 (m, 2H), 2.29-2.15 (m, 2H), 2.11-1.93 (m, 5H), 1.92-1.80 (m, 2H), 1.73-1.58 (m, 2H), 0.99-0.85 (m, 2H), 0.71-0.60 (m, 2H); MS(ES+) m/z 493.2 (M+1).

Example 329

Synthesis of 5-cyclopropyl-2-fluoro-N-(methylsulfonyl)-4-((1-((1-(trifluoromethyl)cyclopentyl)methyl)piperidin-4-yl)methoxy)benzamide trifluoroacetic acid salt

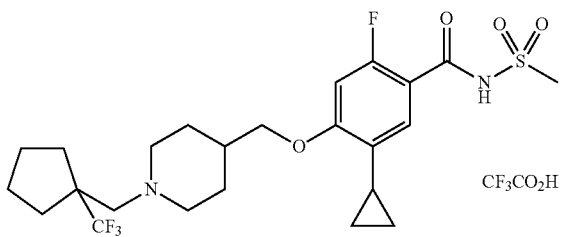 [SMILES: CS(=O)(=O)NC(=O)c1cc(C2CC2)c(OCC2CCN(CC3(C(F)(F)F)CCCC3)CC2)cc1F ; "CF3CO2H"]

Step 1. Preparation of tert-butyl 5-cyclopropyl-2-fluoro-4-((1-((1-(trifluoromethyl)cyclopentyl)methyl)piperidin-4-yl)methoxy)benzoate

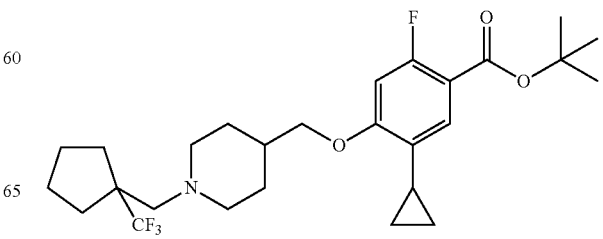

Following the procedure as described in Example 328 step 1, and making variations as required to replace (R)-methyl 5-cyclopropyl-2-fluoro-4-(piperidin-3-yloxy)benzoate with tert-butyl 5-cyclopropyl-2-fluoro-4-(piperidin-4-yl-methoxy)benzoate, and to replace (1-(trifluoromethyl)cyclobutyl)methyl trifluoromethanesulfonate with (1-(trifluoromethyl)cyclopentyl)methyl trifluoromethanesulfonate, the title compound was obtained, as a colorless oil (0.42 g, 54%): MS(ES+) m/z 500.3 (M+1).

Step 2. Preparation of 5-cyclopropyl-2-fluoro-4-((1-((1-(trifluoromethyl)cyclopentyl)methyl)piperidin-4-yl)methoxy)benzoic acid

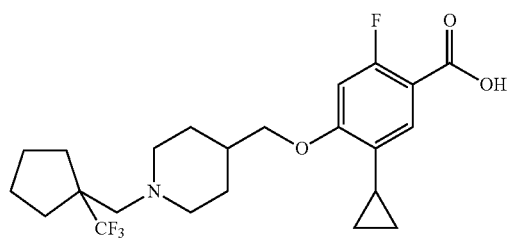 [SMILES: O=C(O)c1cc(C2CC2)c(OCC2CCN(CC3(C(F)(F)F)CCCC3)CC2)cc1F]

Following the procedure as described in Example 3 step 3, and making variations as required to replace (R)-tert-butyl 3-(4-(tert-butoxycarbonyl)-2-cyclopropyl-5-fluorophenoxy)piperidine-1-carboxylate with tert-butyl 5-cyclopropyl-2-fluoro-4-((1-((1-(trifluoromethyl)cyclopentyl)methyl)piperidin-4-yl)methoxy)benzoate, the title compound was obtained as a colorless solid (0.36 g, 97%): MS(ES+) m/z 444.3 (M+1).

Step 3. Preparation of 5-cyclopropyl-2-fluoro-N-(methylsulfonyl)-4-((1-((1-(trifluoromethyl)cyclopentyl)methyl)piperidin-4-yl)methoxy)benzamide trifluoroacetic acid salt

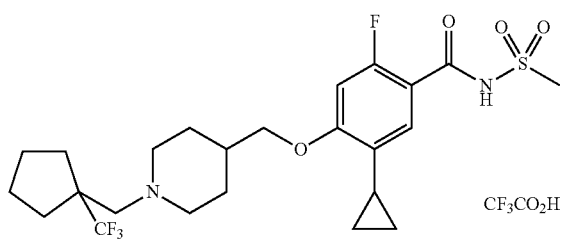 [SMILES: CS(=O)(=O)NC(=O)c1cc(C2CC2)c(OCC2CCN(CC3(C(F)(F)F)CCCC3)CC2)cc1F ; "CF3CO2H"]

Following the procedure as described in Example 17 step 2, and making variations as required to replace (R)-5-cyclopropyl-4-((1-(3,4-dichlorobenzyl)piperidin-3-yl)-oxy)-2-fluorobenzoic acid with 5-cyclopropyl-2-fluoro-4-((1-((1-(trifluoromethyl)cyclopentyl)methyl)piperidin-4-yl)methoxy)benzoic acid, title compound was obtained as a colorless solid (0.04 g, 17%): $^1$H NMR (300 MHz, CDCl$_3$) δ8.82-8.64 (m, 1H), 7.64-7.53 (m, 1H), 6.63-6.49 (m, 1H), 4.00-3.68 (m, 4H), 3.42 (s, 3H), 3.28 (s, 2H), 3.06-2.70 (m, 2H), 2.28-1.69 (m, 14H), 1.01-0.88 (at 2H), 0.71-0.50 (m, 2H); MS(ES+) m/z 521.2 (M+1).

Example 330

Synthesis of 5-cyclopropyl-4-(((2S,3S)-1-(3,5-dichlorobenzyl)-2-methylpiperidin-3-yl)oxy)-2-fluoro-N-(methylsulfonyl)benzamide, trifluoroacetic acid salt

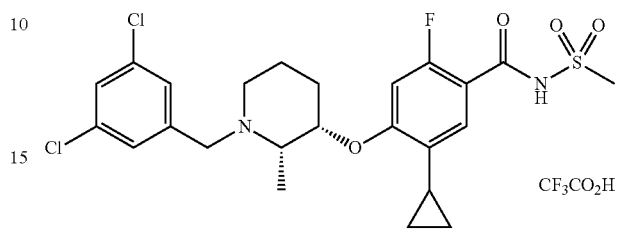

Step 1. Preparation of tert-butyl 4-(((2S,3S)-1-benzyl-2-methylpiperidin-3-yl)oxy)-5-chloro-2-fluorobenzoate

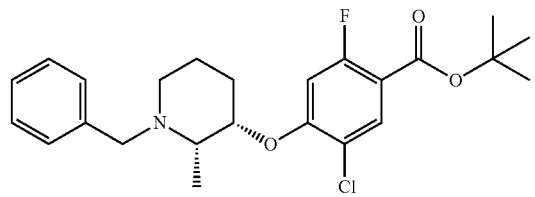 [SMILES: C[C@H]1[C@@H](Oc2cc(F)c(C(=O)OC(C)(C)C)cc2Cl)CCCN1Cc1ccccc1]

Following the procedure as described in Example 1 step 1, and making variation as required to replace (R)-1-benzylpiperidin-3-ol with (2S,3S)-1-benzyl-2-methylpiperidin-3-ol (Peter H. Huy et al., Org. Lett. 2013, 15, 5178), the title compound was obtained as a pale yellow oil (0.15 g, 11%); MS(ES+) m/z 434.2, 436.2 (M+1).

Step 2. tert-butyl 4-(((2S,3S)-1-benzyl-2-methylpiperidin-3-yl)oxy)-5-cyclopropyl-2-fluorobenzoate

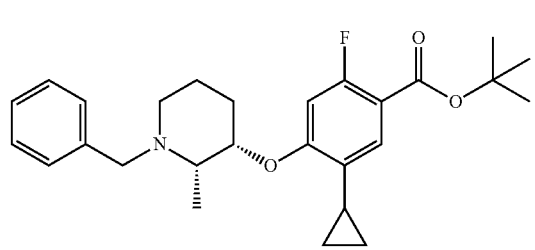 [SMILES: C[C@H]1[C@@H](Oc2cc(F)c(C(=O)OC(C)(C)C)cc2C2CC2)CCCN1Cc1ccccc1]

Following the procedure as described in Example 1 step 2, and making variation as required to replace (R)-tert-butyl 4-((1-benzylpiperidin-3-yl)oxy)-5-chloro-2-fluorobenzoate with tert-butyl 4-(((2S,3S)-1-benzyl-2-methylpiperidin-3-yl)oxy)-5-chloro-2-fluorobenzoate, the title compound was obtained (0.343 g, 96%) as a colorless oil: $^1$H NMR (300 MHz, CDCl$_3$) δ 7.39-7.18 (m, 6H), 6.57-6.48 (m, 1H), 4.51-4.38 (m, 1H), 3.74-3.52 (m, 2H), 3.32-3.18 (m, 1H), 2.59-2.32 (m, 2H), 2.04-1.93 (m, 1H), 1.91-1.58 (m, 4H), 1.54 (s, 9H), 1.07 (d, J=6.6 Hz, 3H), 0.91-0.79 (m, 2H), 0.67-0.52 (m, 2H).

Step 3. Preparation of tert-butyl 5-cyclopropyl-2-fluoro-4-(((2S,3S)-2-methylpiperidin-3-yl)oxy)benzoate

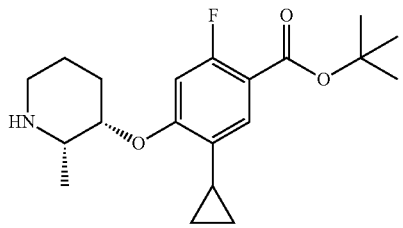 [SMILES: C[C@@H]1NCCC[C@@H]1Oc1cc(F)c(C(=O)OC(C)(C)C)cc1C1CC1]

To a mixture of tert-butyl 4-(((2S,3S)-1-benzyl-2-methylpiperidin-3-yl)oxy)-5-cyclopropyl-2-fluorobenzoate (0.34 g, 0.78 mmol) and ammonium formate (0.49 g, 7.74 mmol) in methanol (16 mL) was added 10% palladium on carbon (0.04 g). The reaction mixture was stirred at reflux for 1 hour, cooled to ambient temperature, and filtered through a pad of diatomaceous earth. The filtrate was concentrated. The residue was diluted with ethyl acetate (100 mL), washed with aqueous saturated, sodium bicarbonate solution (25 mL), water (25 mL), and brine (40 mL); dried over anhydrous magnesium sulfate; filtered and concentrated in vacuo to give the title compound as a colorless solid (0.22 g, 81%): MS(ES+) m/z 349.9 (M+1).

Step 4. Preparation of tert-butyl 5-cyclopropyl-4-(((2S,3S)-1-(3,5-dichlorobenzyl)-2-methylpiperidin-3-yl)oxy-2-fluorobenzoate

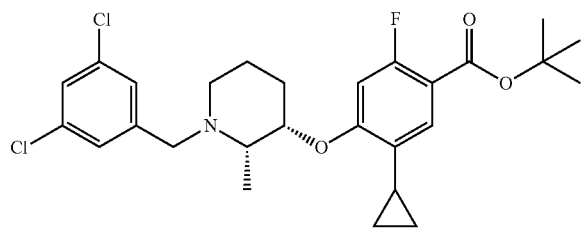 [SMILES: C[C@H]1[C@@H](Oc2cc(F)c(C(=O)OC(C)(C)C)cc2C2CC2)CCCN1Cc1cc(Cl)cc(Cl)c1]

Following the procedure as described in Example 50 step 1, and making variations as required to replace (R)-methyl 5-cyclopropyl-2-fluoro-4-(piperidin-3-yloxy)benzoate with tert-butyl 4-(((2S,3S)-1-benzyl-2-methylpiperidin-3-yl)oxy)-5-cyclopropyl-2-fluorobenzoate, and to replace 1,3-dichloro-5-(1-chloroethyl)benzene with 1,3-dichloro-5-(chloromethyl)benzene, the title compound was obtained as a colorless oil (0.27 g, 84%): MS(ES+) m/z 508.1, 510.1 (M+1).

Step 5. Preparation of 5-cyclopropyl-4-(((2S,3S)-1-(3,5-dichlorobenzyl)-2-methylpiperidin-3-yl)oxy)-2-fluorobenzoic acid

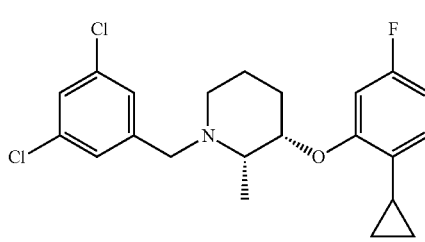

Following the procedure as described in Example 3 step 3, and snaking variation as required to replace (R)-tert-butyl 3-(4-(tert-butoxycarbonyl)-2-cyclopropyl-5-fluorophenoxy)piperidin-1-carboxylate with tert-butyl 5-cyclopropyl-4-(((2S,3S)-1-(3,5-dichlorobenzyl)-2-methylpiperidin-3-yl)oxy)-2-fluorobenzoate, the title compound was obtained as a colorless solid (0.24 g, 99%): MS(ES+) m/z 452.1, 454.0 (M+1).

Step 6. Preparation of 5-cyclopropyl-4-(((2S,3S)-1-(3,5-dichlorobenzyl)-2-methylpiperidin-3-yl)oxy)-2-fluoro-N-(methylsulfonyl)benzamide trifluoroacetic acid salt

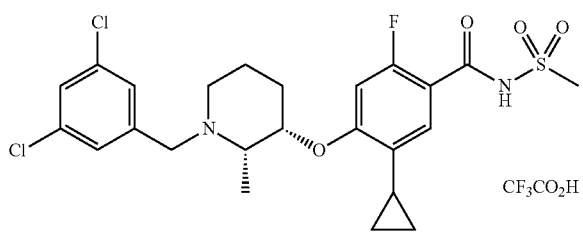 [SMILES: C[C@H]1[C@@H](Oc2cc(F)c(C(=O)NS(C)(=O)=O)cc2C2CC2)CCCN1Cc1cc(Cl)cc(Cl)c1 ; "CF3CO2H"]

Following the procedure as described in Example 17 step 2, and making variations as required to replace (R)-5-cyclopropyl-4-((1-(3,4-dichlorobenzyl)piperidin-3-yl)-oxy)-2-fluorobenzoic acid with 5-cyclopropyl-4-(((2S,3S)-1-(3,5-dichlorobenzyl)-2-methylpiperidin-3-yl)oxy)-2-fluorobenzoic acid, the title compound was obtained as a colorless solid (0.06 g, 36%): $^1$H NMR (300 MHz, CDCl$_3$) δ8.93-8.61 (m, 1H), 7.70-7.53 (m, 1H), 7.50-7.35 (m, 3H), 6.89-6.67 (m, 1H), 5.02-4.83 (m, 1H), 4.46-4.12 (m, 2H), 4.09-3.85 (m, 1H), 3.47-3.33 (m, 3H), 3.31-2.87 (m, 2H), 2.18-1.86 (m, 5H), 1.62-1.39 (m, 3H), 1.03-0.83 (m, 2H), 0.73-0.54 (m, 2H); MS(ES+) m/z 529.1, 531.1 (M+1).

Example 331

Synthesis of 5-cyclopropyl-4-(((2S,3R)-1-(3,5-dichlorobenzyl)-2-methylpiperidin-3-yl)oxy)-2-fluoro-N-(methylsulfonyl)benzamide, trifluoroacetic acid salt

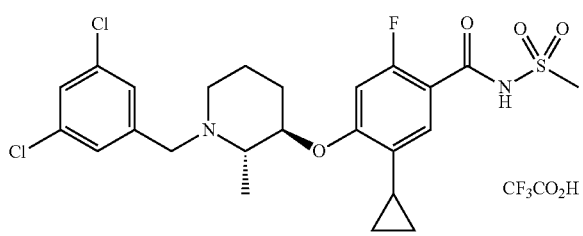 [SMILES: C[C@H]1[C@H](Oc2cc(F)c(C(=O)NS(C)(=O)=O)cc2C2CC2)CCCN1Cc1cc(Cl)cc(Cl)c1 ; "CF3CO2H"]

Step 1. Preparation of tert-butyl 4-(((2S,3R)-1-benzyl-2-methylpiperidin-3-yl)oxy)-5-chloro-2-fluorobenzoate

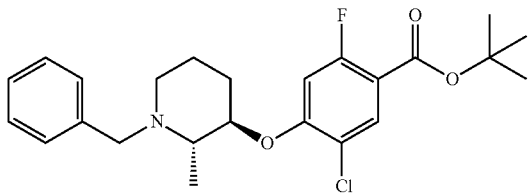 [SMILES: C[C@H]1[C@H](Oc2cc(F)c(C(=O)OC(C)(C)C)cc2Cl)CCCN1Cc1ccccc1]

Following the procedure as described in Example 1 step 1, and making variation as required to replace (R)-1-benzylpiperidin-3-ol with (2S,3R)-1-benzyl-2-methylpiperidin-3-ol (Peter H. Huy et al., *Org. Lett.*, 2013, 75, 5178), the title compound was obtained as a colorless oil (0.26 g, 37%): MS(ES+) m/z 434.1, 436.1 (M+1).

Step 2. Preparation of tert-butyl 4-(((2S,3R)-1-benzyl-2-methylpiperidin-3-yl)oxy)-5-cyclopropyl-2-fluorobenzoate

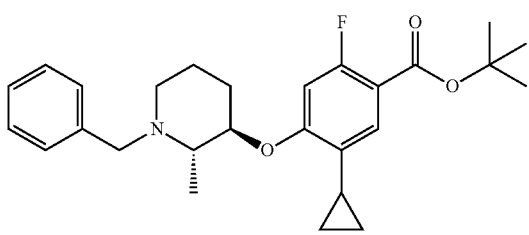 [SMILES: C[C@H]1[C@H](Oc2cc(F)c(C(=O)OC(C)(C)C)cc2C2CC2)CCCN1Cc1ccccc1]

Following the procedure as described in Example 1 step 2, and making variation as required to replace (R)-tert-butyl 4-((1-benzylpiperidin-3-yl)oxy)-5-chloro-2-fluorobenzoate with tert-butyl 4-(((2S,3R)-1-benzyl-2-methylpiperidin-3-yl)oxy)-5-chloro-2-fluorobenzoate, the title compound was obtained as a pale yellow oil (0.21 g, 80%): MS(ES+) m/z 440.4 (M+1).

Step 3. Preparation of tert-butyl 5-cyclopropyl-2-fluoro-4-(((2S,3R)-2-methylpiperidin-3-yl)oxy)benzoate

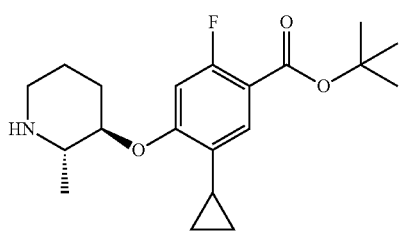 [SMILES: C[C@@H]1NCCC[C@H]1Oc1cc(F)c(C(=O)OC(C)(C)C)cc1C1CC1]

Following the procedure as described in Example 330 step 3, and making variations as required to replace tert-butyl 4-(((2S,3S)-1-benzyl-2-methylpiperidin-3-yl)oxy)-5-cyclopropyl-2-fluorobenzoate with tert-butyl 4-(((2S,3R)-1-benzyl-2-methylpiperidin-3-yl)oxy)-5-cyclopropyl-2-fluorobenzoate, the title compound was obtained as a colorless oil (0.16 g, 95%): MS(ES+) m/z 350.3 (M+1).

Step 4. Preparation of tert-butyl 5-cyclopropyl-4-(((2S,3R)-1-(3,5-dichlorobenzyl)-2-methylpiperidin-3-yl)oxy)-2-fluorobenzoate

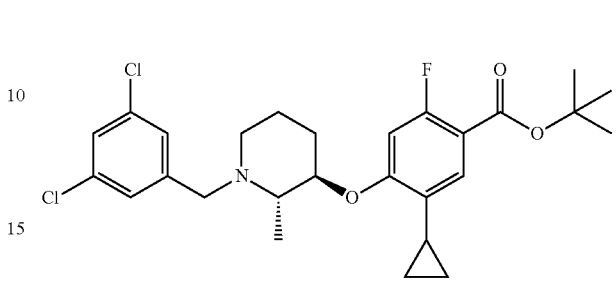

Following the procedure as described in Example 50 step 1, and making variations as required to replace (R)-methyl 5-cyclopropyl-2-fluoro-4-(piperidin-3-yloxy)benzoate with tert-butyl 5-cyclopropyl-2-fluoro-4-(((2S,3R)-2-methylpiperidin-3-yl)oxy)benzoate, and to replace 1,3-dichloro-5-(1-chloroethyl)benzene with 1,3-dichloro-5-(chloromethyl)benzene, the title compound was obtained as a colorless oil (0.15 g, 68%): MS(ES+) m/z 508.1, 510.1 (M+1).

Step 5. Preparation of 5-cyclopropyl-4-(((2S,3R)-1-(3,5-dichlorobenzyl)-2-methylpiperidin-3-yl)oxy)-2-fluorobenzoic acid

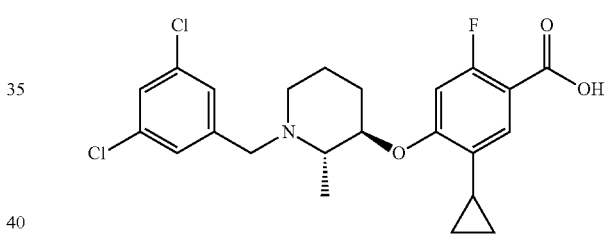

Following the procedure as described in Example 3 step 3, and making variation as required to replace (R)-tert-butyl 3-(4-(tert-butoxycarbonyl)-2-cyclopropyl-5-fluorophenoxy)piperidine-1-carboxylate with tert-butyl 5-cyclopropyl-4-(((2S,3R)-1-(3,5-dichlorobenzyl)-2-methylpiperidin-3-yl)oxy)-2-fluorobenzoate, the title compound was obtained as a colorless solid (0.08 g, 64%): MS(ES+) m/z 452.1, 454.0 (M+1).

Step 6. Preparation of 5-cyclopropyl-4-(((2S,3R)-1-(3,5-dichlorobenzyl)-2-methylpiperidin-3-yl)oxy)-2-fluoro-N-(methylsulfonyl)benzamide, trifluoroacetic acid salt

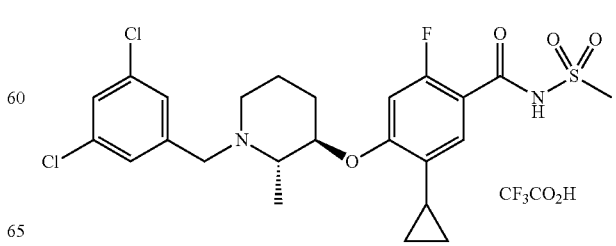

Following the procedure as described in Example 17 step 2, and making variations as required to replace (R)-5-cyclopropyl-4-((1-(3,4-dichlorobenzyl)piperidin-3-yl)-oxy)-2-fluorobenzoic acid with 5-cyclopropyl-4-(((2S,3R)-1-(3,5-dichlorobenzyl)-2-methylpiperidin-3-yl)oxy)-2-fluorobenzoic acid, the title compound was obtained as a colorless solid (0.03 g, 27%); ¹H NMR (300 MHz, CDCl₃) δ8.88-8.66 (m, 1H), 7.67-7.58 (m, 1H), 7.52-7.36 (m, 3H), 6.79-6.64 (m, 1H), 4.89-4.58 (m, 2H), 4.12-3.90 (m, 1H), 3.54-3.21 (m, 5H), 3.00-2.75 (m, 1H), 2.44-1.93 (m, 5H), 1.84-1.64 (m, 3H), 1.06-0.90 (m, 2H), 0.80-0.54 (m, 2H); MS(ES+) m/z 529.1, 531.1 (M+1).

Example 332

Synthesis of (R)-4-((1-(2-chloro-4-fluorobenzyl)piperidin-3-yl)methoxy)-5-cyclopropyl-2-fluoro-N-(methylsulfonyl)benzamide

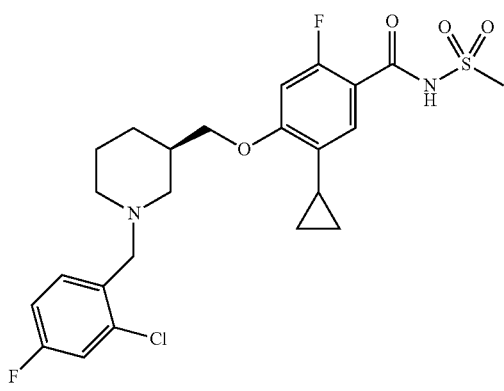 [SMILES: CS(=O)(=O)NC(=O)c1cc(C2CC2)c(OC[C@@H]2CCCN(Cc3ccc(F)cc3Cl)C2)cc1F]

Step 1. Preparation of (R)-tert-butyl 3-((4-(tert-butoxycarbonyl)-2-chloro-5-fluorophenoxy)methyl)piperidine-1-carboxylate

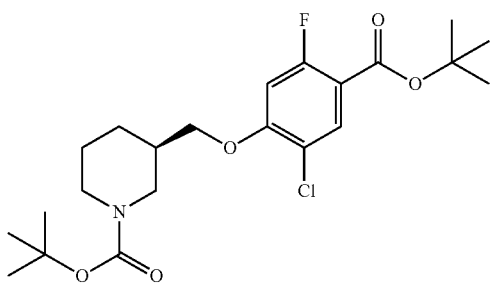 [SMILES: CC(C)(C)OC(=O)c1cc(Cl)c(OC[C@@H]2CCCN(C(=O)OC(C)(C)C)C2)cc1F]

Following the procedure as described in Example 1 step 1, and making variation as required to replace (R)-1-benzylpiperidin-3-ol with (R)-tert-butyl 3-(hydroxymethyl)piperidine-1-carboxylate, the title compound was obtained (13.11 g, 79%) as a colorless oil: MS(ES+) m/z 444.2, 446.2 (M+1).

Step 2. Preparation of (R)-tert-butyl 3-((4-(tert-butoxycarbonyl)-2-cyclopropyl-5-fluorophenoxy)methyl)piperidine-1-carboxylate

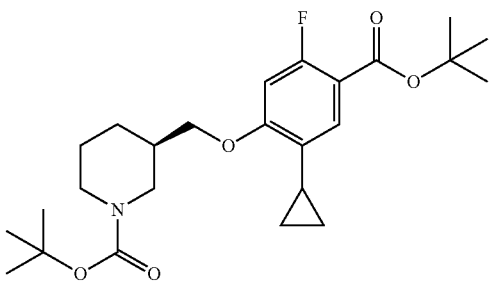 [SMILES: CC(C)(C)OC(=O)c1cc(C2CC2)c(OC[C@@H]2CCCN(C(=O)OC(C)(C)C)C2)cc1F]

Following the procedure as described in Example 1 step 2, and making variation as required to replace (R)-tert-butyl 4-((1-benzylpiperidin-3-yl)oxy)-5-chloro-2-fluorobenzoate with (R)-tert-butyl 3-((4-(tert-butoxycarbonyl)-2-chloro-5-fluorophenoxy)methyl)piperidine-1-carboxylate, the title compound was obtained as a colorless solid (8.61 g, 65%): MS(ES+) m/z 450.3 (M+1).

Step 3. Preparation of (R)-methyl 5-cyclopropyl-2-fluoro-4-(piperidin-3-ylmethoxy)benzoate

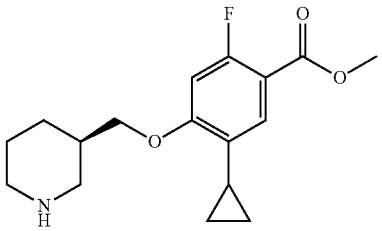 [SMILES: COC(=O)c1cc(C2CC2)c(OC[C@@H]2CCCNC2)cc1F]

Following the procedure as described in Example 34 step 1, and making variations as required to replace (R)-tert-butyl 3-(4-(tert-butoxycarbonyl)-2-cyclopropyl-5-fluorophenoxy)piperidine-1-carboxylate with (R)-tert-butyl 3-((4-(tert-butoxycarbonyl)-2-cyclopropyl-5-fluorophenoxy)methyl)piperidine-1-carboxylate, the title compound was obtained as a colorless oil (5.89 g, 99%); MS(ES+) m/z 308.2 (M+1).

Step 4. Preparation of (R)-methyl 4-((1-(2-chloro-4-fluorobenzyl)piperidin-3-yl)methoxy)-5-cyclopropyl-2-fluorobenzoate

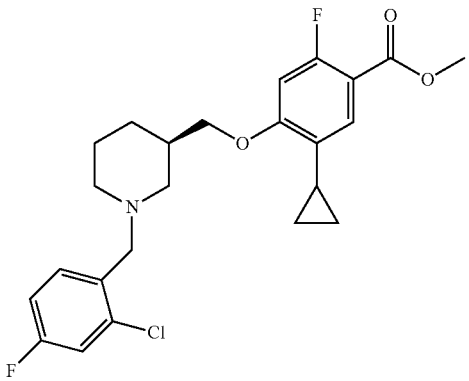 [SMILES: COC(=O)c1cc(C2CC2)c(OC[C@@H]2CCCN(Cc3ccc(F)cc3Cl)C2)cc1F]

Following the procedure as described in Example 34 step 2, and making variations as required to replace (R)-methyl 5-cyclopropyl-2-fluoro-4-(piperidin-3-yloxy)benzoate with (R)-methyl 5-cyclopropyl-2-fluoro-4-(piperidin-3-yl-methoxy)benzoate, and to replace 1-(bromomethyl)-4-fluoro-2-(trifluoromethyl)benzene with 1-(bromomethyl)-2-chloro-4-fluorobenzene, the title compound was obtained as a colorless oil (4.06 g, 94%): MS(ES+) m/z 450.1, 452.1 (M+1).

Step 5. Preparation of (R)-4-((1-(2-chloro-4-fluorobenzyl)piperidin-3-yl)methoxy)-5-cyclopropyl-2-fluorobenzoic acid

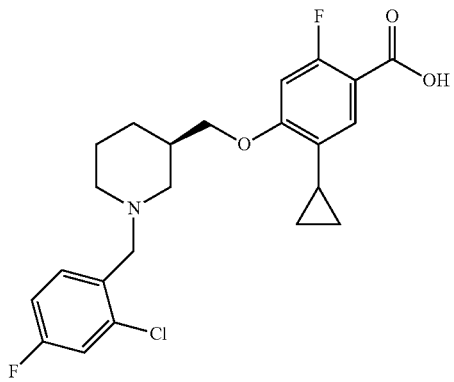 [SMILES: O=C(O)c1cc(C2CC2)c(OC[C@@H]2CCCN(Cc3ccc(F)cc3Cl)C2)cc1F]

Following the procedure as described in Example 50 step 2, and making variations as required to replace methyl 4-((1-(3-fluorobenzyl)piperidin-4-yl)methoxy)-5-cyclopropyl-2-fluorobenzoate with (R)-methyl 4-((1-(2-chloro-4-fluorobenzyl)piperidin-3-yl)methoxy)-5-cyclopropyl-2-fluorobenzoate, the title compound was obtained as a colorless solid (3.80 g, 97%); MS(ES+) m/z 436.1, 438.1 (M+1).

Step 6. Preparation of (R)-4-((1-(2-chloro-4-fluorobenzyl)piperidin-3-yl)methoxy)-5-cyclopropyl-2-fluoro-N-(methylsulfonyl)benzamide

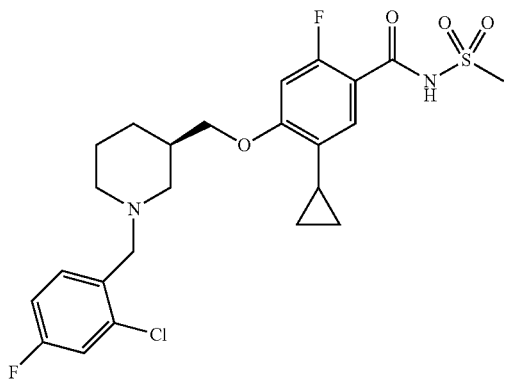 [SMILES: CS(=O)(=O)NC(=O)c1cc(C2CC2)c(OC[C@@H]2CCCN(Cc3ccc(F)cc3Cl)C2)cc1F]

Following the procedure as described in Example 17 step 2, and making variations as required to replace (R)-5-cyclopropyl-4-((1-(3,4-dichlorobenzyl)piperidin-3-yl)-oxy)-2-fluorobenzoic acid with (R)-4-((1-(2-chloro-4-fluorobenzyl)piperidin-3-yl)methoxy)-5-cyclopropyl-2-fluorobenzoic acid, the title compound was obtained as a colorless solid (0.25 g, 35%): $^1$H NMR (300 MHz, CDCl$_3$) δ11.53 (br s, 1H), 7.59-7.48 (m, 1H), 7.47-7.39 (m, 1H), 7.25-7.09 (m, 2H), 6.96-6.85 (m, 1H), 4.09-3.85 (m, 2H), 3.78-3.54 (m, 2H), 3.26 (s, 3H), 3.01-2.78 (m, 2H), 2.36-2.02 (m, 3H), 1.91-1.47 (m, 4H), 1.29-1.12 (m, 1H), 0.86-0.68 (m, 2H), 0.64-0.52 (m, 2H); MS(ES+) m/z 513.2, 515.1 (M+1).

Example 333

Synthesis of (R)—N-(azetidin-1-ylsulfonyl)-4-((1-(2-chloro-4-fluorobenzyl)piperidin-3-yl)methoxy-5-cyclopropyl-2-fluorobenzamide

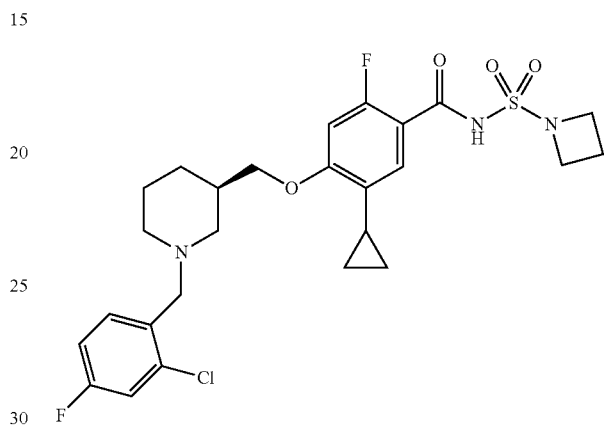

Following the procedure as described in Example 17 step 2, and making variations as required to replace (R)-5-cyclopropyl-4-((1-(3,4-dichlorobenzyl)piperidin-3-yl)-oxy)-2-fluorobenzoic acid with (R)-4-((1-(2-chloro-4-fluorobenzyl)piperidin-3-yl)methoxy)-5-cyclopropyl-2-fluorobenzoic acid, and to replace methanesulfonamide with azetidine-1-sulfonamide, the title compound was obtained as a colorless solid (0.14 g, 19%): $^1$H NMR (300 MHz, CDCl$_3$) δ8.65 (s, 1H), 7.62-7.55 (m, 1H), 7.47-7.38 (m, 1H), 7.12-7.04 (m, 1H), 6.96-6.86 (m, 1H), 6.61-6.51 (m, 1H), 4.33-4.14 (m, 4H), 4.01-3.82 (m, 2H), 3.64-3.49 (m, 2H), 3.00-2.86 (m, 1H), 2.83-2.69 (m, 1H), 2.37-2.03 (m, 5H), 1.99-1.61 (m, 4H), 1.37-1.17 (m, 1H), 0.97-0.75 (m, 2H), 0.71-0.53 (m, 2H): MS(ES+) m/z 554.2, 556.2 (M+1).

Example 334

Synthesis of (R)-5-cyclopropyl-4-((1-(3,5-dichlorobenzyl)piperidin-3-yl)methoxy)-2-fluoro-N-(methylsulfonyl)benzamide

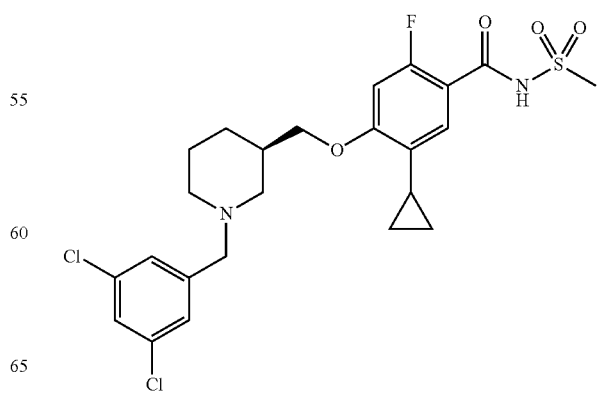

Step 1. Preparation of (R)-methyl 5-cyclopropyl-4-((1-(3,5-dichlorobenzyl)piperidin-3-yl)methoxy)-2-fluorobenzoate

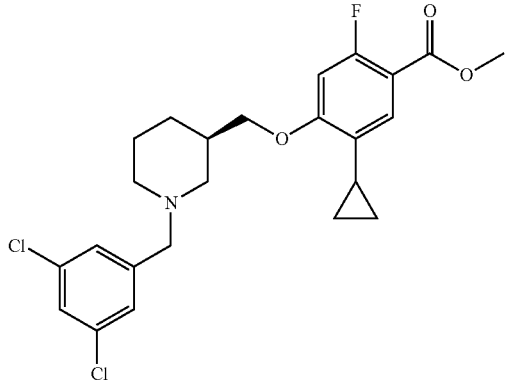 [SMILES: COC(=O)c1cc(C2CC2)c(OC[C@@H]2CCCN(Cc3cc(Cl)cc(Cl)c3)C2)cc1F]

Following the procedure as described in Example 50 step 1, and making variations as required to replace (R)-methyl 5-cyclopropyl-2-fluoro-4-(piperidin-3-yloxy)benzoate with (R)-methyl 5-cyclopropyl-2-fluoro-4-(piperidin-3-ylmethoxy)benzoate, and to replace 1,3-dichloro-5-(1-chloroethyl)benzene with 1,3-dichloro-5-(chloromethyl)benzene, the title compound was obtained as a colorless oil (0.68 g, 89%): MS(ES+) m/z 466.2, 468.1 (M+1).

Step 2. Preparation of (R)-5-cyclopropyl-4-((1-(3,5-dichlorobenzyl)piperidin-3-yl)methoxy)-2-fluorobenzoic acid

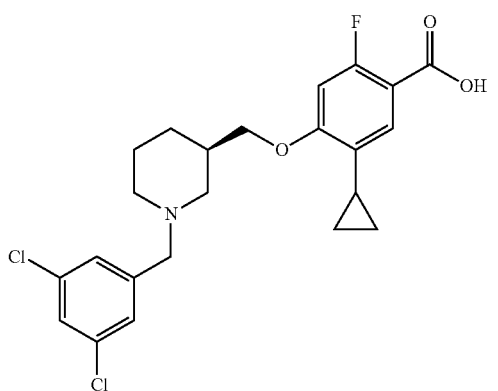 [SMILES: O=C(O)c1cc(C2CC2)c(OC[C@@H]2CCCN(Cc3cc(Cl)cc(Cl)c3)C2)cc1F]

Following the procedure as described in Example 50 step 2, and making variations as required to replace methyl 4-((1-(3-fluorobenzyl)piperidin-4-yl)methoxy)-5-cyclopropyl-2-fluorobenzoate with (R)-methyl 5-cyclopropyl-4-((1-(3,5-dichlorobenzyl)piperidin-3-yl)methoxy)-2-fluorobenzoate, the title compound was obtained as a colorless solid (0.60 g, 91%): MS(ES+) m/z 452.1, 454.1 (M+1).

Step 3. Preparation of (R)-5-cyclopropyl-4-((1-(3,5-dichlorobenzyl)piperidin-3-yl)methoxy)-2-fluoro-N-(methylsulfonyl)benzamide

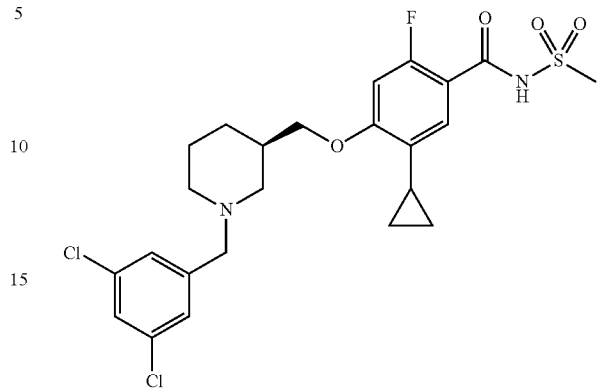

Following the procedure as described in Example 17 step 2, and making variations as required to replace (R)-5-cyclopropyl-4-((1-(3,4-dichlorobenzyl)piperidin-3-yl)-oxy)-2-fluorobenzoic acid with (R)-5-cyclopropyl-4-((1-(3,5-dichlorobenzyl)piperidin-3-yl)methoxy)-2-fluorobenzoic acid, the title compound was obtained as a colorless solid (0.14 g, 39%): $^1$H NMR (300 MHz, CDCl$_3$) δ 8.68 (s, 1H), 7.59-7.53 (m, 1H), 7.25-7.18 (m, 3H), 6.59-6.52 (m, 1H), 3.96-3.82 (m, 2H), 3.53-3.35 (m, 5H), 2.96-2.84 (m, 1H), 2.81-2.67 (m, 1H), 2.33-2.06 (m, 2H), 2.05-1.63 (m, 5H), 1.36-1.16 (m, 1H), 0.95-0.75 (m, 2H), 0.69-0.51 (m, 2H); MS(ES+) m/z 529.1, 531.1 (M+1).

Example 335

Synthesis of (S)-4-((1-(2-chloro-4-fluorobenzyl)piperidin-3-yl)methoxy)-5-cyclopropyl-2-fluoro-N-(methylsulfonyl)benzamide

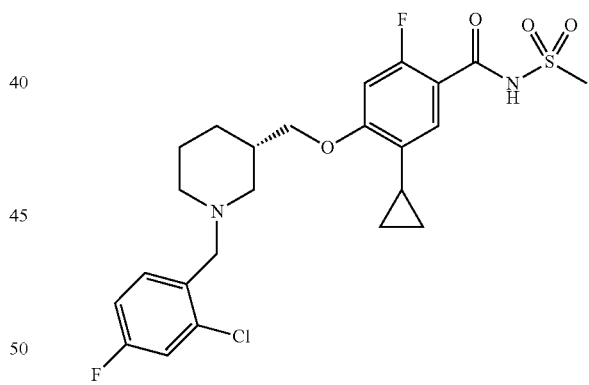

Step 1. Preparation of (S)-tert-butyl 3-((4-(tert-butoxycarbonyl)-2-chloro-5-fluorophenoxy)methyl)piperidine-1-carboxylate

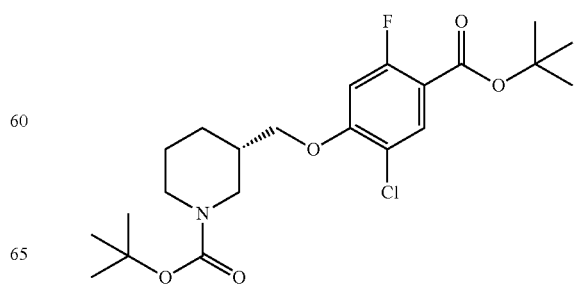

Following the procedure as described in Example 1 step 1, and making variation as required to replace (R)-1-benzylpiperidin-3-ol with (S)-tert-butyl 3-(hydroxymethyl)piperidine-1-carboxylate, the title compound was obtained as a colorless oil (12.94 g, 78%): MS(ES+) m/z 444.2, 446.2 (M+1).

Step 2. Preparation of (S)-tert-butyl 3-((4-(tert-butoxycarbonyl)-2-cyclopropyl-5-fluorophenoxy)methyl)piperidine-1-carboxylate

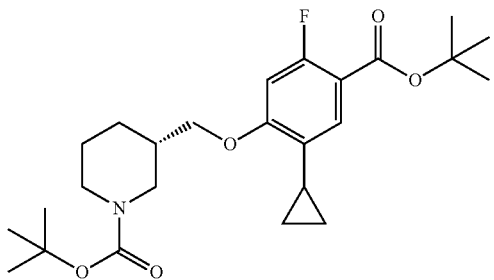 [SMILES: CC(C)(C)OC(=O)c1cc(C2CC2)c(OC[C@H]2CCCN(C(=O)OC(C)(C)C)C2)cc1F]

Following the procedure as described in Example 1 step 2, and making variation as required to replace (R)-tert-butyl 4-((1-benzylpiperidin-3-yl)oxy)-5-chloro-2-fluorobenzoate with (S)-tert-butyl 3-((4-(tert-butoxycarbonyl)-2-chloro-5-fluorophenoxy)methyl)piperidine-1-carboxylate, the title compound was obtained as a colorless solid (10.22 g, 78%): MS(ES+) m/z 450.3 (M+1).

Step 3. Preparation of (S)-methyl-5-cyclopropyl-2-fluoro-4-(piperidin-3-ylmethoxy)benzoate

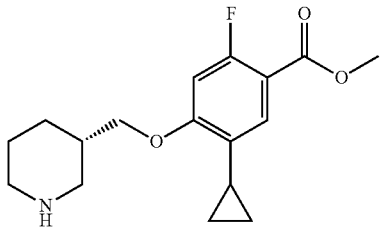 [SMILES: COC(=O)c1cc(C2CC2)c(OC[C@H]2CCCNC2)cc1F]

Following the procedure as described in Example 34 step 1, and making variations as required to replace (R)-tert-butyl 3-(4-(tert-butoxycarbonyl)-2-cyclopropyl-5-fluorophenoxy)piperidine-1-carboxylate with (R)-tert-butyl 3-(4-(tert-butoxycarbonyl)-2-cyclopropyl-5-fluorophenoxy)piperidine-1-carboxylate, the title compound was obtained as a pale yellow oil (6.99 g, 99%): MS(ES+) m/z 308.2 (M+1).

Step 4. Preparation of (S)-methyl 4-((1-(2-chloro-4-fluorobenzyl)piperidin-3-yl)methoxy)-5-cyclopropyl-2-fluorobenzoate

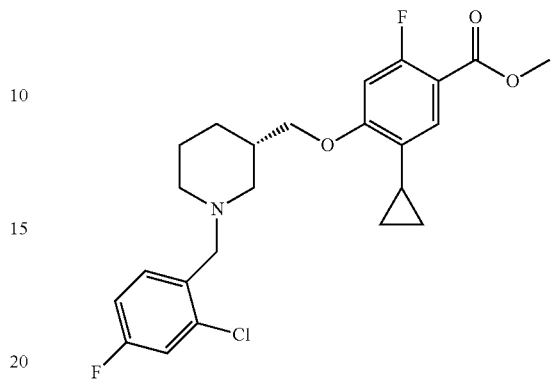

Following the procedure as described in Example 34 step 2, and snaking variations as required to replace (R)-methyl 5-cyclopropyl-2-fluoro-4-(piperidin-3-yloxy)benzoate with (S)-methyl 5-cyclopropyl-2-fluoro-4-(piperidin-3-ylmethoxy)benzoate, and to replace 1-(bromomethyl)-4-fluoro-2-(trifluoromethyl)benzene with 1-(bromomethyl)-2-chloro-4-fluorobenzene, the title compound was obtained as a colorless oil (1.85 g, 42%): MS(ES+) m/z 450.2, 452.2 (M+1).

Step 5. Preparation of (S)-4-((1-(2-chloro-4-fluorobenzyl)piperidin-3-yl)methoxy)-5-cyclopropyl-2-fluorobenzoic acid

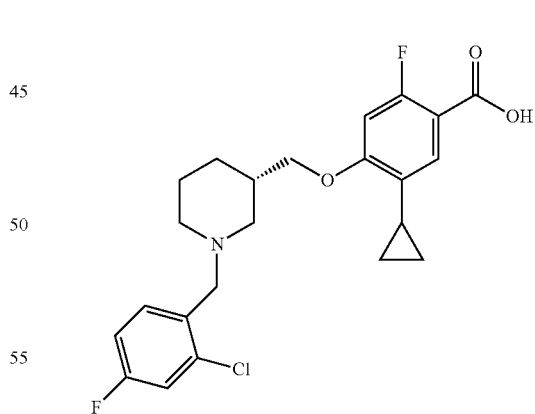

Following the procedure as described in Example 50 step 2, and making variations as required to replace methyl 4-((1-(3-fluorobenzyl)piperidin-4-yl)methoxy)-5-cyclopropyl-2-fluorobenzoate with (S)-methyl 4-((1-(2-chloro-4-fluorobenzyl)piperidin-3-yl)methoxy)-5-cyclopropyl-2-fluorobenzoate, the title compound was obtained as a colorless solid (1.78 g, 99%): MS(ES+) m/z 436.2, 438.1 (M+1).

Step 6. Preparation of (S)-4-((1-(2-chloro-4-fluorobenzyl)piperidin-3-yl)methoxy)-5-cyclopropyl-2-fluoro-N-(methylsulfonyl)benzamide

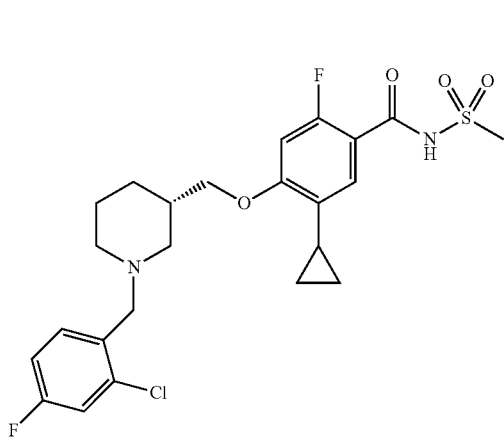 [SMILES: CS(=O)(=O)NC(=O)c1cc(C2CC2)c(OC[C@H]2CCCN(Cc3ccc(F)cc3Cl)C2)cc1F]

Following the procedure as described in Example 17 step 2, and making variations as required to replace (R)-5-cyclopropyl-4-((1-(3,4-dichlorobenzyl)piperidin-3-yl)-oxy)-2-fluorobenzoic acid with (S)-4-((1-(2-chloro-4-fluorobenzyl)piperidin-3-yl)methoxy)-5-cyclopropyl-2-fluorobenzoic acid, title compound was obtained as a colorless solid (0.19 g, 37%): $^1$H NMR (300 MHz, DMSO-$d_6$) δ11.53 (brs, 1H), 7.58-7.48 (m, 1H), 7.47-7.38 (m, 1H), 7.24-7.09 (m, 2H), 6.96-6.86 (m, 1H), 4.08-3.85 (m, 2H), 3.79-3.56 (m, 2H), 3.26 (s, 3H), 3.01-2.78 (m, 2H), 2.34-2.21 (m, 1H), 2.20-2.02 (m, 2H), 1.92-1.50 (m, 4H), 1.31-1.12 (m, 1H), 0.85-0.69 (m, 2H), 0.65-0.53 (m, 2H); MS(ES+) m/z 513.2, 515.2 (M+1).

Example 336

Synthesis of (S)-5-cyclopropyl-4-((1-(3,5-dichlorobenzyl)piperidin-3-yl)methoxy)-2-fluoro-N-(methylsulfonyl)benzamide

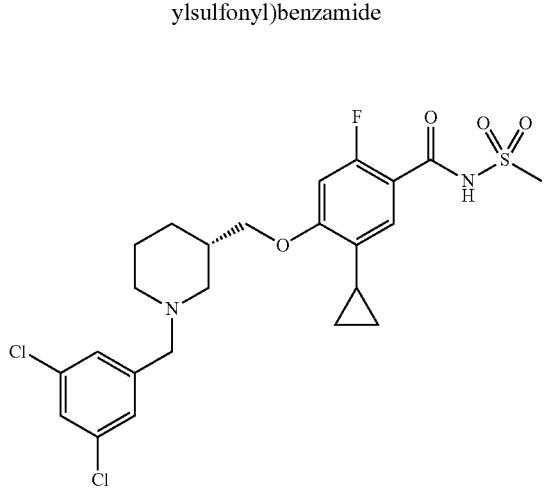

Step 1. Preparation of (S)-methyl 5-cyclopropyl-4-((1-(3,5-dichlorobenzyl)piperidin-3-yl)methoxy)-2-fluorobenzoate

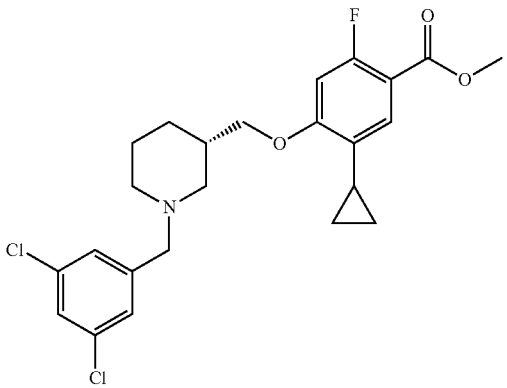 [SMILES: COC(=O)c1cc(C2CC2)c(OC[C@H]2CCCN(Cc3cc(Cl)cc(Cl)c3)C2)cc1F]

Following the procedure as described in Example 50 step 1, and making variations as required to replace (R)-methyl 5-cyclopropyl-2-fluoro-4-(piperidin-3-yloxy)benzoate with (S)-methyl 5-cyclopropyl-2-fluoro-4-(piperidin-3-ylmethoxy)benzoate, and to replace 1,3-dichloro-5-(1-chloroethyl)benzene with 1,3-dichloro-5-(chloromethyl)benzene, the title compound was obtained as a colorless oil (0.65 g, 86%); MS(ES+) m/z 466.2, 468.2 (M+1).

Step 2 Preparation of (S)-5-cyclopropyl-4-((1-(3,5-dichlorobenzyl)piperidin-3-yl)methoxy)-2-fluorobenzoic acid

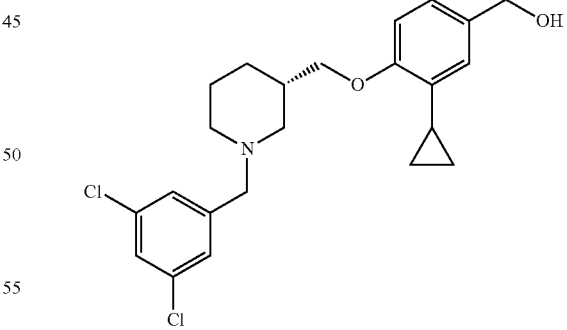

Following the procedure as described in Example 50 step 2, and making variations as required to replace methyl 4-((1-(3-fluorobenzyl)piperidin-4-yl)methoxy)-5-cyclopropyl-2-fluorobenzoate with (S)-methyl 5-cyclopropyl-4-((1-(3,5-dichlorobenzyl)piperidin-3-yl)methoxy)-2-fluorobenzoic, the title compound was obtained as a colorless solid (0.52 g, 83%): MS(ES+) m/z 452.1, 454.2 (M+1).

Step 3. Preparation of (S)-5-cyclopropyl-4-((1-(3,5-dichlorobenzyl)piperidin-3-yl)methoxy)-2-fluoro-N-(methylsulfonyl)benzamide

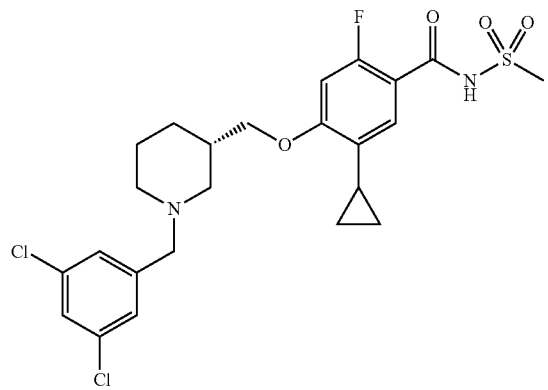 [SMILES: CS(=O)(=O)NC(=O)c1cc(C2CC2)c(OC[C@H]2CCCN(Cc3cc(Cl)cc(Cl)c3)C2)cc1F]

Following the procedure as described in Example 17 step 2, and making variations as required to replace (R)-5-cyclopropyl-4-((1-(3,4-dichlorobenzyl)piperidin-3-yl)-oxy)-2-fluorobenzoic acid with (S)-5-cyclopropyl-4-((1-(3,5-dichlorobenzyl)piperidin-3-yl)methoxy)-2-fluorobenzoic acid, the title compound was obtained as a colorless solid (0.07 g, 20%): $^1$H NMR (300 MHz, CDCl$_3$) δ 8.78 (s, 1H), 7.60-7.50 (m, 1H), 7.24-7.20 (m, 3H), 6.61-6.50 (m, 1H), 3.99-3.82 (m, 2H), 3.55-3.32 (m, 5H), 2.97-2.83 (m, 1H), 2.82-2.67 (m, 1H), 2.32-2.05 (m, 2H), 2.05-1.60 (m, 5H), 1.33-1.15 (m, 1H), 0.95-0.75 (m, 2H), 0.68-0.48 (m, 2H); MS(ES+) m/z 529.1, 531.1 (M+1).

Example 337 and Example 338

Synthesis of 5-cyclopropyl-4-(((S)-1-((R)-1-(3,5-dichlorobenzyl)ethyl)piperidin-3-yl)methoxy)-2-fluoro-N-(methylsulfonyl)benzamide, trifluoroacetic acid salt

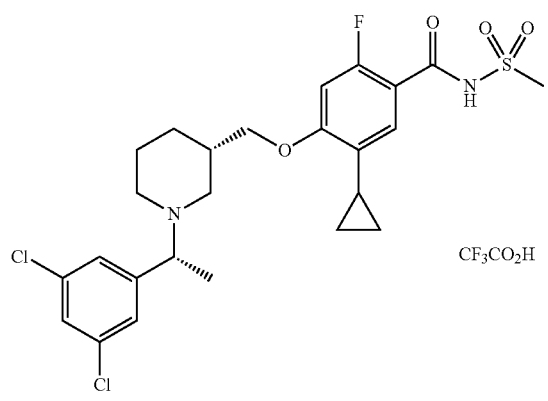 [SMILES: C[C@H](c1cc(Cl)cc(Cl)c1)N1CCC[C@H](COc2cc(F)c(C(=O)NS(C)(=O)=O)cc2C2CC2)C1 ; "CF3CO2H"]

and 5-cyclopropyl-4-(((S)-1-((S)-1-(3,5-dichlorophenyl)ethyl)piperidin-3-yl)methoxy)-2-fluoro-N-(methylsulfonyl)benzamide, trifluoroacetic acid salt

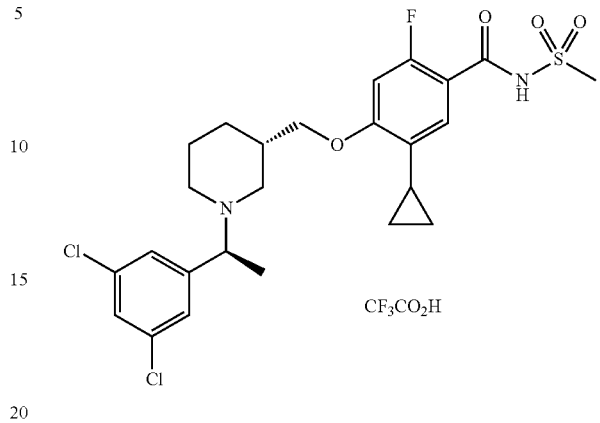

Step 1. Preparation of methyl 5-cyclopropyl-4-(((3S)-1-(3,5-dichlorophenyl)ethyl)piperidin-3-yl)methoxy)-2-fluorobenzoate

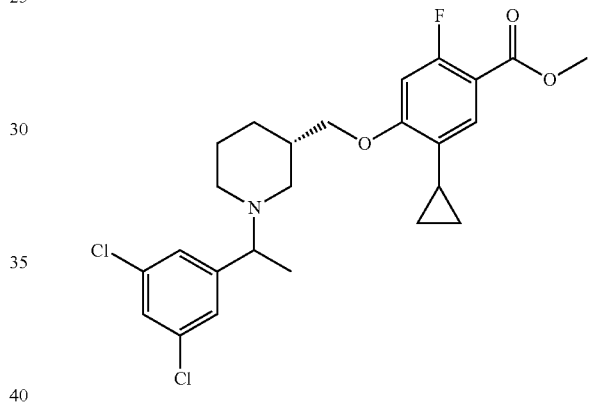

Following the procedure as described in Example 50 step 1, and making variations as required to replace (R)-methyl 5-cyclopropyl-2-fluoro-4-(piperidin-3-yloxy)benzoate with (S)-methyl 5-cyclopropyl-2-fluoro-4-(piperidin-3-ylmethoxy)benzoate, the title compound was obtained as a pale yellow oil (1.92 g, 75%): MS(ES+) m/z 480.2, 482.2 (M+1).

Step 2. Preparation of 5-cyclopropyl-4-(((3S)-1-(1-(3,5-dichlorophenyl)ethyl)piperidin-3-yl)methoxy)-2-fluorobenzoic acid

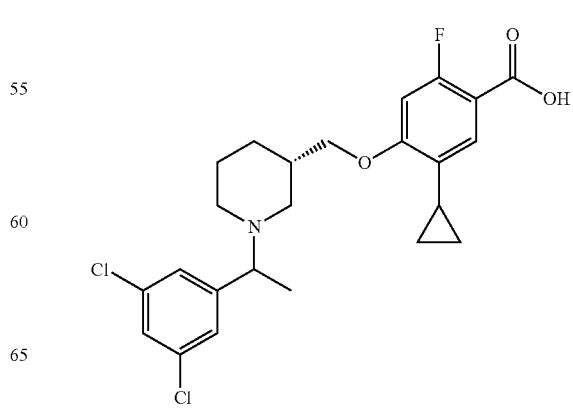

Following the procedure as described in Example 50 step 2, and making variations as required to replace methyl 4-((1-(3-fluorobenzyl)piperidin-4-yl)methoxy)-5-cyclopropyl-2-fluorobenzoate with methyl 5-cyclopropyl-4-(((3S)-1-(1-(3,5-dichlorophenyl)ethyl)piperidin-3-yl)methoxy)-2-fluorobenzoate, the title compound was obtained as a colorless solid (1.72 g, 92%); MS(ES+) m/z 452.1, 454.2 (M+1).

Step 3. Preparation of 5-cyclopropyl-4-(((S)-1-((R)-1-(3,5-dichlorophenyl)ethyl)piperidin-3-yl)methoxy)-2-fluoro-N-(methylsulfonyl)benzamide, trifluoroacetic acid salt

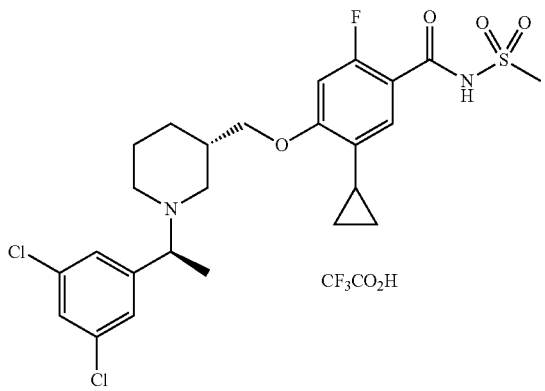

CF₃CO₂H

And 5-cyclopropyl-4-(((S)-1-((S)-1-(3,5-dichlorophenyl)ethyl)piperidin-3-yl)methoxy)-2-fluoro-N-(methylsulfonyl)benzamide, trifluoroacetic acid salt

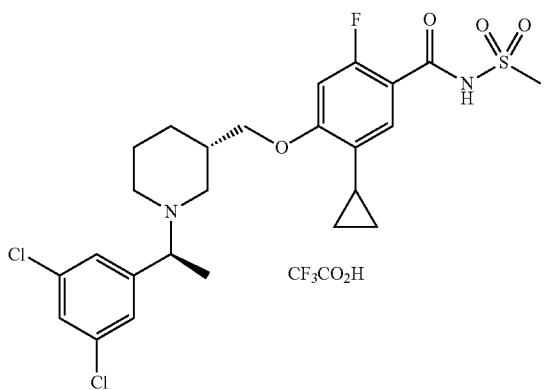

CF₃CO₂H

Following the procedure as described in Example 17 step 2, and making variations as required to replace (R)—S-cyclopropyl-4-((1-(3,4-dichlorobenzyl)piperidin-3-yl)oxy)-2-fluorobenzoic acid with 5-cyclopropyl-4-(((3S)-1-(1-(3,5-dichlorophenyl)ethyl)piperidin-3-yl)methoxy)-2-fluorobenzoic acid, a mixture of diastereomers was obtained. The mixture of diastereomers was then purified by preparative HPLC. The first eluting fraction was arbitrarily assigned as 5-cyclopropyl-4-(((S)-1-((R)-1-(3,5-dichlorophenyl)ethyl)piperidin-3-yl)methoxy)-2-fluoro-N-(methylsulfonyl)benzamide, trifluoroacetic acid salt (0.03 g, 4%): ¹H NMR (300 MHz, DMSO-d₆, 1 drop of D₂O) δ7.80-7.75 (m, 1H), 7.68-7.63 (m, 2H), 7.19-7.12 (m, 1H), 6.98-6.90 (m, 1H), 4.62-4.51 (m, 1H), 4.11-4.04 (m, 1H), 3.94-3.84 (m, 1H), 3.79-3.67 (m, 1H), 3.36-3.28 (m, 4H), 2.85-2.63 (m, 2H), 2.36-2.20 (m, 1H), 2.04-1.91 (m, 1H), 1.88-1.73 (m, 2H), 1.73-1.58 (m, 4H), 1.39-1.26 (m, 1H), 0.80-0.51 (m, 4H); MS(ES+) m/z 543.2, 545.1 (M+1).

The second eluting fraction was arbitrarily assigned as 5-cyclopropyl-4-(((S)-1-((S)-1-(3,5-dichlorophenyl)ethyl)piperidin-3-yl)methoxy-2-fluoro-N-(methylsulfonyl)benzamide, trifluoroacetic acid salt (0.03 g, 4%): ¹H NMR (300 MHz, CDCl3) δ13.00 (br s, 1H), 8.81-8.64 (m, 1H), 7.66-7.57 m, 1H), 7.50-7.43 (m, 1H), 7.37-7.30 (m, 2H), 6.58-6.49 (m, 1H), 4.51-4.36 (m, 1H), 4.07-3.77 (m, 3H), 3.64-3.52 (m, 1H), 3.41 (s, 3H), 2.83-2.65 (m, 1H), 2.58-2.39 (m, 2H), 2.26-2.09 (m, 1H), 2.08-1.91 (m, 2H), 1.91-1.71 (m, 4H), 1.50-1.32 (m, 1H), 0.92-0.76 (m, 2H), 0.71-0.50 (m, 2H); MS(ES+) m/z 543.2, 545.1 (M+1).

Example 339

Synthesis of (S)—N-(azetidin-1-ylsulfonyl)-4-((1-(2-chloro-4-fluorobenzyl)piperidin-3-yl)methoxy)-5-cyclopropyl-2-fluorobenzamide, trifluoroacetic acid salt

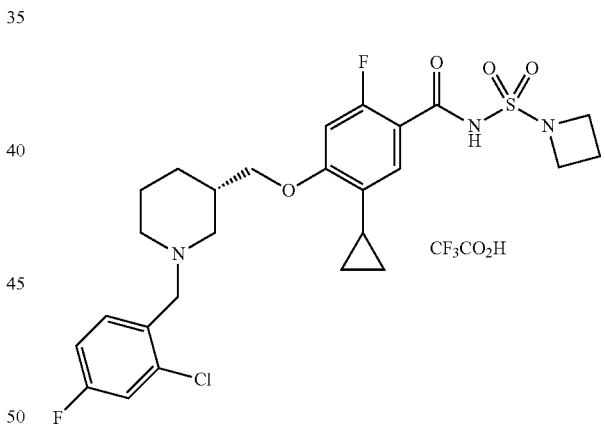

CF₃CO₂H

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with (S)-4-((1-(2-chloro-4-fluorobenzyl)piperidin-3-yl)methoxy)-5-cyclopropyl-2-fluorobenzoic acid, and to replace methanesulfonamide with azetidine-1-sulfonamide, the title compound was obtained as a colorless solid (0.05 g, 7%): ¹H NMR (300 MHz, CDCl₃) δ12.89 (brs, 1H), 8.79-8.49 (m, 1H), 7.79-7.69 (m, 1H), 7.67-7.58 (m, 1H), 7.24-7.17 (m, 1H), 7.17-7.06 (m, 1H), 6.60-6.45 (m, 1H), 4.43 (s, 2H), 4.32-4.16 (m, 4H), 4.08-3.84 (m, 2H), 3.81-3.57 (m, 2H), 2.83-2.63 (m, 2H), 2.34-1.82 (m, 7H), 1.66-1.39 (m, 1H), 0.98-0.81 (m, 2H), 0.73-0.55 (m, 2H); MS(ES+) m/z 554.1, 556.1 (M+1).

Example 340

Synthesis of (S)-4-((1-(2-chloro-4-fluorobenzyl)piperidin-3-yl)methoxy)-5-cyclopropyl-N-(cyclopropylsulfonyl)-2-fluorobenzamide, trifluoroacetic acid salt

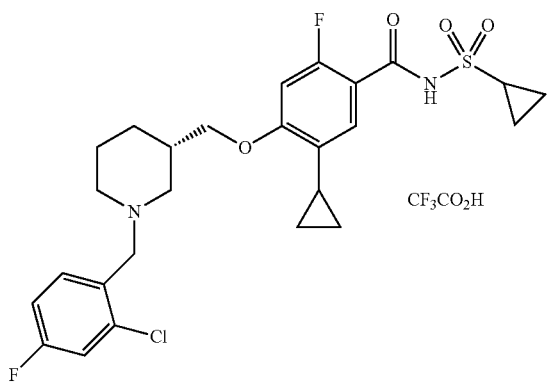 [SMILES: O=C(NS(=O)(=O)C1CC1)c1cc(C2CC2)c(OC[C@H]2CCCN(Cc3ccc(F)cc3Cl)C2)cc1F ; "CF3CO2H"]

Following the procedure as described in Example 17 step 2, and making variations as required to replace (R)-5-cyclopropyl-4-((1-(3,4-dichlorobenzyl)piperidin-3-yl)-oxy)-2-fluorobenzoic acid with (S)-4-((1-(2-chloro-4-fluorobenzyl)piperidin-3-yl)methoxy)-5-cyclopropyl-2-fluorobenzoic acid, and to replace methanesulfonamide wife cyclopropanesulfonamide, the title compound was obtained as a colorless solid (0.17 g, 33%): $^1$H NMR (300 MHz, CDCl$_3$) δ13.17 (br s, 1H), 8.78-8.58 (m, 1H), 7.80-7.70 (m, 1H), 7.64-7.56 (m, 1H), 7.22-7.16 (m, 1H), 7.14-7.05 (m, 1H), 6.58-6.44 (m, 1H), 4.41 (s, 2H), 4.05-3.81 (m, 2H), 3.77-3.55 (m, 2H), 3.14-3.01 (m, 1H), 2.82-2.60 (m, 3H), 2.22-3.79 (m, 4H), 1.58-1.36 (m, 3H), 1.20-1.05 (m, 2H), 0.96-0.79 (m, 2H), 0.72-0.50 (m, 2H): MS(ES+) m/z 539.2, 541.2 (M+1).

Example 341

Synthesis of 5-cyclopropyl-4-(((3R,6R)-1-(3,5-dichlorobenzyl)-6-methylpiperidin-3-yl)methoxy)-2-fluoro-N-(methylsulfonyl)benzamide, trifluoroacetic acid salt

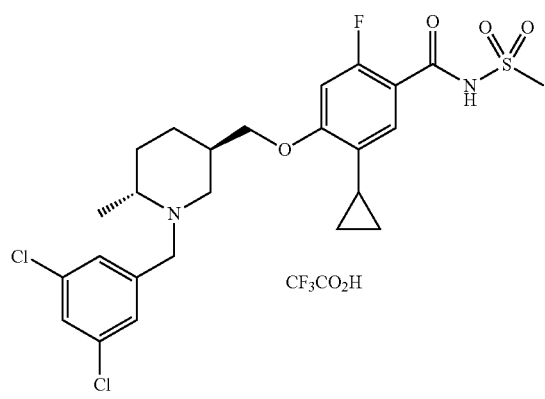 [SMILES: C[C@@H]1CC[C@@H](COc2cc(F)c(C(=O)NS(C)(=O)=O)cc2C2CC2)CN1Cc1cc(Cl)cc(Cl)c1 ; "CF3CO2H"]

Step 1. Preparation of (2R,5R)-benzyl 5-((4-tert-butoxycarbonyl)-2-chloro-5-fluorophenoxy)methyl-2-methylpiperidine-1-carboxylate

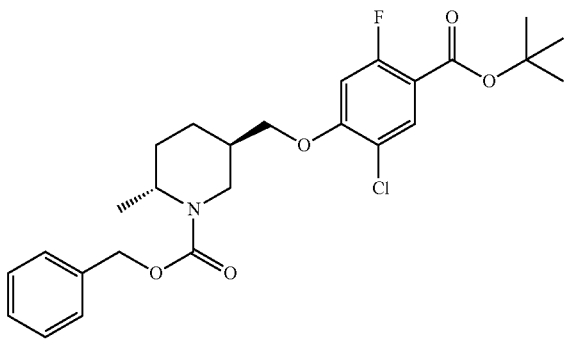 [SMILES: C[C@@H]1CC[C@@H](COc2cc(F)c(C(=O)OC(C)(C)C)cc2Cl)CN1C(=O)OCc1ccccc1]

Following the procedure as described in Example 1 step 1, and making variations as required to replace (R)-1-benzylpiperidin-3-ol with (2R,5R)-benzyl 5-(hydroxymethyl)-2-methylpiperidine-1-carboxylate (WO 2010/048010 A1), the title compound was obtained as a colorless oil (1.61 g, 66%): MS(ES+) m/z 492.2, 494.1 (M+1).

Step 2. Preparation of (2R,5R)-benzyl 5-((4-(tert-butoxycarbonyl)-2-cyclopropyl-5-fluorophenoxy)methyl)-2-methylpiperidine-1-carboxylate

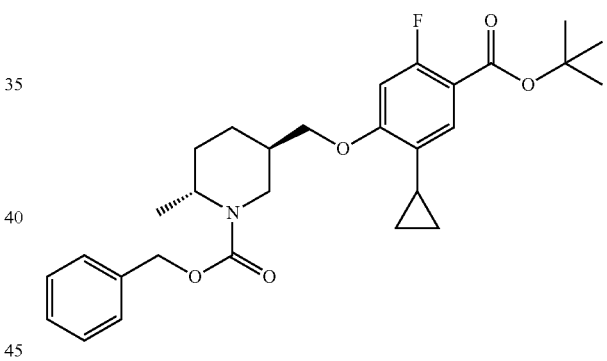

Following the procedure as described to Example 1 step 2, and making variations as required to replace (R)-tert-butyl 4-((1-benzylpiperidin-3-yl)oxy)-5-chloro-2-fluorobenzoate with (2R,5R)-benzyl 5-((4-(tert-butoxycarbonyl)-2-chloro-5-fluorophenoxy)methyl)-2-methylpiperidine-1-carboxylate, the title compound was obtained as a colorless solid (1.46 g, 90%); MS(ES+) m/z 498.3 (M+1).

Step 3. Preparation of tert-butyl 5-cyclopropyl-2-fluoro-4-(((3R,6R)-6-methylpiperidin-3-yl)methoxy)benzoate

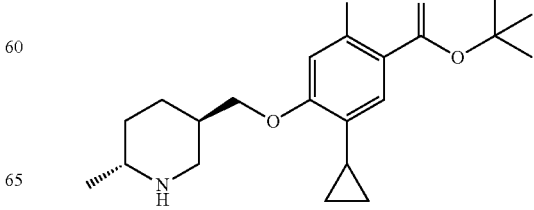

Following the procedure as described in Example 52 step 4, and making variation as required to replace (2R,5R)-benzyl 5-((4-(tert-butoxycarbonyl)-2-cyclopropyl-5-fluorophenoxy)methyl)-2-methylpiperidine-1-carboxylate with (2R,5R)-benzyl 5-((4-(tert-butoxycarbonyl)-2-cyclopropyl-5-fluorophenoxy)methyl)-2-methylpiperidine-1-carboxylate, the title compound was obtained as a colorless oil (1.00 g, 94%); MS(ES+) m/z 304.3 (M+1).

Step 4. Preparation of tert-butyl 5-cyclopropyl-4-(((3R,6R)-1-(3,5-dichlorobenzyl)-6-methylpiperidin-3-yl)methoxy)-2-fluorobenzoate

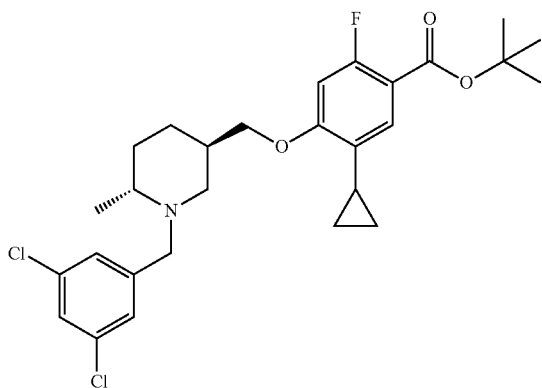 [SMILES: C[C@@H]1CC[C@@H](COc2cc(F)c(C(=O)OC(C)(C)C)cc2C2CC2)CN1Cc1cc(Cl)cc(Cl)c1]

Following the procedure as described in Example 50 step 1, and making variations as required to replace (R)-methyl 5-cyclopropyl-2-fluoro-4-(piperidin-3-yloxy)benzoate with tert-butyl 5-cyclopropyl-2-fluoro-4-(((3R,6R)-6-methylpiperidin-3-yl)methoxy)benzoate, and to replace 1,3-dichloro-5-(1-chloroethyl)benzene with 1,3-dichloro-5-(chloromethyl)benzene, the title compound was obtained as a colorless oil (0.71 g, 98%): MS(ES+) m/z 522.2, 524.2 (M+1).

Step 5. Preparation of 5-cyclopropyl-4-(((3R,6R)-1-(3,5-dichlorobenzyl)-6-methylpiperidin-3-yl)methoxy)-2-fluorobenzoic acid

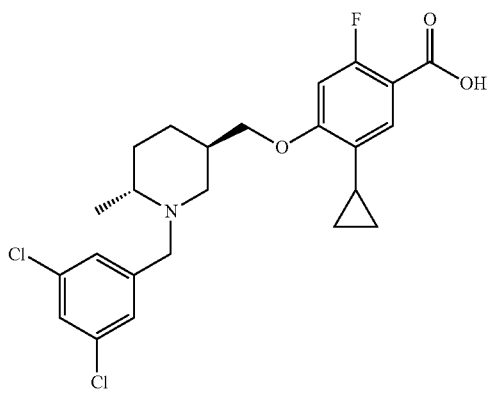 [SMILES: C[C@@H]1CC[C@@H](COc2cc(F)c(C(=O)O)cc2C2CC2)CN1Cc1cc(Cl)cc(Cl)c1]

Following the procedure as described in Example 3 step 3, and making variations as required to replace (R)-tert-butyl 3-(4-(tert-butoxycarbonyl)-2-cyclopropyl-5-fluorophenoxy)piperidine-1-carboxylate with tert-butyl 5-cyclopropyl-4-(((3R,6R)-1-(3,5-dichlorobenzyl)-6-methylpiperidin-3-yl)methoxy)-2-fluorobenzoate, the title compound was obtained as a colorless solid (0.56 g, 88%): MS(ES+) m/z 466.1, 468.1 (M+1).

Step 6. Preparation of 5-cyclopropyl-4-(((3R,6R)-1-(3,5-dichlorobenzyl)-6-methylpiperidin-3-yl)methoxy)-2-fluoro-N-(methylsulfonyl)benzamide, trifluoroacetic acid salt

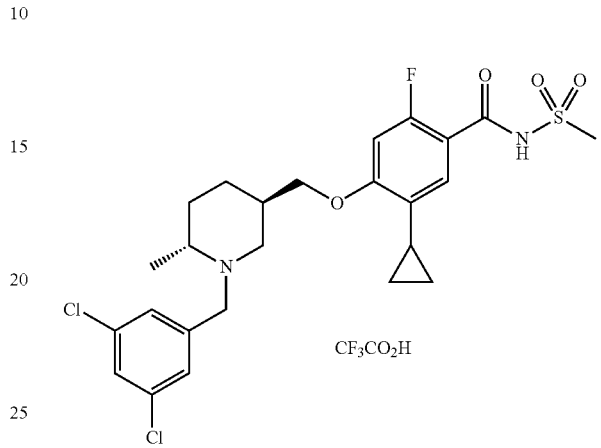

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with 5-cyclopropyl-4-(((3R,6R)-1-(3,5-dichlorobenzyl)-6-methylpiperidin-3-yl)methoxy)-2-fluorobenzoic acid, the title compound was obtained as a colorless solid (0.09 g, 40%): $^1$H NMR (300 MHz, DMSO-$d_6$) δ 8.82-8.62 (m, 1H), 7.67-7.52 (m, 1H), 7.51-7.42 (m, 1H), 7.42-7.34 (m, 2H), 6.57-6.42 (m, 1H), 4.76-4.57 (m, 1H), 4.03-3.76 (m, 3H), 3.53-3.44 (m, 1H), 3.41 (s, 3H), 3.04-2.71 (m, 2H), 2.55-2.37 (m, 1H), 2.28-2.10 (m, 1H), 2.09-1.95 (m, 2H), 1.80-1.61 (m, 4H), 1.56-1.42 (m, 1H), 0.87-0.75 (m, 2H), 0.66-0.49 (m, 2H) MS(ES+) m/z 543.2, 545.2 (M+1).

Example 342

Synthesis of 5-cyclopropyl-4-(((3R,6R)-1-((S)-1-(3,5-dichlorophenyl)ethyl)-6-methylpiperidin-3-yl)methoxy)-2-fluoro-N-(methylsulfonyl)benzamide trifluoroacetic acid salt (arbitrarily assigned)

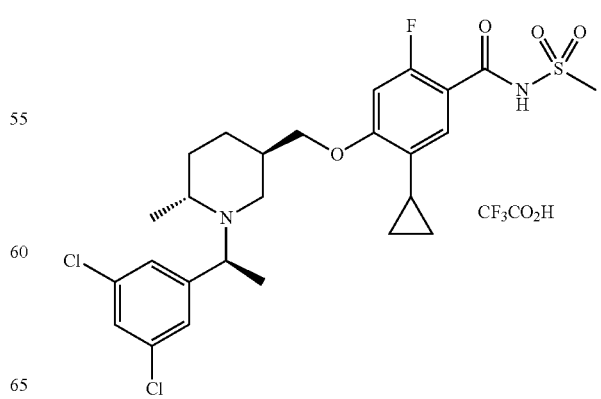

Step 1. Preparation of tert-butyl 5-cyclopropyl-4-(((3R,6R)-1-((S)-1-(3,5-dichlorophenyl)ethyl)-6-methylpiperidin-3-yl)methoxy)-2-fluorobenzoate

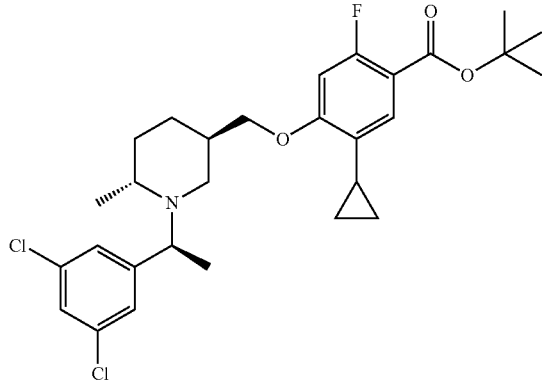 [SMILES: C[C@@H]1CC[C@@H](COc2cc(F)c(C(=O)OC(C)(C)C)cc2C2CC2)CN1[C@@H](C)c1cc(Cl)cc(Cl)c1]

And tert-butyl 5-cyclopropyl-4-(((3R,6R)-1-((R)-1-(3,5-dichlorophenyl)ethyl)-6-methylpiperidin-3-yl)methoxy)-2-fluorobenzoate

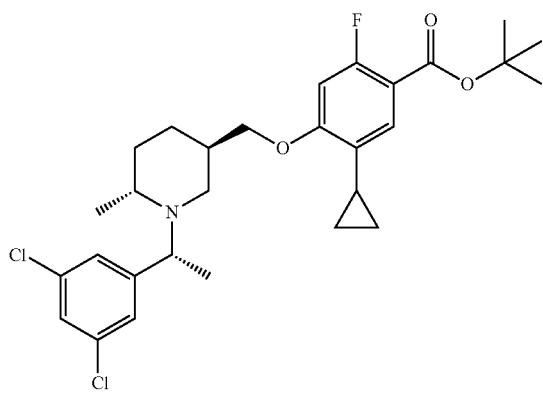 [SMILES: C[C@@H]1CC[C@@H](COc2cc(F)c(C(=O)OC(C)(C)C)cc2C2CC2)CN1[C@H](C)c1cc(Cl)cc(Cl)c1]

Following the procedure as described in Example 50 step 1, and making variations as required to replace (R)-methyl 5-cyclopropyl-2-fluoro-4-(piperidin-3-yloxy)benzoate with tert-butyl 5-cyclopropyl-2-fluoro-4-(((3R,6R)-6-methylpiperidin-3-yl)methoxy)benzoate. The mixture of diastereomers was separated by column chromatography cutting with a gradient of methanol in dichloromethane (0 to 5%). The first eluting fraction was arbitrarily assigned as tert-butyl 5-cyclopropyl-4-(((3R,6R)-1-((S)-1-(3,5-dichlorophenyl)ethyl-6-methylpiperidin-3-yl)methoxy)-2-fluorobenzoate (0.23 g, 32%) as a pale yellow oil: MS(ES+) m/z 536.0, 538.2 (M+1). The second eluting fraction was arbitrarily assigned as tert-butyl 5-cyclopropyl-4-(((3S,6R)-1-((R)-1-(3,5-dichlorophenyl)ethyl)-6-methylpiperidin-3-yl)methoxy)-2-fluorobenzoate (0.23 g, 32%) as a pale yellow oil: MS(ES+) m/z 536.1, 538.1 (M+1).

Step 1. Preparation of 5-cyclopropyl-4-(((3R,6R)-1-((S)-1-(3,5-dichlorophenyl)ethyl)-6-methylpiperidin-3-yl)methoxy)-2-fluorobenzoic acid

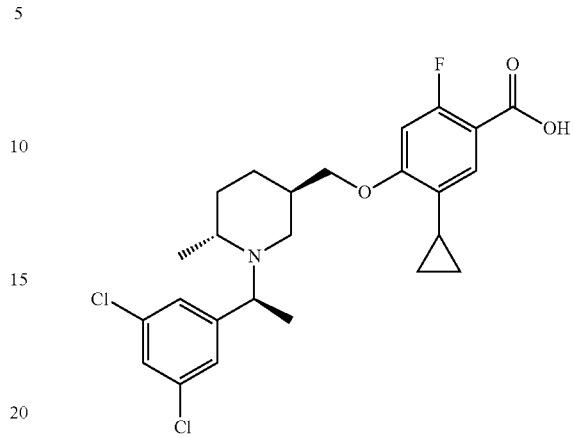

Following the procedure as described in Example 3 step 3, and making variations as required to replace (R)-tert-butyl 3-(4-(tert-butoxycarbonyl)-2-cyclopropyl-5-fluorophenoxy) piperidine-1-carboxylate with tert-butyl 5-cyclopropyl-4-(((3R,6R)-1-((S)-1-(3,5-dichlorophenyl)ethyl)-6-methylpiperidin-3-yl)methoxy)-2-fluorobenzoate, the title compound was obtained as a colorless solid (0.20 g, 99%): MS(ES+) m/z 480.1, 482.1 (M+1).

Step 3. Preparation of 5-cyclopropyl-4-(((3R,6R)-1-((S)-1-(3,5-dichlorophenyl)ethyl)-6-methylpiperidin-3-yl)methoxy)-2-fluoro-N-(methylsulfonyl)benzamide trifluoroacetic acid salt

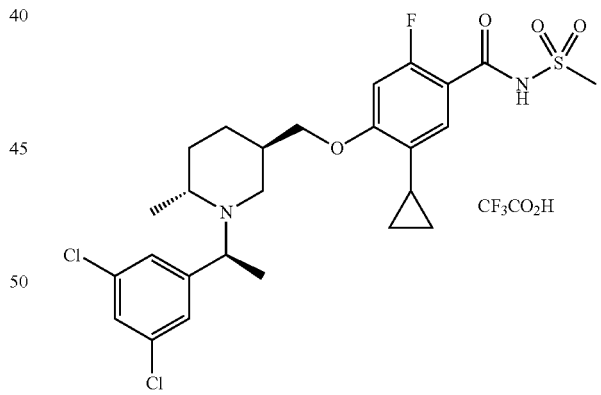

Following the procedure as described in Example 17 step 2, and making variations as required to replace (R)-5-cyclopropyl-4-((1-(3,4-dichlorobenzyl)piperidin-3-yl)-oxy)-2-fluorobenzoic acid with 5-cyclopropyl-4-(((3R,6R)-1-((S)-1-(3,5-dichlorophenyl)ethyl)-6-methylpiperidin-3-yl)methoxy)-2-fluorobenzoic acid, the title compound was obtained as a colorless solid (0.05 g, 38%): ¹H NMR (300 MHz, CDCl₃) δ12.12 (br s, 1H), 8.91-8.53 (m, 1H), 7.65-7.57 (m, 1H), 7.53-7.48 (m, 2H), 7.45-7.39 (m, 1H), 6.56-6.44 (m, 1H), 5.05-4.92 (m, 1H), 4.02-3.76 (m, 2H), 3.41 (s, 3H), 3.27-3.08 (m, 2H), 2.88-2.71 (m, 1H), 2.72-2.56 (m, 2H), 2.36-2.20 (m, 1H), 2.09-1.92 (m, 2H), 1.83-1.49 (m, 7H), 0.94-0.75 (m, 2H), 0.71-0.50 (m, 2H): MS(ES+) m/z 557.0, 559.0 (M+1).

Example 343

Synthesis of 5-cyclopropyl-4-(((3R,6R)-1-((R)-1-(3,5-dichlorophenyl)ethyl)-6-methylpiperidin-3-yl)methoxy)-2-fluoro-N-(methylsulfonyl)benzamide, trifluoroacetic acid salt

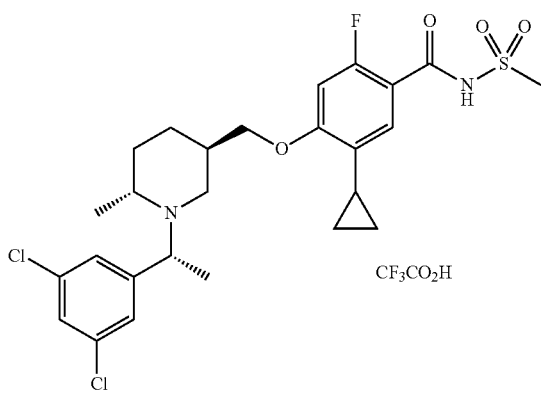 [SMILES: C[C@@H]1CC[C@@H](COc2cc(F)c(C(=O)NS(C)(=O)=O)cc2C2CC2)CN1[C@H](C)c1cc(Cl)cc(Cl)c1 ; "CF3CO2H"]

Step 1. Preparation of 5-cyclopropyl-4-(((3R,6R)-1-((R)-1-(3,5-dichlorophenyl)ethyl)-6-methylpiperidin-3-yl)methoxy)-2-fluorobenzoic acid

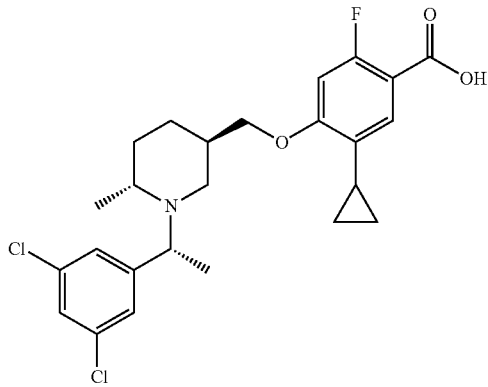 [SMILES: C[C@@H]1CC[C@@H](COc2cc(F)c(C(=O)O)cc2C2CC2)CN1[C@H](C)c1cc(Cl)cc(Cl)c1]

Following the procedure as described in Example 3 step 3, and making variations as required to replace (R)-tert-butyl 3-(4-(tert-butoxycarbonyl)-2-cyclopropyl-5-fluorophenoxy)piperidine-1-carboxylate with tert-butyl 5-cyclopropyl-4-(((3R,6R-1-((R)-1-(3,5-dichlorophenyl)ethyl)-6-methylpiperidin-3-yl)methoxy)-2-fluorobenzoate, the title compound was obtained as a colorless solid (0.21 g, 99%): MS(ES+) m/z 480.1, 482.1 (M+1).

Step 3. Preparation of 5-cyclopropyl-4-(((3R,6R)-1-((R)-1-(3,5-dichlorophenyl)ethyl)-6-methylpiperidin-3-yl)methoxy)-2-fluoro-N-(methylsulfonyl)benzamide, trifluoroacetic acid salt

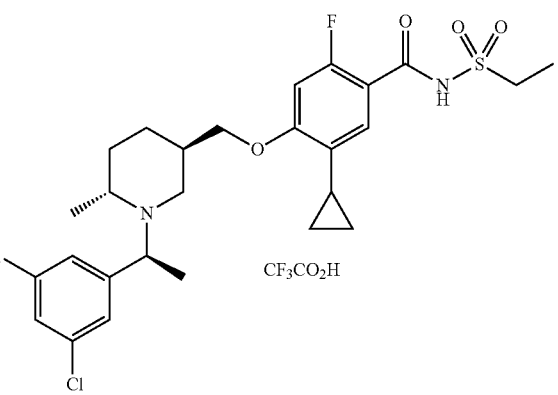

Following the procedure as described in Example 17 step 2, and making variations as required to replace (R)-5-cyclopropyl-4-((1-(3,4-dichlorobenzyl)piperidin-3-yl)oxy)-2-fluorobenzoic acid with 5-cyclopropyl-4-(((3R,6R)-1-((R)-1-(3,5-dichlorophenyl)ethyl)-6-methylpiperidin-3-yl)methoxy)-2-fluorobenzoic acid, the title compound was obtained as a colorless solid (0.05 g, 28%): $^1$H NMR (300 MHz, CDCl$_3$) δ13.00 (br s, 1H), 8.91-8.59 (m, 1H), 7.72-7.59 (m, 1H), 7.54-7.45 (m, 1H), 7.31-7.27 (m, 2H), 6.61-6.51 (m, 1H), 5.04-4.91 (m, 1H), 4.14-3.90 (m, 2H), 3.85-3.73 (m, 1H), 3.42 (s, 3H), 2.96-2.64 (m, 2H), 2.60-2.42 (m, 1H), 2.26-2.06 (m, 1H), 2.04-1.65 (m, 9H), 1.56-1.36 (m, 1H), 0.87-0.73 (m, 2H), 0.67-0.54 (m, 2H); MS(ES+) m/z 557.0, 559.0 (M+1).

Example 344

Synthesis of 5-cyclopropyl-4-(((3R,6R)-1-((S)-1-(3,5-dichlorophenyl)ethyl)-6-methylpiperidin-3-yl)methoxy)-N-(methylsulfonyl)-2-fluorobenzamide, trifluoroacetic acid salt Following the procedure as described in Example 17 step 2, and making variations as required to replace (R)-5-cyclopropyl-4-((1-(3,4-dichlorobenzyl)piperidin-3-yl)oxy)-2-fluorobenzoic acid with 5-cyclopropyl-4-(((3R,6R)-

1-((S)-1-(3,5-dichlorophenyl)ethyl)-6-methylpiperidin-3-yl)methoxy)-2-fluorobenzoic acid, and to replace methanesulfonamide with ethanesulfonamide, the title compound was obtained as a colorless solid (0.05 g, 31%): ¹H NMR (300 MHz, DMSO-d₆) δ11.80 (br s, 1H), 9.19-9.02 (m, 1H), 7.84-7.64 (m, 3H), 7.21-7.10 (m, 1H), 6.98-6.84 (m, 1H), 5.16-4.95 (m, 1H), 4.16-3.95 (m, 1H), 3.87-3.68 (m, 1H), 3.50-3.37 (m, 2H), 3.11-2.85 (m, 2H), 2.30-1.89 (m, 3H), 1.83-1.29 (m, 10H), 1.25-1.14 (m, 3H), 0.79-0.35 (m, 4H); MS(ES+) m/z 571.1, 573.1 (M+1).

Example 345

Synthesis of 5-cyclopropyl-4-(((3R,6R)-1-((R)-1-(3,5-dichlorophenyl)ethyl)-6-methylpiperidin-3-yl)methoxy)-N-(ethylsulfonyl-2-fluorobenzamide, trifluoroacetic acid salt

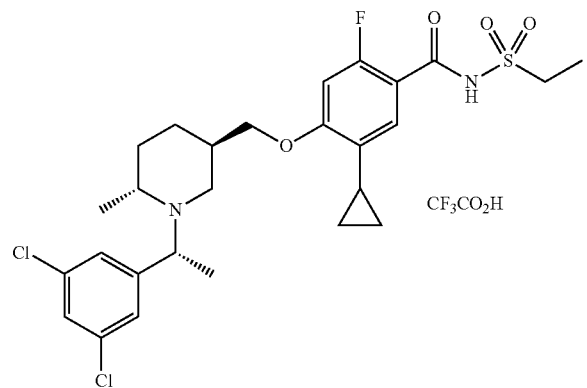 [SMILES: CCS(=O)(=O)NC(=O)c1cc(C2CC2)c(OC[C@@H]2CC[C@@H](C)N([C@H](C)c3cc(Cl)cc(Cl)c3)C2)cc1F ; "CF3CO2H"]

Following the procedure as described in Example 17 step 2, and making variations as required to replace (R)-5-cyclopropyl-4-((1-(3,4-dichlorobenzyl)piperidin-3-yl)-oxy)-2-fluorobenzoic acid with 5-cyclopropyl-4-(((3R,6R)-1-((R)-1-(3,5-dichlorophenyl)ethyl)-6-methylpiperidin-3-yl)methoxy)-2-fluorobenzoic acid, and to replace methanesulfonamide with ethanesulfonamide, the title compound was obtained as a colorless solid (0.02 g, 17%): ¹H NMR (300 MHz, DMSO-d₆) δ11.84 (br s, 1H), 9.71-9.51 (m, 1H), 7.86-7.60 (m, 3H), 7.24-7.14 (m, 1H), 7.03-6.90 (m, 1H), 5.21-4.98 (m, 1H), 4.15-3.99 (m, 2H), 3.94-3.81 (m, 1H), 3.52-3.39 (m, 2H), 2.97-2.80 (m, 1H): 2.47-2.22 (m, 2H), 2.04-1.35 (m, 11H), 1.29-1.18 (m, 3H), 0.82-0.55 (m, 4H); MS(ES+) m/z 571.1, 573.1 (M+1).

Example 346

Synthesis 4-((1-(3-chloro-2-fluoro-5-(trifluoromethyl)benzyl)-4-fluoropiperidin-4-yl)methoxy)-5-cyclopropyl-2-fluoro-N-(methylsulfonyl)benzamide trifluoroacetic acid salt

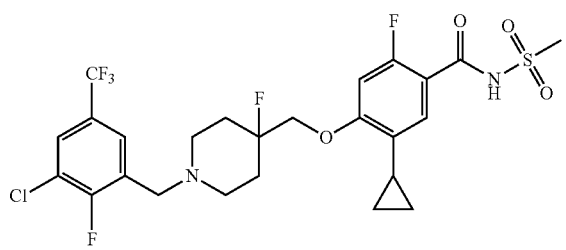 [SMILES: CS(=O)(=O)NC(=O)c1cc(C2CC2)c(OCC2(F)CCN(Cc3cc(C(F)(F)F)cc(Cl)c3F)CC2)cc1F]

Step 1. Preparation of tert-Butyl 4-fluoro-4-(hydroxymethyl)piperidine-1-carboxylate

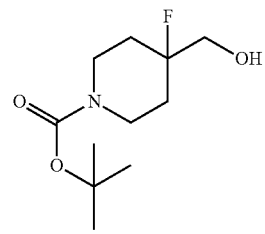 [SMILES: CC(C)(C)OC(=O)N1CCC(F)(CO)CC1]

To a solution of 1-(tert-butoxycarbonyl)-4-fluoropiperidine-4-carboxylic acid (5.00 g, 20.20 mmol) in tetrahydrofuran (100 mL) was added a solution of borane tetrahydrofuran complex (30.3 mL, 30.30 mmol, 1.0 M solution in tetrahydrofuran). The reaction mixture was refluxed for 16 hours, and then another 24 mL of borate tetrahydrofuran complex was added and continued to reflux for another 16 hours. After cooling to ambient temperature the reaction mixture poured onto ice-cold water (50 mL) and saturated ammonium chloride (100 mL), and extracted with ethyl acetate (3×100 mL), dried over anhydrous sodium sulfate and filtered. The filtrate was concentrated to afford the title compound (4.60 g, 98%). Which was used in the next step without further purification: MS (ES+) m/z 234.1 (M+1).

Step 2. Preparation of tert-butyl 4-((4-(tert-butoxycarbonyl)-2-chloro-5-fluorophenoxy)methyl)-4-fluoropiperidine-1-carboxylate

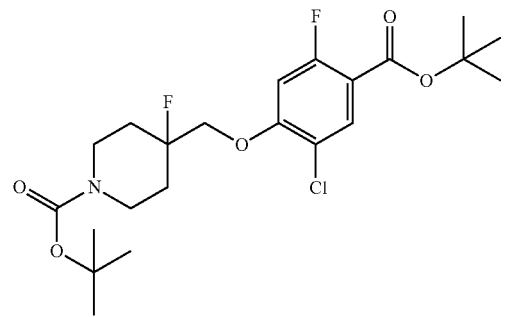 [SMILES: CC(C)(C)OC(=O)c1cc(Cl)c(OCC2(F)CCN(C(=O)OC(C)(C)C)CC2)cc1F]

To a mixture of tert-butyl 4-fluoro-4-(hydroxymethyl)piperidine-1-carboxylate (4.60 g, 19.70 mmol) and tert-butyl 5-chloro-2,4-difluorobenzoate (4.89 g, 19.70 mmol) in dimethyl sulfoxide (50 mL) was added cesium carbonate (9.65 g, 29.60 mmol) and the reaction mixture was heated at 80° C. for 4 hours. After cooling to an ambient temperature, water (50 mL) was added, and then extracted with ethyl acetate (3×100 mL). The organic layer was washed with brine (2×50 mL), dried over anhydrous sodium sulfate and filtered. The filtrate was concentrated in vacuo and the residue was purified by silica gel column chromatography eluting with gradient of 0-30% ethyl acetate in hexanes to afford the title compound as a colorless gum (6.60 g, 73%): ¹H NMR (300 MHz, CDCl₃) δ 7.82 (d, J=7.6 Hz, 1H), 6.58 (d, J=11.8 Hz, 1H), 3.90-4.10 (m, 3H), 3.07 (t, J=12.4 Hz, 2H), 1.98-1.89 (m, 3H), 1.84-1.56 (m, 2H), 1.51 (s, (H), 1.40 (s, 9H): MS (ES+) m/z 464.1, 462.1 (M+1).

Step 3. Preparation of tert-butyl 4-((4-(tert-butoxycarbonyl)-2-cyclopropyl-5-fluorophenoxy)methyl-4-fluoropiperidine-1-carboxylate

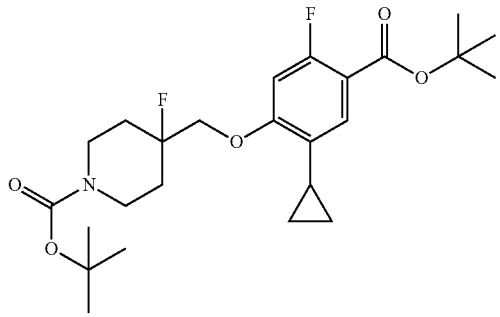 [SMILES: CC(C)(C)OC(=O)c1cc(C2CC2)c(OCC2(F)CCN(C(=O)OC(C)(C)C)CC2)cc1F]

To a mixture of tert-butyl 4-((4-(tert-butoxycarbonyl)-2-chloro-5-fluorophenoxy)methyl)-4-fluoropiperidine-1-carboxylate (6.60 g, 14.30 mmol), cyclopropylboronic acid (3.07 g, 35.80 mmol), potassium phosphate (12.2 g, 57.3 mmol) and tricyclohexylphosphine tetrafluoroborate (0.79 g, 2.15 mmol) in toluene (120 ml) and water (12 mL) under a nitrogen atmosphere was added palladium acetate (0.32 g, 1.43 mmol). The reaction mixture was heated at 100° C. for 16 hours and cooled to ambient temperature. To the reaction mixture was added water (20 mL) and extracted with ethyl acetate (3×100 mL). The combined organic extracts was washed with brine, dried over anhydrous sodium sulfate and filtered. The filtrate was concentrated in vacuo and the residue was purified by column chromatography eluting with 5% ethyl acetate in hexanes to afford the title compound as a colorless gum (4.00 g, 60%): MS (ES+) m/z 468.6 (M+1).

Step 4. Preparation of tert-butyl 5-cyclopropyl-2-fluoro-4-((4-fluoropiperidin-4-yl)methoxy)benzoate hydrochloride

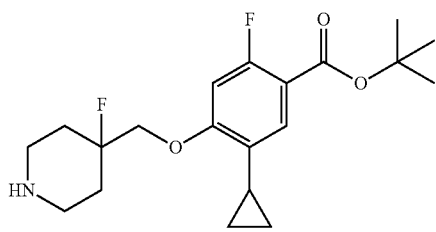 [SMILES: CC(C)(C)OC(=O)c1cc(C2CC2)c(OCC2(F)CCNCC2)cc1F]

To a solution of tert-butyl 4-((4-butoxycarbonyl)-2-cyclopropyl-5-fluorophenoxy)methyl)-4-fluoropiperidine-1-carboxylate (4.00 g, 8.50 mmol) in dioxane (12 mL) was added a solution of hydrogen chloride in dioxane (4M, 4.0 mL, 16.00 mmol). The reaction solution, was stirred at an ambient temperature for 3 hours. The title compound precipitated out from solution was collected by filtration. The filtrate was concentrated to afford another portion of product (1.90 g in total, 61%) as a pale yellow solid: $^1$H NMR (300 MHz, CDCl$_3$) δ 8.97 (br s, 1H), 7.26 (d, J=8.4 Hz, 1H), 6.93 (d, J=12.9 Hz, 1H), 4.23 (d, J=19.9 Hz, 2H), 3.31-3.20 (m 2H), 3.11-2.92 (m, 2H), 2.15-2.06 (m, 2H), 2.04-1.92 (m, 2H), 1.47 (s, 9H), 0.91-0.85 (m, 2H), 0.60-0.54 (m, 2H); MS (ES+) m/z 368.2 (M+1).

Step 5. Preparation of tert-butyl 4-((1-(3-chloro-2-fluoro-5-(trifluoromethyl)benzyl)-4-fluoropiperidin-4-yl)methoxy)-5-cyclopropyl-2-fluorobenzoate

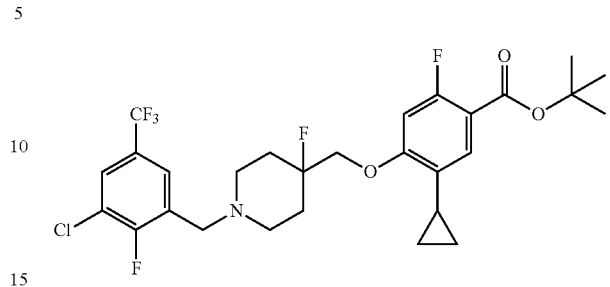

A mixture of tert-butyl 5-cyclopropyl-2-fluoro-4-((4-fluoropiperidin-4-yl)methoxy)benzoate hydrochloride (0.29 g, 0.70 mmol), 1-chloro-3-(chloromethyl)-2-fluoro-5-(trifluoromethyl)benzene (0.18 g, 0.70 mmol) and potassium carbonate (0.24 g, 2.10 mmol) in N,N-dimethylformamide (2 mL) was heated at 90° C. for 10 hours. The solid was filtered off and the filtrate was subjected to column chromatography eluting with 40% ethyl acetate in hexanes to afford the title compound as a gum (0.20 g, 71%): MS (ES+) m/z 578.2, 580.2 (M+1).

Step 6. Preparation of 4-((1-(3-chloro-2-fluoro-5-(trifluoromethyl)benzyl)-4-fluoropiperidin-4-yl)methoxy)-5-cyclopropyl-2-fluorobenzoic acid

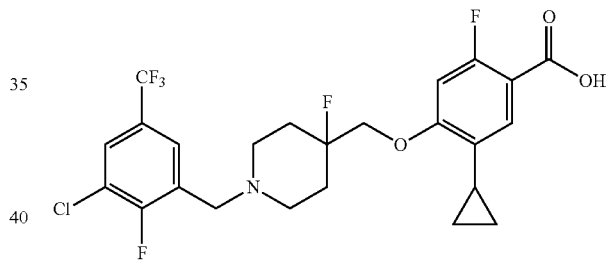

To a solution of tert-butyl 4-((1-(3-chloro-2-fluoro-5-(trifluoromethyl)benzyl)-4-fluoropiperidin-4-yl)methoxy)-5-cyclopropyl-2-fluorobenzoate (029 g, 0.50 mmol) in dichloromethane (5 mL) was added trifluoroacetic acid (2 mL). The reaction mixture was stirred for 3 hours and concentrated in vacuo to afford the title compound as a colorless solid (0.20 g, 76%): MS (ES−) m/z 520.2, 518.2 (M−1).

Step 7. Preparation of 4-((1-(3-chloro-2-fluoro-5-(trifluoromethyl)benzyl)-4-fluoropiperidin-4-yl)methoxy)-5-cyclopropyl-2-fluoro-N-(methylsulfonyl)benzamide, trifluoroacetic acid salt

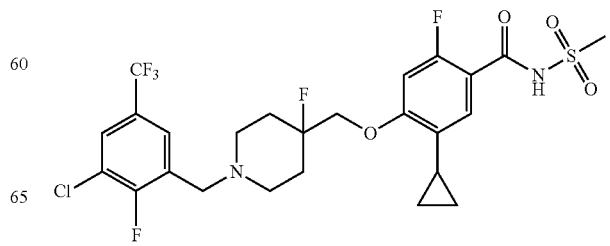

To a mixture of 4-((1-(3-chloro-2-fluoro-5-(trifluoromethyl)benzyl)-4-fluoropiperidin-4-yl)methoxy)-5-cyclopropyl-2-fluorobenzoic acid (0.10 g, 0.19 mmol), 1-ethyl-3-(3-dimethylaminopropyl)carbodiimide (0.068 g, 0.44 mmol), 4-dimethylaminopyridine (0.054 g, 0.44 mmol) was added methanesulfonamide (0.027 g, 0.29 mmol) in dichloromethane (3 mL). After stirring at ambient temperature for 16 hours, the reaction mixture was diluted with ethyl acetate (5 mL), washed with brine (10 mL), dried over anhydrous sodium sulfate and filtered. The filtrate was concentrated in vacuo and the residue was purified by preparative-MPLC to afford the title compound as a colorless solid (0.05 g, 44%): $^1$H NMR (300 MHz, DMSO-d$_6$) δ 11.91 (br s, 1H), 10.24 (br s, 1H), 8.22 (d, J=3 Hz, 1H), 8.00 (d, J=3 Hz, 1H), 71.3 (d, J=9 Hz, 1H), 6.98 (d, J=12 Hz, 1H), 4.65-4.10 (m, 5H), 3.53-3.01 (m, 6H), 2.32-1.81 (m, 5H), 0.94-0.78 (m, 2H), 0.72-0.56 (m, 2H); MS (ES+) m/z 599.1, 601.3 (M+1).

Example 347

Synthesis of 4-((1-(3-chloro-2-fluoro-5-(trifluoromethyl)benzyl)-4-fluoropiperidin-4-yl)methoxy)-5-cyclopropyl-N-(cyclopropylsulfonyl)-2-fluorobenzamide, trifluoroacetic acid salt

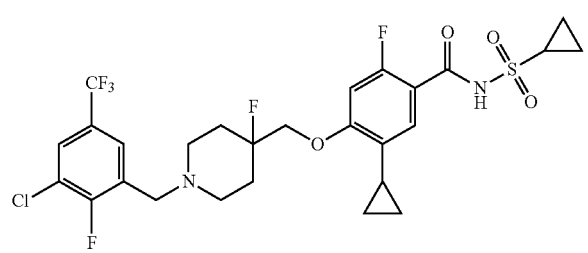 [SMILES: O=C(NS(=O)(=O)C1CC1)c1cc(C2CC2)c(OCC2(F)CCN(Cc3cc(C(F)(F)F)cc(Cl)c3F)CC2)cc1F]

Following the procedure as described in Example 346 step 7 and making non-critical variation as required to replace methanesulfonamide with cyclopropylsulfonamide, the title compound was obtained as a colorless solid (0.04 g, 35%): $^1$H NMR (300 MHz, DMSO-d$_6$) δ 11.89 (br s, 1H), 10.10 (br s, 1H), 8.28 (d, J=6 Hz, 1H), 8.05 (d, J=6 Hz, 1H), 7.15 (d, J=9 Hz, 1H), 7.02 (d, J=15 Hz, 1H), 4.60-4.20 (m, 5H), 3.59-3.16 (m, 4H), 3.14-2.99 (m, 1H), 2.37-1.88 (m, 5H), 1.18-1.04 (m, 3H), 0.96-0.83 (m, 2H), 0.74-0.64 (m, 2H); MS (ES+) m/z 625.1, 627.3 (M+1).

Example 348

Synthesis of 4-((1-(3-chloro-4-(trifluoromethoxy)benzyl)-4-fluoropiperidin-4-yl)methoxy)-5-cyclopropyl-N-(cyclopropylsulfonyl)-2-fluorobenzamide, trifluoroacetic acid salt

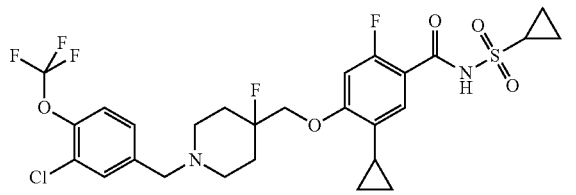 [SMILES: O=C(NS(=O)(=O)C1CC1)c1cc(C2CC2)c(OCC2(F)CCN(Cc3ccc(OC(F)(F)F)c(Cl)c3)CC2)cc1F]

Step 1. Preparation of tert-butyl 4-((1-(3-chloro-4-(trifluoromethoxy)benzyl)-4-fluoropiperidin-4-yl)methoxy)-5-cyclopropyl-2-fluorobenzoate

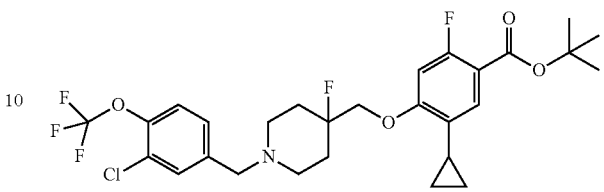

To a solution of tert-butyl 5-cyclopropyl-2-fluoro-4-((4-fluoropiperidin-4-yl)methoxy)benzoate (0.250 g, 0.62 mmol) and 3-chloro-4-(trifluoromethoxy)benzaldehyde (0.17 g, 0.74 mmol) in tetrahydrofuran (5 mL) was added sodium triacetoxyborohydride (0.30 g, 1.40 mmol). The reaction mixture was stirred at ambient temperature for 16 hours and concentrated in vacuo. The residue was subjected to column chromatography to afford the title compound as a colorless gum (0.10 g, 23%): MS (ES+) m/z 576.2, 578.2 (M+1).

Step 2. Preparation of 4-((1-(3-chloro-4-(trifluoromethoxy)benzyl)-4-fluoropiperidin-4-yl)methoxy)-5-cyclopropyl-2-fluorobenzoic acid

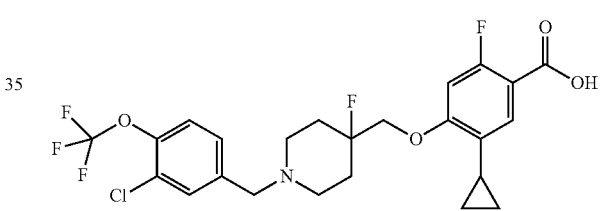

Following the procedure as described in Example 346 step 6, and making non-critical variation as required to replace tert-butyl 4-((4-(tert-butoxycarbonyl)-2-cyclopropyl-5-fluorophenoxy)methyl)-4-fluoropiperidine-1-carboxylate with tert-butyl 4-((1-(3-chloro-4-(trifluoromethoxy)benzyl)-4-fluoropiperidin-4-yl)methoxy)-5-cyclopropyl-2-fluorobenzoate, the title compound was obtained as a colorless solid (0.12 g, quant. yield): MS (ES+) m/z 522.2, 520.2 (M+1).

Step 3. Preparation of 4-((1-(3-chloro-4-(trifluoromethoxy)benzyl)-4-fluoropiperidin-4-yl)methoxy)-5-cyclopropyl-N-(cyclopropylsulfonyl)-2-fluorobenzamide trifluoroacetic acid salt

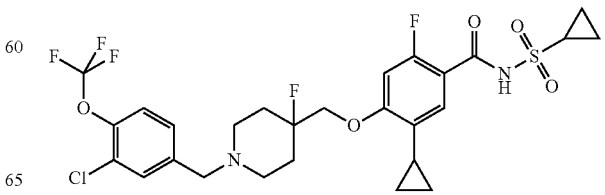

Following the procedure as described in Example 346 step 7 and making non-critical variation as required to replace methanesulfonamide with cyclopropylsulfonamide, the title compound was obtained as a colorless solid (0.02 g, 14%): $^1$H NMR (300 MHz, DMSO-d$_6$) δ 11.80 (br s, H), 10.00 (br s, 1H), 7.90 (s, 1H), 7.75-7.56 (m, 2H), 7.15 (d, J=9 Hz, 1H), 7.03 (d, J=12 Hz, 1H), 4.54-4.2 (m, 4H), 3.25-2.97 (m, 2H), 2.34-1.88 (m, 3H), 2.32-1.85 (m, 5H), 1.21-1.03 (m, 4H), 0.95-0.83 (m, 2H), 0.75-0.61 (m, 2H); MS (ES+) m/z 625.0, 623.1 (M+1).

Example 348

Synthesis of 4-((1-(5-chloro-2-(trifluoromethyl)benzyl)-4-fluoropiperidin-4-yl)methoxy)-5-cyclopropyl-2-fluoro-N-(methylsulfonyl)benzamide, trifluoroacetic acid salt

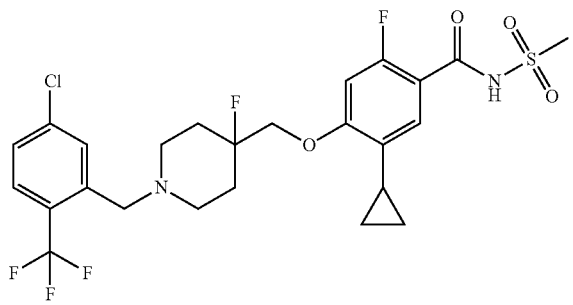 [SMILES: CS(=O)(=O)NC(=O)c1cc(C2CC2)c(OCC2(F)CCN(Cc3cc(Cl)ccc3C(F)(F)F)CC2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-((1-(5-chloro-2-(trifluoromethyl)benzyl)-4-fluoropiperidin-4-yl)methoxy)-5-cyclopropyl-2-fluorobenzoic acid, the title compound was obtained as a colorless solid (0.02 g, 23%): $^1$H NMR (300 MHz, DMSO-d$_6$) δ 11.95 (br, s, 1H), 8.13 (br, s, 1H), 7.96-7.79 (m, 2H), 7.16 (d, J=6 Hz, 1H), 7.02 (d, J=15 Hz, 1H), 4.68-4.41 (m, 2H), 4.39-4.18 (m, 3H), 3.46-3.23 (m, 2H), 3.34 (s, 3H), 2.33-1.93 (m, 6H), 0.93-0.85 (m, 2H), 0.74-0.65 (m, 2H); MS (ES-+) m/z 583.1, 581.2 (M+1).

Example 349

Synthesis of (S)-5-cyclopropyl-4-((1-(1-(3,5-dichlorophenyl)ethyl)-4-fluoropiperidin-4-yl)methoxy)-2-fluoro-N-(methylsulfonyl)benzamide, trifluoroacetic acid salt

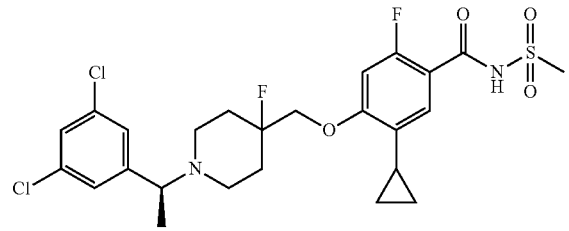 [SMILES: C[C@@H](c1cc(Cl)cc(Cl)c1)N1CCC(F)(COc2cc(F)c(C(=O)NS(C)(=O)=O)cc2C2CC2)CC1]

Step 1. Preparation of (S)-tert-butyl 5-cyclopropyl-4-((1-(1-(3,5-dichlorophenyl)ethyl)-4-fluoropiperidin-4-yl)methoxy)-2-fluorobenzoate

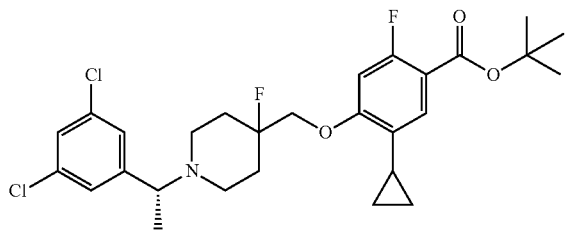 [SMILES: C[C@H](c1cc(Cl)cc(Cl)c1)N1CCC(F)(COc2cc(F)c(C(=O)OC(C)(C)C)cc2C2CC2)CC1]

Following the procedure as described in Example 346 step 5 and making non-critical variations as required to replace 1-chloro-3-(chloromethyl)-2-fluoro-5-(trifluoromethyl)benzene with (R)-1-(3,5-dichlorophenyl)ethyl 4-methylbenzenesulfonate, the title compound was obtained as a colorless solid (0.40 g, 60%): MS (ES+) m/z 542.2, 546.2 (M+1).

Step 2. Preparation of (S)-5-cyclopropyl-4-((1-(1-(3,5-dichlorophenyl)ethyl)-4-fluoropiperidin-4-yl)methoxy)-2-fluorobenzoic acid

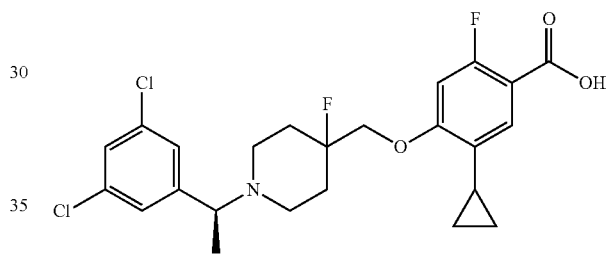

Following the procedure as described in Example 346 step 6, and making non-critical variations as required to replace tert-butyl 4-((4-(tert-butoxycarbonyl)-2-cyclopropyl-5-fluorophenoxy)methyl)-4-fluoropiperidine-1-carboxylate with (R)-tert-butyl 5-cyclopropyl-4-((1-(1-(3,5-dichlorophenyl)ethyl)-4-fluoropiperidin-4-yl)methoxy)-2-fluorobenzoate, the title compound was obtained as a colorless solid (0.20 g, 41%): $^1$H NMR (300 MHz, CDCl$_3$) δ 12.9 (br s, 1H), 7.73 (s, 1H), 7.61 (s, 2H), 7.30 (d, J=8.4 Hz, 1H), 6.93 (d, J=12.9 Hz, 1H), 4.73-4.53 (m, 1H), 4.23 (d, J=20.3 Hz, 2H), 3.81-3.3.63 (m, 1H), 3.26, 3.14 (m, 1H), 3.09-2.90 (m, 2H), 2.15-2.06 (m, 2H), 2.04-1.92 (m, 2H), 1.64 (brs, 3H), 0.89-0.83 (m, 2H), 0.60-0.55 (m 2H); MS(ES+) m/z 486.3, 484.1 (M+1).

Step 3. Preparation of (S)-5-cyclopropyl-4-((1-(1-(3,5-dichlorophenyl)ethyl)-4-fluoropiperidin-4-yl)methoxy)-2-fluoro-N-(methylsulfonyl)benzamide, trifluoroacetic acid salt

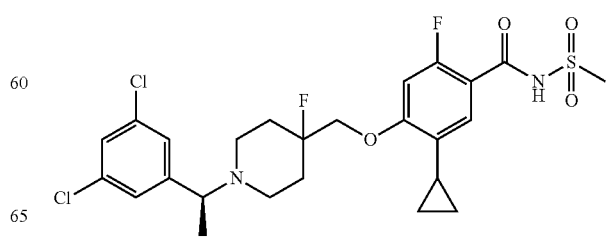

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with (S)-5-cyclopropyl-4-((1-(1-(3,5-dichlorophenyl)ethyl)-4-fluoropiperidin-4-yl)methoxy)-2-fluorobenzoic acid, the title compound (0.05 g, 42% yield) was obtained as a colorless solid: $^1$H NMR (300 MHz, DMSO-$d_6$) δ 11.95 (br s, 1H), 7.87-7.54 (m, 3H), 7.16 (d, J=9 Hz, 1H), 7.02 (d, J=12 Hz, 1H), 4.57 (br, s, 1H), 4.39-4.18 (m, 2H), 3.52 (br, s, 6H), 2.36-1.85 (m, 8H), 1.33-1.14 (m, 1H), 0.89-0.80 (m, 2H), 0.74-0.61 (m, 2H); MS (ES+) m/z 563.3, 561.1 (M+1).

Example 350

Synthesis of (S)-5-cyclopropyl-N-(cyclopropylsulfonyl)-4-((1-(1-(3,5-dichlorophenyl)ethyl)-4-fluoropyridin-4-yl)methoxy)-2-fluorobenzamide

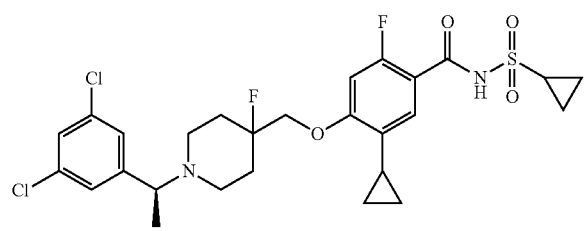 [SMILES: C[C@@H](c1cc(Cl)cc(Cl)c1)N1CCC(F)(COc2cc(F)c(C(=O)NS(=O)(=O)C3CC3)cc2C2CC2)CC1]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with (R)-5-cyclopropyl-4-((1-(1-(3,5-dichlorophenyl)ethyl)-4-fluoropiperidin-4-yl)methoxy)-2-fluorobenzoic acid and to replace methanesulfonamide with cyclopropylsulfonamide, the title compound was obtained as a colorless solid (0.07 g, 57%); $^1$H NMR (300 MHz, DMSO-$d_6$) δ 11.85, (br s, 1H), 10.01 (br s, 1H), 7.73 (s, 1H), 7.615 (d, J=3.0 Hz, 2H), 7.12 (d, J=6.0 Hz, 1H), 6.99 (d, J=15.0 Hz, 1H), 4.6 (brs, 1H), 4.24 (d, J=18.0 Hz, 2H), 3.81-3.62 (m, 1H), 3.27-3.11 (m, 1H), 3.09-2.89 (m, 2H), 2.36-1.83 (m, 5H), 1.73-1.51 (m, 3H), 1.16-1.01 (m, 3H), 0.91-0.78 (m, 2H), 0.71-0.60 (m, 2H); MS(ES+) m/z 589.3, 587.1 (M+1).

Example 351

Synthesis of (R)-5-cyclopropyl-4-((1-(1-(3,5-dichlorophenyl)ethyl)-4-fluoropiperidin-4-yl)methoxy)-2-fluoro-N-(methylsulfonyl)benzamide, trifluoroacetic acid

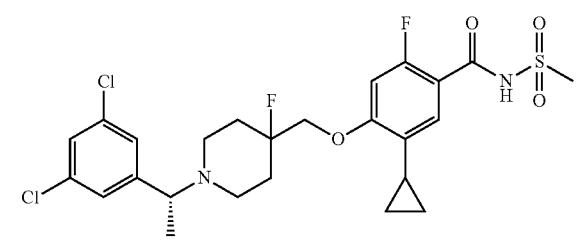 [SMILES: C[C@H](c1cc(Cl)cc(Cl)c1)N1CCC(F)(COc2cc(F)c(C(=O)NS(C)(=O)=O)cc2C2CC2)CC1]

Step 1. Preparation of (R)-tert-butyl 5-cyclopropyl-4-((1-(1-(3,5-dichlorophenyl)ethyl)-4-fluoropiperidin-4-yl)methoxy)-2-fluorobenzoate

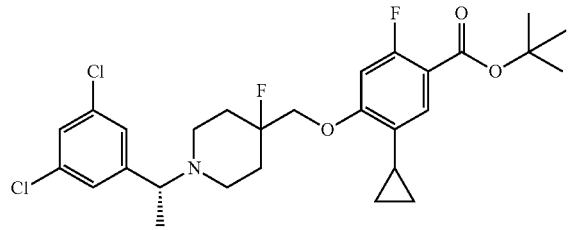 [SMILES: C[C@H](c1cc(Cl)cc(Cl)c1)N1CCC(F)(COc2cc(F)c(C(=O)OC(C)(C)C)cc2C2CC2)CC1]

Following the procedure as described in Example 346 step 5 and making non-critical variations as required to replace 1-chloro-3-(chloromethyl)-2-fluoro-5-(trifluoromethyl)benzene with (S)-1-(3,5-dichlorophenyl)ethyl 4-methylbenzenesulfonate, the title compound was obtained (0.04 g, 60%); MS(ES+) m/z 542.2, 540.2 (M+1).

Step 2. Preparation of (R)-5-cyclopropyl-4-((1-(1-(3,5-dichlorophenyl)ethyl)-4-fluoropiperidin-4-yl)methoxy)-2-fluorobenzoic acid

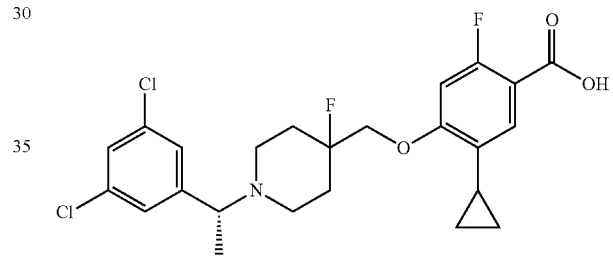

Following the procedure as described in Example 346 step 6 and making non-critical variations as required to replace tert-butyl 4-((4-(tert-butoxycarbonyl)-2-cyclopropyl-5-fluorophenoxy)methyl)-4-fluoropiperidin-1-carboxylate with (S)-tert-butyl 5-cyclopropyl-4-((1-(1-(3,5-dichlorophenyl)ethyl)-4-fluoropiperidin-4-yl)methoxy)-2-fluorobenzoate, the title compound was obtained as a colorless solid (0.12 g, quant. yield): MS(ES+) m/z 484.1, 486.3 (M+1).

Step 3. Preparation of (R)-5-cyclopropyl-4-((1-(1-(3,5-dichlorophenyl)ethyl)-4-fluoropiperidin-4-yl)methoxy)-2-fluoro-N-(methylsulfonyl)benzamide

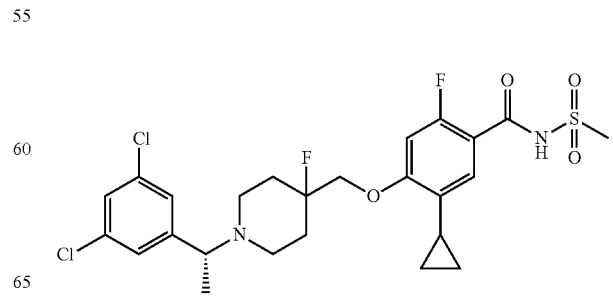

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy-5-cyclopropyl-2-fluorobenzoic acid with (R)-5-cyclopropyl-4-((1-(1-(3,5-dichlorophenyl)ethyl)-4-fluoropiperidin-4-yl)methoxy)-2-fluorobenzoic acid, the title compound was obtained as a colorless solid (0.01 g, 7%): $^1$H NMR (300 MHz, DMSO-$d_6$) δ 11.94 (br s, 1H), 7.87-7.54 (m, 3H), 7.16 (d, J=9.0 Hz, 1H), 7.02 (d, J=12.0 Hz, 1H), 4.57 (brs, 1H), 4.39-4.18 (m, 2H), 3.52 (brs, 6H), 2.36-1.85 (m, 8H), 1.33-1.14 (m, 1H), 0.89-0.80 (m, 2H), 0.74-0.61 (m, 2H); MS(ES+) m/z 563.3, 561.1 (M+1).

Example 352

Synthesis of 4-((1-(bis(3-chlorophenyl)methyl)piperidin-4-yl)methoxy)-5-cyclopropyl-2-fluoro-N-(methylsulfonyl)benzamide, trifluoroacetic acid salt

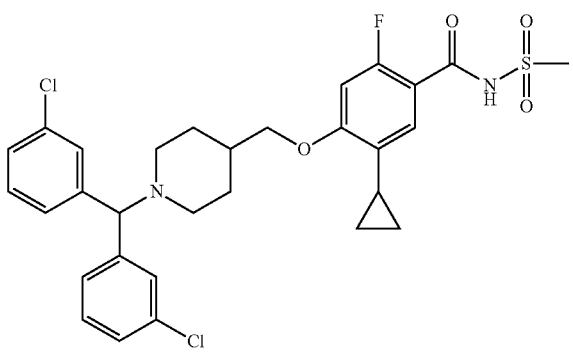 [SMILES: CS(=O)(=O)NC(=O)c1cc(C2CC2)c(OCC2CCN(C(c3cccc(Cl)c3)c3cccc(Cl)c3)CC2)cc1F]

Step 1. Preparation of tert-butyl 4-((1-(bis(3-chlorophenyl)methyl)piperidin-4-yl)methoxy)-5-cyclopropyl-2-fluorobenzoate

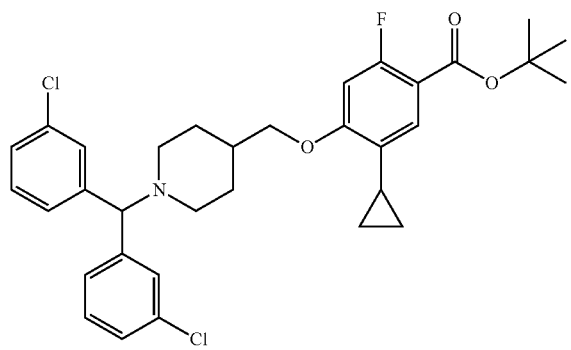 [SMILES: CC(C)(C)OC(=O)c1cc(C2CC2)c(OCC2CCN(C(c3cccc(Cl)c3)c3cccc(Cl)c3)CC2)cc1F]

Following the procedure as described in Example 346 step 5 and making son-critical variations as required to replace of tert-butyl 5-cyclopropyl-2-fluoro-4-((4-fluoropiperidin-4-yl)methoxy)benzoate with tert-butyl 5-cyclopropyl-2-fluoro-4-(piperidin-4-ylmethoxy)benzoate and 1-chloro-3-(chloromethyl)-2-4-5-(trifluoromethyl)benzene with 3,3'-(bromomethylene)bis(chlorobenzene), the title compound was obtained as a colorless solid (0.58 g, 35%): MS(ES+) m/z 586.1, 584.1 (M+1).

Step 2. Preparation of 4-((1-(bis(3-chlorophenyl)methyl)piperidin-4-yl)methoxy)-5-cyclopropyl-2-fluorobenzoic acid

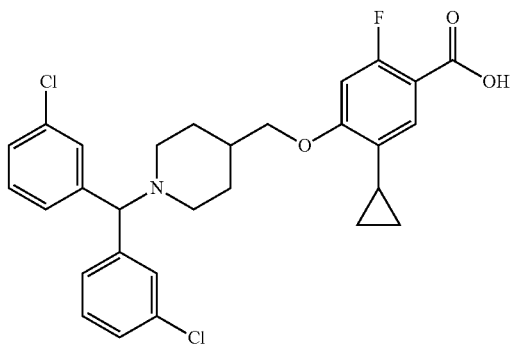 [SMILES: O=C(O)c1cc(C2CC2)c(OCC2CCN(C(c3cccc(Cl)c3)c3cccc(Cl)c3)CC2)cc1F]

Following the procedure as described in Example 346 step 6, and making non-critical variations as required to replace tert-butyl 4-((4-(tert-butoxycarbonyl)-2-cyclopropyl-5-fluorophenoxy)methyl)-4-fluoropiperidin-1-carboxylate with tert-butyl 4-((1-(bis(3-chlorophenyl)methyl)piperidin-4-yl)methoxy)-5-cyclopropyl-2-fluorobenzoate, the title compound was obtained as a colorless solid (0.31 g, 54%): MS(ES+) m/z 530.1, 528.1 (M+1).

Step 3. Preparation of 4-((1-(bis(3-cyclopropyl)methyl)piperidin-4-yl)methoxy)-5-cyclopropyl-2-fluoro-N-(methylsulfonyl)benzamide, trifluoroacetic acid salt

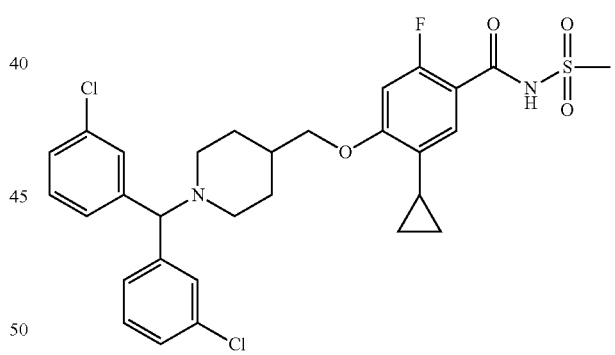

Following the procedure as described is Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-((1-(bis(3-chlorophenyl)methyl)piperidin-4-yl)methoxy)-5-cyclopropyl-2-fluorobenzoic acid, the title compound was obtained as a colorless solid (0.01 g, 38%): $^1$H NMR (300 MHz, DMSO-$d_6$+1% $D_2O$) δ7.72 (s, 2H), 7.63-7.61 (m, 2H), 7.54-7.46 (m, 4H), 7.10 (d, J=8.3 Hz, 1H), 6.93 (d, J=12.9 Hz, 1H), 5.67 (s, 1H), 3.98 (d, J=4.6 Hz, 2H), 3.30 (s, 3H), 3.25-3.21 (m, 2H), 3.09-2.98 (m, 2H), 2.21-2.08 (m, 1H), 2.04-1.97 (m, 3H), 1.72-1.64 (m, 2H), 0.89-0.83 (m, 2H), 0.65-0.60 (m, 2H); MS(ES+) m/z 605.1, 607.3 (M+1).

Example 353

Synthesis of 5-cyclopropyl-4-(((1R,3S,5S)-8-((R)-1-(3,5-dichlorophenyl)ethyl)-8-azabicyclo[3.2.1]octan-3-yl)methoxy)-2-fluoro-N-(methylsulfonyl)benzamide, trifluoroacetic acid salt

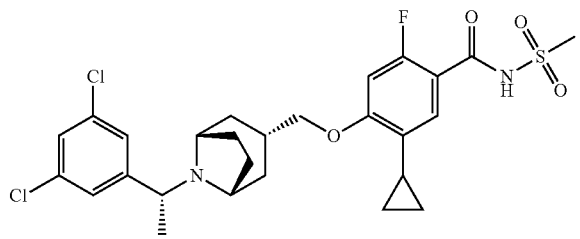 [SMILES: C[C@H](c1cc(Cl)cc(Cl)c1)N1[C@@H]2CC[C@H]1C[C@H](COc1cc(F)c(C(=O)NS(C)(=O)=O)cc1C1CC1)C2]

Following the procedure as described in Example 346 step 5 and making non-critical variations as required to replace of tert-butyl 5-cyclopropyl-2-fluoro-4-((4-fluoropiperidin-4-yl)methoxy)benzoate with 4-((1R,3S,5S)-8-azabicyclo[3.2.1]octan-3-ylmethoxy)-5-cyclopropyl-2-fluoro-N-(methylsulfonyl)benzamide and to replace 1-chloro-3-(chloromethyl)-2-fluoro-5-(trifluoromethyl)benzene with (S)-1,3-dichloro-5-(1-chloroethyl)benzene, the title compound was obtained as a colorless solid (0.03 g, 54%): $^1$H NMR (300 MHz, DMSO-$d_6$) δ 1.89 (br s, 1H), 9.58 (br s, 1H), 7.84-7.74 (m, 2H), 7.73-7.68 (m, 1H), 7.09 (d, J=8.2 Hz, 1H), 6.98 (d, J=12.9 Hz, 1H), 4.54-4.36 (m, 1H), 4.31-4.17 (m, 1H), 4.16-4.06 (m, 1H), 3.96-3.80 (m, 2H), 3.73-3.42 (m, 3H), 3.43-3.34 (m, 1H), 2.39-2.22 (m, 1H), 2.17-1.73 (m, 7H), 1.72-1.52 (m, 4H), 0.91-0.79 (m, 2H), 0.70-0.39 (m, 2H); MS(ES+) m/z 570.1, 571.1 (M+1).

Example 354

Synthesis of 5-cyclopropyl-N-(cyclopropylsulfonyl)-2-fluoro-4-((1-((2-methylthiazol-4-yl)methyl)piperidin-4-yl)methoxy)benzamide, trifluoroacetic acid salt

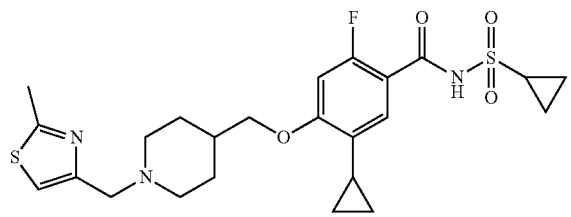 [SMILES: Cc1nc(CN2CCC(COc3cc(F)c(C(=O)NS(=O)(=O)C4CC4)cc3C3CC3)CC2)cs1]

Step 1. Preparation of methyl 5-cyclopropyl-2-fluoro-4-((1-((2-methylthiazol-4-yl)methyl)piperidin-4-yl)methoxy)benzoate

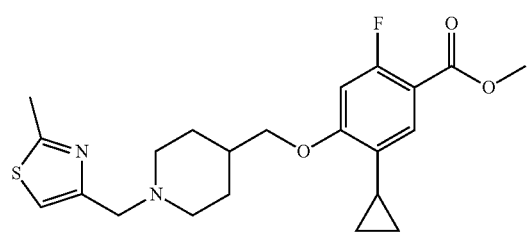 [SMILES: COC(=O)c1cc(C2CC2)c(OCC2CCN(Cc3csc(C)n3)CC2)cc1F]

Following the procedure as described in Example 346 step 5 and making non-critical variations as required to replace tert-butyl 5-cyclopropyl-2-fluoro-4-((4-fluoropiperidin-4-yl)methoxy)benzoate with methyl 5-cyclopropyl-2-fluoro-4-(piperidin-4-ylmethoxy)benzoate hydrochloride and to replace 1-chloro-3-(chloromethyl)-2-fluoro-5-(trifluoromethyl)benzene with 4-(chloromethyl)-2-methylthiazole, the title compound was obtained as a colorless solid (0.20 g, 66%): MS(ES+) m/z 419.2 (M+1).

Step 2. Preparation of 5-cyclopropyl-2-fluoro-4-((1-((2-methylthiazol-4-yl)methyl)piperidin-4-yl)methoxy)benzoic acid

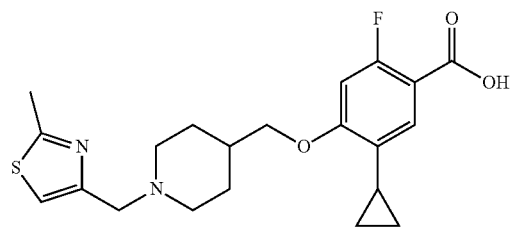 [SMILES: Cc1nc(CN2CCC(COc3cc(F)c(C(=O)O)cc3C3CC3)CC2)cs1]

To a solution of methyl 5-cyclopropyl-2-fluoro-4-((1-((2-methylthiazol-4-yl)methyl)piperidin-4-yl)methoxy)benzoate (0.20 g, 0.48 mmol) in tetrahydrofuran (10 mL) was a added a solution of lithium hydroxide (0.11 g, 4.80 mmol) in water (5 mL). The reaction mixture was refluxed for 5 hours, cooled to ambient temperature, and acidified with 1N hydrochloric acid solution. The reaction mixture was extracted with ethyl acetate (3×10 mL), dried over anhydrous sodium sulfate, filtered.

The filtrate was concentrated in vacuo to afford the title compound as a colorless gum (0.14 g, 72% yield): MS(ES+) m/z 405.2 (M+1).

Step 3. Preparation of 5-cyclopropyl-N-(cyclopropylsulfonyl)-2-fluoro-4-((1-((2-methylthiazol-4-yl)methyl)piperidin-4-yl)methoxy)benzamide

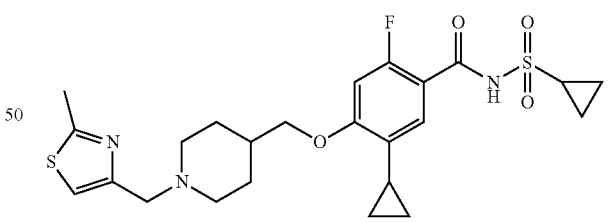

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-((2-methylthiazol-4-yl)methyl)piperidin-4-yl)methoxy)benzoic acid and to replace methanesulfonamide with cyclopropylsulfonamide, the title compound was obtained as a colorless solid (0.03 g, 20%); $^1$H NMR (300 MHz, DMSO-$d_6$) δ 11.86 (br s, 1H), 9.85 (br s, 1H), 7.72 (s, 1H), 7.12 (d, J=9.0 Hz, 1H), 6.98 (d, J=12.8 Hz, 1H), 4.36 (s, 2H), 4.01-3.91 (m, 2H), 3.56-3.39 (m, 2H), 3.13-2.92 (m, 3H), 2.70 (s, 3H), 2.16-

1.82 (m, 4H), 1.77-1.52 (m, 2H), 1.18-1.03 (m, 4H), 0.95-0.82 (m, 2H), 0.74-0.60 (m, 2H): MS(ES+) m/z 508.2 (M+1).

Example 355

Synthesis of 5-cyclopropyl-N-(cyclopropylsulfonyl)-2-fluoro-4-((1-((2-isopropylthiazol-4-yl)methyl)piperidin-4-yl)methoxy)benzamide trifluoroacetic acid salt

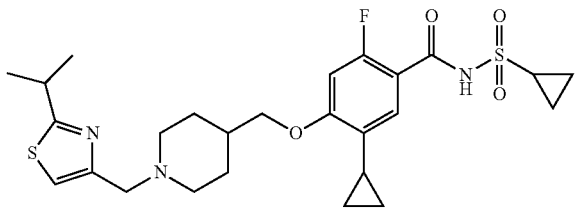 [SMILES: CC(C)c1nc(CN2CCC(COc3cc(F)c(C(=O)NS(=O)(=O)C4CC4)cc3C3CC3)CC2)cs1]

Step 1. Preparation of methyl 5-cyclopropyl-2-fluoro-4-((1-((2-isopropylthiazol-4-yl)methyl)piperidin-4-yl)methoxy)benzoate

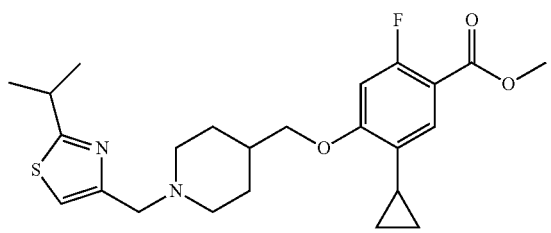 [SMILES: COC(=O)c1cc(C2CC2)c(OCC2CCN(Cc3csc(C(C)C)n3)CC2)cc1F]

Following the procedure as described in Example 346 step 5 and making non-critical variations as required to replace tert-butyl 5-cyclopropyl-2-fluoro-4-((4-fluoropiperidin-4-yl)methoxy)benzoate with methyl 5-cyclopropyl-2-fluoro-4-(piperidin-4-ylmethoxy)benzoate hydrochloride and to replace 1-chloro-3-(chloromethyl)-2-fluoro-5-(trifluoromethyl)benzene with 4-(chloromethyl)-2-isopropylthiazole, the title compound was obtained as a colorless gum (0.23 g, 70%); MS(ES+) m/z 447.2 (M+1).

Step 2. Preparation of 5-cyclopropyl-2-fluoro-4-((1-((2-isopropylthiazol-4-yl)methyl)piperidin-4-yl)methoxy)benzoic acid

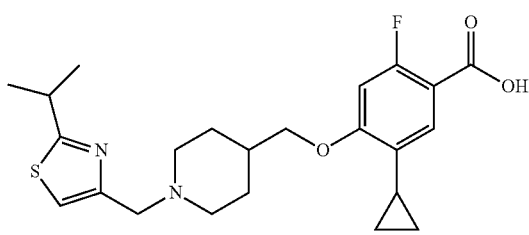 [SMILES: CC(C)c1nc(CN2CCC(COc3cc(F)c(C(=O)O)cc3C3CC3)CC2)cs1]

Following the procedure as described in Example 354 step 2 and making non-critical variations as required to replace methyl 5-cyclopropyl-2-fluoro-4-((1-((2-methylthiazol-4-yl)methyl)piperidin-4-yl)methoxy)benzoate with methyl 5-cyclopropyl-2-fluoro-4-((1-((2-isopropylthiazol-4-yl)methyl)piperidin-4-yl)methoxy)benzoate, the title compound was obtained as a colorless solid (0.15 g, 77%): MS(ES+) m/z 432.2 (M+1).

Step 3. Preparation of 5-cyclopropyl-N-(cyclopropylsulfonyl)-2-fluoro-4-((1-((2-isopropylthiazol-4-yl)methyl)piperidin-4-yl)methoxy)benzamide 2,2,2-trifluoroacetate

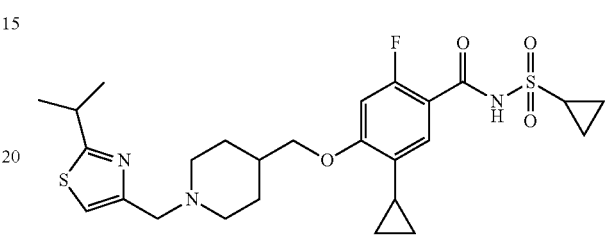

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-((2-isopropylthiazol-4-yl)methyl)piperidin-4-yl)methoxy)benzoic acid and to replace methanesulfonamide with cyclopropylsulfonamide, the title compound was obtained as a colorless solid (0.08 g, 47%): $^1$H NMR (300 MHz, DMSO-d$_6$) δ 11.85 (br s, 1H), 9.81 (s, 1H), 7.76 (s, 1H), 7.12 (d, J=8.2 Hz, 1H), 6.98 (d, J=12.9 Hz, 1H), 4.38 (s, 2H), 4.07-3.86 (m, 2H), 3.41-3.19 (ms 3H), 3.16-2.90 (m, 3H), 2.16-1.84 (m, 4H), 1.75-1.47 (m, 2H), 1.42-1.26 (m, 6H), 1.19-1.00 (m, 4H), 0.95-0.79 (m, 2H), 0.73-0.59 (m, 2H); MS (ES+) m/z 536.2 (M+1).

Example 356

Synthesis of 5-cyclopropyl-N-(cyclopropylsulfonyl)-2-fluoro-4-((1-(5-fluoro-2-(isopropylamino)benzyl)piperidin-4-yl)methoxy)benzamide, trifluoroacetic acid salt

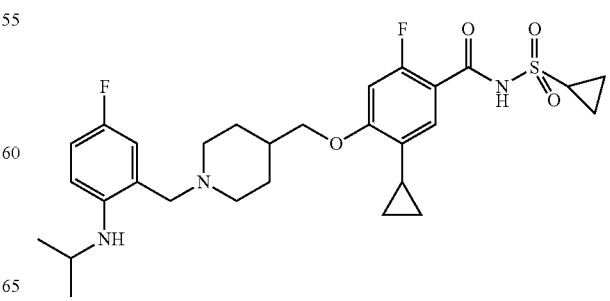

Step 1. Preparation of methyl 4-((1-(2-amino-5-fluorobenzoyl)piperidin-4-yl)methoxy)-5-cyclopropyl-2-fluorobenzoate

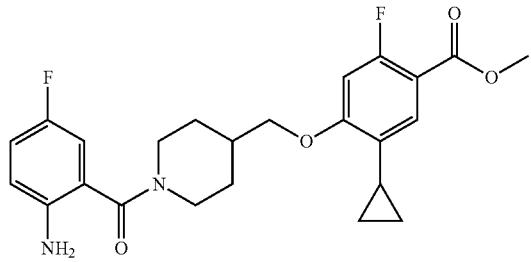 [SMILES: COC(=O)c1cc(C2CC2)c(OCC2CCN(C(=O)c3cc(F)ccc3N)CC2)cc1F]

To a mixture of 2-amino-5-fluorobenzoic acid (0.16 g, 1.00 mmol), benzotriazol-1-yl-oxytripyrrolidinophosphonium hexafluorophosphate (PyBOP) (0.70 g, 1.50 mmol) and N,N-diisopropylethylamine (0.71 g, 4.00 mmol) in dichloromethane (2 mL) was added methyl 5-cyclopropyl-2-fluoro-4-(piperidin-4-ylmethoxy)benzoate (0.52 g, 1.50 mmol). After stirring at an ambient temperature for 16 hours, the reaction mixture was diluted with dichloromethane (10 mL), washed with saturated solution of ammonium chloride (3×5 mL), dried over anhydrous sodium sulfate and filtered. The filtrate was concentrated and the residue was purified by column chromatography eluting with ethyl acetate in hexane to afford the title compound as a colorless solid (0.05 g, 11%): MS(ES+) m/z 445.2 (M+1).

Step 2. Preparation of methyl 4-((1-(2-amino-5-fluorobenzyl)piperidin-4-yl)methoxy)-5-cyclopropyl-2-fluorobenzoate

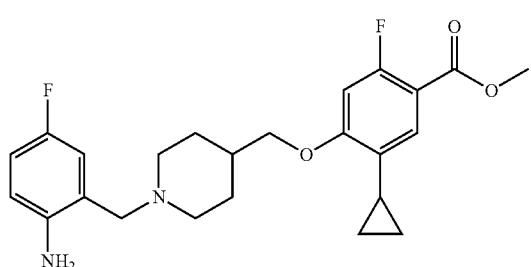

To a solution of methyl 4-((1-(2-amino-5-fluorobenzoyl)piperidin-4-yl)methoxy)-5-cyclopropyl-2-fluorobenzoate (0.18 g, 0.40 mmol) in anhydrous tetrahydrofuran (4 mL), was added borane dimethyl sulfide complex (1.5 mL, 150 mmol). After stirring at ambient temperature for 1 hour, the reaction mixture was added slowly to methanol (50 mL), followed by addition of hydrogen chloride (4.0M in dioxane solution, 5 mL), and then concentrated in vacuo to afford the title compound as a colorless solid (0.10 g, 58%); MS(ES+) m/z 431.2 (M+1).

Step 3. Preparation of methyl 5-cyclopropyl-2-fluoro-4-((1-(5-fluoro-2-(isopropylamino)benzyl)piperidin-4-yl)methoxy)benzoate

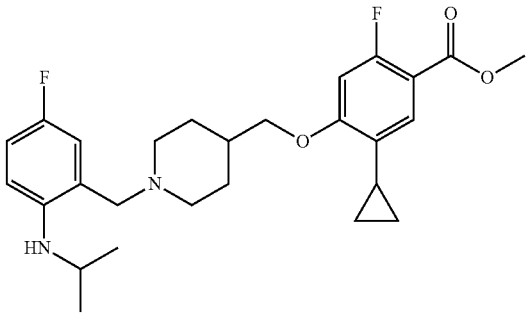 [SMILES: COC(=O)c1cc(C2CC2)c(OCC2CCN(Cc3cc(F)ccc3NC(C)C)CC2)cc1F]

To a 20 mL microwave vial was added methyl 4-((1-(2-amino-5-fluorobenzyl)piperidin-4-yl)methoxy)-5-cyclopropyl-2-fluorobenzoate (0.20 g, 0.50 mmol), methanol (5 mL), sodium cyanoborohydride (0.20 g, 3.00 mmol), acetone (1 mL) an acetic acid (1 mL). The reaction mixture was heated at 130° C. for 15 minutes. After cooling to ambient temperature, the reaction mixture was concentrated and basified with sodium bicarbonate solution, extracted with ethyl acetate (2×20 mL), dried over anhydrous sodium sulfate and filtered. The filtrate was concentrated in vacuo to afford the title compound as a gum (0.12 g, 51%). Which was used in next step without former purification: MS(ES+) m/z 473.2 (M+1).

Step 4. Preparation of 5-cyclopropyl-2-fluoro-4-((1-(5-fluoro-2-(isopropylamino)benzyl)piperidin-4-yl)methoxy)benzoic acid

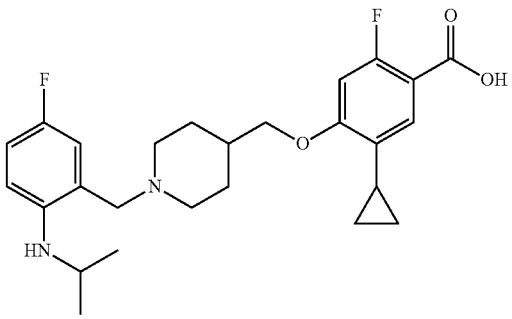 [SMILES: CC(C)Nc1ccc(F)cc1CN1CCC(COc2cc(F)c(C(=O)O)cc2C2CC2)CC1]

Following the procedure as described in Example 354 step 2 and making non-critical variations as required to replace methyl 5-cyclopropyl-2-fluoro-4-((1-((2-methylthiazol-4-yl)methyl)piperidin-4-yl)methoxy)benzoate with methyl 5-cyclopropyl-2-fluoro-4-((1-(5-fluoro-2-(isopropylamino)benzyl)piperidin-4-yl)methoxy benzoate, the title compound was obtained as a gum (0.04 g, 34%). Which was used in next step without anther purification: MS(ES+) m/z 459.6 (M+1).

Step 4. Preparation of 5-cyclopropyl-N-(cyclopropylsulfonyl)-2-fluoro-4-((1-(5-fluoro-2-(isopropylamino)benzyl)piperidin-4-yl)methoxy)benzamide

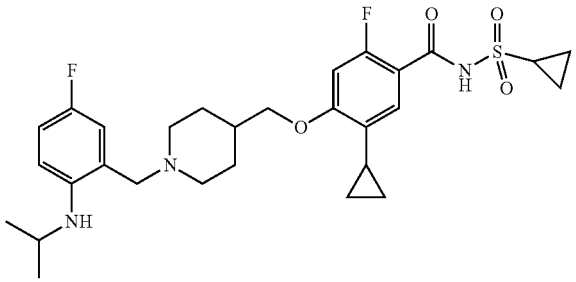 [SMILES: CC(C)Nc1ccc(F)cc1CN1CCC(COc2cc(F)c(C(=O)NS(=O)(=O)C3CC3)cc2C2CC2)CC1]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-(5-fluoro-2-(isopropylamino)benzyl)piperidin-4-yl)methoxy)benzoic acid and to replace methanesulfonamide with cyclopropylsulfonamide, the title compound was obtained as a colorless solid (0.01 g, 23%); $^1$H NMR (300 MHz, DMSO-$d_6$) δ 11.86 (br s, 1H), 7.33 (s, 1H), 7.23-7.06 (m, 3H), 7.04-6.94 (m, 1H), 6.76-6.68 (m, 1H), 4.30 (s, 2H), 3.98 (s, 2H), 3.70-3.54 (m, 1H), 3.50-3.34 (m, 2H), 3.19-2.97 (m, 3H), 2.54 (s, 4H), 2.18-1.92 (m, 3H), 1.75-1.57 (m, 2H), 1.22-1.07 (m, 8H), 0.95-0.85 (m, 2H), 0.73-0.63 (m, 2H); MS (ES+) m/z 562.2 (M+1).

Example 357

Synthesis of 4-((1-((5-chloro-1-methyl-3-(trifluoromethyl)-1H-pyrazol-4-yl)methyl)piperidin-4-yl)methoxy)-5-cyclopropyl-N-(cyclopropylsulfonyl)-2-fluorobenzamide, trifluoroacetic acid salt

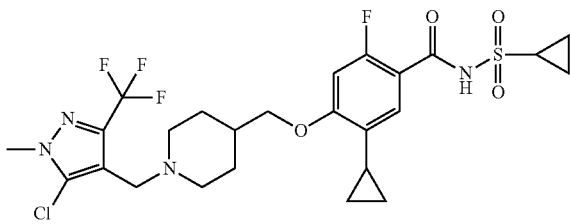 [SMILES: Cn1nc(C(F)(F)F)c(CN2CCC(COc3cc(F)c(C(=O)NS(=O)(=O)C4CC4)cc3C3CC3)CC2)c1Cl]

Step 1. Preparation of methyl 4-((1-((5-chloro-1-methyl-3-(trifluoromethyl)-1H-pyrazol-4-yl)methyl)piperidin-4-yl)methoxy)-5-cyclopropyl-2-fluorobenzoate

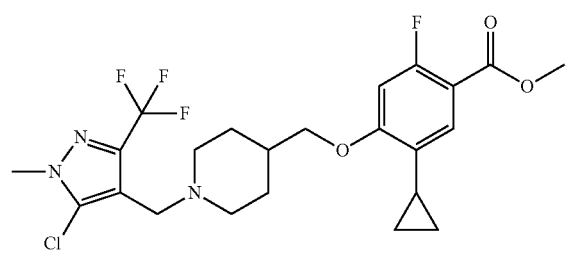

To a mixture of methyl 5-cyclopropyl-2-fluoro-4-(piperidin-4-ylmethoxy)benzoate (0.12 g, 0.40 mmol), 5-chloro-1-methyl-3-(trifluoromethyl)-1H-pyrazole-4-carbaldehyde (0.08 g, 0.40 mmol) in dichloroethane (2 mL) was added sodium triacetoxyborohydride (0.25 g, 1.20 mmol) and acetic acid (0.07 g, 1.20 mmol). After stirring at ambient temperature for 16 hours, the reaction mixture was quenched by addition aqueous ammonium hydroxide solution (28%, 3 mL) and extracted with dichloromethane, dried over anhydrous sodium sulfate and filtered. The filtrate was concentrated in vacuo to afford the title compound as a colorless gum (0.01 g, 50%). Which was used in next step without further purification: MS(ES+) m/z 506.2, 504.2 (M+1).

Step 2. Preparation of 4-((1-((5-chloro-1-methyl-3-(trifluoromethyl)-1H-pyrazol-4-yl)methyl)piperidin-4-yl)methoxy)-5-cyclopropyl-2-fluorobenzoic acid

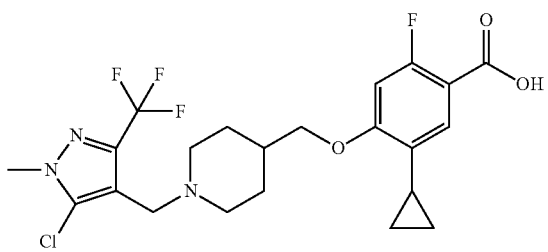 [SMILES: Cn1nc(C(F)(F)F)c(CN2CCC(COc3cc(F)c(C(=O)O)cc3C3CC3)CC2)c1Cl]

Following the procedure as described in Example 354 step 2 and making non-critical variations as required to replace methyl 5-cyclopropyl-2-fluoro-4-((1-((2-methylthiazol-4-yl)methyl)piperidin-4-yl)methoxy)benzoate with methyl 4-((1-((5-chloro-1-methyl-3-(trifluoromethyl)-1H-pyrazol-4-yl)methyl)piperidin-4-yl)methoxy)-5-cyclopropyl-2-fluorobenzoate, the title compound was obtained as a colorless solid (0.10 g, quant. yield): MS (ES+) m/z 492.3, 490.1 (M+1).

Step 3. Preparation of 4-((1-((5-chloro-1-methyl-3-(trifluoromethyl)-1H-pyrazol-4-yl)methyl)piperidin-4-yl)methoxy)-5-cyclopropyl-N-(cyclopropylsulfonyl)-2-fluorobenzamide 2,2,2-trifluoroacetate

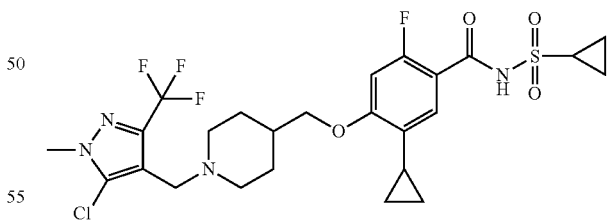

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-((1-((5-chloro-1-methyl-3-(trifluoromethyl)-1H-pyrazol-4-yl)methyl)piperidin-4-yl)methoxy)-5-cyclopropyl-2-fluorobenzoic acid and to replace methanesulfonamide with cyclopropylsulfonamide, the title compound was obtained as a colorless solid (0.01 g, 10%): $^1$H NMR (300 MHz, DMSO-$d_6$) δ 11.85 (br s, 1H), 7.3 (s, 1H), 7.12 (s, 1H), 6.98 (s, 1H), 4.21-4.03 (m, 1H), 3.93 (s, 3H), 3.80-3.20 (m, 6H), 3.1-2.8 (m, 2H), 2.1-1.8 (m, 4H), 1.61-1.42 (m, 2H), 1.21-1.01 (m, 4H), 0.95-0.85 (m, 2H), 0.72-0.55 (m, 2H); MS (ES+) m/z 595.1, 593.2 (M+1).

Example 358

Synthesis of 5-cyclopropyl-4-((1-(1-(3,5-dichlorophenyl)-2-fluoroethyl)piperidin-4-yl)methoxy)-2-fluoro-N-(methylsulfonyl)benzamide, trifluoroacetic acid salt

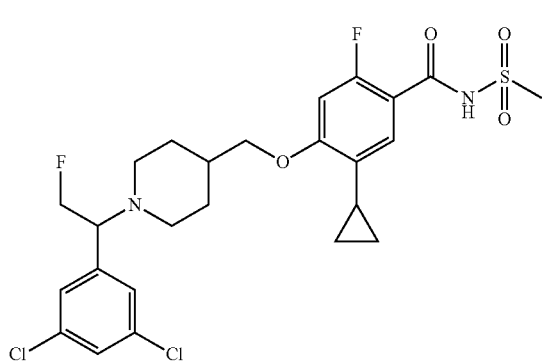 [SMILES: CS(=O)(=O)NC(=O)c1cc(C2CC2)c(OCC2CCN(C(CF)c3cc(Cl)cc(Cl)c3)CC2)cc1F]

Step 1. Preparation of tert-butyl 5-cyclopropyl-4-((1-(1-(3,5-dichlorophenyl)-2-hydroxyethyl)piperidin-4-yl)methoxy)-2-fluorobenzoate

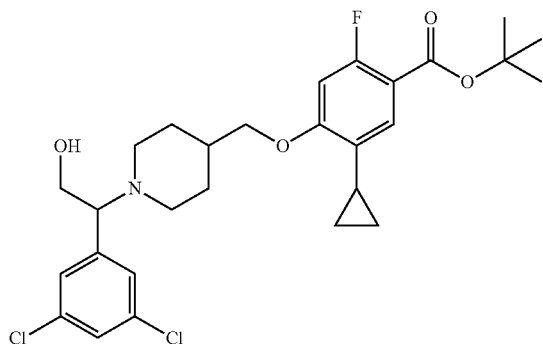 [SMILES: CC(C)(C)OC(=O)c1cc(C2CC2)c(OCC2CCN(C(CO)c3cc(Cl)cc(Cl)c3)CC2)cc1F]

To a mixture of tert-butyl 5-cyclopropyl-2-fluoro-4-(piperidin-4-ylmethoxy)benzoate (1.31 g, 3.75 mmol), glyoxylic acid monohydrate (0.55 g, 5.99 mmol) and 4 Å molecular sieves (1.0 g) in anhydrous toluene (15 mL) was added 3,5-dichlorophenyl)boronic acid (0.79 g, 4.12 mmol). The reaction mixture was refluxed for 16 hours, cooled to ambient temperature and filtered off the solid. The filtrated was concentrated and the residue was redissolved in anhydrous tetrahydrofuran (10 mL). A boron tetrahydrofuran complex (1.0 M in tetrahydrofuran, 25 mL, 25.00 mmol) was added to the solution and stirred at ambient temperature for 16 hours. The reaction mixture was quenched with 1N hydrochloric acid solution (15 mL) and extracted with ethyl acetate (3×25 mL). The combined organic layer was dried over anhydrous sodium sulfate and filtered. The filtrate was concentrated and the residue was purified by column chromatography eluting with ethyl acetate in hexanes to afford the title compound as a gum (0.95 g, 48%). Which was used in the next step without further purification; MS(ES+) m/z 540.2, 538.2 (M+1).

Step 2. Preparation of 5-cyclopropyl-4-((1-(1-(3,5-dichlorophenyl)-2-fluoroethyl)piperidin-4-yl)methoxy)-2-fluoro-N-(methylsulfonyl)benzamide, trifluoroacetic acid salt

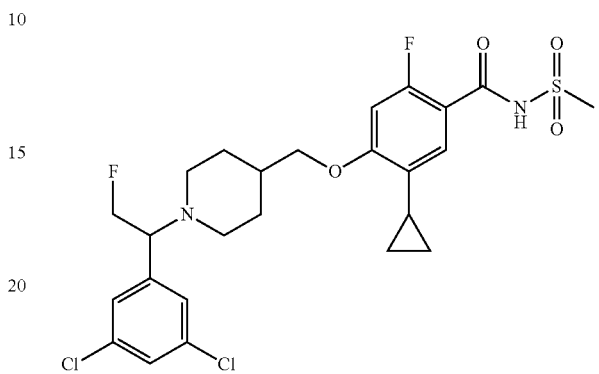

To a solution of tert-butyl 5-cyclopropyl-4-((1-(1-(3,5-dichlorophenyl)-2-hydroxyethyl)piperidin-4-yl)methoxy)-2-fluorobenzoate (0.95 g, 1.77 mmol) in dichloromethane (15 mL) was added methoxyethyl)aminosulfur trifluoride (BAST) (0.57 g, 3.54 mmol). The reaction mixture was stirred at ambient temperature for 16 hours and washed with aqueous sodium bicarbonate solution (3×5 mL), dried over anhydrous sodium sulfate and filtered. The filtrate was concentrated in vacuo and the residue was redissolved in dichloromethane (15 mL). To this solution was added trifluoroacetic acid (5 mL), after stirring at ambient temperature for 3 hours, the reaction mixture was concentrated in vacuo. The residue was redissolved in anhydrous tetrahydrofuran (15 mL). To this solution was added 1-ethyl-3-(3-dimethylaminopropyl)carbodiimide (0.43 g, 3.54 mmol), 4-dimethylaminopyridine (1.08 g, 8.85 mmol) and (0.34 g, 3.54 mmol). After stirring at a ambient temperature for 16 hours. The reaction mixture was diluted with ethyl acetate (15 mL), washed with brine (10 mL), dried over anhydrous sodium sulfate and filtered. The filtrate was concentrated in vacuo and the residue was purified by preparative HPLC to afford the title compound as a colorless solid (0.06 g, 6% in 3 steps): $^1$H NMR (300 MHz, CDCl$_3$) δ 11.84 (br s, 1H), 10.06 (br s, 1H), 7.72 (dd, J=1.79, 1.79 Hz, 1H), 7.54 (s, 2H), 7.11 (d, J=8.31 Hz, 1H), 6.96 (d, J=12.93 Hz, 1H), 6.33-6.03 (m, 1H), 4.11-3.37 (m, 8H), 3.22-2.95 (m, 2H), 2.50 (s, 3H), 2.17-1.87 (m, 2H), 1.83-1.58 (m, 2H), 0.94-0.78 (m, 2H), 0.71-0.61. (m, 2H); MS (ES+) m/z (M+1) 563.1

Example 359

Synthesis of (S)—N-(cyclopropylsulfonyl)-4-((1-(1-(3,5-cyclopropyl)ethyl)piperidin-4-yl)methoxy)-2-fluoro-5-methylbenzamide, trifluoroacetic acid salt

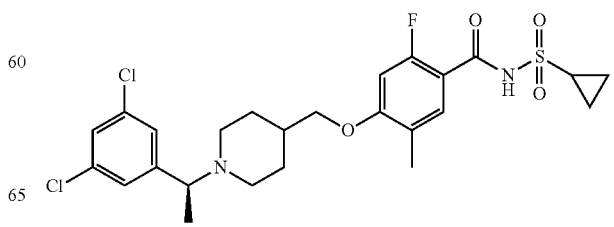

Step 1. Preparation of tert-butyl 4-((1-benzylpiperidin-4-yl)methoxy)-2-4-5-methylbenzoate

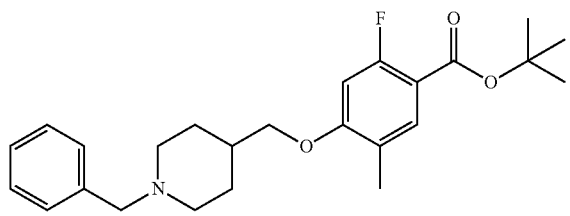 [SMILES: Cc1cc(C(=O)OC(C)(C)C)c(F)cc1OCC1CCN(Cc2ccccc2)CC1]

Following the procedure as described in Example 346 step 2 and making non-critical variations as required to replace tert-butyl 4-fluoro-4-(hydroxymethyl)piperidine-1-carboxylate with (1-benzylpiperidin-4-yl)methanol and to replace tert-butyl 5-chloro-2,4-dichlorobenzoate with tert-butyl 2,4-dichloro-5-methylbenzoate, the title compound was obtained as a colorless foam (0.85 g, 43%): MS(ES+) m/z 416.1, 414.2 (M+1).

Step 2. Preparation of tert-butyl 2-fluoro-5-methyl-4-(piperidin-4-ylmethoxy)benzoate

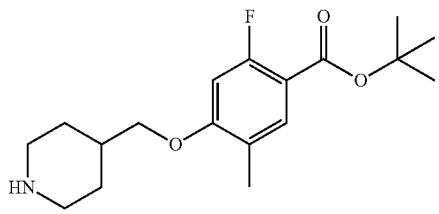 [SMILES: Cc1cc(C(=O)OC(C)(C)C)c(F)cc1OCC1CCNCC1]

To a mixture of tert-butyl 4-((1-benzylpiperidin-4-yl)methoxy)-2-fluoro-5-methylbenzoate (0.63 g, 1.52 mmol), ammonium formate (0.12 g, 1.82 mmol) was added 10% PD/C (0.21 g) in methanol (15 mL). The reaction mixture was refluxed for 1 hour cooled to ambient temperature, filtered through a pad of diatomaceous earth, and washed with methanol. The filtrate was concentrated in vacuo and the residue was directly used in the next step: MS (ES+) m/z 324.2 (M+1).

Step 3. Preparation of (S)-tert-butyl 4-((1-(1-(3,5-dichlorophenyl)ethyl)piperidin-4-yl)methoxy)-2-fluoro-5-methylbenzoate

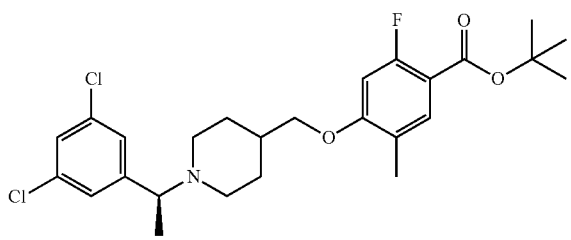 [SMILES: Cc1cc(C(=O)OC(C)(C)C)c(F)cc1OCC1CCN([C@@H](C)c2cc(Cl)cc(Cl)c2)CC1]

Following the procedure as described in Example 345 step 5 and making non-critical variations as required to replace tert-butyl 5-cyclopropyl-2-fluoro-4-((4-fluoropiperidin-4-yl)methoxy)benzoate hydrochloride with tert-butyl 2-fluoro-5-methyl-4-(piperidin-4-ylmethoxy)benzoate, and to replace 1-chloro-3-(chloromethyl)-2-fluoro-5-(trifluoromethyl)benzene with (R)-1-(3,5-dichlorophenyl)ethyl 4-methylbenzenesulfonate, the title compound was obtained as a colorless foam (0.30 g, 82%): MS (ES+) m/z 498.1, 496.2 (M+1).

Step 4. Preparation of (S)-4-((1-(1-(3,5-dichlorophenyl)ethyl)piperidin-4-yl)methoxy-2-fluoro-5-methylbenzoic acid

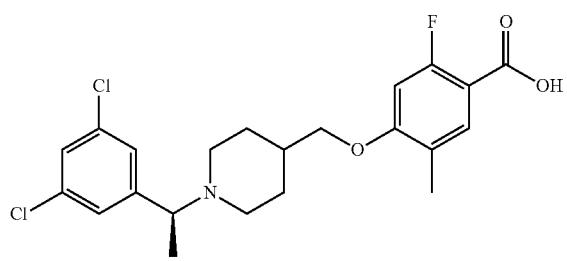 [SMILES: Cc1cc(C(=O)O)c(F)cc1OCC1CCN([C@@H](C)c2cc(Cl)cc(Cl)c2)CC1]

Following the procedure as described in Example 346 step 6, and making non-critical variations as required to replace tert-butyl 4-((4-(tert-butoxycarbonyl)-2-cyclopropyl-5-fluorophenoxy)methyl)-4-fluoropiperidin-1-carboxylate with (S)-tert-butyl 4-((1-(1-(3,5-dichlorophenyl)ethyl)piperidin-4-yl)methoxy)-2-fluoro-5-methylbenzoate, the title compound was obtained as a gum (0.25 g, 0.95%). Which was used in the next step without further purifications: MS (ES−) m/z 438.1, 437.0 (M−1).

Step 5. Preparation of (S)—N-(cyclopropylsulfonyl)-4-((1-(1-(3,5-dichlorophenyl)ethyl)piperidin-4-yl)methoxy)-2-fluoro-5-methylbenzamide trifluoroacetic acid salt

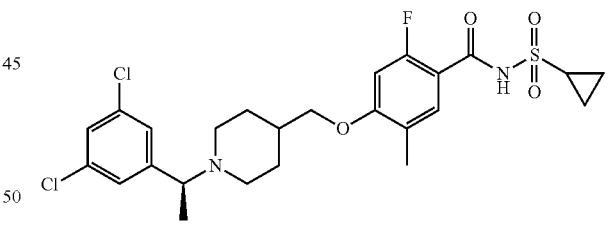

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with (S)-4-((1-(1-(3,5-dichlorophenyl)ethyl)piperidin-4-yl)methoxy)-2-fluoro-5-methylbenzoic acid, and to replace methanesulfonamide with cyclopropylsulfonamide, the title compound was obtained as a colorless solid (0.01 g, 6%): $^1$H NMR (300 MHz, DMSO-$d_6$) δ 11.83 (br s, 1H), 9.49 (br s, 1H), 7.76 (brs, 1H), 7.65 (br s, 2H), 7.49 (d, J=9.0 Hz, 1H), 6.97 (d, J=12.0 Hz, 1H), 4.55 (br s, 1H), 4.00-3.91 (m, 2H), 3.17-3.01 (m, 2H), 2.94-2.75 (m, 2H), 2.31-2.24 (m, 1H), 2.13 (s, 3H), 2.08-1.89 (m, 3H), 1.72-1.48 (m, 5H), 1.19-1.05 (m, 4H); MS (ES+) m/z 545.1, 543.1 (M+1).

Example 360

Synthesis of (S)-4-((1-(1-(3,5-dichloro)ethyl)piperidin-4-yl)methoxy)-2-fluoro-5-methyl-N-(methylsulfonyl)benzamide, trifluoroacetic acid

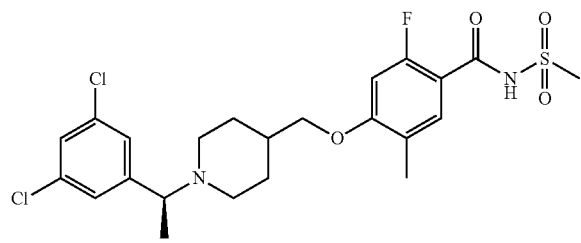 [SMILES: Cc1cc(C(=O)NS(C)(=O)=O)c(F)cc1OCC1CCN([C@@H](C)c2cc(Cl)cc(Cl)c2)CC1]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with (S)-4-((1-(1-(3,5-dichlorophenyl)ethyl)piperidin-4-yl)methoxy)-2-fluoro-5-methylbenzoic acid, the title compound was obtained as a colorless solid (0.04 g, 63%): $^1$H NMR (300 MHz, DMSO-$d_6$) δ 11.89 (br s, 1H), 9.60 (br s, 1H), 7.76 (s, 1H), 7.65 (d, J=3.0 Hz, 2H), 7.50 (d, J=9.0 Hz, 1H), 6.97 (d, J=2.0 Hz, 1H), 4.62-4.49 (m, 1H), 4.01-3.89 (m, 2H), 3.73-3.63 (m, 1H), 3.41-3.33 (m, 1H, 3.34 (s, 3H), 2.92-2.75 (m, 2H), 2.13 (s, 3H), 2.08-1.89 (m, 3H), 1.73-1.53 (m, 5H); MS(ES+) m/z 519.1, 517.1 (M+1).

Example 361

Synthesis of 4-((1-(bis(2-chlorophenyl)methyl)piperidin-4-yl)methoxy)-5-cyclopropyl-2-fluoro-N-(methylsulfonyl)benzamide, trifluoroacetic acid salt

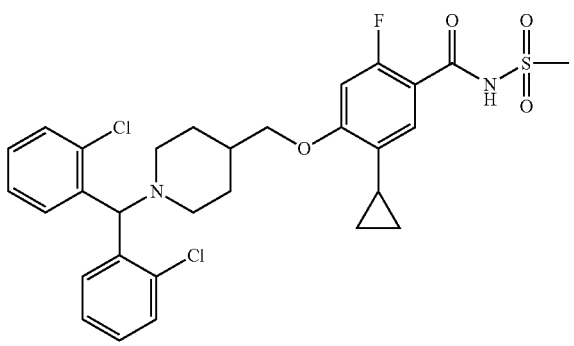 [SMILES: CS(=O)(=O)NC(=O)c1cc(C2CC2)c(OCC2CCN(C(c3ccccc3Cl)c3ccccc3Cl)CC2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-((1-(bis(2-chlorophenyl)methyl)piperidin-4-yl)methoxy)-5-cyclopropyl-2-fluorobenzoic acid, the title compound was obtained as a colorless solid (0.07 g, 39%): $^1$H NMR (300 MHz, DMSO-$d_6$+1% $D_2O$) δ7.76-7.73 (m, 2H), 7.57-7.40 (m, 6H), 7.09 (d, J=8.3 Hz, 1H), 6.91 (d, J=12.9 Hz, 1H), 6.05 (s, 1H), 3.99-3.92 (m, 2H), 3.29 (s, 3H), 3.27-3.18 (m, 2H), 3.17-3.08 (m, 2H), 2.22-2.09 (m, 1H), 2.05-1.94 (m, 3H), 1.69-1.54 (m, 2H), 0.90-0.84 (m, 2H), 0.64-0.59 (m, 2H); MS (ES+) m/z 605.2, 607.1 (M+1).

Example 362

Synthesis of 4-((1-(bis(4-chlorophenyl)methyl)piperidin-4-yl)methoxy)-5-cyclopropyl-2-fluoro-N-(methylsulfonyl)benzamide, trifluoroacetic acid salt

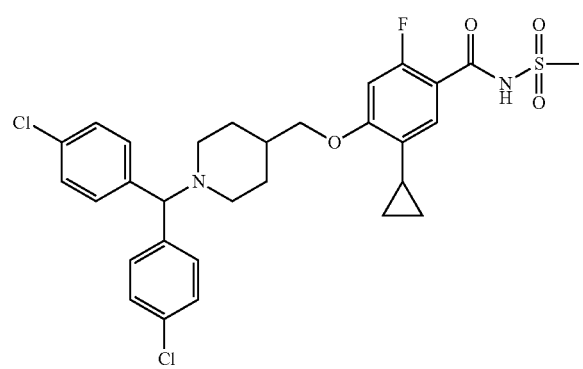 [SMILES: CS(=O)(=O)NC(=O)c1cc(C2CC2)c(OCC2CCN(C(c3ccc(Cl)cc3)c3ccc(Cl)cc3)CC2)cc1F]

Step 1. Preparation of tert-butyl 4-((1-(bis(4-chlorophenyl)methyl)piperidin-4-yl)methoxy)-5-cyclopropyl-2-fluorobenzoate

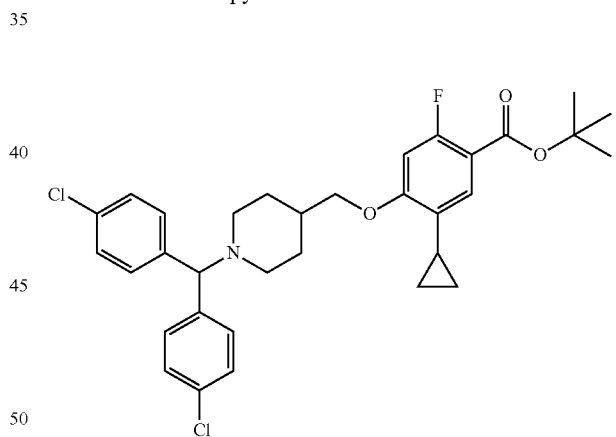

Following the procedure as described in Example 346 step 5 and making non-critical variations as required to replace tert-butyl 5-cyclopropyl-2-fluoro-4-((4-fluoropiperidin-4-yl)methoxy)benzoate with tert-butyl 5-cyclopropyl-2-fluoro-4-(piperidin-4-ylmethoxy)benzoate, and to replace 1-chloro-3-(chloromethyl)-2-fluoro-5-(trifluoromethyl)benzene with 4,4'-(bromomethylene)bis(chlorobenzene), the title compound was obtained as a colorless foam (0.59 g, 95%): $^1$H NMR (300 MHz, CDCl$_3$) δ 7.37-7.21 (m, 9H), 6.48 (d, J=12.7 Hz, 1H), 4.23 (s, 1H), 3.81 (d, J=6.3 Hz, 2H), 2.87 (d, J=12.7 Hz, 1H), 1.99-1.74 (m, 6H), 1.54 (s; 9H), 1.54-1.38 (m, 2H), 0.88-0.81 (m, 2H), 0.62-0.57 (m 2H); MS (ES+) m/z 554.2, 552.2 (M+1).

Step 2. Preparation of 4-((1-(bis(4-chlorophenyl)methyl)piperidin-4-yl)methoxy)-5-cyclopropyl-2-fluorobenzoic acid

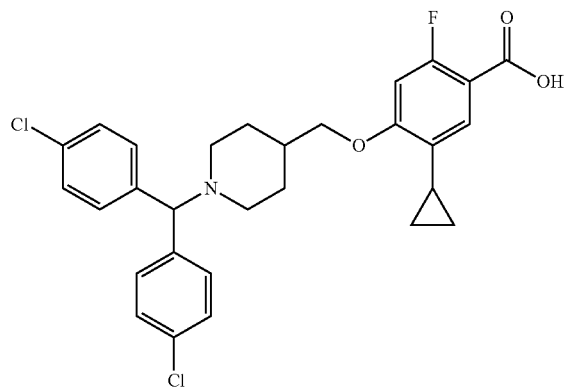 [SMILES: O=C(O)c1cc(C2CC2)c(OCC2CCN(C(c3ccc(Cl)cc3)c3ccc(Cl)cc3)CC2)cc1F]

Following the procedure as described in Example 346 step 6, and making non-critical variations as required to replace tert-butyl 4-((4-(tert-butoxycarbonyl)-2-cyclopropyl-5-fluorophenoxy)methyl)-4-fluoropiperidine-1-carboxylate with tert-butyl 4-((1-(bis(4-chlorophenyl)methyl)piperidin-4-yl)methoxy)-5-cyclopropyl-2-fluorobenzoate, the title compound was obtained, as a gum (0.25 g, 95%). Which was used directly in the next step without further purification: MS (ES−) m/z 438.1, 437.0 (M+1).

Step 3. Preparation of 4-((1-(bis(4-chlorophenyl)methyl)piperidin-4-yl)methoxy)-5-cyclopropyl-2-fluoro-N-(methylsulfonyl)benzamide

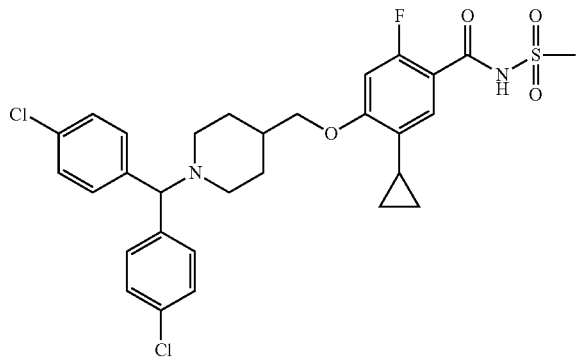 [SMILES: CS(=O)(=O)NC(=O)c1cc(C2CC2)c(OCC2CCN(C(c3ccc(Cl)cc3)c3ccc(Cl)cc3)CC2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-((1-(bis(4-chlorophenyl)methyl)piperidin-4-yl)methoxy)-5-cyclopropyl-2-fluorobenzoic acid, the title compound was obtained as a colorless solid (0.06 g, 36%): $^1$H NMR (300 Mhz, DMSO-$d_6$+1% $D_2O$) δ7.64-7.61 (m, 4H), 7.55-7.52 (m, 4H), 7.09 (d, J=8.3 Hz, 1H), 6.92 (d, =12.9 Hz, 1H), 5.53 (s, 1H), 3.97-3.96 (m, 2H), 3.30 (s, 3H), 3.25-3.18 (m, 2H), 3.08-2.96 (m, 2H), 2.18-2.06 (m, 1H), 2.04-1.90 (m, 3H), 1.71-1.55 (m, 2H), 0.89-0.83 (m, 2H), 0.64-0.59 (m, 2H) (acidic protons were not observed); MS (ES+) m/z 604.9, 606.9 (M+1).

Example 363

Synthesis of 4-((1-(bis(4-fluorophenyl)methyl)piperidin-4-yl)methoxy)-5-cyclopropyl-N-(cyclopropylsulfonyl)-2-fluorobenzamide, trifluoroacetic acid salt

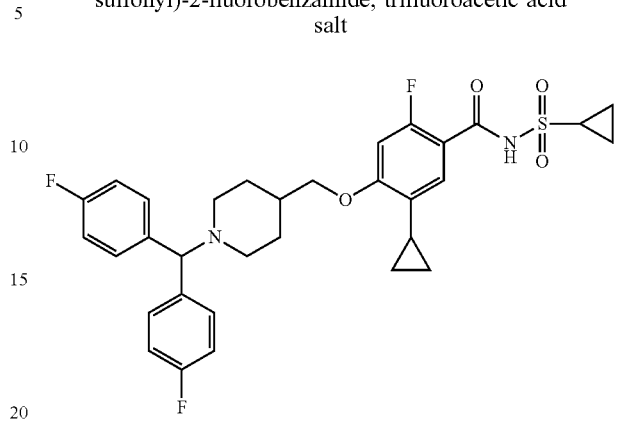

Step 1. Preparation of tert-butyl 4-((1-(bis(4-fluorophenyl)methyl)piperidin-4-yl)methoxy)-5-cyclopropyl-2-fluorobenzoate

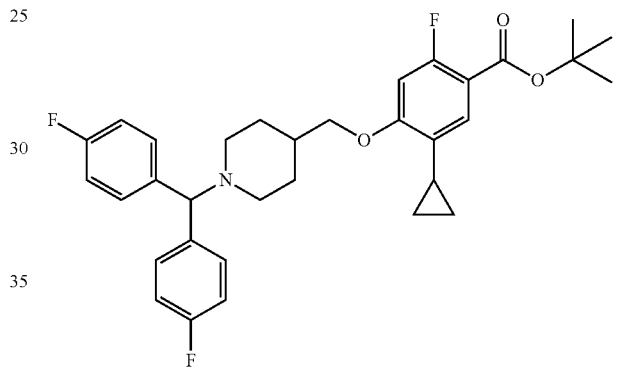

Following the procedure as described in Example 346 step 5 and making non-critical variations as required to replace tert-butyl 5-cyclopropyl-2-fluoro-4-((4-fluoropiperidin-4-yl)methoxy)benzoate with tert-butyl 5-cyclopropyl-2-fluoro-4-(piperidin-4-ylmethoxy)benzoate, and to replace 1-chloro-3-(chloromethyl)-2-fluoro-5-(trifluoromethyl)benzene with 4,4'-(bromomethylene)bis(fluorobenzene), the title compound was obtained as a colorless foam (0.59 g, 95%); MS (ES+) m/z 554.2, 552.2 (M+1).

Step 2. Preparation of 4-((1-(bis(4-fluorophenyl)methyl)piperidin-4-yl)methoxy)-5-cyclopropyl-2-fluorobenzoic acid

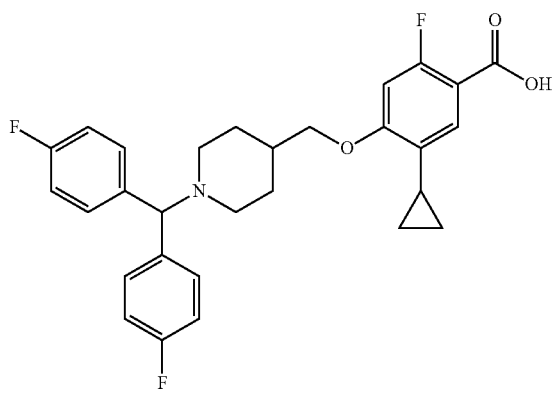 [SMILES: O=C(O)c1cc(C2CC2)c(OCC2CCN(C(c3ccc(F)cc3)c3ccc(F)cc3)CC2)cc1F]

Following the procedure as described in Example 346 step 6, and making non-critical variations as required to replace tert-butyl 4-((4-(tert-butoxycarbonyl)-2-cyclopropyl-5-fluorophenoxy)methyl)-4-fluoropiperidine-1-carboxylate with tert-butyl 4-((1-(bis(4-fluorophenyl)methyl)piperidin-4-yl)methoxy)-5-cyclopropyl-2-fluorobenzoate, the title compound was obtained as a gum (0.57 g, quant. yield). Which was used directly in the next step without further purification: MS(ES−) m/z 493.1, 492.1 (M−1).

Step 3. Preparation of 4-((1-(bis(4-fluorophenyl)methyl)piperidin-4-yl)methoxy)-5-cyclopropyl-N-(cyclopropylsulfonyl)-2-fluorobenzamide, trifluoroacetic acid salt

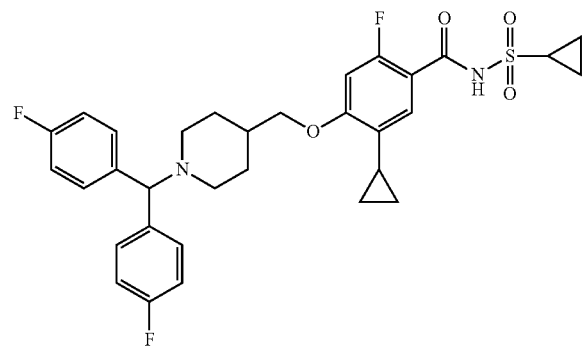 [SMILES: O=C(NS(=O)(=O)C1CC1)c1cc(C2CC2)c(OCC2CCN(C(c3ccc(F)cc3)c3ccc(F)cc3)CC2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-((1-(bis(4-fluorophenyl)methyl)piperidin-4-yl)methoxy)-5-cyclopropyl-2-fluorobenzoic acid, and to replace methanesulfonamide with cyclopropylsulfonamide, the title compound was obtained as a colorless solid (0.02 g, 5%): $^1$H NMR (300 MHz, DMSO-$d_6$) δ 11.82 (br s, 1H), 9.99 (br s, 1H), 7.70-7.62 (m, 2H), 7.38-7.27 (m, 2H), 7.12-6.94 (m, 4H), 6.84-6.72 (m, 2H), 4.02-3.99 (m, 4H), 3.30-3.18 (m, 2H), 3.08-3.00 (m, 1H), 2.07-1.93 (m, 3H), 1.87-1.78 (m, 2H), 1.17-1.04 (m, 4H), 0.87-0.77 (m, 2H), 0.66-0.61 (m, 2H): MS(ES+) m/z 600.1, 599.2 (M+1).

Example 364

Synthesis of 5-cyclopropyl-N-(cyclopropylsulfonyl)-2-fluoro-4-((1-((3-(trifluoromethyl)pyridin-2-yl)methyl)piperidin-4-yl)methoxy)benzamide, trifluoroacetic acid salt

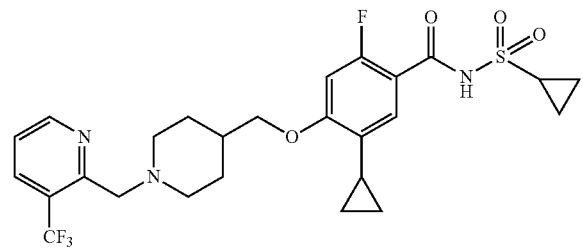 [SMILES: O=C(NS(=O)(=O)C1CC1)c1cc(C2CC2)c(OCC2CCN(Cc3ncccc3C(F)(F)F)CC2)cc1F]

Step 1. Preparation of tert-butyl 5-cyclopropyl-2-fluoro-4-((1-((3-(trifluoromethyl)pyridin-2-yl)methyl)piperidin-4-yl)methoxy)benzoate

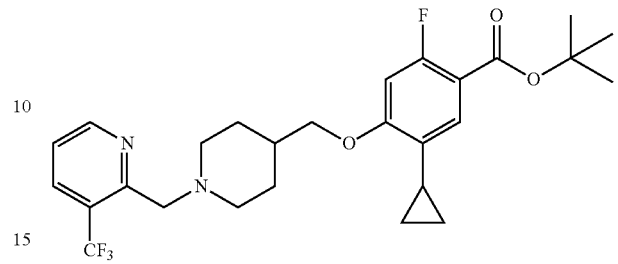

Following the procedure as described in Example 346 step 5 and making non-critical variations as required to replace tert-butyl 5-cyclopropyl-2-fluoro-4-((4-fluoropiperidin-4-yl)methoxy)benzoate with tert-butyl 5-cyclopropyl-2-fluoro-4-(piperidin-4-ylmethoxy)benzoate, and to replace 1-chloro-3-(chloromethyl)-2-fluoro-5-(trifluoromethyl)benzene with 2-(chloromethyl)-3-(trifluoromethyl)pyridine, the title compound was obtained as a colorless foam (0.55 g, 95%): MS(ES+) m/z 410.1, 509.0 (M+1).

Step 2. Preparation of 5-cyclopropyl-2-fluoro-4-((1-((3-(trifluoromethyl)pyridin-2-yl)methyl)piperidin-4-yl)methoxy)benzoic acid

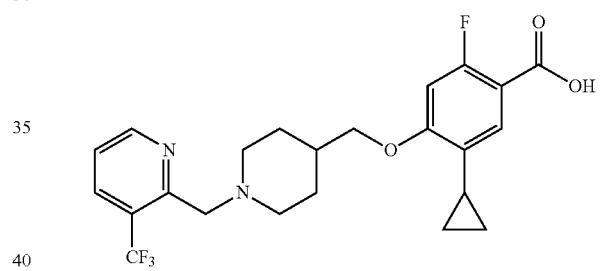

Following the procedure as described in Example 346 step 6, and making non-critical variations as required to replace tert-butyl 4-((4-(tert-butoxycarbonyl)-2-cyclopropyl-5-fluorophenoxy)methyl)-4-fluoropiperidine-1-carboxylate with tert-butyl 5-cyclopropyl-2-fluoro-4-((1-((3-(trifluoromethyl)pyridin-2-yl)methyl)piperidin-4-yl)methoxy)benzoate, the title compound was obtained as a gum (0.49 g, quant. yield). Which was used directly in the next step without further purification: MS(ES−) m/z 493.1, 492.1 (M−1).

Step 3. Preparation of 5-cyclopropyl-N-(cyclopropylsulfonyl)-2-fluoro-4-((1-((3-(trifluoromethyl)pyridin-2-yl)methyl)piperidin-4-yl)methoxy)benzamide, trifluoroacetic acid salt

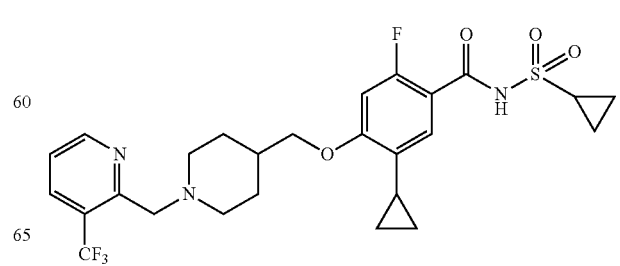

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-((3-(trifluoromethyl)pyridin-2-yl)methyl)piperidin-4-yl)methoxy) benzoic acid, and to replace methanesulfonamide with cyclopropylsulfonamide, the title compound was obtained as a colorless solid (0.07 g, 24%); ¹H NMR (300 MHz, DMSO-d₆) δ 11.83 (br s, 1H), 9.49 (br s, 1H), 8.95 (d, J=4.7 Hz, 1H), 8.32 (d, J=8.2 Hz, 1H), 7.71 (dd, J=7.9, 4.9 Hz, 1H), 7.10 (d, J=8.3H) 1H), 6.97 (d, J=12.9 Hz, 1H), 4.69 (s, 2H), 3.97 (d, J=5.2 Hz, 2H) 1H), 3.64-3.39 (m, 2H), 3.30-3.18 (m, 2H), 3.08-3.00 (m, 1H), 2.07-1.93 (m, 3H), 1.87-1.78 (m, 2H), 1.19-1.05 (m, 4H), 0.92-0.82 (m, 2H), 0.68-0.63 (m, 2H); MS(ES+) m/z 557.1, 556.1 (M+1).

Example 365

Synthesis of 5-cyclopropyl-2-fluoro-N-(methylsulfonyl)-4-((1-((3-(trifluoromethyl)pyridin-2-yl)methyl)piperidin-4-yl)methoxy)benzamide, trifluoroacetic acid salt

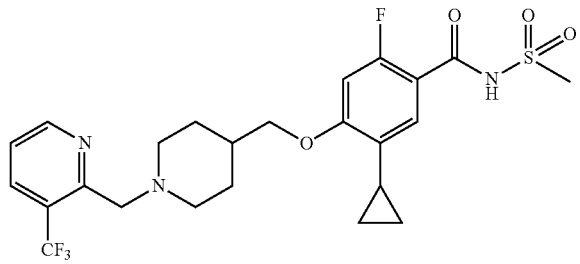 [SMILES: CS(=O)(=O)NC(=O)c1cc(C2CC2)c(OCC2CCN(Cc3ncccc3C(F)(F)F)CC2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-((3-(trifluoromethyl)pyridin-2-yl)methyl)piperidin-4-yl)methoxy) benzoic acid, and to replace methanesulfonamide with cyclopropylsulfonamide, the title compound was obtained as a colorless solid (0.06 g, 23%): ¹H NMR (300 MHz, DMSO-d₆) δ 11.89 (br s, 1H), 9.98 (b rs, 1H), 8.95 (d, J=4.8 Hz, 1H), 8.32 (d, J=7.7 Hz, 1H), 7.71 (dd, J=8.0, 4.9 Hz, 1H), 7.11 (d, J=8.3 Hz, 1H), 6.97 (d, J=12.9 Hz, 1H), 4.69 (s, 2H), 3.97 (d, J=5.1 Hz, 2H) 1H), 3.60-3.48 (m, 2H), 3.30-3.18 (m, 3H), 3.08-3.00 (m, 1H), 2.07-1.93 (m, 3H), 1.87-1.78 (m, 2H), 1.19-1.05 (m, 4H), 0.92-0.82 (m, 2H), 0.68-0.63 (m, 2H): MS(ES+) m/z 531.0, 530.0 (M+1).

Example 366

Synthesis of 4-((1-((4-bromo-5-chloro-2-fluorophenyl)sulfonyl)piperidin-4-yl)methoxy)-5-cyclopropyl-2-fluoro-N-(methylsulfonyl)benzamide

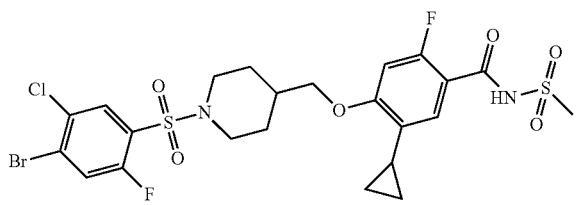 [SMILES: CS(=O)(=O)NC(=O)c1cc(C2CC2)c(OCC2CCN(S(=O)(=O)c3cc(Cl)c(Br)cc3F)CC2)cc1F]

Step 1. Preparation of 4-((1-((4-bromo-5-chloro-2-fluorophenyl)sulfonyl)piperidin-4-yl)methoxy)-5-cyclopropyl-2-fluorobenzoic acid

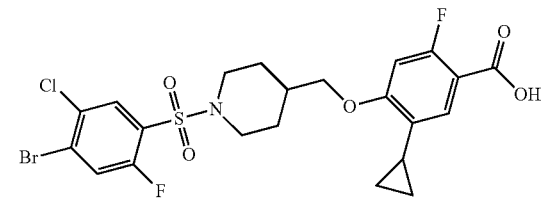 [SMILES: O=C(O)c1cc(C2CC2)c(OCC2CCN(S(=O)(=O)c3cc(Cl)c(Br)cc3F)CC2)cc1F]

To a mixture of tert-butyl 5-cyclopropyl-2-fluoro-4-(piperidin-4-ylmethoxy)benzoate (0.50 g, 1.43 mmol) and triethylamine (0.4 mL) in anhydrous tetrahydrofuran (5 mL) was added 4-bromo-5-chloro-2-fluorobenzene-1-sulfonyl chloride (0.66 g, 2.15 mmol). After stirring at ambient temperature for 16 hours, the reaction mixture was diluted with ethyl acetate (5 mL), washed with 1M aqueous hydrochloric acid solution (3×2 mL), dried over anhydrous sodium sulfate and filtered. The filtrate was concentrated in vacuo and the residue was undissolved in dichloromethane (5 mL) and trifluoroacetic acid (2 mL). The reaction mixture was stirred at ambient temperature for 3 hours and concentrated in vacuo. The residue was triturated with ether to afford the title compound as a colorless solid (0.30 g, 37%). Which was used directly in the next step without any further purification: MS(ES+) m/z 567.1, 565.1 (M+1).

Step 2. Preparation of 4-((1-((4-bromo-5-chloro-2-fluorophenyl)sulfonyl)piperidin-4-yl)methoxy)-5-cyclopropyl-2-fluoro-N-(methylsulfonyl)

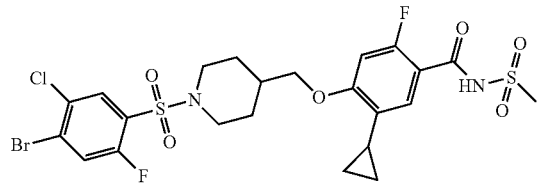 [SMILES: CS(=O)(=O)NC(=O)c1cc(C2CC2)c(OCC2CCN(S(=O)(=O)c3cc(Cl)c(Br)cc3F)CC2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-((1-((4-bromo-5-chloro-2-fluorophenyl)sulfonyl)piperidin-4-yl)methoxy)-5-cyclopropyl-2-fluorobenzoic acid, the title compound was obtained as a colorless solid (0.06 g, 36%): $^1$H NMR (300 MHz, CDCl$_3$) δ 8.70 (d, J=15.0 Hz, 1H), 7.93 (d, J=5.0 Hz, 1H), 7.62-7.49 (m, 2H), 6.56 (d, J=15.0 Hz, 1H), 4.03-3.93 (m, 2H), 3.93-3.86 (m, 2H), 3.41 (s, 3H), 2.73-2.60 (m, 2H), 2.03-1.79 (m, 4H), 1.48-1.27 (m, 2H), 0.95-0.81 (m, 2H), 0.71-0.59 (m, 2H); MS (ES+) m/z 645.0, 643.0 (M+1).

Example 367

Synthesis of 4-((1-((4-bromo-5-chloro-2-fluorophenyl)sulfonyl)piperidin-4-yl)methoxy)-5-cyclopropyl-N-(cyclopropylsulfonyl)-2-fluorobenzamide

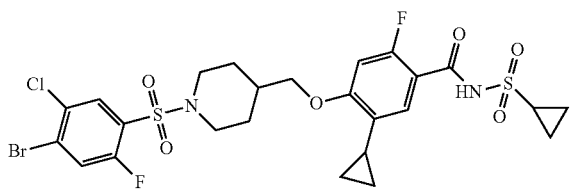 [SMILES: O=C(NS(=O)(=O)C1CC1)c1cc(C2CC2)c(OCC2CCN(S(=O)(=O)c3cc(Cl)c(Br)cc3F)CC2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-((1-((4-bromo-5-chloro-2-fluorophenyl)sulfonyl)piperidin-4-yl)methoxy)-5-cyclopropyl-2-fluorobenzoic acid, and to replace methanesulfonamide with cyclopropylsulfonamide, the title compound was obtained as a colorless solid (0.01 g, 6%): $^1$H NMR (300 MHz, DMSO-d$_6$) δ 11.82, (brs, 1H), 8.16 (d, J=12.0 Hz, 1H), 7.91 (d, J=12.0 Hz, 1H), 7.12 (d, J=6.0 Hz, 1H), 6.94 (d, J=6.0 Hz, 1H), 4.02-3.91 (m, 2H), 3.80-3.68 (m, 2H), 3.13-2.99 (m, 1H), 2.75-2.60 (m, 2H), 2.05-1.79 (m, 2H), 1.44-1.18 (m, 4H), 1.17-1.03 (m, 4H), 0.93-0.79 (m, 2H), 0.71-0.6 (m, 2H); MS(ES+) m/z 671.0, 669.0 (M+1).

Example 368

Synthesis of 4-((1-((4-bromo-3-fluorophenyl)sulfonyl)piperidin-4-yl)methoxy)-5-cyclopropyl-2-fluoro-N-(methylsulfonyl)benzamide

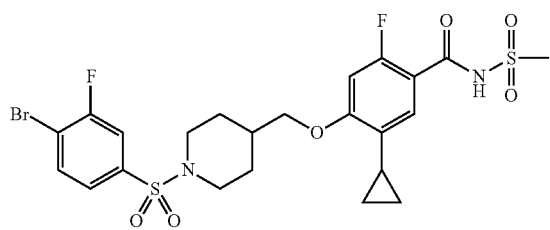 [SMILES: CS(=O)(=O)NC(=O)c1cc(C2CC2)c(OCC2CCN(S(=O)(=O)c3ccc(Br)c(F)c3)CC2)cc1F]

Step 1. Preparation of 4-((1-((4-bromo-3-fluorophenyl)sulfonyl)piperidin-4-yl)methoxy)-5-cyclopropyl-2-fluorobenzoic acid

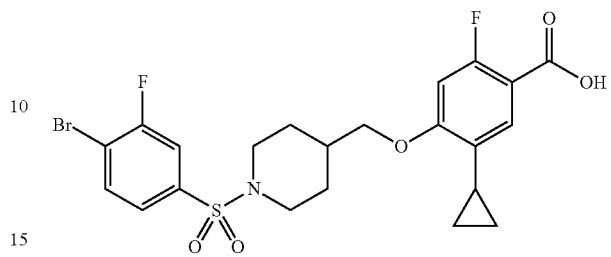

Following the procedure as described in Example 366 step 1 and making non-critical variations as required to replace 4-bromo-5-chloro-2-fluorobenzene-1-sulfonyl chloride with 4-bromo-3-fluorobenzene-1-sulfonyl chloride, the title compound was obtained as a colorless solid (0.30 g, 75%); MS(ES−) m/z 528.1, 526.1 (M−1).

Step 2. Preparation of 4-((1-((4-bromo-3-fluorophenyl)sulfonyl)piperidin-4-yl)methoxy)-5-cyclopropyl-2-fluoro-N-(methylsulfonyl)benzamide

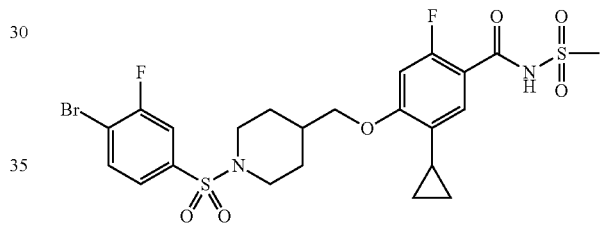

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-((1-((4-bromo-3-fluorophenyl)sulfonyl)piperidin-4-yl)methoxy)-5-cyclopropyl-2-fluorobenzoic acid, the title compound was obtained as a colorless solid (0.05 g, 30%): $^1$H NMR (300 MHz, DMSO-d$_6$) δ11.85 (s, 1H), 7.98 (dd, J=8.3, 6.8 Hz, 1H), 7.72 (dd, J=8.2, 1.9 Hz, 1H), 7.49 (d, J=8.3, 1.8 Hz, 1H), 7.09 (d, J=8.3 Hz, 1H), 6.88 (d, J=12.9 Hz, 1H), 3.93 (d, J=5.9 Hz, 2H), 3.74 (d, J=12.2 Hz, 2H), 3.29 (s, 3H), 2.40-2.32 (m, 2H), 1.99-1.89 (m, 2H), 1.89-1.76 (m, 2H), 1.42-1.30 (m, 2H), 0.89-0.80 (m, 2H), 0.64-0.59 (m, 2H); MS(ES+) m/z 609.1, 607.0 (M+1).

Example 369

Synthesis of 4-((1-((4-bromo-3-fluorophenyl)sulfonyl)piperidin-4-yl)methoxy)-5-cyclopropyl-N-(cyclopropylsulfonyl)-2-fluorobenzamide

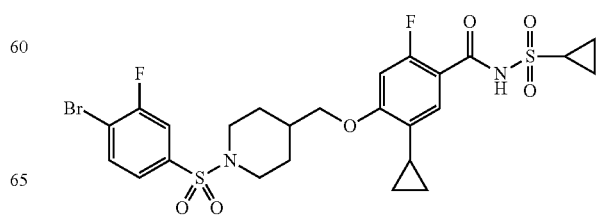

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-((1-((4-bromo-3-fluorophenyl)sulfonyl)piperidin-4-yl)methoxy)-5-cyclopropyl-2-fluorobenzoic acid, and to replace methanesulfonamide with cyclopropylsulfonamide, the title compound was obtained as a colorless solid (0.08 g, 46%): $^1$H NMR (300 MHz, DMSO-$d_6$) δ11.79 (br s, 1H), 7.98 (dd, J=8.3, 6.4 Hz, 1H), 7.72 (dd, J=8.2, 1.9 Hz, 1H), 7.49 (d, J=8.3, 1.8 Hz, 1H), 7.08 (d, J=8.3 Hz, 1H), 6.89 (d, J=12.9 Hz, 1H), 3.90 (d, J=5.4 Hz, 2H), 3.70 (d, J=11.4 Hz, 2H), 3.07-2.98 (m, 1H), 2.36 (t, J=10.9, 10.9, 2H), 1.98-1.87 (m, 1H), 1.43-1.27 (m, 2H), 1.11-1.04 (m, 3H), 0.88-0.78 (m, 4H), 0.64-0.59 (m, 2H); MS(ES+) m/z 635.1, 633.1 (M+1).

Example 370

Synthesis of 5-cyclopropyl-2-fluoro-N-(methylsulfonyl)-4-((1-((2-(trifluoromethyl)phenyl)sulfonyl)piperidin-4-yl)methoxy)benzamide

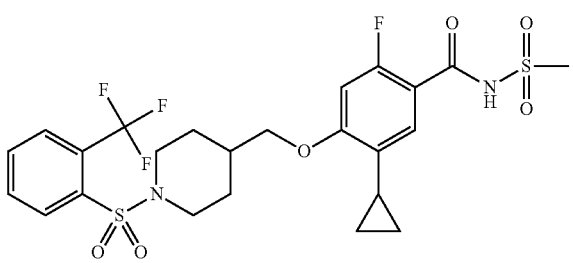 [SMILES: CS(=O)(=O)NC(=O)c1cc(C2CC2)c(OCC2CCN(S(=O)(=O)c3ccccc3C(F)(F)F)CC2)cc1F]

Step 1. Preparation of 5-cyclopropyl-2-fluoro-4-((1-((2-(trifluoromethyl)phenyl)sulfonyl)piperidin-4-yl)methoxy)benzoic acid

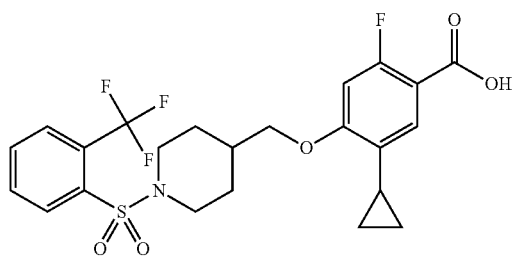 [SMILES: O=C(O)c1cc(C2CC2)c(OCC2CCN(S(=O)(=O)c3ccccc3C(F)(F)F)CC2)cc1F]

Following the procedure as described in Example 366 step 1 and making non-critical variations as required to replace 4-bromo-5-chloro-2-fluorobenzene-1-sulfonyl chloride with 2-(trifluoromethyl)benzene-1-sulfonyl chloride, the title compound (0.24 g, 59% yield) was obtained as a colorless solid: MS(ES−) m/z 500.1 (M−1).

Step 2. Preparation of 5-cyclopropyl-2-fluoro-N-(methylsulfonyl)-4-((1-((2-(trifluoromethyl)phenyl)sulfonyl)piperidin-4-yl)methoxy)

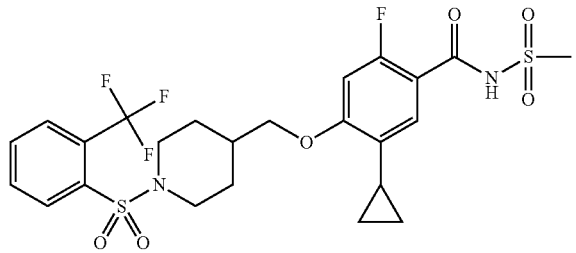 [SMILES: CS(=O)(=O)NC(=O)c1cc(C2CC2)c(OCC2CCN(S(=O)(=O)c3ccccc3C(F)(F)F)CC2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-((2-(trifluoromethyl)phenyl)sulfonyl)piperidin-4-yl)methoxy)benzoic acid, the title compound was obtained as a colorless solid (0.06 g, 36%): $^1$H NMR (300 MHz, DMSO-$d_6$) δ11.86 (br s, 1H), 8.05-7.98 (m, 2H), 7.98-7.84 (m, 2H), 7.09 (d, J=8.3 Hz, 1H), 6.91 (d, J=13.0 Hz, 1H), 3.93 (d, J=5.9 Hz, 2H), 3.74 (d, J=12.2 Hz, 2H), 3.28 (s, 3H), 2.81-2.69 (m, 2H), 1.98-1.89 (m, 2H), 1.85-1.76 (m, 2H), 1.42-1.27 (m, 2H), 0.87-0.80 (m, 2H), 0.65-0.60 (m, 2H): MS(ES+) m/z 579.1 (M+1).

Example 371

Synthesis of 5-cyclopropyl-N-(cyclopropylsulfonyl)-2-fluoro-4-((1-((2-(trifluoromethyl)phenyl)sulfonyl)piperidin-4-yl)methoxy)benzamide

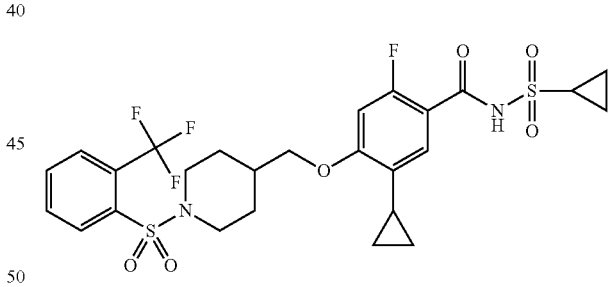

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-((2-(trifluoromethyl)phenyl)sulfonyl)piperidin-4-yl)methoxy)benzoic acid, and to replace methanesulfonamide with cyclopropylsulfonamide, the title compound was obtained as a colorless solid (0.10 g, 66%): $^1$H NMR (300 MHz, DMSO-$d_6$) δ11.80 (brs, 1H), 8.05-7.98 (m, 2H), 7.90-7.87 (m, 2H), 7.09 (d, J=8.3 Hz, 1H), 6.91 (d, J=13.0 Hz, 1H), 6.75 (brs, 1H), 3.94 (d, J=5.9 Hz, 2H), 3.70 (d, J=11.1 Hz, 2H), 3.74 (d, J=12.4 Hz, 2H), 3.07-2.91 (m, 1H), 2.82-2.71 (m, 2H), 2.35-1.89 (m, 2H), 1.89-1.77 (m, 2H), 1.42-1.26 (m, 2H), 1.11-1.02 (m, 3H), 0.89-0.78 (m, 4H), 0.66-0.58 (m, 2H); MS(ES+) m/z 605.2, 507.1 (M+1).

Example 372

Synthesis of 5-cyclopropyl-2-fluoro-N-(methylsulfonyl)-4-((1-((4-(trifluoromethyl)phenyl)sulfonyl)piperidin-4-yl)methoxy)benzamide

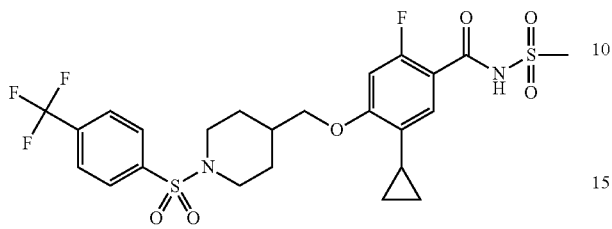

Step 1. Preparation of 5-cyclopropyl-2-fluoro-4-((1-((4-(trifluoromethyl)phenyl)sulfonyl)piperidin-4-yl)methoxy)benzoic acid

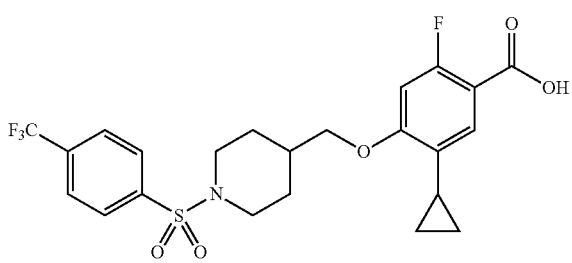 [SMILES: O=C(O)c1cc(C2CC2)c(OCC2CCN(S(=O)(=O)c3ccc(C(F)(F)F)cc3)CC2)cc1F]

Following the procedure as described in Example 366 step 1 and making non-critical variations as required to replace 4-bromo-5-chloro-2-fluorobenzene-1-sulfonyl chloride with 4-(trifluoromethyl)benzene-1-sulfonyl chloride, the title compound was obtained as a colorless solid (0.27 g, 66%): MS(ES+) m/z 502.1 (M+1).

Step 2. Preparation of 5-cyclopropyl-2-fluoro-N-(methylsulfonyl)-4-((1-((4-(trifluoromethyl)phenyl)sulfonyl)piperidin-4-yl)methoxy)benzamide

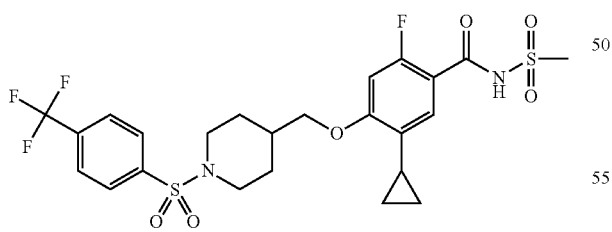

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-((4-(trifluoromethyl)phenyl)sulfonyl)piperidin-4-yl)methoxy)benzoic acid, the title compound was obtained as a colorless solid (0.05 g, 29%): $^1$H NMR (300 MHz, DMSO-$d_6$) δ11.85 (br s, 1H), 8.01. (d, J=8.5 Hz, 2H), 7.93 (d, J=8.4 Hz, 2H), 7.08 (d, J=8.3 Hz, 1H), 6.89 (d, J=13.0 Hz, 1H), 3.89 (d, J=5.4 Hz, 2H), 3.69 (d, J=11.4 Hz, 2H), 3.29 (s, 3H), 2.38-2.27 (m, 2H), 1.98-1.88 (m, 1H), 1.87-1.74 (m, 3H), 1.44-1.26 (m, 2H), 0.86-0.78 (m, 2H), 0.64-0.59 (m, 2H); MS(ES+) m/z 579.1 (M+1).

Example 373

Synthesis of 5-cyclopropyl-N-(cyclopropylsulfonyl)-2-fluoro-4-((1-((4-(trifluoromethyl)phenyl)sulfonyl)piperidin-4-yl)methoxy)benzamide

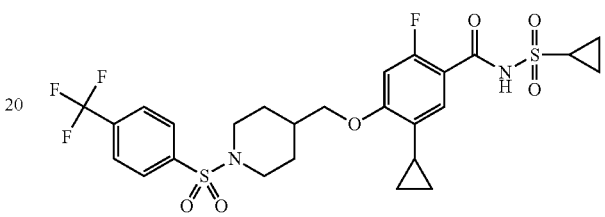

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-((4-(trifluoromethyl)phenyl)sulfonyl)piperidin-4-yl)methoxy)benzoic acid, and to replace methanesulfonamide with cyclopropylsulfonamide, the title compound was obtained as a colorless solid (0.09 g, 58%): $^1$H NMR (300 MHz, DMSO-$d_6$) δ11.78 (br s, 1H), 8.00 (d, J=8.6 Hz, 2H), 7.94 (d, J=8.4 Hz, 2H), 7.08 (d, J=8.3 Hz, 1H), 6.89 (d, J=12.9 Hz, 1H), 6.75 (s, 1H), 3.89 (d, J=5.4 Hz, 2H), 3.70 (d, J=11.1 Hz, 2H), 3.07-2.98 (m, 1H), 2.42-2.26 (m, 2H), 1.98-1.89 (m, 1H), 1.88-1.72 (m, 2H), 1.44-1.28 (m, 2H), 1.11-1.02 (m, 3H), 0.89-0.78 (m, 4H), 0.67-0.58 (m, 2H); MS(ES+) m/z 605.2, 607.1 (M+1).

Example 374

Synthesis of 5-cyclopropyl-2-fluoro-N-(methylsulfonyl)-4-((1-((3-(trifluoromethyl)phenyl)sulfonyl)piperidin-4-yl)methoxy)benzamide

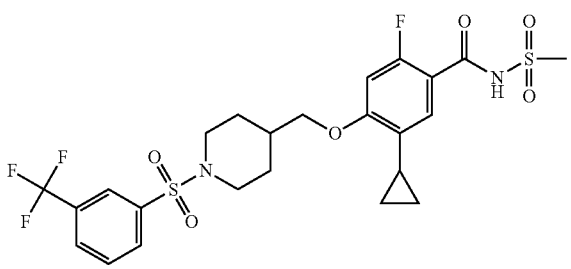 [SMILES: CS(=O)(=O)NC(=O)c1cc(C2CC2)c(OCC2CCN(S(=O)(=O)c3cccc(C(F)(F)F)c3)CC2)cc1F]

Step 1. Preparation of 5-cyclopropyl-2-fluoro-4-((1-((3-(trifluoromethyl)phenyl)sulfonyl)piperidin-4-yl)methoxy)benzoic acid

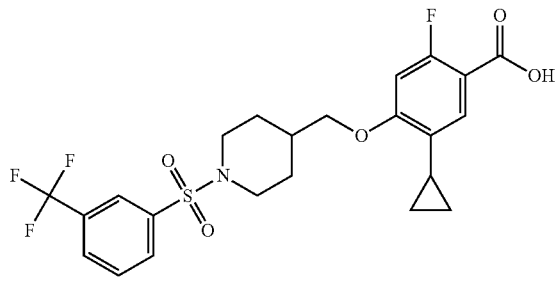 [SMILES: O=C(O)c1cc(C2CC2)c(OCC2CCN(S(=O)(=O)c3cccc(C(F)(F)F)c3)CC2)cc1F]

Following the procedure as described in Example 366 step 1 and making non-critical variations as required to replace 4-bromo-5-chloro-2-fluorobenzene-1-sulfonyl chloride with 3-(trifluoromethyl)benzene-1-sulfonyl chloride, the title compound was obtained as a colorless solid (0.21 g, 52%): MS(ES−) m/z 500.1 (M−1).

Step 2. Preparation of 5-cyclopropyl-2-fluoro-N-(methylsulfonyl)-4-((1-((3-(trifluoromethyl)phenyl)sulfonyl)piperidin-4-yl)methoxy)benzamide

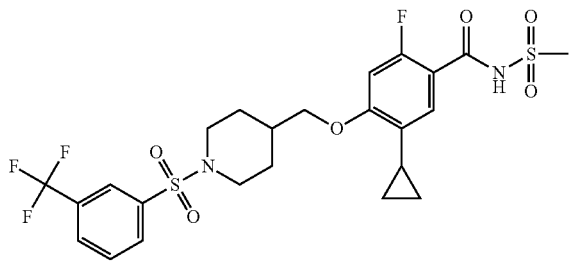 [SMILES: CS(=O)(=O)NC(=O)c1cc(C2CC2)c(OCC2CCN(S(=O)(=O)c3cccc(C(F)(F)F)c3)CC2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-((3-(trifluoromethyl)phenyl)sulfonyl)piperidin-4-yl)methoxy)benzoic acid, the title compound was obtained as a colorless solid (0.08 g, 50%): $^1$H NMR (300 MHz, DMSO-$d_6$) δ 11.89 (br s, 1H), 8.18-8.06 (m, 2H), 8.00-7.88 (m, 2H), 7.11 (d, J=9.0 Hz, 1H), 6.92 (d, J=15.0 Hz, 1H), 3.97-3.88 (m, 2H), 3.82-3.70 (m, 2H), 3.33 (s, 3H), 2.41-2.28 (m, 2H), 2.02-1.91 (m, 1H), 1.88-1.75 (m, 3H), 1.49-1.30 (m, 2H), 0.9-0.8 (m, 2H), 0.7-0.6 (m, 2H): MS(ES−) m/z 577.2 (M−1).

Example 375

Synthesis of 5-cyclopropyl-N-(cyclopropylsulfonyl)-2-fluoro-4-((1-((3-(trifluoromethyl)phenyl)sulfonyl)piperidin-4-yl)methoxy)benzamide

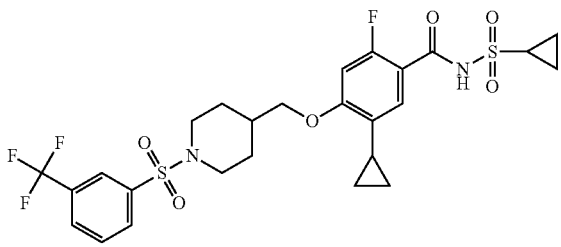 [SMILES: O=C(NS(=O)(=O)C1CC1)c1cc(C2CC2)c(OCC2CCN(S(=O)(=O)c3cccc(C(F)(F)F)c3)CC2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-((3-(trifluoromethyl)phenyl)sulfonylpiperidin-4-yl)methoxy) benzoic acid, and to replace methanesulfonamide with cyclopropylsulfonamide, the title compound was obtained as a colorless solid (0.04 g, 70%); $^1$H NMR (300 MHz, DMSO-$d_6$) δ 11.82 (br s, 1H), 8.18-8.04 (m, 3H), 8.00-7.88 (m, 2H), 7.10 (d, J=9.0 Hz, 1H), 6.91 (d, J=15.0 Hz, 1H), 3.98-3.87 (m, 2H), 3.82-3.70 (m, 2H), 3.12-3.00 (m, 1H), 2.42-2.29 (m, 2H), 2.01-1.91 (m, 1H), 1.91-1.76 (m, 2H), 1.48-1.30 (m, 2H), 1.28-1.04 (m, 4H), 0.93-0.81 (m, 2H), 0.70-0.60 (m, 2H); MS(ES+) m/z 605.2 (M+1).

Example 376

Synthesis of 5-cyclopropyl-2-fluoro-N-(methylsulfonyl)-4-((1-((tetrahydro-2H-pyran-4-yl)sulfonyl)piperidin-4-yl)methoxy)benzamide

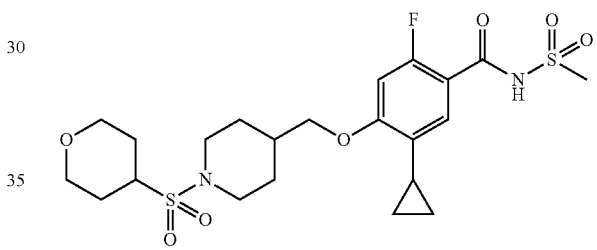

Step 1. Preparation of 5-cyclopropyl-2-fluoro-4-((1-((tetrahydro-2H-pyran-4-yl)sulfonyl)piperidin-4-yl)methoxy)benzoic acid

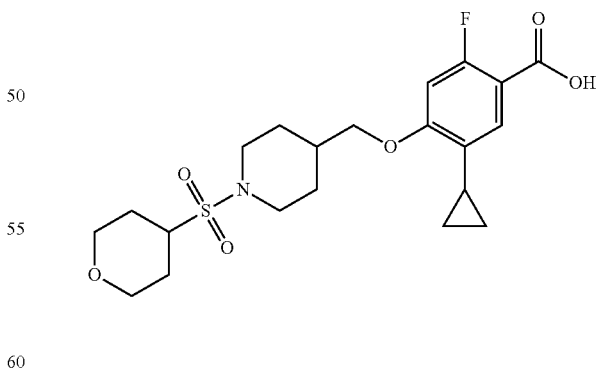

Following the procedure as described in Example 366 step 1 and making non-critical variations as required to replace 4-bromo-5-chloro-2-fluorobenzene-1-sulfonyl chloride with tetrahydro-2H-pyran-4-sulfonyl chloride, the title compound (0.10 g, 26% yield) was obtained as a colorless gum: MS(ES−) m/z 400.2 (M−1).

Step 2. Preparation of 5-cyclopropyl-2-fluoro-N-(methylsulfonyl)-4-((1-((tetrahydro-2H-pyran-4-yl)sulfonyl)piperidin-4-yl)methoxy)benzamide

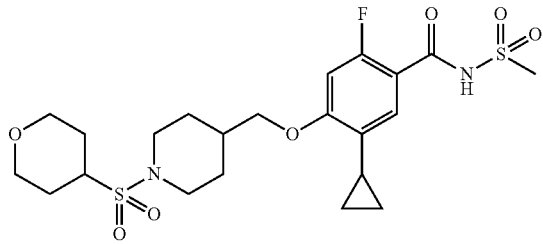 [SMILES: CS(=O)(=O)NC(=O)c1cc(C2CC2)c(OCC2CCN(S(=O)(=O)C3CCOCC3)CC2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-((tetrahydro-2H-pyran-4-yl)sulfonyl)piperidin-4-yl)methoxy)benzoic acid, the title compound was obtained as a colorless solid (0.05 g, 76%): $^{1}$H NMR (300 MHz, DMSO-$d_6$) δ11.87 (br s, 1H), 7.10 (d, J=8.3 Hz, 1H), 6.93 (d, J=13.0 Hz, 1H), 3.96 (d, J=6.1 Hz, 2H), 3.90-3.85 (m, 2H), 3.67-3.63 (m, 2H), 3.43-3.25 (m, 6H), 2.97-2.89 (m, 2H), 2.02-1.93 (m, 2H), 1.83-1.79 (m, 4H), 1.57 (ddd, J=12.4, 12.4, 4.7 Hz, 2H), 1.37-1.23 (m, 2H), 0.89-0.82 (m, 2H), 0.67-0.61 (m, 2H); MS(ES+) m/z 519.1 (M+1).

Example 377

Synthesis of 5-cyclopropyl-N-(cyclopropylsulfonyl)-2-fluoro-4-((1-((tetrahydro-2H-pyran-4-yl)sulfonyl)piperidin-4-yl)methoxy)benzamide

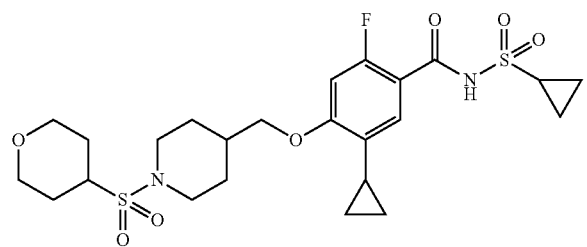 [SMILES: O=C(NS(=O)(=O)C1CC1)c1cc(C2CC2)c(OCC2CCN(S(=O)(=O)C3CCOCC3)CC2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-((tetrahydro-2H-pyran-4-yl)sulfonyl)piperidin-4-yl)methoxy) benzoic acid, and to replace methanesulfonamide with cyclopropylsulfonamide, the title compound was obtained as a colorless solid (0.04 g, 68%); $^{1}$H NMR (300 MHz, DMSO-$d_6$) δ11.80 (br s, 1H), 7.10 (d, J=8.3 Hz, 1H), 6.93 (d, J=13.0 Hz, 1H), 3.96 (d, J=6.1 Hz, 2H), 3.90-3.85 (m, 2H), 3.67-3.63 (m, 2H), 3.43-3.25 (m, 3H), 3.08-2.89 (m, 3H), 2.02-1.93 (m, 2H), 1.83-1.79 (m, 4H), 1.57 (ddd, J=4.6, 12.4, 12.4 Hz, 2H), 1.37-1.23 (m, 2H), 1.09-1.05 (m, 4H), 0.89-0.82 (m, 2H), 0.66-0.61 (m, 2H); MS(ES+) m/z 545.1 (M+1).

Example 378

Synthesis of 5-cyclopropyl-2-fluoro-N-(methylsulfonyl)-4-((1-((4-(trifluoromethoxy)phenyl)sulfonyl)piperidin-4-yl)methoxy)benzamide

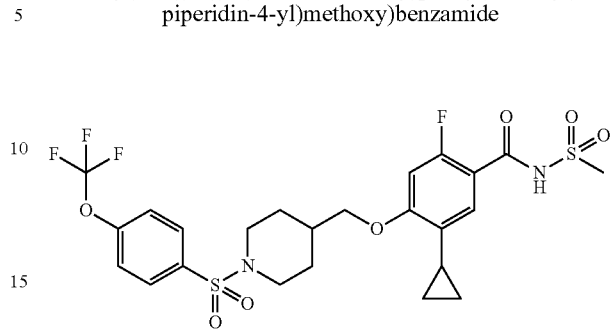

Step 1. Preparation of 5-cyclopropyl-2-fluoro-4-((1-((4-(trifluoromethoxy)phenyl)sulfonyl)piperidin-4-yl)methoxy)benzoic acid

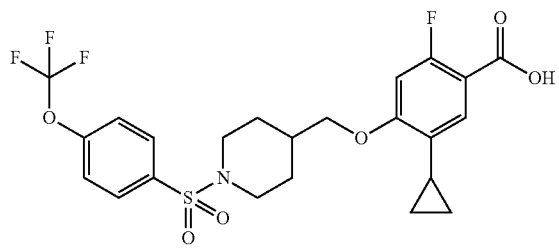 [SMILES: O=C(O)c1cc(C2CC2)c(OCC2CCN(S(=O)(=O)c3ccc(OC(F)(F)F)cc3)CC2)cc1F]

Following the procedure as described in Example 366 step 1 and making non-critical variations as required to replace 4-bromo-5-chloro-2-fluorobenzene-1-sulfonyl chloride with 4-(trifluoromethoxy)benzene-1-sulfonyl chloride, the title compound was obtained as a colorless gum (0.25 g, 60%): MS(ES−) m/z 516.2 (M−1).

Step 2. Preparation of 5-cyclopropyl-2-fluoro-N-(methylsulfonyl)-4-((1-((4-(trifluoromethoxy)phenyl)sulfonyl)piperidin-4-yl)methoxy)benzamide

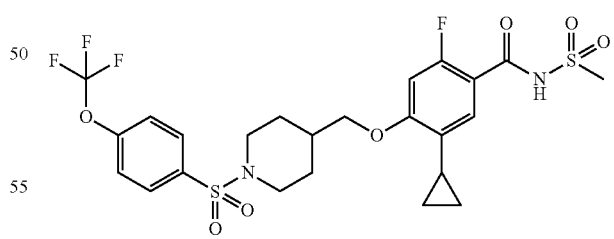

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-((4-(trifluoromethoxy)phenyl)sulfonyl)piperidin-4-yl)methoxy) benzoic acid, the title compound was obtained as a colorless solid (0.06 g, 36%): $^{1}$H NMR (300 MHz, DMSO-$d_6$) δ11.85 (br s, 1H), 7.86 (d, J=8.5 Hz, 2H), 7.60 (d, J=8.5 Hz, 2H), 7.09 (d, J=8.3 Hz, 1H), 6.88 (d, J=12.9 Hz, 1H), 3.89 (d, J=5.1 Hz, 2H), 3.79-3.66 (m, 2H), 3.27 (s, 3H), 2.34-2.26 (m, 2H), 1.98-1.89 (m, 1H), 1.84-1.80 (m, 3H), 1.41-1.29 (m, 2H), 0.86-0.80 (m, 2H), 0.64-0.59 (m, 2H); MS(ES+) m/z 595.0 (M+1).

Example 379

Synthesis of 5-cyclopropyl-N-(cyclopropylsulfonyl)-2-fluoro-4-((1-((4-(trifluoromethoxy)phenyl)sulfonyl)piperidin-4-yl)methoxy)benzamide

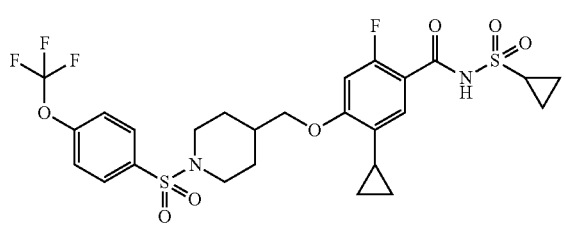 [SMILES: O=C(NS(=O)(=O)C1CC1)c1cc(C2CC2)c(OCC2CCN(S(=O)(=O)c3ccc(OC(F)(F)F)cc3)CC2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-((4-(trifluoromethoxy)phenyl)sulfonyl)piperidin-4-yl)methoxy)benzoic acid, and to replace methanesulfonamide with cyclopropylsulfonamide, the title compound was obtained as a colorless solid (0.01 g, 6%): $^1$H NMR (300 MHz, DMSO-$d_6$) δ 11.79 (br s, 1H), 7.88-7.84 (m, 2H), 7.62-7.59 (m, 2H), 7.08 (d, J=8.3 Hz, 1H), 6.89 (d, J=13.0 Hz, 1H), 3.90 (d, J=5.4 Hz, 2H), 3.70-3.66 (m, 2H), 3.07-2.98 (m, 1H), 2.33-2.26 (m, 2H), 1.98-1.89 (m, 1H), 1.84-1.80 (m, 3H), 1.41-1.28 (m, 2H), 1.08-1.04 (m, 4H), 0.86-0.80 (m, 2H), 0.64-0.59 (m, 2H); MS(ES+) m/z 621.0 (M+1).

Example 380

Synthesis of 5-cyclopropyl-2-fluoro-N-(methylsulfonyl)-4-((1-((3,4,5-trifluorophenyl)sulfonyl)piperidin-4-yl)methoxy)benzamide

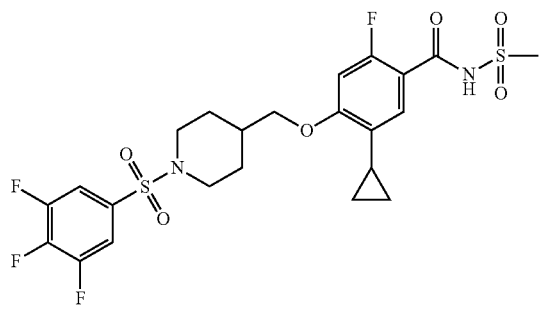 [SMILES: CS(=O)(=O)NC(=O)c1cc(C2CC2)c(OCC2CCN(S(=O)(=O)c3cc(F)c(F)c(F)c3)CC2)cc1F]

Step 1. Preparation of 5-cyclopropyl-2-fluoro-4-((1-((3,4,5-trifluorophenyl)sulfonyl)piperidin-4-yl)methoxy)benzoic acid

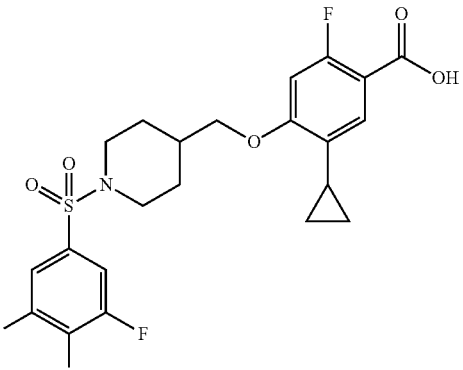

Following the procedure as described in Example 366 step 1 and making non-critical variations as required to replace 4-bromo-5-chloro-2-fluorobenzene-1-sulfonyl chloride with 3,4,5-trifluorobenzene-1-sulfonyl chloride, the title compound was obtained as a colorless gum (0.23 g, 59%): MS(ES+) m/z 488.1 (M+1).

Step 2. Preparation of 5-cyclopropyl-2-fluoro-N-(methylsulfonyl)-4-((1-((3,4,5-trifluorophenyl)sulfonyl)piperidin-4-yl)methoxy)benzamide

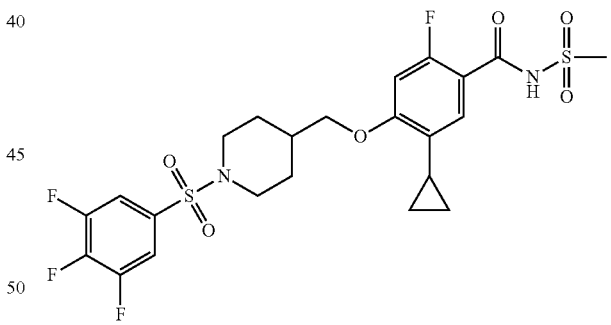

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-((3,4,5-trifluorophenyl)sulfonyl)piperidin-4-yl)methoxy)benzoic acid, the title compound was obtained as a colorless solid (0.08 g, 49%): $^1$H NMR (300 MHz, DMSO-$d_6$) δ 11.89 (br s, 1H), 7.86-7.71 (m, 2H), 7.13 (d, J=9.0 Hz, 1H), (d, J=12.0 Hz, 1H), 4.00-3.89 (m, 2H), 3.77-3.64 (m, 2H), 2.47-2.36 (m, 2H), 2.03-1.91 (m, 2H), 1.90-1.74 (m, 3H), 1.48-1.20 (m, 4H), 0.92-0.81 (m, 2H), 0.70-0.62 (m, 2H).

Example 381

Synthesis of 5-cyclopropyl-N-(cyclopropylsulfonyl)-2-fluoro-4-((1-((3,4,5-trifluorophenyl)sulfonyl)piperidin-4-yl)methoxy)benzamide

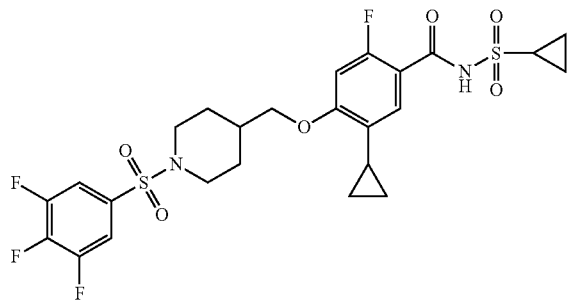 [SMILES: O=C(NS(=O)(=O)C1CC1)c1cc(C2CC2)c(OCC2CCN(S(=O)(=O)c3cc(F)c(F)c(F)c3)CC2)cc1F]

Following the procedure as described in Example 346 step 7 and making non-critical variations as requited to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-((3,4,5-trifluorophenyl)sulfonyl)piperidin-4-yl)methoxy)benzoic acid, and to replace methanesulfonamide with cyclopropylsulfonamide, the title compound was obtained as a color less solid (0.05 g, 31%): $^1$H NMR (300 MHz, DMSO-d$_6$) δ 11.82 (br s, 1H), 7.88-7.75 (m, 2H), 7.11 (d, J=9.0 Hz, 1H), 6.94 (d, J=15.0 Hz, 1H), 3.98-3.89 (m, 2H), 3.77-3.66 (m, 2H), 3.11-3.00 (m, 1H), 2.47-2.37 (m, 3H), 2.04-1.92 (m, 1H), 1.90-1.76 (m, 3H), 1.47-1.31 (m, 2H), 1.16-1.04 (m, 3H), 0.90-0.80 (m, 2H), 0.71-0.61 (m, 2H): MS(ES+) m/z 591.2 (M+1).

Example 382

Synthesis of 4-((1-((3-chloro-4-fluorophenyl)sulfonyl)piperidin-4-yl)methoxy)-5-cyclopropyl-2-fluoro-N-(methylsulfonyl)benzamide

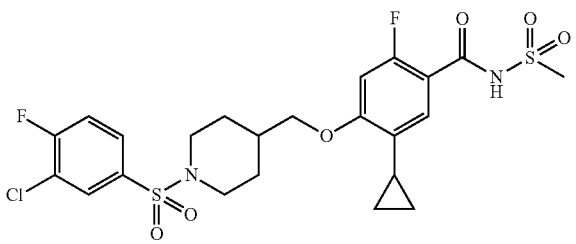 [SMILES: CS(=O)(=O)NC(=O)c1cc(C2CC2)c(OCC2CCN(S(=O)(=O)c3ccc(F)c(Cl)c3)CC2)cc1F]

Step 1. Preparation of 4-((1-((3-chloro-4-fluorophenyl)sulfonyl)piperidin-4-yl)methoxy)-5-cyclopropyl-2-fluorobenzoic acid

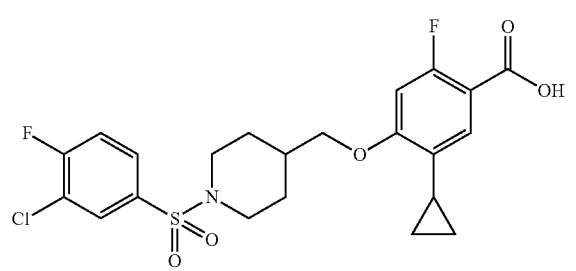 [SMILES: O=C(O)c1cc(C2CC2)c(OCC2CCN(S(=O)(=O)c3ccc(F)c(Cl)c3)CC2)cc1F]

Following the procedure as described in Example 366 step 1 and making non-critical variations as required to replace 4-bromo-5-chloro-2-fluorobenzene-1-sulfonyl chloride with 3-chloro-4-fluorobenzene-1-sulfonyl chloride, the title compound was obtained as a colorless gum (0.23 g, 59%); MS(ES−) m/z 488.1, 486.1 (M−1).

Step 2. Preparation of 4-((1-((3-chloro-4-fluorophenyl)sulfonyl)piperidin-4-yl)methoxy)-5-cyclopropyl-2-fluoro-N-(methylsulfonyl)benzamide

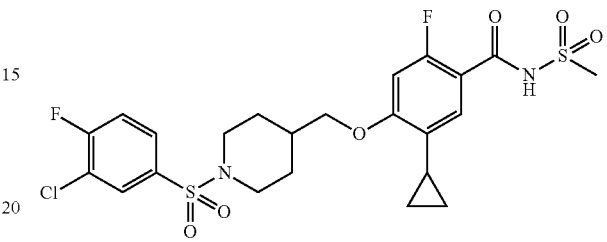

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-((1-((3-chloro-4-fluorophenyl)sulfonyl)piperidin-4-yl)methoxy)-5-cyclopropyl-2-fluorobenzoic acid, the title compound was obtained as a colorless solid (0.03 g, 17%): $^1$H NMR (300 MHz, DMSO-d$_6$) δ11.88 (br s, 1H), 7.93 (dd, J=2.0, 6.8 Hz, 1H), 7.78-7.64 (m, 2H), 7.09 (d, J=8.3 Hz, 1H), 6.87 (d, J=12.9 Hz, 1H), 3.90 (d, J=5.1 Hz, 2H), 3.70-3.66 (m, 2H), 3.25 (s, 3H), 2.38-2.30 (m, 2H), 1.96-1.80 (m, 4H), 1.41-1.27 (m, 2H), 0.86-0.80 (m, 2H), 0.64-0.59 (m, 2H); MS(ES−) m/z 561.1 (M−1).

Example 383

Synthesis of 4-((1-((3-chloro-4-fluorophenyl)sulfonyl)piperidin-4-yl)methoxy)-5-cyclopropyl-N-(cyclopropylsulfonyl)-2-fluorobenzamide

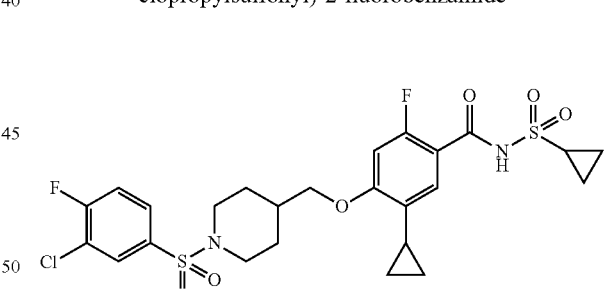

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-((1-((3-chloro-4-fluorophenyl)sulfonyl)piperidin-4-yl)methoxy)-5-cyclopropyl-2-fluorobenzoic acid, and to replace methanesulfonamide with cyclopropylsulfonamide, title compound was obtained as a colorless solid (0.04 g, 25%): $^1$H NMR (300 MHz, DMSO-d$_6$) δ11.78 (br s, 1H), 7.93 (dd, J=2.1, 6.8 Hz, 1H), 7.78-7.64 (m, 2H), 7.08 (d, J=8.3 Hz, 1H), 6.90 (d, J=13.0 Hz, 1H), 3.90 (d, J=5.3 Hz, 2H), 3.70-3.66 (m, 2H), 3.07-2.99 (m, 1H), 2.37-2.30 (m, 2H), 1.98-1.80 (m, 4H), 1.41-1.29 (m, 2H), 1.09-1.05 (m, 4H), 0.86-0.80 (m, 2H), 0.64-0.59 (m, 2H); MS(ES+) m/z 589.0, 591.0 (M+1).

Example 384

Synthesis of 4-((1-((2-chloro-4-(trifluoromethyl)phenyl)sulfonyl)piperidin-4-yl)methoxy)-5-cyclopropyl-2-fluoro-N-(methylsulfonyl)benzamide

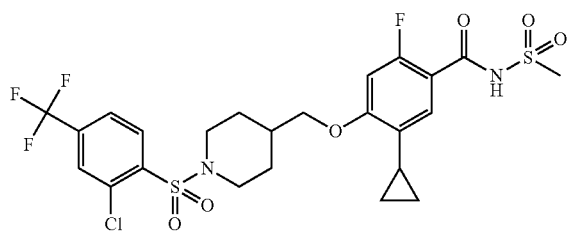

Step 1. Preparation of 4-((1-((2-chloro-4-(trifluoromethyl)phenyl)sulfonyl)piperidin-4-yl)methoxy)-5-cyclopropyl-2-fluorobenzoic acid

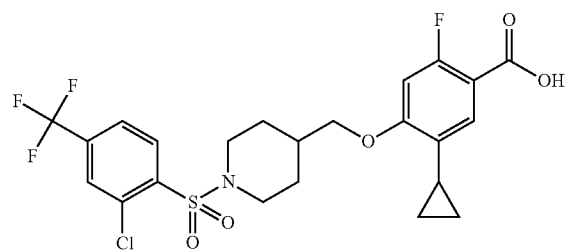 [SMILES: O=C(O)c1cc(C2CC2)c(OCC2CCN(S(=O)(=O)c3ccc(C(F)(F)F)cc3Cl)CC2)cc1F]

Following the procedure as described in Example 366 step 1 and making non-critical variations as required to replace 4-bromo-5-chloro-2-fluorobenzene-1-sulfonyl chloride with 2-chloro-4-(trifluoromethyl)benzene-1-sulfonyl chloride, the title compound was obtained as a colorless gum: (0.26 g, 61%) MS(ES−) m/z 534.0, 532.1 (M−1).

Step 2. Preparation of 4-((1-((2-chloro-4-(trifluoromethyl)phenyl)sulfonyl)piperidin-4-yl)methoxy)-5-cyclopropyl-2-fluoro-N-(methylsulfonyl)benzamide

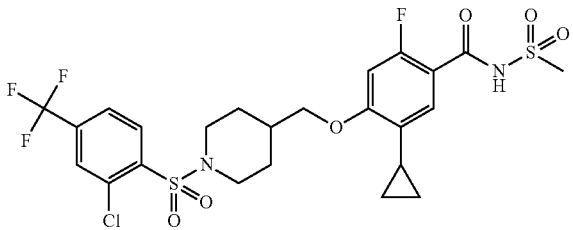 [SMILES: CS(=O)(=O)NC(=O)c1cc(C2CC2)c(OCC2CCN(S(=O)(=O)c3ccc(C(F)(F)F)cc3Cl)CC2)cc1F]

Following the procedure as described in Example 346 step 7 and making non-critical variations as required to replace 4-((1-(3-chloro-2-4-5-(trifluoromethyl)benzyl)-4-fluoropiperidin-4-yl)methoxy)-5-cyclopropyl-2-fluorobenzoic acid with 4-((1-((2-chloro-4-(trifluoromethyl)phenyl)sulfonyl)piperidin-4-yl)methoxy)-5-cyclopropyl-2-fluorobenzoic acid, the title compound was obtained as a colorless solid (0.08 g, 49%): $^1$H NMR (300 MHz, DMSO-$d_6$) δ 11.86 (br s, 1H), 8.16-8.15 (m, 1H), 8.07-8.04 (m, 1H), 7.94 (d, J=8.3 Hz, 1H), 7.09 (d, J=8.3 Hz, 1H), 6.91 (d, J=13.0 Hz, 1H), 3.93 (d, J=5.8 Hz, 2H), 3.80-3.76 (m, 2H), 3.30 (s, 3H), 2.86-2.79 (m, 2H), 1.98-1.89 (m, 4H), 1.39-1.26 (m, 2H), 0.86-0.80 (m, 2H), 0.65-0.60 (m, 2H); MS(ES+) m/z 613.0, 615.0 (M+1).

Example 385

Synthesis of 4-((1-((2-chloro-4-(trifluoromethyl)phenyl)sulfonyl)piperidin-4-yl)methoxy)-5-cyclopropyl-N-(cyclopropylsulfonyl)-2-fluorobenzamide

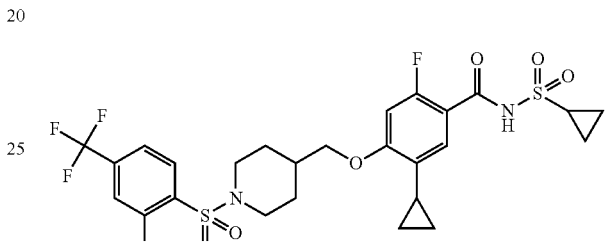

Following the procedure as described in Example 346 step 7 and making non-critical variations as required to replace 4-((1-(3-chloro-2-4-5-(trifluoromethyl)benzyl)-4-fluoropiperidin-4-yl)methoxy)-5-cyclopropyl-2-fluorobenzoic acid with 4-((1-((2-chloro-4-(trifluoromethyl)phenyl)sulfonyl)piperidin-4-yl)methoxy)-5-cyclopropyl-2-fluorobenzoic acid, and to replace methanesulfonamide with cyclopropylsulfonamide, the title compound was obtained as a colorless solid (0.03 g, 14%); $^1$H NMR (300 MHz, DMSO-$d_6$) δ11.79 (br s, 1H), 8.16-8.15 (m, 1H), 8.07-8.04 (m, 1H), 7.94 (d, J=8.3 Hz, 1H), 7.08 (d, J=8.3 Hz, 1H), 6.91 (d, J=13.0 Hz, 1H), 3.93 (d, J=5.8 Hz, 2H), 3.80-3.76 (m, 2H), 3.07-2.99 (m, 1H), 2.86-2.79 (m, 2H), 1.98-1.80 (m, 4H), 1.39-1.26 (m, 2H), 1.09-1.056 (m, 4H), 0.86-0.80 (m, 2H), 0.64-0.59 (m, 2H); MS(ES+) m/z 639.0, 641.0 (M−1).

Example 386

Synthesis of 5-cyclopropyl-2-fluoro-4-((1-((4-fluoro-2-methylphenyl)sulfonyl)piperidin-4-yl)methoxy)-N-(methylsulfonyl)benzamide

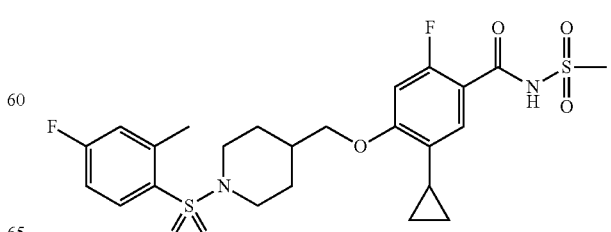

Step 1. Preparation of 5-cyclopropyl-2-fluoro-4-((1-((4-fluoro-2-methylphenyl)sulfonyl)piperidin-4-yl)methoxy)benzoic acid

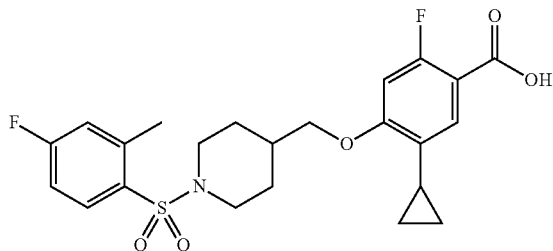 [SMILES: Cc1cc(F)ccc1S(=O)(=O)N1CCC(COc2cc(F)c(C(=O)O)cc2C2CC2)CC1]

Following the procedure as described in Example 366 step 1 and making non-critical variations as required to replace 4-bromo-5-chloro-2-fluorobenzene-1-sulfonyl chloride with 4-fluoro-2-methylbenzene-1-sulfonyl chloride, the title compound was obtained as a colorless gum (0.28 g, 75%): MS(ES−) m/z 464.1 (M−1).

Step 2. Preparation of 5-cyclopropyl-2-fluoro-4-((1-((4-fluoro-2-methylphenyl)sulfonyl)piperidin-4-yl)methoxy)-N-(methylsulfonyl)benzamide

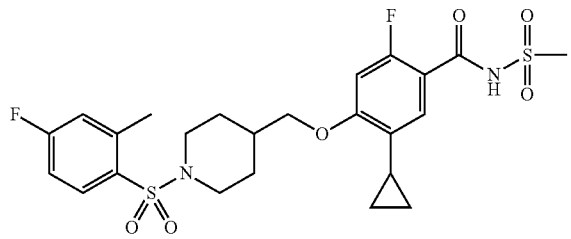 [SMILES: Cc1cc(F)ccc1S(=O)(=O)N1CCC(COc2cc(F)c(C(=O)NS(C)(=O)=O)cc2C2CC2)CC1]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-((4-fluoro-2-methylphenyl)sulfonyl)piperidin-4-yl)methoxy benzoic acid, the title compound was obtained as a colorless solid (0.06 g, 36%): $^1$H NMR (300 MHz, DMSO-$d_6$) δ 11.86 (br s, 1H), 7.84 (dd, J=8.8, 5.9 Hz, 1H), 7.33 (dd, J=10.0, 2.6 Hz, 1H), 7.23 (ddd, J=8.6, 8.6, 2.8 Hz, 1H), 7.09 (d, J=8.3 Hz, 1H), 6.91 (d, J=13.0 Hz, 1H), 3.92 (d, J=5.8, 2H), 3.62 (d, J=12.0, 2H), 3.30 (s, 3H), 2.68-154 (m, 2H), 2.53 (s, 3H), 1.99-1.75 (m, 4H), 1.40-1.26 (m, 2H), 0.87-0.81 (m, 2H), 0.65-0.60 (m, 2H); MS(ES−) m/z 542.0, 541.0 ((M−1).

Example 387

Synthesis of 5-cyclopropyl-N-(cyclopropylsulfonyl)-2-fluoro-4-((1-((4-fluoro-2-methylphenyl)sulfonyl)piperidin-4-yl)methoxy)benzamide

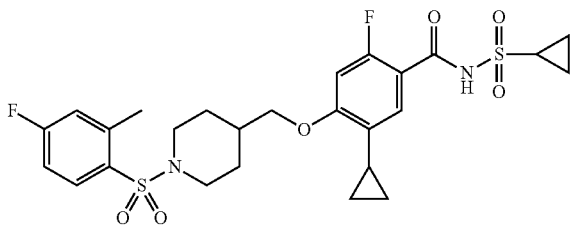 [SMILES: Cc1cc(F)ccc1S(=O)(=O)N1CCC(COc2cc(F)c(C(=O)NS(=O)(=O)C3CC3)cc2C2CC2)CC1]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-(94-fluoro-2-methylphenyl)sulfonyl)piperidin-4-yl)methoxy) benzoic acid, and to replace methanesulfonamide with cyclopropylsulfonamide, the title compound was obtained as a colorless solid (0.01 g, 6%): $^1$H NMR (300 MHz, DMSO-$d_6$) δ 11.79 (br s, 1H), 7.84 (dd, J=8.8, 5.9 Hz, 1H), 7.33 (dd, J=10.0, 2.6 Hz, 1H), 7.23 (ddd, J=8.5, 8.5, 2.7 Hz, 1H), 7.08 (d, J=8.3 Hz, 1H), 6.92 (d, J=12.9 Hz, 1H), 3.92 (d, J=5.8, 2H), 3.63 (d, J=12.1, 2H), 3.30 (s, 3H), 3.08-2.99 (m, 1H), 2.68-154 (m, 2H), 2.53 (s, 3H), 1.99-1.75 (m, 4H), 1.41-1.22 (m, 2H), 1.11-1.01 (m, 4H), 0.87-0.81 (m, 2H), 0.65-0.60 (m, 2H); MS(ES+) m/z 570.0, 569.0 ((M+1).

Example 388

Synthesis of 5-cyclopropyl-2-fluoro-N-(methylsulfonyl)-4-((1-(naphthalen-2-ylsulfonyl)piperidin-4-yl)methoxy)benzamide

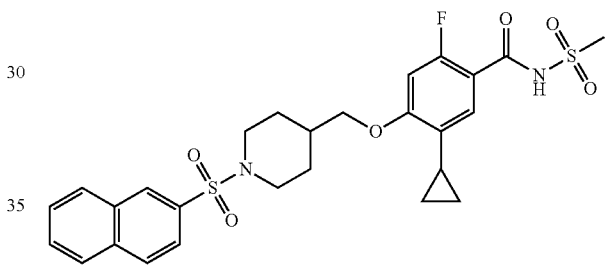

Step 1. Preparation of 5-cyclopropyl-4-fluoro-4-((1-(naphthalen-2-ylsulfonyl)piperidin-4-yl)methoxy)benzoic acid

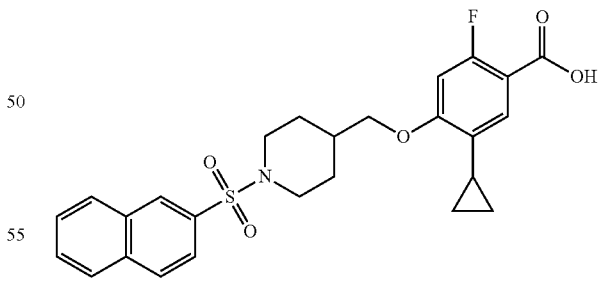

Following the procedure as described in Example 366 step 1 and making non-critical variations as required to replace 4-bromo-5-chloro-2-fluorobenzene-1-sulfonyl chloride with 4-fluoro-2-methylbenzene-1-sulfonyl chloride, the title compound was obtained as a colorless gum (0.28 g, 72%): MS(ES−) m/z 482.1 (M−1).

Step 2. Preparation of 5-cyclopropyl-2-fluoro-N-(methylsulfonyl)-4-((1-(naphthalen-2-ylsulfonyl)piperidin-4-yl)methoxy)benzamide

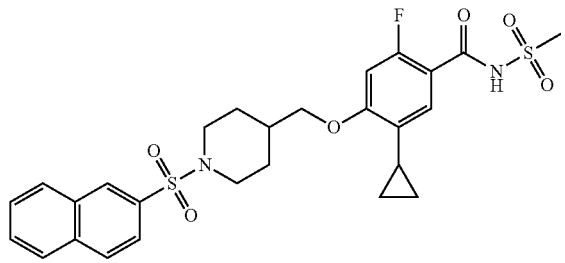 [SMILES: CS(=O)(=O)NC(=O)c1cc(C2CC2)c(OCC2CCN(S(=O)(=O)c3ccc4ccccc4c3)CC2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-(naphthalen-2-ylsulfonyl)piperidin-4-yl)methoxy)benzoic acid, the title compound was obtained as a colorless solid (0.06 g, 36%): $^1$H NMR (300 MHz, DMSO-$d_6$) δ11.84 (br s, 1H), 8.41 (s, 1H), 8.19-8.12 (m, 2H), 8.06-8.04 (m, 1H), 7.75-7.63 (m, 3H), 7.07 (d, J=8.3 Hz, 1H), 6.87 (d, J=13.0 Hz, 1H), 3.87 (d, J=5.6 Hz, 2H), 3.77-3.73 (m, 2H), 3.28 (s, 3H), 2.34-2.27 (m, 2H), 1.93-1.78 (m, 4H), 1.44-1.30 (m, 2H), 0.83-0.76 (m, 2H), 0.62-0.57 (m, 2H); MS(ES+) m/z 561.1 (M+1).

Example 389

Synthesis of 5-cyclopropyl-N-(cyclopropylsulfonyl)-2-fluoro-4-((1-(naphthalen-2-ylsulfonyl)piperidin-4-yl)methoxy)benzamide

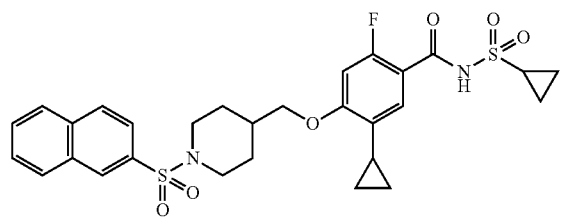 [SMILES: O=C(NS(=O)(=O)C1CC1)c1cc(C2CC2)c(OCC2CCN(S(=O)(=O)c3ccc4ccccc4c3)CC2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-(naphthalen-2-ylsulfonyl)piperidin-4-yl)methoxy)benzoic acid, and to replace methanesulfonamide with cyclopropylsulfonamide, the title compound was obtained as a colorless solid (0.01 g, 6%): $^1$H NMR (300 MHz, DMSO-$d_6$) δ11.77 (br s, 1H), 8.41 (s, 1H), 8.19-8.12 (m, 2H), 8.06-8.03 (m, 1H), 7.75-7.63 (m, 3H), 7.06 (d, J=8.3 Hz, 1H), 6.87 (d, J=13.0 Hz, 1H), 3.87 (d, J=5.5 Hz, 2H), 3.77-3.74 (m, 2H), 3.07-2.98 (m, 1H), 2.34-2.27 (m, 2H), 1.93-1.73 (m, 4H), 1.43-1.32 (m, 2H), 1.09-1.05 (m, 4H), 0.82-0.76 (m, 2H), 0.62-0.56 (m, 2H); MS(ES+) m/z 585.1 (M+1).

Example 390

Synthesis of 4-((1-((4-bromo-3-chlorophenyl)sulfonyl)piperidin-4-yl)methoxy)-5-cyclopropyl-2-fluoro-N-(methylsulfonyl)benzamide

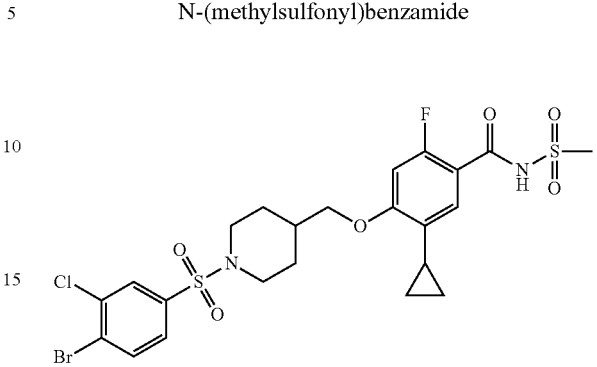

Step 1. Preparation of 4-((1-((4-bromo-3-chlorophenyl)sulfonyl)piperidin-4-yl)methoxy)-5-cyclopropyl-2-fluorobenzoic acid

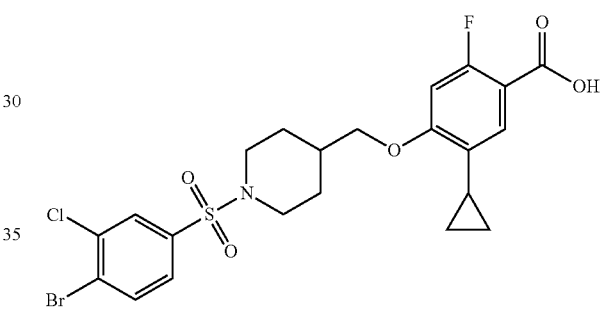

Following the procedure as described in Example 366 step 1 and making non-critical variations as required to replace 4-bromo-5-chloro-2-fluorobenzene-1-sulfonyl chloride with 4-bromo-3-chlorobenzene-1-sulfonyl chloride, the title compound was obtained as a colorless gum (0.34 g, 78%): MS(ES−) m/z 544.0, 542.1 (M−1).

Step 2. Preparation of 4-((1-((4-bromo-3-chlorophenyl)sulfonyl)piperidin-4-yl)methoxy)-5-cyclopropyl-2-fluoro-N-(methylsulfonyl)benzamide

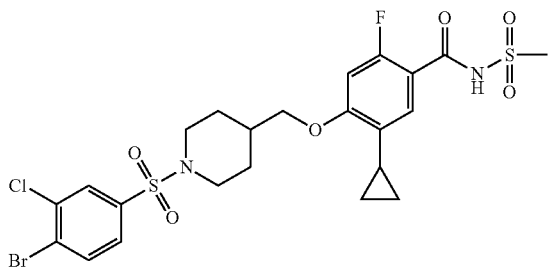 [SMILES: CS(=O)(=O)NC(=O)c1cc(C2CC2)c(OCC2CCN(S(=O)(=O)c3ccc(Br)c(Cl)c3)CC2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-((1-((4-bromo-3-chlorophenyl)sulfonyl)piperidin-4-yl)methoxy)-5-cyclopropyl-2-fluorobenzoic acid, the title compound was obtained as a colorless solid (0.06 g, 36%): $^1$H NMR (300 MHz, d6-DMSO) δ11.89 (br s, 1H), 8.07 (d, J=9.0 Hz, 1H), 7.95-7.89 (d, J=3.0 Hz, 1H), 7.62 (dd, J=12.0, 3.0 Hz, 1H), 7.13 (d, J=9.0, 1H), 6.93 (d, J=12.0 Hz, 1H), 3.98-3.87 (m, 2H), 3.77-3.64 (m, 2H), 3.31 (s, 3H), 2.46-2.32 (m, 2H), 2.03-1.92 (m, 1H), 1.91-1.76 (m, 3H), 1.49-1.30 (m, 2H), 0.94-0.81 (m, 2H), 0.71-0.61 (m, 2H); MS(ES+) m/z 625.0, 627.0 (M+1)

Example 391

Synthesis of 4-((1-((4-bromo-3-chlorophenyl)sulfonyl)piperidin-4-yl)methoxy)-5-cyclopropyl-N-(cyclopropylsulfonyl)-2-fluorobenzamide

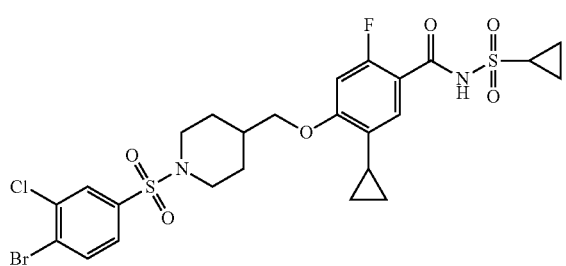 [SMILES: O=C(NS(=O)(=O)C1CC1)c1cc(C2CC2)c(OCC2CCN(S(=O)(=O)c3ccc(Br)c(Cl)c3)CC2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-((1-((4-bromo-3-chlorophenyl)sulfonyl)piperidin-4-yl)methoxy)-5-cyclopropyl-2-fluorobenzoic acid, and to replace methanesulfonamide with cyclopropylsulfonamide, the title compound was obtained as a colorless solid (0.01 g, 6%): $^1$H NMR (300 MHz, DMSO-$d_6$) δ 11.82 (br s, 1H), 8.06 (d, J=9 Hz, 1H), 7.92 (d, J=3 Hz, 1H), 7.62 (dd, J=12 Hz, 3 Hz, 1H), 7.11 (d, J=9 Hz, 1H), 6.93 (d, J=12 Hz, 1H), 3.99-3.89 (m, 2H), 3.76-3.63 (m, 2H), 3.12-2.99 (m, 1H), 2.43-2.32 (m, 3H), 2.01-1.91 (m, 1H), 1.91-1.74 (m, 4H), 1.48-1.29 (m, 2H), 1.16-1.05 (m, 2H), 0.93-0.82 (m, 2H), 0.70-0.61 (m, 2H); MS(ES+) m/z 653.0, 651.0 (M+1).

Example 392

Synthesis of 5-cyclopropyl-2-fluoro-N-(methylsulfonyl)-4-((1-(oxetan-3-ylsulfonyl)piperidin-4-yl)methoxy)benzamide

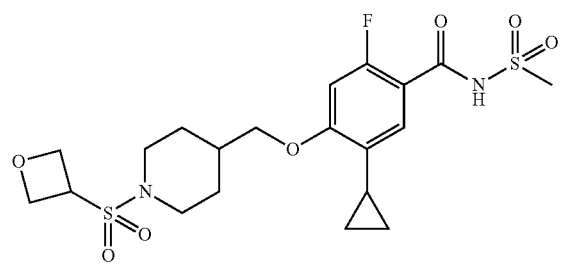 [SMILES: CS(=O)(=O)NC(=O)c1cc(C2CC2)c(OCC2CCN(S(=O)(=O)C3COC3)CC2)cc1F]

Step 1. Preparation of 5-cyclopropyl-2-fluoro-4-((1-(oxetan-3-ylsulfonyl)piperidin-4-yl)methoxy)benzoic acid

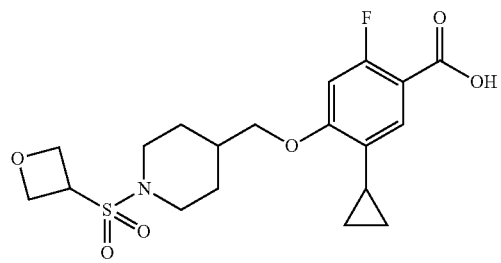 [SMILES: O=C(O)c1cc(C2CC2)c(OCC2CCN(S(=O)(=O)C3COC3)CC2)cc1F]

Following the procedure as described in Example 366 step 1 and making non-critical variations as required to replace 4-bromo-5-chloro-2-fluorobenzene-1-sulfonyl chloride with oxetane-3-sulfonyl chloride, the title compound was obtained as a colorless gum (0.14 g, 39%): MS(ES−) m/z 512.1 (M−1).

Step 2. Preparation of 5-cyclopropyl-2-fluoro-N-(methylsulfonyl)-4-((1-(oxetan-3-ylsulfonyl)piperidin-4-yl)methoxy)benzamide

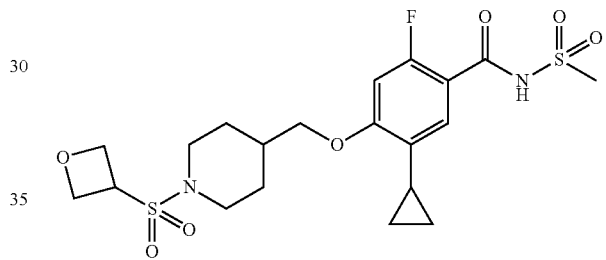

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-(oxetan-3-ylsulfonyl)piperidin-4-yl)methoxy)benzoic acid, the title compound was obtained as a colorless solid (0.03 g, 35%): $^1$H NMR (300 MHz, DMSO-$d_6$) δ11.86 (br s, 1H), 7.10 (d, J=8.3 Hz, 1H), 6.92 (d, J=13.0 Hz, 1H), 4.80-4.66 (m, 5H), 3.94 (d, J=6.0 Hz, 2H), 3.62-3.58 (m, 2H), 3.29 (s, 3H), 2.80-2.72 (m, 2H), 2.02-1.80 (m, 4H), 1.34-1.20 (m, 2H), 0.89-0.82 (m, 2H), 0.66-0.61 (m, 2H); MS(ES−) m/z 489.1 (M−1).

Example 393

Synthesis of 5-cyclopropyl-N-(cyclopropylsulfonyl)-2-fluoro-4-((1-(oxetan-3-ylsulfonyl)piperidin-4-yl)methoxy)benzamide

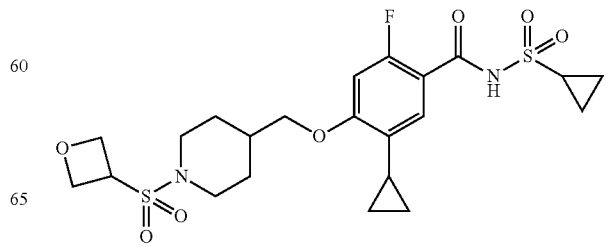

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-(oxetan-3-ylsulfonyl)piperidin-4-yl)methoxy)benzoic acid, and to replace methanesulfonamide with cyclopropylsulfonamide, the title compound was obtained as a colorless solid (0.07 g, 76%): $^1$H NMR (300 MHz, DMSO-$d_6$) δ11.79 (br s, 1H), 7.09 (d, J=8.3 Hz, 1H), 6.93 (d, J=13.0 Hz, 1H), 4.80-4.66 (m, 5H), 3.95 (d, J=6.0 Hz, 2H), 3.62-3.58 (m, 2H), 3.08-3.00 (m, 1H), 2.80-2.73 (m, 2H), 2.02-1.80 (m, 4H), 1.35-1.20 (m, 2H), 1.10-1.06 (m, 4H), 0.89-0.83 (m, 2H), 0.66-0.61 (m, 2H); MS(ES−) m/z 515.2 (M−1).

Example 394

Synthesis of 5-cyclopropyl-N-(cyclopropylsulfonyl)-2-fluoro-4-((1-(methylsulfonyl)piperidin-4-yl)methoxy)benzamide

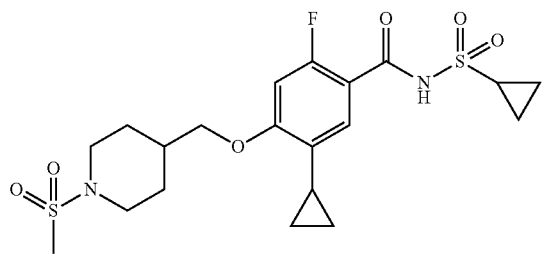 [SMILES: CS(=O)(=O)N1CCC(COc2cc(F)c(C(=O)NS(=O)(=O)C3CC3)cc2C2CC2)CC1]

Step 1. Preparation of methyl 5-cyclopropyl-2-fluoro-4-((1-(methylsulfonyl)piperidin-4-yl)methoxy)benzoate

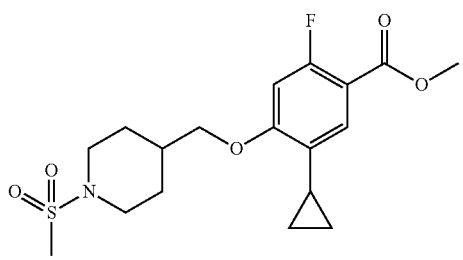 [SMILES: COC(=O)c1cc(C2CC2)c(OCC2CCN(S(C)(=O)=O)CC2)cc1F]

To a cooled (0° C.) solution of 4-bromo-2-chlorobenzyl alcohol (0.75 g, 3.40 mmol) in anhydrous tetrahydrofuran (20 mL) was added methanesulfonyl chloride (0.60 mL, 8.50 mmol) and N,N-diisopropylethylamine (1.5 ml, 8.50 mmol). After stirring at 0° C. under a nitrogen atmosphere for 40 minutes, the reaction mixture was diluted with ethyl acetate (100 mL), washed with 1 M hydrochloric acid solution (100 mL) and brine (100 mL), dried over anhydrous magnesium sulfate, filtered and concentrated in vacuo. The residue was dissolved in anhydrous N,N-dimethylformamide (15 mL), and methyl 5-cyclopropyl-2-fluoro-4-(piperidin-4-ylmethoxy)benzoate hydrochloride (0.98 g, 3.2 mmol) and potassium carbonate (1.52 g, 11.0 mmol) were added to this solution. The reaction mixture was heated at 90° C. under a nitrogen atmosphere for 17 hours, cooled to ambient temperature, diluted with brine (200 mL) and extracted with ethyl acetate (2×150 mL). The combined organic layers were dried over anhydrous magnesium sulfate, filtered, and concentrated in vacuo. The residue was purified by column chromatography, eluting with a 0-50% gradient of ethyl acetate with 10% isopropanol, 10% triethylamine in hexanes to afford the title compound as a colorless solid (0.30 g, 25%); $^1$H NMR (300 MHz, CDCl$_3$) δ7.43 (d, J=8.2 Hz, 1H), 6.52 (d, J=12.6 Hz, 1H), 3.89-3.83 (m, 7H), 2.78 (s, 3H), 2.75-2.67 (m, 2H), 2.02-1.94 (m, 4H), 1.63-1.50 (m, 2H), 0.92-0.87 (m, 2H), 0.65-0.60 (m, 2H); MS(ES+) m/z 386.1 (M+1).

Step 2. Preparation of 5-cyclopropyl-2-fluoro-4-((1-(methylsulfonyl)piperidin-4-yl)methoxy)benzoic acid

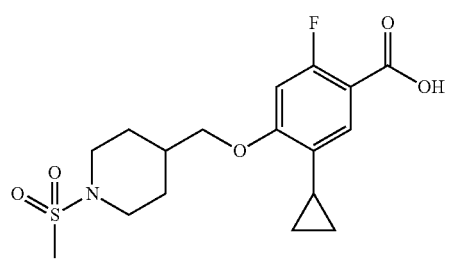 [SMILES: CS(=O)(=O)N1CCC(COc2cc(F)c(C(=O)O)cc2C2CC2)CC1]

To a solution of methyl 5-cyclopropyl-2-fluoro-4-((1-(methylsulfonyl)piperidin-4-yl)methoxy)benzoate (0.30 g, 0.77 mmol) in tetrahydrofuran (10 mL), water (5 mL) was added lithium hydroxide (0.40 g, 17.00 mmol). The mixture was refluxed for 4.5 hours, cooled to ambient temperature. The reaction mixture was acidified with 1 M hydrochloric acid solution (100 mL), extracted with ethyl acetate (100 mL) and dichloromethane (2×100 mL). The combined organic layers were dried over anhydrous magnesium sulfate, filtered and concentrated in vacuo to afford the title compound as a colorless solid (0.16 g) 57%). The aqueous layer contained solid that was filtered, washed with water (50 mL) and diethyl ether (30 mL) to afford additional amount of the title compound as a colorless solid (0.05 g, 18%); MS(ES−) m/z 370.1 (M−1).

Step 3. Preparation of 5-cyclopropyl-N-(cyclopropylsulfonyl)-2-fluoro-4-((1-(methylsulfonyl)piperidin-4-yl)methoxy)benzamide

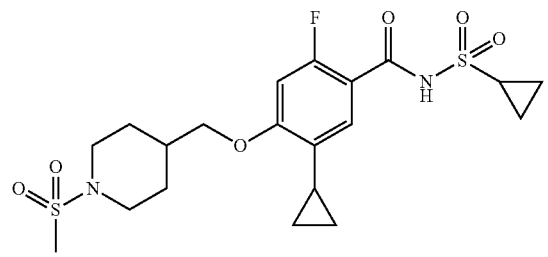 [SMILES: CS(=O)(=O)N1CCC(COc2cc(F)c(C(=O)NS(=O)(=O)C3CC3)cc2C2CC2)CC1]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-(methylsulfonyl)piperidin-4-yl)methoxy)benzoic acid and to replace methanesulfonamide with cyclopropylsulfonamide, the title compound was obtained as a colorless solid (0.06 g, 45%): ¹H NMR (300 MHz, DMSO-d₆) δ11.80 (br s, 1H), 7.09 ((d, J=8.3 Hz, 1H), 6.94 (d, J=13.0 Hz, 1H), 3.97 (d, J=5.8 Hz, 2H), 3.58-3.54 (m, 2H), 3.08-3.00 (m, 1H), 2.82 (s, 3H), 2.75-2.67 (m, 2H), 2.02-1.84 (m, 4H), 1.43-1.30 (m, 2H), 1.09-1.05 (m, 4H), 0.90-0.83 (m, 2H), 0.67-0.62 (m, 2H); MS(ES+) m/z 475.1 (M+1).

Example 395

Synthesis of 5-cyclopropyl-2-fluoro-N-(methylsulfonyl)-4-((1-(methylsulfonyl)piperidin-4-yl)methoxy)benzamide

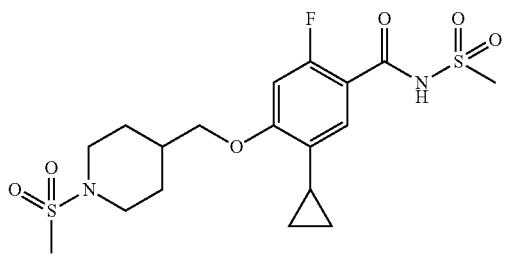

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-2-fluoro-4-((1-(methylsulfonyl)piperidin-4-yl)methoxy)benzoic acid, the title compound was obtained as a colorless solid (0.03 g, 25%): ¹H NMR (300 MHz, DMSO-d₆) δ11.87 (br s, 1H), 7.10 (d, J=8.3 Hz, 1H), 6.94 (d, J=13.0 Hz, 1H), 3.96 (d, J=5.8 Hz, 2H), 3.58-3.54 (m, 2H), 3.30 (s, 3H), 2.82 (s, 3H), 2.75-2.67 (m, 2H), 2.04-1.84 (m, 4H), 1.42-1.30 (m, 2H), 0.90-0.83 (m, 2H), 0.67-0.62 (m, 2H): MS(ES+) m/z 449.0 (M+1).

Example 396

Synthesis of 4-(((1R,3S,5S)-8-(3-chloro-2-fluoro-5-(trifluoromethyl)benzyl)-8-azabicyclo-[3.2.1]octan-3-yl)methoxy)-5-cyclopropyl-N-(cyclopropylsulfonyl)-2-fluorobenzamide, trifluoroacetic acid salt

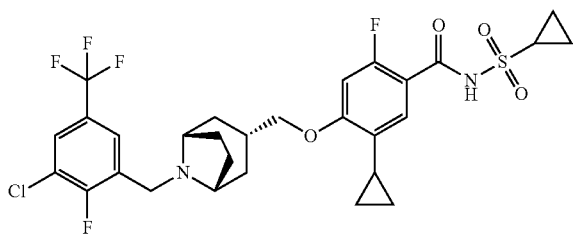 [SMILES: O=C(NS(=O)(=O)C1CC1)c1cc(C2CC2)c(OC[C@@H]2C[C@H]3CC[C@@H](C2)N3Cc2cc(C(F)(F)F)cc(Cl)c2F)cc1F]

Step 1. Preparation of (1R,3S,5S)-benzyl 3-((4-(tert-butoxycarbonyl)-2-chloro-5-fluorophenoxy)methyl)-8-azabicyclo[3.2.1]octane-8-carboxylate

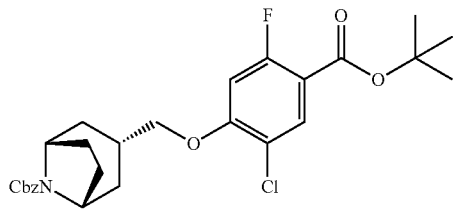 [SMILES: CC(C)(C)OC(=O)c1cc(Cl)c(OC[C@@H]2C[C@H]3CC[C@@H](C2)N3C(=O)OCc2ccccc2)cc1F]

Following the procedure as described in Example 346 step 2 and making non-critical variations as required to replace of tert-butyl 4-fluoro-4-(hydroxymethyl)piperidine-1-carboxylate (4.69 g, 19.70 mmol) with (1R,3S,5S)-benzyl 3-(hydroxymethyl)-8-azabicyclo[3.2.1]octane-8-carboxylate, the title compound was obtained as a colorless gum (7.10 g, 98%): MS(ES+) m/z 506.2, 504.2 (M+1).

Step 2. Preparation of (1R,3S,5S)-benzyl 3-((4-(tert-butoxycarbonyl)-2-cyclopropyl-5-fluorophenoxy)methyl)-8-azabicyclo[3.2.1]octane-8-carboxylate

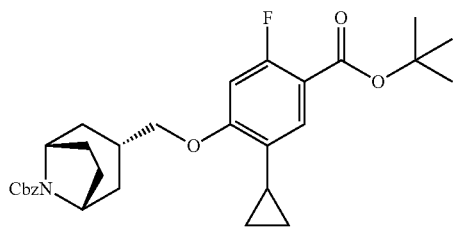 [SMILES: CC(C)(C)OC(=O)c1cc(C2CC2)c(OC[C@@H]2C[C@H]3CC[C@@H](C2)N3C(=O)OCc2ccccc2)cc1F]

Following the procedure as described in Example 346 step 3 and making non-critical variations as required to replace of tert-butyl 4-((4-(tert-butoxycarbonyl)-2-chloro-5-fluorophenoxy)methyl)-4-fluoropiperidine-1-carboxylate with (1R,3S,5S)-benzyl 3-((4-(tert-butoxycarbonyl)-2-chloro-5-fluorophenoxy)methyl)-8-azabicyclo[3.2.1]octane-8-carboxylate, the title compound was obtained as a colorless solid (5.7 g, 80%): ¹H NMR (300 MHz, DMSO-d₆) δ7.34-7.27 (m, 6H), 6.44 (d, J=12.6 Hz, 1H), 5.12 (s, 2H), 4.05 (br s, 2H), 3.75 (d, J=4.8 Hz, 2H), 2.49-2.34 (m, 1H), 2.03-1.88 (m, 3H), 1.76-1.64 (m, 5H) 1.55 (s, 9H), 0.91-0.80 (m, 2H), 0.66-0.61 (m, 2H).

Step 3. Preparation of 4-(((1R,3S,5S)-8-((benzyloxy)carbonyl)-8-azabicyclo[3.2.1]octan-3-yl)methoxy)-5-cyclopropyl-2-fluorobenzoic acid

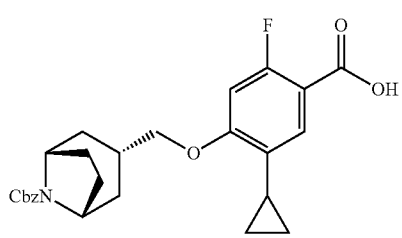 [SMILES: O=C(O)c1cc(C2CC2)c(OC[C@@H]2C[C@H]3CC[C@@H](C2)N3C(=O)OCc2ccccc2)cc1F]

Following the procedure as described in Example 346 step 6, and making non-critical variations as required to replace tert-butyl 4-((4-(tert-butoxycarbonyl)-2-cyclopropyl-5-fluorophenoxy)methyl)-4-fluoropiperidine-1-carboxylate with (1R,3S,5S)-benzyl 5-((4-(tert-butoxycarbonyl)-2-cyclopropyl-5-fluorophenoxy)methyl)-8-azabicyclo[3.2.1]octane-8-carboxylate, the title compound was obtained as a colorless solid (1.30 g, 27%): MS(ES+) m/z 435.1, 454.1 (M+1).

Step 4. Preparation of (1R,3S,5S)-benzyl 3-((2-cyclopropyl-4-((cyclopropylsulfonyl)carbamoyl)-5-fluorophenoxy)methyl)-8-azabicyclo[3.2.1]octane-8-carboxylate

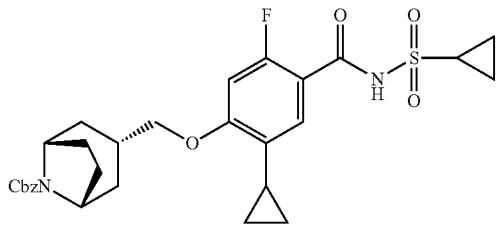 [SMILES: O=C(NS(=O)(=O)C1CC1)c1cc(C2CC2)c(OC[C@@H]2C[C@H]3CC[C@@H](C2)N3C(=O)OCc2ccccc2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-(((1R,3S,5S)-8-((benzyloxy)carbonyl)-8-azabicyclo[3.2.1]octan-3-yl)methoxy)-5-cyclopropyl-2-fluorobenzoic acid, the title compound was obtained as a colorless solid (1.19 g, quant. yield); MS(ES+) m/z 556.2, 555.2 (M+1).

Step 5. Preparation of 4-((1R,3S,5S)-8-azabicyclo[3.2.1]octan-3-ylmethoxy)-5-cyclopropyl-N-(cyclopropylsulfonyl)-2-fluorobenzamide

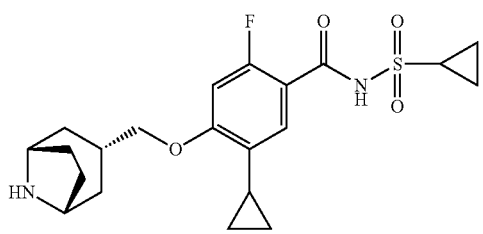 [SMILES: O=C(NS(=O)(=O)C1CC1)c1cc(C2CC2)c(OC[C@@H]2C[C@H]3CC[C@@H](C2)N3)cc1F]

A mixture of (1R,3S,5S)-benzyl 3-((2-cyclopropyl-4-((cyclopropylsulfonyl)carbamoyl)-5-fluorophenoxy)methyl)-8-azabicyclo[3.2.1]octane-8-carboxylate (1.70 g, 3.01 mmol), Pd/C (0.080 g) and acetic acid (0.10 g) in ethanol (60 mL) was stirred at ambient temperature under hydrogen balloon for 2 hours. The solid was filtered and the solvent was concentrated in vacuo to afford the title compound as a beige solid (1.19 g, 94%): MS(ES+) m/z 423.1 (M+1).

Step 6. Preparation of 4-(((1R,3S,5S)-8-(3-chloro-2-fluoro-5-(trifluoromethyl)benzyl)-8-azabicyclo[3.2.1]octan-3-yl)methoxy)-5-cyclopropyl-N-(cyclopropylsulfonyl)-2-fluorobenzamide, trifluoroacetic acid salt

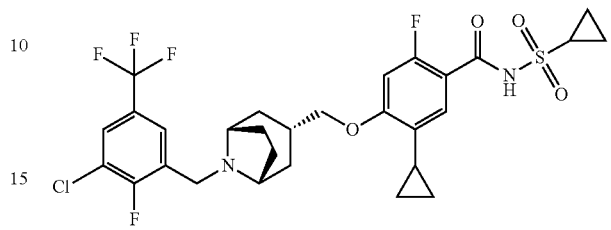

Following the procedure as described in Example 346 step 5 and making non-critical variations as required to replace of tert-butyl 5-cyclopropyl-2-fluoro-4-((4-fluoropiperidin-4-yl)methoxy)benzoate with 4-((1R,3S,5S)-8-azabicyclo[3.2.1]octan-3-ylmethoxy)-5-cyclopropyl-N-(cyclopropylsulfonyl)-2-fluorobenzamide, the title compound was obtained as a colorless solid (0.09 g, 5%): $^1$H NMR (300 MHz, DMSO-$d_6$) δ11.81 (brs, 1H), 9.88 (brs, 1H), 8.25 (d, J=4.9 Hz, 1H), 8.06 (d, J=5.5 Hz, 1H), 7.07 (d, J=8.3 Hz, 1H), 6.98 (d, J=12.9 Hz, 1H), 4.33 (s, 2H), 4.05 (brs, 2H), 3.86 (d, J=6.2 Hz, 2H), 3.08-2.99 (m, 2H), 2.41-2.27 (m, 2H), 2.06-1.96 (m, 3H), 1.83-1.67 (m, 2H), 1.11-1.03 (m, 4H), 0.88-0.80 (m, 2H), 0.66-0.61 (m, 2H); MS(ES+) m/z 634.0, 633.0 (M+1).

Example 397

Synthesis of 4-(((1R,3S,5S)-8-(2-chloro-5-(trifluoromethyl)benzyl)-8-azabicyclo[3.2.1]octan-3-yl)methoxy)-5-cyclopropyl-N-(cyclopropylsulfonyl)-2-fluorobenzamide, trifluoroacetic acid salt

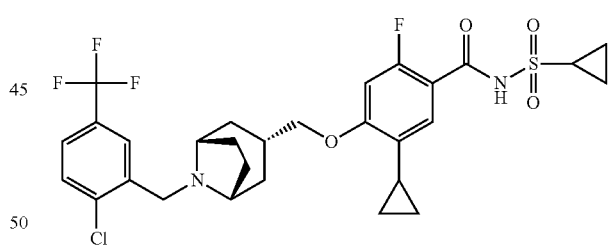

Following the procedure as described in Example 346 step 5 and making non-critical variations as required to replace of tert-butyl 5-cyclopropyl-2-fluoro-4-((4-fluoropiperidin-4-yl)methoxy)benzoate with 4-((1R,3s,5S)-8-azabicyclo[3.2.1]octan-3-ylmethoxy)-5-cyclopropyl-N-(cyclopropylsulfonyl)-2-fluorobenzamide and to replace 1-chloro-3-(chloromethyl)-2-fluoro-5-(trifluoromethyl)benzene with 1-chloro-2-(chloromethyl)-4-(trifluoromethyl)benzene, the title compound was obtained as a colorless solid (0.01 g, 6%): $^1$H NMR (300 MHz, DMSO-$d_6$) δ11.80 (br s, 1H), 9.36 (br s, 1H), 8.19 (s, 1H), 7.09 (d, J=8.3 Hz, 1H), 6.91 (d, J=12.9 Hz, 1H), 6.05 (s, 1H), 3.99-3.92 (m, 2H), 3.29 (s, 3H), 3.27-3.18 (m, 2H), 3.17-3.08 (m, 2H), 2.22-2.09 (m, 1H), 2.05-1.94 (m, 3H), 1.69-1.54 (m, 2H), 0.90-0.84 (m, 2H), 0.64-0.59 (m, 2H); MS(ES+) m/z 617.1, 615.1 (M+1).

Example 398

Synthesis of 4-(((1R,3S,5S)-8-(3-chloro-2-fluoro-5-(trifluoromethyl)benzyl)-8-azabicyclo[3.2.1]octan-3-yl)methoxy)-5-cyclopropyl-2-fluoro-N-(methylsulfonyl)benzamide, trifluoroacetic acid salt

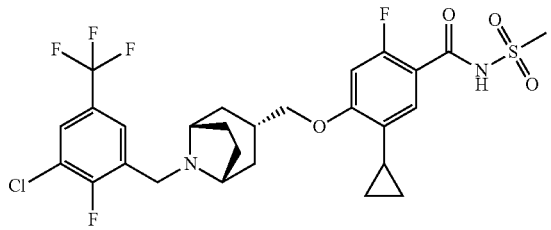 [SMILES: CS(=O)(=O)NC(=O)c1cc(C2CC2)c(OC[C@@H]2C[C@H]3CC[C@@H](C2)N3Cc2cc(C(F)(F)F)cc(Cl)c2F)cc1F]

Step 1. Preparation of (1R,3S,5S)-benzyl 3-((2-cyclopropyl-5-fluoro-4-((methylsulfonyl)carbamoyl)phenoxy)methyl)-8-azabicyclo[3.2.1]octane-8-carboxylate

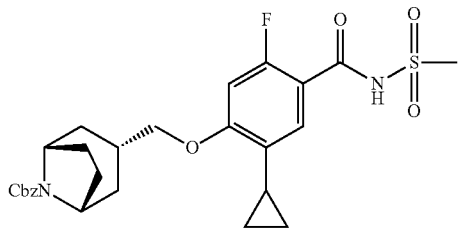 [SMILES: CS(=O)(=O)NC(=O)c1cc(C2CC2)c(OC[C@@H]2C[C@H]3CC[C@@H](C2)N3C(=O)OCc2ccccc2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-(((1R,3S,5S)-8-((benzyloxy)carbonyl)-8-azabicyclo[3.2.1]octan-3-yl)methoxy)-5-cyclopropyl-2-fluorobenzoic acid and to replace methanesulfonamide with cyclopropylsulfonamide, the title compound was obtained as a colorless solid (0.45 g, 14%): $^1$H NMR (300 MHz, CDCl$_3$) δ11.86 (br s, 1H), 7.39-7.25 (m, 5H), 7.10 (d, J=8.3 Hz, 1H), 6.89 (d, J=12.9 Hz, 1H), 5.03 (s, 2H), 4.22-4.14 (m, 2H), 3.85 (d, J=5.1 Hz, 2H), 3.29 (s, 3H), 2.41-2.31 (m, 1H), 1.94-1.84 (m 3H), 1.72-1.44 (m, 6H), 0.85-0.76 (m, 2H), 0.65-0.59 (m, 2H); MS(ES+) m/z 532.1, 531.1 (M+1).

Step 2. Preparation of 4-((1R,3S,5S)-8-azabicyclo[3.2.1]octan-3-ylmethoxy)-5-cyclopropyl-2-fluoro-N-(methylsulfonyl)benzamide

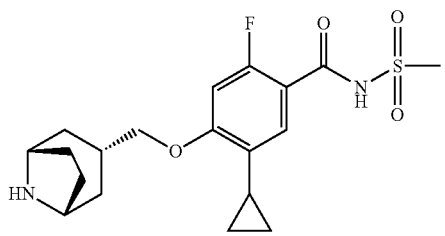 [SMILES: CS(=O)(=O)NC(=O)c1cc(C2CC2)c(OC[C@@H]2C[C@H]3CC[C@@H](C2)N3)cc1F]

Following the procedure as described in Example 396 step 5 and making non-critical variations as required to replace (1R,3S,5S)-benzyl 3-((2-cyclopropyl-4-(cyclopropylsulfonyl)carbamoyl)-5-fluorophenoxy)methyl)-8-azabicyclo[3.2.1]octane-8-carboxylate with (1R,3S,5S)-benzyl 3-((2-cyclopropyl-5-fluoro-4-((methylsulfonyl)carbamoyl)phenoxy)methyl)-8-azabicyclo[3.2.1]octane-8-carboxylate, title compound was obtained as a beige solid (1.10 g, 88%): MS(ES+) m/z 398.1, 397.1 (M+1).

Step 3. Preparation of 4-(((1R,3S,5S)-8-(3-chloro-2-fluoro-5-(trifluoromethyl)benzyl)-8-azabicyclo[3.2.1]octan-3-yl)methoxy)-5-cyclopropyl-2-fluoro-N-(methylsulfonyl)benzamide, trifluoroacetic acid salt

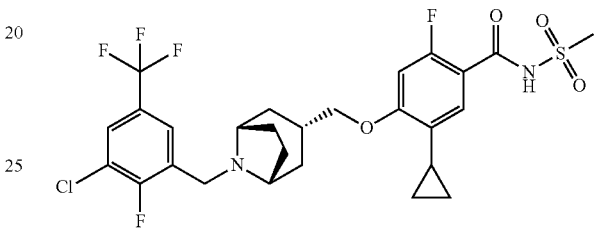

Following the procedure as described in Example 346 step 5 and making non-critical variations as required to replace of tert-butyl 5-cyclopropyl-2-fluoro-4-((4-fluoropiperidin-4-yl)methoxy)benzoate with 4-((1R,3S,5S)-8-azabicyclo[3.2.1]octan-3-ylmethoxy)-5-cyclopropyl-2-fluoro-N-(methylsulfonyl)benzamide, the title compound was obtained as a colorless solid (0.02 g, 14%); $^1$H NMR (300 MHz, DMSO-d$_6$+1% D$_2$O) δ 8.21-8.18 (m, 1H), 8.03-8.01 (m, 1H), 7.08 (d, J=8.2 Hz, 1H), 6.92 (d, J=12.9 Hz, 1H), 4.31 (brs, 2H), 4.04-3.96 (m, 2H), 3.91-3.82 (m, 2H), 3.29 (s, 3H), 2.42-2.27 (m, 3H), 2.04-1.84 (m, 3H), 1.95-1.88 (m, 2H), 1.78-1.67 (m, 2H), 0.90-0.84 (m, 2H), 0.64-0.59 (m, 2H); MS(ES+) m/z 609.0, 607.0 (M+1).

Example 399

Synthesis of 4-(((1R,3S,5S)-8-(2-chloro-5-(trifluoromethyl)benzyl)-8-azabicyclo[3.2.1]octan-3-yl)methoxy)-5-cyclopropyl-2-fluoro-N-(methylsulfonyl)benzamide, trifluoroacetic acid salt

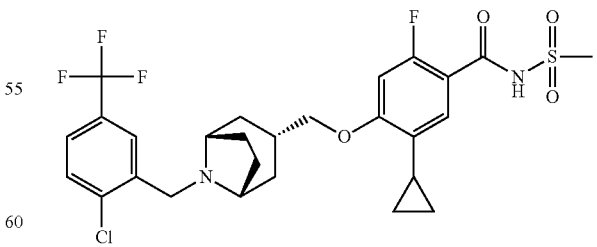

Following the procedure as described in Example 346 step 5 and making non-critical variations as required to replace of tert-butyl 5-cyclopropyl-2-fluoro-4-((4-fluoropiperidin-4-yl)methoxy)benzoate with 4-((1R,3S,5S)-8-azabicyclo[3.2.1]octan-3-ylmethoxy)-5-cyclopropyl-2-fluoro-N-

(methylsulfonyl)benzamide and to replace 1-chloro-3-(chloromethyl)-2-fluoro-5-(trifluoromethyl)benzene with 1-chloro-2-(chloromethyl)-4-(trifluoromethyl)benzene, the title compound was obtained as a colorless solid (0.04 g, 29%): ¹H NMR (300 MHz, DMSO-d₆+1% D₂O) δ8.10 (s, 1H), 7.97-7.76 (m, 2H), 7.04 (d, J=8.1 Hz, 1H), 6.87 (d, J=12.91%, 1H), 4.31 (s, 2H), 4.04-3.94 (m, 2H), 3.92-3.82 (m, 2H), 3.25 (s, 3H), 2.46-2.29 (m, 3H), 2.07-1.95 (m, 3H), 1.94-1.84 (m, 2H), 1.78-1.64 (m, 2H), 0.87-0.81 (m, 2H), 0.59-53 (m, 2H); MS(ES+) m/z 591.0, 589.0 (M+1).

Example 400

Synthesis of 4-((1-(bis(4-chlorophenyl)methyl)piperidin-4-yl)methoxy)-5-cyclopropyl-N-(cyclopropylsulfonyl)-2-fluorobenzamide, trifluoroacetic acid salt

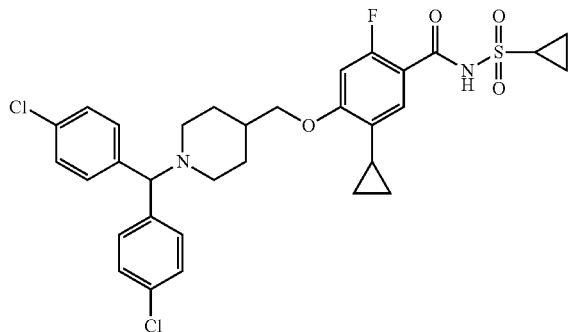 [SMILES: O=C(NS(=O)(=O)C1CC1)c1cc(C2CC2)c(OCC2CCN(C(c3ccc(Cl)cc3)c3ccc(Cl)cc3)CC2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-((1-(bis(4-chlorophenyl)methyl)piperidin-4-yl)methoxy)-5-cyclopropyl-2-fluorobenzoic acid, and to replace methanesulfonamide with the title compound was obtained as a colorless solid (0.07 g, 55%): ¹H NMR (300 MHz, DMSO-d₆+1% D₂O) δ7.63-7.60 (m, 4H), 7.54-7.51 (m, 4H), 7.07 (d, J=8.3 Hz, 1H), 6.91 (d, J=12.9 Hz, 1H), 5.51 (s, 1H), 4.02-3.96 (m, 2H), 3.27-3.19 (m, 2H), 3.06-2.98 (m, 3H), 2.18-2.06 (m, 1H), 2.03-1.94 (m, 3H), 1.71-1.56 (m, 2H), 1.11-1.08 (m, 4H), 0.89-0.83 (m, 2H), 0.62-0.57 (m, 2H); MS(ES+) m/z 631.1, 633.1 (M+1).

Example 401

Synthesis of 4-((1-(bis(3-chlorophenyl)methyl)piperidin-4-yl)methoxy)-5-cyclopropyl-N-(cyclopropylsulfonyl)-2-fluorobenzamide, trifluoroacetic acid salt

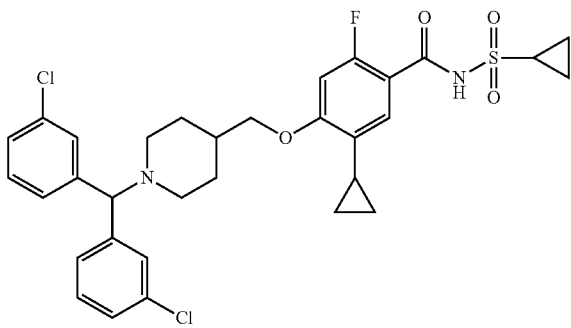 [SMILES: O=C(NS(=O)(=O)C1CC1)c1cc(C2CC2)c(OCC2CCN(C(c3cccc(Cl)c3)c3cccc(Cl)c3)CC2)cc1F]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-((1-(bis(4-chlorophenyl)methyl)piperidin-4-yl)methoxy)-5-cyclopropyl-2-fluorobenzoic acid, and to replace methanesulfonamide with cyclopropylsulfonamide, the title compound was obtained as a colorless solid (0.06 g, 34%): ¹H NMR (300 MHz, DMSO-d₆+1% D₂O) δ7.70 (br s, 2H), 7.61-7.59 (m, 2H), 7.54-7.45 (m, 4H), 7.08 (d, J=8.3 Hz, 1H), 6.92 (d, J=12.9 Hz, 1H), 5.51 (s, 1H), 3.98-3.96 (m, 2H), 3.24-3.21 (m, 2H), 3.07-2.98 (m, 3H), 2.19-2.07 (m, 1H), 2.04-1.95 (m, 3H), 1.73-1.57 (m, 2H), 1.11-1.06 (m, 4H), 0.90-0.83 (m, 2H), 0.63-0.58 (m, 2H); MS (ES+) m/z 631.0, 633.0 (M+1).

Example 402

Synthesis of (S)-5-chloro-4-((1-(1-(3,5-dichlorophenyl)ethyl)piperidin-4-yl)methoxy)-2-fluoro-N-(methylsulfonyl)benzamide, trifluoroacetic acid salt

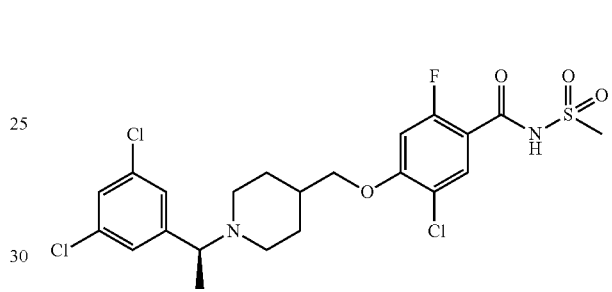

Step 1. Preparation of (S)-tert-butyl 5-chloro-4-((1-(1-(3,5-dichlorophenyl)ethyl)piperidin-4-yl)methoxy)-2-fluorobenzoate

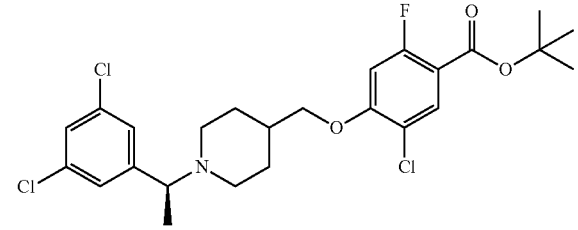 [SMILES: C[C@@H](c1cc(Cl)cc(Cl)c1)N1CCC(COc2cc(F)c(C(=O)OC(C)(C)C)cc2Cl)CC1]

To a solution of tert-butyl 5-chloro-2-fluoro-4-(piperidin-4-ylmethoxy)benzoate hydrochloride (0.13 g, 0.33 mmol) in anhydrous N,N-dimethylformamide (5 mL) was added (R)-1-(3,5-dichlorophenyl)ethyl 4-methylbenzenesulfonate (0.14 g, 0.39 mmol) and potassium carbonate (0.16 g, 1.1 mmol). The reaction mixture was heated to 90° C. under a nitrogen atmosphere for 15 hours, then cooled and diluted with water (100 mL). The mixture was extracted with ethyl acetate (2×100 mL) and the combined organic layers were dried over anhydrous magnesium sulfate, filtered, and concentrated in vacuo. The residue was purified by column chromatography eluting with a gradient of 0-50% ethyl acetate containing 10% isopropanol and 10% triethylamine in hexanes to afford the title compound as a colorless syrup (0.13 g, 73%): ¹H NMR (300 MHz, CDCl₃) δ 7.84 (d, J=7.7 Hz, 1H), 7.20-7.19 (m, 3H), 6.59 (d, J=12.2 Hz, 1H), 4.84 (q, J=6.5 Hz, 1H), 3.83 (d, J=6.1 Hz, 2H), 3.40-3.33 (m, 1H), 3.03-3.00 (m, 1H), 2.81-2.77 (m, 1H), 2.04-1.76 (m, 6H), 1.55 (s, 9H), 1.31 (d, J=6.5 Hz, 3H); MS(ES+) m/z 516.0, 518.0, 520.0 (M+1).

Step 2. Preparation of (S)-5-chloro-4-((1-(1-(3,5-dichlorophenyl)ethyl)piperidin-4-yl)methoxy)-2-fluorobenzoic acid, trifluoroacetic acid salt

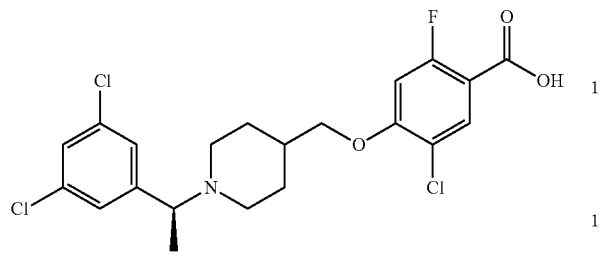

To a solution of (S)-tert-butyl 5-chloro-4-((1-(1-(3,5-dichlorophenyl)ethyl)piperidin-4-yl)methoxy)-2-fluorobenzoate (0.13 g, 0.24 mmol) in dichloromethane (6 mL) was added trifluoroacetic acid (3 mL). The reaction mixture was stirred at ambient temperature for 40 minutes and concentrated in vacuo to afford the title compound as a colorless syrup that was used directly in the next step: MS(ES+): m/z 460.0, 462.0 (M+1).

Step 3. Preparation of (S)-5-chloro-4-((1-(1-(3,5-dichlorophenyl)ethyl)piperidin-4-yl)methoxy)-2-fluoro-N-(methylsulfonyl)benzamide trifluoroacetic acid salt

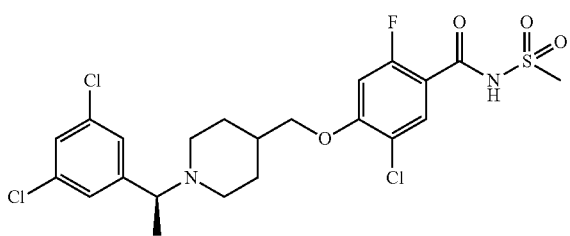 [SMILES: C[C@@H](c1cc(Cl)cc(Cl)c1)N1CCC(COc2cc(F)c(C(=O)NS(C)(=O)=O)cc2Cl)CC1]

To a solution of (S)-5-chloro-4-((1-(1-(3,5-dichlorophenyl)ethyl)piperidin-4-yl)methoxy)-2-fluorobenzoic acid, trifluoroacetic acid salt in anhydrous dichloromethane (10 mL) was added N-(3-dimethylaminopropyl)-N'-ethylcarbodiimide hydrochloride (0.09 g, 0.48 mmol), 4-(dimethylamino)pyridine (0.07 g, 0.54 mmol), and methanesulfonamide (0.04 g, 0.41 mmol). The reaction mixture was stirred at ambient temperature for 16 hours, and then diluted with ethyl acetate (100 mL). The mixture was washed with saturated aqueous ammonium chloride (100 mL), brine (2×100 mL), dried over anhydrous magnesium sulfate, filtered and concentrated in vacuo. The residue was purified by reverse-phase HPLC, eluting with a gradient of 20-80% acetonitrile in water with 0.1% trifluoroacetic acid to afford the title compound as a colorless solid (0.01 g, 1.5% in 2 steps): $^1$H NMR (300 MHz, DMSO-$d_6$) δ12.11 (br s, 1H), 9.42 (br s, 1H), 7.76-7.72 (m, 2H), 7.60 (s, 2H), 7.22 (d, J=12.4 Hz, 1H), 4.50 (brs, 1H), 4.02-4.00 (m, 2H), 3.66-3.59 (m, 1H), 3.34 (brs, 1H), 3.29 (s, 3H), 2.86-2.69 (m, 2H), 2.05-1.89 (m, 3H), 1.61-1.47 (m, 5H); MS(ES+) m/z 537.0, 539.0, 541.0 (M+1).

Example 403

Synthesis of (S)-5-chloro-N-(cyclopropylsulfonyl)-4-((1-(1-(3,5-dichlorophenyl)ethyl)piperidin-4-yl)methoxy)-2-fluorobenzamide, trifluoroacetic acid salt

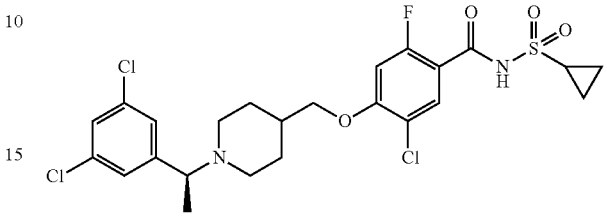

Following the procedure as described in Example 402 Step 3 and making non-critical variations as required to replace methanesulfonamide with cyclopropanesulfonamide, the title compound was obtained as a colorless solid (0.01 g, 13% in 2 steps): $^1$H NMR (300 MHz, DMSO-$d_6$) δ12.03 (br s, 1H), 9.42 (brs, 1H), 7.75-7.72 (m, 2H), 7.60 (s, 2H), 7.23 (d, J=12.4 Hz, 1H), 4.51 (brs, 1H), 4.02-4.00 (m, 2H), 3.67-3.60 (m, 1H), 3.45 (brs, 1H), 3.08-2.99 (m, 1H), 2.86-2.76 (m, 2H), 2.05-1.89 (m, 3H), 1.62-1.47 (m, 5H), 1.10-1.07 (m, 4H); MS(ES+) m/z 503.1, 565.1, 567.0 (M+1).

Example 404

Synthesis of (R)-5-chloro-4-((1-(1-(3,5-dichlorophenyl)ethyl)piperidin-4-yl)methoxy)-2-fluoro-N-(methylsulfonyl)benzamide, trifluoroacetic acid

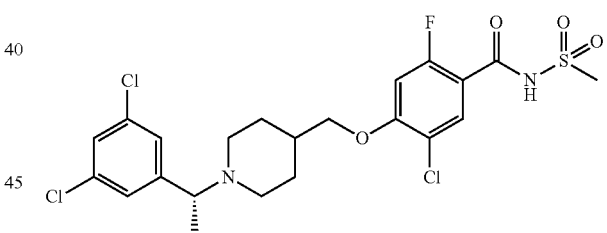

Step 1. Preparation of (R)-tert-butyl 5-chloro-4-((1-(1-(3,5-dichlorophenyl)ethyl)piperidin-4-yl)methoxy)-2-fluorobenzoate

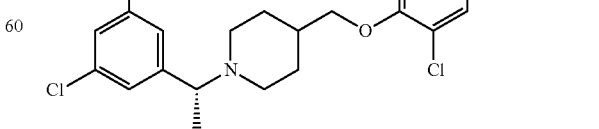

Following the procedure as described in Example 402 step 1 and making non-critical variations to replace (R)-1-

(3,5-dichlorophenyl)ethyl 4-methylbenzenesulfonate with (S)-1-(3,5-dichlorophenyl)ethyl 4-methylbenzenesulfonate, the title compound was obtained as a colorless syrup (0.10 g, 62%): $^1$H NMR (300 MHz, CDCl$_3$) δ7.84 (d, J=7.6 Hz, 1H), 7.20-7.19 (m, 3H), 6.59 (d, J=12.5 Hz, 1H), 4.83 (q, J=6.5, 6.5, 6.4 Hz, 1H), 3.83 (d, J=5.9 Hz, 2H), 3.40-3.34 (m, 1H), 3.03-3.00 (m, 1H), 2.81-2.77 (m, 1H), 2.04-1.76 (m, 6H), 1.55 (s, 9H), 1.31 (d, J=6.2 Hz, 3H); MS(ES+) m/z 516.0, 518.0, 520.0 (M+1).

Step 2. Preparation of (R)-5-chloro-4-((1-(1-(3,5-dichlorophenyl)ethyl)piperidin-4-yl)methoxy)-2-fluorobenzoic acid, trifluoroacetic acid salt

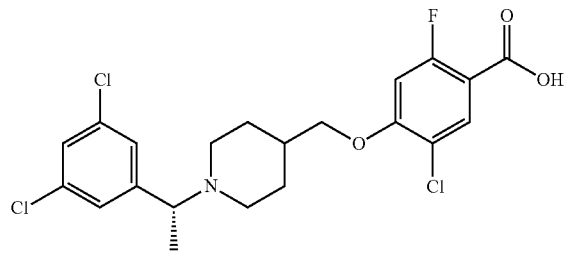 [SMILES: C[C@H](c1cc(Cl)cc(Cl)c1)N1CCC(COc2cc(F)c(C(=O)O)cc2Cl)CC1]

Following the procedure as described in Example 402 step 2 and making non-critical variations as required to replace (S)-tert-butyl 5-chloro-4-((1-(1-(3,5-dichlorophenyl)ethyl)piperidin-4-yl)methoxy)-2-fluorobenzoate with (R)-tert-butyl 5-chloro-4-((1-(1-(3,5-dichlorophenyl)ethyl)piperidin-4-yl)methoxy)-2-fluorobenzoate, the title compound was obtained as a colorless syrup (0.11 g, quant. yield) that was used directly in the next step: MS(ES+) m/z 460.0, 462.0 (M+1).

Step 3. Preparation of (R)-5-chloro-4-((1-(1-(3,5-dichlorophenyl)ethyl)piperidin-4-yl)methoxy)-2-fluoro-N-(methylsulfonyl)benzamide, trifluoroacetic acid salt

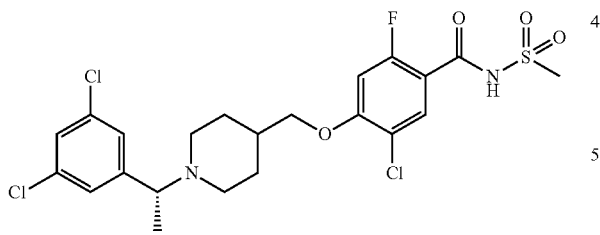

Following the procedure as described in Example 402 step 3 and making non-critical variations as required to (S)-5-chloro-4-((1-(1-(3,5-dichlorophenyl)ethyl)piperidin-4-yl)methoxy)-2-fluorobenzoic acid, trifluoroacetic acid salt with (R)-5-chloro-4-((1-(1-(3,5-dichlorophenyl)ethyl)piperidin-4-yl)methoxy)-2-fluorobenzoic acid, trifluoroacetic acid salt, the title compound was obtained as a colorless solid (0.01 g, 20% in 2 steps): $^1$H NMR (300 MHz, DMSO-d$_6$) δ12.08 (br s, 1H), 9.46 (br s, 1H), 7.76-7.72 (m, 2H), 7.60 (s, 2H), 7.21 (d, J=12.4 Hz, 1H), 4.48 (br s, 1H), 4.02-4.00 (m, 2H), 3.64-3.57 (m, 1H), 3.32 (br s, 1H), 3.27 (s, 3H), 2.83-2.73 (m, 2H), 2.04-1.88 (m, 3H), 1.60-1.46 (m, 5H); MS(ES+) m/z 537.0, 539.0, 541.0 (M+1).

Example 405

Synthesis of (R)-5-chloro-N-(cyclopropylsulfonyl)-4-((1-(1-(3,5-dichlorophenyl)ethyl)piperidin-4-yl)methoxy)-2-fluorobenzamide, trifluoroacetic acid salt

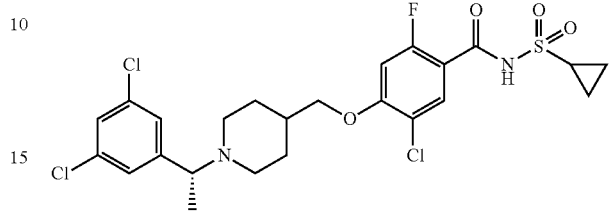

Following the procedure as described in Example 402 step 3 and making non-critical variations as required to replace (S)-5-chloro-4-((1-(1-(3,5-dichlorophenyl)ethyl)piperidin-4-yl)methoxy)-2-fluorobenzoic acid, trifluoroacetic acid salt with (R)-5-chloro-4-((1-(1-(3,5-dichlorophenyl)ethyl)piperidin-4-yl)methoxy)-2-fluorobenzoic acid, trifluoroacetic acid salt and to replace methanesulfonamide with cyclopropanesulfonamide, the title compound was obtained as a colorless solid (0.01 g, 13% over 2 steps); $^1$H NMR (300 MHz, DMSO-d$_6$) δ12.01 (br s, 1H), 0.48 (br s, 1H), 7.75-7.70 (m, 2H), 7.58 (s, 2H), 7.21 (d, J=12.4 Hz, 1H), 4.44 (br s, 1H), 4.02-4.00 (m, 2H), 3.62-3.53 (m, 1H), 3.44 (br s, 1H), 3.06-2.97 (m, 1H), 2.77-2.69 (m, 2H), 2.01-1.87 (m, 3H), 1.58-1.45 (m, 5H), 1.08-1.04 (m, 4H); MS(ES+) m/z 563.2, 565.3 (M+1).

Example 406

Synthesis of 5-chloro-4-((1-(3-chloro-5-(trifluoromethoxy)benzyl)piperidin-4-yl)methoxy)-2-fluoro-N-(methylsulfonyl)benzamide, trifluoroacetic acid salt

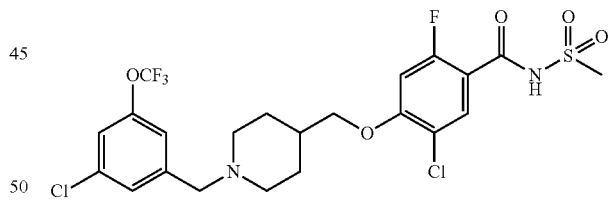

Step 1. Preparation of 3-chloro-5-(trifluoromethoxy)benzyl 4-methylbenzenesulfonate

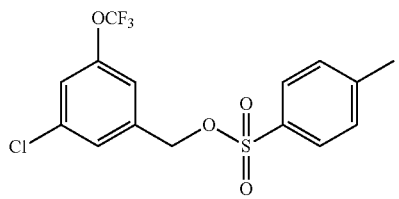 [SMILES: Cc1ccc(S(=O)(=O)OCc2cc(Cl)cc(OC(F)(F)F)c2)cc1]

To a cooled (0° C.) solution of 3-chloro-5-(trifluoromethoxy)benzaldehyde (0.45 g, 2.00 mmol) in anhydrous methanol (10 mL) was added sodium borohydride (0.15 g, 4.00 mmol). After stirring at 0° C. under a nitrogen atmosphere for 1 hour, the reaction mixture was quenched with saturated aqueous ammonium chloride (3 ml), diluted with ethyl acetate (100 mL), washed with 1 M hydrochloric acid solution (2×75 mL), dried over anhydrous magnesium sulfate, filtered, and concentrated in vacuo. The residue was dissolved in anhydrous dichloromethane (30 mL) and to this solution was added 4-methylbenzene-1-sulfonyl chloride (0.47 g, 2.5 mmol), triethylamine (1.4 mL, 9.9 mmol), and 4-dimethylaminopyridine (0.031 g, 0.25 mmol). The reaction mixture was stirred at ambient temperature for 2.5 hours, then diluted with dichloromethane (100 mL), washed with water (100 mL) and brine (100 mL), dried over anhydrous magnesium sulfate, filtered, and concentrated in vacuo. The residue was purified by column chromatography, eluting with a gradient of 0-10% ethyl acetate in hexanes to afford the title compound as a colorless syrup (0.25 g, 33%): $^1$H NMR (300 MHz, CDCl$_3$) δ7.75 (d, J=8.1 Hz, 2H), 7.31 (d, J=8.1 Hz, 2H), 7.14 (br s, 2H), 6.96 (br s, 1H), 5.01 (s, 2H), 2.42 (s, 3H).

Step 2. Preparation of tert-butyl 5-chloro-4-((1-(3-chloro-5-(trifluoromethoxy)benzyl)piperidin-4-yl)methoxy)-2-fluorobenzoate

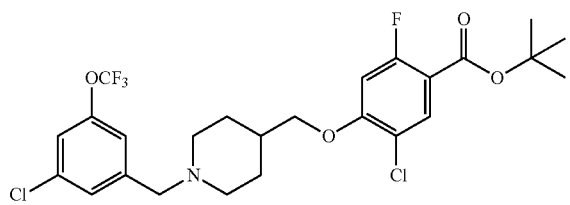 [SMILES: CC(C)(C)OC(=O)c1cc(Cl)c(OCC2CCN(Cc3cc(Cl)cc(OC(F)(F)F)c3)CC2)cc1F]

Following the procedure as described in Example 402 step 1 and making non-critical variations to replace (R)-1-(3,5-dichlorophenyl)ethyl 4-methylbenzenesulfonate with 3-chloro-5-(trifluoromethoxy)benzyl 4-methylbenzenesulfonate, the title compound was obtained as a colorless syrup (0.27 g, 83%): $^1$H NMR (300 MHz, CDCl$_3$) δ7.85 (d, J=7.7 Hz, 1H), 7.26 (br s, 1H), 7.10 (brs, 2H), 6.60 (d, J=12.1 Hz, 1H), 3.85 (d, J=6.3 Hz, 2H), 3.47 (s, 2H), 2.89-2.85 (m, 2H), 2.07-2.00 (m, 2H), 1.90-1.82 (m, 3H), 1.56 (s, 9H), 1.48-1.39 (m, 2H); MS(ES+) m/z 552.0, 554.0 (M+1).

Step 3. Preparation of 5-chloro-4-((1-(3-chloro-5-(trifluoromethoxy)benzyl)piperidin-4-yl)methoxy)-2-fluorobenzoic acid, trifluoroacetic acid salt

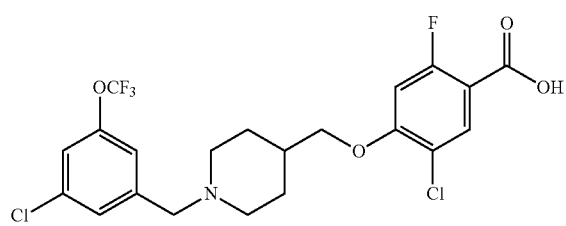 [SMILES: O=C(O)c1cc(Cl)c(OCC2CCN(Cc3cc(Cl)cc(OC(F)(F)F)c3)CC2)cc1F]

Following the procedure as described in Example 402 Step 2 and making non-critical variations as required to replace (S)-tert-butyl 5-chloro-4-((1-(1-(3,5-dichlorophenyl)ethylpiperidin-4-yl)methoxy)-2-fluorobenzoate with tert-butyl 5-chloro-4-((1-(3-chloro-5-(trifluoromethoxy)benzyl)piperidin-4-yl)methoxy)-2-fluorobenzoate, the title compound was obtained as a light yellow syrup (0.29 g, 98%) that was used directly in the next reaction: MS(ES+) m/z 498.0, 496.0 (M+1).

Step 4. Preparation of 5-chloro-4-((1-(3-chloro-5-(trifluoromethoxy)benzyl)piperidin-4-yl)methoxy)-2-fluoro-N-(methylsulfonyl)benzamide, trifluoroacetic acid salt

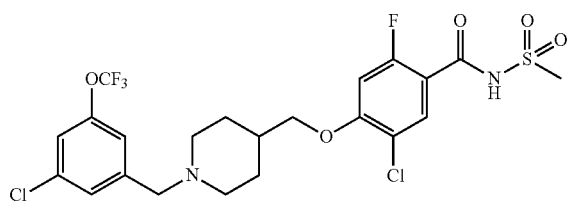 [SMILES: CS(=O)(=O)NC(=O)c1cc(Cl)c(OCC2CCN(Cc3cc(Cl)cc(OC(F)(F)F)c3)CC2)cc1F]

Following the procedure as described in Example 402 step 3 and making non-critical variations as required to replace (S)-5-chloro-4-((1-(1-(3,5-dichlorophenyl)ethyl)piperidin-4-yl)methoxy)-2-fluorobenzoic acid, trifluoroacetic acid salt with 5-chloro-4-((1-(3-chloro-5-(trifluoromethoxy)benzyl)piperidin-4-yl)methoxy)-2-fluorobenzoic acid, trifluoroacetic acid salt, the title compound (0.05 g, 41% in 2 steps) was obtained as a colorless solid: $^1$H NMR (300 MHz, DMSO-d$_6$) δ11.90 (br s, 1H), 9.80 (br s, 1H), 7.75 (d, J=7.3 Hz, 1H), 7.67-7.64 (m, 2H), 7.52 (s, 1H), 7.21 (d, J=12.4 Hz, 1H), 4.27 (brs, 2H), 4.04-4.02 (m, 2H), 3.32 (brs, 2H), 3.27 (s, 3H), 2.97-2.85 (m, 2H), 2.06-1.90 (m, 3H), 1.59-1.46 (m, 2H); MS(ES+) m/z 573.0, 575.0 (M+1).

Example 407

Synthesis of 5-chloro-4-((1-(3-chloro-5-(trifluoromethoxy)benzyl)piperidin-4-yl)methoxy)-N-(cyclopropylsulfonyl)-2-fluorobenzamide, trifluoroacetic acid salt

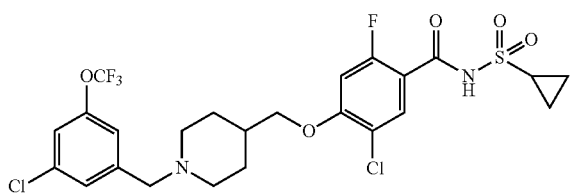 [SMILES: O=C(NS(=O)(=O)C1CC1)c1cc(Cl)c(OCC2CCN(Cc3cc(Cl)cc(OC(F)(F)F)c3)CC2)cc1F]

Following the procedure as described in Example 402 step 3 and making non-critical variations as required to replace (S)-5-chloro-4-((1-(1-(3,5-dichlorophenyl)ethyl)piperidin-4-yl)methoxy)-2-fluorobenzoic acid, trifluoroacetic acid salt with 5-chloro-4-((1-(3-chloro-5-(trifluoromethoxy)benzyl)piperidin-4-yl)methoxy)-2-fluorobenzoic acid, trifluoroacetic acid salt and to replace methanesulfonamide with cyclopropanesulfonamide, the title compound was obtained as a colorless solid (0.05 g, 46% over 2 steps): $^1$H NMR (300 MHz, DMSO-d$_6$) δ12.04 (br s, 1H), 9.75 (br s, 1H), 7.74 (d, J=7.5 Hz, 1H), 7.69-7.66 (m, 2H), 7.54 (s, 1H), 7.24 (d, J=12.4 Hz, 1H), 4.33 (brs, 2H), 4.04-4.02 (m, 2H), 3.43-3.40 (m, 2H), 3.08-2.93 (m, 3H), 2.07-1.92 (d, J=3H), 1.60-1.47 (m, 2H), 1.11-1.08 (m, 4H); MS(ES+) m/z 599.3, 601.0 (M+1).

Example 408

Synthesis of N-(azetidin-1-ylfulfonyl)-5-chloro-4-((1-(3-chloro-5-(trifluoromethoxy)benzyl)piperidin-4-yl)methoxy)-2-fluorobenzamide, trifluoroacetic acid suit

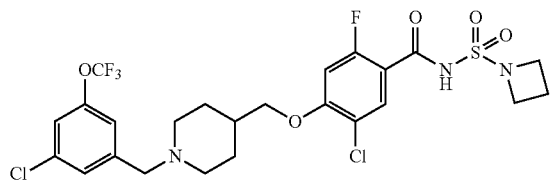 [SMILES: O=C(NS(=O)(=O)N1CCC1)c1cc(Cl)c(OCC2CCN(Cc3cc(Cl)cc(OC(F)(F)F)c3)CC2)cc1F]

Following the procedure as described in Example 402 step 3 and making non-critical variations as required to replace (S)-5-chloro-4-((1-(1-(3,5-dichlorophenyl)ethyl)piperidin-4-yl)methoxy)-2-fluorobenzoic acid, trifluoroacetic acid salt with 5-chloro-4-((1-(3-chloro-5-(trifluoromethoxy)benzyl)piperidin-4-yl)methoxy)-2-fluorobenzoic acid, trifluoroacetic acid salt and to replace methanesulfonamide with azetidine-1-sulfonamide, the title compound was obtained as a colorless solid (0.06 g, 53% in 2 steps): $^1$H NMR (300 MHz, DMSO-$d_6$) δ11.82 (br s, 1H), 9.57 (br s, 1H), 7.77 (d, J=7.4 Hz, 1H), 7.70-7.66 (m, 2H), 7.54 (s, 1H), 7.24 (d, J=12.2 Hz, 1H), 4.32 (br s, 2H), 4.04-3.99 (m, 6H), 3.43-3.39 (m, 2H), 3.01-2.92 (m, 2H), 2.19-1.93 (m, 5H), 1.58-1.45 (m, 2H): MS(ES+) m/z 613.9, 615.9 (M+1).

Example 409

Synthesis of 4-((1-(3-chloro-5-(trifluoromethoxy)benzyl)piperidin-4-yl)methoxy)-5-cyano-N-(cyclopropylsulfonyl)-2-fluorobenzamide, trifluoroacetic acid salt

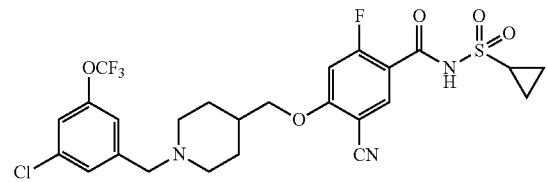 [SMILES: N#Cc1cc(C(=O)NS(=O)(=O)C2CC2)c(F)cc1OCC1CCN(Cc2cc(Cl)cc(OC(F)(F)F)c2)CC1]

Step 1. Preparation of tert-butyl 4-((1-(3-chloro-5-(trifluoromethoxy)benzyl)piperidin-4-yl)methoxy)-5-cyano-2-fluorobenzoate

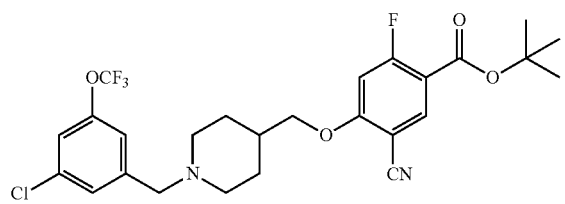 [SMILES: CC(C)(C)OC(=O)c1cc(C#N)c(OCC2CCN(Cc3cc(Cl)cc(OC(F)(F)F)c3)CC2)cc1F]

Following the procedure as described in Example 402 step 1 and making non-critical variations as required to replace tert-butyl 5-chloro-2-fluoro-4-(piperidin-4-ylmethoxy)benzoate hydrochloride with tert-butyl 5-cyano-2-fluoro-4-(piperidin-4-ylmethoxy)benzoate, trifluoroacetic salt and to replace (R)-1-(3,5-dichlorophenyl)ethyl 4-methylbenzenesulfonate with 3-chloro-5-(trifluoromethoxy)benzyl 4-methylbenzenesulfonate, the title compound was obtained as a colorless syrup (0.03 g, 7%): $^1$H NMR (300 MHz; CDCl$_3$) δ8.12 (d, J=8.0 Hz, 1H), 7.26 (br s, 1H), 7.09 (br s, 2H), 6.65 (d, J=12.1 Hz, 1H), 3.90 (d, J=6.6 Hz, 2H), 3.47 (s, 2H), 2.89-2.85 (m, 2H), 2.07-1.84 (m, 5H), 1.56 (s, 9H), 1.45-1.32 (m, 2H); MS(ES+) m/z 543.3, 545.1 (M+1).

Step 2. Preparation of 4-((1-(3-chloro-5-(trifluoromethoxy)benzyl)piperidin-4-yl)methoxy)-5-cyano-2-fluorobenzoic acid, trifluoroacetic acid salt

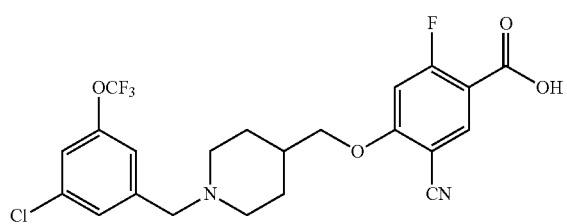 [SMILES: N#Cc1cc(C(=O)O)c(F)cc1OCC1CCN(Cc2cc(Cl)cc(OC(F)(F)F)c2)CC1]

Following the procedure as described in Example 402 step 2 and making non-critical variations as required to replace (S)-tert-butyl 5-chloro-4-((1-(1-(3,5-dichlorophenyl)ethyl)piperidin-4-yl)methoxy)-2-fluorobenzoate with tert-butyl 4-((1-(3-chloro-5-(trifluoromethoxy)benzyl)piperidin-4-yl)methoxy)-5-cyano-2-fluorobenzoate, the title compound was obtained as a colorless solid (0.03 g, quant. yield) that was used directly in the next step: MS(ES+) m/z 487.0 (M+1).

Step 3. Preparation of 4-((1-(3-chloro-5-(trifluoromethoxy)benzyl)piperidin-4-yl)methoxy)-5-cyano-N-(cyclopropylsulfonyl)-2-fluorobenzamide, trifluoroacetic acid salt

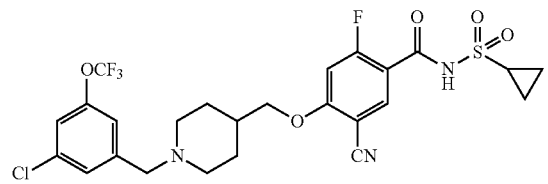 [SMILES: N#Cc1cc(C(=O)NS(=O)(=O)C2CC2)c(F)cc1OCC1CCN(Cc2cc(Cl)cc(OC(F)(F)F)c2)CC1]

Following the procedure as described in Example 402 step 3 and making non-critical variations as required to replace (S)-5-chloro-4-((1-(1-(3,5-dichlorophenyl)ethyl)piperidin-4-yl)methoxy)-2-fluorobenzoic acid, trifluoroacetic acid salt with 4-((1-(3-chloro-5-(trifluoromethoxy)benzyl)piperidin-4-yl)methoxy)-5-cyano-2-fluorobenzoic acid, trifluoroacetic acid salt and to replace methanesulfonamide with cyclopropanesulfonamide, the title compound (0.02 g, 43% in 2 steps) was obtained as a colorless solid: $^1$H NMR (300 MHz, DMSO-$d_6$+5% D$_2$O) δ8.12 (d, J=7.8 Hz, 1H), 7.67-7.64 (m, 2H), 7.52 (s, 1H), 7.31 (d, J=12.6 Hz, 1H), 4.31 (s, 2H), 4.09-4.07 (m, 2H), 3.43-3.39 (m, 2H), 3.06-

2.93 (m, 3H), 2.11-1.03 (m, 1H), 1.96-1.92 (m, 2H), 1.57-1.44 (m, 1H), 1.10-1.07 (m, 4H); MS(ES+) m/z 592.0, 590.0 (M+1).

Example 410

Synthesis of 4-((1-((3-(2-chlorophenyl)-1,2,4-oxadiazol-5-yl)methyl)piperidin-4-yl)methoxy)-5-cyclopropyl-2-fluoro-N-(methylsulfonyl)benzamide, trifluoroacetic acid salt

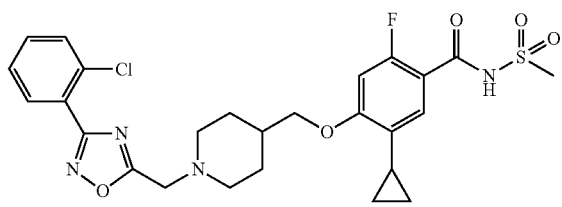 [SMILES: CS(=O)(=O)NC(=O)c1cc(C2CC2)c(OCC2CCN(Cc3nc(-c4ccccc4Cl)no3)CC2)cc1F]

Step 1. Preparation of methyl 4-((1-((3-(2-chlorophenyl)-1,2,4-oxadiazol-5-yl)methyl)piperidin-4-yl)methoxy)-5-cyclopropyl-2-fluorobenzoate

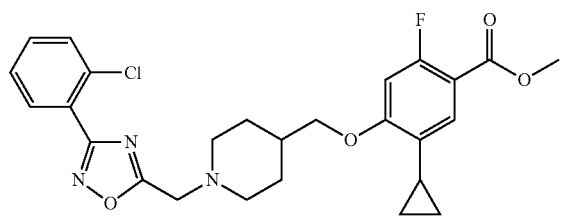 [SMILES: COC(=O)c1cc(C2CC2)c(OCC2CCN(Cc3nc(-c4ccccc4Cl)no3)CC2)cc1F]

Following the procedure as described in Example 402 step 1 and making non-critical variations as required to replace tert-butyl 5-chloro-2-fluoro-4-(piperidin-4-ylmethoxy)benzoate hydrochloride with methyl 5-cyclopropyl-2-fluoro-4-(piperidin-4-ylmethoxy)benzoate hydrochloride and to replace (R)-1-(3,5-dichlorophenyl)ethyl 4-methylbenzenesulfonate with 5-(chloromethyl)-3-(2-chlorophenyl)-1,2,4-oxadiazole and adding tetra-n-butylammonium iodide to the reaction mixture, the title compound was obtained as a colorless syrup (1.13 g, 85%): $^1$H NMR (300 MHz, CDCl$_3$) δ7.92 (dd, J=2.0, 7.4 Hz, 1H), 7.52 (dd, J=1.3, 7.8 Hz, 1H), 7.46-7.34 (m, 3H), 6.52 (6, J=12.7 Hz, 1H), 3.97 (s, 2H), 3.86-3.83 (m, 5H), 3.09-3.05 (m, 2H), 2.37-2.29 (m, 2H), 2.05-1.96 (m, 1H), 1.89-1.86 (m, 3H), 1.61-1.47 (m, 2H), 0.92-0.85 (m, 2H), 0.64-0.59 (m, 2H); MS (ES+) m/z 500.0, 502.0 (M+1).

Step 2. Preparation of 4-((1-((3-(2-chlorophenyl)-1,2,4-oxadiazol-5-yl)methyl)piperidin-4-yl)methoxy)-5-cyclopropyl-2-fluorobenzoic acid

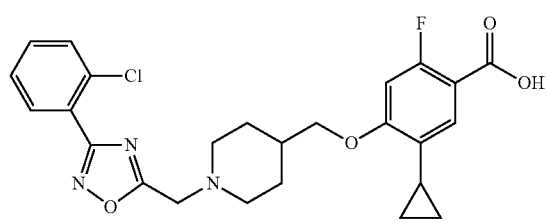 [SMILES: O=C(O)c1cc(C2CC2)c(OCC2CCN(Cc3nc(-c4ccccc4Cl)no3)CC2)cc1F]

Following the procedure as described in Example 354 step 2 and making non-critical variations as required to replace 5-cyclopropyl-2-fluoro-4-((1-((2-methylthiazol-4-yl)methyl)piperidin-4-yl)methoxy)benzoate with fluoro 4-((1-(93-(2-chlorophenyl)-1,2,4-oxadiazol-5-yl)methyl)piperidin-4-yl)methoxy-5-cyclopropyl-2-fluorobenzene, the title compound was obtained following trituration in diethyl ether (10 mL) as a colorless solid (0.43 g, 39%): MS(ES+) m/z 488.0, 486.0 (M+1).

Step 3. Preparation of 4-((1-((3-(2-chlorophenyl)-1,2,4-oxadiazol-5-yl)methyl)piperidin-4-yl)methoxy)-5-cyclopropyl-2-methyl-N-(methylsulfonyl)benzamide, trifluoroacetic acid salt

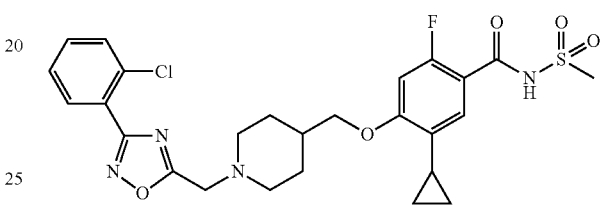

Following the procedure as described in Example 402 step 3 and making non-critical variations as required to replace (S)-5-chloro-4-((1-(1-(3,5-dichlorophenyl)ethyl)piperidin-4-yl)methoxy)-2-fluorobenzoic acid, trifluoroacetic acid salt with 4-((1-((3-(2-chlorophenyl)-1,2,4-oxadiazol-5-yl)methyl)piperidin-4-yl)methoxy)-5-cyclopropyl-2-fluorobenzoic acid, the title compound was obtained as a colorless solid (0.08 g, 39%); $^1$H NMR (300 MHz, DMSO-d$_6$) δ11.76 (br s, 2H), 7.93 (dd, J=1.8, 7.6 Hz, 1H), 7.70-7.52 (m, 3H), 7.10 (d, J=8.3 Hz, 5H), 6.94 (d, J=13.0 Hz, 1H), 4.68 (br s, 2H), 3.97 (d, J=5.1 Hz, 2H), 3.53-3.48 (m, 2H), 3.30 (s, 3H), 3.03-2.92 (m, 2H), 2.05-1.92 (m, 4H), 1.66-1.54 (m, 2H), 0.89-0.83 (m, 2H), 0.67-0.62 (m, 2H); MS(ES+) m/z 562.9, 564.9 (M+1).

Example 411

Synthesis of 5-cyclopropyl-N-(cyclopropylsulfonyl)-4-((1-((3,5-dichlorophenyl)(phenyl)methyl)piperidin-4-yl)methoxy)-2-fluorobenzamide, trifluoroacetic acid salt

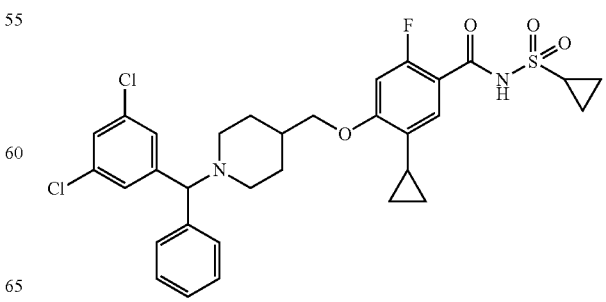

Step 1. Preparation of methyl 5-cyclopropyl-4-((1-((3,5-dichlorophenyl)(phenyl)methyl)piperidin-4-ylmethoxy)-2-fluorobenzoate

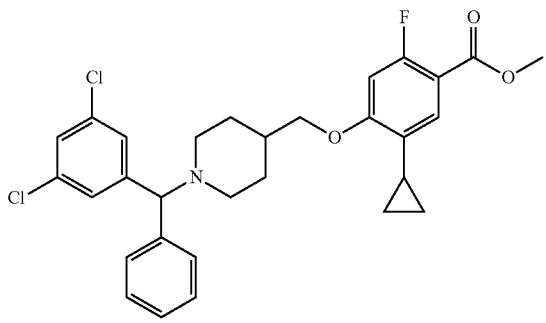 [SMILES: COC(=O)c1cc(C2CC2)c(OCC2CCN(C(c3ccccc3)c3cc(Cl)cc(Cl)c3)CC2)cc1F]

Following the procedure as described in Example 402 step 1 and making non-critical variations as required to replace tert-butyl 5-chloro-2-fluoro-4-(piperidin-4-ylmethoxy)benzoate hydrochloride with methyl 5-cyclopropyl-2-fluoro-4-(piperidin-4-ylmethoxy)benzoate hydrochloride and to replace (R)-1-(3,5-dichlorophenyl)ethyl 4-methylbenzenesulfonate with 1-(bromo(phenyl)methyl)-3,5-dichlorobenzene and adding tetra-n-butylammonium iodide to the reaction mixture, the title compound was obtained as a colorless syrup (0.66 g, 70%): $^1$H NMR (300 MHz, CDCl$_3$) δ7.42 (d, J=8.3 Hz, 1H), 7.33-7.21 (m, 7H), 7.16-7.15 (m, 1H), 6.52 (d, J=12.8 Hz, 1H), 4.21 (s, 1H), 3.86-3.82 (m, 5H), 2.92-2.84 (m, 2H), 2.02-1.76 (m, 6H), 1.54-1.37 (m, 2H). 0.90-0.84 (m, 2H), 0.64-0.58 (m, 2H); MS(ES+) m/z 544.0, 542.0 (M+1).

Step 2. Preparation of 5-cyclopropyl-4-((1-((3,5-dichlorophenyl)(phenyl)methyl)piperidin-4-yl)methoxy)-2-fluorobenzoic acid

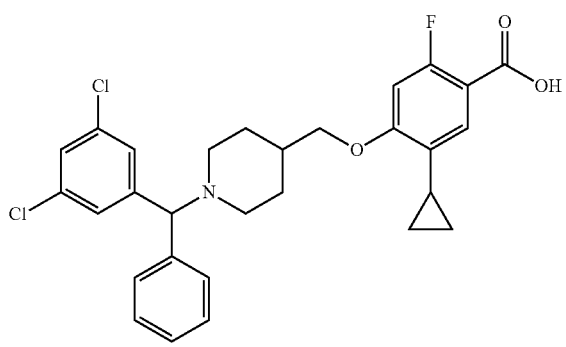 [SMILES: O=C(O)c1cc(C2CC2)c(OCC2CCN(C(c3ccccc3)c3cc(Cl)cc(Cl)c3)CC2)cc1F]

To a solution of methyl 5-cyclopropyl-4-((1-((3,5-dichlorophenyl)(phenyl)methyl)piperidin-4-yl)methoxy)-2-fluorobenzoate (0.66 g, 1.20 mmol) in tetrahydrofuran (20 mL) and water (5 mL) was added lithium hydroxide (0.30 g, 12.00 mmol). The reaction mixture was refluxed for 16 hours, then cooled to ambient temperature, diluted with 1 M hydrochloric acid solution (100 mL) and extracted with dichloromethane (100 mL). The solid present in the organic layer was filtered and washed with diethyl ether (20 mL) to afford the title compound as a colorless solid (0.25 g, 39%). The aqueous layer was further extracted with dichloromethane (2×75 mL). The organic layers were combined with the filtrate from the previous filtration, dried over anhydrous magnesium sulfate, filtered, and concentrated in vacuo to afford additional amount of the title compound as a colorless solid (0.32 g, 50%): MS(ES+) m/z 528.1, 530.0 (M+1).

Step 3. Preparation of 5-cyclopropyl-N-(cyclopropylsulfonyl)-4-((1-((3,5-dichlorophenyl)(phenyl)methyl)piperidin-4-yl)methoxy)-2-fluorobenzamide trifluoroacetic acid salt

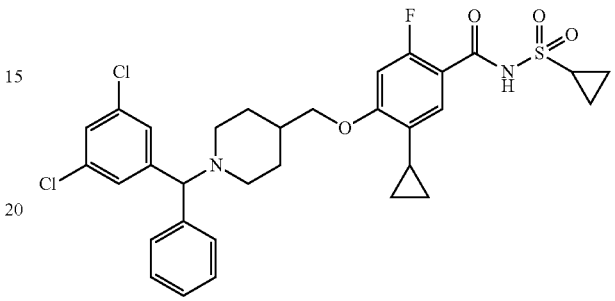

Following the procedure as described in Example 402 step 3 and making non-critical variations as required to replace (S)-5-chloro-4-((1-(1-(3,5-dichlorophenyl)ethyl)piperidin-4-yl)methoxy)-2-fluorobenzoic acid, trifluoroacetic acid salt with 5-cyclopropyl-4-((1-((3,5-dichlorophenyl)(phenyl)methyl)piperidin-4-yl)methoxy)-2-dichlorobenzoic acid, and to replace methanesulfonamide with cyclopropanesulfonamide, the title compound was obtained as a colorless solid (0.00 g, 30%): $^1$H NMR (300 MHz, DMSO-d$_6$+5% D$_2$O) δ7.69 (s, 2H), 7.61-7.56 (m, 3H), 7.47-7.35 (m, 3H), 7.06 (d, J=8.3 Hz, 1H), 6.91 (d, J=12.9 Hz, 1H), 5.44 (brs, 1H), 3.96-3.94 (m, 2H), 3.29-3.11 (m, 2H), 3.05-2.86 (m, 3H), 2.10-1.92 (m, 4H), 1.66-1.54 (m, 2H), 1.08-1.02 (m, 4H), 0.86-0.80 (m, 2H), 0.61-0.56 (m, 2H); MS(ES+) m/z 631.1, 633.0 (M+1).

Example 412

Synthesis of 5-cyclopropyl-4-((1-((3,5-dichlorophenyl)(phenyl)methyl)piperidin-4-yl)methoxy)-2-fluoro-N-(methylsulfonyl)benzamide, trifluoroacetic acid salt

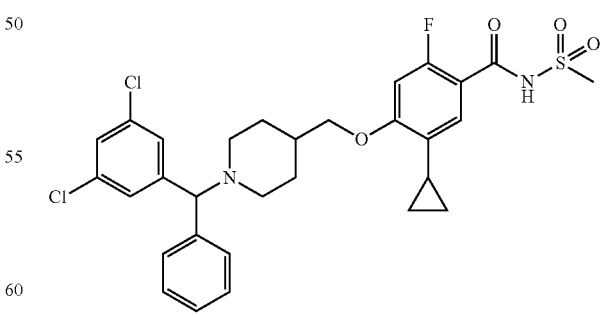

Following the procedure as described in Example 402 step 3 and making non-critical variations as required to replace (S)-5-chloro-4-((1-(1-(3,5-dichlorophenyl)ethyl)piperidin-4-yl)methoxy)-2-fluorobenzoic acid, trifluoroacetic acid salt with 5-cyclopropyl-4-((1-((3,5-dichlorophenyl)

(phenyl)methyl)piperidin-4-yl)methoxy)-2-fluorobenzoic acid, the title compound was obtained as a colorless solid (0.03 g, 11%): ¹H NMR (300 MHz, DMSO-d₆+5% D₂O) δ7.69 (s, 2H), 7.62-7.57 (m, 3H), 7.48-7.35 (m, 3H), 7.07 (d, J=8.3 Hz, 1H), 6.92 (d, J=12.9 Hz, 1H), 5.44 (brs, 1H), 3.96-3.95 (m, 2H), 3.28 (s, 3H), 3.19-2.28 (m, 4H), 2.07-1.92 (m, 4H), 1.65-1.55 (m, 2H), 0.86-0.80 (m, 2H), 0.63-0.58 (m, 2H); MS(ES+) m/z 605.1, 607.1 (M+1).

Example 413

Synthesis of 4-((1-(4-bromo-2-chlorobenzyl)piperidin-4-yl)methoxy-5-cyclopropyl-2-fluoro-N-(methylsulfonyl)benzamide, trifluoroacetic acid salt

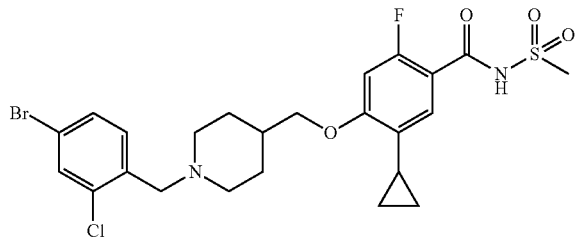 [SMILES: CS(=O)(=O)NC(=O)c1cc(C2CC2)c(OCC2CCN(Cc3ccc(Br)cc3Cl)CC2)cc1F]

Step 1. Preparation of methyl 4-((1-(4-bromo-2-chlorobenzyl)piperidin-4-yl)methoxy)-5-cyclopropyl-2-fluorobenzoate

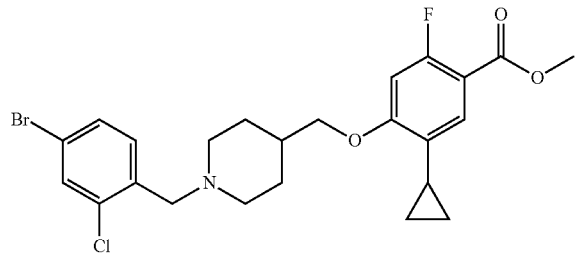 [SMILES: COC(=O)c1cc(C2CC2)c(OCC2CCN(Cc3ccc(Br)cc3Cl)CC2)cc1F]

Following the procedure as described in Example 402 step 1 and making non-critical variations as required to replace tert-butyl 5-chloro-2-fluoro-4-(piperidin-4-ylmethoxy)benzoate hydrochloride with methyl 5-cyclopropyl-2-fluoro-4-(piperidin-4-ylmethoxy)benzoate hydrochloride and to replace (R)-1-(3,5-dichlorophenyl)ethyl 4-methylbenzenesulfonate with 4-bromo-2-chloro-1-(chloromethyl)benzene and adding tetra-n-butylammonium iodide to the reaction mixture, the title compound was obtained as a light yellow solid (1.55 g, 86%): ¹H NMR (300 MHz, CDCl₃) δ7.49 (br s, 1H), 7.44-7.35 (m, 3H), 6.52 (dd, J=2.5, 12.8 Hz, 1H), 3.87-3.82 (m, 5H), 3.55 (d, J=2.5 Hz, 2H), 2.93-2.89 (m, 2H), 2.16-1.81 (m, 6H), 1.50-1.38 (m, 2H), 0.92-0.85 (m, 2H), 0.65-0.61 (m, 2H): MS(ES+) m/z 514.0, 512.0, 510.0 (M+1).

Step 2. Preparation of 4-((1-(4-bromo-2-chlorobenzyl)piperidin-4-yl)methoxy)-5-cyclopropyl-2-fluorobenzoic acid

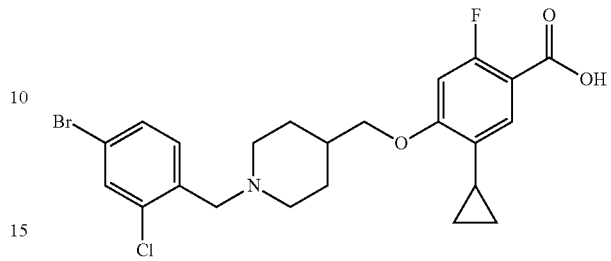

Following the procedure as described in Example 411 step 2 and making non-critical variations as required to replace methyl 4-((1-(bis(4-fluorophenyl)methyl)piperidin-4-yl)methoxy)-5-cyclopropyl-2-fluorobenzoate with methyl 4-((1-(4-bromo-2-chlorobenzyl)piperidin-4-yl)methoxy)-5-cyclopropyl-2-fluorobenzoate, the title compound was obtained following trituration in diethyl ether (10 ml) as a light pink solid (0.10 g, 22%): MS(ES+) m/z 500.0, 498.2, 496.0 (M+1).

Step 3. Preparation of 4-((1-(4-bromo-2-chlorobenzyl)piperidin-4-yl)methoxy)-5-cyclopropyl-2-fluoro-N-(methylsulfonyl)benzamide, trifluoroacetic acid salt

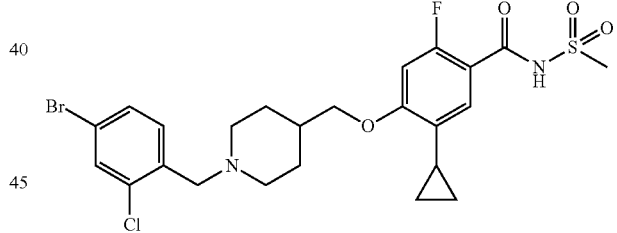

Following the procedure as described in Example 402 step 3 and making non-critical variations as required to replace (S)-5-chloro-4-((1-(1-(3,5-dichlorophenyl)ethyl)piperidin-4-yl)methoxy)-2-fluorobenzoic acid, trifluoroacetic acid salt with 4-((1-(4-bromo-2-chlorobenzyl)piperidin-4-yl)methoxy)-5-cyclopropyl-2-fluorobenzoic acid, the title compound was obtained as a colorless solid (0.02 g, 21%): ¹H NMR (300 MHz, DMSO-d₆) δ11.86 (br s, 1H), 9.48 (br s, 1H), 7.89 (d, J=1.7 Hz, 1H), 7.70 (dd, J=1.7, 8.3 Hz, 1H), 7.60 (d, J=8.3 Hz, 1H), 7.10 (d, J=8.3 Hz, 1H), 6.94 (d, J=12.9 Hz, 1H), 4.35 (s, 2H), 3.94 (brs, 2H), 3.40 (br s, 2H), 3.30 (s, 3H), 3.14-3.04 (m, 2H), 2.08-1.92 (m, 4H), 1.62-1.47 (m, 2H), 0.88-0.82 (m, 2H), 0.68-0.62 (m, 2H); MS(ES+) m/z 577.0, 575.0, 573.0 (M+1).

Example 414

Synthesis of 4-((1-(4-bromo-2-chlorobenzyl)piperidin-4-yl)methoxy)-5-cyclopropyl-N-(cyclopropylsulfonyl)-2-fluorobenzamide, trifluoroacetic acid salt

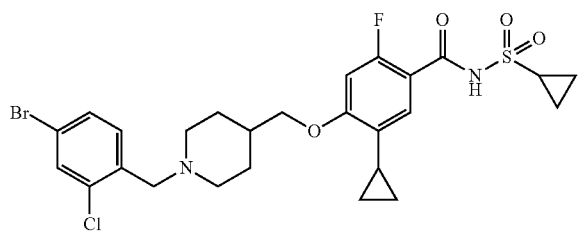 [SMILES: O=C(NS(=O)(=O)C1CC1)c1cc(C2CC2)c(OCC2CCN(Cc3ccc(Br)cc3Cl)CC2)cc1F]

Following the procedure as described in Example 402 step 3 and making non-critical variations as required to replace (S)-5-chloro-4-((1-(1-(3,5-dichlorophenyl)ethyl)piperidin-4-yl)methoxy)-2-fluorobenzoic acid, trifluoroacetic acid salt with 4-((1-(4-bromo-2-chlorobenzyl)piperidin-4-yl)methoxy)-5-cyclopropyl-2-fluorobenzoic acid, and to replace methanesulfonamide with cyclopropanesulfonamide, the title compound was obtained as a colorless solid (0.02 g, 26%): $^1$H NMR (300 MHz, DMSO-$d_6$) δ11.80 (br s, 1H), 9.46 (br s, 1H), 7.89 (d, J=1.6 Hz, 1H), 7.70 (dd, J=1.6, 8.3 Hz, 1H), 7.60 (d, J=8.3 Hz, 1H), 7.09 (d, J=8.3 Hz, 1H), 6.95 (d, J=12.9 Hz, 1H), 4.35 (s, 2H), 3.95-3.94 (m, 2H), 3.39 (br s, 2H), 3.13-2.99 (m, 3H), 2.04-1.93 (m, 4H), 1.61-1.46 (m, 2H), 1.09-1.06 (m, 4H), 0.89-0.82 (m, 2H), 0.67-0.62 (m, 2H); MS (ES+) m/z 603.0, 601.0, 599.0 (M+1).

Example 415

Synthesis of 4-((1-(2-chloro-4-cyclopropylbenzyl)piperidin-4-yl)methoxy)-5-cyclopropyl-2-fluoro-N-(methylsulfonyl)benzamide, trifluoroacetic acid salt

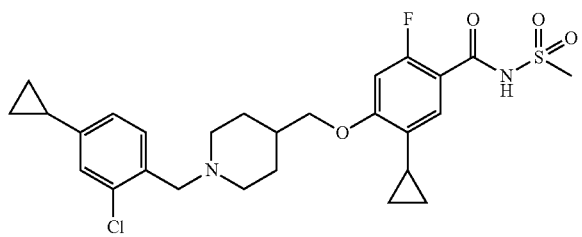 [SMILES: CS(=O)(=O)NC(=O)c1cc(C2CC2)c(OCC2CCN(Cc3ccc(C4CC4)cc3Cl)CC2)cc1F]

Step 1. Preparation of methyl 4-((1-(2-chloro-4-cyclopropylbenzyl)piperidin-4-yl)methoxy)-5-cyclopropyl-2-fluorobenzoate

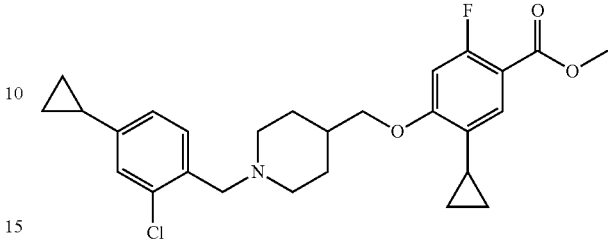

To a solution of methyl 4-((1-(4-bromo-2-chlorobenzyl)piperidin-4-yl)methoxy)-5-cyclopropyl-2-fluorobenzoate (1.03 g, 2.02 mmol) in anhydrous 1,4-dioxane (15 mL) was added cyclopropylboronic acid (1.06 g, 12.30 mmol), tribasic potassium phosphate (1.74 g, 8.22 mmol), and tetrakis(triphenylphosphine)palladium(0) (0.48 g, 0.42 mmol). The suspension was degassed with argon and heated at 100° C. for 30 minutes in a microwave reactor. After cooling to ambient temperature, the reaction mixture was diluted with ethyl acetate (100 mL), washed with saturated aqueous ammonium chloride (2×100 mL), dried over anhydrous magnesium sulfate, filtered and concentrated in vacuo. The residue was purified, by column chromatography eluting with a 0-20% gradient of ethyl acetate with 10% isopropanol, 10% triethylamine in hexanes to afford the title compound as a yellow syrup (0.94 g, 99%); $^1$H NMR (300 MHz, CDCl$_3$) δ7.42 (d, J=8.3 Hz, 1H), 7.31 (d, J=7.9 Hz, 1H), 7.02 (d, J=1.6 Hz, 1H), 6.92 (dd, J=1.6, 7.9 Hz, 1H), 6.52 (d, J=12.8 Hz, 1H), 3.86-3.81 (m, 5H), 3.57 (s, 2H), 2.96-2.92 (m, 2H), 2.13-1.96 (m, 3H), 1.87-1.80 (m, 4H), 1.49-1.37 (m, 2H), 0.98-0.85 (m, 4H), 0.55-0.50 (m, 4H); MS(ES+) m/z 474.1, 472.1 (M+1).

Step 2. Preparation of 4-((1-(2-chloro-4-cyclopropylbenzyl)piperidin-4-yl)methoxy)-5-cyclopropyl-2-fluorobenzoic acid

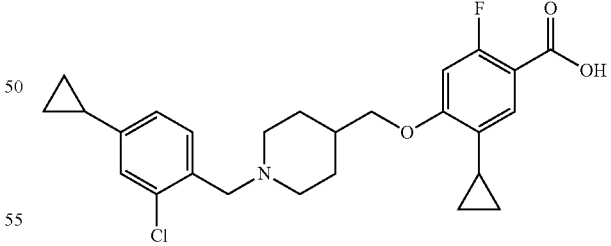

To a solution of methyl 4-((1-(2-chloro-4-cyclopropylbenzyl)piperidin-4-yl)methoxy)-5-cyclopropyl-2-fluorobenzoate (0.93 g, 2.00 mmol) in tetrahydrofuran (25 mL) and water (7 mL) was added lithium hydroxide (0.48 g, 20.00 mmol). The mixture was refluxed for 1.5 hours and cooled to ambient temperature. The reaction mixture was acidified with 1 M aqueous hydrochloric acid solution (10 mL), diluted with saturated aqueous ammonium chloride (150 mL) and extracted with ethyl acetate (2×150 mL). The combined organic layers were dried over anhydrous magnesium sulfate, filtered and concentrated in vacuo. The residue was triturated in diethyl ether (15 mL) to afford the title compound as a colorless solid (0.16 g, 18%). The aqueous layer contained white solid that was filtered, washed with water (100 mL) and diethyl, ether (40 mL) to afford additional amount of the title compound as a colorless solid (0.24 g, 27%): $^1$H NMR (300 MHz, DMSO-d6) δ10.25 (br s, 1H), 7.70 (d, J=7.9 Hz, 1H), 7.27-7.25 (m, 2H), 7.11 (d, J=7.9 Hz, 1H), 6.88 (d, J=13.0 Hz, 1H), 4.31 (d, J=3.7 Hz, 2H), 3.92 (d, J=5.4 Hz, 2H), 3.40-3.31 (m, 5H), 3.11-3.00 (m, 2H), 2.06-1.90 (m, 5H), 1.76-1.68 (m, 2H), 1.01-0.95 (m, 2H), 0.89-0.83 (m, 2H), 0.75-0.70 (m, 2H), 0.57-0.52 (m, 2H); MS(ES+) m/z 460.0, 558.2 (M+1).

Step 3. Preparation of 4-((1-(2-chloro-4-cyclopropylbenzyl)piperidin-4-yl)methoxy)-5-cyclopropyl-2-fluoro-N-(methylsulfonyl)benzamide, trifluoroacetic acid salt

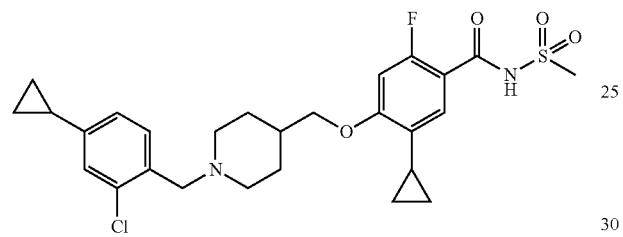

Following the procedure as described in Example 402 Step 3 and making non-critical variations as required to replace (S)-5-chloro-4-((1-(1-(3,5-dichlorophenyl)ethyl)piperidin-4-yl)methoxy-2-fluorobenzoic acid, trifluoroacetic acid salt with 4-((1-(2-chloro-4-cyclopropylbenzyl)piperidin-4-yl)methoxy)-5-cyclopropyl-2-fluorobenzoic acid, the title compound was obtained as a colorless solid (9.06 g, 36%): $^1$H NMR (300 MHz, DMSO-d$_6$) δ11.84 (brs, 1H), 9.57 (brs, 1H), 7.51 (d, J=8.0 Hz, 1H), 7.28-7.27 (m, 1H), 7.14-7.08 (m, 2H), 6.94 (d, J=12.9 Hz, 1H), 4.33 (s, 2H), 3.94 (s, 2H), 3.39 (br s, 2H), 3.30 (s, 3H), 3.12-3.04 (m, 2H), 2.10-1.92 (m, 5H), 1.64-1.55 (m, 2H), 1.02-0.96 (m, 2H), 0.88-0.82 (m, 2H), 0.75-0.70 (m, 2H), 0.67-0.62 (m, 2H); MS(ES+) m/z 537.1, 535.1 (M+1).

Example 416

Synthesis of 4-((1-(2-chloro-4-cyclopropylbenzyl) piperidin-4-yl)methoxy)-5-cyclopropyl-N-(cyclopropylsulfonyl)-2-fluorobenzamide, trifluoroacetic acid salt

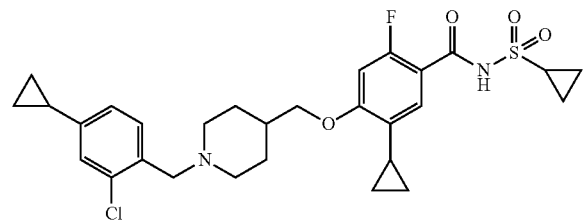 [SMILES: O=C(NS(=O)(=O)C1CC1)c1cc(C2CC2)c(OCC2CCN(Cc3ccc(C4CC4)cc3Cl)CC2)cc1F]

Following the procedure as described in Example 402 step 3 and making non-critical variations as required to replace (S)-5-chloro-4-((1-(1-(3,5-dichlorophenyl)ethyl)piperidin-4-yl)methoxy)-2-fluorobenzoic acid, trifluoroacetic acid salt with 4-((1-(2-chloro-4-cyclopropylbenzyl)piperidin-4-yl)methoxy-5-cyclopropyl-2-fluorobenzoic acid and to replace methanesulfonamide with cyclopropanesulfonamide, the title compound was obtained as a colorless solid (0.05 g, 26%): $^1$H NMR (300 MHz, DMSO-d$_6$) δ1.81 (br s, 1H), 9.47 (br s, 1H), 7.51 (d, J=8.0 Hz, 1H), 7.29-7.28 (m, 1H), 7.14-7.07 (m, 2H), 6.95 (d, J=13.0 Hz, 1H), 4.33 (s, 2H), 3.94-3.93 (m, 2H), 3.43-3.40 (m, 2H), 3.13-2.99 (m, 3H), 2.07-1.92 (m, 5H), 1.62-1.50 (m, 2H), 1.09-1.06 (m, 4H), 1.02-0.96 (m, 2H), 0.88-0.82 (m, 2H), 0.75-0.70 (m, 2H), 0.67-0.62 (m, 2H); MS(ES+) m/z 563.1, 561.2 (M+1).

Example 417

Synthesis of N-(azetidin-1-ylsulfonyl)-4-((1-(2-chloro-4-cyclopropylbenzyl)piperidin-4-yl) methoxy)-5-cyclopropyl-2-fluorobenzamide, trifluoroacetic acid salt

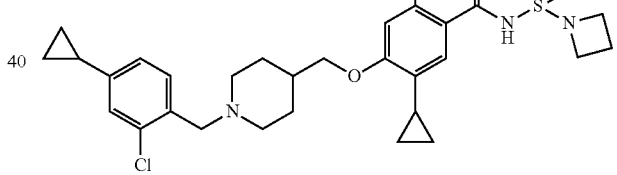

Following the procedure as described in Example 402 step 3 and making non-critical variations as required to replace (S)-5-chloro-4-((1-(1-(3,5-dichlorophenyl)ethyl)piperidin-4-yl)methoxy)-2-fluorobenzoic acid, trifluoroacetic acid salt with 4-((1-(2-chloro-4-cyclopropylbenzyl)piperidin-4-yl)methoxy-5-cyclopropyl-2-fluorobenzoic acid and to replace methanesulfonamide with azetidine-1-sulfonamide, the title compound was obtained as a colorless solid (0.06 g, 23%): $^1$H NMR (300 MHz, DMSO-d$_6$) δ11.59 (br s, 1H), 9.38 (br s, 1H), 7.51 (d, J=8.0 Hz, 1H), 7.29-7.28 (m, 1H), 7.15-7.07 (m, 2H), 6.95 (d, J=12.8 Hz, 1H), 4.33 (s, 2H), 4.01 (t, J=7.7 Hz, 4H), 3.94-3.93 (m, 2H), 3.44-3.40 (m, 2H), 3.12-3.04 (m, 2H), 2.18-1.91 (m, 7H), 1.62-1.50 (m, 2H), 1.02-0.96 (m, 1H), 0.89-0.82 (m, 2H), 0.75-0.70 (m, 2H), 0.68-0.63 (m, 2H); MS(ES+) m/z 578.0, 576.0 (M+1).

Example 418

Synthesis of 4-((1-(bis(4-fluorophenyl)methyl)piperidin-4-yl)methoxy)-5-cyclopropyl-2-fluoro-N-(methylsulfonyl)benzamide, trifluoroacetic acid salt

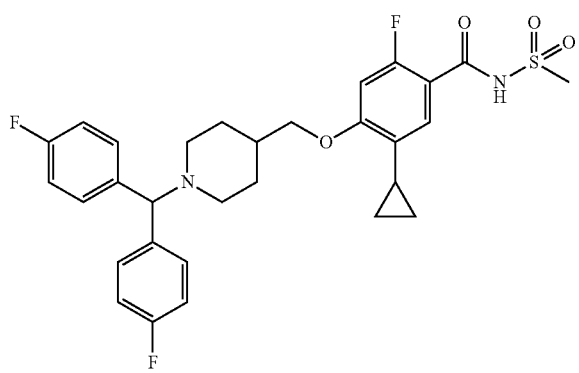 [SMILES: CS(=O)(=O)NC(=O)c1cc(C2CC2)c(OCC2CCN(C(c3ccc(F)cc3)c3ccc(F)cc3)CC2)cc1F]

Step 1. Preparation of methyl 4-((1-(bis(4-fluorophenyl)methyl)piperidin-4-yl)methoxy)-5-cyclopropyl-2-fluorobenzoate

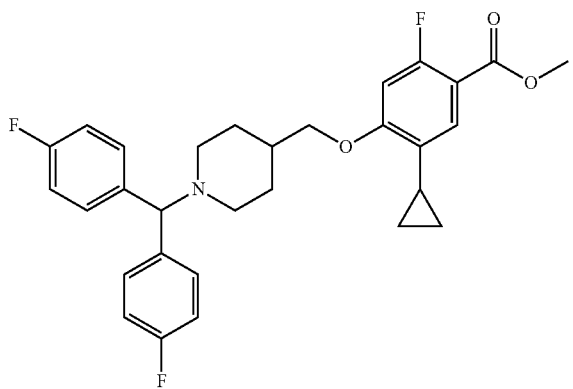 [SMILES: COC(=O)c1cc(C2CC2)c(OCC2CCN(C(c3ccc(F)cc3)c3ccc(F)cc3)CC2)cc1F]

Following the procedure as described in Example 402 step 1 and making non-critical variations as required to replace tert-butyl 5-chloro-2-fluoro-4-(piperidin-4-ylmethoxy)benzoate hydrochloride with methyl 5-cyclopropyl-2-fluoro-4-(piperidin-4-ylmethoxy)benzoate hydrochloride and to replace (R)-1-(3,5-dichlorophenyl)ethyl 4-methylbenzenesulfonate with 4,4'-(bromomethylene)bis(fluorobenzene) and adding tetra-n-butylammonium iodide to the reaction mixture, the title compound was obtained as a light yellow syrup (0.19 g, 18%): $^1$H NMR (300 MHz, CDCl$_3$) δ7.42 (d, J=8.3 Hz, 1H), 7.36-7.29 (m, 4H), 6.98-6.92 (m, 4H), 6.52 (d, J=12.8 Hz, 1H), 4.26 (s, 1H), 3.86 (s, 3H), 3.83 (d, J=6.1 Hz, 2H), 2.90-2.86 (m, 2H), 2.01-1.96 (m, 1H), 1.91-1.77 (m, 5H), 1.49-1.38 (m, 2H), 0.90-0.83 (m, 2H), 0.64-0.58 (m, 2H); MS(ES+) m/z 510.2 (M+1).

Step 2. Preparation of 4-((1-(bis(4-fluorophenyl)methyl)piperidin-4-yl)methoxy)-5-cyclopropyl-2-fluorobenzoic acid

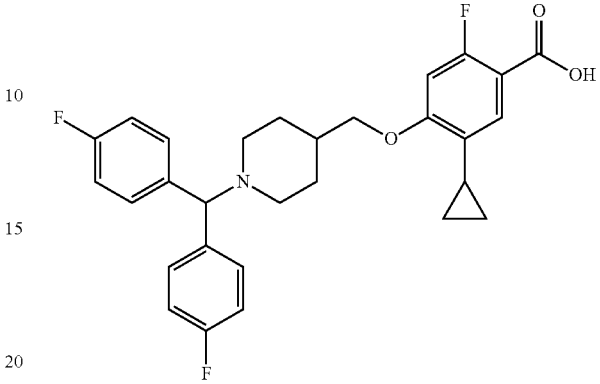

To a solution of methyl 4-((1-(bis(4-fluorophenyl)methyl)piperidin-4-ylmethoxy)-5-cyclopropyl-2-fluorobenzoate (0.19 g, 0.38 mmol) in tetrahydrofuran (10 mL) and water (3 mL) was added lithium hydroxide (0.10 g, 4.10 mmol). The mixture was refluxed for 6 hours, and then cooled to ambient temperature. The mixture was diluted with 1 M hydrochloric acid solution (100 mL) and extracted with ethyl acetate (2×100 mL). The combined organic layers were dried over anhydrous magnesium sulfate, filtered, and concentrated in vacuo to afford the title compound as a colorless syrup (0.19 g, quant. yield) that was used directly in the next reaction: MS(ES+) m/z 496.0 (M+1).

Step 3. Preparation of 4-((1-(bis(4-fluorophenyl)methyl)piperidin-4-yl)methoxy)-5-cyclopropyl-2-fluoro-N-(methylsulfonyl)benzamide, trifluoroacetic acid salt

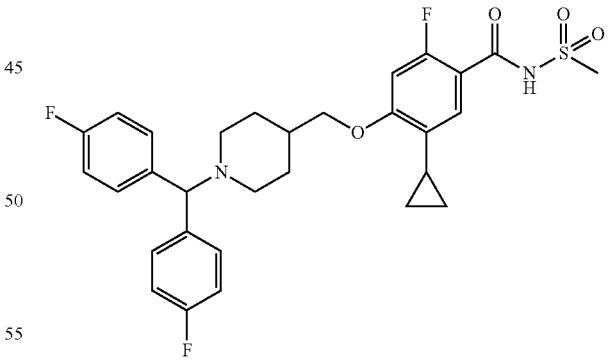

Following the procedure as described in Example 402 Step 3 and making non-critical variations as required to replace (S)-5-chloro-4-((1-(1-(3,5-dichlorophenyl)ethyl)piperidin-4-yl)methoxy)-2-fluorobenzoic acid, trifluoroacetic acid salt with 4-((1-(bis(4-fluorophenyl)methyl)piperidin-4-yl)methoxy)-5-cyclopropyl-2-fluorobenzoic acid, the title compound was obtained as a colorless solid (0.04 g, 27% in 2 steps): $^1$H NMR (300 MHz, DMSO-d$_6$) δ11.88 (br s, 1H), 9.98 (br s, 1H), 7.67 (br s, 4H), 7.31 (brs, 4H), 7.09 (d, J=8.2 Hz, 1H), 6.95 (d, J=13.0 Hz, 1H), 5.62-5.59 (m, 1H), 3.95

(d, J=5.0 Hz, 2H), 3.30 (s, 3H), 3.26-3.22 (m, 2H), 3.04-2.95 (m, 2H), 2.05-1.96 (m, 3H), 1.84-1.81 (m, 1H), 1.60-1.55 (m, 2H), 0.87-0.82 (m, 2H), 0.66-0.61 (m, 2H); MS(ES+) m/z 573.1 (M+1).

Example 419

Synthesis of N-azetidin-1-ylsulfonyl)-4-((1-(bis(4-fluorophenyl)methyl)piperidin-4-yl)methoxy)-5-cyclopropyl-2-fluorobenzamide, trifluoroacetic acid salt

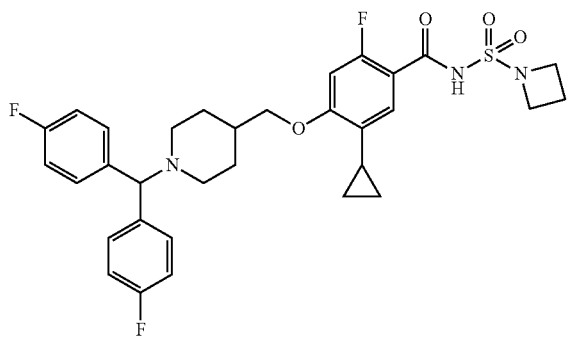 [SMILES: O=C(NS(=O)(=O)N1CCC1)c1cc(C2CC2)c(OCC2CCN(C(c3ccc(F)cc3)c3ccc(F)cc3)CC2)cc1F]

Following the procedure as described in Example 402 Step 3 and making non-critical variations as featured to replace (S)-5-chloro-4-((1-(1-(3,5-dichlorophenyl)ethylpiperidin-4-yl)methoxy)-2-fluorobenzoic acid, trifluoroacetic acid salt with 4-((1-(bis(4-fluorophenyl)methyl)piperidin-4-yl)methoxy)-5-cyclopropyl-2-fluorobenzoic acid, and to replace methanesulfonamide with azetidine-1-sulfonamide, the title compound was obtained as a colorless solid (0.04 g, 28%): $^1$H NMR (300 MHz, DMSO-$d_6$) δ11.59 (br s, 1H), 10.24 (br s, 1H), 7.72 (br s, 4H), 7.31 (br s, 4H), 7.09 (d, J=8.2 Hz, 1H), 6.96 (d, J=12.5 Hz, 1H), 4.01 (t, J=7.7, 7.7 Hz, 4H), 3.95 (d, J=4.4 Hz, 2H), 3.26-3.22 (m, 2H), 3.04-2.96 (m, 2H), 2.15-1.97 (m, 4H), 1.85-1.65 (m, 2H), 1.14 (t, J=7.3, 7.3 Hz, 2H), 0.87-0.82 (m, 2H), 0.66-0.61 (m, 2H); MS(ES+) m/z 614.1 (M+1).

Example 420

Synthesis of 5-cyclopropyl-4-((1-((3,5-dichlorophenyl)(phenyl)methyl)-3-methylazetidin-3-yl)methoxy)-2-fluoro-N-(methylsulfonyl)benzamide, trifluoroacetic acid salt

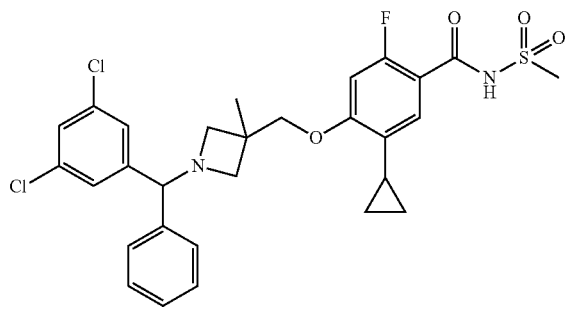 [SMILES: CC1(COc2cc(F)c(C(=O)NS(C)(=O)=O)cc2C2CC2)CN(C(c2ccccc2)c2cc(Cl)cc(Cl)c2)C1]

Step 1. Preparation of methyl 5-cyclopropyl-4-((1-((3,5-dichlorophenyl)(phenyl)methyl)-3-methylazetidin-3-yl)methoxy)-2-fluorobenzoate

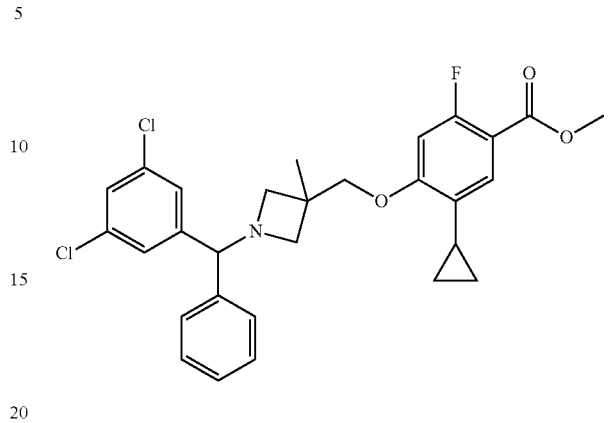

Following the procedure as described in Example 402 step 1 and making non-critical variations as required to replace tert-butyl 5-chloro-2-fluoro-4-(piperidin-4-ylmethoxy)benzoate hydrochloride with methyl 5-cyclopropyl-2-fluoro-4-((3-methylazetidin-3-yl)methoxy)benzoate hydrochloride, and to replace (R)-1-(3,5-dichlorophenyl)ethyl 4-methylbenzenesulfonate with 1-(bromo(phenyl)methyl)-3,5-dichlorobenzene and adding iodide to the reaction mixture, the title compound was obtained as a light yellow syrup (0.56 g, 62%); $^1$H NMR (300 MHz, CDCl$_3$) δ7.47 (d, J=8.3 Hz, 1H), 7.37-7.20 (m, 7H), 7.16-7.15 (m, 1H), 6.61 (d, J=12.6 Hz, 1H), 4.32 (s, 1H), 4.02 (s, 2H), 3.88 (s, 3H), 3.21 (dd, J=7.4, 12.0 Hz, 2H), 2.89 (dd, J=7.4, 9.8 Hz, 2H), 2.06-1.97 (m, 1H), 1.38 (s, 3H), 0.92-0.86 (m, 2H), 0.67-0.62 (m, 2H); MS(ES+) m/z 530.0, 528.0 (M+1).

Step 2. Preparation of 5-cyclopropyl-4-((1-((3,5-dichlorophenyl)(phenyl)methyl)-3-methylazetidin-3-yl)methoxy)-2-fluorobenzoic acid

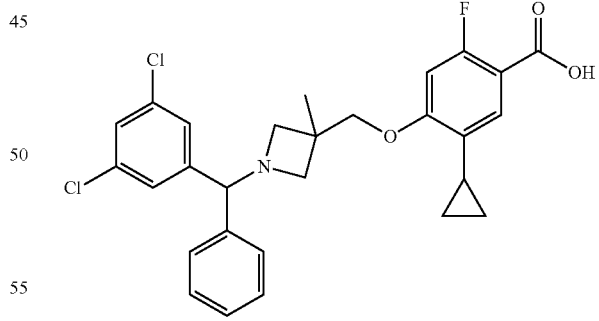

Following the procedure as described in Example 402 step 2 and making non-critical variations as required to replace methyl 4-((1-(bis(4-fluorophenyl)methyl)piperidin-4-yl)methoxy)-5-cyclopropyl-2-fluorobenzoate with methyl 5-cyclopropyl-4-((1-((3,5-dichlorophenyl)(phenyl)methyl)-3-methylazetidin-3-yl)methoxy)-2-fluorobenzoate, the title compound was obtained following trituration in diethyl ether (15 mL) (0.44 g, 80%) as a colorless solid: MS(ES+) m/z 516.1, 514.1. (M+1).

Step 3. Preparation of methyl-5-cyclopropyl-4-((1-((3,5-dichlorophenyl)(phenyl)methyl)-3-methylazetidin-3-yl)methoxy)-2-fluoro-N-(methylsulfonyl)benzamide, trifluoroacetic acid salt

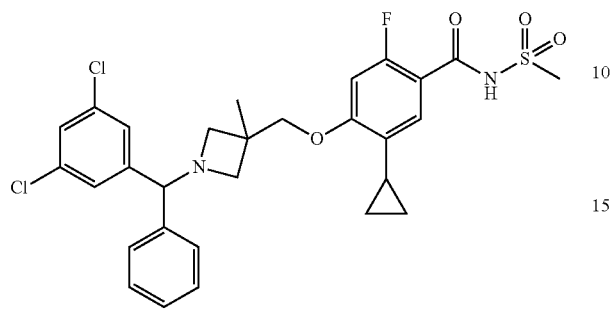

Following the procedure as described in Example 402 step 3 and making non-critical variations as required to replace (S)-5-chloro-4-((1-(1-(3,5-dichlorophenyl)ethyl)piperidin-4-yl)methoxy)-2-fluorobenzoic acid, trifluoroacetic acid salt with 5-cyclopropyl-4-((1-((3,5-dichlorophenyl)(phenyl)methyl)-3-methylazetidin-3-yl)methoxy)-2-fluorobenzoic acid, the title compound was obtained as a colorless solid (0.11 g, 37%): $^1$H NMR (300 MHz, DMSO-d$_6$+ 5% D$_2$O) δ7.60 (s, 1H), 7.52-7.51 (m, 2H), 7.45-7.35 (m, 5H), 7.13 (d, J=8.3 Hz, 1H), 6.91 (d, J=12.8 Hz, 1H), 5.50 (brs, 1H), 4.13 (brs, 2H), 3.89-3.57 (m, 4H), 3.29 (s, 3H), 2.04-1.95 (m, 1H), 1.40 (s, 3H), 0.85-0.78 (m, 2H), 0.65-0.56 (m, 2H): MS(ES+) m/z 592.9, 590.9 (M+1).

Example 421

Synthesis of 5-cyclopropyl-N-(cyclopropylsulfonyl)-4-((1-((3,5-dichlorophenyl)(phenyl)methyl)-3-methylazetidin-3-yl)methoxy)-2-fluorobenzamide, trifluoroacetic acid salt

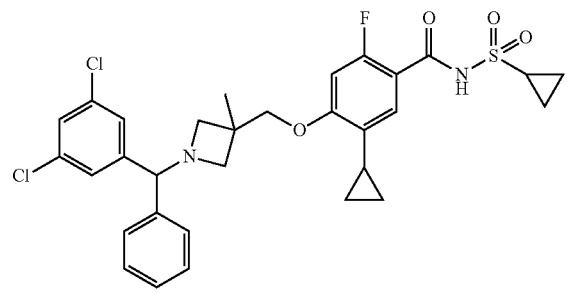 [SMILES: CC1(COc2cc(F)c(C(=O)NS(=O)(=O)C3CC3)cc2C2CC2)CN(C(c2ccccc2)c2cc(Cl)cc(Cl)c2)C1]

Following the procedure as described in Example 402 step 3 and making non-critical variations as required to replace (S)-5-chloro-4-((1-(1-(3,5-dichlorophenyl)ethyl)piperidin-4-yl)methoxy)-2-fluorobenzoic acid, trifluoroacetic acid salt with 5-cyclopropyl-4-((1-((3,5-dichlorophenyl)(phenyl)methyl)-3-methylazetidin-3-yl)methoxy)-2-fluorobenzoic acid and to replace methanesulfonamide with cyclopropanesulfonamide, the title compound was obtained as a colorless solid (0.14 g, 47%): $^1$H NMR (300 MHz, DMSO-d$_4$+5% D$_2$O) δ76.1 (s, 1H), 7.54-7.53 (m, 2H), 7.47-7.35 (m, 5H), 7.12 (d, J=8.3 Hz, 1H), 6.91 (d, J=12.8 Hz, 1H), 5.60 (br s, 1H), 4.14 (br s, 2H), 3.98-3.91 (m, 2H), 3.82-3.76 (m, 2H), 3.06-2.98 (m, 1H), 2.04-1.94 (m, 1H), 1.42 (s, 3H), 1.09-1.06 (m, 4H), 0.84-0.78 (m, 2H), 0.62-0.57 (m, 2H); MS(ES+) m/z 616.9, 618.9 (M+1).

Example 422

Synthesis of (R)-4-((1-(3-chloro-5-(trifluoromethoxy)benzyl)piperidin-3-yl)oxy)-5-cyclopropyl-2-fluoro-N-(methylsulfonyl)benzamide, trifluoroacetic acid salt

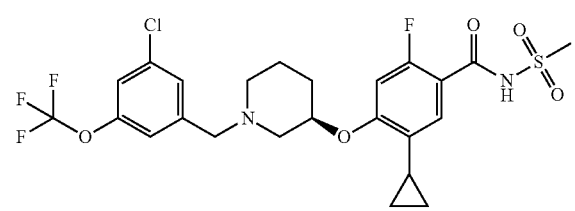 [SMILES: CS(=O)(=O)NC(=O)c1cc(C2CC2)c(O[C@@H]2CCCN(Cc3cc(Cl)cc(OC(F)(F)F)c3)C2)cc1F]

Step 1. Preparation of (R)-4-((1-(tert-butoxycarbonyl)piperidin-3-yl)oxy)-5-cyclopropyl-2-fluorobenzoic acid

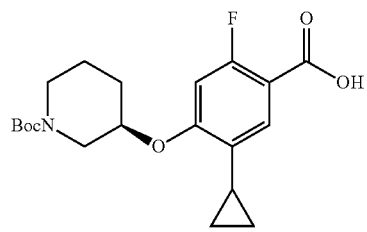 [SMILES: CC(C)(C)OC(=O)N1CCC[C@@H](Oc2cc(F)c(C(=O)O)cc2C2CC2)C1]

To a solution of (R)-tert-butyl 3-(4-(tert-butoxycarbonyl)-2-cyclopropyl-5-fluorophenoxy)piperidine-1-carboxylate (3.50 g, 8.05 mmol) in dichloromethane (20 mL) trifluoroacetic acid (5 mL) was added. The mixture was stirred for 1.5 hours and then a saturated aqueous solution of sodium bicarbonate (25 mL) was added followed by di-tert-butyl dicarbonate (1.93 g, 8.85 mmol). The reaction mixture was stirred for 1 hour, acidified with 1M aqueous hydrochloric acid solution to pH=1 and then extracted with dichloromethane (2×20 mL). The organic layers were combined, dried over anhydrous sodium sulfate, filtered and concentrated to give the title compound as a colorless solid (3.05 g, quant. yield): MS(ES+) m/z 380.2 (M+1).

Step 2. Preparation of (R)-tert-butyl 3-(2-cyclopropyl-5-fluoro-4-((methylsulfonyl)carbamoyl)phenoxy)piperidine-1-carboxylate

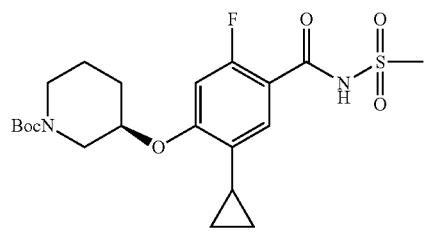 [SMILES: CC(C)(C)OC(=O)N1CCC[C@@H](Oc2cc(F)c(C(=O)NS(C)(=O)=O)cc2C2CC2)C1]

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy-5-cyclopropyl-2-fluorobenzoic acid with (R)-4-((1-(tert-butoxycarbonyl)piperidin-3-yl)oxy)-5-cyclopropyl-2-fluorobenzoic acid and the residue was purified by column chromatography eluting with gradient of 0% to 10% methanol containing 1% ammonia in dichloromethane, the title compound was obtained as a colorless solid (2.76 g, 75%): $^1$H NMR (300 MHz, CDCl$_3$) δ8.89-8.45 (brs, 1H), 7.56 (d, J=9.0 Hz, 1H), 6.61 (d, J=14.5 Hz, 1H), 4.41-4.25 (m, 1H), 3.81-3.25 (m, 7H), 2.10-1.75 (m, 4H), 1.66-1.17 (m, 10H), 0.96-0.81 (m, 2H), 0.75-0.52 (m, 2H).

Step 3. Preparation of (R)-5-cyclopropyl-2-fluoro-N-(methylsulfonyl)-4-(piperidin-3-yloxy)benzamide, trifluoroacetic acid salt

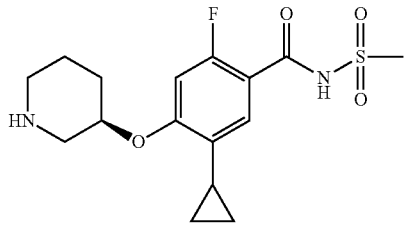 [SMILES: CS(=O)(=O)NC(=O)c1cc(C2CC2)c(O[C@@H]2CCCNC2)cc1F]

Following the procedure as described in Example 346 step 6, and making non-critical variations as required to replace tert-butyl 4-((4-tert-butoxycarbonyl)-2-cyclopropyl-5-fluorophenoxy)methyl)-4-fluoropiperidine-1-carboxylate with (R)-tert-butyl 3-(2-cyclopropyl-5-fluoro-4-((methylsulfonyl)carbamoyl)phenoxy)piperidine-1-carboxylate, the title compound was obtained as a colorless solid (2.75 g, quant. yield): MS(ES+) m/z 357.1 (M+1).

Step 4. (R)-4-((1-(3-chloro-5-(trifluoromethoxy) benzyl)piperidin-3-yl)oxy)-5-cyclopropyl-2-fluoro-N-(methylsulfonyl)benzamide, trifluoroacetic acid salt

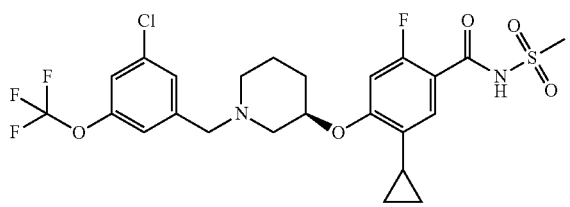 [SMILES: CS(=O)(=O)NC(=O)c1cc(C2CC2)c(O[C@@H]2CCCN(Cc3cc(Cl)cc(OC(F)(F)F)c3)C2)cc1F]

To a stirred solution of (R)-5-cyclopropyl-2-fluoro-N-(methylsulfonyl)-4-(piperidin-3-yloxy)benzamide trifluoroacetate (0.05 g, 0.10 mmol) and 3-chloro-5-(trifluoromethoxy)benzaldehyde (0.033 g, 0.15 mmol) in tetrahydrofuran (1 mL) was added sodium triacetoxyborohydride (0.073 g, 0.23 mmol). After stirring at ambient temperature for 16 hours, the reaction was quenched by adding 1 n aqueous hydrochloric acid solution (0.4 mL) and the mixture was purified by column chromatography eluting with 5% methanol in dichloromethane to give an oil, which was further purified by preparative HPLC to afford the title compound as a colorless solid (0.03 g, 45%): $^1$H NMR (300 MHz, DMSO-d$_6$) δ12.19-11.69 (m, 1H), 10.04-9.66 (m, 1H), 7.76-7.62 (m, 2H), 7.61-7.49 (m, 1H), 7.14-7.01 (m, 2H), 5.01-4.58 (m, 1H), 4.57-4.18 (m, 2H), 3.67-2.77 (m, 7H), 2.42-1.49 (m, 5H), 0.96-0.76 (m, 2H), 0.73-0.60 (m, 2H); MS(ES+) m/z 567.0, 565.0 (M+1).

Example 423

Synthesis of (R)-5-cyclopropyl-4-((1-(2,4-dimethylbenzyl)piperidin-3-yl)oxy)-2-fluoro-N-(methylsulfonyl)benzamide, trifluoroacetic acid salt

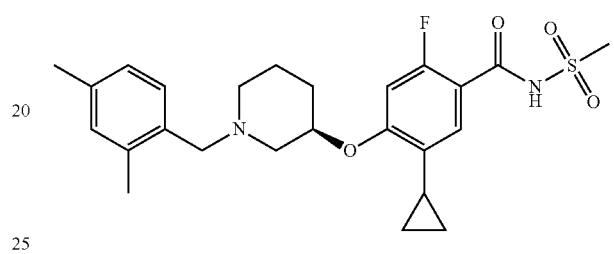

Following the procedure as described in Example 422 step 4, and making variation as required to replace 3-chloro-5-(trifluoromethoxy)benzaldehyde with 2,4-dimethylbenzaldehyde, the title compound was obtained as a colorless solid (0.02 g, 50%): $^1$H NMR (300 MHz, DMSO-d$_6$) δ12.21-11.69 (m, 1H), 9.97-8.99 (as, 1H), 7.45-7.28 (m, 1H), 7.20-6.98 (m, 4H), 4.98-4.62 (m, 1H), 4.45-4.22 (m, 2H), 3.74-2.86 (m, 7H), 2.42-2.28 (m, 3H), 2.25 (s, 3H), 2.21-1.42 (m, 5H), 0.94-0.79 (m, 2H), 0.75-0.59 (m, 2H); MS(ES+) m/z 475.2 (M+1).

Example 424

Synthesis of (R)-4-((1-(2-chloro-4-methylbenzyl) piperidin-3-yl)oxy)-5-cyclopropyl-2-fluoro-N-(methylsulfonyl)benzamide, trifluoroacetic acid salt

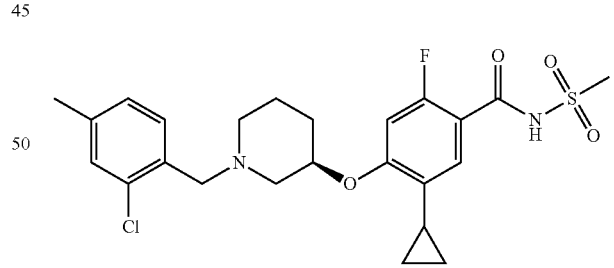

Following the procedure as described in Example 422 step 4 and making variation as required to replace 3-chloro-5-(trifluoromethoxy)benzaldehyde with 2-chloro-4-methylbenzaldehyde, the title compound was obtained as a colorless solid (0.03 g, 61%): $^1$H NMR (300 MHz, DMSO-d$_6$) δ12.24-11.69 (m, 1H), 9.78-9.46 (m, 1H), 7.57 (d, J=7.41 Hz, 1H), 7.41 (s, 1H), 7.25 (d, J=8.00 Hz, 1H), 7.18-7.01 (m, 2H), 5.03-4.65 (m, 1H), 4.54-4.37 (m, 2H), 3.75-3.35 (m, 2H), 3.31 (s, 3H), 3.28-2.89 (m, 2H), 2.30 (s, 3H), 2.25-1.51 (m, 5H), 0.94-0.79 (m, 2H), 0.74-0.60 (m, 2H); MS(ES+) m/z 497.0, 495.0 (M+1).

Example 425

Synthesis of (R)-4-((1-(4-(tert-butyl)benzyl)piperidin-3-yl)oxy)-5-cyclopropyl-2-fluoro-N-(methylsulfonyl)benzamide, trifluoroacetic acid salt

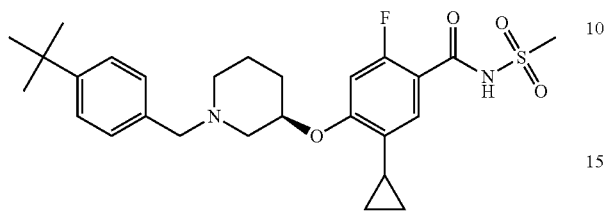

Following the procedure as described in Example 422 step 4 and making variation as required to replace 3-chloro-5-(trifluoromethoxy)benzaldehyde with 4-(tert-butyl)benzaldehyde, the title compound was obtained as a colorless solid (0.03 g, 61%): $^1$H NMR (300 MHz, DMSO-$d_6$) δ12.14-11.80 (m, 1H), 9.96-9.16 (m, 1H), 7.52-7.33 (m, 4H), 7.17-6.98 (m, 2H), 4.99-4.58 (m, 1H), 4.46-4.17 (m, 2H), 3.72-3.37 (m, 2H), 3.36-2.78 (m, 5H), 2.42-1.49 (m, 5H), 1.25 (s, 9H), 0.94-0.80 (m, 2H), 0.74-0.59 (m, 2H); MS(ES+) m/z 503.2 (M+1).

Example 426

Synthesis of (R)-4-((1-([1,1'-biphenyl]-4-ylmethyl)piperidin-3-yl)oxy)-5-cyclopropyl-2-fluoro-N-(methylsulfonyl)benzamide, trifluoroacetic acid salt

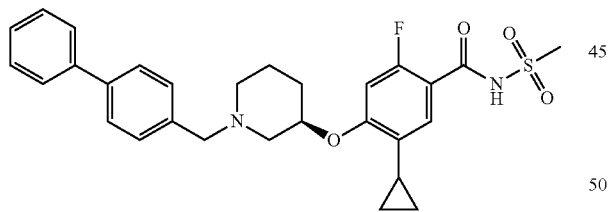

Following the procedure as described in Example 422 step 4 and making variation as required to replace 3-chloro-5-(trifluoromethoxy)benzaldehyde with [1,1'-biphenyl]-4-carbaldehyde, the title compound was obtained as a colorless solid (0.02 g, 36%): $^1$H NMR (300 MHz, DMSO-$d_6$) δ12.14-11.77 (m, 1H), 10.15-9.40 (m, 1H), 7.76 (d, J=8.1 Hz, 2H), 7.67 (d, J=7.3 Hz, 2H), 7.64-7.54 (m, 2H), 7.46 (t, J=7.5 Hz, 2H), 7.41-7.33 (m, 1H), 7.19-7.01 (m, 2H), 5.02-4.61 (m, 1H), 4.55-4.29 (m, 2H), 3.76-3.44 (m, 2H), 3.40-2.86 (m, 5H), 2.42-1.53 (m, 5H), 0.95-0.79 (m, 2H), 0.72-0.61 (m, 2H); MS (ES+) m/z 523.2 (M+1).

Example 427

Synthesis of (R)-4-((1-(5-chloro-2-hydroxybenzyl)piperidin-3-yl)oxy)-5-cyclopropyl-2-fluoro-N-(methylsulfonyl)benzamide, trifluoroacetic acid salt

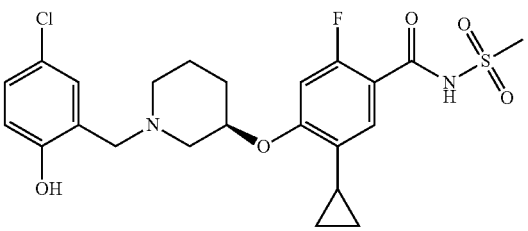 [SMILES: CS(=O)(=O)NC(=O)c1cc(C2CC2)c(O[C@@H]2CCCN(Cc3cc(Cl)ccc3O)C2)cc1F]

Following the procedure as described in Example 422 step 4 and making variation as required to replace 3-chloro-5-(trifluoromethoxy)benzaldehyde with 5-chloro-2-hydroxybenzaldehyde, the title compound was obtained as a colorless solid (0.04 g, 59%): $^1$H NMR (300 MHz, DMSO-$d_6$) δ12.10-11.77 (m, 1H), 10.72-10.50 (m, 1H), 10.16-9.18 (m, 1H), 7.58-7.47 (m, 1H), 7.30 (dd, J=8.6, 2.1 Hz, 1H), 7.17-7.03 (m, 2H), 6.93 (d, J=8.4 Hz, 1H), 5.01-4.68 (m, 1H), 4.35-4.21 (m, 2H), 3.70-2.85 (m, 7H), 2.41-1.56 (m, 5H), 0.95-0.79 (m, 2H), 0.72-0.61 (m, 2H); MS(ES+) m/z 499.1, 497.1 (M+1).

Example 428

Synthesis of (R)-5-cyclopropyl-4-((1-(2,4-diethoxybenzyl)piperidin-3-yl)oxy)-2-fluoro-N-(methylsulfonyl)benzamide, trifluoroacetic acid salt

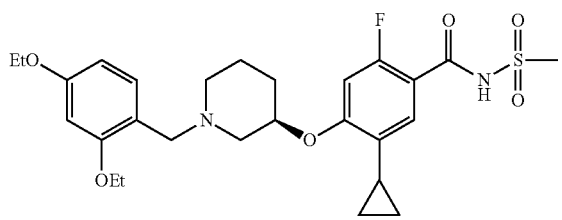 [SMILES: CCOc1ccc(CN2CCC[C@@H](Oc3cc(F)c(C(=O)NS(C)(=O)=O)cc3C3CC3)C2)c(OCC)c1]

Following the procedure as described in Example 422 step 4 and making variation as required to replace 3-chloro-5-(trifluoromethoxy)benzaldehyde with 2,4-diethoxybenzaldehyde, the title compound was obtained as a colorless solid (0.04 g, 77%): $^1$H NMR (300 MHz, DMSO-$d_6$) δ12.13-11.74 (m, 1H), 9.87-9.15 (m, 1H), 7.34 (dd, J=8.7, 8.7 Hz, 1H), 7.18-7.02 (m, 2H), 6.62-6.52 (m, 2H), 5.02-4.65 (m, 1H), 4.38-4.16 (m, 2H), 4.11-3.96 (m, 4H), 3.69-2.82 (m, 7H), 2.43-2.09 (m, 1H), 2.08-1.56 (m, 4H), 1.38-1.22 (m, 6H), 0.93-0.78 (m, 2H), 0.76-0.57 (m, 2H); MS(ES+) m/z 535.1 (M+1).

Example 429

Synthesis of (R)-5-cyclopropyl-4-((1-((2,3-dihydrobenzo[b][1,4]dioxin-6-yl)methyl)piperidin-3-yl)oxy)-2-fluoro-N-(methylsulfonyl)benzamide, trifluoroacetic acid salt

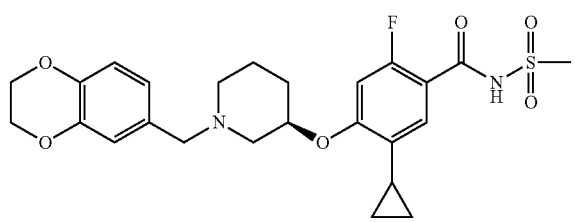 [SMILES: CS(=O)(=O)NC(=O)c1cc(C2CC2)c(O[C@@H]2CCCN(Cc3ccc4c(c3)OCCO4)C2)cc1F]

Following the procedure as described in Example 422 step 4 and making variation as required to replace 3-chloro-5-(trifluoromethoxy)benzaldehyde with 2,3-dihydrobenzo[b][1,4]dioxine-6-carbaldehyde, the title compound was obtained as a colorless solid (0.03 g, 64%): $^1$H NMR (300 MHz, DMSO-$d_6$) δ12.09-11.82 (m, 1H), 9.90-9.22 (m, 1H), 7.18-6.99 (m, 3H), 6.98-6.87 (m, 2H), 4.98-4.60 (m, 1H), 4.39-4.09 (m, 6H), 3.69-2.75 (m, 7H), 2.38-1.49 (m, 5H), 0.95-0.79 (m, 2H), 0.75-0.60 (m, 2H); MS(ES+) m/z 505.1 (M+1).

Example 430

Synthesis of (R)-5-cyclopropyl-4-((1-(3,4-dimethoxybenzyl)piperidin-3-yl)oxy)-2-fluoro-N-(methylsulfonyl)benzamide, trifluoroacetic acid salt

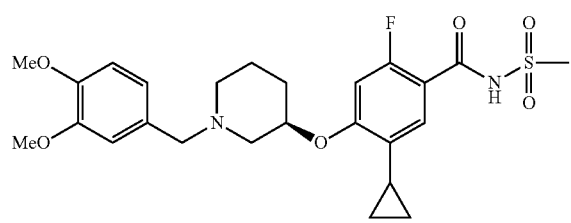 [SMILES: COc1ccc(CN2CCC[C@@H](Oc3cc(F)c(C(=O)NS(C)(=O)=O)cc3C3CC3)C2)cc1OC]

Following the procedure as described in Example 422 step 4 and making variation as required to replace 3-chloro-5-(trifluoromethoxy)benzaldehyde with 3,4-dimethoxybenzaldehyde, the title compound was obtained as a colorless solid (0.03 g, 71%): $^1$H NMR (300 MHz, DMSO-$d_6$) δ12.09-11.81 (m, 1H), 9.95-9.19 (m, 1H), 7.18-6.94 (m, 5H), 4.97-4.62 (m, 1H), 4.43-4.13 (m, 2H), 3.80-3.68 (m, 6H), 3.67-3.36 (m, 2H), 3.31 (s, 3H), 3.25-2.82 (m, 2H), 2.39-2.10 (m, 1H), 2.09-1.52 (m, 4H), 0.97-0.76 (m, 2H), 0.74-0.61 (m, 2H); MS(ES+) m/z 507.1 (M+1).

Example 431

Synthesis of (R)-5-cyclopropyl-2-fluoro-4-((1-(4-fluoro-2-methylbenzyl)piperidin-3-yl)oxy)-N-(methylsulfonyl)benzamide, trifluoroacetic acid salt

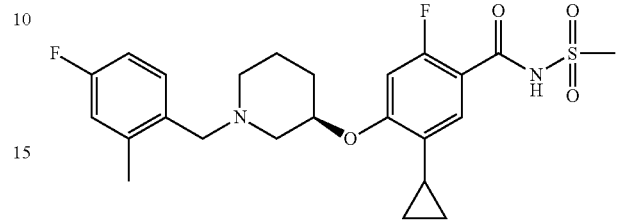

Following the procedure as described in Example 422 step 4 and making variation as required to replace 3-chloro-5-(trifluoromethoxy)benzaldehyde with 4-fluoro-2-methylbenzaldehyde, the title compound was obtained as a colorless solid (0.03 g, 82%): $^1$H NMR (300 MHz, DMSO-$d_6$) δ12.13-11.78 (m, 1H), 9.82-9.03 (m, 1H), 7.63-7.43 (m, 1H), 7.23-7.00 (m, 4H), 4.96-4.62 (m, 1H), 4.44-4.27 (m, 2H), 3.71-2.91 (m, 7H), 2.43-2.13 (m, 4H), 2.13-1.47 (m, 4H), 0.94-0.79 (m, 2H), 0.75-0.60 (m, 2H); MS(ES+) m/z 479.0 (M+1).

Example 432

Synthesis of (R)-4-((1-(2-chloro-4-methoxybenzyl)piperidin-3-yl)oxy)-5-cyclopropyl-2-fluoro-N-(methylsulfonyl)benzamide, trifluoroacetic acid salt

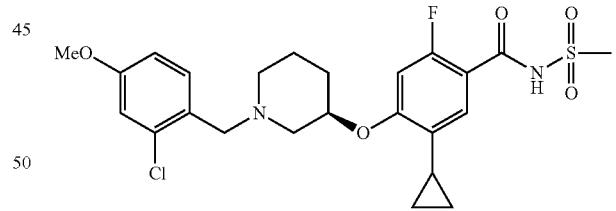

Following the procedure as described in Example 422 step 4 and making variation as required to replace 3-chloro-5-(trifluoromethoxy)benzaldehyde with 2-chloro-4-methoxybenzaldehyde, the title compound was obtained as a colorless solid (0.03 g, 67%): $^1$H NMR (300 MHz, DMSO-$d_6$) δ12.17-11.73 (m, 1H), 9.99-9.27 (m, 1H), 7.67-7.52 (m, 1H), 7.20-6.97 (m, 4H), 5.03-4.60 (m, 1H), 4.48-4.34 (m, 2H), 3.78 (s, 3H), 3.67-2.88 (m, 7H), 2.42-1.51 (m, 5H), 0.95-0.78 (m, 2H), 0.76-0.61 (m, 2H); MS(ES+) m/z 513.1, 511.1 (M+1).

Example 433

Synthesis of (R)-4-((1-(3-chloro-4-(trifluoromethyl)benzyl)piperidin-3-yl)oxy)-5-cyclopropyl-2-fluoro-N-(methylsulfonyl)benzamide, trifluoroacetic acid salt

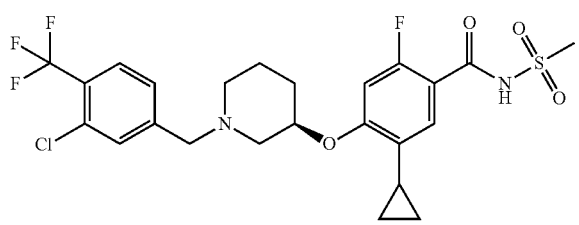 [SMILES: CS(=O)(=O)NC(=O)c1cc(C2CC2)c(O[C@@H]2CCCN(Cc3ccc(C(F)(F)F)c(Cl)c3)C2)cc1F]

Following the procedure as described in Example 422 step 4 and making variation as required to replace 3-chloro-5-(trifluoromethoxy)benzaldehyde with 3-chloro-4-(trifluoromethyl)benzaldehyde, the title compound was obtained as a colorless solid (0.03 g, 69%): $^1$H NMR (300 MHz, DMSO-$d_6$) δ 12.19-11.63 (m, 1H), 9.79-9.50 (m, 1H), 8.12-7.95 (m, 1H), 7.91-7.69 (m, 2H), 7.16-6.98 (m, 2H), 5.00-4.58 (m, 1H), 4.56-4.27 (m, 2H), 3.70-2.77 (m, 7H), 2.42-1.48 (m, 5H), 0.97-0.76 (m, 2H), 0.75-0.59 (m, 2H); MS(ES+) m/z 551.0, 549.0 (M+1).

Example 434

Synthesis of (R)-5-cyclopropyl-2-fluoro-4-((1-(4-methoxy-2-fluorobenzyl)piperidin-3-yl)oxy)-N-(methylsulfonyl)benzamide, trifluoroacetic acid salt

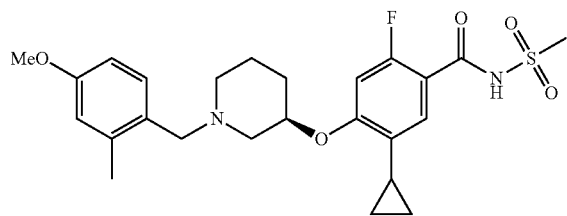 [SMILES: COc1ccc(CN2CCC[C@@H](Oc3cc(F)c(C(=O)NS(C)(=O)=O)cc3C3CC3)C2)c(C)c1]

Following the procedure as described in Example 422 step 4 and making variation as required to replace 3-chloro-5-(trifluoromethoxy)benzaldehyde with 4-methoxy-2-methylbenzaldehyde, the title compound was obtained as a colorless solid (0.03 g, 71%): $^1$H NMR (300 MHz, DMSO-$d_6$) δ12.09-11.80 (m, 1H), 9.72-8.85 (m, 1H), 7.41 (dd, J=16.1, 8.6 Hz, 1H), 7.17-7.00 (m, 2H), 6.89-6.78 (m, 2H), 4.96-4.63 (m, 1H), 4.39-4.20 (m, 2H), 3.72 (s, 3H), 3.68-3.36 (m, 2H), 3.31 (m, 3H), 3.24-2.91 (m, 2H), 2.34 (s, 3H), 2.27-1.51 (m, 5H), 0.94-0.79 (m, 2H), 0.74-0.58 (m, 2H); MS(ES+) m/z 491.2 (M+1).

Example 435

Synthesis of (R)-4-((1-(3-Chloro-4-methylbenzyl)piperidin-3-yl)oxy)-5-cyclopropyl-2-fluoro-N-(methylsulfonyl)benzamide, trifluoroacetic acid salt

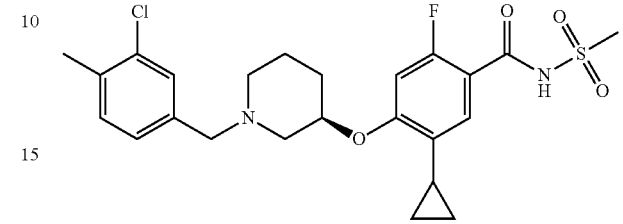

Following the procedure as described in Example 422 step 4 and making variation as required to replace 3-chloro-5-(trifluoromethoxy)benzaldehyde with 3-chloro-4-methylbenzaldehyde, the title compound was obtained as a colorless solid (0.04 g, 91%): $^1$H NMR (300 MHz, DMSO-$d_6$) δ12.16-11.76 (m, 1H), 9.74-9.43 (m, 1H), 7.58-7.43 (m, 2H), 7.41-7.28 (m, 1H), 7.19-7.01 (m, 2H), 4.97-4.64 (m, 1H), 4.44-4.20 (m, 2H), 3.70-3.39 (m, 2H), 3.31 (s, 3H), 3.26-2.85 (m, 2H), 2.31 (s, 3H), 2.26-1.46 (m, 5H), 0.95-0.77 (m, 2H), 0.73-0.61 (m, 2H); MS(ES+) m/z 491.1, 495.1 (M+1).

Example 436

Synthesis of (R)-5-cyclopropyl-4-((1-(3,5-dimethylbenzyl)piperidin-3-yl)oxy)-2-fluoro-N-(methylsulfonyl)benzamide, trifluoroacetic acid salt

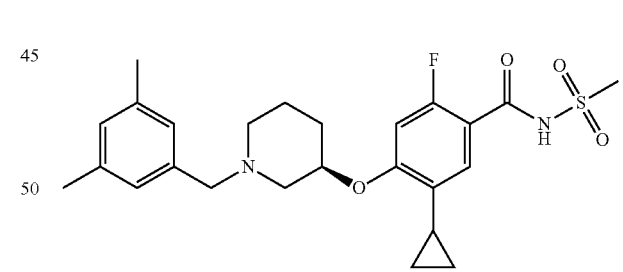

Following the procedure as described in Example 422 step 4 and making variation as required to replace 3-chloro-5-(trifluoromethoxy)benzaldehyde with 3,5-dimethylbenzaldehyde, the title compound was obtained as a colorless solid (0.02 g, 51%): $^1$H NMR (300 MHz, DMSO-$d_6$) δ12.21-11.75 (m, 1H), 10.27-9.47 (m, 1H), 7.20-6.96 (m, 5H), 5.00-4.62 (m, 1H), 4.43-4.12 (m, 2H), 3.70-3.37 (m, 2H), 3.31 (s, 3H), 3.27-2.85 (m, 2H), 2.42-2.11 (m, 7H), 2.07-1.54 (m, 4H), 0.94-0.77 (m, 2H), 0.75-0.57 (m, 2H); MS(ES+) m/z 475.2 (M+1).

Example 437

Synthesis of (R)-5-cyclopropyl-2-fluoro-N-(methylsulfonyl)-4-((1-(3-(trifluoromethoxy)benzyl)piperidin-3-yl)oxy)benzamide, trifluoroacetic acid salt

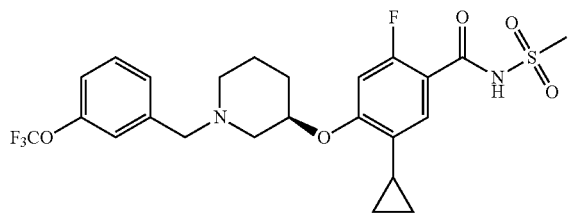 [SMILES: CS(=O)(=O)NC(=O)c1cc(C2CC2)c(O[C@@H]2CCCN(Cc3cccc(OC(F)(F)F)c3)C2)cc1F]

Following the procedure as described in Example 422 step 4 and making variation as required to replace 3-chloro-5-(trifluoromethoxy)benzaldehyde with 3-(trifluoromethoxy)benzaldehyde, the title compound was obtained as a colorless solid (0.02 g, 33%): $^1$H NMR (300 MHz, DMSO-$d_6$) δ12.23-11.62 (m, 1H), 9.77-9.45 (m, 1H), 7.68-7.39 (m, 3H), 7.20-6.98 (m, 2H), 5.03-4.59 (m, 1H), 4.59-4.26 (m, 2H), 3.67-2.77 (m, 7H), 2.42-1.48 (m, 5H), 1.20-0.57 (m, 4H); MS(ES+m/z 531.1 (M+1).

Example 438

Synthesis of (R)-5-cyclopropyl-2-fluoro-4-((1-(2-methoxy-4-(trifluoromethoxy)benzyl)piperidin-3-yl)oxy)-N-(methylsulfonyl)benzamide, trifluoroacetic acid salt

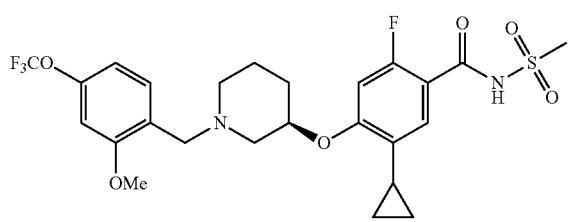 [SMILES: COc1cc(OC(F)(F)F)ccc1CN1CCC[C@@H](Oc2cc(F)c(C(=O)NS(C)(=O)=O)cc2C2CC2)C1]

Following the procedure as described in Example 422 step 4 and making variation as required to replace 3-chloro-5-(trifluoromethoxy)benzaldehyde with 2-methoxy-4-(trifluoromethoxy)benzaldehyde, the title compound was obtained as a colorless solid (0.04 g, 60%); $^1$H NMR (300 MHz, DMSO-$d_6$) δ12.18-11.73 (m, 1H), 9.25-9.01 (m, 1H), 7.63-7.49 (m, 1H), 7.19-6.98 (m, 4H), 5.00-4.61 (m, 1H), 4.41-4.24 (m, 2H), 3.90-3.77 (m, 3H), 3.74-2.83 (m, 7H), 2.42-1.53 (m, 5H), 0.95-0.79 (m, 2H), 0.74-0.61 (m, 2H); MS(ES+) m/z 561.1 (M+1).

Example 439

Synthesis of (R)-5-cyclopropyl-4-((1-(3,4-dimethylbenzyl)piperidin-3-yl)oxy)-2-fluoro-N-(methylsulfonyl)benzamide, trifluoracetic acid salt

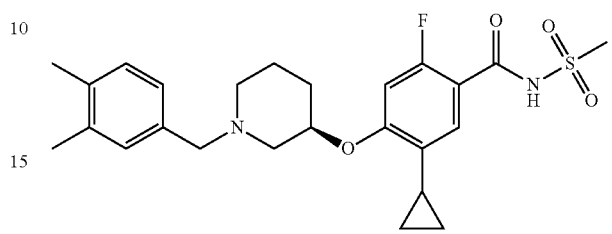

Following the procedure as described in Example 426 step 4 and making variation as required to replace 3-chloro-5-(trifluoromethoxy)benzaldehyde with 3,4-dimethylbenzaldehyde, the title compound was obtained as a colorless solid (0.03 g, 60%): $^1$H NMR (300 MHz, DMSO-$d_6$) δ12.09-11.80 (m, 1H), 10.35-9.35 (m, 1H), 7.34-7.16 (m, 3H), 7.16-6.98 (m, 2H), 4.98-4.67 (m, 1H), 4.42-4.12 (m, 2H), 3.69-3.36 (m, 2H), 3.31 (s, 3H), 3.27-2.79 (m, 2H), 2.42-2.12 (m, 7H), 2.06-1.51 (m, 4H), 0.95-0.78 (m, 2H), 0.73-0.59 (m, 2H): MS(ES+) m/z 475.2 (M+1).

Example 440

Synthesis of (R)-5-cyclopropyl-4-((1-(3,5-dichlorobenzyl)piperidin-3-yl)oxy)-2-fluoro-N-(methylsulfonylbenzamide

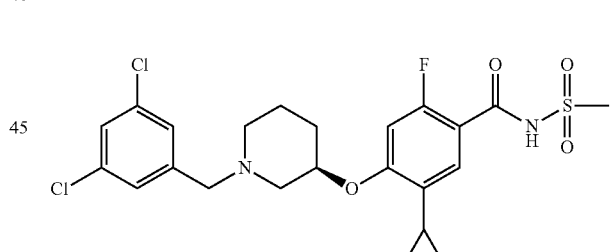

Following the procedure as described in Example 422 step 4 and making variation as required to replace 3-chloro-5-(trifluoromethoxy)benzaldehyde with 3,5-dichlorobenzaldehyde and to purify the residue using column chromatography eluting with 5% methanol containing 0.5% ammonia in dichloromethane, the title compound was obtained as a colorless solid (0.12 g, 72%): $^1$H NMR (300 MHz, CDCl$_3$) δ7.53 (d, J=9.1 Hz, 1H), 7.27-7.16 (m, 3H), 6.55 (d, J=14.5 Hz, 1H), 4.50-4.36 (m, 1H), 3.56-3.41 (m, 2H), 3.39 (s, 3H), 2.86 (d, J=10.4 Hz, 1H), 2.67-2.56 (m, 1H), 2.45-2.33 (m, 1H), 2.32-2.21 (m, 1H), 2.13-1.97 (m, 2H), 1.94-1.78 (m, 1H), 1.74-1.54 (m, 2H), 1.00-0.87 (m, 2H), 0.73-0.59 (m, 2H); MS(ES+) m/z: 515.0, 517.0 (M+1).

Example 441

Synthesis of (R)-4-((1-(2-chloro-4-(methylsulfonyl)benzyl)piperidin-3-yl)oxy)-5-cyclopropyl-2-fluoro-N-(methylsulfonyl)benzamide, trifluoroacetic acid salt

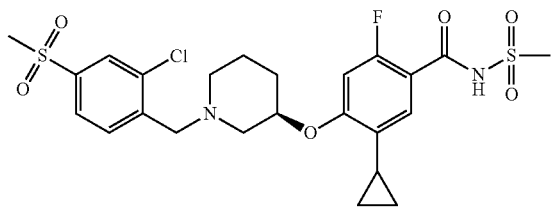

To a stirred solution of (R)-5-cyclopropyl-2-fluoro-N-(methylsulfonyl)-4-(piperidin-3-yloxy)benzamide trifluoroacetate (0.05 g, 0.14 mmol) and 1-(bromomethyl)-2-chloro-4-(methylsulfonyl)benzene (0.06 g, 0.21 mmol) in acetonitrile (2 mL) was added potassium carbonate (0.05 g, 0.34 mmol) and potassium iodide (0.03 g, 0.17 mmol). The reaction mixture was stirred at reflux for 16 hours, cooled to ambient temperature, and then 1N aqueous hydrochloric acid solution (5 mL) was added; extracted with ethyl acetate (3×10 mL) and concentrated in vacuo. The residue was purified by column chromatography eluting with gradient of 0% to 30% ethyl acetate containing 1% formic acid in hexanes to obtained an oil, which was further purified by preparative HPLC (gradient of acetonitrile in water) to afford the title compound (0.04 g, 44%) as a colorless solid: $^1$H NMR (300 MHz, DMSO-$d_6$) δ7.90 (s, 1H), 7.78-7.71 (m, 2H), 7.16 (d, J=8.70 Hz, 1H), 6.85-6.67 (m, 1H), 4.57-4.45 (m, 1H), 3.66 (m, 2H), 3.22 (s, 3H), 2.85-2.72 (m, 2H), 2.62-2.50 (m, 1H), 2.40-2.29 (m, 1H), 2.10-1.97 (m, 1H), 1.97-1.85 (m, 1H), 1.84-1.72 (m, 1H), 1.63-1.44 (m, 2H), 0.90-0.79 (m, 2H), 0.63-0.51 (m, 2H); MS(ES+) m/z: 559.0, 561.0 (M+1).

Example 442

Synthesis of (R)-4-((1-([1,1'-biphenyl]-2-ylmethyl)piperidin-3-yl)oxy)-5-cyclopropyl-2-fluoro-N-(methylsulfonyl)benzamide, trifluoroacetic acid salt

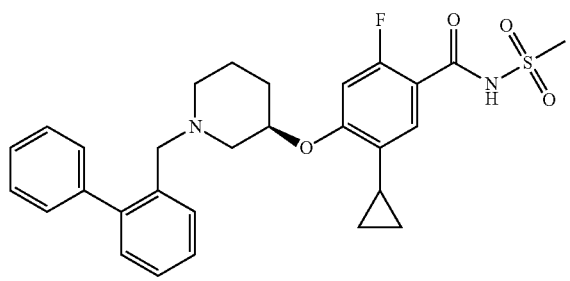 [SMILES: CS(=O)(=O)NC(=O)c1cc(C2CC2)c(O[C@@H]2CCCN(Cc3ccccc3-c3ccccc3)C2)cc1F]

Following the procedure as described in Example 441 and making variation as required to replace 1-(bromomethyl)-2-chloro-4-(methylsulfonyl)benzene with 2-(bromomethyl)-1,1'-biphenyl, the title compound was obtained as a colorless solid (0.02 g, 28%): $^1$H NMR (300 MHz, DMSO-$d_6$) δ12.22-11.69 (m, 1H), 9.66-8.78 (m, 1H), 7.80-7.62 (m, 1H), 7.57-7.21 (m, 8H), 7.17-7.04 (m, 1H), 6.96 (d, J=12.9 Hz, 1H), 4.89-4.11 (m, 5H), 3.41-2.87 (m, 5H), 2.42-1.38 (m, 5H), 0.96-0.77 (m, 2H), 0.76-0.59 (m, 2H); MS(ES+) m/z 523.2 (M+1).

Example 443

Synthesis of (R)-4-((1-([1,1'-biphenyl]-3-ylmethyl)piperidin-3-yl)oxy)-5-cyclopropyl-2-fluoro-N-(methylsulfonyl)benzamide, trifluoroacetic acid salt

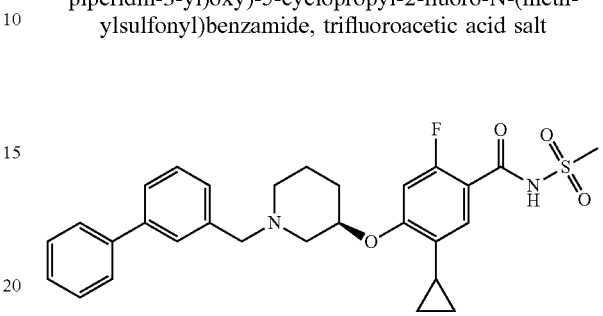

Following the procedure as described in Example 441, and making variation as required to replace 1-(bromomethyl)-2-chloro-4-(methylsulfonyl)benzene with 3-(bromomethyl)-1,1'-biphenyl, the title compound was obtained as a colorless solid (0.01 g, 8%): $^1$H NMR (300 MHz, DMSO-$d_6$) δ12.06-11.82 (m, 1H), 10.20-9.29 (m, 1H), 7.92-7.60 (m, 2H), 7.60-7.42 (m, 6H), 7.42-7.34 (m, 1H), 7.17-6.98 (m, 2H), 4.99-4.62 (m, 1H), 4.60-4.27 (m, 2H), 3.75-3.43 (m, 2H), 3.39-2.89 (m, 5H), 2.43-1.50 (m, 5H), 0.93-0.54 (m, 4H); MS(ES+) m/z 523.2 (M+1).

Example 444

Synthesis of (R)-5-cyclopropyl-2-fluoro-N-(methylsulfonyl)-4-((1l-(spiro[3.5]nonan-7-ylmethyl)piperidin-3-yl)oxy)benzamide, trifluoroacetic acid salt

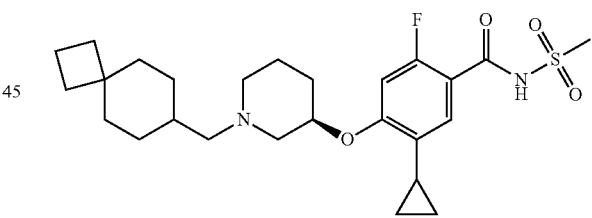

Step 1. Preparation of spiro[3.5]nonan-7-ylmethyl methanesulfonate

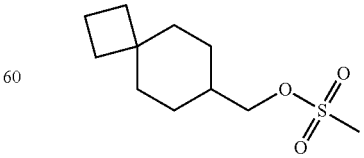

To a solution of spiro[3.5]nonan-7-ylmethanol (0.77 g, 5.00 mmol) and triethylamine (1.05 mL, 7.50 mmol) in dichloromethane (20 mL) was added dropwise methanesulfonyl chloride (0.42 mL, 5.5 mmol) at 0° C. The mixture was stirred for 1.5 hours, and then saturated aqueous solution of ammonium chloride (10 mL) was added and the mixture was extracted with dichloromethane (2×20 mL). The combined organic layers were washed with brine (15 mL), dried over anhydrous sodium sulfate, filtered and concentrated in vacuo to afford the title compound (1.16 g, quant. yield), which was used in the next step without further purification.

Step 2. Preparation of (R)-5-cyclopropyl-2-fluoro-N-(methylsulfonyl)-4-((1-(spiro[3.5]nonan-7-ylmethyl)piperidin-3-yl)oxy)benzamide, trifluoroacetic acid salt

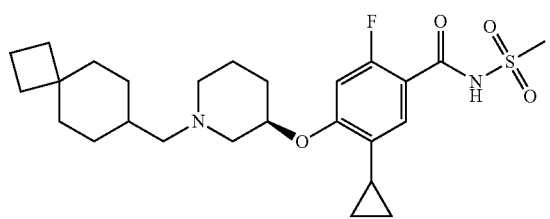 [SMILES: CS(=O)(=O)NC(=O)c1cc(C2CC2)c(O[C@@H]2CCCN(CC3CCC4(CCC4)CC3)C2)cc1F]

Following the procedure as described in Example 441, and making variation as required to replace 1-(bromomethyl)-2-chloro-4-(methylsulfonyl)benzene with spiro[3.5]nonan-7-ylmethyl methanesulfonate, the title compound was obtained as a colorless solid (0.02 g, 31%): $^1$H NMR (300 MHz, DMSO-$d_6$) δ12.09-11.80 (m, 1H), 9.28-8.58 (m, 1H), 7.18-7.01 (m, 2H), 5.03-4.62 (m, 1H), 3.74-3.59 (m, 2H), 3.31 (s, 3H), 3.14-2.81 (m, 4H), 2.43-2.11 (m, 2H), 2.96-1.85 (m, 2H), 1.85-1.44 (m, 12H), 1.30-1.12 (m, 2H), 1.07-0.79 (m, 4H), 0.78-0.56 (m, 2H); MS(ES+) m/z 493.2 (M+1).

Example 445

(Synthesis of (R)-4-((1-(2-chloro-4-fluorobenzyl)-5,5-difluoropiperidin-3-yl)oxy)-5-cyclopropyl-2-fluoro-N-(methylsulfonyl)benzamide

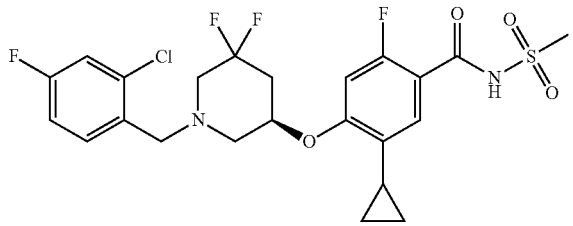 [SMILES: CS(=O)(=O)NC(=O)c1cc(C2CC2)c(O[C@H]2CN(Cc3ccc(F)cc3Cl)CC(F)(F)C2)cc1F]

Step 1. Preparation of (R)-3-((tert-butyldimethylsilyl)oxy)-1-(4-methoxybenzyl)piperidine-2,6-dione

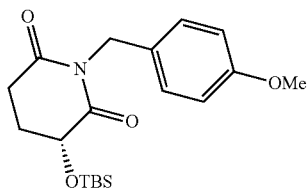 [SMILES: COc1ccc(CN2C(=O)CC[C@@H](O[Si](C)(C)C(C)(C)C)C2=O)cc1]

To a solution of (R)-3-hydroxy-1-(4-methoxybenzyl)piperidine-2,6-dione (prepared accordingly to Yuan-Ping et al., Chirality, 2005, 17, 595-599) (3.50 g, 14.00 mmol) in dichloromethane (20 mL) was added tert-butylchlorodimethylsilane (2.30 g, 15.50 mmol) and imidazole (1.30 g, 19.70 mmol). After stirring at ambient temperature for 1 hour, the reaction mixture was quenched with saturated aqueous ammonium chloride solution (25 mL and extracted with dichloromethane (2×40 mL), washed with brine (30 mL), dried over anhydrous sodium sulfate, filtered and concentrated in vacuo. The residue was purified by column chromatography (0% to 15% ethyl acetate in hexanes) to give the title compound (2.80 g, 55% 0): MS(ES+) m/z 364.1 (M+1).

Step 2. Preparation of (5R)-5-((tert-butyldimethylsilyl)oxy)-6-hydroxy-1-(4-methoxybenzyl)piperidin-2-one

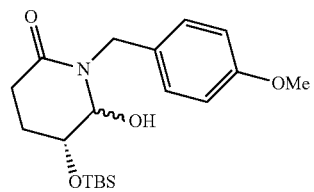 [SMILES: COc1ccc(CN2C(=O)CC[C@@H](O[Si](C)(C)C(C)(C)C)C2O)cc1]

To a solution of (R)-3-((tert-butyldimethylsilyl)oxy)-1-(4-methoxybenzyl)piperidin-2,6-dione (2.80 g, 7.70 mmol) is methanol (10 mL) and dichloromethane (10 mL) under nitrogen atmosphere at −30° C. was added sodium borohydride (1.40 g, 38.50 mmol). Alter stirring for 30 minutes at −30° C. the reaction mixture was warmed to 0° C. over 30 minutes and quenched with saturated aqueous ammonium chloride solution (20 mL) and extracted with dichloromethane (2×15 mL). The combined extracts were dried over anhydrous sodium sulfate, filtered and concentrated in vacuo give an oil (2.70 g, 76%) which was used in the next step without further purification: MS (ES+) m/z 300.2 (M+1).

Step 3. Preparation of (R)-5-((tert-butyldimethylsilyl)oxy)-1-(4-methoxybenzyl)piperidin-2-one

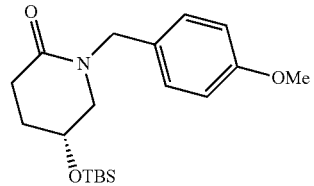 [SMILES: COc1ccc(CN2C[C@H](O[Si](C)(C)C(C)(C)C)CCC2=O)cc1]

To a solution of (5R)-5-((tert-butyldimethylsilyl)oxy)-6-hydroxy-1-(4-methoxybenzyl)piperidin-2-one (2.70 g, 7.60 mmol) and triethylsilane (11.50 g, 77.10 mmol) in dry dichloromethane (20 mL) was added boron trifluoride diethyl ether complex (2.9 mL, 23.00 mmol) at −78° C. under nitrogen atmosphere. After stirring for 30 minutes at −78° C., the reaction mixture was warmed up slowly to 0° C. and stirred at this temperature for 2 hours before it was quenched with saturated aqueous solution of sodium bicarbonate solution (5 mL) and extracted with dichloromethane (2×10 mL). The combined organic layers were dried over anhydrous sodium sulfate, filtered, and concentrated in vacuo to afford the title compound as an oil (1.26 g, 47%): ¹H NMR (300 MHz, CDCl₃) δ7.16 (d, J=8.5 Hz, 2H), 6.82 (d, J=8.6 Hz, 2H), 4.71 (d, J=14.6 Hz, 1H), 4.27 (d, J=14.6 Hz, 1H), 4.08-3.98 (m, 1H), 3.77 (s, 3H), 3.24 (dd, J=12.4, 3.7 Hz, 1H), 3.05 (dd, J=12.3, 4.5 Hz, 1H), 2.68 (m, 1H), 2.39 (td, J=17.6, 5.7 Hz, 1H), 1.91-1.78 (m, 2H), 0.81 (s, 9H), 0.00 (s, 3H), −0.06 (s, 3H).

Step 4. Preparation of (R)-5-hydroxy-1-(4-methoxybenzyl)piperidin-2-one

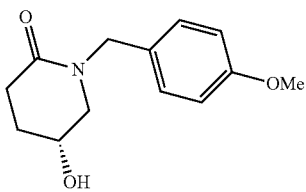 [SMILES: COc1ccc(CN2C[C@H](O)CCC2=O)cc1]

To a solution of (R)-5-((tert-butyldimethylsilyl)oxy)-1-(4-methoxybenzyl)piperidin-2-one (1.25 g, 3.58 mmol) in tetrahydrofuran (10 mL) was added tetra-butylammonium fluoride (1.0M in THF, 5.3 mL, 5.3 mmol) under nitrogen atmosphere. After stirring at ambient temperature for 30 minutes, the reaction mixture was quenched with saturated aqueous ammonium chloride solution (2.5 mL) and extracted with dichloromethane (2×10 mL). The combined extracts were concentrated in vacuo and filtered over a plug of silica gel eluting with 10% hexanes in ethyl acetate followed by ethyl acetate to afford the title compound as oil (0.84 g, quant. yield): MS(ES+) m/z 236.2 (M+1).

Step 5. Preparation of (R)-tert-butyl 5-chloro-2-fluoro-4-((1-(4-methoxybenzyl)-6-oxopiperidin-3-yl)oxy)benzoate

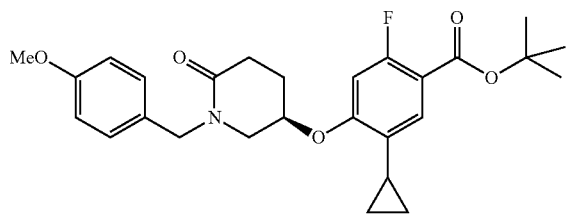 [SMILES: COc1ccc(CN2C[C@H](Oc3cc(F)c(C(=O)OC(C)(C)C)cc3C3CC3)CCC2=O)cc1]

To a solution of (R)-5-hydroxy-1-(4-methoxybenzyl)piperidin-2-one (0.84 g, 3.58 mmol) and tert-butyl 5-chloro-2,4-difluorobenzoate (0.98 g, 3.95 mmol) in dimethylsulfoxide (10 mL) was added cesium carbonate (1.52 g, 10.7 mmol). After stirring for 48 hours at 80° C., the reaction mixture was quenched with saturated aqueous solution of ammonium chloride solution (20 mL) and extracted with dichloromethane (2×10 mL). The organic layers were concentrated under reduced pressure and the residue was purified by chromatography eluting with a gradient of ethyl, acetate in hexanes (50% to 100%) to afford the title compound as a gum (1.38 g, 83%): ¹H NMR (300 MHz, CDCl₃) δ7.80 (d, J=7.7 Hz, 1H), 7.08 (d, J=8.6 Hz, 2H), 6.71 (d, J=8.6 Hz, 2H), 6.46 (d, J=11.9 Hz, 1H), 4.79 (d, J=14.6 Hz, 1H), 4.71-4.62 (m, 1H), 4.17 (d, J=14.6 Hz, 1H), 3.69 (s, 3H), 3.43-3.37 (m, 2H), 2.71 (ddd, J=17.6, 11.1, 6.6 Hz, 1H), 2.46 (ddd, J=17.7, 6.2, 3.1 Hz, 1H), 2.26-2.13 (m, 1H), 2.12-2.00 (m, 1H), 1.52 (s, 9H); MS(ES+) m/z 466.1, 464.1 (M+1).

Step 6. Preparation of (R)-tert-butyl 5-cyclopropyl-2-fluoro-4-((1-(4-methoxybenzyl)-6-oxopiperidin-3-yl)oxy)benzoate

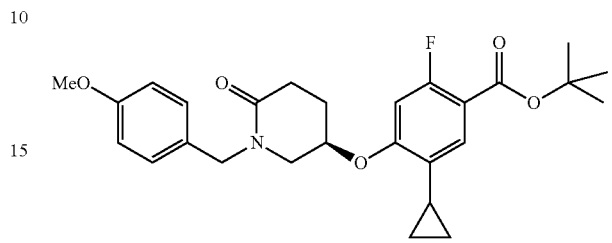

Following the procedure as described in Example 346 step 3 and making variation, as required to replace tert-butyl 4-((4-(tert-butoxycarbonyl)-2-chloro-5-fluorophenoxy)methyl)-4-(fluoropiperidine-1-carboxylate with (R)-tert-butyl 5-chloro-2-fluoro-4-((1-(4-methoxybenzyl)-6-oxopiperidin-3-yl)oxy)benzoate and the reaction mixture was heated at 150° C. for 1 hour under microwave irradiation, the title compound was obtained as a colorless oil (0.90 g, 64%); ¹H NMR (300 MHz, CDCl₃) δ7.32 (d, J=8.4 Hz, 1H), 7.15-7.09 (m, 2H), 6.77-6.70 (m, 2H), 6.39 (d, J=12.4 Hz, 1H), 4.73-4.64 (m, 2H), 4.35-4.28 (m, 1H), 3.72 (s, 3H), 3.47-3.42 (m, 2H), 2.75-2.59 (m, 1H), 2.55-2.42 (m, 1H), 2.30-2.17 (m, 1H), 2.12-2.01 (m, 1H), 1.89-1.76 (m, 1H), 1.53 (s, 9H), 0.89-0.78 (m, 2H), 0.60-0.49 (m, 2H).

Step 7. Preparation of (R)-tert-butyl 5-cyclopropyl-4-((5,5-difluoro-1-(4-methoxy benzyl)-6-oxopiperidin-3-yl)oxy)-2-fluorobenzoate

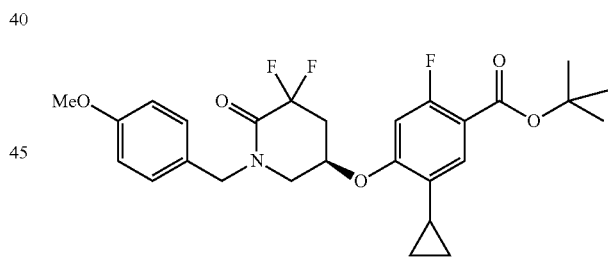

To a solution of diisopropyl amine (0.10 mL, 0.75 mmol) in anhydrous tetrahydrofuran (1 mL) under nitrogen was added butyl lithium solution (1.5M solution in hexanes, 0.46 ml, 0.69 mmol) at −78° C. After stirring at −78° C. for 1 hour, a solution of (R)-tert-butyl 5-cyclopropyl-2-fluoro-4-((1-(4-methoxybenzyl)-6-oxopiperidin-3-yl)oxy)benzoate (0.25 g, 0.53 mmol) in tetrahydrofuran (1.5 mL) was added, stirring was continued at −78° C. for another 1 hour. To this reaction mixture, was added a solution of N-fluorobenzenesulfonimide (0.39 g, 0.75 mmol) in tetrahydrofuran (2 mL) slowly over 10 minutes. The reaction mixture was stirred for 30 minutes at −78° C. and then slowly warmed up to −30° C. over 1 hour. The reaction mixture was cooled to −78° C. again and lithium (1.0 M solution in toluene, 0.8 mL, 0.8 mmol) was added. The reaction mixture was stirred for 30 min at −78° C., a solution of N-fluorobenzenesulfonimide (0.39 g, 0.75 mmol) in tetrahydrofuran (2 mL) was added and the reaction mixture was slowly warmed up to −30° C. over 1 hour and then quenched with a saturated aqueous solution of ammonium chloride solution (10 mL), extracted with ethyl acetate (2×15 mL) and concentrated. The residue was purified by column chromatography eliding with a gradient of 30% to 80% ethyl acetate in hexanes to afford the title compound (0.05 g, 20%); ¹H NMR (300 MHz, CDCl₃) δ7.92 (d, J=7.0 Hz, 1H), 7.62-7.45 (m, 2H), 7.22-7.12 (m, 2H), 6.77 (d, J=8.6 Hz, 2H), 6.40-6.16 (m, 1H), 4.94-4.82 (m, 1H), 4.76-4.64 (m, 1H), 4.47-4.28 (m, 1H), 3.75 (s, 3H), 3.70-3.54 (m, 20), 2.72 (dt, J=14.6, 4.8 Hz, 1H), 1.88-1.59 (m, 2H), 1.54 (s, 9H), 0.90-0.72 (m, 2H), 0.61-0.47 (m, 2H); MS (ES+) m/z 450.1 (M−t-Bu+1).

Step 8. Preparation of (R)-tert-butyl 5-cyclopropyl-4-((5,5-difluoro-1-(4-methoxybenzyl)piperidin-3-yl)oxy)-2-fluorobenzoate

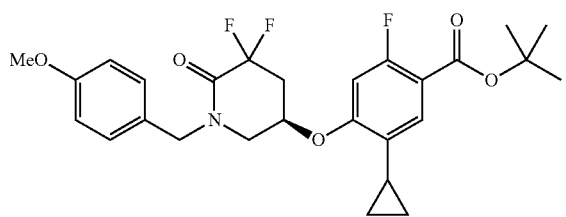 [SMILES: COc1ccc(CN2C[C@H](Oc3cc(F)c(C(=O)OC(C)(C)C)cc3C3CC3)CC(F)(F)C2=O)cc1]

To a solution of (R)-tert-butyl 5-cyclopropyl-4-((5,5-difluoro-1-(4-methoxybenzyl)-6-oxopiperidin-3-yl)oxy)-2-fluorobenzoate (0.05 g, 0.10 mmol) in tetrahydrofuran (1 mL), borane (1.0M in tetrahydrofuran, 0.3 mL, 0.3 mmol) was added. The reaction mixture was stirred for 2 hours at ambient temperature and then quenched with methanol (1 mL). The reaction mixture was concentrated and the residue was purified by column chromatography eluting with a gradient of 0% to 20% ethyl acetate is hexanes to afford the title compound as oil (0.03 g, 61%): ¹H NMR (300 MHz, CDCl₃) δ7.35 (d, J=8.3 Hz, 1H), 7.21 (d, J=8.5 Hz, 2H), 6.85 (d, J=8.5 Hz, 2H), 6.52 (d, J=12.4 Hz, 1H), 4.64-4.49 (m, 1H), 3.78 (s, 3H), 3.68 (d, J=13.1 Hz, 1H), 3.61 (d, J=13.1 Hz, 1H), 3.20-3.09 (m, 1H), 3.08-2.92 (m, 1H), 2.68-2.22 (m, 3H), 2.01-1.89 (m, 2H), 1.55 (s, 9H), 0.85-0.78 (m, 2H), 0.65-0.55 (m, 2H); MS(ES+) m/z 492.1 (M+1).

Step 9. Preparation of (R)-tert-butyl 5-cyclopropyl-4-((5,5-difluoropiperidin-3-yl)oxy)-2-fluorobenzoate trifluoroacetate

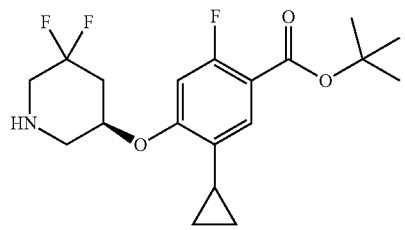 [SMILES: CC(C)(C)OC(=O)c1cc(C2CC2)c(O[C@H]2CNCC(F)(F)C2)cc1F]

To a stirred solution of 4(R)-tert-butyl 5-cyclopropyl-4-((5,5-difluoro-1-(4-methoxybenzyl)piperidin-3-yl)oxy)-2-fluorobenzoate (0.23 g, 0.47 mmol)) in degassed ethyl acetate (5 mL) and trifluoroacetic acid (0.2 mL) was added 10% palladium on carbon (20 mg) and the flask was put under 1 atm of hydrogen gas. The reaction mixture was stirred for 4 hours at ambient temperature, and then filtered over diatomaceous earth and rinsed with ethyl acetate (2×20 mL). The filtrate was concentrated to afford the title compound (0.23 g, quant. yield): MS(ES+) m/z 372.2 (M+1).

Step 10. Preparation of (R)-4-((1-(2-chloro-4-fluorobenzyl)-5,5-difluoropiperidin-3-yl)oxy)-5-cyclopropyl-2-fluorobenzoic acid hydrochloride acid

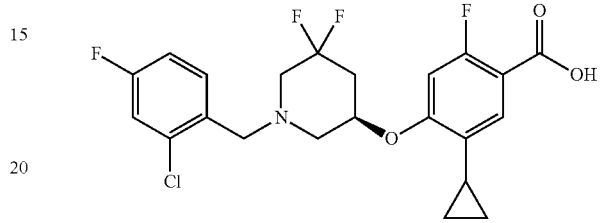

To a stirred solution of (R)-tert-butyl 5-cyclopropyl-4-((5,5-difluoropiperidin-3-yl)oxy)-2-fluorobenzoate trifluoroacetate (0.23 g, 0.47 mmol) in dichloromethane (1 mL) was added trifluoroacetic acid (1 mL). After stirring at ambient temperature for 2 hours, the reaction mixture was concentrated in vacuo. The residue was dissolved in tetrahydrofuran (1 mL), and to the solution was added 2-chloro-4-fluorobenzaldehyde (0.07 g, 0.50 mmol) and sodium triacetoxyborohydride (0.24 g, 0.74 mmol). The reaction mixture was stirred for 16 hours at ambient temperature, quenched with 1N aqueous hydrochloric acid solution (5 mL) and extracted with ethyl acetate (3×10 mL), and concentrated in vacuo. The residue was purified by column chromatography eluting with 40% ethyl acetate (plus 0.5% trifluoroacetic acid) in hexanes to afford the title compound as a colorless solid (0.16 g, 81%); ¹H NMR (300 MHz, CDCl₃) δ7.55-7.41 (m, 2H), 7.10 (dd, J=8.4, 2.6 Hz, 1H), 6.96 (dt, J=8.4, 2.6 Hz, 1H), 6.57 (d, J=12.5 Hz, 1H), 6.47-6.12 (brs, 2H), 4.63 (m, 1H), 3.77 (s, 2H), 3.13 (dd, J=11.4, 3.1 Hz, 1H), 3.02 (dd, J=20.3, 9.1 Hz, 1H), 2.72-2.48 (m, 3H), 2.15-2.05 (m, 1H), 2.01-1.96 (m, 1H), 0.88-0.79 (m, 2H), 0.66-0.58 (m, 2H).

Step 11. Preparation of (R)-4-((1-(2-chloro-4-fluorobenzyl)-5,5-difluoropiperidin-3-yl)oxy)-5-cyclopropyl-2-fluoro-N-(methylsulfonyl)benzamide

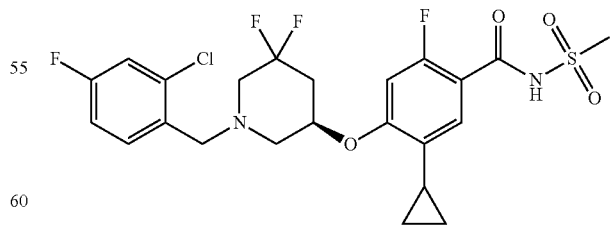

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with (R)-4-((1-(2-chloro-4-fluorobenzyl)-5, 5-difluoropiperidin-3-yl)oxy)-5-cyclopropyl-2-fluorobenzoic acid hydrochloric acid, the title compound was obtained as a colorless solid (0.02 g, 41%): $^1$H NMR (300 MHz, DMSO-$d_6$) δ8.68 (d, J=15.8 Hz, 1H), 7.56 (d, J=9.0 Hz, 1H), 7.46 (dd, J=8.5, 6.2 Hz, 1H), 7.11 (dd, J=8.4, 2.5 Hz, 1H), 6.96 (dt, J=8.3, 2.5 Hz, 1H), 6.57 (d, J=14.1 Hz, 1H), 4.71-4.57 (m, 1H), 3.77 (s, 2H), 3.39 (s, 3H), 3.18-2.94 (m, 2H), 2.75-2.49 (m, 3H), 2.19-1.98 (m, 2H), 0.98-0.83 (m, 2H), 0.68-0.59 (m, 2H); MS(ES+) m/z 537.2, 535.2 (M+1).

Example 446

Synthesis of (R)-5-((1-(2-chloro-4-fluorobenzyl)-5,5-difluoropiperidin-3-yl)oxy)-5-cyclopropyl-2-fluoro-N-(methylsulfonyl)benzamide

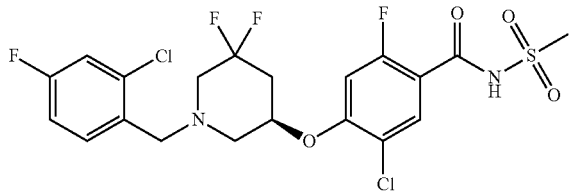 [SMILES: CS(=O)(=O)NC(=O)c1cc(Cl)c(O[C@H]2CN(Cc3ccc(F)cc3Cl)CC(F)(F)C2)cc1F]

Step 1. Preparation of N-(2-chloro-4-fluorobenzyl)-5-oxotetrahydrofuran-2-carboxamide

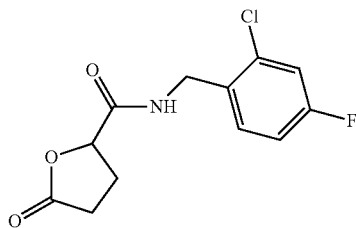 [SMILES: O=C1CCC(C(=O)NCc2ccc(F)cc2Cl)O1]

A mixture of (R)-5-oxotetrahydrofuran-2-carboxylic acid (10.0 g, 76.9 mmol) and thionyl chloride (20.0 g, 307.0 mmol) was refluxed for 10 hours, and then the excess thionyl chloride was removed under reduced pressure. The residue was undissolved in anhydrous dichloromethane (150 mL) and cooled to 0° C. To this solution was added triethylamine (10.1 g, 100.0 mmol) and (2-chloro-4-fluorophenyl)methanamine (12.2 g, 76.9 mmol) successively. After stirring at 0° C. for 3 hours, the reaction mixture was directly poured on a silica column and eluted with 20% to 70% ethyl acetate in hexanes to afford the title compound as a colorless solid (20.80 g, quant. yield): $^1$H NMR (300 MHz, CDCl$_3$): δ7.34 (dd, J=8.5, 6.0 Hz, 1H), 7.13 (dd, J=8.4, 2.6 Hz, 1H), 6.95 (dt, J=8.3, 2.6 Hz, 1H), 6.82-6.68 (m, 1H), 4.86 (t, J=7.4 Hz, 1H), 4.51 (d, J=6.0 Hz, 2H), 2.72-2.50 (m, 3H), 2.45-2.28 (m, 1H).

Step 2. Preparation of (R)-3-((tert-butyldimethylsilyl)oxy)-1-(2-chloro-4-fluorobenzyl)piperidine-2,6-dione

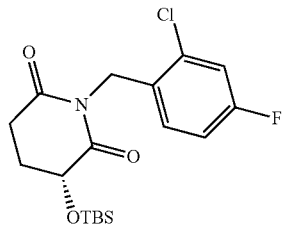 [SMILES: CC(C)(C)[Si](C)(C)O[C@@H]1CCC(=O)N(Cc2ccc(F)cc2Cl)C1=O]

To a solution of N-(2-chloro-4-fluorobenzyl)-5-oxotetrahydrofuran-2-carboxamide (20.8 g, 77.0 mmol) in anhydrous tetrahydrofuran (200 mL) was added a cooled 1.0 M solution of potassium tert-butoxide in anhydrous tetrahydrofuran (46.0 mL, 46.0 mmol) at −78° C. under nitrogen atmosphere. After 10 minutes of stirring at −78° C., the temperature was allowed to arise to −60° C. over 10 min, and then the reaction mixture vas stirred as −60° C. for 1.5 hours. Another portion of potassium tert-butoxide (46.0 mL, 46.0 mmol) was added and the reaction mixture was stirred for another 1.5 hours at −45° C. and then a solution of chloride (12.80 g, 85.70 mmol) in tetrahydrofuran (20 mL) was added dropwise and stirring was continued for 30 minutes at −45° C. The reaction mixture was quenched with saturated aqueous ammonium chloride solution (25 mL) at −45° C., and extracted with ethyl acetate (2×100 mL). The combined extracts were washed with brine (50 mL), dried over anhydrous sodium sulfate, filtered and concentrated under reduced pressure. The residue was purified by flash chromatography eluting with a gradient of 0 to 15% ethyl acetate in hexanes to give the title compound (28.1 g, 93%): $^1$H NMR (300 MHz, CDCl$_3$) δ7.03 (dd, J=8.4, 2.4 Hz, 1H), 6.89 (dd, J=8.5, 6.1 Hz, 1H), 6.79 (dt, J=8.5, 2.4 Hz, 1H), 4.94 (d, J=15.7 Hz, 1H), 4.88 (d, J=15.7 Hz, 1H), 4.35 (dd, J=6.3, 3.7 Hz, 1H), 2.94 (ddd, J=17.8, 8.9, 5.7 Hz, 1H), 2.62 (td, J=17.8, 5.7 Hz, 1H), 2.13-1.97 (m, 2H), 0.85 (s, 9H), 0.08 (s, 3H), 0.05 (s, 3H).

Step 3. Preparation of (5R)-5-((tert-butyldimethylsilyl)oxy)-1-(2-chloro-4-fluorobenzyl)-6-hydroxypiperidin-2-one

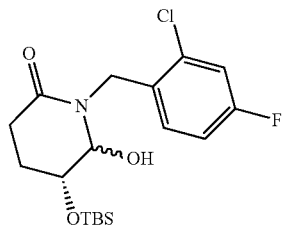 [SMILES: CC(C)(C)[Si](C)(C)O[C@@H]1CCC(=O)N(Cc2ccc(F)cc2Cl)C1O]

Following the procedure as described in Example 445 step 2 and step 3, and making variation as required to replace (R)-3-((tert-butyldimethylsilyl)oxy)-1-(4-methoxybenzyl)piperidin-2,6-dione with (R)-3-((tert-butyldimethylsilyl)oxy)-1-(2-chloro-4-fluorobenzyl)piperidine-2,6-dione, the title compound was obtained (0.68 g, 79% in 2 steps) and used without further purification: MS(ES+) m/z 390.1, 388.1. (M+1).

Step 4. Preparation of (R)-5-((tert-butyldimethylsilyl)oxy)-1-(2-chloro-4-fluorobenzyl)piperidin-2-one

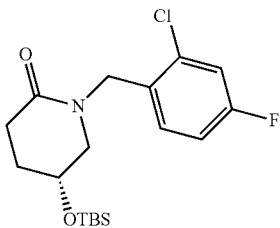 [SMILES: CC(C)(C)[Si](C)(C)O[C@@H]1CCC(=O)N(Cc2ccc(F)cc2Cl)C1]

To a cooled solution (−78° C.) of (5R)-5-((tert-butyldimethylsilyl)oxy)-6-hydroxy-1-(4-methoxybenzyl)piperidin-2-one (2.70 g, 7.60 mmol) and triethylsilane (11.50 g, 77.10 mmol) in anhydrous dichloromethane (20 mL) under nitrogen atmosphere was added boron trifluoride diethyl ether complex (2.9 mL, 23 mmol). The reaction mixture was stirred for 30 minutes at −78° C., and then warmed up slowly to 0% and stirred at this temperature for 2 hours. The reaction mixture was quenched with a saturated aqueous solution of sodium bicarbonate (5 mL) and extracted with dichloromethane (2×10 mL). The combined organic layers were dried over anhydrous sodium sulfate, filtered, and concentrated under reduced pressure to give the title compound as an oil (1.26 g, 47%): $^1$H NMR (300 MHz, CDCl$_3$) (d, J=8.5 Hz, 2H), 6.82 (d, J=8.0 Hz, 2H), 4.71 (d, J=14.6 Hz, 1H), 4.27 (d, J=1.4.6 Hz, 1H), 4.08-3.98 (m, 1H), 3.77 (s, 3H), 3.24 (dd, J=12.4, 3.7 Hz, 1H), 3.05 (dd, J=12.3, 4.5 Hz, 1H), 2.68 (m, 1H), 2.39 (td, J=17.6, 5.7 Hz, 1H), 1.91-1.78 (m, 2H), 0.81 (s, 9H), 0.00 (s, 3H), −0.06 (s, 3H).

Step 4. Preparation of (5R)-5-((tert-butyldimethylsilyl)oxy)-1-(2-chloro-4-fluorobenzyl)-3-fluoropiperidin-2-one

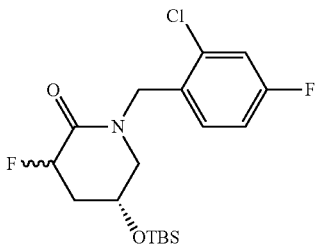 [SMILES: CC(C)(C)[Si](C)(C)O[C@@H]1CC(F)C(=O)N(Cc2ccc(F)cc2Cl)C1]

To a stirred solution of diisopropylamine (0.068 g, 0.67 mmol) in tetrahydrofuran (2 mL) at −78° C. was added n-butyllithium (1.5 M solution in hexanes, 0.41 mL, 0.62 mmol). After stirring for 45 minutes at −78° C., a solution of (R)-5-((tert-butyldimethylsilyl)oxy)-1-(2-chloro-4-fluorobenzyl)piperidin-2-one (0.18 g, 0.48 mmol) in tetrahydrofuran (2 mL) was added dropwise and the reaction mixture was stirred for 40 minutes at −78° C. A solution of N-fluorobenzenesulfonamide (0.21 g, 0.67 mmol) in tetrahydrofuran (1.5 mL) was added via syringe pump over a 10 minutes period and the reaction mixture was stirred at −78° C. for 5 hours and then slowly warmed up to −40° C. The reaction mixture was quenched by addition of saturated aqueous solution of ammonium chloride (10 mL), and extracted with ethyl acetate (2×10 mL). The combined organic phases were washed with water (10 mL) and brine (10 mL), dried over sodium sulfate, filtered and concentrated in vacuo. To the residue was added dichloromethane and methyl tert-butylether (10 mL, 1/1, v/v) the resulting precipitate was removed by inflation. The filtrate was concentrated to give a light yellow residue which was purified by silica gel chromatography using a gradient (0 to 30%) of ethyl acetate in hexanes to give the title compound as a gum (0.08 g, 39%): $^1$H NMR (300 MHz, CDCl$_3$) δ7.29 (dd, J=8.6, 6.1 Hz, 1H), 7.10 (dd, J=8.4, 2.6 Hz, 1H), 6.92 (dt, J=8.4.2.6 Hz, 1H), 5.18 (ddd, J=47.6, 10.1, 6.1 Hz, 1H), 4.99 (d, J=15.5 Hz, 1H), 4.37 (d, J=15.5 Hz, 1H), 4.29-4.20 (m, 1H), 3.44 (dd, J=12.6, 3.3 Hz, 1H), 3.18-3.09 (m, 1H), 2.51-2.35 (m, 1H), 2.23-2.07 (m, 1H), 0.83 (s, 9H), 0.06 (s, 3H), −0.03 (s, 3H).

Step 5. Preparation of (R)-5-((tert-butyldimethylsilyl)oxy)-1-(2-chloro-4-fluorobenzyl)-3,3-difluoropiperidin-2-one

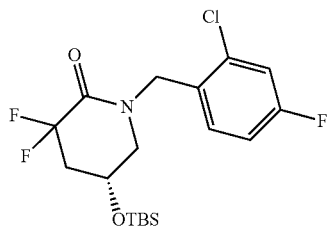 [SMILES: CC(C)(C)[Si](C)(C)O[C@H]1CN(Cc2ccc(F)cc2Cl)C(=O)C(F)(F)C1]

Following the procedure as described in Example 44S step 4, and making variation as required to replace (R)-5-((tert-butyldimethylsilyl)oxy)-1-(2-chloro-4-fluorobenzyl)piperidin-2-one with (5R)-5-((tert-butyldimethylsilyl)oxy)-1-(2-chloro-4-fluorobenzyl)-3-fluoropiperidin-2-one, the title compound was obtained as a colorless solid (0.075 g, 99%): $^1$H NMR (300 MHz, CDCl$_3$) δ7.35 (dd, J=8.6, 6.1 Hz, 1H), 7.12 (dd, J=8.4, 2.6 Hz, 1H), 6.96 (dt, J=8.4, 8.3, 2.6 Hz, 1H), 4.83 (d, J=15.3 Hz, 1H), 4.56 (d, J=15.2 Hz, 1H), 4.23-4.13 (m, 1H), 3.44 (dd, J=12.4, 4.0 Hz, 1H), 3.21 (dd, J=12.5, 6.3 Hz, 1H), 2.62-2.27 (m, 2H), 0.82 (s, 9H), 0.05 (s, 3H), −0.01 (s, 3H); MS(ES+) m/z 410.2, 408.2 (M+1).

Step 6. Preparation of (R)-1-(2-chloro-4-fluorobenzyl)-5,5-difluoropiperidin-3-ol

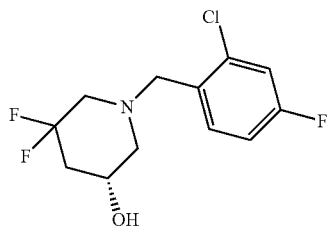 [SMILES: O[C@H]1CN(Cc2ccc(F)cc2Cl)CC(F)(F)C1]

To a solution of (R)-5-((tert-butyldimethylsilyl)oxy)-1-(2-chloro-4-fluorobenzyl)-3,3-difluoropiperidin-2-one (0.015 g, 0.04 mmol) in tetrahydrofuran (1 mL) was added borane (1.0 M solution in tetrahydrofuran, 0.9 mL, 0.9 mmol) under nitrogen atmosphere. After 30 minutes stirring, the reaction mixture was quenched by addition of 6 N hydrochloric acid solution (2.5 mL) and stirring was continued for 2.5 hours. The solution was neutralized by addition, of a saturated aqueous solution of sodium bicarbonate and extracted with dichloromethane (2×10 mL). The combined organic extracts were concentrated under reduced pressure and filtered over a plug of silica gel eluting with 10% ethyl acetate in hexanes followed by 100% ethyl acetate to give the title compound as a colorless oil (0.01 g, 85%): $^1$H NMR (300 MHz, CDCl$_3$) δ 7.38 (dd, J=8.5, 6.2 Hz, 1H), 7.11 (dd, J=8.5, 2.6 Hz, 1H), 6.97 (dt, J=8.3, 2.6 Hz, 1H), 4.05-3.96 (m, 1H), 3.72-3.67 (m, 2H), 2.98-2.83 (m, 1H), 2.82-2.71 (m, 1H), 2.60-2.45 (m, 2H), 2.24-1.90 (m, 2H); MS(ES+) m/z 282.1, 280.1 (M+1).

Step 7. Preparation of (R)-tert-butyl 5-chloro-4-((1-(2-chloro-4-fluorobenzyl)-5,5-difluoropiperidin-3-yl)oxy)-2-fluorobenzoate

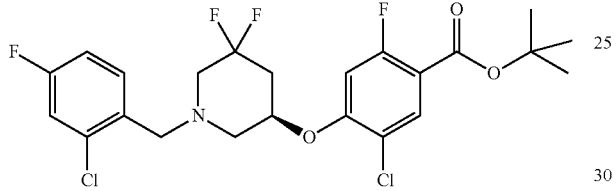

Following the procedure as described in Example 445 step 4 and making variation as required to replace (R)-5-hydroxy-1-(4-methoxybenzyl)piperidin-2-one with (R)-1-(2-chloro-4-fluorobenzyl)-5,5-difluoropiperidin-3-ol, the title compound was obtained as a colorless solid (0.01 g, 67%): $^1$H NMR (300 MHz, CDCl$_3$) δ 7.87 (d, J=7.7 Hz, 1H), 7.47 (dd, J=8.6, 6.3 Hz, 1H), 7.10 (dd, J=8.5, 2.6 Hz, 1H), 6.97 (dt, J=8.3, 8.3, 2.6 Hz, 1H), 6.64 (d, J=11.8 Hz, 1H), 4.65-4.51 (m, 1H), 3.75 (s, 2H), 3.19-2.96 (m, 2H), 2.69-2.42 (m, 3H), 2.12-2.03 (m, 1H), 1.56 (s, 9H); MS(ES+) m/z 510.0, 508.0 (M+1).

Step 8. Preparation of (R)-4-((1-(2-chloro-4-fluorobenzyl)-5,5-difluoropiperidin-3-yl)oxy)-5-cyclopropyl-2-fluoro-N-(methylsulfonyl)benzamide

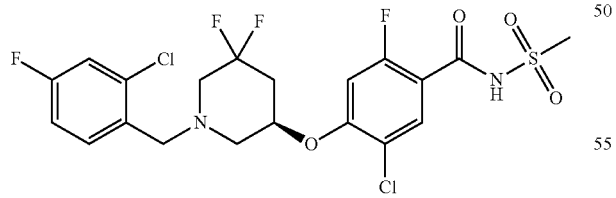

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with (R)-tert-butyl 5-chloro-4-((1-(2-chloro-4-fluorobenzyl)-5,5-difluoropiperidin-3-yl)oxy)-2-fluorobenzoate, the title compound was obtained as a colorless solid (0.004 g, 32%): $^1$H NMR (300 MHz, CDCl$_3$) δ7.77 (d, J=7.4 Hz, 1H), 7.63 (dd, J=8.6, 6.3 Hz, 1H), 7.19 (dd, J=8.7, 2.6 Hz, 1H), 7.09-6.97 (m, 2H), 4.84-4.75 (m, 1H), 3.86-3.79 (m, 2H), 3.33 (s, 3H), 3.09-2.79 (m, 3H), 2.77-2.64 (m, 1H), 2.59-2.41 (m, 1H), 2.33-2.14 (m, 1H); MS(ES+) m/z 531.1, 529.1 (M+1).

Example 447

Synthesis of 5-cyclopropyl-4-(((R)-1-((R)-1-(3,5-dichlorophenyl)-2-methoxyethyl)piperidin-3-yl)oxy)-2-fluoro-N-(methylsulfonyl)benzamide

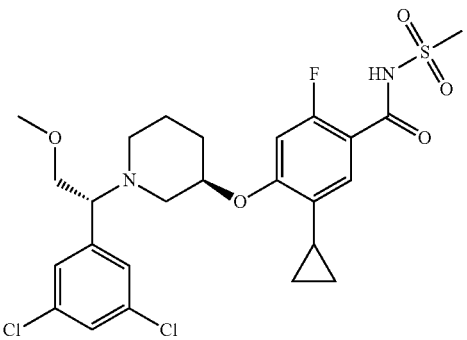

Step 1. Preparation of 2-((R)-3-(2-cyclopropyl-5-fluoro-4-(methoxycarbonyl)phenoxy)piperidin-1-yl-2-(3,5-dichlorophenyl)acetic acid

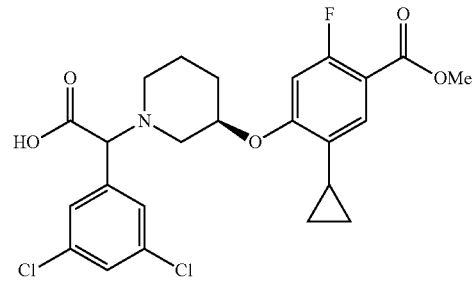 [SMILES: COC(=O)c1cc(C2CC2)c(O[C@@H]2CCCN(C(C(=O)O)c3cc(Cl)cc(Cl)c3)C2)cc1F]

To a stirred solution of (R)-methyl 5-cyclopropyl-2-fluoro-4-(piperidin-3-yloxy)benzoate (0.59 g, 2.00 mmol) in toluene (8 mL) under an atmosphere of nitrogen were added 50% glyoxylic acid in water (0.24 g, 3.20 mmol), molecular sieve 4 Å (0.5 g) and (3,5-dichlorophenyl)boronic acid (0.420 g, 2.20 mmol). The reaction mixture was stirred at 100° C. for 2 hours, cooled to ambient temperature and filtered to remove the molecular sieve. The filtrate was concentrated. The residue (0.15 g, 15%) was used directly in the next step without further purification.

Step 2. Preparation of methyl 5-cyclopropyl-4-(((R)-1-((R)-1-(3,5-dichlorophenyl)-2-hydroxyethyl)piperidin-3-yl)oxy)-2-fluorobenzoate

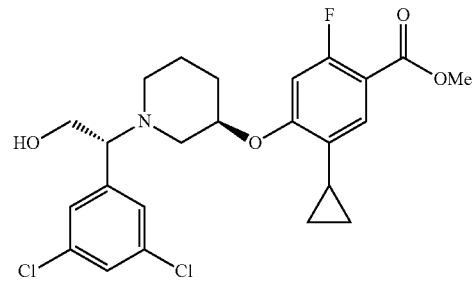 [SMILES: COC(=O)c1cc(C2CC2)c(O[C@@H]2CCCN([C@@H](CO)c3cc(Cl)cc(Cl)c3)C2)cc1F]

To a stirred solution of 2-((R)-3-(2-cyclopropyl-5-fluoro-4-(methoxycarbonyl)phenoxy)piperidin-1-yl)-2-(3,5-dichlorophenyl)acetic acid (0.15 g, 0.30 mmol) in tetrahydrofuran (3 mL) under an atmosphere of nitrogen was added borane in tetrahydrofuran (1.0 M solution in tetrahydrofuran, 1 mL, 1.00 mmol). After stirring at ambient temperature for 16 hours, the reaction mixture was quenched by addition of methanol (2 mL), and concentrated. The residue was purified by chromatography eluting with a gradient (0 to 30%) of ethyl acetate in hexanes to give the title compound (0.09 g, 55%): $^1$H NMR (300 MHz, CDCl$_3$) δ7.43 (d, J=8.4 Hz, 1H), 7.29 (t, J=1.8 Hz, 1H), 7.06 (d, J=1.9 Hz, 2H), 6.54 (d, J=12.8 Hz, 1H), 4.50-4.39 (m, 1H), 3.93-3.82 (m, 4H), 3.69-3.58 (m, 2H), 2.72-2.57 (m, 3H), 2.40-2.27 (m, 1H), 2.03-1.49 (m, 5H), 0.87-0.78 (m, 2H), 0.68-0.57 (m, 2H). The other diastereoisomer methyl 5-cyclopropyl-4-(((R)-1-((S)-1-(3,5-dichlorophenyl)-2-hydroxyethyl)piperidin-3-yl)oxy)-2-fluorobenzoate was also isolated (0.07 g, 45%). $^1$H NMR (300 MHz, CDCl$_3$) δ7.42 (d, J=8.4 Hz, 1H), 7.33-7.29 (m, 1H), 7.10-7.07 (m, 2H), 6.52 (d, J=12.7 Hz, 1H), 4.48-4.35 (m, 1H), 3.96-3.82 (m, 4H), 3.73-3.58 (m, 2H), 2.97-2.88 (m, 1H), 2.61-2.39 (m, 3H), 1.94-1.53 (m, 5H), 0.85-0.79 (m, 2H), 0.67-0.56 (m, 2H).

Step 3. Preparation of methyl 5-cyclopropyl-4-(((R)-1-((R)-1-(3,5-dichlorophenyl)-2-methoxyethyl)piperidin-3-yl)oxy)-2-fluorobenzoate

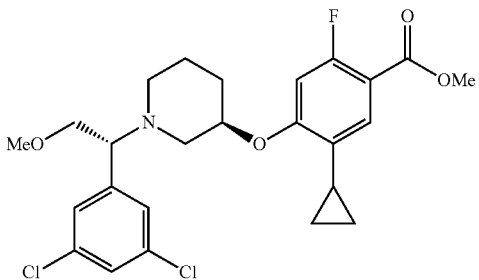 [SMILES: COC[C@@H](c1cc(Cl)cc(Cl)c1)N1CCC[C@@H](Oc2cc(F)c(C(=O)OC)cc2C2CC2)C1]

To a stirred solution of methyl 5-cyclopropyl-4-(((R)-1-((R)-1-(3,5-dichlorophenyl)-2-hydroxyethyl)piperidin-3-yl)oxy)-2-fluorobenzoate (0.08 g, 0.14 mmol) in dimethoxyethane (1 mL) under an atmosphere of nitrogen was added sodium hydride (60% in mineral oil, 0.03 g, 0.69 mmol) and the reaction mixture was stirred for 30 minutes. Methyl iodide (0.030 g, 0.21 mmol) was added to the reaction mixture. After stirring for 16 hours, water (10 mL) was added and the reaction mixture was extracted with dichloromethane (2×10 mL), the combined organic layers were concentrated. The residue was purified by chromatography eluting with a gradient of methanol in dichloromethane (0 to 5%) to give the title compound (0.04 g, 58%): MS(ES+) m/z 498.1, 496.1. (M+1).

Step 4. Preparation of 5-cyclopropyl-4-(((R)-1-((R)-1-(3,5-dichlorophenyl)-2-methoxyethyl)piperidin-3-yl)oxy)-2-fluorobenzoic acid hydrochloride

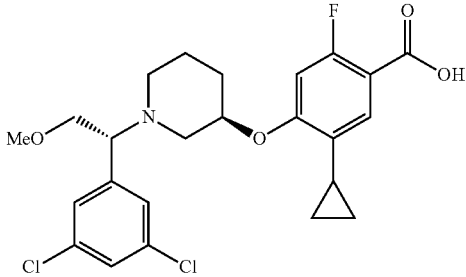 [SMILES: COC[C@@H](c1cc(Cl)cc(Cl)c1)N1CCC[C@@H](Oc2cc(F)c(C(=O)O)cc2C2CC2)C1]

To a stirred solution of methyl 5-cyclopropyl-4-(((3R)-1-(1-(3,5-dichlorophenyl)-2-methoxyethyl)piperidin-3-yl)oxy)-2-fluorobenzoate (0.075 g, 0.15 mmol) in DMSO (1 mL) under an atmosphere of nitrogen were added lithium hydroxide (0.036 g, 1.52 mmol) and the mixture was stirred for 1 hour at 70° C. and then quenched with 1N aqueous hydrochloric acid solution (5 mL) and extracted with dichloromethane (3×10 mL), dried over anhydrous sodium sulfate, filtered and concentrated to give the title compound (0.06 g, 76%) as a colorless solid: MS(ES+) m/z 484.2, 482.2 (M+1).

Step 5. Preparation of 5-cyclopropyl-4-(((R)-1-1-(3,5-dichlorophenyl)-2-methoxyethyl)piperidin-3-yl)oxy)-2-fluoro-N-(methylsulfonyl)benzamide

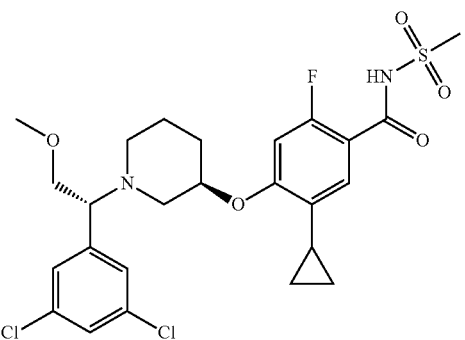

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 5-cyclopropyl-4-(((3R)-1-(1-(3,5-dichlorophenyl)-2-methoxyethyl)piperidin-3-yl)oxy)-2-fluorobenzoic acid hydrochloride (0.06 g, 0.12 mmol), the title compound was obtained as a colorless solid (0.006 g, 9%): $^1$H NMR (300 MHz, CDCl$_3$) δ8.86-8.62 (m, 1H), 7.56 (d, J=8.0 Hz, 1H), 7.52-7.42 (m, 2H), 6.94-6.83 (m, 1H), 5.06-4.92 (m, 1H), 4.48-4.36 (m, 1H), 4.48-4.36 (m, 1H), 4.20-4.08 (m, 1H), 4.06-3.34 (m, 11H), 2.94-2.73 (m, 1H), 2.33-1.94 (m, 3H), 1.77-1.58 (m, 1H), 0.96-0.86 (m, 2H), 0.69-0.59 (m, 2H); MS(ES+) m/z 561.1, 559.1 (M+1).

Example 448

Synthesis of 5-cyclopropyl-4-(((R)-1-((S)-1-(3,5-dichlorophenyl)-2-methoxyethyl)piperidin-3-yl)oxy)-2-4-N-(methylsulfonyl)benzamide, trifluoroacetic acid salt

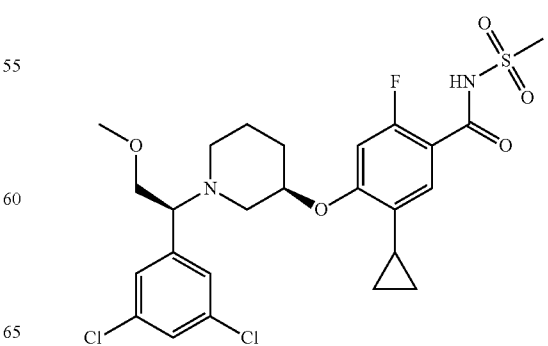

Step 1. Preparation of 2-((R)-3-(2-cyclopropyl-5-fluoro-4-((methylsulfonyl)carbamoyl)phenoxy)piperidin-1-yl)-2-(3,5-dichlorophenyl)acetic acid

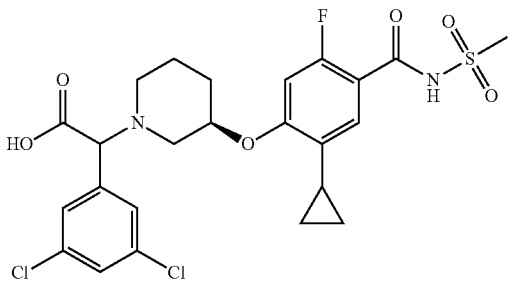 [SMILES: CS(=O)(=O)NC(=O)c1cc(C2CC2)c(O[C@@H]2CCCN(C(C(=O)O)c3cc(Cl)cc(Cl)c3)C2)cc1F]

To a stirred solution of (R)-5-cyclopropyl-2-fluoro-N-(methylsulfonyl)-4-(piperidin-3-yloxy)benzamide (1.50 g, 3.31 mmol) in toluene (10 mL) under an atmosphere of nitrogen was introduced 50% glyoxylic acid in water (0.39 g, 5.30 mmol), molecular sieve 4 Å (0.5 g) and (3,5-dichlorophenyl)boronic acid (0.09 g, 3.04 mmol). The reaction mixture was stirred at 100° C. for 2 hours, cooled to ambient temperature and filtered to remove the molecular sieve. The filtrate was concentrated to give the title compound as a colorless solid (2.16 g, 99%): $^1$H NMR (300 MHz, DMSO-$d_6$) δ11.90-11.82 (m, 1H), 7.70-7.58 (m, 1H), 7.52-7.42 (m, 2H), 7.10 (t, J=1.9 Hz, 1H), 6.98 (dd, J=13.0, 6.0 Hz, 1H), 4.78-4.56 (m, 2H), 3.30 (s, 3H), 3.04-2.92 (m, 1H), 2.90-2.77 (m, 1H), 2.76-2.63 (m, 1H, 2.62-2.51 (m, 1H), 2.19-1.97 (m, 1H), 1.98-1.77 (m, 2H), 1.74-1.47 (m, 2H), 0.95-0.78 (m, 2H), 0.76-0.58 (m, 2H); MS(ES+) m/z 561.0, 559.0 (M+1).

Step 2. Preparation of 5-cyclopropyl-4-(((3R)-1-(1-(3,5-dichlorophenyl)-2-hydroxyethyl)piperidin-3-yl)oxy)-2-4-N-(methylsulfonyl)benzamide

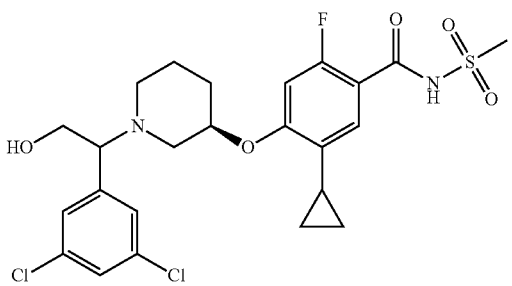 [SMILES: CS(=O)(=O)NC(=O)c1cc(C2CC2)c(O[C@@H]2CCCN(C(CO)c3cc(Cl)cc(Cl)c3)C2)cc1F]

To a stirred solution of 2-((R)-3-(2-cyclopropyl-5-fluoro-4-((methylsulfonyl)carbamoyl)phenoxy)piperidin-1-yl)-2-(3,5-dichlorophenyl)acetic acid (0.80 g, 1.43 mmol) in tetrahydrofuran (8 mL) was added carbonyl diimidazole (0.26 g, 1.57 mmol) under nitrogen. The reaction mixture was reflux for 1 hour and cooled to ambient temperature. To the reaction mixture was added sodium borohydride (0.064 g, 2.0 mmol). After stirring for 2 hours, the reaction mixture was quenched by addition of 1N aqueous hydrochloric acid solution (10 mL) and extracted with dichloromethane (3×20 mL). The combined organics was concentrated, the residue was purified by chromatography eluting with a gradient of 5 to 10% dichloromethane in methanol containing 2% ammonia to afford the title compound as a colorless solid (0.13 g, 14%): $^1$H NMR (300 MHz, DMSO-$d_6$) δ7.47-7.40 (m, 1H), 7.38-7.33 (m, 2H), 7.18-7.09 (m, 1H), 6.86-6.67 (m, 1H), 4.64-4.53 (m, 1H), 4.51-4.37 (m, 1H), 3.80-3.59 (m, 2H), 3.58-3.48 (m, 1H), 3.06-2.57 (m, 5H), 2.38-2.11 (m, 2H), 2.07-1.93 (m, 1H), 1.93-1.77 (m, 1H), 1.76-1.61 (m, 1H), 1.59-1.29 (m, 2H), 0.90-0.76 (m, 2H), 0.65-0.48 (m, 2H): MS(ES+) m/z 547.1, 545.1 (M+1).

Step 3. Preparation of 5-cyclopropyl-4-(((R)-1-((S)-1-(3,5-dichlorophenyl)-2-methoxyethyl)piperidin-3-yl)oxy)-2-fluoro-N-(methylsulfonyl)benzamide, trifluoroacetic acid salt

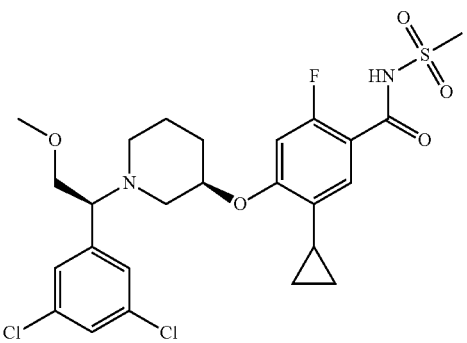

To a solution of 5-cyclopropyl-4-(((3R)-1-(1-(3,5-dichlorophenyl)-2-hydroxyethyl)piperidin-3-yl)oxy)-2-fluoro-N-(methylsulfonyl)benzamide (0.08 g, 0.12 mmol) in dimethoxyethane (1 mL) was added sodium hydride (60% in mineral oil, 0.025 g, 0.62 mmol). The reaction mixture was stirred for 30 minutes and methyl iodide (0.026 g, 0.19 mmol) was added. After stirring for 16 hours, the reaction mixture was quenched by addition of water (10 mL) and extracted with dichloromethane (2×10 mL). The combined organic layers was concentrated and the residue purified by preparative HPLC eluting with a gradient of acetonitrile in water containing 0.1% trifluoroacetic acid to afford the title compound as a colorless solid (0.011 g, 14%): $^1$H NMR (300 MHz, CDCl$_3$) δ 8.82-8.64 (m, 1H), 7.55 (d, J=8.8 Hz, 1H), 7.47-7.38 (m, 3H), 6.88 (d, J=14.4 Hz, 1H), 4.92-4.81 (m, 1H), 4.26-4.19 (m, 1H), 4.12-4.02 (m, 1H), 3.92-3.79 (m, 2H), 3.39 (s, 3H), 3.36 (s, 3H), 3.35-3.28 (m, 1H), 2.79-2.65 (m, 2H), 2.28-2.18 (m, 1H), 2.09-1.96 (m, 2H), 1.71-1.56 (m, 2H), 0.96-0.87 (m, 2H), 0.67-0.59 (m, 2H); MS(ES+) m/z 561.1, 559.1 (M+1).

Example 449

Synthesis of 5-cyclopropyl-4-(((1R,3R,5S)-8-(3,5-dichlorobenzyl)-8-azabicyclo[3.2.1]octan-3-yl)methoxy)-2-fluoro-N-(methylsulfonyl)benzamide

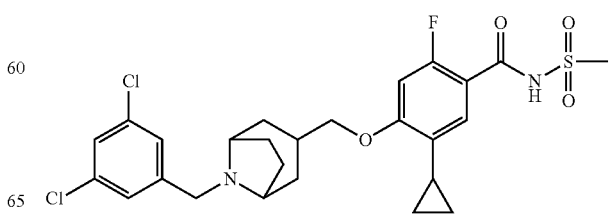

Step 1. Preparation of benzyl 3-((2-cyclopropyl-5-fluoro-4-((methylsulfonyl)carbamoyl)phenoxy)methyl)-8-azabicyclo[3.2.1]octane-8-carboxylate

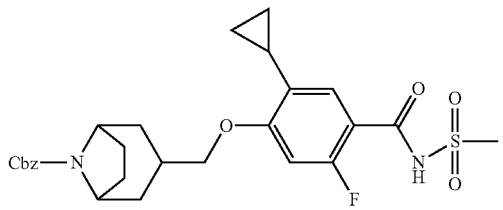 [SMILES: CS(=O)(=O)NC(=O)c1cc(C2CC2)c(OCC2CC3CCC(C2)N3C(=O)OCc2ccccc2)cc1F]

Following the procedure as described in Example 346 Step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-((8-((benzyloxy)carbonyl)-8-azabicyclo[3.2.1]octan-3-yl)methoxy)-5-cyclopropyl-2-fluorobenzoic acid, the title compound was obtained as a colorless solid (0.75 g, 72%): MS(ES+) m/z 531.1 (M+1).

Step 2. Preparation of 4-(8-azabicyclo[3.2.1]octan-3-ylmethoxy)-5-cyclopropyl-2-fluoro-N-(methylsulfonyl)benzamide

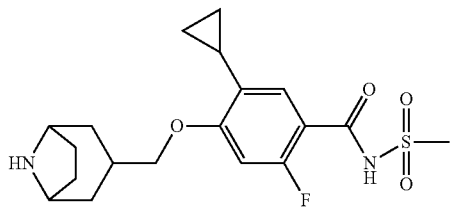 [SMILES: CS(=O)(=O)NC(=O)c1cc(C2CC2)c(OCC2CC3CCC(C2)N3)cc1F]

Following the procedure as described in Example 396 step 5 and making non-critical variations as required to replace (1R,3S,5S)-benzyl 3-((2-cyclopropyl-4-((cyclopropylsulfonyl)carbamoyl)-5-fluorophenoxy)methyl)-8-azabicyclo[3.2.1]octane-8-carboxylate with (1R,3S,5S)-benzyl 3-((2-cyclopropyl-5-fluoro-4-((methylsulfonyl)carbamoyl)phenoxy)methyl)-8-azabicyclo[3.2.1]octan-8-carboxylate, the title compound was obtained (0.55 g, 98%): MS(ES+) m/z 367.1 (M+1).

Step 3. Preparation of 5-cyclopropyl-4-(((1R,3r,5S)-8-(3,5-dichlorobenzyl)-8-azabicyclo[3.2.1]octan-3-yl)methoxy)-2-fluoro-N-(methylsulfonyl)benzamide

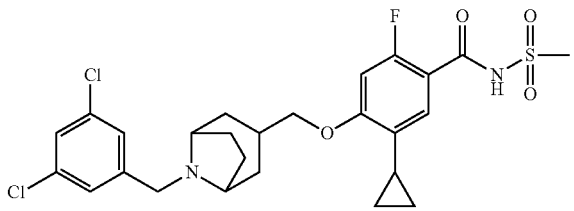 [SMILES: CS(=O)(=O)NC(=O)c1cc(C2CC2)c(OCC2CC3CCC(C2)N3Cc2cc(Cl)cc(Cl)c2)cc1F]

Following the procedure as described in Example 441, and making variation as required to replace 4-(8-azabicyclo[3.2.1]octan-3-ylmethoxy)-N-(azetidin-1-ylsulfonyl)-5-cyclopropyl-2-fluorobenzamideate with 4-(8-azabicyclo[3.2.1]octan-3-ylmethoxy)-5-cyclopropyl-2-fluoro-N-(methylsulfonyl)benzamide and to replace (bromomethylene)dibenzene with 1,3-dichloro-5-(chloromethyl)benzene, the title compound was obtained (0.04 g, 41%). $^1$H NMR (300 MHz, DMSO-$d_6$) δ7.67-7.44 (m, 3H), 7.14 (d, J=8.4 Hz, 1H), 6.79 (d, J=12.9 Hz, 1H), 3.92-3.73 (m, 4H), 3.54-3.36 (m, 2H), 3.05 (s, 3H), 2.33-1.55 (m, 10H), 0.91-0.77 (m, 2H), 0.63-0.53 (m, 2H); MS(ES+) m/z 557.1, 555.1 (M+1).

Example 450

Synthesis of 4-(((1R,4S,6R)-2-((S)-1-(2-chloro-4-fluorophenyl)ethyl)-2-azabicyclo[2.2.1]heptan-6-yl)oxy)-5-cyclopropyl-2-fluoro-N-(methylsulfonyl)benzamide, trifluoroacetic acid salt

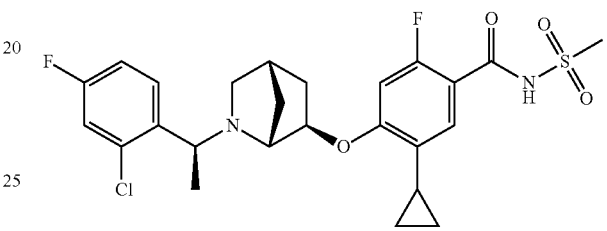

Step 1. Preparation of tert-butyl 5-chloro-2-fluoro-4-(((1R,4S,6R)-2-((S)-1-phenylethyl)-2-azabicyclo[2.2.1]heptan-6-yl)oxy)benzoate

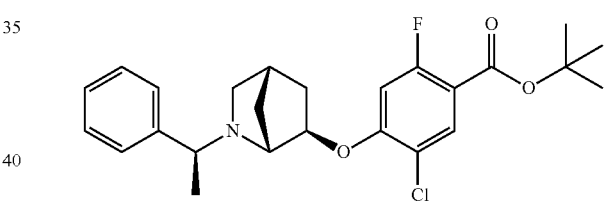

Following the procedure as described in Example 445 step 4 and making variation as required to replace (R)-5-hydroxy-1-(4-methoxybenzyl)piperidin-2-one with (1R,4S,6R)-2-((S)-1-phenylethyl)-2-azabicyclo[2.2.1]heptan-6-ol, and purifying the compound by column chromatography eluting with a gradient of ethyl acetate in hexanes (50% to 100%), the title compound was obtained (2.76 g, 49%). MS(ES+) m/z: 448.1, 446.1 (M+1).

Step 2. Preparation of tert-butyl 5-cyclopropyl-2-fluoro-4-(((1R,4S,6R)-2-((S)-1-phenylethyl)-2-azabicyclo[2.2.1]heptan-6-yl)oxy)benzoate

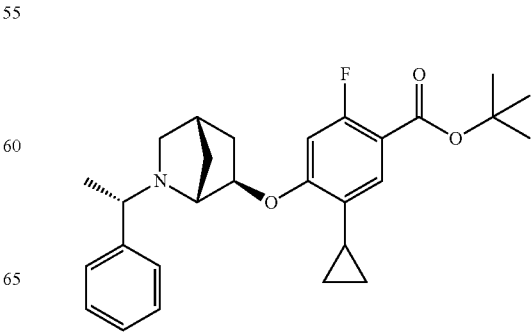

Following the procedure as described in Example 445 step 5, and making variation as required to replace (R)-tert-butyl 5-chloro-2-fluoro-4-((1-(4-methoxybenzyl)-6-oxopiperidin-3-yl)oxy)benzoate with tert-butyl 5-chloro-2-fluoro-4-(((1R,4S,6R)-2-((S)-1-phenylethyl)-2-azabicyclo[2.2.1]heptan-6-yl)oxy)benzoate, the title compound was obtained as a colorless gum (1.82 g, 66%): MS(ES+) m/z 452.2 (M+1).

Step 3. Preparation of tert-butyl 4-((1R,4S,6R)-2-azabicyclo[2.2.1]heptan-6-yloxy)-5-cyclopropyl-2-fluorobenzoate

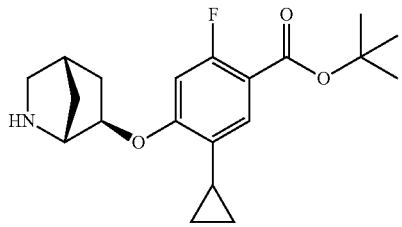 [SMILES: CC(C)(C)OC(=O)c1cc(C2CC2)c(O[C@@H]2C[C@H]3CN[C@@H]2C3)cc1F]

To a stirred solution of tert-butyl 5-cyclopropyl-2-fluoro-4-(((1R,4S,6R)-2-((S)-1-phenylethyl-2-azabicyclo[2.2.1]heptan-6-yl)oxy)benzoate (1.75 g, 3.88 mmol) and ammonium formate (7.3 g, 116 mmol) in methanol (50 mL) and wafer (5 mL) was added 10% palladium on carbon (0.05 g). After stirring for 2 hours at reflux, the reaction mixture was filtered over diatomaceous earth and rinsed with methanol (2×30 mL). The filtrate was concentrated, basified with saturated sodium bicarbonate solution and extracted with dichloromethane (2×40 mL). The combined organic layers were dried over anhydrous sodium sulfate, filtered and concentrated to afford the title compound (1.22 g, 80%): MS(ES+) m/z 348.2 (M+1).

Step 4. Preparation of tert-butyl 4-(((1R,4S,6R)-2-((S)-1-(2-chloro-4-fluorophenyl)ethyl)-2-azabicyclo[2.2.1]heptan-6-yl)oxy)-5-cyclopropyl-2-fluorobenzoate

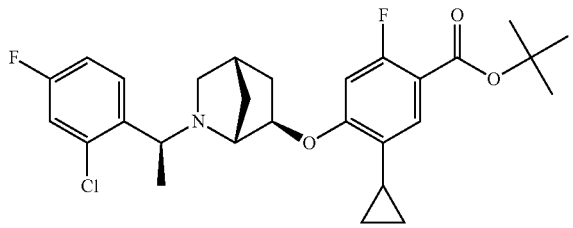 [SMILES: C[C@@H](c1ccc(F)cc1Cl)N1C[C@H]2C[C@@H]1[C@H](Oc1cc(F)c(C(=O)OC(C)(C)C)cc1C1CC1)C2]

And tert-butyl 4-(((1R,4S,6R)-2-((R)-1-(2-chloro-4-fluorophenyl)ethyl)-2-azabicyclo[2.2.1]heptan-6-yl)oxy)-5-cyclopropyl-2-fluorobenzoate

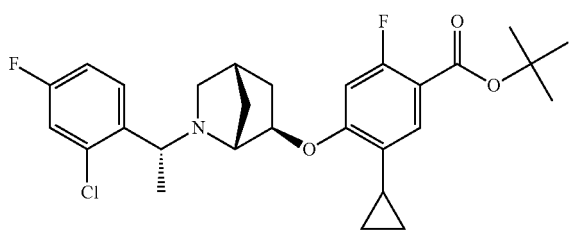 [SMILES: C[C@H](c1ccc(F)cc1Cl)N1C[C@H]2C[C@@H]1[C@H](Oc1cc(F)c(C(=O)OC(C)(C)C)cc1C1CC1)C2]

To a stirred solution of tert-butyl 4-((1R,4S,6R)-2-azabicyclo[2.2.1]heptan-6-yloxy)-5-cyclopropyl-2-fluorobenzoate (1.22 g, 3.51 mmol) in acetonitrile (15 mL) under a nitrogen atmosphere was added 2-chloro-1-(1-chloroethyl)-4-fluorobenzene (0.87 g, 4.55 mmol), potassium carbonate (1.38 g, 10 mmol) and potassium iodide (0.165 g, 1 mmol). After stirring at reflux for 16 hours, the reaction mixture was cooled to ambient temperature, quenched with water (15 mL) and extracted with ethyl acetate (3×20 mL). The combined organic layers was concentrated and the residue was purified by column chromatography (0% to 30% ethyl acetate in hexanes) to give the title compound (0.28 g, 16%). MS(ES+) m/z 504.1 (M+1); its diastereoisomer tert-butyl 4-(((1R,4S,6R)-2-((R)-1-(2-chloro-4-fluorophenyl)ethyl)-2-azabicyclo[2.2.1]heptan-6-yl)oxy-5-cyclopropyl-2-fluorobenzoate was also isolated (0.25 g, 14%): MS(ES+) m/z 504.1 (M+1).

Step 5. Preparation of 4-(((1R,4S,6R)-2-((S)-1-(2-Chloro-4-fluorophenyl)ethyl)-2-azabicyclo[2.2.1] heptan-6-yl)oxy)-5-cyclopropyl-2-fluoro-N-(methylsulfonyl)benzamide, trifluoroacetic acid salt

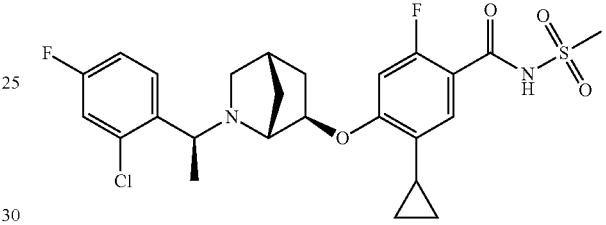

To a stirred solution of tert-butyl 4-(((1R,4S,6R)-2-((S)-1-(2-chloro-4-fluorophenyl)ethyl)-2-azabicyclo[2.2.1]heptan-6-yl)oxy)-5-cyclopropyl-2-fluorobenzoate (0.13 g, 0.26 mmol) in dichloromethane (2 mL) was added trifluoroacetic acid (1 mL). After stirring at ambient temperature for 30 minutes, the reaction mixture was concentrated and co-concentrated with toluene (2×10 mL). The residue was dissolved in dichloromethane (0.5 mL), and to this solution was added 1-ethyl-3-(3-dimethylaminopropyl)carbodiimide (0.11 g, 0.44 mmol), 4-dimethylaminopyridine (0.09 g, 0.78 mmol) and methanesulfonamide (0.03 g, 0.34 mmol). After stirring at ambient temperature for 16 hours, the reaction mixture was quenched with aqueous hydrochloric acid solution (6N, 0.2 mL), diluted with acetonitrile (0.5 mL) and purified by preparative HPLC (gradient of acetonitrile in water +0.1% trifluoroacetic acid) to afford the title compound as a colorless solid (0.06 g, 71%): $^1$H NMR (300 MHz, DMSO-d$_6$) δ12.30-11.64 (br s, 1H), 11.36-10.08 (br s, 1H), 7.99-7.84 (m, 1H), 7.67-7.51 (m, 1H), 7.49-7.38 (m, 1H), 7.23-6.98 (m, 1H), 6.91-6.00 (m, 1H), 5.25-4.47 (m, 2H), 3.86-2.51 (m, 7H), 2.29-2.06 (m, 1H), 2.36-1.79 (m, 3H), 1.78-1.41 (m, 4H), 0.95-0.48 (m, 4H); MS(ES+) m/z 527.1, 525.1 (M+1).

Example 451

Synthesis of 4-(((1R,4s,6R)-2-((R)-1-(2-chloro-4-fluorophenyl)ethyl)-2-azabicyclo[2.2.1]heptan-6-yl)oxy)-5-cyclopropyl-2-fluoro-N-(methylsulfonyl)benzamide, trifluoroacetic acid salt

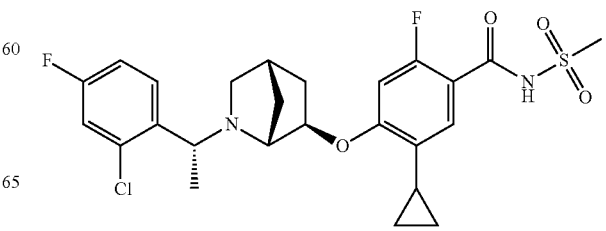

Following the procedure as described in Example 450 step 5 and making variation as required to replace tert-butyl 4-(((1R,4S,6R)-2-((S)-1-(2-chloro-4-fluorophenyl)ethyl)-2-azabicyclo[2.2.1]heptan-6-yl)oxy)-5-cyclopropyl-2-fluorobenzoate with its diastereoisomer tert-butyl 4-(((1R,4S,6R)-2-((R)-1-(2-chloro-4-fluorophenyl)ethyl)-2-azabicyclo[2.2.1]heptan-6-yl)oxy)-5-cyclopropyl-2-fluorobenzoate, the title compound was obtained as a colorless solid (0.04 g, 51%): $^1$H NMR (300 MHz, DMSO-$d_6$) δ12.14-11.78 (br s, 1H), 10.49-10.27 (br s, 1H), 8.15-8.00 (m, 1H), 7.64-7.33 (m, 1H), 7.52-7.39 (m, 1H), 7.11-7.03 (m, 1H), 6.36-6.22 (m, 1H), 5.01-4.80 (m, 2H), 3.64-2.64 (m, 7H), 2.30-1.99 (m, 2H), 1.96-1.78 (m, 2H), 1.75-1.46 (m, 2H), 0.87-0.72 (m, 2H), 0.65-0.53 (m, 2H): MS(ES+) m/z 527.1, 525.1 (M+1).

Example 452

Synthesis of 4-(((R)-1-((R)-1-(2-chloro-4-fluorophenyl)ethyl)-5,5-dimethylpiperidin-3-yl)oxy)-5-cyclopropyl-2-fluoro-N-(methylsulfonyl)benzamide, trifluoroacetic acid salt

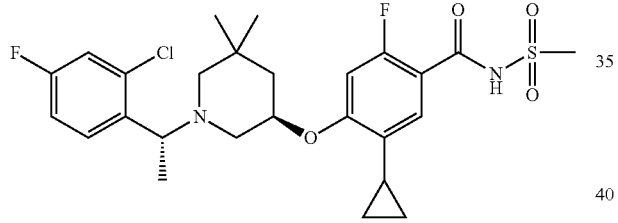

Step 1. Preparation of (R)-tert-butyl 4-((1-benzyl-5,5-dimethylpiperidin-3-yl)oxy)-5-chloro-2-fluorobenzoate

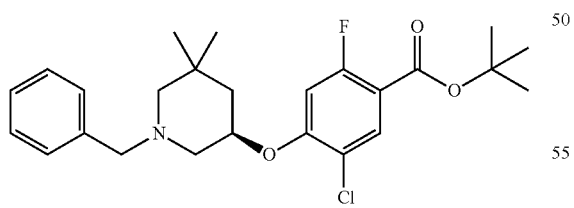

Following the procedure as described in Example 422 step 1 and making variation as required to replace (R)-1-benzylpiperidin-3-ol with (R)-1-benzyl-5,5-dimethylpiperidin-3-ol (prepared accordingly to Ma Y.; Lahue B. R. et al.; U.S. patent 2008/0004287 A1), the title compound was obtained as a colorless solid (0.73 g, 68%): MS(ES+) m/z 450.2, 448.2 (M+1).

Step 2. Preparation of (R)-tert-butyl 4-((1-benzyl-5,5-dimethylpiperidin-3-yl)oxy)-5-cyclopropyl-2-fluorobenzoate

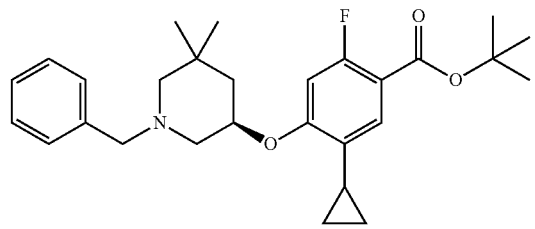 [SMILES: CC1(C)C[C@@H](Oc2cc(F)c(C(=O)OC(C)(C)C)cc2C2CC2)CN(Cc2ccccc2)C1]

Following the procedure as described in Example 422 step 2 and making variation as required to replace (R)-tert-butyl 4-((1-benzylpiperidin-3-yl)oxy)-5-chloro-2-fluorobenzoate with (R)-tert-butyl 4-((1-benzyl-5,5-dimethylpiperidin-3-yl)oxy)-5-chloro-2-fluorobenzoate, the title compound was obtained as oil (0.47 g, 63%): MS(ES+) m/z 454.1 (M+1).

Step 3. Preparation of (R)-tert-butyl 5-cyclopropyl-4-((5,5-dimethylpiperidin-3-yl)oxy)-2-fluorobenzoate

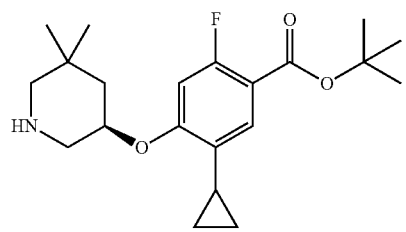 [SMILES: CC1(C)CNC[C@H](Oc2cc(F)c(C(=O)OC(C)(C)C)cc2C2CC2)C1]

Following the procedure as described in Example 450 step 3, and making variation as required to replace tert-butyl 5-cyclopropyl-2-fluoro-4-(((1R,4S,6R)-2-((S)-1-phenylethyl)-2-azabicyclo[2.2.1]heptan-6-yl)oxy)benzoate with (R)-tert-butyl 4-((1-benzyl-5,5-dimethylpiperidin-3-yl)oxy)-5-cyclopropyl-2-fluorobenzoate, the title compound was obtained as an oil (0.38 g, 96%): MS(ES+) m/z 364.2 (M+1).

Step 4. Preparation of tert-butyl 4-(((3R)-1-(1-(2-chloro-4-fluorophenyl)ethyl)-5,5-dimethylpiperidin-3-yl)oxy)-5-cyclopropyl-2-fluorobenzoate

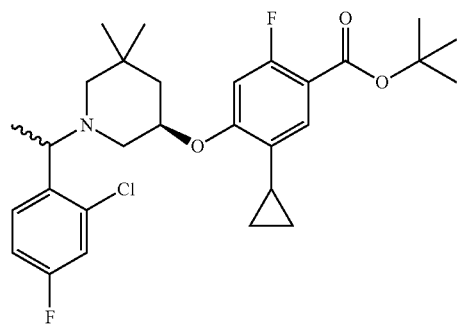 [SMILES: CC(c1ccc(F)cc1Cl)N1C[C@H](Oc2cc(F)c(C(=O)OC(C)(C)C)cc2C2CC2)CC(C)(C)C1]

Following the procedure as described in Example 450 step 4, and snaking variation as required to replace tert-butyl 4-((1R,4S,6R)-2-azabicyclo[2.2.1]heptan-6-yloxy)-5-cyclopropyl-2-fluorobenzoate with (R)-tert-butyl 5-cyclopropyl-4-((5,5-dimethylpiperidin-3-yl)oxy)-2-fluorobenzoate, the title compound was obtained as an oil (0.22 g, 43%); MS(ES+) m/z 522.1, 520.1 (M+1).

Step 5. Preparation of 4-(((R)-1-((R)-1-(2-Chloro-4-fluorophenyl)ethyl)-5,5-dimethylpiperidin-3-yl)oxy)-5-cyclopropyl-2-fluoro-N-(methylsulfonyl)benzamide, trifluoroacetic acid salt

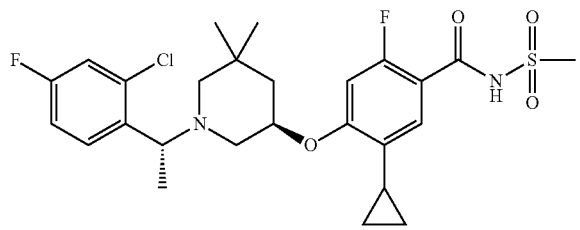 [SMILES: C[C@H](c1ccc(F)cc1Cl)N1C[C@H](Oc2cc(F)c(C(=O)NS(C)(=O)=O)cc2C2CC2)CC(C)(C)C1]

Following the procedure as described in Example 450 step 5, and making variation as required to replace tert-butyl 4-(((1R,4S,6R)-2-((S)-1-(2-chloro-4-fluorophenyl)ethyl)-2-azabicyclo[2.2.1]heptan-6-yl)oxy)-5-cyclopropyl-2-fluorobenzoate with tert-butyl 4-(((3R)-1-(1-(2-chloro-4-fluorophenyl)ethyl)-5,5-dimethylpiperidin-3-yl)oxy)-5-cyclopropyl-2-fluorobenzoate, the title compound was obtained as a colorless solid (0.02 g, 15%): $^1$H NMR (300 MHz, DMSO-$d_6$) δ 7.61 (dd, J=8.7, 6.5 Hz, 1H), 7.35 (dd, J=8.9, 2.6 Hz, 1H), 7.25-7.02 (m, 3H), 6.65-6.50 (m, 2H), 4.56-4.39 (m, 1H), 3.87 (q, J=6.3 Hz, 1H), 3.06-2.74 (m, 4H), 2.39 (d, J=10.7 Hz, 1H), 2.19-2.01 (m, 1H), 2.00-1.85 (m, 2H), 1.80-1.67 (m, 1H), 1.32-1.17 (m, 4H), 0.97 (s, 3H), 0.93 (s, 3H), 0.86-0.73 (m, 2H), 0.60-0.44 (m, 2H); MS(ES+) m/z 543.1, 541.1 (M+1).

Example 453

Synthesis of 5-cyclopropyl-4-((1-(2,4-dichloro-5-fluorobenzyl)piperidin-4-yl)methoxy)-2-fluoro-N-(methylsulfonyl)benzamide, trifluoroacetic acid salt

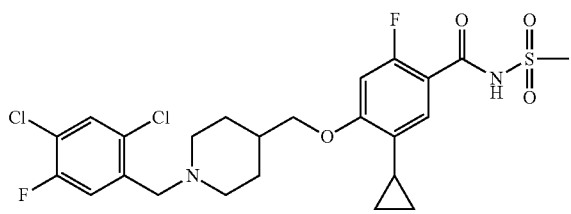 [SMILES: CS(=O)(=O)NC(=O)c1cc(C2CC2)c(OCC2CCN(Cc3cc(F)c(Cl)cc3Cl)CC2)cc1F]

Step 1. Preparation of 4-((1-benzylpiperidin-4-yl)methoxy)-5-cyclopropyl-2-fluoro-N-(methylsulfonyl)benzamide

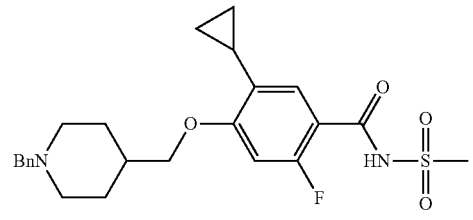 [SMILES: CS(=O)(=O)NC(=O)c1cc(C2CC2)c(OCC2CCN(Cc3ccccc3)CC2)cc1F]

To a solution of tert-butyl 4-((1-benzylpiperidin-4-yl)methoxy)-5-cyclopropyl-2-fluorobenzoate (1.55 g, 3.54 mmol) in dichloromethane (10 mL) was added trifluoroacetic acid (5 mL). The reaction mixture was stirred for 1.5 h and the solvent was concentration in vacuo. The residue was redissolved in anhydrous dichloromethane (10 mL). To this solution, was added 1-ethyl-3-(3-dimethylaminopropyl)carbodiimide (1.37 g, 5.30 mmol), 4-dimethylaminopyridine (1.08 g, 8.84 mmol) and methanesulfonamide (0.37 g, 3.89 mmol). The reaction mixture was stirred at ambient temperature for 16 hours, and then diluted with dichloromethane (20 mL), washed with 1N aqueous hydrochloric acid solution (10 mL), the aqueous layer was extracted with dichloromethane (20 mL). The combined organic layer dried over anhydrous sodium sulfate, filtered and concentrated. The residue was purified by column, chromatography (0% to 10% methanol (1% ammonia) in dichloromethane) to afford the title compound as a gum (1.32 g, 81%): 1H NMR (300 MHz, CDCl$_3$) δ 7.55 (d, J=9.04 Hz, 1H), 7.44-7.36 (m, 5H), 6.52 (d, J=1.4.25 Hz, 1H), 4.16-4.02 (m, 2H), 3.94-3.86 (m, 2H), 3.64-3.43 (m, 2H), 3.39 (s, 3H), 2.68-2.43 (m, 2H), 2.09-1.87 (m, 6H), 0.97-0.85 (m, 2H), 0.65-0.55 (m, 2H).

Step 2. Preparation of 5-cyclopropyl-2-fluoro-N-(fluorosulfonyl)-4-(piperidin-4-ylmethyl)benzamide hydrochloride

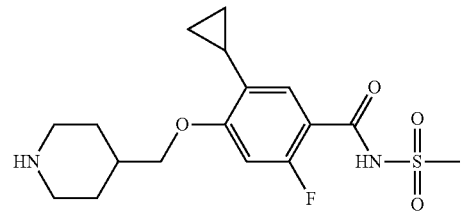 [SMILES: CS(=O)(=O)NC(=O)c1cc(C2CC2)c(OCC2CCNCC2)cc1F]

To a stirred solution of 4-((1-benzylpiperidin-4-yl)methoxy)-5-cyclopropyl-2-fluoro-N-(methylsulfonyl)benzamide (1.25 g, 2.72 mmol)) in degassed ethyl acetate (5 mL) was added 10% palladium on carbon (0.02 g) and the flask was put under 1 atm of hydrogen. The reaction mixture was stirred for 24 hours at ambient temperature, then filtered over diatomaceous earth and rinsed with a 1:1 mixture of methanol and 1 M aqueous hydrochloric acid solution (2×20 mL). The filtrate was concentrated to give the title compound (0.55 g, 55%). MS(ES+) m/z 371.1 (M+1).

Step 3. Preparation of 5-cyclopropyl-4-((1-(2,4-difluoro-5-fluorobenzyl)piperidin-4-yl)methoxy)-2-fluoro-N-(methylsulfonyl)benzamide trifluoroacetate

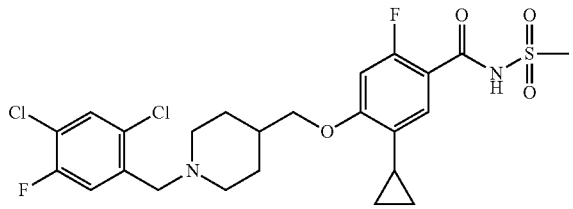 [SMILES: CS(=O)(=O)NC(=O)c1cc(C2CC2)c(OCC2CCN(Cc3cc(F)c(Cl)cc3Cl)CC2)cc1F]

To a stirred solution of 5-cyclopropyl-2-fluoro-N-(methylsulfonyl)-4-(piperidin-4-ylmethoxy)benzamide hydrochloride (0.05 g, 0.12 mmol) in acetonitrile (2 mL) under a nitrogen atmosphere was added 1,5-dichloro-2-(chloromethyl)-4-fluorobenzene (0.04 g, 0.18 mmol), potassium carbonate (0.04 g, 0.30 mmol) and potassium iodide (0.024 g, 0.15 mmol). The reaction mixture was stirred at reflux for 16 hours, cooled to ambient temperature, 1N aqueous hydrochloric acid solution (5 mL) was added and the mixture was extracted with ethyl acetate (3×10 mL), concentrated and purified by column chromatography (0% to 30% ethyl acetate (+1% formic acid) in hexanes) to give an oil which was further purified by preparative HPLC (gradient of acetonitrile in water +0.1% trifluoroacetic acid) to give the title compound as a colorless solid (0.04, 43%). $^1$H NMR (300 MHz, DMSO-$d_6$) δ12.15-11.63 (m, 1H), 9.91-9.31 (m, 1H), 7.99 (d, J=6.88 Hz, 1H), 7.77 (d, J=9.55 Hz, 1H), 7.10 (d, J=8.24 Hz, 1H), 6.95 (d, J=13.00 Hz, 1H), 4.44-4.31 (m, 2H), 4.01-3.90 (m, 2H), 3.53-3.40 (m, 2H), 3.30 (s, 3H), 3.21-3.00 (m, 2H), 2.17-1.88 (m, 4H), 1.68-1.46 (m, 2H), 0.93-0.79 (m, 2H), 0.72-0.60 (m, 2H); MS(ES+) m/z: 547.1, 549.1 (M+1).

Example 454

Synthesis of 5-cyclopropyl-4-((1-(3,5-dichloro-4-fluorobenzyl)piperidin-4-yl)methoxy)-2-fluoro-N-(methylsulfonyl)benzamide, trifluoroacetic acid salt

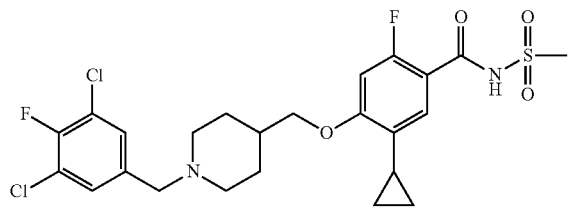 [SMILES: CS(=O)(=O)NC(=O)c1cc(C2CC2)c(OCC2CCN(Cc3cc(Cl)c(F)c(Cl)c3)CC2)cc1F]

Following the procedure as described in Example 453 step 3 and making variation as required to replace 1,5-dichloro-2-(chloromethyl)-4-fluorobenzene with 1,3-dichloro-5-(chloromethyl)-2-fluorobenzene, the title compound was obtained as a colorless solid (0.03 g, 33%): $^1$H NMR (300 MHz, DMSO-$d_6$) δ12.12-11.60 (m, 1H), 0.87-9.63 (m, 1H), 7.83-7.62 (m, 2H), 7.14-7.06 (m, 1H), 6.98-6.90 (m, 1H), 4.35-4.21 (m, 2H), 4.00-3.91 (m, 2H), 3.52-3.36 (m, 2H), 3.30 (s, 3H), 3.04-2.85 (m, 2H), 2.15-1.80 (m, 4H), 1.67-1.45 (m, 2H), 0.92-0.79 (m, 2H), 0.71-0.60 (m, 2H); MS(ES+) m/z 547.0, 549.0 (M+1).

Example 455

Synthesis of 4-((1-(5-chloro-2,4-dichlorobenzyl)piperidin-4-yl)methoxy)-5-cyclopropyl-2-fluoro-N-(methylsulfonyl)benzamide, trifluoroacetic acid salt

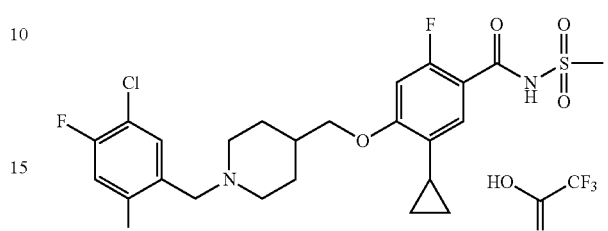

Following the procedure as described in Example 453 step 3, and making variation as required to replace 1,5-dichloro-2-(chloromethyl)-4-fluorobenzene with 1-chloro-5-(chloromethyl)-2,4-dichlorobenzene, the title compound was obtained as a colorless solid (0.02 g, 23%): $^1$H NMR (300 MHz, DMSO-$d_6$) δ12.06-11.74 (m, 1H), 9.65-9.36 (m, 1H), 7.87 (dd, J=7.9, 7.9 Hz, 1H), 7.71 (dd, J=9.6, 9.6 Hz, 1H), 7.10 (d, J=8.2 Hz, 1H), 6.94 (d, J=12.9 Hz, 1H), 4.35-4.22 (m, 2H), 3.99-3.91 (m, 2H), 3.50-3.42 (m, 2H), 3.30 (s, 3H), 3.11-2.93 (m, 2H), 2.13-1.88 (m, 4H), 1.62-1.43 (m, 2H), 0.92-0.80 (m, 2H), 0.70-0.61 (m, 2H); MS(ES+) m/z 533.1, 531.1 (M+1).

Example 456

Synthesis of 4-((1-(3-chloro-4,5-difluorobenzyl)piperidin-4-yl)methoxy)-5-cyclopropyl-2-fluoro-N-(methylsulfonyl)benzamide, trifluoroacetic acid salt

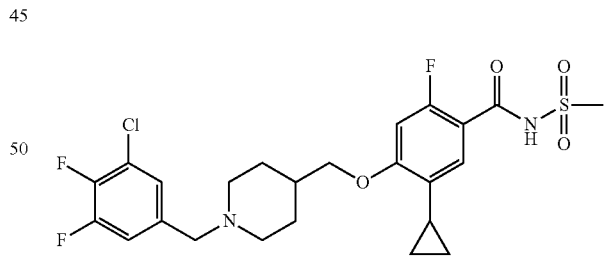

Following the procedure as described in Example 453 step 3, and making variation as required to replace 1,5-dichloro-2-(chloromethyl)-4-fluorobenzene with 1-chloro-5-(chloromethyl)-2,3-difluorobenzene, the title compound was obtained as a colorless solid (0.03, 31%); $^1$H NMR (300 MHz, DMSO-$d_6$) δ11.40-11.06 (m, 1H), 7.50-7.35 (m, 2H), 7.12 (d, J=8.4 Hz, 1H), 6.85 (d, J=12.9 Hz, 1H), 3.91 (d, J=6.0 Hz, 2H), 3.67-3.59 (m, 2H), 3.16 (s, 3H), 2.99-2.82 (m, 2H), 2.23-2.06 (m, 2H), 2.04-1.95 (m, 1H), 1.86-1.72 (m, 3H), 1.46-1.27 (m, 2H), 0.90-0.80 (m, 2H), 0.66-0.55 (m, 2H); MS(ES+) m/z 533.2, 531.2 (M+1).

Example 457

Synthesis of 4-((1-(5-chloro-2-(trifluoromethyl)benzyl)-4-fluoropiperidin-4-yl)methoxy)-5-cyclopropyl-N-(cyclopropylsulfonyl)-2-fluorobenzamide, trifluoroacetic acid salt

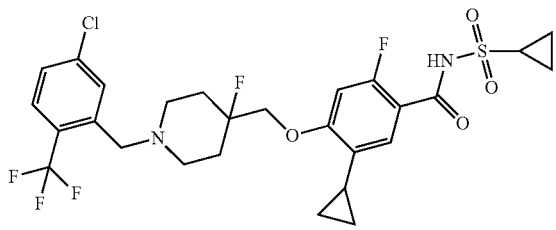 [SMILES: O=C(NS(=O)(=O)C1CC1)c1cc(C2CC2)c(OCC2(F)CCN(Cc3cc(Cl)ccc3C(F)(F)F)CC2)cc1F]

Step 1. Preparation of tert-butyl 4-((1-(5-chloro-2-(trifluoromethyl)benzyl)-4-fluoropiperidin-4-yl)methoxy)-5-cyclopropyl-2-fluorobenzoate

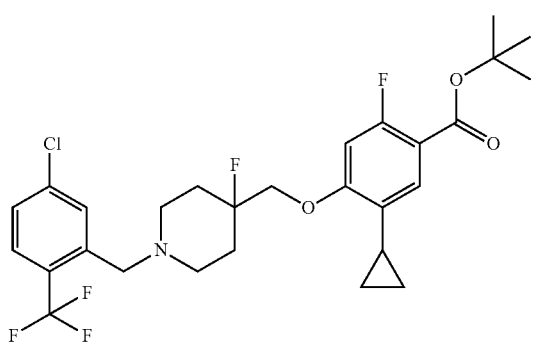 [SMILES: CC(C)(C)OC(=O)c1cc(C2CC2)c(OCC2(F)CCN(Cc3cc(Cl)ccc3C(F)(F)F)CC2)cc1F]

Following the procedure as described in Example 346 step 5 and making non-critical variations as required to replace 1-chloro-3-(chloromethyl)-2-fluoro-5-(trifluoromethyl)benzene with 5-chloro-2-(trifluoromethyl)benzyl methanesulfonate, the title compound was obtained as a colorless gum (0.45 g, 69%): MS(ES+) m/z 562.1, 560.1 (M+1).

Step 2. Preparation of 4-((1-(5-chloro-2-(trifluoromethyl)benzyl)-4-fluoropiperidin-4-yl)methoxy)-5-cyclopropyl-2-fluorobenzoic acid

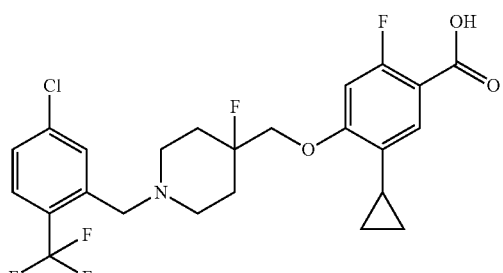

Following the procedure as described in Example 346 step 6, and making non-critical variations as required to replace tert-butyl 4-((4-(tert-butoxycarbonyl)-2-cyclopropyl-5-fluorophenoxy)methyl)-4-fluoropiperidine-1-carboxylate with tert-butyl 4-((1-(5-chloro-2-(trifluoromethyl)benzyl)-4-fluoropiperidin-4-yl)methoxy)-5-cyclopropyl-2-fluorobenzoate to afford the title compound as a colorless solid (0.36 g, 88%): MS(ES+) m/z 506.2, 504.0 (M+1).

Step 3. Preparation of 4-((1-(5-chloro-2-(trifluoromethyl)benzyl)-4-fluoropiperidin-4-yl)methoxy)-5-cyclopropyl-N-(cyclopropylsulfonyl)-2-fluorobenzamide, trifluoroacetic acid salt

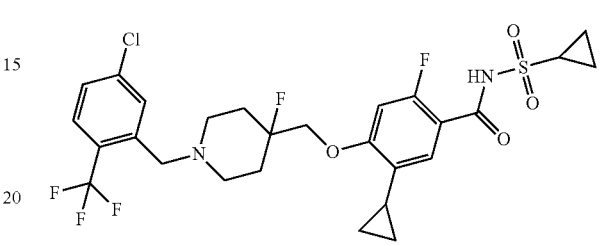

Following the procedure as described in Example 346 step 7 and making non-critical variations as required to replace 4-((1-(3-chloro-2-fluoro-5-(trifluoromethyl)benzyl)-4-fluoropiperidin-4-yl)methoxy)-5-cyclopropyl-2-fluorobenzoic acid with 4-((1-(5-chloro-2-(trifluoromethyl)benzyl)-4-fluoropiperidin-4-yl)methoxy)-5-cyclopropyl-2-fluorobenzoic acid and to replace methanesulfonamide with cyclopropanesulfonamide the title compound was obtained as a colorless solid (0.03 g, 28%); $^1$H NMR (300 MHz, DMSO-$d_6$) δ11.87 (br s, 1H), 9.99 (br s, 1H), 8.13 (br s, 1H), 7.61 (br s, 2H), 7.15 (d, J=8.3 Hz, 1H), 7.03 (d, J=12.8 Hz, 1H), 4.80-4.42 (m, 2H), 4.28 (d, J=20.6 Hz, 2H), 3.60-3.17 (m, 4H), 3.12-3.03 (m, 1H), 2.31-2.17 (m, 2H), 2.08-1.99 (m 3H), 1.14-1.09 (m, 4H), 0.94-0.87 (m, 2H), 0.73-0.67 (m, 2H); MS(ES−) m/z 506.2, 504.0 (M+1).

Example 458

Synthesis of (R)-5-cyclopropyl-4-((2-(3,4-dichlorobenzyl)morpholino)methyl)-2-fluoro-N-(methylsulfonyl)benzamide

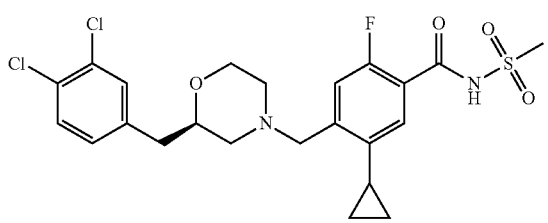 [SMILES: CS(=O)(=O)NC(=O)c1cc(C2CC2)c(CN2CCO[C@H](Cc3ccc(Cl)c(Cl)c3)C2)cc1F]

Step 1. Preparation of (R)-1-chloro-3-(3,4-dichlorophenyl)propan-2-ol

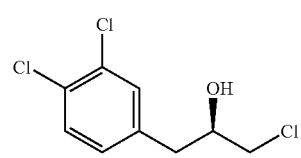 [SMILES: O[C@@H](CCl)Cc1ccc(Cl)c(Cl)c1]

A 50 mL flask charged with magnesium turnings (0.32 g, 13.33 mmol) was heated via heat gun under hi-vac. The flask was cooled to ambient temperature and flushed with argon before freshly distilled diethyl ether (1 mL) and 1,2-dibromoethane (2 drops) were added. The flask was equipped with a condenser before a solution of 4-bromo-1,2-dichlorobenzene (1.68 mL, 13.00 mmol) in diethyl ether (14 mL) was added dropwise so as to maintain a gentle reflux. The cloudy solution was stirred for 1 hour at ambient temperature. After cooling to 0° C., copper iodide (0.21 g, 1.08 mmol) was added. After 10 minutes stirring, a solution of (R)-epichlorohydrin (0.85 mL, 10.80 mmol) in diethyl ether (14 mL) was added dropwise. The reaction mixture was slowly warmed to ambient temperature and stirred overnight, quenched with saturated aqueous ammonium chloride solution (10 mL) at 0° C., and then poured into water (40 mL). The biphasic mixture was stirred until all solids dissolved. The blue aqueous layer was isolated and extracted with ethyl acetate (3×30 mL). The combined organic layers were washed with brine (150 mL); dried over anhydrous sodium sulfate, filtered and concentrated. The residue was purified using flash chromatography [0% to 5% to 10% ethyl acetate in hexanes] to yield the title compound as a colourless oil (2.50 g, 80%): $^1$H NMR (300 MHz, CDCl$_3$) δ7.38 (d, J=8.2 Hz, 1H), 7.35 (d, J=2.0 Hz, 1H), 7.09 (dd, J=2.0, 8.2 Hz, 1H), 4.06-3.90 (m, 1H), 3.62 (dd, J=3.9, 11.2 Hz, 1H), 3.49 (dd, J=6.3, 11.2 Hz, 1H), 2.84 (d, J=5.8 Hz, 1H), 2.83 (d, J=7.1 Hz, 1H), 2.22 (br s, 1H).

Step 2. Preparation of (R)-2-(3,4-dichlorobenzyl)morpholine

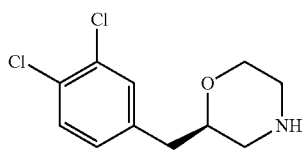 [SMILES: Clc1ccc(C[C@@H]2CNCCO2)cc1Cl]

To a solution of sodium hydroxide (2.50 g, 62.40 mmol) in water (5 mL) was added a solution of (R)-1-chloro-3-(3,4-dichlorophenyl)propan-2-ol (2.50 g, 10.40 mmol) in methanol (1.1 mL). After 5 minutes, 2-aminoethyl hydrogen sulfate (5.86 g, 41.60 mmol) was added in portions (4×1.47 g). The resulting suspension was heated at 40° C. for 5 hours. Toluene (25 mL) and powdered sodium hydroxide (2.50 g, 62.40 mmol) were added. The reaction mixture was stirred overnight at 65° C. After cooling to ambient temperature, the reaction mixture was quenched with water (300 mL). The aqueous layer was isolated and extracted with toluene (2×150 mL). The combined organics were washed with water (50 mL) and brine (50 mL), and concentrated. The residue was purified using flash chromatography [0% to 100-% (80:10:10 ethyl acetate/isopropanol/triethylamime) in hexanes] to yield the title compound as a colourless oil (0.83 g, 32%): MS(ES+) m/z 246.1, 248.1 (M+1).

Step 3. Preparation of tert-butyl 5-cyclopropyl-2-fluoro-4-(iodomethyl)benzoate

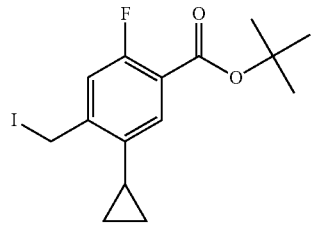 [SMILES: CC(C)(C)OC(=O)c1cc(C2CC2)c(CI)cc1F]

To a suspension of polymer bound triphenylphosphine (2.60 g, 7.80 mmol) in dichloromethane (60 mL) was added imidazole (0.53 g, 7.80 mmol) and iodine (2.00 g, 7.80 mmol). After 5 minutes, tert-butyl 5-cyclopropyl-2-fluoro-4-(hydroxymethyl)benzoate (1.60 g, 6.0 mmol) was added and the reaction mixture was stirred at ambient temperature overnight. The reaction mixture was filtered and the filtrate was washed with saturated aqueous sodium bisulfate solution (50 mL) and water (50 mL). The organic layer was dried over sodium sulfate, decanted and concentrated. The residue was dissolved in ethyl acetate (100 mL) and washed with saturated aqueous sodium bisulfate solution (20 mL), 1N hydrochloric acid solution (20 mL) and brine (20 mL). The organic layer was dried over sodium sulfate, decanted and concentrated to yield the title compound as a yellow solid (2.14 g, 94%): $^1$H NMR (300 MHz, CDCl$_3$) δ7.50 (d, J=7.3 Hz, 1H), 7.05 (d, J=10.9 Hz, 1H), 4.58 (m, 2H), 1.97-1.84 (m, 1H), 1.58 (s. 9H), 1.08-0.99 (m, 2H), 0.78-0.70 (m, 2H).

Step 4. Preparation of (R)-tert-butyl 5-cyclopropyl-4-((2-(3,4-dichlorobenzyl)morpholino)methyl)-2-fluorobenzoate

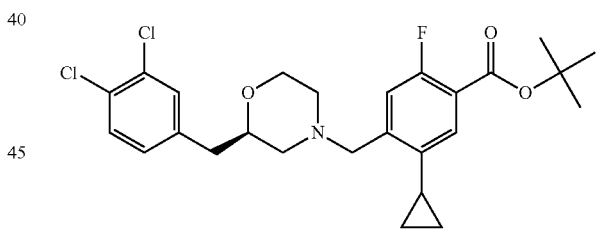

A suspension of tert-butyl 5-cyclopropyl-2-fluoro-4-(iodomethyl)benzoate (0.46 g, 1.22 mmol), (R)-2-(3,4-dichlorobenzyl)morpholine (0.60 g, 2.44 mmol), potassium phosphate (0.52 g, 2.44 mmol) in N,N-dimethyl formamide (22 mL) was heated at 80° C. for 2 hours. The reaction mixture was cooled to ambient temperature, and diluted with water (400 mL) and ethyl acetate (200 mL). The aqueous layer was isolated and extracted with ethyl acetate (3×100 mL). The combined organics were concentrated and the residue was purified by flash chromatography (0% to 10% ethyl acetate in hexanes) to yield the title compound (0.59 g, 97%): $^1$H NMR (300 MHz, CDCl$_3$) δ7.49 (d, J=7.2 Hz, 1H), 7.33 (d, J=8.2 Hz, 1H), 7.32 (d, J=2.0 Hz, 1H), 7.15 (d, J=11.7 Hz, 1H), 7.05 (dd, J=2.0, 8.2 Hz, 1H), 3.84 (d, J=10.6 Hz, 1H), 3.77-3.67 (m, 1H), 3.67-3.54 (m, 3H), 2.80-2.58 (m, 4H), 2.30-2.16 (m, 1H), 2.07-1.90 (m, 2H), 1.58 (s, 9H), 1.00-0.87 (m, 2H), 0.70-0.58 (m, 2H); MS(ES+) m/z 494.2, 496.1 (M+1).

Step 5. Preparation of (R)-5-cyclopropyl-4-((2-(3,4-dichlorobenzyl)morpholino)methyl)-2-fluorobenzoic acid hydrochloride

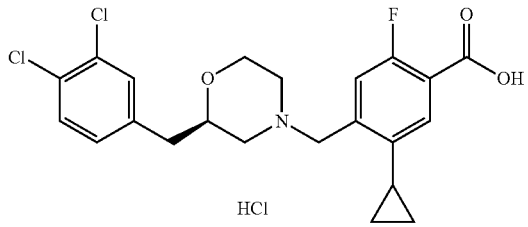 [SMILES: O=C(O)c1cc(C2CC2)c(CN2CCO[C@H](Cc3ccc(Cl)c(Cl)c3)C2)cc1F ; Cl]

A solution of (R)-tert-butyl-5-cyclopropyl-4-((2-(3,4-dichlorobenzyl)morpholino)methyl)-2-fluorobenzoate (0.17 g, 0.34 mmol) and hydrogenchloride (4.0 N solution in 1,4-dioxane, 1.72 mL, 6.88 mmol) in 1,4-dioxane (5 mL) was stirred overnight at ambient temperature, and then heated at 60° C. for 2 hours. The reaction mixture was cooled to ambient temperature and diluted with toluene (10 mL) and concentrated to yield the title compound (0.17 g, quant. yield), which was used without purification: MS(ES+) m/z 438.3, 440.0 (M+1): MS(ES−) m/z 436.1, 438.1 (M−1).

Step 6. Preparation of (R)-5-cyclopropyl-4-((2-(3,4-dichlorobenzyl)morpholino)methyl)-2-fluoro-N-(methylsulfonyl)benzamide

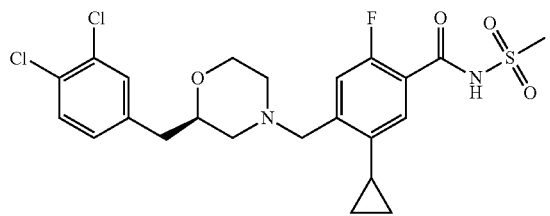 [SMILES: CS(=O)(=O)NC(=O)c1cc(C2CC2)c(CN2CCO[C@H](Cc3ccc(Cl)c(Cl)c3)C2)cc1F]

To a solution of (R)-5-cyclopropyl-4-((2-(3,4-dichlorobenzyl)morpholino)methyl)-2-fluorobenzoic acid hydrochloride (0.17 g, 0.36 mmol) in dichloromethane (10 mL) was added 1-ethyl-3-(3-dimethylaminopropyl)carbodiimide hydrochloride (0.1.0 g, 0.54 mmol), and 4-dimethylaminopyridine (0.10 g, 0.82 mmol). The reaction was stirred at ambient temperature for 10 minutes, methanesulfonamide (0.06 g, 0.58 mmol) was added and stirring was continued at ambient temperature overnight. The reaction mixture was concentrated, diluted with ethyl acetate (20 mL) and washed with 5% aqueous hydrochloric acid solution (10 mL). The organic layer was separated, washed with water and brine, dried over anhydrous sodium sulfate and concentrated. The residue was purified by flash chromatography (0% to 50% ethyl acetate in hexanes) to yield the title compound as a colorless solid (0.09 g, 50%); $^1$H NMR (300 MHz, CDCl$_3$) δ8.94-8.69 (m, 1H), 7.73 (d, J=7.8 Hz, 1H), 7.36-7.31 (m, 3H), 7.05 (d, J=8.1 Hz, 1H), 3.87 (d, J=11.2 Hz, 1H), 3.81-3.57 (m, 4H), 3.42 (s, 3H), 2.83-2.58 (m, 4H), 2.54-2.19 (m, 1H), 2.12-1.99 (m, 1H), 1.99-1.88 (m, 1H), 1.02-0.92 (m, 2H), 0.70-0.59 (m, 2H); MS(ES+) m/z 515.1, 517.1 (M+1), MS(ES−) m/z 513.2, 535.1 (M−1).

Example 459

Preparation of (R)—N-(azetidin-1-ylsulfonyl)-5-cyclopropyl-4-((2-(3,4-dichlorobenzyl) morpholino)methyl)-2-fluorobenzamide

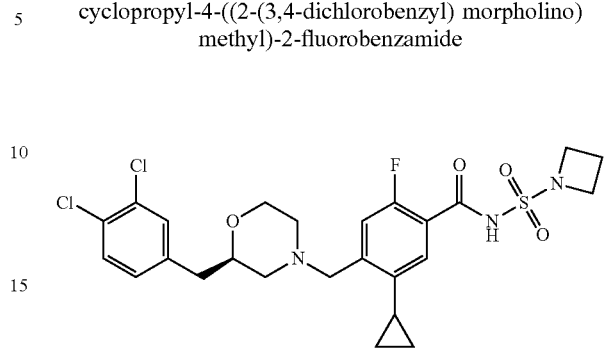

Following the procedure as described in Example 458 step 6 and making non-critical variations as required to replace methanesulfonamide with azetidine-1-sulfonamide, the title compound was obtained as a colorless solid (0.08 g, 41%): $^1$H NMR (300 MHz, CDCl$_3$) δ8.73 (d, J=15.7 Hz, 1H), 7.74 (d, J=7.8 Hz, 1H), 7.36-7.31 (m, 3H), 7.06 (dd, J=2.0, 8.2 Hz, 1H), 4.26 (t, J=7.7 Hz, 4H), 3.89-3.85 (m, 1H), 3.79-3.58 (m, 4H), 2.81-2.58 (m, 4H), 2.33-2.20 (m, 3H), 2.11-1.91 (m, 2H), 1.00-0.92 (m, 2H), 0.71-0.63 (m, 2H); MS(ES+) m/z 556.1, 558.1 (M+1), MS(ES−) m/z 554.2, 556.1 (M−1).

Example 460

Preparation of (R)-5-cyclopropyl-N-(cyclopropylsulfonyl)-4-((2-(3,4-dichlorobenzyl) morpholino)methyl)-2-fluorobenzamide

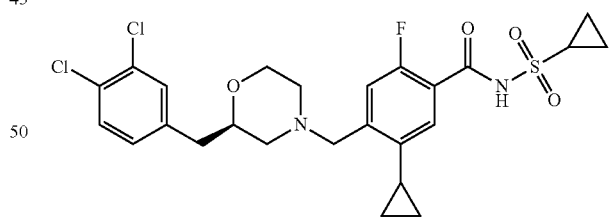

Following the procedure as described in Example 458 step 6 and making non-critical variations as required to replace methanesulfonamide with cyclopropanesulfonamide, the title compound was obtained as a colorless solid (0.07 g, 35%): $^1$H NMR (300 MHz, CDCl$_3$) δ8.78 (d, J=15.0 Hz, 1H), 7.74 (d, J=7.8 Hz, 1H), 7.36-7.31 (m, 3H), 7.05 (dd, J=1.9, 8.2 Hz, 1H), 3.91-3.85 (m, 1H), 3.81-3.57 (m, 4H), 3.16-3.02 (m, 1H), 2.83-2.52 (m, 4H), 2.32-2.19 (m, 1H), 2.08-1.85 (m, 2H), 1.53-1.38 (m, 2H), 1.20-1.06 (m, 2H), 1.00-0.87 (m, 2H), 0.70-0.56 (m, 2H); MS(ES+) m/z 541.1, 543.1 (M+1), MS(ES−) m/z 539.1, 541.1 (M−1).

Example 461

Synthesis of (S)-5-cyclopropyl-4-((2-(3,4-dichlorobenzyl)morpholino)methyl)-2-fluoro-N-(methylsulfonyl)benzamide

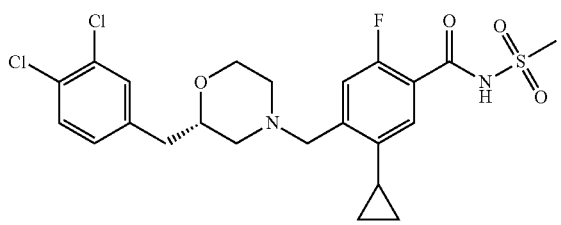 [SMILES: CS(=O)(=O)NC(=O)c1cc(C2CC2)c(CN2CCO[C@@H](Cc3ccc(Cl)c(Cl)c3)C2)cc1F]

Step 1. Preparation of (S)-1-chloro-3-(3,4-dichlorophenyl)propan-2-ol

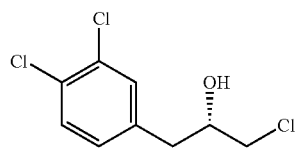 [SMILES: O[C@H](CCl)Cc1ccc(Cl)c(Cl)c1]

Following the procedure as described in Example 458 step 1 and making non-critical variations as required to replace with (S)-epichlorohydrin, the title compound was obtained as a colorless oil (2.70 g, 87%): $^1$H NMR (300 MHz, CDCl$_3$) δ7.39 (d, J=8.2 Hz, 1H), 7.35 (d, J=2.0 Hz, 1H), 7.09 (dd, J=2.0, 8.2 Hz, 1H), 4.10-3.98 (m, 1H), 3.62 (dd, J=3.9, 11.2 Hz, 1H), 3.49 (dd, J=6.3, 11.2 Hz, 1H), 2.85-2.82 (m, 2H), 2.20 (br s, 1H).

Step 2. Preparation of (S)-2-(3,4-dichlorobenzyl)morpholine

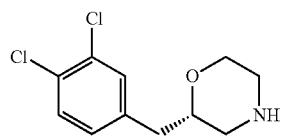

Following the procedure as described in Example 458 step 2 and making non-critical variations as required to replace (R)-1-chloro-3-(3,4-dichlorophenyl)propan-2-ol with (S)-1-chloro-3-(3,4-dichlorophenyl)propan-2-ol, the title compound was obtained as a colorless oil (1.04 g, 37%): MS(ES+) m/z 246.1, 248.1 (M+1).

Step 3. Preparation of (S)-tert-butyl 5-cyclopropyl-4-((2-(3,4-dichlorobenzyl)morpholino)methyl)-2-fluorobenzoate

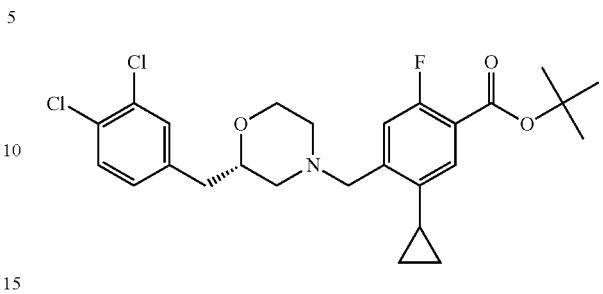

Following the procedure as described in Example 458 step 4 and making non-critical variations as required to replace (R)-2-(3,4-dichlorobenzyl)morpholine with (S)-2-(3,4-dichlorobenzyl)morpholine, the title compound was obtained (0.46 g, 98%): $^1$H NMR (300 MHz, CDCl$_3$) δ7.50 (d, J=7.3 Hz, 1H), 7.34 (d, J=8.2 Hz, 1H), 7.31 (d, J=2.0 Hz, 1H), 7.14 (d, J=11.7 Hz, 1H), 7.05 (dd, J=2.0, 8.2 Hz, 1H), 3.85 (d, J=10.6 Hz, 1H), 3.78-3.66 (m, 1H), 3.66-3.55 (m, 3H), 2.80-2.57 (m, 4H), 2.22 (dt, J=3.0, 11.2 Hz, 1H), 2.05-1.92 (m, 2H), 1.58 (s, 9H), 0.97-0.89 (m, 2H), 0.67-0.59 (m, 2H); MS(ES+) m/z 494.0, 496.0 (M+1).

Step 4. Preparation of (S)-5-cyclopropyl-4-((2-(3,4-dichlorobenzyl)morpholino)methyl)-2-fluorobenzoic acid hydrochloride

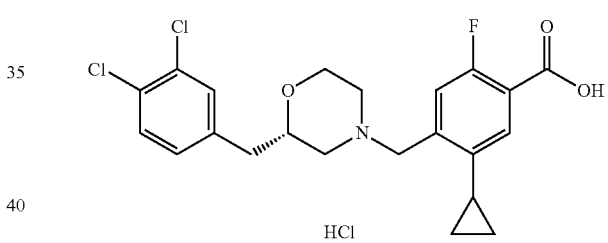

Following the procedure as described in Example 458 step 5 and making non-critical variations as required to replace (R)-tert-butyl 5-cyclopropyl-4-((2-(3,4-dichlorobenzyl)morpholinomethyl)-2-fluorobenzoate with (S)-tert-butyl 5-cyclopropyl-4-((2-(3,4-dichlorobenzyl)morpholino)methyl)-2-fluorobenzoate, the title compound was obtained as a colorless solid (0.43 g, 98%): MS(ES+) m/z 438.1, 440.0 (M+1); MS(ES−) m/z 436.1, 438.1 (M−1).

Step 5. Preparation of (S)-5-cyclopropyl-4-((2-(3,4-dichlorobenzyl)morpholino)methyl)-2-fluoro-N-(methylsulfonyl)benzamide

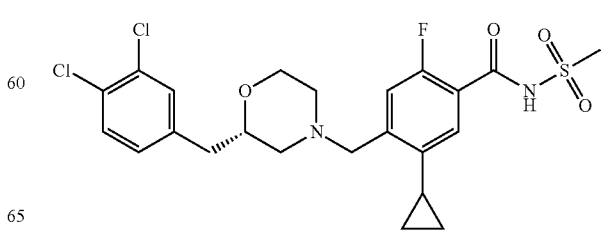

Following the procedure as described in Example 458 step 6 and making non-critical variations as required to replace (R)-5-cyclopropyl-4-((2-(3,4-dichlorobenzyl)morpholino)methyl)-2-fluorobenzoic acid hydrochloride with (S)-5-cyclopropyl-4-((2-(3,4-dichlorobenzyl)morpholino)methyl)-2-fluorobenzoic acid hydrochloride, the title compound was obtained as a colorless solid (0.04 g, 20%): ¹H NMR (300 MHz, CDCl₃) δ8.94-8.69 (m, 1H), 7.73 (d, J=7.8 Hz, 1H), 7.36-7.31 (m, 3H), 7.05 (d, J=8.1 Hz, 1H), 3.87 (d, J=11.2 Hz, 1H), 3.81-3.57 (m, 4H), 3.42 (s, 3H), 2.83-2.58 (m, 4H), 2.34-2.19 (m, 1H), 2.12-1.99 (m, 1H), 1.99-1.88 (m, 1H), 1.02-0.92 (m, 2H), 0.70-0.59 (m, 2H); MS(ES+) m/z 515.1, 517.1 (M+1), MS(ES−) m/z 513.2, 515.2 (M−1).

Example 462

Preparation of (S)-5-cyclopropyl-N-(cyclopropylsulfonyl)-4-((2-(3,4-dichlorobenzyl)morpholino)methyl-2-fluorobenzamide

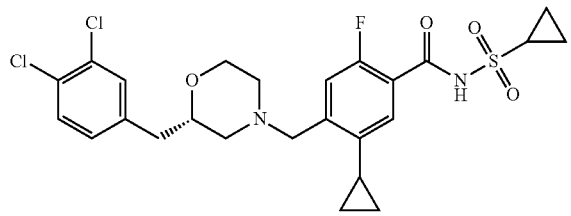 [SMILES: O=C(NS(=O)(=O)C1CC1)c1cc(C2CC2)c(CN2CCO[C@@H](Cc3ccc(Cl)c(Cl)c3)C2)cc1F]

Following the procedure as described in Example 458 step 6 and making non-critical variations as required to replace (R)-5-cyclopropyl-4-((2-(3,4-dichlorobenzyl)morpholinomethyl)-2-fluorobenzoic acid hydrochloride with (S)-5-cyclopropyl-4-((2-(3,4-dichlorobenzyl)morpholino)methyl)-2-fluorobenzoic acid hydrochloride, ane to replace methanesulfonamide with cyclopropanesulfonamide, the title compound was obtained as a colorless solid (0.02 g, 11%): ¹H NMR (300 MHz, CDCl₃) δ8.78 (d, J=13.5 Hz, 1H), 7.74 (d, J=7.8 Hz, 1H), 7.38-7.23 (m, 3H), 7.07-7.04 (m, 1H), 3.94-3.82 (m, 1H), 3.82-3.57 (m, 4H), 3.16-3.04 (m, 1H), 2.83-2.55 (m, 4H), 2.37-2.21 (m, 1H), 2.12-1.88 (m, 2H), 1.53-1.42 (m, 2H), 1.22-1.10 (m, 2H), 1.03-0.92 (m, 2H), 0.72-0.61 (m, 2H); MS(ES+) m/z 541.1, 543.1 (M+1), MS(ES−) m/z 539.2, 541.2 (M−1).

Example 463

Synthesis of (R)-5-cyclopropyl-4-((2-(3,5-dichlorobenzyl)morpholino)methyl)-2-fluoro-N-(methylsulfonyl)benzamide

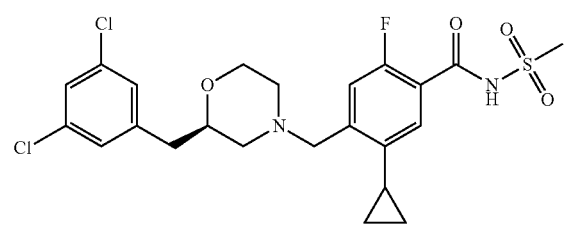 [SMILES: CS(=O)(=O)NC(=O)c1cc(C2CC2)c(CN2CCO[C@H](Cc3cc(Cl)cc(Cl)c3)C2)cc1F]

Step 1. Preparation of (R)-1-chloro-3-(3,5-dichlorophenyl)propan-2-ol

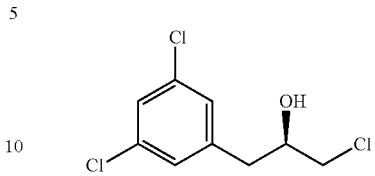

Following the procedure as described in Example 458 step 1 and making non-critical variations as required to replace 4-bromo-1,2-dichlorobenzene with 1-bromo-3,5-dichlorobenzene, the title compound was obtained as a colorless oil (12.93 g, 83%): ¹H NMR (300 MHz, CDCl₃) δ7.27-7.24 (m, 1H), 7.18-7.12 (m, 2H), 4.09-3.98 (m, 1H), 3.62 (dd, J=3.9, 11.2 Hz, 1H), 3.49 (dd, J=6.3, 11.2 Hz, 1H), 2.87-2.79 (m, 2H), 2.22 (br s, 1H).

Step 2. Preparation of (R)-2-(3,5-dichlorobenzyl)morpholine

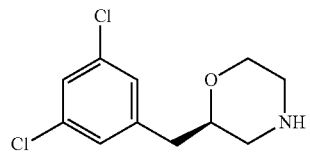 [SMILES: Clc1cc(Cl)cc(C[C@@H]2CNCCO2)c1]

Following the procedure as described in Example 458 step 2 and making non-critical variations as required to replace (R)-1-chloro-3-(3,4-dichlorophenyl)propan-2-ol with (R)-1-chloro-3-(3,5-dichlorophenyl)propan-2-ol, the title compound was obtained as a colorless oil (6.98 g, 53%): MS(ES+) m/z 246.1, 248.1 (M+1).

Step 3. Preparation of (R)-tert-butyl 5-cyclopropyl-4-((2-(3,5-dichlorobenzyl)morpholino)methyl)-2-fluorobenzoate

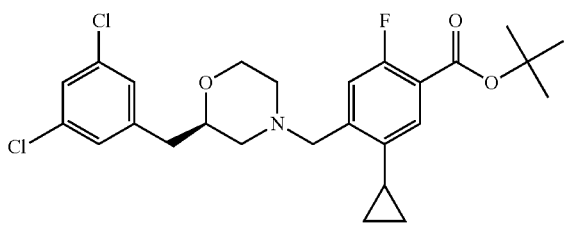 [SMILES: CC(C)(C)OC(=O)c1cc(C2CC2)c(CN2CCO[C@H](Cc3cc(Cl)cc(Cl)c3)C2)cc1F]

To a micromave vial was charged with tert-butyl 5-cyclopropyl-2-fluoro-4-(iodomethyl)benzoate (0.14 g, 0.37 mmol), (R)-2-(3,5-dichlorobenzyl)morpholino (0.18 g, 0.75 mmol), potassium phosphate (0.16 mg, 0.75 mmol) and N,N-dimethyl formamide (8 mL). The suspension was heated in the microwave reactor at 80° C. for 2 hours. The reaction mixture was cooled to ambient temperature and diluted with water (200 mL) and ethyl acetate (100 mL). The aqueous layer was isolated and extracted with ethyl acetate (3×50 mL). The combined organics were concentrated and the residue was purified by flash chromatography (0% to 10% ethyl acetate in hexanes) to yield the title compound (0.18 g, 98%): MS(ES+) m/z 494.2, 496.2 (M+1).

Step 4. Preparation of (R)-5-cyclopropyl-4-((2-(3,5-dichlorobenzyl)morpholino)methyl)-2-fluorobenzoic acid hydrochloride

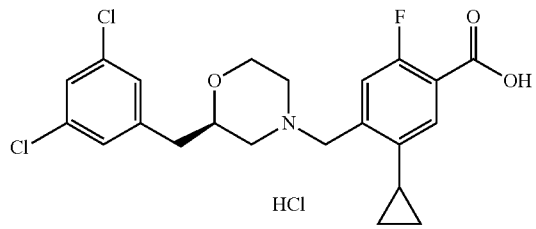 [SMILES: O=C(O)c1cc(C2CC2)c(CN2CCO[C@H](Cc3cc(Cl)cc(Cl)c3)C2)cc1F ; Cl]

Following the procedure as described in Example 458 step 5 and making non-critical variations as required to replace (R)-tert-butyl 5-cyclopropyl-4-((2-(3,4-dichlorobenzyl)morpholino)methyl)-2-fluorobenzoate with (R)-tert-butyl 5-cyclopropyl-4-((2-(3,5-dichlorobenzyl)morpholino)methyl)-2-fluorobenzoate, the title compound was obtained as a colorless solid (0.08 g, 49%): MS(ES+) m/z 437.9, 439.9 (M+1); MS(ES−) m/z 436.0, 438.0 (M−1).

Step 5. Preparation of (R)-5-cyclopropyl-4-((2-(3,5-dichlorobenzyl)morpholino)methyl)-2-fluoro-N-(methylsulfonyl)benzamide

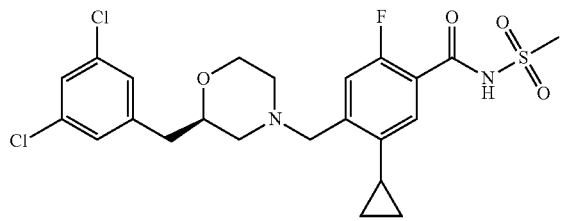 [SMILES: CS(=O)(=O)NC(=O)c1cc(C2CC2)c(CN2CCO[C@H](Cc3cc(Cl)cc(Cl)c3)C2)cc1F]

Following the procedure as described in Example 458 step 6 and making non-critical variations as required to replace (R)-5-cyclopropyl-4-((2-(3,4-dichlorobenzyl)morpholino)methyl)-2-fluorobenzoic acid hydrochloride with (R)-5-cyclopropyl-4-((2-(3,5-dichlorobenzyl)morpholino)methyl)-2-fluorobenzoic acid hydrochloride, the title compound was obtained as a colorless solid (0.05 g, 24%): $^1$H NMR (300 MHz, CDCl$_3$) δ 8.95-8.69 (m, 1H), 7.73 (d, J=7.8 Hz, 1H), 7.34-7.20 (m, 2H), 7.14-7.11 (m, 2H), 3.92-3.83 (m, 1H), 3.81-3.31 (m, 2H), 3.67 (s, 2H), 3.42 (s, 3H), 2.82-2.59 (m, 4H), 2.27 (d, J=3.1, 11.2 Hz, 1H), 2.11-1.89 (m, 2H), 1.02-0.92 (m, 2H), 0.70-0.59 (m, 2H); MS(ES+) m/z 515.1, 517.1 (M+1), MS(ES−) m/z 513.1, 515.1 (M−1).

Example 464

Preparation of (R)-5-cyclopropyl-N-(cyclopropylsulfonyl)-4-((2-(3,5-dichlorobenzyl)morpholino)methyl)-2-fluorobenzamide

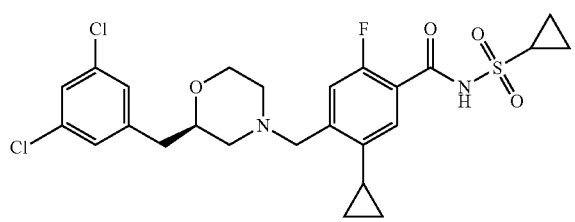 [SMILES: O=C(NS(=O)(=O)C1CC1)c1cc(C2CC2)c(CN2CCO[C@H](Cc3cc(Cl)cc(Cl)c3)C2)cc1F]

Following the procedure as described in Example 458 step 6 and making non-critical variations as required to replace (R)-5-cyclopropyl-4-((2-(3,4-dichlorobenzyl)morpholino)methyl)-2-fluorobenzoic acid hydrochloride with (R)-5-cyclopropyl-4-((2-(3,5-dichlorobenzyl)morpholino)methyl)-2-fluorobenzoic acid hydrochloride, ane to replace methanesulfonamide with cyclopropanesulfonamide, the title compound was obtained as a colorless solid (0.03 g, 22%): $^1$H NMR (300 MHz, CDCl$_3$) δ 8.78 (d, J=15.7 Hz, 1H), 7.74 (d, J=7.8 Hz, 1H), 7.33-7.19 (m, 2H), 7.11-7.07 (m, 2H), 3.92-3.85 (m, 1H), 3.81-3.71 (m, 1H), 3.67 (s, 2H), 3.65-3.60 (m, 1H), 3.16-3.04 (m, 1H), 2.82-2.62 (m, 4H), 2.27 (dt, J=11.2 Hz, 1H), 2.05 (t, J=10.4 Hz, 2H), 2.01-1.90 (m, 1H), 1.51-1.44 (m, 2H), 1.21-1.11 (m, 2H), 1.01-0.94 (m, 2H), 0.71-0.64 (m, 2H); MS(ES+) m/z 541.1, 543.0 (M+1), MS(ES−) m/z 539.1, 541.1 (M−1).

Example 465

Preparation of (R)—N-(azetidin-1-ylsulfonyl)-5-cyclopropyl-4-((2-(3,5-dichlorobenzyl)morpholino)methyl)-2-fluorobenzamide, trifluoroacetic acid salt

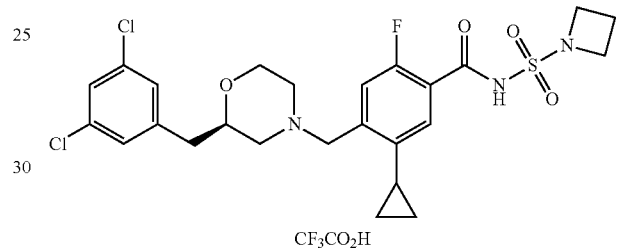

Following the procedure as described in Example 458 step 6 and making non-critical variations as required to replace (R)-5-cyclopropyl-4-((2-(3,4-dichlorobenzyl)morpholino)methyl)-2-fluorobenzoic acid hydrochloride with (R)-5-cyclopropyl-4-((2-(3,5-dichlorobenzyl)morpholino)methyl)-2-fluorobenzoic acid hydrochloride, and to replace methanesulfonamide with azetidine-1-sulfonamide, the title compound was obtained by reverse-phase HPLC purification as a colorless solid (0.04 g, 37%): $^1$H NMR (300 MHz, CDCl$_3$) δ 7.77 (d, J=7.4 Hz, 1H), 7.43 (d, J=11.5 Hz, 1H), 7.27-7.26 (m, 1H), 7.07 (s, 2H), 4.49 (s, 2H), 4.25 (t, J=7.7 Hz, 4H), 4.15-3.88 (m, 3H), 3.55 (d, J=11.1 Hz, 2H), 2.97-2.77 (m, 2H), 2.75-2.64 (m, 1H), 2.63-2.49 (m, 1H), 2.36-2.22 (m, 2H), 1.51-1.44 (m, 2H), 1.93-1.79 (m, 1H), 1.17-1.03 (m, 2H), 0.84-0.70 (m, 2H); MS(ES+) m/z 556.1, 558.1 (M+1), MS(ES−) m/z 554.2, 556.2 (M−1).

Example 466

Synthesis of (R)-4-((2-(2-chloro-4-fluorobenzyl)morpholino)methyl)-5-cyclopropyl-2-fluoro-N-(methylsulfonyl)benzamide, trifluoroacetic acid salt

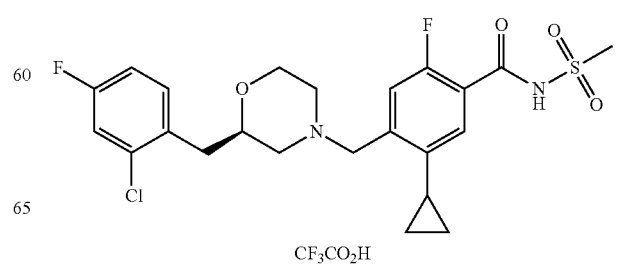

Step 1. Preparation of (R)-1-chloro-3-(2-chloro-4-fluorophenyl)propan-2-ol

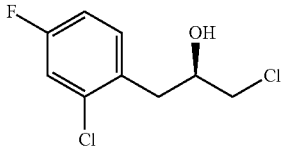 [SMILES: O[C@@H](CCl)Cc1ccc(F)cc1Cl]

Following the procedure as described in Example 458 step 1 and making non-critical variations as required to replace 4-bromo-1,2-dichlorobenzene with 1-bromo-2-chloro-4-fluorobenzene, the title compound was obtained as a colorless oil (3.22 g, 55%); $^1$H NMR (300 MHz, CDCl$_3$) δ7.28 (dd, J=6.2, 8.5 Hz, 1H), 7.12 (dd, J=2.6, 8.5 Hz, 2H), 6.95 (dt, J=2.6, 8.3 Hz, 1H), 4.19-4.09 (m, 1H), 3.72-3.66 (m, 1H), 3.59-3.50 (m, 1H), 3.06-2.90 (m, 2H), 2.17 (br s, 1H).

Step 2. Preparation of (R)-2-(2-chloro-4-fluorobenzyl)morpholine

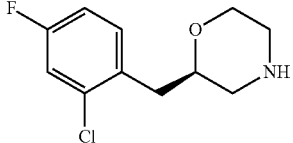

Following the procedure as described in Example 458 step 2 and making non-critical variations as required to replace (R)-1-chloro-3-(3,4-dichlorophenyl)propan-2-ol with (R)-1-chloro-3-(2-chloro-4-fluorophenyl)propan-2-ol, the title compound was obtained as a colorless oil (0.66 g, 20%): MS(ES+) m/z 230.2, 232.2 (M+1).

Step 3. Preparation of (R)-tert-butyl 5-cyclopropyl-4-((2-(2-chloro-4-fluorobenzyl)morpholino)methyl)-2-fluorobenzoate

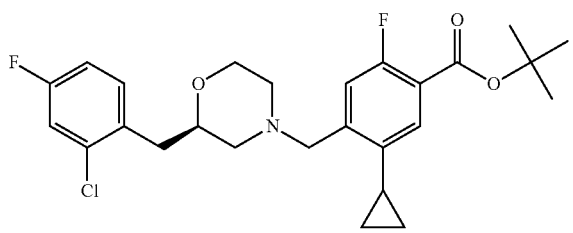 [SMILES: CC(C)(C)OC(=O)c1cc(C2CC2)c(CN2CCO[C@H](Cc3ccc(F)cc3Cl)C2)cc1F]

Following the procedure as described in Example 458 step 4 and making non-critical variations as required to replace (R)-2-(3,4-dichlorobenzyl)morpholine with (R)-2-(2-chloro-4-fluorobenzyl)morpholine, the title compound was obtained (0.47 g, quant. yield): MS(ES+) m/z 478.2, 480.2 (M+1).

Step 4. Preparation of (R)-4-((2-(2-chloro-4-fluorobenzyl)morpholino)methyl)-5-cyclopropyl-2-fluorobenzoic acid hydrochloride

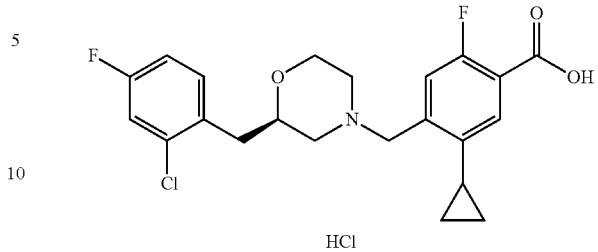

Following the procedure as described in Example 458 step 5 and making non-critical variations as required to replace (R)-tert-butyl 5-cyclopropyl-4-((2-(3,4-dichlorobenzyl)morpholino)methyl)-2-fluorobenzoate with (R)-tert-butyl 5-cyclopropyl-4-((2-(2-chloro-4-fluorobenzyl)morpholino)methyl)-2-fluorobenzoate, the title compound was obtained as a colorless solid (0.45 g, 97%): MS(ES+) m/z 422.0, 424.0 (M+1); MS(ES−) m/z 420.1, 422.1 (M−1).

Step 5. Preparation of (R)-4-((2-(2-chloro-4-fluorobenzyl)morpholino)methyl)-5-cyclopropyl-2-methyl-N-(methylsulfonyl)benzamide, trifluoroacetic acid salt

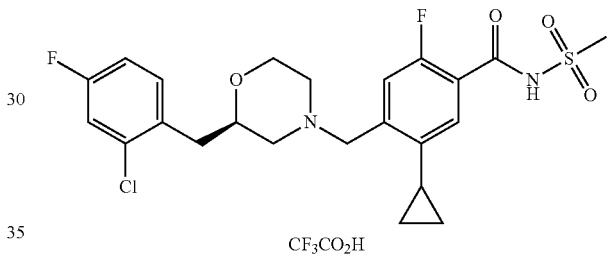

Following the procedure as described in Example 458 step 6 and making non-critical variations as required to replace (R)-5-cyclopropyl-4-((2-(3,4-dichlorobenzyl)morpholino)methyl)-2-fluorobenzoic acid hydrochloride with (R)-4-((2-(2-chloro-4-fluorobenzyl)morpholino)methyl)-5-cyclopropyl-2-fluorobenzoic acid hydrochloride, the title compound was obtained as a colorless solid (0.07 g, 38%): $^1$H NMR (300 MHz, CDCl$_3$) δ7.71 (d, J=7.7 Hz, 1H), 7.38 (d, J=11.5 Hz, 1H), 7.27-7.16 (m, 1H), 7.14-7.07 (m, 1H), 6.98-6.90 (m, 1H), 4.51 (s, 2H), 4.19-4.09 (m, 1H), 4.09-3.68 (m, 2H), 3.57 (dd, J=11.5, 26.0 Hz, 2H), 3.39 (s, 3H), 3.02-2.88 (m, 3H), 2.68 (t, J=11.0 Hz, 1H), 1.94-1.83 (m, 1H), 1.16-1.06 (m, 2H), 0.82-0.75 (m, 2H); MS(ES+) m/z 499.1, 501.1 (M+1); MS(ES−) m/z 497.1, 499.1 (M−1).

Example 467

Preparation of (R)-4-((2-(2-chloro-4-fluorobenzyl)morpholino)methyl)-5-cyclopropyl-N-(cyclopropylsulfonyl)-2-fluorobenzamide, trifluoroacetic acid salt

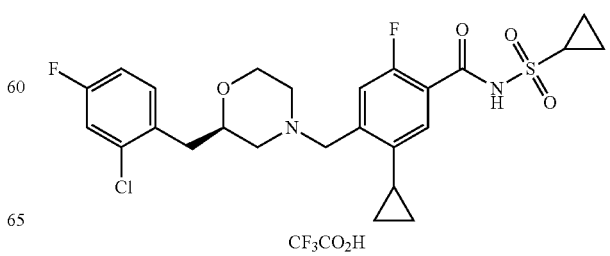

Following the procedure as described in Example 458 step 6 and making non-critical variations as required to replace (R)-5-cyclopropyl-4-((2-(3,4-dichlorobenzyl)morpholinomethyl)-2-fluorobenzoic acid hydrochloride with (R)-4-((2-(2-chloro-4-fluorobenzyl)morpholino)methyl)-5-cyclopropyl-2-fluorobenzoic acid hydrochloride, ane to replace methanesulfonamide with cyclopropanesulfonamide, the title compound was obtained as a colorless solid (0.06 g, 32%): $^1$H NMR (300 MHz, CDCl$_3$) δ7.73 (d, J=7.3 Hz, 1H), 7.37 (d, J=11.5 Hz, 1H), 7.20 (dd, J=6.2, 8.4 Hz, 1H), 7.11 (dd, J=2.3, 8.4 Hz, 1H), 6.94 (dt, J=2.4, 8.2 Hz, 1H), 4.52 (s, 2H), 4.21-3.81 (m, 3H), 3.59 (dd, J=11.2, 26.5 Hz, 2H), 3.14-2.95 (m, 1H), 3.01-2.93 (m, 3H), 2.70 (t, J=10.8 Hz, 1H), 1.95-1.80 (m, 1H), 1.49-1.37 (m, 2H), 1.23-1.37 (m, 4H), 0.80-0.68 (m, 2H); MS (ES+) m/z 525.1, 527.1 (M+1); MS(ES−) m/z 523.1, 525.1 (M−1).

Example 468

Preparation of (R)-N-(azetidin-1-ylsulfonyl)-4-((2-(2-chloro-4-fluorobenzyl)morpholino)methyl)-5-cyclopropyl-2-fluorobenzamide, trifluoroacetic acid salt

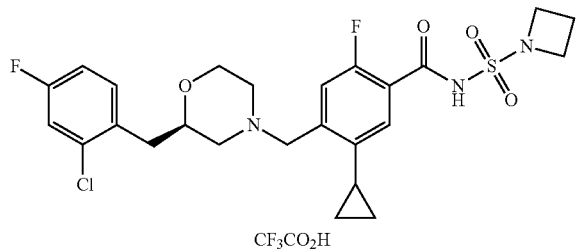 [SMILES: O=C(NS(=O)(=O)N1CCC1)c1cc(C2CC2)c(CN2CCO[C@H](Cc3ccc(F)cc3Cl)C2)cc1F ; "CF3CO2H"]

CF$_3$CO$_2$H

Following the procedure as described in Example 458 step 6 and making non-critical variations as required to replace (R)-5-cyclopropyl-4-((2-(3,4-dichlorobenzyl)morpholino)methyl)-2-fluorobenzoic acid hydrochloride with (R)-4-((2-(2-chloro-4-fluorobenzyl)morpholino)methyl)-5-cyclopropyl-2-fluorobenzoic acid hydrochloride, ane to replace methanesulfonamide with azetidine-1-sulfonamide, the title compound was obtained as a colorless solid (0.06 g, 37%): $^1$H NMR (300 MHz, CDCl$_3$) δ7.77 (d, J=7.72 Hz, 1H), 7.42 (d, J=11.6 Hz, 1H), 7.25-7.20 (m, 1H), 7.14-7.10 (m, 1H), 6.98-6.91 (m, 1H), 4.49 (s, 2H), 4.25 (t, J=7.7 Hz, 4H), 4.20-4.15 (m, 1H), 4.05-3.92 (m, 2H), 3.55 (dd, J=11.2, 26.5 Hz, 2H), 3.02-2.82 (m, 3H), 2.65 (t, J=10.6 Hz, 1H), 2.37-2.22 (m, 2H), 1.96-1.82 (m, 1H), 1.16-1.03 (m, 2H), 0.82-0.69 (m, 2H); MS(ES+) m/z 540.1, 542.1 (M+1); MS(ES−) m/z 538.1, 540.1 (M−1).

Example 469

Synthesis of (R)-5-cyclopropyl-4-((2-(3,5-dichlorobenzyl)-5,5-dimethylmorpholino)methyl)-2-fluoro-N-(methylsulfonyl)benzamide, trifluoroacetic acid salt

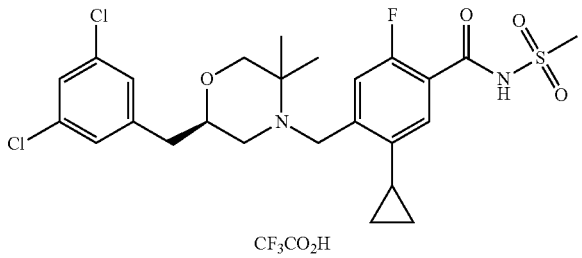 [SMILES: CC1(C)CO[C@H](Cc2cc(Cl)cc(Cl)c2)CN1Cc1cc(F)c(C(=O)NS(C)(=O)=O)cc1C1CC1 ; "CF3CO2H"]

CF$_3$CO$_2$H

Step 1. Preparation of (R)-1-amino-3-(3,5-dichlorophenyl)propan-2-ol

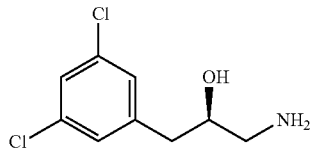 [SMILES: NC[C@H](O)Cc1cc(Cl)cc(Cl)c1]

To a solution of (R)-1-chloro-3-(3,5-dichlorophenyl)propan-2-ol (1.44 g, 6.01 mmol) in N,N-dimethyl formamide (45 mL) was added sodium azide (1.95 g, 30.05 mmol) and sodium iodide (0.54 g, 3.60 mmol). The resulting suspension was heated at 75° C. overnight, cooled to ambient temperature, diluted with ethyl acetate (150 mL) and washed with water (50 mL), 5% aqueous lithium chloride solution (50 mL) and brine (50 mL). The organic layer was dried over anhydrous sodium sulfate, filtered and concentrated. The residue was dissolved in tetrahydrofuran (55 ml) and water (18 mL), and to this solution was added triphenylphosphine (1.85 g, 7.07 mmol). The resulting reaction mixture was heated at 50° C. for 24 hours. Upon cooling to ambient temperature, the reaction mixture was diluted with dichloromethane (200 mL) and 10% aqueous sodium bicarbonate solution (100 mL). The aqueous layer was isolated and extracted with dichloromethane (2×100 mL). The combined organics were washed with brine (100 mL), dried over anhydrous sodium sulfate, filtered and concentrated. The residue was purified by flash chromatography [0% to 100% (85:14:1 dichloromethane/ethanol/ammonium hydroxide) in dichloromethane] to yield the title compound (0.93 g, 70% over 2 steps): MS(ES+) m/z 220.1, 222.1 (M+1).

Step 2. Preparation of (R)-2-chloro-N-(3-(3,5-dichlorophenyl)-2-hydroxypropyl)acetamide

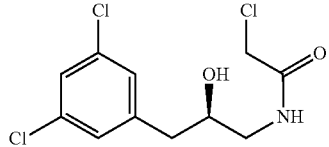 [SMILES: O=C(CCl)NC[C@H](O)Cc1cc(Cl)cc(Cl)c1]

To a cooled (0° C.) solution of (R)-1-amino-3-(3,5-dichlorophenyl)propan-2-ol (0.86 g, 3.91 mmol) and triethylamine (0.718 mL, 5.08 mmol) in 9:1 dichloromethane/acetonitrile (60 mL) was added 2-chloroacetyl chloride (340 µL, 4.29 mmol) dropwise. The resulting solution was stirred at 0° C. for 1.5 hours, and then warmed to ambient temperature and stirred for 30 minutes. The reaction mixture was re-cooled (0° C.) and quenched with 5% aqueous hydrochloric acid solution (1.5 mL). The aqueous layer was isolated and extracted with dichloromethane (2×30 mL). The combined organics were washed with brine (20 mL), dried over sodium sulfate, filtered and concentrated. The residue was triturated with diethyl ether to yield the title compound as a colorless solid (0.87 g, 75%): $^1$H NMR (300 MHz, CDCl$_3$) δ7.27-7.26 (m, 2H), 7.13-7.11 (m, 1H), 6.98 (br s, 1H), 4.09 (s, 2H), 4.05-3.95 (m, 1H), 3.64-3.53 (m 1H), 3.33-3.21 (m, 1H), 2.84-2.64 (m, 2H), 1.58 (br s, 1H); MS(ES+) m/z 296.0, 298.0 (M+1).

Step 3. Preparation of (R)-6-(3,5-dichlorobenzyl)morpholin-3-one

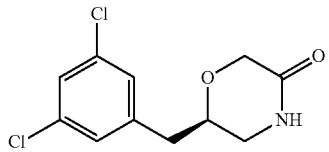 [SMILES: O=C1CO[C@H](Cc2cc(Cl)cc(Cl)c2)CN1]

To a cooled (0° C.) solution of (R)-2-chloro-N-(3-(3,5-dichlorophenyl)-2-hydroxypropyl) acetamide (0.31 g, 1.03 mmol) in isopropanol (2 mL) and toluene (1 mL) was added a solution of potassium tert-butoxide (0.32 g, 2.88 mmol) in isopropanol (3 mL). The reaction was stirred at 0° C. for 1 hour, and then slowly warmed to ambient temperature and stirred overnight. The reaction mixture was neutralized to pH=6 with 5% aqueous hydrochloric acid solution, and then concentrated. The aqueous residue was diluted with toluene (75 mL) and saturated aqueous sodium bicarbonate solution (25 mL). The toluene layer was isolated, washed with brine (20 mL) and then concentrated. The combined aqueous layers were extracted with ethyl acetate (2×50 mL). The combined organics were dried over sodium sulfate, filtered and concentrated. The residue was purified using flash chromatography [0% to 5% methanol, in dichloromethane] to yield the title compound as a colorless solid (0.23 g, 87%): $^1$H NMR (300 MHz, CDCl$_3$) δ7.32-7.12 (m, 2H), 7.11 (s, 1H), 6.32 (br s, 1H), 4.29 (d, J=16.9 Hz, 1H), 4.13 (d, J=16.9 Hz, 1H), 3.96-3.82 (m, 1H), 3.41-3.22 (m, 2H), 2.88 (dd, J=7.4, 14.2 Hz, 1H), 2.74 (dd, J=5.1, 14.2 Hz, 1H), 1.87 (brs, 1H).

Step 4. Preparation of (R)-6-(3,5-dichlorobenzyl)-4-(4-methoxybenzyl)morpholin-3-one

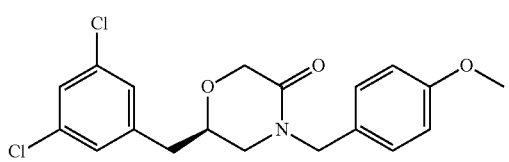 [SMILES: COc1ccc(CN2C[C@@H](Cc3cc(Cl)cc(Cl)c3)OCC2=O)cc1]

To a cooled (0° C.) solution of (R)-6-(3,5-dichlorobenzyl)morpholin-3-one (0.23 g, 0.89 mmol) in N,N-dimethyl formamide (3 mL) was added sodium hydride (60% dispersion, 0.04 g, 1.08 mmol). The resulting suspension was warmed to ambient temperature and stirred for 15 minutes. The pink slurry was re-cooled (0° C.) before 4-methoxybenzylchloride (0.15 mL, 1.08 mmol) was added dropwisely. At this point the slurry was too thick to stir and N,N-dimethyl formamide (2 mL) was added before the reaction mixture was slowly warmed to ambient temperature and stirred overnight. The reaction was cooled (0° C.), quenched with saturated aqueous ammonium chloride solution (5 mL) and diluted with ethyl acetate (50 mL). The aqueous layer was isolated and extracted with ethyl acetate (2×20 mL). The combined organics were washed with brine (20 mL), dried over sodium sulfate, filtered and concentrated. The residue was purified using flash chromatography [0% to 20% to 40% ethyl acetate in hexanes] to yield the title compound as a colourless oil (0.27 g, 79%): $^1$H NMR (300 MHz, CDCl$_3$) δ7.28-7.16 (m, 3H), 7.08-7.03 (m, 2H), 6.91-6.84 (m, 2H), 4.62 (d, J=14.5 Hz, 1H), 4.43 (d, J=14.5 Hz, 1H), 4.19-4.07 (m, 1H), 3.94-3.81 (m, 1H), 3.80 (s, 3H), 3.24-3.02 (m, 2H), 2.96 (s, 1H), 2.88 (s, 1H), 2.77 (dd, J=7.8, 14.3 Hz, 1H), 2.67 (dd, J=4.6, 14.3 Hz, 1H).

Step 5. Preparation of (R)-2-(3,5-dichlorobenzyl)-4-(4-methoxybenzyl)-5,5-dimethylmorpholine

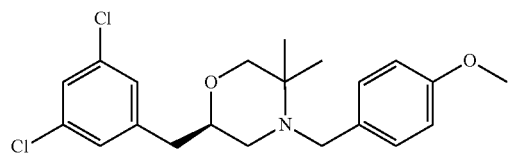 [SMILES: COc1ccc(CN2C[C@@H](Cc3cc(Cl)cc(Cl)c3)OCC2(C)C)cc1]

To a cooled (−10° C.) solution of (R)-6-(3,5-dichlorobenzyl)-4-(4-methoxybenzyl)morpholin-3-one (0.27 g, 0.71 mmol) in tetrahydrofuran (1.5 mL) was added anhydrous zirconium(IV) chloride (0.17 g, 0.72 mmol). After 30 minutes, a solution of methylmagnesium bromide (3.0M in diethyl ether, 1.4 mL, 4.26 mmol) was added dropwisely. After 1 hour at −10° C., the slurry was too thick to stir, so tetrahydrofuran (2 mL) was added. The resulting suspension was stirred at −10° C. for an additional 1 hour, and then slowly warmed to ambient temperature and stirred overnight. The reaction was cooled (0° C.), diluted with diethyl ether (10 ml) and saturated aqueous sodium/potassium tartarate solution (5 mL). The thick slurry was stirred for 15 minutes, resulting in a cloudy yellow biphasic solution. The solid was removed by filtration and rinsed with ethyl acetate and water. The organic layer was isolated and the aqueous layer was extracted with ethyl acetate (2×50 mL). The combined organics were washed with water (20 mL) then brine (20 mL), dried over sodium sulfate, and concentrated. The residue was purified using flash chromatography [0% to 15% to 30% ethyl acetate in hexanes] to yield the title compound as a colourless oil (0.13 g, 46%); MS(ES+) m/z 394.0, 396.0 (M+1).

Step 6. Preparation of (R)-2-(3,5-dichlorobenzyl)-5,5-dimethylmorpholine

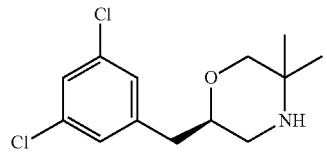 [SMILES: CC1(C)CO[C@H](Cc2cc(Cl)cc(Cl)c2)CN1]

To a solution of (R)-2-(3,5-dichlorobenzyl)-4-(4-methoxybenzyl)-5,5-dimethylmorpholine (0.13 g, 0.32 mmol) in water/acetonitrile (1:1, v/v, 7 mL) was added a solution of ceric ammonium nitrate (535 mg, 0.975 mmol) in methanol (56 mL). The resulting orange solution was stirred at ambient temperature overnight, quenched with 5% aqueous hydrochloric acid solution (20 mL), and then extracted with diethyl ether (3×20 mL). The combined aqueous layer was basified with solid sodium bicarbonate to pH=9 and extracted with ethyl acetate (3×75 mL). The combined ethyl acetate extracts were washed with brine (20 mL), dried over sodium sulfate, filtered and concentrated to give the title compound as a colorless solid (0.08 g, 98%): MS(ES+) m/z 274.1, 276.1 (M+1).

Step 7. Preparation of (R)-tert-butyl 5-cyclopropyl-4-((2-(3,5-dichlorobenzyl)-5,5-dimethyl morpholino)methyl)-2-fluorobenzoate

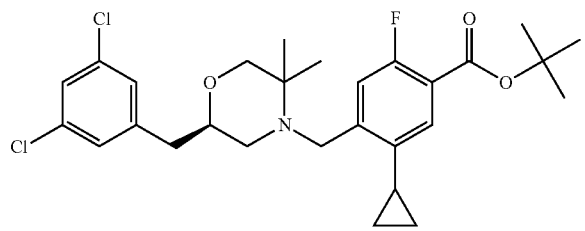 [SMILES: CC(C)(C)OC(=O)c1cc(C2CC2)c(CN2C[C@@H](Cc3cc(Cl)cc(Cl)c3)OCC2(C)C)cc1F]

To a suspension of (R)-2-(3,5-dichlorobenzyl)-5,5-dimethylmorpholine (0.08 g, 0.30 mmol) and potassium carbonate (0.05 g, 0.34 mmol) in N,N-dimethyl formamide (2 mL) was added tert-butyl 5-cyclopropyl-2-fluoro-4-(((methylsulfonyl)oxy)methyl) benzoate (0.12 g, 0.34 mmol). The suspension was stirred at ambient temperature overnight, diluted with water (30 mL) and ethyl acetate (75 mL). The aqueous layer was isolated and extracted with ethyl acetate (3×50 mL). The combined organics were washed with brine (50 mL), and concentrated. The residue was purified by flash chromatography [0% to 10% ethyl acetate in hexanes] to yield the title compound (0.08 g, 54%): MS(ES+) m/z 522.1, 524.1 (M+1).

Step 8. Preparation of (R)-5-cyclopropyl-4-((2-(3,5-dichlorobenzyl)-5,5-dimethylmorpholino)methyl)-2-fluorobenzoic acid hydrochloride

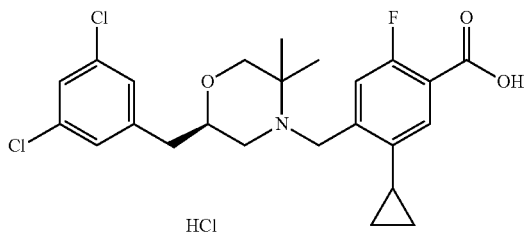 [SMILES: CC1(C)CO[C@H](Cc2cc(Cl)cc(Cl)c2)CN1Cc1cc(F)c(C(=O)O)cc1C1CC1 ; Cl]

Following the procedure as described in Example 458 step 5 and making non-critical variations as required to replace (R)-tert-butyl 5-cyclopropyl-4-((2-(3,4-dichlorobenzyl)morpholino)methyl)-2-fluorobenzoate with (R)-tert-butyl 5-cyclopropyl-4-((2-(3,5-dichlorobenzyl)-5,5-dimethyl morpholino)methyl)-2-fluorobenzoate, the title compound was obtained as a colorless solid (0.08 g, quant. yield): MS(ES+) m/z 466.0, 468.0 (M+1); MS(ES−) m/z 464.1, 466.1 (M−1).

Step 9. Preparation of (R)-5-cyclopropyl-4-((2-(3,5-dichlorobenzyl)-5,5-dimethylmorpholino)methyl)-2-fluoro-N-(methylsulfonyl)benzamide, trifluoroacetic acid

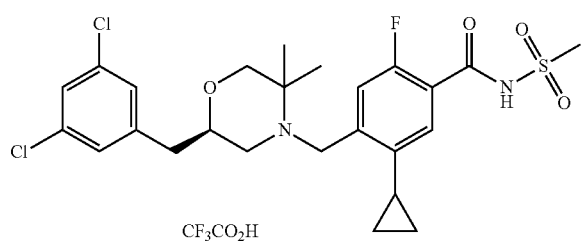 [SMILES: CC1(C)CO[C@H](Cc2cc(Cl)cc(Cl)c2)CN1Cc1cc(F)c(C(=O)NS(C)(=O)=O)cc1C1CC1 ; "CF3CO2H"]

Following the procedure as described in Example 458 step 6 and making non-critical variations as required to replace (R)-5-cyclopropyl-4-((2-(3,4-dichlorobenzyl)morpholino)methyl)-2-fluorobenzoic acid hydrochloride with (R)-5-cyclopropyl-4-((2-(3,5-dichlorobenzyl)-5,5-dimethylmorpholino)methyl)-2-fluorobenzoic acid hydrochloride, the title compound was obtained by reverse-phase HPLC purification as a colorless solid (0.06 g, 56%): $^1$H NMR (300 MHz, CDCl$_3$) δ 7.46 (d, J=7.0 Hz, 1H), 7.31-7.19 (m, 2H), 7.09-7.03 (m, 2H), 4.58 (d, J=13.2 Hz, 1H), 4.06-3.96 (m, 1H), 3.91 (d, J=13.2 Hz, 1H), 3.84 (d, J=12.7 Hz, 1H), 3.58 (d, J=12.6 Hz, 1H), 3.36 (s, 3H), 3.20 (d, J=11.9 Hz, 1H), 2.78 (dd, J=3.5, 14.5 Hz, 1H), 1.90-1.77 (m, 1H), 1.50 (s, 3H), 1.42 (s, 3H), 1.10-0.94 (m, 2H), 0.88-0.79 (m, 2H), 0.61-0.51 (m, 2H); MS (ES+) m/z 543.0, 545.0 (M+1); MS(ES−) m/z 541.0, 543.0 (M−1).

Example 470

Synthesis of 4-(((1R,3r,5S)-3-(3-chloro-2-fluoro-5-(trifluoromethyl)phenoxy)-8-azabicyclo[3.2.1]octan-8-yl)methyl)-5-cyclopropyl-N-(cyclopropylsulfonyl)-2-fluorobenzamide, trifluoroacetic acid salt

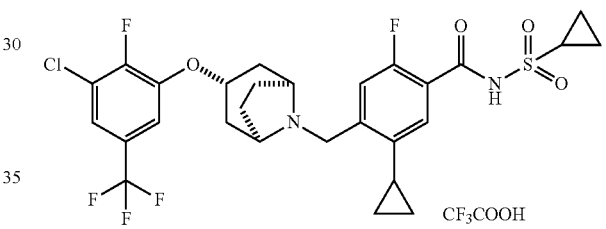

Step 1. Preparation of (1R,3s,5S)-tert-butyl 3-((methylsulfonyl)oxy)-8-azabicyclo[3.2.1]octane-8-carboxylate carboxylate

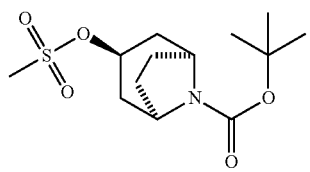 [SMILES: CC(C)(C)OC(=O)N1[C@@H]2CC[C@H]1C[C@H](OS(C)(=O)=O)C2]

To a cold (0° C.) mixture of (1R,3s,5S)-tert-butyl-3-hydroxy-8-azabicyclo[3.2.1]octane-8-carboxylate (7.68 g, 33.80 mmol) and triethylamine (7.1 mL, 50.70 mmol) in anhydrous dichloromethane (100 mL) was added methanesulfonyl chloride (3.1 mL, 40.60 mmol) and the reaction mixture was stirred for 1 hour at 0° C. The organic phase was washed with hydrochloric acid solution (1 N, 10 mL), water (20 mL), and brine (20 mL); dried over anhydrous sodium sulfate. Filtration and concentration of the filtrate in vacuo provided the title compound as a yellowish solid (10.40 g, quant. yield): $^1$H NMR (300 MHz, CDCl$_3$) δ5.09-4.96 (m, 1H), 4.29-4.17 (m, 2H). J=2.97 (s, 3H), 2.10-1.93 (m, 4H), 1.90-1.75 (m, 2H), 1.68-1.59 (m, 2H), 1.44 (s, 9H).

Step 2. Preparation of (1R,3r,5S)-tert-butyl 3-(3-chloro-2-fluoro-5-(trifluoromethyl)phenoxy)-8-azabicyclo[3.2.1]octane-8-carboxylate

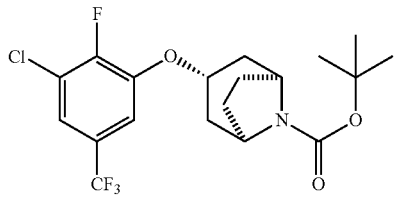 [SMILES: CC(C)(C)OC(=O)N1[C@@H]2CC[C@H]1C[C@@H](Oc1cc(C(F)(F)F)cc(Cl)c1F)C2]

To a mixture of (1R,3s,5S)-tert-butyl 3-hydroxy-8-azabicyclo[3.2.1]octane-8-carboxylate (1.44 g, 4.70 mmol) in anhydrous dimethylformamide (10 mL) was added cesium carbonate (3.06 g, 9.40 mmol) and 3-chloro-2-fluoro-5-(trifluoromethyl)phenol (1.10 g, 4.70 mmol) and the reaction mixture was heated at 80° C. for 16 hours. After cooling to ambient temperature, the reaction mixture was diluted with ethyl acetate (150 mL) and water (20 mL). The organic phase was washed with water (2×15 mL), brine (15 mL), and dried over anhydrous sodium sulfate. After filtration and concentration of the filtrate in vacuo, the residue was purified by flash chromatography (0 to 30% ethyl acetate in hexanes) to afford the title compound as a colorless oil (2.00 g, quant. yield): $^1$H NMR (300 MHz, CDCl$_3$) δ7.19 (d, J=6.5 Hz, 1H), 6.98-6.93 (m, 1H), 4.71-4.65 (m, 1H), 4.25-4.19 (m, 2H), 2.24-2.09 (m, 4H), 2.06-1.90 (m, 4H), 1.46 (s, 9H); MS(ES+) m/z 368.0, 370.0 (M−55).

Step 3. Preparation of (1R,3r,5S)-3-(3-chloro-2-fluoro-5-(trifluoromethyl)phenoxy)-8-azabicyclo[3.2.1]octane

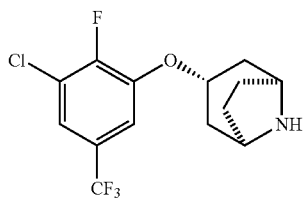 [SMILES: Fc1c(Cl)cc(C(F)(F)F)cc1O[C@H]1C[C@H]2CC[C@@H](C1)N2]

To a mixture of (1R,3r,5S)-tert-butyl 3-(3-chloro-2-fluoro-5-(trifluoromethyl)phenoxy)-8-azabicyclo[3.2.1]octane-8-carboxylate (2.00 g, 4.70 mmol) in dichloromethane (10 mL) was added trifluoroacetic acid (2 mL) and the reaction mixture was stirred at ambient temperature for 16 hours. Alter evaporation of all volatiles in vacuo, the residue was dissolved in dichloromethane (100 mL). The organic phase was washed with sodium hydroxide solution (1 N, 10 mL), water (10 mL), and brine (10 mL), and dried over anhydrous sodium sulfate. Filtration and concentration of the filtrate in vacuo yielded the title compound as a colorless oil (1.50 g, quant. yield): MS (ES+) m/z 324.1, 326.1 (M+1).

Step 4. Preparation of tert-butyl 4-(((1R,3r,5S)-3-(3-chloro-2-fluoro-5-(trifluoromethyl)-phenoxy)-8-azabicyclo[3.2.1]octan-8-yl)methyl)-5-cyclopropyl-2-fluorobenzoate

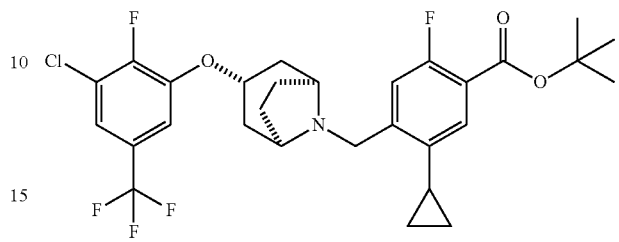

To a mixture of (1R,3r,5S)-3-(3-chloro-2-fluoro-5-(trifluoromethyl)phenoxy)-8-azabicyclo[3.2.1]octane (1.50 g, 4.70 mmol) in anhydrous (10 mL) was added potassium carbonate (1.30 g, 9.40 mmol) and tert-butyl 5-cyclopropyl-2-fluoro-4-(((methylsulfonyl)oxy)methyl)benzoate (1.62 g, 4.70 mmol) and the reaction mixture was stirred at ambient temperature for 16 hours. After dilution with ethyl acetate (150 mL) and addition of water (20 ml), the organic phase was washed with water (2×15 mL), brine (15 mL), and dried over anhydrous sodium sulfate. Filtration and concentration of the filtrate in vacuo gave a residue which was purified by flash chromatography (0 to 20% ethyl acetate in hexanes) to afford the title compound as a colorless oil (1.30 g, 48%): $^1$H NMR (300 MHz, CDCl$_3$) δ7.48 (d, J=7.2 Hz, 1H), 7.35-7.28 (m, 1H), 7.24-7.20 (m, 1H), 4.68-4.60 (m, 1H), 6.98-6.94 (m, 1H), 3.73-3.61 (m, 2H), 3.25-3.08 (m, 2H), 2.27-1.85 (m, 9H), 1.57 (% 9H), 0.95-0.85 (m, 2H), 0.64-0.58 (m, 2H); MS(ES+) m/z 572.1, 574.1 (M+1).

Step 5. 4-(((1R,3r,5S)-3-(3-chloro-2-fluoro-5-(trifluoromethyl)phenoxy)-8-azabicyclo[3.2.1]octan-8-yl)methyl)-5-cyclopropyl-2-fluorobenzoic acid hydrochloride

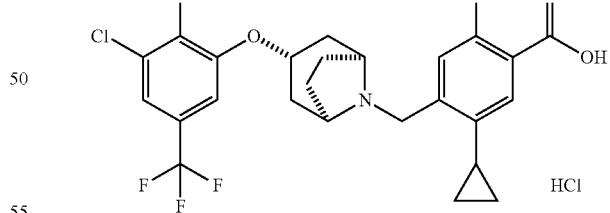

A mixture of tert-butyl 4-(((1-R,3r,5S)-3-(3-chloro-2-fluoro-5-(trifluoromethyl)-phenoxy)-8-azabicyclo[3.2.1]octan-8-yl)methyl)-5-cyclopropyl-2-fluorobenzoate (1.30 g, 2.27 mmol) and concentrated hydrochloric acid (3 mL) in dioxane (20 mL) was stirred at ambient temperature for 16 hours. Concentration of the reaction mixture in vacuo followed by co-evaporation with toluene (2×10 mL) provided the title compound as an off-white solid containing traced of toluene (1.30 g, quant. yield): MS(ES+) m/z 514.1, 516.1 (M+1).

Step 6. Preparation of 4-(((1R,3r,5S)-3-(3-chloro-2-fluoro-5-(trifluoromethyl)phenoxy)-8-azabicyclo[3.2.1]octan-8-yl)methyl)-5-cyclopropyl-N-(cyclopropylsulfonyl)-2-fluorobenzamide, trifluoroacetic acid salt

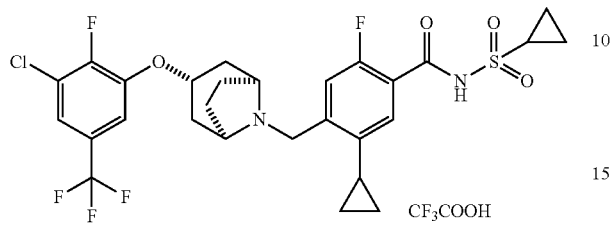

A mixture of 4-(((1R,3r,5S)-3-(3-chloro-2-fluoro-5-(trifluoromethyl)phenoxy)-8-azabicyclo[3.2.1]octan-8-yl)methyl)-5-cyclopropyl-2-fluorobenzoic acid hydrochloride (0.63 g, 1.10 mmol), amide (0.34 g, 3.60 mmol), N-(3-dimethylaminopropyl)-N'-ethylcarbodiimide hydrochloride (0.69 g, 3.60 mmol), and 4-dimethylaminopyridine (0.88 g, 7.20 mmol) in anhydrous dichloromethane (10 mL) was stirred at ambient temperature for 16 hours. The reaction mixture was diluted with ethyl acetate (150 mL) and washed with aqueous hydrochloric acid solution (1 M, 10 mL), water (10 mL) and brine (10 mL). The organic phase was dried over anhydrous sodium sulfate, filtered, and the filtrate concentrated in vacuo. The residue was purified by reverse phase HPLC (acetonitrile in water with 0.1% trifluoroacetic acid) to give the title compound as a colorless solid (0.38 g, 47%): $^1$H NMR (300 MHz, DMSO-$d_6$) $\delta$12.24 (br s, 1H), 9.58 (brs, 1H), 7.67-7.53 (m, 3H), 7.27 (d, J=7.1. Hz, 1H), 5.00-4.92 (m, 1H), 4.42 (brs, 2H), 4.01 (brs, 2H), 3.12-2.99 (m, 1H), 2.46-2.23 (m, 6H), 2.22-2.05 (m, 3H), 1.15-1.05 (m, 4H), 1.04-0.94 (m, 2H), 0.82-0.73 (m, 2H); MS(ES−) m/z 617.1, 619.1 (M−1).

Example 471

Synthesis of 4-(((1R,3r,5S)-3-(3-chloro-2-fluoro-5-(trifluoromethyl)phenoxy)-8-azabicyclo[3.2.1]octan-8-yl)methyl)-5-cyclopropyl-2-fluoro-N-(methylsulfonyl)benzamide 2,2,2-trifluoroacetate

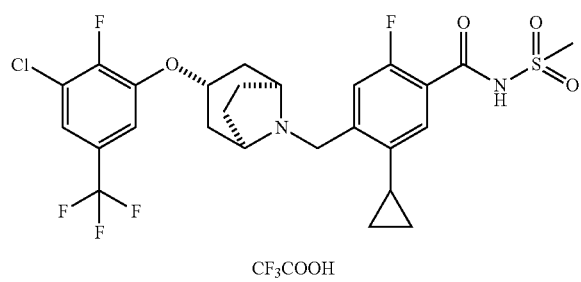

Following the procedure as described in Example 470 step 6, and making variation as required to replace cyclopropanesulfonamide with methanesulfonamide, the title compound was obtained as a colorless solid (0.35 g, 45%): $^1$H NMR (300 MHz, DMSO-$d_6$) $\delta$12.32 (br s, 1H), 9.46 (br s, 1H), 7.67-7.51 (m, 3H), 7.29 (d, J=7.2 Hz, 1H), 4.97 (s, 1H), 4.42 (s, 2H), 4.01 (s, 2H), 3.34 (s, 3H), 2.44-2.26 (m, 6H), 2.22-2.00 (m, 3H), 1.03-0.96 (m, 2H), 0.81-0.74 (m, 2H); MS(ES−) m/z 591.1, 593.1 (M−1).

Example 472

Synthesis of 4-((4-((5-chloro-4-(trifluoromethyl)pyridin-2-yl)oxy)-4-methylpiperidin-1-yl)methyl)-5-cyclopropyl-N-(cyclopropylsulfonyl)-2-fluorobenzamide, trifluoroacetic acid salt

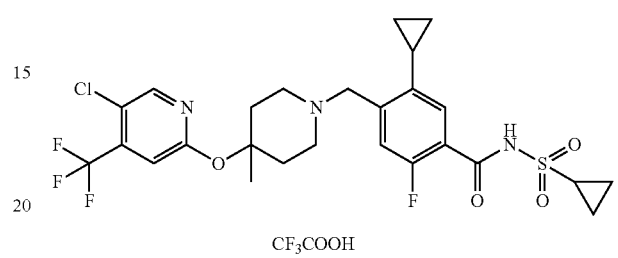

Step 1. Preparation of tert-butyl 4-(bromomethyl)-5-cyclopropyl-2-fluorobenzoate

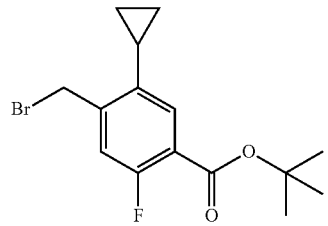 [SMILES: CC(C)(C)OC(=O)c1cc(C2CC2)c(CBr)cc1F]

To a cold (0° C.) mixture of tert-butyl 5-cyclopropyl-2-fluoro-4-(hydroxymethyl)benzoate (1.0 g, 3.80 mmol) and triphenylphosphine (1.48 g, 5.60 mmol) in anhydrous tetrahydrofuran (20 mL) was added tetrabromomethane (1.87 g, 5.60 mmol) and the reaction mixture was stirred for 3 hours at 0° C. After concentration in vacuo, the residue was purified by flash chromatography (0 to 20% ethyl acetate in hexanes) to afford the title compound as an off-white solid (1.24 g, quant. yield): $^1$H NMR (300 MHz, CDCl$_3$) $\delta$7.52 (d, J=7.2 Hz, 1H), 7.06 (d, J=10.8 Hz, 1H), 4.62 (s, 2H), 2.04-1.92 (m, 1H), 1.56 (s, 9H), 1.04-0.96 (m, 2H), 0.74-0.67 (m, 2H).

Step 2. Preparation of tert-butyl 5-cyclopropyl-2-fluoro-4-((4-hydroxy-4-methylpiperidin-1-yl)methyl)benzoate

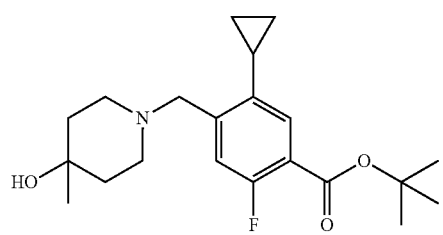 [SMILES: CC1(O)CCN(Cc2cc(F)c(C(=O)OC(C)(C)C)cc2C2CC2)CC1]

Following the procedure as described in Example 470 step 4, and making variations as required to replace (1R,3r,5S)-3-(3-chloro-2-fluoro-5-(trifluoromethyl)phenoxy)-8-azabicyclo[3.2.1]-octane with 4-hydroxy-methylpiperidine, and to replace tert-butyl 5-cyclopropyl-2-fluoro-4-(((methylsulfonyl)oxy)methyl)benzoate with tert-butyl 4-(bromomethyl)-5-cyclopropyl-2-fluorobenzoate, the title compound was obtained as an orange oil (1.10 g, 8:1%); $^1$H NMR (300 MHz, CDCl$_3$) δ7.47 (d, J=7.2 Hz, 1H), 7.17 (d, J=11.9 Hz, 1H), 3.64 (s, 2H), 2.59-2.49 (m, 2H), 2.47-2.36 (m, 2H), 1.99-1.88 (m, 1H), 1.73-1.51 (m, 14H), 1.24 (s, 3H), 0.93-0.85 (m, 2H), 0.63-0.57 (m, 2H).

Step 3. Preparation of tert-butyl 4-((4-((5-chloro-4-(trifluoromethyl)pyridin-2-yl)oxy)-4-methylpiperidin-1-yl)methyl)-5-cyclopropyl-2-fluorobenzoate

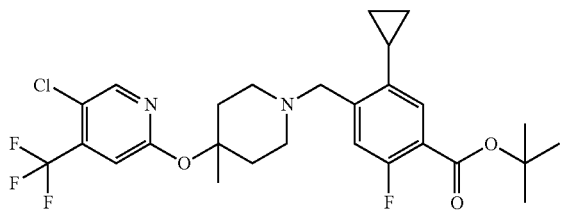 [SMILES: CC(C)(C)OC(=O)c1cc(C2CC2)c(CN2CCC(C)(Oc3cc(C(F)(F)F)c(Cl)cn3)CC2)cc1F]

To a mixture of tert-butyl 5-cyclopropyl-2-fluoro-4-((4-hydroxy-4-methylpiperidin-1-yl)methyl)benzoate (1.08 g, 2.96 mmol) and 2,5-dichloro-4-(trifluoromethyl)pyridine (0.96 g, 4.40 mmol) in anhydrous tetrahydrofuran (5 mL) was added lithium bis(trimethylsilyl)amide (1.0 M in tetrahydrofuran, 4.4 mL, 4.4 mmol) and the reaction-mixture was heated at 80-100° C. for 48 hours. After cooling to ambient temperature, the reaction mixture was diluted with ethyl acetate (100 mL). The organic phase was washed with 1 M aqueous hydrochloric acid solution (10 ml), water (2×10 mL), brine (10 mL), and dried over anhydrous sodium sulfate. Filtration and concentration of the filtrate provided a residue which was purified by flash chromatography (0 to 20% ethyl acetate in hexanes) to afford the title compound as a colorless oil (0.19 g, 12%): $^1$H NMR (300 MHz, CDCl$_3$) δ8.16 (s, 1H), 7.47 (d, J=7.3 Hz, 1H), 7.17 (d, J=11.8 Hz, 1H), 6.98 (s, 1H), 3.62 (s, 2H), 2.62-2.53 (m, 2H), 2.43-2.30 (m, 4H), 1.99-1.88 (m, 1H), 1.83-1.71 (m, 2H), 1.60 (s, 3H), 1.58 (d, J=13.7 Hz, 9H), 0.93-0.85 (m, 2H), 0.63-0.57 (m, 2H); MS(ES+) m/z 543.2, 545.2 (M+1).

Step 4. Preparation of 4-((4-((5-chloro-4-(trifluoromethyl)piperidin-2-yl)oxy)-4-methylpiperidin-1-yl)methyl)-5-cyclopropyl-2-fluorobenzoic acid

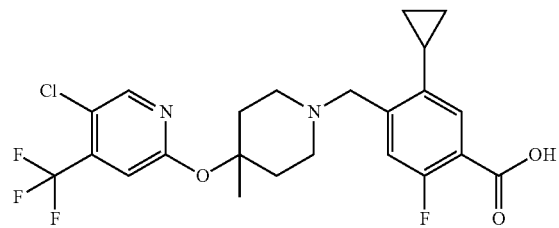 [SMILES: CC1(Oc2cc(C(F)(F)F)c(Cl)cn2)CCN(Cc2cc(F)c(C(=O)O)cc2C2CC2)CC1]

Following the procedure as described in Example 470 step 5, and making variation as required to replace tert-butyl 4-(((1R,3r,5S)-3-(3-chloro-2-fluoro-5-(trifluoromethyl)phenoxy)-8-azabicyclo[3.2.1]octan-8-yl)methyl)-5-cyclopropyl-2-fluorobenzoate with tert-butyl 4-((4-((5-chloro-4-(trifluoromethyl)pyridin-2-yl)oxy)-4-methylpiperidin-1-yl)methyl)-5-cyclopropyl-2-fluorobenzoate, the title compound was obtained as a yellowish solid (0.17 g, quant. yield): MS(ES+) m/z 485.2, 487.1 (M+1).

Step 5. Preparation of 4-((4-((5-chloro-4-(trifluoromethyl)pyridin-2-yl)oxy)-4-fluoropiperidin-1-yl)methyl)-5-cyclopropyl-N-(cyclopropylsulfonyl)-2-fluorobenzamide 2,2,2-trifluoroacetate

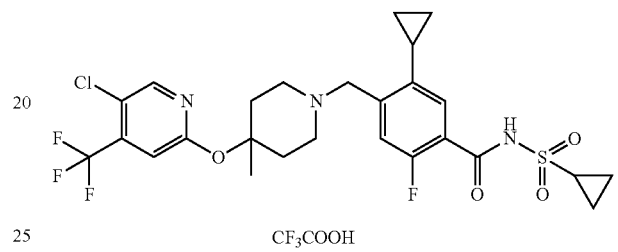

Following the procedure as described in Example 470 Step 6, and making variation as required to replace 4-(((1R,3r,5S)-3-(3-chloro-2-fluoro-5-(trifluoromethyl)phenoxy)-8-azabicyclo[3.2.1]octan-8-yl)methyl)-5-cyclopropyl-2-fluorobenzoic acid hydrochloride with 4-((4-((5-chloro-4-(trifluoromethyl)pyridin-2-yl)oxy)-4-methylpiperidin-1-yl)methyl)-5-cyclopropyl-2-fluorobenzoic acid, the title compound was obtained as a colorless solid (0.07 mg, 3.1%): $^1$H NMR (300 MHz, DMSO-d$_6$) δ12.47 (br s, 1H), 9.24 (br s, 1H), 8.22 (s, 1H), 7.74 (d, J=7.4 Hz, 1H), 7.49 (d, J=11.8 Hz, 1H), 7.03 (s, 1H), 4.46 (s, 2H), 3.58-3.44 (m, 2H), 3.12-2.97 (m, 3H), 2.78-2.67 (m, 2H), 2.28-2.11 (m, 2H), 1.91-1.80 (m, 1H), 1.59 (s, 3H), 1.48-1.40 (m, 2H), 1.19-1.11 (m, 2H), 1.10-1.02 (m, 2H), 0.76-0.69 (m, 2H); MS(ES−) m/z 588.1, 590.0 (M−1).

Example 473

Synthesis of 4-((4-((5-bromo-3-chloropyridin-2-yl)oxy)piperidin-1-yl)methyl)-5-cyclopropyl-N-(cyclopropylsulfonyl)-2-fluorobenzamide, trifluoroacetic acid salt

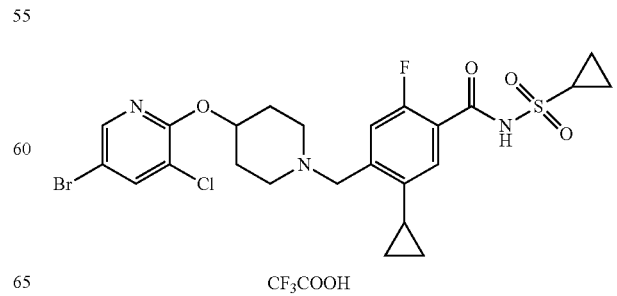

Step 1. Preparation of tert-butyl 4-((5-bromo-3-chloropyridin-2-yl)oxy)piperidine-1-carboxylate

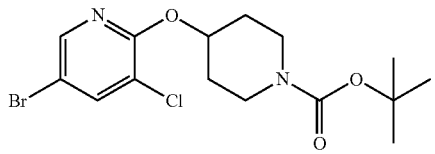 [SMILES: CC(C)(C)OC(=O)N1CCC(Oc2ncc(Br)cc2Cl)CC1]

To a mixture of sodium hydride (60% dispersion in mineral oil, 0.44 g, 11.00 mmol) in anhydrous dimethylformamide (20 mL) was added 1-Boc-4-hydroxypiperidine (2.00 g, 10.00 mmol). The reaction mixture was stirred for 1 hour at ambient temperature after which 5-bromo-2,3-dichloropyridine (2.27 g, 10.00 mmol) was added. The reaction mixture was healed to 70° C. for 16 hours. After cooling to ambient temperature, the reaction mixture was partitioned between water (50 mL) and ethyl acetate (200 mL). The organic phase was washed with brine (20 mL), dried over anhydrous sodium sulfate, and filtered. Concentration of the filtrate in vacuo provided the title compound as yellowish oil (3.90 g, quant. yield), which was used without further purification: MS(ES+) m/z 335.0, 337.0 (M−55).

Step 2. Preparation of 5-bromo-3-chloro-2-(piperidin-4-yloxy)pyridine

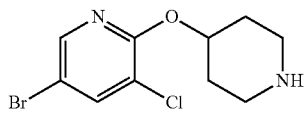

Following the procedure as described in Example 470 step 3, and making variation as required to replace (1R,3r,5S)-tert-butyl 3-(3-chloro-2-fluoro-5-(trifluoromethyl)phenoxy)-8-azabicyclo[3.2.1]octane-8-carboxylate with tert-butyl 4-((5-bromo-3-chloropyridin-2-yl)oxy)piperidine-1-carboxylate, the title compound was isolated as a yellowish oil (2.90 g, quant. yield): MS(ES+) m/z 291.0, 293.0, 295.0 (M+1).

Step 3. Preparation of tert-butyl 4-((4-((5-bromo-3-chloropyridin-2-yl)oxy)piperidin-1-yl)methyl)-5-cyclopropyl-2-fluorobenzoate

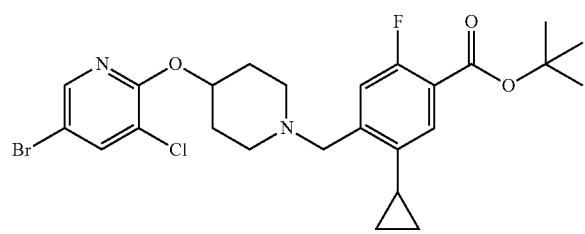 [SMILES: CC(C)(C)OC(=O)c1cc(C2CC2)c(CN2CCC(Oc3ncc(Br)cc3Cl)CC2)cc1F]

Following the procedure as described in Example 470 Step 4, and making variation as required to replace (1R,3r,5S)-3-(3-chloro-2-fluoro-5-(trifluoromethyl)phenoxy)-8-azabicyclo[3.2.1]-octane with 5-bromo-3-chloro-2-(piperidin-4-yloxy)pyridine, the title compound was obtained as a yellowish solid (2.70 g, quant. yield): MS(ES+) m/z 539.2, 541.2 (M+1).

Step 4: Preparation of 4-((4-((5-bromo-3-chloropyridin-2-yl)oxy)piperidin-1-yl)methyl)-5-cyclopropyl-2-fluorobenzoic acid hydrochloride

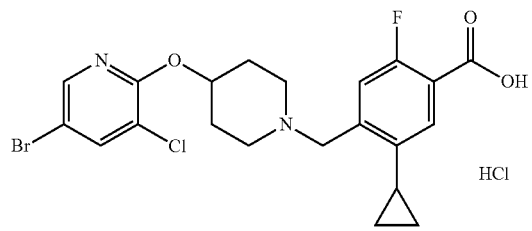 [SMILES: O=C(O)c1cc(C2CC2)c(CN2CCC(Oc3ncc(Br)cc3Cl)CC2)cc1F ; Cl]

Following the procedure as described in Example 470 step 5, and making variation as required to replace tert-butyl 4-(((1R,3r,5S)-3-(3-chloro-2-fluoro-5-(trifluoromethyl)-phenoxy)-8-azabicyclo[3.2.1]octan-8-yl)methyl)-5-cyclopropyl-2-fluorobenzoate with tert-butyl 4-((4-((5-bromo-3-chloropyridin-2-yl)oxy)piperidin-1-yl)methyl-5-cyclopropyl-2-fluorobenzoate, the title compound was isolated as an off-white solid (1.09 g, quant. yield); MS(ES+) m/z 483.0, 485.0 (M+1).

Step 5: Preparation of 4-((4-((5-bromo-3-chloropyridin-2-yl)oxy)piperidin-1-yl)methyl)-5-cyclopropyl-N-(cyclopropylsulfonyl)-2-fluorobenzamide, trifluoroacetic acid salt

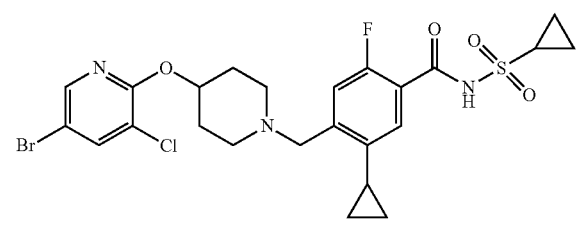

To a mixture of 4-((4-((5-bromo-3-chloropyridin-2-yl)oxy)piperidin-1-yl)methyl)-5-cyclopropyl-2-fluorobenzoic acid hydrochloride (1.09 g, 2.10 mmol) in anhydrous tetrahydrofuran (10 mL) was added 1,1'-carbonyldiimidazole (0.68 g, 4.20 mmol) and 1,8-diazabicyclo[5.4.0]undec-7-ene (0.63 mL, 4.20 mmol) and the reaction mixture was heated at 70° C. for 30 minutes. After cooling to ambient temperature, cyclopropanesulfonamide (0.51 g, 4.20 mmol) and 1,8-diazabicyclo[5.4.0]undec-7-ene (0.63 mL, 4.20 mmol) was added and the reaction mixture was heated at 70° C. for 4 hours. After cooling to ambient temperature, the reaction mixture was diluted with ethyl acetate (200 mL). The organic phase washed with hydrochloric acid (1 N, 1.0 mL), water (10 mL), brine (10 mL), and dried over anhydrous sodium sulfate. Filtration and concentration of the filtrate in vacuo provided the crude product (0.78 g). Half of the crude material (0.39 g) was purified by reverse phase preparative HPLC to give the title compound as a colorless solid (0.20 g, 14%): $^1$H NMR (300 MHz, DMSO-$d_6$) δ 12.38 (br s, 1H), 9.38 (br s, 1H), 8.07 (s, 1H), 7.79 (d, J=2.1. Hz, 1H), 7.74

(d, J=7.3 Hz, 1H), 7.47 (d, J=11.8 Hz, 1H), 5.45 (s, 1H), 4.52 (s, 2H), 3.61-3.45 (m, 2H), 3.27-3.11 (m, 2H), 3.11-3.00 (m, 1H), 2.43-2.27 (m, 2H), 2.27-2.14 (m, 2H), 1.95-1.83 (m, 5H), 1.48-1.38 (m, 2H), 1.18-1.05 (m, 4H), 0.79-0.72 (m, 2H); MS(ES−) m/z 584.0, 586.0, 588.0 (M−1).

Example 474

Synthesis of 4-((4-((3-chloro-5-cyclopropylpyridin-2-yl)oxy)piperidin-1-yl)methyl)-5-cyclopropyl-N-(cyclopropylsulfonyl)-2-fluorobenzamide hydrochloride

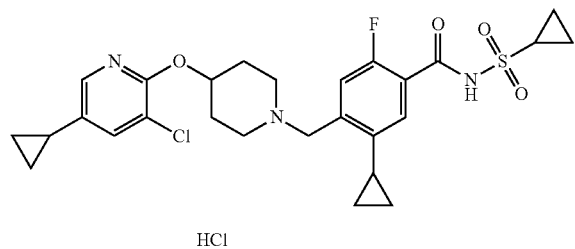 [SMILES: O=C(NS(=O)(=O)C1CC1)c1cc(C2CC2)c(CN2CCC(Oc3ncc(C4CC4)cc3Cl)CC2)cc1F ; Cl]

HCl

To a mixture of 4-((4-((5-bromo-3-chloropyridin-2-yl)oxy)piperidin-1-yl)methyl)-5-cyclopropyl-N-(cyclopropylsulfonyl)-2-fluorobenzamide (0.39 g, 0.67 mmol), cyclopropylboronic acid (0.17 g, 2.00 mmol), potassium phosphate tribasic (0.57 g, 2.7 mmol) in dioxane (10 mL) was added tetrakis(triphenylphosphine)palladium(0) (0.08 g, 0.07 mmol). The reaction mixture was degassed by passing a stream of argon through it and then heated at 110° C. in a sealed vial for 16 hours. After cooling to ambient temperature, the reaction mixture was filtered over diatomaceous earth. The filter cake was washed with dichloromethane (50 mL), and the combined filtrate was concentrated in vacuo. The residue was purified by reverse phase HPLC (acetonitrile in water with 0.1% ammonium hydroxide). The combined fractions were adjusted to pH 1-2 with 1 N hydrochloric acid, and extracted with dichloromethane (3×30 mL). The organic phase was dried over anhydrous sodium sulfate, filtered, and the filtrate concentrated in vacuo to give the title compound as an off-white solid (0.11 g, 29%): ¹H NMR (300 MHz, DMSO-d₆) δ12.66 (br s, 1H), 9.22 (br s, 1H), 8.15 (d, J=11.6 Hz, 1H), 7.83 (d, J=2.0 Hz, 1H), 7.78 (d, J=7.5 Hz, 1H), 7.29 (d, J=2.1 Hz, 1H), 5.40 (s, 1H), 4.39 (s, 2H), 3.37-3.00 (m, 5H), 2.70-2.50 (m, 2H), 2.24-2.07 (m, 2H), 2.01-1.88 (m, 1H), 1.86-1.75 (m, 1H), 1.50-1.40 (m, 2H), 1.19-1.03 (m, 4H), 1.00-0.92 (m, 2H), 0.77-0.70 (m, 2H), 0.64-0.57 (m, 2H); MS(ES+) m/z 548.2, 550.2 (M+1).

Example 475

Synthesis of 5-cyclopropyl-N-(cyclopropylsulfonyl)-4-(((1R,3r,5S)-3-(3,5-dichlorophenoxy)-8-azabicyclo[3.2.1]octan-8-yl)methyl)-2-fluorobenzamide hydrochloride

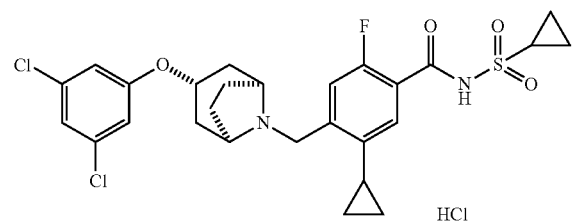

HCl

Step 1. Preparation of (1R,3r,5S)-tert-butyl 3-(3,5-dichlorophenoxy)-8-azabicyclo[3.2.1]octane-8-carboxylate

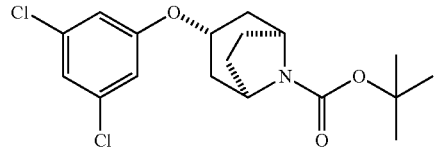

To a mixture of (1R,3r,5S)-tert-butyl 3-hydroxy-8-azabicyclo[3.2.1]octane-8-carboxylate (5.00 g, 22.00 mmol) in toluene (50 mL) was added 3,5-dichloroiodobenzene (0.00 g, 22.00 mmol), cesium carbonate (21.50 g, 66.00 mmol), copper(I) iodide (0.63 g, 3.30 mmol), 3,4,7,8-tetramethyl-1,10-phenantroline (1.60 g, 6.60 mmol) and molecular sieves (4 A, 5.00 g). The reaction mixture was degassed by passing a stream of argon through it and then heated at 80° C. in a sealed vial for 120 hours. After cooling to ambient temperature, the reaction mixture was diluted with ethyl acetate (150 mL) and filtered over diatomaceous earth. Concentration of the filtrate in vacuo gave a residue which was purified by flash chromatography (0 to 20% ethyl acetate in hexanes) to afford the title compound as a yellowish oil (3.80 g, 46%): ¹H NMR (300 MHz, CDCl₃) δ6.93-6.90 (m, 1H), 6.71-6.69 (m, 2H), 4.59-4.53 (m, 1H), 4.28-4.09 (m, 2H), 2.24-1.85 (m, 8H), 1.45 (s, 9H); MS(ES+) m/z 316.1, 318.1 (M−55).

Step 2. Preparation of (1R,3r,5S)-3-(3,5-dichlorophenoxy)-8-azabicyclo[3.2.1]octane

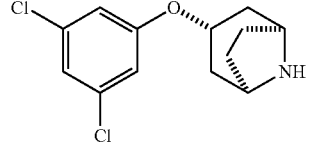

Following the procedure as described in Example 470 Step 3, and making variation as required to replace (1R,3r,5S)-tert-butyl 3-(3-chloro-2-fluoro-5-(trifluoromethyl)phenoxy)-8-azabicyclo[3.2.1]octane-8-carboxylate with (1R,3r,5S)-tert-butyl 3-(3,5-dichlorophenoxy)-8-azabicyclo[3.2.1]octane-8-carboxylate, the title compound was isolated as an off-white solid (2.80 g, quant. yield); MS (ES+) m/z 272.1, 274.1 (M+H).

Step 3. Preparation of tert-butyl 5-cyclopropyl-4-(((1R,3r,5S)-3-(3,5-dichlorophenoxy)-8-azabicyclo[3.2.1]octan-8-yl)methyl)-2-fluorobenzoate

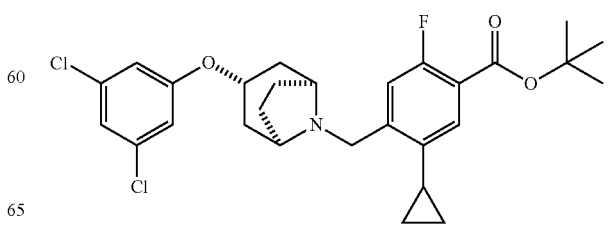

Following the procedure as described in Example 470 step 4, and making variation as required to replace (1R,3r,5S)-3-(3-chloro-2-fluoro-5-(trifluoromethyl)phenoxy)-8-azabicyclo[3.2.1]-octane with (1R,3r,5S)-3-(3,5-dichlorophenoxy)-8-azabicyclo[3.2.1]octane, the title compound was obtained as an off-white foam (4.50 g, 86%): $^1$H NMR (300 MHz, CDCl$_3$) δ7.47 (d, J=7.3 Hz, 1H), 7.32 (d, J=12.1 Hz, 1H), 6.92-6.89 (m, 1H), 6.72-6.69 (m, 2H), 4.54-4.46 (m, 1H), 3.65 (s, 2H) 3.14 (s, 2H), 2.19-2.09 (m, 2H), 2.07-1.99 (m, 4H), 1.95-1.85 (m, 3H), 1.57 (s, 9H), 0.93-0.83 (m, 2H), 0.64-0.58 (m, 2H); MS(ES+) m/z 520.2, 522.2 (M+1).

Step 4 Preparation of 5-cyclopropyl-4-(((1R,3r,5S)-3-(3,5-dichlorophenoxy)-8-azabicyclo[3.2.1]octan-8-yl)methyl)-2-fluorobenzoic acid hydrochloride

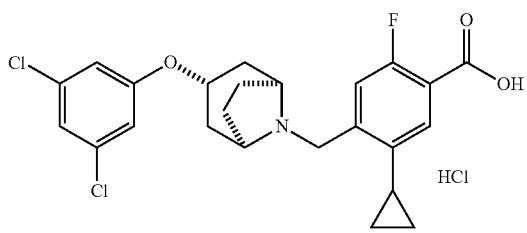

Following the procedure as described in Example 470 Step 5, and making variation as required to replace tert-butyl 4-(((1R,3r,5S)-3-(3-chloro-2-fluoro-5-(trifluoromethyl)-phenoxy)-8-azabicyclo[3.2.1]octan-8-yl)methyl)-5-cyclopropyl-2-fluorobenzoate with tert-butyl 5-cyclopropyl-4-(((1R,3r,5S)-3-(3,5-dichlorophenoxy)-8-azabicyclo[3.2.1] octan-8-yl)methyl)-2-fluorobenzoate, the title compound was obtained as a colorless solid after trituration with diethyl ether (4.40 g, quant. yield): $^1$H NMR (300 MHz, DMSO-d$_6$) δ13.43 (br s, 1H), 10.56 (br s, 1H), 7.92 (d, J=11.6 Hz, 1H), 7.49 (d, J=7.3 Hz, 1H), 7.17-7.09 (m, 3H), 4.84-4.78 (m, 1H), 4.48-4.38 (m, 2H), 3.98 (s, 2H), 2.77-2.65 (m, 2H), 2.40-2.02 (m, 7H), 1.07-0.97 (m, 2H), 0.76-0.66 (m, 2H); MS(ES+) m/z 464.1, 466.1 (M+1).

Step 5. Preparation of 5-cyclopropyl-N-(cyclopropylsulfonyl)-4-(((1R,3r,5S)-3-(3,5-dichlorophenoxy)-8-azabicyclo[3.2.1]octan-8-yl)methyl-2-fluorobenzamide hydrochloride

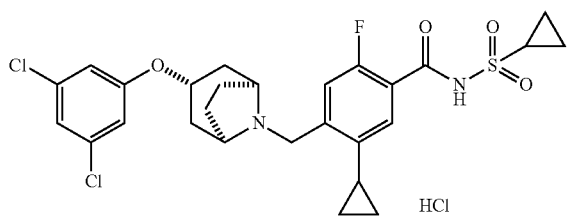

A mixture of 5-cyclopropyl-4-(((1R,3r,5S)-3-(3,5-dichlorophenoxy)-8-azabicyclo[3.2.1]octan-8-yl)methyl)-2-fluorobenzoic acid hydrochloride (4.00 g, 8.00 mmol), cyclopropanesulfonamide (1.16 g, 9.60 mmol), N-(3-dimethylaminopropyl)-N'-ethylcarbodiimide hydrochloride (1.84 g, 9.60 mmol), and 4-dimethylaminopyridine (3.32 g, 28.80 mmol) in anhydrous dichloromethane (50 mL) and anhydrous tetrahydrofuran (50 mL) was stirred at ambient temperature for 16 hours. Additional cyclopropanesulfonamide (1.16 g, 9.60 mmol), N-(3-dimethylaminopropyl)-N'-ethylcarbodiimide hydrochloride (1.84 g, 9.60 mmol), and 4-dimethylaminopyridine (3.52 g, 28.80 mmol) was added and the reaction mixture was stirred for another 16 hours at ambient temperature. The reaction mixture was partitioned between ethyl acetate (300 mL) and 1M aqueous hydrochloric acid solution (20 mL). The organic phase was washed with hydrochloric acid (1 N, 20 mL), water (20 mL) and brine (2×10 mL), dried over anhydrous sodium sulfate and filtered. After concentration of the filtrate in vacuo, the obtained solid residue was triturated with acetonitrile (100 mL) and filtered off. The solid was re-dissolved in dichloromethane (50 mL), filtered and concentrated in vacuo. The residue was dried in vacuo at 40-50° C. provided the title compound as a colorless solid (2.45 g, 51%): $^1$H NMR (300 MHz, CDCl$_3$/CD$_3$OD) δ8.42 (d, J=12.3 Hz, 1H), 7.73 (d, J=7.4 Hz, 1H), 6.97 (t, J=1.6, 1H), 6.71 (d, J=1.7 Hz, 2H), 4.73-4.67 (m, 1H), 4.45 (s, 2H), 3.84 (brs, 2H), 3.33-3.21 (m, 2H), 3.12-3.02 (m, 1H), 2.52-2.42 (m, 2H), 2.33-2.21 (m, 2H), 2.18-2.09 (m, 2H), 1.93-1.82 (m, 1H), 1.50-1.42 (m, 2H), 1.19-1.10 (m, 2H), 1.10-1.01 (m, 2H), 0.78-0.70 (m, 2H); MS(ES−) m/z 567.1, 569.0 (M+1).

Example 476

Synthesis of 5-cyclopropyl-2-fluoro-N-(methylsulfonyl)-4-((4-((5-trifluoromethyl)pyridin-2-yl)oxypiperidin-1-yl)methyl)benzamide, trifluoroacetic acid salt

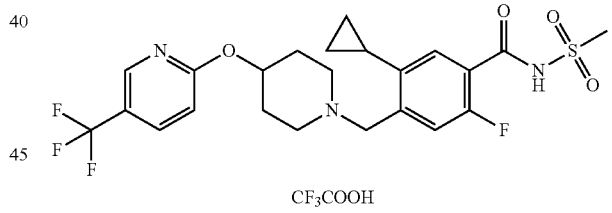

Step 1. Preparation of tert-butyl 4-((5-(trifluoromethyl)pyridin-2-yl)oxy)piperidine-1-carboxylate

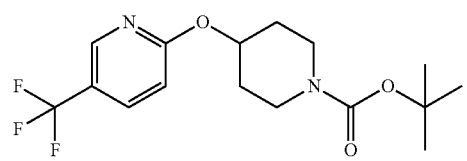 [SMILES: CC(C)(C)OC(=O)N1CCC(Oc2ccc(C(F)(F)F)cn2)CC1]

Following the procedure as described in Example 470 step 1, and making variation as required to replace 5-bromo-2,3-dichloropyridine with 2-chloro-5-trifluoromethylpyridine, the title compound was isolated as a colorless solid (3.65 g, quant. yield): MS(ES+) m/z 291.1 (M−55).

Step 2. Preparation of 2-(piperidin-4-yloxy)-5-trifluoromethyl)pyridine

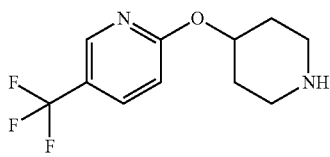 [SMILES: FC(F)(F)c1ccc(OC2CCNCC2)nc1]

Following the procedure as described in Example 470 step 3, and making variation as required to replace (1R,3r,5S)-tert-butyl 3-(3-chloro-2-fluoro-5-(trifluoromethyl)phenoxy)-8-azabicyclo[3.2.1]octane-8-carboxylate with tert-butyl 4-((5-(trifluoromethyl)pyridin-2-yl)oxy)piperidine-1-carboxylate, the title compound was obtained as an off-white solid (2.40 g, quant. yield): $^1$H NMR (300 MHz, CDCl$_3$) δ8.38 (d, J=0.7 Hz, 1H), 7.75 (dd, J=8.7, 2.4 Hz, 1H), 6.78 (d, J=8.7 Hz, 1H), 6.48 (s, 1H), 5.36-5.22 (m, 2H), 3.30-3.16 (m, 2H), 3.06-2.93 (m, 2H), 2.22-2.10 (m, 2H), 1.97-1.83 (m, 2H); MS (ES+) m/z 247.2 (M+1).

Step 3. Preparation of tert-butyl 5-cyclopropyl-2-fluoro-4-((4-((5-(trifluoromethyl)pyridin-2-yl)oxy)piperidin-1-yl)methyl)benzoate

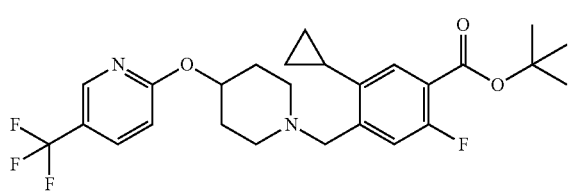 [SMILES: CC(C)(C)OC(=O)c1cc(C2CC2)c(CN2CCC(Oc3ccc(C(F)(F)F)cn3)CC2)cc1F]

Following the procedure as described in Example 470 step 4, and making variation as required to replace (1R,3r,5S)-3-(3-chloro-2-fluoro-5-(trifluoromethyl)phenoxy)-8-azabicyclo[3.2.1]-octane with 2-(piperidin-4-yloxy)-5-(trifluoromethyl)pyridine, the title compound was obtained as light yellowish oil (2.50 g, quant. yield): MS(ES+) m/z 495.2 (M+1).

Step 4. Preparation of 5-cyclopropyl-2-fluoro-4-((4-((5-(trifluoromethyl)pyridin-2-yl)oxy)piperidin-1-yl)methyl)benzoic acid hydrochloride

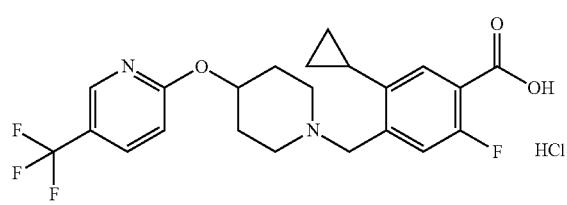 [SMILES: O=C(O)c1cc(C2CC2)c(CN2CCC(Oc3ccc(C(F)(F)F)cn3)CC2)cc1F ; Cl]

Following the procedure as described in Example 470 step 5, and making variation as required to replace tert-butyl 4-(((1R,3r,5S)-3-(3-chloro-2-fluoro-5-(trifluoromethyl)-phenoxy)-8-azabicyclo[3.2.1]octan-8-yl)methyl)-5-cyclopropyl-2-fluorobenzoate with tert-butyl 5-cyclopropyl-2-fluoro-4-((4-((5-(trifluoromethyl)pyridin-2-yl)oxy) piperidin-1-yl)methyl)benzoate, the title compound was obtained as a colorless solid (1.10 g, 95%): MS(ES+) m/z 439.1 (M+1).

Step 5. Preparation of 5-cyclopropyl-2-fluoro-N-(methylsulfonyl)-4-((4-((5-(trifluoromethyl)pyridin-2-yl)oxy)piperidin-1-yl)methylbenzamide, trifluoroacetic acid salt

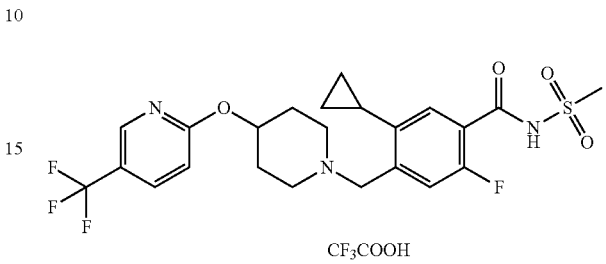

Following the procedure as described in Example 470 Step 6, and making variations as required to replace 4-(((1R,3r,5S)-3-(3-chloro-2-fluoro-5-(trifluoromethyl)phenoxy)-8-azabicyclo[3.2.1]octan-8-yl)methyl)-5-cyclopropyl-2-fluorobenzoic acid hydrochloride with 5-cyclopropyl-2-fluoro-4-((4-((5-(trifluoromethyl)pyridin-2-yl)oxy)piperidin-1-yl)methyl)benzoic acid hydrochloride and cyclopropanesulfonamide with methanesulfonamide, the title compound was obtained as a colorless solid (0.24 g, 33%); $^1$H NMR (300 MHz, DMSO-d$_6$) δ12.44 (br s, 1H), 9.94 (br s, 1H), 8.40 (s, 1H), 7.80 (dd, J=8.7, 1.9 Hz, 1H), 7.68 (d, J=7.3 Hz, 1H), 7.48 (d, J=11.7 Hz, 1H), 6.83 (d, J=8.7 Hz, 1H), 5.46 (s, 1H), 4.52 (s, 2H), 3.81-3.42 (m, 1H), 3.37 (s, 3H), 3.31-2.88 (m, 2H), 2.44-2.29 (m, 2H), 2.29-2.14 (m, 2H), 1.96-1.84 (m, 1H), 1.16-1.02 (m, 2H), 0.80-0.71 (m, 2H); MS(ES−) m/z 514.2 (m−1).

Example 477

Synthesis of 5-cyclopropyl-N-(cyclopropylsulfonyl)-2-fluoro-4-((4-((5-(trifluoromethyl)pyridin-2-yl)oxy)piperidin-1-yl)methyl)benzamide, trifluoroacetic acid salt

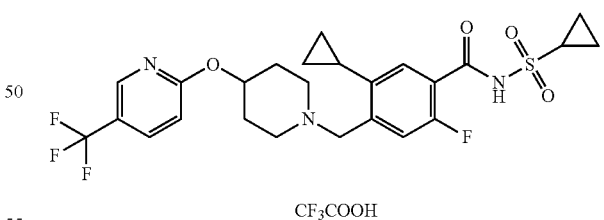

Following the procedure as described in Example 470 step 6, and making variation as required to replace 4-(((1R,3r,5S)-3-(3-chloro-2-fluoro-5-(trifluoromethyl)phenoxy)-8-azabicyclo[3.2.1]octan-8-ylmethyl)-5-cyclopropyl-2-fluorobenzoic acid hydrochloride with 5-cyclopropyl-2-fluoro-4-((4-((5-(trifluoromethyl)pyridin-2-yl)oxy)piperidin-1-yl) methyl)benzoic acid hydrochloride, the title compound was obtained as a colorless solid (0.31 g, 40%): $^1$H NMR (300 MHz, DMSO-d$_6$) δ12.88 (br s, 1H), 9.49 (br s, 1H), 8.40 (s, 1H), 7.80 (dd, J=8.7, 2.1 Hz, 1H), 7.72 (d, J=7.4 Hz, 1H), 7.49 (d, J=11.9 Hz, 1H), 6.83 (d, J=8.7 Hz, 1H), 5.45 (s, 1H), 4.50 (s, 2H), 3.75-3.31 (m, 2H), 3.28-2.83 (m, 3H), 2.46-2.29 (as, 2H), 2.28-2.14 (m, 2H), 1.98-1.83 (m, 1H), 1.47-1.37 (m, 2H), 1.19-1.04 (m, 4H), 0.79-0.71 (m, 2H); MS(ES−) m/z 540.2 (M−).

Example 478

Synthesis of 4-((4-((2-chloro-4-fluorobenzyl)oxy) piperidin-1-yl)methyl)-5-cyclopropyl-2-fluoro-N-(methylsulfonyl)benzamide, trifluoroacetic acid salt

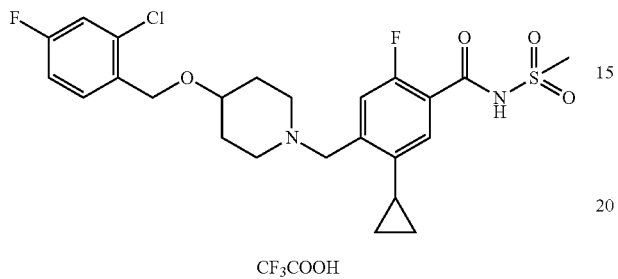

CF₃COOH

Step 1. Preparation of tert-butyl 4-((2-chloro-4-fluorobenzyl)oxy)piperidine-1-carboxylate

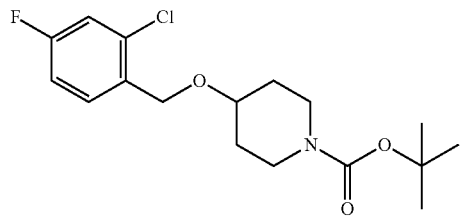 [SMILES: CC(C)(C)OC(=O)N1CCC(OCc2ccc(F)cc2Cl)CC1]

To a mixture of 1-Boc-4-hydroxypiperidine (2.00 g, 10.00 mmol) in anhydrous dimethylformamide (20 mL) was added sodium hydride (60% dispersion in mineral oil, 0.40 g, 10.10 mmol) at 0° C. The reaction mixture was allowed to warm to ambient temperature and stirred for 1 hour. To this reaction mixture was added 2-chloro-4-fluorobenzylbromide (2.45 g, 11.00 mmol) and tetrabutylammonium iodide (0.37 g, 1.00 mmol) and the reaction mixture was stirred for 48 hours at ambient temperature. After addition of water (20 mL) and dilution with ethyl acetate (200 mL), the organic phase was washed with water (3×20 mL), brine (20 mL), and dried over anhydrous sodium sulfate. Filtration and concentration of the filtrate in vacuo provided the title compound as yellowish oil (3.50 g, quant. yield), which was used without further purification: MS(ES+) m/z 288.1, 290.1 (M−55).

Step 2. Preparation of 4-((2-chloro-4-fluorobenzyl)oxy)piperidine

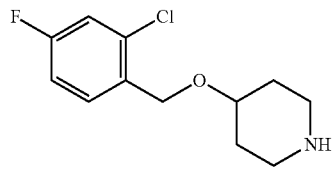 [SMILES: Fc1ccc(COC2CCNCC2)c(Cl)c1]

Following the procedure as described in Example 470 step 3, and making variation as required to replace (1R,3r,5S)-tert-butyl 3-(3-chloro-2-fluoro-5-(trifluoromethyl)phenoxy)-8-azabicyclo[3.2.1]octane-8-carboxylate with tert-butyl 4-((2-chloro-4-fluorobenzyl)oxy)piperidine-1-carboxylate the title compound was obtained as a yellowish oil (1.70 g, 71%): ¹H NMR (300 MHz, CDCl₃) δ7.46 (dd, J=8.4, 0.4 Hz, 1H), 7.08 (dd, J=8.5, 2.6 Hz, 1H), 6.96 (dt, J=8.4, 8.3, 2.6 Hz, 1H), 4.56 (s, 2H), 3.56-3.43 (m, 1H), 3.14-3.04 (m, 2H), 2.68-2.54 (m, 2H), 2.02-1.91 (m, 2H), 1.88-1.79 (m, 1H), 1.58-1.43 (m, 2H).

Step 3. Preparation of tert-butyl 4-((4-((2-chloro-4-fluorobenzyl)oxy)piperidin-1-yl)methyl)-5-cyclopropyl-2-fluorobenzoate

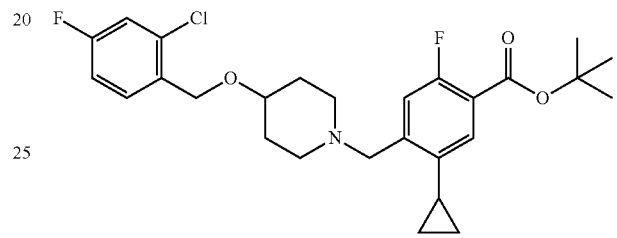

Following the procedure as described in Example 470 step 4, and making variation as required to replace (1R,3r,5S)-3-(3-chloro-2-4-5-(trifluoromethyl)phenoxy)-8-azabicyclo[3.2.1]-octane with 4-((2-chloro-4-fluorobenzyl)oxy) piperidine, the title compound was obtained as a yellowish oil (3.40 g, 97%): MS(ES+) m/z 492.2, 494.2 (M+1).

Step 4. Preparation of 4-((4-((2-chloro-4-fluorobenzyl)oxy)piperidin-1-yl)methyl)-5-cyclopropyl-2-fluorobenzoic acid, trifluoroacetic acid salt

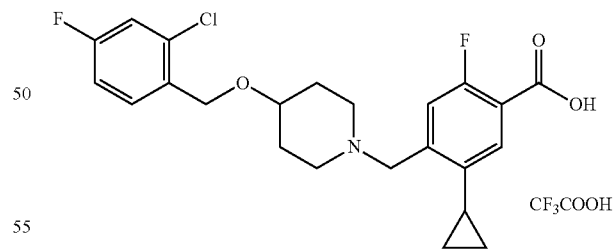

To a mixture of tert-butyl 4-((4-((2-chloro-4-fluorobenzyl)oxy)piperidin-1-yl)methyl)-5-cyclopropyl-2-fluorobenzoate (3.41 g, 6.90 mmol) in dichloromethane (40 mL) was added trifluoroacetic acid (5 mL) and the reaction mixture was stirred at ambient temperature for 16 hours. Concentration of the reaction mixture in vacuo provided the title compound as an off-white solid (3.20 g, 84%): MS(ES+) m/z 436.1, 438.1 (M+1).

Step 5. Preparation of 4-((4-((2-chloro-4-fluorobenzyl)oxy)piperidin-1-yl)methyl)-5-cyclopropyl-2-fluoro-N-(methylsulfonyl)benzamide, trifluoroacetic acid salt

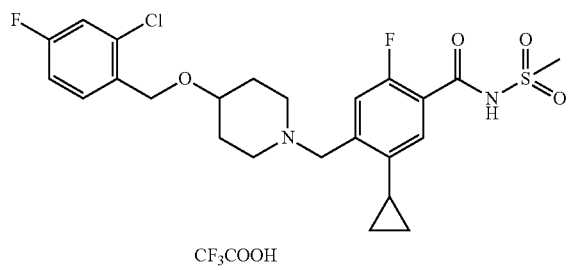 [SMILES: CS(=O)(=O)NC(=O)c1cc(C2CC2)c(CN2CCC(OCc3ccc(F)cc3Cl)CC2)cc1F ; "CF3COOH"]

CF₃COOH

Following the procedure as described in Example 470 step 6, and making variations as required to replace 4-(((1R,3r,5S)-3-(3-chloro-2-fluoro-5-(trifluoromethyl)phenoxy)-8-azabicyclo[3.2.1]octan-8-yl)methyl)-5-cyclopropyl-2-fluorobenzoic acid hydrochloride with 4-((4-((2-chloro-4-fluorobenzyl)oxy)piperidin-1-yl)methyl)-5-cyclopropyl-2-fluorobenzoic acid, trifluoroacetic acid salt and to replace cyclopropanesulfonamide with methanesulfonamide, the title compound was obtained as a colorless solid (0.52 g, 53%): ¹H NMR (300 MHz, DMSO-d₆) δ11.46 (br s, 1H), 9.97 (br s, 1H), 7.68 (d, J=7.4 Hz, 1H), 7.43 (d, J=11.9 Hz, 1H), 7.37 (dd, J=8.4, 6.3 Hz, 1H), 7.13 (dd, J=8.4, 2.3 Hz, 1H), 6.99 (dt, J=8.3, 8.3, 2.4 Hz, 1H), 4.52 (s, 2H), 4.46 (s, 2H), 3.85 (br s, 1H), 3.50-3.40 (m, 2H), 3.37 (s, 3H), 3.25-3.09 (m, 2H), 2.24-2.02 (m, 4H), 1.91-1.80 (m, 1H), 1.12-1.03 (m, 2H), 0.77-0.69 (m, 2H); MS(ES+) m/z 513.2, 515.2 (M+1).

Example 479

Synthesis of N-(azetidin-1-ylsulfonyl)-4-((4-((2-chloro-4-fluorobenzyl)oxy)piperidin-1-yl)methyl)-5-cyclopropyl-2-fluorobenzamide, trifluoroacetic acid salt

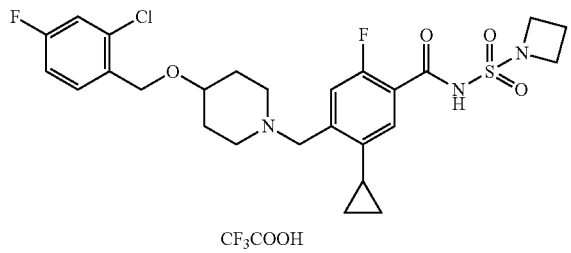 [SMILES: O=C(NS(=O)(=O)N1CCC1)c1cc(C2CC2)c(CN2CCC(OCc3ccc(F)cc3Cl)CC2)cc1F ; "CF3COOH"]

CF₃COOH

Following the procedure as described in Example 470 step 6, and making variations as required to replace 4-(((1R,3r,5S)-3-(3-chloro-2-fluoro-5-(trifluoromethyl)phenoxy)-8-azabicyclo[3.2.1]octan-8-yl)methyl)-5-cyclopropyl-2-fluorobenzoic acid hydrochloride with 4-((4-((2-chloro-4-fluorobenzyl)oxy)piperidin-1-yl)methyl)-5-cyclopropyl-2-fluorobenzoic acid, trifluoroacetic acid salt and to replace cyclopropanesulfonamide with azetidine-1-sulfonamide, the title compound was obtained as a colorless solid (0.18 g, 17%): ¹H NMR (300 MHz, DMSO-d₆) δ13.04 (br s, 1H), 9.04 (br s, 1H), 7.75 (d, J=7.5 Hz, 1H), 7.52 (d, J=12.1 Hz, 1H), 7.37 (dd, J=8.4, 6.2 Hz, 1H), 7.13 (dd, J=8.4, 2.5 Hz, 1H), 6.99 (dt, J=8.3, 8.3, 2.6 Hz, 1H), 4.53 (s, 2H), 4.43 (s, 2H), 4.23 (t, J=7.7, 7.7 Hz, 4H), 3.84 (br s, 1H), 3.48-3.33 (m, 2H), 3.22-3.05 (m, 2H), 2.34-2.14 (m, 4H), 2.13-2.01 (m, 3H), 1.13-1.04 (m, 2H), 0.78-0.71 (m, 2H); MS (ES+) m/z 554.2, 556.2 (M+1).

Example 480

Synthesis of 4-((4-((2-chloro-4-fluorobenzyl)oxy)piperidin-1-yl)methyl)-5-cyclopropyl-N-(cyclopropylsulfonyl)-2-fluorobenzamide, trifluoroacetic acid salt

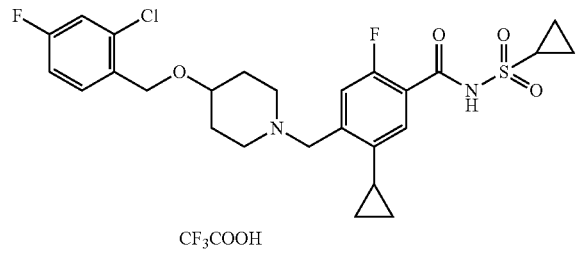 [SMILES: O=C(NS(=O)(=O)C1CC1)c1cc(C2CC2)c(CN2CCC(OCc3ccc(F)cc3Cl)CC2)cc1F ; "CF3COOH"]

CF₃COOH

Following the procedure as described in Example 470 step 6, and making variation as required to replace 4-(((1R,3r,5S)-3-(3-chloro-2-fluoro-5-(trifluoromethyl)phenoxy)-8-azabicyclo[3.2.1]octan-8-yl)methyl)-5-cyclopropyl-2-fluorobenzoic acid hydrochloride with 4-((4-((2-chloro-4-fluorobenzyl)oxy)piperidin-1-yl)methyl)-5-cyclopropyl-2-fluorobenzoic acid 2,2,2-trifluoroacetate, the title compound was obtained as a colorless solid (0.62 g, 60%): ¹H NMR (300 MHz, DMSO-d₆) δ12.13 (br s, 1H), 9.34 (br s, 1H), 7.72 (d, J=7.4 Hz, 1H), 7.46 (d, J=11.9 Hz, 1H), 7.37 (dd, J=8.5, 6.1 Hz, 1H), 7.13 (dd, J=8.4, 2.4 Hz, 1H), 6.99 (dt, J=8.3, 8.3, 2.6 Hz, 1H), 4.32 (s, 2H), 4.45 (s, 2H), 3.85 (s, 1H), 3.50-3.37 (m, 2H), 3.22-2.99 (m, 3H), 2.28-2.01 (m, 4H), 1.92-1.80 (m, 1H), 1.48-1.39 (m, 2H), 1.19-1.03 (m, 4H), 0.77-0.70 (m, 2H); MS(ES+) m/z 539.2, 541.1 (M+1).

Example 481

Synthesis of 4-((1-(3-chloro-5-(trifluoromethyl)pyridin-2-yl)-3-methylazetidin-3-yl)methoxy)-5-cyclopropyl-N-(cyclopropylsulfonyl)-2-fluorobenzamide

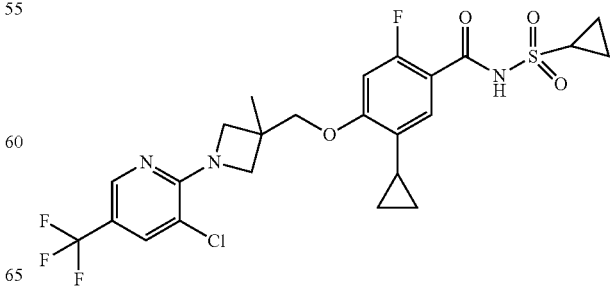

Step 1. Preparation of tert-butyl 3-((4-(tert-butoxy-carbonyl)-2-chloro-5-fluorophenoxy)methyl)-3-methylazetidine-1-carboxylate

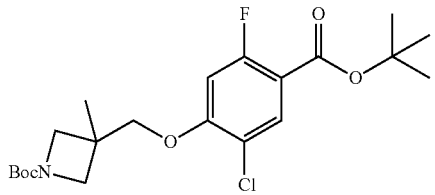 [SMILES: CC1(COc2cc(F)c(C(=O)OC(C)(C)C)cc2Cl)CN(C(=O)OC(C)(C)C)C1]

Following the procedure as described in Example 3 step 1, and making variation as required to (R)-tert-butyl 3-hydroxypiperidin-1-carboxylate with 1-Boc-3-(hydroxymethyl)-3-methylazetidine and purification by flash chromatography (0 to 40% ethyl acetate in hexanes), the title compound was obtained as a yellowish oil (12.40 g, 81%); $^1$H NMR (300 MHz, CDCl$_3$) δ 7.86 (d, J=7.6 Hz, 1H), 6.62 (d, J=11.9 Hz, 1H), 3.95 (s, 2H), 3.90 (d, J=8.5 Hz, 2H), 3.66 (d, J=8.5 Hz, 2H), 1.56 (s, 9H), 1.42 (s, 9H), 1.41 (s, 1H); MS(ES+) m/z 430.1, 432.1 (M+1).

Step 2. Preparation of tert-butyl 3-((4-(tert-butoxycarbonyl)-2-cyclopropyl-5-fluorophenoxy)methyl)-3-methylazetidine-1-carboxylate

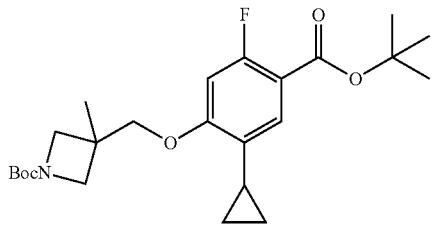 [SMILES: CC1(COc2cc(F)c(C(=O)OC(C)(C)C)cc2C2CC2)CN(C(=O)OC(C)(C)C)C1]

Following the procedure as described in Example 3 step 2, and making variation as required to (R)-tert-butyl 3-(4-(tert-butoxycarbonyl)-2-chloro-5-fluorophenoxy)piperidin-1-carboxylate with tert-butyl 3-((4-(tert-butoxycarbonyl)-2-chloro-5-fluorophenoxy)methyl)-3-methylazetidine-1-carboxylate, the title compound was obtained as a brownish gum (10.80 g, 86%): $^1$H NMR (300 MHz, CDCl$_3$) δ7.40 (d, J=8.3 Hz, 1H), 6.50 (d, J=12.4 Hz, 1H), 3.95 (d, J=8.4 Hz, 2H), 3.90 (s, 2H), 3.64 (d, J=8.4 Hz, 2H), 1.98-1.87 (m, 1H), 1.55 (s, 9H), 1.41 (s, 9H), 1.40 (s, 3H), 0.91-0.82 (m, 2H), 0.62-0.56 (m, 2H).

Step 3. Preparation of methyl 5-cyclopropyl-2-fluoro-4-((3-methylazetidin-3-yl)methoxy)benzoate hydrochloride

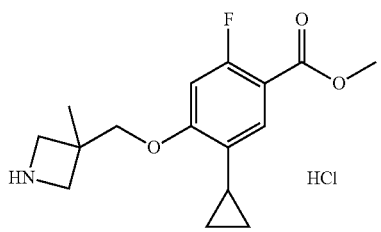 [SMILES: COC(=O)c1cc(C2CC2)c(OCC2(C)CNC2)cc1F ; Cl]

Thionyl chloride (9.0 mL) was added slowly methanol (200 mL) at 0° C. and the mixture was stirred for 1 hour at 0° C. A solution of tert-butyl 3-((4-(tert-butoxycarbonyl)-2-cyclopropyl-5-fluorophenoxy)methyl)-3-methylazetidine-1-carboxylate (10.80 g, 24.80 mmol) in methanol (20 mL) was then added and the reaction mixture was heated under reflux for 6 hours. After cooling to ambient temperature, the reaction mixture was stirred for 16 hours and then concentrated in vacuo. The residue was co-evaporated with toluene (3×10 mL) and triturated in hexanes (20 mL) to provide the title compound as a brownish gum (8.20 g, quant. yield): $^1$H NMR (300 MHz, CDCl$_3$) δ9.98 (br s, 1H), 9.79 (br s, 1H), 7.47 (d, J=8.2 Hz, 1H), 6.57 (d, J=12.2 Hz, 1H), 4.26-4.15 (m, 2H), 4.01 (s, 2H), 3.86 (s, 3H), 3.86-3.79 (m, 2H), 2.11-2.01 (m, 1H), 1.55 (s, 3H), 1.01-0.93 (m, 2H), 0.62-0.56 (m, 2H): MS(ES+) m/z 294.2 (M+1).

Step 4. Preparation of methyl 4-((1-(3-chloro-5-(trifluoromethyl)pyridin-2-yl)-3-methylazetidin-3-yl)methoxy)-5-cyclopropyl-2-fluorobenzoate

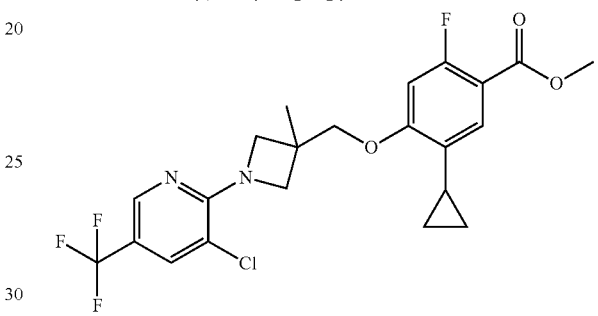

To a mixture of methyl 5-cyclopropyl-2-fluoro-4-((3-methylazetidin-3-yl)methoxy)benzoate hydrochloride (0.60 g, 1.82 mmol) in toluene (10 mL) was added 2-bromo-3-chloro-5-(trifluoromethyl)pyridine (0.71 g, 2.73 mmol), cesium carbonate (1.78 g, 5.46 mmol), bis(dibenzylideneacetone)palladium(0) (0.21 g, 0.36 mmol) and 2,2'-bis(diphenyl-phosphino)-1,1'-binaphthalene (0.22 g, 0.36 mmol). The reaction mixture was degassed by passing a stream of argon through it and then heated at 110° C. in a sealed vial for 16 hours. After cooling to ambient temperature, the reaction mixture was filtered over diatomaceous earth. The filter cake was washed with ethyl acetate (50 mL) and me combined filtrate was concentrated in vacuo. Purification of the residue by purification by flash chromatography (0 to 25% ethyl acetate in hexanes) provided the title compound as an orange gum (0.60 g, 70%): $^1$H NMR (300 MHz, CDCl$_3$) δ8.24-8.22 (m, 1H), 7.56 (d, J=2.0 Hz, 1H), 7.45 (d, J=83 Hz, 1H), 6.56 (d, J=12.5 Hz, 1H), 4.39 (d, J=9.0 Hz, 2H), 4.08 (d, J=9.0 Hz, 2H), 4.00 (s, 2H), 3.86 (s, 3H), 1.88-1.74 (m, 1H), 1.48 (s, 3H), 0.75-0.68 (m, 2H), 0.59-0.53 (m, 2H).

Step 5. Preparation of 4-((1-(3-chloro-5-(trifluoromethyl)pyridin-2-yl)-3-methylazetidin-3-yl)methoxy)-5-cyclopropyl-2-fluorobenzoic acid

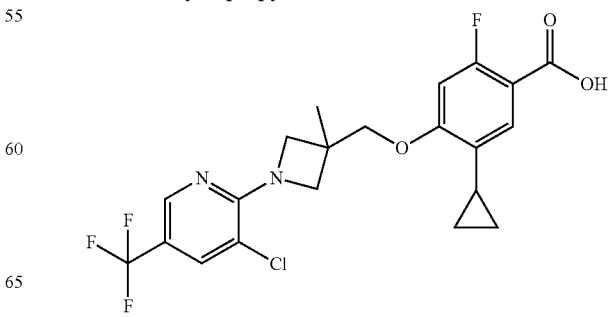

To a mixture of methyl 4-((1-(3-chloro-5-(trifluoromethyl)pyridin-2-yl)-3-methylazetidin-3-yl)methoxy)-5-cyclopropyl-2-fluorobenzoate (0.60 g, 1.27 mmol) is tetrahydrofuran (5 mL) was added a solution of lithium hydroxide monohydrate (0.29 g, 6.95 mmol) in water (5 mL) and the reaction mixture was heated at 80° C. for 3 hours. After cooling to ambient temperature, the reaction mixture was partitioned between dichloromethane (50 mL) and 1 M aqueous hydrochloric acid solution (10 mL). The organic phase was dried over anhydrous sodium sulfate, filtered, and the filtrate concentrated in vacuo to provide the title compound as an off-white solid (0.58 g, 99%): MS(ES+) m/z 459.0, 461.0 (M+1).

Step 6. Preparation of 4-((1-(3-chloro-5-(trifluoromethyl)pyridin-2-yl)-3-methylazetidin-3-yl)methoxy)-5-cyclopropyl-N-(cyclopropylsulfonyl)-2-fluorobenzamide

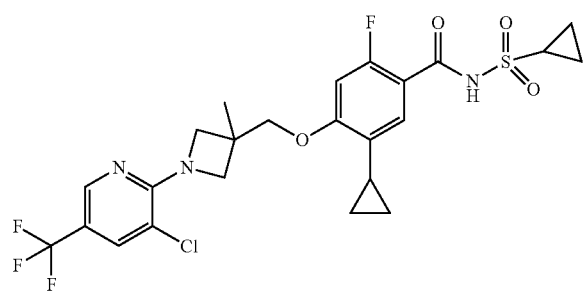 [SMILES: CC1(COc2cc(F)c(C(=O)NS(=O)(=O)C3CC3)cc2C2CC2)CN(c2ncc(C(F)(F)F)cc2Cl)C1]

Following the procedure as described in Example 470 Step 6, and making variation as required to replace 4-(((1R,3r,5S)-3-(3-chloro-2-fluoro-5-(trifluoromethyl)phenoxy)-8-azabicyclo[3.2.1]octan-8-yl)methyl)-5-cyclopropyl-2-fluorobenzoic acid hydrochloride with 4-((1-(3-chloro-5-(trifluoromethyl)pyridin-2-yl)-3-methylazetidin-3-yl)methoxy)-5-cyclopropyl-2-fluorobenzoic acid and purification by flash chromatography (0 to 50% ethyl acetate containing 0.1% trifluoroacetic acid in hexanes), the title compound was obtained as an off-white solid (0.19 g, 54%): $^1$H NMR (300 MHz, DMSO-d$_6$) δ11.85 (br s, 1H), 8.40-8.38 (m, 1H), 7.99 (d, J=1.9 Hz, 1H), 7.12 (d, J=8.3 Hz, 1H), 7.01 (d, J=12.9 Hz, 1H), 4.35 (d, J=9.0 Hz, 2H), 4.12 (s, 2H), 4.06 (d, J=9.0 Hz, 2H), 3.12-3.02 (m, 1H), 1.80-1.69 (m, 1H), 1.43 (s, 3H), 1.15-1.07 (m, 4H), 0.64-0.58 (m, 4H); MS(ES−) m/z 560.1, 562.1 (M−1).

Example 482

Synthesis of 4-((1-(3-chloro-5-(trifluoromethyl)pyridin-2-yl)-3-methylazetidin-3-yl)methoxy)-5-cyclopropyl-N-(ethylsulfonyl)-2-fluorobenzamide

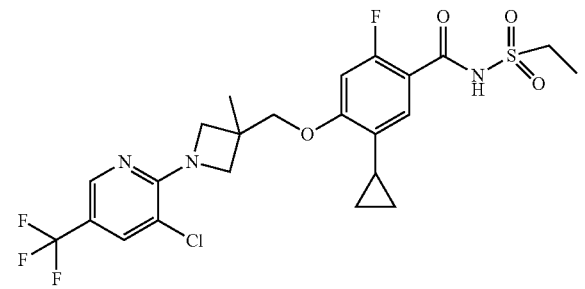 [SMILES: CCS(=O)(=O)NC(=O)c1cc(C2CC2)c(OCC2(C)CN(c3ncc(C(F)(F)F)cc3Cl)C2)cc1F]

Following the procedure as described in Example 470 step 6, and making variation as required to replace 4-(((1R,3r,5S)-3-(3-chloro-2-fluoro-5-(trifluoromethyl)phenoxy)-8-azabicyclo[3.2.1]octan-8-yl)methyl)-5-cyclopropyl-2-fluorobenzoic acid hydrochloride with 4-((1-(3-chloro-5-(trifluoromethyl)pyridin-2-yl)-3-methylazetidin-3-yl)methoxy)-5-cyclopropyl-2-fluorobenzoic acid and cyclopropanesulfonamide with ethanesulfonamide and purification by flash chromatography (0 to 50% ethyl acetate containing 0.1% trifluoroacetic acid in hexanes), the title compound was obtained as an off-white solid (0.19 g, 50%): $^1$H NMR (300 MHz, DMSO-d$_6$) δ11.83 (br s, 1H), 8.40-8.38 (m, 1H), 7.99 (d, J=2.1 Hz, 1H), 7.12 (d, J=8.3 Hz, 1H), 7.00 (d, J=12.8 Hz, 1H), 4.35 (d, J=9.0 Hz, 2H), 4.12 (s, 2H), 4.06 (d, J=9.0 Hz, 2H), 3.46 (q, J=7.3 Hz, 2H), 1.81-1.68 (m, 1H), 1.43 (s, 3H), 1.24 (t, J=7.3 Hz, 3H), 0.64-0.58 (m, 4H); MS(ES−) m/z 548.1, 550.1 (M−1).

Example 483

Synthesis of 4-((1-(5-chloro-3-fluoropyridin-2-yl)-3-methylazetidin-3-yl)methoxy)-5-cyclopropyl-N-(cyclopropylsulfonyl)-2-fluorobenzamide

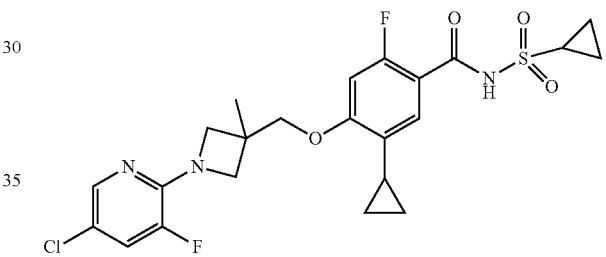

Step 1. Preparation of methyl 4-((1-(5-chloro-3-fluoropyridin-2-yl)-3-methylazetidin-3-yl)methoxy)-5-cyclopropyl-2-fluorobenzoate

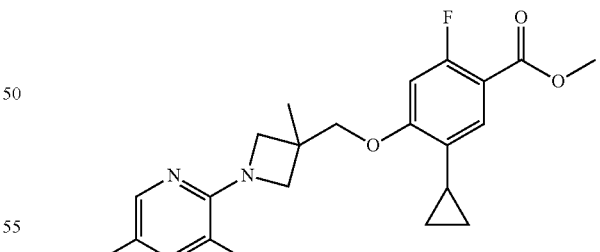

Following the procedure as described in Example 481 step 4, and making variation as required to replace 2-bromo-3-chloro-5-(trifluoromethyl)pyridine with 2-bromo-5-chloro-3-fluoropyridine, the title compound was obtained as an orange gum (0.43 g, 56%): $^1$H NMR (300 MHz, CDCl$_3$) δ7.87-7.85 (m, 1H), 7.44 (d, J=8.3 Hz, 1H), 7.16 (d, J=11.2 Hz, 1H), 6.56 (d, J=12.5 Hz, 1H), 4.18 (d, J=8.3 Hz, 2H), 4.01 (s, 2H), 3.89 (d, J=7.9 Hz, 2H), 3.86 (s, 3H), 1.87-1.75 (m, 1H), 1.48 (s, 3H), 0.77-0.68 (m, 2H), 0.60-0.53 (m, 2H).

Step 2. Preparation of 4-((1-(5-chloro-3-fluoropyridin-2-yl)-3-methylazetidin-3-yl)methoxy)-5-cyclopropyl-2-fluorobenzoic acid

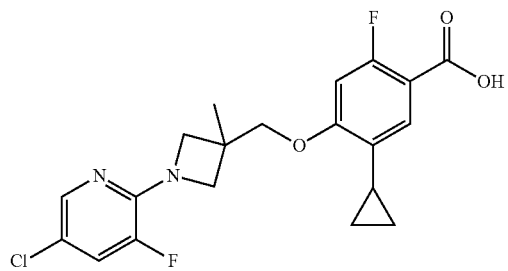 [SMILES: CC1(COc2cc(F)c(C(=O)O)cc2C2CC2)CN(c2ncc(Cl)cc2F)C1]

Following the procedure as described in Example 481 step 5, and making variation as required to replace methyl 4-((1-(3-chloro-5-(trifluoromethyl)pyridin-2-yl)-3-methylazetidin-3-yl)methoxy)-5-cyclopropyl-2-fluorobenzoate with methyl 4-((1-(5-chloro-3-fluoropyridin-2-yl)-3-methylazetidin-3-yl)methoxy)-5-cyclopropyl-2-fluorobenzoate, the title compound was obtained as an off-white solid (0.41 g, 98%): MS(ES−) m/z 409.0, 411.0 (M−1).

Step 3. Preparation of 4-((1-(5-chloro-3-fluoropyridin-2-yl)-3-methylazetidin-3-yl)methoxy)-5-cyclopropyl-N-(cyclopropylsulfonyl)-2-fluorobenzamide

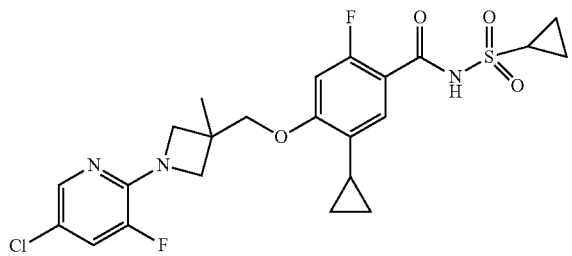 [SMILES: CC1(COc2cc(F)c(C(=O)NS(=O)(=O)C3CC3)cc2C2CC2)CN(c2ncc(Cl)cc2F)C1]

Following the procedure as described in Example 470 step 6, and making variation as required to replace 4-(((1R, 3r,5S)-3-(3-chloro-2-fluoro-5-(trifluoromethyl)phenoxy)-8-azabicyclo[3.2.1]octan-8-yl)methyl)-5-cyclopropyl-2-fluorobenzoic acid hydrochloride with 4-((1-(5-chloro-3-fluoropyridin-2-yl)-3-methylazetidin-3-yl)methoxy)-5-cyclopropyl-2-fluorobenzoic acid and purification by flash chromatography (0 to 50% ethyl acetate containing 0.1% trifluoroacetic acid in hexanes), the title compound was obtained as an off-white solid (0.13 g, 51%): $^1$H NMR (300 MHz, DMSO-$d_6$) δ11.85 (s, 1H), 7.97 (dd, J=2.0, 0.6 Hz, 1H), 7.74 (dd, J=11.8, 2.1 Hz, 1H), 7.12 (d, J=8.3 Hz, 1H), 7.00 (d, J=12.9 Hz, 1H), 4.16-4.10 (m, 4H), 3.85 (dd, J=8.3, 1.2 Hz, 2H), 3.12-3.02 (m, 1H), 1.80-1.69 (m, 1H), 1.43 (s, 3H), 1.16-1.07 (m, 4H), 0.68-0.58 (m, 4H); MS(ES−) m/z 510.1, 512.1 (M−1).

Example 484

Synthesis of 4-((1-(5-chloro-3-fluoropyridin-2-yl)-3-methylazetidin-3-yl)methoxy)-5-cyclopropyl-N-(ethylsulfonyl)-2-fluorobenzamide

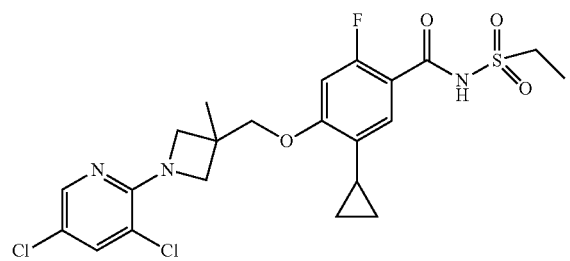 [SMILES: CCS(=O)(=O)NC(=O)c1cc(C2CC2)c(OCC2(C)CN(c3ncc(Cl)cc3Cl)C2)cc1F]

The following the procedure as described in Example 470 step 6, and making variation as required to replace 4-(((1R, 3r,5S)-3-(3-chloro-2-fluoro-5-(trifluoromethyl)phenoxy)-8-azabicyclo[3.2.1]octan-8-yl)methyl)-5-cyclopropyl-2-fluorobenzoic acid hydrochloride with 4-((1-(5-chloro-3-fluoropyridin-2-yl)-3-methylazetidin-3-yl)methoxy)-5-cyclopropyl-2-fluorobenzoic acid and cyclopropanesulfonamide with ethanesulfonamide, the title compound was obtained as an off-white solid (0.08 g, 30%): $^1$H NMR (300 MHz, DMSO-$d_6$) δ11.83 (br s, 1H), 7.97 (d, J=1.9 Hz, 1H), 7.74 (dd, J=11.8, 2.0 Hz, 1H), 7.12 (d, J=8.3 Hz, 1H), 7.00 (d, J=12.9 Hz, 1H), 4.17-4.09 (m, 4H), 3.85 (dd, J=8.3, 1.2 Hz, 2H), 3.40 (q, J=7.4, 7.3, 7.3 Hz, 2H), 1.81-1.70 (m, 1H), 1.43 (s, 3H), 1.24 (t, J=7.3, 7.3 Hz, 3H), 0.68-0.58 (m, 4H); MS(ES−) m/z 498.1, 500.1 (M−1).

Example 485

Synthesis of 4-((1-(5-chloro-6-(trifluoromethyl)pyridin-2-yl)-3-methylazetidin-3-yl)methoxy)-5-cyclopropyl-N-(cyclopropylsulfonyl)-2-fluorobenzamide

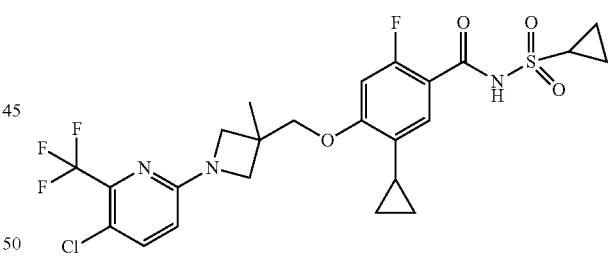

Step 1. Preparation of methyl 4-((1-(5-chloro-6-(trifluoromethyl)pyridin-2-yl)-3-methylazetidin-3-yl)methoxy)-5-cyclopropyl-2-fluorobenzoate

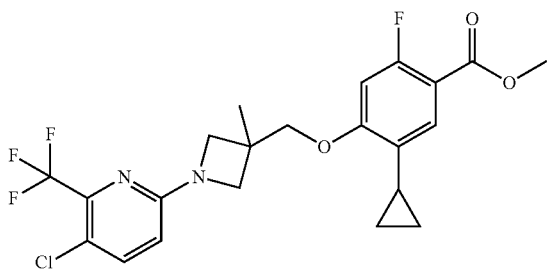 [SMILES: COC(=O)c1cc(C2CC2)c(OCC2(C)CN(c3ccc(Cl)c(C(F)(F)F)n3)C2)cc1F]

Following the procedure as described in Example 481 step 4, and making variation as required to replace 2-bromo-3-chloro-5-(trifluoromethyl)pyridine with 3,6-dichloro-2-(trifluoromethyl)pyridine, the title compound was obtained as an orange gum (0.66 g, 51%): $^1$H NMR (300 MHz, CDCl$_3$) δ7.48 (d, J=8.8 Hz, 1H), 7.43 (d, J=8.3 Hz, 1H), 6.55 (d, J=12.4 Hz, 1H), 6.36 (d, J=8.8 Hz, 1H), 4.10 (d, J=8.2 Hz, 2H), 3.99 (s, 2H), 3.86 (s, 3H), 3.81 (d, J=8.2 Hz, 2H), 1.82-1.70 (m, 1H), 1.50 (s, 3H), 0.74-0.65 (m, 2H), 0.58-0.52 (m, 2H).

Step 2. Preparation of 4-((1-(5-chloro-6-(trifluoromethyl)pyridin-2-yl)-3-methylazetidin-3-yl)methoxy)-5-cyclopropyl-2-fluorobenzoic acid

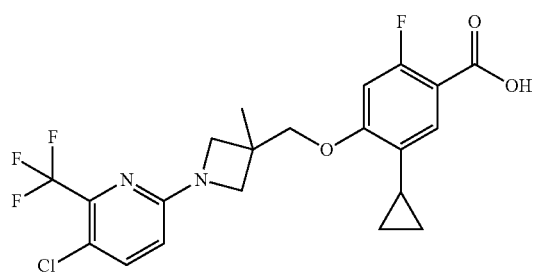 [SMILES: CC1(COc2cc(F)c(C(=O)O)cc2C2CC2)CN(c2ccc(Cl)c(C(F)(F)F)n2)C1]

Following the procedure as described in Example 481 Step 5, and making variation as required to replace methyl 4-((1-(3-chloro-5-(trifluoromethyl)pyridin-2-yl)-3-methylazetidin-3-yl)methoxy)-5-cyclopropyl-2-fluorobenzoate with methyl 4-((1-(5-chloro-6-(trifluoromethyl)pyridin-2-yl)-3-methylazetidin-3-yl)methoxy)-5-cyclopropyl-2-fluorobenzoate, the title compound was obtained as an off-white solid (0.63 g, 99%): MS(ES+) m/z 459.0, 461.0 (M+1).

Step 3. Preparation of 4-((1-(5-chloro-6-(trifluoromethyl)pyridin-2-yl)-3-methylazetidin-3-yl)methoxy)-5-cyclopropyl-N-(cyclopropylsulfonyl)-2-fluorobenzamide

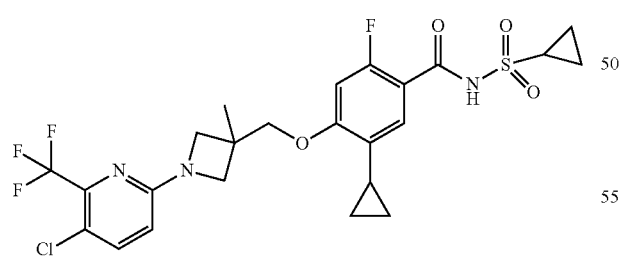

Following the procedure as described in Example 470 step 6, and making variation as required to replace 4-(((1R,3r,5S)-3-(3-chloro-2-fluoro-5-(trifluoromethyl)phenoxy)-8-azabicyclo[3.2.1]octan-8-yl)methyl)-5-cyclopropyl-2-fluorobenzoic acid hydrochloride with -((1-(5-chloro-6-(trifluoromethyl)pyridin-2-yl)-3-methylazetidin-3-yl)methoxy)-5-cyclopropyl-2-fluorobenzoic acid and purification by flash chromatography (0 to 50% ethyl acetate containing 0.1% trifluoroacetic acid in hexanes), the title compound was obtained as a colorless solid (0.11 g, 28%): $^1$H NMR (300 MHz, DMSO-d$_6$) δ11.85 (br s, 1H), 7.81 (d, J=8.9 Hz, 1H), 7.10 (d, J=8.3 Hz, 1H), 6.99 (d, J=12.9 Hz, 1H), 6.78-6.68 (m, 1H), 4.10 (s, 2H), 4.05 (d, J=8.5 Hz, 2H), 3.81 (d, J=8.5 Hz, 2H), 3.13-3.00 (m, 1H), 1.72-1.61 (m, 1H), 1.44 (s, 3H), 1.15-1.06 (m, 4H), 0.62-0.55 (m, 4H); MS(ES−) m/z 560.1, 562.1 (M−1).

Example 486 and Example 487

Synthesis of 4-((1-(4-chloro-5-(trifluoromethyl)pyridin-2-yl)-3-methylazetidin-3-yl)methoxy)-5-cyclopropyl-N-(cyclopropylsulfonyl)-2-fluorobenzamide, trifluoroacetic acid salt

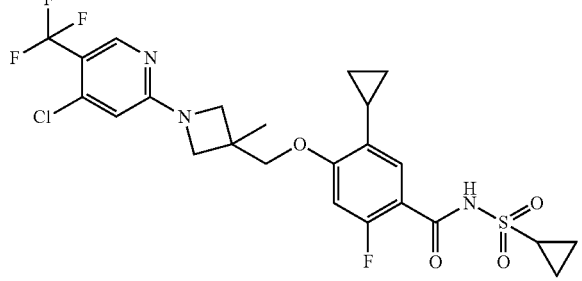

And 4-((1-(2-chloro-5-(trifluoromethyl)pyridin-4-yl)-3-methylazetidin-3-yl)methoxy)-5-cyclopropyl-N-(cyclopropylsulfonyl)-2-fluorobenzamide, trifluoroacetic acid salt

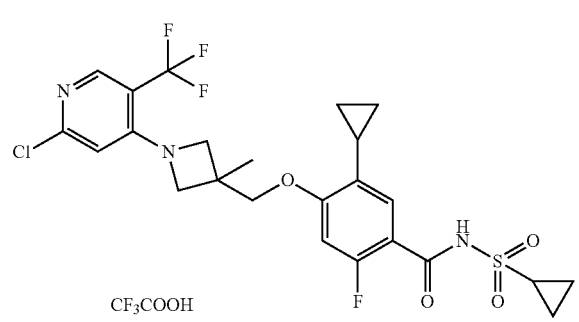 [SMILES: CC1(COc2cc(F)c(C(=O)NS(=O)(=O)C3CC3)cc2C2CC2)CN(c2cc(Cl)ncc2C(F)(F)F)C1 ; "CF3COOH"]

Step 1. Preparation of methyl 4-((1-(4-chloro-5-(trifluoromethyl)pyridin-2-yl)-3-methylazetidin-3-yl)methoxy)-5-cyclopropyl-2-fluorobenzoate and methyl 4-((1-(2-chloro-5-(trifluoromethyl)pyridin-4-yl)-3-methylazetidin-3-yl)methoxy)-5-cyclopropyl-2-fluorobenzoate

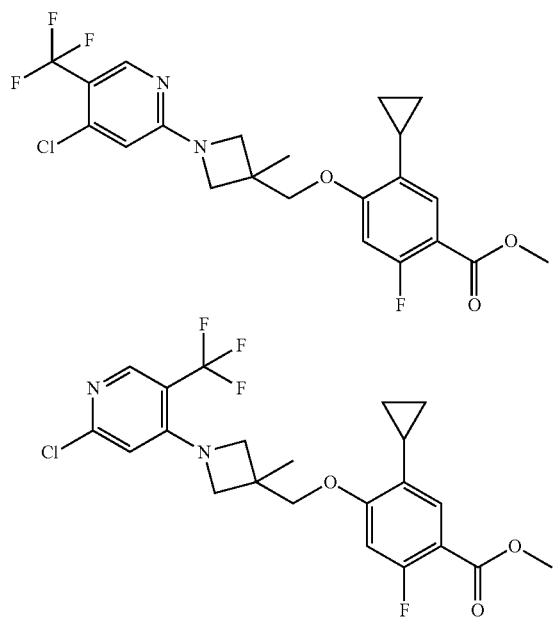

Following the procedure as described in Example 481 Step 4, and making variation as required to replace 2-bromo-3-chloro-5-(trifluoromethyl)pyridine with 2,4-dichloro-5-(trifluoromethyl)pyridine, a 2.5:1 mixture of the title compounds was obtained as an orange gum (0.40 g, 31%). Major isomer: $^{19}$F NMR (282 MHz, CDCl$_3$) δ −55.5 (s, 3F), −108.8 (s, 1F), Minor isomer: $^{19}$F NMR (282 MHz, CDCl$_3$) δ −60.5 (s, 3F), −108.9 (s, 1F).

Step 2. Preparation of 4-((1-(4-chloro-5-(trifluoromethyl)pyridin-2-yl)-3-methylazetidin-3-yl)methoxy)-5-cyclopropyl-2-fluorobenzoic acid and 4-((1-(2-chloro-5-(trifluoromethyl)pyridin-4-yl)-3-methylazetidin-3-yl)methoxy)-5-cyclopropyl-2-fluorobenzoic acid

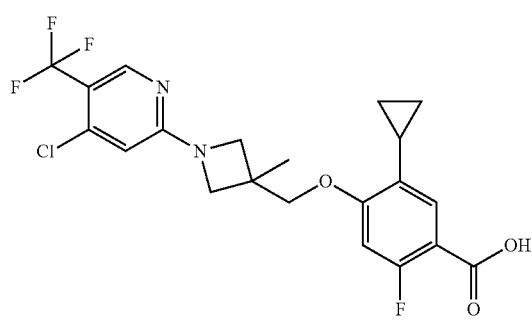

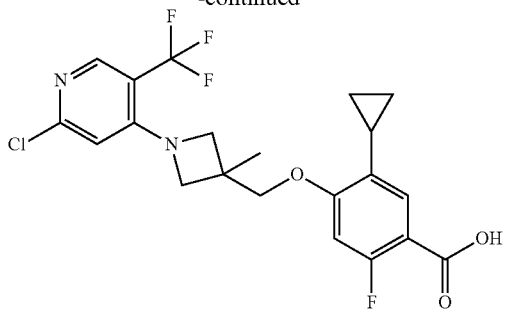

Following the procedure as described in Example 481 Step 5, and making variation as required to replace methyl 4-((1-(3-chloro-5-(trifluoromethyl)pyridin-2-yl)-3-methylazetidin-3-yl)methoxy)-5-cyclopropyl-2-fluorobenzoate with a mixture of methyl 4-((1-(4-chloro-5-(trifluoromethyl)pyridin-2-yl)-3-methylazetidin-3-yl)methoxy)-5-cyclopropyl-2-fluorobenzoate and methyl 4-((1-(2-chloro-5-(trifluoromethyl)pyridin-4-yl)-3-methylazetidin-3-yl)methoxy)-5-cyclopropyl-2-fluorobenzoate, a mixture of the title compounds was obtained as a yellowish solid (0.33 g, 76%): MS(ES+) m/z 459.1, 461.1 (M+1).

Step 3. Preparation of 4-((1-(4-chloro-5-(trifluoromethyl)pyridin-2-yl)-3-methylazetidin-3-yl)methoxy)-5-cyclopropyl-N-(cyclopropylsulfonyl)-2-fluorobenzamide, trifluoroacetic acid salt

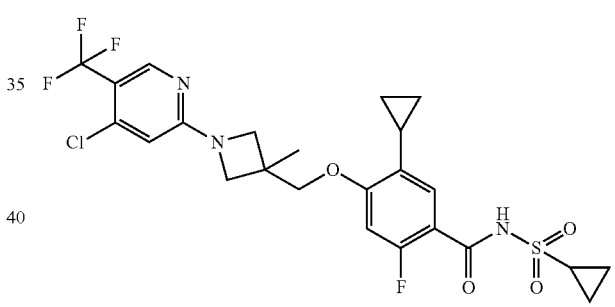

CF$_3$COOH

And 4-((1-(2-chloro-5-(trifluoromethyl)pyridin-4-yl)-3-methylazetidin-3-yl)methoxy)-5-cyclopropyl-N-(cyclopropylsulfonyl)-2-fluorobenzamide, trifluoroacetic acid salt

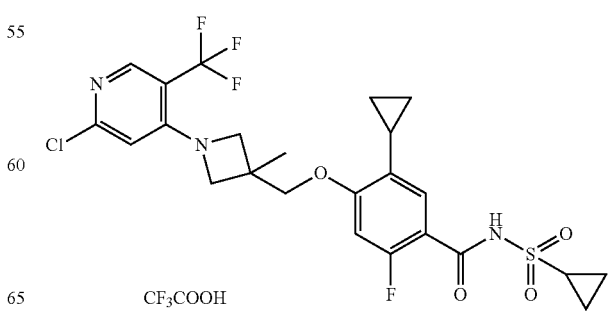

CF$_3$COOH

Following the procedure as described in Example 470 step 6, and making variation as required to replace 4-(((1R,3r,5S)-3-(3-chloro-2-fluoro-5-(trifluoromethyl)phenoxy)-8-azabicyclo[3.2.1]octan-8-yl)methyl)-5-cyclopropyl-2-fluorobenzoic acid hydrochloride with a mixture of 4-((1-(4-chloro-5-(trifluoromethyl)pyridin-2-yl)-3-methylazetidin-3-yl)methoxy)-5-cyclopropyl-2-fluorobenzoic acid and 4-((1-(2-chloro-5-(trifluoromethyl)pyridin-4-yl)-3-methylazetidin-3-yl)methoxy)-5-cyclopropyl-2-fluorobenzoic acid, the title compounds were obtained after reverse phase HPLC purification: the first fraction is 4-((1-(2-Chloro-5-(trifluoromethyl)pyridin-4-yl)-3-methylazetidin-3-yl)methoxy)-5-cyclopropyl-N-(cyclopropylsulfonyl)-2-fluorobenzamide, trifluoroacetic acid salt (0.07 g, 18%): $^1$H NMR (300 MHz, DMSO-d$_6$) δ11.86 (br s, 1H), 8.27 (s, 1H), 7.14 (d, J=8.3 Hz, 1H), 7.02 (d, J=12.9 Hz, 1H), 6.58 (s, 1H), 4.19 (d, J=8.9 Hz, 2H), 4.14 (s, 2H), 3.96 (d, J=8.9 Hz, 2H), 3.13-3.02 (m, 1H), 1.88-1.76 (m, 1H), 1.42 (s, 3H), 1.16-1.07 (m, 4H), 0.66-0.58 (m, 4H); MS(ES+) m/z 562.1, 564.1 (M+1). The second fraction is 4-((1-(4-Chloro-5-(trifluoromethyl)pyridin-2-yl)-3-methylazetidin-3-yl)methoxy)-5-cyclopropyl-N-(cyclopropylsulfonyl)-2-fluorobenzamide, trifluoroacetic acid salt (0.19 g, 46%): $^1$H NMR (300 MHz, DMSO-d$_6$) δ11.85 (s, 1H), 8.39 (s, 1H), 7.11 (d, J=8.3 Hz, 1H), 7.01 (d, J=12.9 Hz, 3H), 6.75 (s, 1H), 4.14-4.07 (m, 4H), 3.86 (d, J=8.9 Hz, 2H), 3.12-3.02 (m, 1H), 1.76-1.64 (m, 1H), 1.44 (s, 3H), 1.14-1.07 (m, 4H), 0.64-0.58 (m, 4H); MS(ES+) m/z 562.1, 564.1 (M+1).

Example 488

Synthesis of 5-cyclopropyl-N-(cyclopropylsulfonyl)-2-fluoro-4-((3-methyl-1-(5-(trifluoromethyl)pyridin-2-yl)azetidin-2-3-yl)methoxy)benzamide, trifluoroacetic acid salt

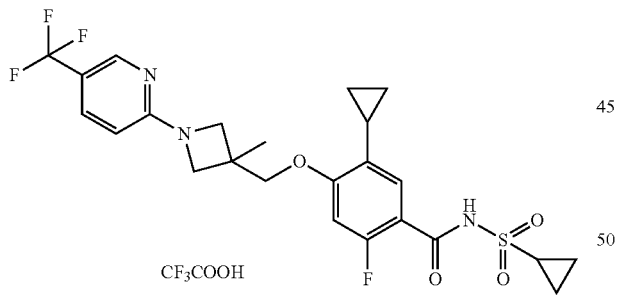

To a mixture of 4-((1-(4-chloro-5-(trifluoromethyl)pyridin-2-yl)-3-methylazetidin-3-yl)methoxy)-5-cyclopropyl-N-(cyclopropylsulfonyl)-2-fluorobenzamide, trifluoroacetic acid salt (0.10 g, 0.18 mmol) in ethyl acetate (5 mL) and acetic acid (1 mL) was added palladium on carbon (10 wt %, wet, 50 mg) and the reaction mixture was stirred under an atmosphere of hydrogen for 16 hours. The reaction mixture was filtered over diatomaceous earth, the filter cake washed with ethyl acetate (20 mL), and the combined filtrate concentrated in vacuo. Purification of the residue by reverse phase HPLC provided the title compound as a colorless solid (0.02 g, 16%): $^1$H NMR (300 MHz, DMSO-d$_6$) δ8.67 (d, J=16.3 Hz, 1H), 8.43 (s, 1H), 7.80 (d, J=8.2 Hz, 1H), 7.61 (d, J=9.1 Hz, 1H), 6.61 (d, J=13.3 Hz, 1H), 6.51. (d, J=8.8 Hz, 1H), 4.41 (d, J=8.7 Hz, 2H), 4.12 (d, J=8.8 Hz, 2H), 4.07 (s, 2H), 3.14-3.02 (m, 1H), 1.86-1.73 (m, 1H), 1.57 (s, 3H), 1.48-1.40 (m, 2H), 1.19-1.09 (m, 2H), 0.78-0.70 (m, 2H), 0.63-0.55 (m, 2H); MS(ES+) m/z 528.0 (M+1).

Example 489

Synthesis of 5-cyclopropyl-N-(cyclopropylsulfonyl)-2-fluoro-4-((3-methyl-1-(3-(trifluoromethyl)pyridin-4-yl)azetidin-3-yl)methoxy)benzamide, trifluoroacetic acid salt

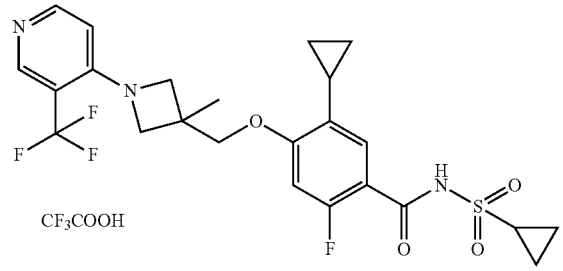 [SMILES: "CF3COOH" ; CC1(COc2cc(F)c(C(=O)NS(=O)(=O)C3CC3)cc2C2CC2)CN(c2ccncc2C(F)(F)F)C1]

Following the procedure as described in Example 488, and making variation as required to replace 4-((1-(4-chloro-5-(trifluoromethyl)pyridin-2-yl)-3-methylazetidin-3-yl)methoxy)-5-cyclopropyl-N-(cyclopropylsulfonyl)-2-fluorobenzamide, trifluoroacetic acid salt, with 4-((1-(2-chloro-5-(trifluoromethyl)pyridin-4-yl)-3-methylazetidin-3-yl)methoxy)-5-cyclopropyl-N-(cyclopropylsulfonyl)-2-fluorobenzamide, the title compound was obtained as a colorless solid (0.01 g, 33%): $^1$H NMR (300 MHz, DMSO-d$_6$) δ8.79-8.55 (m, 2H), 8.36 (br s, 1H), 7.63 (d, J=8.9 Hz, 1H), 6.62 (d, J=13.7 Hz, 1H), 6.53 (br s, 1H), 4.53 (br s, 2H), 4.19 (br s, 2H), 4.07 (s, 2H), 3.13-3.00 (m, 1H), 1.84-1.72 (m, 1H), 1.59 (s, 3H), 1.48-1.38 (m, 2H), 1.17-1.08 (m, 2H), 0.77-0.68 (m, 2H), 0.62-0.54 (m, 2H); MS(ES+) m/z 528.1 (M+1).

Example 490

Synthesis of (R)-5-cyclopropyl-2-fluoro-N-(methylsulfonyl)-4-((1-(5-trifluoromethyl)pyridin-2-yl)piperidin-3-yl)oxy)benzamide, trifluoroacetic acid salt

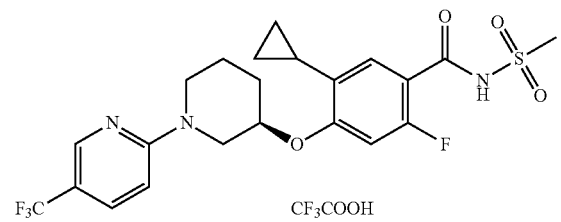 [SMILES: CS(=O)(=O)NC(=O)c1cc(C2CC2)c(O[C@@H]2CCCN(c3ccc(C(F)(F)F)cn3)C2)cc1F ; "CF3COOH"]

Step 1. Preparation of (R)-methyl 5-cyclopropyl-2-fluoro-4-((1-(5-(trifluoromethyl-pyridin-2-yl)piperidin-3-yl)oxy)benzoate

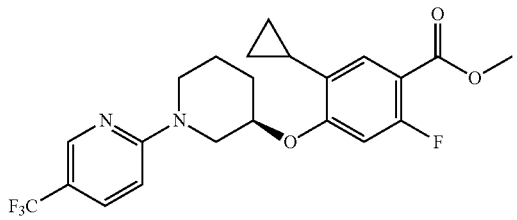 [SMILES: COC(=O)c1cc(C2CC2)c(O[C@@H]2CCCN(c3ccc(C(F)(F)F)cn3)C2)cc1F]

Following the procedure as described in Example 481 Step 4 and making variation as required to replace methyl 5-cyclopropyl-2-fluoro-4-((3-methylazetidin-3-yl)methoxy)benzoate hydrochloride with (R)-methyl 5-cyclopropyl-2-fluoro-4-(piperidin-3-yloxy)benzoate and 2-bromo-5-chloro-5-(trifluoromethyl)pyridine with 2-chloro-5-(trifluoromethyl)pyridine, the title compound was obtained as a yellowish oil (0.58 g, 44%); $^1$H NMR (300 MHz, CDCl$_3$) δ8.35-8.33 (m, 1H), 7.56 (dd, J=9.1, 2.5 Hz, 1H), 7.36 (d, J=8.3 Hz, 1H), 6.74 (d, J=12.9 Hz, 1H), 6.61 (d, J=9.0 Hz, 1H), 4.47-4.38 (m, 1H), 4.17 (dd, J=13.5, 2.7 Hz, 1H), 3.86 (s, 3H), 3.80-3.64 (m, 3H), 2.18-2.05 (m, 1H), 2.04-1.87 (m, 2H), 1.78-1.57 (m, 2H), 0.74-0.67 (m, 2H), 0.55-0.46 (m, 2H): MS(ES+) m/z 439.2 (M+1).

Step 2. Preparation of (R)-5-cyclopropyl-2-fluoro-4-((1-(5-(trifluoromethyl)pyridin-2-yl)piperidin-3-yl)oxy)benzoic acid

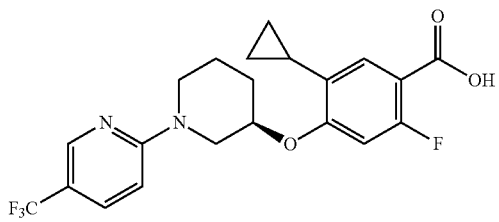 [SMILES: O=C(O)c1cc(C2CC2)c(O[C@@H]2CCCN(c3ccc(C(F)(F)F)cn3)C2)cc1F]

Following the procedure as described in Example 481 Step 5 and making variation as required to replace methyl 4-((1-(3-chloro-5-(trifluoromethyl)pyridin-2-yl)-3-methylazetidin-3-yl)methoxy)-5-cyclopropyl-2-fluorobenzoate with (R)-methyl 5-cyclopropyl-2-fluoro-4-((1-(5-(trifluoromethyl)pyridin-2-yl)piperidin-3-yl)oxy)benzoate, the title compound was obtained as an orange gum (0.55 g, quant. yield); MS(ES+) m/z 425.1 (M+1).

Step 3. Preparation of (R)-5-cyclopropyl-2-fluoro-N-(fluorosulfonyl)-4-((1-(5-(trifluoromethyl)pyridin-2-yl)piperidin-3-yl)oxy)benzamide, trifluoroacetic acid salt

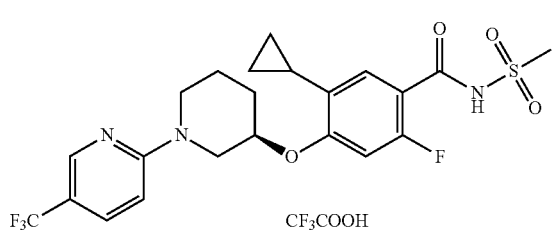 [SMILES: CS(=O)(=O)NC(=O)c1cc(C2CC2)c(O[C@@H]2CCCN(c3ccc(C(F)(F)F)cn3)C2)cc1F ; "CF3COOH"]

Following the procedure as described in Example 470 Step 6, and making variation as required to replace 4-(((1R,3r,5S)-3-(3-chloro-2-fluoro-5-(trifluoromethyl)phenoxy)-8-azabicyclo[3.2.1]octan-8-yl)methyl)-5-cyclopropyl-2-fluorobenzoic acid hydrochloride with (R)-5-cyclopropyl-2-fluoro-4-((1-(5-(trifluoromethyl)pyridin-2-yl)piperidin-3-yl)oxy)benzoic acid and cyclopropanesulfonamide with methanesulfonamide, the title compound was obtained as a colorless solid (0.16 g, 39%); $^1$H NMR (300 MHz, DMSO-d$_6$) δ10.59 (br s, 1H), 8.86-8.71 (m, 1H), 8.37-8.34 (m, 1H), 7.73 (dd, J=9.3, 2.3 Hz, 1H), 7.47 (d, J=9.0 Hz, 1H), 6.83 (d, J=9.3 Hz, 1H), 6.76-6.69 (m, 1H), 4.65-4.56 (m, 1H), 4.10 (dd, J=14.0, 5.3 Hz, 1H), 4.02 (dd, J=1.4.0, 2.7 Hz, 1H), 3.90 (ddd, J=1.3.5, 5.9, 3.2 Hz, 1H), 3.63 (ddd, J=13.7, 8.6, 3.4 Hz, 1H), 3.39 (s, 3H), 2.15-1.94 (m, 3H), 1.81-1.60 (m, 2H), 0.78-0.61 (m, 2H), 0.58-0.41 (m, 2H); MS(ES−) m/z 500.2 (M−1).

Example 491

Synthesis of (R)-5-cyclopropyl-N-(cyclopropylsulfonyl)-2-fluoro-4-((1-(5-(trifluoromethyl)pyridin-2-yl)piperidin-3-yl)oxy)benzamide, trifluoroacetic acid salt

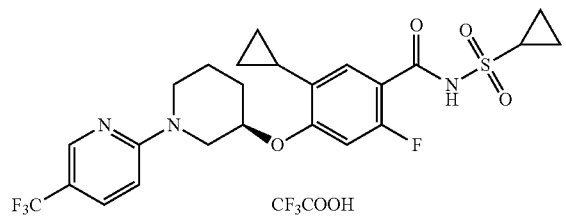 [SMILES: O=C(NS(=O)(=O)C1CC1)c1cc(C2CC2)c(O[C@@H]2CCCN(c3ccc(C(F)(F)F)cn3)C2)cc1F ; "CF3COOH"]

Following the procedure as described in Example 470 step 6, and making variation as required to replace 4-(((1R,3r,5S)-3-(3-chloro-2-fluoro-5-(trifluoromethyl)phenoxy)-8-azabicyclo[3.2.1]octan-8-yl)methyl)-5-cyclopropyl-2-fluorobenzoic acid hydrochloride with (R)-5-cyclopropyl-2-fluoro-4-((1-(5-(trifluoromethyl)pyridin-2-yl)piperidin-3-yl)oxy)benzoic acid, the title compound was obtained as a colorless solid (0.16 g, 39%): $^1$H NMR (300 MHz, DMSO-d$_6$) δ9.89 (br s, 1H), 8.75 (d, J=15.1 Hz, 1H), 7.72 (dd, J=9.3, 2.3 Hz, 1H), 7.48 (d, J=9.0 Hz, 1H), 6.82 (d, J=9.3 Hz, 1H), 6.73 (d, J=14.2 Hz, 1H), 4.64-4.53 (m, 1H), 4.12-3.99 (m, 2H), 3.89 (ddd, J=13.4, 6.3, 3.3 Hz, 1H), 3.63 (ddd, J=13.7, 8.2, 3.3 Hz, 1H), 3.07 (tt, J=8.1, 8.1, 4.8, 4.8 Hz, 1H), 2.15-1.92 (m, 3H), 1.80-1.60 (m, 3H), 1.47-1.38 (m, 2H), 1.18-1.08 (m, 2H), 0.79-0.61 (m, 2H), 0.58-0.43 (m, 2H); MS(ES−) m/z 526.2 (M−1).

Example 492

Synthesis of (R)-5-cyclopropyl-N-(cyclopropylsulfonyl)-2-fluoro-4-((1-(pyridin-2-yl)piperidin-3-yl)oxy)benzamide

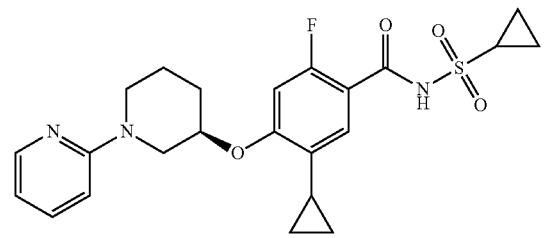 [SMILES: O=C(NS(=O)(=O)C1CC1)c1cc(C2CC2)c(O[C@@H]2CCCN(c3ccccn3)C2)cc1F]

Step 1. Preparation of (R)-tert-butyl 5-cyclopropyl-2-fluoro-4-((1-(pyridin-2-yl)piperidin-3-yl)oxy)benzoate

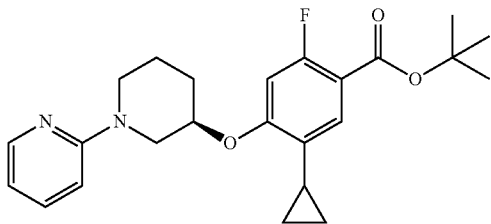 [SMILES: CC(C)(C)OC(=O)c1cc(C2CC2)c(O[C@@H]2CCCN(c3ccccn3)C2)cc1F]

Following the procedure as described in Example 481 Step 4 and making variations as required to replace methyl 5-cyclopropyl-2-fluoro-4-((3-methylazetidin-3-yl)methoxy)benzoate hydrochloride with (R)-methyl 5-cyclopropyl-2-fluoro-4-(piperidin-3-yloxy)benzoate, and to replace 2-bromo-3-chloro-5-(trifluoromethyl)pyridine with 2-bromopyridine, and to replace cesium carbonate with potassium tert-butoxide, the title compound was obtained as a yellowish oil (0.27 g, 32%): MS(ES+) m/z 413.3 (M+1).

Step 2. Preparation of (R)-5-cyclopropyl-2-fluoro-4-((1-(pyridin-2-yl)piperidin-3-yl)oxy)benzoic acid

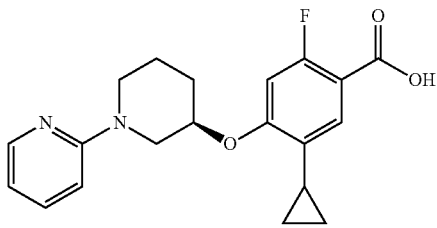 [SMILES: O=C(O)c1cc(C2CC2)c(O[C@@H]2CCCN(c3ccccn3)C2)cc1F]

Following the procedure as described in Example 478 step 4, and making variation as required to replace tert-butyl 4-((4-((2-chloro-4-fluorobenzyl)oxy)piperidin-1-yl)methyl)-5-cyclopropyl-2-fluorobenzoate with (R)-tert-butyl 5-cyclopropyl-2-fluoro-4-((1-(pyridin-2-yl)piperidin-3-yl)oxy)benzoate, the title compound was obtained as a yellowish oil (0.23 g, quant. yield): MS(ES+) m/z 357.2 (M+1).

Step 3. Preparation of (R)-5-cyclopropyl-N-(cyclopropylsulfonyl)-2-fluoro-4-((1-(pyridin-2-yl)piperidin-3-yl)oxy)benzamide

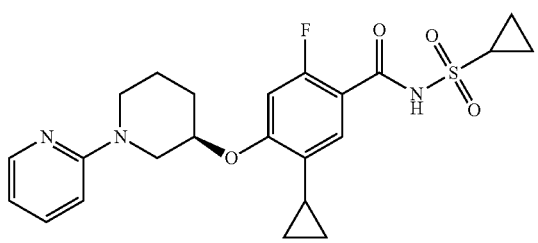 [SMILES: O=C(NS(=O)(=O)C1CC1)c1cc(C2CC2)c(O[C@@H]2CCCN(c3ccccn3)C2)cc1F]

Following the procedure as described in Example 470 Step 6, and making variation as required to replace 4-(((1R,3r,5S)-3-(3-chloro-2-fluoro-5-(trifluoromethyl)phenoxy)-8-azabicyclo[3.2.1]octan-8-yl)methyl)-5-cyclopropyl-2-fluorobenzoic acid hydrochloride with (R)-5-cyclopropyl-2-fluoro-4-((1-(pyridin-2-yl)piperidin-3-yl)oxybenzoic acid and purification by flash chromatography (0-100% ethyl acetate in hexanes), the title compound was obtained as a colorless solid (0.03 g, 20%): $^1$H NMR (300 MHz, CDCl$_3$) δ8.71 (s, 1H), 8.15 (ddd, J=5.0, 1.9, 0.6 Hz, 1H), 7.52 (d, J=9.1 Hz, 1H), 7.44 (ddd, J=8.9, 7.1, 1.9 Hz, 1H), 6.95 (d, J=15.0 Hz, 1H), 6.65 (d, J=8.6 Hz, 1H), 6.59 (dd, J=7.1, 5.0 Hz, 1H), 4.46-4.32 (m, 2H), 3.81-3.71 (m, 1H), 3.45-3.32 (m, 2H), 3.13-3.01 (m, 1H), 2.23-2.11 (m, 1H), 1.97-1.81 (m, 3H), 1.70-1.60 (m, 1H), 1.47-1.39 (m, 2H), 1.16-1.08 (m, 2H), 0.85-0.76 (m, 2H), 0.60-0.53 (m, 2H); MS(ES−) m/z 458.3 (M−1).

Example 493

Synthesis of (R)—N-(azetidin-1-ylsulfonyl)-5-cyclopropyl-2-fluoro-4-((1-(pyridin-2-yl)piperidin-3-yl)oxy)benzamide

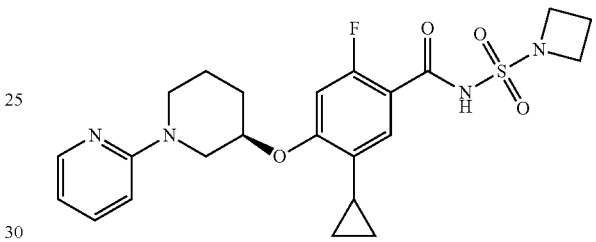

Following the procedure as described in Example 470 Step 6, and making variations as required to replace 4-(((1R,3r,5S)-3-(3-chloro-2-fluoro-5-(trifluoromethyl)phenoxy)-8-azabicyclo[3.2.1]octan-8-yl)methyl)-5-cyclopropyl-2-fluorobenzoic acid hydrochloride with (R)-5-cyclopropyl-2-fluoro-4-((1-(pyridin-2-yl)piperidin-3-yl)oxy)benzoic acid, and to replace cyclopropanesulfonamide with azetidine-1-sulfonamide and purification by flash chromatography (0-100% ethyl acetate in hexanes), the title compound was obtained as a colorless solid (0.04 g, 28%): $^1$H NMR (300 MHz, CDCl$_3$) δ8.67 (d, J=14.1 Hz, 1H), 8.15 (dd, J=4.9, 1.8 Hz, 1H), 7.53 (d, J=9.1 Hz, 1H), 7.44 (ddd, J=8.8, 7.2, 1.9 Hz, 1H), 6.96 (d, J=14.7 Hz, 1H), 6.65 (d, J=8.6 Hz, 1H), 6.59 (dd, J=7.1, 5.0 Hz, 1H), 4.46-4.33 (m, 2H), 4.23 (t, J=8.1, 8.1 Hz, 4H), 3.81-3.71 (m, 1H), 3.45-3.33 (m, 2H), 2.31-2.12 (m, 3H), 1.97-1.82 (m, 3H), 1.72-1.60 (m, 1H), 0.85-0.77 (m, 2H), 0.62-0.55 (m, 2H); MS(ES−) m/z 473.3 (M−1).

Example 494

Synthesis of (R)-5-cyclopropyl-N-(cyclopropylsulfonyl)-2-fluoro-4-((1-(5-fluoropyridin-2-yl)piperidin-3-yl)oxy)benzamide, trifluoroacetic acid salt

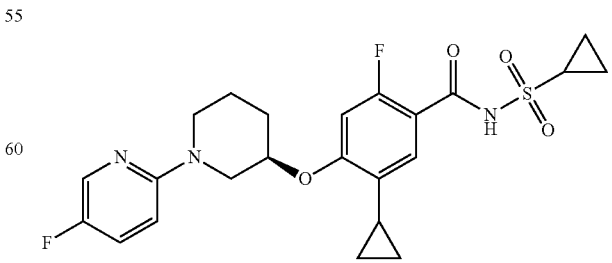

CF$_3$COOH

Step 1. Preparation of (R)-tert-butyl 5-cyclopropyl-2-fluoro-4-((1-(5-fluoropyridin-2-yl)piperidin-3-yl)oxy)benzoate

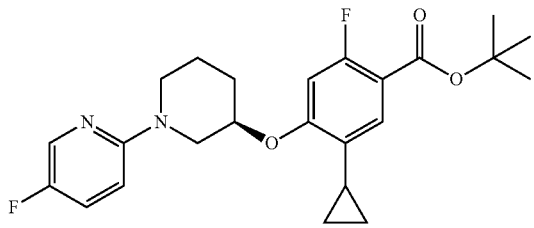 [SMILES: CC(C)(C)OC(=O)c1cc(C2CC2)c(O[C@@H]2CCCN(c3ccc(F)cn3)C2)cc1F]

Following the procedure as described in Example 481 step 4 and making variation as required to replace methyl 5-cyclopropyl-2-fluoro-4-((3-methylazetidin-3-yl)methoxy)benzoate hydrochloride with (R)-methyl 5-cyclopropyl-2-fluoro-4-(piperidin-3-yloxy)benzoate, 2-bromo-3-chloro-5-(trifluoromethyl)pyridine with 2-chloro-5-fluoropyridine, and cesium carbonate with potassium tert-butoxide, the title compound was obtained as a yellowish oil (0.22 g, 26%): MS(ES+) m/z 431.1 (M+1).

Step 2. Preparation of (R)-5-cyclopropyl-2-fluoro-4-((1-(5-fluoropyridin-2-yl)piperidin-3-yl)oxy)benzoic acid

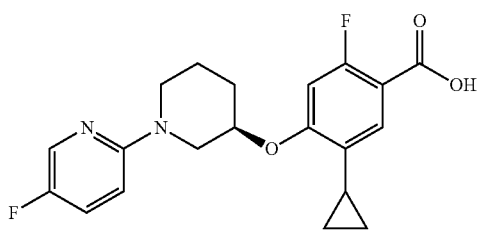 [SMILES: O=C(O)c1cc(C2CC2)c(O[C@@H]2CCCN(c3ccc(F)cn3)C2)cc1F]

Following the procedure as described in Example 478 step 4, and making variation as required to replace tert-butyl 4-((4-((2-chloro-4-fluorobenzyl)oxy)piperidin-1-yl)methyl)-5-cyclopropyl-2-fluorobenzoate with (R)-tert-butyl 5-cyclopropyl-2-fluoro-4-((1-(5-fluoropyridin-2-yl)piperidin-3-yl)oxy)benzoate, the title compound was obtained as an orange oil (0.04 g, quant. yield): MS(ES+) m/z 374.9 (M+1).

Step 3. Preparation of (R)-5-cyclopropyl-N-(cyclopropylsulfonyl)-2-fluoro-4-((1-(5-fluoropyridin-2-yl)piperidin-3-yl)oxy)benzamide, trifluoroacetic acid salt

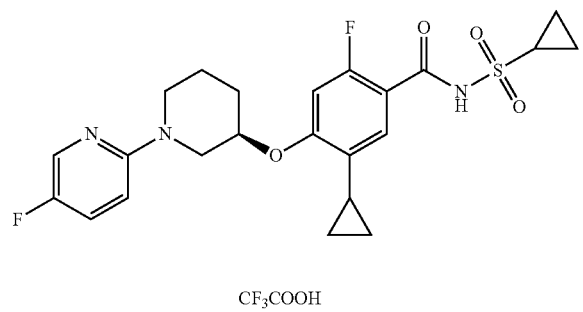 [SMILES: O=C(NS(=O)(=O)C1CC1)c1cc(C2CC2)c(O[C@@H]2CCCN(c3ccc(F)cn3)C2)cc1F ; "CF3COOH"]

Following the procedure as described in Example 470 step 6, and making variation as required to replace 4-(((1R,3r,5S)-3-(3-chloro-2-fluoro-5-(trifluoromethyl)phenoxy)-8-azabicyclo[3.2.1]octan-8-yl)methyl)-5-cyclopropyl-2-fluorobenzoic acid hydrochloride with (R)-5-cyclopropyl-2-fluoro-4-((1-(5-fluoropyridin-2-yl)piperidin-3-yl)oxy)benzoic acid and purification by flash chromatography (50% ethyl acetate in hexanes, then 0-10% methanol in dichloromethane) and treatment with trifluoroacetic acid, the title compound was obtained as a colorless solid (0.12 g, 39%): $^1$H NMR (300 MHz, DMSO-$d_6$) δ 8.72 (d, J=15.5 Hz, 1H), 8.01 (d, J=2.8 Hz, 1H), 7.51 (d, J=9.1 Hz, 1H), 7.32-7.25 (m, 1H), 6.86 (d, J=1.4.5 Hz, 1H), 6.66 (dd, J=9.3, 3.2 Hz, 1H), 5.06 (br s, 1H), 4.51-4.42 (m, 1H), 4.19 (dd, J=13.2, 2.0 Hz, 1H), 3.72-3.61 (m, 1H), 3.54-3.39 (m, 2H), 3.15-3.02 (m, 1H), 2.21-2.08 (m, 1H), 2.00-1.78 (m, 3H), 1.75-1.60 (m, 1H), 1.47-1.37 (m, 2H), 1.20-1.08 (m, 2H), 0.84-0.76 (m, 2H), 0.61-0.52 (m, 2H); MS(ES+) m/z 478.2 (M+1).

Example 495

Synthesis of (R)-5-cyclopropyl-N-(cyclopropylsulfonyl)-4-((1-(2-(3,5-dichlorophenyl)propan-2-yl)oxy)-2-fluorobenzamide, trifluoroacetic acid salt

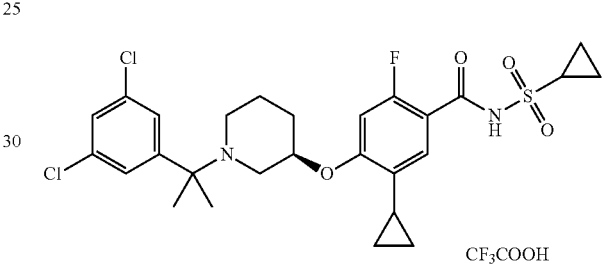

Step 1. Preparation of (R)-methyl 5-cyclopropyl-4-((1-(2-(3,5-dichlorophenyl)propan-2-yl)piperidin-3-yl)oxy)-2-fluorobenzoate

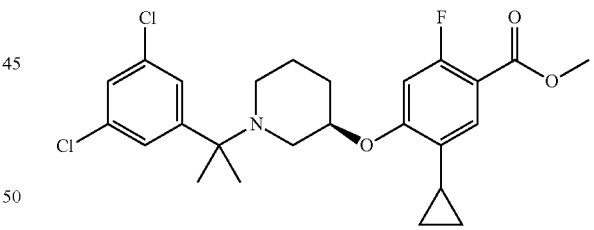

To a mixture of (R)-methyl 5-cyclopropyl-2-fluoro-4-(piperidin-3-yloxy)benzoate (1.00 g, 3.41 mmol) in anhydrous tetrahydrofuran (20 mL) was added 4-dimethylaminopyridine (0.08 g, 0.68 mmol), triethylamine (0.95 mL, 6.82 mmol) and 3,5-dichlorobenzyl chloride (0.86 g, 4.11 mmol). After stirring at ambient temperature for 16 hours, the reaction mixture was diluted with ethyl acetate (200 mL), washed with aqueous hydrochloric acid solution (1 N, 1.0 mL), water (10 mL), brine (10 mL), and dried over anhydrous sodium sulfate. Filtration and concentration of the filtrate in vacuo gave a residue which was purified by flash chromatography (0-100% ethyl acetate in hexanes) to provide (R)-methyl 5-cyclopropyl-4-((1-(3,5-dichlorobenzoyl)piperidin-3-yl)oxy)-2-fluorobenzoate as yellowish oil (1.31 g, 82%).

To a mixture of (R)-methyl 5-cyclopropyl-4-((1-(3,5-dichlorobenzoyl)piperidin-3-yl)oxy)-2-fluorobenzoate (1.31 g, 2.81 mmol) and 2,6-di-tert-butyl-4-methylpyridine (0.69 g, 3.37 mmol) in anhydrous dichloromethane (40 mL) was added trifluoromethanesulfonic anhydride (0.57 ml, 3.37 mmol) at −78° C. The reaction mixture was stirred for 2 hours at −78° C., after which methyl lithium (1.6 M solution in diethyl ether, 8.8 mL 14.10 mmol) was added to it. After stirring for 1 hour at −78° C., the reaction mixture was warmed to −60° C., and stirred for additional 2 hours. After addition of saturated ammonium chloride solution (20 mL) and dichloromethane (200 mL), the mixture was allowed to warm to ambient temperature. The organic phase was washed with aqueous hydrochloric acid solution (1 N, 10 mL), water (10 mL), brine (10 mL), and dried over anhydrous sodium sulfate. Filtration and concentration, of the filtrate in vacuo gave a residue which was purified by flash chromatography (0-30% ethyl acetate in hexanes) to provide the title compound as a colorless oil (0.23 g, 17%): $^1$H NMR (300 MHz, CDCl$_3$) δ7.42-7.37 (m, 3H), 7.19 (t, J=1.9, 1.9 Hz, 1H), 6.42 (d, J=12.9 Hz, 1H), 4.37-4.28 (m, 1H), 3.85 (s, 3H), 2.93-2.85 (m, 1H), 2.67-2.58 (m, 1H), 2.39-2.21 (m, 2H), 2.09-1.97 (m, 2H), 1.86-1.74 (m, 1H), 1.64-1.48 (m, 2H), 1.29 (s, 3H), 1.27 (s, 3H), 0.94-0.82 (m, 2H), 0.66-0.59 (m, 2H); MS(ES+) m/z 480.2, 482.2 (M+1).

Step 2. Preparation of (R)-5-cyclopropyl-4-((1-(2-(3,5-dichlorophenyl)propan-2-yl)piperidin-3-yl)oxy)-2-fluorobenzoic acid

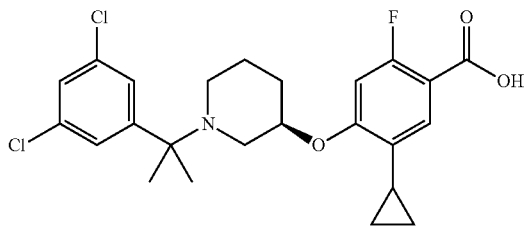 [SMILES: CC(C)(c1cc(Cl)cc(Cl)c1)N1CCC[C@@H](Oc2cc(F)c(C(=O)O)cc2C2CC2)C1]

Following the procedure as described in Example 481 Step 5 and making variation as required to replace methyl 4-((1-(3-chloro-5-(trifluoromethyl)pyridin-2-yl)-3-methylazetidin-3-yl)methoxy)-5-cyclopropyl-2-fluorobenzoate with (R)-methyl 5-cyclopropyl-4-((1-(2-(3,5-dichlorophenyl)propan-2-yl)piperidin-3-yl)oxy)-2-fluorobenzoate, the title compound was obtained as a yellowish oil (0.23 g, quant. yield): MS(ES−) m/z 466.2, 468.2 (M−1).

Step 3. Preparation of (R)-5-cyclopropyl-N-(cyclopropylsulfonyl)-4-((1-(2-(3,5-dichlorophenyl)propan-2-yl)piperidin-3-yl)oxy)-2-fluorobenzamide, trifluoroacetic acid salt

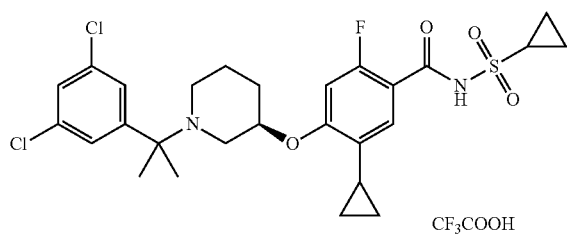 [SMILES: CC(C)(c1cc(Cl)cc(Cl)c1)N1CCC[C@@H](Oc2cc(F)c(C(=O)NS(=O)(=O)C3CC3)cc2C2CC2)C1 ; "CF3COOH"]

Following the procedure as described in Example 473 Step 5, and making variation as required to replace 4-((4-((5-bromo-3-chloropyridin-2-yl)oxy)piperidin-1-yl)methyl)-5-cyclopropyl-2-fluorobenzoic acid hydrochloride with (R)-5-cyclopropyl-4-((1-(2-(3,5-dichlorophenyl)propan-2-yl)piperidin-3-yl)oxy)-2-fluorobenzoic acid, the title compound was as a colorless solid (0.19 g, 67%); $^1$H NMR (300 MHz, CDCl$_3$) δ 8.74 (d, J=13.3 Hz, 1H), 7.55 (d, J=1.7 Hz, 2H), 7.53 (d, J=9.0 Hz, 1H), 7.45 (t, J=1.7 Hz, 1H), 6.92 (d, J=14.1 Hz, 1H), 5.15-5.04 (m, 1H), 3.75-3.65 (m, 1H), 3.43-3.35 (m, 1H), 3.11-3.01 (m, 1H), 2.67-2.50 (m, 2H), 2.39-1.89 (m, 4H), 1.89 (s, 3H), 1.86 (s, 3H), 1.60-1.48 (m, 1H), 1.47-1.38 (m, 2H), 1.16-1.08 (m, 2H), 0.93-0.84 (m, 2H), 0.65-0.58 (m, 2H); MS(ES−) m/z 567.2, 569.2 (M−1)

Example 496

Synthesis of 4-(((1R,3r,5S)-3-(3-chloro-5-(trifluoromethoxy)phenoxy)-8-azabicyclo[3.2.1]octan-8-yl)methyl)-5-cyclopropyl-N-(cyclopropylsulfonyl)-2-fluorobenzamide, trifluoroacetic acid salt

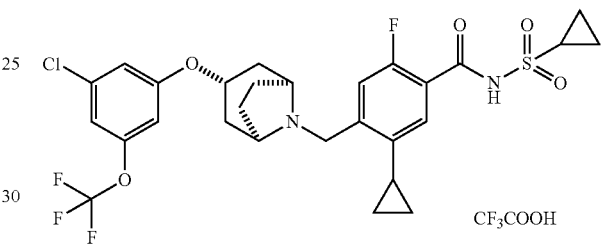

Step 1. Preparation of (1R,3r,5S)-tert-butyl 3-(3-chloro-5-(trifluoromethoxy)phenoxy)-8-azabicyclo[3.2.1]octane-8-carboxylate

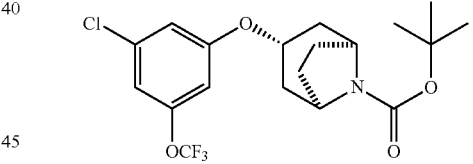

Following the procedure as described in Example 470 step 2, and making variation as required to replace 3-chloro-2-fluoro-5-(trifluoromethyl)phenol with 3-chloro-5-(trifluoromethoxy)-phenol, the title compound was obtained as a colorless oil (2.0 g, quant. yield): $^1$H NMR (300 MHz, CDCl$_3$) δ6.82-6.79 (m, 1H), 6.75-6.72 (m, 1H), 6.57-6.53 (m, 1H), 4.60-4.54 (m, 1H), 4.23-4.17 (m, 2H), 2.19-1.87 (m, 8H), 1.46 (s, 9H); MS(ES+) m/z 366.0, 368.0 (M−55).

Step 2. Preparation of (1R,3r,5S)-3-(3-chloro-5-(trifluoromethoxy)phenoxy)-8-azabicyclo[3.2.1]octane

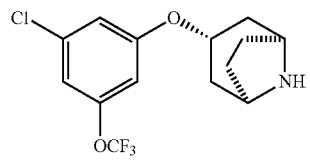 [SMILES: FC(F)(F)Oc1cc(Cl)cc(O[C@H]2C[C@H]3CC[C@@H](C2)N3)c1]

Following the procedure as described in Example 470 step 3, and making variation as required to replace (1R3r,5S)-tert-butyl 3-(3-chloro-2-fluoro-5-(trifluoromethyl)phenoxy)-8-azabicyclo[3.2.1]octane-8-carboxylate with (1R,3r,5S)-tert-butyl 3-(3-chloro-5-(trifluoromethoxy)phenoxy)-8-azabicyclo[3.2.1]octane-8-carboxylate, the title compound was isolated as a colorless oil (1.50 g, quant. yield): MS(ES+) m/z 322.1, 324.1 (M+1).

Step 3. Preparation of tert-butyl 4-(((1R,3r,5S)-3-(3-chloro-5-(trifluoromethoxy)phenoxy)-8-azabicyclo[3.2.1]octan-8-yl)methyl)-5-cyclopropyl-2-fluorobenzoate

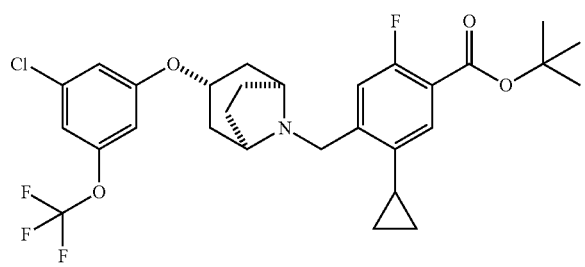 [SMILES: CC(C)(C)OC(=O)c1cc(C2CC2)c(CN2[C@@H]3CC[C@H]2C[C@@H](Oc2cc(Cl)cc(OC(F)(F)F)c2)C3)cc1F]

Following the procedure as described in Example 470 Step 4, and making variation as required to replace (1R,3r,5S)-3-(3-chloro-2-fluoro-5-(trifluoromethyl)phenoxy)-8-azabicyclo[3.2.1]-octane with (1R,3r,5S)-3-(3-chloro-5-(trifluoromethoxy)phenoxy)-8-azabicyclo[3.2.1]octane, the title compound was isolated as a colorless oil (1.75 g, 65%); $^1$H NMR (300 MHz, CDCl$_3$) δ7.48 (d, J=7.1 Hz, 1H), 7.36-7.28 (m, 1H), 6.81-6.77 (m 1H), 6.74 (t, J=2.0 Hz, 1H), 6.58-6.53 (m, 1H), 4.58-4.46 (m, 1H), 3.74-3.58 (m 2H), 3.23-3.05 (m, 2H), 2.23-1.83 (m, 9H), 1.57 (s, 9H), 0.95-0.83 (m, 2H), 0.65-0.57 (m, 2H); MS(ES+) m/z 570.1, 572.1 (M+1).

Step 4. Preparation of 4-(((1R,3r,5S)-3-(3-chloro-5-(trifluoromethoxy)phenoxy)-8-azabicyclo[3.2.1]octan-8-yl)methyl)-5-cyclopropyl-2-fluorobenzoic acid hydrochloride

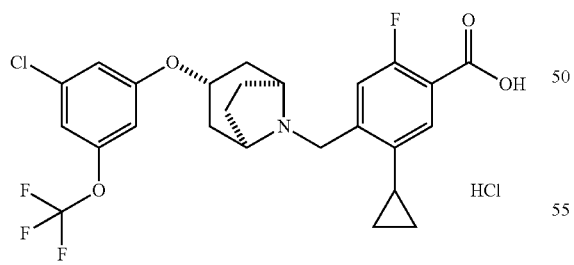

Following the procedure as described in Example 470 Step 5, and making variation as required to replace tert-butyl 4-(((1R,3r,5S)-3-(3-chloro-2-fluoro-5-(trifluoromethyl)-phenoxy)-8-azabicyclo[3.2.1]octan-8-yl)methyl)-5-cyclopropyl-2-fluorobenzoate with tert-butyl 4-(((1R,3r,5S)-3-(3-chloro-5-(trifluoromethoxy)phenoxy)-8-azabicyclo[3.2.1]octan-8-yl)methyl)-5-cyclopropyl-2-fluorobenzoate, the title compound was isolated as a colorless solid (1.64 g, 96%): MS(ES+) m/z 516.1, 518.1 (M+1).

Step 5. Preparation of 4-(((1R,3r,5S)-3-(3-chloro-5-(trifluoromethoxy)phenoxy)-8-azabicyclo[3.2.1]octan-8-yl)methyl)-5-cyclopropyl-N-(cyclopropylsulfonyl)-2-fluorobenzamide, trifluoroacetic acid salt

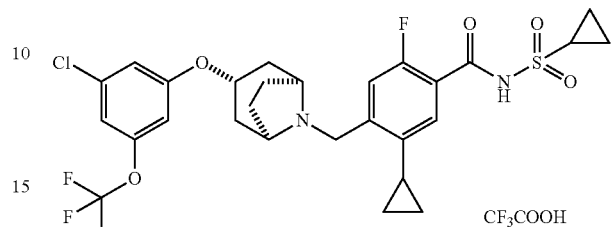

Following the procedure as described in Example 473 step 5, and snaking variation as required to replace 4-((4-((5-bromo-3-chloropyridin-2-yl)oxy)piperidin-1-yl) methyl)-5-cyclopropyl-2-fluorobenzoic acid hydrochloride with (of 4-(((1R,3r,5S)-3-(3-chloro-5-(trifluoromethoxy) phenoxy)-8-azabicyclo[3.2.1]octan-8-yl)methyl)-5-cyclopropyl-2-fluorobenzoic acid hydrochloride, the title compound was as a colorless solid (0.45 g, 62%): $^1$H NMR (300 MHz, CDCl$_3$10% CD$_3$OD) δ7.47 (d, J=7.3 Hz, 1H), 7.41 (d, J=11.2 Hz, 1H), 6.79 (brs, 1H), 6.74-6.71 (m, 1H), 6.53 (brs, 1H), 4.62-4.55 (m, 1H), 4.37 (s, 2H), 3.88 (br s, 2H), 3.04-2.93 (m, 1H), 2.75-2.62 (m, 2H), 2.49-2.38 (m, 2H), 2.33-2.22 (m, 2H), 2.12 (d, J=15.6 Hz, 2H), 1.85-1.74 (m, 1H), 1.37-1.28 (m, 2H), 1.11-0.94 (m, 4H), 0.71-0.62 (m, 2H); MS(ES+) m/z: 617.1, 619.1 (M+1).

Example 497

Synthesis of 5-cyclopropyl-2-fluoro-N-(methylsulfonyl)-4-((4-(2-(trifluoromethyl)phenoxy)piperidin-1-yl)methyl)benzamide

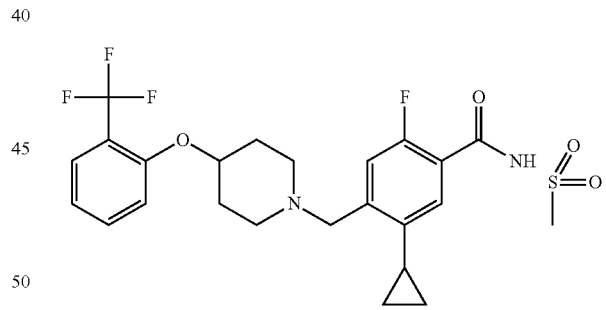

Step 1. Preparation of tert-butyl 5-cyclopropyl-2-fluoro-4-((4-(2-(trifluoromethyl)phenoxy)piperidin-1-yl)methyl)benzoate

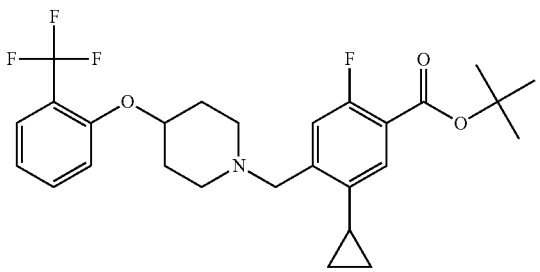

Following the procedure as described in Example 53 step 3, and making variation as required to replace (S)-3-(3,5-dichlorophenoxy)piperidine, trifluoroacetic acid salt with 4-(2-(trifluoromethyl)phenoxy)piperidine, hydrochloride salt, the title compound was obtained as an oil (1.38 g, 66%): ¹H NMR (300 MHz, CDCl₃) δ7.55 (d, J=8.3 Hz, 1H), 7.50-7.39 (m, 2H), 7.20 (d, J=12.1 Hz, 1H), 6.99-6.90 (m, 2H), 4.58-4.47 (m, 1H), 3.64 (s, 2H), 2.74-2.62 (m, 2H), 2.50-2.35 (m, 2H), 2.03-1.83 (m, 5H), 1.56 (s, 9H), 0.96-0.86 (m, 2H), 0.64-0.56 (m, 2H); MS(ES+) m/z 494.3 (M+1).

Step 2. Preparation of 5-cyclopropyl-2-fluoro-4-((4-(2-(trifluoromethyl)phenoxy)piperidin-1-yl)methyl) benzoic acid, trifluoroacetic acid salt

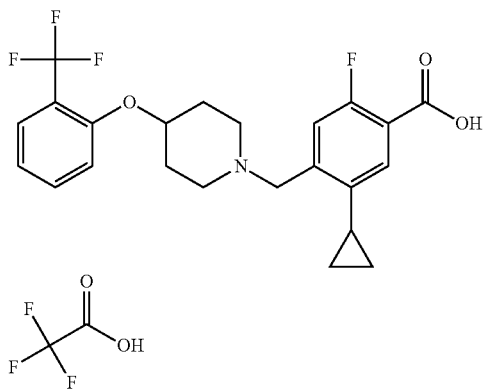

Following the procedure as described in Example 53 step 4, and making variation as required to replace (S)-tert-butyl 5-cyclopropyl-4-((3-(3,5-dichlorophenoxy)piperidin-1-yl)methyl)-2-fluorobenzoate with tert-butyl 5-cyclopropyl-2-fluoro-4-((4-(2-(trifluoromethyl)phenoxy)piperidin-1-yl)methyl)benzoate, the title compound was obtained as an colorless solid (1.54 g, quant. yield): MS(ES+) m/z 438.1 (M+1).

Step 3. Preparation of 5-cyclopropyl-2-fluoro-N-(methylsulfonyl)-4-((4-(2-(trifluoromethyl)phenoxy)piperidin-1-yl)methyl)benzamide

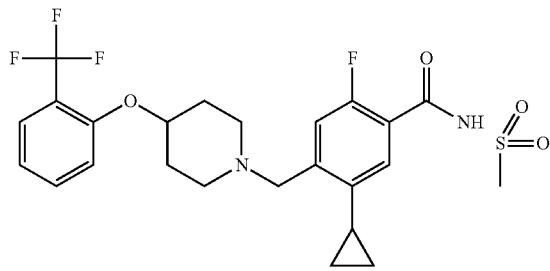

Following the procedure as described in Example 53 step 5, and making variation as required to replace cyclopropanesulfonamide with methylsulfonamide and to replace (S)-5-cyclopropyl-4-((3-(3,5-dichlorophenoxy)piperidin-1-yl)methyl)-2-fluorobenzoic acid with 5-cyclopropyl-2-fluoro-4-((4-(2-(trifluoromethyl)phenoxy)piperidin-1-yl)methyl)benzoic acid, trifluoroacetic acid salt, and purification by flash chromatography (0-75% methanol+ 0.4% ammonium hydroxide in dichloromethane), the title compound was obtained as a colorless solid (0.20 g, 53%); ¹H NMR (300 MHz, CDCl₃) δ7.69 (d, J=7.6 Hz, 1H), 7.57 (d, J=7.7 Hz, 1H), 7.51-7.37 (m, 2H), 7.04-6.93 (m, 2H), 6.50 (br s, 1H), 4.77-4.68 (m, 1H), 4.09 (s, 2H), 3.29 (s, 3H), 3.04-2.89 (m, 4H), 2.36-2.22 (m, 2H), 2.12-2.00 (m, 2H), 1.94-1.82 (m, 1H) 1.05-0.97 (m, 2H), 0.70-0.63 (m, 2H); MS(ES+) m/z 515.2 (M+1).

Example 498

Synthesis of 5-cyclopropyl-N-(cyclopropylsulfonyl)-2-fluoro-4-((4-(2-(trifluoromethyl)phenoxy)piperidin-1-yl)methyl)benzamide

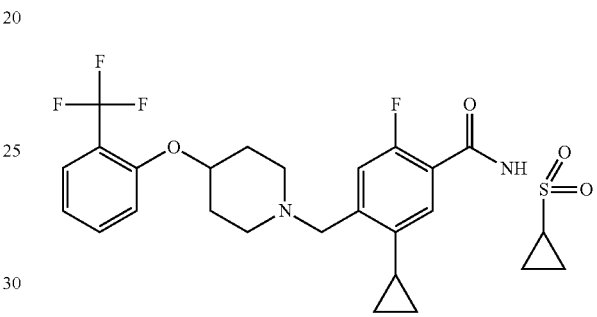

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-2-fluoro-4-((4-(2-(trifluoromethyl)phenoxy)piperidin-1-yl)methyl)benzoic acid, trifluoroacetic acid salt the title compound was obtained as a colorless solid (0.22 g, 50%): ¹M NMR (300 MHz, CDCl₃) δ 7.70 (d, J=7.7 Hz, 1H), 7.56 (d, J=7.7 Hz, 1H), 7.50-7.37 (m, 2H), 7.02-6.92 (m, 2H), 6.57 (br s, 1H), 4.73-4.62 (m, 1H), 3.99 (s, 2H), 3.08-2.97 (m, 1H), 2.95-2.76 (m, 4H), 2.27-2.12 (m, 2H), 2.08-1.96 (m, 2H), 1.95-1.84 (m, 1H), 1.45-1.36 (m, 2H), 1.16-1.05 (m, 2H), 1.04-0.94 (m, 2H), 0.70-0.61 (m, 2H); MS(ES+) m/z 541.2 (M+1).

Example 499

Synthesis of 5-cyclopropyl-2-fluoro-N-(methylsulfonyl)-4-((4-(4-(trifluoromethyl)phenoxy)piperidin-1-yl)methyl)benzamide

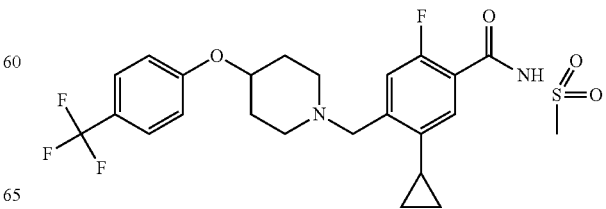

Step 1. Preparation of tert-butyl 5-cyclopropyl-2-fluoro-4-((4-(4-trifluoromethyl)phenoxy)piperidin-1-yl)methyl)benzoate

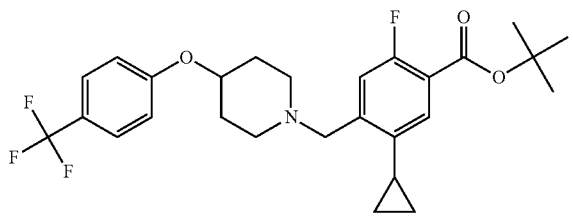 [SMILES: CC(C)(C)OC(=O)c1cc(C2CC2)c(CN2CCC(Oc3ccc(C(F)(F)F)cc3)CC2)cc1F]

Following the procedure as described in Example 53 step 3, and making variation as required to replace (S)-3-(3,5-dichlorophenoxy)piperidine, trifluoroacetic acid salt with 4-(4-(trifluoromethyl)phenoxy)piperidine, hydrochloride salt, the title compound was obtained as an oil (1.24 g, 60%): $^1$H NMR (300 MHz, CDCl$_3$) δ7.54-7.45 (m, 3H), 7.18 (d, J=11.8 Hz, 1H), 6.94 (d, J=9.1 Hz, 2H), 4.46-4.34 (m, 1H), 3.65 (s, 2H), 2.79-2.67 (m, 1H), 2.44-2.27 (m, 2H), 2.07-1.90 (m, 3H), 1.89-1.75 (m, 2H), 1.56 (s, 9H), 0.95-0.87 (m, 2H), 0.65-0.57 (m, 2H); MS(ES+) m/z 494.1 (M+1).

Step 2. Preparation of 5-cyclopropyl-2-fluoro-4-((4-(4-(trifluoromethyl)phenoxy)piperidin-1-yl)methyl) benzoic acid, 2trifluoroacetic acid salt

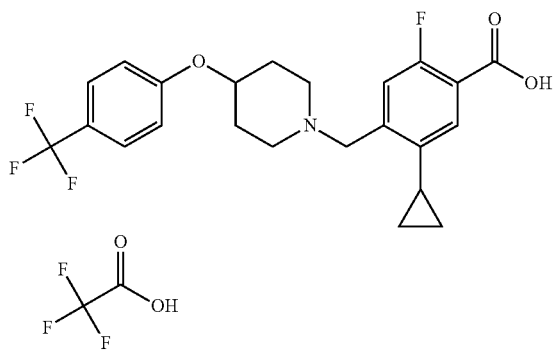

Following the procedure as described in Example 53 step 4, and making variation as required to replace (S)-tert-butyl 5-cyclopropyl-4-((3-(3,5-dichlorophenoxy)piperidin-1-yl) methyl)-2-fluorobenzoate with tert-butyl 5-cyclopropyl-2-fluoro-4-((4-(4-(trifluoromethyl)phenoxy)piperidin-1-yl) methyl)benzoate, the title compound was obtained as an colorless solid (1.38 g, quant. yield): MS(ES+) m/z 438.2 (M+1).

Step 3. Preparation of 5-cyclopropyl-2-fluoro-N-(methylsulfonyl)-4-((4-(4-(trifluoromethyl)phenoxy) piperidin-1-yl)methyl)benzamide

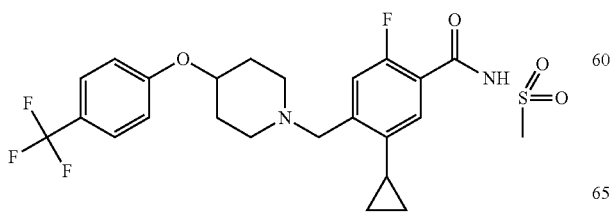

Following the procedure as described in Example 53 step 5, and making variation as required to replace cyclopropanesulfonamide with methylsulfonamide and to replace (S)-5-cyclopropyl-4-((3-(3,5-dichlorophenoxy)piperidin-1-yl)methyl)-2-fluorobenzoic acid with 5-cyclopropyl-2-fluoro-4-((4-(4-(trifluoromethyl)phenoxy)piperidin-1-yl) methyl)benzoic acid, trifluoroacetic acid salt, the title compound was obtained as a colorless solid (0.18 g, 48%): $^1$H NMR (300 MHz, CDCl$_3$) δ7.69 (d, J=7.6 Hz, 1H), 7.52 (4.9-8.6 Hz, 2H), 7.39 (d, J=13.1 Hz, 1H), 6.94 (d, J=8.6 Hz, 2H), 6.22 (br s, 1H), 4.56-4.43 (m, 1H), 3.88 (s, 2H), 3.37 (s, 3H), 2.90-2.79 (m, 2H), 2.72-2.59 (m, 2H), 2.21-2.08 (m, 2H), 1.99-1.86 (m, 3H), 1.03-0.94 (m, 2H), 0.70-0.62 (m, 2H); MS(ES-+) m/z 515.2 (M+1).

Example 500

Synthesis of 5-cyclopropyl-N-(cyclopropylsulfonyl)-2-fluoro-4-((4-(4-(trifluoromethyl)phenoxy) piperidin-1-yl)methyl)benzamide

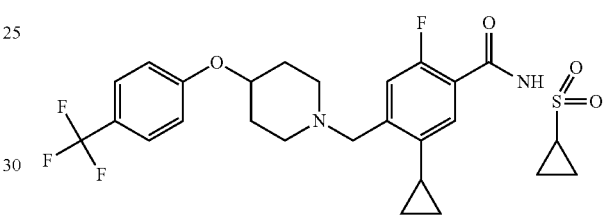

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-2-fluoro-4-((4-(4-(trifluoromethyl)phenoxy)piperidin-1-yl)methyl)benzoic acid, trifluoroacetic acid salt, the title compound was obtained as a colorless solid (0.20 g, 51%); 7.69 (d, J=7.6 Hz, 1H), 7.53 (d, J=8.6 Hz, 2H), 7.46 (d, J=12.5 Hz, 1H), 6.95 (d, J=8.6 Hz, 2H), 4.67-4.55 (m, 1H), 4.17 (s, 2H), 3.16-2.91 (m, 5H), 2.37-2.58 (m, 2H), 2.11-1.97 (m, 2H), 1.96-1.85 (m, 1H), 1.46-1.37 (m, 2H), 1.18-0.99 (m, 4H), 0.74-0.65 (m, 2H); MS(ES+) m/z 541.2 (M+1).

Example 501

Synthesis of 5-cyclopropyl-2-fluoro-N-(methylsulfonyl)-4-((4-(3-(trifluoromethyl)phenoxy)piperidin-1-yl)methyl)benzamide, trifluoroacetic acid salt

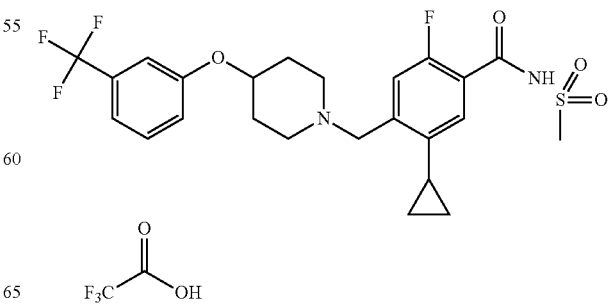

Step 1. Preparation of tert-butyl 5-cyclopropyl-2-fluoro-4-((4-(3-(trifluoromethyl)phenoxy)piperidin-1-yl)methyl)benzoate

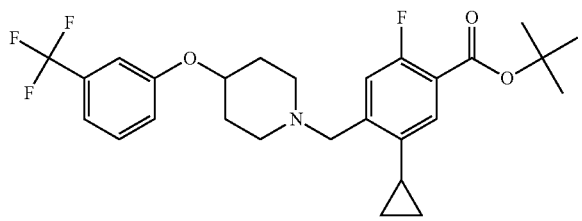 [SMILES: CC(C)(C)OC(=O)c1cc(C2CC2)c(CN2CCC(Oc3cccc(C(F)(F)F)c3)CC2)cc1F]

Following the procedure as described in Example 53 step 3, and making variation as required to replace (S)-3-(3,5-dichlorophenoxy)piperidine, trifluoroacetic acid salt with 4-(3-(trifluoromethyl)phenoxy)piperidine, the title compound was obtained as an oil (0.69 g, 79%); $^1$H NMR (300 MHz, CDCl$_3$) δ7.48 (d, J=7.3 Hz, 1H), 7.35 (dd, J=8.0, 8.0 Hz, 1H), 7.22-7.09 (m, 3H), 7.07-7.02 (m, 1H), 4.43-4.34 (m, 1H), 3.67 (s, 2H), 2.79-2.68 (m, 2H), 2.43-2.32 (m, 2H), 2.05-1.92 (m, 3H), 1.89-1.76 (m, 2H), 1.56 (s, 9H), 0.95-0.88 (m, 2H), 0.65-0.58 (m, 2H); MS(ES+) m/z 494.3 (M+1).

Step 2. Preparation of 5-cyclopropyl-2-fluoro-4-((4-(3-(trifluoromethyl)phenoxy)pyridin-1-yl)methyl)benzoic acid, trifluoroacetic acid salt

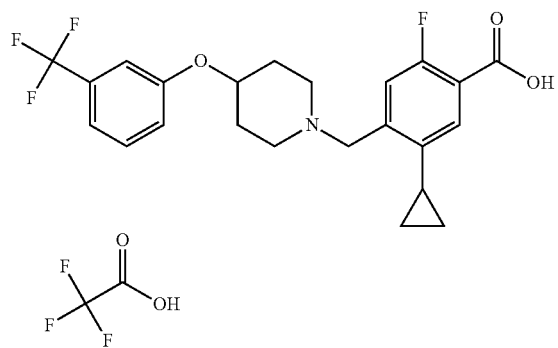

Following the procedure as described in Example 53 step 4, and making variation as required to replace (S)-tert-butyl 5-cyclopropyl-4-((3-(3,5-dichlorophenoxy)pyridin-1-yl)methyl)-2-fluorobenzoate of tert-butyl 5-cyclopropyl-2-fluoro-4-((4-(3-(trifluoromethyl)phenoxy)pyridin-1-yl)methyl)benzoate, the title compound was obtained as an colorless solid (0.77 g, quant. yield): MS(ES+) m/z 438.2 (M+1).

Step 3. Preparation of 5-cyclopropyl-2-fluoro-N-(methylsulfonyl)-4-((4-(3-(trifluoromethyl)phenoxy)pyridin-1-yl)methyl)benzamide, trifluoroacetic acid salt

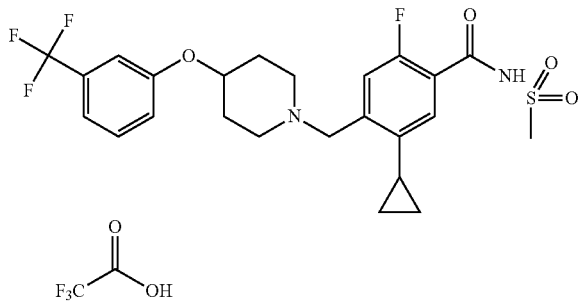

Following the procedure as described in Example 53 step 5, and making variations as required to replace cyclopropanesulfonamide with methylsulfonamide and to replace (S)-5-cyclopropyl-4-((3-(3,5-dichlorophenoxy)pyridin-1-yl)methyl)-2-fluorobenzoic acid with 5-cyclopropyl-2-fluoro-4-((4-(3-(trifluoromethyl)phenoxy)pyridin-1-yl) methyl)benzoic acid trifluoroacetic acid salt and purification by preparative HPLC, the title compound was obtained as a colorless solid (0.06 g, 14%): $^1$H NMR (300 MHz, DMSO-d$_6$) δ12.24 (br s, 1H), 9.49 (br s, 1H), 7.65-7.45 (m, 2H), 7.34-7.22 (m, 4H), 4.92-4.74 (m, 1H), 4.52 (br s, 2H), 3.78-3.49 (m, 2H), 3.33 (s, 3H), 3.27-3.15 (m, 2H), 2.25-1.95 (m, 5H), 1.03-0.95 (m, 2H), 0.81-0.73 (m, 2H); MS(ES+) m/z 515.0 (M+1).

Example 502

Synthesis of 5-cyclopropyl-N-(cyclopropylsulfonyl)-2-fluoro-4-((4-(3-(trifluoromethyl)phenoxy)pyridin-1-yl)methyl)benzamide, trifluoroacetic acid salt

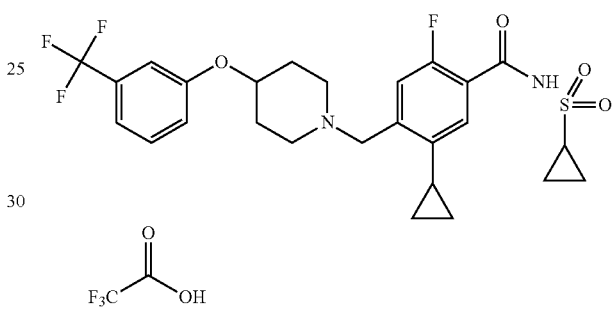

Following the procedure as described in Example 53 step 5, and making variation as required to replace (S)-5-cyclopropyl-4-((3-(3,5-dichlorophenoxy)pyridin-1-yl)methyl)-2-fluorobenzoic acid with 5-cyclopropyl-2-fluoro-4-((4-(3-(trifluoromethyl)phenoxy)pyridin-1-yl)methyl)benzoic acid trifluoroacetic acid salt and purification by preparative HPLC, the title compound was obtained as a colorless solid (0.10 g, 22%): $^1$H NMR (300 MHz, CDCl$_3$) δ 12.78 (br s, 1H), 9.24 (br s, 1H), 7.76 (d, J=7.6 Hz, 1H), 7.63 (d, J=11.9 Hz, 1H), 7.46-7.38 (m, 1H), 7.28-7.21 (m, 1H), 7.14-7.10 (m, 1H), 7.07-7.02 (m, 1H), 4.78-4.69 (m, 1H), 4.49 (s, 2H), 3.55-3.42 (m, 2H), 3.25-3.11 (m, 2H), 3.11-3.00 (m, 1H), 2.56-2.38 (m, 2H), 2.23-2.10 (m, 2H), 1.97-1.86 (m, 1H), 1.48-1.40 (m, 2H), 1.19-1.07 (m, 4H), 0.80-0.72 (m, 2H); MS(ES+) m/z 541.0 (M+1).

Example 503

Synthesis of 4-((4-(4-chlorophenoxy)pyridin-1-yl)methyl)-5-cyclopropyl-2-fluoro-N-(methylsulfonyl)benzamide, trifluoroacetic acid salt

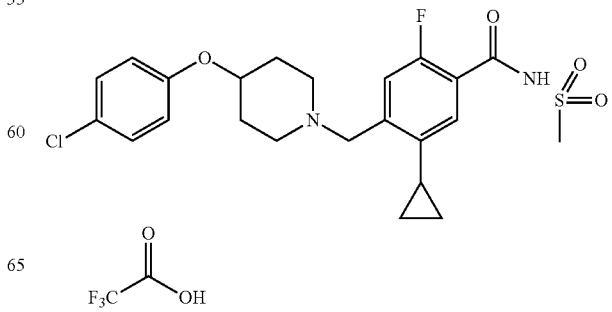

Step 1. Preparation of tert-butyl 4-((4-(4-chlorophenoxy)pyridin-1-yl)methyl)-5-cyclopropyl-2-fluorobenzoate

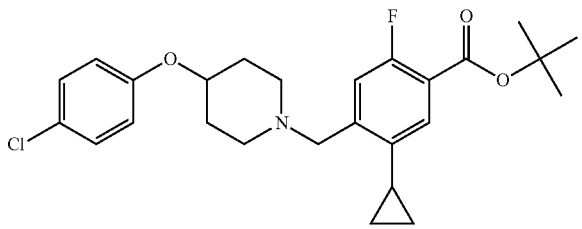 [SMILES: CC(C)(C)OC(=O)c1cc(C2CC2)c(CN2CCC(Oc3ccc(Cl)cc3)CC2)cc1F]

Following the procedure as described in Example 53 step 3, and making variation as required to replace (S)-3-(3,5-dichlorophenoxy)pyridin, trifluoroacetic acid salt with 4-(4-chlorophenoxy)piperidine, the title compound was obtained as an oil (0.85 g, 93%); $^1$H NMR (300 MHz, CDCl$_3$) δ7.48 (d, J=7.4 Hz, 1H), 7.23-7.14 (m, 3H), 6.84-6.78 (m, 2H), 4.33-4.23 (m, 1H), 3.65 (s, 2H), 2.77-2.66 (m, 2H), 2.40-2.28 (m, 2H), 2.03-1.90 (m, 3H), 1.86-1.72 (m, 2H), 1.56 (s, 9H), 0.94-0.87 (m, 2H), 0.64-0.57 (m, 2H); MS(ES+) m/z 460.3, 462.2 (M+1).

Step 2. Preparation of 4-((4-(4-chlorophenoxy)pyridin-1-yl)methyl)-5-cyclopropyl-2-fluorobenzoic acid, trifluoroacetic acid salt

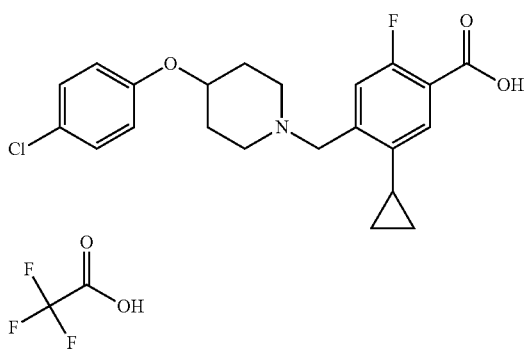

Following the procedure as described in Example 53 step 4, and making variation as required to replace (S)-tert-butyl 5-cyclopropyl-4-((3-(3,5-dichlorophenoxy)pyridin-1-yl)methyl)-2-fluorobenzoate with tert-butyl 4-((4-(4-chlorophenoxy)pyridin-1-ylmethyl)-5-cyclopropyl-2-fluorobenzoate, the title compound was obtained as an colorless solid (0.96 g, quant. yield): MS(ES+) m/z 404.2, 406.2 (M+1).

Step 3. Preparation of 4-((4-(4-chlorophenoxy)pyridin-1-yl)methyl)-5-cyclopropyl-2-fluoro-N-(methylsulfonyl)benzamide, trifluoroacetic acid salt

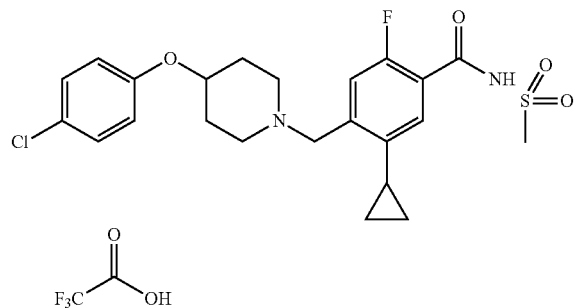

Following the procedure as described in Example 53 step 5, and making variations as required to replace cyclopropanesulfonamide with methylsulfonamide and to replace (S)-5-cyclopropyl-4-((3-(3,5-dichlorophenoxy)pyridin-1-yl)methyl)-2-fluorobenzoic acid with 4-((4-(4-chlorophenoxy)pyridin-1-yl)methyl)-5-cyclopropyl-2-fluorobenzoic acid, trifluoroacetic acid salt, and purification by preparative HPLC, the title compound was obtained as a colorless solid (0.06 g, 11%); $^1$H NMR (300 MHz, CDCl$_3$+10% CD$_3$OD) δ7.35-7.28 (m, 2H), 7.14-7.07 (m, 2H), 6.76-6.69 (m, 2H), 4.51-4.45 (m, 1H), 4.36 (s, 2H), 3.23 (s, 3H), 3.21-3.09 (m, 4H), 2.19-2.07 (m, 2H), 2.05-1.94 (m, 2H), 1.88-1.77 (m, 1H), 1.00-0.92 (m, 2H), 0.64-0.57 (m, 2H); MS(ES+) m/z 481.1, 483.2 (M+1).

Example 504

Synthesis of 4-((4-(4-chlorophenoxy)pyridin-1-yl)methyl-5-cyclopropyl-N-(cyclopropylsulfonyl)-2-fluorobenzamide, trifluoroacetic acid salt

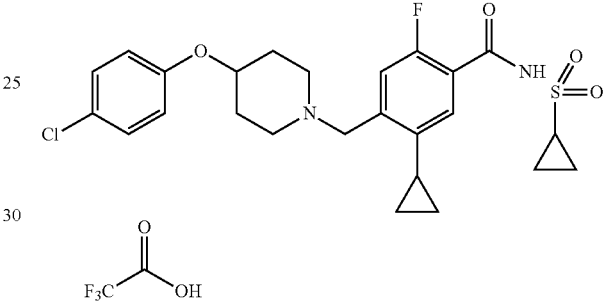

Following the procedure as described in Example 53 step 5, and making variations as required to replace (S)-5-cyclopropyl-4-((3-(3,5-dichlorophenoxy)pyridin-1-yl)methyl)-2-fluorobenzoic acid with 4-((4-(4-chlorophenoxy)pyridin-1-yl)methyl)-5-cyclopropyl-2-fluorobenzoic acid, trifluoroacetic acid salt, and purification by preparative HPLC, the title compound was obtained as a colorless solid (0.07 g, 12%): $^1$H NMR (300 MHz, DMSO-d$_6$) δ12.19 (br s, 1H), 9.49 (br s, 1H), 7.49 (d, J=11.1 Hz, 1H), 7.32 (d, J=8.6 Hz, 2H), 7.23 (d, J=7.0 Hz, 1H), 7.01 (d, J=8.5 Hz, 2H), 4.77-4.35 (m, 3H), 3.71-3.16 (m, 4H), 3.09-2.99 (m, 1H), 2.28-1.93 (m, 4H), 1.86-1.67 (m, 1H), 1.15-1.06 (m, 4H), 1.02-0.94 (m, 2H), 0.79-0.72 (m, 2H); MS(ES+) m/z 507.2, 509.1 (M+1).

Example 505

Synthesis of 4-((4-(2-chloro-4-fluorophenoxy)pyridin-1-yl)methyl)-5-cyclopropyl-2-fluoro-N-(methylsulfonyl)benzamide trifluoroacetic acid salt

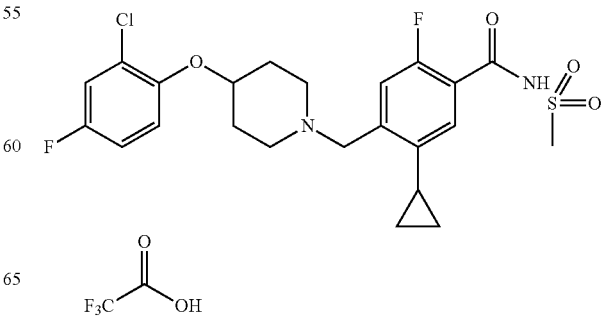

Step 1, Preparation of tert-butyl 4-((4-(2-chloro-4-fluorophenoxy)pyridin-1-yl)methyl)-5-cyclopropyl-2-fluorobenzoate

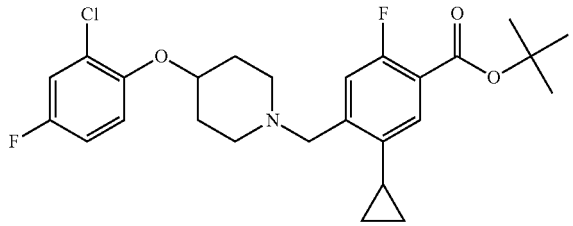 [SMILES: CC(C)(C)OC(=O)c1cc(C2CC2)c(CN2CCC(Oc3ccc(F)cc3Cl)CC2)cc1F]

Following the procedure as described in Example 53 step 3, and making variation as required to replace (S)-3-(3,5-dichlorophenoxy)pyridin, trifluoroacetic acid salt with 4-(2-chloro-4-fluorophenoxy)pyridin, the title compound was obtained as an oil (1.42 g, 68%): $^1$H NMR (300 MHz, CDCl$_3$) δ7.48 (d, J=7.3 Hz, 1H), 7.22-7.15 (m, 1H), 6.98-6.80 (m, 3H), 4.33-4.18 (m, 1H), 3.65 (s, 2H), 2.80-2.68 (m, 2H), 2.41-2.26 (m, 2H), 2.02-1.72 (m, 5H), 1.56 (s, 9H), 0.95-0.87 (m, 2H), 0.65-0.57 (m, 2H); MS(ES+) m/z 478.3, 480.2 (M+1).

Step 2. Preparation of 4-((4-(2-chloro-4-fluorophenoxy)pyridin-1-yl)methyl)-5-cyclopropyl-2-fluorobenzoic acid, trifluoroacetic acid salt

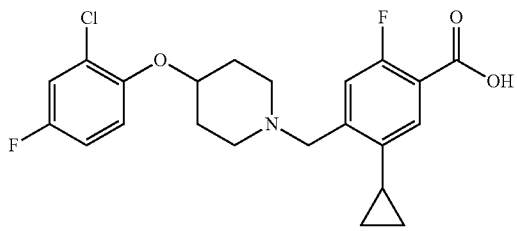

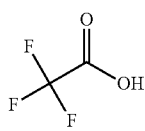

Following the procedure as described in Example 53 step 4, and making variation as required to replace (S)-tert-butyl 5-cyclopropyl-4-((3-(3,5-dichlorophenoxy)pyridin-1-yl)methyl)-2-fluorobenzoate with tert-butyl 4-((4-(2-chloro-4-fluorophenoxy)pyridin-1-yl)methyl)-5-cyclopropyl-2-fluorobenzoate, the title compound was obtained as an colorless solid (1.59 g, quant. yield): MS(ES+) m/z 422.2, 424.1 (M+1).

Step 3. Preparation of 4-((4-(2-chloro-4-fluorophenoxy)pyridin-1-yl)methyl)-5-cyclopropyl-2-fluoro-N-(methylsulfonyl)benzamide, trifluoroacetic acid salt

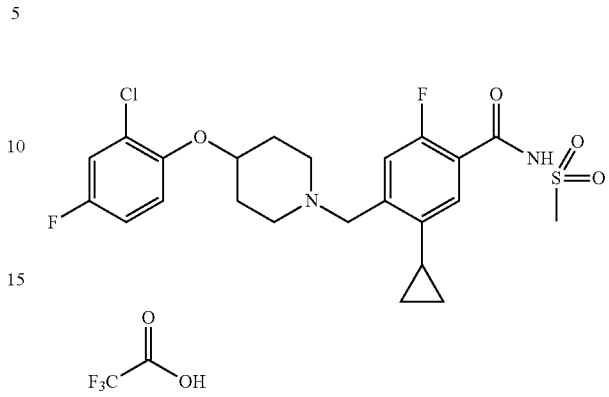

Following the procedure as described in Example 53 step 5, and making variations as required to replace cyclopropanesulfonamide with methylsulfonamide and to replace (S)-5-cyclopropyl-4-((3-(3,5-dichlorophenoxy)-1-yl)methyl)-2-fluorobenzoic acid with -((4-(2-chloro-4-fluorophenoxy)pyridin-1-yl)methyl)-5-cyclopropyl-2-fluorobenzoic acid, trifluoroacetic acid salt and purification by preparative HPLC, the title compound was obtained as a colorless solid (0.10 g, 23%): $^1$H NMR (300 MHz, DMSO-d$_6$) δ12.19 (br s, 1H), 9.81 (br s, 1H), 7.53-7.41 (m, 2H), 7.31-7.23 (m, 2H), 7.21-7.13 (m, 1H), 4.74-4.38 (m, 3H), 3.77-3.44 (m, 2H), 3.32 (s, 3H), 3.29-3.17 (m, 2H), 2.18-2.03 (m, 3H), 2.00-1.80 (m, 2H), 1.02-0.94 (m, 2H), 0.80-0.72 (m, 2H); MS(ES+) m/z 499.2, 501.1 (M+1).

Example 506

Synthesis of 4-((4-(2-chloro-4-fluorophenoxy)pyridin-1-yl)methyl)-5-cyclopropyl-N-(cyclopropylsulfonyl)-2-fluorobenzamide, trifluoroacetic acid salt

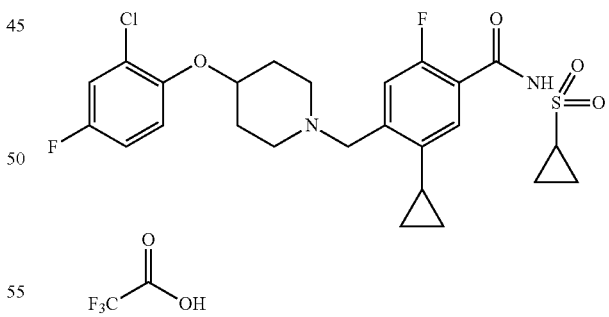

Following the procedure as described in Example 53 step 3, and making variations as required to replace (S)-5-cyclopropyl-4-((3-(3,5-dichlorophenoxy)pyridin-1-yl)methyl)-2-fluorobenzoic acid with 4-((4-(2-chloro-4-fluorophenoxy)pyridin-1-yl)methyl)-5-cyclopropyl-2-fluorobenzoic acid, trifluoroacetic acid salt, and purification by preparative HPLC, the title compound was obtained as a purification by preparative HPLC, the title compound was obtained as a colorless solid (0.13 g, 29%); $^1$H NMR (300 MHz, DMSO-d$_6$) δ12.28 (br s, 1H), 9.92 (br s, 1H), 7.56-

7.49 (m, 1H), 7.44 (dd, J=8.4, 3.1 Hz, 1H), 7.31-7.22 (m, 2H), 7.21-7.13 (m, 1H), 4.76-4.68 (m, 1H), 4.56 (s, 2H), 3.53-3.33 (m, 2H), 3.31-3.15 (m, 2H), 3.11-3.00 (m, 1H), 2.31-1.97 (m, 4H), 1.91-1.77 (m, 1H), 1.15-1.06 (m, 4H), 1.03-0.94 (m, 2H), 0.81-0.73 (m, 2H): MS(ES+) m/z 525.2, 527.2 (M+1).

Example 507

Synthesis of 4-((4-(2-chloro-4-fluorophenoxy)pyridin-1-yl)methyl)-5-cyclopropyl-N-(cyclopropylsulfonyl)-2-fluorobenzamide, trifluoroacetic acid salt

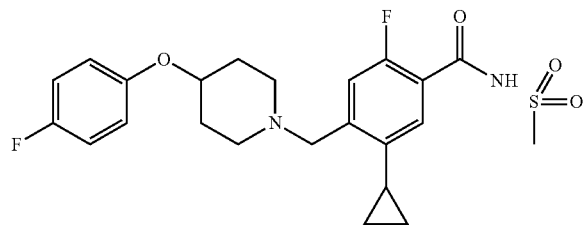

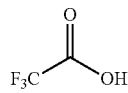

Step 1. Preparation of tert-butyl 5-cyclopropyl-2-fluoro-4-((4-(4-fluorophenoxy)pyridin-1-yl)methyl)benzoate

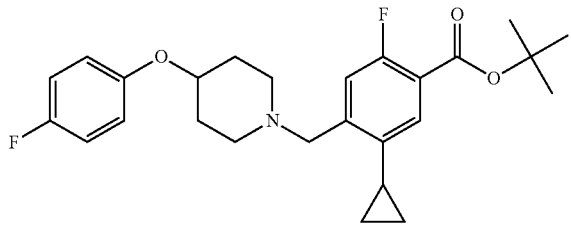

Following the procedure as described in Example 53 step 3, and making variation as required to replace acid (S)-3-(3,5-dichlorophenoxy)pyridin, trifluoroacetic acid salt with 4-(4-fluorophenoxy)pyridin, the title compound was obtained as an oil (1.92 g, quant. yield): ¹H NMR (300 MHz, CDCl₃) δ7.47 (d, J=7.5 Hz, 1H), 7.17 (d, J=11.8 Hz, 1H), 6.97-6.88 (m, 2H), 6.86-6.79 (m, 2H), 4.27-4.17 (m, 1H), 3.63 (s, 2H), 2.77-2.67 (m, 2H), 2.36-2.25 (m, 2H), 2.00-1.89 (m, 3H), 1.1.84-1.71 (m, 2H), 1.55 (s, 9H), 0.94-0.86 (m, 2H), 0.63-0.57 (m, 2H); MS(ES+) m/z 444.2 (M+1).

Step 2. Preparation of 5-cyclopropyl-2-fluoro-4-((4-(4-fluorophenoxy)piperidin-1-yl)methyl)benzoic acid, trifluoroacetic acid salt

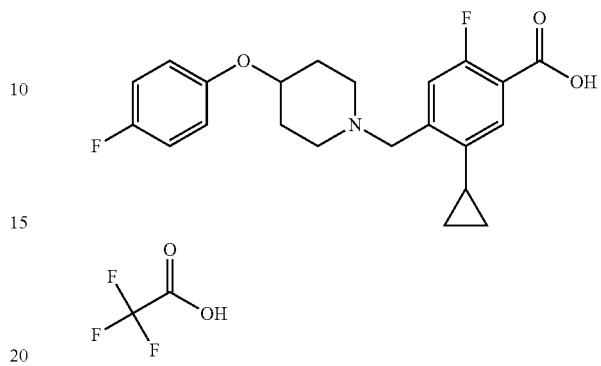

Following the procedure as described in Example 53 step 4, and making variation as required to replace (S)-tert-butyl 5-cyclopropyl-4-((3-(3,5-dichlorophenoxy)piperidin-1-yl)methyl)-2-fluorobenzoate with tert-butyl 5-cyclopropyl-2-fluoro-4-((4-(4-fluorophenoxy)piperidin-1-yl)methyl)benzoate, the title compound was obtained as an colorless solid (2.43 g, quant. yield): MS(ES+) m/z 388.2 (M+1).

Step 3. Preparation of 4-((4-(2-chloro-4-fluorophenoxy)piperidin-1-yl)methyl)-5-cyclopropyl-N-(cyclopropylsulfonyl)-2-fluorobenzamide, trifluoroacetic acid salt

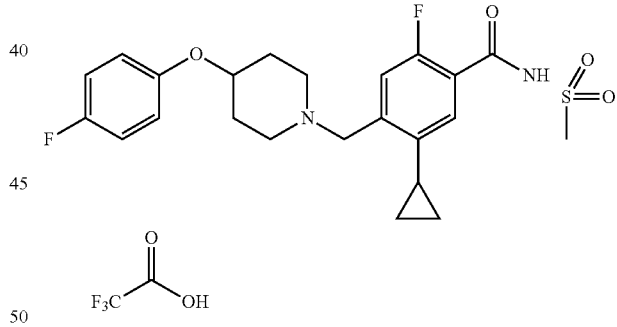

Following the procedure as described in Example 53 step 5, and making variations as required to replace cyclopropanesulfonamide with methylsulfonamide and to replace (S)-5-cyclopropyl-4-((3-(3,5-dichlorophenoxy)piperidin-1-yl)methyl)-2-fluorobenzoic acid with 5-cyclopropyl-2-fluoro-4-((4-(4-fluorophenoxy)piperidin-1-yl)methyl)benzoic acid, trifluoroacetic acid salt, and purification by preparative HPLC the title compound was obtained as a colorless solid (0.05 g, 12%): ¹H NMR (300 MHz, DMSO-d₆) δ12.28 (br s, 1H), 9.68 (br s, 1H), 7.51 (d, J=11.2 Hz, 1H), 7.25 (d, J=6.9 Hz, 1H), 7.16-7.06 (m, 2H), 7.95-6.94 (m, 2H), 4.71-4.41 (m, 3H), 4.21-3.72 (m, 4H), 3.33 (s, 3H), 2.26-2.09 (m, 2H), 2.07-1.93 (m, 2H), 1.86-1.70 (m, 1H), 1.04-0.95 (m, 2H), 0.81-0.73 (m, 2H); MS(ES+) m/z 465.2 (M+1).

Example 508

Synthesis of 5-cyclopropyl-N-(cyclopropylsulfonyl)-2-fluoro-4-((4-(4-fluorophenoxy)piperidin-1-yl)methyl)benzamide, trifluoroacetic acid salt

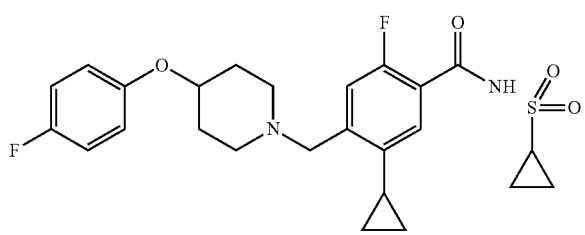

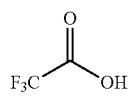

Following the procedure as described in Example 53 step 5, and making variations as required replace (S)-5-cyclopropyl-4-((3-(3,5-dichlorophenoxy)piperidin-1-yl)methyl)-2-fluorobenzoic acid with 5-cyclopropyl-2-fluoro-4-((4-(4-fluorophenoxy)piperidin-1-yl)methyl)benzoic acid, trifluoroacetic acid salt and purification by preparative HPLC, the title compound was obtained as a colorless solid (0.06 g, 14%): $^1$H NMR (300 MHz, DMSO-$d_6$) δ12.26 (brs, 1H), 9.86 (br s, 1H), 7.52 (d, J=11.1 Hz, 1H), 7.23 (d, J=7.2 Hz, 1H), 7.16-7.06 (m, 2H), 7.05-6.95 (m, 2H), 4.73-4.70 (m, 3H), 4.13-3.70 (m, 2H), 3.50-3.31 (m, 2H), 3.11-3.00 (m, 1H), 2.27-1.93 (m, 4H), 1.88-1.70 (m, 1H), 1.15-1.06 (m, 4H), 1.03-0.94 (m, 2H), 0.80-0.72 (m, 2H); MS(ES+) m/z 491.2 (M+1).

Example 509

Synthesis of 5-cyclopropyl-4-((4-(3,4-dichlorophenoxy)piperidin-1-yl)methyl)-2-fluoro-N-(methylsulfonyl)benzamide, trifluoroacetic acid salt)

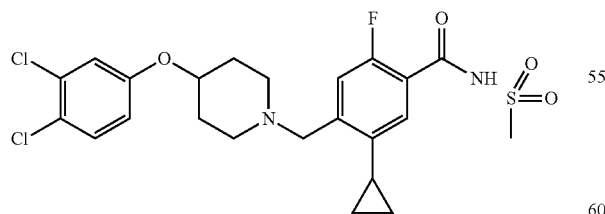

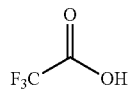

Step 1. Preparation of tert-butyl 5-cyclopropyl-4-((4-(3,4-dichlorophenoxy)piperidin-1-yl)methyl)-2-fluorobenzoate

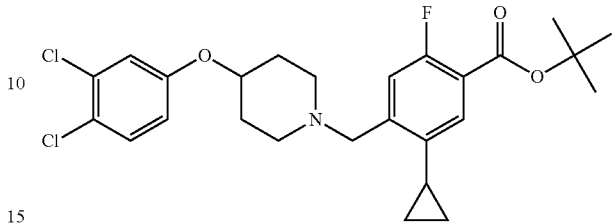

Following the procedure as described in Example 53 step 3, and making variation as required to replace (S)-3-(3,5-dichlorophenoxy)piperidin, trifluoroacetic and salt with 4-(3,4-dichlorophenoxy)piperidin, the title compound was obtained as an oil (1.75 g, quant.): $^1$H NMR (300 MHz, CDCl$_3$) δ7.47 (d, J=7.2 Hz, 1H), 7.26 (d, J=8.9 Hz, 1H), 7.15 (d, J=11.8 Hz, 1H), 6.97 (d, J=2.7 Hz, 1H), 6.72 (dd, J=8.9, 2.8 Hz, 1H), 4.32-4.21 (m, 1H), 3.63 (s, 2H), 2.74-2.64 (m, 2H), 2.38-2.27 (m, 2H), 2.00-1.88 (m, 3H), 1.84-1.71 (m, 2H), 1.55 (s, 9H), 0.94-0.85 (m, 2H), 0.64-0.56 (m, 2H); MS(ES+) m/z 494.1, 496.1 (M+1).

Step 2. Preparation of 5-cyclopropyl-4-((4-(3,4-dichlorophenoxy)piperidin-1-yl)methyl)-2-fluorobenzoic acid, trifluoroacetic acid salt

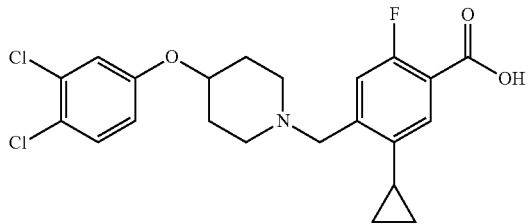

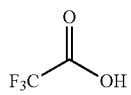

Following the procedure as described in Example 53 step 4, and making variation as required to replace (S)-tert-butyl 5-cyclopropyl-4-((3-(3,5-dichlorophenoxy)piperidin-1-yl)methyl)-2-fluorobenzoate with tert-butyl 5-cyclopropyl-4-((4-(3,4-dichlorophenoxy)piperidin-1-yl)methyl)-2-fluorobenzoate and purification by trituration with diethyl ether, the title compound was obtained as an colorless solid (1.54 g, 69%): MS(ES+) m/z 438.1, 440.1 (M+1).

Step 3. Preparation of 5-cyclopropyl-4-((4-(3,4-dichlorophenoxy)piperidin-1-yl)methyl)-2-fluoro-N-(methylsulfonyl)benzamide, trifluoroacetic acid salt

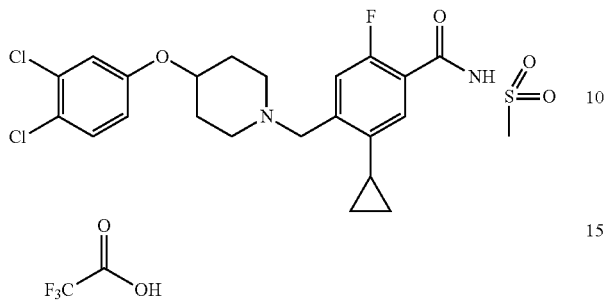

Following the procedure as described in Example 53 step 5, and making variation as required to replace cyclopropanesulfonamide with methylsulfonamide and (S)-5-cyclopropyl-4-((3-(3,5-dichlorophenoxy)piperidin-1-yl)methyl)-2-fluorobenzoic acid with 5-cyclopropyl-4-((4-(3,4-dichlorophenoxy)piperidin-1-yl)methyl)-2-fluorobenzoic acid, trifluoroacetic acid salt and purification by preparative HPLC, the title compound was obtained as a colorless solid (0.40 g, 69%); $^1$H NMR (300 MHz, DMSO-$d_6$) δ12.28 (br s, 1H), 10.00 (br s, 1H), 7.55-7.47 (m, 2H), 7.32 (d, J=2.4 Hz, 1H), 7.25 (d, J=7.1 Hz, 1H), 7.07-6.98 (m, 1H), 4.82-4.65 (m, 1H), 4.56 (s, 2H), 4.38-3.94 (m, 2H), 3.34 (s, 3H), 3.30-3.18 (m, 2H), 2.24-2.09 (m, 3H), 2.01-1.76 (m, 2H), 1.05-0.94 (m, 2H), 0.80-0.72 (m, 2H): MS(ES+) m/z 515.7, 517.1 (M+1).

Example 510

Synthesis of 5-cyclopropyl-N-(cyclopropylsulfonyl)-4-((4-(3,4-dichlorophenoxy)piperidin-1-yl)methyl)-2-fluorobenzamide, trifluoroacetic acid salt

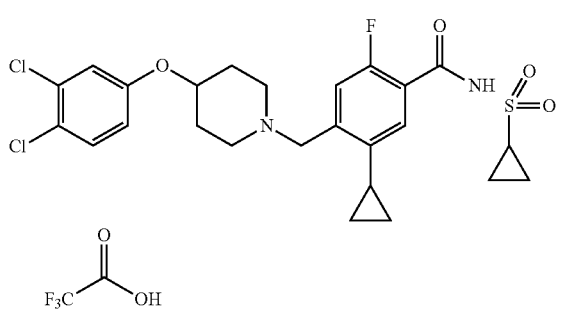

Following the procedure as described in Example 53 step 5, and making variations as required to replace (S)-5-cyclopropyl-4-((3-(3,5-dichlorophenoxy)piperidin-1-yl)methyl)-2-fluorobenzoic acid with 5-cyclopropyl-4-((4-(3,4-dichlorophenoxy)piperidin-1-yl)methyl)-2-fluorobenzoic acid, trifluoroacetic acid salt and purification by preparative HPLC, the title compound was obtained as a colorless solid (0.45 g, 69%): $^1$H NMR (300 MHz, DMSO-$d_6$) δ12.28 (br s, 1H), 9.98 (br s, 1H), 7.57-7.47 (m, 2H), 7.36-7.28 (m, 1H), 7.23 (d, J=7.0 Hz, 1H), 7.08-6.94 (m, 1H), 4.85-4.69 (m, 1H), 4.57 (s, 2H), 3.59-3.16 (m, 4H), 3.10-2.98 (m, 1H), 2.26-2.09 (m, 2H), 2.09-1.94 (m, 2H), 1.89-1.71 (m, 1H), 1.15-1.06 (m, 4H), 1.03-0.94 (m, 2H), 0.81-0.72 (m, 2H); MS(ES+) m/z 541.1, 543.1 (M+1).

Example 511

Synthesis of 5-cyclopropyl-4-((4-((3,5-dichlorobenzyl)oxy)piperidin-1-yl)methyl)-2-fluoro-N-(methylsulfonyl)benzamide, trifluoroacetic acid salt

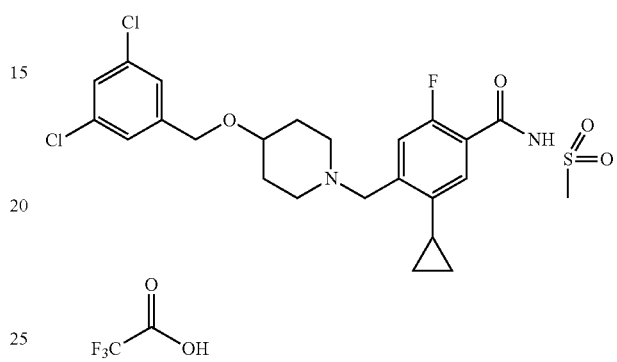

Step 1. Preparation of tert-butyl 4-((3,5-dichlorobenzyl)oxy)piperidin-1-carboxylate

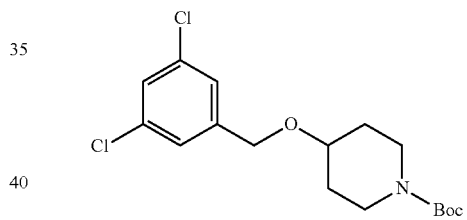

Following the procedure as described in Example 478 step 1, and making variation as required to replace 2-chloro-4-fluorobenzylbromide with 3,5-dichlorobenzyl chloride, the title compound was isolated as a yellowish oil (1.29 g, 77%).

Step 2. Preparation of 4-((3,5-dichlorobenzyl)oxy)piperidin, trifluoroacetic acid salt

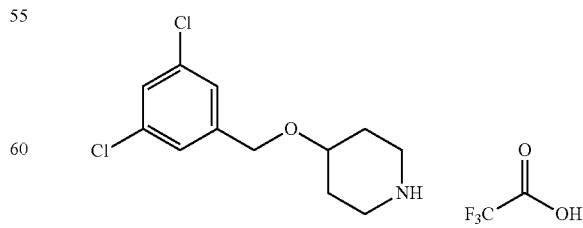

A solution of tert-butyl 4-((3,5-dichlorobenzyl)oxy)piperidine-1-carboxylate (1.98 g, 5.50 mmol) in dichloromethane (50 mL) was treated with trifluoroacetic acid (15 mL).

Step 3. Preparation of tert-butyl 5-cyclopropyl-4-((4-((3,5-dichlorobenzyl)oxy)piperidin-1-yl)methyl)-2-fluorobenzoate

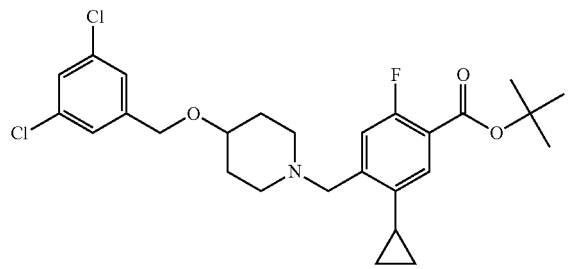 [SMILES: CC(C)(C)OC(=O)c1cc(C2CC2)c(CN2CCC(OCc3cc(Cl)cc(Cl)c3)CC2)cc1F]

Following the procedure as described in Example 53 step 3, and making variation as required to replace (S)-3-(3,5-dichlorophenoxy)piperidine, trifluoroacetic acid salt with 4-((3,5-dichlorobenzyl)oxy)piperidine, trifluoroacetic acid salt, the title compound was obtained as an oil (1.44 g, 51% in 2 steps); $^1$H NMR (300 MHz, CDCl$_3$) δ7.47 (d, J=7.3 Hz, 1H), 7.25-7.19 (m, 3H), 7.16 (d, J=11.8 Hz, 1H), 4.46 (s, 2H), 3.61 (s, 2H), 3.48-3.37 (m, 1H), 2.78-2.08 (m, 2H), 2.27-2.14 (m, 2H), 1.99-1.84 (m, 3H), 1.74-1.60 (m, 2H), 1.56 (s, 9H), 0.94-0.85 (m, 2H), 0.63-0.56 (m, 2H); MS (ES+) m/z 508.2, 510.2 (M+1).

Step 4. Preparation of 5-cyclopropyl-4-((4-((3,5-dichlorobenzyl)oxy)piperidin-1-yl)methyl)-2-fluorobenzoic acid, trifluoroacetic acid salt

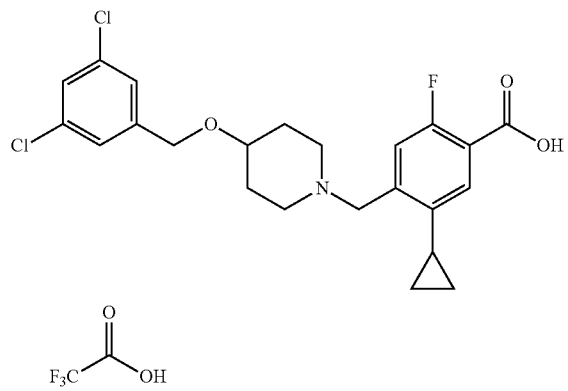

Following the procedure as described in Example 53 step 4, and making variation as required to replace (S)-tert-butyl 5-cyclopropyl-4-((3-(3,5-dichlorophenoxy)piperidin-1-yl)methyl)-2-fluorobenzoate with tert-butyl 5-cyclopropyl-4-((4-((3,5-dichlorobenzyl)oxy)piperidin-1-yl)methyl)-2-fluorobenzoate the title compound was obtained as an colorless solid (1.29 g, 81%): MS(ES+) m/z 452.1, 454.1 (M+1).

Step 5. Preparation of 5-cyclopropyl-4-((4-((3,5-dichlorobenzyl)oxy)piperidin-1-yl)methyl)-2-fluoro-N-(methylsulfonyl)benzamide, trifluoroacetic acid salt

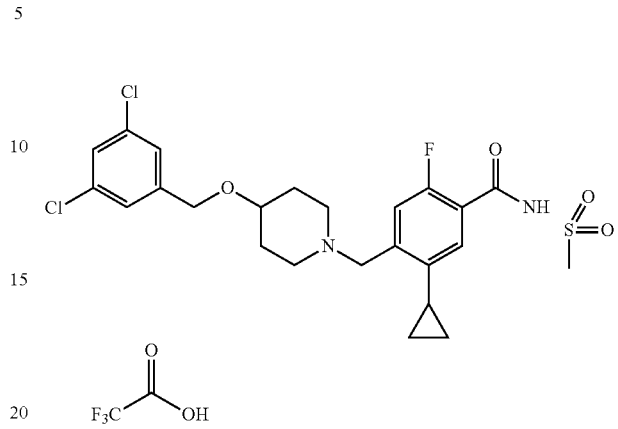

Following the procedure as described in Example 53 step 5, and making variations as required to replace cyclopropanesulfonamide with methylsulfonamide and to replace (S)-5-cyclopropyl-4-((3-(3,5-dichlorophenoxy)piperidin-1-yl)methyl)-2-fluorobenzoic acid with 5-cyclopropyl-4-((4-((3,5-dichlorobenzyl)oxy)piperidin-1-yl)methyl)-2-fluorobenzoic acid, trifluoroacetic acid salt and purification by preparative HPLC, the title compound was obtained as a colorless solid (0.25 g, 51%): $^1$H NMR (300 MHz, DMSO-d$_6$) δ12.26 (br s, 1H), 9.63 (br s, 1H), 7.54-7.45 (m, 2H), 7.42-7.32 (m, 2H), 7.24 (d, J=7.3 Hz, 1H), 4.51 (br s, 4H), 3.81-3.66 (m, 1H), 3.34 (s, 3H), 3.30-3.20 (m, 2H), 3.18-3.07 (m, 1H), 2.24-1.97 (m, 3H), 1.93-1.80 (m, 2H), 1.73-1.54 (m, 1H), 1.02-0.93 (m, 2H), 0.80-0.71 (m, 2H): MS(ES+) m/z 529.1, 531.1 (M+1).

Example 512

Synthesis of 5-cyclopropyl-N-(cyclopropylsulfonyl)-4-((4-((3,5-dichlorobenzyl)oxy)piperidin-1-yl)methyl)-2-fluorobenzamide, trifluoroacetic acid salt

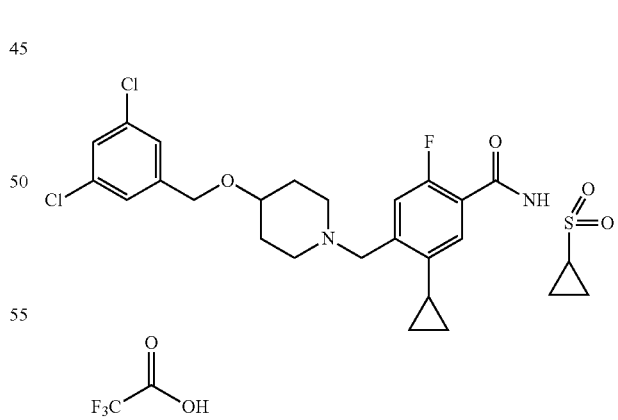

Following the procedure as described in Example 53 step 5, and making variations as required to replace (S)-5-cyclopropyl-4-((3-(3,5-dichlorophenoxy)piperidin-1-yl)methyl)-2-fluorobenzoic acid with 5-cyclopropyl-4-((4-((3,5-dichlorobenzyl)oxy)piperidin-1-yl)methyl)-2-fluorobenzoic acid, trifluoroacetic acid salt and purification by preparative HPLC, the title compound was obtained as a colorless solid (0.31 g, 61%): ¹H NMR (300 MHz, DMSO-d₆) δ12.24 (br s, 1H), 9.53 (br s, 1H), 7.53-7.45 (m, 2H), 7.42-7.33 (m, 2H), 7.23 (d, J=7.3 Hz, 1H), 4.51 (br s, 4H), 3.79-3.66 (m, 1H), 3.64-3.49 (m, 1H), 3.42-3.12 (m, 3H), 3.11-3.00 (m, 1H), 2.21-1.98 (m, 3H), 1.93-1.79 (m, 1H), 1.73-1.53 (m, 1H), 1.16-1.06 (m, 4H), 1.01-0.93 (m, 2H), 0.79-0.71, (m, 2H): MS(ES+) m/z 555.2, 557.2 (M+1).

Example 513

Synthesis of 5-cyclopropyl-2-fluoro-4-((4-(fluoromethyl)-4-(4-fluorophenyl)piperidin-1-yl)methyl)-N-(methylsulfonyl)benzamide, trifluoroacetic acid salt

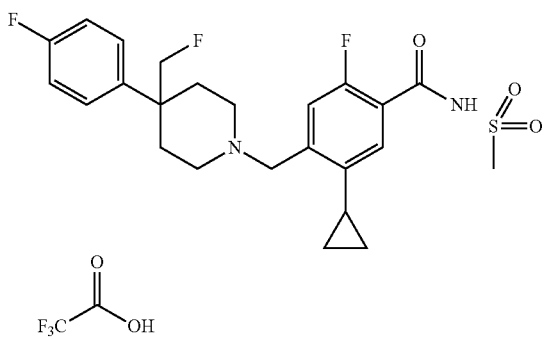

Step 1. Preparation of (4-(4-fluorophenyl)piperidin-4-yl)methanol, trifluoroacetic acid salt

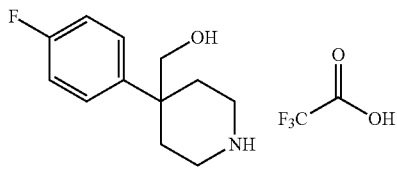 [SMILES: OCC1(c2ccc(F)cc2)CCNCC1 ; O=C(O)C(F)(F)F]

To a solution of tert-butyl 4-(4-fluorophenyl)-4-(hydroxymethyl)piperidin-1-carboxylate (1.51 g, 4.88 mmol) in dichloromethane (50 mL) was added trifluoroacetic acid (15 mL). The resulting solution was stirred at ambient temperature for 1.5 hours and then concentrated in vacuo to provided the title compound (1.58 g, quant. yield): MS(ES+) m/z 210.2 (M+1).

Step 2. Preparation of tert-butyl 5-cyclopropyl-2-4-((4-(4-fluorophenyl)-4-(hydroxymethyl)piperidin-1-yl)methyl)benzoate

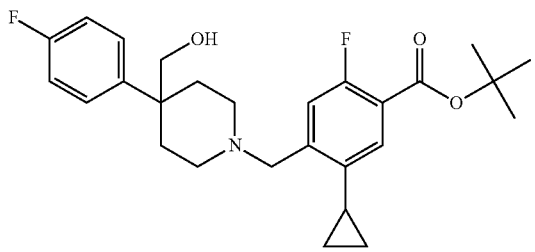 [SMILES: CC(C)(C)OC(=O)c1cc(C2CC2)c(CN2CCC(CO)(c3ccc(F)cc3)CC2)cc1F]

Following the procedure as described in Example 53 step 3, and making variation as required to replace (S)-3-(3,5-dichlorophenoxy)piperidine, trifluoroacetic acid salt with (4-(4-fluorophenyl)piperidin-4-yl)methanol, trifluoroacetic acid salt, the title compound was obtained as an oil (0.78 g, 35%): ¹H NMR (300 MHz, CDCl₃) δ7.45 (d, J=7.3 Hz, 1H), 7.33-7.26 (m, 2H), 7.17 (d, J=11.9 Hz, 1H), 7.12-7.00 (m, 2H), 4.19-4.11 (m, 1H), 3.60-3.50 (m, 4H), 3.32-3.21 (m, 1H), 3.14-3.03 (m, 1H), 2.68-2.57 (m, 2H), 2.33-2.21 (m, 1H), 2.20-2.10 (m, 1H), 1.98-1.79 (m, 3H), 1.55 (s, 9H), 0.90-0.82 (m, 2H), 0.61-0.54 (m, 2H): MS(ES+) m/z 458.3 (M+1).

Step 3. Preparation of tert-butyl 5-cyclopropyl-2-fluoro-4-((4-(fluoromethyl)-4-(4-fluorophenyl)piperidin-1-yl)methyl)benzoate

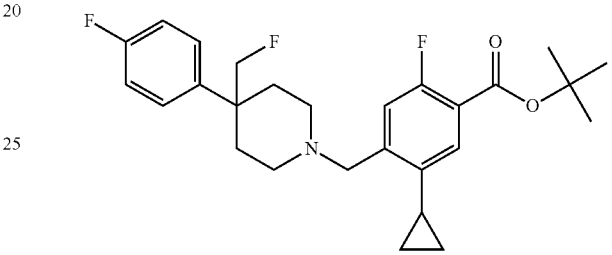

To a solution of tert-butyl 5-cyclopropyl-2-fluoro-4-((4-(4-fluorophenyl)-4-(hydroxymethyl)piperidin-1-yl)methyl)benzoate (0.78 g, 1.70 mmol) in dichloromethane (40 mL) under nitrogen, was added with diethylaminosulfur trifluoride (0.45 mL, 3.4 mmol) at 0° C. The resulting solution was stirred at 0° C. for 2.5 hours and then quenched with saturated sodium bicarbonate (30 mL). The mixture was extracted with ethyl acetate (80 mL) and the combined organic extracts were washed with saturated sodium bicarbonate (3×30 mL), saturated ammonium chloride (40 mL), brine (40 mL), dried over anhydrous sodium sulfate, filtered, and concentrated in vacuo. The residue was purified by flash chromatography (0-25% ethyl acetate in hexanes) to provide the title compound as a colorless oil (0.39 g, 50%); ¹H NMR (300 MHz, CDCl₃) δ7.47 (d, J=7.2 Hz, 1H), 7.21-7.09 (m, 3H), 7.01-6.91 (m, 2H), 3.64 (s, 2H), 2.85 (d, J=22.9 Hz, 2H), 2.71-2.59 (m, 2H), 2.41-2.28 (m, 2H), 1.97-1.85 (m, 1H), 1.79-1.61 (m, 4H), 1.55 (s, 9H), 0.93-0.85 (m, 2H), 0.63-0.55 (m, 2H); MS(ES+) m/z 460.3 (M+1).

Step 4. Preparation of 5-cyclopropyl-2-fluoro-4-((4-(fluoromethyl)-4-(4-fluorophenyl)piperidin-1-yl)methyl)benzoic acid

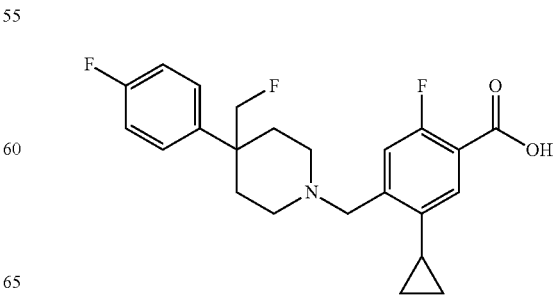

To a solution of tert-butyl 5-cyclopropyl-2-fluoro-4-((4-(fluoromethyl)-4-(4-fluorophenyl)piperidin-1-yl)methyl)benzoate (0.39 g, 0.85 mmol) in 1,4-dioxane (10 mL) was added concentrated hydrochloric acid (5 mL). The resulting solution was stirred at ambient temperature for 4 hours. The reaction mixture was diluted with ethyl acetate (60 mL), washed with water (60 mL), saturated ammonium chloride (50 mL), brine (2×40 mL), dried over anhydrous sodium sulfate, filtered the solid, and concentrated in vacuo to provide the title compound (0.24 g, 71.%): MS(ES+) m/z 404.2 (M+1).

Step 5. Preparation of 5-cyclopropyl-2-fluoro-4-((4-(fluoromethyl)-4-(4-fluorophenyl)piperidin-1-yl)methyl)-N-(methylsulfonyl)benzamide, trifluoroacetic acid salt

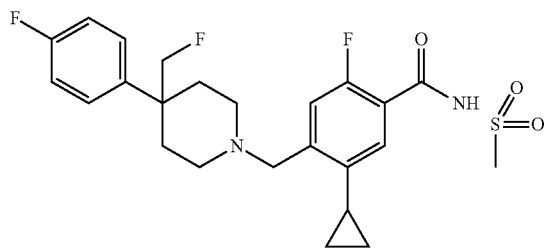

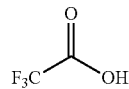

Following the procedure as described in Example 53 step 5, and making variations as required to replace cyclopropanesulfonamide with methylsulfonamide and to replace (S)-5-cyclopropyl-4-((3-(3,5-dichlorophenoxy)piperidin-1-yl)methyl)-2-fluorobenzoic acid with 5-cyclopropyl-2-fluoro-4-((4-(fluoromethyl)-4-(4-fluorophenyl)piperidin-1-yl)methyl)benzoic acid and purification by preparative HPLC, the title compound was obtained as a colorless solid (0.045 g, 26%); $^1$H NMR (300 MHz, DMSO-d$_6$) δ12.22 (br s, 1H), 9.49 (br s, 1H), 7.45 (d, J=10.8 Hz, 1H), 7.28-7.19 (m, 3H), 7.17-7.08 (m, 2H), 4.50 (s, 2H.), 4.14-3.60 (m, 2H), 3.33 (s, 3H), 3.30-3.10 (m, 2H), 2.96 (d, J=20.6 Hz, 2H), 2.17-2.05 (m, 1H), 2.02-1.75 (m, 4H), 1.03-0.89 (m, 2H), 0.78-0.69 (m, 2H); MS(ES+) m/z 481.2 (M+1).

Example 514

Synthesis of 5-cyclopropyl-N-(cyclopropylsulfonyl)-2-fluoro-4-((4-(fluoromethyl)-4-(4-fluorophenyl)piperidin-1-yl)methyl)benzamide, trifluoroacetic acid salt

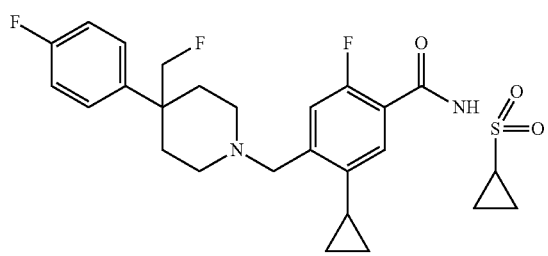

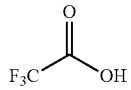

Following the procedure as described in Example 53 step 3, and making variations as required to replace (S)-5-cyclopropyl-4-((3-(3,5-dichlorophenoxy)piperidin-1-yl)methyl)-2-fluorobenzoic acid with 5-cyclopropyl-2-fluoro-4-((4-(fluoromethyl)-4-(4-fluorophenyl)piperidin-1-yl)methyl)benzoic acid, and purification by preparative HPLCs), the title compound was obtained as a colorless solid (0.07 g, 39%); $^1$H NMR (300 MHz, DMSO-d$_6$) δ12.24 (brs, 1H), 9.53 (br s, 1H), 7.46 (d, J=11.1 Hz, 1H), 7.27-7.18 (m, 3H), 7.17-7.08 (m, 2H), 4.52 (s, 2H), 4.09-3.64 (m, 2H), 3.37-3.13 (m, 2H), 3.09-3.02 (m, 1H), 2.96 (d, J=19.7 Hz, 2H), 2.17-2.05 (m, 1H), 2.02-1.73 (m, 4H), 1.16-1.04 (m, 4H), 1.01-0.91 (m, 2H), 0.79-0.68 (m, 2H); MS(ES+) m/z 507.2 (M+1).

Example 515

Synthesis of 5-cyclopropyl-2-fluoro-4-((4-(4-fluorophenyl)-4-(methoxymethyl)piperidin-1-yl)methyl)-N-(methylsulfonyl)benzamide, trifluoroacetic acid salt

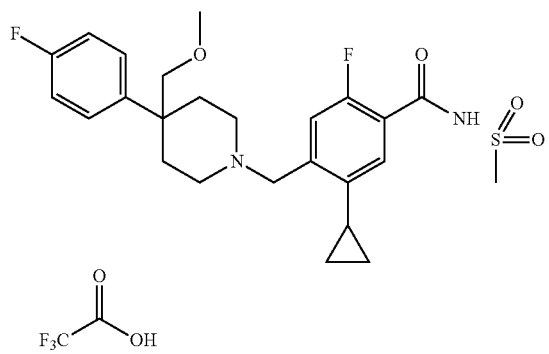

Step 1. Preparation of tert-butyl 5-cyclopropyl-2-fluoro-4-((4-(4-fluorophenyl)-4-(methoxymethyl)piperidin-1-yl)methyl)benzoate

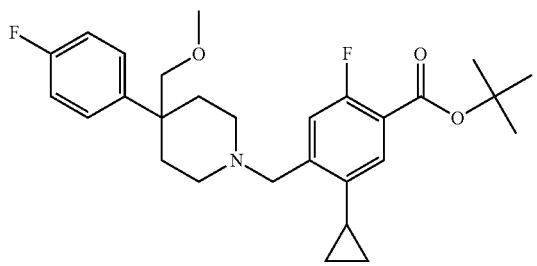 [SMILES: COCC1(c2ccc(F)cc2)CCN(Cc2cc(F)c(C(=O)OC(C)(C)C)cc2C2CC2)CC1]

To a solution of tert-butyl 5-cyclopropyl-2-fluoro-4-((4-(4-fluorophenyl)-4-(hydroxymethyl)piperidin-1-yl)methyl)benzoate (1.39 g, 3.04 mmol) and methyliodide (0.53 mL, 8.5 mmol) in anhydrous tetrahydrofuran (40 mL) at −78° C.

was treated with 1.0 M lithium bis(trimethylsilyl)amide in tetrahydrofuran (8.5 mL, 8.5 mmol) under nitrogen. The resulting solution was stirred −78° C. for 30 minutes and then warmed to ambient temperature and stirred for 18 hours. The reaction mixture was diluted with ethyl acetate (100 mL), washed with saturated ammonium chloride (2×50 mL), brine (2×40 mL), dried over anhydrous sodium sulfate, filtered the solid, and concentrated in vacuo. The residue was purified by flash chromatography (0-25% ethyl acetate in hexanes) to provide the title compound as a colorless oil (0.48 g, 34%): $^1$H NMR (300 MHz, CDCl$_3$) δ7.45 (d, J=7.3 Hz, 1H), 7.33-7.26 (m, 2H), 7.17 (d, J=11.8 Hz, 1H), 7.05-6.96 (m, 2H), 3.54 (s, 2H), 3.31 (s, 2H), 3.19 (s, 3H), 2.66-2.54 (m, 2H), 2.33-2.21 (m, 2H), 2.17-2.06 (m, 2H), 2.02-1.84 (m, 3H), 1.56 (s, 9H), 0.90-0.81 (m, 2H), 0.61-0.53 (m, 2H): MS(ES+) m/z 472.3 (M+1).

Step 2. Preparation of 5-cyclopropyl-2-fluoro-4-((4-(4-fluorophenyl)-4-(methoxymethyl)piperidin-1-yl)methyl)benzoic acid

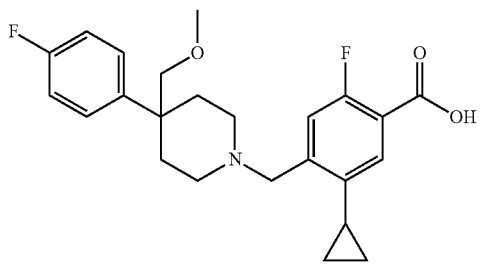 [SMILES: COCC1(c2ccc(F)cc2)CCN(Cc2cc(F)c(C(=O)O)cc2C2CC2)CC1]

Following the procedure as described in Example 513 step 4, and making variation as required to replace tert-butyl 5-cyclopropyl-2-fluoro-4-((4-(fluoromethyl)-4-(4-fluorophenyl)piperidin-1-yl)methyl)benzoate with tert-butyl 5-cyclopropyl-2-fluoro-4-((4-(4-fluorophenyl)-4-(methoxymethyl)piperidin-1-yl)methyl)benzoate, the title compound was obtained as a colorless solid (0.26 g, 62%): MS(ES+) m/z 461.2 (M+1).

Step 3. Preparation of 5-cyclopropyl-2-fluoro-4-((4-(4-fluorophenyl)-4-(methoxymethyl)piperidin-1-yl)methyl)-N-(methylsulfonyl)benzamide, trifluoroacetic acid salt

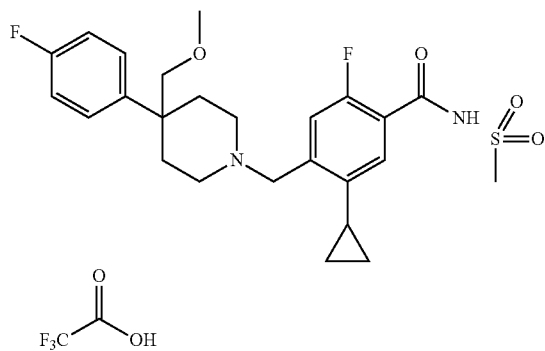

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-2-fluoro-4-((4-(4-fluorophenyl)-4-(methoxymethyl)piperidin-1-yl)methyl)benzoic acid, and to replace cyclopropanesulfonamide with methylsulfonamide, and purification by preparative HPLC, the title compound was obtained as a colorless solid (0.04 g, 21%): $^1$H NMR (300 MHz, DMSO-d$_6$) δ 12.31 (br s, 1H), 9.54 (br s, 1H), 7.54-7.30 (my 3H), 7.25-7.02 (m, 3H), 5.74-4.82 (m, 1H), 4.63-4.34 (m, 2H), 3.73-3.55 (m, 1H), 3.38-3.27 (m, 5H), 3.18-3.08 (m, 4H), 2.92-2.74 (m, 1H), 2.43-2.37 (m, 1H), 2.28-2.02 (m, 3H), 1.99-1.84 (m, 1H), 1.04-0.85 (m, 2H), 0.81-0.66 (m, 2H); MS(ES+) m/z 493.2 (M+1).

Example 516

Synthesis of 5-cyclopropyl-N-(cyclopropylsulfonyl)-2-fluoro-4-((4-(4-fluorophenyl)-4-(methoxymethyl)piperidin-1-yl)methyl)benzamide, trifluoroacetic acid salt

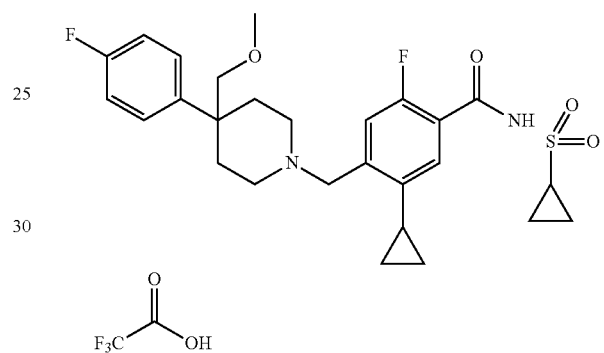

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-2-fluoro-4-((4-(4-fluorophenyl)-4-(methoxymethyl)piperidin-1-yl)methyl)benzoic acid, and purification by preparative HPLC, the title compound was obtained as a colorless solid (0.045 g, 23%); $^1$H NMR (300 MHz, DMSO-d$_6$) δ 12.24 (br s, 1H), 9.51 (br s, 1H), 7.54-7.31 (m, 3H), 7.26-7.07 (m, 3H), 4.64-4.53 (m, 1H), 4.42 (s, 2H), 3.72-3.57 (m, 1H), 3.42-3.26 (m, 2H), 3.19-3.09 (m, 4H), 3.08-3.00 (m, 1H), 2.92-2.75 (m, 1H), 2.44-2.35 (m, 1H), 2.29-2.01 (m, 3H), 2.00-1.85 (m, 1H), 1.17-1.06 (m, 4H), 1.04-0.84 (m, 2H), 0.82-0.65 (m, 2H); MS(ES+) m/z 519.2 (M+1).

Example 517

Synthesis of 5-cyclopropyl-4-((4-(3,5-dichlorobenzyl)piperazin-1-yl)methyl)-2-fluoro-N-(methylsulfonyl)benzamide, trifluoroacetic acid salt

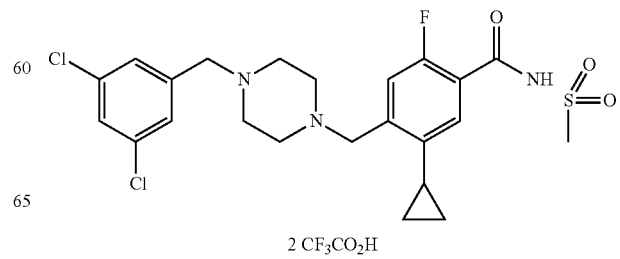

Step 1. Preparation of tert-butyl 4-(3,5-dichlorobenzyl)piperazine-1-carboxylate

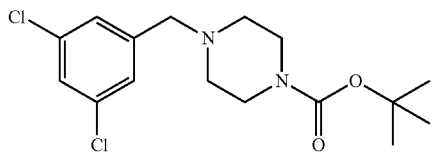 [SMILES: CC(C)(C)OC(=O)N1CCN(Cc2cc(Cl)cc(Cl)c2)CC1]

To a mixture of tert-butyl piperazine-1-carboxylate (1.00 g, 5.37 mmol) and potassium carbonate (1.34 g, 9.76 mmol) in anhydrous dimethylformamide (50 mL) was added 1,3-dichloro-5-(chloromethyl)benzene (0.95 g, 4.88 mmol) under nitrogen. The resulting mixture was stirred at ambient temperature for 2 days. The reaction mixture was diluted with ethyl acetate (200 mL), washed with water (100 mL), saturated ammonium chloride (2×50 mL), brine (2×40 mL), dried over anhydrous sodium sulfate, filtered and concentrated in vacuo. The residue was purified by flash chromatography (3:1 hexanes:ethyl acetate) to provide the title compound as a colorless oil (1.22 g, 73%): $^1$H NMR (300 MHz, CDCl$_3$) δ 7.25-7.17 (m, 3H), 3.45-3.35 (m, 6H), 2.39-2.30 (m, 4H), 1.42 (s, 9H); MS(ES+) m/z 345.1, 347.1 (M+1).

Step 2. Preparation of 1-(3,5-dichlorobenzyl)piperazine dihydrochloride

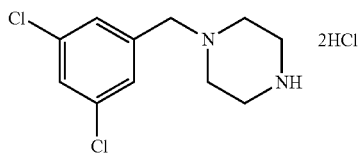 [SMILES: Clc1cc(Cl)cc(CN2CCNCC2)c1]

To a mixture of tert-butyl 4-(3,5-dichlorobenzyl)piperazine-1-carboxylate (1.22 g, 3.53 mmol) in 1,4-dioxane (20 mL) was added concentrated hydrochloric acid (5 mL). The mixture was stirred for 2 hours and then concentrated in vacuo to provide the title compound as a colorless solid (1.12 g, quant. yield): MS(ES+) m/z 245.1, 247.1 (M+1).

Step 3. Preparation of tert-butyl 5-cyclopropyl-4-((4-(3,5-dichlorobenzyl)piperazin-1-yl)methyl)-2-fluorobenzoate

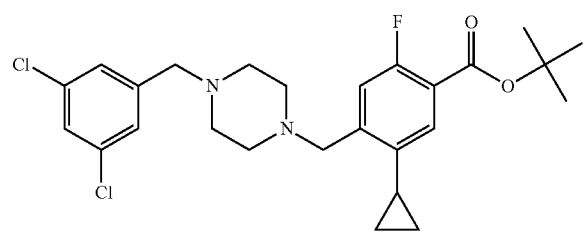 [SMILES: CC(C)(C)OC(=O)c1cc(C2CC2)c(CN2CCN(Cc3cc(Cl)cc(Cl)c3)CC2)cc1F]

Following the procedure as described in Example 53 step 3, and making variation as required to replace (S)-3-(3,5-dichlorophenoxy)piperidine, trifluoroacetic acid salt with 1-(3,5-dichlorobenzyl)piperazine dihydrochloride, the title compound was obtained as an oil (1.74 g, quant. yield): $^1$H NMR (300 MHz, CDCl$_3$) δ7.46 (d, J=7.2 Hz, 1H), 7.25-7.10 (m, 4H), 3.63 (s, 2H), 3.43 (s, 2H), 2.59-2.35 (m, 8H), 1.98-1.87 (m, 1H), 1.55 (s, 9H), 0.94-0.86 (m, 2H), 0.67-0.55 (m, 2H); MS(ES+) m/z 508.2, 508.2 (M+1).

Step 4. Preparation of 5-cyclopropyl-4-((4-(3,5-dichlorobenzyl)piperazin-1-yl)methyl)-2-fluorobenzoic acid dihydrochloride

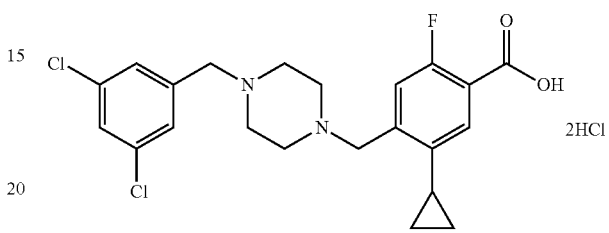

To a solution of tert-butyl 5-cyclopropyl-4-((4-(3,5-dichlorobenzyl)piperazin-1-yl)methyl)-2-fluorobenzoate (1.81 g, 3.67 mmol) in 1,4-dioxane (35 mL) was added concentrated hydrochloric acid (1.5 mL). The resulting mixture was stirred for 2 hours and then concentrated in vacuo. The residue was triturated with water to provide the title compound as a colorless solid (1.5 g, 94%): MS(ES+) m/z 437.0, 439.0 (M+1).

Step 5. Preparation of 5-cyclopropyl-4-((4-(3,5-dichlorobenzyl)piperazin-1-yl)methyl)-2-fluoro-N-(methylsulfonyl)benzamide, trifluoroacetic acid salt

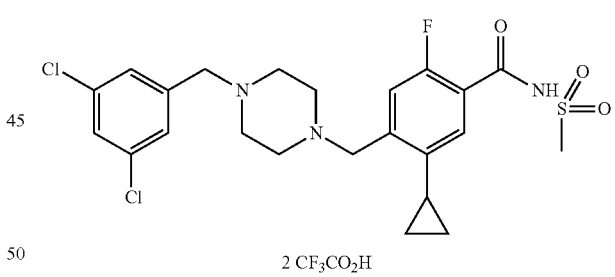

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-((4-(3,5-dichlorobenzyl)piperazin-1-yl)methyl)-2-fluorobenzoic acid dihydrochloride, and to replace cyclopropanesulfonamide with methylsulfonamide, and purification by preparative HPLC, the title compound was obtained as a colorless solid (0.08 g, 21%): $^1$H NMR (300 MHz, DMSO-d$_6$) δ12.19 (br s, 1H), 9.74 (br s, 1H), 7.66 (s, 1H), 7.51 (s, 2H), 7.32 (d, J=11.6 Hz, 1H), 7.22 (d, J=7.1 Hz, 1H), 5.76 (br s, 1H), 4.11 (br s, 2H), 3.97 (br s, 2H), 3.33 (s, 3H), 3.27-2.65 (m, 8H), 2.11-1.98 (m, 1H), 1.01-0.86 (m, 2H), 0.77-0.59 (m, 2H); MS(ES+) m/z 514.1, 516.1 (M+1).

Example 518

Synthesis of 5-cyclopropyl-N-(cyclopropylsulfonyl)-4-((4-(3,5-dichlorobenzyl)piperazin-1-yl)methyl)-2-fluorobenzamide, trifluoroacetic acid salt

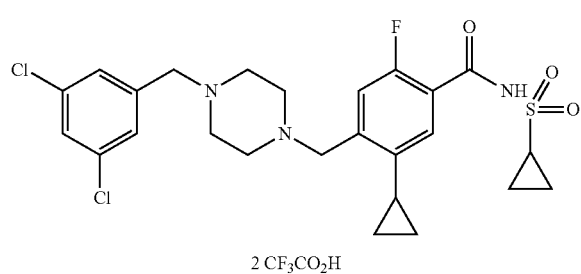

2 CF₃CO₂H

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-((4-(3,5-dichlorobenzyl)piperazin-1-yl)methyl)-2-fluorobenzoic acid dihydrochloride, and purification by preparative HPLC, the title compound was obtained as a colorless solid (0.20 g, 34%): ¹H NMR (300 MHz, DMSO-d₆) δ12.13 (br s, 1H), 7.65 (s, 1H), 7.54-7.49 (m, 2H), 7.33 (d, J=11.3 Hz, 1H), 7.20 (d, J=7.6 Hz, 1H), 4.10 (br s, 2H), 3.97 (br s, 2H), 3.33-2.59 (m, 9H), 2.10-1.99 (m, 1H), 1.15-1.03 (m, 4H), 0.96-0.87 (m, 2H), 0.72-0.63 (m, 2H); MS(ES+) m/z 540.2, 542.2 (M+1).

Example 519

Synthesis of 4-((4-(4-chloro-3-(trifluoromethyl)phenoxy)piperidin-1-yl)methyl)-5-cyclopropyl-2-fluoro-N-(methylsulfonyl)benzamide, trifluoroacetic acid salt

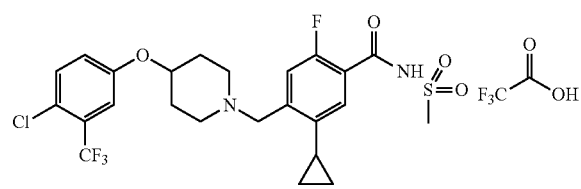

Step 1. Preparation of tert-butyl 5-cyclopropyl-2-fluoro-4-((4-hydroxypiperidin-1-yl)methyl)benzoate

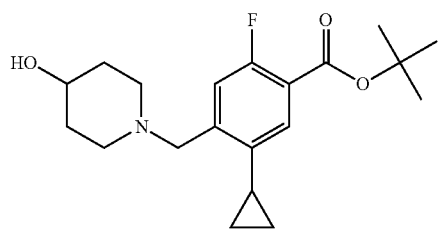 [SMILES: CC(C)(C)OC(=O)c1cc(C2CC2)c(CN2CCC(O)CC2)cc1F]

Following the procedure as described in Example 53 step 3, and making variation as required to replace (S)-3-(3,5-dichlorophenoxy)piperidine, trifluoroacetic acid salt with piperidin-4-ol, the title compound was obtained as an oil (0.98 g, 94%); ¹H NMR (300 MHz, CDCl₃) δ7.45 (d, J=7.3 Hz, 1H), 7.16 (d, J=11.8 Hz, 1H), 3.57-3.64 (m, 1H), 3.61 (s, 2H), 2.77-2.68 (m, 2H), 2.25-2.13 (m, 2H), 1.97-1.76 (m, 4H), 1.64-1.57 (m, 1H), 1.54 (s, 9H), 0.92-0.84 (m, 2H), 0.62-0.55 (m, 2H); MS(ES+) m/z 350.3 (M+1).

Step 2. Preparation of tert-butyl 5-cyclopropyl-2-fluoro-4-((4-((methylsulfonyl)oxy)piperidin-1-yl)methyl)benzoate

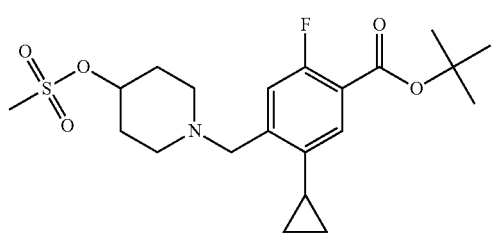 [SMILES: CC(C)(C)OC(=O)c1cc(C2CC2)c(CN2CCC(OS(C)(=O)=O)CC2)cc1F]

To a solution of tert-butyl 5-cyclopropyl-2-fluoro-4-((4-hydroxypiperidin-1-yl)methyl)benzoate (0.98 g, 2.80 mmol) and triethylamine (0.59 mL, 4.2 mmol) in dichloromethane (40 mL) at 0° C. was added methanesulfonyl chloride (0.26 mL, 3.36 mmol) under nitrogen. The resulting mixture was stirred at 0° C. for 1 hour. The mixture was washed with saturated ammonium chloride (40 mL), brine (40 mL), dried over anhydrous sodium sulfate, filtered the solid, and concentrated in vacuo to dryness to provide the title compound as a colorless oil (1.20 g, quant. yield): ¹H NMR (300 Mhz, CDCl₃) δ 7.47 (d, J=7.3 Hz, 1H), 7.14 (d, J=11.8 Hz, 1H), 7.81-4.71 (m, 1H), 3.64 (s, 2H), 3.00 (s, 3H), 2.76-2.65 (m, 2H), 2.43-2.28 (m, 2H), 2.09-1.83 (m, 5H), 1.55 (s, 9H), 0.94-0.86 (m, 2H), 0.63-0.56 (m, 2H): MS(ES+) m/z 428.2 (M+1).

Step 3. Preparation of tert-butyl 4-((4-(4-chloro-3-(trifluoromethyl)phenoxy)piperidin-1-yl)methyl)-5-cyclopropyl-2-fluorobenzoate

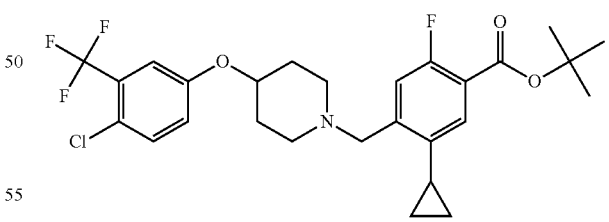

To a mixture of tert-butyl 5-cyclopropyl-2-fluoro-4-((4-((methylsulfonyl)oxy)piperidin-1-yl)methyl)benzoate (1.20 g, 2.80 mmol) and 4-chloro-3-(trifluoromethyl)phenol (0.61 g, 3.08 mmol) in anhydrous dimethylformamide (50 mL) was added potassium carbonate (0.43 g, 3.08 mmol). The reaction mixture was heated at 90° C. under nitrogen for 7 hours, cooled to ambient temperature and diluted with ethyl acetate (150 mL), washed with water (100 mL), saturated ammonium chloride (100 mL), brine (100 mL), dried over anhydrous sodium sulfate, filtered and concentrated in vacuo.

The residue was purified by flash chromatography (0-25% ethyl acetate in hexanes) to provide the title compound as a colorless oil (0.71 g, 48%): MS(ES+) m/z 528.1, 530.1 (M+1).

Step 4. Preparation of 4-((4-(4-chloro-3-(trifluoromethyl)phenoxy)piperidin-1-yl)methyl)-5-cyclopropyl-2-fluorobenzoic acid hydrochloride

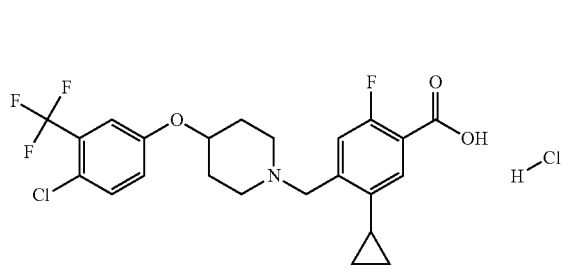 [SMILES: O=C(O)c1cc(C2CC2)c(CN2CCC(Oc3ccc(Cl)c(C(F)(F)F)c3)CC2)cc1F ; Cl]

Following the procedure as described in Example 517 step 4, and making variation as required to replace tert-butyl 5-cyclopropyl-4-((4-(3,5-dichlorobenzyl)piperazin-1-yl)methyl)-2-fluorobenzoate with tert-butyl 4-((4-(4-chloro-3-(trifluoromethyl)phenoxy)piperidin-1-yl)methyl)-5-cyclopropyl-2-fluorobenzoate and purification by trituration with diethyl ether, the title compound was obtained as a colorless solid (0.32 g, 47%): MS(ES+) m/z 472.0, 474.0 (M+1).

Step 5. Preparation of 4-((4-(4-chloro-3-(trifluoromethyl)phenoxy)piperidin-1-yl)methyl)-5-cyclopropyl-2-fluoro-N-(methylsulfonyl)benzamide, trifluoroacetic acid salt

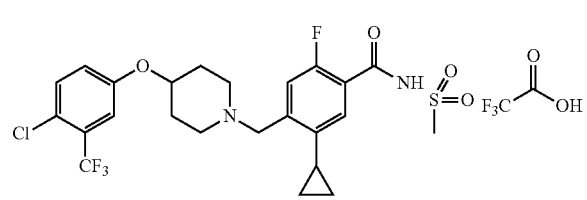

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 4-((4-(4-chloro-3-(trifluoromethyl)phenoxy)piperidin-1-yl)methyl)-5-cyclopropyl-2-fluorobenzoic acid hydrochloride, and to replace cyclopropanesulfonamide with methylsulfonamide, and purification by preparative HPLC, the title compound was obtained as a colorless solid (0.05 g, 24%): $^1$H NMR (300 MHz, DMSO-$d_6$) δ 12.30 (br s, 1H), 9.67 (br s, 1H), 7.63 (d, J=8.9 Hz, 1H), 7.51 (d, J=11.1 Hz, 1H), 7.44-7.30 (m, 2H), 7.25 (d, J=7.0 Hz, 1H), 4.95-4.76 (m, 1H), 4.54 (s, 2H), 4.26-3.74 (m, 2H), 3.47-3.12 (m, 6H), 2.28-1.74 (m, 4H), 1.06-0.92 (m, 2H), 0.82-0.71 (m, 2H); MS(ES+) m/z 549.1, 551.1 (M+1).

Example 520

Synthesis of 4-((4-(4-chloro-3-(trifluoromethyl)phenoxy)piperidin-1-yl)methyl)-5-cyclopropyl-N-(cyclopropylsulfonyl)-2-fluorobenzamide, trifluoroacetic acid salt

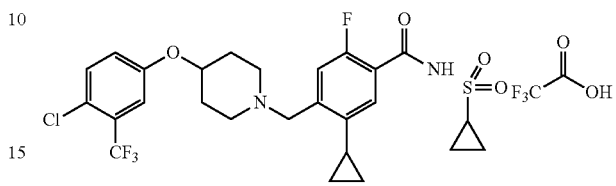

Following the procedure as described in Example 53 step 5, and making variation as required to replace fluorobenzoic acid hydrochloride, and purification by preparative HPLC, the title compound was obtained as a colorless (0.07 g, 32%): $^1$H NMR (300 MHz, DMSO-$d_6$) δ 12.22 (br s, 1H), 9.69 (br s, 1H), 7.63 (d, J=8.7 Hz, 1H), 7.51 (d, J=11.1 Hz, 1H), 7.44-7.30 (m, 2H), 7.23 (d, J=7.2 Hz, 1H), 7.92-4.79 (m, 1H), 4.54 (s, 2H), 4.23-3.76 (m, 2H), 3.50-3.31 (m, 2H), 3.10-3.00 (m, 1H), 2.28-1.70 (m, 5H), 1.15-1.06 (m, 4H), 1.03-0.95 (m, 2H), 0.81-0.72 (m, 2H); MS (ES+) m/z 575.2, 577.1 (M+1).

Example 521

Synthesis of 4-((4-((5-chloro-4-(trifluoromethyl)pyridin-2-yl)oxy)piperidin-1-yl)methyl)-5-cyclopropyl-2-fluoro-N-(methylsulfonyl)benzamide, trifluoroacetic acid salt

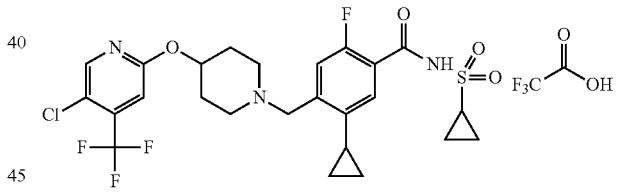

Step 1. Preparation of tert-butyl 4-((5-chloro-4-(trifluoromethyl)pyridin-2-yl)oxy)piperidine-1-carboxylate

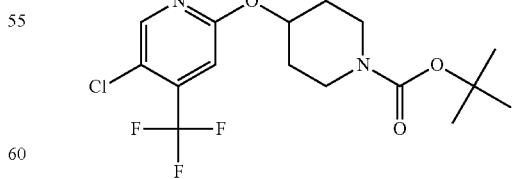

To a solution of tert-butyl 4-hydroxypiperidine-1-carboxylate (1.03 g, 5.09 mmol) in anhydrous 1,2-dimethoxyethane (35 mL) was added (60% sodium hydride in mineral oil, 0.20 g, 5.09 mmol) under nitrogen. The resulting mixture was stirred for 1 hour at ambient temperature and then added 2,5-dichloro-4-(trifluoromethyl)pyridine (1.00 g, 4.63 mmol). The reaction mixture was refluxed for 2 hours and cooled to ambient temperature. The reaction mixture was diluted with ethyl acetate (100 mL), washed with water (50 mL), saturated ammonium chloride (2×50 mL), brine (50 mL), dried over anhydrous sodium sulfate, filtered, and concentrated in vacuo to provide the title compound as an oil (1.76 g, quant. yield); $^{1}$H NMR (300 MHz, CDCl$_3$) δ 8.18 (s, 1H), 6.99 (s, 1H), 5.21-5.11 (m, 1H), 3.80-3.66 (m, 2H), 3.30-3.19 (m, 2H), 1.99-1.88 (m, 2H), 1.75-1.61 (m, 2H), 1.43 (s, 9H); MS(ES+) m/z 325.0, 326.9 (M−55).

Step 2. Preparation of tert-butyl 4-((4-((5-chloro-4-(trifluoromethyl)pyridin-2-yl)oxy)piperidin-1-yl)methyl)-5-cyclopropyl-2-fluorobenzoate

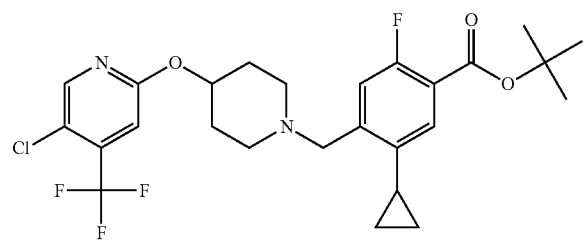 [SMILES: CC(C)(C)OC(=O)c1cc(C2CC2)c(CN2CCC(Oc3cc(C(F)(F)F)c(Cl)cn3)CC2)cc1F]

To a mixture of tert-butyl 4-((5-chloro-4-(trifluoromethyl)pyridin-2-yl)oxy)piperidine-1-carboxylate (1.76 g, 4.63 mmol) in 1,4-dioxane (30 mL) was added concentrated hydrochloric acid (10 mL). The resulting mixture was stirred for 5 hours and then concentrated in vacuo. The residue was dissolved in anhydrous dimethylformamide (70 mL), and to this solution was added potassium carbonate (2.21 g, 16.00 mmol) and tert-butyl 5-cyclopropyl-2-fluoro-4-(((methylsulfonyl)oxy)methyl)benzoate (1.38 g, 4.00 mmol). The resulting mixture was stirred under nitrogen at ambient temperature for 18 hours diluted with ethyl acetate (150 mL), washed with water (1.00 mL), saturated ammonium chloride (2×70 mL), brine (70 mL), dried over anhydrous sodium sulfate, filtered and concentrated in vacuo. The residue was purified by flash chromatography (0-80% ethyl acetate in hexanes) to provide the title compound as a colorless oil (1.92 g, 91%): $^{1}$H NMR (300 MHz, CDCl$_3$) δ 8.19 (s, 1H), 7.48 (d, J=7.1 Hz, 1H), 7.18 (d, J=11.8 Hz, 1H), 7.00 (s, 1H), 5.12-5.02 (m, 1H), 3.64 (s, 2H), 2.78-2.67 (m, 2H), 2.41-2.31 (m, 2H), 2.05-1.90 (m, 3H), 1.86-1.73 (m, 2H), 1.56 (s, 9H), 0.94-0.86 (m, 2H), 0.65-0.38 (m, 2H); MS(ES+) m/z 529.2, 531.2 (M+1H).

Step 3. Preparation of 4-((4-((5-chloro-4-(trifluoromethyl)pyridin-2-yl)oxy)piperidin-1-yl)methyl)-5-cyclopropyl-2-fluorobenzoic acid hydrochloride

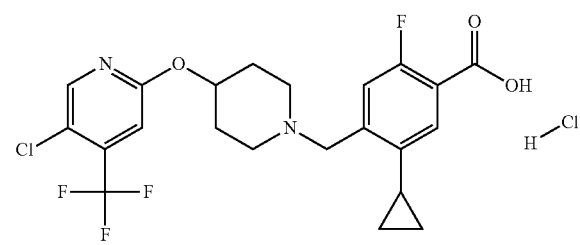 [SMILES: O=C(O)c1cc(C2CC2)c(CN2CCC(Oc3cc(C(F)(F)F)c(Cl)cn3)CC2)cc1F ; Cl]

Following the procedure as described in Example 517 step 4, and making variation as required to replace tert-butyl 5-cyclopropyl-4-((4-(3,5-dichlorobenzyl)piperazin-1-yl)methyl)-2-fluorobenzoate with tert-butyl 4-((4-((5-chloro-4-(trifluoromethyl)pyridin-2-yl)oxy)piperidin-1-yl)methyl)-5-cyclopropyl-2-fluorobenzoate, the title compound was obtained us a colorless solid (1.85 g, quant. yield): MS(ES+) m/z 472.9, 475.1 (M+1H).

Step 4. Preparation of 4-((4-((5-chloro-4-(trifluoromethyl)pyridin-2-yl)oxy)piperidin-1-yl)methyl)-5-cyclopropyl-2-fluoro-N-(methylsulfonyl)benzamide, trifluoroacetic acid salt

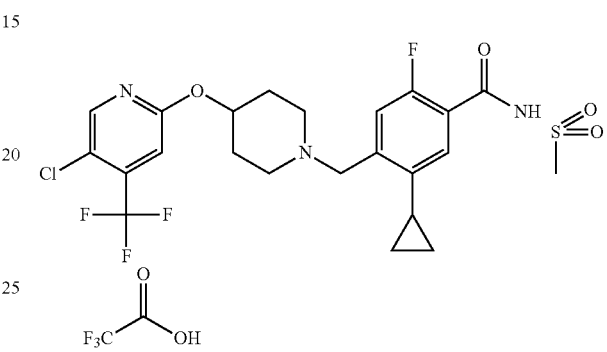

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 4-((4-((5-chloro-4-(trifluoromethyl)pyridin-2-yl)oxy)piperidin-1-yl)methyl)-5-cyclopropyl-2-fluorobenzoic acid hydrochloride, and to replace cyclopropanesulfonamide with methylsulfonamide, and purification by preparative-HPLC, the title compound was obtained as a colorless solid (0.45 g, 67%): $^{1}$H NMR (300 MHz, DMSO-d$_6$) δ 12.28 (br s, 1H), 9.92 (br s, 1H), 8.49 (s, 1H), 7.51 (d, J=10.9 Hz, 1H), 7.30 (s, 1H), 7.25 (d, J=7.1 Hz, 1H), 5.33-5.15 (m, 1H), 4.55 (s, 2H), 3.51-3.24 (m, 7H), 2.34-2.00 (m, 4H), 1.93-1.75 (m, 1H), 1.04-0.91 (m, 2H), 0.81-0.70 (m, 2H); MS(ES+) m/z 550.1, 552.1 (M+1).

Example 522

Synthesis of 4-((4-((5-chloro-4-(trifluoromethyl)pyridin-2-yl)oxy)piperidin-1-yl)methyl)-5-cyclopropyl-N-(cyclopropylsulfonyl)-2-fluorobenzamide, trifluoroacetic acid salt

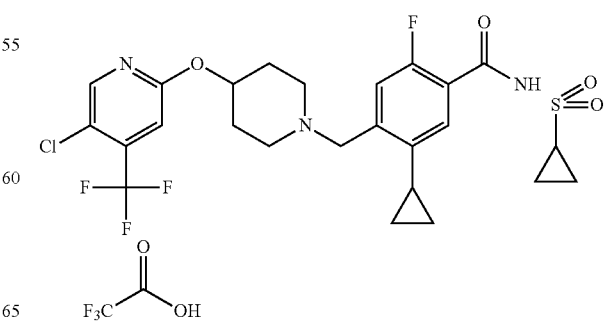

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 4-((4-((5-chloro-4-(trifluoromethyl)pyridin-2-yl)oxy)piperidin-1-yl)methyl)-5-cyclopropyl-2-fluorobenzoic acid hydrochloride, and purification by preparative HPLC, the title compound was obtained as a colorless solid (0.35 g, 51%): $^1$H NMR (300 MHz, DMSO-$d_6$) δ 12.24 (br s, 1H), 10.16 (br s, 1H), 8.48 (s, 1H), 7.53 (d, J=10.9 Hz, 1H), 7.30 (s, 1H), 7.23 (d, J=7.1 Hz, 1H), 5.32-5.14 (m, 1H), 4.56 (s, 1H), 3.52-3.24 (m, 4H), 3.11-3.00 (m, 5H), 2.33-1.98 (m, 4H), 1.96-1.82 (m, 1H), 1.17-1.06 (m, 4H), 1.03-0.94 (m, 2H), 0.81-0.71 (m, 2H); MS(ES+) m/z 576.1, 578.3 (M+1).

Example 523

Synthesis of 4-((4-((3-chloro-5-(trifluoromethyl)pyridin-2-yl)oxy)piperidin-1-yl)methyl)-5-cyclopropyl-2-fluoro-N-(methylsulfonyl)benzamide, trifluoroacetic acid salt

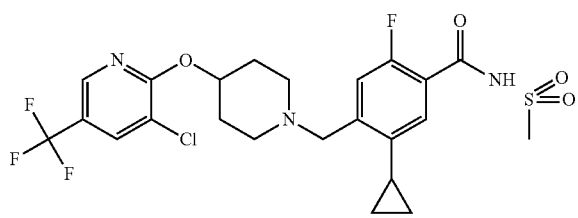

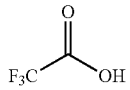

Step 1. Preparation of tert-butyl 4-((3-chloro-5-(trifluoromethyl)pyridin-2-yl)oxy)piperidine-1-carboxylate

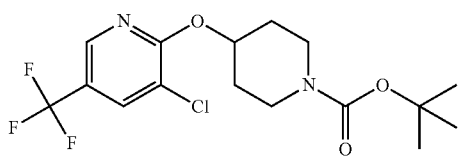 [SMILES: CC(C)(C)OC(=O)N1CCC(Oc2ncc(C(F)(F)F)cc2Cl)CC1]

Following the procedure as described in Example 521 step 1, and making variation as required so replace 2,5-dichloro-4-(trifluoromethyl)pyridine with 3-chloro-2-fluoro-5-(trifluoromethyl)pyridine, the title compound was obtained as a colorless solid (1.76 g, quant. yield): $^1$H NMR (300 MHz, CDCl$_3$) δ 8.25 (s, 1H), 7.80 (s, 1H), 5.38-5.28 (m, 1H), 3.87-3.72 (m, 4H), 3.04-2.90 (m, 2H), 1.86-1.72 (m, 2H), 1.40 (s, 9H); MS(ES-H m/z 324.9, 326.9 (M−55).

Step 2. Preparation of tert-butyl 4-((4-((3-chloro-5-(trifluoromethyl)pyridin-2-yl)oxy)piperidin-1-yl)methyl)-5-cyclopropyl-2-fluorobenzoate

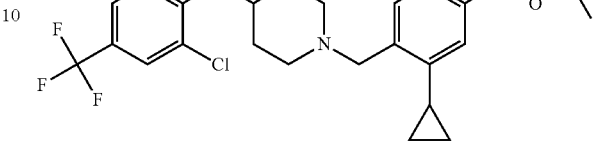

Following the procedure as described in Example 521 step 2, and making variation as required to replace tert-butyl 4-((5-chloro-4-(trifluoromethyl)pyridin-2-yl)oxy)piperidine-1-carboxylate with tert-butyl 4-((3-chloro-5-(trifluoromethyl)pyridin-2-yl)oxy)piperidine-1-carboxylate, the title compound was obtained as a colorless solid (0.52 g, 25%): $^1$H NMR (300 MHz, CDCl$_3$) δ 8.29-8.26 (m, 1H), 7.81 (d, J=2.1 Hz, 1H), 7.48 (d, J=7.1 Hz, 1H), 7.19 (d, J=11.7 Hz, 1H), 5.28-5.19 (m, 1H), 3.66 (s, 2H), 2.79-2.68 (m, 2H); 2.46-2.35 (m, 2H), 2.09-1.82 (m, 5H), 1.56 (s, 9H), 0.96-0.87 (m, 2H), 0.65-0.58 (m, 2H); MS(ES+) m/z 529.3, 531.2 (M+1).

Step 3. Preparation of 4-((4-((3-chloro-5-(trifluoromethyl)pyridin-2-yl)oxy)piperidin-1-yl)methyl)-5-cyclopropyl-2-fluorobenzoic acid hydrochloride

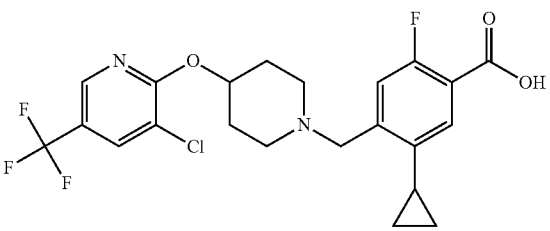

Following the procedure as described in Example 517 step 4, and making variation as required to replace tert-butyl 5-cyclopropyl-4-((4-(3,5-dichlorobenzyl)piperazin-1-yl)methyl)-2-fluorobenzoate with tert-butyl 4-((4-((3-chloro-5-(trifluoromethyl)pyridin-2-yl)oxy)piperidin-1-yl)methyl)-5-cyclopropyl-2-fluorobenzoate, the title compound was obtained as a colorless solid (0.50 g, quant. yield): MS(ES+) m/z: 472.9, 473.1 (M+1H).

Step 4. Preparation of 4-((4-((3-chloro-5-(trifluoromethyl)pyridin-2-yl)oxy)piperidin-1-yl)methyl)-5-cyclopropyl-2-fluoro-N-(methylsulfonyl)benzamide, trifluoroacetic acid salt

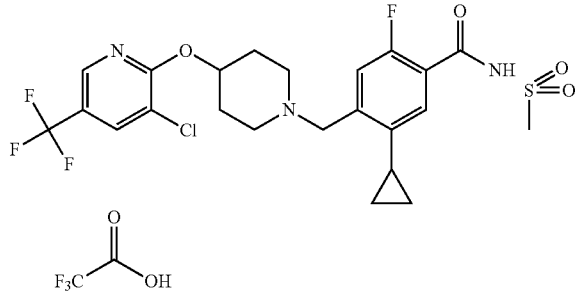

Following the procedure as described in Example 53 step 5, and making variation as required to replace with (S)-5-cyclopropyl-4-((3-(3,5-dichlorophenoxy)piperidin-1-yl)methyl)-2-fluorobenzoic acid with 4-((4-((3-chloro-5-(trifluoromethyl)pyridin-2-yl)oxy)piperidin-1-yl)methyl)-5-cyclopropyl-2-fluorobenzoic acid hydrochloride, and to replace cyclopropanesulfonamide with methylsulfonamide, and purification by preparative HPLC, the title compound was obtained as a colorless solid (0.11 g, 39%): $^1$H NMR (300 MHz, DMSO-$d_6$) δ 12.31 (br s, 1H), 9.87 (br s, 1H), 8.55-8.51 (m, 1H), 8.43-8.39 (m, 1H), 7.52 (d, J=11.1 Hz, 1H), 7.26 (d, J=7.1 Hz, 1H), 5.49-5.24 (m, 1H), 4.56 (s, 2H), 3.55-3.14 (m, 7H), 2.38-2.06 (m, 4H), 2.03-1.82 (m, 1H), 1.05-0.93 (m, 2H), 0.83-0.70 (m, 2H); MS(ES−) m/z 550.1, 552.1 (M+1).

Example 524

Synthesis of 4-((4-((3-chloro-5-(trifluoromethyl)pyridin-2-yl)oxy)piperidin-1-yl)methyl)-5-cyclopropyl-N-(cyclopropylsulfonyl)-2-fluorobenzamide, trifluoroacetic acid salt

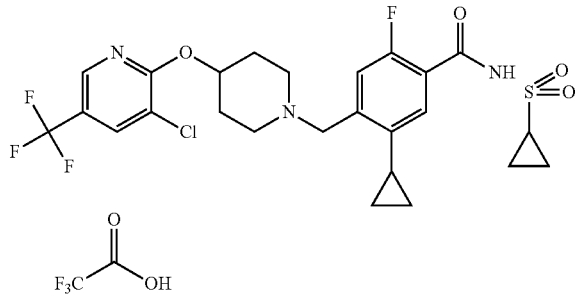

Following the procedure as described in Example 53 step 3, and making variation as required to replace (S)-5-cyclopropyl-4-((3-(3,5-dichlorophenoxy)piperidin-1-yl)methyl)-2-fluorobenzoic acid with 4-((4-((3-chloro-5-(trifluoromethyl)pyridin-2-yl)oxy)piperidin-1-yl)methyl)-5-cyclopropyl-2-fluorobenzoic acid hydrochloride, and purification by preparative HPLC, the title compound was obtained as a colorless solid (0.11 g, 38%): $^1$H NMR (300 MHz, DMSO-$d_6$) δ 12.22 (br s, 1H), 9.96 (brs, 1H), 8.55-8.51 (m, 1H), 8.43-8.39 (m, 1H), 7.55 (d, J=10.9 Hz, 1H), 7.24 (d, J=7.1 Hz, 1H), 5.48-5.25 (m, 1H), 4.56 (s, 2H), 3.56-3.16 (m, 4H), 3.11-3.00 (m, 1H), 2.38-2.07 (m, 4H), 2.01-1.82 (m, 1H), 1.15-1.06 (m, 4H), 1.04-0.94 (m, 2H), 0.80-0.72 (m, 2H); MS(ES+) m/z 576.1, 578.1 (M+1).

Example 525

Synthesis of 4-((4-((3-chloro-5-(trifluoromethyl)pyridin-2-yl)oxy)piperidin-1-yl)methyl)-5-cyclopropyl-N-(cyclopropylsulfonyl)-2-fluorobenzamide, trifluoroacetic acid salt

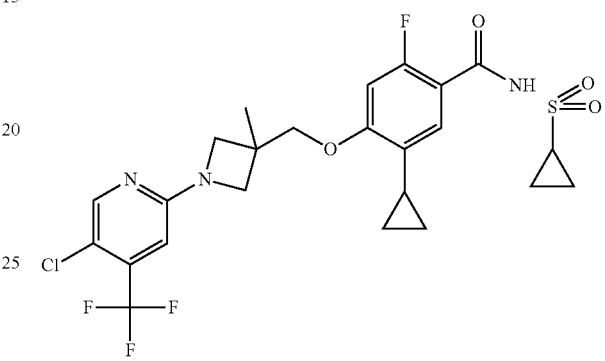

Step 1. Preparation of methyl 4-((1-(5-chloro-4-(trifluoromethyl)pyridin-2-yl)-3-methylazetidin-3-yl)methoxy)-5-cyclopropyl-2-fluorobenzoate

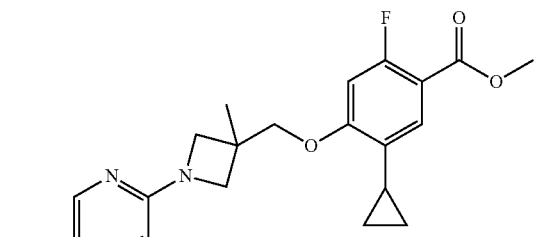

To a degassed mixture of methyl 5-cyclopropyl-2-fluoro-4-((3-methylazetidin-3-yl)methoxy)benzoate hydrochloride (0.15 g, 0.46 mmol), 2,5-dichloro-4-(trifluoromethyl)pyridine (0.15 g, 0.68 mmol) and cesium carbonate (0.58 g, 1.77 mmol) in anhydrous toluene (5.0 mL) was added rac-2,2'-bis(diphenylphosphino)-1,1'-binaphthyl (0.06 g, 0.091 mmol) and bis(dibenzylideneacetone)palladium(0) (0.03 g, 0.046 mmol). The resulting mixture was heated at 100° C. in a sealed tube for 30 hours. The reaction mixture was diluted with ethyl acetate (30 mL), washed with water (30 mL), saturated ammonium chloride (30 mL), brine (30 mL), dried over anhydrous sodium sulfate, filtered, and concentrated in vacuo. The residue was purified by HPLC to provide the title compound as a colorless solid (0.10 g, 46%): MS(ES+) m/z 473.1, 475.1 (M+1).

Step 2. Preparation of 4-((1-(5-chloro-4-(trifluoromethyl)pyridin-2-yl)-3-methylazetidin-3-yl)methoxy)-5-cyclopropyl-2-fluorobenzoic acid

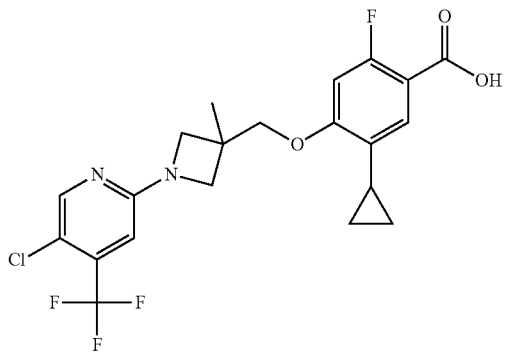 [SMILES: CC1(COc2cc(F)c(C(=O)O)cc2C2CC2)CN(c2cc(C(F)(F)F)c(Cl)cn2)C1]

To a mixture of methyl 4-((1-(5-chloro-4-(trifluoromethyl)pyridin-2-yl)-3-methylazetidin-3-yl)methoxy)-5-cyclopropyl-2-fluorobenzoate (0.10 g, 0.21 mmol) and lithium hydroxide monohydrate (0.09 g, 2.10 mmol) in tetrahydrofuran (20 mL) and water (10 mL) was refluxed for 7 hours. The mixture was diluted with ethyl acetate (50 mL), washed with 1.0 N hydrochloride acid solution (30 mL), brine (3×30 mL), dried over anhydrous sodium sulfate, filtered, and concentrated in vacuo to provide the title compound as a colorless solid (0.07 g, 67%): MS(ES+) m/z 458.9, 460.9 (M+1).

Step 3. Preparation of 4-((4-((3-chloro-5-(trifluoromethyl)piperidin-2-yl)oxy)piperidin-1-yl)methyl)-5-cyclopropyl-N-(cyclopropylsulfonyl)-2-fluorobenzamide, trifluoroacetic acid salt

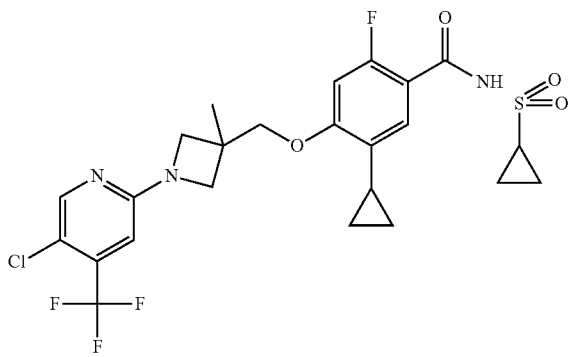

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 4-((1-(5-chloro-4-(trifluoromethyl)pyridin-2-yl)-3-methylazetidin-3-yl)methoxy)-5-cyclopropyl-2-fluorobenzoic acid, and purification by preparative HPLC, the title compound was obtained as a colorless solid, (0.03 g, 38%): $^1$H NMR (300 MHz, DMSO-$d_6$) δ11.81 (s, 1H), 8.27 (s, 1H), 7.06 (d, J=8.3 Hz, 1H), 6.96 (d, J=13.0 Hz, 1H), 6.75 (s, 1H), 4.07 (s, 2H), 4.03 (d, J=8.6 Hz, 2H), 3.79 (d, J=8.6 Hz, 2H), 3.08-2.98 (m, 1H), 1.71-1.59 (m, 1H), 1.40 (s, 3H), 1.12-1.03 (m, 4H), 0.59-0.53 (m, 4H); MS(ES+) m/z 562.1, 564.1 (M+1).

Example 526

Synthesis of 5-cyclopropyl-4-((4-((3,5-dichlorophenyl)sulfonyl)piperidin-1-yl)methyl)-2-fluoro-N-(methylsulfonyl)benzamide, trifluoroacetic acid salt

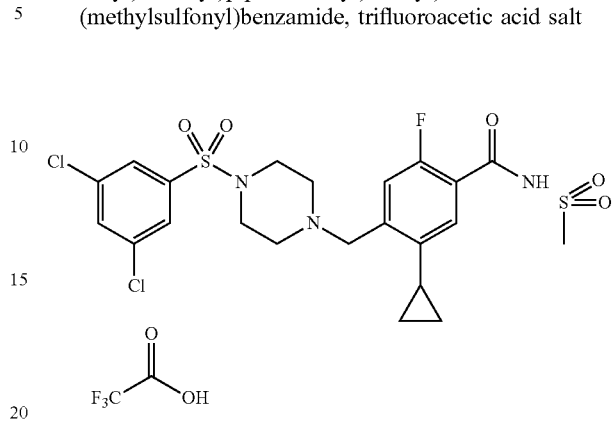

Step 1. Preparation of tert-butyl 4-((3,5-dichlorophenyl)sulfonyl)piperazine-1-carboxylate

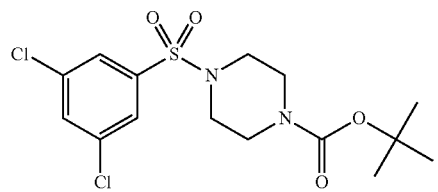 [SMILES: CC(C)(C)OC(=O)N1CCN(S(=O)(=O)c2cc(Cl)cc(Cl)c2)CC1]

To a solution of perfluorophenyl 3,5-dichlorobenzenesulfonate (2.30 g, 5.85 mmol) and triethylamine (1.63 mL, 11.7 mmol) in dichloromethane (50 mL) was added with tert-butyl piperazine-1-carboxylate (1.31 g, 7.02 mmol) at ambient temperature. The resulting mixture was stirred at ambient temperature for 18 hours under nitrogen, diluted with ethyl acetate (100 mL), washed with saturated ammonium chloride (2×50 mL), saturated sodium bicarbonate (50 mL), brine (30 mL), dried over anhydrous sodium sulfate, filtered and concentrated in vacuo. The residue was purified by flash chromatography (0-20% ethyl acetate in hexanes) to provide the title compound as a colorless solid (1.87 g, 81%): $^1$H NMR (300 MHz, CDCl$_3$) δ7.00-7.54 (m, 3H), 3.50 (d, J=4.8 Hz, 4H), 2.99 (t, J=5.1 Hz, 4H), 1.39 (s, 9H); MS(ES+) m/z 294.9, 296.9 (M−Boc+2).

Step 2. Preparation of 1-((3,5-dichlorophenyl)sulfonyl)piperazine hydrochloride

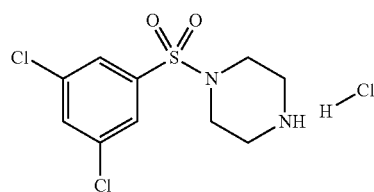

Following the procedure as described in Example 517 step 4, and making variation as required to replace tert-butyl 5-cyclopropyl-4-((4-(3,5-dichlorobenzyl)piperazin-1-yl)methyl)-2-fluorobenzoate with tert-butyl 4-((3,5-dichlorophenyl)sulfonyl)piperazine-1-carboxylate, the title compound was obtained as a colorless solid (1.57 g, quant. yield); MS(ES+) m/z 295.0, 297.0 (M+1).

Step 2. Preparation of tert-butyl 5-cyclopropyl-4-((4-((3,5-dichlorophenyl)sulfonyl)piperazin-1-yl)methyl)-2-fluorobenzoate

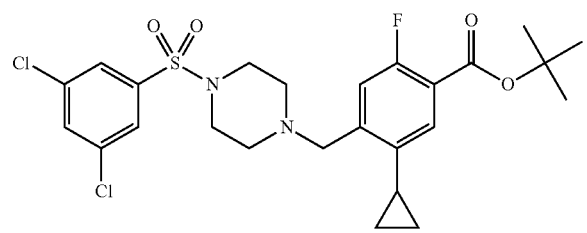

Following the procedure as described in Example 53 step 3, and making variation as required to replace (S)-3-(3,5-dichlorophenoxy)piperidine, trifluoroacetic acid salt with 1-((3,5-dichlorophenyl)sulfonyl)piperazine hydrochloride and purification by flash chromatography (0-20% ethyl acetate in hexanes), the title compound was obtained as an foam (1.81 g, 70%): $^1$H NMR (300 MHz, CDCl$_3$) δ 7.61-7.55 (m, 3H), 7.45 (d, J=7.5 Hz, 1H), 7.04 (d, J=11.7 Hz, 1H), 3.64 (s, 2H), 3.11-3.00 (m, 4H), 2.61-2.51 (m, 4H), 1.92-1.79 (m, 1H), 1.54 (s, 9H), 0.91-0.83 (m, 2H), 0.62-0.54 (m, 2H); MS(ES+) m/z 543.0, 345.0 (M+1).

Step 3. Preparation of 5-cyclopropyl-4-((4-((3,5-dichlorophenyl)sulfonyl)piperazin-1-yl)methyl)-2-fluorobenzoic acid hydrochloride

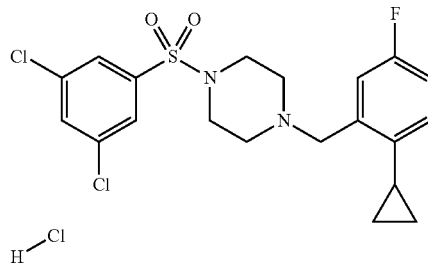

Following the procedure as described in Example 517 step 4, and making variation as required to replace tert-butyl 5-cyclopropyl-4-((4-(3,5-dichlorobenzyl)piperazin-1-yl)methyl)-2-fluorobenzoate with tert-butyl 5-cyclopropyl-4-((4-((3,5-dichlorophenyl)sulfonyl)piperazin-1-yl)methyl)-2-fluorobenzoate, the title compound was obtained as a colorless solid (1.74 g, quant. yield): MS (ES+) m/z 478.0, 489.0 (M+1).

Step 4. Preparation of 5-cyclopropyl-4-((4-((3,5-dichlorophenyl)sulfonyl)piperazin-1-yl)methyl)-2-fluoro-N-(methylsulfonyl)benzamide, trifluoroacetic acid salt

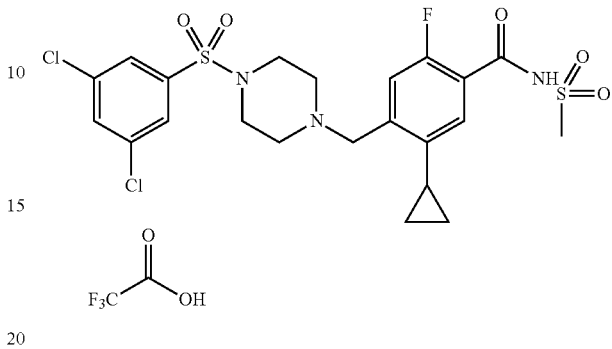

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-((4-((3,5-dichlorophenyl)sulfonyl)piperazin-1-yl)methyl)-2-fluorobenzoic acid hydrochloride, and to replace cyclopropanesulfonamide with methylsulfonamide, and purification by preparative HPLC, the title compound was obtained as a colorless solid (0.18 g, 43%): $^1$H NMR (300 MHz, DMSO-d$_6$) δ 11.97 (br s, 1H), 8.07-8.04 (m, 1H), 7.74 (d, J=1.7 Hz, 2H), 7.32 (d, J=11.3 Hz, 1H), 7.21 (d, J=7.2 Hz, 1H), 5.68 (br s, 1H), 4.20 (s, 2H), 3.32 (s, 3H), 3.29-2.90 (m, 8H), 2.08-1.97 (m, 1H), 0.97-0.87 (m, 2H), 0.72-0.64 (m, 2H); MS(ES+) m/z 504.0, 566.0 (M+1).

Example 527

Synthesis of 5-cyclopropyl-N-(cyclopropylsulfonyl)-4-((4-((3,5-dichlorophenyl)sulfonyl)piperazin-1-yl)methyl)-2-fluorobenzamide, trifluoroacetic acid salt

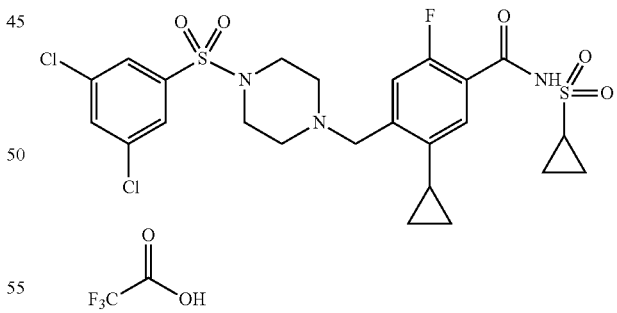

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-((4-((3,5-dichlorophenyl)sulfonyl)piperazin-1-yl)methyl)-2-fluorobenzoic acid hydrochloride, and purification by preparative HPLC, the title compound was obtained as a colorless solid (0.19 g, 43%): $^1$H NMR (300 MHz, DMSO-d$_6$) δ 12.01 (brs, 1H), 8.04 (dd, J=1.7 Hz, 1H), 7.74 (d, J=1.7 Hz, 2H), 7.31 (0.9-11.4 Hz, 1H), 7.19 (d, J=7.1 Hz, 1H), 5.05 (brs, 1H), 4.13 (s, 2H), 3.29-2.76 (m, 9H), 2.07-1.95 (m, 1H), 1.14-1.05 (m, 4H), 0.96-0.87 (m, 2H), 0.71-0.63 (m, 2H): MS(ES+) m/z 590.0, 592.0 (M+1).

Example 528

Synthesis of 5-cyclopropyl-N-(cyclopropylsulfonyl)-4-(((1R,3s,5S)-3-(3,5-dichlorophenoxy)-8-azabicyclo[3.2.1]octan-8-yl)methyl)-2-fluorobenzamide, trifluoroacetic acid salt

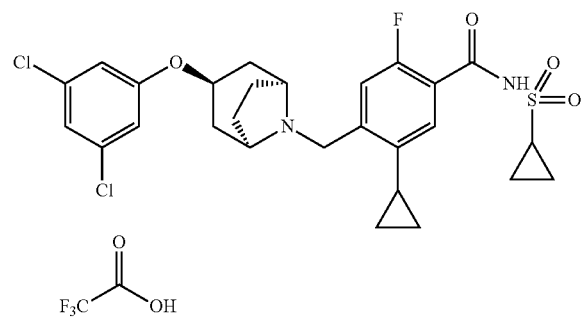

Step 1. Preparation of tert-butyl 5-cyclopropyl-2-fluoro-4-(((1R,3r,5S)-3-hydroxy-8-azabicyclo[3.2.1]octan-8-yl)methyl)benzoate

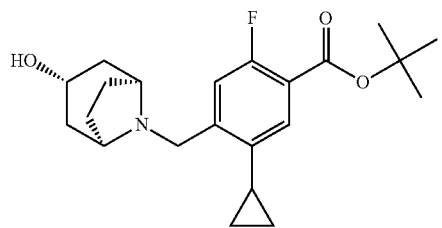 [SMILES: CC(C)(C)OC(=O)c1cc(C2CC2)c(CN2[C@@H]3CC[C@H]2C[C@@H](O)C3)cc1F]

Following the procedure as described in Example 470 Step 4, and making variation as required to replace (1R,3r,5S)-3-(3-chloro-2-fluoro-5-(trifluoromethyl)phenoxy)-8-azabicyclo[3.2.1]-octane with nortropine, the title compound was obtained as a yellowish solid (2.16 g, 99%): $^1$H NMR (300 MHz, CDCl$_3$) δ7.46 (d, J=7.3 Hz, 1H), 7.31 (d, J=12.2 Hz, 1H), 4.09-4.03 (m, 1H), 3.63 (s, 2H), 3.13-3.07 (m, 2H), 2.16-1.94 (m, 6H), 1.92-1.81 (m, 1H), 1.70 (br s, 1H), 1.65 (br s, 1H), 1.57-1.57 (m, 1H), 1.56 (s, 9H), 0.91-0.83 (m, 2H), 0.62-0.56 (m, 2H).

Step 2. Preparation of tert-butyl 5-cyclopropyl-2-fluoro-4-(((1R,3r,5S)-3-((methylsulfonyl)oxy)-8-azabicyclo[3.2.1]octan-8-yl)methyl)benzoate

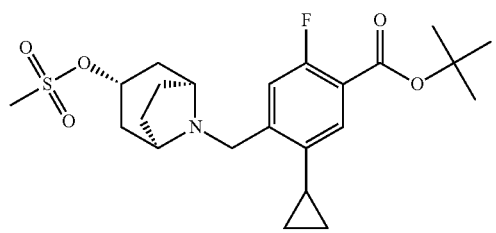 [SMILES: CC(C)(C)OC(=O)c1cc(C2CC2)c(CN2[C@@H]3CC[C@H]2C[C@@H](OS(C)(=O)=O)C3)cc1F]

Following the procedure as described in Example 519 step 2, and making variation as required to replace tert-butyl 5-cyclopropyl-2-fluoro-4-((4-hydroxypiperidin-1-yl)methyl)benzoate with tert-butyl 5-cyclopropyl-2-fluoro-4-(((1R,3r,5S)-3-hydroxy-8-azabicyclo[3.2.1]octan-8-yl)methyl)benzoate, the title compound was obtained as an foam (1.21 g, quant. yield): MS(ES+) m/z 454.2 (M+1).

Step 3. Preparation of tert-butyl 5-cyclopropyl-4-(((1R,3s,5S)-3-(3,5-dichlorophenoxy)-8-azabicyclo[3.2.1]octan-8-ylmethyl)-2-fluorobenzoate

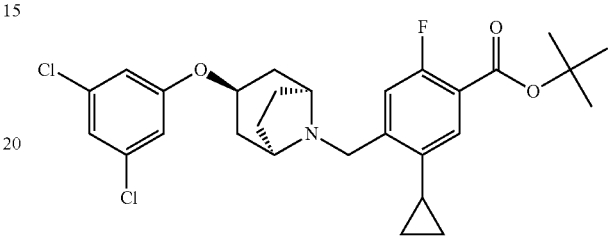

Following the procedure as described in Example 519 step 3, and making variation as required to replace 4-chloro-3-(trifluoromethyl)phenol with 3,5-dichlorophenol and to replace tert-butyl 5-cyclopropyl-2-fluoro-4-((4-((methylsulfonyl)oxypiperidin-1-yl)methyl)benzoate with tert-butyl 5-cyclopropyl-2-fluoro-4-(((1R,3r,5S)-3-((methylsulfonyl)oxy)-8-azabicyclo[3.2.1]octan-8-yl)methyl)benzoate, the title compound was obtained as an colorless oil (0.70 g, 36%); $^1$H NMR (300 MHz, CDCl$_3$) δ 7.47 (d, J=7.3 Hz, 1H), 7.30 (d, J=12.1 Hz, 1H), 6.91-6.87 (m, 1H), 6.76-6.69 (m, 2H), 4.53-4.40 (m, 1H), 3.75 (s, 2H), 3.32-3.24 (m, 2H), 2.15-1.76 (m, 7H), 1.72-1.64 (m, 2H), 1.57 (s, 9H), 0.94-0.85 (m, 2H), 0.64-0.56 (m, 2H); MS(ES+) m/z 520.2, 522.2 (M+1).

Step 4. Preparation of 5-cyclopropyl-4-(((1R,3s,5S)-3-(3,5-dichlorophenoxy)-8-azabicyclo[3.2.1]octan-8-yl)methyl)-2-fluorobenzoic acid hydrochloride

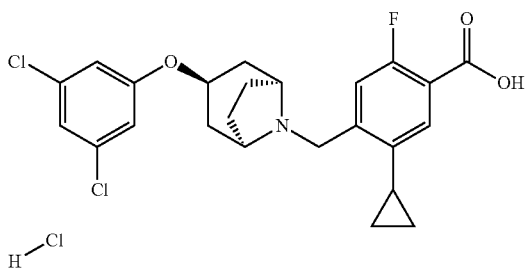

Following the procedure as described in Example 518 step 4, and making variation as required to replace tert-butyl 5-cyclopropyl-4-((4-(3,5-dichlorobenzyl)piperazin-1-yl)methyl)-2-fluorobenzoate with tert-butyl 5-cyclopropyl-4-(((1R,3s,5S)-3-(3,5-dichlorophenoxy)-8-azabicyclo[3.2.1]octan-8-yl)methyl)-2-fluorobenzoate, the title compound was obtained as a colorless solid (0.67 g, quant. yield): MS(ES+) m/z 464.1, 466.1 (M+1).

Step 5. Preparation of 5-cyclopropyl-N-(cyclopropylsulfonyl)-4-(((1R,3s,5S)-3-(3,5-dichlorophenoxy)-8-azabicyclo[3.2.1]octan-8-yl)methyl)-2-fluorobenzamide, trifluoroacetic acid salt

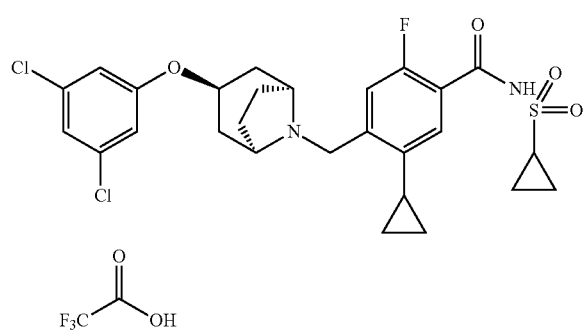

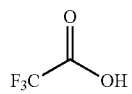

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-(((1R,3s,5S)-3-(3,5-dichlorophenoxy)-8-azabicyclo[3.2.1]octan-8-yl)methyl)-2-fluorobenzoic acid hydrochloride, and purification by preparative HPLC, the title compound was obtained as a colorless solid (0.04 g, 4%): $^1$H NMR (300 MHz, DMSO-$d_6$) δ 12.25 (br s, 1H), 9.63 (brs, 1H), 7.57 (d, J=11.4 Hz, 1H), 7.26 (d, J=7.1 Hz, 1H), 7.16-7.09 (m, 3H), 4.97-4.83 (m, 1H), 4.38 (s, 2H), 4.03 (s, 2H), 3.10-2.98 (m, 1H), 2.42-2.17 (m, 6H), 2.15-1.94 (m, 3H), 1.17-1.06 (m, 4H), 1.03-0.93 (m, 2H), 0.82-0.72 (m, 2H); MS(ES+) m/z 567.1, 569.1 (M+1).

Example 529

Synthesis of (R)-4-((1-(2-(3-chlorophenyl)propan-2-yl)piperidin-3-yl)oxy)-5-cyclopropyl-2-fluoro-N-(methylsulfonyl)benzamide, trifluoroacetic acid salt

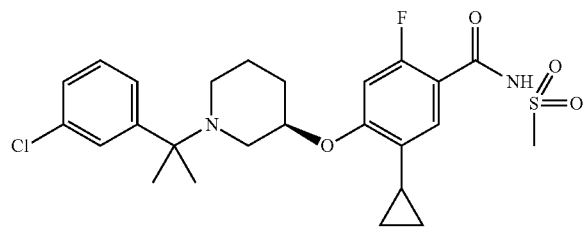

Step 1. Preparation of methyl (R)-5-((1-(2-(3-chlorophenyl)propan-2-yl)piperidin-3-yl)oxy)-5-cyclopropyl-2-fluorobenzoate

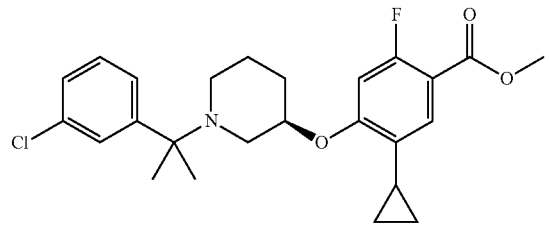 [SMILES: COC(=O)c1cc(C2CC2)c(O[C@@H]2CCCN(C(C)(C)c3cccc(Cl)c3)C2)cc1F]

Following the procedure as described in Example 493 step 1, and making variation as required to replace 3,5-dichlorobenzoyl chloride with 3-chlorobenzoyl chloride, the title compound was obtained as a yellowish oil (0.72 g, 24% in 2 steps): $^1$H NMR (300 MHz, CDCl$_3$) δ 7.53-7.48 (m, 1H), 7.42-7.35 (m, 2H), 7.21-7.16 (m, 2H), 6.39 (d, J=1.30 Hz, 1H), 4.35-4.24 (m, 1H), 3.85 (s, 3H), 2.96-2.87 (m, 1H), 2.74-2.64 (m, 1H), 2.34-2.20 (m, 2H), 2.09-1.97 (m, 2H), 1.86-1.77 (m, 1H), 1.63-1.50 (m, 2H), 1.30 (s, 3H), 1.30 (s, 3H), 0.92-0.84 (m, 2H), 0.65-0.59 (m, 2H); MS (ES+) m/z 446.2, 448.2 (M+1).

Step 2. Preparation of (R)-4-((1-(2-(3-chlorophenyl)propan-2-yl)piperidin-3-yl)oxy)-5-cyclopropyl-2-fluorobenzoic acid

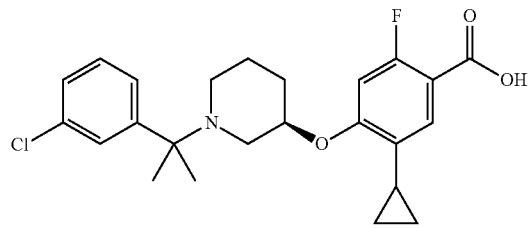 [SMILES: CC(C)(c1cccc(Cl)c1)N1CCC[C@@H](Oc2cc(F)c(C(=O)O)cc2C2CC2)C1]

Following the procedure as described in Example 481 step 5 and making variation as required to replace methyl 4-((1-(3-chloro-5-(trifluoromethyl)pyridin-2-yl)-3-methylazetidin-3-yl)methoxy)-5-cyclopropyl-2-fluorobenzoate with (R)-methyl 4-((1-(2-(3-chlorophenyl)propan-2-yl)piperidin-3-yl)oxy)-5-cyclopropyl-2-fluorobenzoate, the title compound was obtained as an orange amorphous solid (0.47 g, 68%): MS(ES+) m/z 432.2, 434.2 (M+1).

Step 3. Preparation of (R)-4-((1-(2-(3-chlorophenyl)propan-2-yl)piperidin-3-yl)oxy)-5-cyclopropyl-2-fluoro-N-(methylsulfonyl)benzamide, trifluoroacetic acid salt

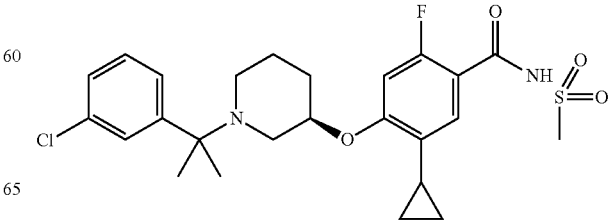

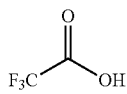

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with (R)-4-((1-(2-(3-chlorophenyl)propan-2-yl)piperidin-3-yl)oxy)-5-cyclopropyl-2-fluorobenzoic acid, and to replace cyclopropanesulfonamide with methylsulfonamide, and purification by preparative HPLC, the title compound was obtained as a colorless solid (0.08 g, 24%): $^1$H NMR (300 MHz, CDCl$_5$) δ 12.12 (br s, 1H), 8.85-8.65 (m, 1H), 7.67-7.58 (m, 1H), 7.57-7.49 (m, 2H), 7.46-7.40 (m, 2H), 6.96 (d, J=14.0 Hz, 1H), 5.18-5.05 (m, 1H), 3.78-3.66 (m, 1H), 3.47-3.32 (m, 4H), 2.60-2.43 (m, 2H), 2.38-2.08 (m, 2H), 2.03-1.93 (m, 2H), 1.90 (s, 3H), 1.88 (s, 3H), 1.57-1.41 (m, 1H), 0.93-0.82 (m, 2H), 0.65-0.56 (m, 2H); MS(ES+) m/z 509.1, 511.1 (M+1).

Example 530

Synthesis of (R)-4-((1-(2-(3-chlorophenyl)propan-2-yl)piperidin-3-yl)oxy)-5-cyclopropyl-N-(cyclopropylsulfonyl)-2-fluorobenzamide, trifluoroacetic acid salt

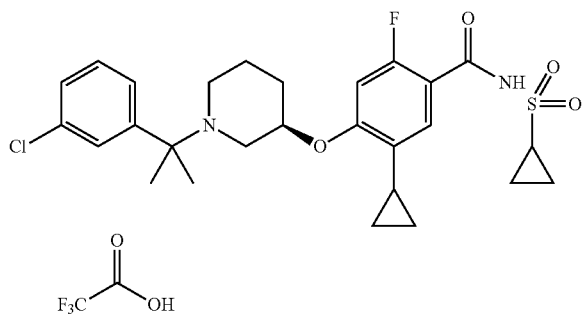

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with R)-4-((1-(2-(3-chlorophenyl)propan-2-yl)piperidin-3-yl)oxy)-5-cyclopropyl-2-fluorobenzoic acid, and purification by preparative HPLC, the title compound was obtained as a colorless solid (0.08 g, 23%): $^1$H NMR (300 MHz, CDCl$_3$) δ 11.92 (br s, 1H), 8.72 (d, J=15.5 Hz, 1H), 7.67-7.58 (m, 1H), 7.57-7.49 (m, 2H), 7.47-7.40 (m, 2H), 6.96 (d, =14.0 Hz, 1H), 5.18-5.04 (m, 1H), 3.78-3.65 (m, 1H), 3.46-5.34 (m, 1H), 3.11-3.01 (m, 1H), 2.61-2.43 (m, 2H), 2.37-2.10 (m, 2H), 2.04-1.93 (m, 2H). 1.91 (s, 3H), 1.87 (s, 3H), 1.57-1.39 (m, 3H), 1.16-1.07 (m, 2H), 0.92-0.84 (m, 2H), 0.64-0.57 (m, 2H); MS(ES+) m/z 535.2, 537.1 (M+1).

Example 531

Synthesis of 5-cyclopropyl-N-(cyclopropylsulfonyl)-4-((4-((3,5-dichlorophenyl)thio)piperidin-1-yl)methyl)-2-fluorobenzamide, trifluoroacetic acid salt

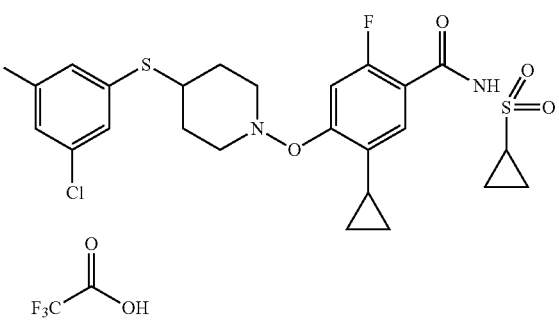

Step 1. Preparation of tert-butyl 4-((methylsulfonyl)oxy)piperidine-1-carboxylate

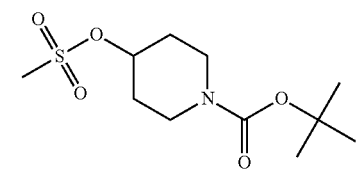 [SMILES: CC(C)(C)OC(=O)N1CCC(OS(C)(=O)=O)CC1]

Following the procedure as described in Example 519 step 2, and making variation as required to replace tert-butyl 5-cyclopropyl-2-fluoro-4-((4-hydroxypiperidin-1-yl)methyl)benzoate with tert-butyl 4-hydroxypiperidine-1-carboxylate, the title compound was obtained as a colorless solid (7.32 g, quant. yield): $^1$H NMR (300 MHz, CDCl$_3$) δ 4.88-4.78 (m, 1H), 3.71-3.60 (m, 2H), 3.30-3.19 (m, 2H), 2.99 (s, 3H), 1.97-1.86 (m, 2H), 1.82-1.70 (m, 2H) 1.41 (s, 9H); MS(ES+) m/z 302.1 (M+23).

Step 2. Preparation of tert-butyl 4-((3,5-dichlorophenyl)thio)piperidine-1-carboxylate

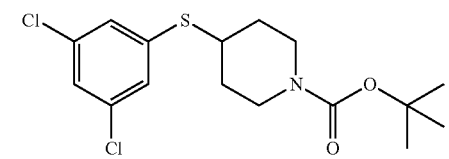 [SMILES: CC(C)(C)OC(=O)N1CCC(Sc2cc(Cl)cc(Cl)c2)CC1]

Following the procedure as described in Example 519 step 3, and making variation as required to replace 4-chloro-3-(trifluoromethyl)phenol with 3,5-dichlorobenzenethiol and tert-butyl 5-cyclopropyl-2-fluoro-4-((4-((methylsulfonyl)oxy)-1-yl)methyl)benzoate with tert-butyl 4-((methylsulfinyl)oxy)piperidin-1-carboxylate, the title compound was obtained as an colorless solid (3.66 g, 64%): $^1$H NMR (300 MHz, CDCl$_3$) δ 7.22-7.16 (m, 3H), 3.99-3.81 (m, 2H), 3.29-3.17 (m, 1H), 2.98-2.85 (m, 2H), 1.94-1.83 (m, 2H), 1.58-1.45 (m, 2H), 1.41 (s, 9H); MS(ES+) m/z 306.0, 308.0 (M−Boc+2H).

Step 3. Preparation of 4-((3,5-dichlorophenyl)thio)piperidine hydrochloride

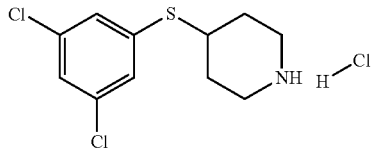

Following the procedure as described in Example 517 step 2, and making variation as required to replace tert-butyl 4-(3,5-dichlorobenzyl)piperazine-1-carboxylate with tert-butyl 4-((3,5-dichlorophenyl)thio)piperidine-1-carboxylate, the title compound was obtained as a colorless solid (0.19 g, quant. yield): MS(ES+) m/z: 262.1, 264.1. (M+1).

Step 4. Preparation of tert-butyl 5-cyclopropyl-4-((4-((3,5-dichlorophenyl)thio)piperidin-1-yl)methyl)-2-fluorobenzoate

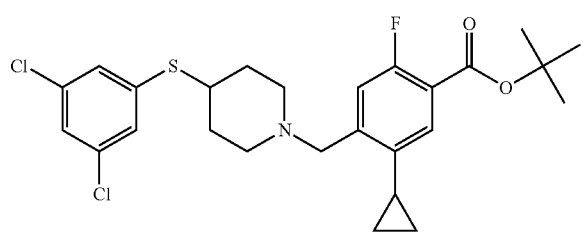 [SMILES: CC(C)(C)OC(=O)c1cc(C2CC2)c(CN2CCC(Sc3cc(Cl)cc(Cl)c3)CC2)cc1F]

Following the procedure as described in Example 53 step 3, and making variation as required to replace (S)-3-(3,5-dichlorophenoxy)piperidine, trifluoroacetic acid salt with 4-((3,5-dichlorophenyl)thio)piperidine hydrochloride, the title compound was obtained as an oil (0.29 g, quant. yield): MS(ES+) m/z 510.0, 512.0 (M+1).

Step 5. Preparation of 5-cyclopropyl-4-((4-((3,5-dichlorophenyl)thio)piperidin-1-yl)methyl)-2-fluorobenzoic acid hydrochloride

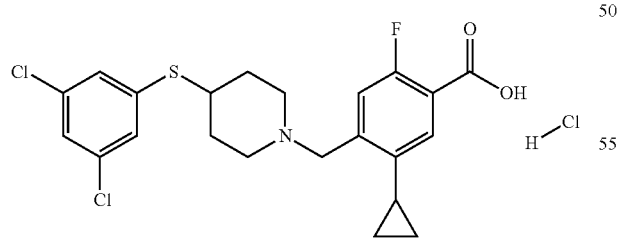

Following the procedure as described in Example 517 step 2, and making variation as required to replace tert-butyl 4-(3,5-dichlorobenzyl)piperazine-1-carboxylate with tert-butyl 5-cyclopropyl-4-((4-((3,5-dichlorophenyl)thio)piperidin-1-yl)methyl)-2-fluorobenzoate, the title compound was obtained as a colorless solid (0.28 g, quant. yield): MS(ES+) m/z 454.0, 456.1 (M+1).

Step 6. Preparation of 5-cyclopropyl-N-(cyclopropylsulfonyl)-4-((4-((3,5-dichlorophenyl)thio)piperidin-1-yl)methyl)-2-fluorobenzamide, trifluoroacetic acid salt

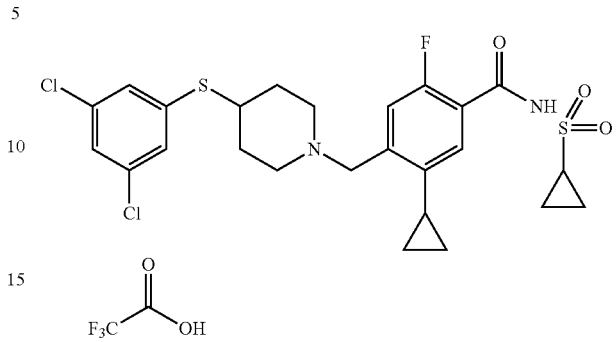

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-((4-((3,5-dichlorophenyl)thio)piperidin-1-yl)methyl)-2-fluorobenzoic acid hydrochloride, and purification by preparative HPLC, the title compound was obtained as a colorless solid (0.09 g, 22%): $^1$H NMR (300 MHz, CDCl$_3$) δ 9.43 (br s, 2H), 7.71 (d, J=7.2 Hz, 1H), 7.43 (d, J=12.1 Hz, 1H), 7.27-7.20 (m, 3H), 4.43 (s, 2H), 3.61-3.15 (m, 5H), 3.09-2.99 (m, 1H), 2.50-2.20 (m, 2H), 2.07-1.91 (m, 2H), 1.91-1.81 (m, 1H), 1.46-1.37 (m, 2H), 1.19-1.04 (m, 4H), 0.79-0.69 (m, 2H); MS (ES+) m/z 557.1, 559.1 (M+1).

Example 532

Synthesis of 5-cyclopropyl-4-((4-((3,5-dichlorophenyl)sulfonyl)piperidin-1-yl)methyl)-2-fluoro-N-(methylsulfonyl)benzamide, trifluoroacetic acid salt

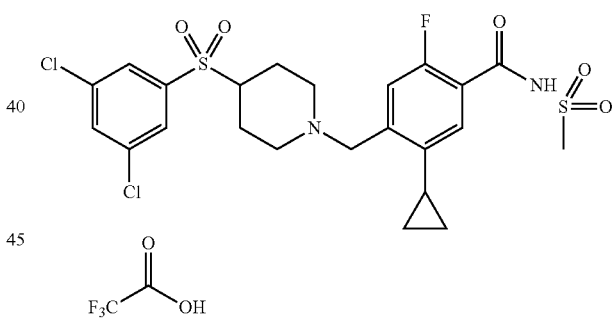

Step 1. Preparation of tert-butyl 4-((3,5-dichlorophenyl)sulfonyl)piperidine-1-carboxylate and tert-butyl 4-((3,5-dichlorophenyl)sulfinyl)piperidine-1-carboxylate

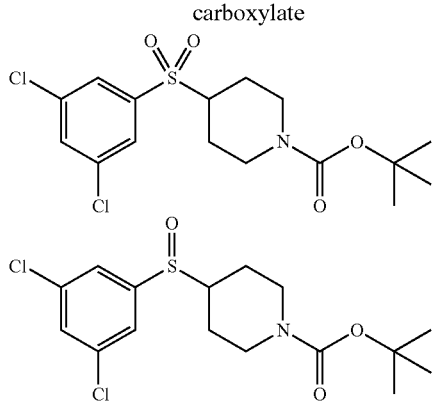

To a solution of tert-butyl 4-((3,5-dichlorophenyl)thio)piperidine-1-carboxylate (3.66 g, 10.10 mmol) in dichloromethane (100 mL) at 0° C. was added m-chloroperoxybenzoic acid (77%, 3.40 g, 15.15 mmol). The resulting mixture was stirred at 0° C. for 3 hours and then concentrated in vacuo to about 40 mL volume. The mixture was diluted with ethyl acetate (150 mL), washed with saturated sodium thiosulfate (100 mL), 1.0 M aqueous sodium hydroxide solution (3×50 mL), brine (50 mL), dried over anhydrous sodium sulfate, filtered the solid, and concentrated in vacuo. The residue was purified by flash chromatography (0-50% ethyl acetate in hexanes) to provide tert-butyl 4-((3,5-dichlorophenyl)sulfonyl)piperidine-1-carboxylate (2.12 g, 53%) and tert-butyl 4-((3,5-dichlorophenyl)sulfinyl)piperidine-1-carboxylate (1.35 g, 34%) as a colorless solids. Analytical data for tert-butyl-4-((3,5-dichlorophenyl)sulfonyl)piperidine-1-carboxylate: $^1$H NMR (300 MHz, CDCl$_3$) δ 7.73-7.68 (m, 2H), 7.64-7.60 (m, 1H), 4.31-4.15 (m, 2H), 3.10-2.97 (m, 1H), 2.72-2.56 (m, 2H), 1.99-1.89 (m, 2(1), 1.67-1.51 (m, 2H), 1.41 (s, 9H): MS (ES+) m/z 294.0, 296.0 (M−Boc+H). Analytical data for tert butyl 4-((3,5-dichlorophenyl)sulfinyl)piperidine-1-carboxylate: $^1$H NMR (300 MHz, CDCl$_3$) δ 7.46-7.44 (m, 1H), 7.43-7.41 (m, 2H), 4.27-4.12 (m, 2H), 2.76-2.59 (m, 3H), 1.86-1.76 (m, 1H), 1.68-1.54 (m, 3H), 1.40 (s, 9H); MS(ES+) m/z 378.0, 380.0 (M+1).

Step 2. Preparation of 4-((3,5-dichlorophenyl)sulfonyl)piperidine hydrochloride

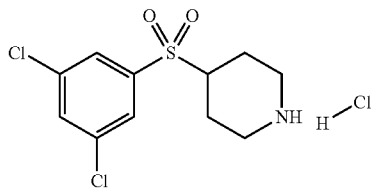

Following the procedure as described in Example 517 step 2, and making variation as required to replace tert-butyl 4-(3,5-dichlorobenzyl)piperazine-1-carboxylate with tert-butyl 4-((3,5-dichlorophenyl)sulfonyl)piperidine-1-carboxylate, the title compound was obtained as a colorless solid (1.78 g, quant. yield): MS(ES+) m/z 294.1, 296.1 (M+1).

Step 3. Preparation of tert-butyl 5-cyclopropyl-4-((4-((3,5-dichlorophenyl)sulfonyl)piperidin-1-yl)methyl)-2-fluorobenzoate

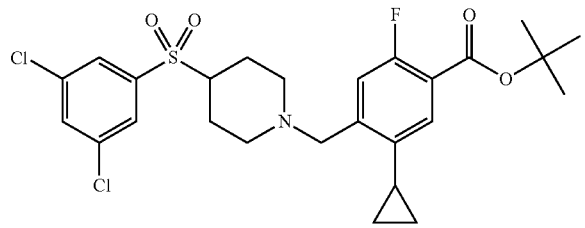 [SMILES: CC(C)(C)OC(=O)c1cc(C2CC2)c(CN2CCC(S(=O)(=O)c3cc(Cl)cc(Cl)c3)CC2)cc1F]

Following the procedure as described in Example 53 step 3, and making variation as required to replace (S)-3-(3,5-dichlorophenoxy)piperidine, trifluoroacetic acid salt with 4-((3,5-dichlorophenyl)sulfonyl)piperidine hydrochloride, the title compound was obtained as a colorless solid (2.63, quant. yield): MS(ES+) m/z 542.0, 544.0 (M+1).

Step 4. Preparation of 5-cyclopropyl-4-((4-((3,5-dichlorophenyl)sulfonyl)piperidin-1-yl)methyl)-2-fluorobenzoic acid hydrochloride

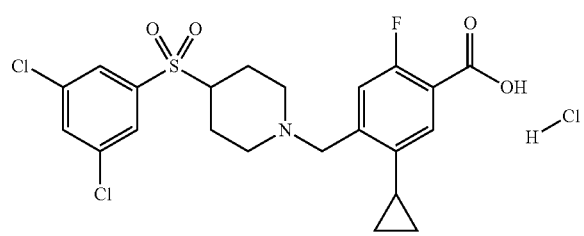

Following the procedure as described in Example 517 step 2, and making variation as required to replace tert-butyl 4-(3,5-dichlorobenzyl)piperazine-1-carboxylate with tert-butyl 5-cyclopropyl-4-((4-((3,5-dichlorophenyl)sulfonyl)piperidin-1-yl)methyl)-2-fluorobenzoate, the title compound was obtained as a colorless solid (2.59 g, 90%); MS(ES+) m/z 486.0, 488.1 (M+1).

Step 5. Preparation of 5-cyclopropyl-4-((4-((3,5-dichlorophenyl)sulfonyl)piperidin-1-yl)methyl)-2-fluoro-N-(methylsulfonyl)benzamide, trifluoroacetic acid salt

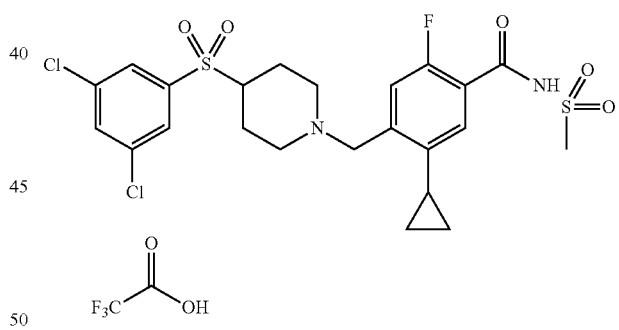

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-((4-((3,5-dichlorophenyl)sulfonyl)piperidin-1-yl)methyl)-2-fluorobenzoic acid hydrochloride, and to replace cyclopropanesulfonamide with methylsulfonamide, and purification by preparative HPLC, the title compound was obtained as a colorless solid (0.11 g, 20%): $^1$H NMR (300 MHz, DMSO-d$_6$) δ 12.17 (brs, 1H), 9.85 (br s, 1H), 8.12 (dd, J=1.7, 1.7 Hz, 1H), 7.84 (d, J=1.7 Hz, 2H), 7.39 (d, J=11.1 Hz, 1H), 7.23 (d, J=7.1 Hz, 1H), 4.32 (s, 2H), 3.75-3.59 (m, 3H), 3.32 (s, 3H), 2.98-2.75 (m, 2H), 2.10-1.96 (m, 3H), 1.88-1.68 (m, 2H), 0.98-0.88 (m, 2H), 0.76-0.66 (m, 2H); MS(ES+) m/z 563.0, 565.0 (M+1).

Example 533

Synthesis of 5-cyclopropyl-N-(cyclopropylsulfonyl)-4-((4-((3,5-dichlorophenyl)sulfonyl)piperidin-1-yl)methyl)-2-fluorobenzamide, trifluoroacetic acid salt

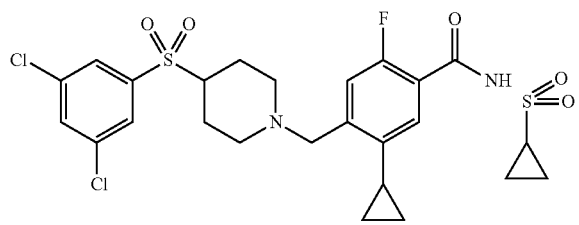

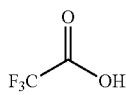

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-((4-((3,5-dichlorophenyl)sulfonyl)piperidin-1-yl)methyl)-2-fluorobenzoic acid hydrochloride, and purification by preparative HPLC, the title compound was obtained as a colorless solid (0.04 g, 7%): $^1$H NMR (300 MHz, CDCl$_3$+10% CD$_3$OD) δ 7.65-7.61 (m, 2H), 7.60-7.57 (m, 1H), 7.38 (d, J=7.1 Hz, 1H), 7.16 (d, J=11.4 Hz, 1H), 4.02 (s, 2H), 3.28-3.20 (m, 2H), 3.17-3.06 (m, 1H), 3.02-2.91 (m, 1H), 2.66-2.51 (m, 2H), 2.11-2.00 (m, 2H), 1.97-1.74 (m, 3H), 1.34-1.25 (m, 2H), 1.08-0.98 (m, 2H), 0.95-0.86 (m, 2H), 0.62-0.54 (m, 2H); MS(ES+) m/z 589.1, 591.1 (M+1).

Example 534

Synthesis of 5-cyclopropyl-4-((4-((3,5-dichlorophenyl)sulfinyl)piperidin-1-yl)methyl)-2-fluoro-N-(methylsulfonyl)benzamide, trifluoroacetic acid salt

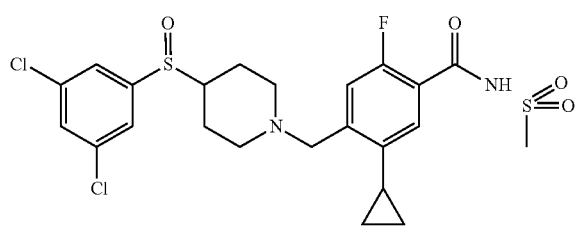

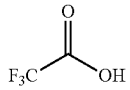

Step 1. Preparation of 4-((3,5-dichlorophenyl)sulfinyl)piperidine hydrochloride

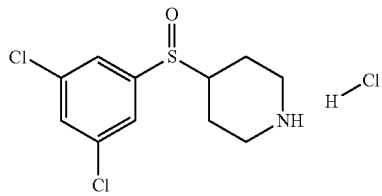

Following the procedure as described in Example 517 step 2, and making variation as required to replace tert-butyl 4-(3,5-dichlorobenzyl)piperazine-1-carboxylate with tert-butyl 4-((3,5-dichlorophenyl)sulfinyl)piperidine-1-carboxylate, the title compound was obtained as a colorless solid (1.12 g, quant. yield): MS(ES+) m/z: 278.1, 280.1 (M+1).

Step 2. Preparation of tert-butyl 5-cyclopropyl-4-((4-((3,5-dichlorophenyl)sulfinyl)piperidin-1-yl)methyl)-2-fluorobenzoate

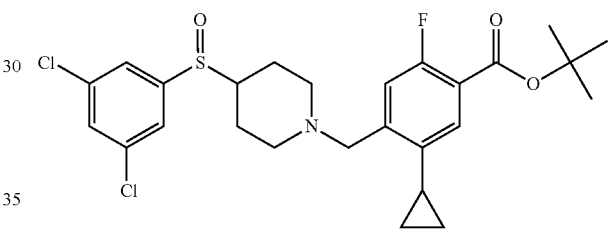

Following the procedure as described in Example 53 step 3, and making variation as required to replace (S)-3-(3,5-dichlorophenoxy)piperidine, trifluoroacetic acid salt with 4-((3,5-dichlorophenyl)sulfinyl)piperidine hydrochloride, the title compound was obtained as a colorless solid (1.40 g, 80%): MS(ES+) m/z 526.1, 528.1 (M+1).

Step 3. Preparation of 5-cyclopropyl-4-((4-((3,5-dichlorophenyl)sulfinyl)piperidin-1-yl)methyl)-2-fluorobenzoic acid hydrochloride

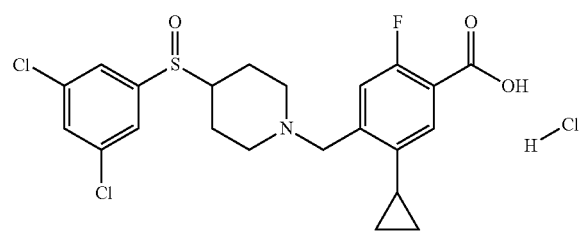 [SMILES: O=C(O)c1cc(C2CC2)c(CN2CCC(S(=O)c3cc(Cl)cc(Cl)c3)CC2)cc1F ; Cl]

Following the procedure as described in Example 517 step 2, and making variation as required to replace tert-butyl 4-(3,5-dichlorobenzyl)piperazine-1-carboxylate with tert-butyl 5-cyclopropyl-4-((4-((3,5-dichlorophenyl)sulfinyl)piperidin-1-yl)methyl)-2-fluorobenzoate, the title compound was obtained as a colorless solid (1.35 g, quant. yield): MS(ES+) m/z 470.0, 472.1 (M+1).

Step 4. Preparation of 5-cyclopropyl-4-((4-((3,5-dichlorophenyl)sulfinyl)piperidin-1-yl)methyl)-2-fluoro-N-(methylsulfonyl)benzamide, trifluoroacetic acid salt

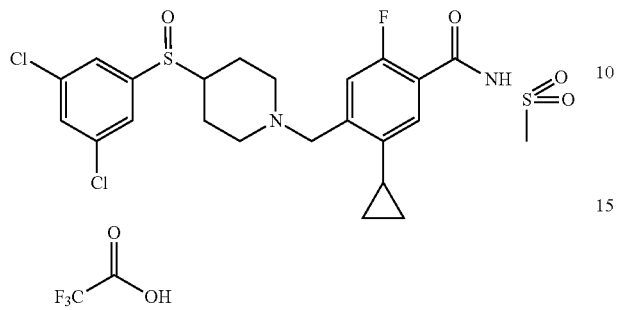

Following the procedure as described in Example 53 step 5, and making variation its required to replace (S)-5-cyclopropyl-4-((3-(3,5-dichlorophenoxy)piperidin-1-yl)methyl)-2-fluorobenzoic acid with 5-cyclopropyl-4-((4-((3,5-dichlorophenyl)sulfinyl)piperidin-1-yl)methyl)-2-fluorobenzoic acid hydrochloride, and to replace cyclopropanesulfonamide with methylsulfonamide, and purification by preparative HPLC, the title compound was obtained as a colorless solid (0.05 g, 9%); $^1$H NMR (300 MHz, CDCl$_3$+10% CD$_3$OD) δ 7.46-7.37 (m, 3H), 7.26-7.20 (m, 2H), 4.19 (s, 2H), 3.42-3.33 (m, 2H), 3.31-3.24 (m, 4H), 2.88-2.70 (m, 2H), 2.08-1.87 (m, 4H), 1.86-1.76 (m, 1H), 1.00-0.91 (m, 2H), 0.66-0.58 (m, 2H) (Note: Note: exchangeable protons not observed.); MS(ES+) m/z 547.0, 549.0 (M+1).

Example 535

Synthesis of 5-cyclopropyl-N-(cyclopropylsulfonyl)-4-((4-((3,5-dichlorophenyl)sulfinyl)piperidin-1-yl)methyl)-2-fluorobenzamide, trifluoroacetic acid salt

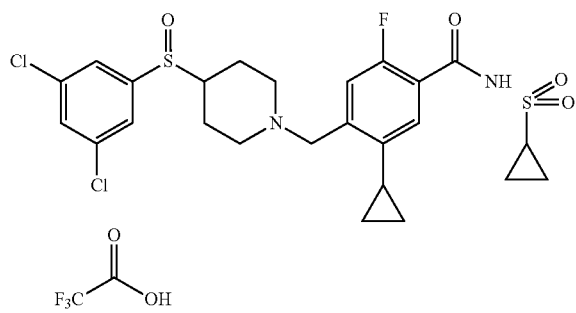

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-((4-((3,5-dichlorophenyl)sulfinyl)piperidin-1-yl)methyl)-2-fluorobenzoic acid hydrochloride, and purification by preparative HPLC, the title compound was obtained as a colorless solid (0.05 g, 8%): $^1$H NMR (300 MHz, CDCl$_3$+10% CD$_3$OD) δ 7.47-7.42 (m, 2H), 7.42-7.39 (m, 2H), 7.29-7.23 (m, 1H), 4.26 (s, 2H), 3.33-3.27 (m, 2H), 3.05-2.95 (m, 1H), 2.94-2.84 (m, 2H), 2.82-2.72 (m, 1H), 2.13-2.03 (m, 2H), 2.02-1.93 (m, 2H), 1.88-1.77 (m, 1H), 1.39-1.30 (m, 2H), 1.12-1.03 (m, 2H), 1.02-0.95 (m, 2H), 0.68-0.60 (m, 2H); MS(ES+) m/z 573.1, 575.1 (M+1).

Example 536

Synthesis of 4-((4-(3-Chloro-2-fluoro-5-(trifluoromethyl)phenoxy)piperidin-1-yl)methyl)-5-cyclopropyl-2-fluoro-N-(methylsulfonyl)benzamide, trifluoroacetic acid salt

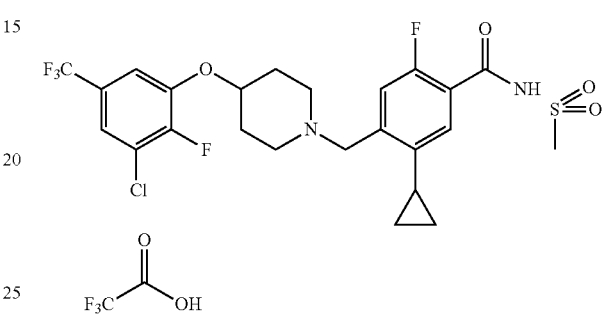

Step 1. Preparation of tert-butyl 4-(3-chloro-2-fluoro-5-(trifluoromethyl)phenoxy)piperidine-1-carboxylate

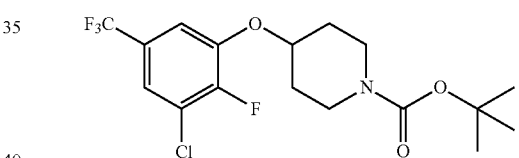

Following the procedure as described in Example 519 step 3, and making variation as required to replace 4-chloro-3-(trifluoromethyl)phenol with 3-chloro-2-fluoro-5-(trifluoromethyl)phenol and tert-butyl 5-cyclopropyl-2-fluoro-4-((4-((methylsulfonyl)oxy)piperidin-1-yl)methyl)benzoate with tert-butyl 4-((methylsulfinyl)oxy)piperidine-1-carboxylate, the title compound was obtained as an colorless oil (2.67 g, 69%): $^1$H NMR (300 MHz, CDCl$_3$) δ 7.29-7.25 (m, 1H), 7.11-7.06 (m, 1H), 4.55-4.46 (m, 1H), 3.74-3.63 (m, 2H), 3.41-3.29 (m, 2H), 1.97-1.85 (m, 2H), 1.83-1.71 (m, 2H), 1.44 (s, 9H); MS(ES+) m/z 342.0, 344.0 (M−55).

Step 2. Preparation of 4-(3-chloro-2-fluoro-5-(trifluoromethyl)phenoxy)piperidine hydrochloride

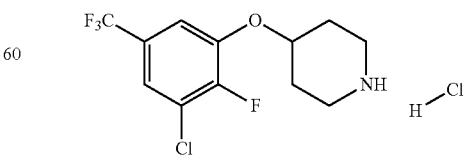

Following the procedure as described in Example 517 step 2, and making variation as required to replace tert-butyl 4-(3,5-dichlorobenzyl)piperazine-1-carboxylate with tert-butyl 4-(3-chloro-2-fluoro-5-(trifluoromethyl)phenoxy)piperidine-1-carboxylate, the title compound was obtained as a colorless solid (2.24 g, quant. yield): MS (ES+) m/z 298.1, 300.1 (M+1).

Step 3. Preparation of tert-butyl 4-((4-(3-chloro-2-fluoro-5-(trifluoromethyl)phenoxy)piperidin-1-yl)methyl)-5-cyclopropyl-2-fluorobenzoate

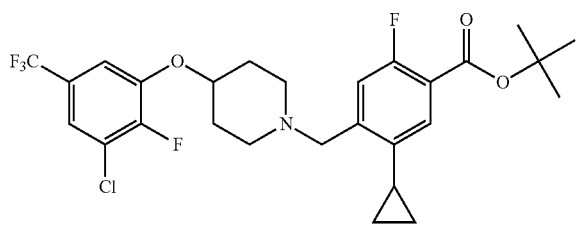 [SMILES: CC(C)(C)OC(=O)c1cc(C2CC2)c(CN2CCC(Oc3cc(C(F)(F)F)cc(Cl)c3F)CC2)cc1F]

Following the procedure as described in Example 53 step 3, and making variation as required to replace (S)-3-(3,5-dichlorophenoxy)piperidine, trifluoroacetic acid salt with 4-(3-chloro-2-fluoro-5-(trifluoromethyl)phenoxy)piperidine hydrochloride, the title compound was obtained as a colorless solid (2.00, 66%): MS(ES+): m/z 546.2, 548.2 (M+1).

Step 4. Preparation of 4-((4-(3-chloro-2-fluoro-5-(trifluoromethyl)phenoxypiperidine-1-yl)methyl)-5-cyclopropyl-2-fluorobenzoic acid hydrochloride

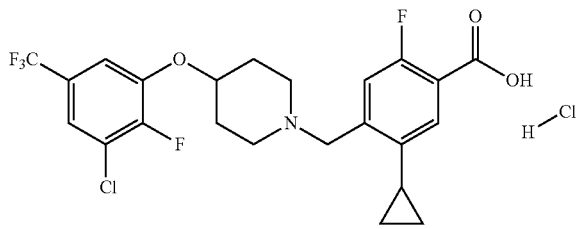

Following the procedure as described in Example 517 step 2, and making variation as required to replace tert-butyl 4-(3,5-dichlorobenzyl)piperazine-1-carboxylate with tert-butyl 4-((4-(3-chloro-2-fluoro-5-(trifluoromethyl)phenoxy)piperidin-1-yl)methyl)-5-cyclopropyl-2-fluorobenzoate, the title compound was obtained as a colorless solid (1.93 g, quant. yield): MS(ES+) m/z 490.1, 492.1 (M+1).

Step 5. Preparation of -((4-(3-Chloro-5-(trifluoromethyl)phenoxy)piperidin-1-yl)methyl)-5-cyclopropyl-2-fluoro-N-(methylsulfonyl)benzamide, trifluoroacetic acid salt

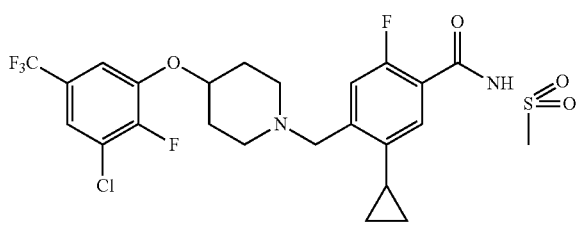

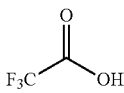

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 4-((4-(3-chloro-2-fluoro-5-(trifluoromethyl)phenoxy)piperidin-yl)methyl)-5-cyclopropyl-2-fluorobenzoic acid hydrochloride, and to replace cyclopropanesulfonamide with methylsulfonamide, and purification by preparative HPLC, the title compound was obtained as a colorless solid (0.22 g, 38%): $^1$H NMR (300 MHz, DMSO-$d_6$) δ 12.19 (br s, 1H), 10.27 (br s, 1H), 7.68-7.61 (m, 2H), 7.52 (d, J=11.1 Hz, 1H), 7.25 (d, J=7.1 Hz, 1H), 4.95-4.77 (m, 1H), 4.57 (s, 2H), 3.45-3.36 (m, 2H), 3.34 (s, 3H), 3.31-3.23 (m, 2H), 2.24-2.10 (m, 3H), 2.06-1.98 (m, 2H), 1.03-0.95 (m, 2H), 0.81-0.73 (m, 2H): MS(ES+) m/z 567.1, 569.1 (M+1).

Example 537

Synthesis of 4-((4-(3-chloro-2-fluoro-5-(trifluoromethyl)phenoxy)piperidin-1-yl)methyl)-5-cyclopropyl-N-(cyclopropylsulfonyl)-2-fluorobenzamide, trifluoroacetic acid salt

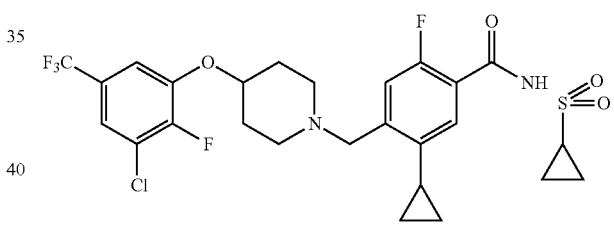

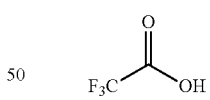

Following the procedure as described in Example 53 step 3, and making variation as required to replace (S)-5-cyclopropyl-4-((3-(3,5-dichlorophenoxy)piperidin-1-yl)methyl)-2-fluorobenzoic acid with 4-((4-(3-chloro-2-fluoro-5-(trifluoromethyl)phenoxy)piperidin-1-yl)methyl)-5-cyclopropyl-2-fluorobenzoic acid hydrochloride, and purification by preparative HPLC, the title compound was obtained as a colorless solid (0.25 g, 43%): $^1$H NMR (300 MHz, CDCl$_3$+10% CD$_3$OD) δ7.40 (d, J=7.1 Hz, 1H), 7.34-7.25 (m, 2H), 7.13-7.08 (m, 1H), 4.67-4.59 (m, 1H), 4.41 (s, 2H), 3.42-3.30 (m, 2H), 3.29-3.15 (m, 2H), 3.02-2.91 (m, 1H), 2.32-2.17 (m, 2H), 2.53-2.01 (m, 2H), 1.90-1.79 (m, 1H), 1.34-1.26 (m, 2H), 1.08-0.96 (m, 4H), 0.69-0.61 (m, 2H); MS(ES+) m/z 593.1, 595.1 (M+1).

Example 538

Synthesis of (R)-4-((1-(tert-butyl)piperidin-3-yl)oxy)-5-cyclopropyl-2-fluoro-N-(methylsulfonyl)benzamide

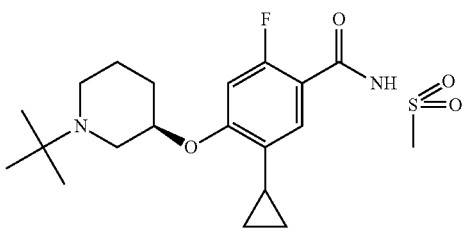

Step 1. Preparation of methyl (R)-4-((1-acetylpiperidin-3-yl)oxy)-5-cyclopropyl-2-fluorobenzoate

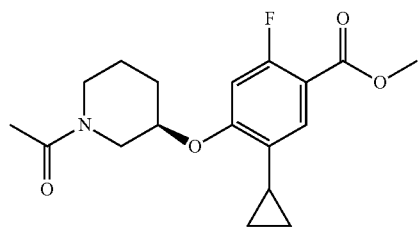 [SMILES: COC(=O)c1cc(C2CC2)c(O[C@@H]2CCCN(C(C)=O)C2)cc1F]

To a solution of methyl (R)-5-cyclopropyl-2-fluoro-4-(piperidin-3-yloxy)benzoate (2.00 g, 6.82 mmol), triethylamine (1.90 mL, 13.64 mmol), and 4-dimethylaminopyridine (0.20 g, 1.64 mmol) in dichloromethane (60 mL) was added acetic anhydride (1.29 mL, 13.64 mmol) under nitrogen. The resulting solution was stated at ambient temperature for 18 hours. The reaction mixture was concentrated in vacuo, diluted with ethyl acetate (100 mL), washed with aqueous saturated ammonium chloride solution (2×50 mL), aqueous saturated sodium bicarbonate solution (2×50 mL), and brine (30 mL); dried over anhydrous sodium sulfate, filtered and concentrated in vacuo. The residue was purified by flash chromatography (50-100% ethyl acetate in hexanes) to provide the title compound as a colorless solid (1.28 g, 56%); MS(ES+) m/z 336.1 (M+1).

Step 2. Preparation of methyl (R)-4-((1-(tert-butyl)piperidin-3-yl)oxy)-5-cyclopropyl-2-fluorobenzoate

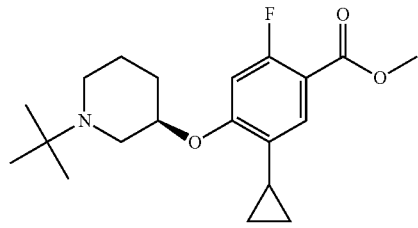 [SMILES: COC(=O)c1cc(C2CC2)c(O[C@@H]2CCCN(C(C)(C)C)C2)cc1F]

To a solution of methyl (R)-4-((1-acetylpiperidin-3-yl)oxy)-5-cyclopropyl-2-fluorobenzoate (1.28 g, 3.82 mmol) and 2,6-di-tert-butyl-4-methylpyridine (0.94 g, 4.58 mmol) in anhydrous dichloromethane (70 mL) at −78° C. under nitrogen was added bifluoromethanesulfonic anhydride (0.77 mL, 4.58 mmol) dropwise. The resulting mixture was stirred at −78° C. for 2 hours and then added methyl lithium (1.6 M in diethyl ether, 11.9 ml, 19.04 mmol) dropwise. The resulting mixture was stirred at −78° C. for 1 hour and then quenched cold with aqueous saturated ammonium chloride solution (50 mL). The mixture was warmed to ambient temperature, the organic layer was washed with brine (50 mL), dried over anhydrous sodium sulfate, filtered and concentrated in vacuo. The residue was purified by preparative HPLC to provide the title compound as a colorless solid (0.40 g, 30%): $^1$H NMR (300 MHz, CDCl$_3$) δ7.39 (d, J=8.4 Hz, 1H), 6.46 (d, J=12.8 Hz, 1H), 4.67-4.39 (m, 1H), 3.84 (s, 3H), 3.46-3.31 (m, 1H), 3.16-2.98 (m, 1H), 2.32-2.11 (m, 3H), 2.05-1.93 (m, 1H), 1.91-1.69 (m, 2H), 1.50-1.34 (m, 1H), 1.15 (s, 9H), 0.90-0.81 (m, 2H), 0.66-0.55 (m, 2H); MS(ES+) m/z 350.3 (M+1).

Step 3. Preparation of (R)-4-((1-(tert-butyl)piperidin-3-yl)oxy)-5-cyclopropyl-2-fluoro-N-(methylsulfonyl)benzamide

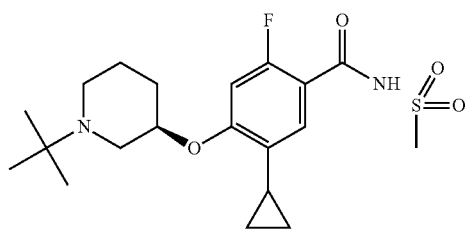

To a mixture of (R)-4-((1-(tert-butyl)piperidin-3-yl)oxy)-5-cyclopropyl-2-fluorobenzoate (0.14 g, 0.40 mmol) and sodium hydroxide (0.12 g, 2.85 mmol) in tetrahydrofuran (10 mL) and water (2.5 mL) was refluxed for 6 hours. The reaction mixture was cooled to ambient temperature and added 1.0 N aqueous hydrochloride acid solution (5 mL) and concentrated in vacuo. The residue was dissolved in anhydrous dimethylformamide (5 mL), and dichloromethane (5 mL). To this solution was added methanesulfonamide (0.06 g, 0.60 mmol), N-(3-dimethylaminopropyl)-N'-ethylcarbodiimide hydrochloride (0.12 g, 0.60 mmol) and 4-dimethylaminopyridine (0.20 g, 1.60 mmol). The resulting mixture was stirred for 20 hours at ambient temperature, and diluted with 1.0 N aqueous hydrochloric acid solution (15 ml) and brine (15 mL); extracted with dichloromethane:methanol (20:1 v/v, 2×50 mL); dried over anhydrous sodium sulfate, filtered and concentrated is vacuo. The residue was purified by preparative HPLC to provide the title compound as a colorless solid, (0.03 g, 18%): $^1$H NMR (300 MHz, CDCl$_3$+10% CD$_3$OD) δ7.29 (d, J=8.9 Hz, 1H), 6.54 (d, J=13.1, Hz, 1H), 4.31-4.38 (m, 1H), 3.47-3.37 (m, 1H), 3.29-3.18 (m, 1H), 3.09 (s, 3H), 2.37-2.23 (m, 2H), 2.19-2.07 (m, 1H), 1.94-1.73 (m, 3H), 1.44-1.29 (m, 1H), 1.19 (s, 9H), 0.81-0.73 (m, 2H), 0.58-0.49 (m, 2H); MS(ES+) m/z 413.2 (M+1).

Example 539

Synthesis of (R)-4-((1-(tert-butyl)piperidin-3-yl)oxy)-5-cyclopropyl-N-(cyclopropylsulfonyl)-2-fluorobenzamide

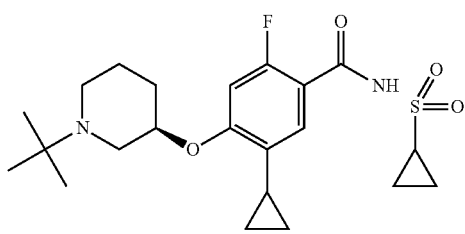

Following the procedure as described in Example 538 step 3, and making variation as required to replace methylsulfonamide with cyclopropanesulfonamide, the title compound was obtained as a colorless solid (0.04 g, 23%): $^1$H NMR (300 MHz, CDCl$_3$+10% CD$_3$OD) δ7.33 (d, J=8.7 Hz, 1H), 6.58 (d, J=13.4 Hz, 1H), 4.44-4.31 (m, 1H), 3.36-3.24 (m, 1H), 3.11-2.98 (m, 1H), 2.95-2.84 (m, 1H), 2.23-2.05 (m, 3H), 1.98-1.87 (m, 1H), 1.85-1.57 (m, 2H), 1.43-5.29 (m, 1H), 1.27-1.20 (m, 2H), 1.09 (s, 9H), 1.01-0.92 (m, 2H), 0.84-0.74 (m, 2H), 0.58-0.50 (m, 2H); MS(ES+) m/z 439.2 (M+1).

Example 540

Synthesis of 5-cyclopropyl-4-((4-(1-3,5-dichlorophenyl)ethyl)piperazin-1-yl)methyl)-2-fluoro-N-(methylsulfonyl)benzamide

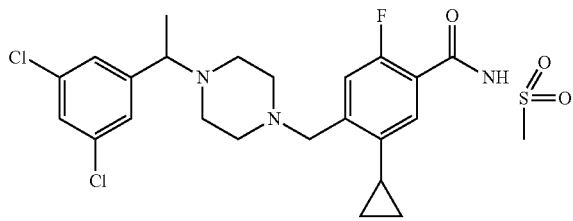

Step 1. Preparation of tert-butyl 4-(1-(3,5-dichlorophenyl)ethyl)piperazine-1-carboxylate

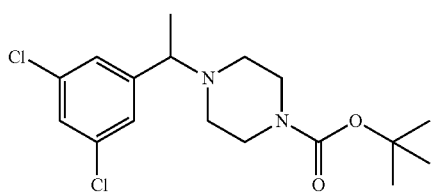 [SMILES: CC(c1cc(Cl)cc(Cl)c1)N1CCN(C(=O)OC(C)(C)C)CC1]

To a solution of tert-butyl piperazine-1-carboxylate (3.13 g, 16.83 mmol) and 1-(3,5-dichlorophenyl)ethan-1-one (3.50 g, 18.51 mmol) in anhydrous tetrahydrofuran (80 mL) was added titanium isopropoxide (IV) (10.2 mL, 33.66 mmol) under nitrogen. The resulting mixture was refluxed for 18 hours, cooled to −42° C. and added anhydrous methanol (3.0 mL) and sodium triacetoxyborohydride (7.13 g, 33.66 mmol). After stirring for 5 hours at −42° C., the reaction mixture was added acetic acid (3.85 mL, 67.32 mmol) and allowed to warm to ambient temperance. The reaction mixture was stirred for 18 hours and then refluxed for 16 hours, cooled to ambient temperature and diluted with ethyl acetate (200 mL) and 1.0 M aqueous sodium hydroxide solution (100 mL). The mixture was filtered and the layers were separated. The organic layer was washed with 1.0 M aqueous sodium hydroxide solution (3×50 mL) and brine (3×50 mL); dried over anhydrous sodium sulfate, filtered and concentrated in vacuo. The residue was purified by flash chromatography (0-50% ethyl acetate in hexanes) to provide the title compound as an oil (2.70 g, 45%): $^1$H NMR (300 MHz, CDCl$_3$) δ7.21-7.15 (m, 3H), 3.43-3.33 (m, 4H), 3.29 (q, J=6.7 Hz, 1H), 2.45-2.21 (m, 4H), 1.41 (s, 9H), 1.27 (d, J=6.6 Hz, 3H); MS(ES+) m/z 359.1, 361.1 (M+1).

Step 2. Preparation of 1-(1-(3,5-dichlorophenyl)ethyl)piperazine

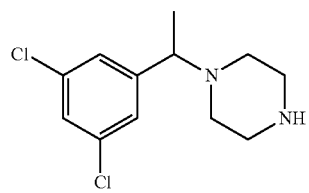 [SMILES: CC(c1cc(Cl)cc(Cl)c1)N1CCNCC1]

To a solution of tert-butyl 4-(1-(3,5-dichlorophenyl)ethyl)piperazine-1-carboxylate (2.70 g, 7.51 mmol) in dichloromethane (100 mL) was added trifluoroacetic acid (25 mL). The resulting solution was stirred at ambient temperature for 1 hour and then concentrated in vacuo. To the residue was added 1.0 M aqueous sodium hydroxide solution (50 mL) and extracted with dichloromethane (2×80 mL). The combined organic extracts were washed with brine (50 mL), dried over anhydrous sodium sulfate, filtered and concentrated in vacuo to provide the title compound as a colorless oil (1.80 g, 92%): MS(ES+) m/z 259.1, 261.2 (M+1).

Step 3. Preparation of tert-butyl 5-cyclopropyl-4-((4-(1-(3,5-dichlorophenyl)ethyl)piperazin-1-yl)methyl)-2-fluorobenzoate

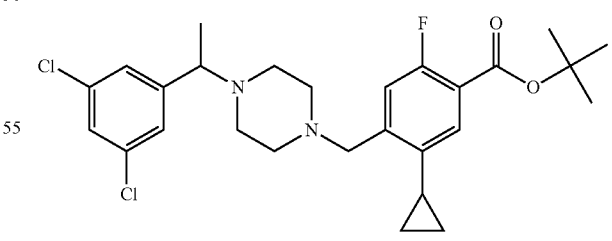

Following the procedure as described in Example 53 step 3, and making variation as required to replace (S)-3-(3,5-dichlorophenoxy)piperidine trifluoroacetic acid salt with 1-(1-(3,5-dichlorophenyl)ethyl)piperazine, the title compound was obtained as a colorless oil (3.53 g, quant. yield): $^1$H NMR (300 MHz, CDCl$_3$) δ7.51-7.43 (m, 1H), 7.27-7.09 (m, 2H), 3.61 (s, 2H), 3.34-3.22 (m, 1H), 2.58-2.28 (m, 8H), 1.98-1.85 (m, 1H), 1.55 (s, 9H), 1.33-1.23 (m, 3H), 0.94-9.83 (m, 2H), 0.66-0.53 (m, 2H); MS(ES+) m/z 507.2, 509.2 (M+1).

Step 4. Preparation of 5-cyclopropyl-4-((4-(1-(3,5-dichlorophenyl)ethyl)piperazin-1-yl)methyl)-2-fluorobenzoic acid dihydrochloride

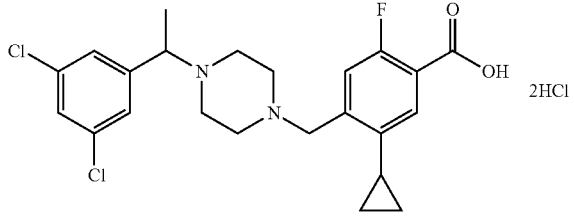 [SMILES: CC(c1cc(Cl)cc(Cl)c1)N1CCN(Cc2cc(F)c(C(=O)O)cc2C2CC2)CC1]

Following the procedure as described in Example 517 step 2, and making variation as required to replace tert-butyl 4-(3,5-dichlorobenzyl)piperazine-1-carboxylate with tert-butyl 5-cyclopropyl-4-((4-(1-(3,5-dichlorophenyl)ethyl)piperazin-1-yl)methyl)-2-fluorobenzoate, the title compound was obtained as a colorless solid (1.82 g, quant. yield): MS(ES+) m/z 451.0, 453.0 (M+1).

Step 5. Preparation of 5-cyclopropyl-4-((4-(1-(3,5-dichlorophenyl)ethyl)piperazin-1-yl)methyl)-2-fluoro-N-methylsulfonyl)benzamide

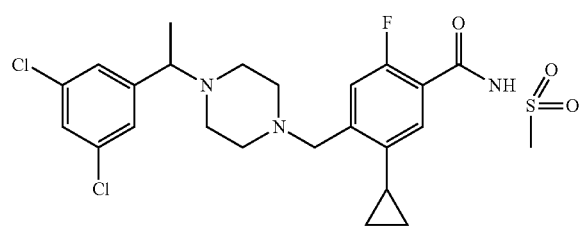

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-((4-(1-(3,5-dichlorophenyl)ethyl)piperazin-1-yl)methyl)-2-fluorobenzoic acid dihydrochloride, and to replace cyclopropanesulfonamide with methylsulfonamide, and purification by preparative HPLC, the title compound was obtained as a colorless solid (0.01 g, 1%): $^1$H NMR (300 MHz, CDCl$_3$+10% CD$_3$OD) δ7.50-7.43 (m, 1H), 7.18-7.09 (m, 4H), 3.59 (s, 2H), 3.31-3.19 (m, 4H), 2.50-2.25 (m, 8H), 1.88-1.79 (m, 1H), 1.29-1.20 (m, 3H), 0.90-0.81 (m, 2H), 0.59-0.50 (m, 2H); MS(ES+) m/z 528.1, 530.1 (M+1).

Example 541

Synthesis of 5-cyclopropyl-N-(cyclopropylsulfonyl)-4-((4-(1-(3,5-dichlorophenyl)ethyl)piperazin-1-yl)methyl)-2-fluorobenzamide

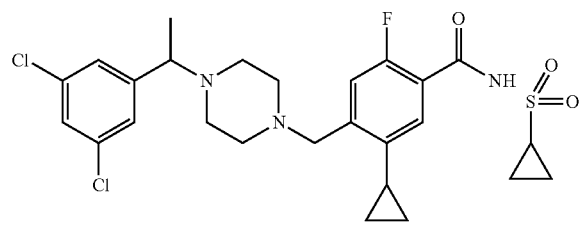

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-((4-(1-(3,5-dichlorophenyl)ethyl)piperazin-1-yl)methyl)-2-fluorobenzoic acid dihydrochloride, and purification by preparative HPLC, the title compound was obtained as a colorless solid (0.08 g, 8%); $^1$H NMR (300 MHz, CDCl$_3$+10% CD$_3$OD) δ7.47 (d, J=7.9 Hz, 1H), 7.17-7.09 (m, 4H) 3.28-3.18 (m, 3H), 3.01-2.91 (m, 1H), 2.55-2.39 (m, 8H), 1.89-1.78 (m, 1H), 1.35-126 (m, 2H), 1.24 (d, J=6.8 Hz, 3H), 1.07-0.98 (m, 2H), 0.89-0.60 (m, 2H), 0.57-0.49 (m, 2H); MS(ES+) m/z 554.1, 556.1 (M+1).

Example 542

Synthesis of 4-((1-(5-chloro-4-(trifluoromethyl)pyridin-2-yl)azetidin-3-yl)methoxy)-5-cyclopropyl-2-fluoro-N-(methylsulfonyl)benzamide

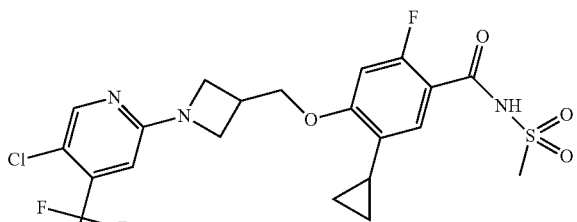

Step 1. Preparation of tert-butyl 3-((4-(tert-butoxycarbonyl)-2-chloro-5-fluorophenoxy)methyl)azetidin-1-carboxylate

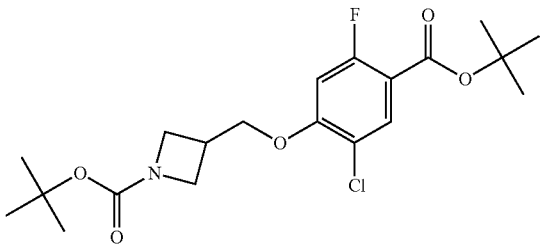 [SMILES: CC(C)(C)OC(=O)c1cc(Cl)c(OCC2CN(C(=O)OC(C)(C)C)C2)cc1F]

To a mixture of tert-butyl 3-(hydroxymethyl)azetidine-1-carboxylate (8.94 g, 47.86 mmol), tert-butyl 5-chloro-2,4-dichlorobenzoate (14.28 g, 57.43 mmol) in anhydrous dimethylsulfimide (250 mL) was added cesium carbonate (28.10 g, 86.15 mmol). The reaction mixture was heated at 85° C. under nitrogen for 6 hours, cooled to ambient temperature and diluted with ethyl acetate (500 mL), washed with water (250 mL), aqueous saturated ammonium, chloride solution (2×200 mL) and brine (2×100 mL); dried over anhydrous sodium sulfate, filtered and concentrated in vacuo. The residue was purified by flash chromatography (0-25% ethyl acetate in hexanes) to provide the title compound as a colorless solid (19.30 g, 81%): $^1$H NMR (300 MHz, CDCl$_3$) δ7.83 (d, J=7.7 Hz, 1H), 6.61 (d, J=11.8 Hz, 1H), 4.13-4.07 (m, 2H), 4.40 (d, J=8.4 Hz, 2H), 3.80 (dd, J=8.6, 5.2 Hz, 2H), 3.07-2.91 (m, 1H), 1.53 (s, 9H), 1.40 (s, 9H); MS(ES+) m/z 416.2, 418.2 (M+1).

Step 2. Preparation of tert-butyl 3-((4-(tert-butoxy-carbonyl)-2-cyclopropyl-5-fluorophenoxy)methyl)azetidine-1-carboxylate

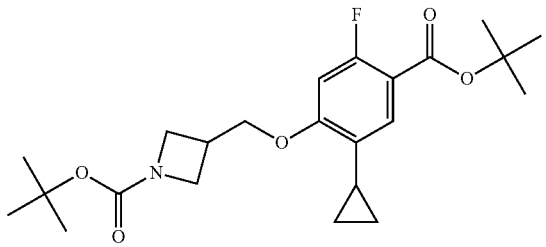 [SMILES: CC(C)(C)OC(=O)c1cc(C2CC2)c(OCC2CN(C(=O)OC(C)(C)C)C2)cc1F]

To a degassed mixture of tert-butyl 3-((4-(tert-butoxycarbonyl)-2-chloro-5-fluorophenoxy)methyl)azetidine-1-carboxylate (8.45 g, 20.32 mmol), cyclopropylboronic acid (43.49 g, 40.64 mmol), and potassium phosphate (tribasic, 17.30 g, 81.28 mmol) in toluene (200 mL) and water (20 mL) was added tricyclohexylphosphine tetrafluoroborate (1.50 g, 4.06 mmol) and palladium (II) acetate (0.46 g, 2.03 mmol). The resulting mixture was refluxed under nitrogen for 18 hours, cooled to ambient temperature and filtered. The filtrate was diluted with ethyl acetate (200 mL), washed with water (100 mL), aqueous saturated ammonium chloride solution (100 mL) and brine (100 mL); dried over anhydrous sodium sulfate, filtered and concentrated in vacuo. The residue was purified by flash chromatography (0-18% ethyl acetate in hexanes) to provide the title compound as a colorless solid (8.35 g, 98%): $^1$H NMR (300 MHz, CDCl$_3$) δ7.37 (d, J=8.3 Hz, 1H), 6.49 (d, J=12.4 Hz, 1H), 4.10-4.01 (m, 4H), 3.86 (dd, J=8.6, 5.5 Hz, 2H), 3.07-2.95 (m, 1H), 1.99-1.87 (m, 1H), 1.54 (s, 9H), 1.40 (s, 9H), 0.90-0.80 (m, 2H), 0.63-0.53 (m, 2H); MS(ES+) m/z 422.2 (M+1).

Step 3. Preparation of methyl 4-(azetidin-3-yl-methoxy)-5-cyclopropyl-2-fluorobenzoate hydrochloride

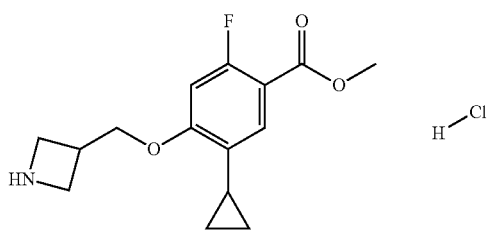 [SMILES: COC(=O)c1cc(C2CC2)c(OCC2CNC2)cc1F ; Cl]

To anhydrous methanol (80 mL) under nitrogen was added thionyl chloride (5.00 mL, 68.97 mmol) dropwise at 0° C. The resulting mixture was stirred at 0° C. for 1 hour and then added a solution of (8.35 g, 19.81 mmol) in anhydrous methanol (10 mL). The resulting mixture was stirred at 0° C. for 2 hours, at ambient temperature for 18 hours and refluxed for 4 hours, and then concentrated in vacuo. The residue was dissolved in anhydrous toluene (50 mL) and concentrated in vacuo to provide the title compound as a colorless solid (6.26 g, quant. yield): MS(ES+) m/z 280.2 (M+1).

Step 4. Preparation of methyl 4-((1-(5-chloro-4-(trifluoromethyl)pyridin-2-yl)azetidin-3-yl)methoxy)-5-cyclopropyl-2-fluorobenzoate

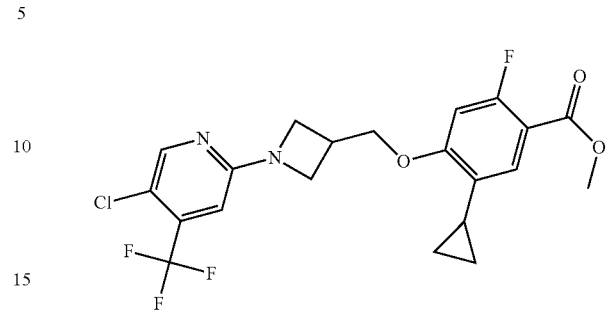

Following the procedure as described in Example 525 step 1, and making variation as required to replace methyl 5-cyclopropyl-2-fluoro-4-((3-methylazetidin-3-yl)methoxy)benzoate hydrochloride with methyl 4-(azetidin-3-yl-methoxy)-5-cyclopropyl-2-benzoate hydrochloride and purification by flash chromatography (2:1 of hexanes:ethyl acetate), the title compound was obtained as a colorless oil (0.51 g, 53%): $^1$H NMR (300 MHz, CDCl$_3$) δ8.18 (s, 1H), 7.42 (d, J=1.4 Hz, 1H), 6.56 (d, J=12.4 Hz, 1H), 6.48 (s, 1H), 4.28-4.20 (m, 2H), 4.18 (d, J=5.7 Hz, 2H), 4.02 (dd, J=8.2, 5.3 Hz, 2H), 3.86 (s, 3H), 3.34-3.20 (m, 1H), 1.86-1.75 (m, 1H), 0.77-0.69 (m, 2H), 0.60-0.53 (m, 2H); MS(ES+) m/z 459.1, 461.0 (M+1).

Step 5. Preparation of 4-((1-(5-chloro-4-(trifluoromethyl)pyridin-2-yl)azetidin-3-yl)methoxy)-5-cyclopropyl-2-fluorobenzoic acid

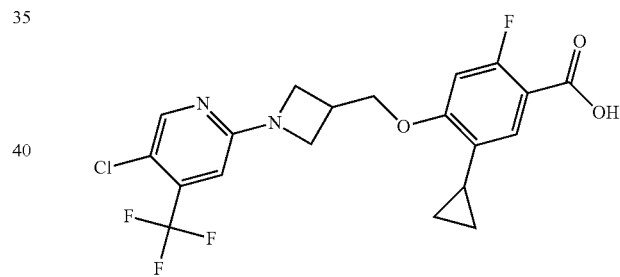

Following the procedure as described in Example 525 step 2, and making variation as required to replace methyl 4-((1-(5-chloro-4-(trifluoromethyl)pyridin-2-yl)-3-methylazetidin-3-yl)methoxy)-5-cyclopropyl-2-fluorobenzoate with methyl 4-((1-(5-chloro-4-(trifluoromethyl)pyridin-2-yl)azetidin-3-yl)methoxy)-5-cyclopropyl-2-fluorobenzoate, the title compound was obtained as a colorless solid (0.49 g, quant. yield): MS(ES+) m/z 445.1, 447.0 (M+1).

Step 6. Preparation of -((1-(5-chloro-4-(trifluoromethyl)pyridin-2-yl)azetidin-3-yl)methoxy)-5-cyclopropyl-2-fluoro-N-(methylsulfonyl)benzamide

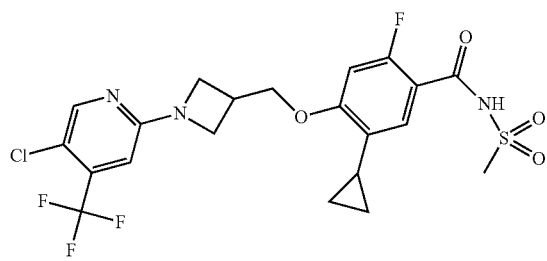 [SMILES: CS(=O)(=O)NC(=O)c1cc(C2CC2)c(OCC2CN(c3cc(C(F)(F)F)c(Cl)cn3)C2)cc1F]

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 4-((1-(5-chloro-4-(trifluoromethyl)pyridin-2-yl)azetidin-3-yl)methoxy)-5-cyclopropyl-2-fluorobenzoic acid, and to replace cyclopropanesulfonamide with methylsulfonamide, the title compound was obtained as a colorless solid (0.12 g, 42%): $^1$H NMR (300 MHz, CDCl$_3$) δ8.70 (d, J=14.0 Hz, 1H), 8.17 (s, 1H), 7.54 (d, J=9.1 Hz, 1H), 6.59 (d, J=14.2 Hz, 1H), 0.48 (s, 1H), 4.28-4.19 (m, 4H), 4.06-3.98 (m, 2H), 3.38 (s, 3H), 3.33-3.23 (m, 1H), 1.87-1.76 (m, 1H), 0.80-0.72 (m, 2H), 0.61-0.54 (m, 2H); MS(ES+) m/z 522.0, 524.0 (M+1).

Example 543

Synthesis of 4-((1-(5-chloro-4-(trifluoromethyl)pyridin-2-yl)azetidin-3-yl)methoxy)-5-cyclopropyl-N-(cyclopropylsulfonyl)-2-fluorobenzamide

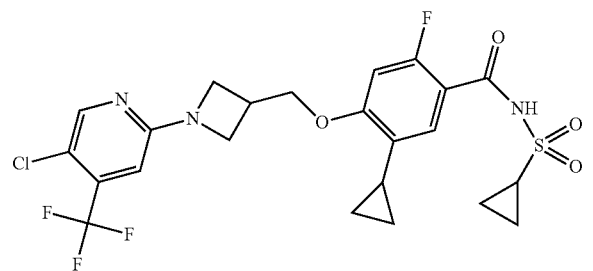 [SMILES: O=C(NS(=O)(=O)C1CC1)c1cc(C2CC2)c(OCC2CN(c3cc(C(F)(F)F)c(Cl)cn3)C2)cc1F]

Following the procedure as described in Example 53 step 5, and making variation as required to replace (S)-5-cyclopropyl-4-((3-(3,5-cyclophenoxy)piperidin-1-yl)methyl)-2-fluorobenzoic acid with 4-((1-(5-chloro-4-(trifluoromethyl)pyridin-2-yl)azetidin-3-yl)methoxy)-5-cyclopropyl-2-fluorobenzoic acid, the title compound was obtained as a colorless solid (0.07 g, 23%): $^1$H NMR (300 MHz, CDCl$_3$) δ8.66 (d, J=15.9 Hz, 1H), 8.18 (s, 1H), 7.56 (d, J=8.9 Hz, 1H), 6.59 (d, J=14.1 Hz, 1H), 6.49 (s, 1H), 4.30-4.19 (m, 4H), 4.06-3.98 (m, 2H), 3.35-3.22 (m, 1H), 3.12-3.02 (m, 1H), 1.89-1.77 (m, 1H), 1.47-1.39 (m, 2H), 1.17-1.08 (m, 2H), 0.81-0.72 (m, 2H), 0.64-0.54 (m, 2H); MS(ES+) m/z 548.0, 550.0 (M+1).

Example 544

Synthesis of 5-cyclopropyl-4-((3-(3,5-dichlorophenoxy)azetidin-1-yl)methyl)-2-fluoro-N-(methylsulfonyl)benzamide, trifluoroacetic acid salt

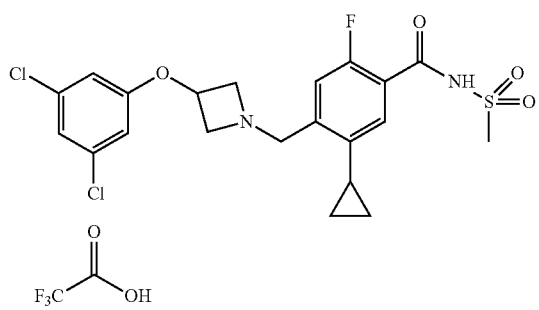

Step 1. Preparation of tert-butyl 3-((methylsulfonyl)oxy)azetidine-1-carboxylate

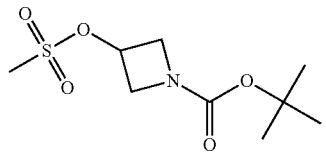 [SMILES: CC(C)(C)OC(=O)N1CC(OS(C)(=O)=O)C1]

Following the procedure as described in Example 519 step 2, and making variation as required to replace tert-butyl 5-cyclopropyl-2-fluoro-4-((4-hydroxypiperidin-1-yl)methyl)benzoate with tert-butyl 3-hydroxyazetidine-1-carboxylate, the title compound was obtained as a colorless oil (16.76 g, quant. yield): $^1$H NMR (300 MHz, CDCl$_3$) δ5.18-5.08 (m, 1H), 4.21 (dd, J=11.1, 6.7 Hz, 2H), 4.02 (dd, J=4.1, 11.0 Hz, 2H), 3.00 (s, 3H), 1.37 (s, 9H).

Step 2. Preparation of tert-butyl 3-(3,5-dichlorophenoxy)azetidine-1-carboxylate

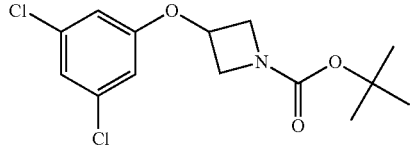 [SMILES: CC(C)(C)OC(=O)N1CC(Oc2cc(Cl)cc(Cl)c2)C1]

Following the procedure as described in Example 519 step 3, and making variation as required to replace 4-chloro-3-(trifluoromethyl)phenol with 3,5-dichlorophenol, and to replace tert-butyl 5-cyclopropyl-2-fluoro-4-((4-((methylsulfonyl)oxypiperidin-1-yl)methyl)benzoate with tert-butyl 3-((methylsulfonyl)oxy)azetidine-1-carboxylate, the title compound was obtained as an colorless solid (7.06 g, 97%): $^1$H NMR (300 MHz, CDCl$_3$) δ6.98-6.93 (m, 1H), 6.62-6.57 (m, 2H), 4.84-4.75 (m, 1H), 4.26 (dd, J=9.8, 6.4 Hz, 2H), 3.94 (dd, J=9.9, 4.1 Hz, 2H), 1.41 (s, 9H); MS(ES+) m/z 262.1, 264.1 (M−55).

Step 3. Preparation of 3-(3,5-dichlorophenoxy)azetidine

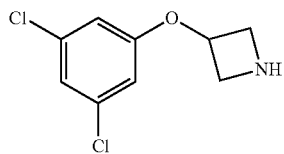 [SMILES: Clc1cc(Cl)cc(OC2CNC2)c1]

Following the procedure as described in Example 540 step 2, and making variation as required to replace tert-butyl 4-(1-(3,5-dichlorophenyl)ethyl)piperidine-1-carboxylate with tert-butyl 3-(3,5-dichlorophenoxy)azetidine-1-carboxylate, the title compound was obtained as an colorless oil (4.84 g, quant. yield); MS(ES+) m/z 218.1, 220.1 (M+1).

Step 4. Preparation of tert-butyl 5-cyclopropyl-4-((3-(3,5-dichlorophenoxy)azetidin-1-yl)methyl)-2-fluorobenzoate fluorobenzoate

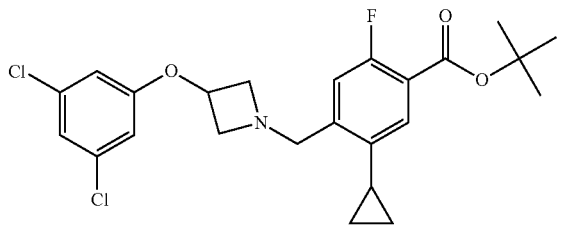 [SMILES: CC(C)(C)OC(=O)c1cc(C2CC2)c(CN2CC(Oc3cc(Cl)cc(Cl)c3)C2)cc1F]

Following the procedure as described in Example 53 step 3, and making variation as required to replace (S)-3-(3,5-phenoxy)piperidine, trifluoroacetic acid salt with 3-(3,5-dichlorophenoxy)azetidine, the title compound was obtained as a colorless oil (1.81 g, 65%); $^1$H NMR (300 MHz, CDCl$_3$) δ7.47 (d, J=7.3 Hz, 1H), 7.09 (d, J=11.7 Hz, 1H), 6.95-6.92 (m, 1H), 6.67-6.62 (m, 2H), 4.81-4.71 (m, 1H), 3.91-3.80 (m, 4H), 3.22-3.11 (m, 2H), 1.90-1.76 (m, 1H), 1.55 (s, 9H), 0.96-0.85 (m, 2H): 0.66-0.55 (m, 2H); MS(ES+) m/z 466.1, 468.1 (M+1).

Step 5. Preparation of 5-cyclopropyl-4-((3-(3,5-dichlorophenoxy)azetidin-1-yl)methyl)-2-fluorobenzoic acid hydrochloride

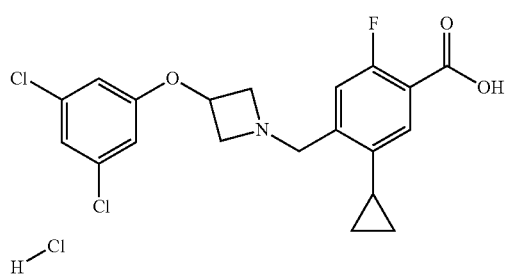

Following the procedure as described in Example 517 step 2, and making variation as required to replace tert-butyl 4-(3,5-dichlorobenzyl)piperidin-1-carboxylate with tert-butyl 5-cyclopropyl-4-((3-(3,5-dichlorophenoxy)azetidin-1-yl)methyl)-2-fluorobenzoate, the title compound was obtained as a colorless solid (1.73 g, quant. yield): MS(ES+) m/z 410.0, 412.0 (M+1).

Step 6. Preparation of 5-cyclopropyl-4-((3-(3,5-dichlorophenoxy)azetidin-1-yl)methyl)-2-fluoro-N-(methylsulfonyl)benzamide, trifluoroacetic acid salt

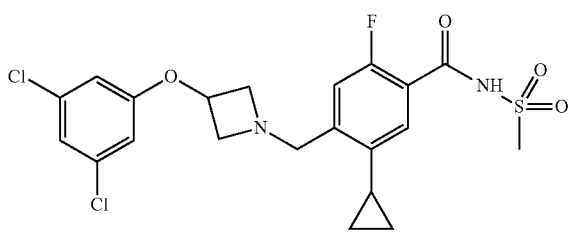

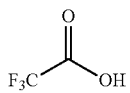

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-((3-(3,5-dichlorophenoxy)azetidin-1-yl)methyl)-2-fluorobenzoic acid hydrochloride, and to replace cyclopropanesulfonamide with methylsulfonamide, and purification by preparative HPLC, the title compound was obtained as a colorless solid (0.60 g, 99%): $^1$H NMR (300 MHz, CDCl$_3$+50% CD$_3$OD) δ8.00-7.93 (m, 1H), 7.78-7.68 (m, 1H), 7.55-7.49 (m, 1H), 7.26-7.18 (m, 2H), 5.66-5.55 (m, 1H), 5.24-5.08 (m, 4H), 4.60-4.49 (m, 2H), 3.84 (s, 3H), 2.46-2.35 (m, 1H), 1.62-1.49 (m, 2H), 1.26-1.16 (m, 2H); MS(ES+) m/z 487.0, 489.0 (M+1).

Example 545

Synthesis of 5-cyclopropyl-N-(cyclopropylsulfonyl)-4-((3-(3,5-dichlorophenoxy)azetidin-1-yl)methyl)-2-fluorobenzamide, trifluoroacetic acid salt

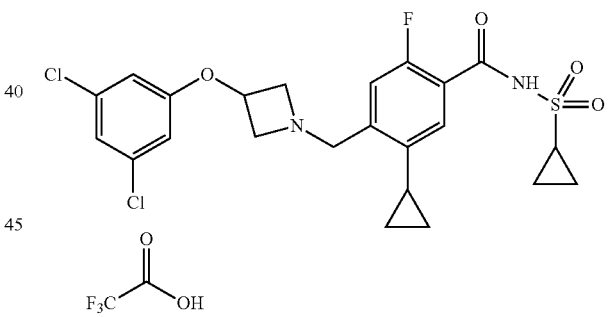

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-((3-(3,5-dichlorophenoxy)azetidin-1-yl)methyl)-2-fluorobenzoic acid hydrochloride, and purification by preparative HPLC, the title compound was obtained as a colorless solid (0.40 g, 64%); $^1$H NMR (300 MHz, CDCl$_3$+10% CD$_3$OD) δ7.48 (d, J=7.1 Hz, 1H), 7.17 (d, J=10.8 Hz, 1H), 7.00-6.95 (m, 1H), 6.67-6.62 (m, 2H), 5.10-5.00 (m, 1H), 4.67-4.66 (m, 2H), 4.59 (s, 2H), 3.99-3.90 (m, 2H), 3.05-2.94 (m, 1H), 1.88-1.76 (m, 1H), 1.38-1.30 (m, 2H), 1.12-0.96 (m, 4H), 0.69-0.62 (m, 2H) (Note: exchangeable protons not observed.); MS(ES+) m/z 513.0, 515.0 (M+1).

Example 546

Synthesis of 5-cyclopropyl-4-((4-(2,4-dichlorophenoxy)piperidin-1-yl)methyl)-2-fluoro-N-(methylsulfonyl)benzamide, trifluoroacetic acid salt

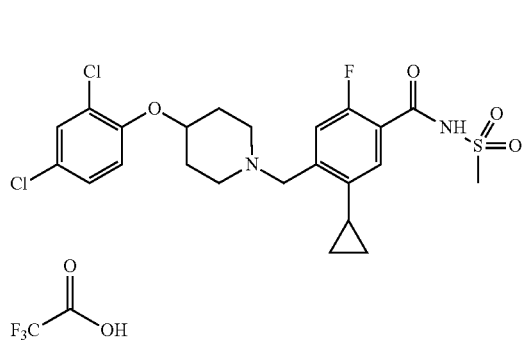

Step 1. Preparation of tert-butyl 4-(2,4-dichlorophenoxy)piperidine-1-carboxylate

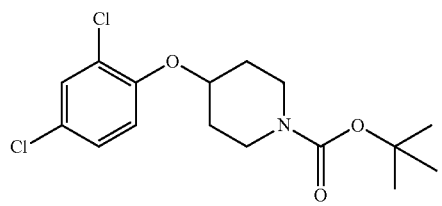 [SMILES: CC(C)(C)OC(=O)N1CCC(Oc2ccc(Cl)cc2Cl)CC1]

Following the procedure as described in Example 519 step 3, and making variation as required to replace 4-chloro-3-(trifluoromethyl)phenol with 2,4-dichlorophenol, and to replace tert-butyl 5-cyclopropyl-2-fluoro-4-((4-((methylsulfonyl)oxy)piperidin-1-ylmethyl)benzoate with tert-butyl 4-((methylsulfonyl)oxy)piperidine-1-carboxylate, the title compound was obtained as an colorless solid (3.16 g, 81%): $^1$H NMR (300 MHz, CDCl$_3$) δ7.33 (d, J=2.4 Hz, 1H), 7.12 (dd, J=8.7, 2.6 Hz, 1H), 6.84 (d, J=8.7 Hz, 1H), 4.50-4.41 (m, 1H), 3.60 (ddd, J=13.4, 8.0, 3.9 Hz, 2H), 3.48-3.35 (m, 2H), 1.91-1.71 (m, 4H), 1.42 (s, 9H); MS(ES+) m/z: 290.1, 292.1 (M−t-Bu+2H).

Step 2. Preparation of 4-(2,4-dichlorophenoxy)piperidine

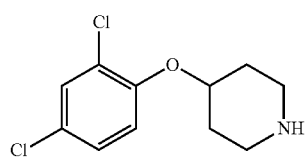 [SMILES: Clc1ccc(OC2CCNCC2)c(Cl)c1]

Following the procedure as described in Example 540 step 2, and making variation as required to replace tert-butyl 4-(1-(3,5-dichlorophenyl)ethyl)piperidine-1-carboxylate with tert-butyl 4-(2,4-dichlorophenoxy)piperidine-1-carboxylate, the title compound was obtained as an colorless oil (1.96 g, 87%): MS(ES+) m/z 246.1, 248.1. (M+1).

Step 3. Preparation of tert-butyl 5-cyclopropyl-4-((4-(2,4-dichlorophenoxy)piperidin-1-yl)methyl)-2-fluorobenzoate

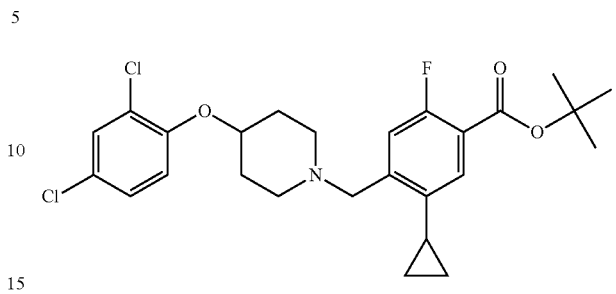

Following the procedure as described in Example 53 step 3, and making variation as required to replace (S)-3-(3,5-dichlorophenoxy)piperidine, trifluoroacetic acid salt with 4-(2,4-dichlorophenoxy)piperidine, the title compound was obtained as a colorless oil (2.76 g, 93%): $^1$H NMR (300 MHz, CDCl$_3$) δ7.47 (d, J=7.3 Hz, 1H), 7.34 (d, J=2.3 Hz, 1H), 7.21-7.10 (m, 2H), 6.85 (d, J=8.9 Hz, 1H), 4.40-4.30 (m, 1H), 3.64 (s, 2H), 2.78-2.67 (m, 2H), 2.42-2.30 (m, 2H), 2.01-1.80 (m, 5H), 1.56 (s, 9H), 0.94-0.86 (m, 2H), 0.65-0.56 (m, 2H): MS(ES+) m/z 494.1, 496.1 (M+1).

Step 4. Preparation of 5-cyclopropyl-4-((4-(2,4-dichlorophenoxy)piperidin-1-yl)methyl)-2-fluorobenzoic acid hydrochloride

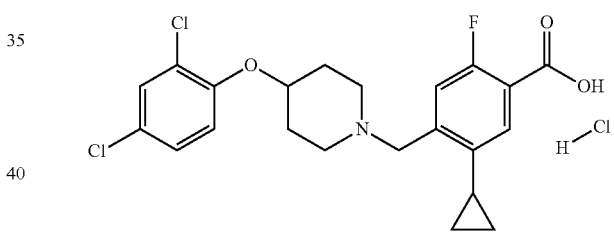

Following the procedure as described in Example 517 step 2, and making variation as required to replace tert-butyl 4-(3,5-dichlorobenzyl)piperidine-1-carboxylate with tert-butyl 5-cyclopropyl-4-((4-(2,4-dichlorophenoxy)piperidin-1-yl)methyl)-2-fluorobenzoate, the title compound was obtained as a colorless solid (2.65 g, quant. yield): MS(ES+) m/z 438.1, 440.1 (M+1).

Step 5. Preparation of 5-cyclopropyl-4-((4-(2,4-dichlorophenoxy)piperidin-1-yl)methyl)-2-fluoro-N-(methylsulfonyl)benzamide, trifluoroacetic acid salt

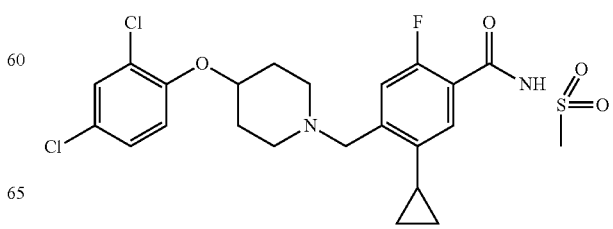

-continued

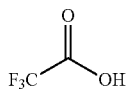

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-((4-(2,4-dichlorophenoxy)piperidin-1-yl)methyl)-2-fluorobenzoic acid hydrochloride, and to replace cyclopropanesulfonamide with methylsulfonamide, and purification by preparative HPLC, the title compound was obtained as a colorless solid (0.25 g, 40%): $^1$H NMR (300 MHz, CDCl$_3$+10% CD$_3$OD) δ7.42 (d, J=7.1 Hz, 1H), 7.36-7.28 (m, 2H), 7.16-7.09 (m, 1H), 6.86-6.80 (m, 1H), 4.69-4.59 (m, 1H), 4.42 (s, 2H), 3.40-3.17 (m, 7H), 2.27-2.00 (m, 4H), 1.89-1.77 (m, 1H), 1.06-0.95 (m, 2H), 0.70-0.61 (m, 2H); MS(ES+) m/z 515.0, 517.0 (M+1).

Example 547

Synthesis of 5-cyclopropyl-N-(cyclopropylsulfonyl)-4-((4-(2,4-dichlorophenoxy)piperidin-1-yl)methyl)-2-fluorobenzamide, trifluoroacetic acid salt

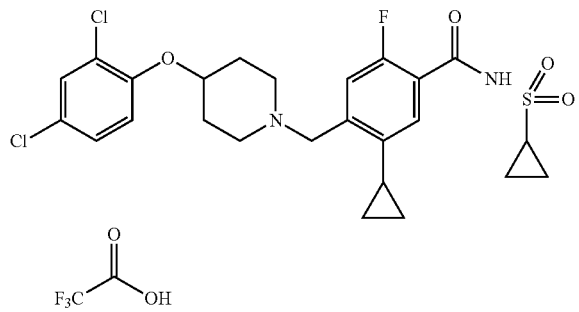

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-((4-(2,4-dichlorophenoxy)-1-yl)methyl)-2-fluorobenzoic acid hydrochloride, and purification by preparative HPLC, the title compound was obtained as a colorless solid (0.33 g, 50%); $^1$H NMR (300 MHz, CDCl$_3$+10% CD$_3$OD) δ7.49-7.43 (m, 1H), 7.37-7.28 (m, 2H), 7.16-7.10 (m, 1H), 6.87-6.80 (m, 1H), 4.69-4.61 (m, 1H), 4.43 (s, 2H), 3.48-3.15 (m, 4H), 3.04-2.92 (m, 1H), 2.30-2.14 (m, 2H), 2.13-2.01 (m, 2H), 1.89-1.77 (m, 1H), 1.39-1.28 (m, 2H), 1.13-0.94 (m, 4H), 0.72-0.63 (m, 2H); MS(ES+) m/z 541.1, 543.1 (M+1).

Example 548

Synthesis of 4-((4-(3-chloro-5-(trifluoromethoxy)phenoxy)piperidin-1-yl)methyl)-5-cyclopropyl-2-fluoro-N-(methylsulfonyl)benzamide, trifluoroacetic acid salt

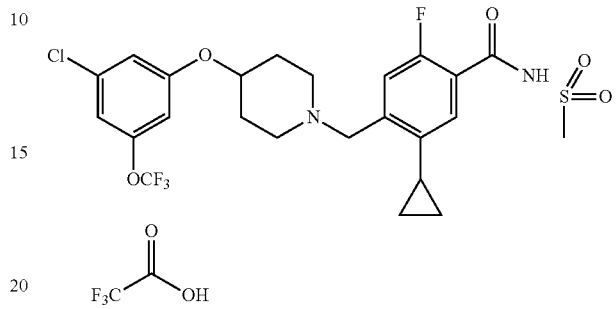

Step 1. Preparation of tert-butyl 4-(3-chloro-5-(trifluoromethoxy)phenoxy)piperidine-1-carboxylate

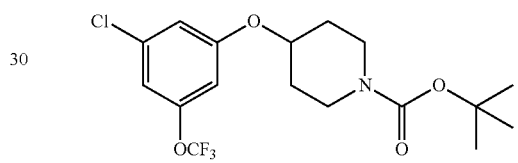

Following the procedure as described in Example 519 step 3, and making variation as required to replace 4-chloro-3-(trifluoromethyl)phenol with 3-chloro-5-(trifluoromethoxy)phenol, and to replace tert-butyl 5-cyclopropyl-2-fluoro-4-((4-((methylsulfonyl)oxy)piperidin-1-yl)methyl)benzoate with tert-butyl 4-((methylsulfonyl)oxy)piperidine-1-carboxylate, the title compound was obtained as an colorless solid (2.41 g, 65%): $^1$H NMR (300 MHz, CDCl$_3$) δ6.82-6.78 (m, 2H), 6.64-6.61 (m, 1H), 4.46-4.37 (m, 1H), 3.64 (ddd, J=13.4, 7.6, 3.9 Hz, 2H), 3.33 (ddd, J=13.5, 7.6, 3.9 Hz, 2H), 1.95-1.82 (m, 2H), 1.77-1.64 (m, 2H), 1.44 (s, 9H); MS(ES+) m/z 340.1, 342.1 (M−t-Bu+2H).

Step 2. Preparation of 4-(3-chloro-5-(trifluoromethoxy)phenoxy)piperidine

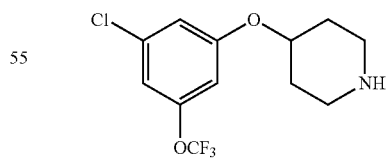

Following the procedure as described in Example 540 step 2, and making variation as required to replace tert-butyl 4-(1-(3,5-dichlorophenyl)ethyl)piperidine-1-carboxylate with tert-butyl 4-(3-chloro-5-(trifluoromethoxy)phenoxy)piperidine-1-carboxylate, the title compound was obtained as an colorless oil (1.55 g, 86%): MS(ES+) m/z 296.1, 298.1 (M+1).

Step 3. Preparation of tert-butyl 4-((4-(3-chloro-5-(trifluoromethoxy)phenoxy)piperidin-1-yl)methyl)-5-cyclopropyl-2-fluorobenzoate

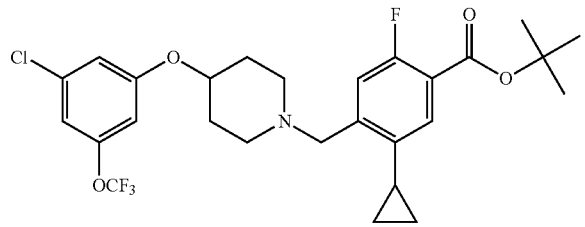 [SMILES: CC(C)(C)OC(=O)c1cc(C2CC2)c(CN2CCC(Oc3cc(Cl)cc(OC(F)(F)F)c3)CC2)cc1F]

Following the procedure as described in Example 53 step 3, and making variation as required to replace (S)-3-(3,5-dichlorophenoxy)piperidine, trifluoroacetic acid salt with 4-(3-chloro-5-(trifluoromethoxy)phenoxy)piperidine, the title compound was obtained as a colorless oil (2.15 g, 76%): ¹H NMR (300 MHz, CDCl₃) δ7.48 (d, J=7.1 Hz, 1H), 7.17 (d, J=11.6 Hz, 1H), 6.84-6.76 (m, 2H), 6.67-6.61 (m, 1H), 4.35-4.26 (m, 1H), 3.64 (s, 2H), 2.76-2.64 (m, 2H), 2.41-2.29 (m, 2H), 2.03-1.89 (m, 3H), 1.87-1.74 (m, 2H), 1.56 (s, 9H), 0.96-0.87 (m, 2H), 0.65-0.57 (m, 2H); MS(ES+) m/z 544.2, 546.2 (M+1).

Step 4. Preparation of 4-((4-(3-chloro-5-(trifluoromethoxy)phenoxy)piperidin-1-yl)methyl)-5-cyclopropyl-2-fluorobenzoic acid hydrochloride

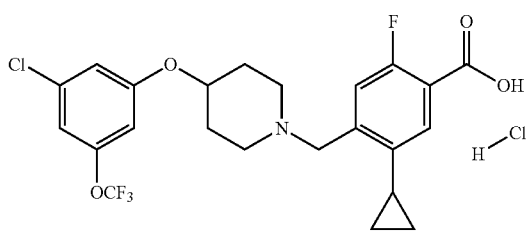

Following the procedure as described in Example 517 step 2, and making variation as required to replace tert-butyl 4-(3,5-dichlorobenzyl)piperidine-1-carboxylate with tert-butyl 4-((4-(3-chloro-5-(trifluoromethoxy)phenoxy)piperidin-1-yl)methyl)-5-cyclopropyl-2-fluorobenzoate, the title compound was obtained as a colorless solid (2.07 g, quant. yield): MS(ES+) m/z 488.1, 490.1 (M+1).

Step 5. Preparation of 4-((4-(3-chloro-5-(trifluoromethoxy)phenoxy)piperidin-1-yl)methyl)-5-cyclopropyl-2-fluoro-N-(methylsulfonyl)benzamide, trifluoroacetic acid salt

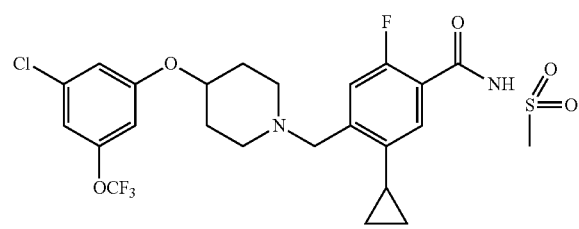

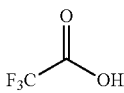

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 4-((4-(3-chloro-5-(trifluoromethoxy)phenoxy)piperidin-1-yl)methyl)-5-cyclopropyl-2-fluorobenzoic acid hydrochloride, and to replace cyclopropanesulfonamide with methylsulfonamide, and purification by preparative HPLC, the title compound was obtained as a colorless solid (0.15 g, 22%): ¹H NMR (300 MHz, CDCl₃+10% CD₃OD) δ7.42 (d, J=7.3 Hz, 1H), 7.33 (d, J=11.1 Hz, 1H), 6.84-6.78 (m, 2H), 6.65-6.60 (m, 1H), 4.64-4.55 (m, 1H), 4.41 (s, 2H), 3.45-3.33 (m, 2H), 3.30 (s, 3H), 3.24-3.11 (m, 2H), 2.33-2.19 (m, 2H), 2.15-2.03 (m, 2H), 1.91-1.80 (m, 1H), 1.08-0.99 (m, 2H), 0.73-0.64 (m, 2H); MS(ES+) m/z 565.2, 567.2 (M+1).

Example 549

Synthesis of 4-((4-(3-chloro-5-(trifluoromethoxy)phenoxy)piperidin-1-yl)methyl)-5-cyclopropyl-N-(cyclopropylsulfonyl)-2-fluorobenzamide, trifluoroacetic acid salt

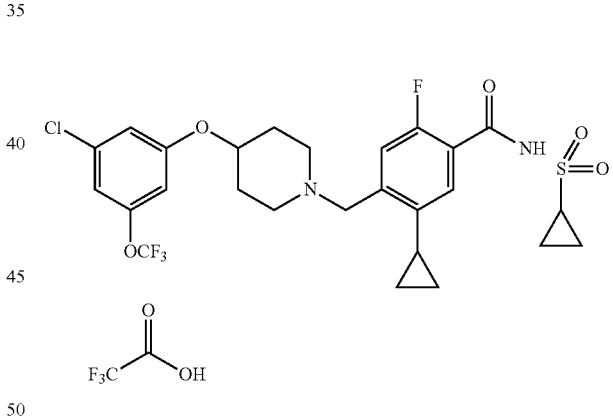

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 4-((4-(3-chloro-5-(trifluoromethoxy)phenoxy)piperidin-1-yl)methyl)-5-cyclopropyl-2-fluorobenzoic acid hydrochloride, and purification by preparative HPLC, the title compound was obtained as a colorless solid (0.15 g, 21%): ¹H NMR (300 MHz, CDCl₃+10% CD₃OD) δ7.43 (d, J=7.0 Hz, 1H), 7.32 (d, 10.9 Hz, 1H), 6.82-6.77 (m, 2H), 6.64-6.59 (m, 1H), 4.62-4.57 (m, 1H), 4.41 (s, 2H), 3.35-3.25 (m, 2H), 3.23-3.09 (m, 2H), 3.04-2.93 (m, 1H), 2.32-2.17 (m, 2H), 2.13-2.01 (m, 2H), 1.91-1.79 (m, 1H), 1.37-3.28 (m, 2H), 1.13-0.97 (m, 4H), 0.71-0.62 (m, 2H): MS(ES+) m/z 591.1, 593.1 (M+1).

Example 550

Synthesis of 4-(((1R,3r,5S)-3-((5-chloro-4-(trifluoromethyl)pyridin-2-yl)oxy)-8-azabicyclo[3.2.1]octan-8-yl)methyl)-5-cyclopropyl-2-fluoro-N-(methylsulfonyl)benzamide, trifluoroacetic acid salt

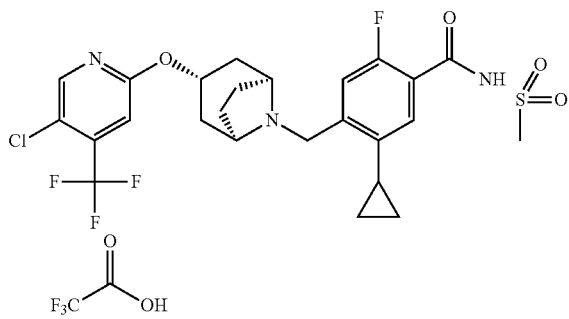

Step 1. Preparation of tert-butyl (1R,3r,5S)-3-hydroxy-8-azabicyclo[3.2.1]octane-8-carboxylate

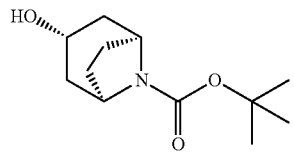

To a mixture of (1R,3r,5S)-8-azabicyclo[3.2.1]octan-3-ol (4.20 g, 33.02 mmol) and 1.0 M aqueous sodium hydroxide solution (50 mL, 50.0 mmol) in tetrahydrofuran (100 mL) was added di-tert-butyl dicarbonate (8.65 g, 39.62 mmol). The resulting mixture was stirred at ambient temperature for 18 hours, and diluted with diethyl ether (200 mL); washed with brine (4×70 mL); dried over anhydrous sodium sulfate, filtered concentrated in vacuo. The residue was triturated with hexanes to provide the title compound as a colorless solid (6.87 g, 91.%): $^1$H NMR (300 MHz, CDCl$_3$) δ4.24-4.02 (m, 3H), 2.19-1.95 (m, 4H), 1.95-1.83 (m, 2H), 1.76-1.59 (m, 3H), 1.41 (s, 9H).

Step 2. Preparation of tert-butyl (1R,3r,5S)-3-((5-chloro-4-(trifluoromethyl)pyridin-2-yl)oxy)-8-azabicyclo[3.2.1]octane-8-carboxylate

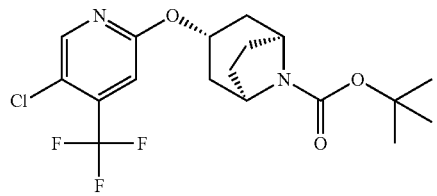 [SMILES: CC(C)(C)OC(=O)N1[C@@H]2CC[C@H]1C[C@@H](Oc1cc(C(F)(F)F)c(Cl)cn1)C2]

Following the procedure as described in Example 521 step 1, and making variation as required to replace tert-butyl 4-hydroxypiperidine-1-carboxylate with tert-butyl (1R,3r,5S)-3-hydroxy-8-azabicyclo[3.2.1]octane-8-carboxylate, the title compound was obtained as a colorless solid (1.57 g, 84%): $^1$H NMR (300 MHz, CDCl$_3$) δ8.20 (s, 1H), 6.95 (s, 1H), 5.37-5.29 (m, 1H), 4.29-4.08 (m, 2H), 2.26-1.82 (m, 8H), 1.45 (s, 9H); MS(ES+) m/z 351.1, 353.1 (M−55).

Step 3. Preparation of (1R,3r,5S)-3-((5-chloro-4-(trifluoromethyl)pyridin-2-yl)oxy)-8-azabicyclo[3.2.1]octane

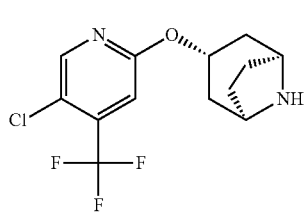 [SMILES: FC(F)(F)c1cc(O[C@H]2C[C@H]3CC[C@@H](C2)N3)ncc1Cl]

Following the procedure as described in Example 540 step 2, and making variation as required to replace tert-butyl 4-(1-(3,5-dichlorophenyl)ethyl)piperidine-1-carboxylate with tert-butyl (1R,3r,5S)-3-((5-chloro-4-(trifluoromethyl)pyridin-2-yl)oxy)-8-azabicyclo[3.2.1]octane-8-carboxylate, the title compound was obtained as an colorless oil (1.18 g, quant. yield): MS(ES+) m/z 307.2, 309.2 (M+1).

Step 4. Preparation of tert-butyl 4-(((1R,3r,5S)-3-((5-chloro-4-(trifluoromethyl)pyridin-2-yl)oxy)-8-azabicyclo[3.2.1]octan-8-yl)methyl)-5-cyclopropyl-2-fluorobenzoate

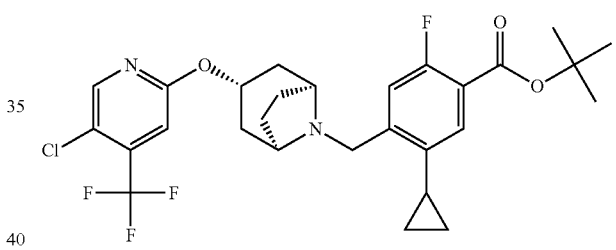

Following the procedure as described in Example 53 step 3, and making variation as required to replace (S)-3-(3,5-dichlorophenoxy)piperidine, trifluoroacetic acid salt with (1R,3r,5S)-3-((5-chloro-4-(trifluoromethyl)pyridin-2-yl)oxy)-8-azabicyclo[3.2.1]octane, the title compound was obtained as a colorless oil (1.62 g, 76%): $^1$H NMR (300 MHz, CDCl$_3$) δ8.20 (s, 1H), 7.47 (d, J=7.3 Hz, 1H), 7.32 (d, J=12.1 Hz, 1H), 6.95 (s, 1H), 5.30-5.24 (m, 1H), 3.67 (s, 2H), 3.19-3.12 (m, 2H), 2.23-2.13 (m, 2H), 2.10-2.00 (m, 4H), 1.95-1.82 (m, 3H), 1.56 (s, 9H), 0.93-0.84 (m, 2H), 0.64-0.57 (m, 2H); MS(ES+) m/z 555.2, 557.2 (M+1).

Step 5. Preparation of 4-(((1R,3r,5S)-3-((5-chloro-4-(trifluoromethyl)pyridin-2-yl)oxy)-8-azabicyclo[3.2.1]octan-8-yl)methyl)-5-cyclopropyl-2-fluorobenzoic acid hydrochloride

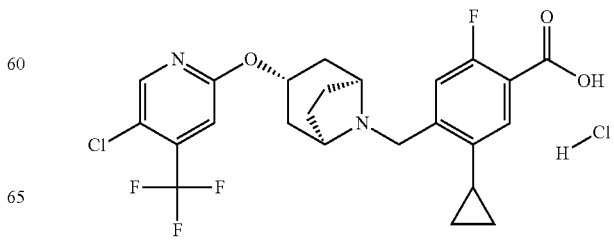

Following the procedure as described in Example 517 step 2, and making variation as required to replace tert-butyl 4-(3,5-dichlorobenzyl)piperidin-1-carboxylate with tert-butyl 4-(((1R,3r,5S)-3-((5-chloro-4-(trifluoromethyl)pyridin-2-yl)oxy)-8-azabicyclo[3.2.1]octan-8-yl)methyl)-5-cyclopropyl-2-fluorobenzoate, the title compound was obtained as a colorless solid (1.56 g, quant. yield): MS(ES+) m/z: 409.0, 501.0 (M+1).

Step 6. Preparation of 4-(((1R,3r,5S)-3-((5-chloro-4-(trifluoromethyl)pyridin-2-yl)oxy)-8-azabicyclo[3.2.1]octan-8-yl)methyl)-5-cyclopropyl-2-fluoro-N-(methylsulfonyl)benzamide, trifluoroacetic acid salt

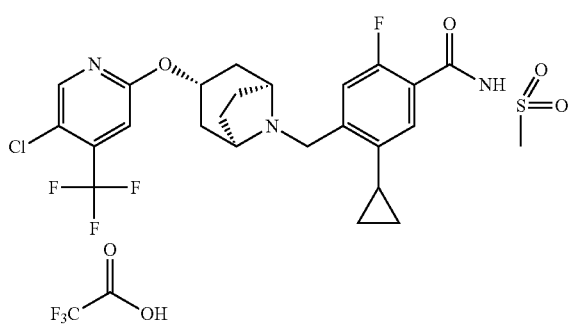

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 4-(((1R,3r,5S)-3-((5-chloro-4-(trifluoromethyl)pyridin-2-yl)oxy)-8-azabicyclo[3.2.1]octan-8-yl)methyl)-5-cyclopropyl-2-fluorobenzoic acid hydrochloride, and to replace cyclopropanesulfonamide with methylsulfonamide, and purification by preparative HPLC, the title compound was obtained as a colorless solid (0.14 g, 20%): $^1$H NMR (300 MHz, CDCl$_3$+10% CD$_3$OD) δ8.18 (s, 1H), 7.50-7.37 (m, 2H), 6.94 (s, 1H), 5.37-5.27 (m, 1H), 4.40 (s, 2H), 3.98-3.83 (m, 2H), 3.29 (s, 3H), 2.80-2.63 (m, 2H), 2.52-2.41 (m, 2H), 2.38-2.25 (m, 2H), 2.19-2.08 (m, 2H), 1.86-1.75 (m, 1H), 1.05-0.95 (m, 2H), 0.71-0.62 (m, 2H); MS(ES+) m/z 576.1, 578.1 (M+1).

Example 551

Synthesis of 4-(((1R,3r,5S)-3-((5-chloro-4-(trifluoromethyl)pyridin-2-yl)oxy)-8-azabicyclo[3.2.1]octan-8-yl)methyl)-5-cyclopropyl-N-(cyclopropylsulfonyl)-2-fluorobenzamide, trifluoroacetic acid salt

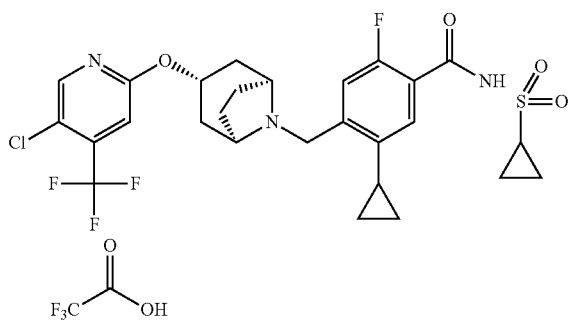

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 4-(((1R,3r,5S)-3-((5-chloro-4-(trifluoromethyl)pyridin-2-yl)oxy)-8-azabicyclo[3.2.1]octan-8-yl)methyl)-5-cyclopropyl-2-fluorobenzoic acid hydrochloride, and purification by preparative HPLC, the title compound was obtained as a colorless solid (0.16 g, 22%): $^1$H NMR (300 MHz, CDCl$_3$+10% CD$_3$OD) δ8.18 (s, 1H), 7.51-7.40 (m, 2H), 6.94 (s, 1H), 5.36-5.28 (m, 1H), 4.38 (s, 2H), 3.95-3.85 (m, 2H), 3.04-2.94 (m, 1H), 2.76-2.63 (m, 2H), 2.52-2.41 (m, 21H), 2.37-2.23 (m, 2H), 2.20-2.07 (m, 2H), 1.87-1.74 (m, 1H), 1.39-1.29 (m, 2H), 1.11-0.93 (m, 4H), 0.72-0.63 (m, 2H); MS(ES+) m/z 602.1, 604.1 (M+1).

Example 552

Synthesis of 4-(((1R,3r,5S)-3-((3-chloro-5-(trifluoromethyl)pyridin-2-yl)oxy)-8-azabicyclo[3.2.1]octan-8-yl)methyl)-5-cyclopropyl-2-fluoro-N-(methylsulfonyl)benzamide, trifluoroacetic acid salt

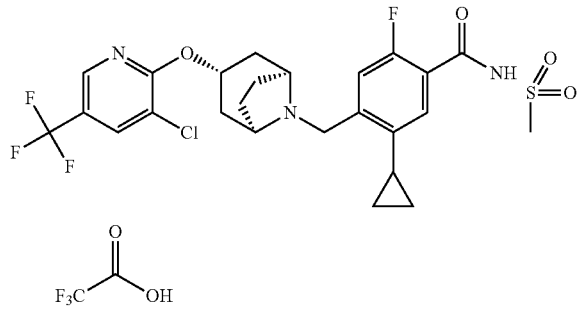

Step 1. Preparation of tert-butyl (1R,3r,5S)-3-((3-chloro-5-(trifluoromethyl)pyridin-2-yl)oxy)-8-azabicyclo[3.2.1]octane-8-carboxylate

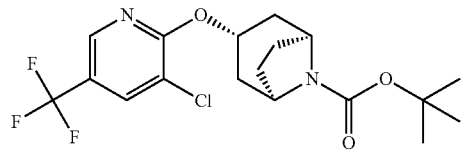 [SMILES: CC(C)(C)OC(=O)N1[C@@H]2CC[C@H]1C[C@@H](Oc1ncc(C(F)(F)F)cc1Cl)C2]

Following the procedure as described in Example 52 in step 1, and making variation as required to replace 2,5-dichloro-4-(trifluoromethyl)pyridine with 3-chloro-2-fluoro-5-(trifluoromethyl)pyridine and tert-butyl 4-hydroxypiperidine-1-carboxylate with tert-butyl (1R,3r,5S)-3-hydroxy-8-azabicyclo[3.2.1]octane-8-carboxylate, the title compound was obtained as a colorless solid (1.22 g, 34%): $^1$H NMR (300 MHz, CDCl$_3$) δ8.77 (s, 1H), 7.71 (s, 1H), 5.53-5.46 (m, 1H), 4.31-4.12 (m, 2H), 2.30-2.08 (m, 4H), 2.05-1.81 (m, 4H), 1.45 (s, 9H); MS(ES+) m/z 351.1, 353.1 (M−55).

Step 2. Preparation of (1R,3r,5S)-3-((3-chloro-5-(trifluoromethyl)pyridin-2-yl)oxy)-8-azabicyclo[3.2.1]octan

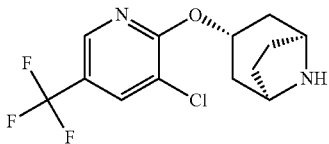 [SMILES: FC(F)(F)c1cnc(O[C@H]2C[C@H]3CC[C@@H](C2)N3)c(Cl)c1]

Following the procedure as described in Example 540 step 2, and making variation as required to replace tert-butyl 4-(1-(3,5-dichlorophenyl)ethyl)piperazine-1-carboxylate with tert-butyl (1R,3r,5S)-3-((3-chloro-5-(trifluoromethyl)pyridin-2-yl)oxy)-8-azabicyclo[3.2.1]octane-8-carboxylate, the title compound was obtained as an colorless oil (0.39 g, 42%): MS(ES+) m/z 307.0, 309.0 (M+1).

Step 3. Preparation of tert-butyl 4-(((1R,3r,5S)-3-((3-chloro-5-(trifluoromethyl)pyridin-2-yl)oxy)-8-azabicyclo[3.2.1]octan-8-yl)methyl)-5-cyclopropyl-2-fluorobenzoate

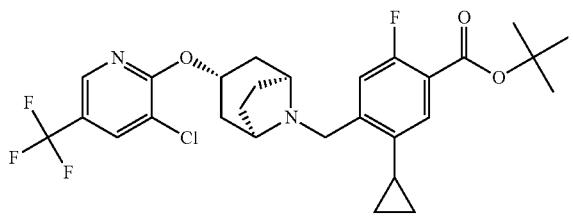 [SMILES: CC(C)(C)OC(=O)c1cc(C2CC2)c(CN2[C@@H]3CC[C@H]2C[C@@H](Oc2ncc(C(F)(F)F)cc2Cl)C3)cc1F]

Following the procedure as described in Example 53 step 3, and making variation as required to replace (S)-3-(3,5-dichlorophenoxy)piperidine, trifluoroacetic acid salt with (1R,3r,5S)-3-((3-chloro-5-(trifluoromethyl)pyridin-2-yl)oxy)-8-azabicyclo[3.2.1]octane, the title compound was obtained as a colorless oil (0.68 g, 97%): $^1$H NMR (300 MHz, CDCl$_3$) δ8.30-8.26 (m, 1H), 7.82 (d, J=2.2 Hz, 1H), 7.48 (d, J=7.3 Hz, 1H), 7.34 (d, J=12.1 Hz, 1H), 5.44 (t, J=5.2 Hz, 1H), 3.68 (s, 2H), 3.21-3.13 (m, 2H), 2.27-2.16 (m, 4H), 2.10-1.99 (m, 2H), 1.96-1.84 (m, 3H), 1.56 (s, 9H), 0.93-0.85 (m, 2H), 0.65-0.57 (m, 2H); MS(ES+) m/z 555.2, 557.2 (M+1).

Step 4. Preparation of 4-(((1R,3r,5S)-3-((3-chloro-5-(trifluoromethyl)pyridin-2-yl)oxy)-8-azabicyclo[3.2.1]octan-8-yl)methyl)-5-cyclopropyl-2-fluorobenzoic acid hydrochloride

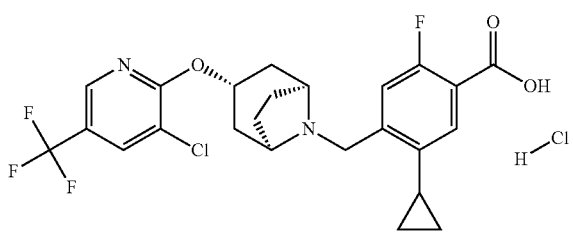

Following the procedure as described in Example 517 step 2, and making variation as required to replace tert-butyl 4-(3,5-dichlorobenzyl)piperazine-1-carboxylate with tert-butyl 4-(((1R,3r,5S)-3-((3-chloro-5-trifluoromethyl)pyridin-2-yl)oxy)-8-azabicyclo[3.2.1]octan-8-yl)methyl)-5-cyclopropyl-2-fluorobenzoate, the title compound was obtained as a colorless solid (0.66 g, quant. yield): MS(ES+) m/z 499.1, 501.1 (M+1).

Step 5. Preparation of 4-(((1R,3r,5S)-3-((3-chloro-5-(trifluoromethyl)pyridin-2-yl)oxy)-8-azabicyclo[3.2.1]octan-8-yl)methyl)-5-cyclopropyl-2-fluoro-N-(methylsulfonyl)benzamide, trifluoroacetic acid salt

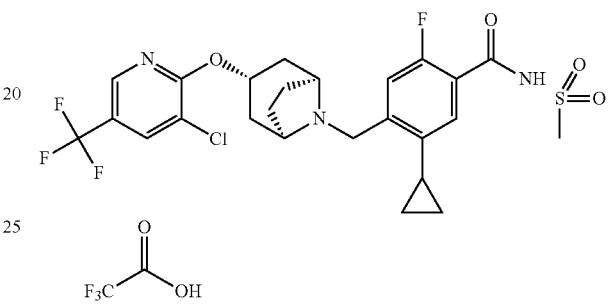

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with -(((1R,3r,5S)-3-((3-chloro-5-(trifluoromethyl)pyridin-2-yl)oxy)-8-azabicyclo[3.2.1]octan-8-yl)methyl)-5-cyclopropyl-2-fluorobenzoic acid hydrochloride, and to replace cyclopropanesulfonamide with methylsulfonamide, and purification by preparative HPLC, the title compound was obtained as a colorless solid (0.12 g, 29%): $^1$H NMR (300 MHz, CDCl$_3$+10% CD$_3$OD) δ8.24 (s, 1H), 7.83 (s, 1H), 7.50-7.41 (m, 2H), 5.53-5.46 (m, 1H), 4.42 (s, 2H), 3.97-3.87 (m, 2H), 3.30 (s, 3H), 2.80-2.68 (m, 2H), 2.66-2.54 (m, 2H), 2.38-2.25 (m, 2H), 2.20-2.09 (m, 2H), 1.87-1.75 (m, 1H), 1.05-0.95 (m, 2H), 0.72-0.63 (m, 2H); MS(ES+) m/z 576.0, 578.0 (M+1).

Example 553

Synthesis of 4-(((1R,3r,5S)-3-((3-chloro-5-(trifluoromethyl)pyridin-2-yl)oxy)-8-azabicyclo[3.2.1]octan-8-yl)methyl)-5-cyclopropyl-2-fluoro-N-(methylsulfonyl)benzamide, trifluoroacetic acid salt

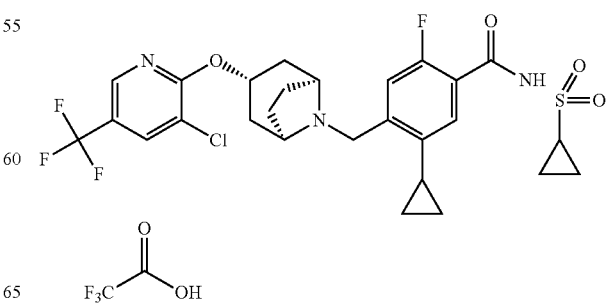

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with -(((1R,3r,5S)-3-((3-chloro-5-(trifluoromethyl)pyridin-2-yl)oxy)-8-azabicyclo[3.2.1]octan-8-yl)methyl)-5-cyclopropyl-2-fluorobenzoic acid hydrochloride, and purification by preparative HPLC, the title compound was obtained as a colorless solid (0.12 g, 27%): $^1$H NMR (300 MHz, CDCl$_3$+10% CD$_3$OD) δ8.24 (s, 1H), 7.83 (s, 1H), 7.52-7.41 (m, 2H), 5.53-5.46 (m, 1H), 4.42 (s, 2H), 3.97-3.87 (m, 2H), 3.05-2.95 (m, 1H), 2.80-2.68 (m, 2H), 2.66-2.54 (m, 2H), 2.38-2.25 (m, 2H), 2.20-2.09 (m, 2H), 1.87-1.75 (m, 1H), 1.38-1.29 (m, 2H), 1.13-0.94 (m, 4H), 0.73-0.62 (m, 2H): MS(ES+) m/z 602.1, 604.0 (M+1).

Example 554

Synthesis of 4-((1-(5-chloro-4-(trifluoromethyl)pyridin-2-yl)piperidin-4-yl)methoxy)-5-cyclopropyl-2-4-N-(methylsulfonyl)benzamide

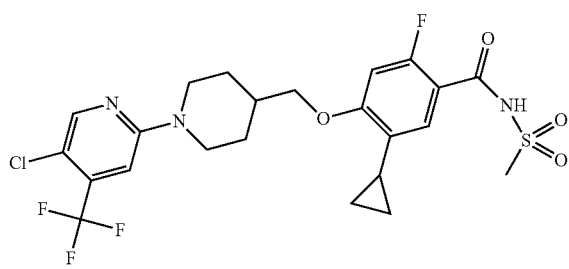 [SMILES: CS(=O)(=O)NC(=O)c1cc(C2CC2)c(OCC2CCN(c3cc(C(F)(F)F)c(Cl)cn3)CC2)cc1F]

Step 1. Preparation of tert-butyl 4-((4-(tert-butoxycarbonyl)-2-chloro-5-fluorophenoxy)methyl)piperidin-1-carboxylate

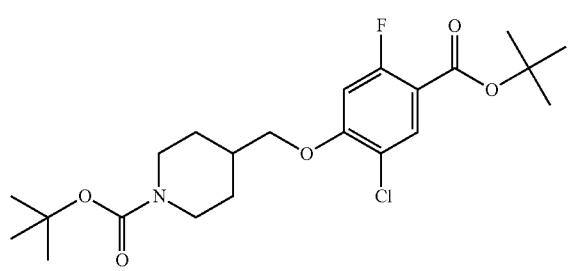 [SMILES: CC(C)(C)OC(=O)c1cc(Cl)c(OCC2CCN(C(=O)OC(C)(C)C)CC2)cc1F]

Following the procedure as described in Example 542 step 1, and making variation as required to replace tert-butyl 3-(hydroxymethyl)azetidine-1-carboxylate with tert-butyl 4-(hydroxymethyl)piperidin-1-carboxylate, the title compound was obtained as a colorless solid (7.39 g, 69%): $^1$H NMR (300 MHz, CDCl$_3$) δ7.85 (d, J=7.6 Hz, 1H), 6.59 (d, J=11.9 Hz, 1H), 4.23-4.05 (m, 2H), 3.84 (d, J=6.2 Hz, 2H), 2.81-2.64 (m, 2H), 2.10-1.94 (m, 1H), 1.87-1.77 (m, 2H), 1.55 (s, 9H), 1.44 (s, 9H), 1.36-1.20 (m, 2H); MS(ES+) m/z 444.1, 446.2 (M+1).

Step 2. Preparation of tert-butyl 4-((4-(tert-butoxycarbonyl)-2-cyclopropyl-5-fluorophenoxy)methyl)piperidin-1-carboxylate

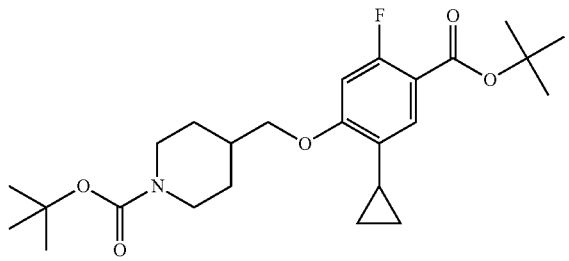 [SMILES: CC(C)(C)OC(=O)c1cc(C2CC2)c(OCC2CCN(C(=O)OC(C)(C)C)CC2)cc1F]

Following the procedure as described in Example 542 step 2, and making variation as required to replace tert-butyl 3-((4-(tert-butoxycarbonyl)-2-chloro-5-fluorophenoxy)methyl)azetidine-1-carboxylate with tert-butyl 4-((4-(tert-butoxycarbonyl)-2-chloro-5-fluorophenoxy)methyl)piperidin-1-carboxylate, the title compound was obtained as a colorless solid (8.12 g, 97%): $^1$H NMR (300 MHz, CDCl$_3$) δ7.35 (d, J=8.3 Hz, 1H), 6.47 (d, J=12.4 Hz, 1H), 4.23-4.04 (m, 2H), 3.81 (d, J=6.2 Hz, 2H), 2.81-2.64 (m, 2H), 2.05-1.91 (m, 2H), 1.85-1.75 (m, 2H), 1.53 (s, 9H), 1.43 (s, 9H), 1.38-1.26 (m, 2H), 0.89-0.81 (m, 2H), 0.63-0.56 (m, 2H); MS(ES+) m/z: 450.2 (M+1).

Step 3. Preparation of methyl 5-cyclopropyl-2-fluoro-4-(piperidin-4-ylmethoxy)benzoate hydrochloride

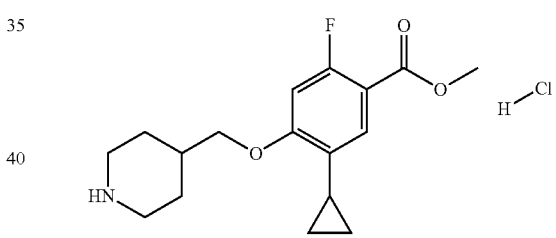

Following the procedure as described in Example 542 step 3, and making variation as required to tert-butyl 3-((4-(tert-butoxycarbonyl)-2-cyclopropyl-5-fluorophenoxy)methyl)azetidine-1-carboxylate with tert-butyl 4-((4-(tert-butoxycarbonyl)-2-cyclopropyl-5-fluorophenoxy)methyl)piperidin-1-carboxylate, the title compound was obtained as a colorless solid (6.21 g, quant. yield): MS(ES+) m/z 308.2 (M+1).

Step 4. Preparation of methyl 4-((1-(5-chloro-4-(trifluoromethyl)pyridin-2-yl)piperidin-4-yl)methoxy)-5-cyclopropyl-2-fluorobenzoate

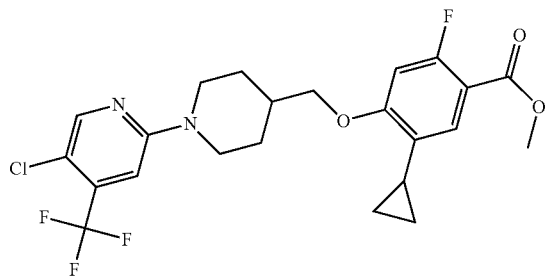 [SMILES: COC(=O)c1cc(C2CC2)c(OCC2CCN(c3cc(C(F)(F)F)c(Cl)cn3)CC2)cc1F]

Following the procedure as described in Example 525 step 1, and making variation as required to replace methyl 5-cyclopropyl-2-fluoro-4-((3-methylazetidin-3-yl)methoxy)benzoate hydrochloride with methyl 5-cyclopropyl-2-fluoro-4-(piperidin-4-ylmethoxy)benzoate hydrochloride and purification by flash chromatography, the title compound was obtained as a colorless oil (0.71 g, 56%): $^1$H NMR (300 MHz, CDCl$_3$) δ8.19 (s, 1H), 7.42 (d, J=8.4 Hz, 1H), 6.86 (s, 1H), 6.52 (d, J=12.5 Hz, 1H), 4.41-4.31 (m, 2H), 3.90-3.83 (m, 5H), 2.94 (dt, J=13.0, 2.6 Hz, 2H), 2.23-2.08 (m, 1H), 2.01-1.90 (m, 3H), 1.44 (dq, J=12.4, 4.0 Hz, 2H), 0.94-0.82 (m, 2H), 0.67-0.57 (m, 2H); MS(ES+) m/z 487.1, 489.1 (M+1).

Step 5. Preparation of 4-((1-(5-chloro-4-(trifluoromethyl)pyridin-2-yl)piperidin-4-yl)methoxy)-5-cyclopropyl-2-fluorobenzoic acid

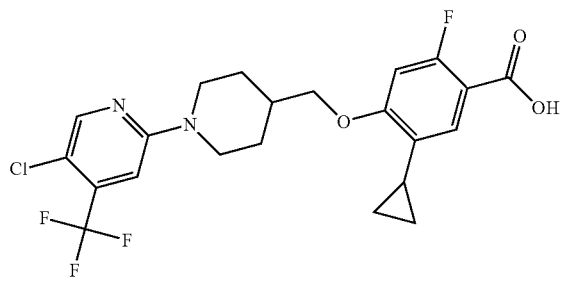 [SMILES: O=C(O)c1cc(C2CC2)c(OCC2CCN(c3cc(C(F)(F)F)c(Cl)cn3)CC2)cc1F]

Following the procedure as described in Example 525 step 2, and making variation as required to replace methyl 4-((1-(5-chloro-4-(trifluoromethyl)pyridin-2-yl)-3-methylazetidin-3-yl)methoxy)-5-cyclopropyl-2-fluorobenzoate with methyl 4-((1-(5-chloro-4-(trifluoromethyl)pyridin-2-yl)piperidin-4-yl)methoxy)-5-cyclopropyl-2-fluorobenzoate, the title compound was obtained as a colorless solid (0.49 g, 71%): MS(ES+) m/z 473.1, 475.1 (M+1).

Step 6. Preparation of 4-((1-(5-chloro-4-(trifluoromethyl)pyridin-2-yl)piperidin-4-yl)methoxy)-5-cyclopropyl-2-fluoro-N-(methylsulfonyl)benzamide

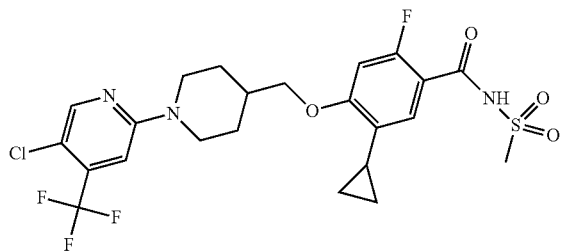 [SMILES: CS(=O)(=O)NC(=O)c1cc(C2CC2)c(OCC2CCN(c3cc(C(F)(F)F)c(Cl)cn3)CC2)cc1F]

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 4-((1-(5-chloro-4-(trifluoromethyl)pyridin-2-yl)piperidin-4-yl)methoxy)-5-cyclopropyl-2-fluorobenzoic acid, and to replace cyclopropanesulfonamide with methylsulfonamide, the title compound was obtained as a colorless solid (0.15 g, 55%): $^1$H NMR (300 MHz, CDCl$_3$) δ8.68 (br s, 1H), 8.20 (s, 1H), 7.56 (d, J=8.7 Hz, 1H), 6.86 (s, 1H), 6.55 (d, =14.1 Hz, 1H), 4.41-4.32 (m, 2H), 3.89 (d, J=6.28 Hz, 2H), 3.39 (s, 3H), 2.95 (dt, J=13.0, 2.6 Hz, 2H), 2.25-2.10 (m, 1H), 2.05-1.91 (m, 3H), 1.45 (dq, J=12.5, 3.6 Hz, 2H), 0.95-0.86 (m, 2H), 0.68-0.58 (m, 2H); MS(ES+) m/z 550.0, 552.0 (M+1).

Example 555

Synthesis of 4-((1-(5-chloro-4-(trifluoromethyl)pyridin-2-yl)piperidin-4-yl)methoxy)-5-cyclopropyl-N-(cyclopropylsulfonyl)-2-fluorobenzamide

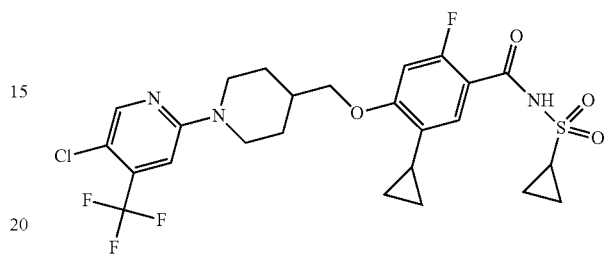

Following the procedure as described in Example 53 step 3, and making variation as required to replace (S)-5-cyclopropyl-4-((3-(3,5-dichlorophenoxy)piperidin-1-yl)methyl)-2-fluorobenzoic acid with 4-((1-(5-chloro-4-(trifluoromethyl)pyridin-2-yl)piperidin-4-yl)methoxy)-5-cyclopropyl-2-fluorobenzoic acid, the title compound was obtained as a colorless solid (0.14 g, 49%); $^1$H NMR (300 MHz, CDCl$_3$) δ8.67 (br s, 1H), 8.20 (s, 1H), 7.57 (d, J=9.1 Hz, 1H), 0.86 (s, 1H), 6.55 (d, J=14.1 Hz, 1H), 4.41-4.31 (m, 2H), 3.89 (d, J=6.1 Hz, 2H), 3.12-3.03 (m, 1H), 3.00-2.89 (m, 2H), 2.25-2.09 (m, 1H), 2.05-1.90 (m, 3H), 1.53-1.37 (m, 4H), 1.17-1.07 (m, 2H), 0.94-0.85 (m, 2H), 0.67-0.59 (m, 2H): MS(ES+) m/z 576.0, 578.0 (M+1).

Example 556

Synthesis of 4-((1-(5-chloro-4-(trifluoromethyl)pyridin-2-yl)-4-methylpiperidin-4-yl)methoxy)-5-cyclopropyl-2-fluoro-N-(methylsulfonyl)benzamide

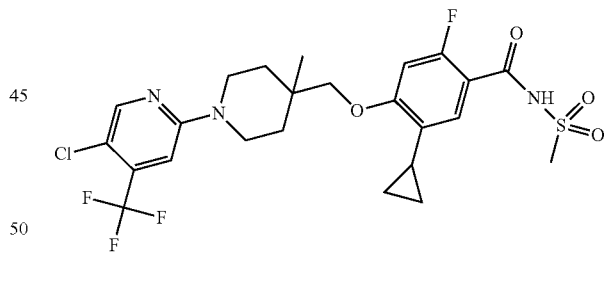

Step 1. Preparation of tert-butyl 4-((4-(tert-butoxycarbonyl)-2-chloro-5-fluorophenoxy)methyl)-4-methylpiperidine-1-carboxylate

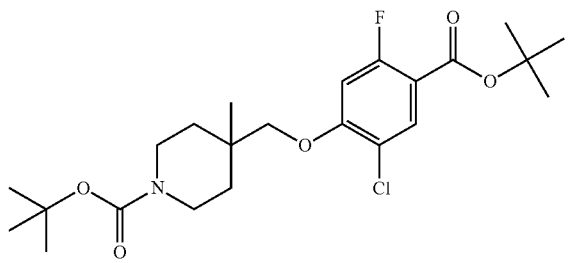 [SMILES: CC1(COc2cc(F)c(C(=O)OC(C)(C)C)cc2Cl)CCN(C(=O)OC(C)(C)C)CC1]

Following the procedure as described in Example 542 step 1, and making variation as required to replace tert-butyl 3-(hydroxymethyl)azetidine-1-carboxylate with tert-butyl 4-(hydroxymethyl)-4-methylpiperidin-1-carboxylate, the title compound was obtained as a colorless solid (15.19 g, 76%): ¹H NMR (300 MHz, CDCl₃) δ7.83 (d, J=7.6 Hz, 1H), 6.58 (d, J=11.9 Hz, 1H), 3.76-3.62 (m, 4H), 3.22-3.10 (m, 2H), 1.65-1.56 (m, 2H), 1.54 (s, 9H), 5.48-1.39 (m, 11H), 1.13 (s, 3H); MS(ES+) m/z 458.1, 460.0 (M+1).

Step 2. Preparation of tert-butyl 4-((4-(tert-butoxy-carbonyl)-2-cyclopropyl-5-fluorophenoxy)methyl)-4-methylpiperidine-1-carboxylate

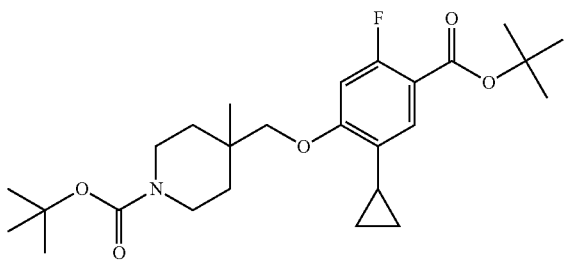 [SMILES: CC1(COc2cc(F)c(C(=O)OC(C)(C)C)cc2C2CC2)CCN(C(=O)OC(C)(C)C)CC1]

Following the procedure as described in Example 542 step 2, and making variation as required to replace tert-butyl 3-(94-(tert-butoxycarbonyl)-2-chloro-5-fluorophenoxy) methyl)azetidine-1-carboxylate with tert-butyl 4-((4-(tert-butoxycarbonyl)-2-chloro-5-fluorophenoxy)methyl)-4-methylpiperidine-1-carboxylate, the title compound was obtained as a colorless solid (9.91 g, 69%): ¹H NMR (300 MHz, CDCl₃) δ7.38 (d, J=8.4 Hz, 1H), 6.47 (d, J=12.5 Hz, 1H), 3.77-3.61 (m, 4H), 3.23-3.09 (m, 2H), 2.00-1.88 (m, 1H), 1.69-1.57 (m, 2H), 1.54 (s, 9H), 1.48-1.38 (m, 11H), 1.13 (s, 3H), 0.89-0.82 (m, 2H), 0.62-0.55 (m, 2H); MS(ES+) m/z: 464.2 (M+1).

Step 3. Preparation of methyl 5-cyclopropyl-2-fluoro-4-((4-methylpiperidin-4-yl)methoxy)benzoate hydrochloride

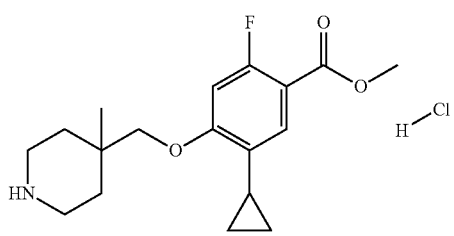 [SMILES: COC(=O)c1cc(C2CC2)c(OCC2(C)CCNCC2)cc1F ; Cl]

Following the procedure as described in Example 542 step 3, and making variation as required to tert-butyl 3-((4-(tert-butoxycarbonyl)-2-cyclopropyl-5-fluorophenoxy) methyl)azetidine-1-carboxylate with tert-butyl 4-((4-(tert-butoxycarbonyl)-2-cyclopropyl-5-fluorophenoxy)methyl)-4-methylpiperidine-1-carboxylate, the title compound was obtained as a colorless solid (7.65 g, quant. yield): MS(ES+) m/z 322.2 (M+1).

Step 4. Preparation of methyl 4-((1-(5-chloro-4-(trifluoromethyl)pyridin-2-yl)-4-methylpiperidin-4-yl)methoxy)-5-cyclopropyl-2-fluorobenzoate

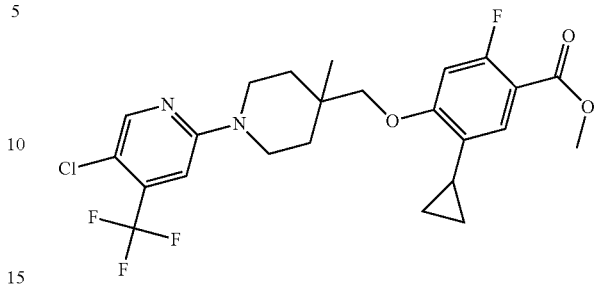

Following the procedure as described in Example 525 step 1, and making variation as required to replace methyl 5-cyclopropyl-2-fluoro-4-((3-methylazetidin-3-yl)methoxy) benzoate hydrochloride with methyl 5-cyclopropyl-2-fluoro-4-((4-methylpiperidin-4-yl)methoxy)benzoate hydrochloride, the title compound was obtained as a colorless oil (0.87 g, 67%): ¹H NMR (300 MHz, CDCl₃) δ8.19 (s, 1H), 7.45 (d, J=8.4 Hz, 1H), 6.84 (s, 1H), 6.52 (d, J=12.5 Hz, 1H), 3.94-3.83 (m, 5H), 3.73 (s, 2H), 3.43-3.31 (m, 2H), 1.99-1.86 (m, 1H), 1.84-1.72 (m, 2H), 1.63-1.52 (m, 2H), 1.20 (s, 3H), 0.88-0.79 (m, 2H), 0.64-0.55 (m, 2H); MS(ES−) m/z 501.1, 503.1 (M+1).

Step 5. Preparation of 4-((1-(5-chloro-4-(trifluoromethyl)pyridin-2-yl)-4-methylpiperidin-4-yl) methoxy)-5-cyclopropyl-2-fluorobenzoic acid

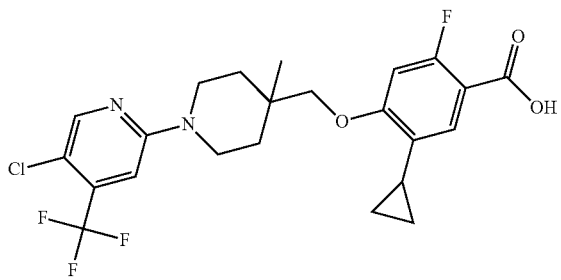 [SMILES: CC1(COc2cc(F)c(C(=O)O)cc2C2CC2)CCN(c2cc(C(F)(F)F)c(Cl)cn2)CC1]

Following the procedure as described in Example 525 step 2, and making variation as required to replace methyl 4-((1-(5-chloro-4-(trifluoromethyl)pyridin-2-yl)-3-methyl-azetidin-3-yl)methoxy)-5-cyclopropyl-2-fluorobenzoate with methyl 4-((1-(5-chloro-4-(trifluoromethyl)pyridin-2-yl)-4-methylpiperidin-4-yl)methoxy)-5-cyclopropyl-2-fluorobenzoate, the title compound was obtained as a colorless solid (0.85 g, quant. yield): MS(ES+) m/z 487.1, 489.1 (M+1).

Step 6. Preparation of 4-((1-(5-chloro-4-(trifluoromethyl)pyridin-2-yl)-4-methylpiperidin-4-yl) methoxy)-5-cyclopropyl-2-fluoro-N-(methylsulfonyl)benzamide

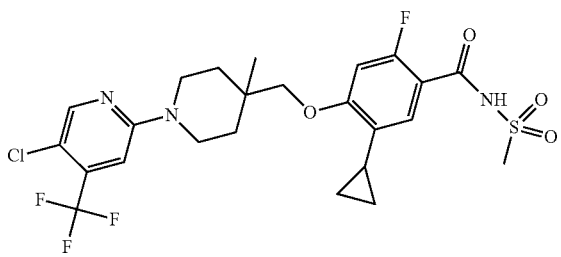 [SMILES: CC1(COc2cc(F)c(C(=O)NS(C)(=O)=O)cc2C2CC2)CCN(c2cc(C(F)(F)F)c(Cl)cn2)CC1]

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 4-((1-(5-chloro-4-(trifluoromethyl)pyridin-2-yl)-4-methylpiperidin-4-yl)methoxy)-5-cyclopropyl-2-fluorobenzoic acid, and to replace cyclopropanesulfonamide with methylsulfonamide, the title compound was obtained as a colorless solid (0.40 g, 82%): $^1$H NMR (300 MHz, CDCl$_3$) δ 8.71 (br s, 1H), 8.18 (s, 1H), 7.65 (d, J=9.1 Hz, 1H), 8.84 (s, 1H), 6.56 (d, J=14.1 Hz, 1H), 3.95-3.84 (m, 2H), 3.76 (s, 2H), 3.42-3.30 (m, 5H), 1.98-1.87 (m, 1H), 1.84-1.71 (m, 2H), 1.63-1.53 (m, 2H), 1.21 (s, 3H), 0.91-0.82 (m, 2H), 0.64-0.56 (m, 2H); MS(ES+) m/z 564.0, 566.0 (M+1).

Example 557

Synthesis of 4-((1-(5-chloro-4-(trifluoromethyl)pyridin-2-yl)-4-methylpiperidin-4-yl)methoxy)-5-cyclopropyl-N-(cyclopropylsulfonyl)-2-fluorobenzamide

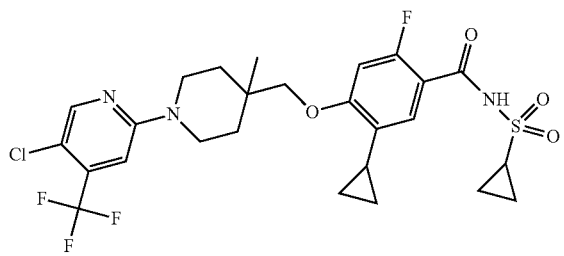 [SMILES: CC1(COc2cc(F)c(C(=O)NS(=O)(=O)C3CC3)cc2C2CC2)CCN(c2cc(C(F)(F)F)c(Cl)cn2)CC1]

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 4-((1-(5-chloro-4-(trifluoromethyl)pyridin-2-yl)-4-methylpiperidin-4-yl)methoxy)-5-cyclopropyl-2-fluorobenzoic acid, the title compound was obtained as a colorless solid (0.35 g, 68%): $^1$H NMR (300 MHz, CDCl$_3$) δ8.67 (d, J=13.6 Hz, 1H), 8.19 (s, 1H), 7.58 (d, J=9.1 Hz, 1H), 6.84 (s, 1H), 6.55 (d, J=14.1 Hz, 1H), 3.97-3.84 (m, 2H), 3.76 (s, 2H), 3.43-3.29 (m, 2H), 3.13-3.01 (m, 1H), 1.99-1.87 (m, 1H), 1.85-1.72 (m, 2H), 1.64-1.51 (m, 2H), 1.46-1.38 (m, 2H), 1.21 (s, 3H), 1.16-1.07 (m, 2H), 0.91-0.81 (m, 2H), 0.65-0.56 (m, 2H): MS(ES+) m/z 590.0, 592.0 (M+1).

Example 558

Synthesis of 5-cyclopropyl-4-(((1S,4S)-5-((3,5-dichlorophenyl)sulfonyl)-2,5-diazabicyclo[2.2.1]heptan-2-yl)methyl)-2-fluoro-N-(methylsulfonyl)benzamide, trifluoroacetic acid salt

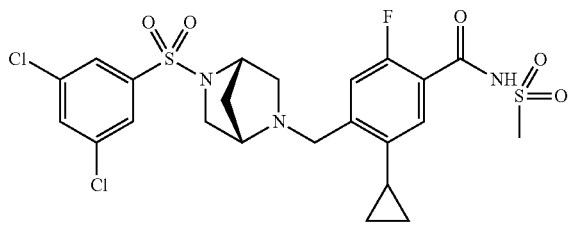

-continued

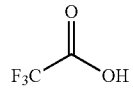

Step 1. Preparation of tert-butyl (1S,4S)-5-(4-(tert-butoxycarbonyl)-2-cyclopropyl-5-fluorobenzyl)-2,5-diazabicyclo[2.2.1]heptane-2-carboxylate

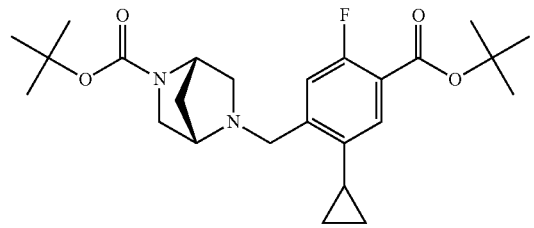 [SMILES: CC(C)(C)OC(=O)c1cc(C2CC2)c(CN2C[C@@H]3C[C@H]2CN3C(=O)OC(C)(C)C)cc1F]

Following the procedure as described in Example 53 step 3, and making variation as required to replace (S)-3-(3,5-dichlorophenoxy)piperidine, trifluoroacetic acid salt with tert-butyl (1S,4S)-2,5-diazabicyclo[2.2.1]heptane-2-carboxylate, the title compound was obtained as a colorless solid (2.61 g, 67%): $^1$H NMR (300 MHz, CDCl$_3$) δ7.46 (d, J=7.1 Hz, 1H), 7.18 (d, J=12.1 Hz, 1H), 4.41-4.22 (m, 1H), 3.94-3.77 (m, 2H), 3.65-3.39 (m, 2H), 3.23-3.13 (m, 1H), 2.98-2.82 (m, 1H), 2.75-2.43 (m, 1H), 1.93-1.80 (m, 2H), 1.77-1.60 (m, 1H), 1.55 (s, 9H), 1.44 (s, 9H), 0.94-0.86 (m, 2H), 0.64-0.55 (m, 2H); MS(ES+) m/z 447.2 (M+1).

Step 2. Preparation of methyl 4-(((1S,4S)-2,5-diazabicyclo[2.2.1]heptan-2-yl)methyl)-5-cyclopropyl-2-fluorobenzoate hydrochloride

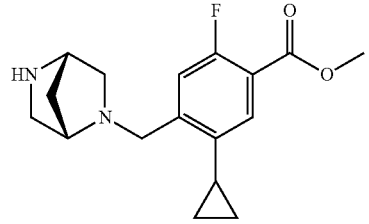 [SMILES: COC(=O)c1cc(C2CC2)c(CN2C[C@@H]3C[C@H]2CN3)cc1F]

Following the procedure as described in Example 542 step 3, and making variation as required to tert-butyl 3-((4-(tert-butoxycarbonyl)-2-cyclopropyl-5-fluorophenoxy)methyl)azetidine-1-carboxylate with tert-butyl (1S,4S)-5-(4-(tert-butoxycarbonyl)-2-cyclopropyl-5-fluorobenzyl)-2,5-diazabicyclo[2.2.1]heptane-2-carboxylate, the title compound was obtained as a colorless solid (2.12 g, 96%): MS(ES+) m/z 305.2 (M+1).

Step 3. Preparation of methyl 5-cyclopropyl-4-(((1S,4S)-5-((3,5-dichlorophenyl)sulfonyl)-2,5-diazabicyclo[2.2.1]heptan-2-yl)methyl)-2-fluorobenzoate

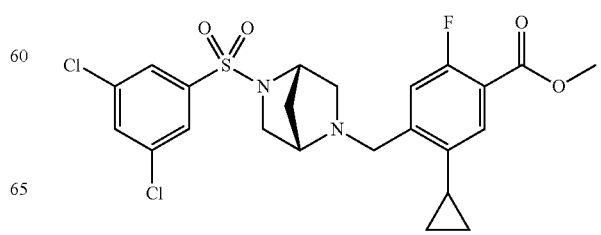

To a mixture of methyl 4-(((1S,4S)-2,5-diazabicyclo[2.2.1]heptan-2-yl)methyl)-5-cyclopropyl-2-fluorobenzoate hydrochloride (0.38 g, 1.00 mmol) and 4-dimethylaminopyridine (0.61 g, 5.00 mmol) in dichloromethane (10 mL) was added 3,5-dichlorobenzenesulfonyl chloride (0.37 g, 1.50 mmol). The reaction mixture was stirred at ambient temperature in a sealed tube for 5 hours, was diluted with ethyl acetate (50 mL); washed with water (40 mL), aqueous saturated sodium bicarbonate solution (50 mL) and brine (50 mL); dried over anhydrous sodium sulfate, filtered and concentrated in vacuo. The residue was purified by flash chromatography (0-40% ethyl acetate in hexanes) to provide the title compound as a colorless solid (0.51 g, quant. yield): ¹H NMR (300 MHz, CDCl₃) δ7.73-7.68 (m, 2H), 7.58-7.50 (m, 2H), 7.11 (d, J=11.8 Hz, 1H), 4.34 (s, 1H), 3.93-3.81 (m, 5H), 3.64 (d, J=9.5 Hz, 1H), 3.49 (s, 1H), 3.10 (dd, J=9.5, 2.1 Hz, 1H), 2.89 (dd, J=9.7, 2.1 Hz, 1H), 2.68 (d, J=9.7 Hz, 1H), 1.88-1.76 (m, 2H), 1.30 (d, J=9.7 Hz, 1H), 0.94-0.86 (m, 2H), 0.63-0.56 (m, 2H); MS(ES+) m/z 513.0, 515.0 (M+1).

Step 4. Preparation of 5-cyclopropyl-4-(((1S,4S)-5-((3,5-dichlorophenyl)sulfonyl)-2,5-diazabicyclo[2.2.1]heptan-2-yl)methyl)-2-fluorobenzoic acid

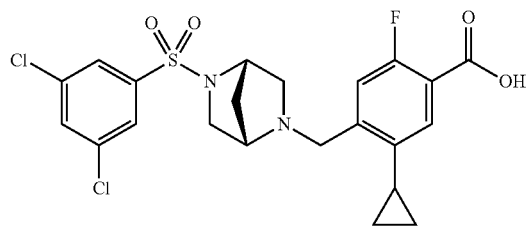 [SMILES: O=C(O)c1cc(C2CC2)c(CN2C[C@@H]3C[C@H]2CN3S(=O)(=O)c2cc(Cl)cc(Cl)c2)cc1F]

Following the procedure as described in Example 525 step 2, and making variation as required to replace methyl 4-((1-(5-chloro-4-(trifluoromethyl)pyridin-2-yl)-3-methylazetidin-3-yl)methoxy)-5-cyclopropyl-2-fluorobenzoate with methyl 5-cyclopropyl-4-(((1S,4S)-5-((3,5-dichlorophenyl)sulfonyl)-2,5-diazabicyclo[2.2.1]heptan-2-yl)methyl)-2-fluorobenzoate, the title compound was obtained as a colorless solid (0.51 g, quant. yield): MS(ES+) m/z 499.0, 501.0 (M+1).

Step 5. Preparation of 5-cyclopropyl-4-(((1S,4S)-5-((3,5-dichlorophenyl)sulfonyl)-2,5-diazabicyclo[2.2.1]heptan-2-yl)methyl)-2-fluoro-N-(methylsulfonyl)benzamide, trifluoroacetic acid salt

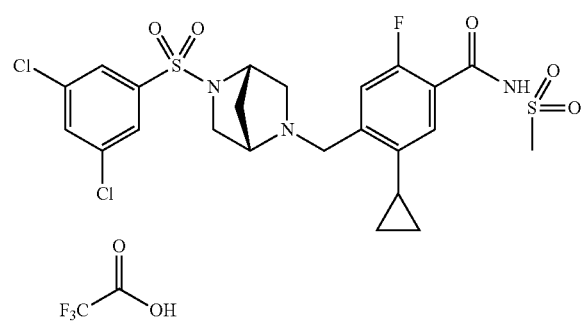

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 4-((1-(5-chloro-4-(trifluoromethyl)pyridin-2-yl)-4-methylpiperidin-4-yl)methoxy)-5-cyclopropyl-2-fluorobenzoic acid, and to replace cyclopropanesulfonamide with methylsulfonamide, and purification by preparative HPLC, the title compound was obtained as a colorless solid (0.15 g, 43%): ¹H NMR (300 MHz, CDCl₃+10% CD₃OD) δ7.67-7.62 (m, 2H), 7.57-7.53 (m, 1H), 7.48-7.41 (m, 1H), 7.30-7.22 (m, 1H), 4.55-4.33 (m, 3H), 4.24 (s, 1H), 3.84 (d, J=11.1 Hz, 1H), 3.39-3.20 (m, 6H), 2.14 (d, J=11.1 Hz, 1H), 1.86-1.74 (m, 1H), 1.63 (d, J=11.6 Hz, 1H), 1.05-0.95 (m, 2H), 0.69-0.59 (m, 2H); MS(ES+) m/z 575.9, 577.9 (M+1).

Example 559

Synthesis of 5-cyclopropyl-N-(cyclopropylsulfonyl)-4-(((1S,4S)-5-((3,5-dichlorophenyl)sulfonyl)-2,5-diazabicyclo[2.2.1]heptan-2-yl)methyl)-2-fluorobenzamide, trifluoroacetic acid salt

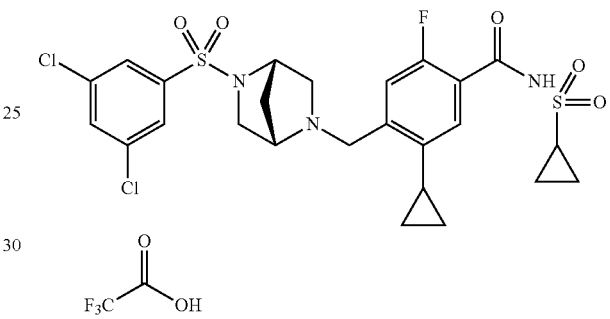

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 4-((1-(5-chloro-4-(trifluoromethyl)pyridin-2-yl)-4-methylpiperidin-4-yl)methoxy)-5-cyclopropyl-2-fluorobenzoic acid, and purification by preparative HPLC, the title compound was obtained as a colorless solid (0.20 g, 56%): ¹H NMR (300 MHz, CDCl₃+10% CD₃OD) δ7.64 (d, J=1.7 Hz, 2H), 7.57-7.54 (m, 1H), 7.47 (d, J=7.3 Hz, 1H), 7.258 (d, J=11.4 Hz, 1H), 4.49-4.28 (m, 3H), 4.17 (s, 1H), 3.82 (d, J=11.4 Hz, 1H), 3.35-3.20 (m, 3H), 3.05-2.94 (m, 1H), 2.15-2.06 (m, 1H), 1.86-1.74 (m, 1H), 1.60 (d, J=11.3 Hz, 1H), 1.37-1.29 (m, 2H), 1.22-0.94 (m, 4H), 0.67-0.59 (m, 2H); MS(ES+) m/z 602.3, 603.9 (M+1).

Example 560

Synthesis of 4-(((1R,3r,5S)-3-(3-chloro-5-(trifluoromethoxy)phenoxy)-8-azabicyclo[3.2.1]octan-8-yl)methyl)-5-cyclopropyl-2-fluoro-N-(methylsulfonyl)benzamide, trifluoroacetic acid salt

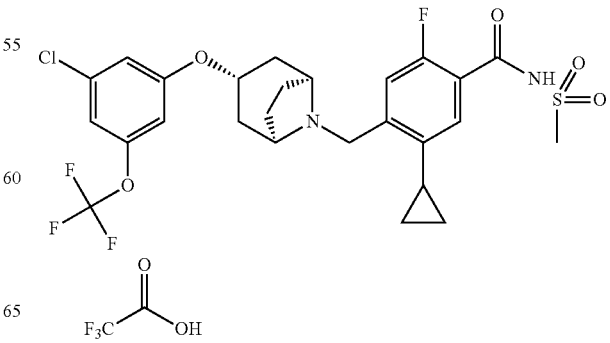

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 4-(((1R,3r,5S)-3-(3-chloro-5-(trifluoromethoxy)phenoxy)-8-azabicyclo[3.2.1]octan-8-yl)methyl)-5-cyclopropyl-2-fluorobenzoic acid hydrochloride, and to replace cyclopropanesulfonamide with methylsulfonamide, and purification by preparative HPLC, the title compound was obtained as a colorless solid (0.36 g, 51%): $^1$H NMR (300 MHz, CDCl$_3$+10%, CD$_3$OD) δ7.47-7.39 (m, 2H), 6.81-6.78 (m, 1H), 6.75-6.72 (m, 1H), 6.56-6.52 (m, 1H), 4.62-4.56 (m, 1H), 4.38 (s, 2H), 3.90 (brs, 2H), 3.29 (s, 3H), 2.75-2.64 (m, 2H), 2.50-2.40 (m, 2H), 2.16-2.24 (m, 2H), 2.13 (d, J=16.4 Hz, 2H), 1.85-1.74 (m, 1H), 1.03-0.95 (m, 2H), 0.70-0.63 (m, 2H); MS(ES+) m/z 591.1, 593.1 (M+1).

Example 561

Synthesis of 4-((4-((5-chloro-4-(trifluoromethyl)pyridin-2-yl)oxy)-3,3-dimethylpiperidin-1-yl)methyl)-5-cyclopropyl-2-fluoro-N-(methylsulfonyl)benzamide, trifluoroacetic acid salt

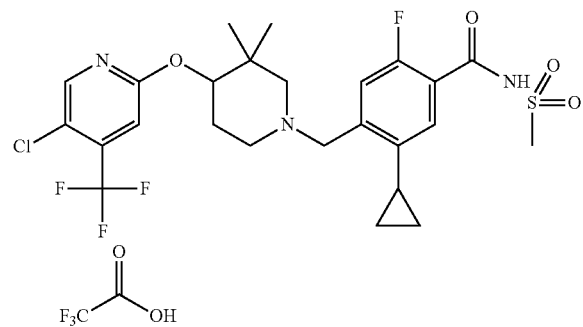

Step 1. Preparation of tert-butyl 3,3-dimethyl-4-oxopiperidine-1-carboxylate

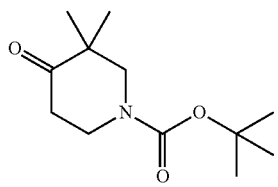 [SMILES: CC(C)(C)OC(=O)N1CCC(=O)C(C)(C)C1]

To a solution of tert-butyl 4-oxopiperidine-1-carboxylate (15.0 g, 75.30 mmol) in anhydrous tetrahydrofuran (400 mL) at 0° C. was added sodium hydride (60% in mineral oil, 6.04 g, 151.00 mmol) under nitrogen. After stirring for 10 minutes, methyl iodide (11.7 mL, 188.00 mmol) was added; the reaction mixture was stirred at 0° C. for 1 hour and stirred at ambient temperature for 3 hours. The reaction mixture was quenched by slowly addition of water (10 mL) and concentrated in vacuo to remove about 300 mL of tetrahydrofuran. The residue was diluted with ethyl acetate (300 mL), washed with aqueous saturated ammonium chloride solution (2×250 mL) and brine (100 mL); dried over anhydrous sodium sulfate, filtered and concentrated in vacuo. The residue was triturated with hexanes to provide the title compound as a colorless solid (6.68 g, 39%): $^1$H NMR (300 MHz, CDCl$_3$) δ3.68 (d, J=6.2 Hz, 2H), 3.39 (s, 2H), 2.45 (t, J=6.2 Hz, 2H), 1.45 (s, 9H), 1.07 (s, 6H).

Step 2. Preparation of tert-butyl 4-hydroxy-3,3-dimethylpiperidine-1-carboxylate

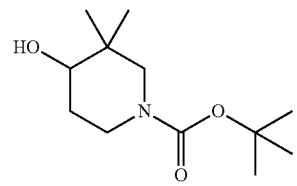 [SMILES: CC(C)(C)OC(=O)N1CCC(O)C(C)(C)C1]

To a solution of 3,3-dimethyl-4-oxopiperidine-1-carboxylate (4.88 g, 21.47 mmol) in anhydrous methanol (50 mL) at 0° C. was added sodium borohydride (0.87 g, 21.97 mmol) portionwise under nitrogen. The resulting mixture was stirred at 0° C. for 1 hour and then stirred at ambient temperature for 2 hours. The reaction mixture was concentrated in vacuo and the residue was diluted with ethyl acetate (200 mL), washed with 1.0 M aqueous hydrochloric acid solution (100 mL) and brine (2×70 mL); dried over anhydrous sodium sulfate, filtered and concentrated in vacuo to provide the title compound as a colorless solid (4.92 g, quant. yield): $^1$H NMR (300 MHz, CDCl$_3$) δ 3.92-3.68 (m, 1H), 3.58-3.41 (m, 1H), 3.37 (dd, J=9.2, 4.0 Hz, 1H), 3.07-2.93 (m, 1H), 2.69 (d, J=13.3 Hz, 1H), 1.77-1.65 (m, 1H), 1.60-1.46 (m, 1H), 1.42 (s, 9H), 0.92 (s, 3H), 0.85 (s, 3H); MS(ES+) m/z 230.2 (M+1).

Step 3. Preparation of tert-butyl 4-((5-chloro-4-(trifluoromethyl)pyridin-2-yl)oxy)-3,3-dimethylpiperidine-1-carboxylate

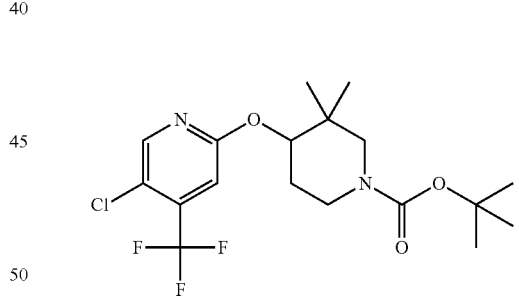

To a mixture of tert-butyl 4-hydroxy-3,3-dimethylpiperidine-1-carboxylate (4.58 g, 19.97 mmol) and 2,5-dichloro-4-(trifluoromethyl)pyridine (5.18 g, 23.96 mmol) in anhydrous dimethylsulfoxide (150 mL) was added cesium carbonate (19.52 g, 59.91 mmol). The reaction mixture was heated at 90° C. under nitrogen for 18 hours, cooled to ambient temperature, diluted with ethyl acetate (300 mL), washed with water (150 mL) and brine (3×100 mL), dried over anhydrous sodium sulfate, filtered and concentrated in vacuo. The residue was purified by flash chromatography (0-12% ethyl acetate in hexanes) to provide the title compound as a colorless oil (4.55 g, 56%): $^1$H NMR (300 MHz, CDCl$_3$) δ8.18 (s, 1H), 7.01. (s, 1H), 4.91 (dd, J=8.3, 3.8 Hz, 1H), 3.80-3.60 (m, 1H), 3.55-3.43 (m, 1H), 3.25 (ddd, J=13.5, 8.7, 3.9 Hz, 1H), 2.97 (d, J=13.7 Hz, 1H), 1.98-1.83

(m, 1H), 1.73-1.58 (m, 1H), 1.44 (s, 9H), 0.97 (s, 3H), 0.95 (s, 3H); MS(ES+) m/z 353.0, 355.0 (M−55).

Step 4. Preparation of 5-chloro-2-((3,3-dimethylpiperidin-4-yl)oxy)-4-(trifluoromethyl)pyridine

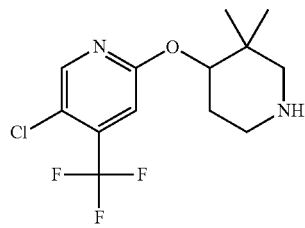 [SMILES: CC1(C)CNCCC1Oc1cc(C(F)(F)F)c(Cl)cn1]

Following the procedure as described in Example 540 step 2, and making variation as required to replace tert-butyl 4-(1-(3,5-dichlorophenyl)ethyl)piperazine-1-carboxylate with tert-butyl 4-((5-chloro-4-(trifluoromethyl)pyridin-2-yl)oxy)-3,3-dimethylpiperidine-1-carboxylate, the title compound was obtained as an colorless oil (3.77 g, quant. yield): MS(ES+) m/z 309.1, 311.1 (M+1).

Step 5. Preparation of tert-butyl 4-((4-((5-chloro-4-(trifluoromethyl)pyridin-2-yl)oxy)-3,3-dimethylpiperidin-1-yl)methyl)-5-cyclopropyl-2-fluorobenzoate

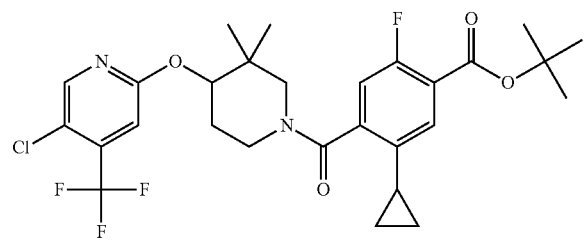 [SMILES: CC(C)(C)OC(=O)c1cc(C2CC2)c(C(=O)N2CCC(Oc3cc(C(F)(F)F)c(Cl)cn3)C(C)(C)C2)cc1F]

Following the procedure as described in Example 53 step 3, and making variation as required to replace (S)-3-(3,5-dichlorophenoxy)piperidine, trifluoroacetic acid salt with 5-chloro-2-((3,3-dimethylpiperidin-4-yl)oxy)-4-(trifluoromethyl)pyridine, the title compound was obtained as a colorless solid (5.46 g, 79%): $^1$H NMR (300 MHz, CDCl$_3$) δ 8.18 (s, 1H), 7.47 (d, J=7.3 Hz, 1H), 7.17 (d, J=11.9 Hz, 1H), 7.07 (s, 1H), 4.83 (dd, J=8.6, 3.9 Hz, 1H), 3.59 (s, 2H), 2.74-2.62 (m, 1H), 2.43 (d, J=10.9 Hz, 1H), 2.37-2.26 (m, 1H), 2.08-1.91 (m, 3H), 1.83-1.68 (m, 1H), 1.56 (s, 9H), 1.07 (s, 3H), 0.98-0.86 (m, 5H), 0.65-0.58 (m, 2H); MS(ES+) m/z 515.0, 516.9 (M+1).

Step 6. Preparation of 4-((4-((5-chloro-4-(trifluoromethyl)pyridin-2-yl)oxy)-3,3-dimethylpiperidin-1-yl)methyl)-5-cyclopropyl-2-fluorobenzoic acid hydrochloride

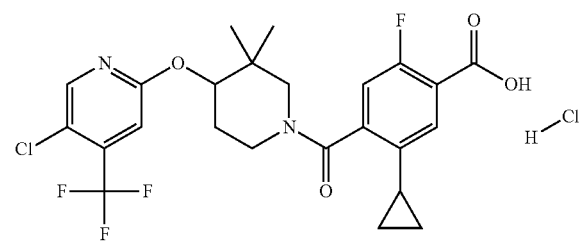

Following the procedure as described in Example 517 step 2, and making variation as required to replace tert-butyl 4-(3,5-dichlorobenzyl)piperazine-1-carboxylate with tert-butyl 4-((4-((5-chloro-4-(trifluoromethyl)pyridin-2-yl)oxy)-3,3-dimethylpiperidin-1-yl)methyl)-5-cyclopropyl-2-fluorobenzoate, the title compound was obtained as a colorless solid (1.59 g, quant. yield): MS(ES+) m/z 501.1, 503.1 (M+1).

Step 7. Preparation of 4-((4-((5-chloro-4-(trifluoromethyl)pyridin-2-yl)oxy)-3,3-dimethylpiperidin-1-yl)methyl)-5-cyclopropyl-2-fluoro-N-(methylsulfonyl)benzamide, trifluoroacetic acid salt

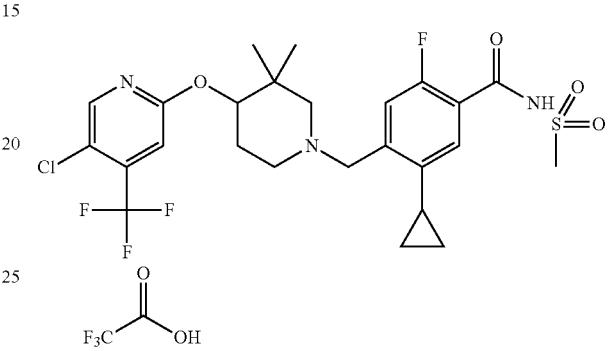

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 4-((4-((5-chloro-4-(trifluoromethyl)pyridin-2-yl)oxy)-3,3-dimethylpiperidin-1-yl)methyl)-5-cyclopropyl-2-fluorobenzoic acid hydrochloride, and to replace cyclopropanesulfonamide with methylsulfonamide, and purification by preparative HPLC, the title compound was obtained as a colorless solid (0.35 g, 34%); $^1$H NMR (300 MHz, DMSO-d$_6$+5% D$_2$O) δ 8.45 (s, 1H), 7.49 (d, J=11.2 Hz, 1H), 7.32 (s, 1H), 7.25 (d, J=7.1 Hz, 1H), 5.06-4.91 (m, 1H), 4.43 (br s, 2H), 3.33 (s, 3H), 3.29-2.91 (m, 4H), 2.20-2.04 (m, 2H), 2.02-1.80 (m, 1H), 1.21-0.86 (m, 8H), 0.81-0.68 (m, 2H); MS(ES+) m/z 578.1, 580.1 (M+1).

Example 562

Synthesis of 4-((4-((5-chloro-4-(trifluoromethyl)pyridin-2-yl)oxy)-3,3-dimethylpiperidin-1-yl)methyl)-5-cyclopropyl-N-(cyclopropylsulfonyl)-2-fluorobenzamide, trifluoroacetic acid salt

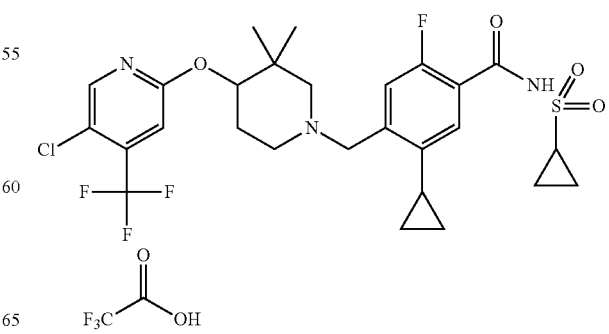

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 4-((4-((5-chloro-4-(trifluoromethyl)pyridin-2-yl)oxy)-3,3-dimethylpiperidin-1-yl)methyl)-5-cyclopropyl-2-fluorobenzoic acid hydrochloride, and purification by preparative HPLC, the title compound was obtained as a colorless solid (0.50 g, 47%): $^1$H NMR (300 MHz, CDCl$_3$+10% CD$_3$OD) δ8.14 (s, 1H), 7.46 (d, J=7.3 Hz, 1H), 7.39 (d, J=11.2 Hz, 1H), 7.00 (s, 1H), 4.99-4.92 (m, 1H), 4.48-4.32 (m, 2H), 3.56-3.32 (m, 1H), 3.21-3.08 (m, 1H), 3.05-2.97 (m, 5H), 2.96-2.88 (m, 1H), 2.87-2.74 (m, 1H), 2.35-2.19 (m, 1H), 2.08-1.95 (m, 1H), 1.92-1.81 (m, 1H), 1.38-1.29 (m, 2H), 1.20-0.89 (m, 10H), 0.70-0.63 (m, 2H); MS(ES+) m/z 604.2, 606.2 (M+1).

Example 563

Synthesis of 5-cyclopropyl-N-(cyclopropylsulfonyl)-4-(((1S,4S)-5-((R)-1-(3,5-dichlorophenyl)ethyl)-2,5-diazabicyclo[2.2.1]heptan-2-yl)methyl)-2-fluorobenzamide, trifluoroacetic acid salt

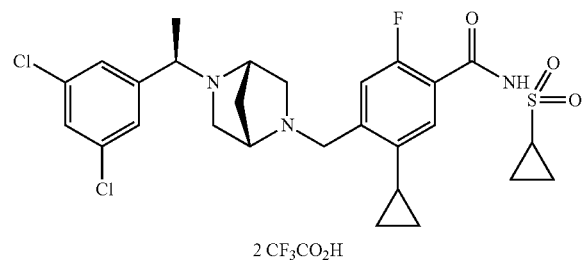

2 CF$_3$CO$_2$H

Step 1. Preparation of methyl 5-cyclopropyl-4-(((1S,4S)-5-((R)-1-(3,5-dichlorophenyl)ethyl)-2,5-diazabicyclo[2.2.1]heptan-2-yl)methyl)-2-fluorobenzoate and methyl 5-cyclopropyl-4-(((1S,4S)-5-((S)-1-(3,5-dichlorophenyl)ethyl)-2,5-diazabicyclo[2.2.1]heptan-2-yl)methyl)-2-fluorobenzoate

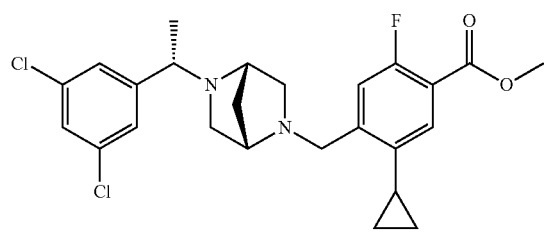

To a solution of methyl 4-(((1S,4S)-2,5-diazabicyclo[2.2.1]heptan-2-yl)methyl)-5-cyclopropyl-2-fluorobenzoate dihydrochloride (0.38 g, 1.00 mmol) and 1-(3,5-dichlorophenyl)ethyl 4-methylbenzenesulfonate (0.41 g, 1.20 mmol) in anhydrous dimethylformamide (10 mL) was added potassium carbonate (0.55 g, 4.00 mmol). The reaction mixture was heated at 80° C. in a sealed tube for 6 hours, cooled to ambient temperature, diluted with ethyl acetate (80 mL), washed with water (50 mL) and brine (50 mL), dried over anhydrous sodium sulfate, filtered and concentrated in vacuo. The residue was purified by preparative HPLC. The first eluting fraction was arbitrarily assigned as methyl 5-cyclopropyl-4-(((1S,4S)-5-((R)-1-(3,5-dichlorophenyl)ethyl)-2,5-diazabicyclo[2.2.1]heptan-2-yl)methyl)-2-fluorobenzoate as a colorless oil (0.05 g, 10%)) and the second eluting fraction was arbitrarily assigned as methyl 5-cyclopropyl-4-(((1S,4S)-5-((S)-1-(3,5-dichlorophenyl)ethyl)-2,5-diazabicyclo[2.2.1]heptan-2-yl)methyl)-2-fluorobenzoate as a colorless oil (0.05 g, 10%)). Analytical data for methyl 5-cyclopropyl-4-(((1S,4S)-5-((R)-1-(3,5-dichlorophenyl)ethyl)-2,5-diazabicyclo[2.2.1]heptan-2-yl)methyl)-2-fluorobenzoate: $^1$H NMR (300 MHz, CDCl$_3$) δ7.54 (d, J=7.3 Hz, 1H), 7.31-7.17 (m, 4H), 3.97-3.85 (m, 4H), 3.75 (d, J=15.6 Hz, 1H), 3.65-3.54 (m, 1H), 3.25 (d, J=11.4 Hz, 2H), 2.94-2.85 (m, 2H), 2.70 (d, J=9.7 Hz, 1H), 2.48 (dd, J=10.2, 2.4 Hz, 1H), 1.93-1.81 (m, 1H), 1.77-1.87 (m, 2H), 1.31 (d, J=0.4 Hz, 3H), 0.96-0.88 (m, 2H), 0.65-0.57 (m, 2H); MS (ES+) m/z: 477.1, 479.1 (M+1). Analytical data for methyl 5-cyclopropyl-4-(((1S,4S)-5-((S)-1-(3,5-dichlorophenyl)ethyl)-2,5-diazabicyclo[2.2.1]heptan-2-yl)methyl)-2-fluorobenzoate: $^1$H NMR (300 MHz, CDCl$_3$) δ7.54 (d, J=7.3 Hz, 1H), 7.30-7.17 (m, 4H), 3.93 (d, J=15.7 Hz, 1H), 3.88 (s, 3H), 3.79 (d, J=15.7 Hz, 1H), 3.54 (q, J=5.9 Hz, 1H), 3.48 (s, 1H), 3.25 (s, 1H), 2.88 (d, J=9.9 Hz, 1H), 2.72-2.60 (m, 2H), 2.54 (d, J=9.6 Hz, 1H), 1.93-1.82 (m, 1H), 1.81-1.69 (m, 2H), 1.22 (d, J=5.9 Hz, 3H), 0.96-0.88 (m, 2H), 0.68-0.56 (m, 2H); MS(ES+) m/z 477.1, 479.1 (M+1).

Step 2. Preparation of 5-cyclopropyl-N-(cyclopropylsulfonyl)-4-(((1S,4S)-5-((R)-1-(3,5-dichlorophenyl)ethyl-2,5-diazabicyclo[2.2.1]heptan-2-yl)methyl)-2-fluorobenzamide, trifluoroacetic acid salt

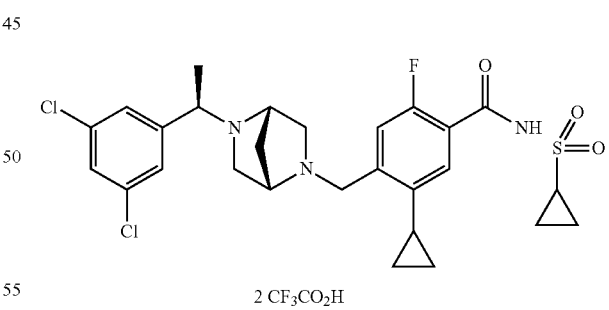

2 CF$_3$CO$_2$H

Following the procedure as described in Example 538 step 3, and making variation as required to replace (R)-4-((1-(tert-butyl)piperidin-3-yl)oxy)-5-cyclopropyl-2-fluorobenzoate with methyl 5-cyclopropyl-4-(((1S,4S)-5-((R)-1-(3,5-dichlorophenyl)ethyl)-2,5-diazabicyclo[2.2.1]heptan-2-yl)methyl)-2-fluorobenzoate, and to replace methylsulfonamide with cyclopropanesulfonamide, and purification by HPLC, the title compound was obtained as a colorless solid (0.07 g, 26%): $^1$H NMR (300 MHz, DMSO-d$_6$+5% D$_2$O) δ7.64-7.57 (m, 3H), 7.37 (d, J=11.5 Hz, 1H), 7.19 (d, J=7.1 Hz, 1H), 4.37-3.98 (m, 4H), 3.79 (br s, 1H), 3.38-3.23 (m, 2H), 3.10-2.86 (m, 3H), 2.20-2.03 (m, 2H), 2.02-1.92 (m, 1H), 1.52 (d, J=6.2 Hz, 3H), 1.13-1.04 (m, 4H), 0.95-0.87 (m, 2H), 0.70-0.60 (m, 2H); MS(ES+) m/z 566.1, 568.1 (M+1).

Example 564

Synthesis of 5-cyclopropyl-N-(cyclopropylsulfonyl)-4-(((1S,4S)-5-((S)-1-(3,5-dichlorophenyl)ethyl)-2,5-diazabicyclo[2.2.1]heptan-2-yl)methyl)-2-fluorobenzamide, trifluoroacetic acid salt

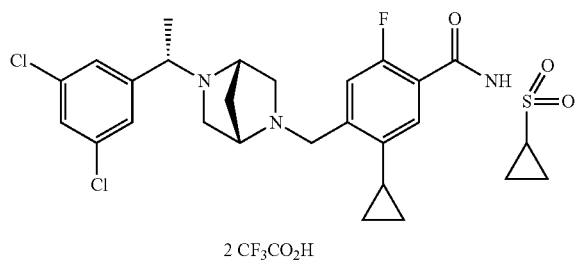

2 CF$_3$CO$_2$H

Following the procedure as described in Example 538 step 3, and making variation as required to replace (R)-4-((1-(tert-butyl)piperidin-3-yl)oxy)-5-cyclopropyl-2-fluorobenzoate with methyl 5-cyclopropyl-4-(((1S,4S)-5-((S)-1-(3,5-dichlorophenyl)ethyl)-2,5-diazabicyclo[2.2.1]heptan-2-yl)methyl)-2-fluorobenzoate, and to replace methylsulfonamide with cyclopropanesulfonamide, and purification by HPLC, the title compound was obtained as a colorless solid (0.07 g, 17%): $^1$H NMR (300 MHz, DMSO-d$_6$+5% D$_2$O) δ7.62 (s, 1H), 7.55 (s, 2H), 7.39 (d, J=11.7 Hz, 1H), 7.21 (d, J=7.1 Hz, 1H), 4.39-4.08 (m, 3H), 3.90 (br s, 2H), 3.39-3.25 (m, 2H), 3.22-3.10 (m, 1H), 3.08-2.99 (m, 1H), 2.98-2.89 (m, 1H), 2.26-2.08 (m, 2H), 2.04-1.93 (m, 1H), 1.41 (d, J=6.5 Hz, 3H), 1.16-1.03 (m, 4H), 0.97-0.87 (m, 2H), 0.73-0.61 (m, 2H) (Note: Exchangeable protons not observed.); MS(ES+) m/z 566.2, 568.2 (M+1).

Example 565

Synthesis of 5-cyclopropyl-4-(((S)-4-((R)-1-(3,5-dichlorophenyl)ethyl)-3-methylpiperazin-1-yl)methyl)-2-fluoro-N-(methylsulfonyl)benzamide

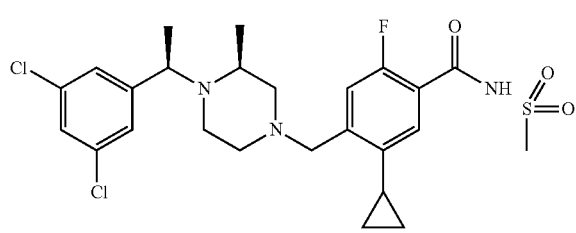

Step 1. Preparation of 1-benzyl 4-(tert-butyl) (S)-2-methylpiperazine-1,4-dicarboxylate

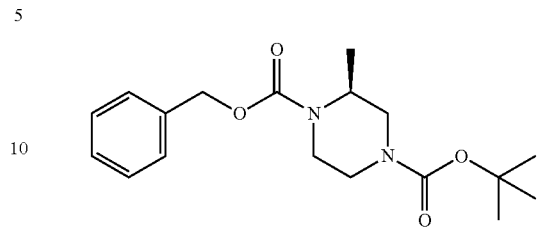

To a solution of tert-butyl (S)-3-methylpiperazine-1-carboxylate (6.35 g, 31.71 mmol), triethylamine (4.98 mL, 34.88 mmol) and 4-dimethylaminopyridine (0.10 g, 0.82 mmol) in dichloromethane (80 mL) under nitrogen at 0° C. was added dropwise benzyl chloroformate (8.84 mL, 63.42 mmol). The resulting mixture was stirred at 0° C. for 2 hours and then at ambient temperature for 18 hours, quenched with water (10 mL) and stirred for 1 hour. The mixture was diluted with diluted with ethyl acetate (150 mL), washed with aqueous saturated ammonium chloride solution (2×80 mL) and brine (80 mL); dried over anhydrous sodium sulfate, filtered and concentrated in vacuo to provide the title compound as an oil (10.45 g, 99%); $^1$H NMR (300 MHz, CDCl$_3$) δ7.39-7.25 (m, 5H), 5.11 (s, 2H), 4.37-4.23 (m, 1H), 4.10-3.71 (m, 3H), 3.15-2.91 (m, 2H), 2.86-2.69 (m, 1H), 1.43 (s, 9H), 1.14 (d, J=6.8 Hz, 3H); MS(ES+) m/z 235.2 (M−99).

Step 2. Preparation of benzyl (S)-2-methylpiperazine-1-carboxylate

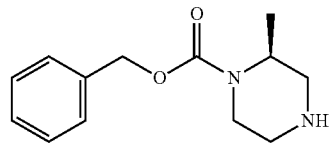 [SMILES: C[C@H]1CNCCN1C(=O)OCc1ccccc1]

To a solution of 1-benzyl 4-(tert-butyl) (S)-2-methylpiperazine-1,4-dicarboxylate (10.45 g, 31.25 mmol) in dichloromethane (70 mL) was added trifluoroacetic acid (35 mL). After stirring at ambient temperature for 5 hours, the reaction mixture was concentrated in vacuo and the residue was dissolved in diethyl ether (80 mL) and extracted with 1.0 M aqueous hydrochloric acid solution (2×25 mL).

The combined aqueous layers were basified with 2.0 M aqueous sodium hydroxide solution to pH=9, and extracted with diethyl ether (2×100 mL), the combined organic layers were washed with brine (2×50 mL); dried over anhydrous sodium sulfate; filtered and concentrated in vacuo to provide the title compound as an oil (6.28 g, 86%): $^1$H NMR (300 MHz, CDCl$_3$) δ7.36-7.23 (m, 5H), 5.13 (d, J=12.7 Hz, 1H), 5.08 (d, J=12.7 Hz, 1H), 4.27-4.16 (m, 1H), 3.88-3.79 (m, 1H), 3.02 (td, J=12.7, 3.3 Hz, 1H), 2.95-2.83 (m, 2H), 2.76-2.70 (m, 1H), 2.64 (td, J=12.7, 3.6 Hz, 1H), 1.21 (d, J=7.0 Hz, 3H): MS(ES+) m/z 235.1 (M+1).

Step 3. Preparation of benzyl (S)-4-(4-(tert-butoxycarbonyl)-2-cyclopropyl-5-(fluorobenzyl)-2-methyl-piperazine-1-carboxylate

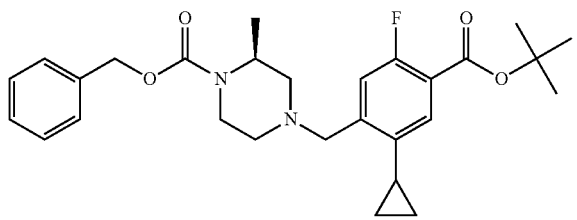 [SMILES: C[C@H]1CN(Cc2cc(F)c(C(=O)OC(C)(C)C)cc2C2CC2)CCN1C(=O)OCc1ccccc1]

Following the procedure as described in Example 53 step 3, and making variation as required to replace (S)-3-(3,5-dichlorophenoxy)piperidine, trifluoroacetic acid salt with benzyl (S)-2-methylpiperazine-1-carboxylate, the title compound was obtained as a colorless solid (6.58 g, 84%): $^1$H NMR (300 MHz, CDCl$_3$) δ7.47 (d, J=7.3 Hz, 1H), 7.38-7.25 (m, 5H), 7.14 (d, J=11.7 Hz, 1H), 5.17-5.07 (m, 2H), 4.34-4.23 (m, 1H), 3.95-3.65 (m, 1H), 3.58 (s, 2H), 3.17 (td, J=12.4-3.0 Hz, 1H), 2.74 (d, J=11.1 Hz, 1H), 2.59 (d, J=11.1 Hz, 1H), 2.22 (dd, J=11.1, 3.8 Hz, 1H), 2.08 (td, J=11.8, 3.3 Hz, 1H), 2.01-1.90 (m, 1H), 1.56 (s, 9H), 1.26 (d, J=6.7 Hz, 3H), 0.94-0.86 (m, 2H), 0.64-0.57 (m, 2H); MS (ES+) m/z 48331 (M+1).

Step 4. Preparation of tert-butyl (S)-5-cyclopropyl-2-fluoro-4-((3-methylpiperazin-1-yl)methyl)benzoate

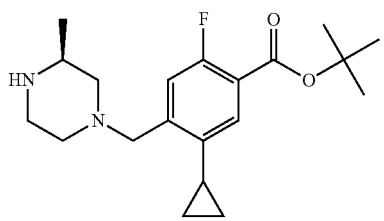 [SMILES: C[C@H]1CN(Cc2cc(F)c(C(=O)OC(C)(C)C)cc2C2CC2)CCN1]

To a degassed mixture of 10% palladium on carbon (50% wetted powder, 2.0 g) in methanol (50 mL) was added a solution of benzyl (S)-4-(4-(tert-butoxycarbonyl)-2-cyclopropyl-5-fluorobenzyl)-2-methylpiperazine-1-carboxylate (5.51 g, 11.42 mmol) in methanol (50 mL). The resulting mixture was bubbled with hydrogen gas for 2 minutes and then held under 1 atmosphere of hydrogen for 2 hours. The reaction mixture was hobbled with nitrogen, filtered through diatomaceous earth, and concentrated in vacuo to provide the title compound as a colorless oil (3.98 g, quant. yield): MS(ES+) m/z: 349.3 (M+1).

Step 5. Preparation of tert-butyl 5-cyclopropyl-4-(((S)-4-((R)-1-(3,5-dichlorophenyl)ethyl)-3-methyl-piperazin-1-yl)methyl)-2-fluorobenzoate and tert-butyl 5-cyclopropyl-4-(((S)-4-((S)-1-(3,5-dichlorophenyl)ethyl)-3-methylpiperazin-1-yl)methyl)-2-fluorobenzoate

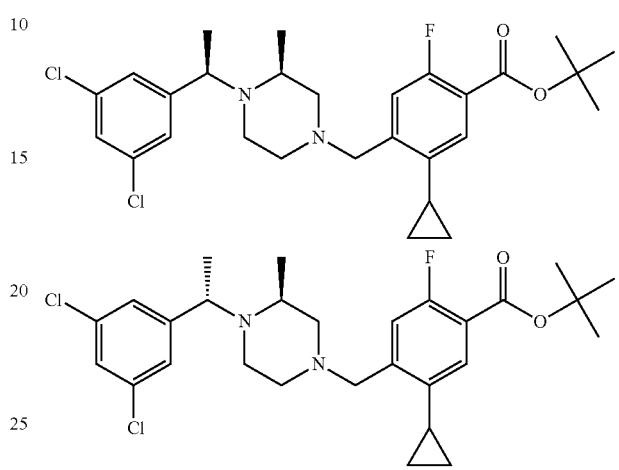

Following the procedure as described in Example 563 step 1, and making variation as required to replace methyl 4-(((1S,4S)-2,5-diazabicyclo[2.2.1]heptan-2-yl)methyl)-5-cyclopropyl-2-fluorobenzoate dihydrochloride with tert-butyl (S)-5-cyclopropyl-2-fluoro-4-((3-methylpiperazin-1-yl)methyl)benzoate and purification by flash chromatography (0-15% ethyl acetate (+10% isopropanol, +10% triethylamine) in hexanes. The first eluting fraction was arbitrarily assigned fraction was arbitrarily assigned as tert-butyl 5-cyclopropyl-4-(((S)-4-((S)-1-(3,5-dichlorophenyl)ethyl)-3-methylpiperazin-1-yl)methyl)-2-fluorobenzoate (3.27 g, 66%) MS(ES+) m/z: 521.2, 523.2 (M+1).

Step 6. Preparation of 5-cyclopropyl-4-(((S)-4-((R)-1-(3,5-dichlorophenyl)ethyl)-3-methylpiperazin-1-yl)methyl)-2-fluorobenzoic acid hydrochloride

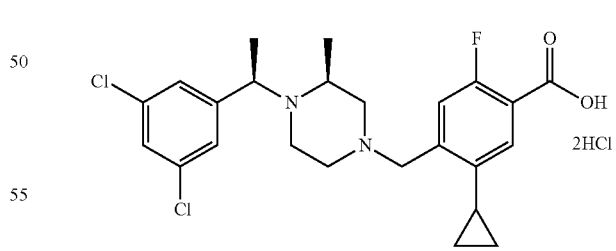

Following the procedure as described in Example 517 step 2, and making variation as required to replace tert-butyl 4-(3,5-dichlorobenzyl)piperazine-1-carboxylate with tert-butyl 5-cyclopropyl-4-(((S)-4-((R)-1-(3,5-dichlorophenyl)ethyl)-3-methylpiperazin-1-yl)methyl)-2-fluorobenzoate, the title compound was obtained as a colorless solid (1.49 g, quant. yield): MS(ES+) m/z 465.0, 467.0 (M+1).

819

Step 7. Preparation of 5-cyclopropyl-4-(((S)-4-((R)-1-(3,5-dichloro phenyl)ethyl)-3-methylpiperazin-1-yl)methyl)-2-fluoro-N-(methylsulfonyl)benzamide

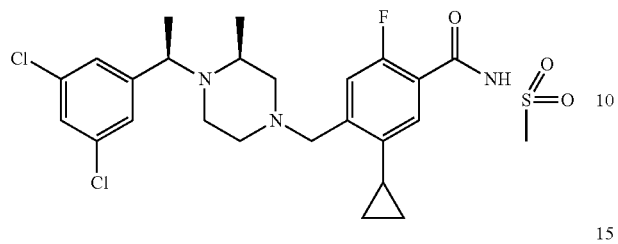

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-(((S)-4-((R)-1-(3,5-dichlorophenyl)ethyl)-3-methylpiperazin-1-yl)methyl)-2-fluorobenzoic acid hydrochloride, and to replace cyclopropanesulfonamide with methylsulfonamide, and purification by preparative HPLC, the title compound was obtained as a colorless solid (0.07 g, 9%): $^1$H NMR (300 MHz, CDCl$_3$) δ7.69 (d, J=7.7 Hz, 1H), 7.32-7.25 (m, 3H), 7.20-7.18 (m, 1H), 3.98-3.85 (m, 1H), 3.62 (s, 2H), 3.39 (s, 3H), 3.04-2.92 (m, 1H), 2.65-2.57 (m, 1H), 2.50-2.41 (m, 1H), 2.36-2.19 (m, 4H), 1.98-1.87 (m, 1H), 1.24 (d, J=6.7 Hz, 3H), 1.10 (d, J=6.3 Hz, 3H), 0.98-0.91 (m, 2H), 0.66-0.59 (m, 2H); MS(ES+) m/z 542.1, 544.1 (M+1).

Example 566

Synthesis of 5-cyclopropyl-N-(cyclopropylsulfonyl)-4-(((S)-4-((R)-1-(3,5-dichlorophenyl)ethyl)-3-methylpiperazin-1-yl)methyl)-2-fluorobenzamide

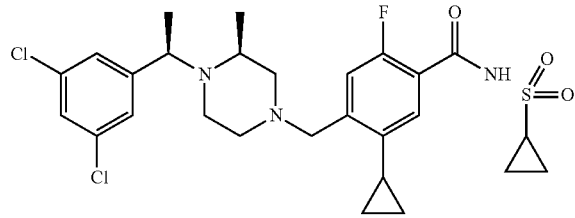

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-(((S)-4-((R)-1-(3,5-dichlorophenyl)ethyl)-3-methylpiperazin-1-yl)methyl)-2-fluorobenzoic acid hydrochloride, and purification by preparative HPLC, the title compound was obtained as a colorless solid (0.11 g, 14%): $^1$H NMR (300 MHz, CDCl$_3$) δ8.74 (br s, 1H), 7.70 (d, J=7.8 Hz, 1H), 7.34-7.25 (m, 3H), 7.21-7.17 (m, 1H), 3.97-3.84 (m, 1H), 3.61 (s, 2H), 3.13-3.03 (m, 1H), 3.02-2.91 (m, 1H), 2.65-2.57 (m, 4H), 2.50-2.40 (m, 1H), 2.35-0.217 (m, 4H), 1.98-1.87 (m, 1H), 1.48-1.40 (m, 2H), 1.24 (d, J=6.5 Hz, 3H), 1.17-1.06 (m, 5H), 0.98-0.90 (m, 2H), 0.66-0.59 (m, 2H); MS(ES+) m/z 568.2, 570.2 (M+1).

820

Example 507

Synthesis of 5-cyclopropyl-4-(((S)-4-((S)-1-(3,5-dichlorophenyl)ethyl)-3-methylpiperazin-1-yl)methyl)-2-fluoro-N-(methylsulfonyl)benzamide

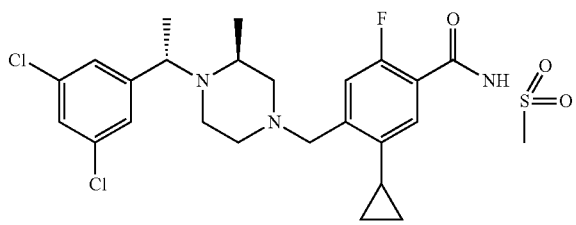

Step 1. Preparation of 5-cyclopropyl-4-(((S)-4-((S)-1-(3,5-dichlorophenyl)ethyl)-3-methylpiperazin-1-yl)methyl)-2-fluorobenzoic acid dihydrochloride

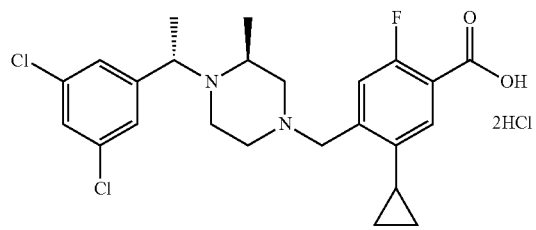 [SMILES: C[C@H]1CN(Cc2cc(F)c(C(=O)O)cc2C2CC2)CCN1[C@@H](C)c1cc(Cl)cc(Cl)c1]

Following the procedure as described in Example 517 step 2, and making variation as required to replace tert-butyl 4-(3,5-dichlorobenzyl)piperazine-1-carboxylate with tert-butyl 5-cyclopropyl-4-(((S)-4-(((S)-1-(3,5-dichlorophenyl)ethyl)-3-methylpiperazin-1-yl)methyl)-2-fluorobenzoate, the title compound was obtained as a colorless solid (3.38 g, quant.): MS(ES+) m/z 465.0, 467.0 (M+1).

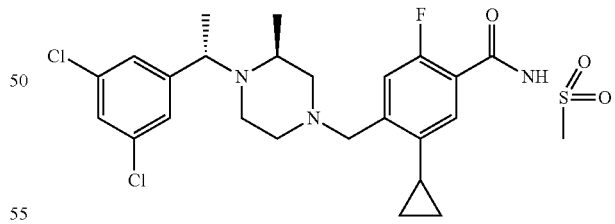

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-(((S)-4-((S)-1-(3,5-dichlorophenyl)ethyl)-3-methylpiperazin-1-yl)methyl)-2-fluorobenzoic acid hydrochloride, and to replace cyclopropanesulfonamide with methylsulfonamide, and purification by preparative HPLC, the title compound was obtained as a colorless solid (0.003 g, 0.2%): MS(ES+) m/z 542.2, 544.2 (M+1).

Example 568

Synthesis of 5-cyclopropyl-N-(cyclopropylsulfonyl)-4-(((S)-4-((S)-1-(3,5-dichlorophenyl)ethyl)-3-methylpiperazin-1-yl)methyl)-2-fluorobenzamide

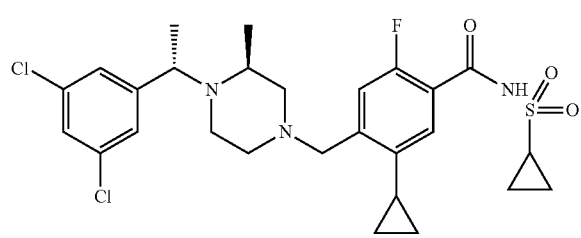

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-(((S)-4-((S)-1-(3,5-dichlorophenyl)ethyl)-3-methylpiperazin-1-yl)methyl)-2-fluorobenzoic acid hydrochloride, and purification by preparative HPLC, the title compound was obtained as a colorless solid (0.004 g, 0.2%): MS (ES+) m/z 568.2, 570.2 (M+1).

Example 569

Synthesis of 5-cyclopropyl-4-(((R)-4-((R)-1-(3,5-dichlorophenyl)ethyl)-3-methylpiperazin-1-yl)methyl)-2-4-N-(methylsulfonyl)benzamide

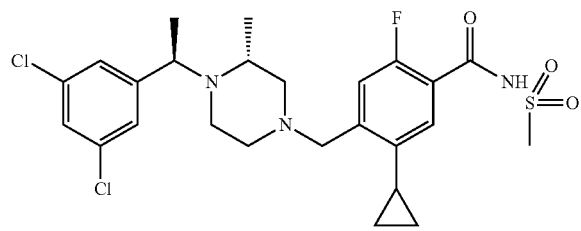

Step 1. Preparation of 1-benzyl 4-(tert-butyl) (R)-2-methylpiperazine-1,4-dicarboxylate

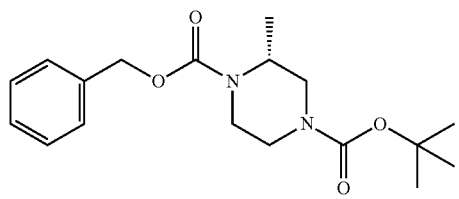 [SMILES: C[C@@H]1CN(C(=O)OC(C)(C)C)CCN1C(=O)OCc1ccccc1]

Following the procedure as described in Example 565 step 1, and making variation as required to replace tert-butyl (S)-3-methylpiperazine-1-carboxylate with tert-butyl (R)-3-methylpiperazine-1-carboxylate, the title compound was obtained as a colorless oil (10.60 g, quant. yield): $^1$H NMR (300 MHz, CDCl$_3$) δ7.39-7.26 (m, 5H), 5.16-5.06 (m, 2H), 4.37-4.23 (m, 1H), 4.12-3.70 (m, 3H), 3.16-2.91 (m, 2H), 2.88-2.68 (m, 1H), 1.43 (s, 9H), 1.14 (d, J=6.7 Hz, 3H): MS(ES+) m/z 235.2 (M−Boc+H).

Step 2. Preparation of benzyl (R)-2-methylpiperazine-1-carboxylate

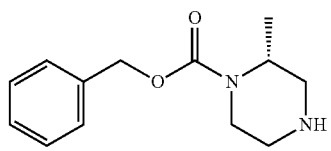 [SMILES: C[C@@H]1CNCCN1C(=O)OCc1ccccc1]

Following the procedure as described in Example 565 step 2, and making variation as required to replace 1-benzyl 4-(tert-butyl) (S)-2-methylpiperazine-1,4-dicarboxylate with 1-benzyl 4-(tert-butyl) (R)-2-methylpiperazine-1,4-dicarboxylate, the title compound was obtained as a colorless oil (6.80 g, 82%): $^1$H NMR (300 MHz, CDCl$_3$) δ7.36-7.24 (m, 5H), 5.16-5.05 (m, 2H), 4.27-4.17 (m, 1H), 3.88-3.79 (m, 1H), 3.02 (td, J=12.5, 3.3 Hz, 11.3), 2.95-2.82 (m, 2H), 2.77-2.70 (m, 1H), 2.64 (td, J=12.3, 3.5 Hz, 1H), 1.49 (br s, 1H), 1.21 (d, J=6.5 Hz, 3H); MS(ES+) m/z: 235.1 (M+1).

Step 3. Preparation of benzyl (R)-4-(4-(tert-butoxycarbonyl)-2-cyclopropyl-5-fluorobenzyl)-2-methylpiperazine-1-carboxylate

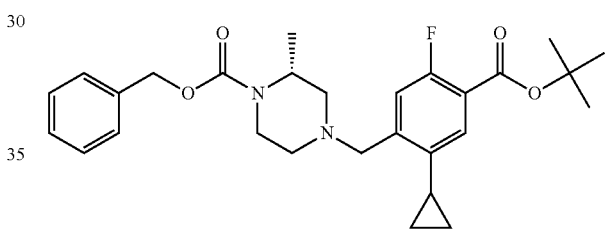

Following the procedure as described in Example 53 step 3, and making variation as required to replace (S)-3-(3,5-dichlorophenoxy)piperidine, trifluoroacetic acid salt with benzyl (R)-2-methylpiperazine-1-carboxylate, the title compound was obtained as a colorless solid (7.04 g, 90%): $^1$H NMR (300 MHz, CDCl$_3$) δ7.47 (d, J=7.4 Hz, 1H), 7.36-7.25 (m, 5H), 7.14 (d, J=11.8 Hz, 1H), 5.17-5.07 (m, 2H), 4.34-4.23 (m, 1H), 3.95-3.86 (m, 1H), 3.58 (s, 2H), 3.17 (td, J=12.7, 3.2 Hz, 1H), 2.74 (d, J=11.0 Hz, 1H), 2.59 (d, J=11.1 Hz, 1H), 2.22 (dd, J=11.0, 3.5 Hz, 1H), 2.08 (td, J=11.6, 3.3 Hz, 1H), 2.01-1.90 (m, 1H), 1.56 (s, 9H), 1.26 (d, J=6.8 Hz, 3H), 0.94-0.86 (m, 2H), 0.65-0.57 (m, 2H); MS(ES+) m/z 483.1 (M+1).

Step 4. Preparation of tert-butyl (R)-5-cyclopropyl-2-fluoro-4-((3-methylpiperazin-1-yl)methyl)benzoate

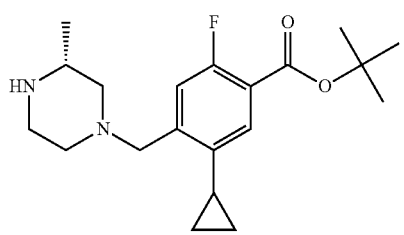 [SMILES: C[C@@H]1CN(Cc2cc(F)c(C(=O)OC(C)(C)C)cc2C2CC2)CCN1]

Following the procedure as described in Example 565 step 4, and making variation as required to replace benzyl (S)-4-(4-(tert-butoxycarbonyl)-2-cyclopropyl-5-fluorobenzyl)-2-methylpiperazine-1-carboxylate with benzyl (R)-4-(4-(tert-butoxycarbonyl)-2-cyclopropyl-5-fluorobenzyl)-2-methylpiperazine-1-carboxylate, the title compound was obtained as a colorless oil (4.19 g, 98%): MS(ES+) m/z 349.1 (M+1).

Step 5. Preparation of 534-butyl 5-cyclopropyl-4-(((R)-4-((R)-1-(3,5-dichlorophenyl)ethyl)-3-methylpiperazin-1-yl)methyl)-2-fluorobenzoate and tert-butyl 5-cyclopropyl-4-(((R)-4-((S)-1-(3,5-dichlorophenyl)ethyl)-3-methylpiperazin-1-yl)methyl)-2-fluorobenzoate

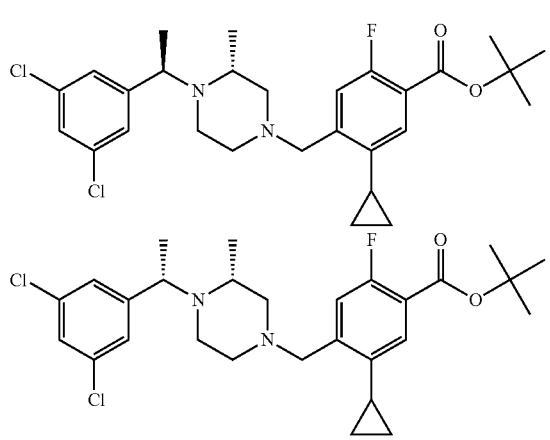

Following the procedure as described in Example 563 step 1, and making variation as required to replace methyl 4-(((1S,4S)-2,5-diazabicyclo[2.2.1]heptan-2-yl)methyl)-5-cyclopropyl-2-fluorobenzoate dihydrochloride with tert-butyl (R)-5-cyclopropyl-2-fluoro-4-((3-methylpiperazin-1-yl)methyl)benzoate and purification by flash chromatography (0-15% ethyl acetate (+10% isopropanol, +10% triethylamine) in hexanes. The first eluting fraction was arbitrarily assigned as tert-butyl 5-cyclopropyl-4-(((R)-4-((R)-1-(3,5-dichlorophenyl)ethyl)-3-methylpiperazin-1-yl)methyl)-2-fluorobenzoate (1.12 g, 24%)): MS (ES+) m/z: 521.2, 523.2 (M+1). The second eluting fraction was arbitrarily assigned as tert-butyl 5-cyclopropyl-4-(((R)-4-((S)-1-(3,5-dichlorophenyl)ethyl)-3-methylpiperazin-1-yl)methyl)-2-fluorobenzoate (2.07 g, 44%): MS(ES+) m/z 521.2, 523.2 (M+1).

Step 6. Preparation of 5-cyclopropyl-4-(((R)-4-((R)-1-(3,5-dichlorophenyl)ethyl)-3-methylpiperazin-1-yl)methyl)-2-fluorobenzoic acid dihydrochloride

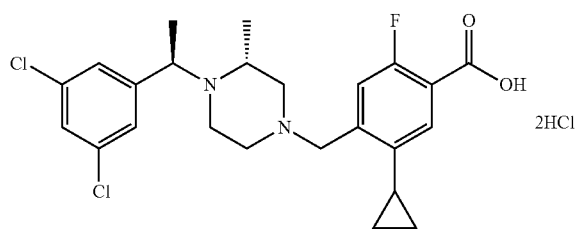 [SMILES: C[C@@H]1CN(Cc2cc(F)c(C(=O)O)cc2C2CC2)CCN1[C@H](C)c1cc(Cl)cc(Cl)c1]

Following the procedure as described in Example 517 step 2, and making variation as required to replace tert-butyl 4-(3,5-dichlorobenzyl)piperazine-1-carboxylate with tert-butyl 5-cyclopropyl-4-(((R)-4-((R)-1-(3,5-dichlorophenyl)ethyl)-3-methylpiperazin-1-yl)methyl)-2-fluorobenzoate, the title compound was obtained as a colorless solid (1.16 g, quant. yield): MS(ES+) m/z 465.1, 467.1 (M+1).

Step 2. Preparation of 5-cyclopropyl-4-(((R)-4-((R)-1-(3,5-dichlorophenyl)ethyl)-3-methylpiperazin-1-yl)methyl)-2-fluoro-N-(methylsulfonyl)benzamide

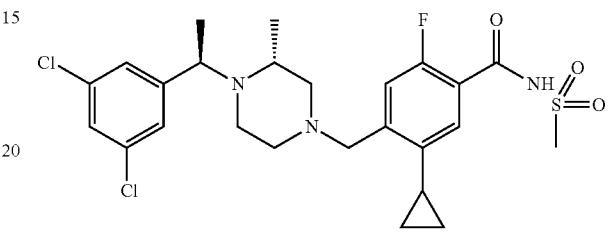

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-((R)-4-((R)-1-(3,5-dichlorophenyl)ethyl)-3-methylpiperazin-1-yl)methyl)-2-fluorobenzoic acid hydrochloride, and to replace cyclopropanesulfonamide with methylsulfonamide, and purification by preparative HPLC, the title compound was obtained as a colorless solid (0.13 g, 22%): $^1$H NMR (300 MHz, CDCl$_3$) δ7.44 (d, J=7.7 Hz, 1H), 7.27 (d, J=1.6 Hz, 2H), 7.17 (dd, J=1.7 Hz, 1H), 7.02 (d, J=12.2 Hz, 1H), 6.78 (br s, 1H), 3.93-3.81 (m, 1H), 3.52 (s, 2H), 3.02 (s, 3H), 2.96-2.84 (m, 1H), 2.61-2.51 (m, 1H), 2.45-2.35 (m, 1H), 2.31-2.11 (m, 3H), 1.99-1.96 (m, 1H), 1.93-1.84 (m, 1H), 1.20 (d, J=1.05, 3H), (d, J=6.2 Hz, 3H), 0.87-0.80 (m, 2H), 0.60-0.52 (m, 2H); MS(ES+) m/z 543.1, 544.1 (M+1).

Example 570

Synthesis of 5-cyclopropyl-N-(cyclopropylsulfonyl)-4-(((R)-4-((R)-1-(3,5-dichlorophenyl)ethyl)-3-methylpiperazin-1-yl)methyl)-2-fluorobenzamide

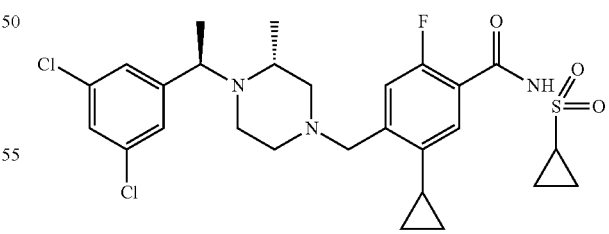

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-((R)-4-((R)-1-(3,5-dichlorophenyl)ethyl)-3-methylpiperazin-1-yl)methyl)-2-fluorobenzoic acid hydrochloride, and purification by preparative HPLC, the title compound was obtained as a colorless solid (0.18 g, 30%): $^1$H NMR (300 MHz, CDCl$_3$)

δ7.69 (d, J=7.8 Hz, 1H), 7.32-7.23 (m, 3H), 7.21-7.17 (m, 1H), 3.98-3.83 (m, 1H), 3.61 (s, 2H), 3.12-3.02 (m, 1H), 3.02-2.92 (m, 1H), 2.65-2.57 (m, 1H), 2.51-2.40 (m, 1H), 2.35-2.19 (m, 4H), 2.00-1.87 (m, 1H), 1.47-1.39 (m, 2H), 1.24 (d, J=6.5 Hz, 3H), 1.17-1.06 (m, 5H), 0.98-0.90 (m, 2H) 0.66-0.59 (m, 2H); MS(ES+) m/z 568.2, 570.2 (M+1).

Example 571

Synthesis of 5-cyclopropyl-4-(((R)-4-((S)-1-(3,5-dichlorophenyl)ethyl)-3-methylpiperazin-1-yl)methyl)-2-fluoro-N-(methylsulfonyl)benzamide

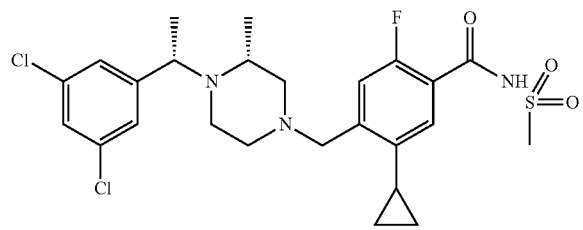

Step 1. Preparation of 5-cyclopropyl-4-(((R)-4-((S)-1-(3,5-dichlorophenyl)ethyl)-3-methylpiperazin-1-yl)methyl)-2-fluorobenzoic acid hydrochloride

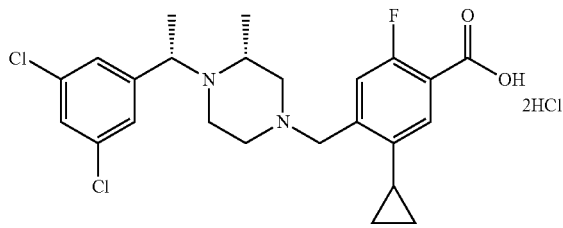 [SMILES: C[C@@H]1CN(Cc2cc(F)c(C(=O)O)cc2C2CC2)CCN1[C@@H](C)c1cc(Cl)cc(Cl)c1]

Following the procedure as described in Example 517 step 2, and making variation as required to replace tert-butyl 4-(3,5-dichlorobenzyl)piperazine-1-carboxylate with tert-butyl 5-cyclopropyl-4-(((R)-4-((S)-1-(3,5-dichlorophenyl)ethyl)-3-methylpiperazin-1-yl)methyl)-2-fluorobenzoate, the title compound was obtained as a colorless solid (2.14 g, quant.): MS(ES+) m/z 465.1, 467.1 (M+1).

Step 2. Preparation of 5-cyclopropyl-4-(((R)-4-((S)-1-(3,5-dichlorophenyl)ethyl)-3-methylpiperazin-1-yl)methyl)-2-4-N-(methylsulfonyl)benzamide

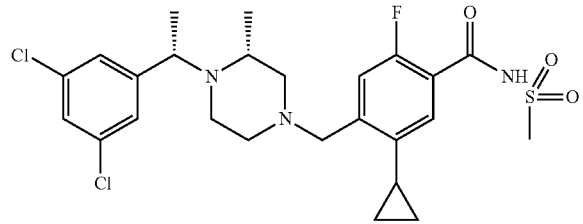

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-(((R)-4-((S)-1-(3,5-dichlorophenyl)ethyl)-3-methylpiperazin-1-yl)methyl)-2-fluorobenzoic acid hydrochloride, and to replace cyclopropanesulfonamide with methylsulfonamide, and purification by preparative HPLC, the title compound was obtained as a colorless solid (0.005 g, 0.5%): ¹H NMR (300 MHz, CDCl₃) δ7.46 (d, J=7.5 Hz, 1H), 7.22-7.18 (m, 1H), 7.17-7.13 (m, 2H), 6.99 (d, J=12.2 Hz, 1H), 3.91-3.78 (m, 1H), 3.51 (s, 2H), 3.02 (s, 3H), 2.79-2.67 (m, 1H), 2.54-2.35 (m, 3H), 2.21-2.11 (m, 2H), 1.94-1.82 (m, 1H), 1.31 (d, J=6.8 Hz, 3H), 1.25-1.20 (m, 2H), 1.00 (d, J=6.1 Hz, 3H), 0.88-0.78 (m, 2H), 0.59-0.52 (m, 2H); MS(ES−) m/z 540.2, 542.2 (M−1).

Example 572

Synthesis of 5-cyclopropyl-N-(cyclopropylsulfonyl)-4-(((R)-4-((S)-1-(3,5-dichlorophenyl)ethyl)-3-methylpiperazin-1-yl)methyl)-2-fluorobenzamide

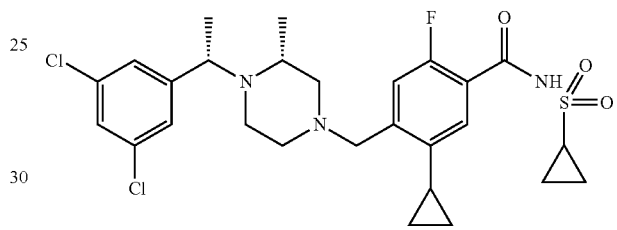

Following the procedure as described in Example 53 step 5, and making variation as required to replace (S)-5-cyclopropyl-4-((3-(3,5-dichlorophenoxy)piperidin-1-yl)methyl)-2-fluorobenzoic acid with 5-cyclopropyl-4-(((R)-4-((S)-1-(3,5-dichlorophenyl)ethyl)-3-methylpiperazin-1-yl)methyl)-2-fluorobenzoic acid hydrochloride, and purification by preparative HPLC, the title compound was obtained as a colorless solid (0.01 g, 1%): ¹H NMR (300 MHz, CDCl₃) δ8.74 (br s, 1H), 7.69 (d, J=7.8 Hz, 1H), 7.28-7.20 (m, 2H), 7.19-7.13 (m, 2H), 3.94-3.81 (m, 1H), 3.59 (s, 2H), 3.12-3.02 (m, 1H), 2.93-2.72 (m, 1H), 2.58-2.42 (m, 3H), 2.25-2.16 (m, 1H), 1.97-1.86 (m, 1H), 1.66-1.49 (m, 2H), 1.47-1.40 (m, 2H), 1.33 (d, J=6.5 Hz, 3H), 1.17-1.08 (m, 2H), 1.05 (d, J=6.3 Hz, 3H), 0.97-0.89 (m, 2H), 0.65-0.57 (m, 2H); MS(ES+) m/z 568.2, 570.2 (M+1).

Example 573

Synthesis of (S)-4-((1-(2-chloro-4-fluorobenzyl)piperidin-3-yl)oxy)-5-cyclopropyl-2-fluoro-N-(methylsulfonyl)

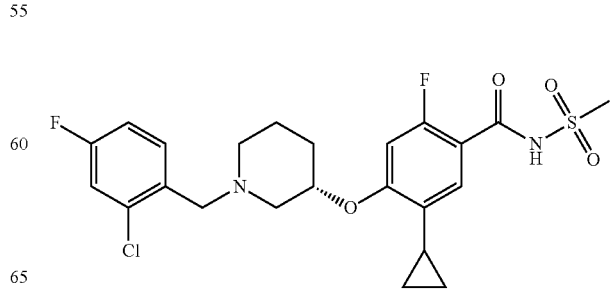

Following the procedure as described in Example 3 step 5, and making variation as required to replace (R)-5-cyclopropyl-4-((1-(3,5-dichlorobenzyl)piperidin-3-yl)methyl)-2-fluorobenzoic acid with (S)-4-((1-(2-chloro-4-fluorobenzyl)piperidin-3-yl)oxy)-5-cyclopropyl-2-fluorobenzoic acid, and to replace cyclopropylsulfonamide with methanesulfonamide, the title compound was obtained as a colorless solid (0.09 g, 55%): $^1$H NMR (300 MHz, CDCl$_3$) δ7.55 (d, J=9.2 Hz, 1H), 7.46-7.41 (m, 1H), 7.11-7.08 (m, 1H), 6.96-6.89 (m, 1H), 6.58 (d, J=14.6 Hz, 1H), 4.46-4.41 (m, 1H), 3.63 (s, 2H), 3.41 (s, 3H), 2.99-2.96 (m, 1H), 2.73-2.70 (m, 1H), 2.48-2.42 (m, 1H), 2.36-2.29 (m, 1H), 2.10-2.02 (m, 2H), 1.92-1.86 (m, 1H), 1.72-1.56 (m, 2H), 0.96-0.90 (m, 2H), 0.69-0.64 (m, 2H); MS(ES+) m/z 498.9, 500.9 (M+1); MS(ES−) m/z 497.2, 499.2 (M−1).

Example 574

Synthesis of 4-((1-benzhydryl-4-methylpiperidin-4-yl)methoxy)-5-cyclopropyl-2-fluoro-N-(methylsulfonyl)benzamide

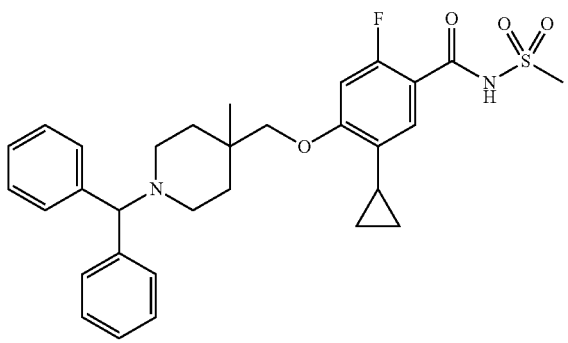 [SMILES: CC1(COc2cc(F)c(C(=O)NS(C)(=O)=O)cc2C2CC2)CCN(C(c2ccccc2)c2ccccc2)CC1]

Steps 1-2: Preparation of tert-butyl 4-((2-cyclopropyl-5-fluoro-4-((methylsulfonyl)carbamoyl)-phenoxy)methyl)-4-methylpiperidine-1-carboxylate The compound was prepared in a similar manner to Example 598 starting from 5-chloro-2,4-difluoro-N-methyl-sulfonyl-benzamide and tert-butyl 3-(hydroxymethyl)-3-methylazetidine-1-carboxylate.

Step 3: Preparation of 4-((1-benzhydryl-4-methylpiperidin-4-yl)methoxy)-5-cyclopropyl-2-fluoro-N-(methylsulfonyl)benzamide A mixture of 4-((1-benzhydryl-4-methylpiperidin-4-yl)methoxy)-5-cyclopropyl-2-fluoro-N-(methylsulfonyl)benzamide (55 mg), trifluoroacetic acid (0.23 ml) in dichloromethane (0.68 ml) was stirred at 0° C. for 10 min then at rt for 1 h. The contents were concentrated under vacuum. To the residue were added acetonitrile (2.3 mL), benzhydryl bromide (29 mg), and cesium carbonate (266 mg). The mixture was heated at 50° C. for 4 hr. Extra benzhydryl bromide (6 mg) was added. The mixture was heated at 50° C. for 16 hr. Acidified with 0.5M NaH$_2$PO$_4$, the contents were extracted with DCM (2×). The combined extracts were dried (Na$_2$SO$_4$). The crude was purified with HPLC (19.8 mg). LCMS (Method F): RT=4.71 min, m/z: 551.2 [M+H]$^+$. $^1$H NMR (400 MHz, DMSO-d6) δ 11.84 (s, 1H), 7.49-7.36 (m, 4H), 7.36-7.24 (m, 4H), 7.24-7.11 (m, 3H), 6.93 (d, J=12.9 Hz, 1H), 4.35 (s, 1H), 3.84 (s, 2H), 2.31-2.15 (m, 2H), 2.04-1.94 (m, 1H), 1.76-1.60 (m, 2H), 1.55-1.35 (m, 2H), 1.06 (s, 3H), 0.92-0.80 (m, 2H), 0.68-0.58 (m, 2H).

Example 575

Synthesis of 5-cyclopropyl-4-((1-(3,4-dichlorobenzyl)-4-methylpiperidin-4-yl)methoxy)-2-fluoro-N-(methylsulfonyl)benzamide

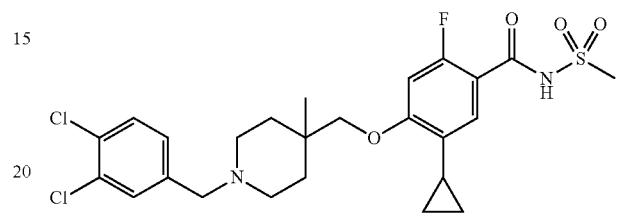

The compound was prepared in a similar manner to Example 73 starting from tert-butyl 4-((2-cyclopropyl-5-fluoro-4-((methylsulfonyl)carbamoyl)phenoxy)methyl)-4-methylpiperidine-1-carboxylate (Example 73 step 1-2) and 3,4-dichlorobenzaldehyde. LCMS (Method F): Rt=4.73 min, m/z: 543.2 [M+H]$^+$. $^1$H NMR (400 MHz, DMSO-d6) δ 7.67-7.58 (m, 2H), 7.35 (dd, J=8.3, 2.0 Hz, 1H), 7.20 (d, J=8.4 Hz, 1H), 6.87 (d, J=12.8 Hz, 1H), 3.83 (s, 2H), 3.72 (s, 2H), 3.15 (s, 3H), 2.78-2.62 (m, 2H), 2.07-1.95 (m, 1H), 1.76-1.64 (m, 2H), 1.57-1.43 (m, 2H), 1.09 (s, 3H), 0.94-0.83 (m, 2H), 0.68-0.55 (m, 2H).

Example 576

Synthesis of 5-cyclopropyl-2-fluoro-4-((1-((6-methoxypyridin-2-yl)methyl)-4-methylpiperidin-4-yl)methoxy)-N-methylsulfonyl)benzamide

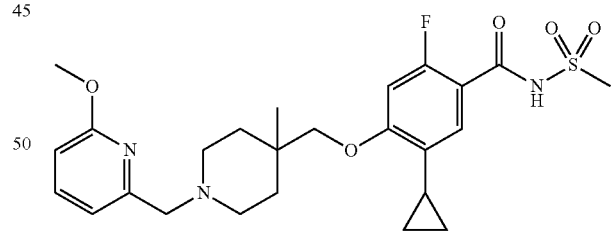

The compound was prepared in a similar manner to Example 73 starting from tert-butyl 4-((2-cyclopropyl-5-fluoro-4-((methylsulfonyl)carbamoyl)phenoxy)methyl)-4-methylpiperidine-1-carboxylate (Example 73 step 1-2) and 6-methoxypicolinaldehyde.

LCMS (Method F): Rt=4.25 min, m/z: 506.2 [M+H]$^+$. $^1$H NMR (400 MHz, DMSO-d6) δ 7.77-7.69 (m, 1H), 7.22 (d, J=8.5 Hz, 1H), 7.06 (d, J=7.3 Hz, 1H), 6.80 (dd, J=26.4, 10.5 Hz, 1H), 4.02-3.89 (m, 2H), 3.86 (s, 3H), 3.85 (d, J=1.2 Hz, 2H), 3.05 (s, 3H), 3.01-2.75 (m, 4H), 2.06-1.97 (m, 1H), 1.87-1.74 (m, 2H), 1.58 (s, 2H), 1.12 (s, 3H), 0.91-0.83 (m, 2H), 0.63-0.56 (m, 2H).

Example 577

Synthesis of 5-cyclopropyl-4-((1-(4,5-dichloro-2-fluorobenzoyl)-4-methylpiperidin-4-yl)methoxy)-2-fluoro-N-(methylsulfonyl)benzamide

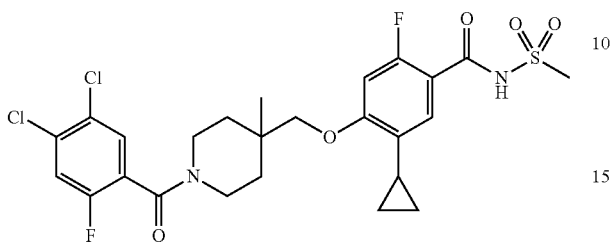

To a solution of tert-butyl 4-((2-cyclopropyl-5-fluoro-4-((methylsulfonyl)carbamoyl)-phenoxy)methyl-4-methylpiperidine-1-carboxylate (Example 73 steps 1-2, 56 mg) in dichloromethane (0.7 mL) at 0° C. was added trifluoroacetic acid (0.17 mL). The mixture was stirred at 0° C. for 10 min then at rt for 1 h. The contents were concentrated under vacuum. To the residue was added dichloromethane (2.3 mL), 4,5-dichloro-2-fluorobenzoic acid (28 mg), DIPEA (0.09 mL, cooled with ice-bath), and HBTU (30 mg). The mixture was stirred at rt for 1 hr. Acidified with 1:4 mixture of 0.5 M HCl and 0.5 M NaH$_2$PO$_4$, the contents were extracted with DCM (2×). The combined DCM solutions were dried (Na$_2$SO$_4$). After filtration and concentration. The crude was purified with HPLC (41 mg). LCMS (Method F): RT=6.50 min, m/z: 575.2 [M+H]$^+$. $^1$H NMR (400 MHz, DMSO-d6) δ 11.85 (s, 1H), 7.82 (d, J=8.9 Hz, 1H), 7.73 (d, J=6.4 Hz, 1H), 7.18 (d, J=8.3 Hz, 1H), 7.00-6.91 (m, 1H), 4.01-3.85 (m, 3H), 3.49-3.38 (m, 1H), 2.05-1.95 (m, 1H), 1.74-1.55 (m, 2H), 1.56-1.45 (m, 1H), 1.45-1.35 (m, 1H), 1.15 (s, 3H), 0.93-0.84 (m, 2H), 0.70-0.61 (m, 2H).

Example 578

Synthesis of 5-cyclopropyl-4-((1-(2,5-dichlorobenzoyl)-4-methylpiperidin-4-yl)methoxy)-2-fluoro-N-(methylsulfonyl)benzamide

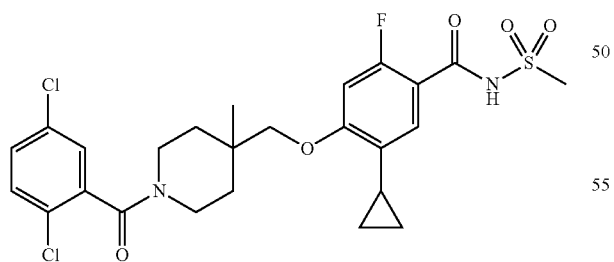

The compound was prepared in a similar manner to Example 589 from tert-butyl 4-((2-cyclopropyl-5-fluoro-4-((methylsulfonyl)carbamoyl)phenoxy)methyl)-4-methylpiperidine-1-carboxylate and 2,5-dichlorobenzoic acid. LCMS (Method F): RT=6.256 min, m/z: 557.2 [M+H]$^+$. $^1$H NMR (400 MHz, DMSO-d6) δ 11.85 (s, 1H), 7.62-7.43 (m, 3H), 7.19 (t, J=8.0 Hz, 1H), 6.93 (dd, J=12.9, 6.2 Hz, 1H), 3.99 (s, 1H), 3.89 (d, J=4.9 Hz, 2H), 3.41 (d, J=13.9 Hz, 1H), 3.26-3.17 (m, 4H), 2.01 (d, J=4.9 Hz, 1H), 1.78-1.46 (m, 4H), 1.40 (d, J=13.6 Hz, 1H), 1.14 (d, J=9.5 Hz, 3H), 0.93-0.82 (m, 2H), 0.70-0.58 (m, 2).

Example 579

Synthesis of 4-((1-(4-chloro-2-(trifluoromethyl)benzyl)piperidin-4-yl)methoxy)-5-cyclopropyl-2-fluoro-N-(methylsulfonyl)benzamide

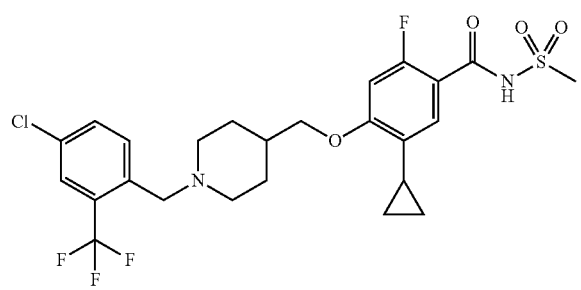 [SMILES: CS(=O)(=O)NC(=O)c1cc(C2CC2)c(OCC2CCN(Cc3ccc(Cl)cc3C(F)(F)F)CC2)cc1F]

To a solution of 5-cyclopropyl-2-fluoro-N-methylsulfonyl-4-(4-piperidylmethoxy)benzamide hydrochloride (60 mg) in 1,2-dichloroethane (2.2 mL) at 0° C. was added DIPEA (0.075 mL), followed by 4-fluoro-2-(trifluoromethyl)benzaldehyde (39 mg) and sodium triacetoxyborohydride (91 mg). The mixture was stirred at rt for 20 hr. Diluted with 0.5 M NaH$_2$PO$_4$, the contents were extracted with DCM (3×). The combined org solutions were dried (Na$_2$SO$_4$). After filtration and concentration, the residue was purified with HPLC (55 mg). LCMS (Method G): RT=4.36 min, m/z: 563.14 [M+H]$^+$. $^1$H NMR (400 MHz, DMSO-d6) δ 11.74 (s, 1H), 7.81 (d, J=8.5 Hz, 1H), 7.78-7.72 (m, 2H), 7.15 (d, J=8.4 Hz, 1H), 6.92 (d, J=12.9 Hz, 1H), 3.95 (d, J=6.0 Hz, 2H), 3.62 (s, 2H), 3.27 (s, 3H), 2.83 (d, J=11.1 Hz, 2H), 2.16-1.97 (m, 3H), 1.90-1.74 (m, 3H), 1.46-1.31 (m, 2H), 0.92-0.85 (m, 2H), 0.69-0.62 (m, 2H).

Example 580

Synthesis of 4-((1-(2-chloro-5-(trifluoromethyl)benzyl)piperidin-4-yl)methoxy)-5-cyclopropyl-2-fluoro-N-(methylsulfonyl)benzamide

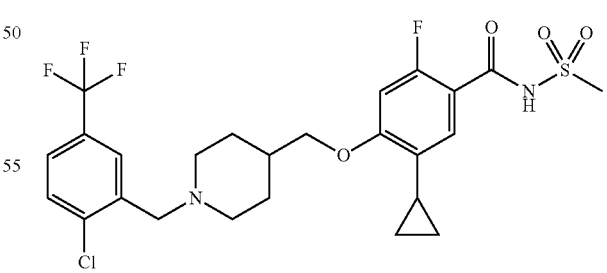

The compound was prepared in a similar manner to Example 591 from 5-cyclopropyl-2-fluoro-N-methylsulfonyl-4-(4-piperidylmethoxy)benzamide hydrochloride and 2-chloro-5-(trifluoromethyl)benzaldehyde. LCMS (Method G): RT=4.25 min, m/z: 563.14 [M+H]$^+$. $^1$H NMR (400 MHz, DMSO-d6) δ 11.61 (s, 1H), 7.86 (d, J=2.0 Hz, 1H), 7.73-7.64 (m, 2H), 7.16 (d, J=8.4 Hz, 1H), 6.91 (d, J=12.9

Hz, 1H), 3.97 (d, J=6.0 Hz, 2H), 3.72 (s, 2H), 3.26 (s, 3H), 2.92 (d, J=11.2 Hz, 2H), 2.24 (t, J=11.6 Hz, 2H), 2.08-1.96 (m, 1H), 1.92-1.75 (m, 3H), 1.51-1.35 (m, 2H), 0.92-0.83 (m, 2H), 0.69-0.61 (m, 2H).

Example 581

Synthesis of 4-((1-(3-chloro-2-fluoro-5-(trifluoromethyl)benzyl)piperidin-4-yl)methoxy)-5-cyclopropyl-2-fluoro-N-(methylsulfonyl)benzamide

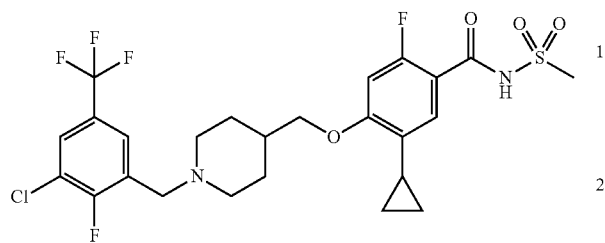

Step 1: Preparation of methyl 4-[[1-[[3-chloro-2-fluoro-5-(trifluoromethyl)phenyl]methyl]-4-piperidyl]methoxy]-5-cyclopropyl-2-fluoro-benzoate To a solution of methyl 5-cyclopropyl-2-fluoro-4-(4-piperidylmethoxy)benzoate hydrochloride (A, 0.362 g, 1.00 mmol, ~95% pure) in 1,2-dichloroethane (6.0 mL) at 0° C. was added DIPEA, (2.0 equiv., 2.00 mmol, 100 mass %), followed by 3-chloro-2-fluoro-5-(trifluoromethyl)benzaldehyde (350 mg) and sodium triacetoxyborohydride (636 mg). The mixture was stirred at rt for 20 hr. Diluted with aqueous sodium bicarbonate solution, the contents were extracted with DCM (3×). The combined org solutions were dried (Na$_2$SO$_4$). After filtration and concentration, the crude was purified with flash chromatography (0-40% EtOAc/heptane) to afford the product (498 mg).

Step 2: Preparation of 4-[[1-[[3-chloro-2-fluoro-5-(trifluoromethyl)phenyl]methyl]-4-piperidyl]methoxy]-5-cyclopropyl-2-fluoro-benzoic acid To a mixture of methyl 4-[[1-[[3-chloro-2-fluoro-5-(trifluoromethyl)phenyl]methyl]-4-piperidyl]methoxy]-5-cyclopropyl-2-fluoro-benzoate (A, 0.480 g, 0.927 mmol) and KOH (57 mg) in methanol (4.6 mL) was slowly added water (0.46 mL). The resulting mixture was stirred at 40° C. for 16 hr. Extra 0.1 eq of KOH was added. The mixture was heated at 60° c. for 20 hr. LCMS showed completion. The contents were concentrated under-vacuum. Used as-is.

Step 3: Preparation of 4-[[1-[[3-chloro-2-fluoro-5-(trifluoromethyl)phenyl]methyl]-4-piperidyl]methoxy]-5-cyclopropyl-2-fluoro-N-methylsulfonyl-benzamide A mixture of crude 4-[[1-[[3-chloro-2-fluoro-5-(trifluoromethyl)phenyl]methyl]-4-piperidyl]methoxy]-5-cyclopropyl-2-fluoro-benzoic acid potassium salt (60.0 mg) from the previous step, methanesulfonamide (41 mg), HBTU (62 mg) and DIPEA (0.037 mL) is 1,2-dichloroethane (1.6 mL) was stirred at 40° C. for 16 hr. LCMS showed completion. Acidified with 0.5M NaH$_2$PO$_4$, the contents were extracted with DCM (3×). The combined extracts were dried (Na$_2$SO$_4$). The crude was purified with HPLC (16.2 mg). LCMS (Method G): RT=5.71 min, m/z: 581.1 [M+H]$^+$. $^1$H NMR (400 MHz, DMSO-d6) δ 11.59 (s, 1H), 8.05-7.98 (m, 1H), 7.83-7.75 (m, 1H), 7.15 (d, J=8.3 Hz, 1H), 6.89 (d, J=12.9 Hz, 1H), 3.94 (d, J=5.9 Hz, 2H), 3.73 (s, 2H), 3.24 (s, 3H), 2.91 (d, J=11.2 Hz, 2H), 2.25-2.10 (m, 2H), 2.05-1.96 (m, 1H), 1.80 (d, J=11.9 Hz, 3H), 1.39 (d, J=11.9 Hz, 2H), 0.93-0.83 (m, 2H), 0.69-0.61 (m, 2H).

Example 582

Synthesis of 4-((1-(3-chloro-2-fluoro-5-(trifluoromethyl)benzyl)piperidin-4-yl)methoxy)-5-cyclopropyl-N-(cyclopropylsulfonyl)-2-fluorobenzamide

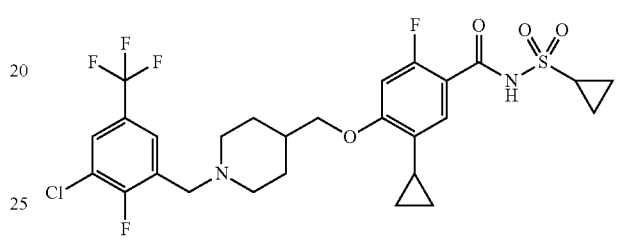

The compound was prepared in a similar manner to Example 587 from 4-[[1-[[3-chloro-2-fluoro-5-(trifluoromethyl)phenyl]methyl]-4-piperidyl]methoxy]-5-cyclopropyl-2-fluoro-benzoic acid and cyclopropanesulfonamide. LCMS (Method F): RT=4.98 min, m/z: 607.2 [M+H]$^+$. $^1$H NMR (400 MHz, DMSO-d6) δ 11.69 (s, 1H), 8.03-7.97 (m, 1H), 7.80-7.74 (m, 1H), 7.16 (d, J=8.5 Hz, 1H), 6.83 (d, J=12.9 Hz, 1H), 3.92 (d, J=5.8 Hz, 2H), 3.70-3.63 (m, 2H), 3.04-2.93 (m, 1H), 2.86 (d, J=11.1 Hz, 2H), 2.14-2.05 (m, 3H), 2.04-1.96 (m, 1H), 1.78 (d, J=10.9 Hz, 3H), 1.44-1.31 (m, 2H), 1.04-0.91 (m, 3H), 9.90-0.83 (m, 2H), 0.65-0.58 (m, 2H).

Example 583

Synthesis of N-(azetidin-1-ylsulfonyl)-4-((1-(3-chloro-2-fluoro-5-(trifluoromethyl)benzyl)piperidin-4-yl)methoxy)-5-cyclopropyl-2-fluorobenzamide

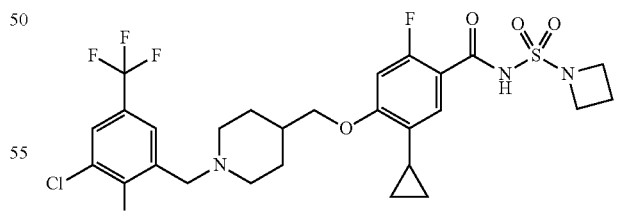

The compound was prepaid in a similar manner to Example 587 from 4-[[1-[[3-chloro-2-fluoro-5-(trifluoromethyl)phenyl]methyl]-4-piperidyl]methoxy]-5-cyclopropyl-2-fluoro-benzoic acid and azetidine-1-sulfonamide. LCMS (Method F): RT=5.04 min, m/z: 622.2 [M+H]$^+$. $^1$H NMR (400 MHz, DMSO-d6) δ 11.47 (s, 1H), 8.03-7.97 (m, 1H), 7.81-7.74 (m, 1H), 7.15 (d, J=8.3 Hz, 1H), 6.90 (d, J=12.8 Hz, 1H), 4.06-3.90 (m, 6H), 3.68 (s, 2H), 2.88 (d, J=11.1 Hz, 2H), 2.19-2.06 (m, 4H), 2.06-1.97 (m, 1H), 1.79 (d, J=11.4 Hz, 3H) 1.46-1.31 (m, 2H), 0.93-0.84 (m, 2H), 0.69-0.61 (m, 2H).

Example 584

Synthesis of 4-((1-(4-chloro-2-(trifluoromethyl)benzyl)piperidin-4-yl)methoxy)-5-cyclopropyl-2-fluoro-N-(methylsulfonyl)benzamide

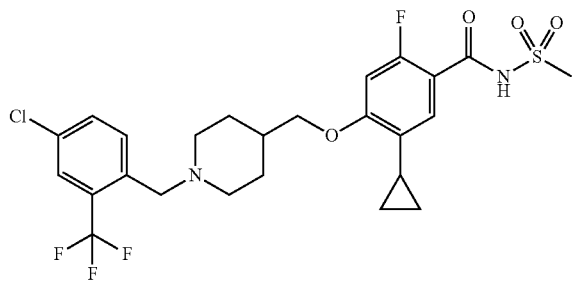 [SMILES: CS(=O)(=O)NC(=O)c1cc(C2CC2)c(OCC2CCN(Cc3ccc(Cl)cc3C(F)(F)F)CC2)cc1F]

The compound was prepared in a similar manner to Example 585 from 5-cyclopropyl-2-fluoro-N-methylsulfonyl-4-(4-piperidylmethoxy)benzamide hydrochloride and 4-chloro-2-(trifluoromethyl)benzaldehyde. LCMS (Method G): RT=4.36 min, m/z: 563.14 [M+H]$^+$. $^1$H NMR (400 MHz, DMSO-d6) δ 11.74 (s, 1H), 7.81 (d, J=8.5 Hz, 1H), 7.78-7.72 (m, 2H), 7.15 (d, J=8.4 Hz, 1H), 6.92 (d, J=12.9 Hz, 1H), 3.95 (d, J=6.0 Hz, 2H), 3.62 (s, 2H), 3.27 (s, 3H), 2.83 (d, J=11.1 Hz, 2H), 2.16-1.97 (m, 3H), 1.90-1.74 (m, 3H), 1.46-1.31 (m, 2H), 0.92-0.85 (m, 2H), 0.69-0.62 (m, 2H)

Example 585

Synthesis of 4-((1-(4-bromo-2-(trifluoromethyl)benzyl)piperidin-4-yl)methoxy)-5-cyclopropyl-2-fluoro-N-(methylsulfonyl)benzamide

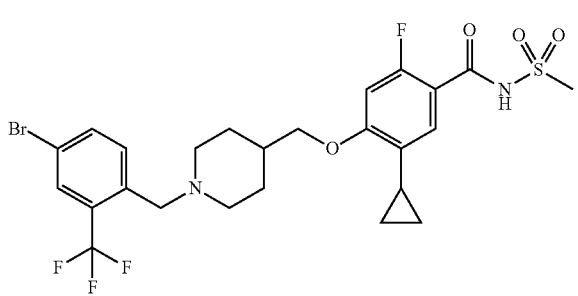

The compound was prepared in a similar manner to Example 585 from 5-cyclopropyl-2-fluoro-N-methylsulfonyl-4-(4-piperidylmethoxy)benzamide hydrochloride and 4-bromo-2-(trifluoromethyl)benzaldehyde. LCMS (Method G): RT=4.44 min, m/z: 609.09 [M+H]$^+$. $^1$H NMR (400 MHz, DMSO-d6) δ 11.74 (s, 1H), 7.93-7.82 (m, 2H), 7.74 (d, J=8.4 Hz, 1H), 7.15 (d, J=8.4 Hz, 1H), 6.92 (d, J=13.0 Hz, 1H), 3.96 (d, J=6.1 Hz, 2H), 3.61, (s, 2H), 3.28 (s. 3H), 2.89-2.77 (m, 2H), 2.17-1.96 (m, 3H), 1.90-1.72 (m, 3H), 1.46-1.31 (m, 2H), 0.94-0.82 (m, 2H), 0.71-0.61 (m, 2H).

Example 586

Synthesis of 5-cyclopropyl-2-fluoro-4-((1-(4-fluoro-2-(trifluoromethyl)benzyl)piperidin-4-yl)methoxy)-N-(methylsulfonyl)benzamide

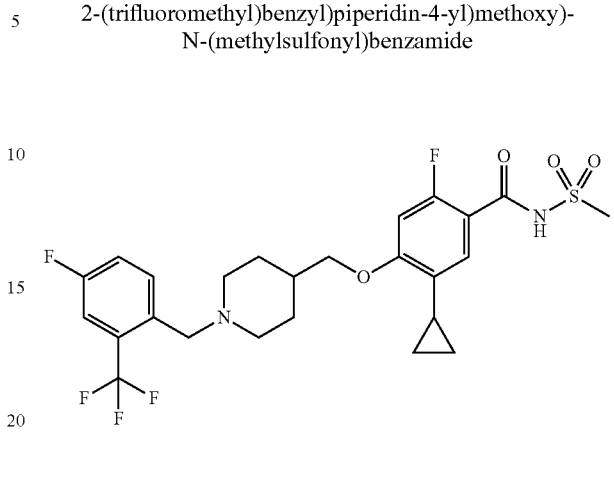

The compound was prepared in a similar manner to Example 585 from 5-cyclopropyl-2-fluoro-N-methylsulfonyl-4-(4-piperidylmethoxy)benzamide hydrochloride and 4-fluoro-2-(trifluoromethyl)benzaldehyde. LCMS (Method G): RT=4.18 min, m/z: 547.17 [M+H]$^+$. $^1$H NMR (400 MHz, DMSO-d6) δ 11.71 (s, 1H), 7.82 (dd, J=8.6, 5.8 Hz, 1H), 7.61-7.49 (m, 2H), 7.15 (d, J=8.3 Hz, 1H), 6.92 (d, J=13.0 Hz, 1H), 3.95 (d, J=6.2 Hz, 2H), 3.62 (s, 2H), 2.84 (d, J=11.1 Hz, 2H), 2.17-1.96 (m, 3H), 1.90-1.73 (m, 3H), 1.46-1.31 (m, 2H), 0.93-0.84 (m, 2H), 0.69-0.62 (m, 2H).

Example 587

Synthesis of 4-((1-(4-bromo-3-chlorobenzyl)piperidin-4-yl)methoxy)-5-cyclopropyl-2-fluoro-N-(methylsulfonyl)benzamide

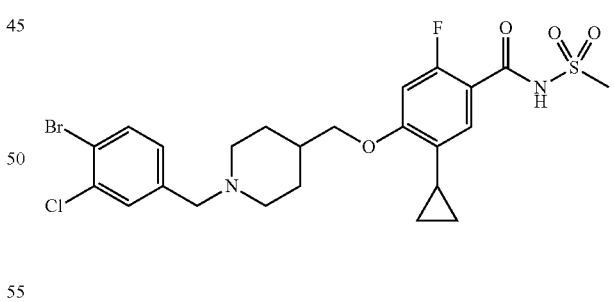

The compound was prepared in a similar manner to Example 585 from 5-cyclopropyl-2-fluoro-N-methylsulfonyl-4-(4-piperidylmethoxy)benzamide hydrochloride and 4-bromo-2-chlorobenzaldehyde. LCMS (Method G): RT=4.13 min, m/z: 575.06 [M+H]$^+$. $^1$H NMR (400 MHz, DMSO-d6) δ 7.76 (d, J=8.2 Hz, 1H), 7.61 (d, J=2.0 Hz, 1H), 7.27 (dd, J=8.2, 2.0 Hz, 1H), 7.17 (d, J=8.4 Hz, 1H), 6.86 (d, J=12.9 Hz, 1H), 3.94 (d, J=5.9 Hz, 2H), 3.67 (s, 2H), 3.16 (s, 3H), 2.97 (d, J=11.2 Hz, 2H), 2.25 (s, 2H), 2.06-1.96 (m, 1H), 1.83 (d, J=12.8 Hz, 3H), 1.42 (d, J=12.2 Hz, 2H), 0.92-0.83 (m, 2H), 0.67-0.58 (m, 2H).

Example 588

Synthesis of 4-((1-(4-bromo-2,5-difluorobenzyl)piperidin-4-yl)methoxy)-5-cyclopropyl-2-fluoro-N-(methylsulfonyl)benzamide

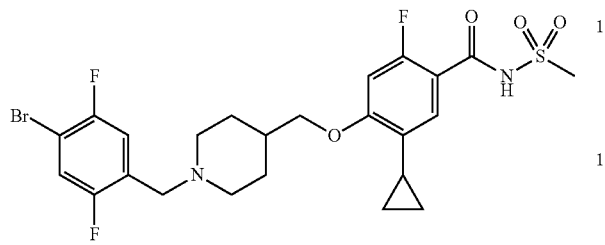

The compound was prepared in a similar manner to Example 585 from 5-cyclopropyl-2-fluoro-N-methylsulfonyl-4-(4-piperidylmethoxy)benzamide hydrochloride and 4-bromo-2,5-difluorobenzaldehyde. LCMS (Method G): RT=41.9 min, m/z: 577.08 [M+H]$^+$. $^1$H NMR (400 MHz, DMSO-d6) δ 11.46 (s, 1H), 7.71 (dd, J=8.9, 5.7 Hz, 1H), 7.44 (dd, J=9.1, 6.2 Hz, 1H), 7.15 (d, J=8.3 Hz, 1H), 6.89 (d, J=12.9 Hz, 1H), 3.94 (d, J=5.9 Hz, 2H), 3.62 (s, 2H), 3.23 (s, 3H), 2.93 (d, J=11.2 Hz, 2H), 2.19 (t, J=11.5 Hz, 2H), 2.05-1.96 (m, 1H), 1.80 (d, J=12.4 Hz, 3H), 1.48-1.32 (m, 2H), 0.92-0.83 (m, 2H), 0.68-0.60 (m, 2H).

Example 589

Synthesis of 4-((1-(4-bromo-2-fluorobenzyl)piperidin-4-yl)methoxy)-5-cyclopropyl-2-fluoro-N-(methylsulfonyl)benzamide

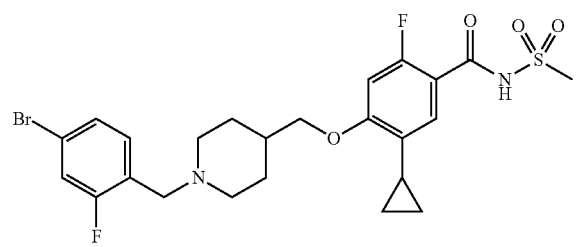 [SMILES: CS(=O)(=O)NC(=O)c1cc(C2CC2)c(OCC2CCN(Cc3ccc(Br)cc3F)CC2)cc1F]

The compound was prepared in a similar manner to Example 585 from 5-cyclopropyl-2-fluoro-N-methylsulfonyl-4-(4-piperidylmethoxy)benzamide hydrochloride and 4-bromo-2-fluorobenzaldehyde. LCMS (Method G): RT=4.18 min, m/z: 559.09 [M+H]$^+$. $^1$H NMR (400 MHz, DMSO-d6) δ 7.54 (dd, J=9.7, 1.8 Hz, 1H), 7.47-7.37 (m, 2H), 7.16 (d, J=8.5 Hz, 1H), 6.87 (d, J=12.9 Hz, 1H), 3.93 (d, J=5.9 Hz, 2H), 3.67 (s, 2H), 3.19 (s, 3H), 2.96 (d, J=11.2 Hz, 2H), 2.24 (s, 2H), 2.05-1.96 (m, 1H), 1.81 (d, J=11.8 Hz, 3H), 1.47-1.32 (m, 2H), 0.92-0.83 (m, 2H), 0.67-0.59 (m, 2H).

Example 590

Synthesis of 4-((1-(3-chloro-5-cyanobenzyl)piperidin-4-yl)methoxy)-5-cyclopropyl-2-fluoro-N-(methylsulfonyl)benzamide

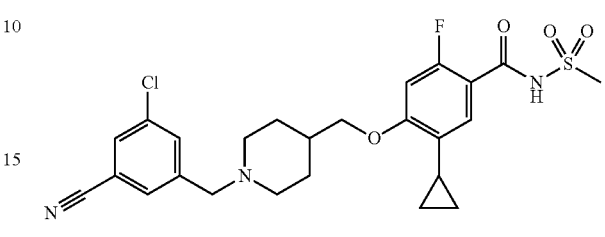

The compound was prepared in a similar manner to Example 585 from 5-cyclopropyl-2-fluoro-N-(methylsulfonyl)-4-(4-piperidylmethoxy)benzamide hydrochloride and 3-chloro-5-formylbenzonitrile. LCMS (Method G): RT=3.96 min, m/z: 520.15 [M+H]$^+$. $^1$H NMR (400 MHz, DMSO-d6) δ 11.42 (s, 1H), 7.96 (t, J=1.8 Hz, 1H), 7.81-7.74 (m, 2H), 7.16 (d, J=8.4 Hz, 1H), 6.89 (d, J=12.9 Hz, 1H), 3.95 (d, J=5.9 Hz, 2H), 3.68 (s, 2H), 3.22 (s, 3H), 2.92 (d, J=11.2 Hz, 2H), 2.19 (m, J=11.6 Hz, 2H), 2.06-1.95 (m, 1H), 1.91-1.74 (m, 3H), 1.50-1.32 (m, 2H), 0.94-0.82 (m, 2H), 0.69-0.60 (m, 2H).

Example 591

Synthesis of 4-((1-(3-cyano-4-fluorobenzyl)piperidin-4-yl)methoxy)-5-cyclopropyl-2-fluoro-N-(methylsulfonyl)benzamide

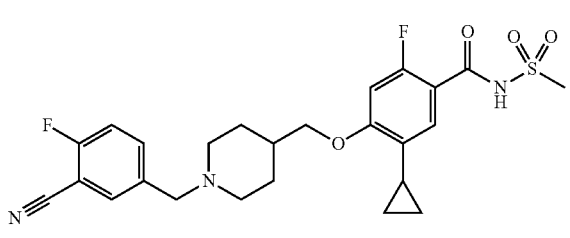 [SMILES: CS(=O)(=O)NC(=O)c1cc(C2CC2)c(OCC2CCN(Cc3ccc(F)c(C#N)c3)CC2)cc1F]

The compound was prepared in a similar manner to Example 585 from 5-cyclopropyl-2-fluoro-N-methylsulfonyl-4-(4-piperidylmethoxy)benzamide hydrochloride and 2-fluoro-5-formylbenzonitrile. LCMS (Method G): RT=3.85 min, m/z: 504.17 [M+H]$^+$.

$^1$H NMR (400 MHz, DMSO-d6) δ 7.87 (dd, J=6.3, 2.2 Hz, 1H), 7.80-7.72 (m, 1H), 7.57-7.48 (m, 1H), 7.16 (d, J=8.4 Hz, 1H), 6.88 (d, J=12.9 Hz, 1H), 3.94 (d, J=6.0 Hz, 2H), 3.70 (s, 2H), 3.19 (s, 3H), 2.96 (d, J=11.3 Hz, 2H), 2.24 (t, J=11.6 Hz, 2H), 2.05-1.96 (m, 1H), 1.92-1.76 (m, 3H), 1.49-1.33 (m, 2H), 0.92-0.83 (m, 2H), 0.68-0.60 (m, 2H).

Example 592

Synthesis of 5-cyclopropyl-2-fluoro-N-(methylsulfonyl)-4-((1-(6-(trifluoromethyl)pyridin-2-yl)piperidin-4-yl)methoxy)benzamide

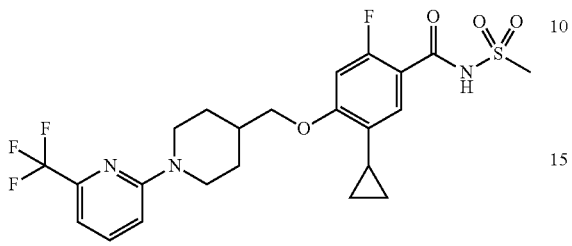

Step 1: Preparation of 5-chloro-2-fluoro-N-methylsulfonyl-4-[[1-[6-(trifluoromethyl)-2-pyridyl]-4-piperidyl]methoxy]benzamide To solution of (1-[6-(trifluoromethyl)pyridin-2-yl]piperidin-4-yl)methanol (169 mg) and 5-chloro-2,4-difluoro-N-methylsulfonyl-benzamide (175 mg) in DMSO (2.5 mL) at 14° C. (bath) was added potassium tert-butoxide (1.75 mg). The mixture was stirred at rt for 1 hr. Diluted with EtOAc, the contents were washed with ¼ mixture of 0.5M NaH$_2$PO$_4$ (2×) and brine (1×), dried (Na$_2$SO$_4$). After filtration and concentration, the crude was purified with flash chromatography (0-2% MeOH/DCM with 0.5% HCO$_2$H) to give the product (205 mg).

Step 2: Preparation of 5-cyclopropyl-2-fluoro-N-(methylsulfonyl)-4-((1-(6-(trifluoromethyl)-2-pyridin-2-yl)piperidin-4-yl)methoxy)benzamide A mixture of 5-chloro-2-fluoro-N-methylsulfonyl-4-[[1-[6-(trifluoromethyl)-2-pyridyl]-4-piperidyl]methoxy]benzamide (205 mg), cyclopropylboronic acid (109 mg), and potassium phosphate (523 mg) in water (0.4 mL) and toluene (8.0 mL) was purged with nitrogen for 10 min. Tricyclohexylphosphoniumtetrafluoroborate (46 mg) and palladium acetate (14 mg) were added. The resulting mixture was stirred under nitrogen at 95° C. for 40 hr. Acidified with ¼ mixture of 0.5 M HCl and 0.5 M NaH$_2$PO$_4$, the contents were extracted with DCM (2×). The combined DCM solution were dried (Na$_2$SO$_4$). After filtration and concentration, the crude was purified with HPLC (37.5 mg). LCMS (Method G): RT=7.99 min, m/z: 516.2 [M+H]$^+$. $^1$H NMR (400 MHz, DMSO-d6) δ 11.84 (s, 1H), 7.76-7.67 (m, 1H), 7.15 (dd, J=9.8, 8.6 Hz, 2H), 6.98 (d, J=7.2 Hz, 1H), 6.90 (d, J=12.9 Hz, 1H), 4.38 (d, J=13.2 Hz, 2H), 3.98 (d, J=6.2 Hz, 2H), 3.23 (s, 3H), 2.94 (td, J=12.7, 2.6 Hz, 2H), 2.12 (s, 1H), 2.04-1.94 (m, 1H), 1.92-1.81 (m, 2H), 1.43-1.28 (m, 2H), 0.88-0.80 (m, 2H), 0.68-0.59 (m, 2H).

Example 593

Synthesis of 4-((1-(3-chloro-2-fluoro-5-(trifluoromethyl)benzyl)-3-methylazetidin-3-yl)methoxy)-5-cyclopropyl-2-fluoro-N-(methylsulfonyl)benzamide

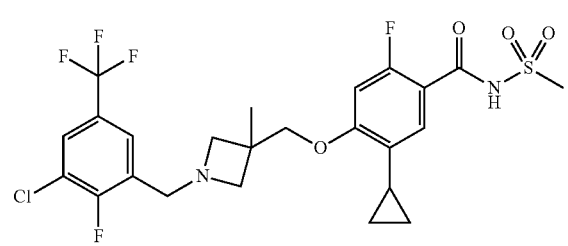 [SMILES: CC1(COc2cc(F)c(C(=O)NS(C)(=O)=O)cc2C2CC2)CN(Cc2cc(C(F)(F)F)cc(Cl)c2F)C1]

Steps 1-2: Preparation of tert-butyl 3-[[2-cyclopropyl-5-fluoro-4-(methylsulfonylcarbamoyl)phenoxy]methyl]-3-methyl-azetidine-1-carboxylate The compound was prepared in a similar manner to Example 598 starting 5-chloro-2,4-difluoro-N-methylsulfonyl-benzamide and tert-butyl 3-(hydroxymethyl)-3-methyl-azetidine-1-carboxylate

Step 3: Preparation of 4-((1-(3-chloro-2-fluoro-5-(trifluoromethyl)benzyl)-3-methylazetidin-3-yl)methoxy)-5-cyclopropyl-2-fluoro-N-(methylsulfonyl)benzamide The compound was prepared in a similar manner to Example 73 starting from tert-butyl 3-[[2-cyclopropyl-5-fluoro-4-(methylsulfonylcarbamoyl)phenoxy]methyl]-3-methyl-azetidine-1-carboxylate and 3-chloro-2-fluoro-5-(trifluoromethyl)benzaldehyde. LCMS (Method G): RT=5.66 min, m/z: 567.1 [M+H]$^+$. $^1$H NMR (400 MHz, DMSO-d6) δ 11.68 (s, 1H), 8.01 (dd, J=6.5, 2.2 Hz, 1H), 7.74 (dd, J=5.9, 2.3 Hz, 1H), 7.20 (d, J=8.5 Hz, 1H), 6.94 (d, J=12.8 Hz, 1H), 4.06 (s, 2H), 3.84 (s, 2H), 3.39 (d, J=7.3 Hz, 2H), 3.23 (s, 3H), 3.14 (d, J=7.3 Hz, 2H), 2.09-1.98 (m, 1H), 1.36 (s, 3H), 0.92-0.82 (m, 2H), 0.70-0.61 (m, 2H).

Example 594

Synthesis of 5-Cyclopropyl-4-((1-(3,5-dichloro-2-cyanobenzyl)piperidin-4-yl)methoxy)-2-fluoro-N-(methylsulfonyl)benzamide

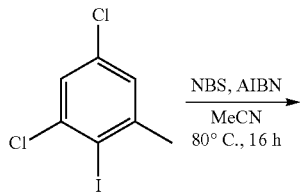

839
-continued

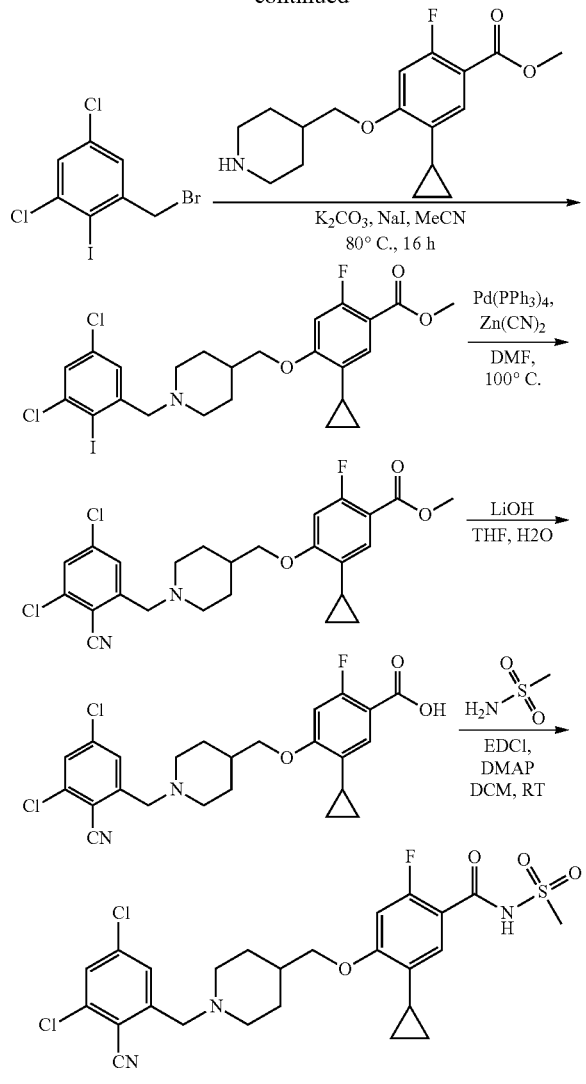

594

Step 1: Preparation of 1-(bromomethyl)-3,5-dichloro-2-iodobenzene

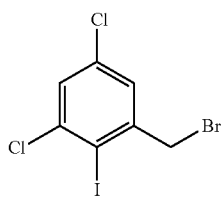 [SMILES: Clc1cc(Cl)c(I)c(CBr)c1]

2,2'-azobis(2-methylpropionitrile) (149 mg, 0.91 mmol) was added to a solution of 1,5-dichloro-2-iodo-3-methylbenzene (2.6 g, 9.1 mmol) and N-bromosuccinimide (1.8 g, 10.0 mmol) in acetonitrile (70 mL), the reaction mixture was stirred at 80° C. for 16 h, diluted with water (50 mL) and extracted with ethyl acetate (100 mL×3), the combined organic layers were washed with brine (50 mL), dried, over anhydrous sodium sulfate, filtered and concentrated. The residue was purified by silica gel column chromatography (eluting with petroleum ether) to afford the target compound (1.26 g, yield: 38%) as a white solid. $^1$H NMR (500 MHz, CDCl$_3$): δ 7.44-7.43 (m, 1H), 7.41-7.40 (m, 1H), 4.61 (s, 2H).

Step 2: Preparation of methyl 5-cyclopropyl-4-((1-(3,5-dichloro-2-iodobenzyl)piperidin-4-yl)methoxy)-2-fluorobenzoate

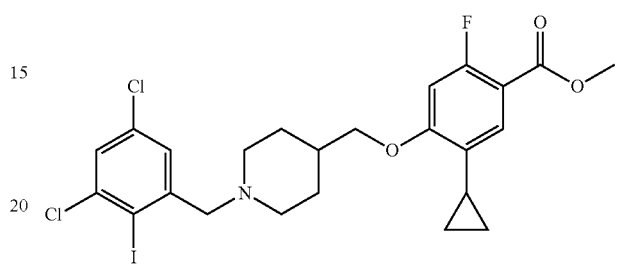

A mixture of 1-(bromomethyl)-3,5-dichloro-2-iodobenzene (200 mg, 0.55 mmol), methyl 5-cyclopropyl-2-fluoro-4-(piperidin-4-ylmethoxy)benzoate hydrochloride (188.7 mg, 0.55 mmol), sodium iodide (245.9 mg, 1.65 mmol) and potassium carbonate (227.7 mg, 1.65 mmol) in acetonitrile (40 mL) was stirred at 80° C. for 16 h. The reaction mixture was diluted with ethyl acetate (100 mL) and brine (50 mL), and the organic layer was separated, washed with brine (20 mL), dried over anhydrous sodium sulfate, filtered and concentrated. The residue was purified, by silica gel chromatography (eluting with 20% ethyl acetate in petroleum ether) to give the target compound (240 mg, 74%) as a pale yellow oil. LCMS (ESI) m/z: 592.0 [M+H]$^+$.

Step 3: Preparation of methyl 5-cyclopropyl-4-((1-(3,5-dichloro-2-cyanobenzyl)piperidin-4-yl) methoxy)-2-fluorobenzoate

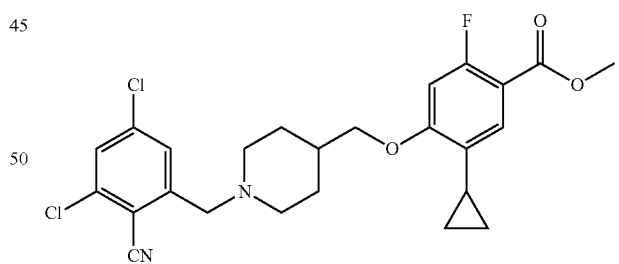

A mixture of methyl 5-cyclopropyl-4-((1-(3,5-dichloro-2-iodobenzyl)piperidin-4-yl)methoxy)-2-fluorobenzoate (150 mg, 0.25 mmol) and copper cyanide (45.0 mg, 0.50 mmol) in N-methylpyrolidone (5.0 mL) was stirred under microwave at 150° C. for 1.0 h. The reaction mixture was diluted with ethyl acetate (300 mL), filtered, the filtrate was washed with water (50 mL) and brine (50 mL), dried over anhydrous sodium sulfate, filtered and concentrated. The residue was purified by silica gel chromatography (eluting with 20% ethyl acetate in petroleum ether) to give the target compound (35.0 mg, 14%) as a pale yellow oil. LCMS (ESI) m/z: 491.1 [M+H]$^+$.

841

Step 4: Preparation of 5-cyclopropyl-4-((1-(3,5-dichloro-2-cyanobenzyl)piperidin-4-yl)methoxy)-2-fluorobenzoic acid

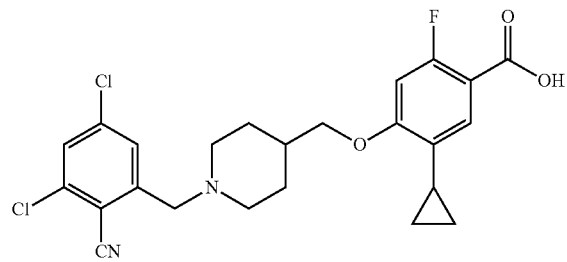 [SMILES: N#Cc1c(Cl)cc(Cl)cc1CN1CCC(COc2cc(F)c(C(=O)O)cc2C2CC2)CC1]

A mixture of methyl 5-cyclopropyl-4-((1-(3,5-dichloro-2-cyanobenzyl)piperidin-4-yl)methoxy)-2-fluorobenzoate (35 mg, 0.07 mmol) and lithium hydroxide (42 mg, 1.75 mmol) in THF (5 mL) and water (5 mL) was stirred at room temperature for 16 h. The mixture was adjusted to pH 2-3 with HCl (2M), extracted with ethyl acetate (10×2 mL), the combined organic layers were washed with brine (10 mL), dried over anhydrous sodium sulfate, filtered and concentrated to give the crude product as a pale yellow solid. The solid was used in next step without further purification. LCMS (ESI) m/z: 477.1 [M+H]+.

Step 5: Preparation of 5-Cyclopropyl-4-((1-(3,5-dichloro-2-cyanobenzyl)piperidin-4-yl)methoxy)-2-fluoro-N-(methylsulfonyl)benzamide

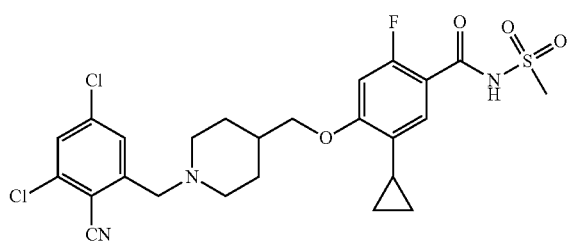 [SMILES: CS(=O)(=O)NC(=O)c1cc(C2CC2)c(OCC2CCN(Cc3cc(Cl)cc(Cl)c3C#N)CC2)cc1F]

A mixture of 5-cyclopropyl-4-((1-(3,5-dichloro-2-cyanobenzyl)piperidin-4-yl)methoxy)-2-fluorobenzoic acid (30 mg, 0.07 mmol), methanesulfonamide (11 mg, 0.11 mmol), 1-ethyl-(3-dimethylaminopropyl)carbodiimide hydrochloride (27 mg, 0.14 mmol) and N,N-dimethyl-4-aminopyridine (17 mg, 0.14 mmol) in DCM (4 mL) was stirred at room temperature for 1.6 h. The reaction mixture was diluted with DCM (30 mL), washed with HCl (20 M, 5 mL), water (5 mL) and brine (10 mL), dried over anhydrous sodium sulfate, filtered and concentrated. The residue was purified by reverse phase Combiflash (30-40% MeCN in 0.1% $NH_4HCO_3$) to give the target product (23 mg, 38%) as a white solid. LCMS (ESI) Method A: RT=5.68 mm, m/z: 554.1 [M+H]+. $^1$H NMR (400 MHz, DMSO-$d_6$) δ 7.91 (d, J=4.0 Hz, 1H), 7.65 (d, J=4.0 Hz, 1H), 7.15 (d, J=8.4 Hz, 1H), 6.90 (d, J=16.0 Hz, 1H), 3.95 (d, J=4.0 Hz, 2H), 3.67 (s, 2H), 3.23 (s, 3H), 2.87-2.84 (m, 2H), 2.18-2.12 (m, 2H), 1.99-2.02 (m, 1H), 1.80-1.77 (m, 3H), 1.39-1.36 (m, 1H), 0.90-0.87 (m, 1H), 0.67-0.64 (m, 2H).

842

Example 595

Synthesis of 4-((1-(3-chloro-2-fluoro-5-(trifluoromethyl)benzyl)-4-cyanopiperidin-4-yl)methoxy)-5-cyclopropyl-2-fluoro-N-(methylsulfonyl)benzamide

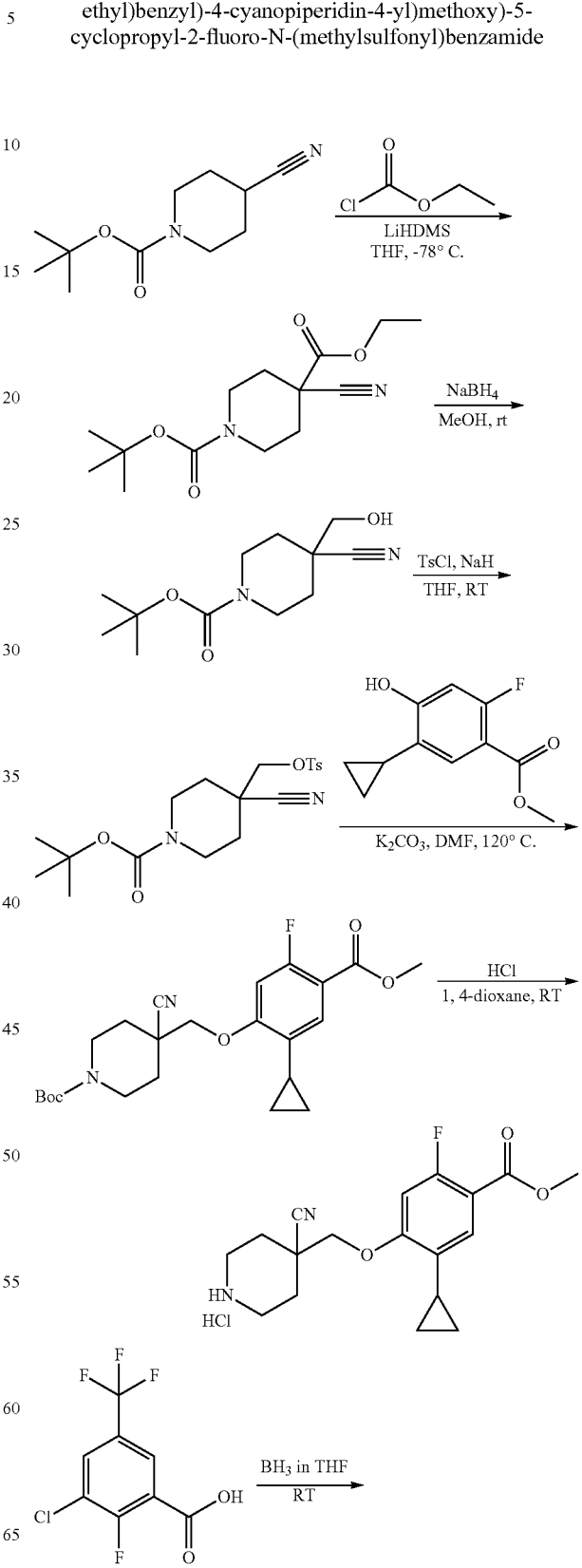

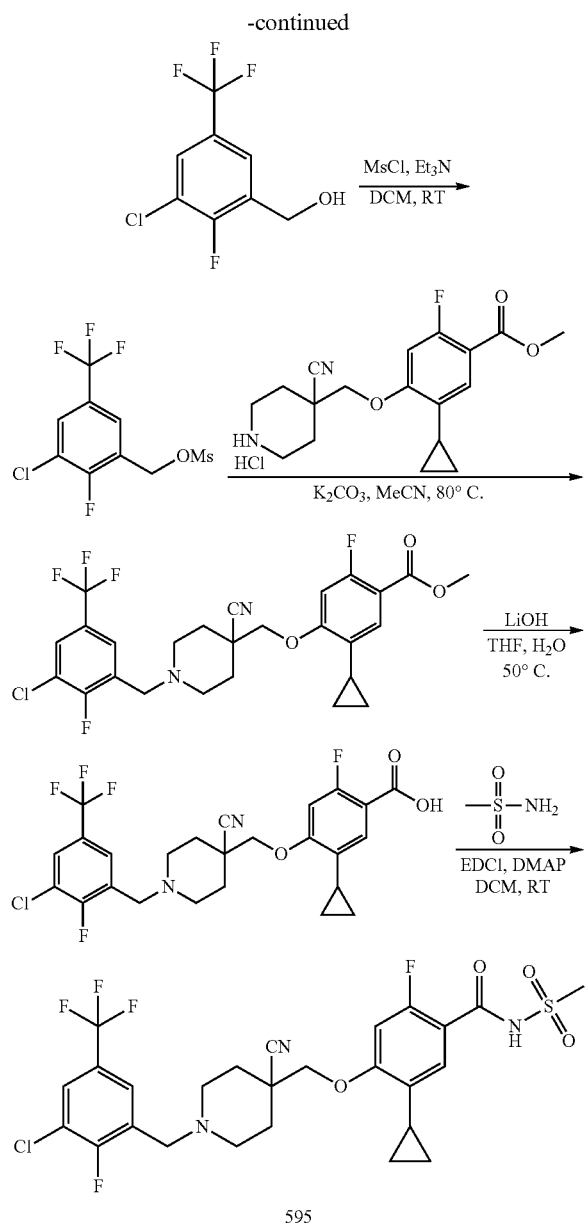

595

Step 1: Preparation of 1-(tert-butyl) 4-ethyl
4-cyanopiperidine-1,4-dicarboxylate

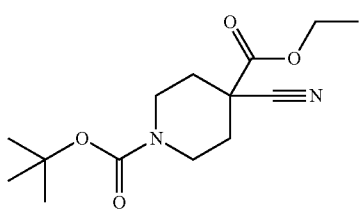 [SMILES: CCOC(=O)C1(C#N)CCN(C(=O)OC(C)(C)C)CC1]

Lithium hexamethyldisilazide (1 M, 20 mL, 20 mmol) was added dropwise to a solution of tert-butyl 4-cyanopiperidine-1-carboxylate (2.1 g, 10 mmol) in anhydrous THF (30 mL) at −78° C. The resulting mixture was stirred at this temperature for 1 h, then ethyl carbonochloridate (2.2 g, 20 mmol) was added at −78° C. and stirred at this temperature for 1 h. The reaction was quenched with sodium bicarbonate aqueous solution (1 M, 30 mL) and extracted with ethyl acetate (100 mL×3), the combined organic layers were washed with brine (20 mL), dried over anhydrous sodium sulfate, filtered and concentrated. The crude product was purified by silica column chromatography (eluting with 10-25% ethyl acetate in petroleum ether) to give product as colorless oil (2.8 g, 99%), LCMS (ESI) m/z: 183.1 [M−99]⁺.

Step 2: Preparation of tert-butyl
4-cyano-4-(hydroxymethyl)piperidine-1-carboxylate

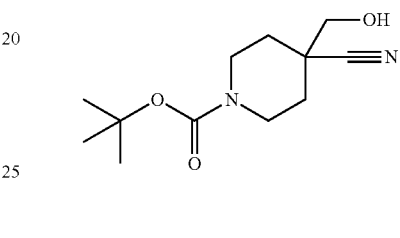

Sodium borohydride (1.5 g, 40 mmol) was added to a solution, of 1-tert-butyl 4-ethyl 4-cyanopiperidine-1,4-dicarboxylate (2.8 g, 10 mmol) in MeOH (30 mL) at 0° C., the reaction mixture was stirred at room temperature for 1 h. The solvent was removed under reduced pressure and the crude was diluted with water (30 ml), extracted with ethyl acetate (50 mL×3), washed with brine (20 ml), dried over anhydrous sodium sulfate, filtered and concentrated to get crude product (2.4 g, 99%). The crude was used directly in the next step without further purification.

Step 3: Preparation of tert-butyl
4-cyano-4-(tosyloxymethyl)piperidine-1-carboxylate

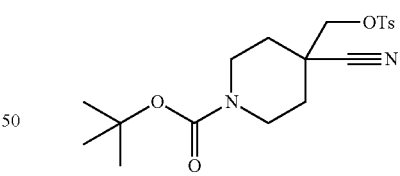

Sodium hydride (2.0 g, 50 mmol) was added to an ice-cooled solution of tert-butyl 4-cyano-4-(hydroxymethyl)piperidine-1-carboxylate (2.4 g, 10 mmol) in anhydrous THF (20 mL) and stirred for 1 h, then a solution of tosyl chloride (3.8 g, 20 mmol) in THF (10 mL) was added and the mixture was stirred at room temperature for 16 h. The mixture was quenched with water (40 mL), extracted with ethyl acetate (50 mL×3), washed with brine (40 mL), dried over anhydrous sodium sulfate, filtered and concentrated. The crude product was purified by silica column chromatography (eluting with 25% ethyl acetate in petroleum ether) to give product as white solid (2.0 g, 50%). LCMS (ESI) m/z: 295.1 [M−99]⁺.

Step 4: Preparation of tert-butyl 4-cyano-4-((2-cyclopropyl-5-fluoro-4-(methoxycarbonyl)-phenoxy)methyl)piperidine-1-carboxylate

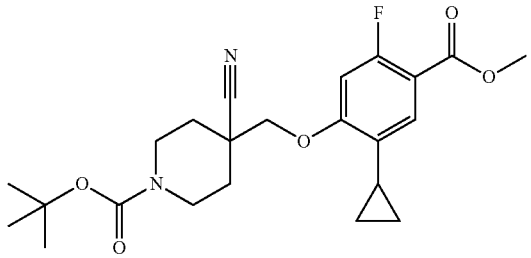 [SMILES: COC(=O)c1cc(C2CC2)c(OCC2(C#N)CCN(C(=O)OC(C)(C)C)CC2)cc1F]

A mixture of tert-butyl 4-cyano-4-(tosyloxymethyl)piperidine-1-carboxylate (1.0 g, 2.5 mmol), methyl 5-cyclopropyl-2-fluoro-4-hydroxybenzoate (525 mg, 2.5 mmol) and potassium carbonate (1.1 g, 7.5 mmol) in DMF (10 mL) in a sealed tube was stirred at 120° C. for 4 h. The reaction mixture was diluted with water (40 mL), extracted with ethyl acetate (50 mL×3), washed with brine (20 mL), dried over anhydrous sodium sulfate, filtered and concentrated to get crude product (1.0 g, 93%). The crude was used directly in the next step without further purification. LCMS (ESI) m/z: 433.1 [M+1]$^+$.

Step 5: Preparation of methyl 4-((4-cyanopiperidin-4-yl)methoxy)-5-cyclopropyl-2-fluorobenzoate hydrochloride

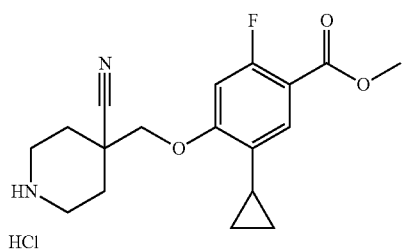 [SMILES: COC(=O)c1cc(C2CC2)c(OCC2(C#N)CCNCC2)cc1F ; Cl]

Hydrochloride is 1,4-dioxane (4 M, 20 mL) was added to a solution of tert-butyl 4-cyano-4-((2-cyclopropyl-5-fluoro-4-(methoxycarbonyl)phenoxy)methyl)piperidine-1-carboxylate (1.0 g, 2.3 mmol) is 1,4-dioxane, the reaction mixture was stirred at room temperature for 1 h. The solution was concentrated to give a brown solid, which was recrystallized in ethyl acetate (4 mL) to give the target compound as a gray solid (0.6 g, 74%), LCMS (ESI) m/z: 333.1 [M−HCl+1]$^+$.

Step 6: Preparation of (3-chloro-2-fluoro-5-(trifluoromethyl)phenyl)methanol

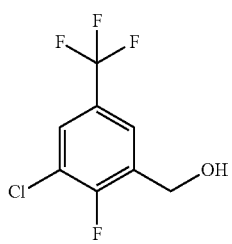 [SMILES: OCc1cc(C(F)(F)F)cc(Cl)c1F]

Borane-tetrahydrofuran complex (1M, 20 mL, 20 mmol) was mixed with 3-chloro-2-fluoro-5-(trifluoromethyl)benzoic acid (480 mg, 2 mmol) at 0° C., the reaction mixture was stirred at room temperature for 1 h, quenched with MeOH (20 mL). The solvents were removed under reduced pressure to give crude product (400 mg, 87%) which was used directly in the next step without further purification. LCMS (ESI) m/z: 227.1 [M−1]$^+$.

Step 7: Preparation of 3-chloro-2-fluoro-5-(trifluoromethyl)benzyl methanesulfonate

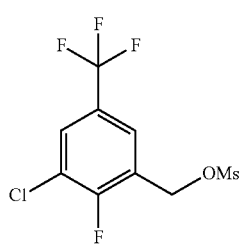 [SMILES: CS(=O)(=O)OCc1cc(C(F)(F)F)cc(Cl)c1F]

Methanesulfonyl chloride (60 mg, 0.52 mmol) was added dropwise to a mixture of (3-chloro-2-fluoro-5-(trifluoromethyl)phenyl)methanol (100 mg, 0.44 mmol) and triethylamine (90 mg, 0.88 mmol) in DCM (10 mL) at 0° C. The reaction mixture was stirred at room temperature for 16 h, diluted with DCM (20 mL), washed with water (10 mL×2), dried over anhydrous sodium sulfate, filtered and concentrated to get crude product (130 mg, 96%). The crude was used directly in the next step without further purification. LCMS (ESI) m/z: 307.1 [M+1]$^+$.

Step 8: Preparation of methyl 4-((1-(3-chloro-2-fluoro-5-(trifluoromethyl)benzyl)-4-cyanopiperidin-4-yl)methoxy)-5-cyclopropyl-2-fluorobenzoate

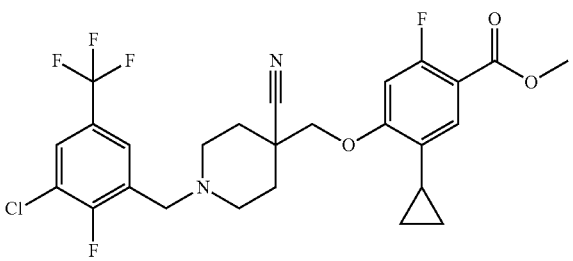 [SMILES: COC(=O)c1cc(C2CC2)c(OCC2(C#N)CCN(Cc3cc(C(F)(F)F)cc(Cl)c3F)CC2)cc1F]

A mixture of 3-chloro-2-fluoro-5-(trifluoromethyl)benzyl methanesulfonate (100 mg, 0.33 mmol), methyl 4-((4-cyanopiperidin-4-yl)methoxy)-5-cyclopropyl-2-fluorobenzoate hydrochloride (122 mg, 0.33 mmol) and potassium carbonate (137 mg, 0.99 mmol) in acetonitrile (10 mL) was stirred at 80° C. for br 16 h. The reaction mixture was diluted with ethyl acetate (100 mL) and brine (50 mL), washed with brine (50 mL), dried over anhydrous sodium sulfate, filtered and concentrated. The residue was purified by silica gel chromatography (eluting with 20% ethyl acetate in petroleum ether) to give the target compound (80 mg, 45%) as a pale yellow oil, LCMS (ESI) m/z: 543.0 [M+H]$^+$.

847

Step 9: Preparation of 4-((1-(3-chloro-2-fluoro-5-(trifluoromethyl)benzyl)-4-cyanopiperidin-4-yl)methoxy)-5-cyclopropyl-2-fluorobenzoic acid

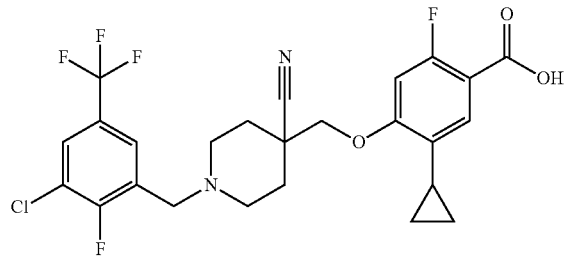 [SMILES: N#CC1(COc2cc(F)c(C(=O)O)cc2C2CC2)CCN(Cc2cc(C(F)(F)F)cc(Cl)c2F)CC1]

A mixture of methyl 4-((1-(3-chloro-2-fluoro-5-(trifluoromethyl)benzyl)-4-cyanopiperidin-4-yl)methoxy)-5-cyclopropyl-2-fluorobenzoate (80 mg, 0.15 mmol) and lithium hydroxide (36 mg, 1.5 mmol) in THF (3 mL) and water (3 mL) was stirred at 50° C. for 3 h. The reaction mixture was adjusted pH 2-3 with HCl (2M), extracted with ethyl acetate (10×2 mL), washed with brine (10 mL), dried over anhydrous sodium sulfate, filtered and concentrated to give the product (77 mg, 99%) as a pale yellow solid. LCMS (ESI) m/z: 529.1 [M+H]$^+$.

Step 10: Preparation of 4-((1-(3-chloro-2-fluoro-5-(trifluoromethyl)benzyl)-4-cyanopiperidin-4-yl)methoxy)-5-cyclopropyl-2-fluoro-N-(methylsulfonyl)benzamide

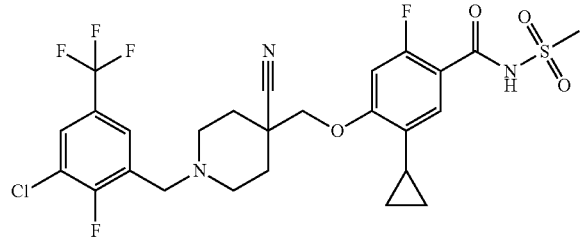 [SMILES: CS(=O)(=O)NC(=O)c1cc(C2CC2)c(OCC2(C#N)CCN(Cc3cc(C(F)(F)F)cc(Cl)c3F)CC2)cc1F]

A mixture of 4-((1-(3-chloro-2-fluoro-5-(trifluoromethyl)benzyl)-4-cyanopiperidin-4-yl)methoxy)-5-cyclopropyl-2-fluorobenzoic acid (77 mg, 0.16 mmol), methanesulfonamide (23 mg, 0.24 mmol), 1-ethyl-(3-dimethylaminopropyl)carbodiimide hydrochloride (61 mg, 0.32 mmol) and N,N-dimethyl-4-aminopyridine (39 mg, 0.32 mmol) in DCM (4 mL) was stirred at room temperature for 16 h. The reaction mixture was diluted with DCM (100 mL), washed with HCl (2.0 M, 20 mL) and brine (50 mL), dried over anhydrous sodium sulfate, filtered and concentrated. The residue was purified by reverse phase combiflash (40-50% MeCN in 0.1% NH$_4$HCO$_3$) to give the target product (40 mg, 41%) as white solid. LCMS (ESI) Method A: RT=5.91 min, m/z: 606.0 [M+H]$^+$. $^1$H NMR (400 MHz, DMSO-d$_6$) δ 8.03 (d, J=5.2 Hz, 1H), 7.8 (d, J=3.2 Hz, 1H), 7.21 (d, J=7.6 Hz, 1H), 6.92-6.87 (m, 1H), 4.21 (s, 2H), 3.72 (s, 2H), 3.14 (s, 3H), 2.91-2.88 (m, 2H), 2.33-2.76 (m, 2H), 2.06-2.03 (m, 3H), 1.77-1.71 (m, 2H), 0.90-0.87 (m, 2H), 0.65-0.62 (m, 2H).

Examples 596-598

Using procedures similar to those described herein the following compounds of formula (I) were also prepared.

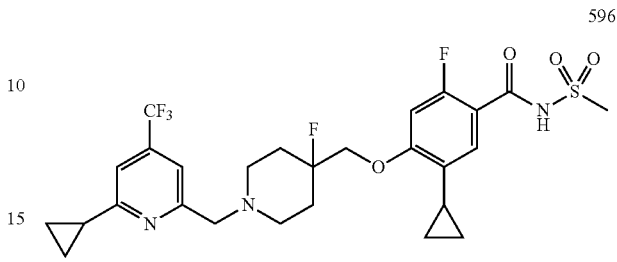

596

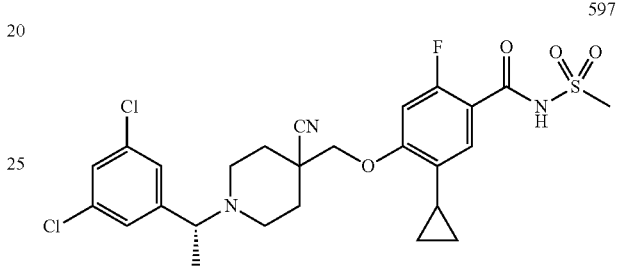

597

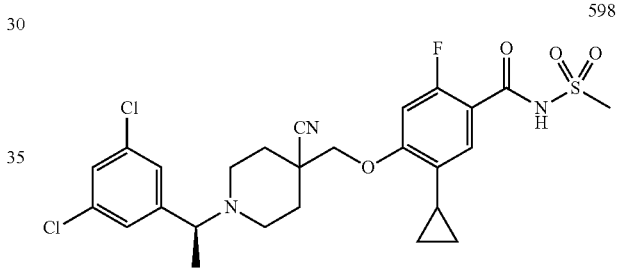

598

Example 596: M+H 588.23; Example 597: M+H 568.22; and Example 598: M+H 568.22

Example 599

Electrophysiological Assay (EP) (In vitro Assay)

Patch voltage clamp electrophysiology allows for the direct measurement and quantification of block of voltage-gated sodium channels (NaV's), and allows the determination of the time- and voltage-dependence of block which has been interpreted as differential binding to the resting, open, and inactivated states of the sodium channel (Hille, B., Journal of General Physiology (1977), 69: 497-515).

The following patch voltage clamp electrophysiology studies were performed on representative compounds of the invention using human embryonic kidney cells (HEK), permanently transfected with an expression vector containing the full-length cDNA coding for the desired human sodium channel α-subunit, grown in culture media containing 10% FBS, 1% PSG, and 0.5 mg/mL G418 at 37° C. with 5% CO2. HEK cells used for the electrophysiology (EP) recordings had a passage number of less than 40 for all studies and were used within three days from the time of plating, NaV1.7 and NaV1.5 cDNAs (NM_002977 and AC137587; SCN5A, respectively) were stably expressed in HEK-293 cells. The β1 subunit was coexpressed in both the NaV1.7 and NaV1.5 cell lines.

Sodium currents were measured rising the patch clamp technique in the whole-cell configuration using either a PatchXpress automated voltage clamp or manually using an Axopatch 200B (Axon Instruments) or Model 2400 (A-M systems) amplifier. The manual voltage clamp protocol was as follows: Borosilicate glass micropipettes were fire-polished to a tip diameter yielding a resistance of 2-4 Mohms in the working solutions. The pipette was filled with a solution comprised of: 5 mM NaCl, 10 mM CsCl, 120 mM CsF, 0.1 mM CaCl2, 2 mM MgCl2, 10 mM HEPES, 10 mM EGTA; and adjusted to pH 7.2 with CsOH. The external solution had the following composition: 140 mM NaCl, 5 mM KCl, 2 mM CaCl2, 1 mM MgCl2, 10 mM HEPES; and adjusted to pH 7.4 with NaOH. In some studies, the external sodium was reduced by equimolar replacement with choline. Osmolality in the CsF internal and NaCl external solutions was adjusted to 300 mOsm/kg and 310 mOsm/kg with glucose, respectively. All recordings were performed at ambient temperature in a bath chamber with a volume of 150 µL. Control sodium currents were measured in 0.5% DMSO. Controls and representative compounds of the invention were applied to the recording chamber through a 4-pinch or 8-pinch valve bath perfusion system manufactured by ALA Scientific Instruments.

Currents were recorded at 40 kHz sampling frequency, filtered at 5 Hz, and stored using a Digidata-1322A analogue/digital interface with the pClamp software (Axon instruments). Series resistance compensation was applied (60-80%). Cells were rejected if currents showed inadequate voltage control (as judged by the IV relationship during stepwise activation). All statistics in this study are given as mean±SD.

The membrane potential was maintained at a voltage where reactivation of the channel is complete (which was −60 mV for both NaV1.7 and NaV1.5). The voltage is then stepped back to a very negative (Vhold=150 mV) voltage for 20 ms and then a test poise is applied to quantify the compound block. The 20 ms brief repolarization was long enough for compound-free channels to completely recover from fast inactivation, but the compound-bound channels recovered more slowly such that negligible recovery could occur during this interval. The percent decrease in sodium current following wash-on of compound was taken as the percent block of sodium channels. Data for representative compounds of formula (I) is provided in Table 1.

Example 600

Tritiated Sulfonamide Binding to Membranes

Isolated from Cells that Heterologously Express hNav1.7 and the β1 Subunit

Preparation of membranes containing recombinantly expressed sodium channels: Frozen recombinant cell pellets were thawed on ice and diluted to 4 times the cell pellet weight with ice cold 50 mM TrisHCl, pH 7.4 buffer. The cell suspensions were homogenized on ice using a motorized glass douncehomogeniser. Homogenates were further diluted 8.4 times with ice cold 50 mM TrisHCl, pH 7.4 buffer and then centrifuged at 200×g at 4° C. for 15 min. The supersatants were collected and centrifuged at 10000×g at 4° C. for 50 min. The pellets were then re-suspended in 100 mMNaCl, 20 mM TrisHCl, pH. 7.4 buffer containing 1% v/v protease inhibitors (Calbiochem) and re-homogenized on ice. The homogenized membranes were then processed through a syringe equipped with a 26 gauge needle. Protein concentrations were determined by Bradford Assay and the membranes were stored at −80° C.

Radioligand Binding Studies: Saturation experiments. A representative compound of formula (I) having a methyl group was tritiated. Three tritiums were incorporated in place of methyl hydrogens to generate [$^3$H]compound. Binding of this radioligand was preformed in 5 mL borosilicate glass test tubes at room temperature. Binding was initiated by adding membranes to increasing concentrations of [$^3$H] compound in 100 mM NaCl, 20 mM TrisHCl, pH 7.4 buffer containing 0.01% w/v bovine serum albumin (BSA) for 18 h. Non-specific binding was determined in the presence of 1 µM unlabelled compound. After 18 h, the reactants were filtered through GF/C glass fiber filters presoaked in 0.5% w/v polyethylene imine. Filters were washed with 15 mL ice cold 100 mM NaCl, 20 mM TrisHCl, pH7.4 buffer containing 0.25% BSA to separate bound from free ligand. [$^3$H] compound bound to filters was quantified by liquid scintillation counting.

Competitive binding experiments: Binding reactions were preformed its 96-well polypropylene plates at room temperature for 18 h. In 360 µL, membranes were incubated with 100 pM [$^3$H]compound and increasing concentrations of Test Compound. Non-specific binding was defined in the presence of 1 µM unlabelled compound. Reactions were transferred and filtered through 96-well glass fiber/C filter plates presoaked with 0.5% polyethylene imine. The filtered reactions were washed 5 times with 200 µL ice cold butter containing 0.25% BSA. Bound radioactivity was determined by liquid scintillation counting.

Data Analysis: For saturation experiments, non-specific binding was subtracted from total binding to provide specific binding and these values were recalculated in terms of pmol ligand bound per mg protein. Saturation curves were constructed and dissociation constants were calculated using the single site ligand binding model: Beq=(Bmax*X)/(X+KD), where Beq is the amount of ligand bound at equilibrium, Bmax is the maximum receptor density, Kd is the dissociation constant for the ligand, and X is the tree ligand concentration. For competition studies percent inhibition was determined and $IC_{50}$ values were calculated using a 4 parameter logistic model (% inhibition=(A+((B−A)/(1+((x/C)^D)))) using XLfit, where A and B are the maximal and minimal inhibition respectively, C is the $IC_{50}$ concentration and D is the (Hill) slope.

Representative compounds, when tested in this model, demonstrated affinities as set forth in Table 1.

TABLE 1

| Example | Structure | Ligand Binding Assay (μM) | NaV1.7 EP (μM) | NaV1.5 EP (μM) |
|---|---|---|---|---|
| 1 | 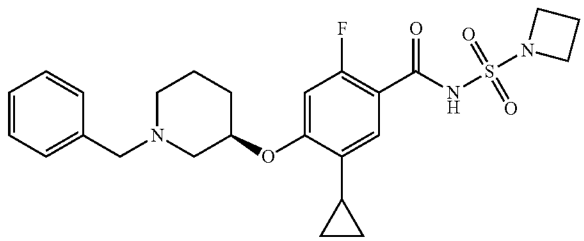 [SMILES: O=C(NS(=O)(=O)N1CCC1)c1cc(C2CC2)c(O[C@@H]2CCCN(Cc3ccccc3)C2)cc1F] | 0.0356 | 0.0226 | 2.7559 |
| 2 | 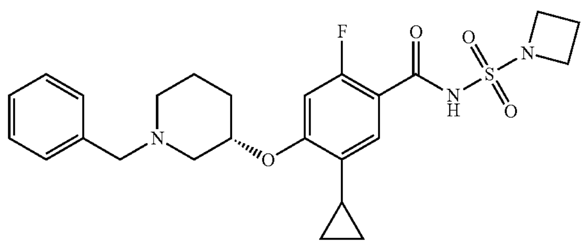 [SMILES: O=C(NS(=O)(=O)N1CCC1)c1cc(C2CC2)c(O[C@H]2CCCN(Cc3ccccc3)C2)cc1F] | 4.1167 | 1.0769 | |
| 3 | 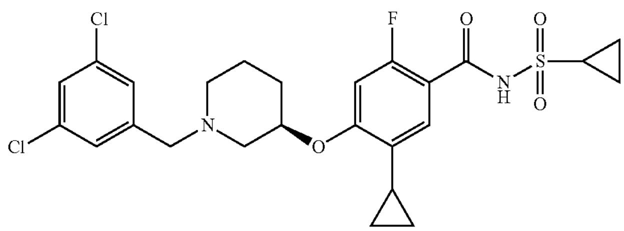 [SMILES: O=C(NS(=O)(=O)C1CC1)c1cc(C2CC2)c(O[C@@H]2CCCN(Cc3cc(Cl)cc(Cl)c3)C2)cc1F] | 0.0026 | | |
| 4 | 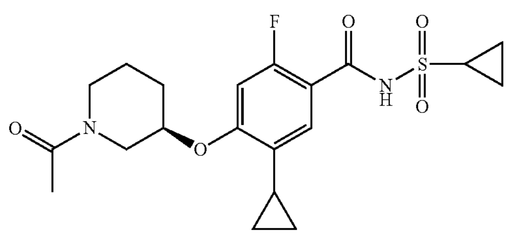 [SMILES: CC(=O)N1CCC[C@@H](Oc2cc(F)c(C(=O)NS(=O)(=O)C3CC3)cc2C2CC2)C1] | 6.5995 | | |
| 5 | 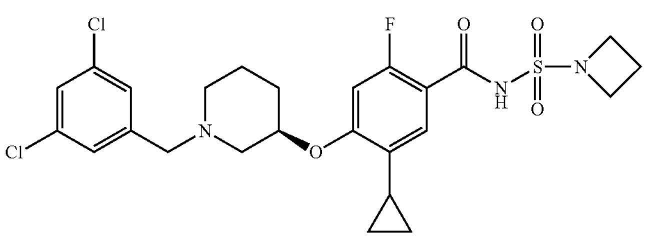 [SMILES: O=C(NS(=O)(=O)N1CCC1)c1cc(C2CC2)c(O[C@@H]2CCCN(Cc3cc(Cl)cc(Cl)c3)C2)cc1F] | 0.0071 | | |
| 6 | 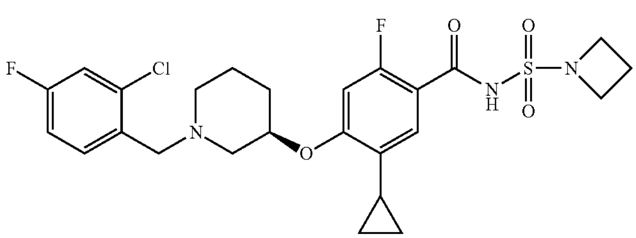 [SMILES: O=C(NS(=O)(=O)N1CCC1)c1cc(C2CC2)c(O[C@@H]2CCCN(Cc3ccc(F)cc3Cl)C2)cc1F] | 0.0030 | 0.0009 | 0.0331 |

TABLE 1-continued

| Example | Structure | Ligand Binding Assay (µM) | NaV1.7 EP (µM) | NaV1.5 EP (µM) |
|---|---|---|---|---|
| 7 | 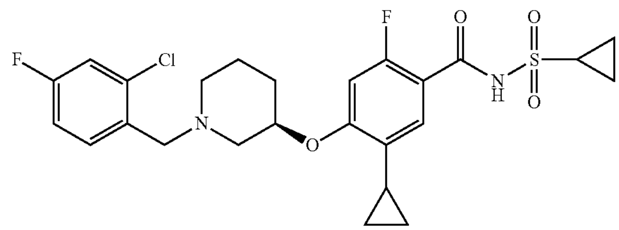 [SMILES: O=C(NS(=O)(=O)C1CC1)c1cc(C2CC2)c(O[C@@H]2CCCN(Cc3ccc(F)cc3Cl)C2)cc1F] | 0.0035 | | |
| 8 | 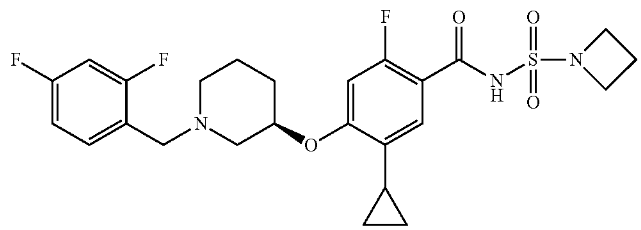 [SMILES: O=C(NS(=O)(=O)N1CCC1)c1cc(C2CC2)c(O[C@@H]2CCCN(Cc3ccc(F)cc3F)C2)cc1F] | 0.0081 | | |
| 9 | 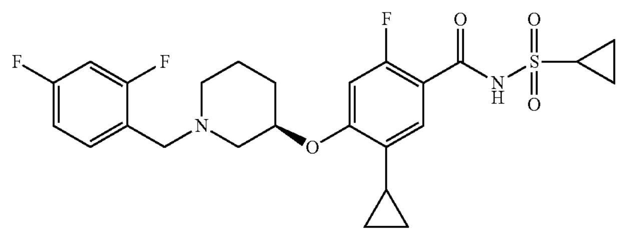 [SMILES: O=C(NS(=O)(=O)C1CC1)c1cc(C2CC2)c(O[C@@H]2CCCN(Cc3ccc(F)cc3F)C2)cc1F] | 0.0035 | | |
| 10 | 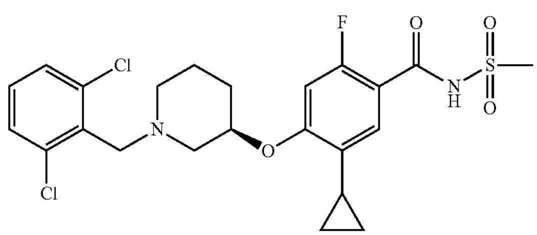 [SMILES: CS(=O)(=O)NC(=O)c1cc(C2CC2)c(O[C@@H]2CCCN(Cc3c(Cl)cccc3Cl)C2)cc1F] | 0.0041 | | |
| 11 | 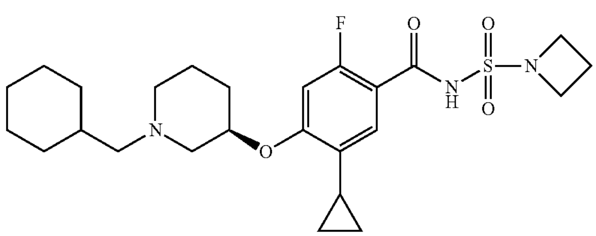 [SMILES: O=C(NS(=O)(=O)N1CCC1)c1cc(C2CC2)c(O[C@@H]2CCCN(CC3CCCCC3)C2)cc1F] | 0.0474 | | |
| 12 | 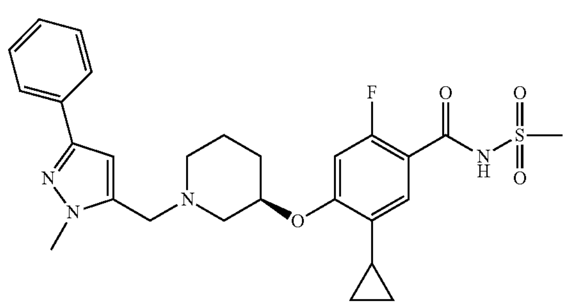 [SMILES: Cn1nc(-c2ccccc2)cc1CN1CCC[C@@H](Oc2cc(F)c(C(=O)NS(C)(=O)=O)cc2C2CC2)C1] | 0.0113 | | |

TABLE 1-continued
| Example | Structure | Ligand Binding Assay (μM) | NaV1.7 EP (μM) | NaV1.5 EP (μM) |
|---|---|---|---|---|
| 13 | 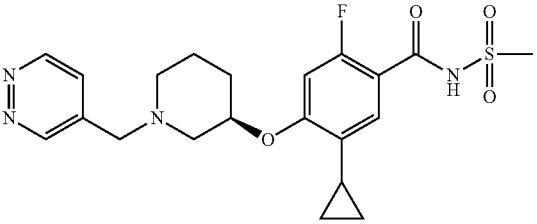 [SMILES: CS(=O)(=O)NC(=O)c1cc(C2CC2)c(O[C@@H]2CCCN(Cc3ccnnc3)C2)cc1F] | 1.4894 | | |
| 14 | 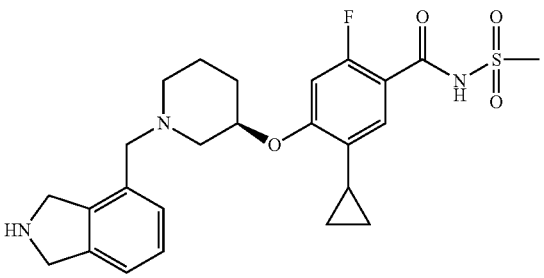 [SMILES: CS(=O)(=O)NC(=O)c1cc(C2CC2)c(O[C@@H]2CCCN(Cc3cccc4c3CNC4)C2)cc1F] | 0.3181 | | |
| 15 | 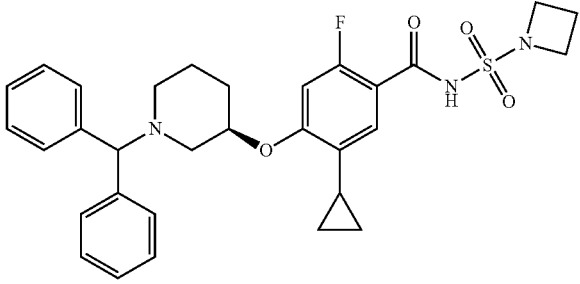 [SMILES: O=C(NS(=O)(=O)N1CCC1)c1cc(C2CC2)c(O[C@@H]2CCCN(C(c3ccccc3)c3ccccc3)C2)cc1F] | 0.0048 | | |
| 16 | 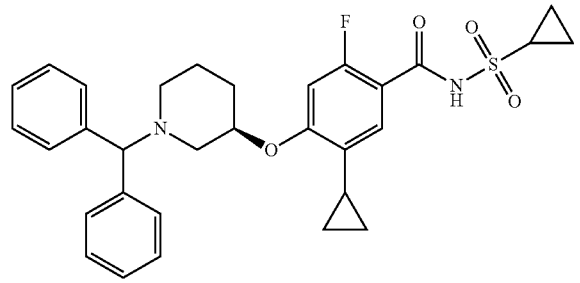 [SMILES: O=C(NS(=O)(=O)C1CC1)c1cc(C2CC2)c(O[C@@H]2CCCN(C(c3ccccc3)c3ccccc3)C2)cc1F] | 0.0034 | | |
| 17 | 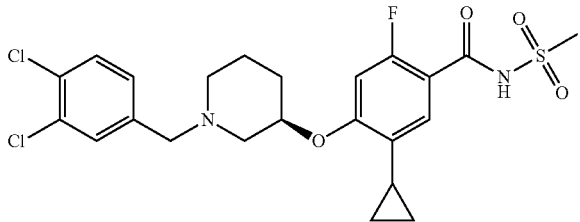 [SMILES: CS(=O)(=O)NC(=O)c1cc(C2CC2)c(O[C@@H]2CCCN(Cc3ccc(Cl)c(Cl)c3)C2)cc1F] | 0.0048 | | |

TABLE 1-continued

| Example | Structure | Ligand Binding Assay (μM) | NaV1.7 EP (μM) | NaV1.5 EP (μM) |
|---|---|---|---|---|
| 18 | 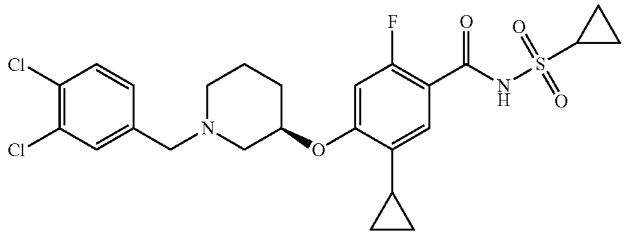 [SMILES: O=C(NS(=O)(=O)C1CC1)c1cc(C2CC2)c(O[C@@H]2CCCN(Cc3ccc(Cl)c(Cl)c3)C2)cc1F] | 0.0026 | | |
| 19 | 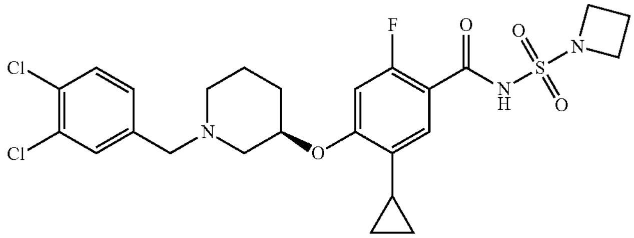 [SMILES: O=C(NS(=O)(=O)N1CCC1)c1cc(C2CC2)c(O[C@@H]2CCCN(Cc3ccc(Cl)c(Cl)c3)C2)cc1F] | 0.0049 | | |
| 20 | 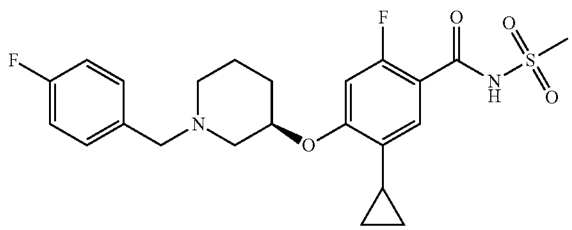 [SMILES: CS(=O)(=O)NC(=O)c1cc(C2CC2)c(O[C@@H]2CCCN(Cc3ccc(F)cc3)C2)cc1F] | 0.0309 | | |
| 21 | 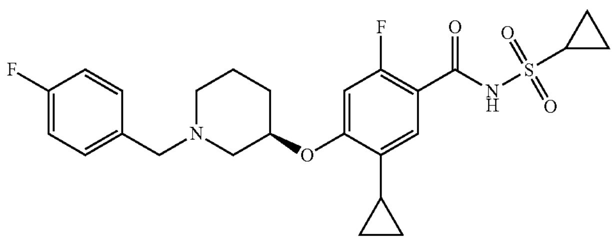 [SMILES: O=C(NS(=O)(=O)C1CC1)c1cc(C2CC2)c(O[C@@H]2CCCN(Cc3ccc(F)cc3)C2)cc1F] | 0.0112 | | |
| 22 | 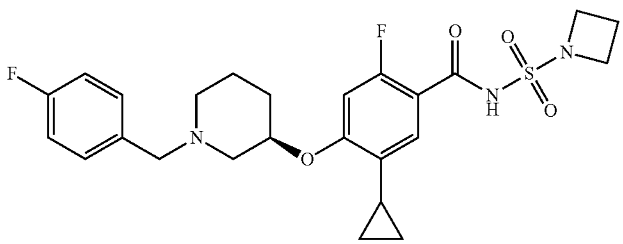 [SMILES: O=C(NS(=O)(=O)N1CCC1)c1cc(C2CC2)c(O[C@@H]2CCCN(Cc3ccc(F)cc3)C2)cc1F] | 0.0182 | | |
| 23 | 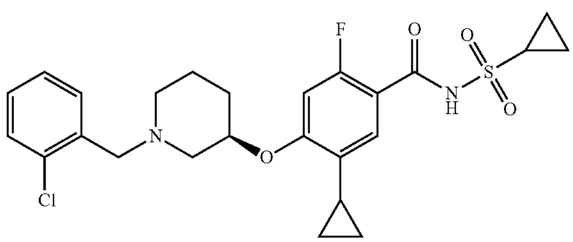 [SMILES: O=C(NS(=O)(=O)C1CC1)c1cc(C2CC2)c(O[C@@H]2CCCN(Cc3ccccc3Cl)C2)cc1F] | 0.0017 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 24 | 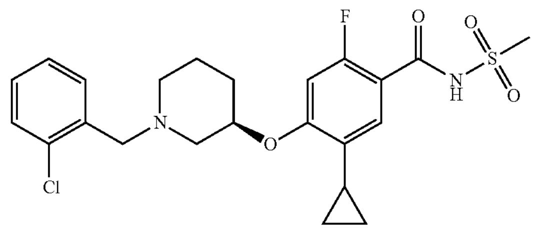 [SMILES: CS(=O)(=O)NC(=O)c1cc(C2CC2)c(O[C@@H]2CCCN(Cc3ccccc3Cl)C2)cc1F] | 0.0060 | | |
| 25 | 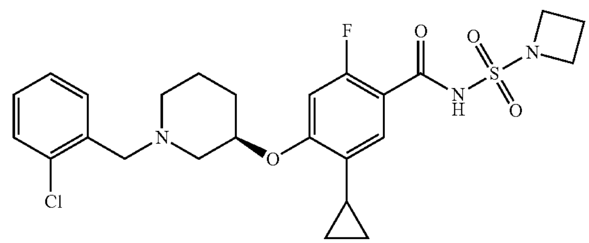 [SMILES: O=C(NS(=O)(=O)N1CCC1)c1cc(C2CC2)c(O[C@@H]2CCCN(Cc3ccccc3Cl)C2)cc1F] | 0.0032 | | |
| 26 | 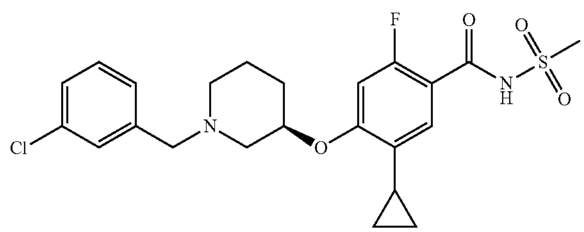 [SMILES: CS(=O)(=O)NC(=O)c1cc(C2CC2)c(O[C@@H]2CCCN(Cc3cccc(Cl)c3)C2)cc1F] | 0.0061 | | |
| 27 | 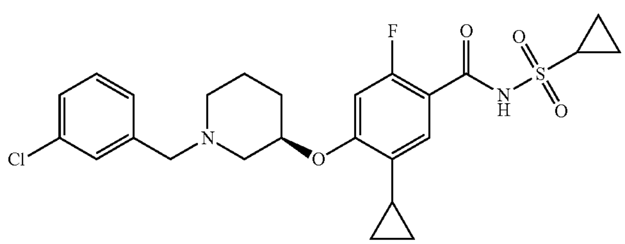 [SMILES: O=C(NS(=O)(=O)C1CC1)c1cc(C2CC2)c(O[C@@H]2CCCN(Cc3cccc(Cl)c3)C2)cc1F] | 0.0036 | | 0.1689 |
| 28 | 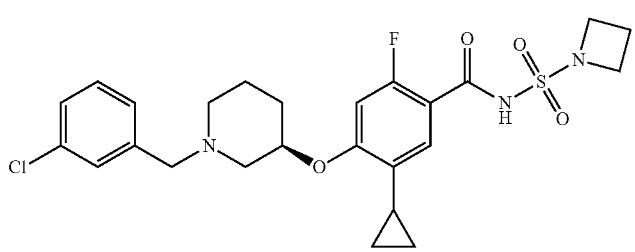 [SMILES: O=C(NS(=O)(=O)N1CCC1)c1cc(C2CC2)c(O[C@@H]2CCCN(Cc3cccc(Cl)c3)C2)cc1F] | 0.0074 | | |
| 29 | 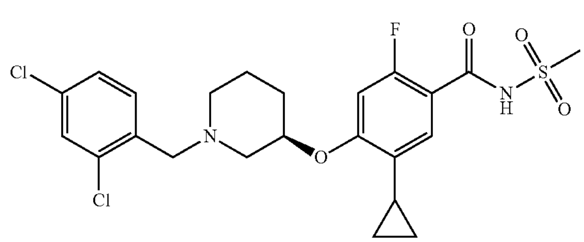 [SMILES: CS(=O)(=O)NC(=O)c1cc(C2CC2)c(O[C@@H]2CCCN(Cc3ccc(Cl)cc3Cl)C2)cc1F] | 0.0017 | | |

TABLE 1-continued

| Example | Structure | Ligand Binding Assay (μM) | NaV1.7 EP (μM) | NaV1.5 EP (μM) |
|---|---|---|---|---|
| 30 | 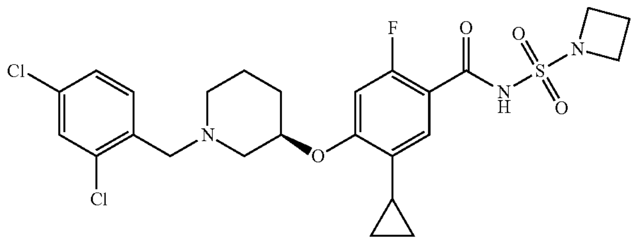 [SMILES: O=C(NS(=O)(=O)N1CCC1)c1cc(C2CC2)c(O[C@@H]2CCCN(Cc3ccc(Cl)cc3Cl)C2)cc1F] | 0.0027 | | |
| 31 | 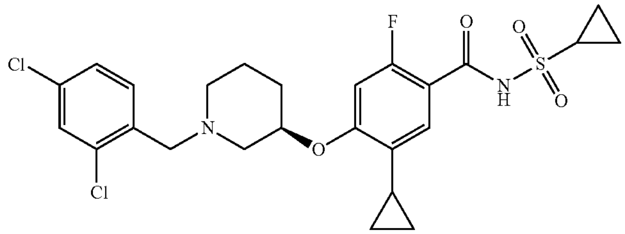 [SMILES: O=C(NS(=O)(=O)C1CC1)c1cc(C2CC2)c(O[C@@H]2CCCN(Cc3ccc(Cl)cc3Cl)C2)cc1F] | 0.0026 | | |
| 32 | 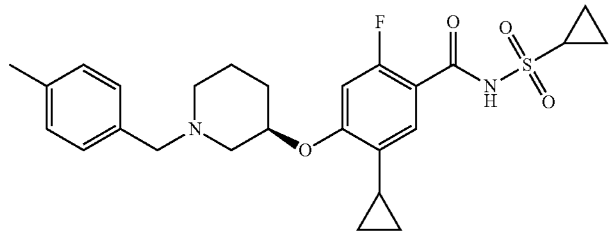 [SMILES: Cc1ccc(CN2CCC[C@@H](Oc3cc(F)c(C(=O)NS(=O)(=O)C4CC4)cc3C3CC3)C2)cc1] | 0.0054 | | |
| 33 | 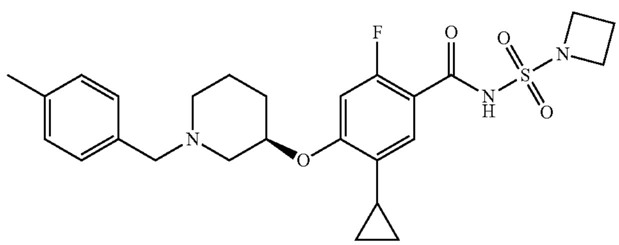 [SMILES: Cc1ccc(CN2CCC[C@@H](Oc3cc(F)c(C(=O)NS(=O)(=O)N4CCC4)cc3C3CC3)C2)cc1] | 0.0132 | | |
| 34 | 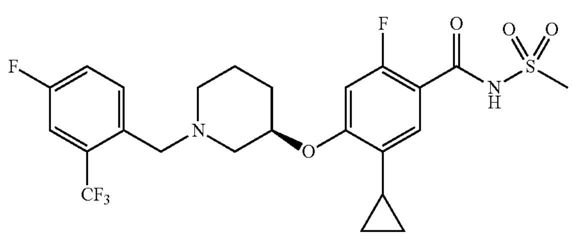 [SMILES: CS(=O)(=O)NC(=O)c1cc(C2CC2)c(O[C@@H]2CCCN(Cc3ccc(F)cc3C(F)(F)F)C2)cc1F] | 0.0019 | | |
| 35 | 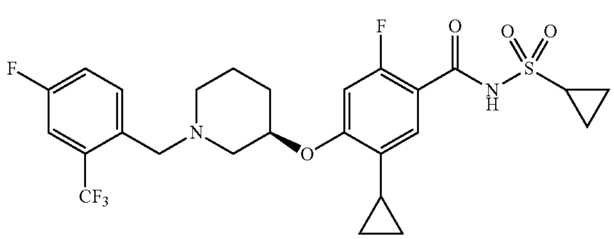 [SMILES: O=C(NS(=O)(=O)C1CC1)c1cc(C2CC2)c(O[C@@H]2CCCN(Cc3ccc(F)cc3C(F)(F)F)C2)cc1F] | 0.0024 | | |

TABLE 1-continued

| Example | Structure | Ligand Binding Assay (μM) | NaV1.7 EP (μM) | NaV1.5 EP (μM) |
|---|---|---|---|---|
| 36 | 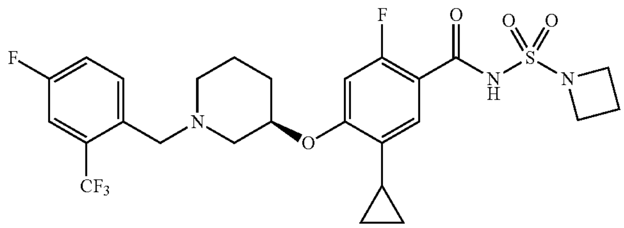 [SMILES: O=C(NS(=O)(=O)N1CCC1)c1cc(C2CC2)c(O[C@@H]2CCCN(Cc3ccc(F)cc3C(F)(F)F)C2)cc1F] | 0.0036 | | |
| 37 | 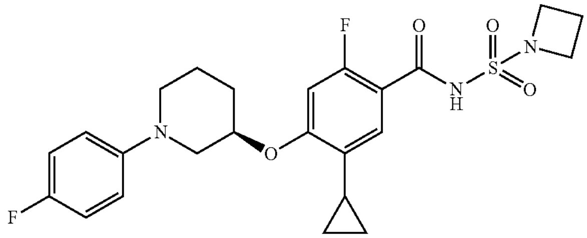 [SMILES: O=C(NS(=O)(=O)N1CCC1)c1cc(C2CC2)c(O[C@@H]2CCCN(c3ccc(F)cc3)C2)cc1F] | 0.0151 | | |
| 38 | 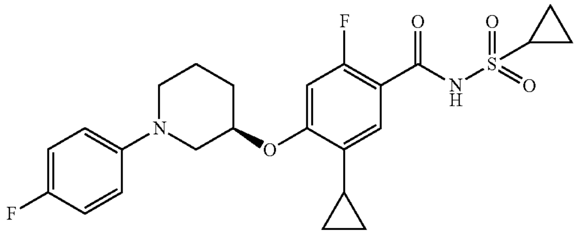 [SMILES: O=C(NS(=O)(=O)C1CC1)c1cc(C2CC2)c(O[C@@H]2CCCN(c3ccc(F)cc3)C2)cc1F] | 0.0039 | | |
| 39 | 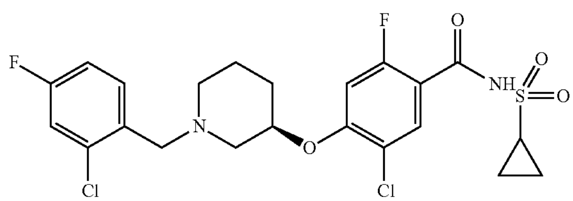 | 0.0068 | | |
| 40 | 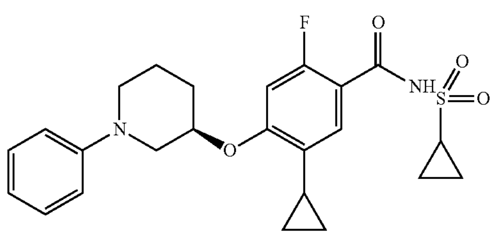 | 0.0084 | | |
| 41 | 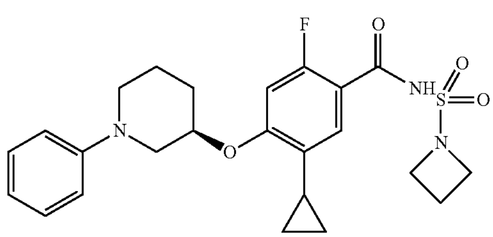 | 0.0134 | | |

TABLE 1-continued
| Example | Structure | Ligand Binding Assay (μM) | NaV1.7 EP (μM) | NaV1.5 EP (μM) |
|---|---|---|---|---|
| 42 | 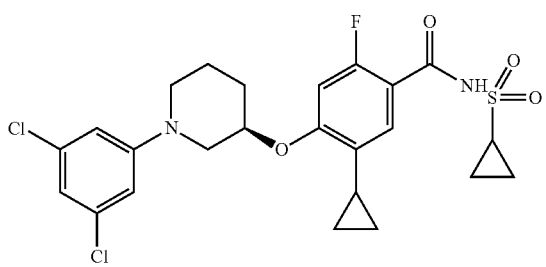 | 0.0021 | | |
| 43 | 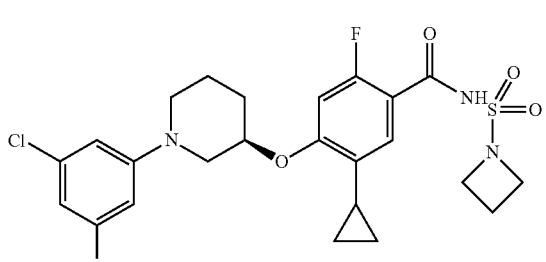 | 0.0049 | | |
| 44 | 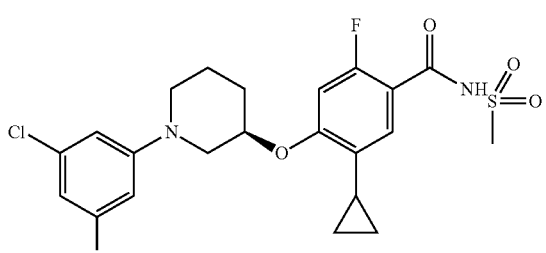 | 0.0036 | | |
| 45 | 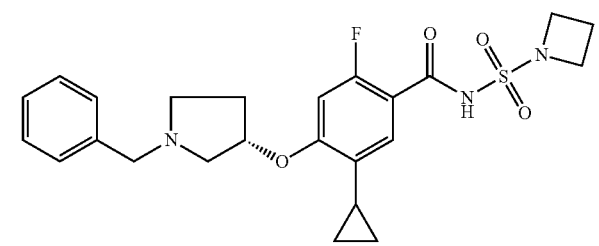 [SMILES: O=C(NS(=O)(=O)N1CCC1)c1cc(C2CC2)c(O[C@H]2CCN(Cc3ccccc3)C2)cc1F] | 4.5841 | | |
| 46 | 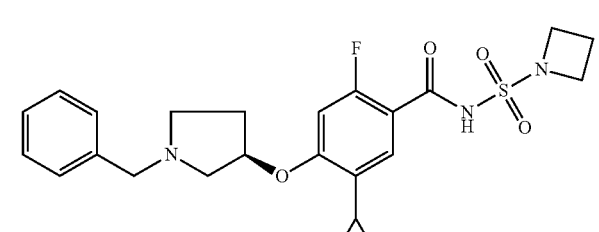 | 0.9205 | | |

TABLE 1-continued

| Example | Structure | Ligand Binding Assay (μM) | NaV1.7 EP (μM) | NaV1.5 EP (μM) |
|---|---|---|---|---|
| 47 | 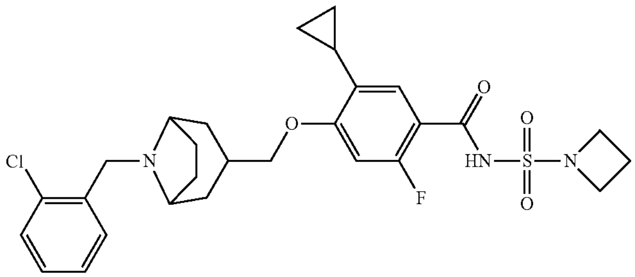 [SMILES: O=C(NS(=O)(=O)N1CCC1)c1cc(C2CC2)c(OCC2CC3CCC(C2)N3Cc2ccccc2Cl)cc1F] | 0.0251 | | |
| 48 | 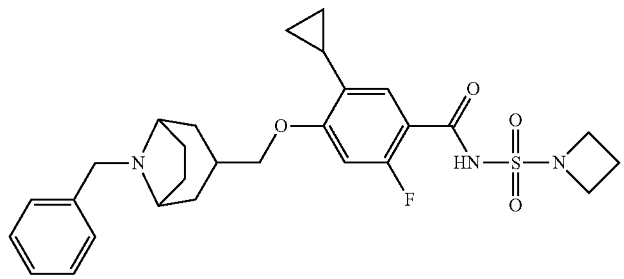 [SMILES: O=C(NS(=O)(=O)N1CCC1)c1cc(C2CC2)c(OCC2CC3CCC(C2)N3Cc2ccccc2)cc1F] | 2.8179 | | |
| 49 | 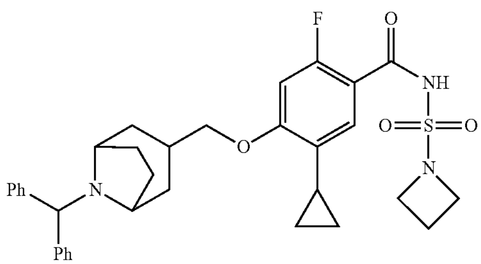 [SMILES: O=C(NS(=O)(=O)N1CCC1)c1cc(C2CC2)c(OCC2CC3CCC(C2)N3C(c2ccccc2)c2ccccc2)cc1F] | 0.0043 | 0.0054 | 0.199 |
| 50 | 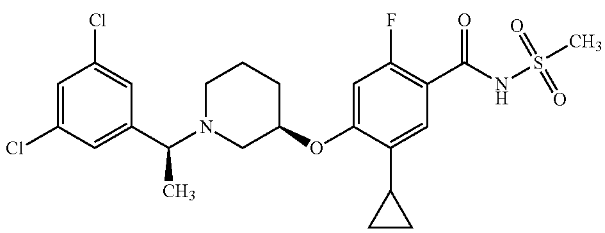 [SMILES: C[C@@H](c1cc(Cl)cc(Cl)c1)N1CCC[C@@H](Oc2cc(F)c(C(=O)NS(C)(=O)=O)cc2C2CC2)C1] | 0.0019 | | |
| 51 | 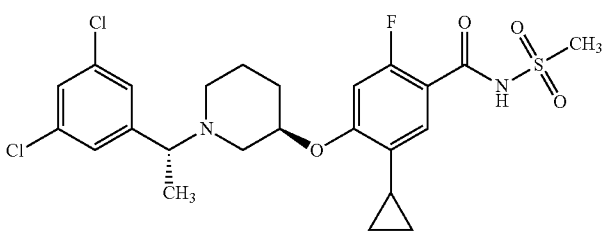 [SMILES: C[C@H](c1cc(Cl)cc(Cl)c1)N1CCC[C@@H](Oc2cc(F)c(C(=O)NS(C)(=O)=O)cc2C2CC2)C1] | 0.0021 | | |
| 52 | 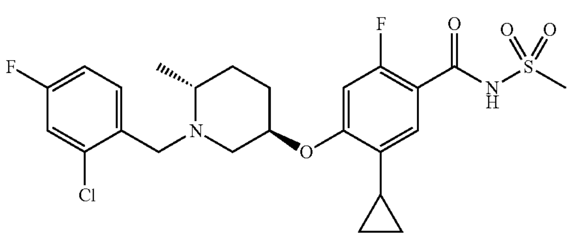 [SMILES: C[C@@H]1CC[C@@H](Oc2cc(F)c(C(=O)NS(C)(=O)=O)cc2C2CC2)CN1Cc1ccc(F)cc1Cl] | <0.0016 | | |

TABLE 1-continued

| Example | Structure | Ligand Binding Assay (μM) | NaV1.7 EP (μM) | NaV1.5 EP (μM) |
|---|---|---|---|---|
| 53 | 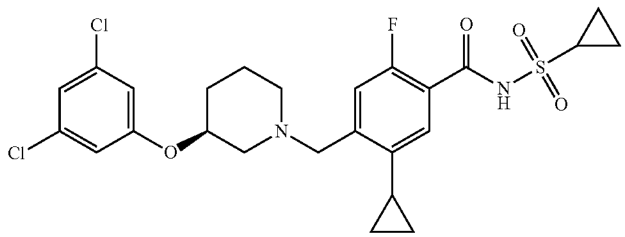 [SMILES: O=C(NS(=O)(=O)C1CC1)c1cc(C2CC2)c(CN2CCC[C@H](Oc3cc(Cl)cc(Cl)c3)C2)cc1F] | 0.0080 | | |
| 54 | 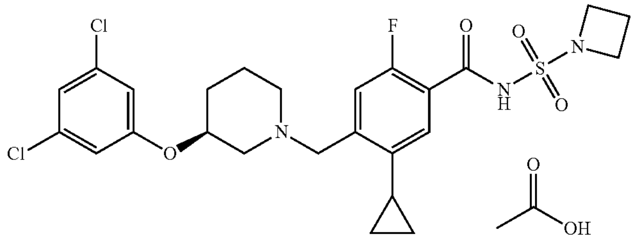 | 0.0220 | | |
| 55 | 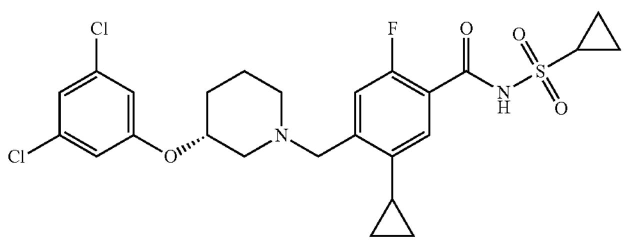 [SMILES: O=C(NS(=O)(=O)C1CC1)c1cc(C2CC2)c(CN2CCC[C@@H](Oc3cc(Cl)cc(Cl)c3)C2)cc1F] | 0.0233 | | |
| 56 | 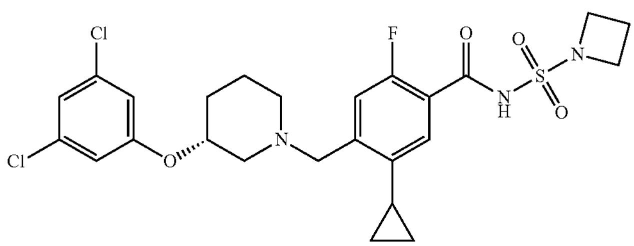 [SMILES: O=C(NS(=O)(=O)N1CCC1)c1cc(C2CC2)c(CN2CCC[C@@H](Oc3cc(Cl)cc(Cl)c3)C2)cc1F] | 0.0635 | | |
| 57 | 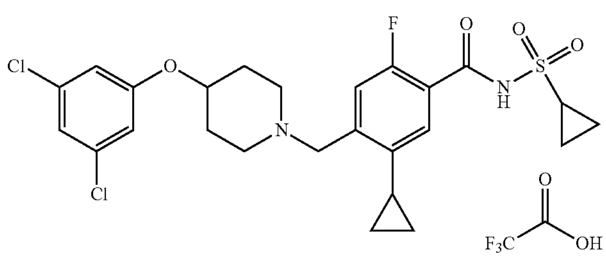 | 0.0038 | | |
| 58 | 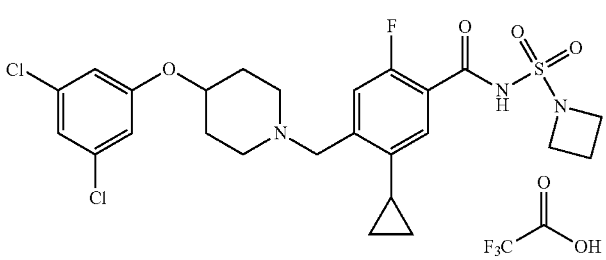 | | | |

TABLE 1-continued

| Example | Structure | Ligand Binding Assay (µM) | NaV1.7 EP (µM) | NaV1.5 EP (µM) |
|---|---|---|---|---|
| 59 | 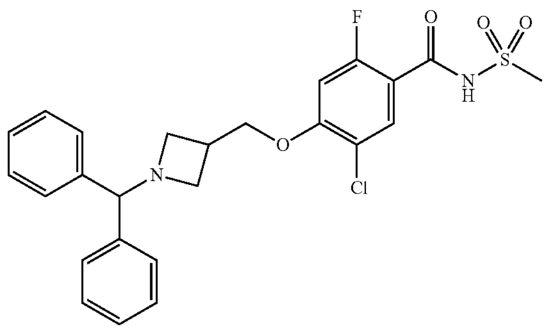 [SMILES: CS(=O)(=O)NC(=O)c1cc(Cl)c(OCC2CN(C(c3ccccc3)c3ccccc3)C2)cc1F] | 0.076 | | |
| 60 | 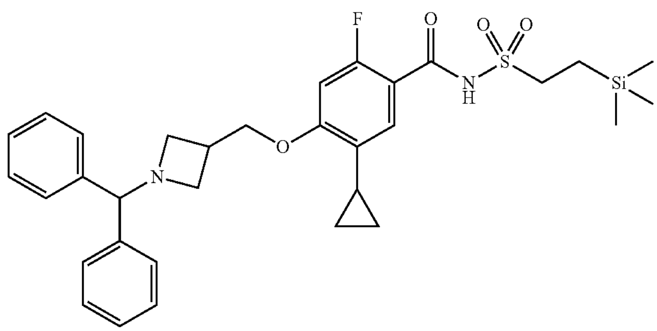 [SMILES: C[Si](C)(C)CCS(=O)(=O)NC(=O)c1cc(C2CC2)c(OCC2CN(C(c3ccccc3)c3ccccc3)C2)cc1F] | 1.6 | | |
| 61 | 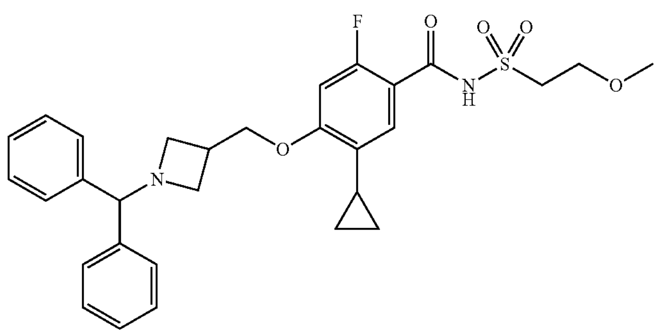 [SMILES: COCCS(=O)(=O)NC(=O)c1cc(C2CC2)c(OCC2CN(C(c3ccccc3)c3ccccc3)C2)cc1F] | 0.057 | | |
| 62 | 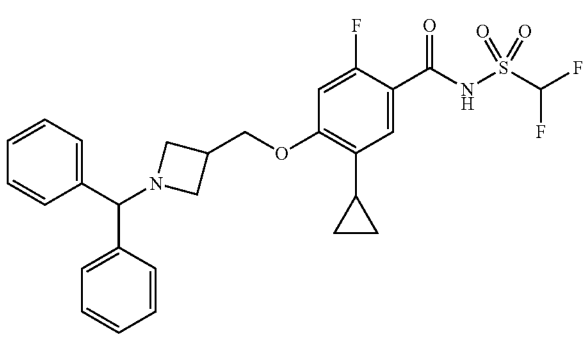 [SMILES: O=C(NS(=O)(=O)C(F)F)c1cc(C2CC2)c(OCC2CN(C(c3ccccc3)c3ccccc3)C2)cc1F] | 0.047 | | |

TABLE 1-continued

| Example | Structure | Ligand Binding Assay (μM) | NaV1.7 EP (μM) | NaV1.5 EP (μM) |
|---|---|---|---|---|
| 63 | 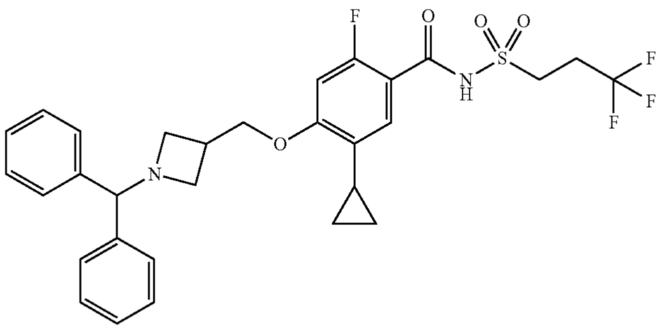 [SMILES: O=C(NS(=O)(=O)CCC(F)(F)F)c1cc(C2CC2)c(OCC2CN(C(c3ccccc3)c3ccccc3)C2)cc1F] | 0.046 | | |
| 64 | 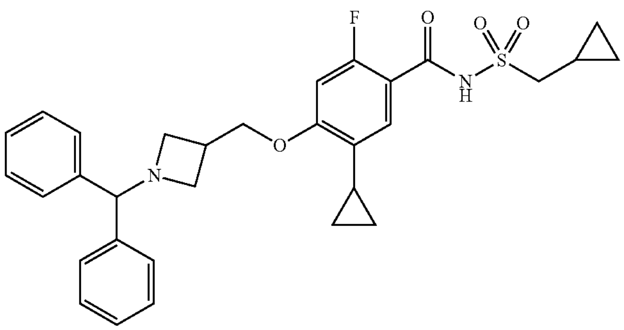 [SMILES: O=C(NS(=O)(=O)CC1CC1)c1cc(C2CC2)c(OCC2CN(C(c3ccccc3)c3ccccc3)C2)cc1F] | 0.0047 | | |
| 65 | 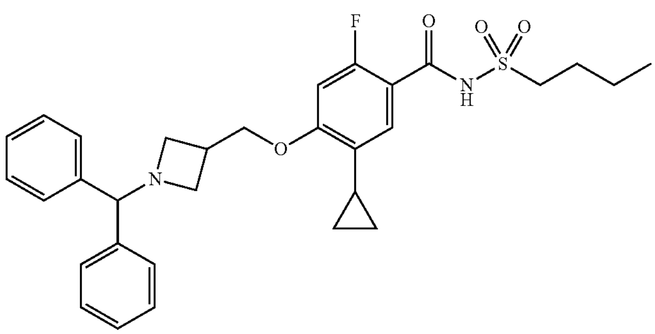 [SMILES: CCCCS(=O)(=O)NC(=O)c1cc(C2CC2)c(OCC2CN(C(c3ccccc3)c3ccccc3)C2)cc1F] | 0.034 | | |
| 66 | 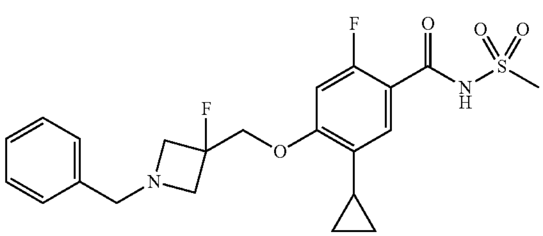 [SMILES: CS(=O)(=O)NC(=O)c1cc(C2CC2)c(OCC2(F)CN(Cc3ccccc3)C2)cc1F] | 0.091 | | |
| 67 | 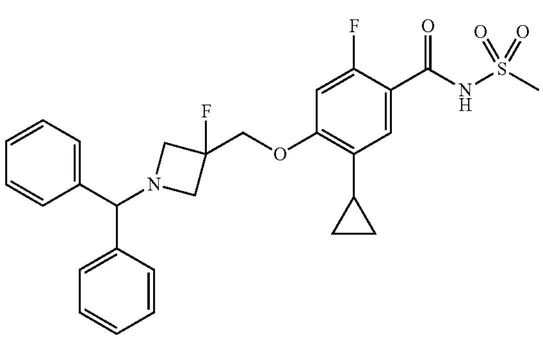 [SMILES: CS(=O)(=O)NC(=O)c1cc(C2CC2)c(OCC2(F)CN(C(c3ccccc3)c3ccccc3)C2)cc1F] | 0.0079 | | |

TABLE 1-continued
| Example | Structure | Ligand Binding Assay (μM) | NaV1.7 EP (μM) | NaV1.5 EP (μM) |
|---------|-----------|---------------------------|----------------|----------------|
| 68 | 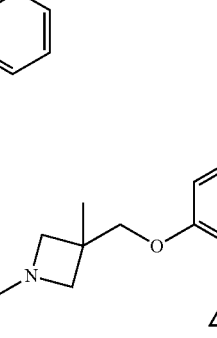 | 0.0064 | | |
| 69 | 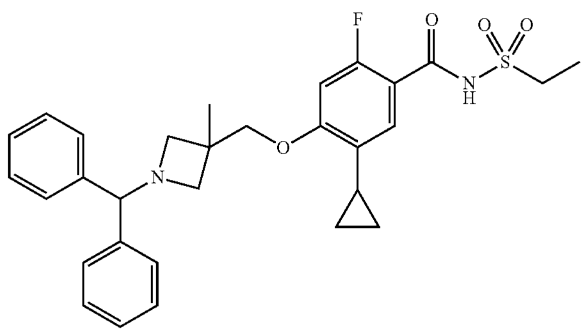 [SMILES: CCS(=O)(=O)NC(=O)c1cc(C2CC2)c(OCC2(C)CN(C(c3ccccc3)c3ccccc3)C2)cc1F] | 0.0061 | | |
| 70 | 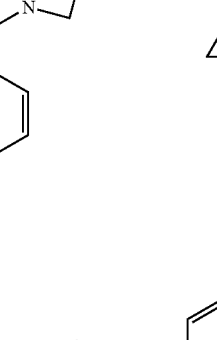 | 0.006 | | |
| 71 | 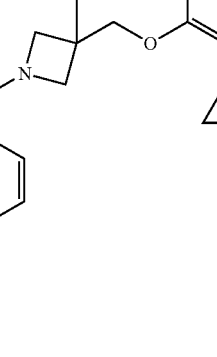 | 0.0031 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 72 | 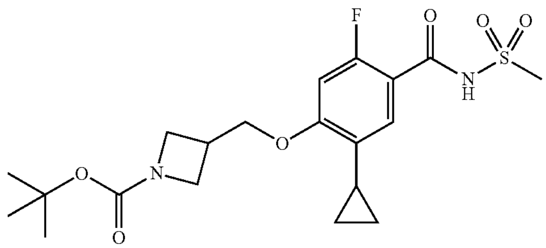 [SMILES: CC(C)(C)OC(=O)N1CC(COc2cc(F)c(C(=O)NS(C)(=O)=O)cc2C2CC2)C1] | 0.75 | | |
| 73 | 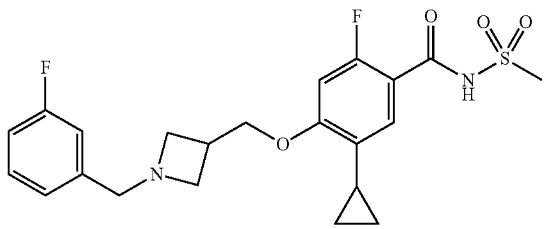 [SMILES: CS(=O)(=O)NC(=O)c1cc(C2CC2)c(OCC2CN(Cc3cccc(F)c3)C2)cc1F] | 1.3 | | |
| 74 | 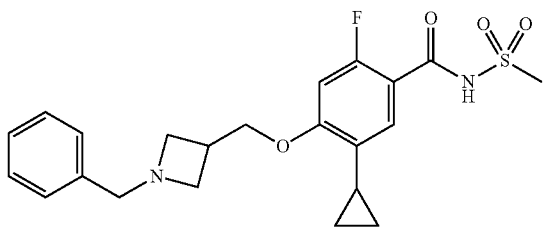 [SMILES: CS(=O)(=O)NC(=O)c1cc(C2CC2)c(OCC2CN(Cc3ccccc3)C2)cc1F] | 3.6 | | |
| 75 | 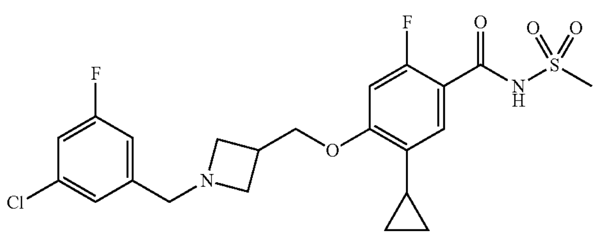 [SMILES: CS(=O)(=O)NC(=O)c1cc(C2CC2)c(OCC2CN(Cc3cc(F)cc(Cl)c3)C2)cc1F] | 0.074 | | |
| 76 | 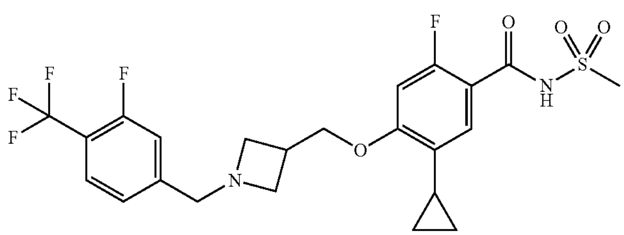 [SMILES: CS(=O)(=O)NC(=O)c1cc(C2CC2)c(OCC2CN(Cc3ccc(C(F)(F)F)c(F)c3)C2)cc1F] | 0.042 | | |
| 77 | 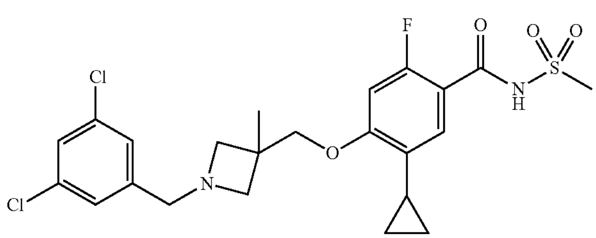 [SMILES: CC1(COc2cc(F)c(C(=O)NS(C)(=O)=O)cc2C2CC2)CN(Cc2cc(Cl)cc(Cl)c2)C1] | 0.0064 | | |

TABLE 1-continued

| Example | Structure | Ligand Binding Assay (μM) | NaV1.7 EP (μM) | NaV1.5 EP (μM) |
|---|---|---|---|---|
| 78 | 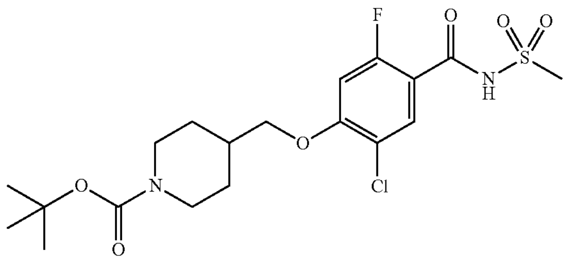 [SMILES: CC(C)(C)OC(=O)N1CCC(COc2cc(F)c(C(=O)NS(C)(=O)=O)cc2Cl)CC1] | 0.49 | | |
| 79 | 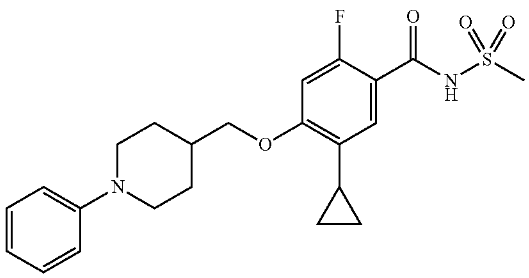 [SMILES: CS(=O)(=O)NC(=O)c1cc(C2CC2)c(OCC2CCN(c3ccccc3)CC2)cc1F] | 0.0099 | | |
| 80 | 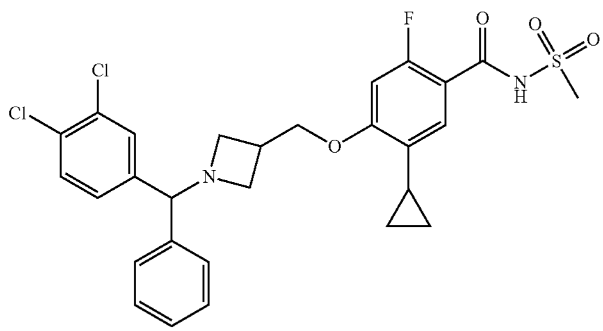 | 0.00405 | | |
| 81 | 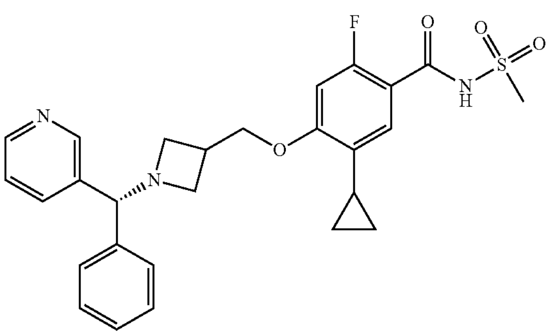 [SMILES: CS(=O)(=O)NC(=O)c1cc(C2CC2)c(OCC2CN([C@H](c3ccccc3)c3cccnc3)C2)cc1F] | 0.63 | | |
| 82 | 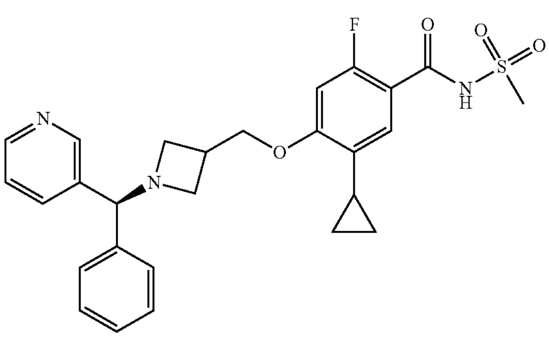 [SMILES: CS(=O)(=O)NC(=O)c1cc(C2CC2)c(OCC2CN([C@@H](c3ccccc3)c3cccnc3)C2)cc1F] | 0.408 | | |

TABLE 1-continued

| Example | Structure | Ligand Binding Assay (μM) | NaV1.7 EP (μM) | NaV1.5 EP (μM) |
|---|---|---|---|---|
| 83 | 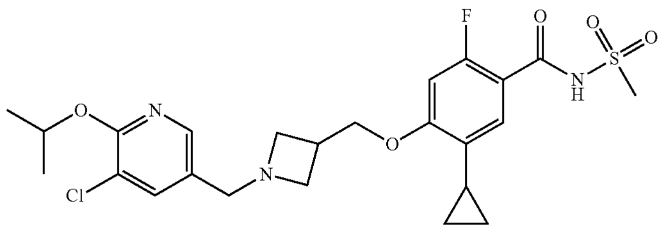 [SMILES: CC(C)Oc1ncc(CN2CC(COc3cc(F)c(C(=O)NS(C)(=O)=O)cc3C3CC3)C2)cc1Cl] | 0.059 | | |
| 84 | 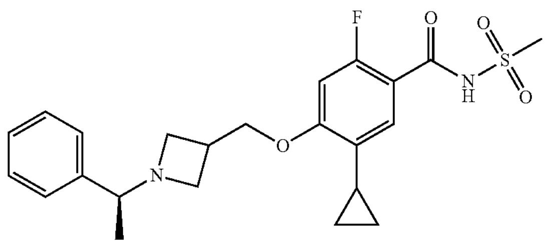 [SMILES: C[C@@H](c1ccccc1)N1CC(COc2cc(F)c(C(=O)NS(C)(=O)=O)cc2C2CC2)C1] | 1.24 | | |
| 85 | 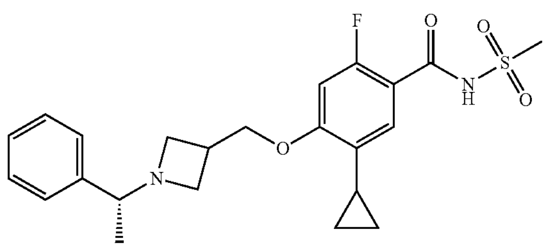 [SMILES: C[C@H](c1ccccc1)N1CC(COc2cc(F)c(C(=O)NS(C)(=O)=O)cc2C2CC2)C1] | 1.86 | | |
| 86 | 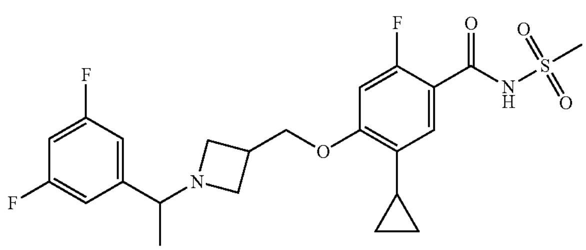 [SMILES: CC(c1cc(F)cc(F)c1)N1CC(COc2cc(F)c(C(=O)NS(C)(=O)=O)cc2C2CC2)C1] | 0.0495 | | |
| 87 | 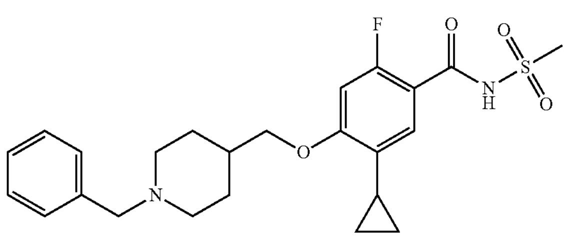 [SMILES: CS(=O)(=O)NC(=O)c1cc(C2CC2)c(OCC2CCN(Cc3ccccc3)CC2)cc1F] | 0.278 | | |
| 88 | 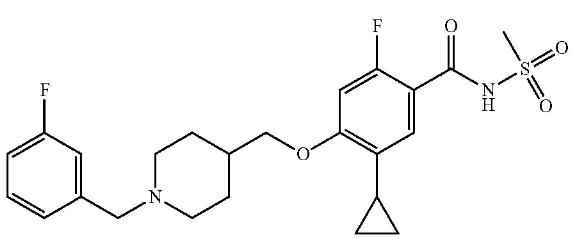 [SMILES: CS(=O)(=O)NC(=O)c1cc(C2CC2)c(OCC2CCN(Cc3cccc(F)c3)CC2)cc1F] | 0.0928 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 89 | 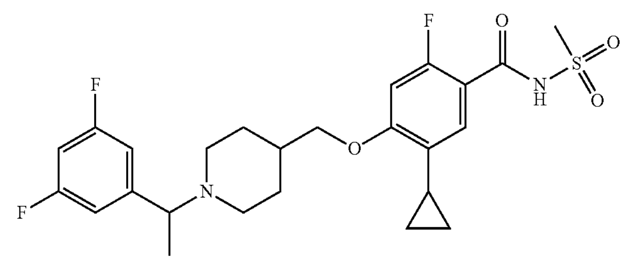 [SMILES: CC(c1cc(F)cc(F)c1)N1CCC(COc2cc(F)c(C(=O)NS(C)(=O)=O)cc2C2CC2)CC1] | 0.0223 | | |
| 90 | 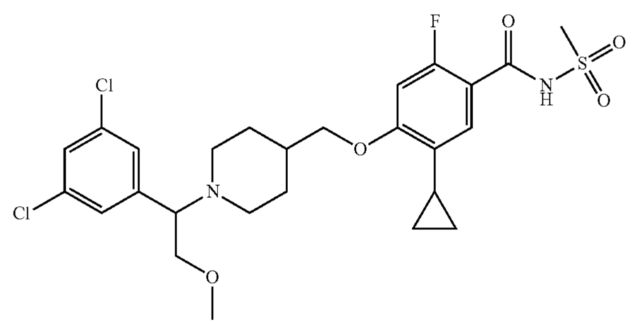 [SMILES: COCC(c1cc(Cl)cc(Cl)c1)N1CCC(COc2cc(F)c(C(=O)NS(C)(=O)=O)cc2C2CC2)CC1] | 0.00287 | | |
| 91 | 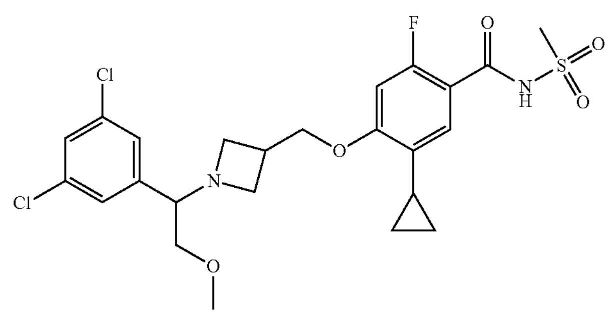 [SMILES: COCC(c1cc(Cl)cc(Cl)c1)N1CC(COc2cc(F)c(C(=O)NS(C)(=O)=O)cc2C2CC2)C1] | 0.0147 | | |
| 92 | 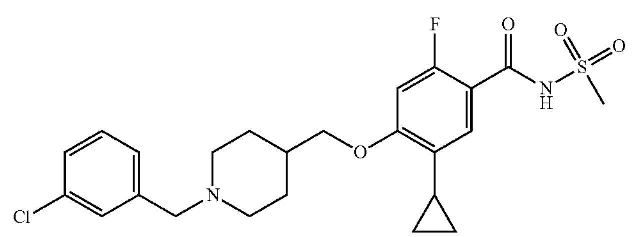 [SMILES: CS(=O)(=O)NC(=O)c1cc(C2CC2)c(OCC2CCN(Cc3cccc(Cl)c3)CC2)cc1F] | 0.0305 | | |
| 93 | 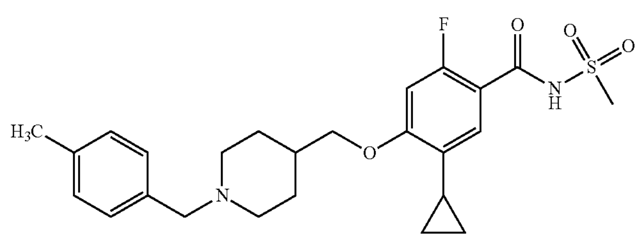 [SMILES: Cc1ccc(CN2CCC(COc3cc(F)c(C(=O)NS(C)(=O)=O)cc3C3CC3)CC2)cc1] | 0.173 | | |

TABLE 1-continued

| Example | Structure | Ligand Binding Assay (μM) | NaV1.7 EP (μM) | NaV1.5 EP (μM) |
|---|---|---|---|---|
| 94 | 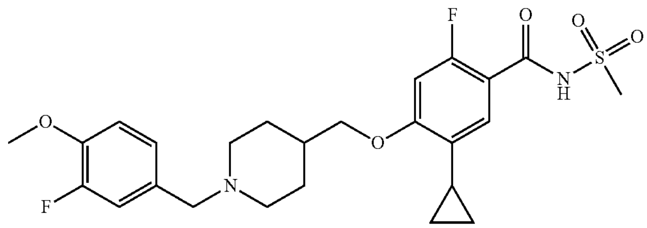 [SMILES: COc1ccc(CN2CCC(COc3cc(F)c(C(=O)NS(C)(=O)=O)cc3C3CC3)CC2)cc1F] | 0.15 | | |
| 95 | 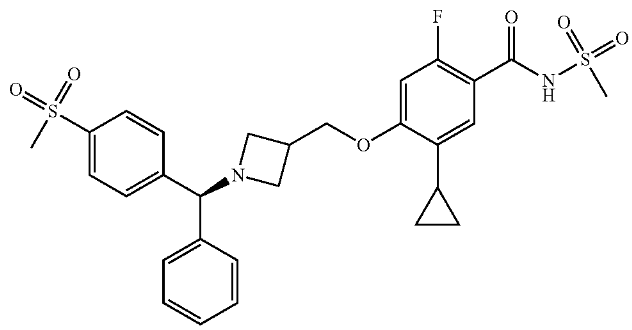 [SMILES: CS(=O)(=O)NC(=O)c1cc(C2CC2)c(OCC2CN([C@@H](c3ccccc3)c3ccc(S(C)(=O)=O)cc3)C2)cc1F] | 1.06 | | |
| 96 | 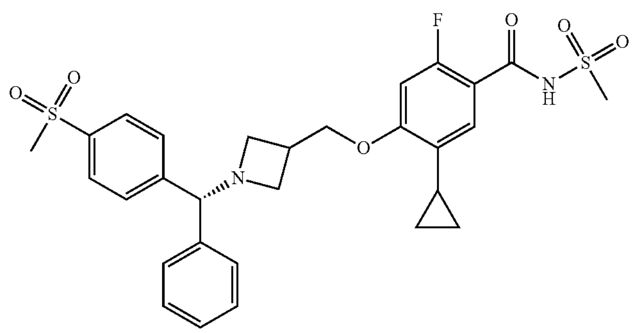 [SMILES: CS(=O)(=O)NC(=O)c1cc(C2CC2)c(OCC2CN([C@H](c3ccccc3)c3ccc(S(C)(=O)=O)cc3)C2)cc1F] | 0.429 | | |
| 97 | 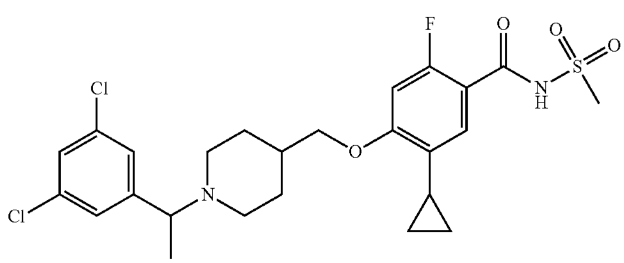 | 0.00269 | | |
| 98 | 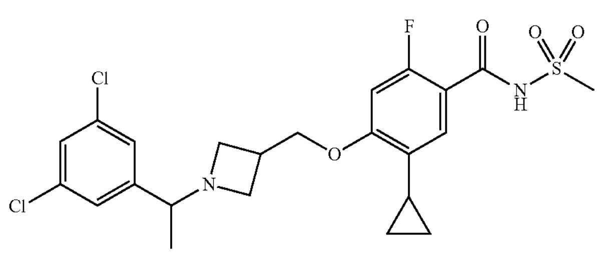 [SMILES: CC(c1cc(Cl)cc(Cl)c1)N1CC(COc2cc(F)c(C(=O)NS(C)(=O)=O)cc2C2CC2)C1] | 0.00751 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 99 | 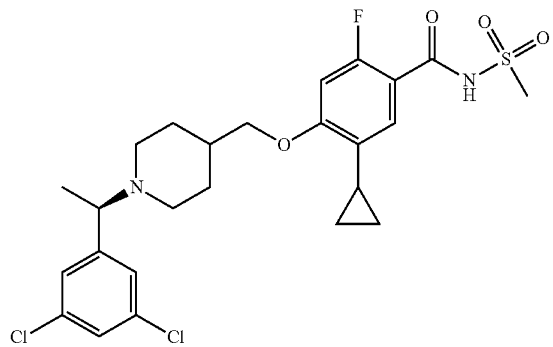 [SMILES: C[C@H](c1cc(Cl)cc(Cl)c1)N1CCC(COc2cc(F)c(C(=O)NS(C)(=O)=O)cc2C2CC2)CC1] | 0.00389 | | |
| 100 | 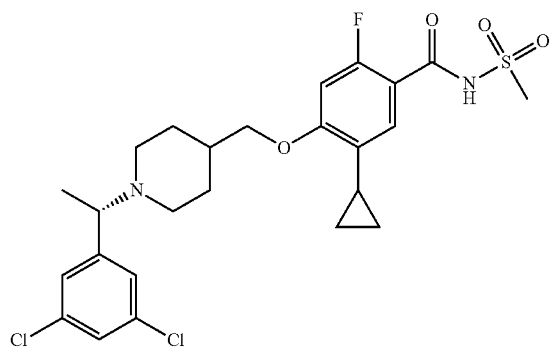 [SMILES: C[C@@H](c1cc(Cl)cc(Cl)c1)N1CCC(COc2cc(F)c(C(=O)NS(C)(=O)=O)cc2C2CC2)CC1] | 0.00419 | 0.0058 | 0.552 |
| 101 | 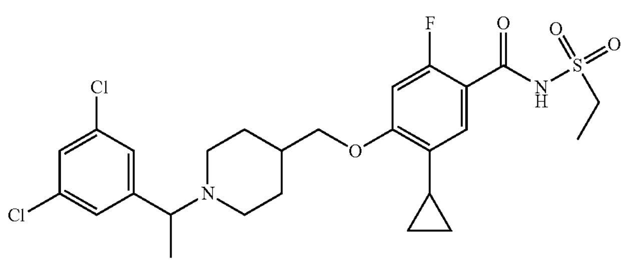 [SMILES: CCS(=O)(=O)NC(=O)c1cc(C2CC2)c(OCC2CCN(C(C)c3cc(Cl)cc(Cl)c3)CC2)cc1F] | 0.00376 | | |
| 102 | 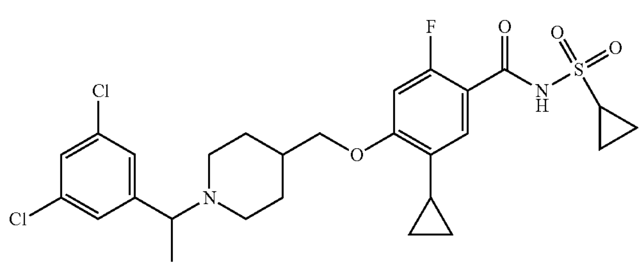 [SMILES: CC(c1cc(Cl)cc(Cl)c1)N1CCC(COc2cc(F)c(C(=O)NS(=O)(=O)C3CC3)cc2C2CC2)CC1] | 0.00254 | | |
| 103 | 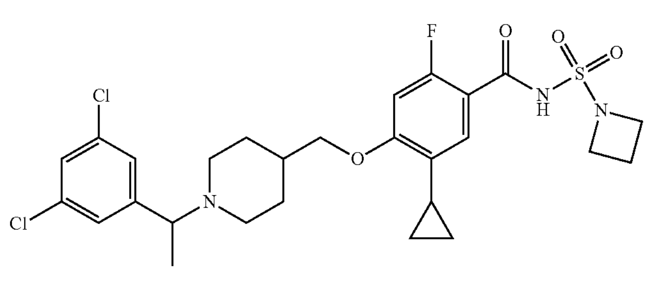 [SMILES: CC(c1cc(Cl)cc(Cl)c1)N1CCC(COc2cc(F)c(C(=O)NS(=O)(=O)N3CCC3)cc2C2CC2)CC1] | 0.00524 | | |

TABLE 1-continued
| Example | Structure | Ligand Binding Assay (μM) | NaV1.7 EP (μM) | NaV1.5 EP (μM) |
|---|---|---|---|---|
| 104 | 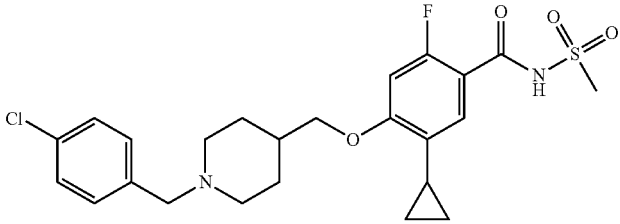 [SMILES: CS(=O)(=O)NC(=O)c1cc(C2CC2)c(OCC2CCN(Cc3ccc(Cl)cc3)CC2)cc1F] | 0.0451 | | |
| 105 | 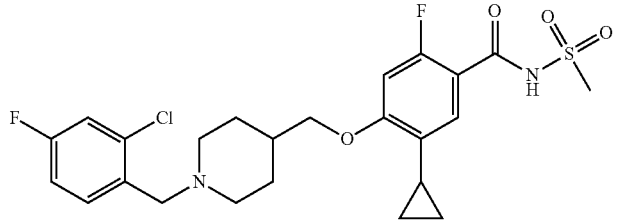 [SMILES: CS(=O)(=O)NC(=O)c1cc(C2CC2)c(OCC2CCN(Cc3ccc(F)cc3Cl)CC2)cc1F] | 0.0163 | | |
| 106 | 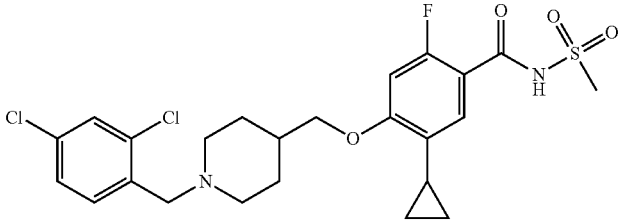 [SMILES: CS(=O)(=O)NC(=O)c1cc(C2CC2)c(OCC2CCN(Cc3ccc(Cl)cc3Cl)CC2)cc1F] | 0.0048 | | |
| 107 | 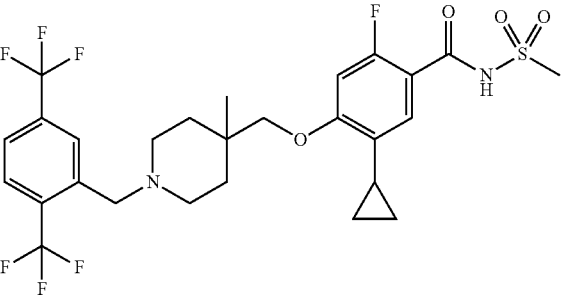 [SMILES: CC1(COc2cc(F)c(C(=O)NS(C)(=O)=O)cc2C2CC2)CCN(Cc2cc(C(F)(F)F)ccc2C(F)(F)F)CC1] | 0.0021 | | |
| 108 | 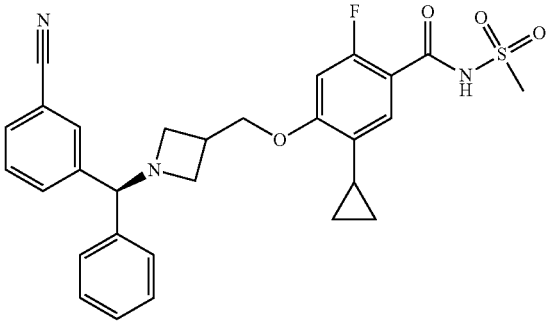 [SMILES: CS(=O)(=O)NC(=O)c1cc(C2CC2)c(OCC2CN([C@@H](c3ccccc3)c3cccc(C#N)c3)C2)cc1F] | 0.094 | | |

TABLE 1-continued

| Example | Structure | Ligand Binding Assay (μM) | NaV1.7 EP (μM) | NaV1.5 EP (μM) |
|---|---|---|---|---|
| 109 | 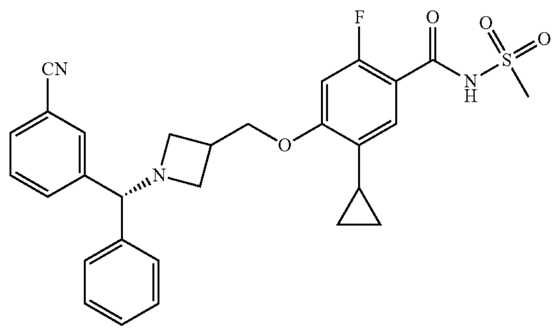 [SMILES: CS(=O)(=O)NC(=O)c1cc(C2CC2)c(OCC2CN([C@H](c3ccccc3)c3cccc(C#N)c3)C2)cc1F] | 0.0536 | | |
| 110 | 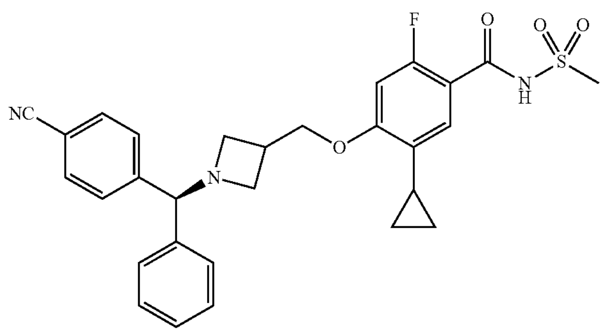 [SMILES: CS(=O)(=O)NC(=O)c1cc(C2CC2)c(OCC2CN([C@@H](c3ccccc3)c3ccc(C#N)cc3)C2)cc1F] | 0.0411 | | |
| 111 | 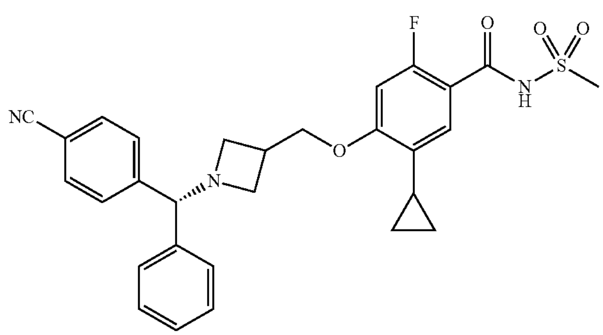 [SMILES: CS(=O)(=O)NC(=O)c1cc(C2CC2)c(OCC2CN([C@H](c3ccccc3)c3ccc(C#N)cc3)C2)cc1F] | 0.0204 | | |
| 112 | 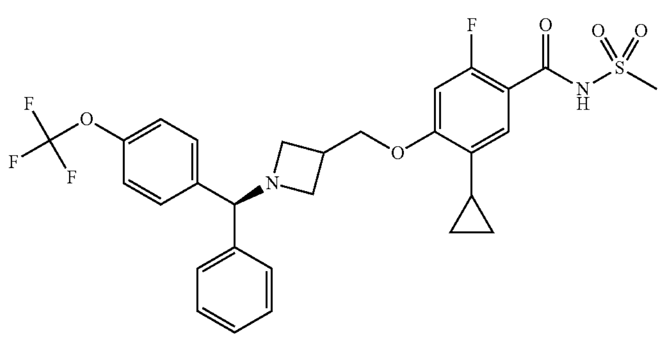 [SMILES: CS(=O)(=O)NC(=O)c1cc(C2CC2)c(OCC2CN([C@@H](c3ccccc3)c3ccc(OC(F)(F)F)cc3)C2)cc1F] | 0.00335 | | |

TABLE 1-continued

| Example | Structure | Ligand Binding Assay (μM) | NaV1.7 EP (μM) | NaV1.5 EP (μM) |
|---|---|---|---|---|
| 113 | 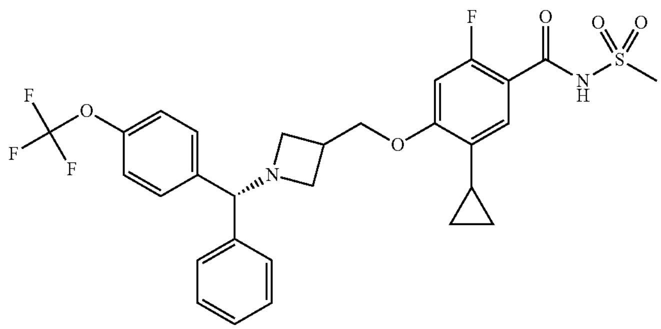 [SMILES: CS(=O)(=O)NC(=O)c1cc(C2CC2)c(OCC2CN([C@H](c3ccccc3)c3ccc(OC(F)(F)F)cc3)C2)cc1F] | 0.0111 | | |
| 114 | 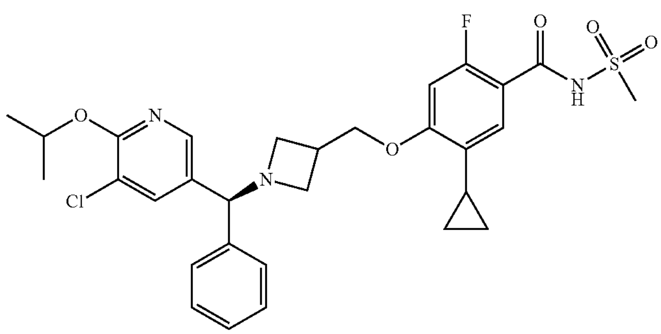 [SMILES: CC(C)Oc1ncc([C@H](c2ccccc2)N2CC(COc3cc(F)c(C(=O)NS(C)(=O)=O)cc3C3CC3)C2)cc1Cl] | 0.00727 | | |
| 115 | 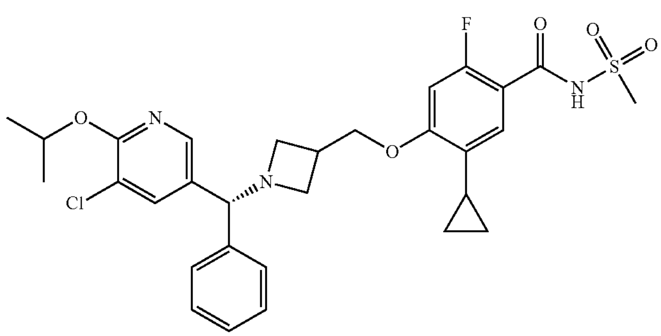 [SMILES: CC(C)Oc1ncc([C@@H](c2ccccc2)N2CC(COc3cc(F)c(C(=O)NS(C)(=O)=O)cc3C3CC3)C2)cc1Cl] | 0.0042 | | |
| 116 | 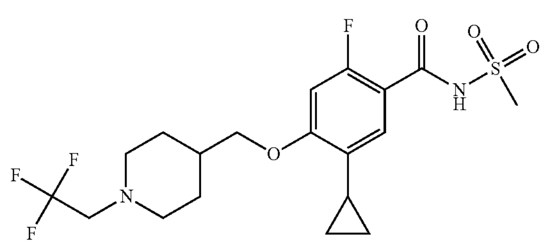 [SMILES: CS(=O)(=O)NC(=O)c1cc(C2CC2)c(OCC2CCN(CC(F)(F)F)CC2)cc1F] | 0.0775 | | |
| 117 | 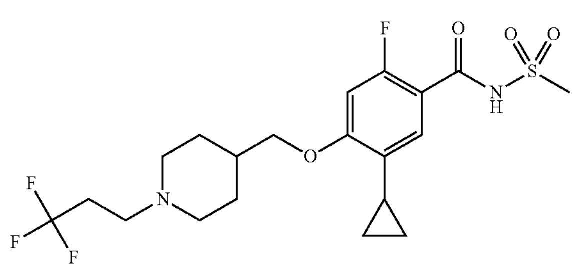 [SMILES: CS(=O)(=O)NC(=O)c1cc(C2CC2)c(OCC2CCN(CCC(F)(F)F)CC2)cc1F] | 0.411 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 118 | 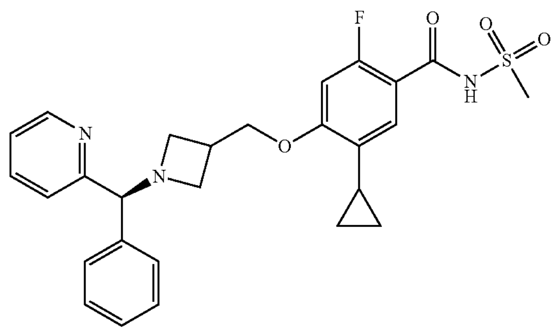 [SMILES: CS(=O)(=O)NC(=O)c1cc(C2CC2)c(OCC2CN([C@@H](c3ccccc3)c3ccccn3)C2)cc1F] | 0.417 | | |
| 119 | 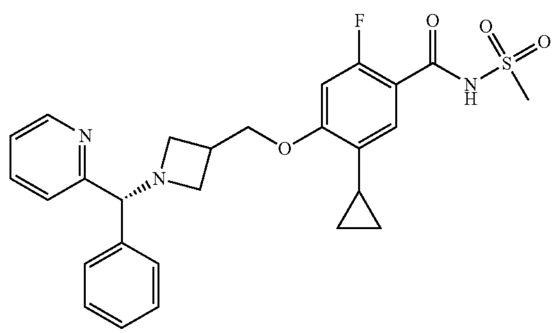 [SMILES: CS(=O)(=O)NC(=O)c1cc(C2CC2)c(OCC2CN([C@H](c3ccccc3)c3ccccn3)C2)cc1F] | 0.306 | | |
| 120 | 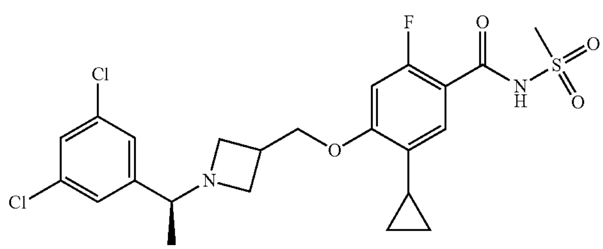 [SMILES: C[C@@H](c1cc(Cl)cc(Cl)c1)N1CC(COc2cc(F)c(C(=O)NS(C)(=O)=O)cc2C2CC2)C1] | 0.0206 | | |
| 121 | 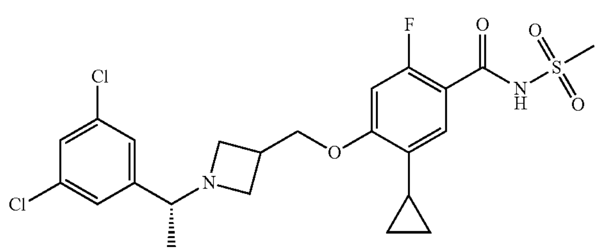 [SMILES: C[C@H](c1cc(Cl)cc(Cl)c1)N1CC(COc2cc(F)c(C(=O)NS(C)(=O)=O)cc2C2CC2)C1] | 0.0301 | | |
| 122 | 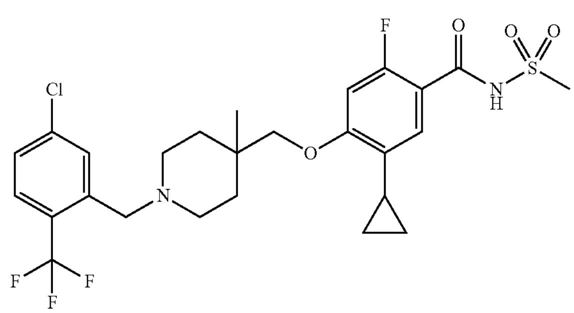 [SMILES: CC1(COc2cc(F)c(C(=O)NS(C)(=O)=O)cc2C2CC2)CCN(Cc2cc(Cl)ccc2C(F)(F)F)CC1] | 0.0024 | | |

TABLE 1-continued

| Example | Structure | Ligand Binding Assay (μM) | NaV1.7 EP (μM) | NaV1.5 EP (μM) |
| --- | --- | --- | --- | --- |
| 123 | 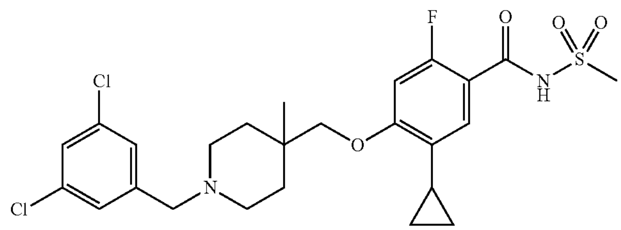 [SMILES: CC1(COc2cc(F)c(C(=O)NS(C)(=O)=O)cc2C2CC2)CCN(Cc2cc(Cl)cc(Cl)c2)CC1] | 0.0029 | | |
| 124 | 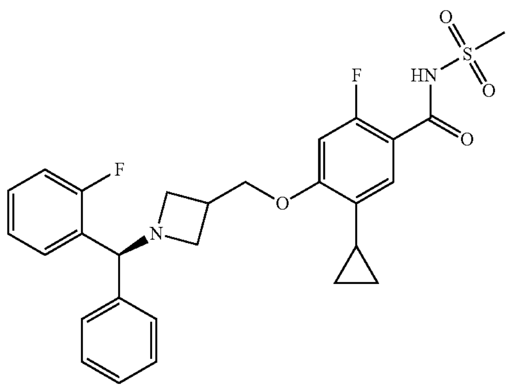 [SMILES: CS(=O)(=O)NC(=O)c1cc(C2CC2)c(OCC2CN([C@@H](c3ccccc3)c3ccccc3F)C2)cc1F] | 0.0713 | | |
| 125 | 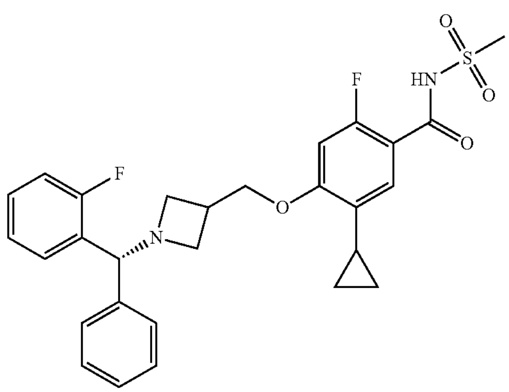 [SMILES: CS(=O)(=O)NC(=O)c1cc(C2CC2)c(OCC2CN([C@H](c3ccccc3)c3ccccc3F)C2)cc1F] | 0.025 | | |
| 126 | 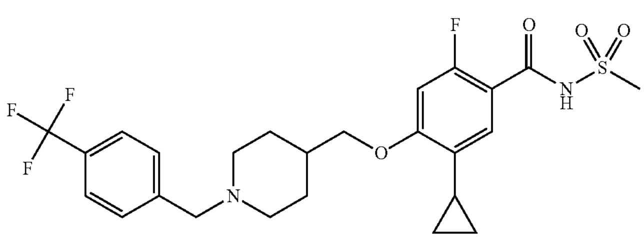 [SMILES: CS(=O)(=O)NC(=O)c1cc(C2CC2)c(OCC2CCN(Cc3ccc(C(F)(F)F)cc3)CC2)cc1F] | 0.282 | | |
| 127 | 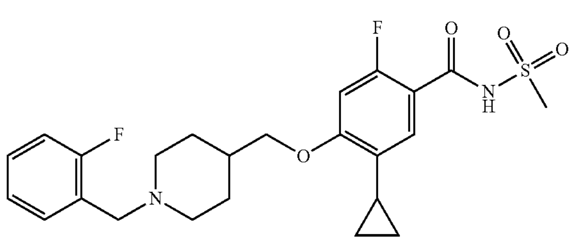 [SMILES: CS(=O)(=O)NC(=O)c1cc(C2CC2)c(OCC2CCN(Cc3ccccc3F)CC2)cc1F] | 0.578 | | |

TABLE 1-continued
| Example | Structure | Ligand Binding Assay (μM) | NaV1.7 EP (μM) | NaV1.5 EP (μM) |
|---|---|---|---|---|
| 128 | 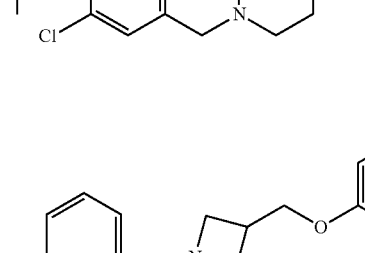 | 0.0056 | | |
| 129 | 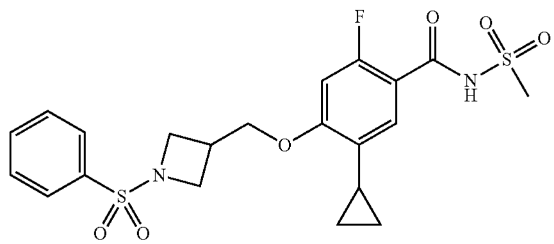 [SMILES: CS(=O)(=O)NC(=O)c1cc(C2CC2)c(OCC2CN(S(=O)(=O)c3ccccc3)C2)cc1F] | 1.37 | | |
| 130 | 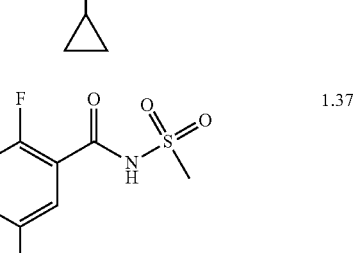 | 0.0035 | | |
| 131 | 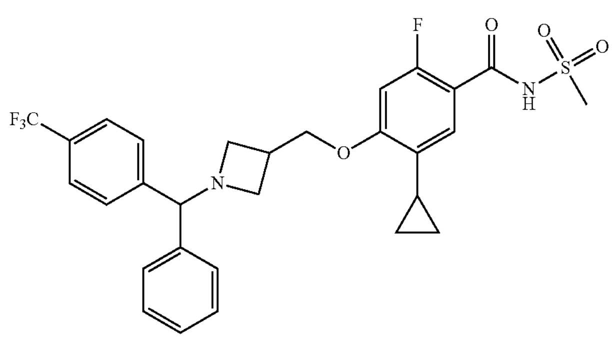 [SMILES: CS(=O)(=O)NC(=O)c1cc(C2CC2)c(OCC2CN(C(c3ccccc3)c3ccc(C(F)(F)F)cc3)C2)cc1F] | 0.00299 | | |
| 132 | 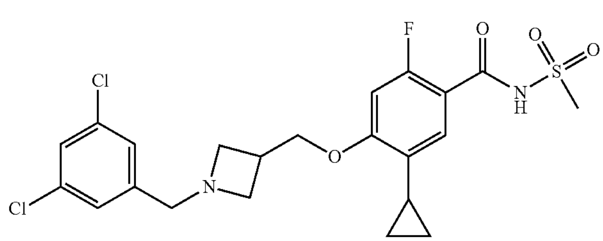 [SMILES: CS(=O)(=O)NC(=O)c1cc(C2CC2)c(OCC2CN(Cc3cc(Cl)cc(Cl)c3)C2)cc1F] | 0.014 | | |

TABLE 1-continued

| Example | Structure | Ligand Binding Assay (μM) | NaV1.7 EP (μM) | NaV1.5 EP (μM) |
|---|---|---|---|---|
| 133 | 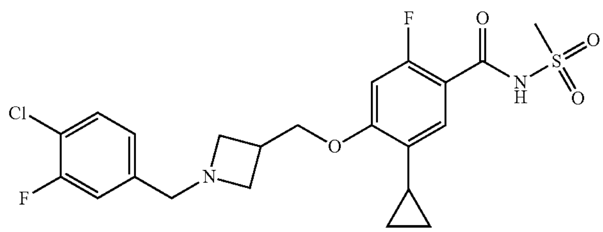 [SMILES: CS(=O)(=O)NC(=O)c1cc(C2CC2)c(OCC2CN(Cc3ccc(Cl)c(F)c3)C2)cc1F] | 0.118 | | |
| 134 | 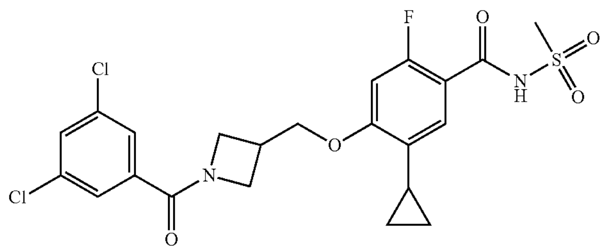 [SMILES: CS(=O)(=O)NC(=O)c1cc(C2CC2)c(OCC2CN(C(=O)c3cc(Cl)cc(Cl)c3)C2)cc1F] | 0.346 | | |
| 135 | 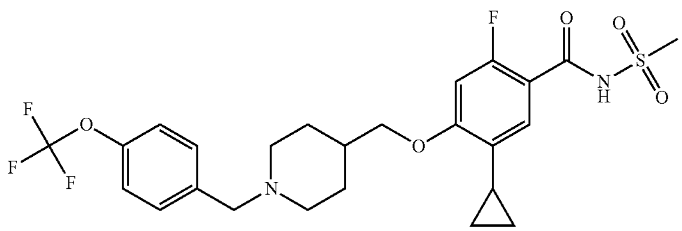 [SMILES: CS(=O)(=O)NC(=O)c1cc(C2CC2)c(OCC2CCN(Cc3ccc(OC(F)(F)F)cc3)CC2)cc1F] | 0.0155 | | |
| 136 | 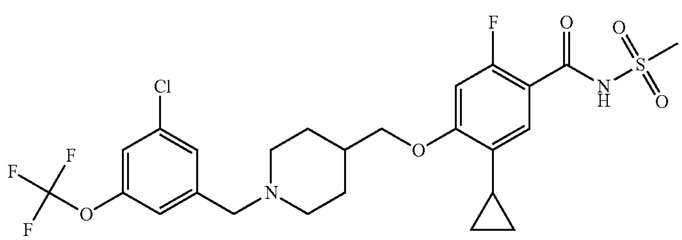 [SMILES: CS(=O)(=O)NC(=O)c1cc(C2CC2)c(OCC2CCN(Cc3cc(Cl)cc(OC(F)(F)F)c3)CC2)cc1F] | 0.00188 | | |
| 137 | 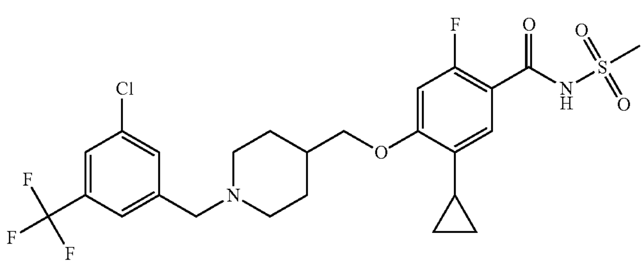 [SMILES: CS(=O)(=O)NC(=O)c1cc(C2CC2)c(OCC2CCN(Cc3cc(Cl)cc(C(F)(F)F)c3)CC2)cc1F] | 0.00205 | | |
| 138 | 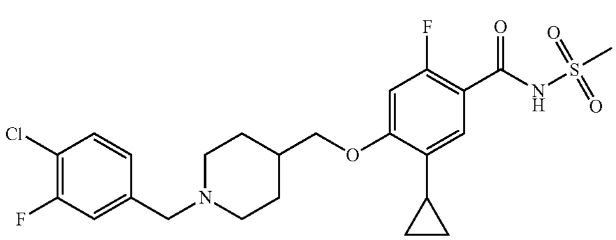 [SMILES: CS(=O)(=O)NC(=O)c1cc(C2CC2)c(OCC2CCN(Cc3ccc(Cl)c(F)c3)CC2)cc1F] | 0.0112 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 139 | 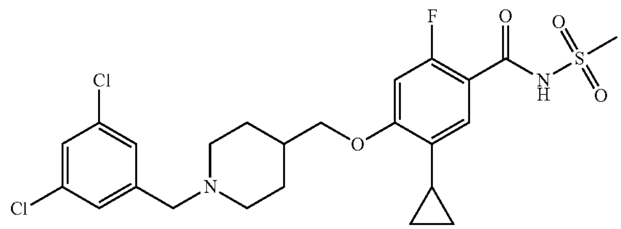 [SMILES: CS(=O)(=O)NC(=O)c1cc(C2CC2)c(OCC2CCN(Cc3cc(Cl)cc(Cl)c3)CC2)cc1F] | 0.0049 | | |
| 140 | 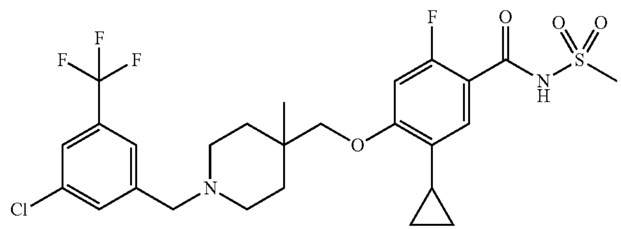 [SMILES: CC1(COc2cc(F)c(C(=O)NS(C)(=O)=O)cc2C2CC2)CCN(Cc2cc(Cl)cc(C(F)(F)F)c2)CC1] | 0.0035 | | |
| 141 | 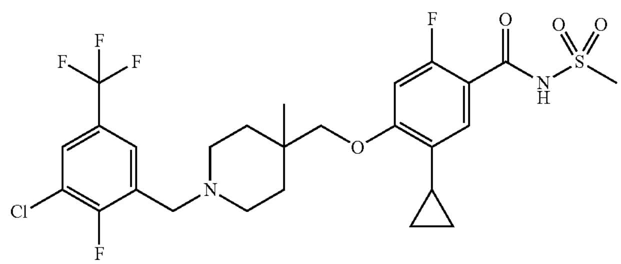 [SMILES: CC1(COc2cc(F)c(C(=O)NS(C)(=O)=O)cc2C2CC2)CCN(Cc2cc(C(F)(F)F)cc(Cl)c2F)CC1] | 0.0039 | | |
| 142 | 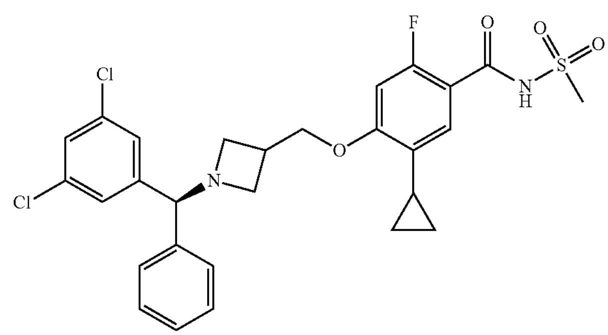 [SMILES: CS(=O)(=O)NC(=O)c1cc(C2CC2)c(OCC2CN([C@@H](c3ccccc3)c3cc(Cl)cc(Cl)c3)C2)cc1F] | 0.00657 | | |
| 143 | 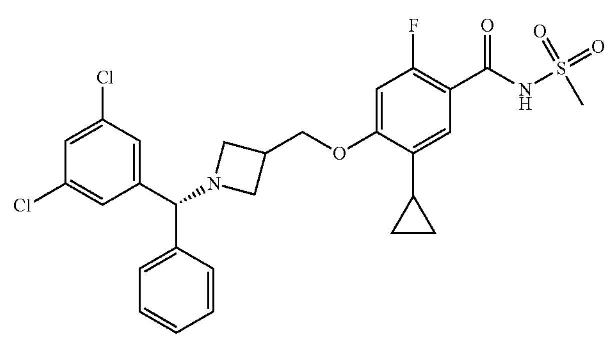 [SMILES: CS(=O)(=O)NC(=O)c1cc(C2CC2)c(OCC2CN([C@H](c3ccccc3)c3cc(Cl)cc(Cl)c3)C2)cc1F] | 0.0026 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 144 | 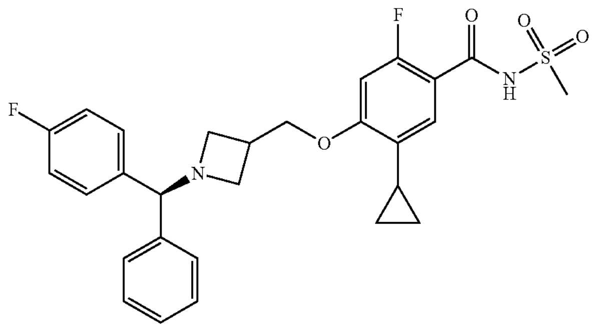 [SMILES: CS(=O)(=O)NC(=O)c1cc(C2CC2)c(OCC2CN([C@@H](c3ccccc3)c3ccc(F)cc3)C2)cc1F] | 0.00915 | | |
| 145 | 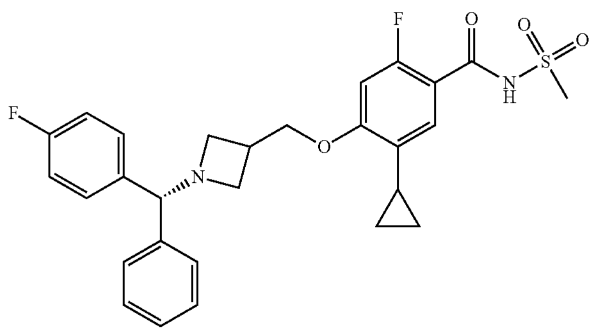 [SMILES: CS(=O)(=O)NC(=O)c1cc(C2CC2)c(OCC2CN([C@H](c3ccccc3)c3ccc(F)cc3)C2)cc1F] | 0.00622 | | |
| 146 | 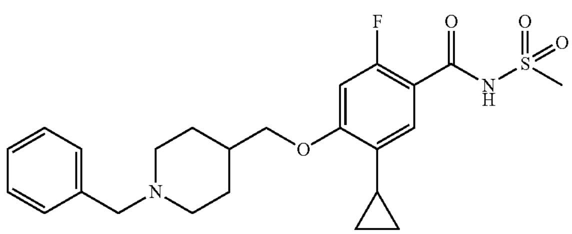 [SMILES: CS(=O)(=O)NC(=O)c1cc(C2CC2)c(OCC2CCN(Cc3ccccc3)CC2)cc1F] | 0.276 | | |
| 147 | 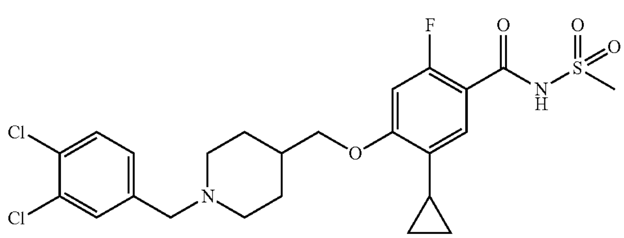 [SMILES: CS(=O)(=O)NC(=O)c1cc(C2CC2)c(OCC2CCN(Cc3ccc(Cl)c(Cl)c3)CC2)cc1F] | 0.00603 | | |
| 148 | 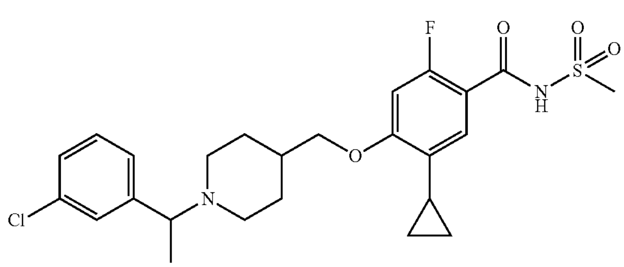 [SMILES: CC(c1cccc(Cl)c1)N1CCC(COc2cc(F)c(C(=O)NS(C)(=O)=O)cc2C2CC2)CC1] | 0.015 | | |

TABLE 1-continued
| Example | Structure | Ligand Binding Assay (µM) | NaV1.7 EP (µM) | NaV1.5 EP (µM) |
|---|---|---|---|---|
| 149 | 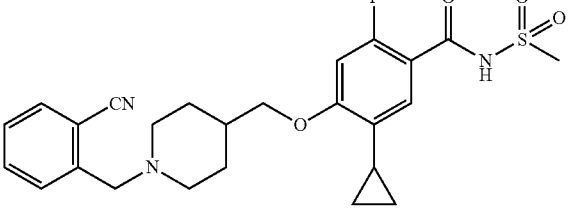 | 0.0737 | | |
| 150 | 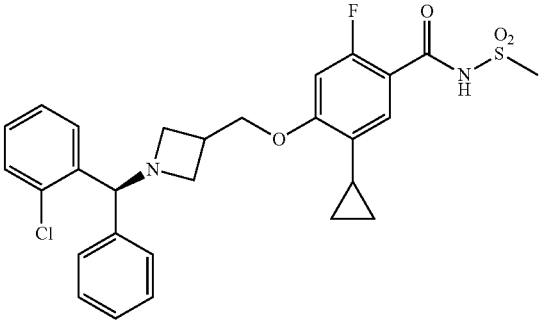 [SMILES: CS(=O)(=O)NC(=O)c1cc(C2CC2)c(OCC2CN([C@@H](c3ccccc3)c3ccccc3Cl)C2)cc1F] | 0.100 | | |
| 151 | 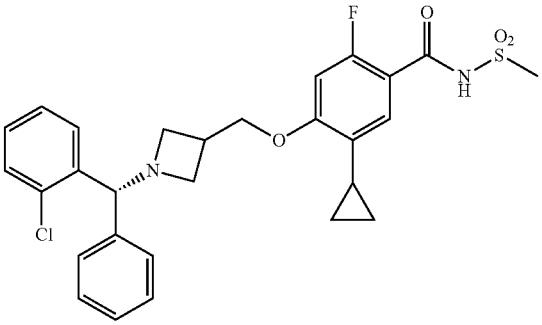 [SMILES: CS(=O)(=O)NC(=O)c1cc(C2CC2)c(OCC2CN([C@H](c3ccccc3)c3ccccc3Cl)C2)cc1F] | 0.00994 | | |
| 152 | 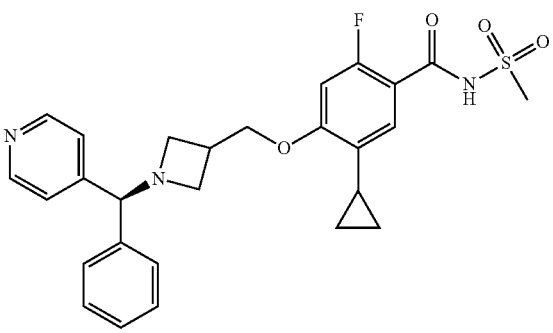 [SMILES: CS(=O)(=O)NC(=O)c1cc(C2CC2)c(OCC2CN([C@@H](c3ccccc3)c3ccncc3)C2)cc1F] | 0.443 | | |
| 153 | 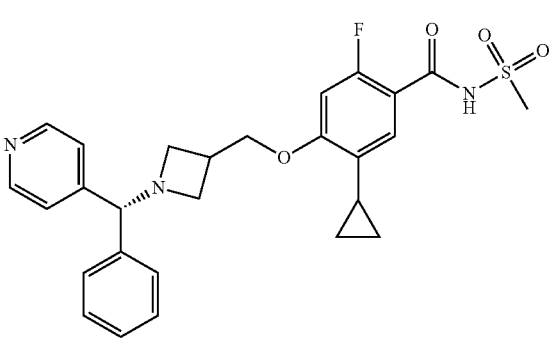 [SMILES: CS(=O)(=O)NC(=O)c1cc(C2CC2)c(OCC2CN([C@H](c3ccccc3)c3ccncc3)C2)cc1F] | 0.439 | | |

TABLE 1-continued

| Example | Structure | Ligand Binding Assay (μM) | NaV1.7 EP (μM) | NaV1.5 EP (μM) |
|---|---|---|---|---|
| 154 | 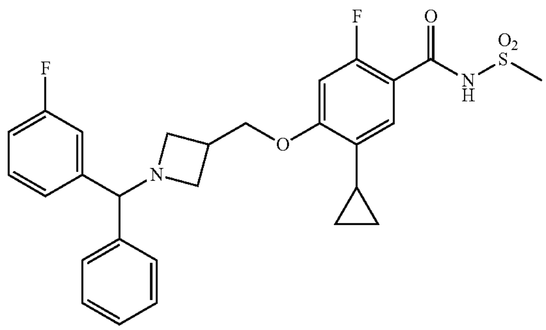 [SMILES: CS(=O)(=O)NC(=O)c1cc(C2CC2)c(OCC2CN(C(c3ccccc3)c3cccc(F)c3)C2)cc1F] | 0.00912 | | |
| 155 | 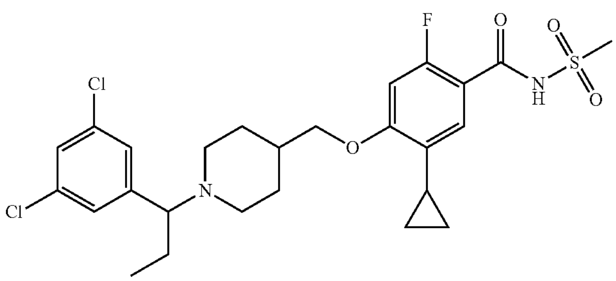 [SMILES: CCC(c1cc(Cl)cc(Cl)c1)N1CCC(COc2cc(F)c(C(=O)NS(C)(=O)=O)cc2C2CC2)CC1] | 0.00202 | | |
| 156 | 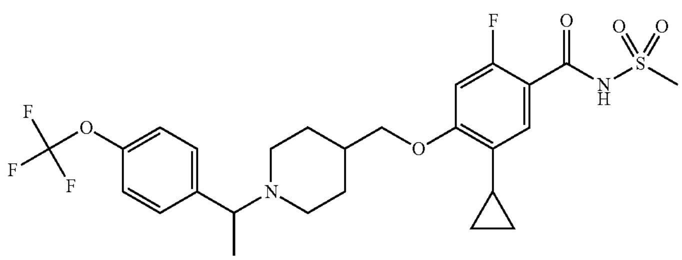 [SMILES: CC(c1ccc(OC(F)(F)F)cc1)N1CCC(COc2cc(F)c(C(=O)NS(C)(=O)=O)cc2C2CC2)CC1] | 0.021 | | |
| 157 | 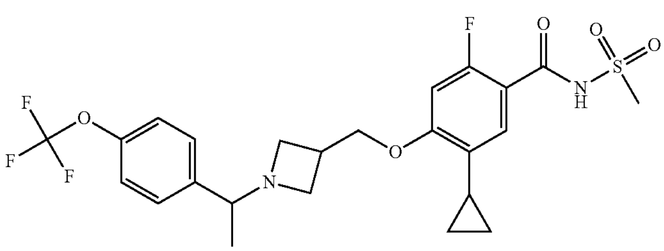 [SMILES: CC(c1ccc(OC(F)(F)F)cc1)N1CC(COc2cc(F)c(C(=O)NS(C)(=O)=O)cc2C2CC2)C1] | 0.0351 | | |
| 158 | 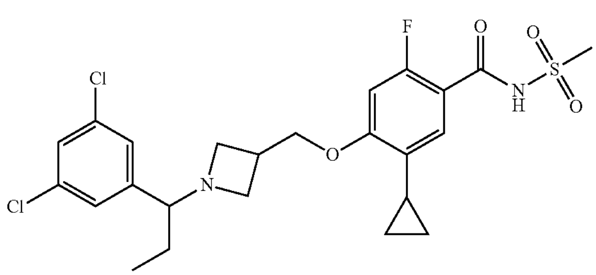 [SMILES: CCC(c1cc(Cl)cc(Cl)c1)N1CC(COc2cc(F)c(C(=O)NS(C)(=O)=O)cc2C2CC2)C1] | 0.0123 | | |

TABLE 1-continued

| Example | Structure | Ligand Binding Assay (μM) | NaV1.7 EP (μM) | NaV1.5 EP (μM) |
|---|---|---|---|---|
| 159 | 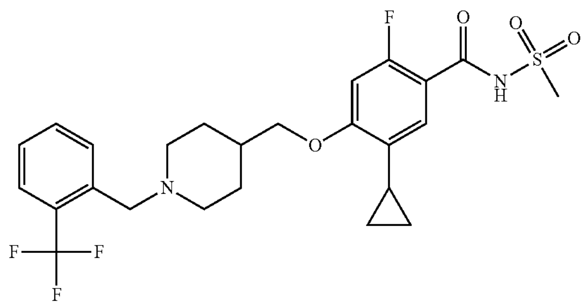 [SMILES: CS(=O)(=O)NC(=O)c1cc(C2CC2)c(OCC2CCN(Cc3ccccc3C(F)(F)F)CC2)cc1F] | 0.00542 | | |
| 160 | 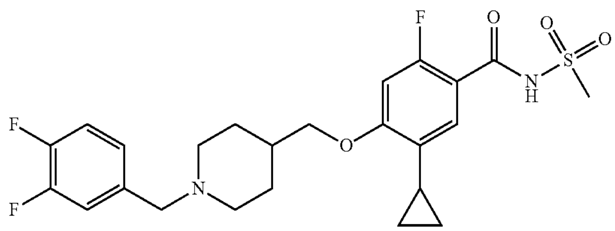 [SMILES: CS(=O)(=O)NC(=O)c1cc(C2CC2)c(OCC2CCN(Cc3ccc(F)c(F)c3)CC2)cc1F] | 0.0628 | | |
| 161 | 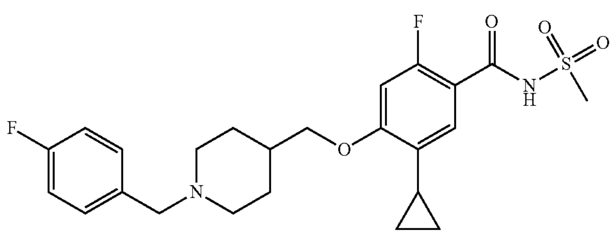 [SMILES: CS(=O)(=O)NC(=O)c1cc(C2CC2)c(OCC2CCN(Cc3ccc(F)cc3)CC2)cc1F] | 0.284 | | |
| 162 | 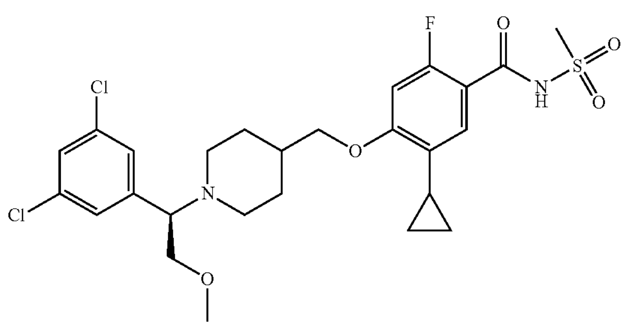 [SMILES: COC[C@@H](c1cc(Cl)cc(Cl)c1)N1CCC(COc2cc(F)c(C(=O)NS(C)(=O)=O)cc2C2CC2)CC1] | 0.0039 | 0.0028 | |
| 163 | 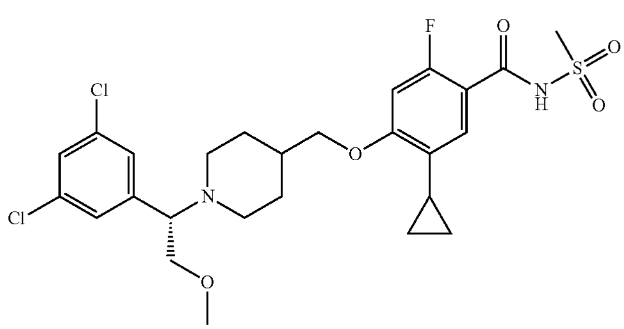 [SMILES: COC[C@H](c1cc(Cl)cc(Cl)c1)N1CCC(COc2cc(F)c(C(=O)NS(C)(=O)=O)cc2C2CC2)CC1] | 0.0036 | | |

TABLE 1-continued
| Example | Structure | Ligand Binding Assay (μM) | NaV1.7 EP (μM) | NaV1.5 EP (μM) |
|---|---|---|---|---|
| 164 | 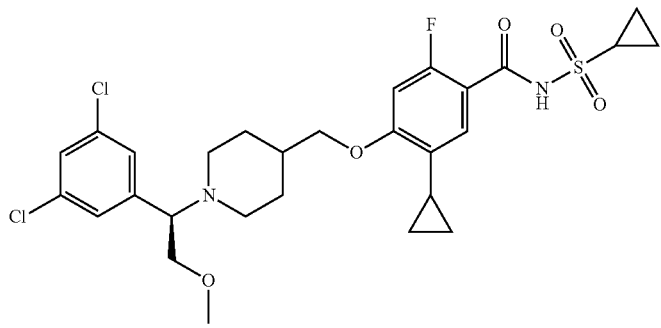 [SMILES: COC[C@@H](c1cc(Cl)cc(Cl)c1)N1CCC(COc2cc(F)c(C(=O)NS(=O)(=O)C3CC3)cc2C2CC2)CC1] | 0.0043 | 0.0033 | |
| 165 | 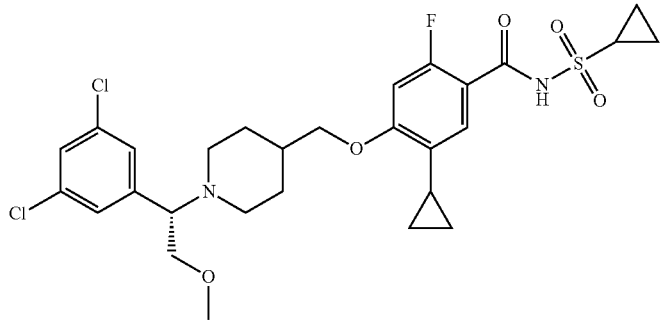 [SMILES: COC[C@H](c1cc(Cl)cc(Cl)c1)N1CCC(COc2cc(F)c(C(=O)NS(=O)(=O)C3CC3)cc2C2CC2)CC1] | 0.0023 | 0.0024 | 0.049 |
| 166 | 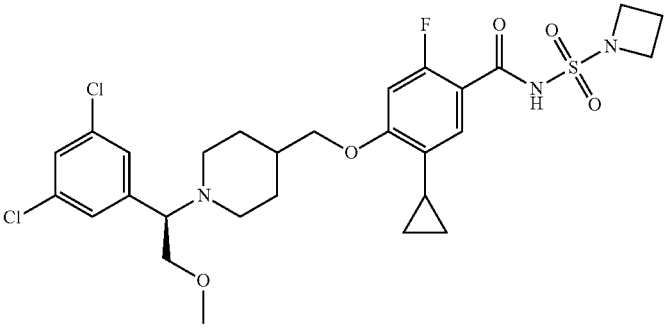 [SMILES: COC[C@@H](c1cc(Cl)cc(Cl)c1)N1CCC(COc2cc(F)c(C(=O)NS(=O)(=O)N3CCC3)cc2C2CC2)CC1] | 0.0039 | | |
| 167 | 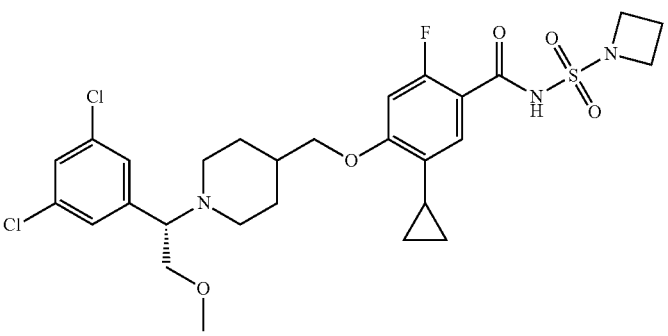 [SMILES: COC[C@H](c1cc(Cl)cc(Cl)c1)N1CCC(COc2cc(F)c(C(=O)NS(=O)(=O)N3CCC3)cc2C2CC2)CC1] | 0.0049 | 0.0042 | |

TABLE 1-continued

| Example | Structure | Ligand Binding Assay (μM) | NaV1.7 EP (μM) | NaV1.5 EP (μM) |
|---------|-----------|---------------------------|-----------------|-----------------|
| 168 | 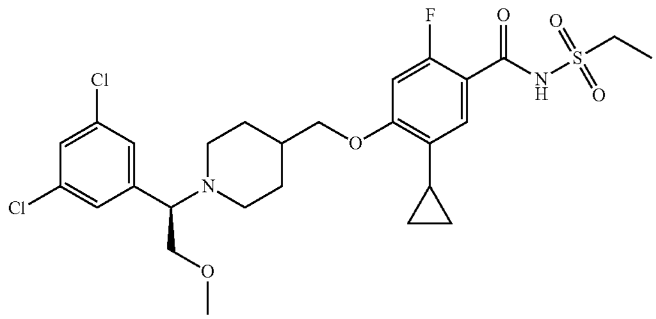 [SMILES: CCS(=O)(=O)NC(=O)c1cc(C2CC2)c(OCC2CCN([C@@H](COC)c3cc(Cl)cc(Cl)c3)CC2)cc1F] | 0.0062 | 0.003 | 0.078 |
| 169 | 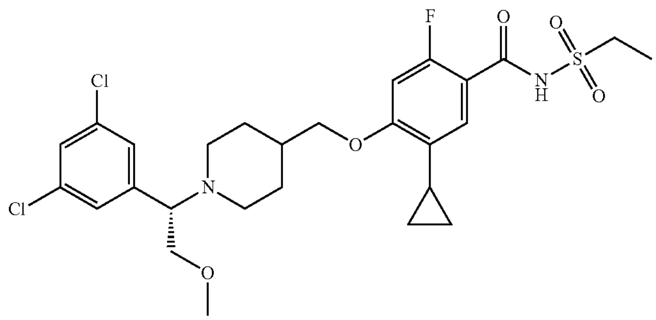 [SMILES: CCS(=O)(=O)NC(=O)c1cc(C2CC2)c(OCC2CCN([C@H](COC)c3cc(Cl)cc(Cl)c3)CC2)cc1F] | 0.0063 | 0.003 | 0.28 |
| 170 | 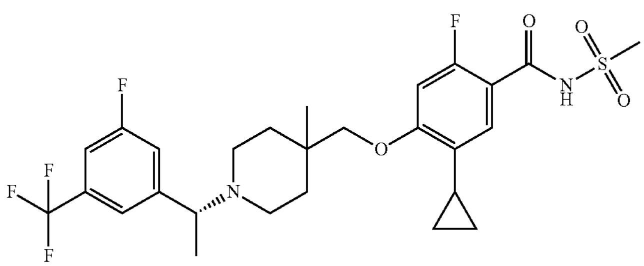 [SMILES: C[C@H](c1cc(F)cc(C(F)(F)F)c1)N1CCC(C)(COc2cc(F)c(C(=O)NS(C)(=O)=O)cc2C2CC2)CC1] | 0.005 | | |
| 171 | 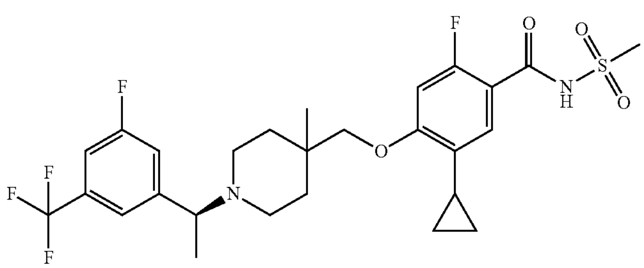 [SMILES: C[C@@H](c1cc(F)cc(C(F)(F)F)c1)N1CCC(C)(COc2cc(F)c(C(=O)NS(C)(=O)=O)cc2C2CC2)CC1] | 0.005 | | |
| 172 | 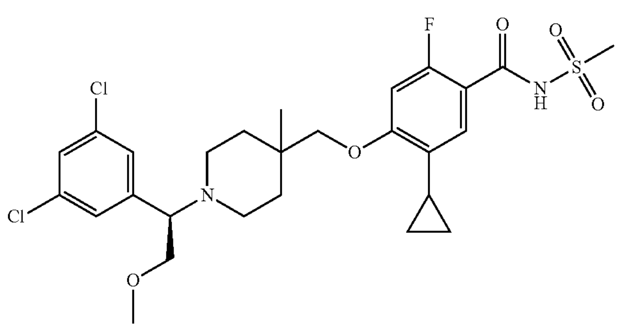 [SMILES: COC[C@@H](c1cc(Cl)cc(Cl)c1)N1CCC(C)(COc2cc(F)c(C(=O)NS(C)(=O)=O)cc2C2CC2)CC1] | 0.0039 | | |

TABLE 1-continued

| Example | Structure | Ligand Binding Assay (μM) | NaV1.7 EP (μM) | NaV1.5 EP (μM) |
|---|---|---|---|---|
| 173 | 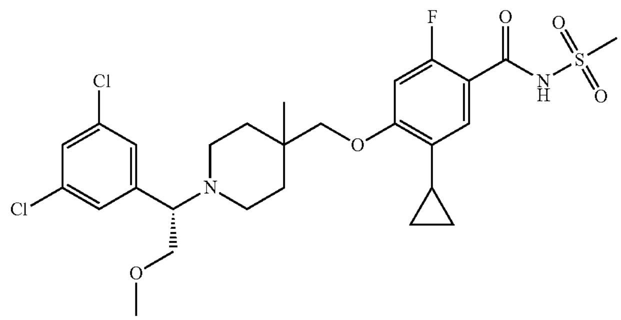 [SMILES: COC[C@H](c1cc(Cl)cc(Cl)c1)N1CCC(C)(COc2cc(F)c(C(=O)NS(C)(=O)=O)cc2C2CC2)CC1] | 0.0039 | | |
| 174 | 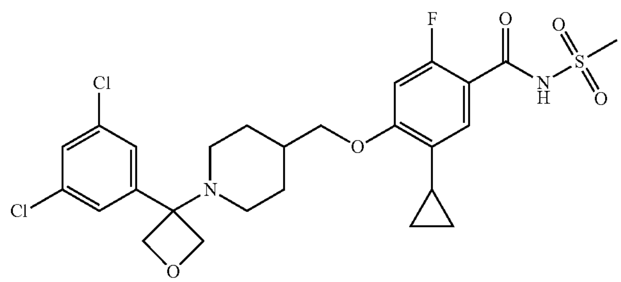 [SMILES: CS(=O)(=O)NC(=O)c1cc(C2CC2)c(OCC2CCN(C3(c4cc(Cl)cc(Cl)c4)COC3)CC2)cc1F] | 0.012 | | |
| 175 | 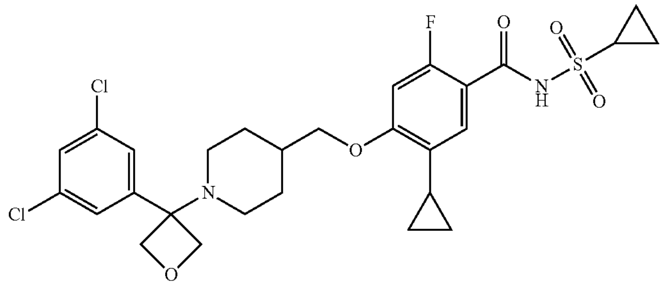 [SMILES: O=C(NS(=O)(=O)C1CC1)c1cc(C2CC2)c(OCC2CCN(C3(c4cc(Cl)cc(Cl)c4)COC3)CC2)cc1F] | 0.0052 | | |
| 176 | 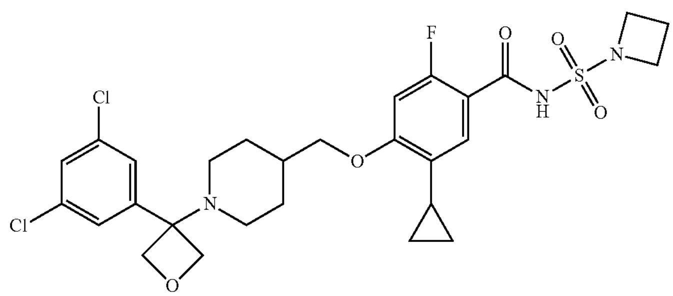 [SMILES: O=C(NS(=O)(=O)N1CCC1)c1cc(C2CC2)c(OCC2CCN(C3(c4cc(Cl)cc(Cl)c4)COC3)CC2)cc1F] | 0.0091 | | |
| 177 | 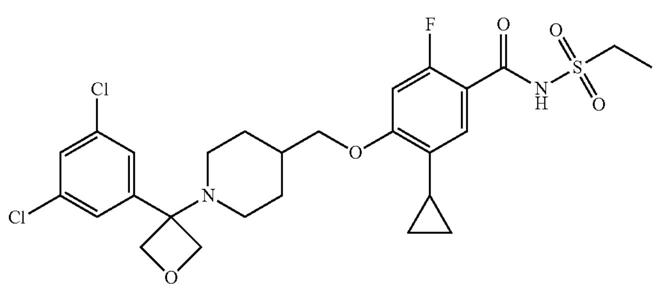 [SMILES: CCS(=O)(=O)NC(=O)c1cc(C2CC2)c(OCC2CCN(C3(c4cc(Cl)cc(Cl)c4)COC3)CC2)cc1F] | 0.0083 | | |

TABLE 1-continued

| Example | Structure | Ligand Binding Assay (μM) | NaV1.7 EP (μM) | NaV1.5 EP (μM) |
|---|---|---|---|---|
| 178 | 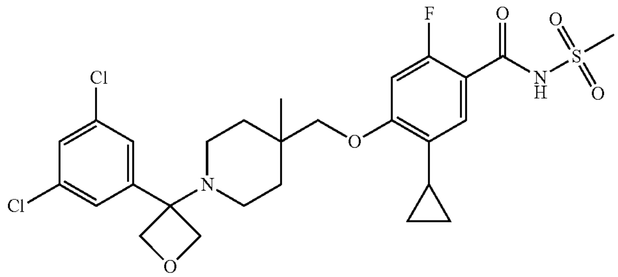 [SMILES: CC1(COc2cc(F)c(C(=O)NS(C)(=O)=O)cc2C2CC2)CCN(C2(c3cc(Cl)cc(Cl)c3)COC2)CC1] | 0.0076 | | |
| 179 | 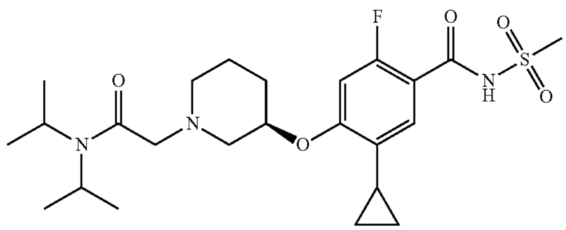 [SMILES: CC(C)N(C(=O)CN1CCC[C@@H](Oc2cc(F)c(C(=O)NS(C)(=O)=O)cc2C2CC2)C1)C(C)C] | 1.8 | | |
| 180 | 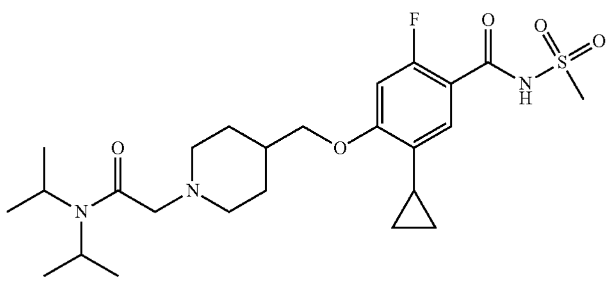 [SMILES: CC(C)N(C(=O)CN1CCC(COc2cc(F)c(C(=O)NS(C)(=O)=O)cc2C2CC2)CC1)C(C)C] | 9.9 | | |
| 181 | 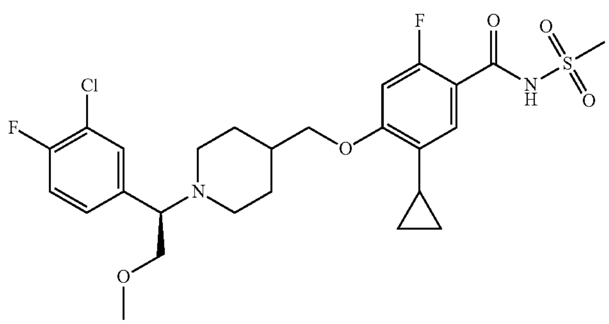 [SMILES: COC[C@@H](c1ccc(F)c(Cl)c1)N1CCC(COc2cc(F)c(C(=O)NS(C)(=O)=O)cc2C2CC2)CC1] | 0.011 | | |
| 182 | 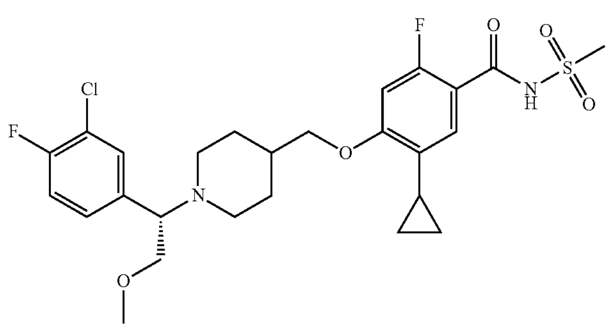 [SMILES: COC[C@H](c1ccc(F)c(Cl)c1)N1CCC(COc2cc(F)c(C(=O)NS(C)(=O)=O)cc2C2CC2)CC1] | 0.014 | | |

TABLE 1-continued

| Example | Structure | Ligand Binding Assay (μM) | NaV1.7 EP (μM) | NaV1.5 EP (μM) |
|---|---|---|---|---|
| 183 | 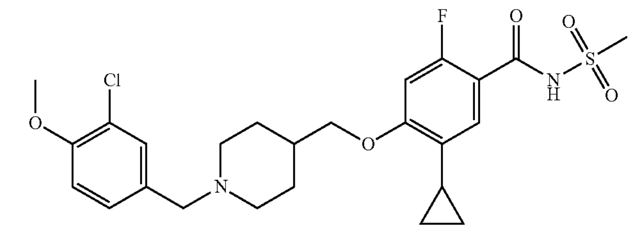 [SMILES: COc1ccc(CN2CCC(COc3cc(F)c(C(=O)NS(C)(=O)=O)cc3C3CC3)CC2)cc1Cl] | 0.047 | | |
| 184 | 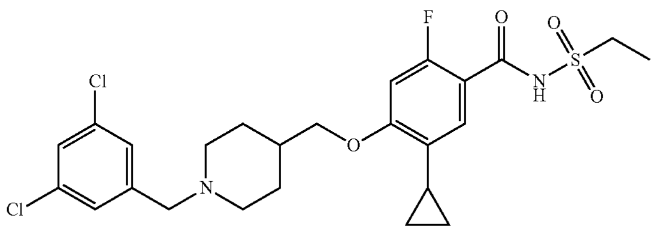 [SMILES: CCS(=O)(=O)NC(=O)c1cc(C2CC2)c(OCC2CCN(Cc3cc(Cl)cc(Cl)c3)CC2)cc1F] | 0.0051 | | |
| 185 | 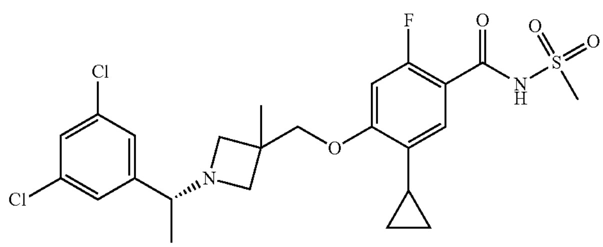 [SMILES: C[C@H](c1cc(Cl)cc(Cl)c1)N1CC(C)(COc2cc(F)c(C(=O)NS(C)(=O)=O)cc2C2CC2)C1] | 0.007 | | |
| 186 | 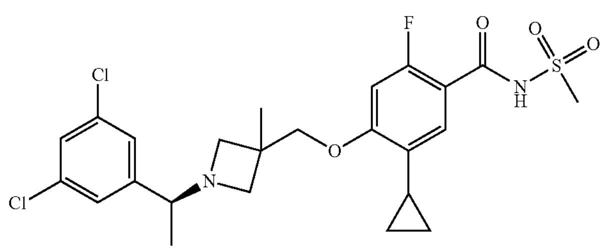 [SMILES: C[C@@H](c1cc(Cl)cc(Cl)c1)N1CC(C)(COc2cc(F)c(C(=O)NS(C)(=O)=O)cc2C2CC2)C1] | 0.004 | | |
| 187 | 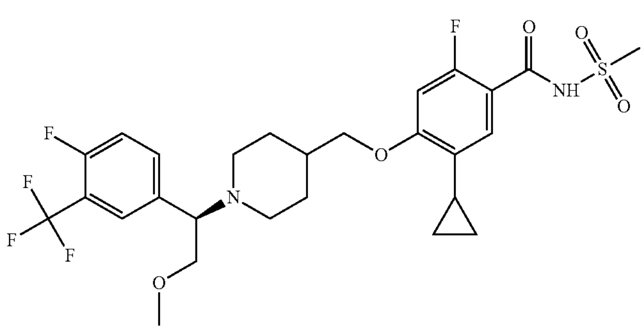 [SMILES: COC[C@@H](c1ccc(F)c(C(F)(F)F)c1)N1CCC(COc2cc(F)c(C(=O)NS(C)(=O)=O)cc2C2CC2)CC1] | 0.005 | | |

TABLE 1-continued

| Example | Structure | Ligand Binding Assay (μM) | NaV1.7 EP (μM) | NaV1.5 EP (μM) |
|---|---|---|---|---|
| 188 | 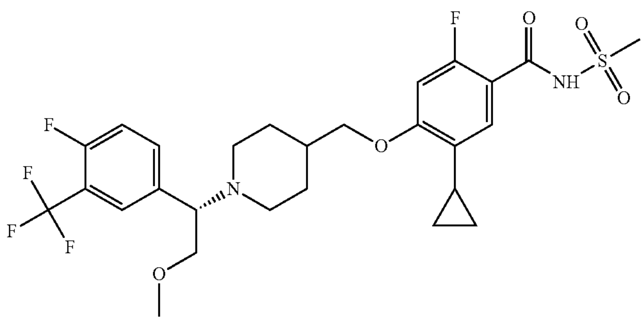 [SMILES: COC[C@H](c1ccc(F)c(C(F)(F)F)c1)N1CCC(COc2cc(F)c(C(=O)NS(C)(=O)=O)cc2C2CC2)CC1] | 0.0052 | | |
| 189 | 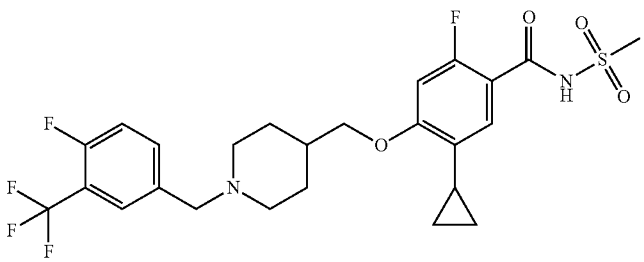 [SMILES: CS(=O)(=O)NC(=O)c1cc(C2CC2)c(OCC2CCN(Cc3ccc(F)c(C(F)(F)F)c3)CC2)cc1F] | 0.016 | | |
| 190 | 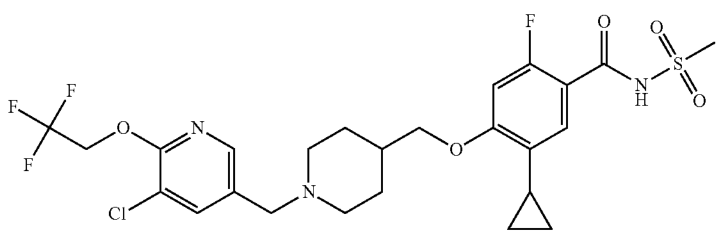 [SMILES: CS(=O)(=O)NC(=O)c1cc(C2CC2)c(OCC2CCN(Cc3cnc(OCC(F)(F)F)c(Cl)c3)CC2)cc1F] | 0.056 | | |
| 191 | 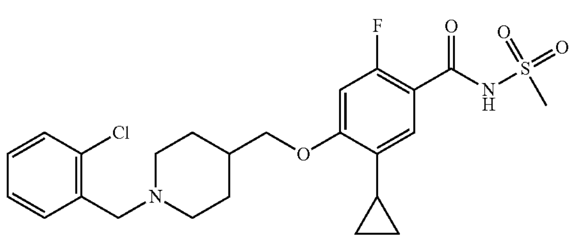 [SMILES: CS(=O)(=O)NC(=O)c1cc(C2CC2)c(OCC2CCN(Cc3ccccc3Cl)CC2)cc1F] | 0.032 | | |
| 192 | 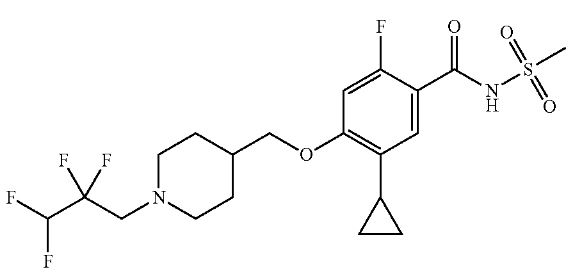 [SMILES: CS(=O)(=O)NC(=O)c1cc(C2CC2)c(OCC2CCN(CC(F)(F)C(F)F)CC2)cc1F] | 0.034 | | |

TABLE 1-continued
| Example | Structure | Ligand Binding Assay (μM) | NaV1.7 EP (μM) | NaV1.5 EP (μM) |
|---|---|---|---|---|
| 193 | 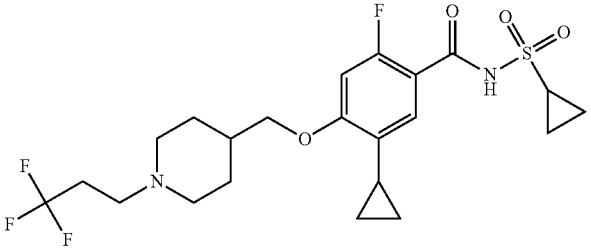 [SMILES: O=C(NS(=O)(=O)C1CC1)c1cc(C2CC2)c(OCC2CCN(CCC(F)(F)F)CC2)cc1F] | 0.052 | | |
| 194 | 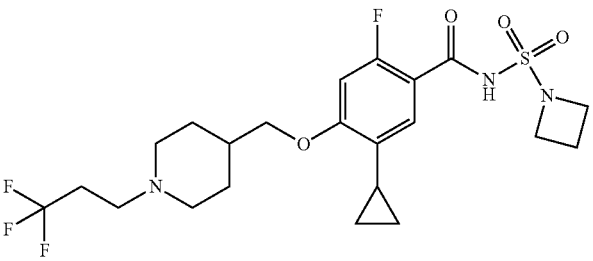 [SMILES: O=C(NS(=O)(=O)N1CCC1)c1cc(C2CC2)c(OCC2CCN(CCC(F)(F)F)CC2)cc1F] | 0.18 | | |
| 195 | 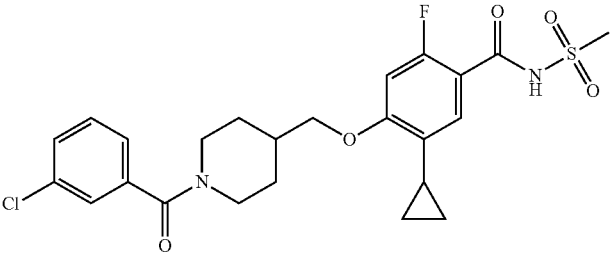 [SMILES: CS(=O)(=O)NC(=O)c1cc(C2CC2)c(OCC2CCN(C(=O)c3cccc(Cl)c3)CC2)cc1F] | 0.35 | | |
| 196 | 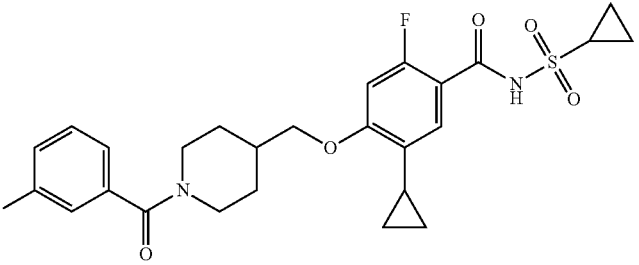 | 0.043 | | |
| 197 | 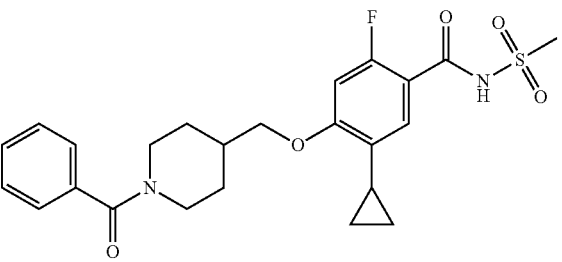 [SMILES: CS(=O)(=O)NC(=O)c1cc(C2CC2)c(OCC2CCN(C(=O)c3ccccc3)CC2)cc1F] | 3.2 | | |

TABLE 1-continued
| Example | Structure | Ligand Binding Assay (μM) | NaV1.7 EP (μM) | NaV1.5 EP (μM) |
|---|---|---|---|---|
| 198 | 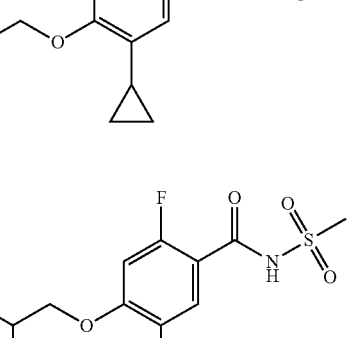 | 0.55 | | |
| 199 | 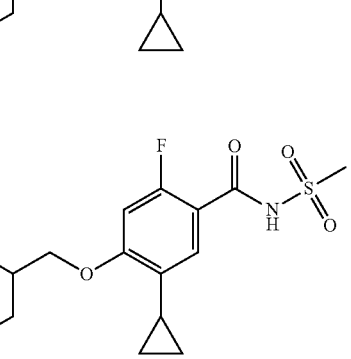 | 1.4 | | |
| 200 | 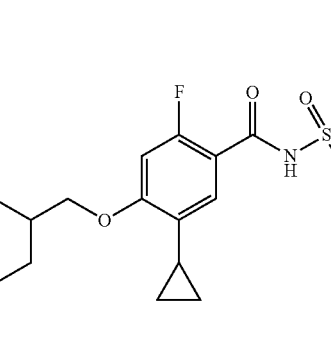 | 9.4 | | |
| 201 | 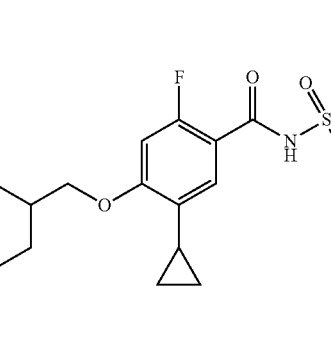 | 0.005 | | |
| 202 | 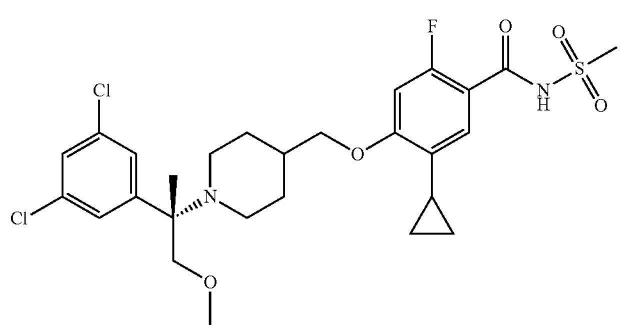 [SMILES: COC[C@](C)(c1cc(Cl)cc(Cl)c1)N1CCC(COc2cc(F)c(C(=O)NS(C)(=O)=O)cc2C2CC2)CC1] | 0.0016 | | |

TABLE 1-continued

| Example | Structure | Ligand Binding Assay (μM) | NaV1.7 EP (μM) | NaV1.5 EP (μM) |
|---|---|---|---|---|
| 203 | 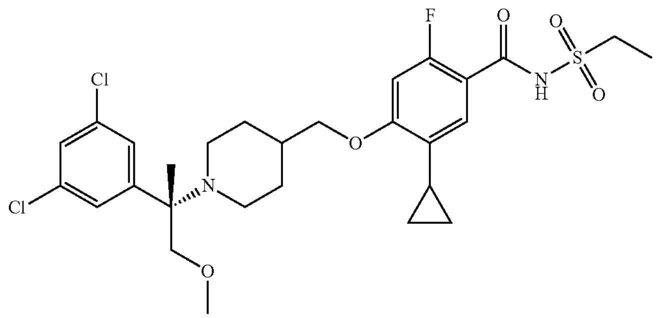 [SMILES: CCS(=O)(=O)NC(=O)c1cc(C2CC2)c(OCC2CCN([C@](C)(COC)c3cc(Cl)cc(Cl)c3)CC2)cc1F] | 0.0036 | | |
| 204 | 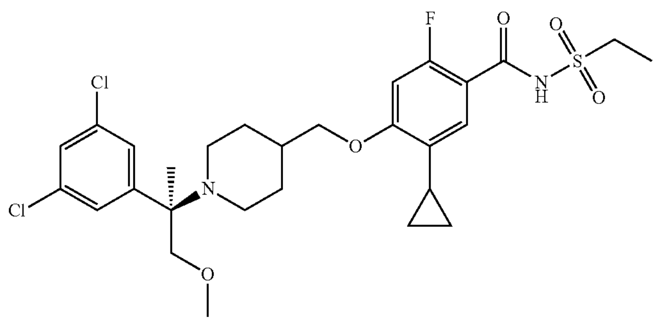 [SMILES: CCS(=O)(=O)NC(=O)c1cc(C2CC2)c(OCC2CCN([C@@](C)(COC)c3cc(Cl)cc(Cl)c3)CC2)cc1F] | 0.0027 | | |
| 205 | 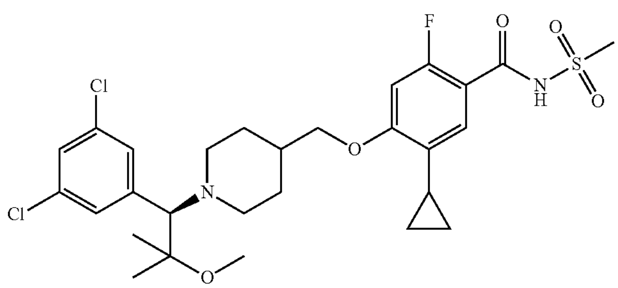 [SMILES: COC(C)(C)[C@@H](c1cc(Cl)cc(Cl)c1)N1CCC(COc2cc(F)c(C(=O)NS(C)(=O)=O)cc2C2CC2)CC1] | 0.0025 | | |
| 206 | 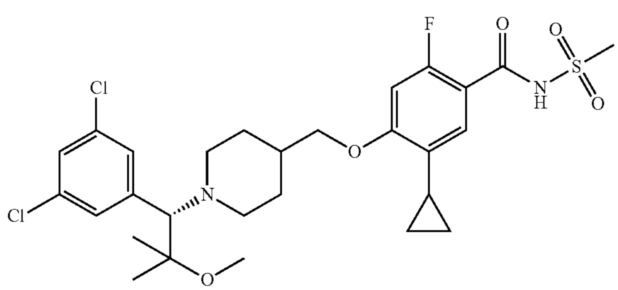 [SMILES: COC(C)(C)[C@H](c1cc(Cl)cc(Cl)c1)N1CCC(COc2cc(F)c(C(=O)NS(C)(=O)=O)cc2C2CC2)CC1] | 0.0018 | | |
| 207 | 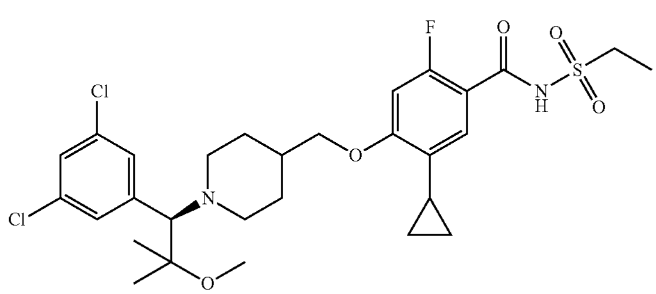 [SMILES: CCS(=O)(=O)NC(=O)c1cc(C2CC2)c(OCC2CCN([C@H](c3cc(Cl)cc(Cl)c3)C(C)(C)OC)CC2)cc1F] | 0.0017 | | |

TABLE 1-continued

| Example | Structure | Ligand Binding Assay (µM) | NaV1.7 EP (µM) | NaV1.5 EP (µM) |
|---|---|---|---|---|
| 208 | 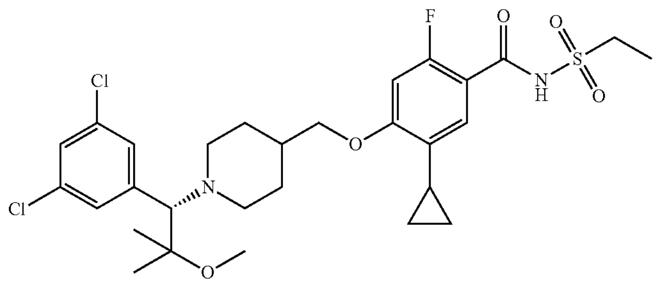 [SMILES: CCS(=O)(=O)NC(=O)c1cc(C2CC2)c(OCC2CCN([C@@H](c3cc(Cl)cc(Cl)c3)C(C)(C)OC)CC2)cc1F] | 0.0016 | 0.003 | 0.013 |
| 209 | 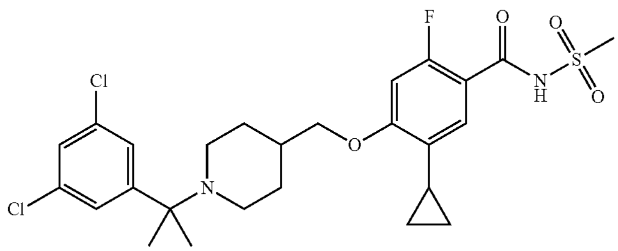 [SMILES: CC(C)(c1cc(Cl)cc(Cl)c1)N1CCC(COc2cc(F)c(C(=O)NS(C)(=O)=O)cc2C2CC2)CC1] | 0.0017 | 0.0158 | |
| 210 | 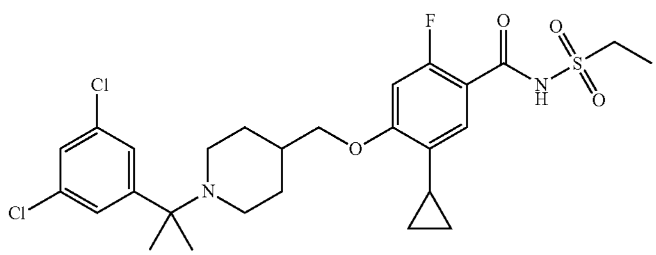 [SMILES: CCS(=O)(=O)NC(=O)c1cc(C2CC2)c(OCC2CCN(C(C)(C)c3cc(Cl)cc(Cl)c3)CC2)cc1F] | 0.0019 | | |
| 211 | 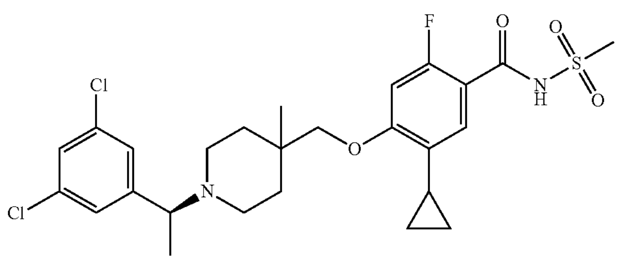 [SMILES: C[C@@H](c1cc(Cl)cc(Cl)c1)N1CCC(C)(COc2cc(F)c(C(=O)NS(C)(=O)=O)cc2C2CC2)CC1] | 0.0017 | | |
| 212 | 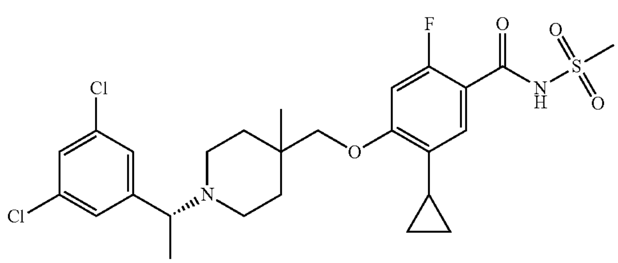 [SMILES: C[C@H](c1cc(Cl)cc(Cl)c1)N1CCC(C)(COc2cc(F)c(C(=O)NS(C)(=O)=O)cc2C2CC2)CC1] | 0.0027 | | |
| 213 | 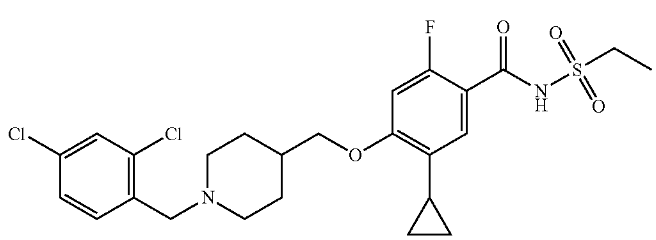 [SMILES: CCS(=O)(=O)NC(=O)c1cc(C2CC2)c(OCC2CCN(Cc3ccc(Cl)cc3Cl)CC2)cc1F] | 0.0025 | | |

TABLE 1-continued

| Example | Structure | Ligand Binding Assay (μM) | NaV1.7 EP (μM) | NaV1.5 EP (μM) |
|---|---|---|---|---|
| 214 | 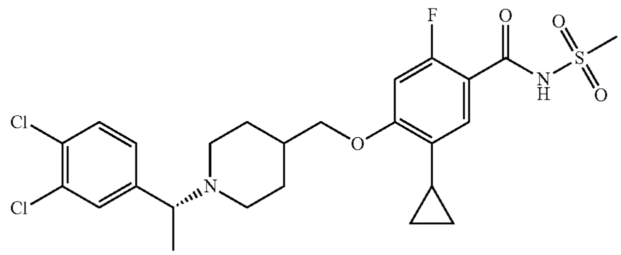 [SMILES: C[C@H](c1ccc(Cl)c(Cl)c1)N1CCC(COc2cc(F)c(C(=O)NS(C)(=O)=O)cc2C2CC2)CC1] | 0.0031 | | |
| 215 | 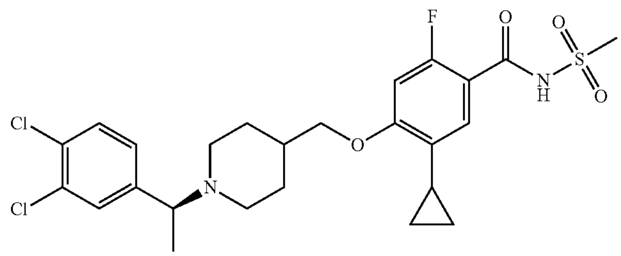 [SMILES: C[C@@H](c1ccc(Cl)c(Cl)c1)N1CCC(COc2cc(F)c(C(=O)NS(C)(=O)=O)cc2C2CC2)CC1] | 0.0048 | | |
| 216 | 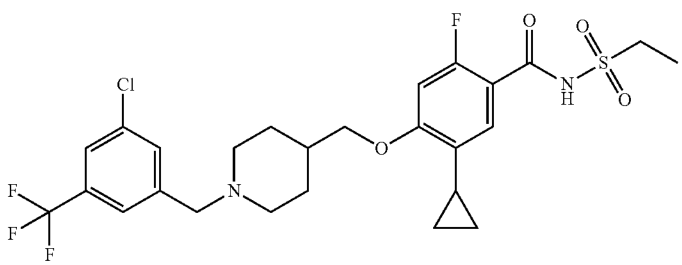 [SMILES: CCS(=O)(=O)NC(=O)c1cc(C2CC2)c(OCC2CCN(Cc3cc(Cl)cc(C(F)(F)F)c3)CC2)cc1F] | 0.005 | | |
| 217 | 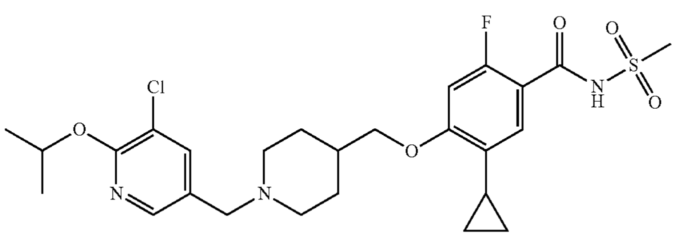 [SMILES: CC(C)Oc1ncc(CN2CCC(COc3cc(F)c(C(=O)NS(C)(=O)=O)cc3C3CC3)CC2)cc1Cl] | 0.0056 | 0.0025 | 0.19 |
| 218 | 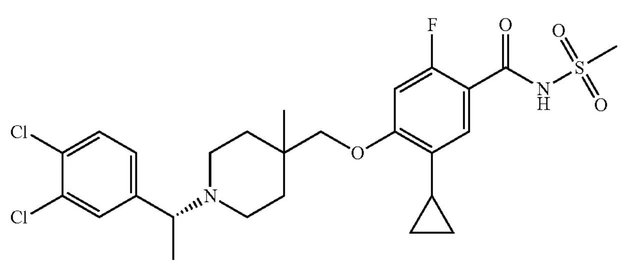 [SMILES: C[C@H](c1ccc(Cl)c(Cl)c1)N1CCC(C)(COc2cc(F)c(C(=O)NS(C)(=O)=O)cc2C2CC2)CC1] | 0.0078 | | |
| 219 | 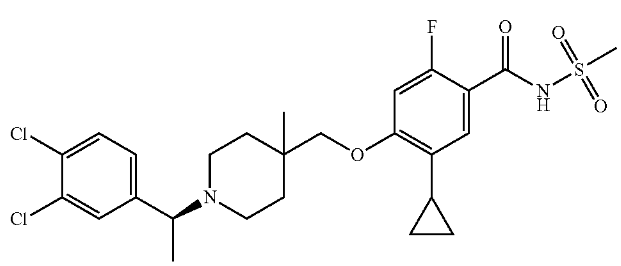 [SMILES: C[C@@H](c1ccc(Cl)c(Cl)c1)N1CCC(C)(COc2cc(F)c(C(=O)NS(C)(=O)=O)cc2C2CC2)CC1] | 0.0083 | | |

TABLE 1-continued

| Example | Structure | Ligand Binding Assay (μM) | NaV1.7 EP (μM) | NaV1.5 EP (μM) |
|---|---|---|---|---|
| 220 | 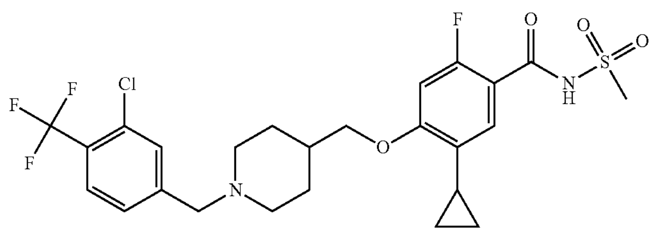 [SMILES: CS(=O)(=O)NC(=O)c1cc(C2CC2)c(OCC2CCN(Cc3ccc(C(F)(F)F)c(Cl)c3)CC2)cc1F] | 0.017 | | |
| 221 | 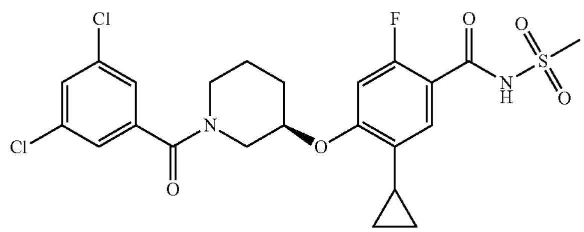 [SMILES: CS(=O)(=O)NC(=O)c1cc(C2CC2)c(O[C@@H]2CCCN(C(=O)c3cc(Cl)cc(Cl)c3)C2)cc1F] | 1.8 | | |
| 222 | 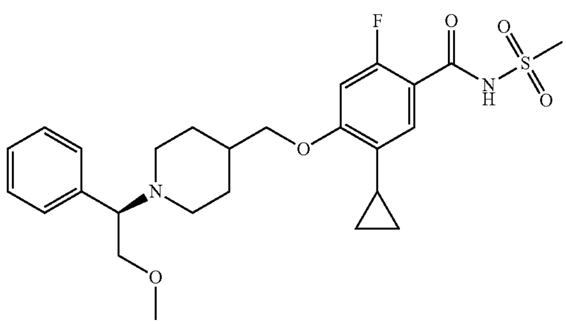 [SMILES: COC[C@@H](c1ccccc1)N1CCC(COc2cc(F)c(C(=O)NS(C)(=O)=O)cc2C2CC2)CC1] | 0.16 | | |
| 223 | 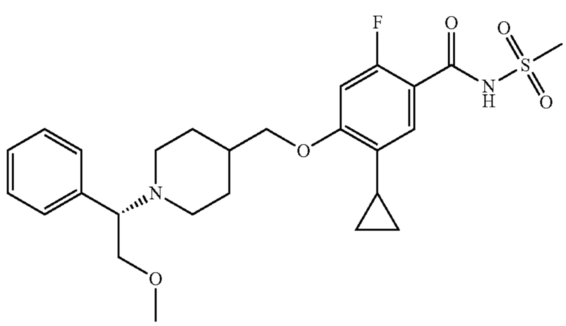 [SMILES: COC[C@H](c1ccccc1)N1CCC(COc2cc(F)c(C(=O)NS(C)(=O)=O)cc2C2CC2)CC1] | 0.25 | | |
| 224 | 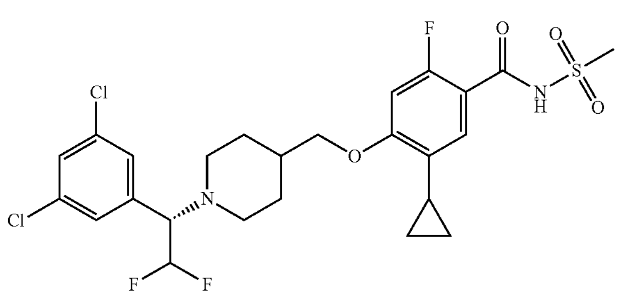 [SMILES: CS(=O)(=O)NC(=O)c1cc(C2CC2)c(OCC2CCN([C@@H](c3cc(Cl)cc(Cl)c3)C(F)F)CC2)cc1F] | 0.0045 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 225 | 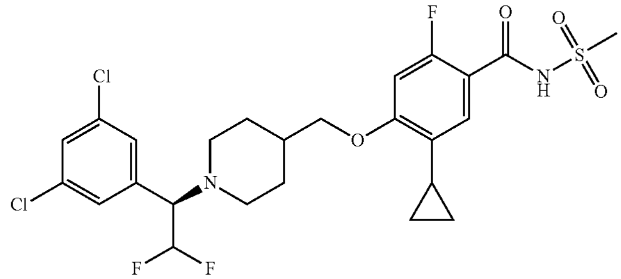 [SMILES: CS(=O)(=O)NC(=O)c1cc(C2CC2)c(OCC2CCN([C@H](c3cc(Cl)cc(Cl)c3)C(F)F)CC2)cc1F] | 0.017 | | |
| 226 | 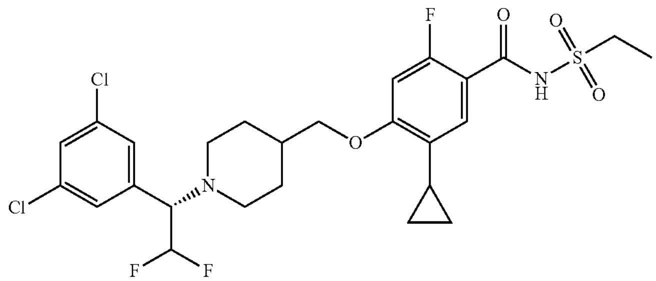 [SMILES: CCS(=O)(=O)NC(=O)c1cc(C2CC2)c(OCC2CCN([C@@H](c3cc(Cl)cc(Cl)c3)C(F)F)CC2)cc1F] | 0.012 | | |
| 227 | 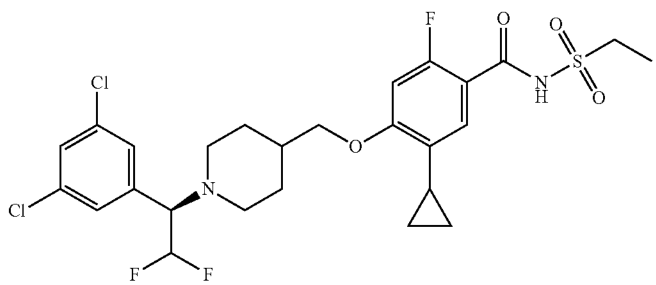 [SMILES: CCS(=O)(=O)NC(=O)c1cc(C2CC2)c(OCC2CCN([C@H](c3cc(Cl)cc(Cl)c3)C(F)F)CC2)cc1F] | 0.0081 | | |
| 228 | 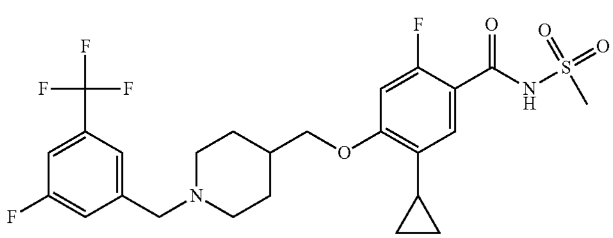 [SMILES: CS(=O)(=O)NC(=O)c1cc(C2CC2)c(OCC2CCN(Cc3cc(F)cc(C(F)(F)F)c3)CC2)cc1F] | 0.0051 | 0.031 | 4.1 |
| 229 | 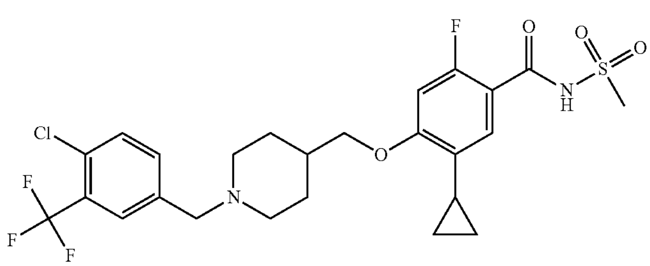 [SMILES: CS(=O)(=O)NC(=O)c1cc(C2CC2)c(OCC2CCN(Cc3ccc(Cl)c(C(F)(F)F)c3)CC2)cc1F] | 0.0073 | | |

TABLE 1-continued
| Example | Structure | Ligand Binding Assay (μM) | NaV1.7 EP (μM) | NaV1.5 EP (μM) |
|---|---|---|---|---|
| 230 | 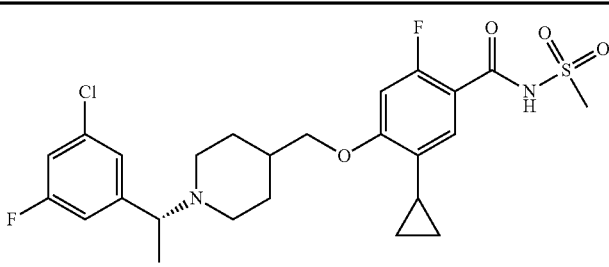 | 0.0044 | | |
| 231 | 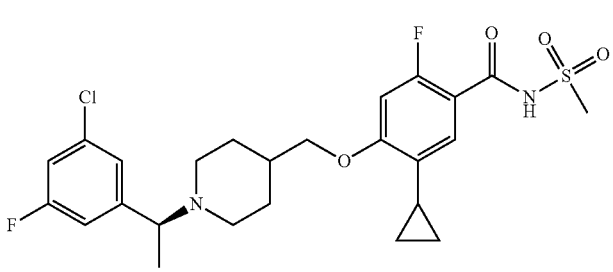 [SMILES: C[C@@H](c1cc(F)cc(Cl)c1)N1CCC(COc2cc(F)c(C(=O)NS(C)(=O)=O)cc2C2CC2)CC1] | 0.0059 | | |
| 232 | 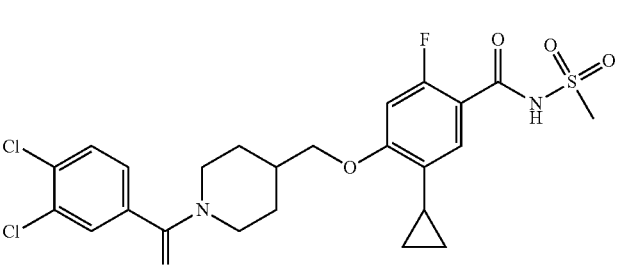 | 0.064 | | |
| 233 | 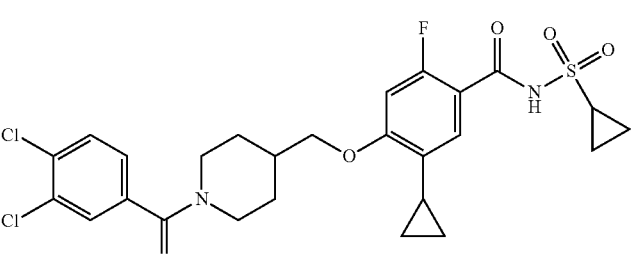 | 0.031 | | |
| 234 | 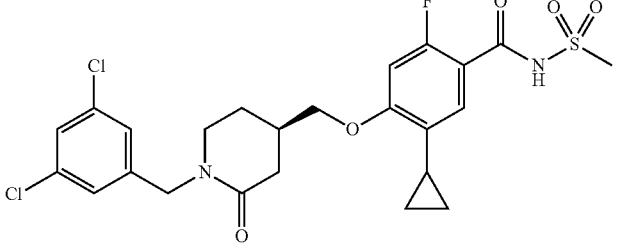 | 0.17 | | |

TABLE 1-continued

| Example | Structure | Ligand Binding Assay (μM) | NaV1.7 EP (μM) | NaV1.5 EP (μM) |
|---|---|---|---|---|
| 235 | 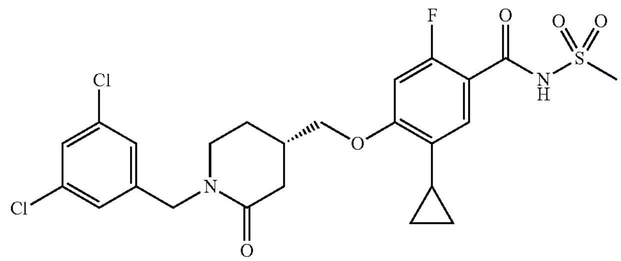 [SMILES: CS(=O)(=O)NC(=O)c1cc(C2CC2)c(OC[C@H]2CCN(Cc3cc(Cl)cc(Cl)c3)C(=O)C2)cc1F] | 0.21 | | |
| 236 | 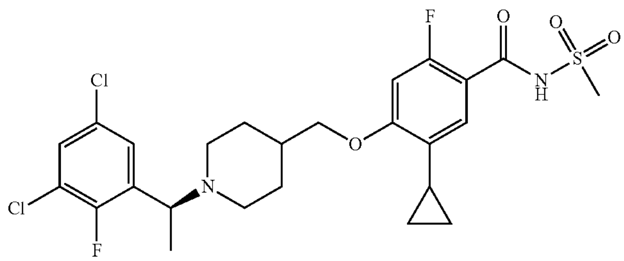 [SMILES: C[C@@H](c1cc(Cl)cc(Cl)c1F)N1CCC(COc2cc(F)c(C(=O)NS(C)(=O)=O)cc2C2CC2)CC1] | 0.0016 | | |
| 237 | 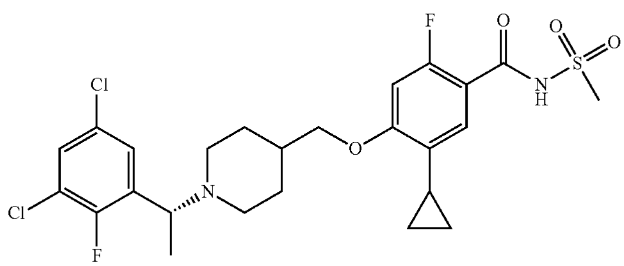 [SMILES: C[C@H](c1cc(Cl)cc(Cl)c1F)N1CCC(COc2cc(F)c(C(=O)NS(C)(=O)=O)cc2C2CC2)CC1] | 0.0029 | | |
| 238 | 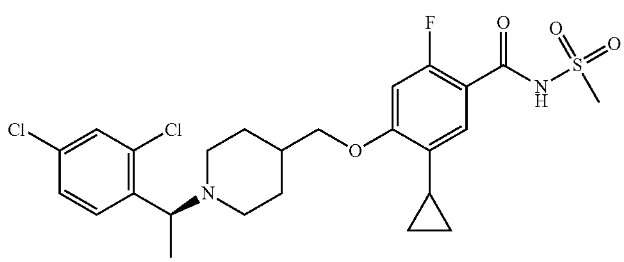 [SMILES: C[C@@H](c1ccc(Cl)cc1Cl)N1CCC(COc2cc(F)c(C(=O)NS(C)(=O)=O)cc2C2CC2)CC1] | 0.0022 | | |
| 239 | 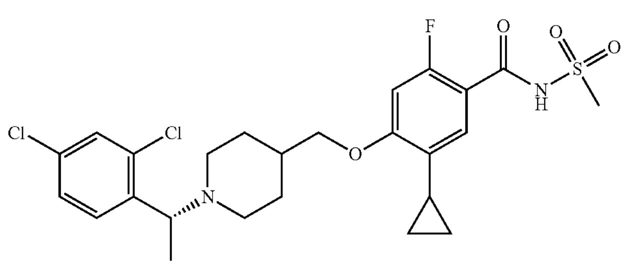 [SMILES: C[C@H](c1ccc(Cl)cc1Cl)N1CCC(COc2cc(F)c(C(=O)NS(C)(=O)=O)cc2C2CC2)CC1] | 0.0034 | | |

TABLE 1-continued

| Example | Structure | Ligand Binding Assay (μM) | NaV1.7 EP (μM) | NaV1.5 EP (μM) |
|---|---|---|---|---|
| 240 | 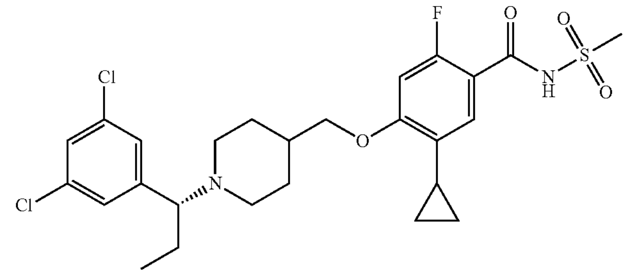 [SMILES: CC[C@H](c1cc(Cl)cc(Cl)c1)N1CCC(COc2cc(F)c(C(=O)NS(C)(=O)=O)cc2C2CC2)CC1] | 0.0024 | | |
| 241 | 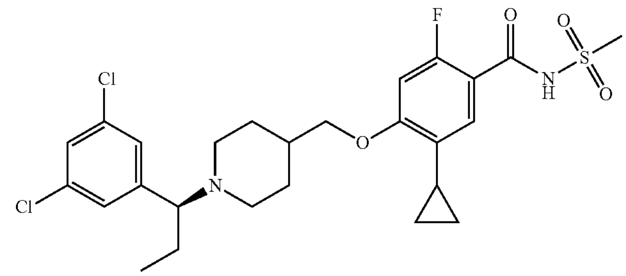 [SMILES: CC[C@@H](c1cc(Cl)cc(Cl)c1)N1CCC(COc2cc(F)c(C(=O)NS(C)(=O)=O)cc2C2CC2)CC1] | 0.0027 | | |
| 242 | 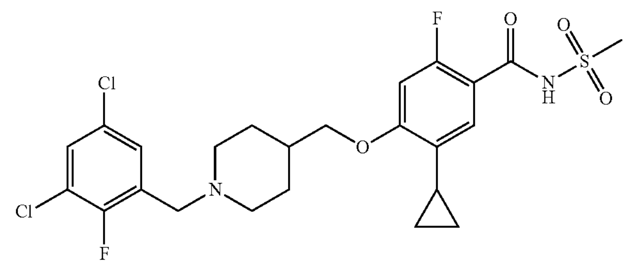 [SMILES: CS(=O)(=O)NC(=O)c1cc(C2CC2)c(OCC2CCN(Cc3cc(Cl)cc(Cl)c3F)CC2)cc1F] | 0.003 | | |
| 243 | 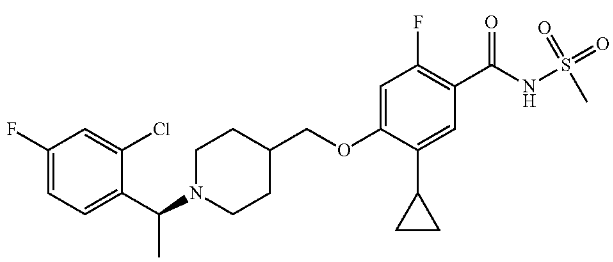 [SMILES: C[C@@H](c1ccc(F)cc1Cl)N1CCC(COc2cc(F)c(C(=O)NS(C)(=O)=O)cc2C2CC2)CC1] | 0.011 | | |
| 244 | 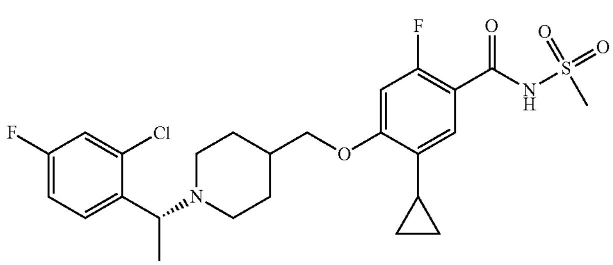 [SMILES: C[C@H](c1ccc(F)cc1Cl)N1CCC(COc2cc(F)c(C(=O)NS(C)(=O)=O)cc2C2CC2)CC1] | 0.012 | | |

TABLE 1-continued
| Example | Structure | Ligand Binding Assay (μM) | NaV1.7 EP (μM) | NaV1.5 EP (μM) |
|---|---|---|---|---|
| 245 | 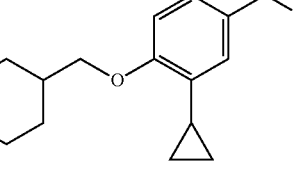 | 0.0079 | | |
| 246 | 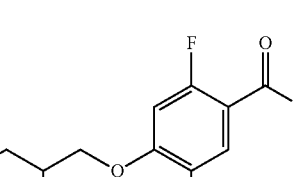 | 0.0077 | | |
| 247 | 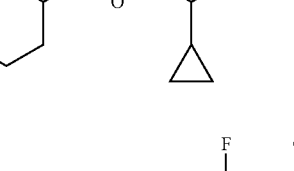 | 0.0089 | | |
| 248 | 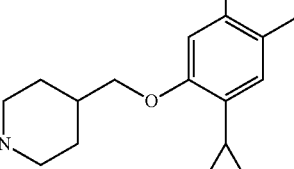 | 0.01 | | |
| 249 | 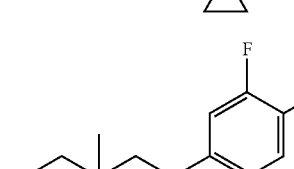 | 0.039 | | |
| 250 | 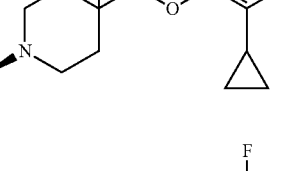 | 0.043 | | |

TABLE 1-continued

| Example | Structure | Ligand Binding Assay (μM) | NaV1.7 EP (μM) | NaV1.5 EP (μM) |
|---|---|---|---|---|
| 251 | 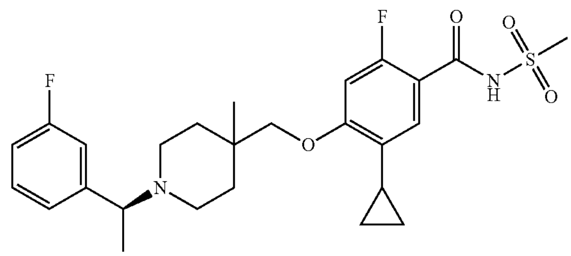 [SMILES: C[C@@H](c1cccc(F)c1)N1CCC(C)(COc2cc(F)c(C(=O)NS(C)(=O)=O)cc2C2CC2)CC1] | 0.049 | | |
| 252 | 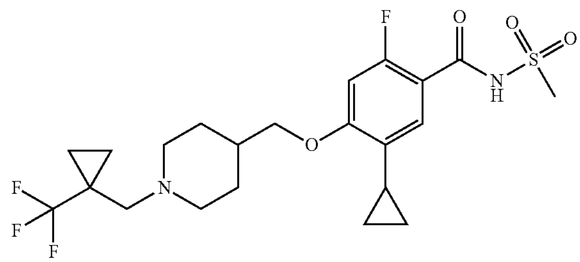 [SMILES: CS(=O)(=O)NC(=O)c1cc(C2CC2)c(OCC2CCN(CC3(C(F)(F)F)CC3)CC2)cc1F] | 0.05 | | |
| 253 | 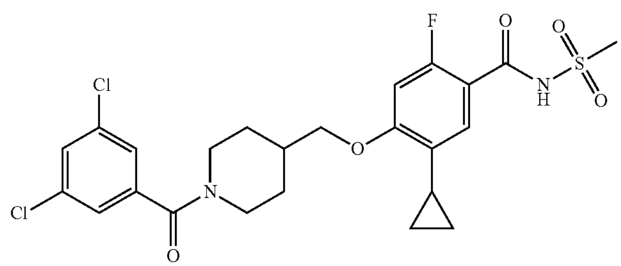 [SMILES: CS(=O)(=O)NC(=O)c1cc(C2CC2)c(OCC2CCN(C(=O)c3cc(Cl)cc(Cl)c3)CC2)cc1F] | 0.02 | | |
| 254 | 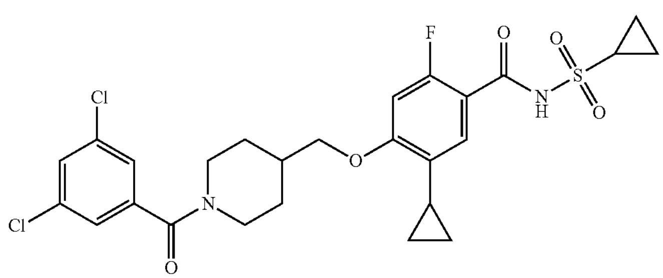 [SMILES: O=C(NS(=O)(=O)C1CC1)c1cc(C2CC2)c(OCC2CCN(C(=O)c3cc(Cl)cc(Cl)c3)CC2)cc1F] | 0.026 | | |
| 255 | 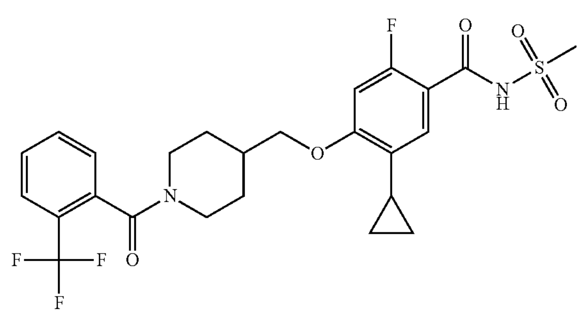 [SMILES: CS(=O)(=O)NC(=O)c1cc(C2CC2)c(OCC2CCN(C(=O)c3ccccc3C(F)(F)F)CC2)cc1F] | 1.1 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 256 | 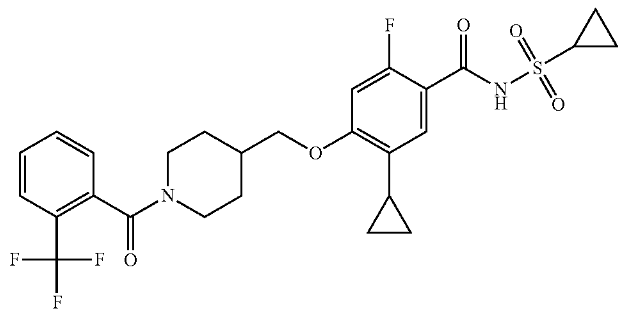 [SMILES: O=C(NS(=O)(=O)C1CC1)c1cc(C2CC2)c(OCC2CCN(C(=O)c3ccccc3C(F)(F)F)CC2)cc1F] | 0.29 | | |
| 257 | 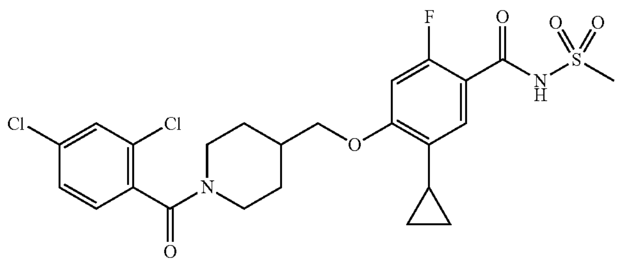 [SMILES: CS(=O)(=O)NC(=O)c1cc(C2CC2)c(OCC2CCN(C(=O)c3ccc(Cl)cc3Cl)CC2)cc1F] | 0.27 | | |
| 258 | 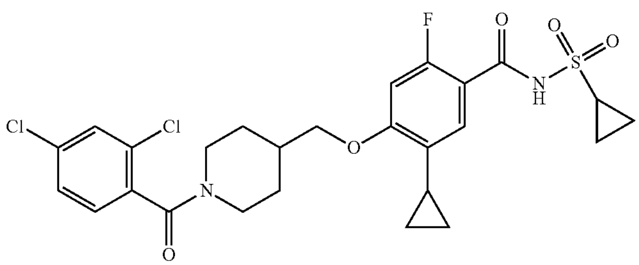 [SMILES: O=C(NS(=O)(=O)C1CC1)c1cc(C2CC2)c(OCC2CCN(C(=O)c3ccc(Cl)cc3Cl)CC2)cc1F] | 0.065 | | |
| 259 | 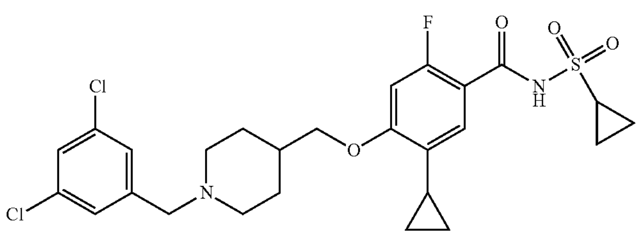 [SMILES: O=C(NS(=O)(=O)C1CC1)c1cc(C2CC2)c(OCC2CCN(Cc3cc(Cl)cc(Cl)c3)CC2)cc1F] | 0.0022 | 0.023 | 0.11 |
| 260 | 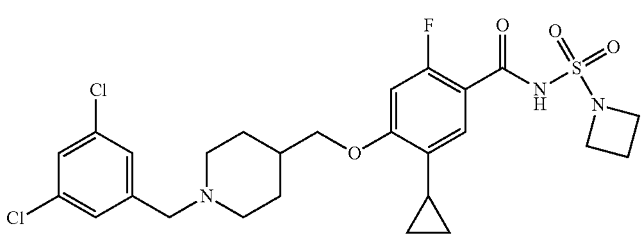 [SMILES: O=C(NS(=O)(=O)N1CCC1)c1cc(C2CC2)c(OCC2CCN(Cc3cc(Cl)cc(Cl)c3)CC2)cc1F] | 0.0048 | | |
| 261 | 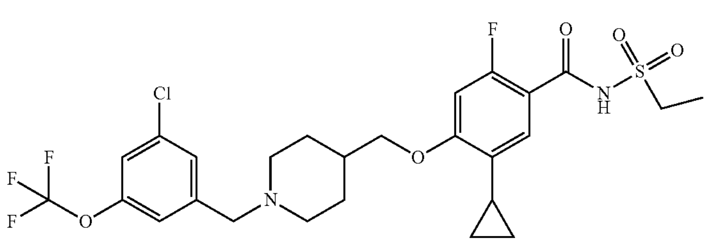 [SMILES: CCS(=O)(=O)NC(=O)c1cc(C2CC2)c(OCC2CCN(Cc3cc(Cl)cc(OC(F)(F)F)c3)CC2)cc1F] | 0.0048 | | |

TABLE 1-continued

| Example | Structure | Ligand Binding Assay (μM) | NaV1.7 EP (μM) | NaV1.5 EP (μM) |
|---|---|---|---|---|
| 262 | 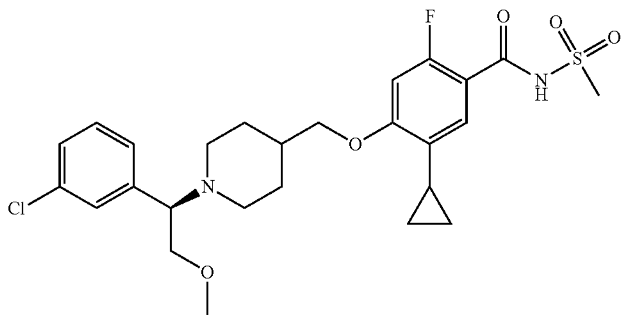 [SMILES: COC[C@@H](c1cccc(Cl)c1)N1CCC(COc2cc(F)c(C(=O)NS(C)(=O)=O)cc2C2CC2)CC1] | 0.018 | | |
| 263 | 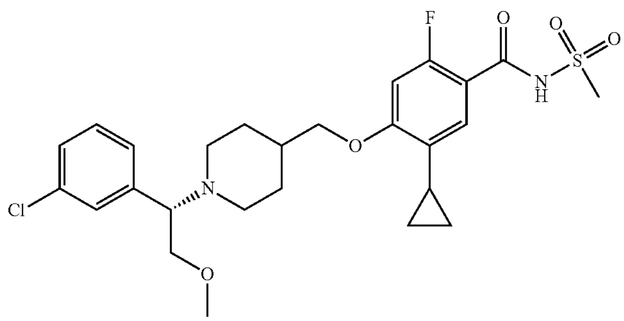 [SMILES: COC[C@H](c1cccc(Cl)c1)N1CCC(COc2cc(F)c(C(=O)NS(C)(=O)=O)cc2C2CC2)CC1] | 0.02 | | |
| 264 | 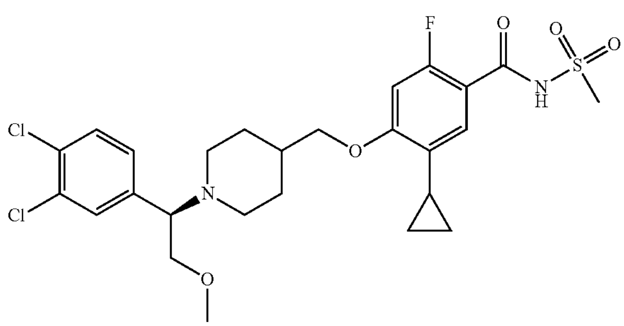 [SMILES: COC[C@@H](c1ccc(Cl)c(Cl)c1)N1CCC(COc2cc(F)c(C(=O)NS(C)(=O)=O)cc2C2CC2)CC1] | 0.0092 | | |
| 265 | 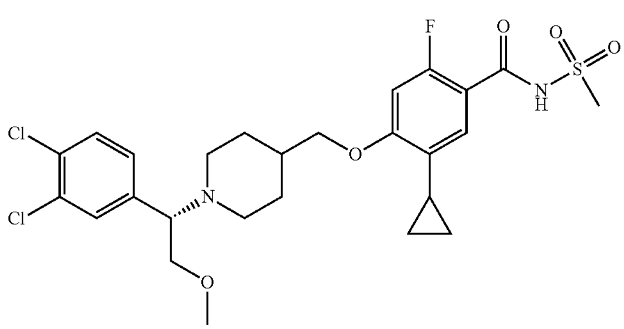 [SMILES: COC[C@H](c1ccc(Cl)c(Cl)c1)N1CCC(COc2cc(F)c(C(=O)NS(C)(=O)=O)cc2C2CC2)CC1] | 0.10 | | |

TABLE 1-continued
| Example | Structure | Ligand Binding Assay (μM) | NaV1.7 EP (μM) | NaV1.5 EP (μM) |
|---|---|---|---|---|
| 266 | 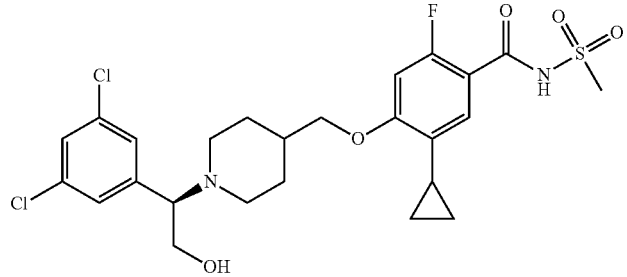 [SMILES: CS(=O)(=O)NC(=O)c1cc(C2CC2)c(OCC2CCN([C@@H](CO)c3cc(Cl)cc(Cl)c3)CC2)cc1F] | 0.091 | | |
| 267 | 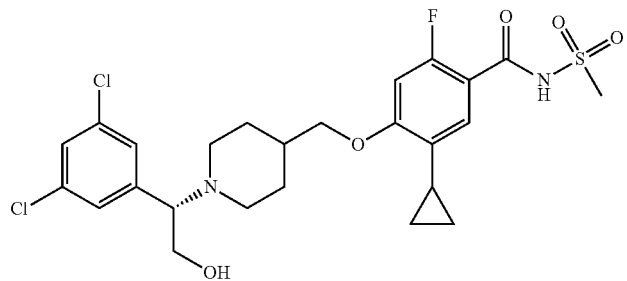 [SMILES: CS(=O)(=O)NC(=O)c1cc(C2CC2)c(OCC2CCN([C@H](CO)c3cc(Cl)cc(Cl)c3)CC2)cc1F] | 0.047 | | |
| 268 | 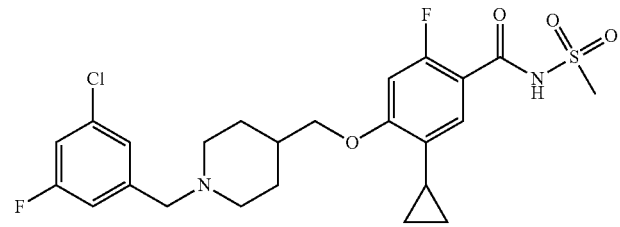 [SMILES: CS(=O)(=O)NC(=O)c1cc(C2CC2)c(OCC2CCN(Cc3cc(F)cc(Cl)c3)CC2)cc1F] | 0.006 | 0.0028 | |
| 269 | 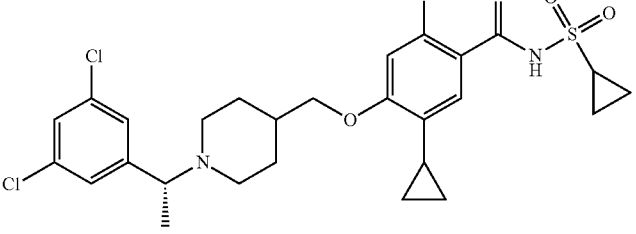 | 0.0034 | | |
| 270 | 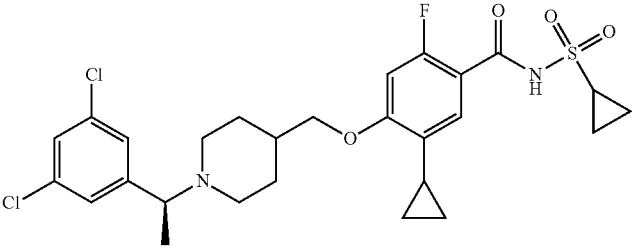 [SMILES: C[C@@H](c1cc(Cl)cc(Cl)c1)N1CCC(COc2cc(F)c(C(=O)NS(=O)(=O)C3CC3)cc2C2CC2)CC1] | 0.005 | 0.0058 | |

TABLE 1-continued
| Example | Structure | Ligand Binding Assay (μM) | NaV1.7 EP (μM) | NaV1.5 EP (μM) |
|---|---|---|---|---|
| 271 | 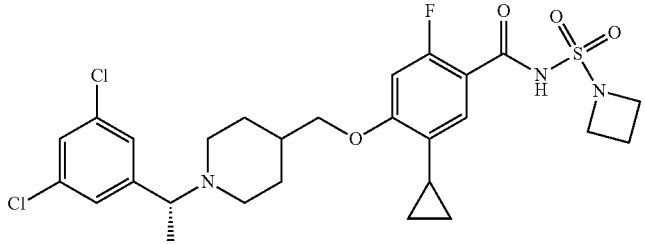 | 0.0037 | | |
| 272 | 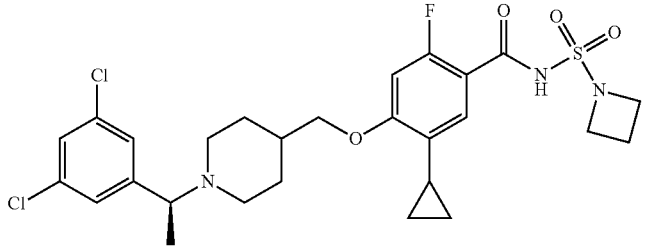 [SMILES: C[C@@H](c1cc(Cl)cc(Cl)c1)N1CCC(COc2cc(F)c(C(=O)NS(=O)(=O)N3CCC3)cc2C2CC2)CC1] | 0.0042 | | |
| 273 | 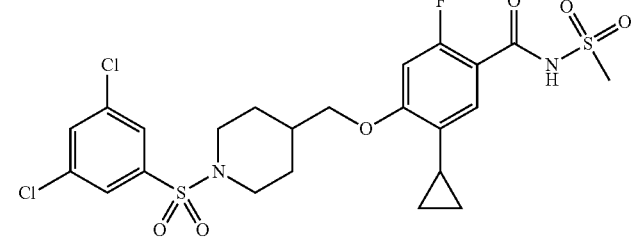 | 0.0085 | | |
| 274 | 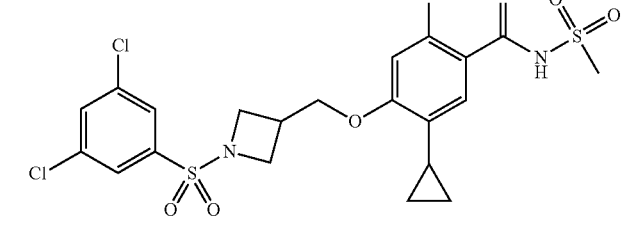 | 0.068 | | |
| 275 | 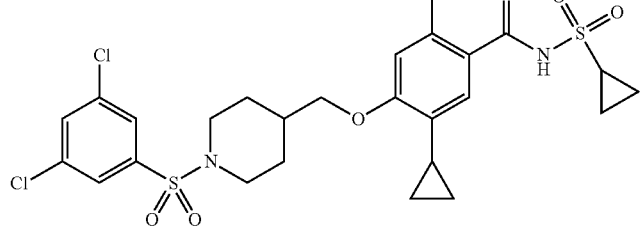 | 0.0069 | | |
| 276 | 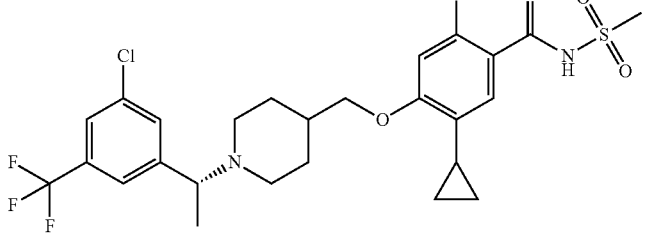 | 0.0057 | | |

TABLE 1-continued

| Example | Structure | Ligand Binding Assay (μM) | NaV1.7 EP (μM) | NaV1.5 EP (μM) |
| --- | --- | --- | --- | --- |
| 277 | 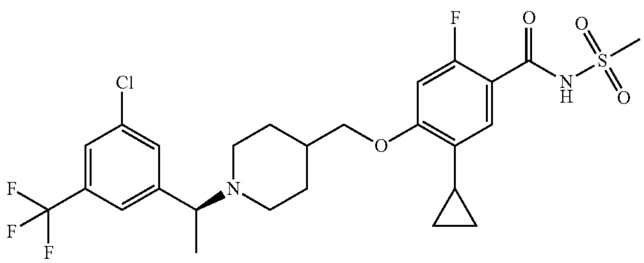 [SMILES: C[C@@H](c1cc(Cl)cc(C(F)(F)F)c1)N1CCC(COc2cc(F)c(C(=O)NS(C)(=O)=O)cc2C2CC2)CC1] | 0.004 | | |
| 278 | 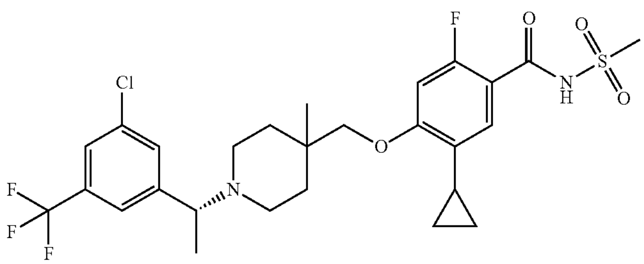 [SMILES: C[C@H](c1cc(Cl)cc(C(F)(F)F)c1)N1CCC(C)(COc2cc(F)c(C(=O)NS(C)(=O)=O)cc2C2CC2)CC1] | 0.0033 | | |
| 279 | 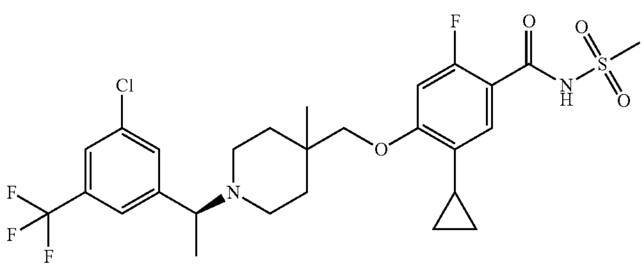 | 0.004 | | |
| 280 | 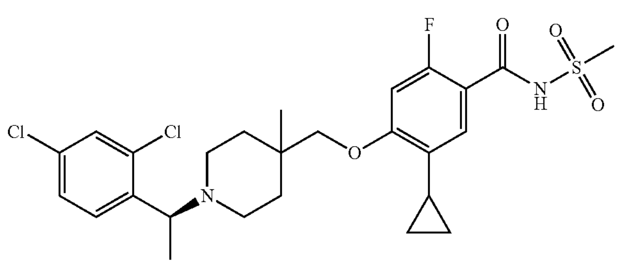 [SMILES: C[C@@H](c1ccc(Cl)cc1Cl)N1CCC(C)(COc2cc(F)c(C(=O)NS(C)(=O)=O)cc2C2CC2)CC1] | 0.0081 | | |
| 281 | 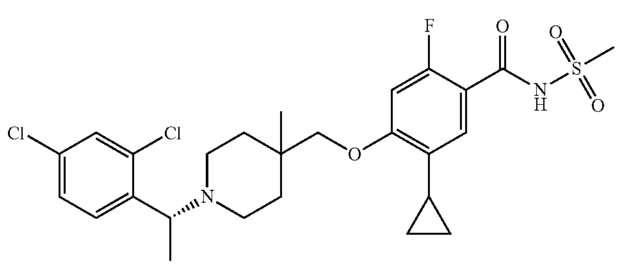 [SMILES: C[C@H](c1ccc(Cl)cc1Cl)N1CCC(C)(COc2cc(F)c(C(=O)NS(C)(=O)=O)cc2C2CC2)CC1] | 0.0047 | | |

TABLE 1-continued

| Example | Structure | Ligand Binding Assay (μM) | NaV1.7 EP (μM) | NaV1.5 EP (μM) |
|---|---|---|---|---|
| 282 | 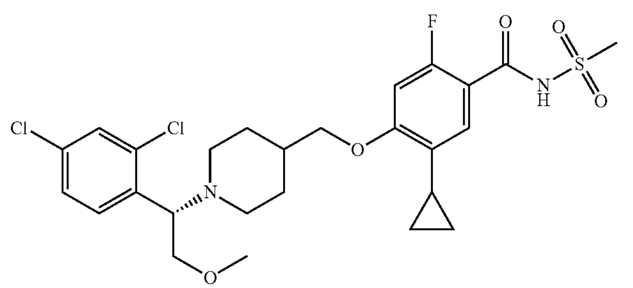 [SMILES: COC[C@H](c1ccc(Cl)cc1Cl)N1CCC(COc2cc(F)c(C(=O)NS(C)(=O)=O)cc2C2CC2)CC1] | 0.0044 | | |
| 283 | 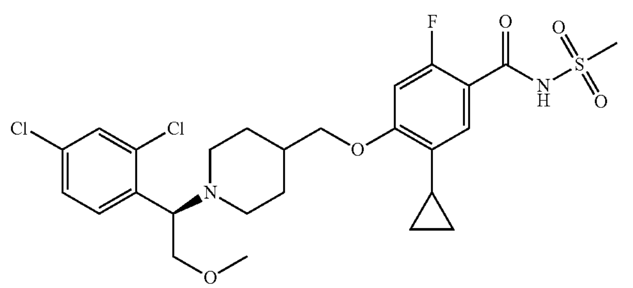 [SMILES: COC[C@@H](c1ccc(Cl)cc1Cl)N1CCC(COc2cc(F)c(C(=O)NS(C)(=O)=O)cc2C2CC2)CC1] | 0.004 | | |
| 284 | 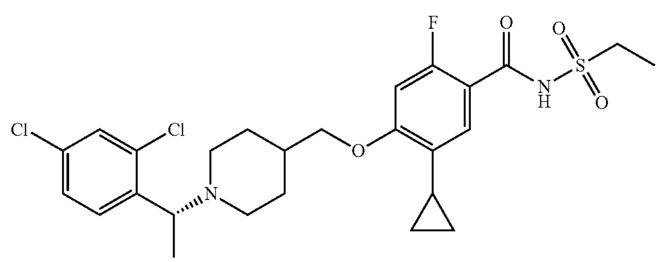 [SMILES: CCS(=O)(=O)NC(=O)c1cc(C2CC2)c(OCC2CCN([C@H](C)c3ccc(Cl)cc3Cl)CC2)cc1F] | 0.0036 | | |
| 285 | 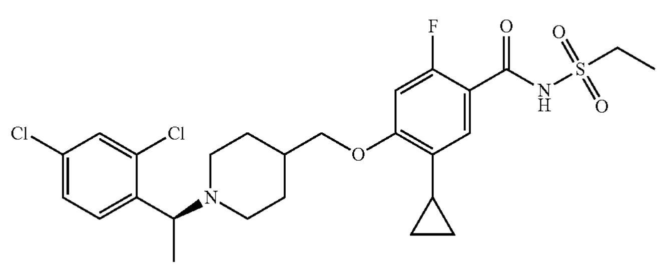 [SMILES: CCS(=O)(=O)NC(=O)c1cc(C2CC2)c(OCC2CCN([C@@H](C)c3ccc(Cl)cc3Cl)CC2)cc1F] | 0.0033 | | |
| 286 | 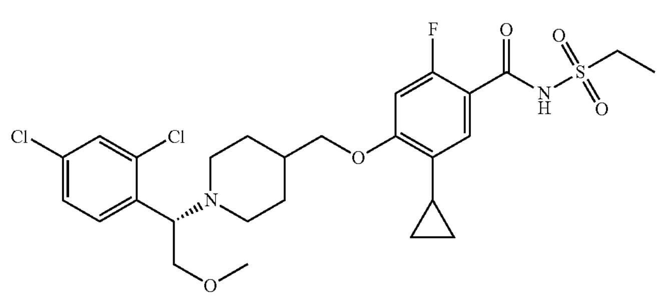 [SMILES: CCS(=O)(=O)NC(=O)c1cc(C2CC2)c(OCC2CCN([C@H](COC)c3ccc(Cl)cc3Cl)CC2)cc1F] | 0.0054 | | |

TABLE 1-continued

| Example | Structure | Ligand Binding Assay (μM) | NaV1.7 EP (μM) | NaV1.5 EP (μM) |
|---|---|---|---|---|
| 287 | 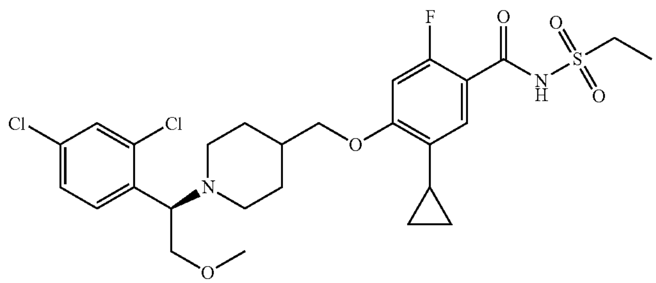 [SMILES: CCS(=O)(=O)NC(=O)c1cc(C2CC2)c(OCC2CCN([C@@H](COC)c3ccc(Cl)cc3Cl)CC2)cc1F] | 0.0035 | | |
| 288 | 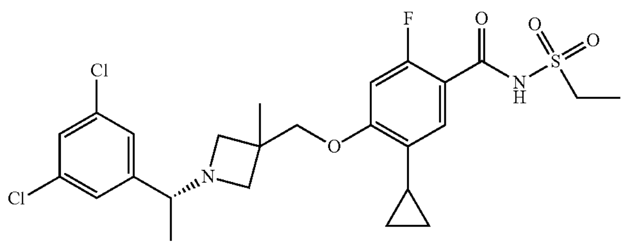 [SMILES: CCS(=O)(=O)NC(=O)c1cc(C2CC2)c(OCC2(C)CN([C@H](C)c3cc(Cl)cc(Cl)c3)C2)cc1F] | 0.0035 | | |
| 289 | 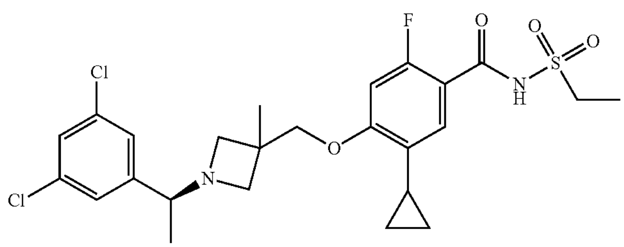 [SMILES: CCS(=O)(=O)NC(=O)c1cc(C2CC2)c(OCC2(C)CN([C@@H](C)c3cc(Cl)cc(Cl)c3)C2)cc1F] | 0.0035 | | |
| 290 | 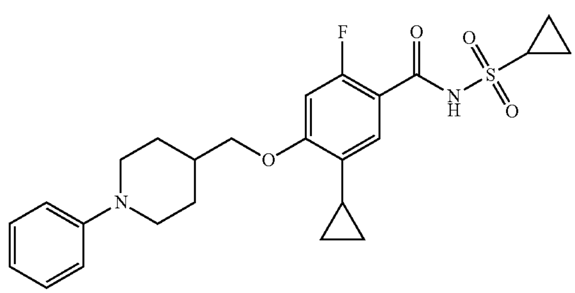 [SMILES: O=C(NS(=O)(=O)C1CC1)c1cc(C2CC2)c(OCC2CCN(c3ccccc3)CC2)cc1F] | 0.0048 | | |
| 291 | 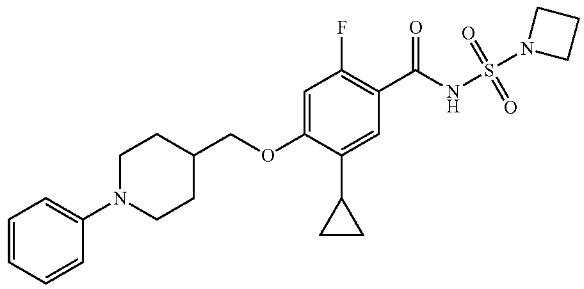 [SMILES: O=C(NS(=O)(=O)N1CCC1)c1cc(C2CC2)c(OCC2CCN(c3ccccc3)CC2)cc1F] | 0.011 | | |

TABLE 1-continued

| Example | Structure | Ligand Binding Assay (μM) | NaV1.7 EP (μM) | NaV1.5 EP (μM) |
|---|---|---|---|---|
| 292 | 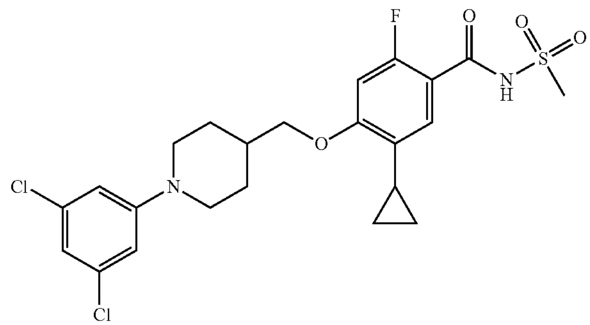 [SMILES: CS(=O)(=O)NC(=O)c1cc(C2CC2)c(OCC2CCN(c3cc(Cl)cc(Cl)c3)CC2)cc1F] | 0.0029 | | |
| 293 | 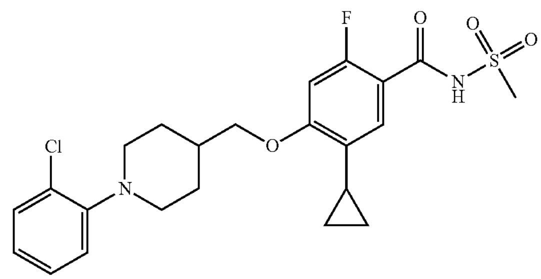 [SMILES: CS(=O)(=O)NC(=O)c1cc(C2CC2)c(OCC2CCN(c3ccccc3Cl)CC2)cc1F] | 0.0052 | | |
| 294 | 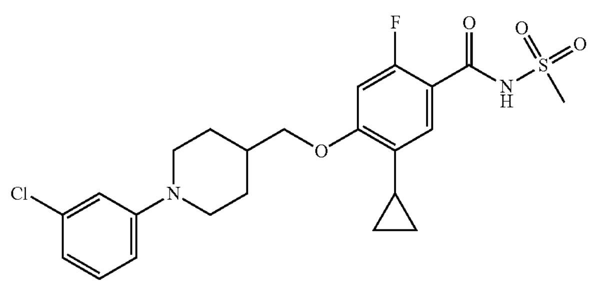 [SMILES: CS(=O)(=O)NC(=O)c1cc(C2CC2)c(OCC2CCN(c3cccc(Cl)c3)CC2)cc1F] | 0.0038 | | |
| 295 | 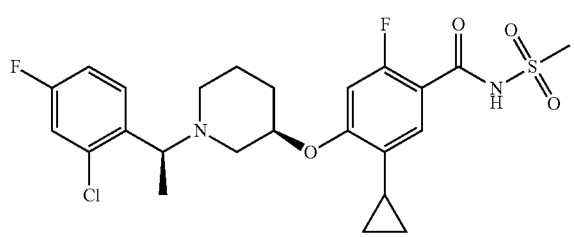 [SMILES: C[C@@H](c1ccc(F)cc1Cl)N1CCC[C@@H](Oc2cc(F)c(C(=O)NS(C)(=O)=O)cc2C2CC2)C1] | 0.0023 | | |
| 296 | 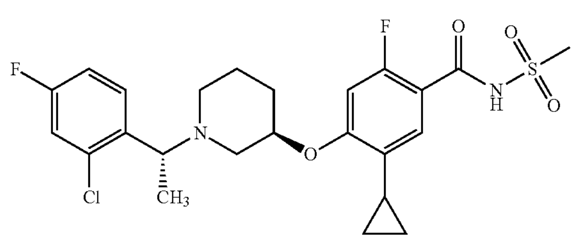 | 0.0081 | | |

TABLE 1-continued

| Example | Structure | Ligand Binding Assay (μM) | NaV1.7 EP (μM) | NaV1.5 EP (μM) |
|---|---|---|---|---|
| 297 | 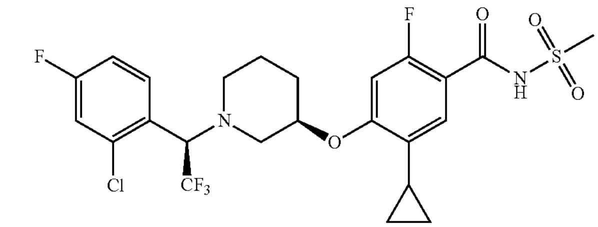 [SMILES: CS(=O)(=O)NC(=O)c1cc(C2CC2)c(O[C@@H]2CCCN([C@H](c3ccc(F)cc3Cl)C(F)(F)F)C2)cc1F] | 0.0108 | | |
| 298 | 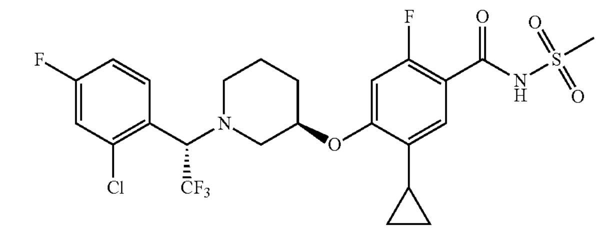 | 0.0046 | | |
| 299 | 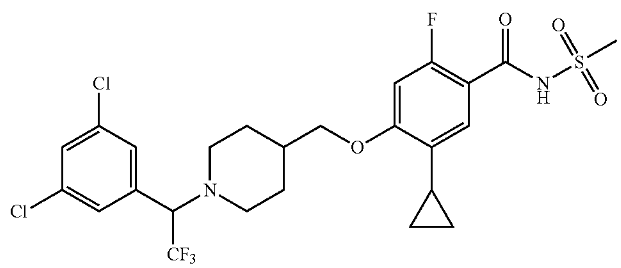 [SMILES: CS(=O)(=O)NC(=O)c1cc(C2CC2)c(OCC2CCN(C(c3cc(Cl)cc(Cl)c3)C(F)(F)F)CC2)cc1F] | 0.0019 | | |
| 300 | 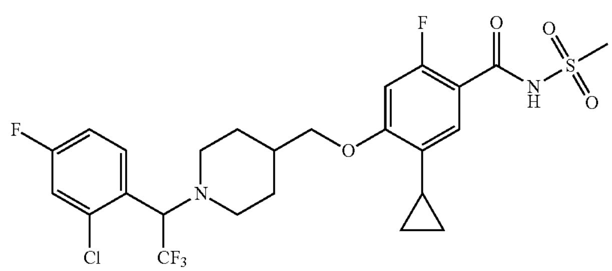 [SMILES: CS(=O)(=O)NC(=O)c1cc(C2CC2)c(OCC2CCN(C(c3ccc(F)cc3Cl)C(F)(F)F)CC2)cc1F] | 0.0016 | | |
| 301 | 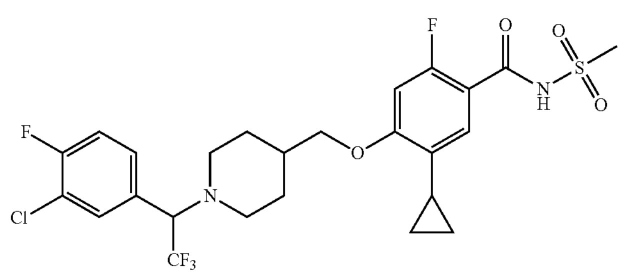 [SMILES: CS(=O)(=O)NC(=O)c1cc(C2CC2)c(OCC2CCN(C(c3ccc(F)c(Cl)c3)C(F)(F)F)CC2)cc1F] | 0.003 | | |
| 302 | 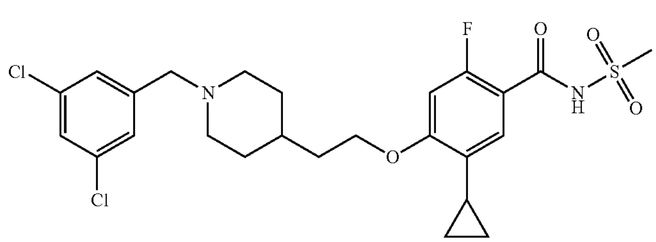 [SMILES: CS(=O)(=O)NC(=O)c1cc(C2CC2)c(OCCC2CCN(Cc3cc(Cl)cc(Cl)c3)CC2)cc1F] | 0.0057 | | |

TABLE 1-continued

| Example | Structure | Ligand Binding Assay (μM) | NaV1.7 EP (μM) | NaV1.5 EP (μM) |
|---|---|---|---|---|
| 303 | 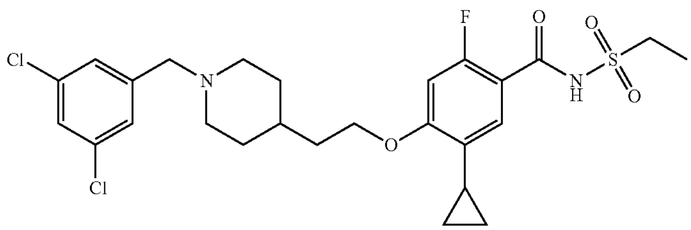 [SMILES: CCS(=O)(=O)NC(=O)c1cc(C2CC2)c(OCCC2CCN(Cc3cc(Cl)cc(Cl)c3)CC2)cc1F] | 0.0065 | | |
| 304 | 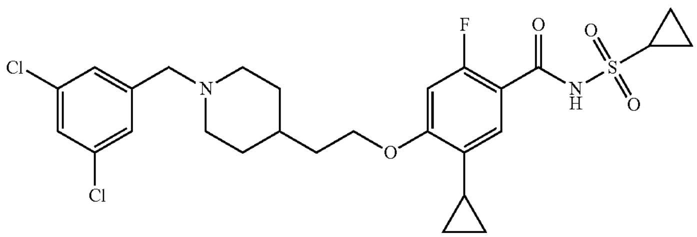 [SMILES: O=C(NS(=O)(=O)C1CC1)c1cc(C2CC2)c(OCCC2CCN(Cc3cc(Cl)cc(Cl)c3)CC2)cc1F] | 0.0037 | | |
| 305 | 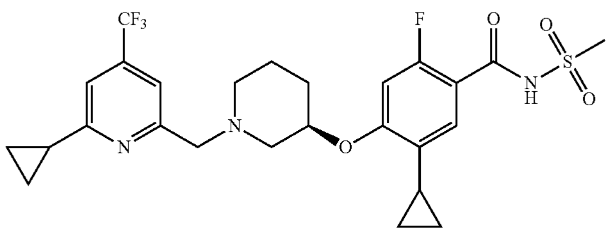 [SMILES: CS(=O)(=O)NC(=O)c1cc(C2CC2)c(O[C@@H]2CCCN(Cc3cc(C(F)(F)F)cc(C4CC4)n3)C2)cc1F] | 0.0039 | | |
| 306 | 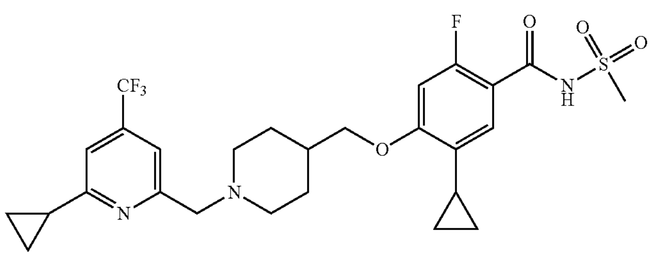 [SMILES: CS(=O)(=O)NC(=O)c1cc(C2CC2)c(OCC2CCN(Cc3cc(C(F)(F)F)cc(C4CC4)n3)CC2)cc1F] | 0.0060 | | |
| 307 | 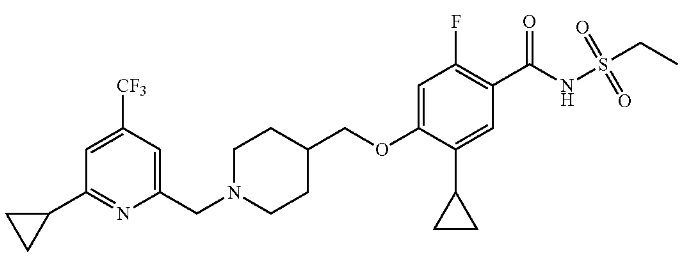 [SMILES: CCS(=O)(=O)NC(=O)c1cc(C2CC2)c(OCC2CCN(Cc3cc(C(F)(F)F)cc(C4CC4)n3)CC2)cc1F] | 0.0067 | | |
| 308 | 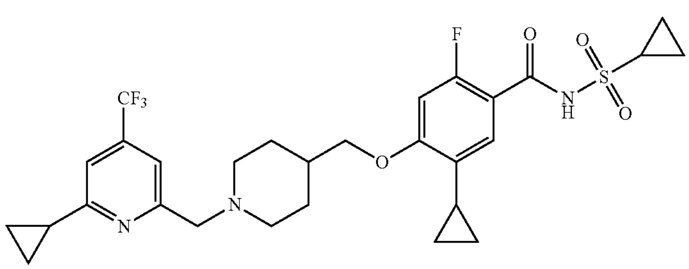 [SMILES: O=C(NS(=O)(=O)C1CC1)c1cc(C2CC2)c(OCC2CCN(Cc3cc(C(F)(F)F)cc(C4CC4)n3)CC2)cc1F] | 0.0060 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 309 | 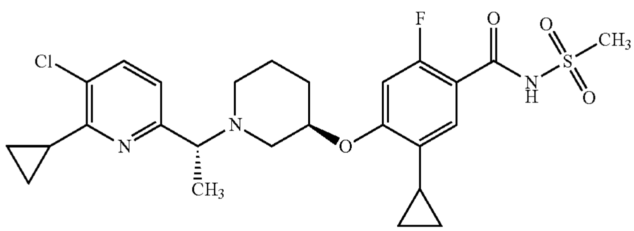 [SMILES: C[C@H](c1ccc(Cl)c(C2CC2)n1)N1CCC[C@@H](Oc2cc(F)c(C(=O)NS(C)(=O)=O)cc2C2CC2)C1] | 0.0027 | 0.003 | 0.38 |
| 310 | 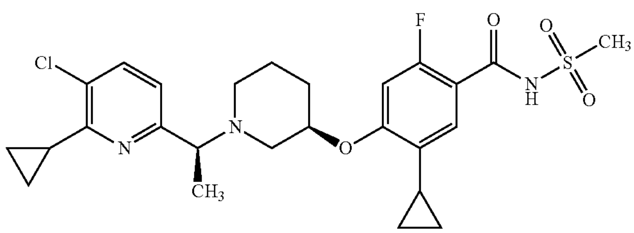 [SMILES: C[C@@H](c1ccc(Cl)c(C2CC2)n1)N1CCC[C@@H](Oc2cc(F)c(C(=O)NS(C)(=O)=O)cc2C2CC2)C1] | 0.0023 | | |
| 311 | 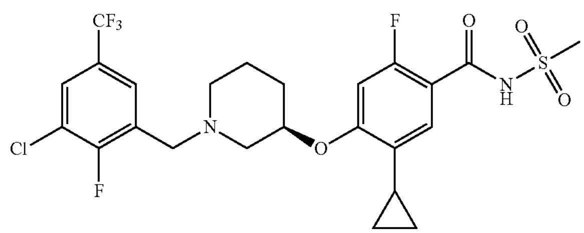 [SMILES: CS(=O)(=O)NC(=O)c1cc(C2CC2)c(O[C@@H]2CCCN(Cc3cc(C(F)(F)F)cc(Cl)c3F)C2)cc1F] | 0.0029 | | |
| 312 | 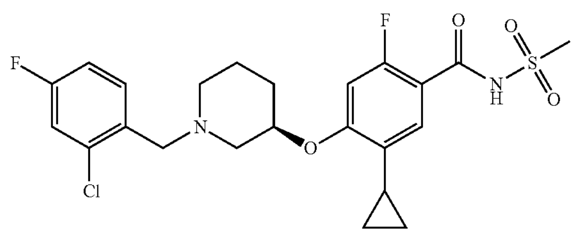 [SMILES: CS(=O)(=O)NC(=O)c1cc(C2CC2)c(O[C@@H]2CCCN(Cc3ccc(F)cc3Cl)C2)cc1F] | 0.0022 | <0.001 | 0.31 |
| 313 | 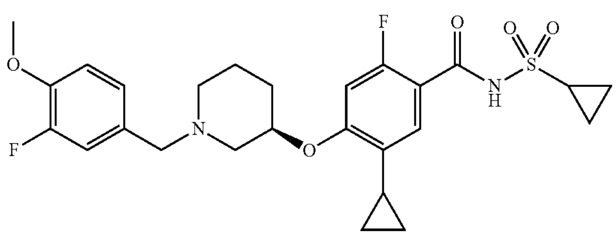 [SMILES: COc1ccc(CN2CCC[C@@H](Oc3cc(F)c(C(=O)NS(=O)(=O)C4CC4)cc3C3CC3)C2)cc1F] | 0.0091 | | |
| 314 | 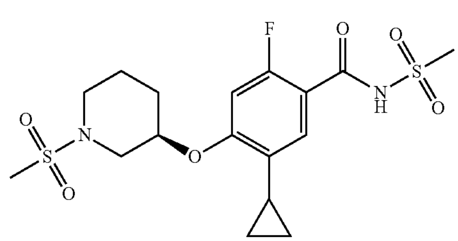 | >10 | | |

TABLE 1-continued

| Example | Structure | Ligand Binding Assay (μM) | NaV1.7 EP (μM) | NaV1.5 EP (μM) |
|---|---|---|---|---|
| 315 | 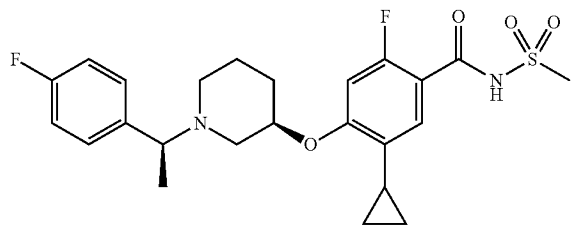 [SMILES: C[C@@H](c1ccc(F)cc1)N1CCC[C@@H](Oc2cc(F)c(C(=O)NS(C)(=O)=O)cc2C2CC2)C1] | 0.0191 | | |
| 316 | 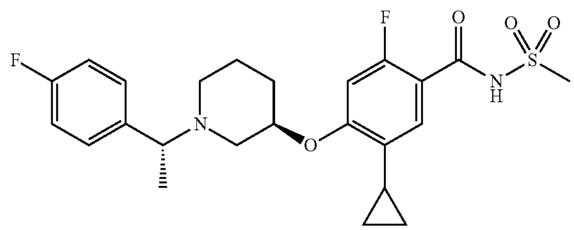 [SMILES: C[C@H](c1ccc(F)cc1)N1CCC[C@@H](Oc2cc(F)c(C(=O)NS(C)(=O)=O)cc2C2CC2)C1] | 0.0372 | | |
| 317 | 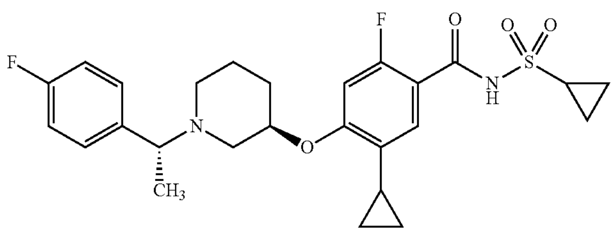 [SMILES: C[C@H](c1ccc(F)cc1)N1CCC[C@@H](Oc2cc(F)c(C(=O)NS(=O)(=O)C3CC3)cc2C2CC2)C1] | 0.0060 | | |
| 318 | 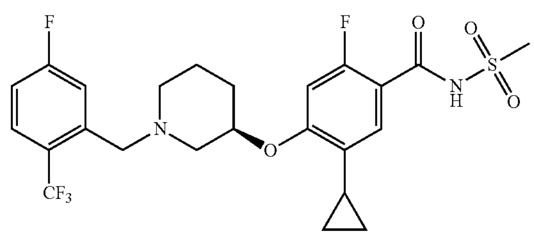 [SMILES: CS(=O)(=O)NC(=O)c1cc(C2CC2)c(O[C@@H]2CCCN(Cc3cc(F)ccc3C(F)(F)F)C2)cc1F] | 0.0026 | | |
| 319 | 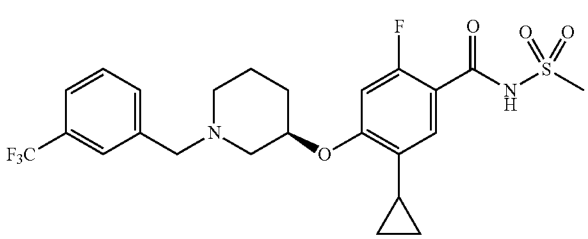 [SMILES: CS(=O)(=O)NC(=O)c1cc(C2CC2)c(O[C@@H]2CCCN(Cc3cccc(C(F)(F)F)c3)C2)cc1F] | 0.0054 | | |
| 320 | 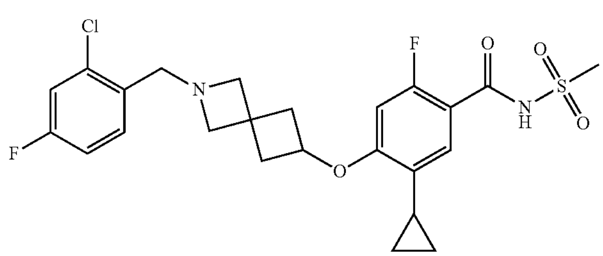 [SMILES: CS(=O)(=O)NC(=O)c1cc(C2CC2)c(OC2CC3(C2)CN(Cc2ccc(F)cc2Cl)C3)cc1F] | 0.2133 | | |

TABLE 1-continued
| Example | Structure | Ligand Binding Assay (μM) | NaV1.7 EP (μM) | NaV1.5 EP (μM) |
|---|---|---|---|---|
| 321 | 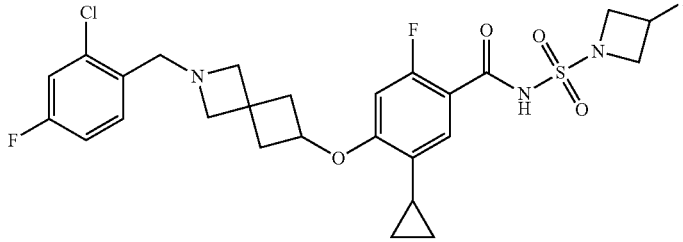 | 0.1907 | | |
| 322 | 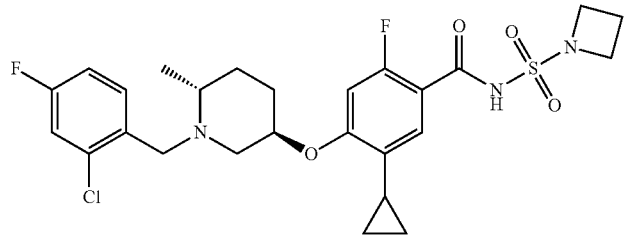 [SMILES: C[C@@H]1CC[C@@H](Oc2cc(F)c(C(=O)NS(=O)(=O)N3CCC3)cc2C2CC2)CN1Cc1ccc(F)cc1Cl] | 0.0019 | | |
| 323 | 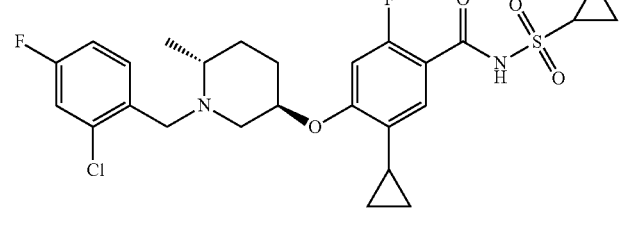 | 0.0019 | | |
| 324 | 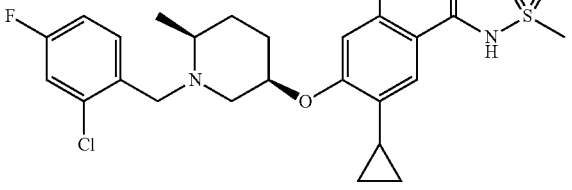 | 0.0027 | | |
| 325 | 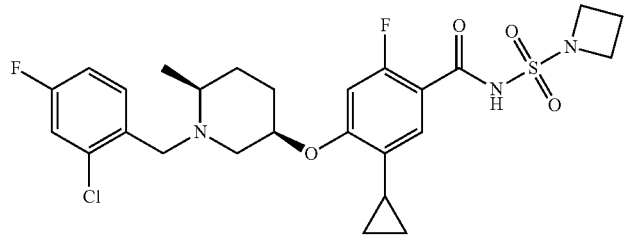 [SMILES: C[C@H]1CC[C@@H](Oc2cc(F)c(C(=O)NS(=O)(=O)N3CCC3)cc2C2CC2)CN1Cc1ccc(F)cc1Cl] | 0.0024 | | |
| 326 | 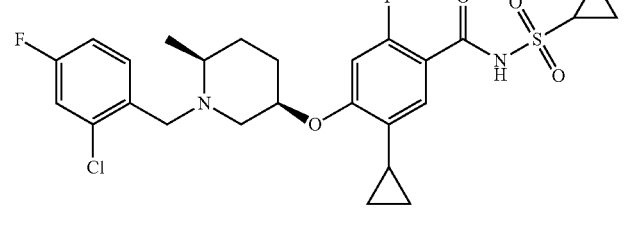 | 0.0029 | | |

TABLE 1-continued

| Example | Structure | Ligand Binding Assay (μM) | NaV1.7 EP (μM) | NaV1.5 EP (μM) |
|---|---|---|---|---|
| 327 | 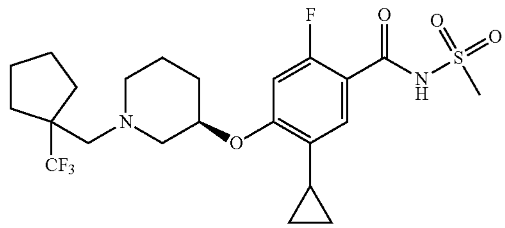 [SMILES: CS(=O)(=O)NC(=O)c1cc(C2CC2)c(O[C@@H]2CCCN(CC3(C(F)(F)F)CCCC3)C2)cc1F] | 0.0027 | | |
| 328 | 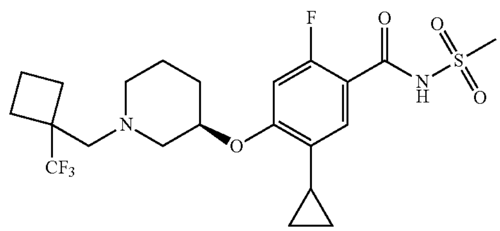 [SMILES: CS(=O)(=O)NC(=O)c1cc(C2CC2)c(O[C@@H]2CCCN(CC3(C(F)(F)F)CCC3)C2)cc1F] | 0.0064 | | |
| 329 | 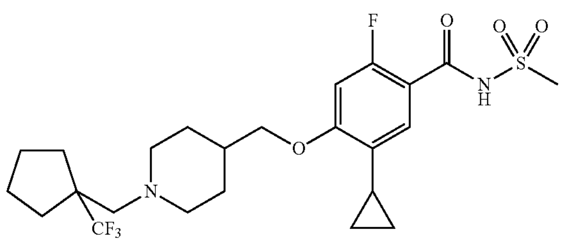 [SMILES: CS(=O)(=O)NC(=O)c1cc(C2CC2)c(OCC2CCN(CC3(C(F)(F)F)CCCC3)CC2)cc1F] | 0.0033 | | |
| 330 | 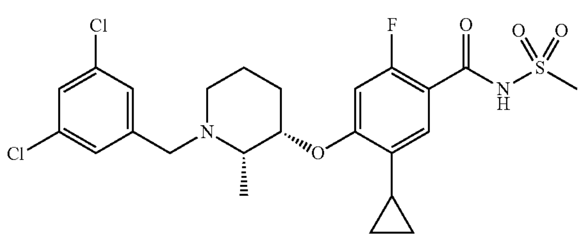 [SMILES: C[C@H]1[C@@H](Oc2cc(F)c(C(=O)NS(C)(=O)=O)cc2C2CC2)CCCN1Cc1cc(Cl)cc(Cl)c1] | 0.0319 | | |
| 331 | 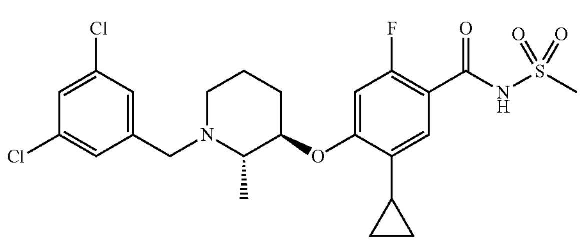 [SMILES: C[C@H]1[C@H](Oc2cc(F)c(C(=O)NS(C)(=O)=O)cc2C2CC2)CCCN1Cc1cc(Cl)cc(Cl)c1] | 0.0322 | | |

TABLE 1-continued
| Example | Structure | Ligand Binding Assay (μM) | NaV1.7 EP (μM) | NaV1.5 EP (μM) |
|---|---|---|---|---|
| 332 | 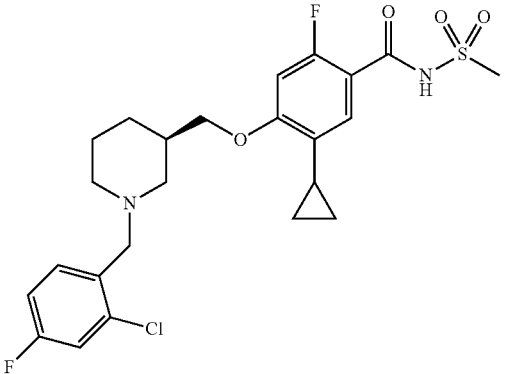 [SMILES: CS(=O)(=O)NC(=O)c1cc(C2CC2)c(OC[C@@H]2CCCN(Cc3ccc(F)cc3Cl)C2)cc1F] | 0.0352 | | |
| 333 | 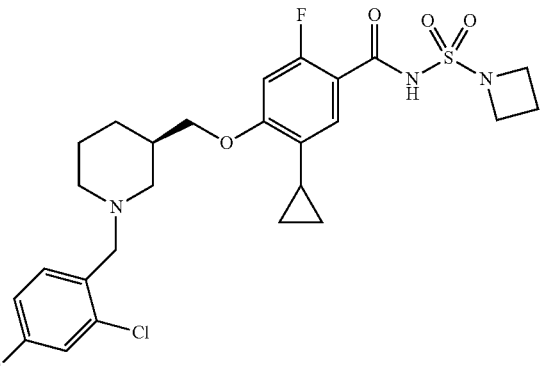 | 0.0207 | | |
| 334 | 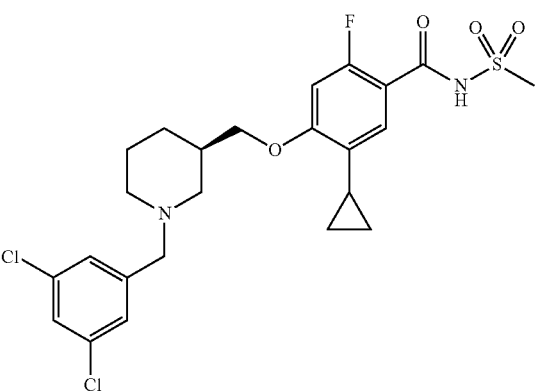 [SMILES: CS(=O)(=O)NC(=O)c1cc(C2CC2)c(OC[C@@H]2CCCN(Cc3cc(Cl)cc(Cl)c3)C2)cc1F] | 0.0071 | | |
| 335 | 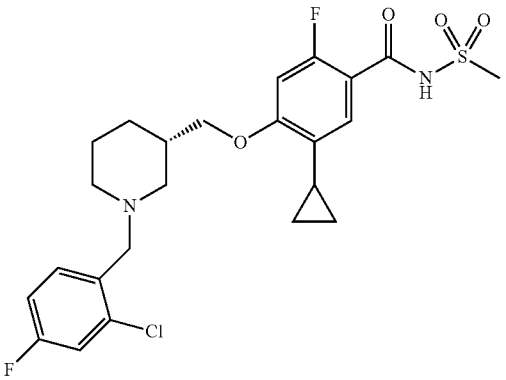 [SMILES: CS(=O)(=O)NC(=O)c1cc(C2CC2)c(OC[C@H]2CCCN(Cc3ccc(F)cc3Cl)C2)cc1F] | 0.0143 | | |

TABLE 1-continued
| Example | Structure | Ligand Binding Assay (μM) | NaV1.7 EP (μM) | NaV1.5 EP (μM) |
|---|---|---|---|---|
| 336 | 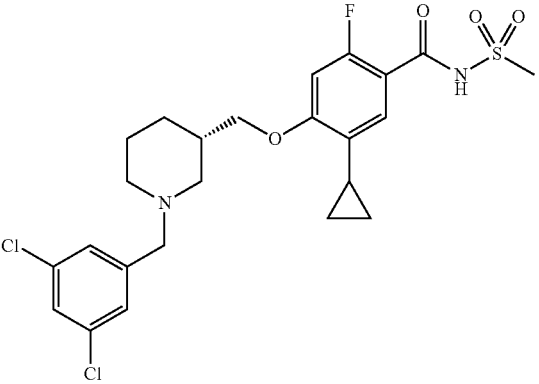 [SMILES: CS(=O)(=O)NC(=O)c1cc(C2CC2)c(OC[C@H]2CCCN(Cc3cc(Cl)cc(Cl)c3)C2)cc1F] | 0.0049 | | |
| 337 | 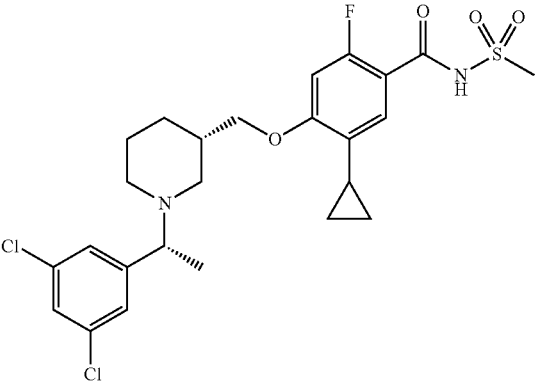 [SMILES: C[C@H](c1cc(Cl)cc(Cl)c1)N1CCC[C@H](COc2cc(F)c(C(=O)NS(C)(=O)=O)cc2C2CC2)C1] | 0.01108 | | |
| 338 | 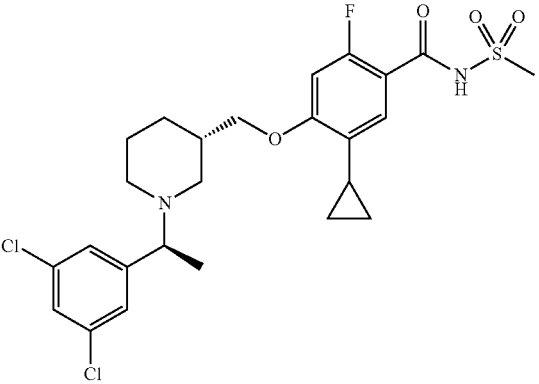 [SMILES: C[C@@H](c1cc(Cl)cc(Cl)c1)N1CCC[C@H](COc2cc(F)c(C(=O)NS(C)(=O)=O)cc2C2CC2)C1] | 0.0074 | | |
| 339 | 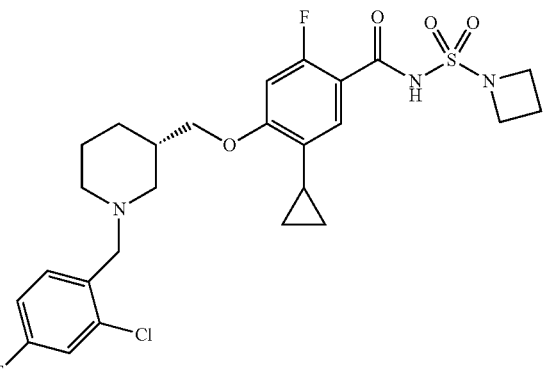 | 0.0165 | | |

TABLE 1-continued
| Example | Structure | Ligand Binding Assay (μM) | NaV1.7 EP (μM) | NaV1.5 EP (μM) |
|---|---|---|---|---|
| 340 | 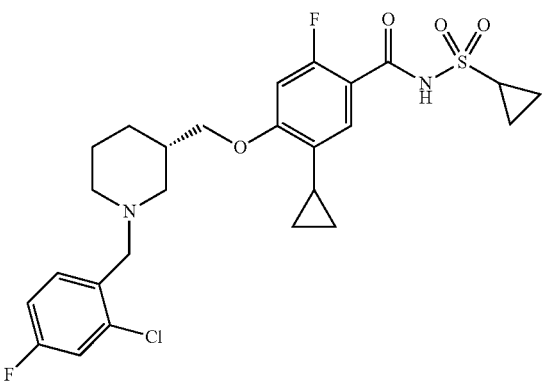 [SMILES: O=C(NS(=O)(=O)C1CC1)c1cc(C2CC2)c(OC[C@H]2CCCN(Cc3ccc(F)cc3Cl)C2)cc1F] | 0.0047 | | |
| 341 | 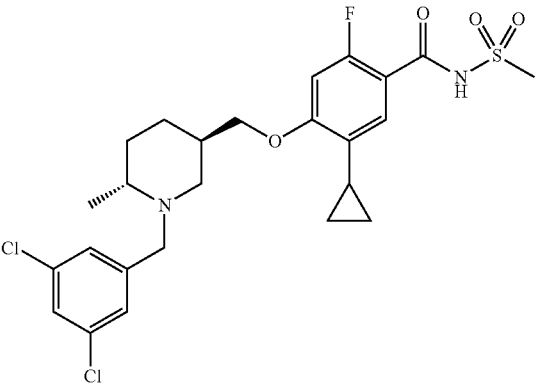 [SMILES: C[C@@H]1CC[C@@H](COc2cc(F)c(C(=O)NS(C)(=O)=O)cc2C2CC2)CN1Cc1cc(Cl)cc(Cl)c1] | 0.0044 | | |
| 342 | 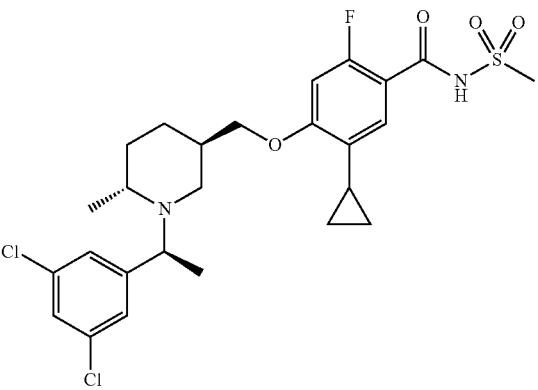 [SMILES: C[C@@H]1CC[C@@H](COc2cc(F)c(C(=O)NS(C)(=O)=O)cc2C2CC2)CN1[C@@H](C)c1cc(Cl)cc(Cl)c1] | 0.0057 | | |

TABLE 1-continued

| Example | Structure | Ligand Binding Assay (μM) | NaV1.7 EP (μM) | NaV1.5 EP (μM) |
|---|---|---|---|---|
| 343 | 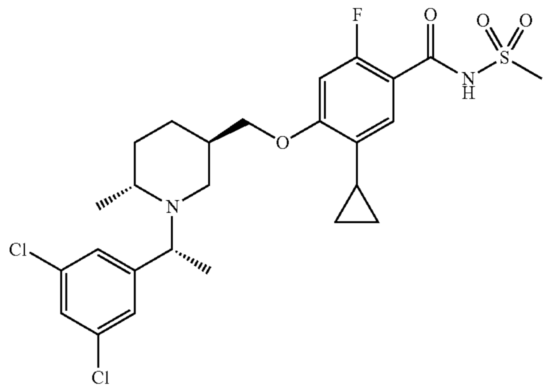 [SMILES: C[C@@H]1CC[C@@H](COc2cc(F)c(C(=O)NS(C)(=O)=O)cc2C2CC2)CN1[C@H](C)c1cc(Cl)cc(Cl)c1] | 0.0084 | | |
| 344 | 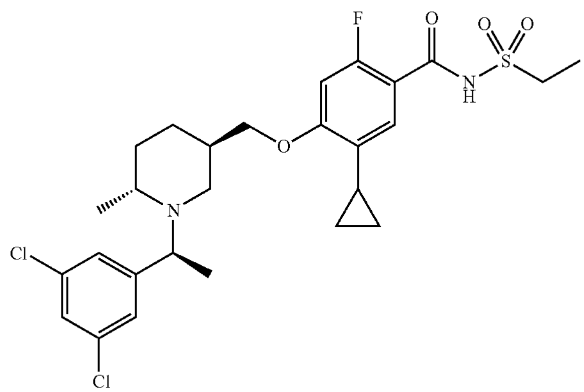 [SMILES: CCS(=O)(=O)NC(=O)c1cc(C2CC2)c(OC[C@@H]2CC[C@@H](C)N([C@@H](C)c3cc(Cl)cc(Cl)c3)C2)cc1F] | 0.0069 | | |
| 345 | 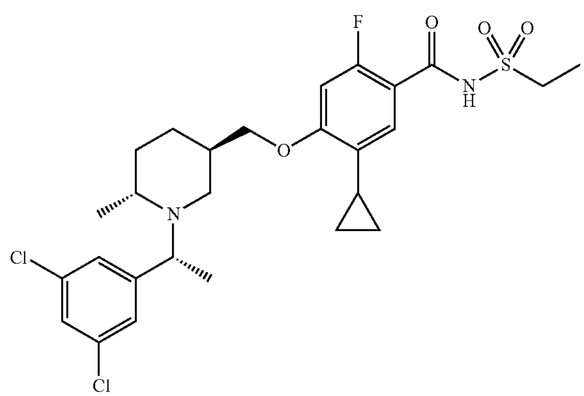 [SMILES: CCS(=O)(=O)NC(=O)c1cc(C2CC2)c(OC[C@@H]2CC[C@@H](C)N([C@H](C)c3cc(Cl)cc(Cl)c3)C2)cc1F] | 0.0078 | | |
| 346 | 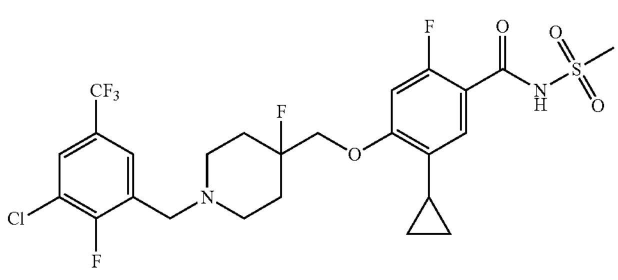 [SMILES: CS(=O)(=O)NC(=O)c1cc(C2CC2)c(OCC2(F)CCN(Cc3cc(C(F)(F)F)cc(Cl)c3F)CC2)cc1F] | 0.0044 | 0.0022 | 682 |

TABLE 1-continued
| Example | Structure | Ligand Binding Assay (μM) | NaV1.7 EP (μM) | NaV1.5 EP (μM) |
|---|---|---|---|---|
| 347 | 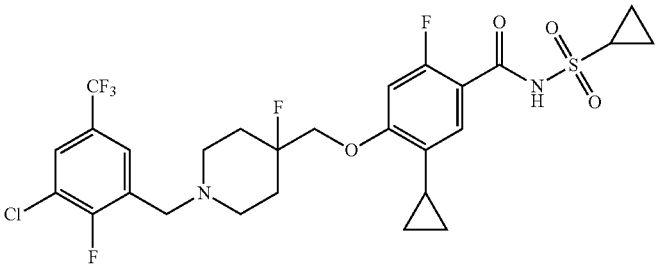 [SMILES: O=C(NS(=O)(=O)C1CC1)c1cc(C2CC2)c(OCC2(F)CCN(Cc3cc(C(F)(F)F)cc(Cl)c3F)CC2)cc1F] | 0.0063 | | |
| 348 | 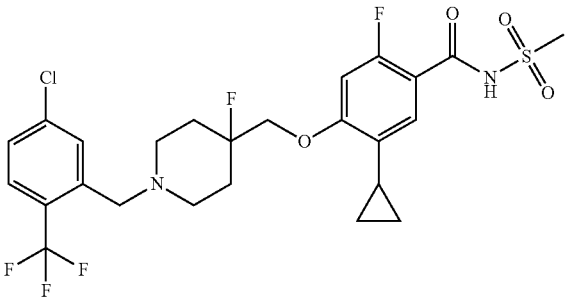 [SMILES: CS(=O)(=O)NC(=O)c1cc(C2CC2)c(OCC2(F)CCN(Cc3cc(Cl)ccc3C(F)(F)F)CC2)cc1F] | 0.0045 | | |
| 349 | 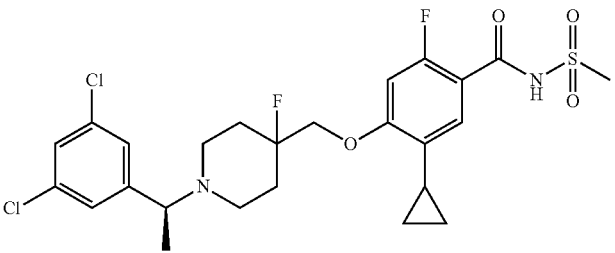 [SMILES: C[C@@H](c1cc(Cl)cc(Cl)c1)N1CCC(F)(COc2cc(F)c(C(=O)NS(C)(=O)=O)cc2C2CC2)CC1] | 0.0040 | | |
| 350 | 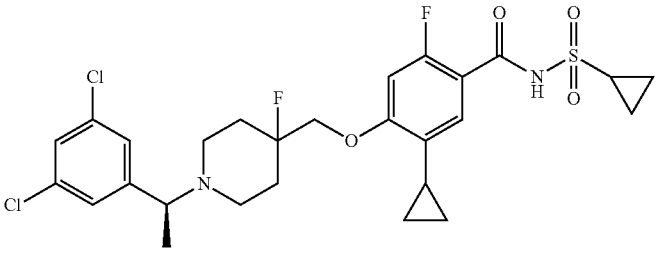 [SMILES: C[C@@H](c1cc(Cl)cc(Cl)c1)N1CCC(F)(COc2cc(F)c(C(=O)NS(=O)(=O)C3CC3)cc2C2CC2)CC1] | 0.0045 | | |
| 351 | 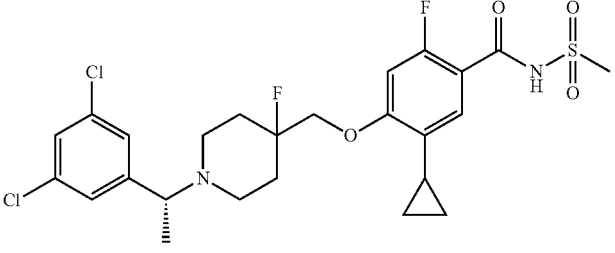 [SMILES: C[C@H](c1cc(Cl)cc(Cl)c1)N1CCC(F)(COc2cc(F)c(C(=O)NS(C)(=O)=O)cc2C2CC2)CC1] | 0.0053 | | |

TABLE 1-continued

| Example | Structure | Ligand Binding Assay (μM) | NaV1.7 EP (μM) | NaV1.5 EP (μM) |
|---|---|---|---|---|
| 352 | 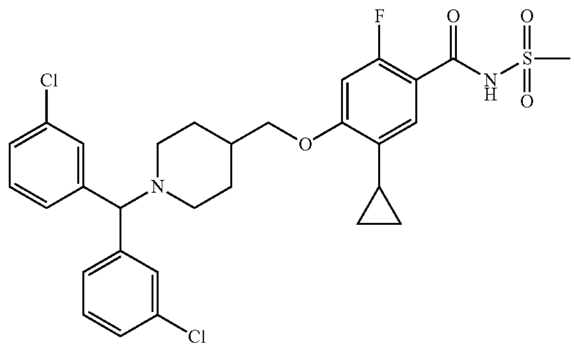 [SMILES: CS(=O)(=O)NC(=O)c1cc(C2CC2)c(OCC2CCN(C(c3cccc(Cl)c3)c3cccc(Cl)c3)CC2)cc1F] | 0.0020 | | |
| 353 | 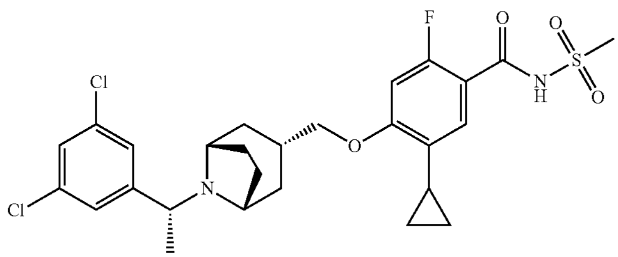 [SMILES: C[C@H](c1cc(Cl)cc(Cl)c1)N1[C@@H]2CC[C@H]1C[C@H](COc1cc(F)c(C(=O)NS(C)(=O)=O)cc1C1CC1)C2] | 0.011 | | |
| 354 | 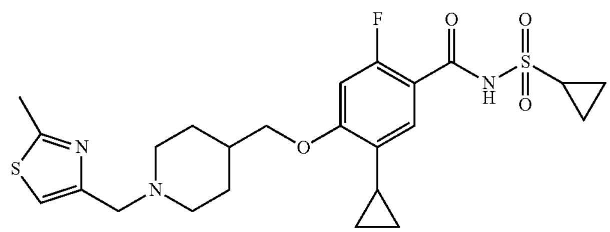 [SMILES: Cc1nc(CN2CCC(COc3cc(F)c(C(=O)NS(=O)(=O)C4CC4)cc3C3CC3)CC2)cs1] | 2.6695 | | |
| 355 | 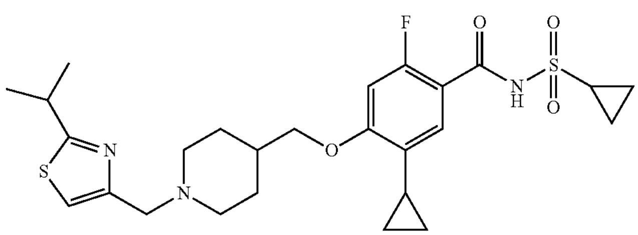 [SMILES: CC(C)c1nc(CN2CCC(COc3cc(F)c(C(=O)NS(=O)(=O)C4CC4)cc3C3CC3)CC2)cs1] | 0.11876 | | |
| 356 | 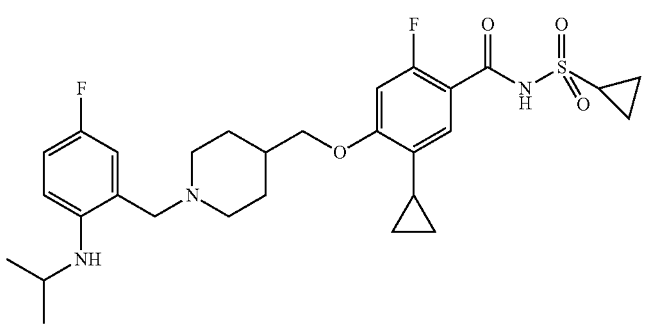 [SMILES: CC(C)Nc1ccc(F)cc1CN1CCC(COc2cc(F)c(C(=O)NS(=O)(=O)C3CC3)cc2C2CC2)CC1] | 0.0058 | | |

TABLE 1-continued

| Example | Structure | Ligand Binding Assay (μM) | NaV1.7 EP (μM) | NaV1.5 EP (μM) |
|---|---|---|---|---|
| 357 | 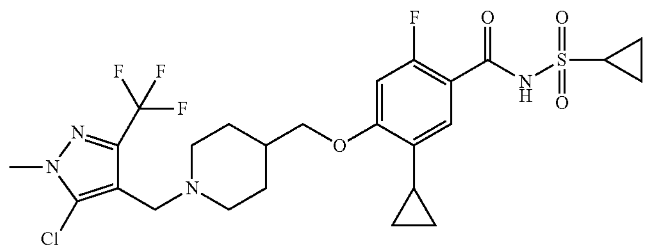 [SMILES: Cn1nc(C(F)(F)F)c(CN2CCC(COc3cc(F)c(C(=O)NS(=O)(=O)C4CC4)cc3C3CC3)CC2)c1Cl] | 0.0130 | | |
| 358 | 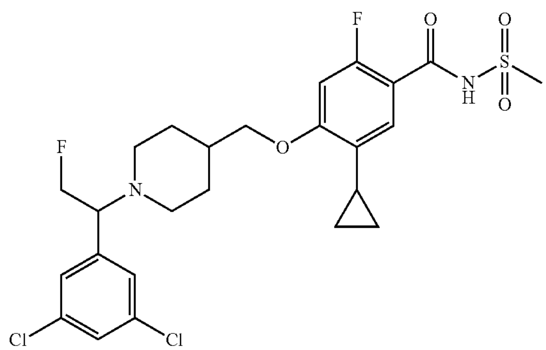 [SMILES: CS(=O)(=O)NC(=O)c1cc(C2CC2)c(OCC2CCN(C(CF)c3cc(Cl)cc(Cl)c3)CC2)cc1F] | 0.0140 | | |
| 359 | 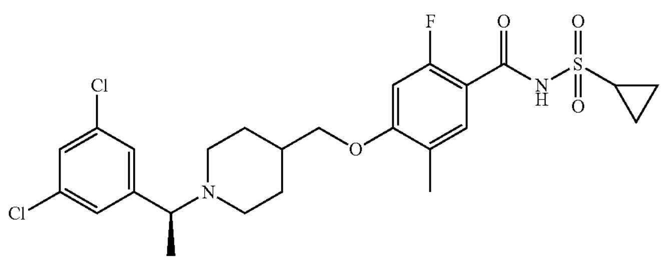 [SMILES: Cc1cc(C(=O)NS(=O)(=O)C2CC2)c(F)cc1OCC1CCN([C@@H](C)c2cc(Cl)cc(Cl)c2)CC1] | 0.0114 | | |
| 360 | 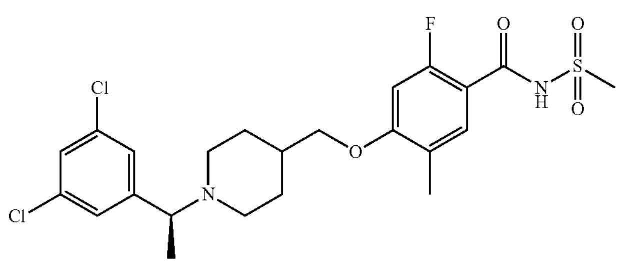 [SMILES: Cc1cc(C(=O)NS(C)(=O)=O)c(F)cc1OCC1CCN([C@@H](C)c2cc(Cl)cc(Cl)c2)CC1] | 0.0128 | | |
| 361 | 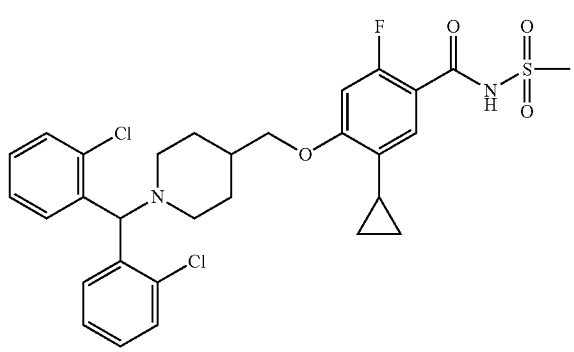 [SMILES: CS(=O)(=O)NC(=O)c1cc(C2CC2)c(OCC2CCN(C(c3ccccc3Cl)c3ccccc3Cl)CC2)cc1F] | 0.0020 | | |

TABLE 1-continued

| Example | Structure | Ligand Binding Assay (μM) | NaV1.7 EP (μM) | NaV1.5 EP (μM) |
|---|---|---|---|---|
| 362 | 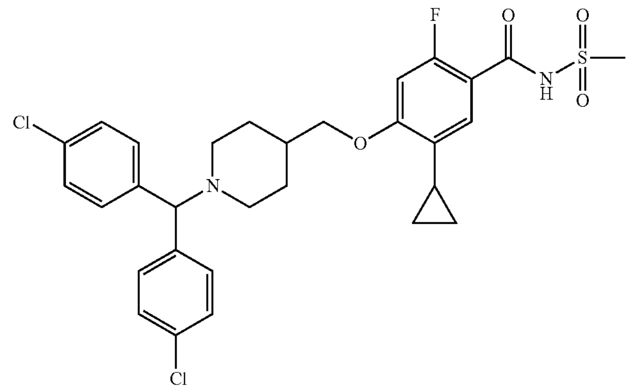 [SMILES: CS(=O)(=O)NC(=O)c1cc(C2CC2)c(OCC2CCN(C(c3ccc(Cl)cc3)c3ccc(Cl)cc3)CC2)cc1F] | 0.0029 | | |
| 363 | 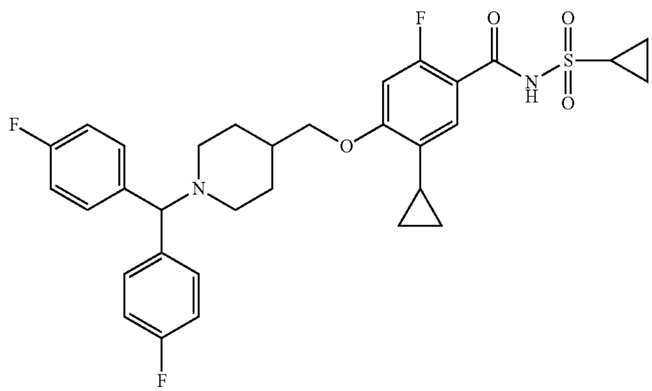 [SMILES: O=C(NS(=O)(=O)C1CC1)c1cc(C2CC2)c(OCC2CCN(C(c3ccc(F)cc3)c3ccc(F)cc3)CC2)cc1F] | 0.0058 | | |
| 364 | 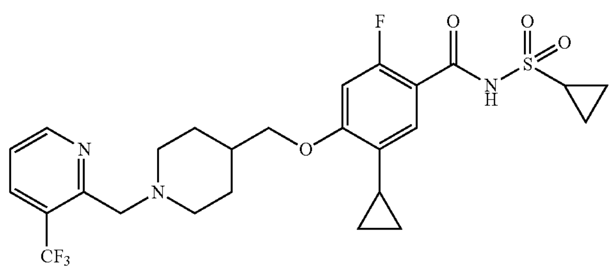 [SMILES: O=C(NS(=O)(=O)C1CC1)c1cc(C2CC2)c(OCC2CCN(Cc3ncccc3C(F)(F)F)CC2)cc1F] | 0.0806 | | |
| 365 | 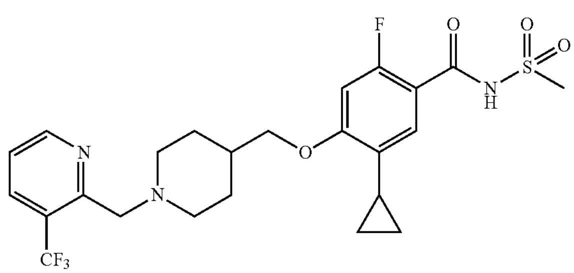 [SMILES: CS(=O)(=O)NC(=O)c1cc(C2CC2)c(OCC2CCN(Cc3ncccc3C(F)(F)F)CC2)cc1F] | 0.3272 | | |
| 366 | 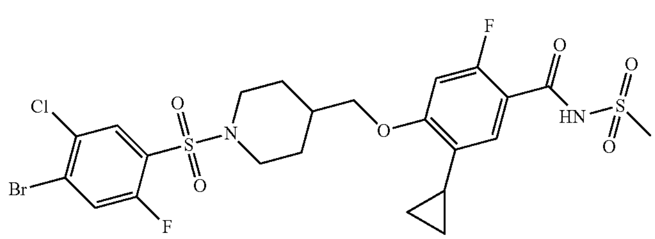 [SMILES: CS(=O)(=O)NC(=O)c1cc(C2CC2)c(OCC2CCN(S(=O)(=O)c3cc(Cl)c(Br)cc3F)CC2)cc1F] | 0.0091 | | |

TABLE 1-continued

| Example | Structure | Ligand Binding Assay (μM) | NaV1.7 EP (μM) | NaV1.5 EP (μM) |
|---|---|---|---|---|
| 367 | 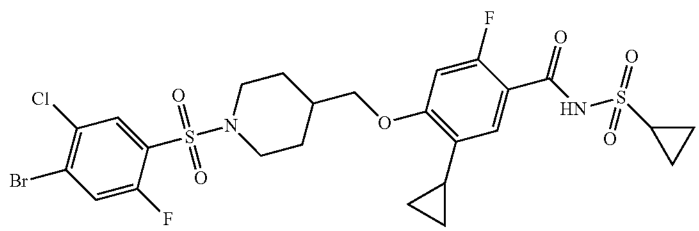 [SMILES: O=C(NS(=O)(=O)C1CC1)c1cc(C2CC2)c(OCC2CCN(S(=O)(=O)c3cc(Cl)c(Br)cc3F)CC2)cc1F] | 0.0083 | | |
| 368 | 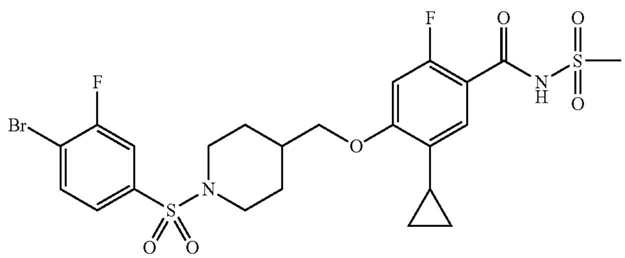 [SMILES: CS(=O)(=O)NC(=O)c1cc(C2CC2)c(OCC2CCN(S(=O)(=O)c3ccc(Br)c(F)c3)CC2)cc1F] | 0.0251 | | |
| 369 | 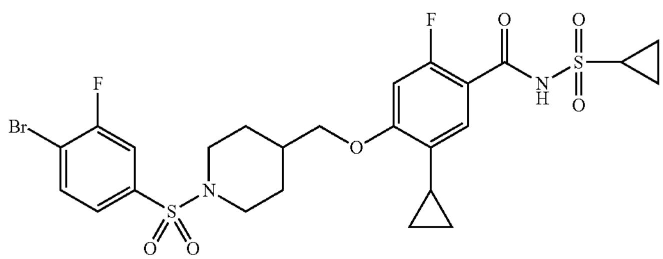 [SMILES: O=C(NS(=O)(=O)C1CC1)c1cc(C2CC2)c(OCC2CCN(S(=O)(=O)c3ccc(Br)c(F)c3)CC2)cc1F] | 0.0145 | | |
| 370 | 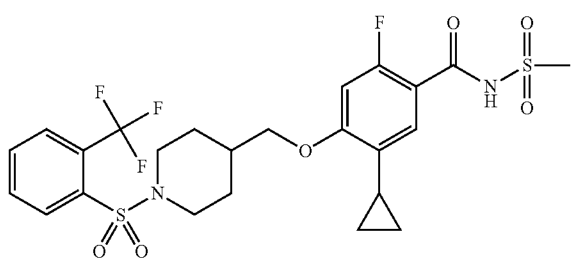 [SMILES: CS(=O)(=O)NC(=O)c1cc(C2CC2)c(OCC2CCN(S(=O)(=O)c3ccccc3C(F)(F)F)CC2)cc1F] | 0.0308 | | |
| 371 | 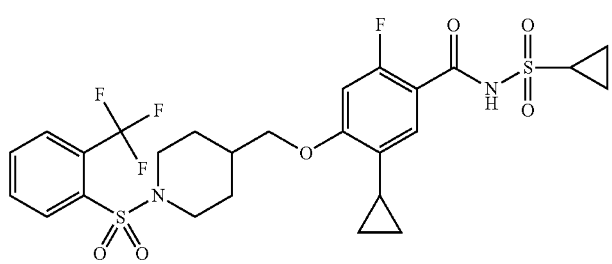 [SMILES: O=C(NS(=O)(=O)C1CC1)c1cc(C2CC2)c(OCC2CCN(S(=O)(=O)c3ccccc3C(F)(F)F)CC2)cc1F] | 0.0203 | | |
| 372 | 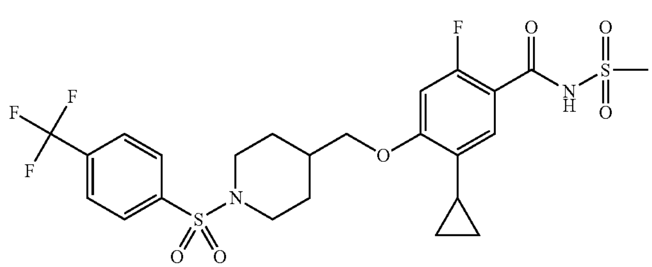 [SMILES: CS(=O)(=O)NC(=O)c1cc(C2CC2)c(OCC2CCN(S(=O)(=O)c3ccc(C(F)(F)F)cc3)CC2)cc1F] | 0.04923 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 373 | 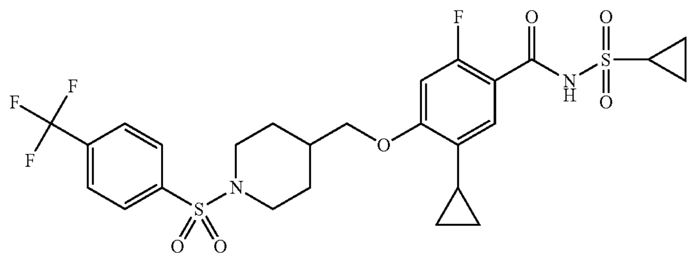 [SMILES: O=C(NS(=O)(=O)C1CC1)c1cc(C2CC2)c(OCC2CCN(S(=O)(=O)c3ccc(C(F)(F)F)cc3)CC2)cc1F] | 0.0197 | | |
| 374 | 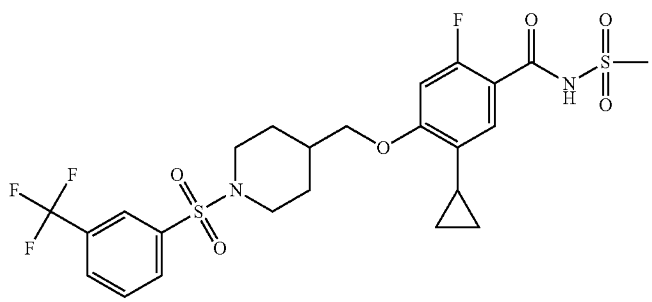 [SMILES: CS(=O)(=O)NC(=O)c1cc(C2CC2)c(OCC2CCN(S(=O)(=O)c3cccc(C(F)(F)F)c3)CC2)cc1F] | 0.0231 | | |
| 375 | 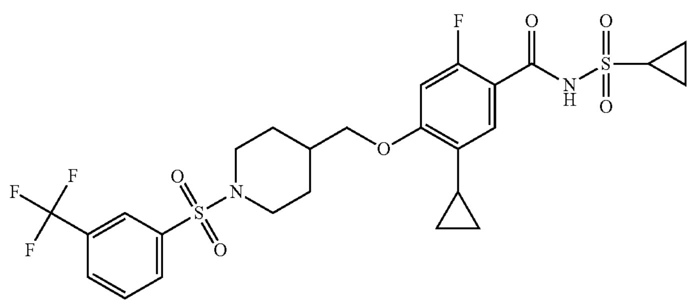 [SMILES: O=C(NS(=O)(=O)C1CC1)c1cc(C2CC2)c(OCC2CCN(S(=O)(=O)c3cccc(C(F)(F)F)c3)CC2)cc1F] | 0.0146 | | |
| 376 | 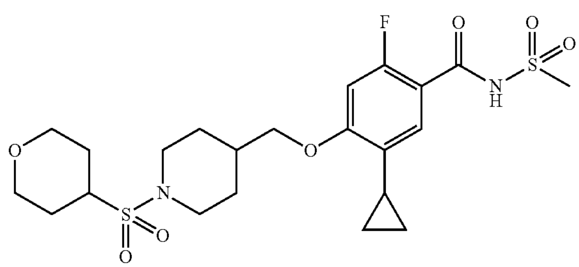 [SMILES: CS(=O)(=O)NC(=O)c1cc(C2CC2)c(OCC2CCN(S(=O)(=O)C3CCOCC3)CC2)cc1F] | 2.4491 | | |
| 377 | 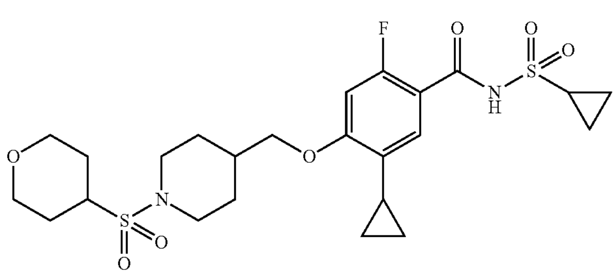 [SMILES: O=C(NS(=O)(=O)C1CC1)c1cc(C2CC2)c(OCC2CCN(S(=O)(=O)C3CCOCC3)CC2)cc1F] | 1.2589 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 378 | 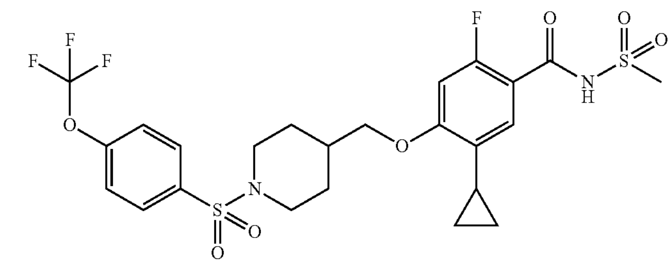 [SMILES: CS(=O)(=O)NC(=O)c1cc(C2CC2)c(OCC2CCN(S(=O)(=O)c3ccc(OC(F)(F)F)cc3)CC2)cc1F] | 0.0459 | | |
| 379 | 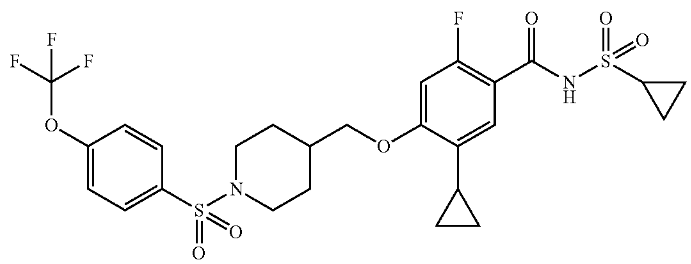 [SMILES: O=C(NS(=O)(=O)C1CC1)c1cc(C2CC2)c(OCC2CCN(S(=O)(=O)c3ccc(OC(F)(F)F)cc3)CC2)cc1F] | 0.0172 | | |
| 380 | 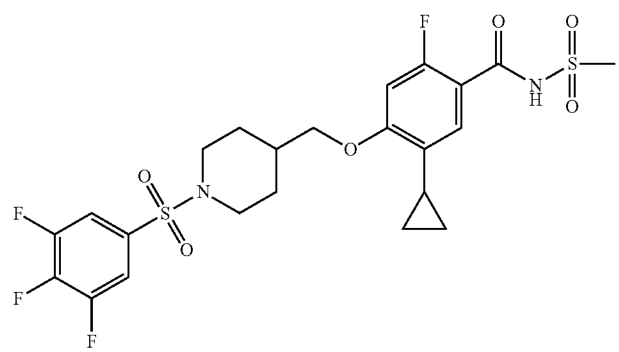 [SMILES: CS(=O)(=O)NC(=O)c1cc(C2CC2)c(OCC2CCN(S(=O)(=O)c3cc(F)c(F)c(F)c3)CC2)cc1F] | 0.0409 | | |
| 381 | 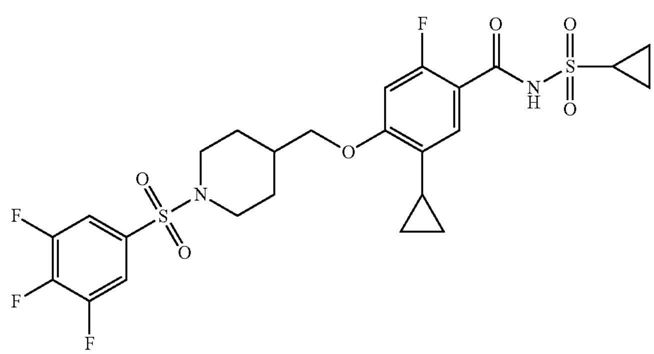 [SMILES: O=C(NS(=O)(=O)C1CC1)c1cc(C2CC2)c(OCC2CCN(S(=O)(=O)c3cc(F)c(F)c(F)c3)CC2)cc1F] | 0.0148 | | |
| 382 | 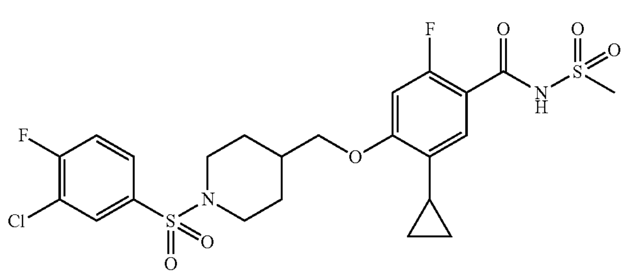 [SMILES: CS(=O)(=O)NC(=O)c1cc(C2CC2)c(OCC2CCN(S(=O)(=O)c3ccc(F)c(Cl)c3)CC2)cc1F] | 0.0407 | | |

TABLE 1-continued

| Example | Structure | Ligand Binding Assay (μM) | NaV1.7 EP (μM) | NaV1.5 EP (μM) |
|---|---|---|---|---|
| 383 | 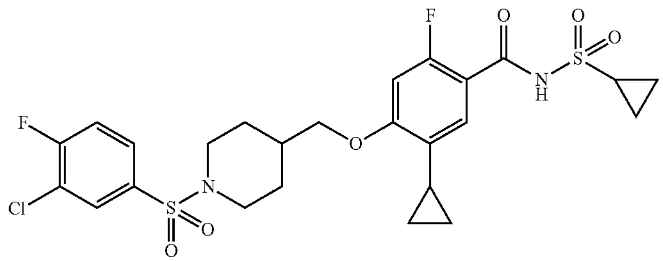 [SMILES: O=C(NS(=O)(=O)C1CC1)c1cc(C2CC2)c(OCC2CCN(S(=O)(=O)c3ccc(F)c(Cl)c3)CC2)cc1F] | 0.0148 | | |
| 384 | 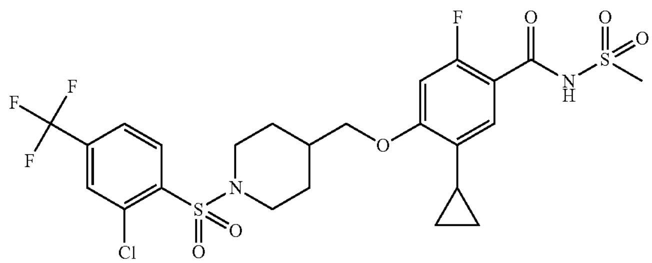 [SMILES: CS(=O)(=O)NC(=O)c1cc(C2CC2)c(OCC2CCN(S(=O)(=O)c3ccc(C(F)(F)F)cc3Cl)CC2)cc1F] | 0.0163 | | |
| 385 | 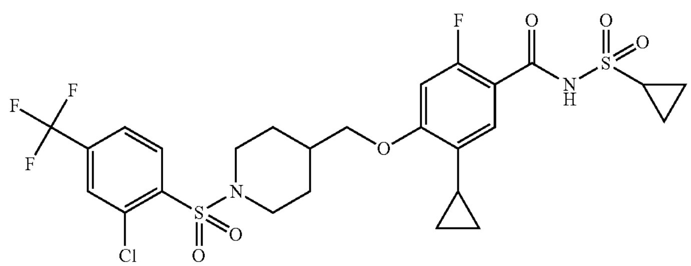 [SMILES: O=C(NS(=O)(=O)C1CC1)c1cc(C2CC2)c(OCC2CCN(S(=O)(=O)c3ccc(C(F)(F)F)cc3Cl)CC2)cc1F] | 0.0100 | | |
| 386 | 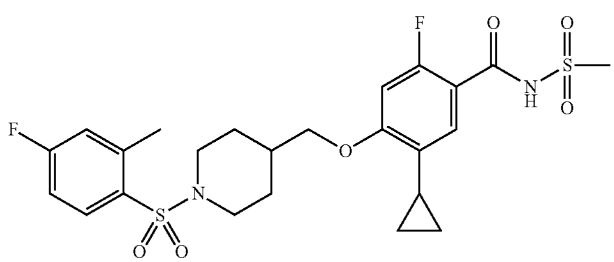 [SMILES: Cc1cc(F)ccc1S(=O)(=O)N1CCC(COc2cc(F)c(C(=O)NS(C)(=O)=O)cc2C2CC2)CC1] | 0.0521 | | |
| 387 | 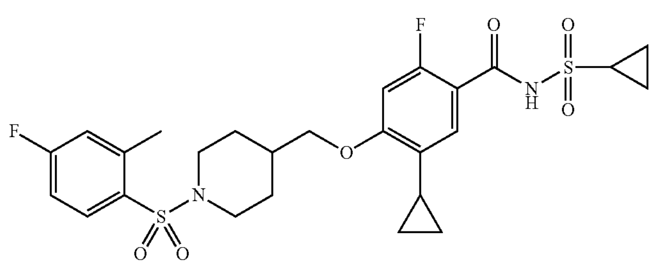 [SMILES: Cc1cc(F)ccc1S(=O)(=O)N1CCC(COc2cc(F)c(C(=O)NS(=O)(=O)C3CC3)cc2C2CC2)CC1] | 0.0133 | | |

TABLE 1-continued

| Example | Structure | Ligand Binding Assay (μM) | NaV1.7 EP (μM) | NaV1.5 EP (μM) |
|---|---|---|---|---|
| 388 | 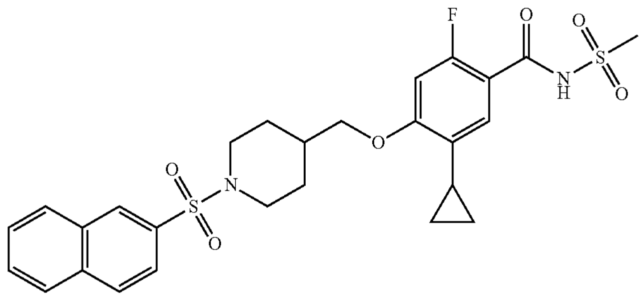 [SMILES: CS(=O)(=O)NC(=O)c1cc(C2CC2)c(OCC2CCN(S(=O)(=O)c3ccc4ccccc4c3)CC2)cc1F] | 0.0163 | | |
| 389 | 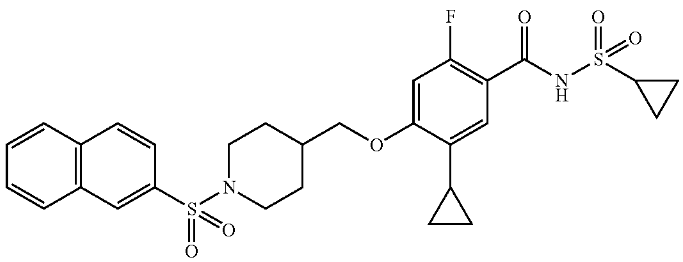 [SMILES: O=C(NS(=O)(=O)C1CC1)c1cc(C2CC2)c(OCC2CCN(S(=O)(=O)c3ccc4ccccc4c3)CC2)cc1F] | 0.0088 | | |
| 390 | 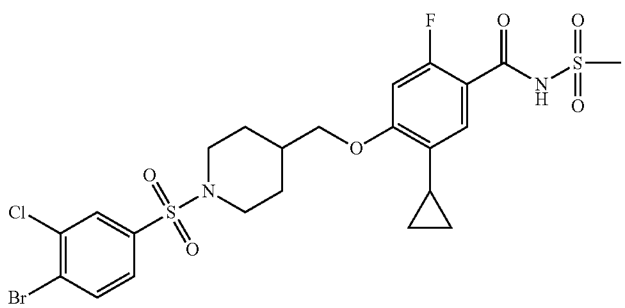 [SMILES: CS(=O)(=O)NC(=O)c1cc(C2CC2)c(OCC2CCN(S(=O)(=O)c3ccc(Br)c(Cl)c3)CC2)cc1F] | 0.0185 | | |
| 391 | 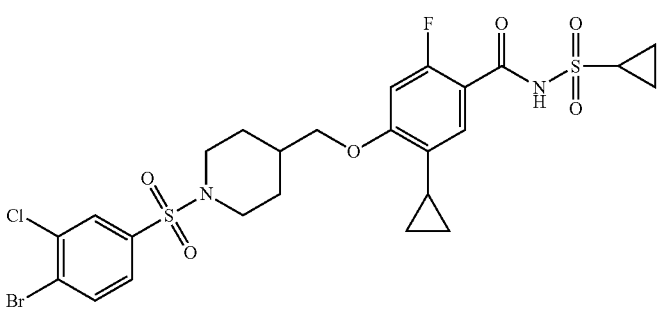 [SMILES: O=C(NS(=O)(=O)C1CC1)c1cc(C2CC2)c(OCC2CCN(S(=O)(=O)c3ccc(Br)c(Cl)c3)CC2)cc1F] | 0.0101 | | |
| 392 | 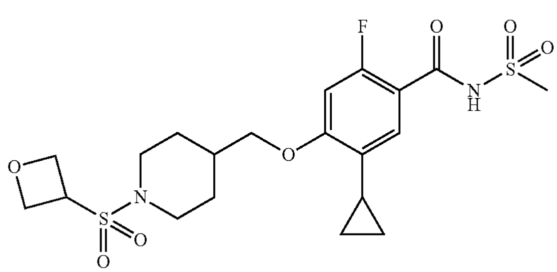 [SMILES: CS(=O)(=O)NC(=O)c1cc(C2CC2)c(OCC2CCN(S(=O)(=O)C3COC3)CC2)cc1F] | 2.0625 | | |

TABLE 1-continued

| Example | Structure | Ligand Binding Assay (μM) | NaV1.7 EP (μM) | NaV1.5 EP (μM) |
|---|---|---|---|---|
| 393 | 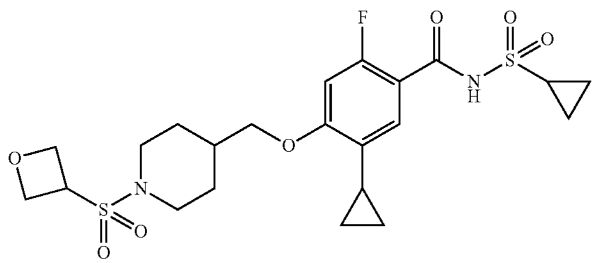 [SMILES: O=C(NS(=O)(=O)C1CC1)c1cc(C2CC2)c(OCC2CCN(S(=O)(=O)C3COC3)CC2)cc1F] | 1.3750 | | |
| 394 | 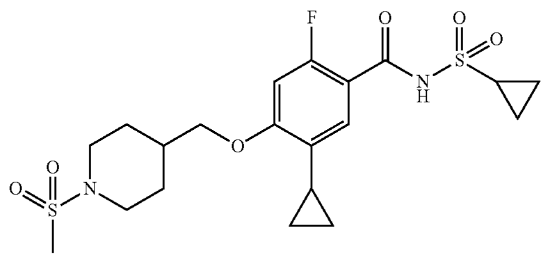 [SMILES: CS(=O)(=O)N1CCC(COc2cc(F)c(C(=O)NS(=O)(=O)C3CC3)cc2C2CC2)CC1] | 6.0057 | | |
| 395 | 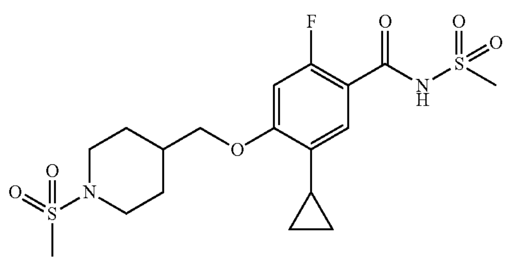 [SMILES: CS(=O)(=O)NC(=O)c1cc(C2CC2)c(OCC2CCN(S(C)(=O)=O)CC2)cc1F] | >10 | | |
| 396 | 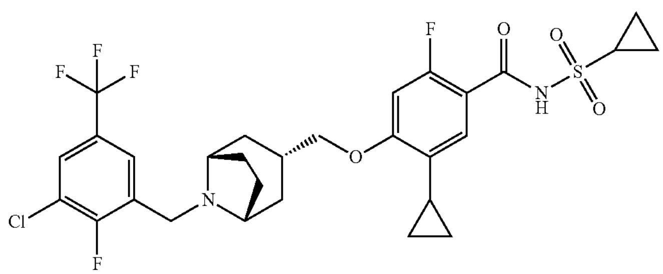 [SMILES: O=C(NS(=O)(=O)C1CC1)c1cc(C2CC2)c(OC[C@@H]2C[C@H]3CC[C@@H](C2)N3Cc2cc(C(F)(F)F)cc(Cl)c2F)cc1F] | 0.0148 | | |
| 397 | 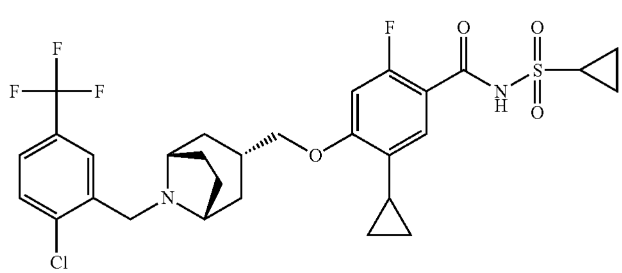 [SMILES: O=C(NS(=O)(=O)C1CC1)c1cc(C2CC2)c(OC[C@@H]2C[C@H]3CC[C@@H](C2)N3Cc2cc(C(F)(F)F)ccc2Cl)cc1F] | 0.0057 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 398 | 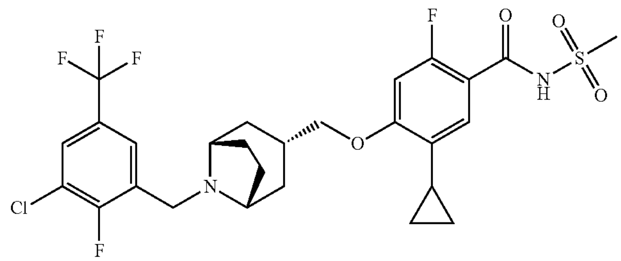 [SMILES: CS(=O)(=O)NC(=O)c1cc(C2CC2)c(OC[C@@H]2C[C@H]3CC[C@@H](C2)N3Cc2cc(C(F)(F)F)cc(Cl)c2F)cc1F] | 0.0051 | | |
| 399 | 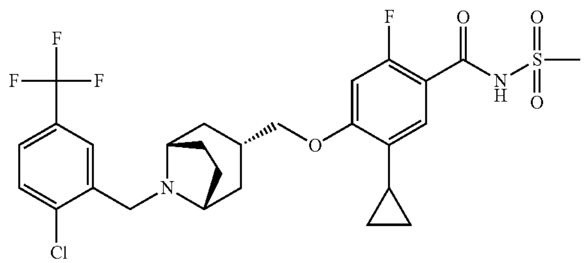 [SMILES: CS(=O)(=O)NC(=O)c1cc(C2CC2)c(OC[C@@H]2C[C@H]3CC[C@@H](C2)N3Cc2cc(C(F)(F)F)ccc2Cl)cc1F] | 0.0046 | | |
| 400 | 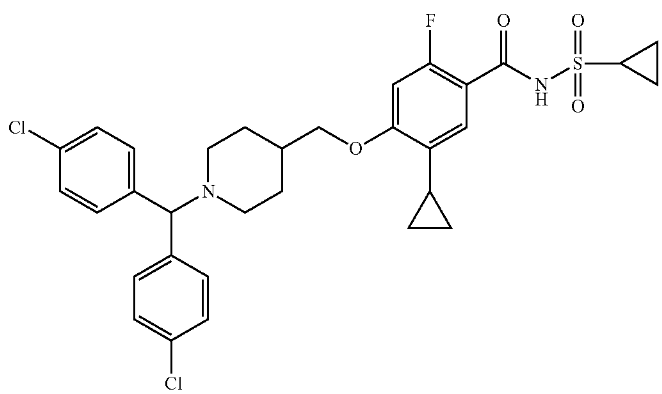 [SMILES: O=C(NS(=O)(=O)C1CC1)c1cc(C2CC2)c(OCC2CCN(C(c3ccc(Cl)cc3)c3ccc(Cl)cc3)CC2)cc1F] | 0.0021 | | |
| 401 | 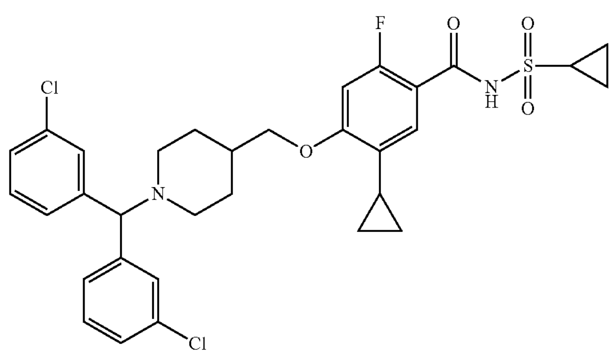 [SMILES: O=C(NS(=O)(=O)C1CC1)c1cc(C2CC2)c(OCC2CCN(C(c3cccc(Cl)c3)c3cccc(Cl)c3)CC2)cc1F] | 0.0031 | | |
| 402 | 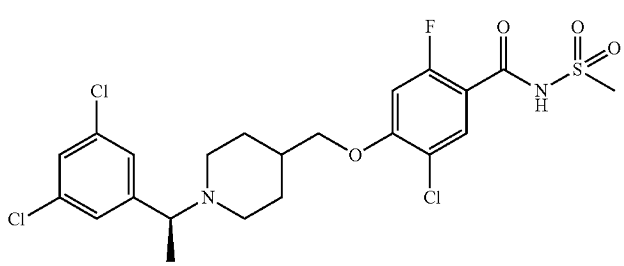 [SMILES: C[C@@H](c1cc(Cl)cc(Cl)c1)N1CCC(COc2cc(F)c(C(=O)NS(C)(=O)=O)cc2Cl)CC1] | 0.0224 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 403 | 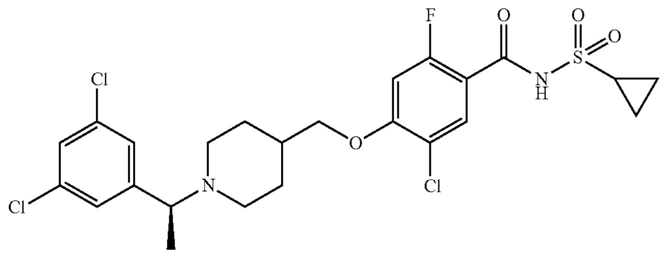 [SMILES: C[C@@H](c1cc(Cl)cc(Cl)c1)N1CCC(COc2cc(F)c(C(=O)NS(=O)(=O)C3CC3)cc2Cl)CC1] | 0.0170 | | |
| 404 | 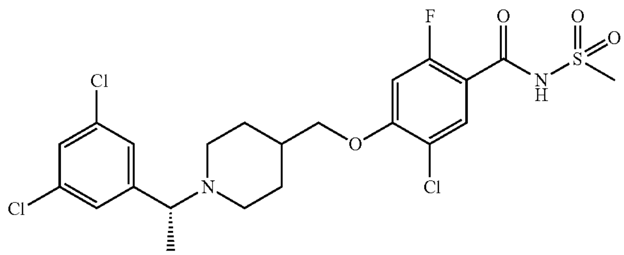 [SMILES: C[C@H](c1cc(Cl)cc(Cl)c1)N1CCC(COc2cc(F)c(C(=O)NS(C)(=O)=O)cc2Cl)CC1] | 0.0201 | | |
| 405 | 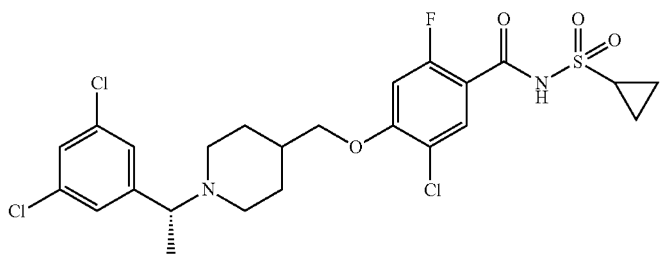 [SMILES: C[C@H](c1cc(Cl)cc(Cl)c1)N1CCC(COc2cc(F)c(C(=O)NS(=O)(=O)C3CC3)cc2Cl)CC1] | 0.0150 | | |
| 406 | 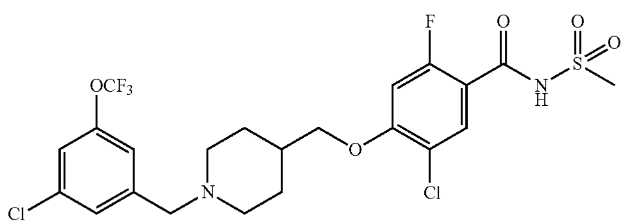 [SMILES: CS(=O)(=O)NC(=O)c1cc(Cl)c(OCC2CCN(Cc3cc(Cl)cc(OC(F)(F)F)c3)CC2)cc1F] | 0.0176 | | |
| 407 | 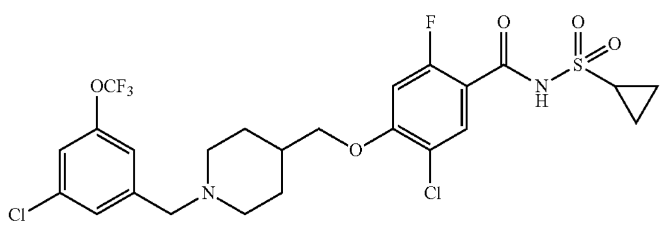 [SMILES: O=C(NS(=O)(=O)C1CC1)c1cc(Cl)c(OCC2CCN(Cc3cc(Cl)cc(OC(F)(F)F)c3)CC2)cc1F] | 0.0067 | | |
| 408 | 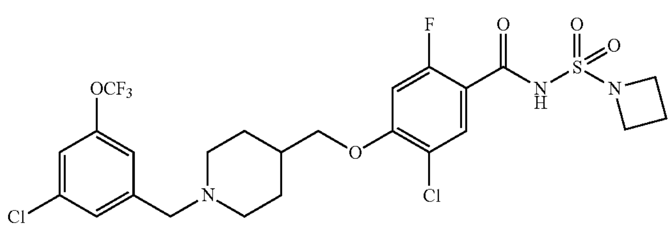 [SMILES: O=C(NS(=O)(=O)N1CCC1)c1cc(Cl)c(OCC2CCN(Cc3cc(Cl)cc(OC(F)(F)F)c3)CC2)cc1F] | 0.0227 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 409 | 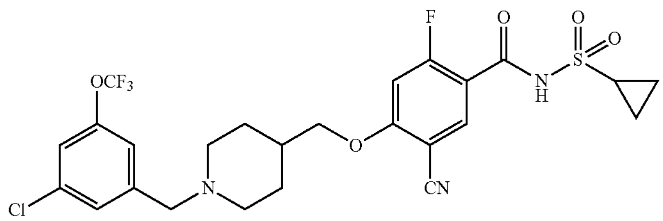 [SMILES: N#Cc1cc(C(=O)NS(=O)(=O)C2CC2)c(F)cc1OCC1CCN(Cc2cc(Cl)cc(OC(F)(F)F)c2)CC1] | 0.0540 | | |
| 410 | 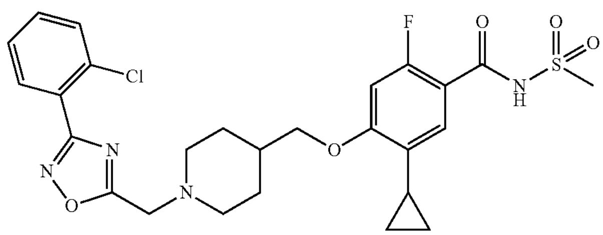 [SMILES: CS(=O)(=O)NC(=O)c1cc(C2CC2)c(OCC2CCN(Cc3nc(-c4ccccc4Cl)no3)CC2)cc1F] | 0.0109 | | |
| 411 | 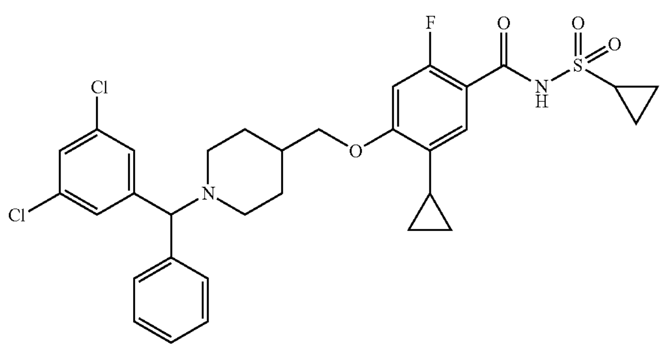 [SMILES: O=C(NS(=O)(=O)C1CC1)c1cc(C2CC2)c(OCC2CCN(C(c3ccccc3)c3cc(Cl)cc(Cl)c3)CC2)cc1F] | 0.0008 | | |
| 412 | 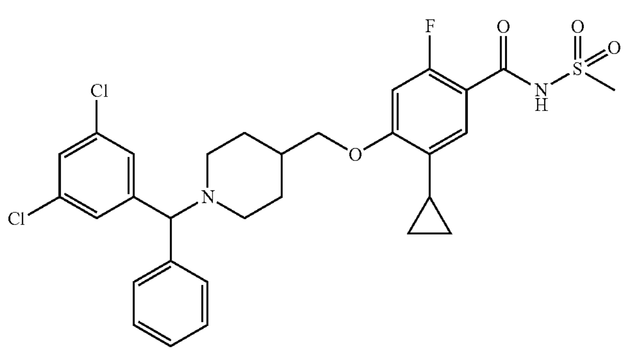 [SMILES: CS(=O)(=O)NC(=O)c1cc(C2CC2)c(OCC2CCN(C(c3ccccc3)c3cc(Cl)cc(Cl)c3)CC2)cc1F] | 0.0015 | | |
| 413 | 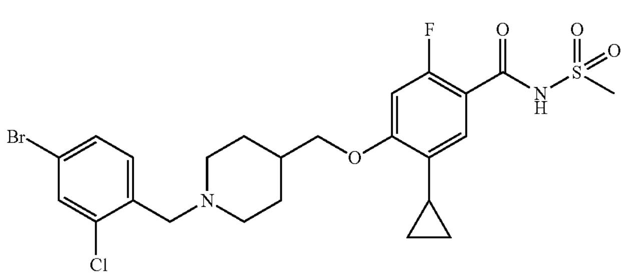 [SMILES: CS(=O)(=O)NC(=O)c1cc(C2CC2)c(OCC2CCN(Cc3ccc(Br)cc3Cl)CC2)cc1F] | 0.0060 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 414 | 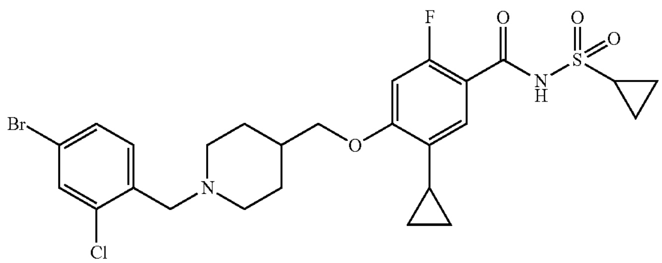 [SMILES: O=C(NS(=O)(=O)C1CC1)c1cc(C2CC2)c(OCC2CCN(Cc3ccc(Br)cc3Cl)CC2)cc1F] | 0.0038 | | |
| 415 | 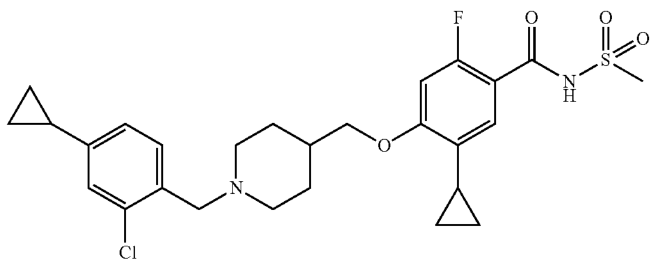 [SMILES: CS(=O)(=O)NC(=O)c1cc(C2CC2)c(OCC2CCN(Cc3ccc(C4CC4)cc3Cl)CC2)cc1F] | 0.0061 | | |
| 416 | 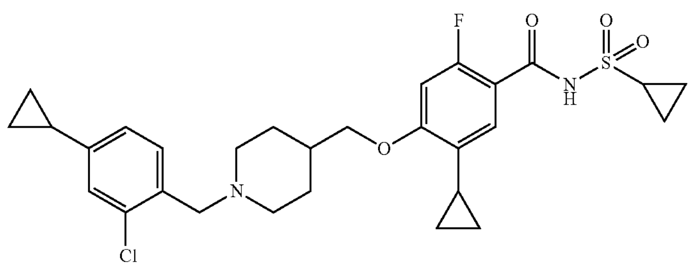 [SMILES: O=C(NS(=O)(=O)C1CC1)c1cc(C2CC2)c(OCC2CCN(Cc3ccc(C4CC4)cc3Cl)CC2)cc1F] | 0.0053 | | |
| 417 | 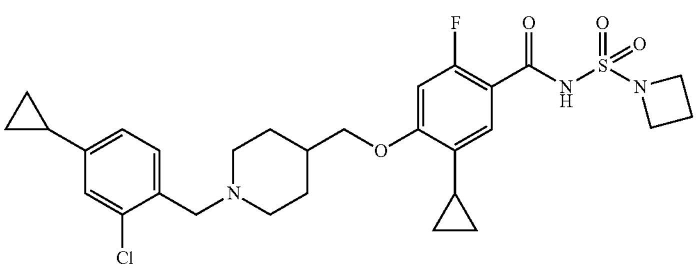 [SMILES: O=C(NS(=O)(=O)N1CCC1)c1cc(C2CC2)c(OCC2CCN(Cc3ccc(C4CC4)cc3Cl)CC2)cc1F] | 0.0057 | | |
| 418 | 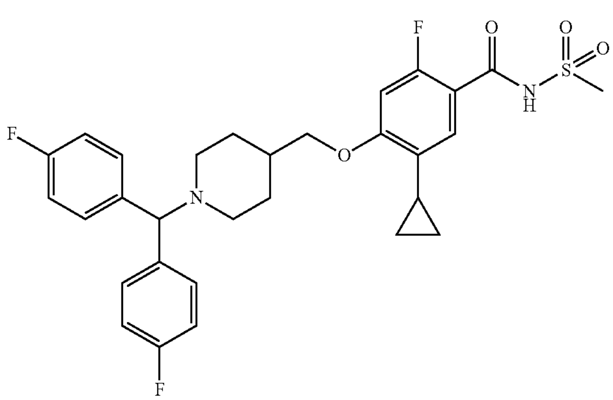 [SMILES: CS(=O)(=O)NC(=O)c1cc(C2CC2)c(OCC2CCN(C(c3ccc(F)cc3)c3ccc(F)cc3)CC2)cc1F] | 0.0032 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 419 | 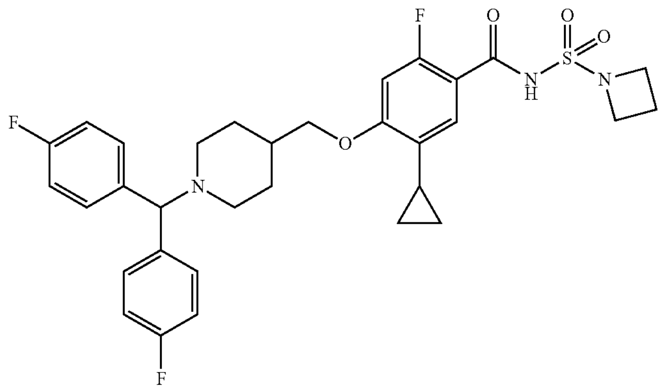 [SMILES: O=C(NS(=O)(=O)N1CCC1)c1cc(C2CC2)c(OCC2CCN(C(c3ccc(F)cc3)c3ccc(F)cc3)CC2)cc1F] | 0.0052 | | |
| 420 | 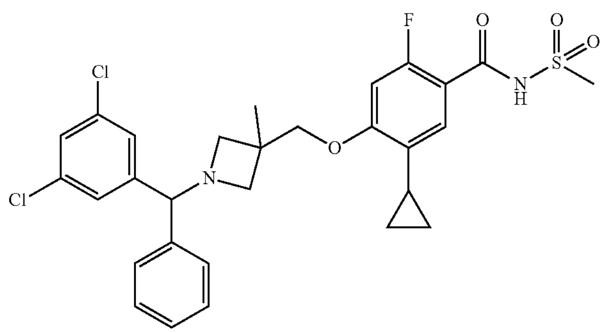 [SMILES: CC1(COc2cc(F)c(C(=O)NS(C)(=O)=O)cc2C2CC2)CN(C(c2ccccc2)c2cc(Cl)cc(Cl)c2)C1] | 0.0024 | | |
| 421 | 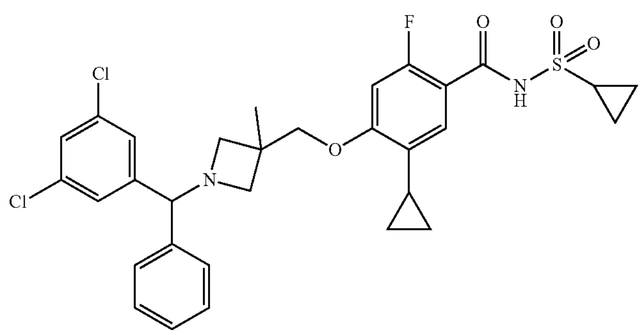 [SMILES: CC1(COc2cc(F)c(C(=O)NS(=O)(=O)C3CC3)cc2C2CC2)CN(C(c2ccccc2)c2cc(Cl)cc(Cl)c2)C1] | 0.0025 | | |
| 422 | 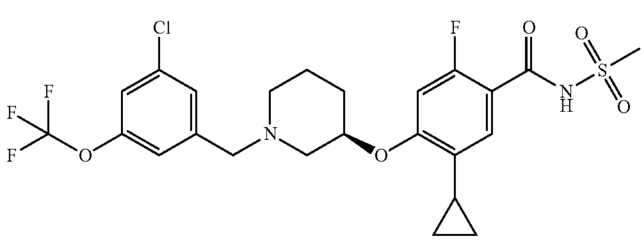 [SMILES: CS(=O)(=O)NC(=O)c1cc(C2CC2)c(O[C@@H]2CCCN(Cc3cc(Cl)cc(OC(F)(F)F)c3)C2)cc1F] | 0.0013 | | |
| 423 | 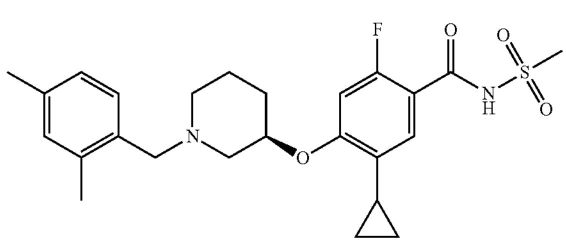 | 0.0021 | | |

TABLE 1-continued

| Example | Structure | Ligand Binding Assay (μM) | NaV1.7 EP (μM) | NaV1.5 EP (μM) |
|---|---|---|---|---|
| 424 | 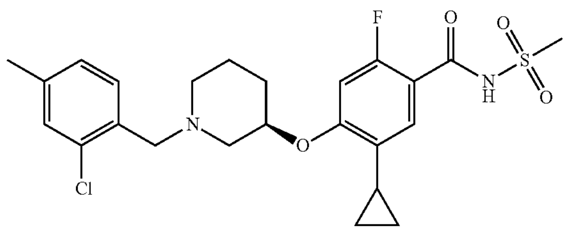 | 0.0025 | | |
| 425 | 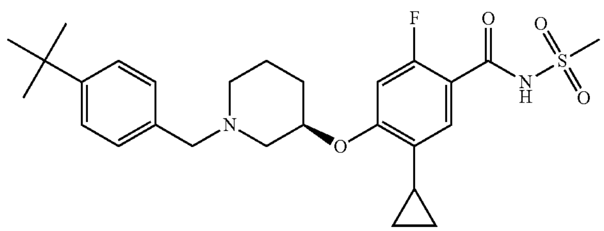 [SMILES: CC(C)(C)c1ccc(CN2CCC[C@@H](Oc3cc(F)c(C(=O)NS(C)(=O)=O)cc3C3CC3)C2)cc1] | 0.0029 | | |
| 426 | 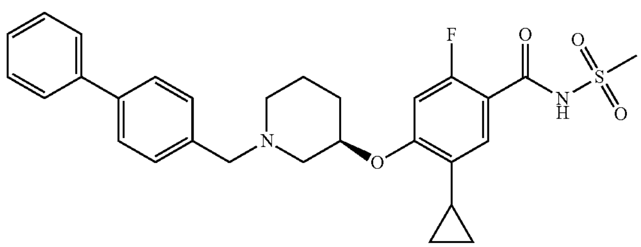 [SMILES: CS(=O)(=O)NC(=O)c1cc(C2CC2)c(O[C@@H]2CCCN(Cc3ccc(-c4ccccc4)cc3)C2)cc1F] | 0.0031 | | |
| 427 | 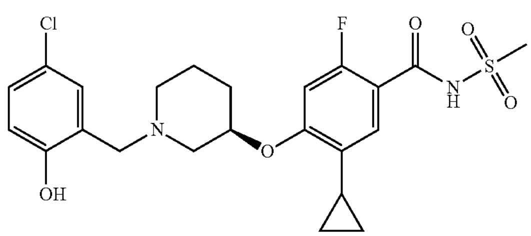 [SMILES: CS(=O)(=O)NC(=O)c1cc(C2CC2)c(O[C@@H]2CCCN(Cc3cc(Cl)ccc3O)C2)cc1F] | 0.0190 | | |
| 428 | 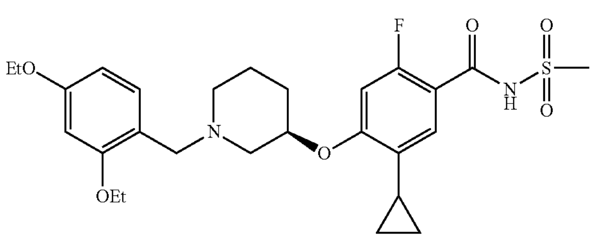 [SMILES: CCOc1ccc(CN2CCC[C@@H](Oc3cc(F)c(C(=O)NS(C)(=O)=O)cc3C3CC3)C2)c(OCC)c1] | 0.0234 | | |
| 429 | 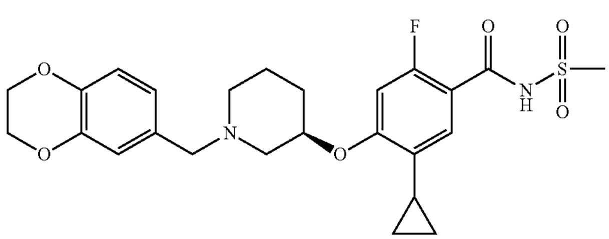 [SMILES: CS(=O)(=O)NC(=O)c1cc(C2CC2)c(O[C@@H]2CCCN(Cc3ccc4c(c3)OCCO4)C2)cc1F] | 0.0519 | | |

TABLE 1-continued

| Example | Structure | Ligand Binding Assay (μM) | NaV1.7 EP (μM) | NaV1.5 EP (μM) |
|---|---|---|---|---|
| 430 | 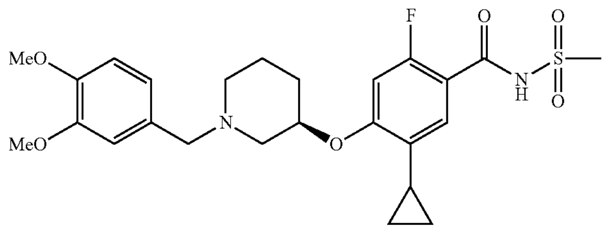 [SMILES: COc1ccc(CN2CCC[C@@H](Oc3cc(F)c(C(=O)NS(C)(=O)=O)cc3C3CC3)C2)cc1OC] | 0.5327 | | |
| 431 | 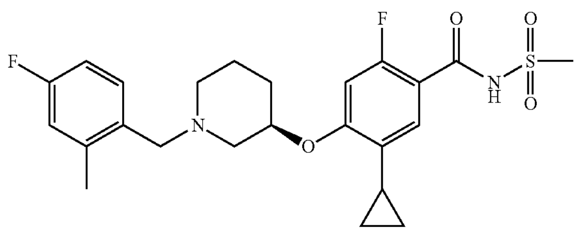 [SMILES: Cc1cc(F)ccc1CN1CCC[C@@H](Oc2cc(F)c(C(=O)NS(C)(=O)=O)cc2C2CC2)C1] | 0.0032 | | |
| 432 | 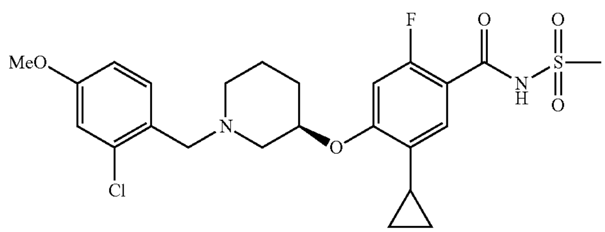 [SMILES: COc1ccc(CN2CCC[C@@H](Oc3cc(F)c(C(=O)NS(C)(=O)=O)cc3C3CC3)C2)c(Cl)c1] | 0.0033 | | |
| 433 | 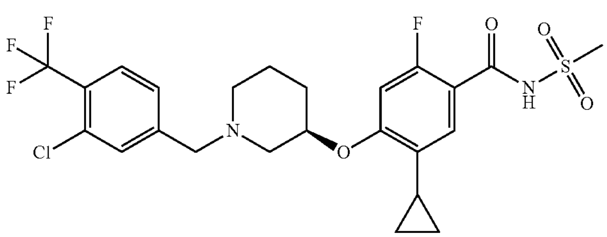 [SMILES: CS(=O)(=O)NC(=O)c1cc(C2CC2)c(O[C@@H]2CCCN(Cc3ccc(C(F)(F)F)c(Cl)c3)C2)cc1F] | 0.0062 | | |
| 434 | 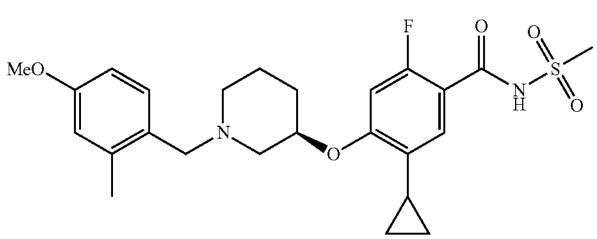 [SMILES: COc1ccc(CN2CCC[C@@H](Oc3cc(F)c(C(=O)NS(C)(=O)=O)cc3C3CC3)C2)c(C)c1] | 0.0050 | 0.0128 | |
| 435 | 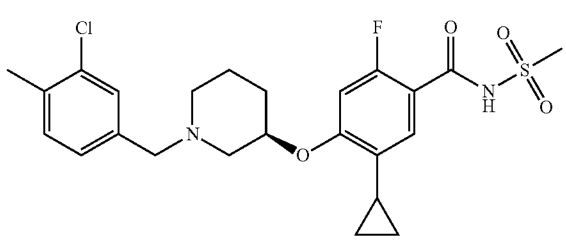 | 0.0054 | | |

TABLE 1-continued

| Example | Structure | Ligand Binding Assay (μM) | NaV1.7 EP (μM) | NaV1.5 EP (μM) |
|---|---|---|---|---|
| 436 | 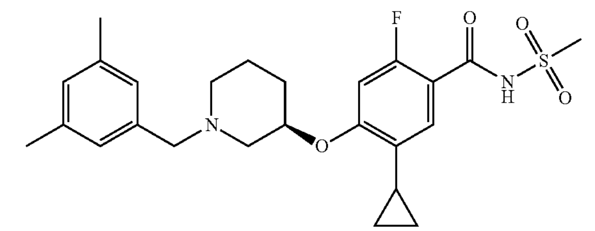 | 0.0054 | | |
| 437 | 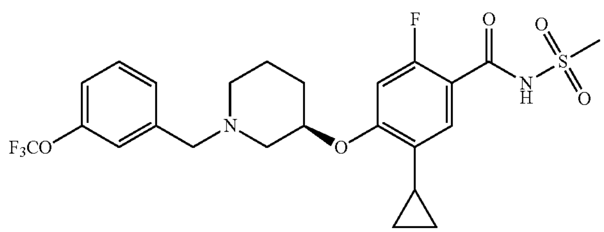 [SMILES: CS(=O)(=O)NC(=O)c1cc(C2CC2)c(O[C@@H]2CCCN(Cc3cccc(OC(F)(F)F)c3)C2)cc1F] | 0.0073 | | |
| 438 | 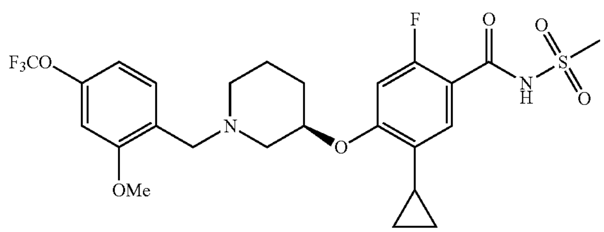 [SMILES: COc1cc(OC(F)(F)F)ccc1CN1CCC[C@@H](Oc2cc(F)c(C(=O)NS(C)(=O)=O)cc2C2CC2)C1] | 0.0095 | | |
| 439 | 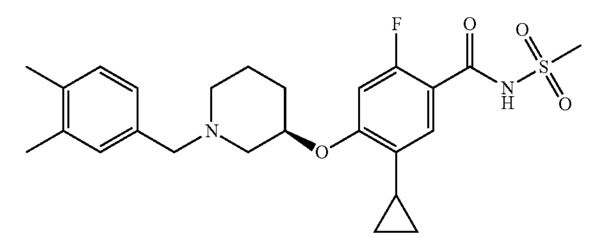 | 0.0110 | | |
| 440 | 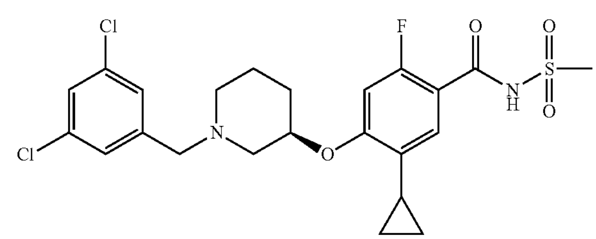 [SMILES: CS(=O)(=O)NC(=O)c1cc(C2CC2)c(O[C@@H]2CCCN(Cc3cc(Cl)cc(Cl)c3)C2)cc1F] | 0.0003 | | |
| 441 | 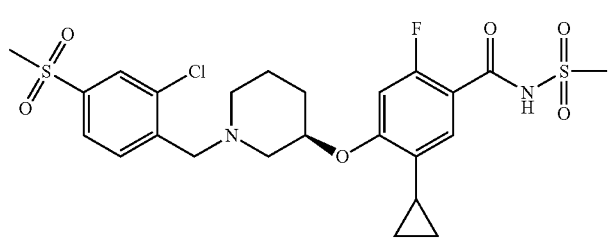 | 0.1378 | | |

TABLE 1-continued

| Example | Structure | Ligand Binding Assay (μM) | NaV1.7 EP (μM) | NaV1.5 EP (μM) |
|---|---|---|---|---|
| 442 | 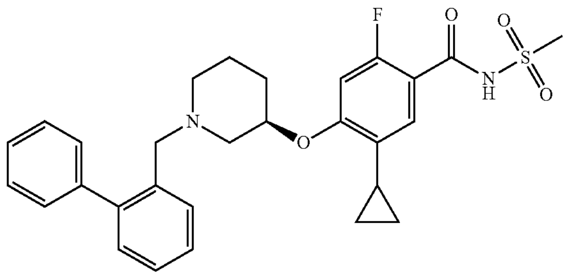 [SMILES: CS(=O)(=O)NC(=O)c1cc(C2CC2)c(O[C@@H]2CCCN(Cc3ccccc3-c3ccccc3)C2)cc1F] | 0.0031 | | |
| 443 | 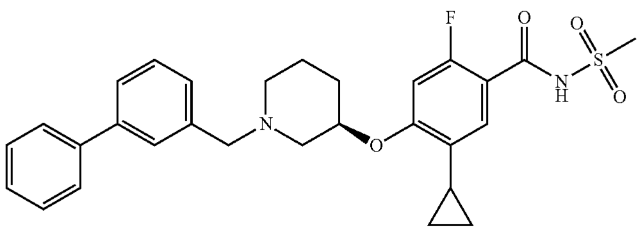 [SMILES: CS(=O)(=O)NC(=O)c1cc(C2CC2)c(O[C@@H]2CCCN(Cc3cccc(-c4ccccc4)c3)C2)cc1F] | 0.0034 | | |
| 444 | 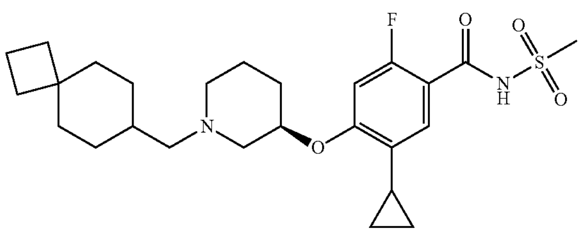 [SMILES: CS(=O)(=O)NC(=O)c1cc(C2CC2)c(O[C@@H]2CCCN(CC3CCC4(CCC4)CC3)C2)cc1F] | 0.0045 | | |
| 445 | 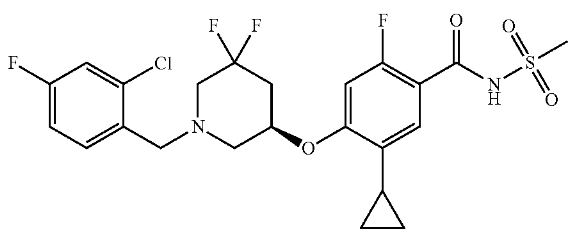 [SMILES: CS(=O)(=O)NC(=O)c1cc(C2CC2)c(O[C@H]2CN(Cc3ccc(F)cc3Cl)CC(F)(F)C2)cc1F] | 0.0061 | | |
| 446 | 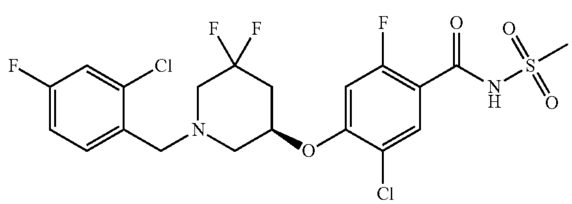 [SMILES: CS(=O)(=O)NC(=O)c1cc(Cl)c(O[C@H]2CN(Cc3ccc(F)cc3Cl)CC(F)(F)C2)cc1F] | 0.0565 | | |
| 447 | 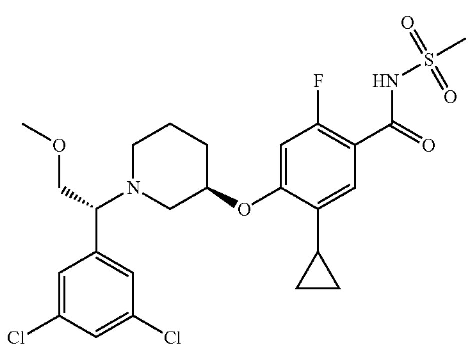 | 0.0060 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 448 | 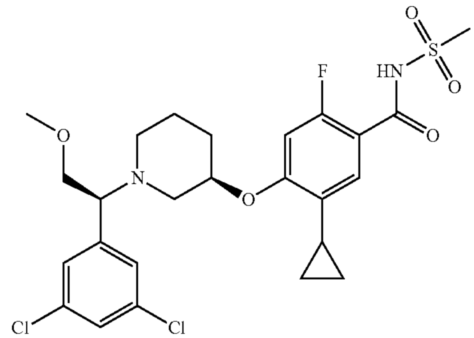 | 0.0105 | | |
| 449 | 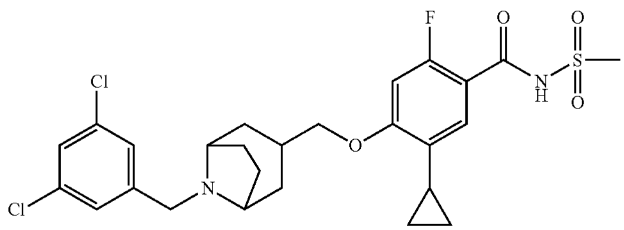 [SMILES: CS(=O)(=O)NC(=O)c1cc(C2CC2)c(OCC2CC3CCC(C2)N3Cc2cc(Cl)cc(Cl)c2)cc1F] | 0.0171 | | |
| 450 | 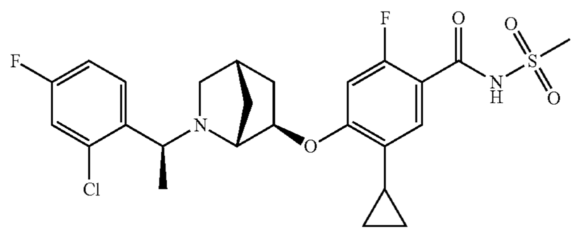 [SMILES: C[C@@H](c1ccc(F)cc1Cl)N1C[C@H]2C[C@@H]1[C@H](Oc1cc(F)c(C(=O)NS(C)(=O)=O)cc1C1CC1)C2] | 0.0099 | | |
| 451 | 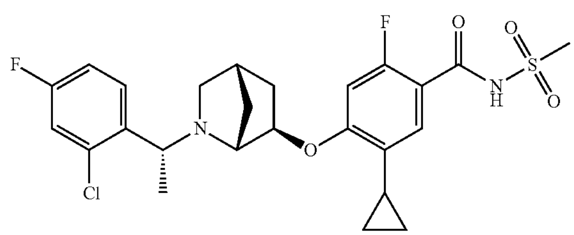 [SMILES: C[C@H](c1ccc(F)cc1Cl)N1C[C@H]2C[C@@H]1[C@H](Oc1cc(F)c(C(=O)NS(C)(=O)=O)cc1C1CC1)C2] | 0.0257 | | |
| 452 | 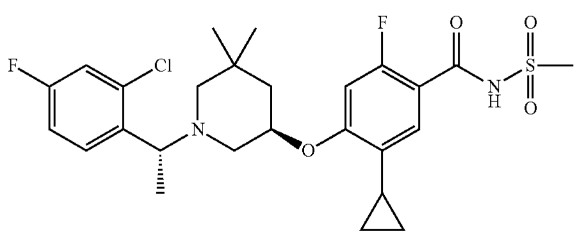 [SMILES: C[C@H](c1ccc(F)cc1Cl)N1C[C@H](Oc2cc(F)c(C(=O)NS(C)(=O)=O)cc2C2CC2)CC(C)(C)C1] | 0.0432 | | |
| 453 | 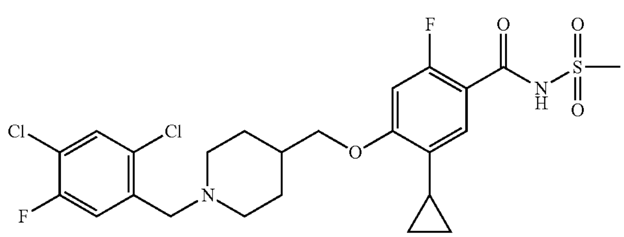 [SMILES: CS(=O)(=O)NC(=O)c1cc(C2CC2)c(OCC2CCN(Cc3cc(F)c(Cl)cc3Cl)CC2)cc1F] | 0.0030 | | |

TABLE 1-continued

| Example | Structure | Ligand Binding Assay (μM) | NaV1.7 EP (μM) | NaV1.5 EP (μM) |
|---|---|---|---|---|
| 454 | 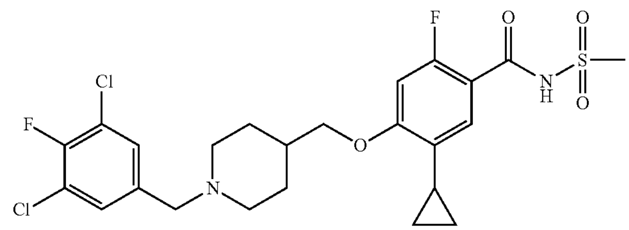 [SMILES: CS(=O)(=O)NC(=O)c1cc(C2CC2)c(OCC2CCN(Cc3cc(Cl)c(F)c(Cl)c3)CC2)cc1F] | 0.0050 | | |
| 455 | 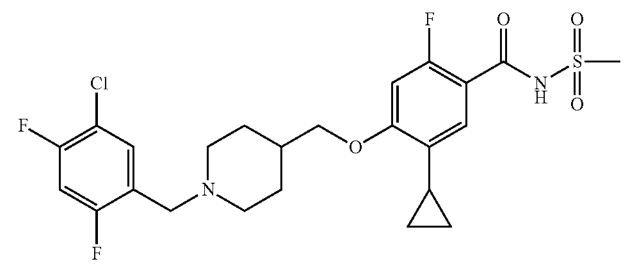 [SMILES: CS(=O)(=O)NC(=O)c1cc(C2CC2)c(OCC2CCN(Cc3cc(Cl)c(F)cc3F)CC2)cc1F] | 0.0085 | | |
| 456 | 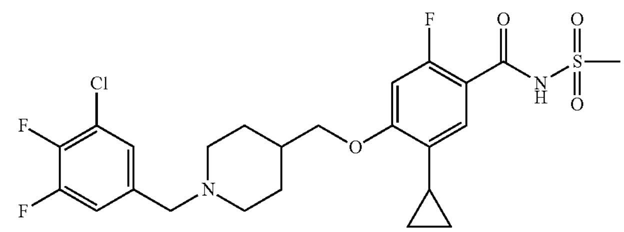 [SMILES: CS(=O)(=O)NC(=O)c1cc(C2CC2)c(OCC2CCN(Cc3cc(F)c(F)c(Cl)c3)CC2)cc1F] | 0.0093 | | |
| 457 | 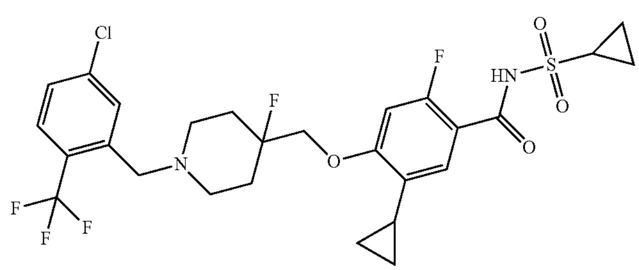 [SMILES: O=C(NS(=O)(=O)C1CC1)c1cc(C2CC2)c(OCC2(F)CCN(Cc3cc(Cl)ccc3C(F)(F)F)CC2)cc1F] | 0.0048 | | |
| 458 | 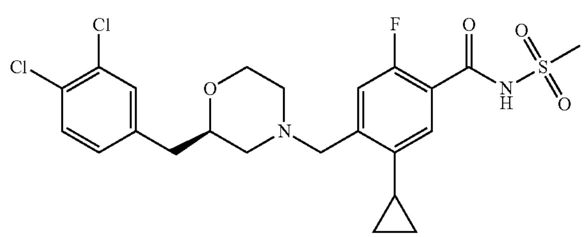 [SMILES: CS(=O)(=O)NC(=O)c1cc(C2CC2)c(CN2CCO[C@H](Cc3ccc(Cl)c(Cl)c3)C2)cc1F] | 0.0044 | | |
| 459 | 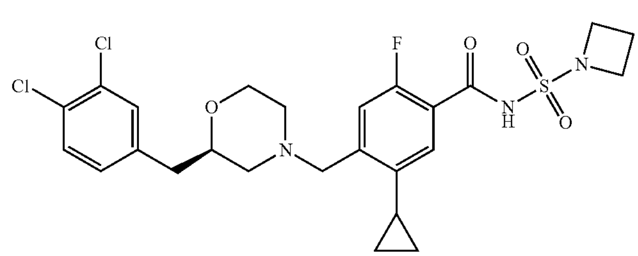 [SMILES: O=C(NS(=O)(=O)N1CCC1)c1cc(C2CC2)c(CN2CCO[C@H](Cc3ccc(Cl)c(Cl)c3)C2)cc1F] | 0.0125 | | |

TABLE 1-continued

| Example | Structure | Ligand Binding Assay (μM) | NaV1.7 EP (μM) | NaV1.5 EP (μM) |
|---|---|---|---|---|
| 460 | 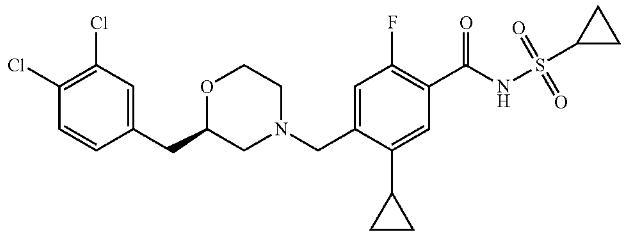 [SMILES: O=C(NS(=O)(=O)C1CC1)c1cc(C2CC2)c(CN2CCO[C@H](Cc3ccc(Cl)c(Cl)c3)C2)cc1F] | 0.0050 | | |
| 461 | 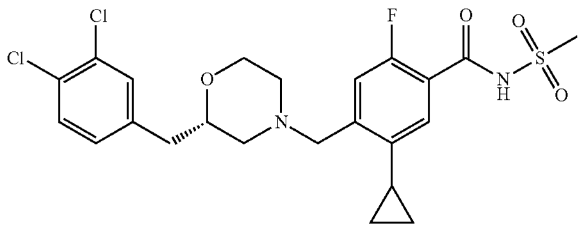 [SMILES: CS(=O)(=O)NC(=O)c1cc(C2CC2)c(CN2CCO[C@@H](Cc3ccc(Cl)c(Cl)c3)C2)cc1F] | 0.0421 | | |
| 462 | 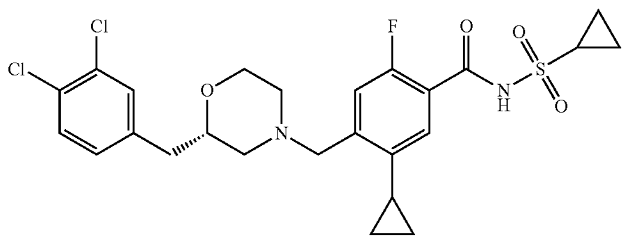 [SMILES: O=C(NS(=O)(=O)C1CC1)c1cc(C2CC2)c(CN2CCO[C@@H](Cc3ccc(Cl)c(Cl)c3)C2)cc1F] | 0.0363 | | |
| 463 | 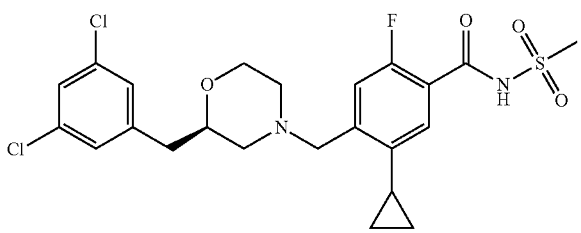 [SMILES: CS(=O)(=O)NC(=O)c1cc(C2CC2)c(CN2CCO[C@H](Cc3cc(Cl)cc(Cl)c3)C2)cc1F] | 0.0038 | <0.003 | 0.6688 |
| 464 | 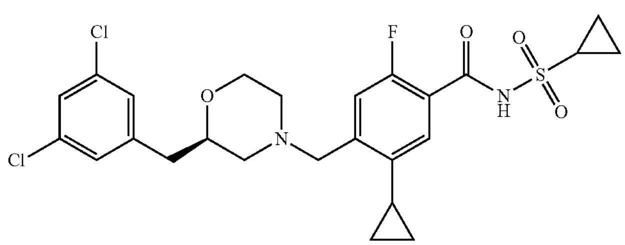 [SMILES: O=C(NS(=O)(=O)C1CC1)c1cc(C2CC2)c(CN2CCO[C@H](Cc3cc(Cl)cc(Cl)c3)C2)cc1F] | 0.0027 | <0.0030 | 0.109 |
| 465 | 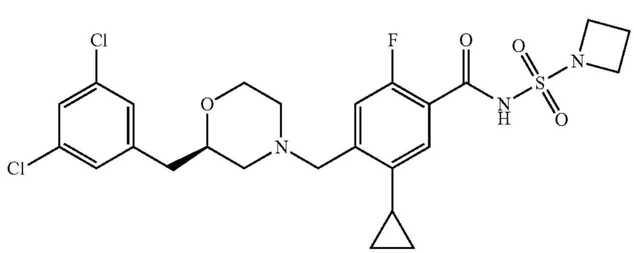 [SMILES: O=C(NS(=O)(=O)N1CCC1)c1cc(C2CC2)c(CN2CCO[C@H](Cc3cc(Cl)cc(Cl)c3)C2)cc1F] | 0.0128 | | |

TABLE 1-continued

| Example | Structure | Ligand Binding Assay (µM) | NaV1.7 EP (µM) | NaV1.5 EP (µM) |
|---|---|---|---|---|
| 466 | 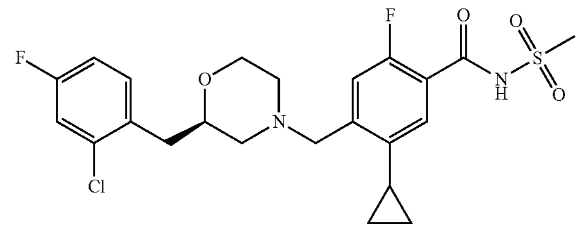 [SMILES: CS(=O)(=O)NC(=O)c1cc(C2CC2)c(CN2CCO[C@H](Cc3ccc(F)cc3Cl)C2)cc1F] | 0.0073 | | |
| 467 | 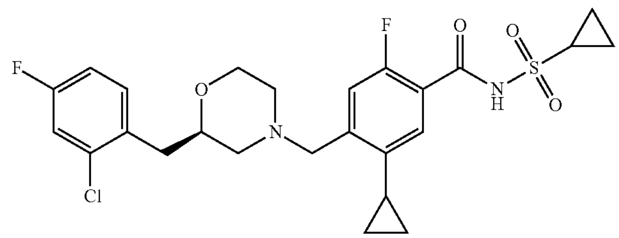 [SMILES: O=C(NS(=O)(=O)C1CC1)c1cc(C2CC2)c(CN2CCO[C@H](Cc3ccc(F)cc3Cl)C2)cc1F] | 0.0043 | | |
| 468 | 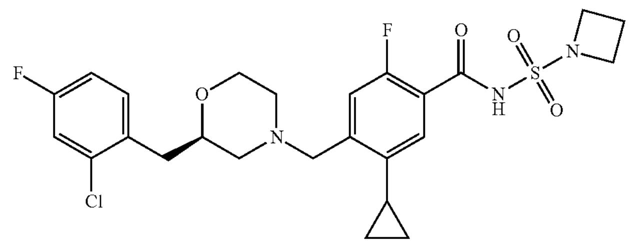 [SMILES: O=C(NS(=O)(=O)N1CCC1)c1cc(C2CC2)c(CN2CCO[C@H](Cc3ccc(F)cc3Cl)C2)cc1F] | 0.0113 | | |
| 469 | 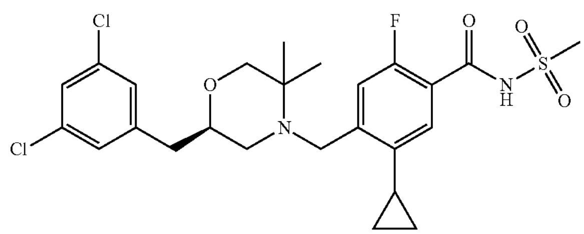 [SMILES: CC1(C)CO[C@H](Cc2cc(Cl)cc(Cl)c2)CN1Cc1cc(F)c(C(=O)NS(C)(=O)=O)cc1C1CC1] | 0.0989 | | |
| 470 | 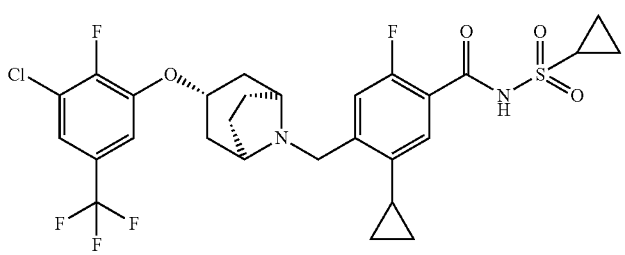 | 0.0038 | | |
| 471 | 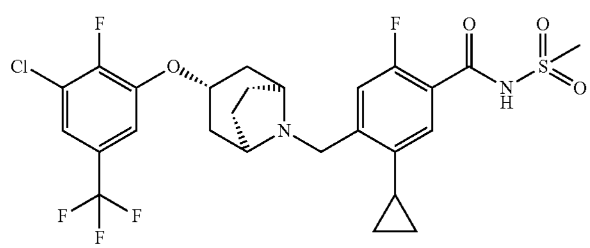 | 0.0037 | | |

TABLE 1-continued

| Example | Structure | Ligand Binding Assay (µM) | NaV1.7 EP (µM) | NaV1.5 EP (µM) |
| --- | --- | --- | --- | --- |
| 472 | 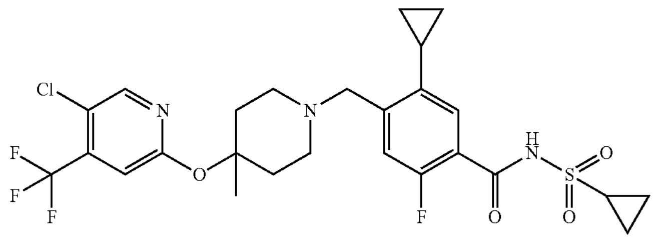 [SMILES: CC1(Oc2cc(C(F)(F)F)c(Cl)cn2)CCN(Cc2cc(F)c(C(=O)NS(=O)(=O)C3CC3)cc2C2CC2)CC1] | 0.0036 | | |
| 473 | 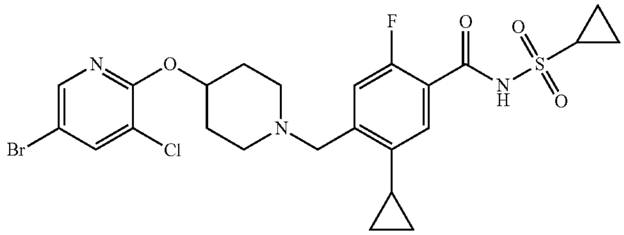 [SMILES: O=C(NS(=O)(=O)C1CC1)c1cc(C2CC2)c(CN2CCC(Oc3ncc(Br)cc3Cl)CC2)cc1F] | 0.0095 | | |
| 474 | 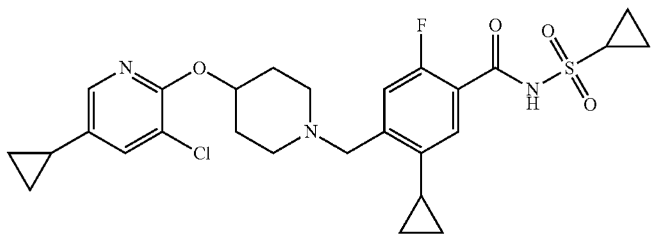 [SMILES: O=C(NS(=O)(=O)C1CC1)c1cc(C2CC2)c(CN2CCC(Oc3ncc(C4CC4)cc3Cl)CC2)cc1F] | 0.0056 | <0.0030 | 0.4493 |
| 475 | 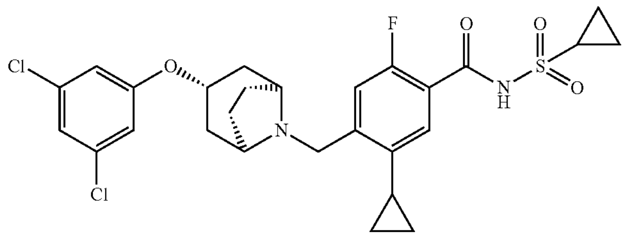 | 0.0031 | 0.0018 | 0.8140 |
| 476 | 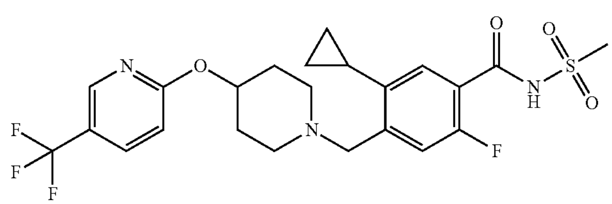 [SMILES: CS(=O)(=O)NC(=O)c1cc(C2CC2)c(CN2CCC(Oc3ccc(C(F)(F)F)cn3)CC2)cc1F] | 0.0372 | | |
| 477 | 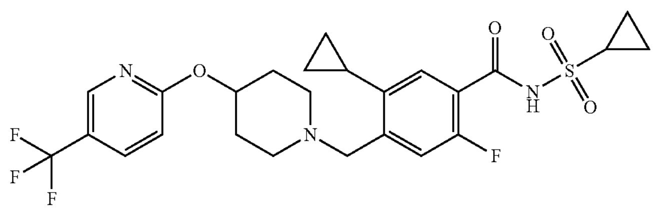 [SMILES: O=C(NS(=O)(=O)C1CC1)c1cc(C2CC2)c(CN2CCC(Oc3ccc(C(F)(F)F)cn3)CC2)cc1F] | 0.0142 | | |

TABLE 1-continued
| Example | Structure | Ligand Binding Assay (µM) | NaV1.7 EP (µM) | NaV1.5 EP (µM) |
|---|---|---|---|---|
| 478 | 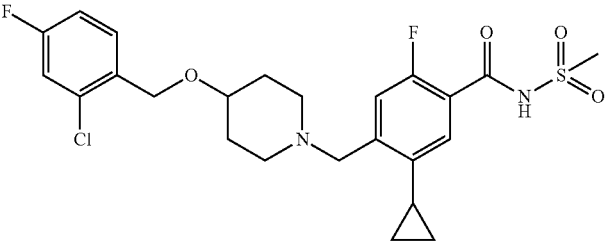 [SMILES: CS(=O)(=O)NC(=O)c1cc(C2CC2)c(CN2CCC(OCc3ccc(F)cc3Cl)CC2)cc1F] | 0.0381 | | |
| 479 | 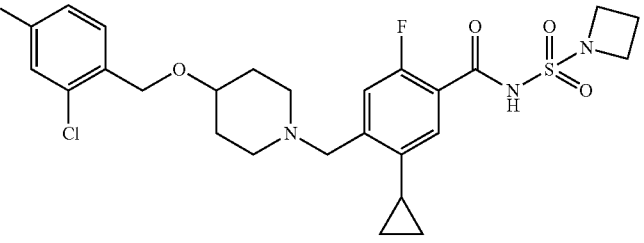 | 0.0553 | | |
| 480 | 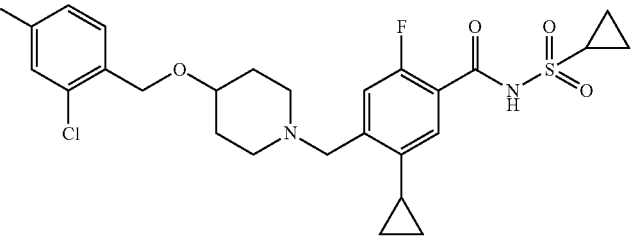 | 0.0218 | | |
| 481 | 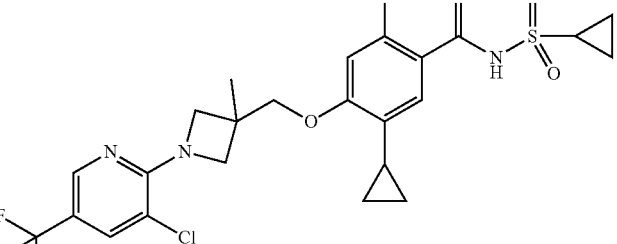 | 0.0031 | | |
| 482 | 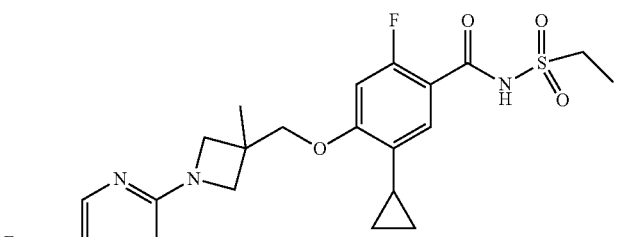 | 0.0033 | | |

TABLE 1-continued
| Example | Structure | Ligand Binding Assay (μM) | NaV1.7 EP (μM) | NaV1.5 EP (μM) |
|---|---|---|---|---|
| 483 | 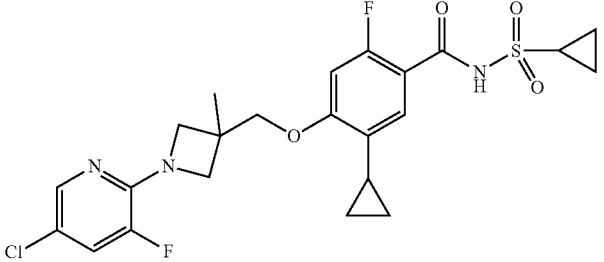 [SMILES: CC1(COc2cc(F)c(C(=O)NS(=O)(=O)C3CC3)cc2C2CC2)CN(c2ncc(Cl)cc2F)C1] | 0.0052 | | |
| 484 | 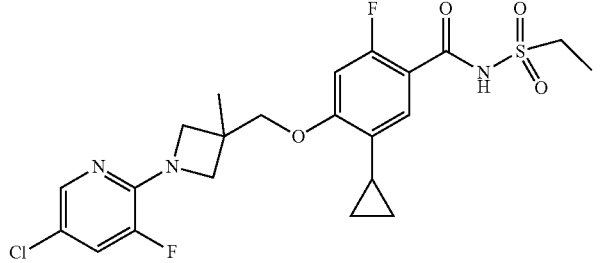 [SMILES: CCS(=O)(=O)NC(=O)c1cc(C2CC2)c(OCC2(C)CN(c3ncc(Cl)cc3F)C2)cc1F] | 0.0092 | | |
| 485 | 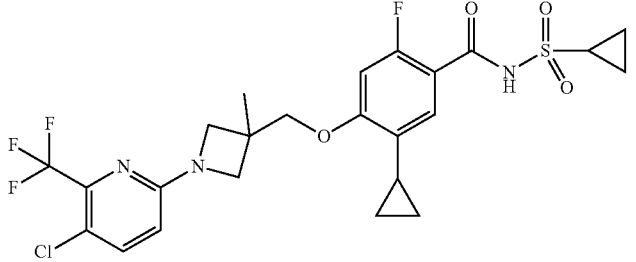 [SMILES: CC1(COc2cc(F)c(C(=O)NS(=O)(=O)C3CC3)cc2C2CC2)CN(c2ccc(Cl)c(C(F)(F)F)n2)C1] | 0.0045 | | |
| 486 | 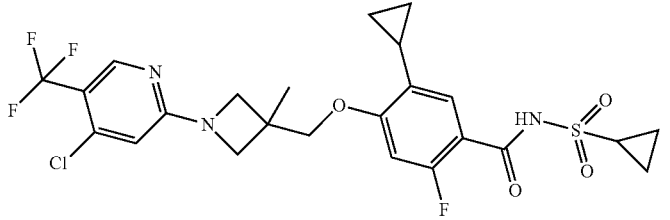 [SMILES: CC1(COc2cc(F)c(C(=O)NS(=O)(=O)C3CC3)cc2C2CC2)CN(c2cc(Cl)c(C(F)(F)F)cn2)C1] | 0.0056 | | |
| 487 | 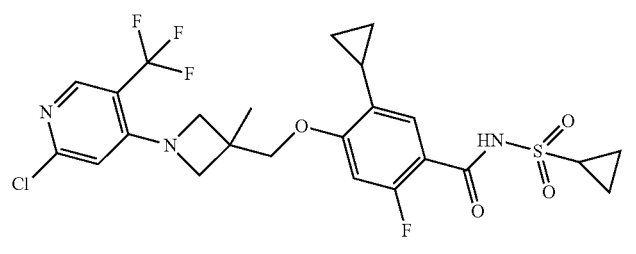 [SMILES: CC1(COc2cc(F)c(C(=O)NS(=O)(=O)C3CC3)cc2C2CC2)CN(c2cc(Cl)ncc2C(F)(F)F)C1] | 0.0135 | | |
| 488 | 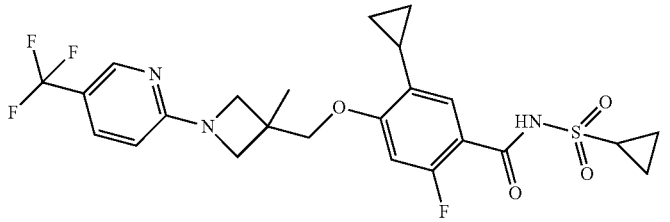 [SMILES: CC1(COc2cc(F)c(C(=O)NS(=O)(=O)C3CC3)cc2C2CC2)CN(c2ccc(C(F)(F)F)cn2)C1] | 0.0092 | | |

TABLE 1-continued

| Example | Structure | Ligand Binding Assay (μM) | NaV1.7 EP (μM) | NaV1.5 EP (μM) |
|---|---|---|---|---|
| 489 | 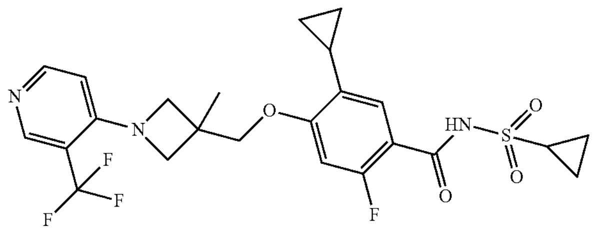 [SMILES: CC1(COc2cc(F)c(C(=O)NS(=O)(=O)C3CC3)cc2C2CC2)CN(c2ccncc2C(F)(F)F)C1] | 0.1031 | | |
| 490 | 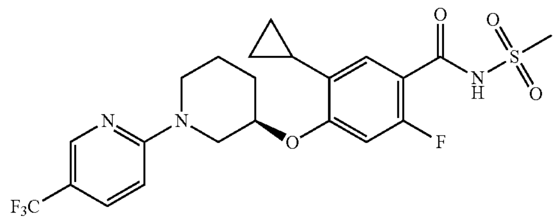 [SMILES: CS(=O)(=O)NC(=O)c1cc(C2CC2)c(O[C@@H]2CCCN(c3ccc(C(F)(F)F)cn3)C2)cc1F] | 0.0423 | | |
| 491 | 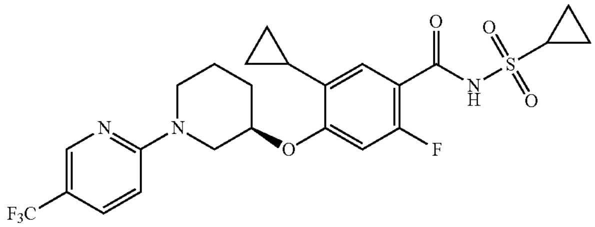 [SMILES: O=C(NS(=O)(=O)C1CC1)c1cc(C2CC2)c(O[C@@H]2CCCN(c3ccc(C(F)(F)F)cn3)C2)cc1F] | 0.0283 | | |
| 492 | 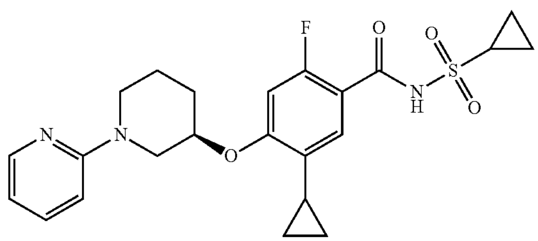 [SMILES: O=C(NS(=O)(=O)C1CC1)c1cc(C2CC2)c(O[C@@H]2CCCN(c3ccccn3)C2)cc1F] | 0.0938 | | |
| 493 | 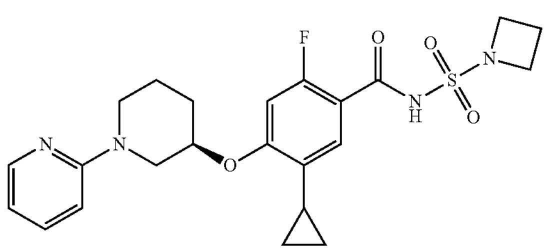 [SMILES: O=C(NS(=O)(=O)N1CCC1)c1cc(C2CC2)c(O[C@@H]2CCCN(c3ccccn3)C2)cc1F] | 0.2427 | | |
| 494 | 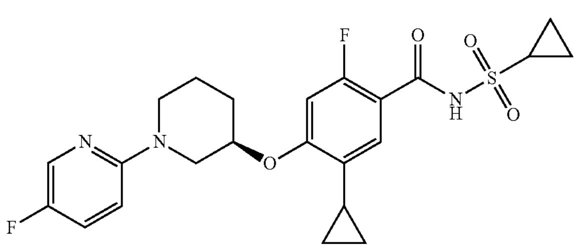 [SMILES: O=C(NS(=O)(=O)C1CC1)c1cc(C2CC2)c(O[C@@H]2CCCN(c3ccc(F)cn3)C2)cc1F] | 0.0527 | | |

TABLE 1-continued
| Example | Structure | Ligand Binding Assay (μM) | NaV1.7 EP (μM) | NaV1.5 EP (μM) |
|---|---|---|---|---|
| 495 | 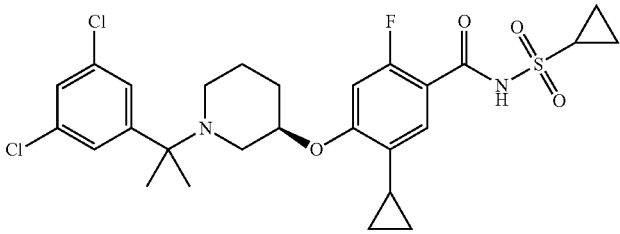 [SMILES: CC(C)(c1cc(Cl)cc(Cl)c1)N1CCC[C@@H](Oc2cc(F)c(C(=O)NS(=O)(=O)C3CC3)cc2C2CC2)C1] | 0.0044 | 0.0002 | 0.0154 |
| 496 | 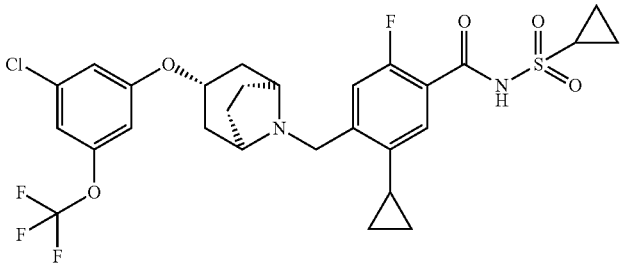 | 0.0022 | | |
| 497 | 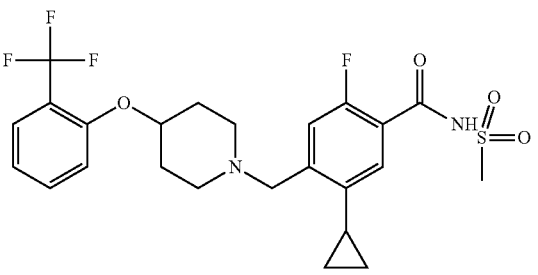 | 0.0143 | | |
| 498 | 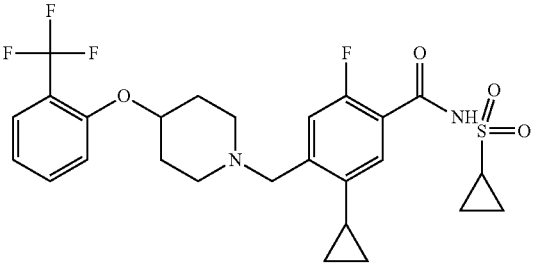 | 0.0874 | | |
| 499 | 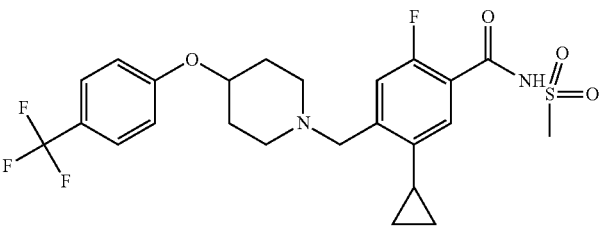 | 0.0136 | | |
| 500 | 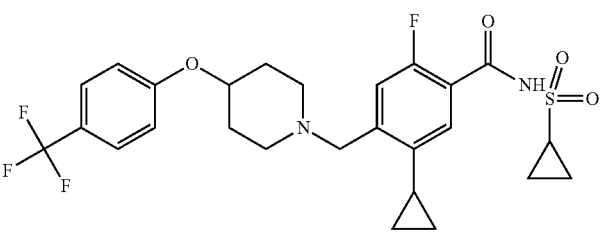 | 0.0078 | | |

TABLE 1-continued

| Example | Structure | Ligand Binding Assay (μM) | NaV1.7 EP (μM) | NaV1.5 EP (μM) |
|---|---|---|---|---|
| 501 | 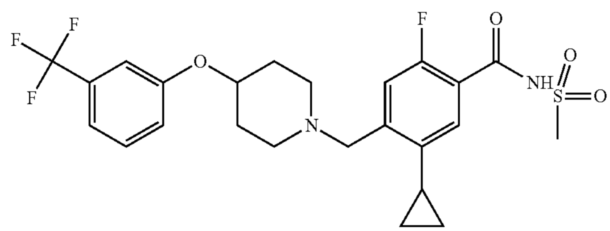 | 0.0134 | | |
| 502 | 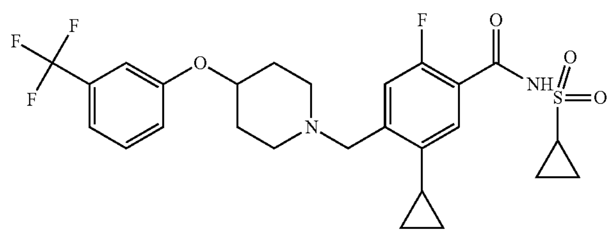 | 0.0068 | | |
| 503 | 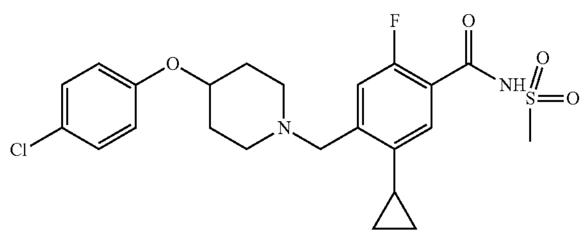 | 0.0296 | | |
| 504 | 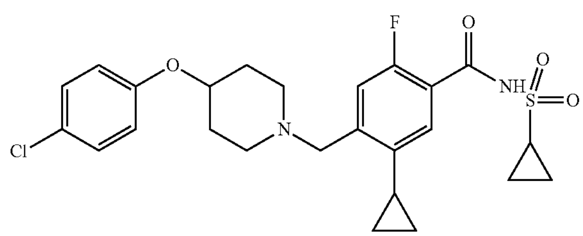 | 0.0162 | | |
| 505 | 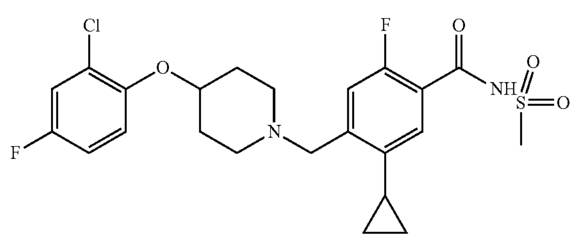 | 0.0278 | | |
| 506 | 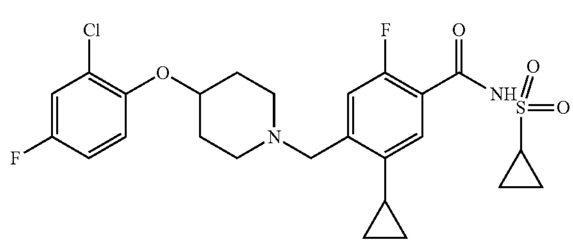 | 0.0143 | | |

TABLE 1-continued

| Example | Structure | Ligand Binding Assay (μM) | NaV1.7 EP (μM) | NaV1.5 EP (μM) |
|---|---|---|---|---|
| 507 | 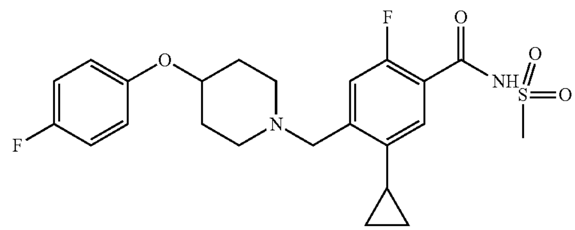 | 0.0817 | | |
| 508 | 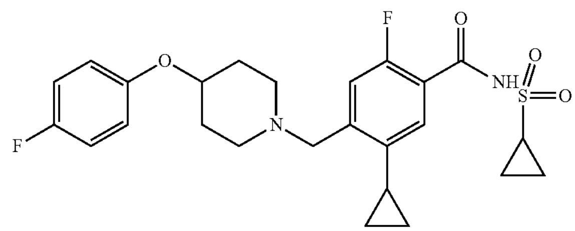 | 0.0440 | | |
| 509 | 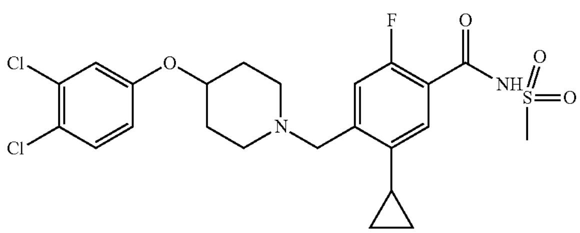 | 0.0131 | | |
| 510 | 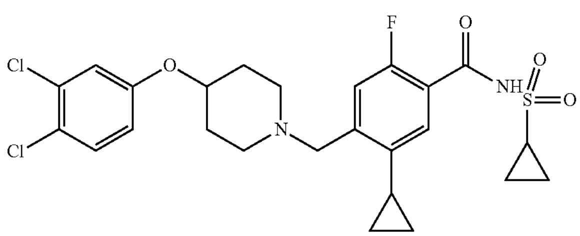 | 0.0091 | | |
| 511 | 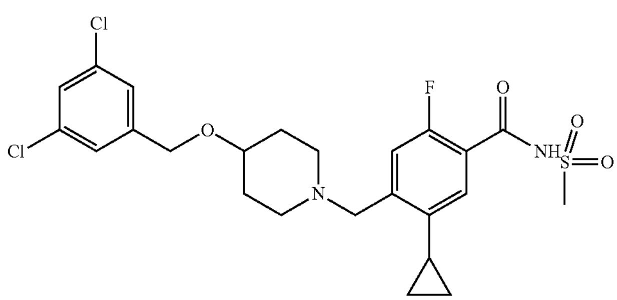 | 0.0235 | | |
| 512 | 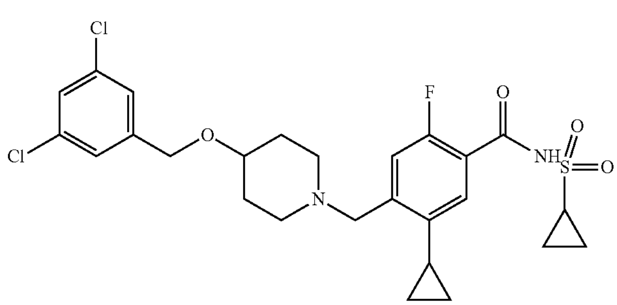 | 0.0167 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 513 | 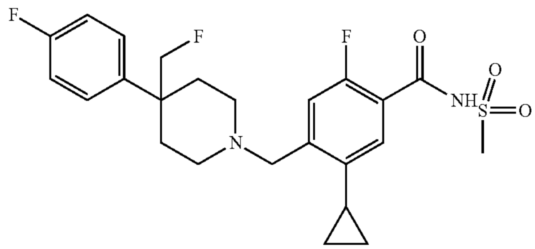 | 0.0698 | | |
| 514 | 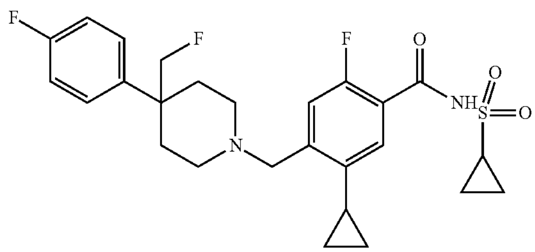 | 0.0244 | | |
| 515 | 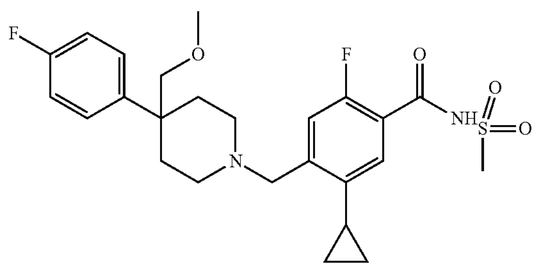 | 0.3843 | | |
| 516 | 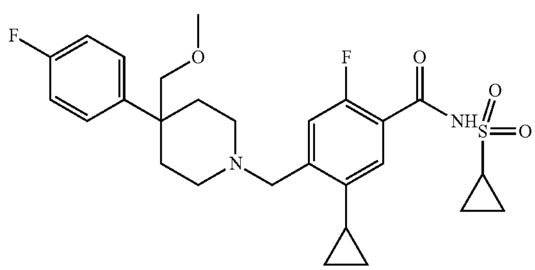 | 0.2131 | | |
| 517 | 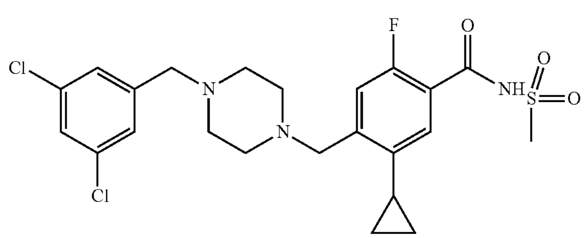 | 0.0150 | | |
| 518 | 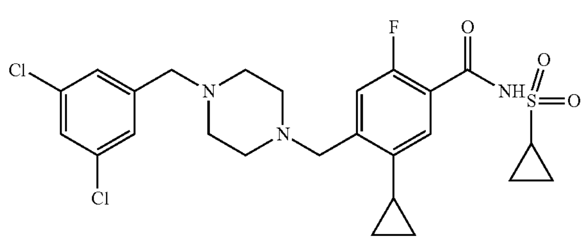 | 0.0082 | | |

TABLE 1-continued

| Example | Structure | Ligand Binding Assay (μM) | NaV1.7 EP (μM) | NaV1.5 EP (μM) |
|---|---|---|---|---|
| 519 | 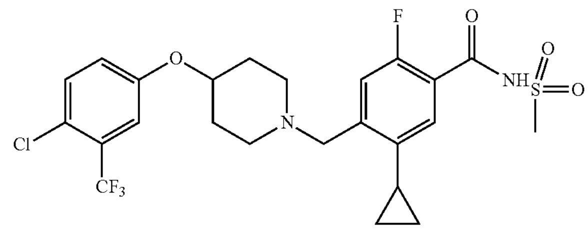 | 0.0081 | | |
| 520 | 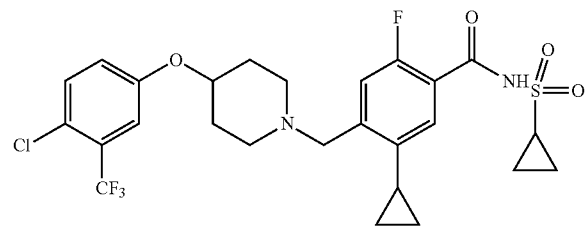 | 0.0073 | | |
| 521 | 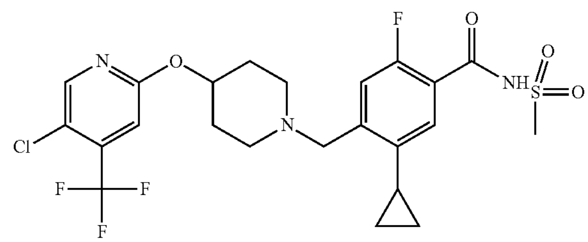 | 0.0079 | | |
| 522 | 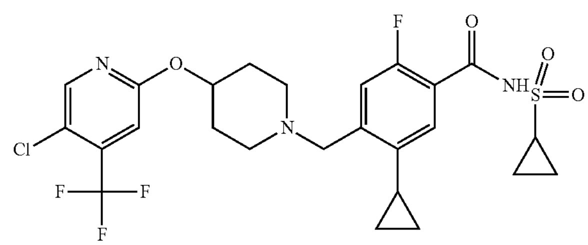 | 0.0052 | | |
| 523 | 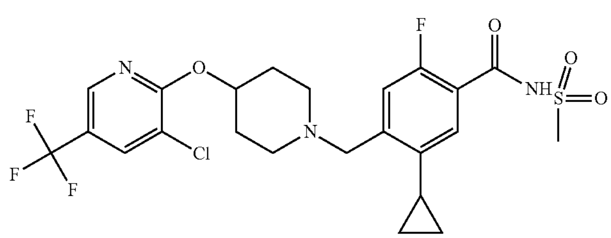 | 0.0058 | | |
| 524 | 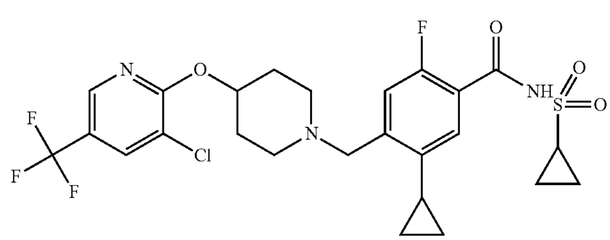 | 0.0114 | | |

TABLE 1-continued
| Example | Structure | Ligand Binding Assay (μM) | NaV1.7 EP (μM) | NaV1.5 EP (μM) |
|---|---|---|---|---|
| 525 | 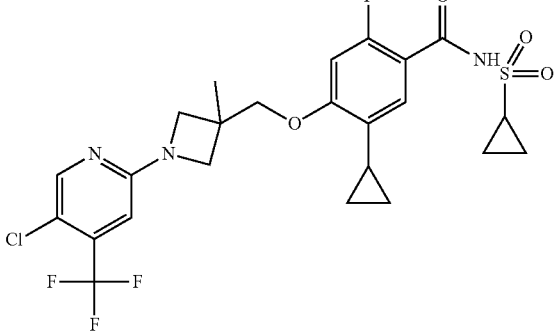 | 0.0065 | 0.0048 | 0.1134 |
| 526 | 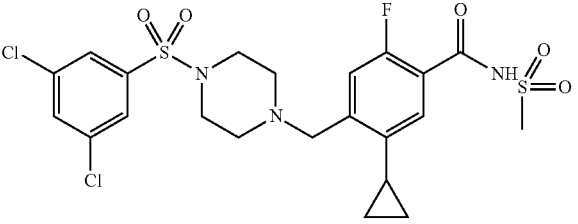 | 0.0202 | | |
| 527 | 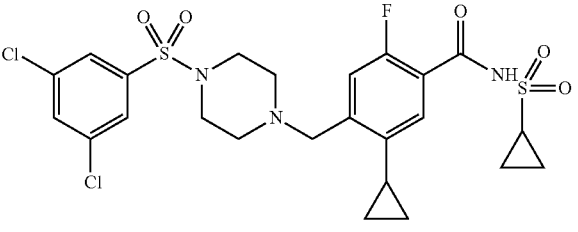 | 0.0099 | | |
| 528 | 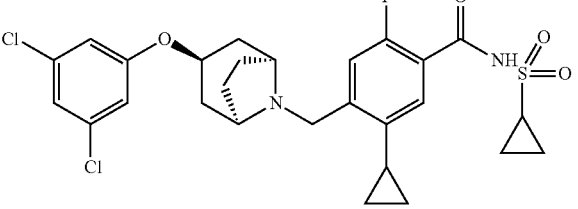 | 0.0034 | | |
| 529 | 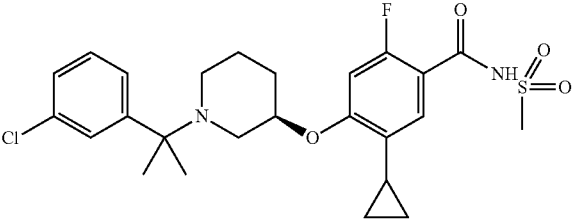 | 0.0024 | | |
| 530 | 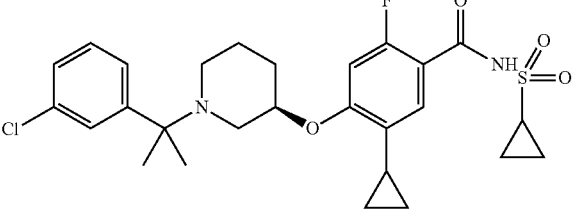 | 0.0023 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 531 | 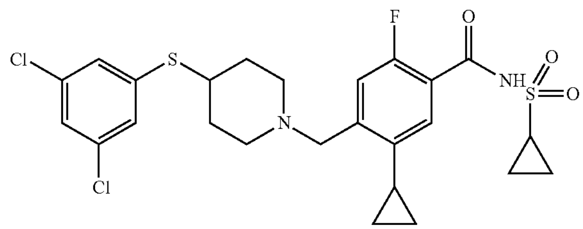 | 0.0022 | | |
| 532 | 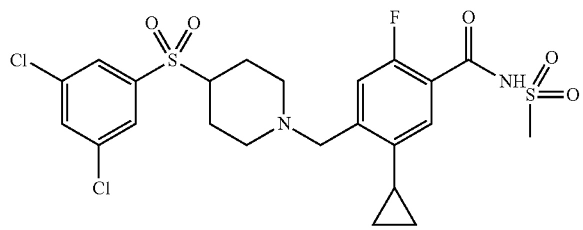 | 0.2205 | | |
| 533 | 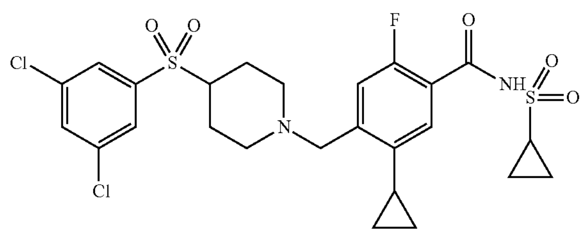 | 0.1268 | | |
| 534 | 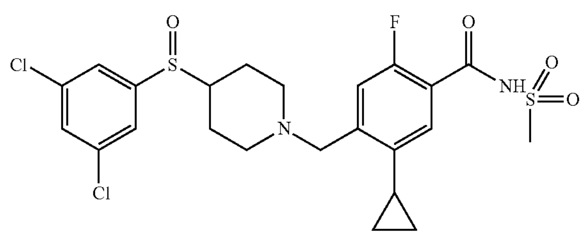 | 0.8789 | | |
| 535 | 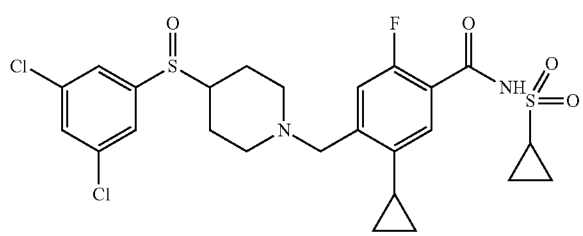 | 0.7204 | | |
| 536 | 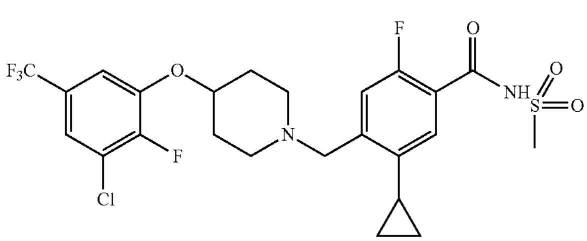 | 0.0050 | | |

TABLE 1-continued
| Example | Structure | Ligand Binding Assay (μM) | NaV1.7 EP (μM) | NaV1.5 EP (μM) |
|---|---|---|---|---|
| 537 | 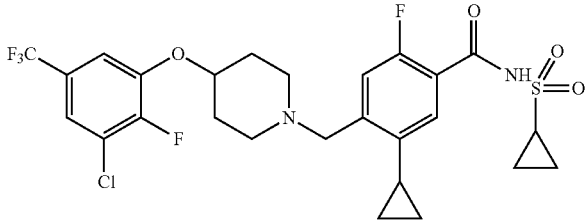 | 0.0057 | | |
| 538 | 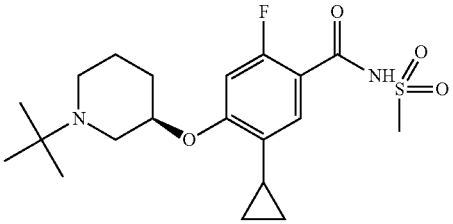 | 7.1223 | | |
| 539 | 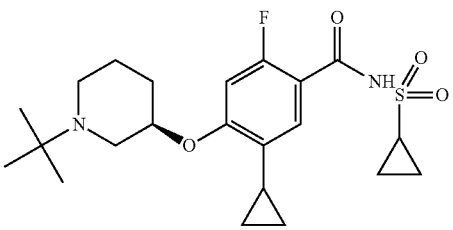 | 2.2782 | | |
| 540 | 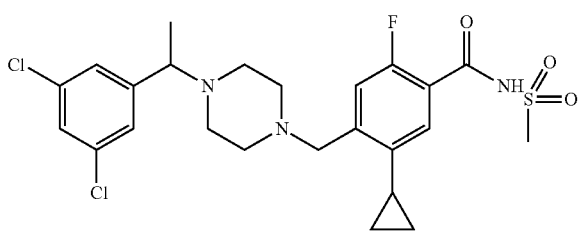 | 0.0078 | | |
| 541 | 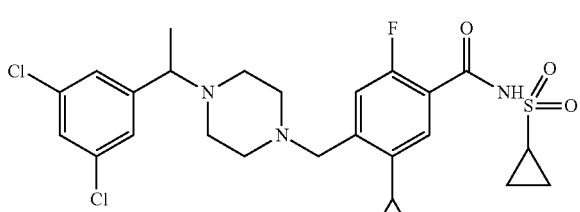 | 0.0059 | | |
| 542 | 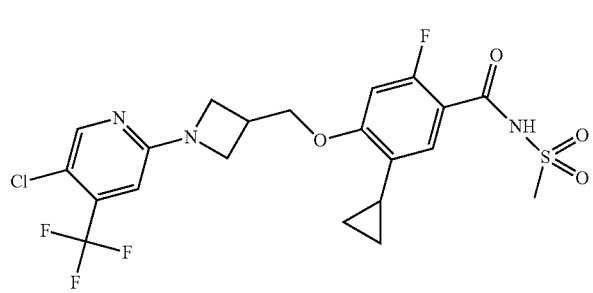 [SMILES: CS(=O)(=O)NC(=O)c1cc(C2CC2)c(OCC2CN(c3cc(C(F)(F)F)c(Cl)cn3)C2)cc1F] | 0.0270 | | |

TABLE 1-continued

| Example | Structure | Ligand Binding Assay (μM) | NaV1.7 EP (μM) | NaV1.5 EP (μM) |
|---|---|---|---|---|
| 543 | 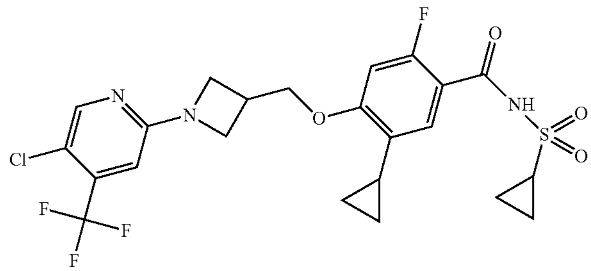 [SMILES: O=C(NS(=O)(=O)C1CC1)c1cc(C2CC2)c(OCC2CN(c3cc(C(F)(F)F)c(Cl)cn3)C2)cc1F] | 0.0117 | | |
| 544 | 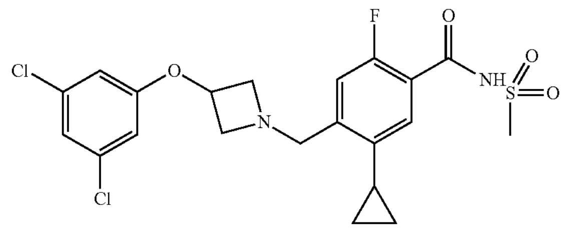 | 0.0153 | | |
| 545 | 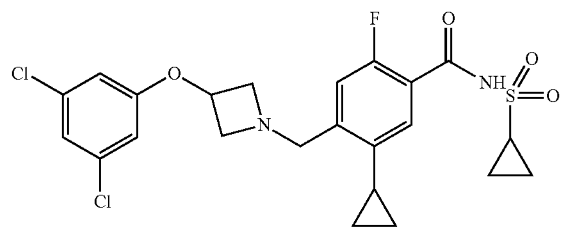 | 0.0034 | | |
| 546 | 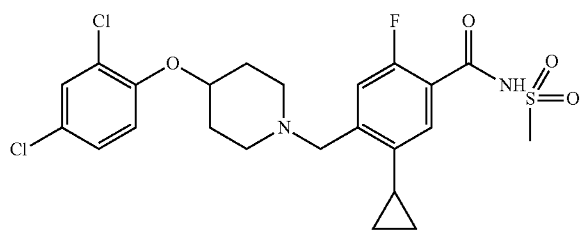 | 0.0119 | | |
| 547 | 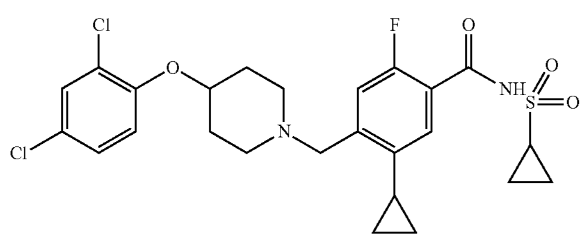 | 0.0082 | | |
| 548 | 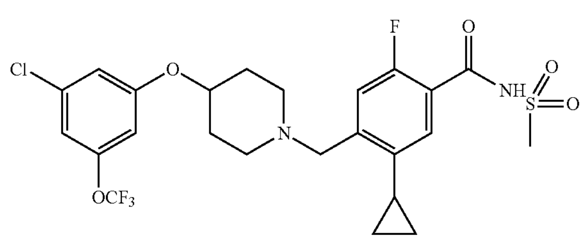 | 0.0037 | | |

TABLE 1-continued

| Example | Structure | Ligand Binding Assay (μM) | NaV1.7 EP (μM) | NaV1.5 EP (μM) |
|---|---|---|---|---|
| 549 | 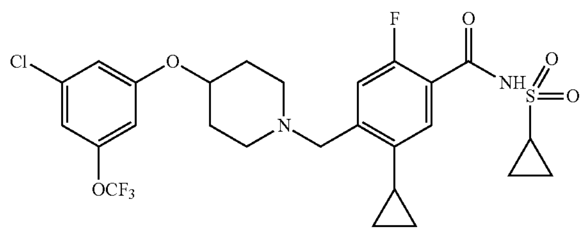 | 0.0044 | | |
| 550 | 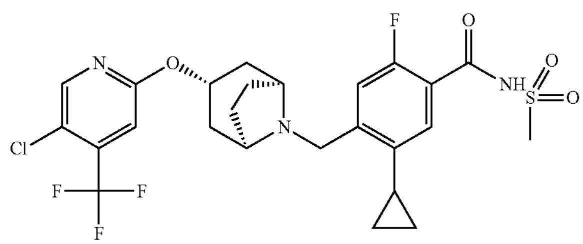 | 0.0136 | | |
| 551 | 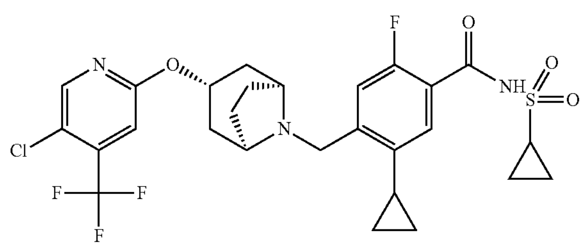 | 0.0075 | | |
| 552 | 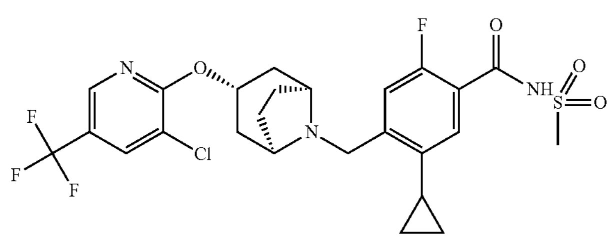 | 0.0070 | | |
| 553 | 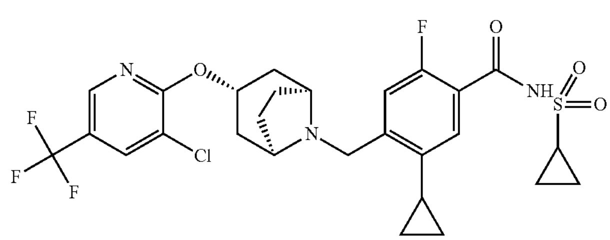 | 0.0061 | | |
| 554 | 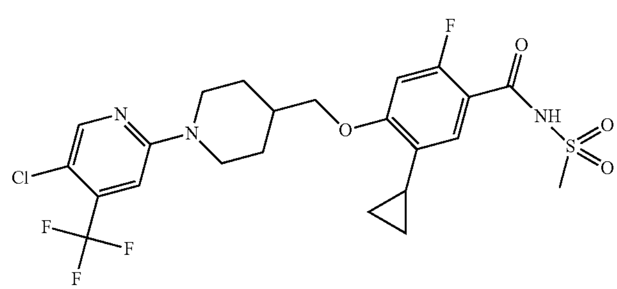 [SMILES: CS(=O)(=O)NC(=O)c1cc(C2CC2)c(OCC2CCN(c3cc(C(F)(F)F)c(Cl)cn3)CC2)cc1F] | 0.0032 | | |

TABLE 1-continued
| Example | Structure | Ligand Binding Assay (μM) | NaV1.7 EP (μM) | NaV1.5 EP (μM) |
|---|---|---|---|---|
| 555 | 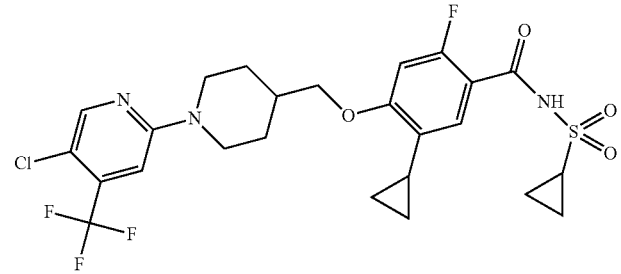 [SMILES: O=C(NS(=O)(=O)C1CC1)c1cc(C2CC2)c(OCC2CCN(c3cc(C(F)(F)F)c(Cl)cn3)CC2)cc1F] | 0.0029 | | |
| 556 | 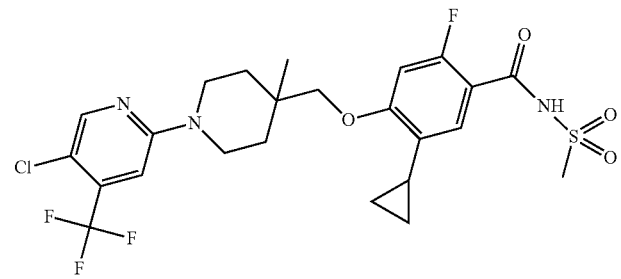 [SMILES: CC1(COc2cc(F)c(C(=O)NS(C)(=O)=O)cc2C2CC2)CCN(c2cc(C(F)(F)F)c(Cl)cn2)CC1] | 0.0021 | | |
| 557 | 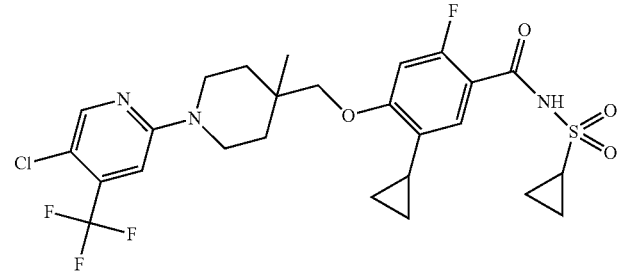 [SMILES: CC1(COc2cc(F)c(C(=O)NS(=O)(=O)C3CC3)cc2C2CC2)CCN(c2cc(C(F)(F)F)c(Cl)cn2)CC1] | 0.0027 | | |
| 558 | 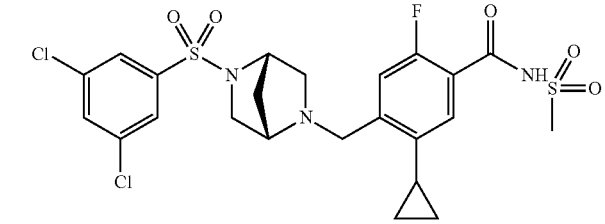 | 0.0371 | | |
| 559 | 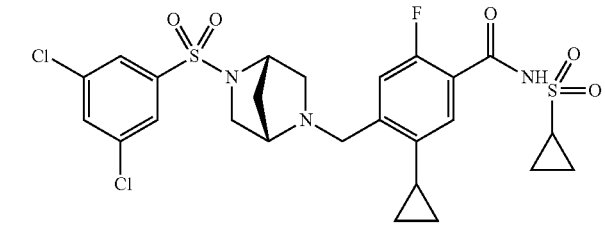 | 0.0189 | | |

TABLE 1-continued

| Example | Structure | Ligand Binding Assay (µM) | NaV1.7 EP (µM) | NaV1.5 EP (µM) |
|---|---|---|---|---|
| 560 | 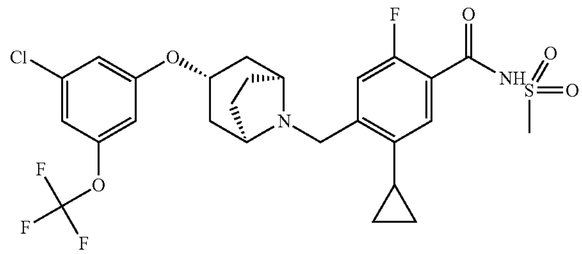 | 0.0028 | | |
| 561 | 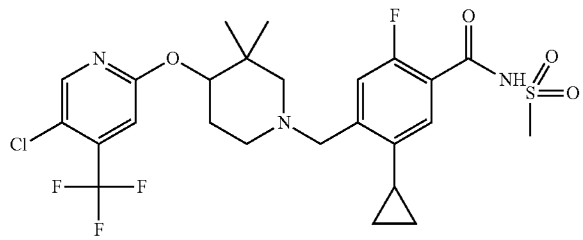 | 0.0028 | | |
| 562 | 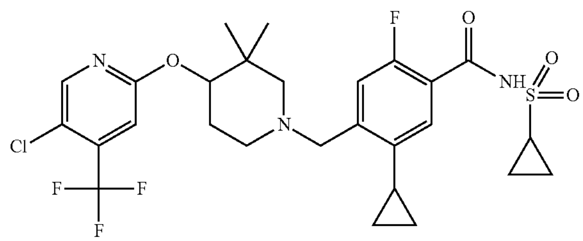 | 0.0031 | | |
| 563 | 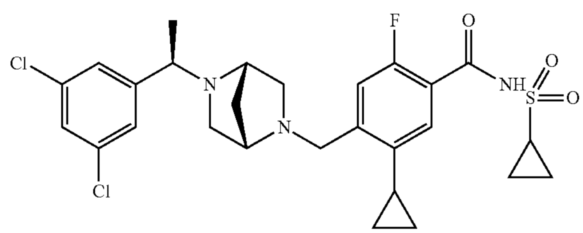 | 0.0042 | | |
| 564 | 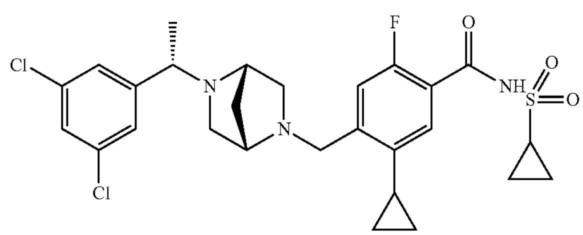 | 0.0036 | | |
| 565 | 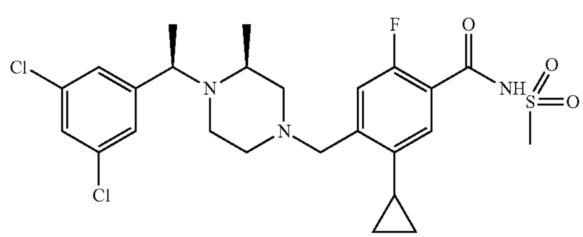 | 0.0041 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 566 | 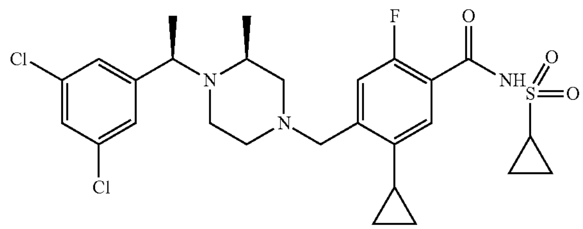 | 0.0027 | | |
| 567 | 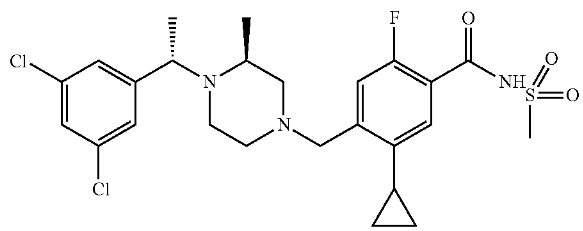 | 0.0152 | | |
| 568 | 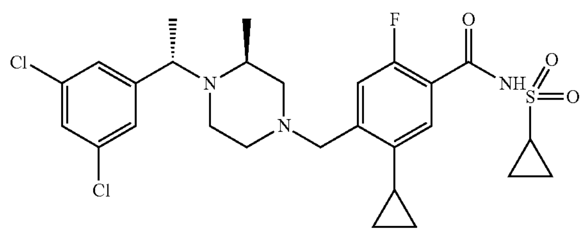 | 0.0095 | | |
| 569 | 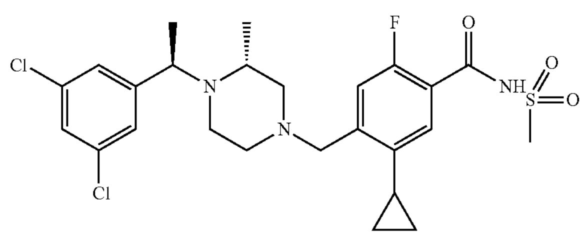 | 0.0048 | | |
| 570 | 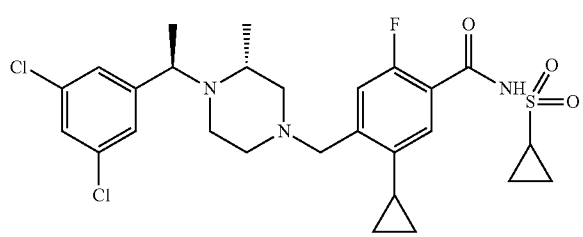 | 0.0029 | | |
| 571 | 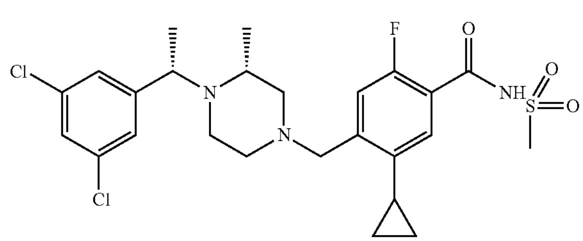 | 0.0443 | | |

TABLE 1-continued

| Example | Structure | Ligand Binding Assay (μM) | NaV1.7 EP (μM) | NaV1.5 EP (μM) |
|---------|-----------|---------------------------|----------------|----------------|
| 572 | 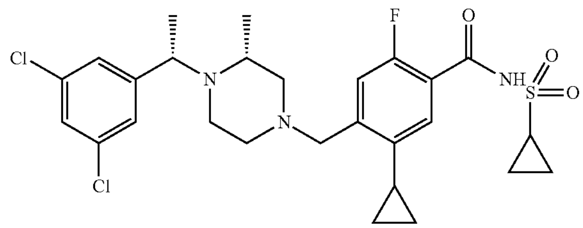 | 0.0216 | | |
| 573 | 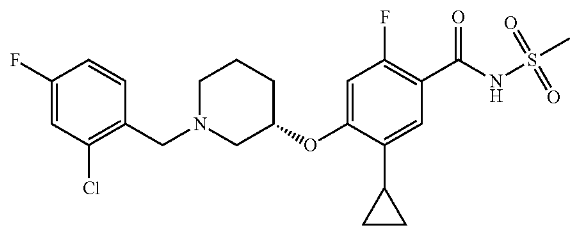 [SMILES: CS(=O)(=O)NC(=O)c1cc(C2CC2)c(O[C@H]2CCCN(Cc3ccc(F)cc3Cl)C2)cc1F] | 0.1072 | | |
| 574 | 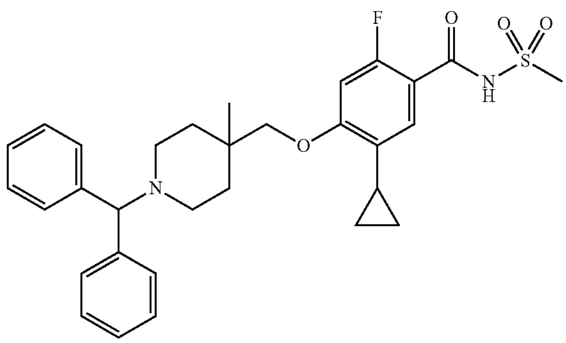 [SMILES: CC1(COc2cc(F)c(C(=O)NS(C)(=O)=O)cc2C2CC2)CCN(C(c2ccccc2)c2ccccc2)CC1] | 0.0029 | | |
| 575 | 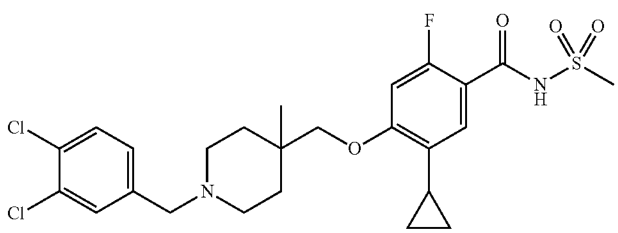 [SMILES: CC1(COc2cc(F)c(C(=O)NS(C)(=O)=O)cc2C2CC2)CCN(Cc2ccc(Cl)c(Cl)c2)CC1] | 0.0045 | | |
| 576 | 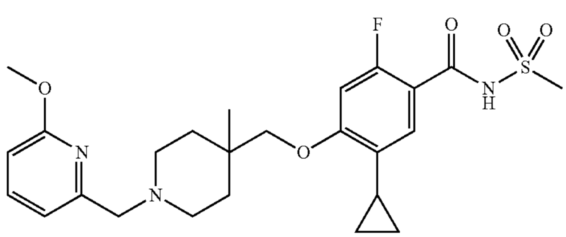 [SMILES: COc1cccc(CN2CCC(C)(COc3cc(F)c(C(=O)NS(C)(=O)=O)cc3C3CC3)CC2)n1] | 0.27 | | |
| 577 | 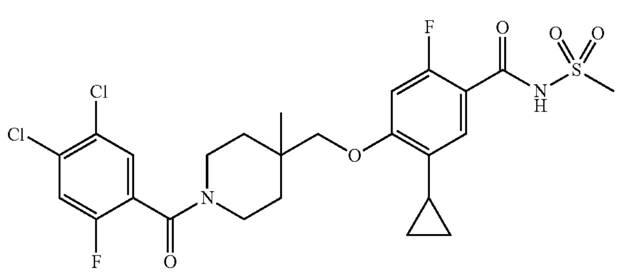 [SMILES: CC1(COc2cc(F)c(C(=O)NS(C)(=O)=O)cc2C2CC2)CCN(C(=O)c2cc(Cl)c(Cl)cc2F)CC1] | 0.04 | | |

TABLE 1-continued
| Example | Structure | Ligand Binding Assay (μM) | NaV1.7 EP (μM) | NaV1.5 EP (μM) |
|---|---|---|---|---|
| 578 | 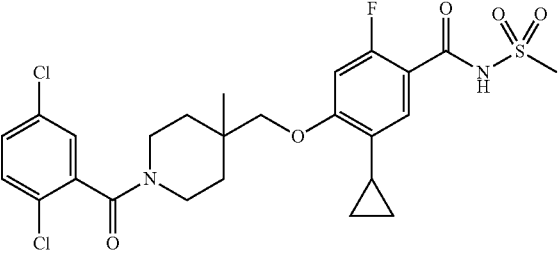 [SMILES: CC1(COc2cc(F)c(C(=O)NS(C)(=O)=O)cc2C2CC2)CCN(C(=O)c2cc(Cl)ccc2Cl)CC1] | 0.18 | | |
| 579 | 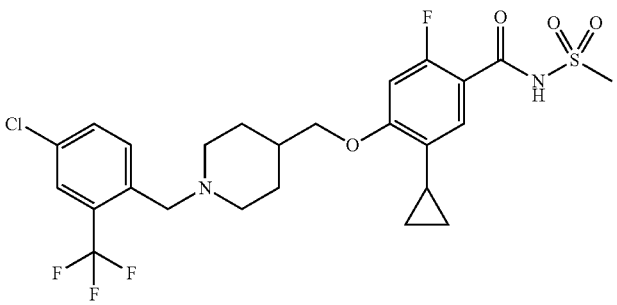 [SMILES: CS(=O)(=O)NC(=O)c1cc(C2CC2)c(OCC2CCN(Cc3ccc(Cl)cc3C(F)(F)F)CC2)cc1F] | 0.0029 | | |
| 580 | 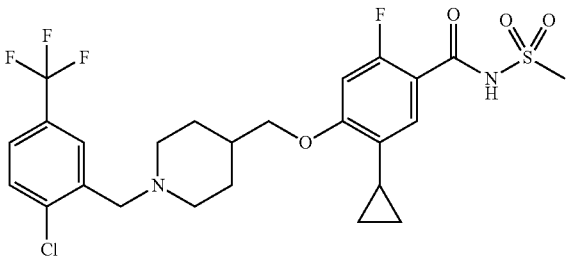 [SMILES: CS(=O)(=O)NC(=O)c1cc(C2CC2)c(OCC2CCN(Cc3cc(C(F)(F)F)ccc3Cl)CC2)cc1F] | 0.0037 | | |
| 581 | 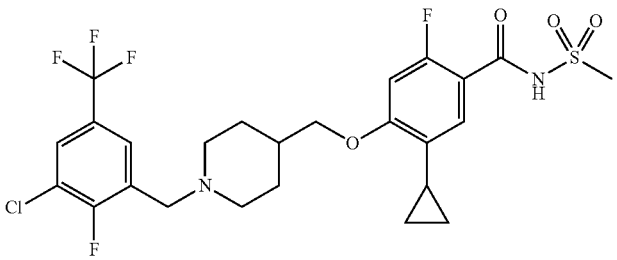 [SMILES: CS(=O)(=O)NC(=O)c1cc(C2CC2)c(OCC2CCN(Cc3cc(C(F)(F)F)cc(Cl)c3F)CC2)cc1F] | 0.0038 | | |
| 582 | 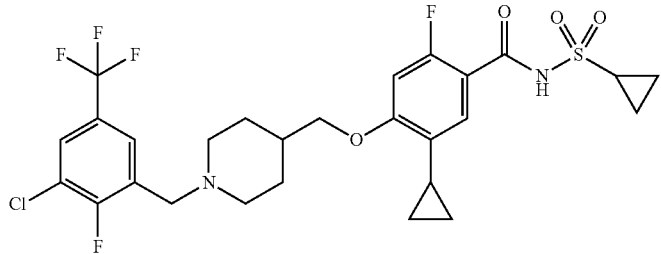 [SMILES: O=C(NS(=O)(=O)C1CC1)c1cc(C2CC2)c(OCC2CCN(Cc3cc(C(F)(F)F)cc(Cl)c3F)CC2)cc1F] | 0.0042 | | |

TABLE 1-continued

| Example | Structure | Ligand Binding Assay (μM) | NaV1.7 EP (μM) | NaV1.5 EP (μM) |
|---|---|---|---|---|
| 583 | 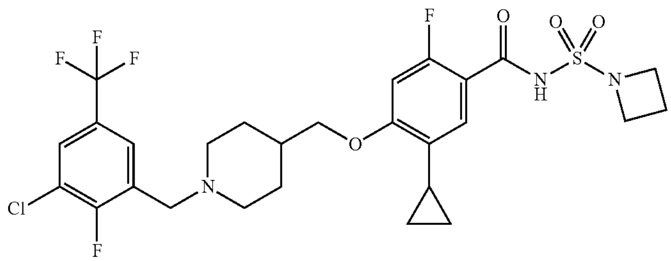 [SMILES: O=C(NS(=O)(=O)N1CCC1)c1cc(C2CC2)c(OCC2CCN(Cc3cc(C(F)(F)F)cc(Cl)c3F)CC2)cc1F] | 0.0034 | | |
| 584 | 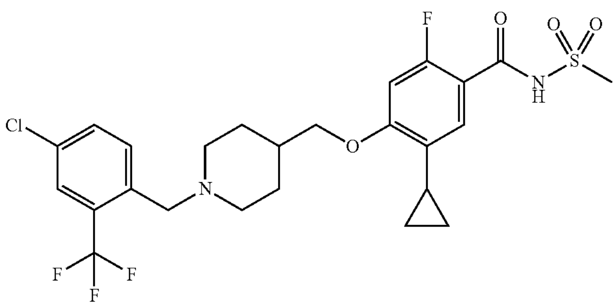 | 0.0029 | | |
| 585 | 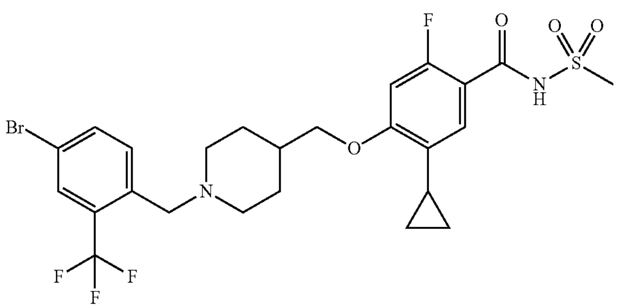 [SMILES: CS(=O)(=O)NC(=O)c1cc(C2CC2)c(OCC2CCN(Cc3ccc(Cl)cc3C(F)(F)F)CC2)cc1F] | 0.0035 | | |
| 586 | 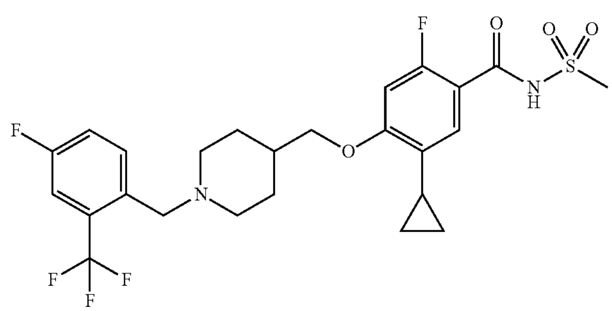 [SMILES: CS(=O)(=O)NC(=O)c1cc(C2CC2)c(OCC2CCN(Cc3ccc(F)cc3C(F)(F)F)CC2)cc1F] | 0.0052 | | |
| 587 | 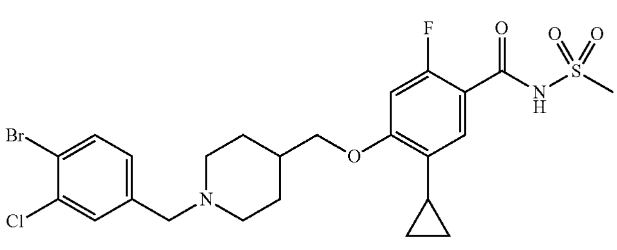 [SMILES: CS(=O)(=O)NC(=O)c1cc(C2CC2)c(OCC2CCN(Cc3ccc(Br)c(Cl)c3)CC2)cc1F] | 0.0051 | | |

TABLE 1-continued

| Example | Structure | Ligand Binding Assay (μM) | NaV1.7 EP (μM) | NaV1.5 EP (μM) |
|---|---|---|---|---|
| 588 | 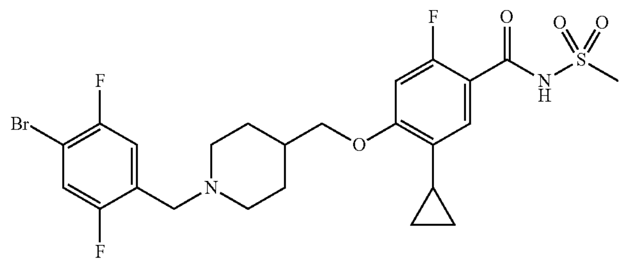 [SMILES: CS(=O)(=O)NC(=O)c1cc(C2CC2)c(OCC2CCN(Cc3cc(F)c(Br)cc3F)CC2)cc1F] | 0.0069 | | |
| 589 | 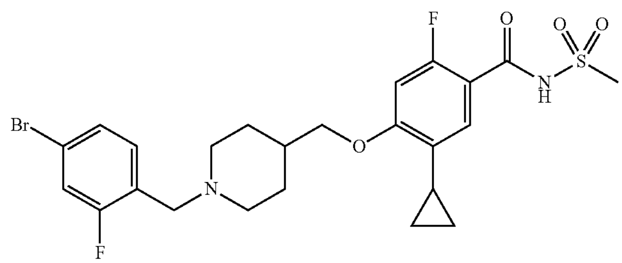 [SMILES: CS(=O)(=O)NC(=O)c1cc(C2CC2)c(OCC2CCN(Cc3ccc(Br)cc3F)CC2)cc1F] | 0.011 | | |
| 590 | 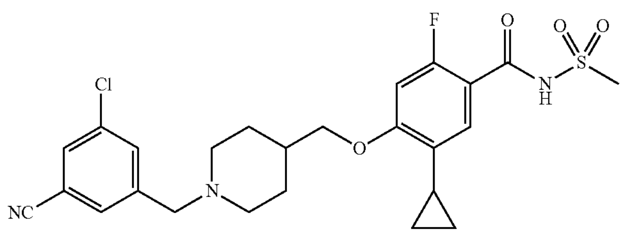 [SMILES: CS(=O)(=O)NC(=O)c1cc(C2CC2)c(OCC2CCN(Cc3cc(Cl)cc(C#N)c3)CC2)cc1F] | 0.026 | | |
| 591 | 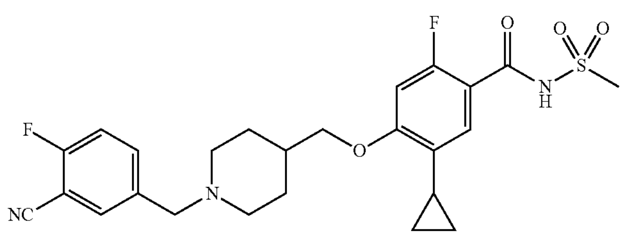 [SMILES: CS(=O)(=O)NC(=O)c1cc(C2CC2)c(OCC2CCN(Cc3ccc(F)c(C#N)c3)CC2)cc1F] | 0.24 | | |
| 592 | 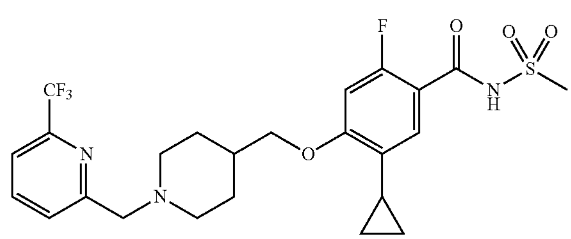 [SMILES: CS(=O)(=O)NC(=O)c1cc(C2CC2)c(OCC2CCN(Cc3cccc(C(F)(F)F)n3)CC2)cc1F] | 0.0054 | | |
| 593 | 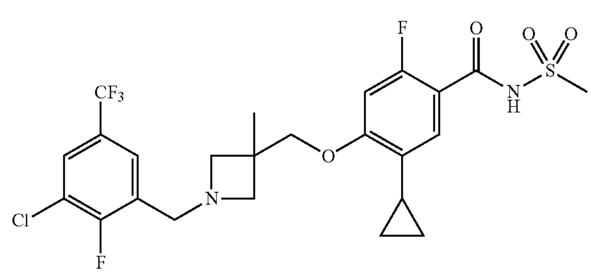 [SMILES: CC1(COc2cc(F)c(C(=O)NS(C)(=O)=O)cc2C2CC2)CN(Cc2cc(C(F)(F)F)cc(Cl)c2F)C1] | 0.0099 | | |

TABLE 1-continued

| Example | Structure | Ligand Binding Assay (μM) | NaV1.7 EP (μM) | NaV1.5 EP (μM) |
|---|---|---|---|---|
| 594 | 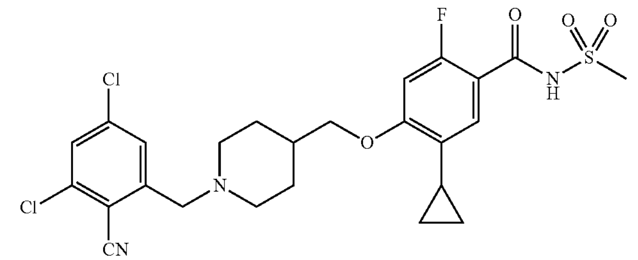 [SMILES: CS(=O)(=O)NC(=O)c1cc(C2CC2)c(OCC2CCN(Cc3cc(Cl)cc(Cl)c3C#N)CC2)cc1F] | 0.137 | 0.0084 | 0.623 |
| 595 | 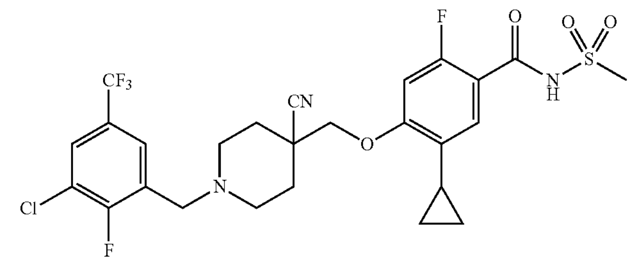 [SMILES: CS(=O)(=O)NC(=O)c1cc(C2CC2)c(OCC2(C#N)CCN(Cc3cc(C(F)(F)F)cc(Cl)c3F)CC2)cc1F] | 0.0343 | | |
| 596 | 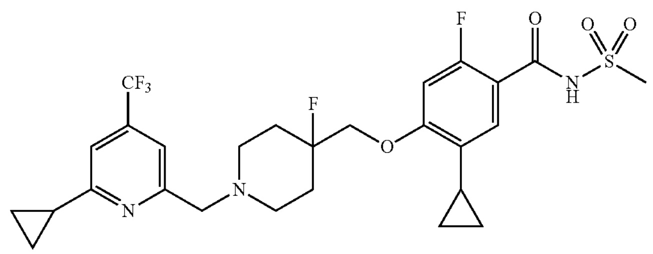 [SMILES: CS(=O)(=O)NC(=O)c1cc(C2CC2)c(OCC2(F)CCN(Cc3cc(C(F)(F)F)cc(C4CC4)n3)CC2)cc1F] | 0.0599 | | |
| 597 | 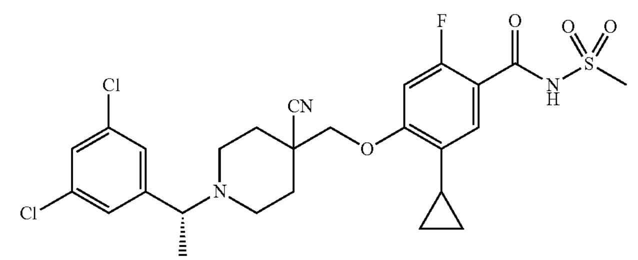 [SMILES: C[C@H](c1cc(Cl)cc(Cl)c1)N1CCC(C#N)(COc2cc(F)c(C(=O)NS(C)(=O)=O)cc2C2CC2)CC1] | 0.0276 | | |
| 598 | 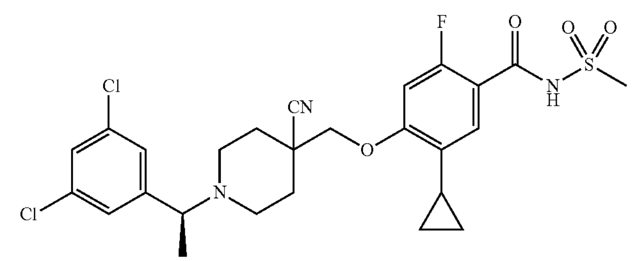 [SMILES: C[C@@H](c1cc(Cl)cc(Cl)c1)N1CCC(C#N)(COc2cc(F)c(C(=O)NS(C)(=O)=O)cc2C2CC2)CC1] | 0.258 | | |

Example 601

Analgesia Induced by Sodium Channel Blockers

Heat Induced Tail Flick Latency Test

In this test, the analgesia effect produced by administering a compound of the invention can be observed through heat-induced tail-flick in mice. The test includes a heat source consisting of a projector lamp with a light beam focused and directed to a point on the tail of a mouse being tested. The tail-flick latencies, which are assessed prior to drug treatment, and in response to a noxious heat stimulus, i.e., the response time from applying radiant heat on the dorsal surface of the tail to the occurrence of tail flick, are measured and recorded at 40, 80, 120, and 160 minutes.

For the first part of this study, 65 animals undergo assessment of baseline tail flick latency once a day over two consecutive days. These animals are then randomly assigned to one of the 11 different treatment groups including a vehicle control, a morphine control, and 9 compounds at 30 mg/Kg are administered intramuscularly. Following dose administration, the animals are closely monitored for signs of toxicity including tremor or seizure, hyperactivity, shallow, rapid or depressed breathing and failure to groom. The optimal incubation time for each compound is determined via regression analysis. The analgesic activity of the test compounds is expressed as a percentage of the maximum possible effect (% MPE) and is calculated using the following formula:

$$\% \, MPE \frac{\text{Postdrug latency} - \text{Predrug latency}}{\text{Cut-off time (10 s)} - \text{Predrug latency}} \times 100\%$$

where:

Postdrug latency=the latency time for each individual animal taken before the tail is removed (flicked) from the heat source after receiving drug.

Predrug latency=the latency time for each individual animal taken before the tail is flicked from the heat source prior to receiving drug.

Cut-off time (10 s)=is the maximum exposure to the heat source.

Acute Pain (Formalin Test)

The formalin test is used as art animal model of acute pain. In the formalin test, animals are briefly habituated to the plexiglass test chamber on the day prior to experimental day for 20 minutes. On the test day, animals are randomly injected with the test articles. At 30 minutes after drug administration, 50 µL of 10% formalin is injected subcutaneously into the plantar surface of the left hind paw of the rats. Video data acquisition begins immediately after formalin administration, for duration of 90 minutes.

The images are captured using the Actimetrix Limelight software which stores files under the *.llii extension, and then converts it into the MPEG-4 coding. The videos are then analyzed using behaviour analysis software "The Observer 5.1", (Version 5.0, Noldus Information Technology, Wageningen. The Netherlands). The video analysis is conducted by watching the animal behaviour and scoring each according to type, and defining the length of the behaviour (Dubuisson and Dennis, 1977). Scored behaviours include: (1) normal behaviour, (2) putting no weight on the paw, (3) raising the paw, (4) licking/biting or scratching the paw. Elevation, favoring, or excessive licking, biting and scratching of the injected paw indicate a pain response. Analgesic response or protection from compounds is indicated if both paws are resting on the floor with no obvious favoring, excessive licking, biting or scratching of the injected paw.

Analysis of the formalin test data is done according to two factors: (1) Percent Maximal Potential Inhibitory Effect (% MPIE) and (2) pain score. The % MPIEs is calculated by a series of steps, where the first is to sum the length of non-normal behaviours (behaviours 1, 2, 3) of each animal. A single value for the vehicle group is obtained by averaging all scores within the vehicle treatment group. The following calculation yields the MPIE value for each animal:

*MPIE* (%)=100−[(treatment sum/average vehicle value)×100%]

The pain score is calculated from a weighted scale as described above. The duration of the behaviour is multiplied by the weight (rating of the severity of the response), and divided by the total length of observation to determine a pain rating for each animal. The calculation is represented by the following formula:

Pain rating=[0($T_0$)+1($T_1$)+2($T_2$)+3($t_3$)]/($T_0$+$T_1$+$T_2$+$T_3$)

CPA Induced Chronic Inflammatory Pain

In this test, tactile allodynia is assessed with calibrated von Frey filaments. Following a full week of acclimatization to the vivarium facility, 150 µL of the "Complete Freund's Adjuvant" (CPA) emulsion (CFA suspended in an oil/saline (1:1) emulsion at a concentration of 0.5 mg/mL) is injected subcutaneously into the plantar surface of the left hind paw of rats under light isofluraneanaesthesia. Animals are allowed to recover from the anaesthesia and the baseline thermal and mechanical nociceptive thresholds of all animals are assessed one week after the administration of CFA. All animals are habituated to the experimental equipment for 20 minutes on the day prior to the start of the experiment. The test and control articles are administrated to the animals, and the nociceptive thresholds measured at defined time points after drug administration to determine the analgesic responses to each of the six available treatments. The time points used are previously determined to show the highest analgesic effect for each test compound.

Thermal nociceptive thresholds of the animals are assessed using the Hargreaves test. Animals are placed in a Plexiglas enclosure set on top of an elevated glass platform with heating units. The glass platform is thermostatically controlled at a temperature of approximately 30° C. for all test trials. Animals are allowed to accommodate for 20 minutes following placement into the enclosure until all exploration behaviour ceases. The Model 226 Plantar/Tail Stimulator Analgesia Meter (IITC, Woodland Hills, Calif.) is used to apply a radiant heat beam from underneath the glass platform to the plantar surface of the hind paws. During all test trials, the idle intensity and active intensity of the heat source are set at 1 and 45 respectively, and a cut off time of 20 seconds is employed to prevent tissue damage.

The response thresholds of animals to tactile stimuli are measured using the Model 2290 Electrovonfreyanesthesiometer (IITC Life Science, Woodland Hills, Calif.) following the Hargreaves test. Animals are placed in an elevated Plexiglas enclosure set on a mire mesh surface. After 10 minutes of accommodation, pre-calibrated Von Frey hairs are applied perpendicularly to the plantar surface of both paws of the animals in an ascending order starting from the 0.1 g hair, with sufficient force to cause slight buckling of the hair against the paw. Testing continues until the hair with the lowest force to induce a rapid flicking of the paw is determined or when the cut off force of approximately 20 g is reached. This cut off force is used because it represent approximately 10% of the animals' body weight and it serves to prevent raising of the entire limb due to the use of stiller hairs, which would change the nature of the stimulus.

Postoperative Models of Nociception

In this model, the hypealgesia caused by an intra-planar incision in the paw is measured by applying increased tactile stimuli to the paw until the animal withdraws its paw from the applied stimuli. While animals are anaesthetized under 3.5% isoflurane, which is delivered via a nose cone, a 1 cm longitudinal incision is made using a number 10 scalpel blade in the plantar aspect of the left hind paw through the skin and fascia, starting 0.5 cm from the proximal edge of the heel and extending towards the toes. Following the incision, the skin is apposed using 2, 3-0 sterilized silk sutures. The injured site is covered with Polysporin and Betadine. Animals are returned to their home cage for overnight recovery.

The withdrawal thresholds of animals to tactile stimuli for both operated (ipsilateral) and unoperated (contralateral) paws can be measured using the Model 2290 Electrovonfreyanesthesiometer (IITC Life Science, Woodland Hills, Calif.). Animals are placed in an elevated Plexiglas enclosure set on a mire mesh surface. After at least 10 minutes of acclimatization, pre-calibrated Von Frey hairs are applied perpendicularly to the plantar surface of both paws of the animals in an ascending order starting from the 10 g hair, with sufficient force to cause slight buckling of the hair against the paw. Testing continues until the hair with the lowest force to induce a rapid flicking of the paw is determined or when the cut off force of approximately 20 g is reached. This cut off force is used because it represent approximately 10% of the animals' body weight and it serves to prevent raising of the entire limb due to the use of stiffer hairs, which would change the nature of the stimulus.

Neuropathic Pain Model; Chronic Constriction Injury

Briefly, an approximately 3 cm incision is made through the skin and the fascia at the mid thigh level of the animals' left hind leg using a no. 10 scalpel blade. The left sciatic nerve is exposed via blunt dissection through, the biceps lemons with care to minimize haemorrhagia. Four loose ligatures are tied along the sciatic nerve using 4-0 non-degradable sterilized silk sutures at intervals of 1 to 2 mm apart. The tension of the loose ligatures is tight enough to induce slight constriction of the sciatic nerve when viewed under a dissection microscope at a magnification of 4 fold. In the sham-operated animal, the left sciatic nerve is exposed without further manipulation. Antibacterial ointment is applied directly into the wound, and the muscle is closed using sterilized sutures. Betadine is applied onto the muscle and its surroundings, followed by skin closure with surgical clips.

The response thresholds of animals to tactile stimuli are measured using the Model 2290 Electrovonfreyanesthesiometer (IITC Life Science, Woodland Hills, Calif.). Animals are placed in an elevated Plexiglas enclosure set on a mire mesh surface. After 10 minutes of accommodation, pre-calibrated Von Frey hairs are applied perpendicularly to the plantar surface of both paws of the animals in an ascending order starting from the 0.1 g hair, with sufficient force to cause slight buckling of the hair against the paw. Testing continues until the hair with the lowest force to induce a rapid flicking of the paw is determined or when the cut off force of approximately 20 g is reached. This cut off force is used because it represents approximately 10% of the animals' body weight and it serves to prevent raising of the entire limb due to the use of stiffer hairs, which would change the nature of the stimulus.

Thermal nociceptive thresholds of the animals are assessed using the Hargreaves test. Following the measurement of tactile thresholds, animals are placed in a Plexiglass enclosure set on top of an elevated glass platform with beating units. The glass platform is thermostatically controlled at a temperature of approximately 24 to 26° C. for all test trials. Animals are allowed to accommodate for 10 minutes following placement into the enclosure until all exploration behaviour ceases. The Model 226 Plantar/Tail Stimulator Analgesia Meter (IITC, Woodland Hills, Calif.) is used to apply a radiant heat beam from underneath the glass platform to the plantar surface of the hind paws. During all test trials, the idle intensity and active intensity of the heat source are set at 1 and 55 respectively, and a cut off time of 20 seconds is used to prevent tissue damage.

Neuropathic pass model: Spinal Nerve Ligation

The spinal nerve ligation (SNL) neuropathic pain model is used as an animal (i.e. rat) model of neuropathic pain. In the SNL test, the lumbar roots of spinal nerves L5 and L6 are tightly ligated to cause nerve injury, which results in the development of mechanical hyperalgesia, mechanical allodynia and thermal hypersensitivity. The surgery is performed two weeks before the test day in order for the pain state to fully develop in the animals. Several spinal nerve ligation variations are used to characterize the analgesic properties of a compound of the invention.

Ligation of the L5 spinal serve;
Ligation of the L5 and L6 spinal nerves:
Ligation and transection of the L5 spinal nerve;
Ligation and transection of the L5 and L6 spinal nerves; or
Mild irritation of the L4 spinal nerve in combination with any one of the above (1)-(4).

While the animals are anaesthetized under 3.5% isofluorane delivered via a nose cone, an approximately 2.5 cm longitudinal incision is made using a number 10 scalpel blade in the skin just lateral to the dorsal midline, using the level of the posterior iliac crests as the midpoint of the incision. Following the incision, the isofluorane is readjusted to maintenance levels (1.5%-2.5%). At mid-sacral region, an incision is made with the scalpel blade, sliding the blade along the side of the vertebral column (in the saggital plane) until the blade hits the sacrum. Scissors tips are introduced through the incision and the muscle and ligaments are removed from the spine to expose 2-3 cm of the vertebral column. The muscle and fascia are cleared from the spinal vertebra in order to locate the point where the nerve exits from the vertebra. A small glass hook is placed medial to the spinal nerves and the spinal nerves are gently elevated from the surrounding tissues. Once the spinal nerves have been isolated, a small length of non-degradable 6-0 sterilized silk thread is wound, twice around the ball at the tip of the glass hook and passed back under the nerve. The spinal nerves are then firmly Heated by tying a knot, ensuring mat the nerve bulges on both sides of the ligature. The procedure may be repeated as needed. In some animals, the L4 spinal nerve may be lightly rubbed (up to 20 times) with the small glass hook to maximise the development of neuropathic pain. Antibacterial ointment is applied directly into the incision, and the muscle is closed using sterilized sutures. Betadine is applied onto the muscle and its surroundings, followed by skin closure with surgical staples or sterile non-absorbable monofilament 5-0 nylon sutures.

The analgesic effect produced by topical administration of a compound of the invention to the animals can then be observed by measuring the paw withdrawal threshold of animals to mechanical tactile stimuli. These may be measured using either the mechanical allodynia procedure or the mechanical hyperalgesia procedure as described below. After establishment of the appropriate baseline measurements by either method, topical formulation of a compound of the invention is applied on the ipsilateral ankle and foot. The animals are then placed in plastic tunnels for 15 minutes to prevent them front licking the treated area and removing the compound. Animals are placed in the acrylic enclosure for 15 minutes before testing the ipsilateral paw by either of the methods described below, and the responses are recorded at 0.5, 1.0 and 2.0 hour post treatment.

Mechanical Allodynia Method

The pain threshold of animals to mechanical allodynia for both operated and control animals can be measured approximately 14 days post-surgery using manual calibrated von Frey filaments as follows. Animals are placed in an elevated plexiglass enclosure set on a mire mesh surface. Animals are allowed to acclimate for 20-30 minutes. Pre-calibrated Von Frey hairs are applied perpendicularly to the plantar surface of the ipsilateral paw of the animals starting from the 2.0 g hair, with sufficient force to cause slight buckling of the hair against the paw to establish the baseline measurements. Stimuli are presented in a consecutive manner, either in an ascending or descending order until the first change in response is noted, after which four additional responses are recorded for a total of six responses. The six responses measured in grams are entered into a formula as described by Chaplan, S. R. et al., J. Neurosci. Methods, 1994 July; 53(1):55-63, and a 50% withdrawal threshold is calculated. This constitutes the mechanical allodynia value.

B. Mechanical Hyperalgesia Method

The response thresholds of animals to tactile stimuli were measured using the Model 2290 Electrovonfreyanesthesiometer (IITC Life Science, Woodland Hills, Calif.). Animals were placed in an elevated Plexiglas enclosure set on a wire mesh surface. After 15 minutes of accommodation in this enclosure, a von Frey hair was applied perpendicularly to the plantar surface of the ipsilateral hind paws of the animals, with sufficient force, measured in grams, to elicit a crisp response of the paw. The response indicated a withdrawal from the painful stimulus and constituted the efficacy endpoint. The data were expressed as percent change from baseline threshold measured in grams.

Example 602

In Vivo Assay for Treatment of Pruritis

The compounds of the invention can be evaluated for their activity as antipruritic agents by in vivo test using rodent models. One established model for peripherally elicited pruritus is through the injection of serotonin into the rostral back area (neck) in hairless rats. Prior to serotonin injections (e.g., 2 mg/mL, 50 μL), a dose of a compound of the present invention can be applied systemically through oral, intravenous or intraperitoneal routes or topically to a circular area fixed diameter (e.g. 18 mm). Following dosing, the serotonin injections are given in the area of the topical dosing. After serotonin injection the animal behaviour is monitored by video recording for 20 min-1.5 h, and She number of scratches in this time compared to vehicle treated animals. Thus, application of a compound of the current invention could suppress serotonin-induced scratching in rats.

All of the U.S. patents, U.S. patent application publications, U.S. patent applications, foreign patents, foreign patent applications and non patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

The invention claimed is:

1. A compound selected from the group consisting of:

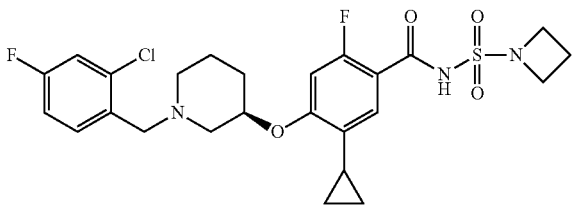

(R)—N-(azetidin-1-ylsulfonyl)-4-((1-(2-chloro-4-fluorobenzyl)piperidin-3-yl)oxy)-5-cyclopropyl-2-fluorobenzamide,

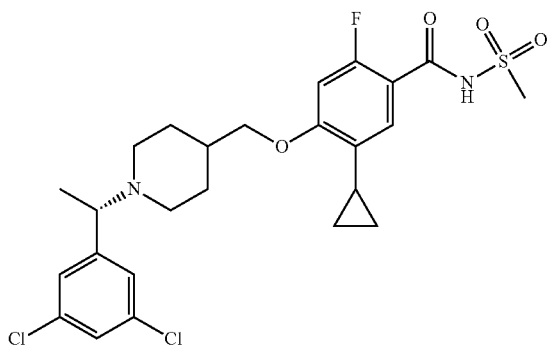 [SMILES: C[C@@H](c1cc(Cl)cc(Cl)c1)N1CCC(COc2cc(F)c(C(=O)NS(C)(=O)=O)cc2C2CC2)CC1]

(S)-5-cyclopropyl-4-((1-(1-(3,5-dichlorophenyl)ethyl)piperidin-4-yl)methoxy)-2-fluoro-N-(methylsulfonyl)benzamide,

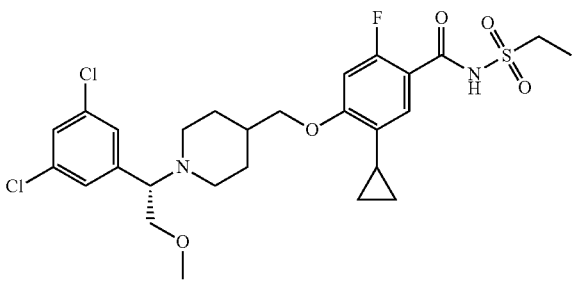 [SMILES: CCS(=O)(=O)NC(=O)c1cc(C2CC2)c(OCC2CCN([C@H](COC)c3cc(Cl)cc(Cl)c3)CC2)cc1F]

(S)-5-cyclopropyl-4-((1-(1-(3,5-dichlorophenyl)-2-methoxyethyl)piperidin-4-yl)methoxy)-N-(ethylsulfonyl)-2-fluorobenzamide,

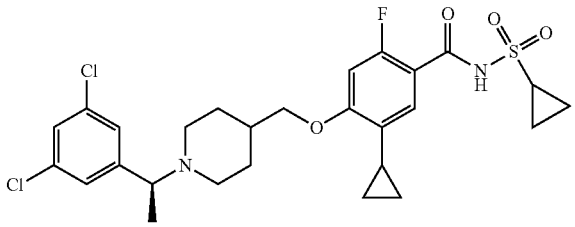 [SMILES: C[C@@H](c1cc(Cl)cc(Cl)c1)N1CCC(COc2cc(F)c(C(=O)NS(=O)(=O)C3CC3)cc2C2CC2)CC1]

(S)-5-cyclopropyl-N-(cyclopropylsulfonyl)-4-((1-(1-(3,5-dichlorophenyl)ethyl)piperidin-4-yl)methoxy)-2-fluorobenzamide,

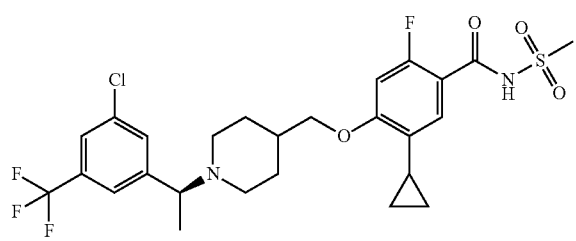 [SMILES: C[C@@H](c1cc(Cl)cc(C(F)(F)F)c1)N1CCC(COc2cc(F)c(C(=O)NS(C)(=O)=O)cc2C2CC2)CC1]

(S)-4-((1-(1-(3-chloro-5-(trifluoromethyl)phenyl)ethyl)piperidin-4-yl)methoxy)-5-cyclopropyl-2-fluoro-N-(methylsulfonyl)benzamide,

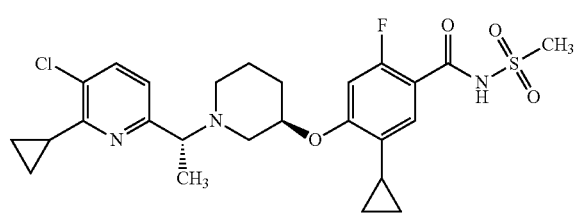 [SMILES: C[C@H](c1ccc(Cl)c(C2CC2)n1)N1CCC[C@@H](Oc2cc(F)c(C(=O)NS(C)(=O)=O)cc2C2CC2)C1]

4-(((R)-1-((R)-1-(5-chloro-6-cyclopropylpyridin-2-yl)ethyl)piperidin-3-yl)oxy-5-cyclopropyl-2-fluoro-N-(methylsulfonyl)benzamide,

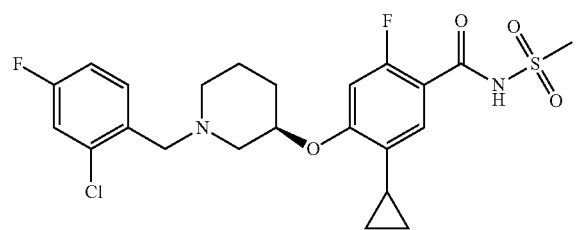 [SMILES: CS(=O)(=O)NC(=O)c1cc(C2CC2)c(O[C@@H]2CCCN(Cc3ccc(F)cc3Cl)C2)cc1F]

(R)-4-((1-(2-chloro-4-fluorobenzyl)piperidin-3-yl)oxy)-5-cyclopropyl-2-fluoro-N-(methylsulfonyl)benzamide,

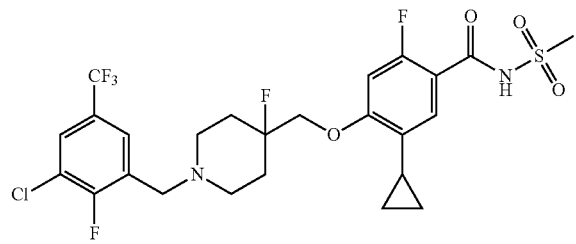 [SMILES: CS(=O)(=O)NC(=O)c1cc(C2CC2)c(OCC2(F)CCN(Cc3cc(C(F)(F)F)cc(Cl)c3F)CC2)cc1F]

4-((1-(3-chloro-2-fluoro-5-(trifluoromethyl)benzyl)-4-fluoropiperidin-4-yl)methoxy)-5-cyclopropyl-2-fluoro-N-(methylsulfonyl)benzamide, and

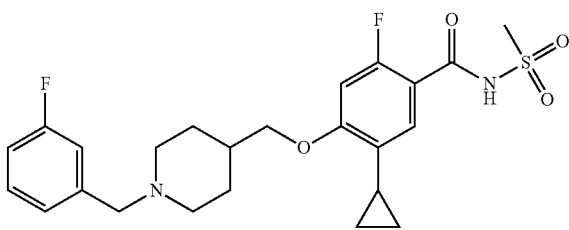 [SMILES: CS(=O)(=O)NC(=O)c1cc(C2CC2)c(OCC2CCN(Cc3cccc(F)c3)CC2)cc1F]

4-((1-(3-fluorobenzyl)piperidin-4-yl)methoxy)-5-cyclopropyl-2-fluoro-N-(methylsulfonyl)benzamide, and pharmaceutically acceptable salts thereof.

2. The compound of claim 1 which is:

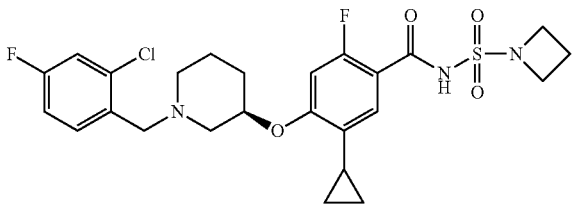

(R)—N-(azetidin-1-ylsulfonyl)-4-((1-(2-chloro-4-fluorobenzyl)piperidin-3-yl)oxy)-5-cyclopropyl-2-fluorobenzamide or a pharmaceutically acceptable salt thereof.

3. The compound of claim 1 which is:

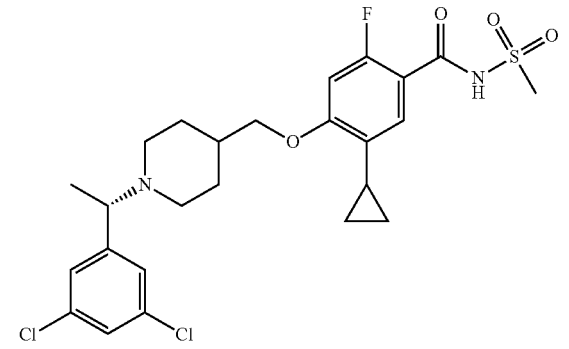 [SMILES: C[C@@H](c1cc(Cl)cc(Cl)c1)N1CCC(COc2cc(F)c(C(=O)NS(C)(=O)=O)cc2C2CC2)CC1]

(S)-5-cyclopropyl-4-((1-(1-(3,5-dichlorophenyl)ethyl)piperidin-4-yl)methoxy)-2-fluoro-N-(methylsulfonyl)benzamide or a pharmaceutically acceptable salt thereof.

4. The compound of claim 1 which is:

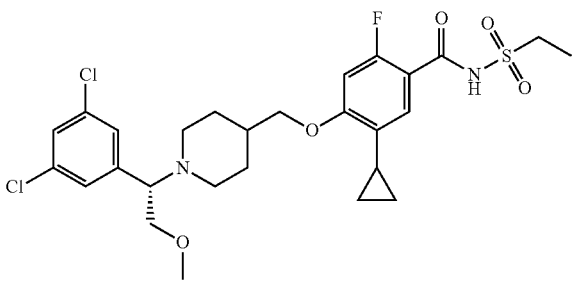 [SMILES: CCS(=O)(=O)NC(=O)c1cc(C2CC2)c(OCC2CCN([C@H](COC)c3cc(Cl)cc(Cl)c3)CC2)cc1F]

(S)-5-cyclopropyl-4-((1-(1-(3,5-dichlorophenyl)-2-methoxyethyl)piperidin-4-yl)methoxy)-N-(ethylsulfonyl)-2-fluorobenzamide or a pharmaceutically acceptable salt thereof.

5. The compound of claim 1 which is:

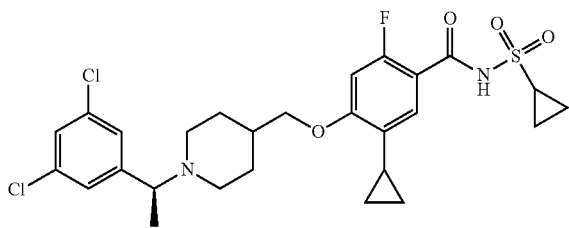 [SMILES: C[C@@H](c1cc(Cl)cc(Cl)c1)N1CCC(COc2cc(F)c(C(=O)NS(=O)(=O)C3CC3)cc2C2CC2)CC1]

(S)-5-cyclopropyl-N-(cyclopropylsulfonyl)-4-((1-(1-(3,5-dichlorophenyl)ethyl)piperidin-4-yl)methoxy)-2-fluorobenzamide or a pharmaceutically acceptable salt thereof.

6. The compound of claim 1 which is:

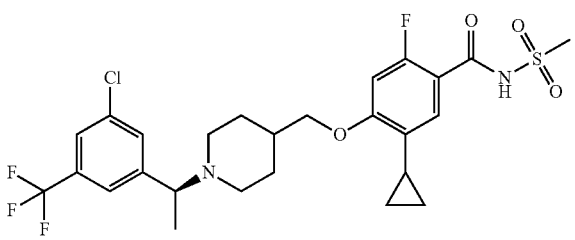 [SMILES: C[C@@H](c1cc(Cl)cc(C(F)(F)F)c1)N1CCC(COc2cc(F)c(C(=O)NS(C)(=O)=O)cc2C2CC2)CC1]

(S)-4-((1-(1-(3-chloro-5-(trifluoromethyl)phenyl)ethyl)piperidin-4-yl)methoxy)-5-cyclopropyl-2-fluoro-N-(methylsulfonyl)benzamide or a pharmaceutically acceptable salt thereof.

7. The compound of claim 1 which is:

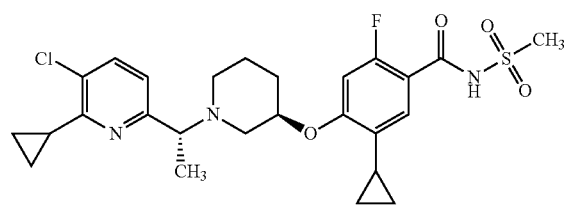 [SMILES: C[C@H](c1ccc(Cl)c(C2CC2)n1)N1CCC[C@@H](Oc2cc(F)c(C(=O)NS(C)(=O)=O)cc2C2CC2)C1]

4-(((R)-1-((R)-1-(5-chloro-6-cyclopropylpyridin-2-yl)ethyl)piperidin-3-yl)oxy)-5-cyclopropyl-2-fluoro-N-(methylsulfonyl)benzamide or a pharmaceutically acceptable salt thereof.

8. The compound of claim 1 which is:

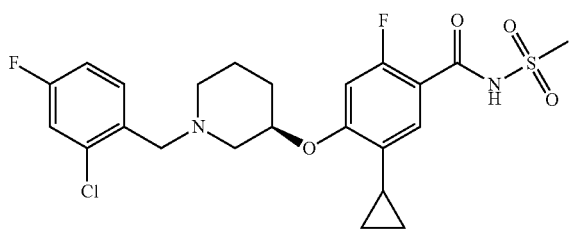 [SMILES: CS(=O)(=O)NC(=O)c1cc(C2CC2)c(O[C@@H]2CCCN(Cc3ccc(F)cc3Cl)C2)cc1F]

(R)-4-((1-(2-chloro-4-fluorobenzyl)piperidin-3-yl)oxy)-5-cyclopropyl-2-fluoro-N-(methylsulfonyl)benzamide or a pharmaceutically acceptable salt thereof.

9. The compound of claim 1 which is:

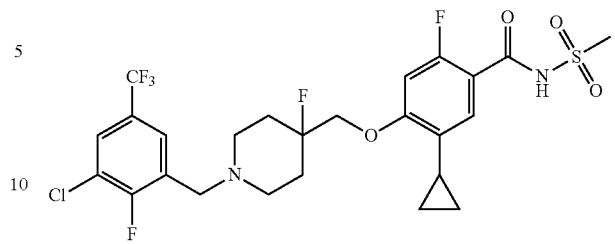

4-((1-(3-chloro-2-fluoro-5-(trifluoromethyl)benzyl)-4-fluoropiperidin-4-yl)methoxy)-5-cyclopropyl-2-fluoro-N-(methylsulfonyl)benzamide or a pharmaceutically acceptable salt thereof.

10. The compound of claim 1 which is:

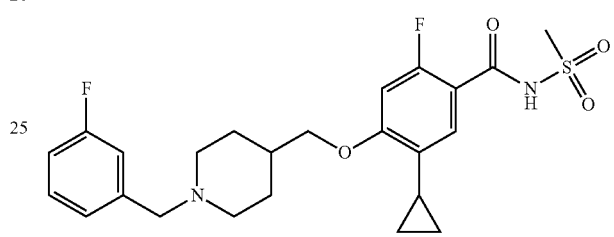

4-((1-(3-fluorobenzyl)piperidin-4-yl)methoxy)-5-cyclopropyl-2-fluoro-N-(methylsulfonyl)benzamide or a pharmaceutically acceptable salt thereof.

11. The compound of claim 1 which is:

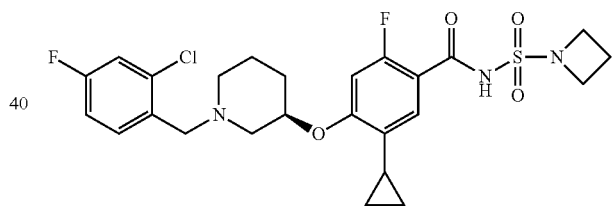

(R)—N-(azetidin-1-ylsulfonyl)-4-((1-(2-chloro-4-fluorobenzyl)piperidin-3-yl)oxy)-5-cyclopropyl-2-fluorobenzamide.

12. The compound of claim 1 which is:

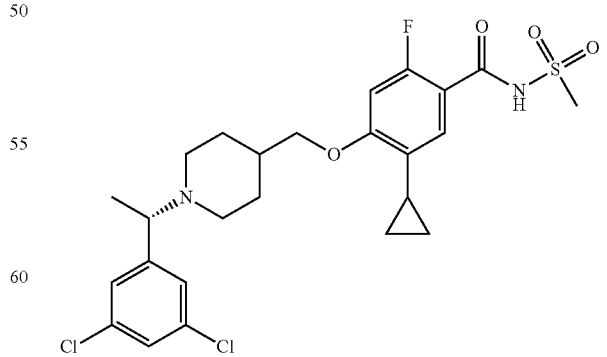

(S)-5-cyclopropyl-4-((1-(1-(3,5-dichlorophenyl)ethyl)piperidin-4-yl)methoxy)-2-fluoro-N-(methylsulfonyl)benzamide.

13. The compound of claim 1 which is:

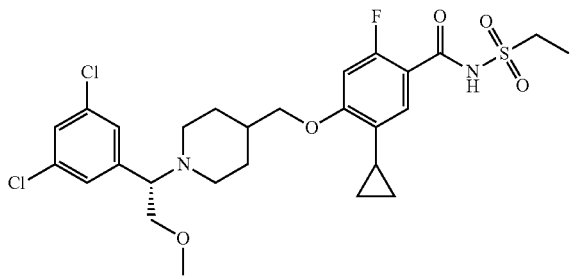 [SMILES: CCS(=O)(=O)NC(=O)c1cc(C2CC2)c(OCC2CCN([C@H](COC)c3cc(Cl)cc(Cl)c3)CC2)cc1F]

(S)-5-cyclopropyl-4-((1-(1-(3,5-dichlorophenyl)-2-methoxyethyl)piperidin-4-yl)methoxy)-N-(ethylsulfonyl)-2-fluorobenzamide.

14. The compound of claim 1 which is:

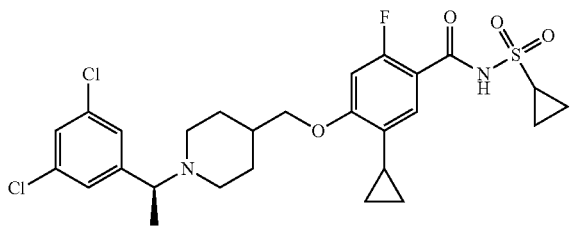 [SMILES: C[C@@H](c1cc(Cl)cc(Cl)c1)N1CCC(COc2cc(F)c(C(=O)NS(=O)(=O)C3CC3)cc2C2CC2)CC1]

(S)-5-cyclopropyl-N-(cyclopropylsulfonyl)-4-((1-(1-(3,5-dichlorophenyl)ethyl)piperidin-4-yl)methoxy)-2-fluorobenzamide.

15. The compound of claim 1 which is:

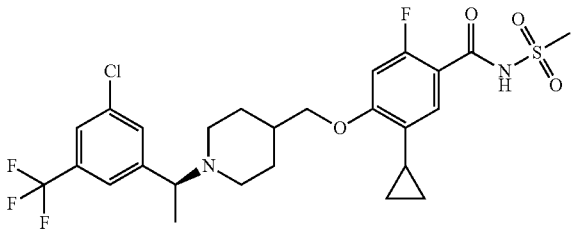 [SMILES: C[C@@H](c1cc(Cl)cc(C(F)(F)F)c1)N1CCC(COc2cc(F)c(C(=O)NS(C)(=O)=O)cc2C2CC2)CC1]

(S)-4-((1-(1-(3-chloro-5-(trifluoromethyl)phenyl)ethyl)piperidin-4-yl)methoxy)-5-cyclopropyl-2-fluoro-N-(methylsulfonyl)benzamide.

16. The compound of claim 1 which is:

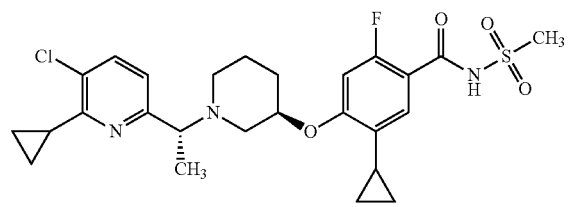 [SMILES: C[C@H](c1ccc(Cl)c(C2CC2)n1)N1CCC[C@@H](Oc2cc(F)c(C(=O)NS(C)(=O)=O)cc2C2CC2)C1]

4-(((R)-1-((R)-1-(5-chloro-6-cyclopropylpyridin-2-yl)ethyl)piperidin-3-yl)oxy)-5-cyclopropyl-2-fluoro-N-(methylsulfonyl)benzamide.

17. The compound of claim 1 which is:

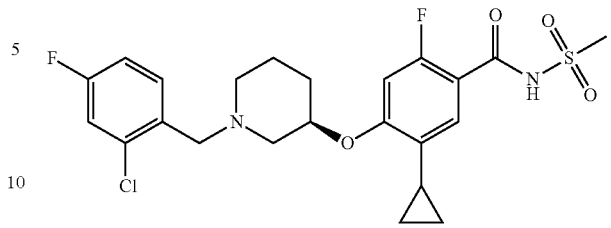

(R)-4-((1-(2-chloro-4-fluorobenzyl)piperidin-3-yl)oxy)-5-cyclopropyl-2-fluoro-N-(methylsulfonyl)benzamide.

18. The compound of claim 1 which is:

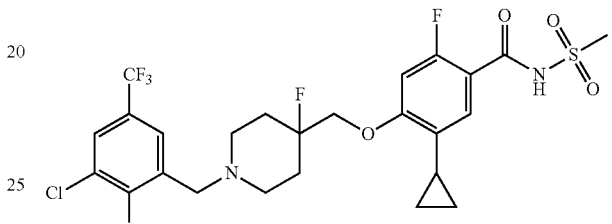

4-((1-(3-chloro-2-fluoro-5-(trifluoromethyl)benzyl)-4-fluoropiperidin-4-yl)methoxy)-5-cyclopropyl-2-fluoro-N-(methylsulfonyl)benzamide.

19. The compound of claim 1 which is:

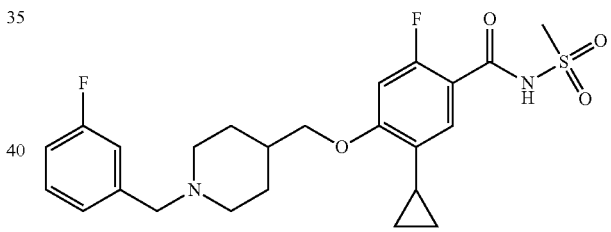

4-((1-(3-fluorobenzyl)piperidin-4-yl)methoxy)-5-cyclopropyl-2-fluoro-N-(methylsulfonyl)benzamide.

20. A pharmaceutical composition comprising a compound or a pharmaceutically acceptable salt thereof as described in claim 1, and a pharmaceutically acceptable excipient.

21. A pharmaceutical composition comprising the compound or a pharmaceutically acceptable salt thereof as described in claim 2, and a pharmaceutically acceptable excipient.

22. A pharmaceutical composition comprising the compound or a pharmaceutically acceptable salt thereof as described in claim 3, and a pharmaceutically acceptable excipient.

23. A pharmaceutical composition comprising the compound or a pharmaceutically acceptable salt thereof as described in claim 4, and a pharmaceutically acceptable excipient.

24. A pharmaceutical composition comprising the compound or a pharmaceutically acceptable salt thereof as described in claim 5, and a pharmaceutically acceptable excipient.

25. A pharmaceutical composition comprising the compound or a pharmaceutically acceptable salt thereof as described in claim 6, and a pharmaceutically acceptable excipient.

26. A pharmaceutical composition comprising the compound or a pharmaceutically acceptable salt thereof as described in claim 7, and a pharmaceutically acceptable excipient.

27. A pharmaceutical composition comprising the compound or a pharmaceutically acceptable salt thereof as described in claim 8, and a pharmaceutically acceptable excipient.

28. A pharmaceutical composition comprising the compound or a pharmaceutically acceptable salt thereof as described in claim 9, and a pharmaceutically acceptable excipient.

29. A pharmaceutical composition comprising the compound or a pharmaceutically acceptable salt thereof as described in claim 10, and a pharmaceutically acceptable excipient.

30. A pharmaceutical composition comprising the compound as described in claim 11, and a pharmaceutically acceptable excipient.

31. A pharmaceutical composition comprising the compound as described in claim 12, and a pharmaceutically acceptable excipient.

32. A pharmaceutical composition comprising the compound as described in claim 13, and a pharmaceutically acceptable excipient.

33. A pharmaceutical composition comprising the compound as described in claim 14, and a pharmaceutically acceptable excipient.

34. A pharmaceutical composition comprising the compound as described in claim 15, and a pharmaceutically acceptable excipient.

35. A pharmaceutical composition comprising the compound as described in claim 16, and a pharmaceutically acceptable excipient.

36. A pharmaceutical composition comprising the compound as described in claim 17, and a pharmaceutically acceptable excipient.

37. A pharmaceutical composition comprising the compound as described in claim 18, and a pharmaceutically acceptable excipient.

38. A pharmaceutical composition comprising the compound as described in claim 19, and a pharmaceutically acceptable excipient.

\* \* \* \* \*

UNITED STATES PATENT AND TRADEMARK OFFICE
CERTIFICATE OF CORRECTION

PATENT NO.        : 9,546,164 B2                                          Page 1 of 1
APPLICATION NO.   : 14/603273
DATED             : January 17, 2017
INVENTOR(S)       : Jean-Christophe Andrez et al.

It is certified that error appears in the above-identified patent and that said Letters Patent is hereby corrected as shown below:

On the Title Page

Item (56), Other Publications, Priest et al., please delete "9382 – 8387" and insert -- 9382 – 9387 --;

Item (56), Other Publications, Roberts et al., please delete "Heteroaryl Acyl" and insert -- Heteroaryl Acyl Sulfamide Synthesis via --;

Item (56), Other Publications, Tamaoka, please delete "42(2)" and insert -- 42(9) --;

Item (56), Other Publications, Deng et al., please delete "DOI: 10.1021j0049410e" and insert -- DOI: 10.1021jjm049410e --;

In the Claims

Column 1081, Line 32, Claim 1, please delete "oxy-5" and insert -- oxy)-5 -- therefor.

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*